US012715855B2

(12) United States Patent
Han et al.

(10) Patent No.: US 12,715,855 B2
(45) Date of Patent: Aug. 25, 2026

(54) FERROPTOSIS INHIBITORS—DIARYLAMINE PARA-ACETAMIDES

(71) Applicant: SIRONAX LTD., Grand Cayman (KY)

(72) Inventors: Jianguang Han, Beijing (CN); Zhiyuan Zhang, Beijing (CN)

(73) Assignee: SIRONAX LTD., Grand Cayman (KY)

( * ) Notice: Subject to any disclaimer, the term of this patent is extended or adjusted under 35 U.S.C. 154(b) by 830 days.

(21) Appl. No.: 17/908,583

(22) PCT Filed: Mar. 2, 2021

(86) PCT No.: PCT/CN2021/078601
§ 371 (c)(1),
(2) Date: Sep. 1, 2022

(87) PCT Pub. No.: WO2021/175200
PCT Pub. Date: Sep. 10, 2021

(65) Prior Publication Data

US 2023/0159492 A1 May 25, 2023

(30) Foreign Application Priority Data

Mar. 2, 2020 (WO) ................ PCT/CN2020/077408

(51) Int. Cl.

| | |
|---|---|
| *C07C 211/55* | (2006.01) |
| *A61K 31/16* | (2006.01) |
| *A61P 35/00* | (2006.01) |
| *C07D 211/34* | (2006.01) |
| *C07D 401/12* | (2006.01) |

(52) U.S. Cl.
CPC .......... *C07D 401/12* (2013.01); *C07D 211/34* (2013.01)

(58) Field of Classification Search
CPC ..... C07C 211/55; C07D 401/12; A61K 31/16; A61P 35/00
See application file for complete search history.

(56) References Cited

U.S. PATENT DOCUMENTS

| | | | |
|---|---|---|---|
| 4,436,921 | A | 3/1984 | Hori et al. |
| 2007/0105943 | A1 | 5/2007 | Nakamoto et al. |
| 2019/0248774 | A1 | 8/2019 | Pham et al. |

FOREIGN PATENT DOCUMENTS

| | | | |
|---|---|---|---|
| CA | 1131640 | A | 9/1982 |
| CN | 103404518 | A | 11/2013 |
| EP | 1 780 197 | A1 | 5/2007 |
| JP | S5630893 | A | 3/1981 |
| JP | 4249551 | A | 9/1992 |
| JP | H04249551 | A | 9/1992 |
| JP | 2006522127 | A | 9/2006 |
| JP | 2010524914 | A | 7/2010 |
| JP | 2010532381 | A | 10/2010 |
| JP | 2012518672 | A | 8/2012 |
| JP | 2013112740 | A | 6/2013 |
| JP | 2013522253 | A | 6/2013 |
| KR | 20159997208 | A | 8/2015 |
| WO | 9931073 | A1 | 6/1999 |
| WO | 2000039101 | A1 | 7/2000 |
| WO | 2003032994 | A1 | 4/2003 |
| WO | 2004002944 | A1 | 1/2004 |
| WO | 2004002964 | A2 | 1/2004 |
| WO | 2004087652 | A1 | 10/2004 |
| WO | WO 2006094800 | A2 | 9/2006 |
| WO | WO 2007/054725 | A2 | 5/2007 |
| WO | 2008129380 | A1 | 10/2008 |
| WO | WO 2009006389 | A2 | 1/2009 |
| WO | WO 2009006404 | A2 | 1/2009 |
| WO | 2010097372 | A1 | 9/2010 |
| WO | WO 2011113606 | A1 | 9/2011 |
| WO | 2012022795 | A1 | 2/2012 |
| WO | WO 2013152039 | A1 | 10/2013 |
| WO | 2014026242 | A1 | 2/2014 |
| WO | 2014026243 | A1 | 2/2014 |
| WO | 2016001077 | A1 | 1/2016 |
| WO | WO 2019008011 | A1 | 1/2019 |
| WO | 2019103952 | A1 | 5/2019 |
| WO | WO 2020/010280 | A1 | 1/2020 |
| WO | WO 2020/259683 | A1 | 12/2020 |

OTHER PUBLICATIONS

Feng, Yansheng et al., "Liproxstatin-1 protects the mouse myocardium against ischemia/reperfusion injury by decreasing VDAC1 levels and restoring GPX4 levels," Biochemical and Biophysical Research Communications, vol. 520,3: 606-611, (2019).*

Stockwell, Brent et al., "Ferroptosis: a regulated cell death nexus linking metabolism, redox biology, and disease," Cell, 2017, 171(2): 273-285.*

T. Hori et al., Studies on antitumor-active 2,3-dioxopiperazine derivatives. IV. Synthesis and structure-antitumor activity relationship of 1-(4-(2-pyridylamino)benzyl)-2,3-dioxopiperazine derivatives, Chemical & Pharmaceutical Bulletin, 29(6), pp. 1594-1605 (1981).

CAS. "CAS RN 2419344-98-0, 2471334-68-4" STN Registry, Jun. 5, 2020.

CAS. "CAS RN 2249343-87-9, 1462467-50-0, 1242513-60-5, 1242513-59-2" STN Registry, Sep. 24, 2010.

(Continued)

*Primary Examiner* — Bruck Kifle

(74) *Attorney, Agent, or Firm* — Troutman Pepper Locke LLP

(57) ABSTRACT

Provided are compounds that inhibit ferroptosis activity, or modulate or inhibit a disease associated with ferroptosis dysregulation, such as neuropathy, ischemia reperfusion injury, acute kidney failure and cancer, including corresponding sulfonamides, and pharmaceutically acceptable salts, hydrates and stereoisomers thereof. The compounds are employed in pharmaceutical compositions, and methods of making and use, including treating a person in need thereof with an effective amount of the compound or composition, and detecting a resultant improvement in the person's health or condition.

20 Claims, No Drawings

(56) References Cited

OTHER PUBLICATIONS

C. Baumgartner et al., Structure-Based Design and Synthesis of the First Weak Non-Phosphate Inhibitors for IspF, an Enzyme in the Non-Mevalonate Pathway of Isoprenoid Biosynthesis, *Helvetica Chimica Acta*, Dec. 31, 2007, vol. 90.
R. Li et al., Designing of novel ERRy inverse agonists by molecular modeling studies of docking and 3D-QSAR on hydroxytamoxifen derivatives, Medicinal Chemistry Reaearch, Aug. 13, 2019, vol. 28, No. 10.
S. Berge et al., Pharmaceutical Salts, Journal of Pharmaceutical Sciences, 1977, vol. 66, No. 1, pp. 1-19.
International Search Report and Written Opinion of International Patent Application No. PCT/CN2021/078601, mailed May 31, 2021.
Extended European Search Report in counterpart European Patent Application No. 21763577.0 dated Apr. 25, 2024.
JM. Lapierre et al., Discovery of 3-(3-(4-(1-Aminocyclobutyl)phenyl)-5-phenyl-3H-imidazo[4,5-b]pyridin-2-yl)pyridin-2-amine (ARQ 092): An Orally Bioavailable, Selective, and Potent Allosteric AKT Inhibitor, Journal of Medicinal Chemistry, 59(13), pp. 6455-6469 (2016).
K. Yoshikawa et al., Identification of alpha-substituted acylamines as novel, potent, and orally active mGluR5 negative allosteric modulators, Bioorganic & Medicinal Chemistry Letters, 25(16), 3135-3141 (2015).
CAS. “1366468-50-9. 1366458-57-2, 1366301-88-3, 1366301-11-2”, STN Registry, dated Apr. 11, 2012.

* cited by examiner

FERROPTOSIS INHIBITORS—DIARYLAMINE PARA-ACETAMIDES

CROSS-REFERENCE TO RELATED APPLICATION

This is a national stage application of International Application No. PCT/CN2021/078601, filed on Mar. 2, 2021, which claims priority to PCT/CN2020/077408, filed on Mar. 2, 2020, all of which are incorporated herein by reference.

INTRODUCTION

Ferroptosis is a type of programmed cell death dependent on iron and characterized by the accumulation of lipid peroxides, and is genetically and biochemically distinct from other forms of regulated cell death such as apoptosis, autophagy and necrosis. Dysregulated ferroptosis has been implicated in a number of diseases, including neuropathy, ischemia reperfusion injury, acute kidney failure and cancer.

SUMMARY OF THE INVENTION

The invention provides compounds that modulate or inhibit ferroptosis activity, or modulate or inhibit a disease associated with ferroptosis dysregulation, such as neuropathy, ischemia reperfusion injury, acute kidney failure and cancer, and prodrugs thereof, which are hydrolyzed, typically in the gut or blood, to yield the corresponding compounds/inhibitors.

In an aspect the invention provides a compound of formula I, or a salt, hydrate or stereoisomer thereof, or the corresponding sulfonamide:

I

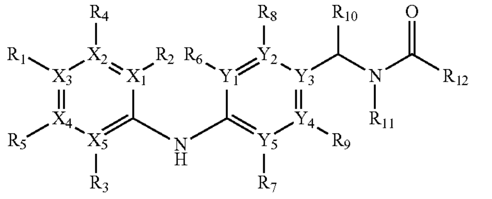

wherein:

R1-R11 are independently H, substituted or unsubstituted heteroatom or substituted or unsubstituted hydrocarbyl, substituted or unsubstituted heterohydrocarbyl;

R12 is substituted or unsubstituted heteroatom, or substituted or unsubstituted hydrocarbyl, or substituted or unsubstituted heterohydrocarbyl;

R11-R-12 may be joined to form a substituted or unsubstituted C3-C18 or C3-C10 or C3-C6 heterocycle; and X1-X5 and Y1-Y5 are independently C or N.

In embodiments:

R1 is H, substituted or unsubstituted heteroatom, substituted or unsubstituted alkyl, substituted or unsubstituted, heteroalkyl, substituted or unsubstituted aryl, or substituted or unsubstituted heteroaryl;

R1 is substituted or unsubstituted OH or $NH_2$, substituted or unsubstituted C1-C9 alkyl, or substituted or unsubstituted C1-C9 heteroalkyl;

R1 is substituted or unsubstituted OH or $NH_2$;

R1 is NR'R", wherein R' and R" are independently substituted or unsubstituted hydrocarbyl, or substituted or unsubstituted heterohydrocarbyl, which may be linked to form an optionally substituted C4-C9 heterocycle;

R1 is NR'R", forming substituted or unsubstituted piperidin-1-yl, such as 4-$CF_3$piperidin-1-yl;

R2-R10 are independently H, halide, substituted or unsubstituted OH or $NH_2$, or substituted or unsubstituted alkyl, or substituted or unsubstituted heteroalkyl;

R2-R10 are independently H, halide or substituted or unsubstituted lower alkyl, such as F-substituted C1-C4 alkyl;

R2-R10 are H;

R11 is H, OH or substituted or unsubstituted C1-C4 alkyl;

R11 H or OH;

R11 is H;

R12 is substituted or unsubstituted alkyl, or substituted or unsubstituted heteroalkyl, or substituted or unsubstituted aryl, or substituted or unsubstituted heteroaryl;

R12 is substituted or unsubstituted C3-C9 cycloalkyl, substituted or unsubstituted C3-C9 heterocycloalkyl, substituted or unsubstituted C5-C9 aryl, or substituted or unsubstituted C5-C9 heteroaryl;

R12 is 1-ethyl, pyrrolidin-2-one-4-yl;

R11-R12 are joined in a substituted or unsubstituted C3-C10 heterocycle;

R11-R12 are joined in a C5-C6 heterocycle, such as substituted or unsubstituted piperazin-2-one, such as wherein position 4 is substituted with methyl or ethyl;

0, 1, 2 or 3 of X1-X4, and 0, 1, 2 or 3 of Y1-Y4 are N;

0, 1 or 2 of X1-X4, and 0, 1 or 2 of Y1-Y4 are N;

only Y2 and X4, or Y2 and Y4, or X2 and Y2, or X2 and Y4, or X4 and X2, or X4 and Y4 are N; or only X2, X3, X4, Y2 or Y4 is N; or any combination of the foregoing substituents.

In an aspect the invention provides a compound disclosed herein, or a salt, hydrate or stereoisomer thereof:

In an aspect the invention provides a pharmaceutical composition comprising a therapeutically effective amount of a compound for formula I (supra) in predetermined, unit dosage form and one or more pharmaceutically acceptable excipients.

In an aspect the invention provides use of a compound or composition disclosed herein in the manufacture of a medicament to inhibit ferroptosis activity, or modulate or inhibit a disease associated with ferroptosis dysregulation, such as neuropathy, ischemia reperfusion injury, acute kidney failure and cancer in a person in need thereof.

In an aspect the invention provides a compound or composition disclosed herein to inhibit ferroptosis activity, or modulate or inhibit a disease associated with ferroptosis dysregulation, such as neuropathy, ischemia reperfusion injury, acute kidney failure and cancer, in a person in need thereof, or in the manufacture of a medicament thereof in a person in need thereof.

In an aspect the invention provides a method of using a compound or composition disclosed herein to inhibit ferroptosis activity, or modulate or inhibit a disease associated with ferroptosis dysregulation, such as neuropathy, ischemia reperfusion injury, acute kidney failure and cancer, in a person in need thereof, and optionally detecting a resultant improvement in the person's health or condition.

The invention encompasses all combination of the particular embodiments recited herein, as if each combination had been laboriously recited.

DESCRIPTION OF PARTICULAR EMBODIMENTS OF THE INVENTION

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

The term "alkyl" refers to a hydrocarbon group selected from linear and branched saturated hydrocarbon groups of 1-18, or 1-12, or 1-6 carbon atoms. Examples of the alkyl group include methyl, ethyl,1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), and 1,1-dimethylethyl or t-butyl ("t-Bu"). Other examples of the alkyl group include 1-pentyl, 2-pentyl, 3-pentyl, 2-methyl-2-butyl, 3-methyl-2-butyl, 3-methyl-1-butyl, 2-methyl-1-butyl, 1 -hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl and 3,3-dimethyl-2-butyl groups.

Lower alkyl means 1-8, preferably 1-6, more preferably 1-4 carbon atoms; lower alkenyl or alkynyl means 2-8, 2-6 or 2-4 carbon atoms.

The term "alkenyl" refers to a hydrocarbon group selected from linear and branched hydrocarbon groups comprising at least one C═C double bond and of 2-18, or 2-12, or 2-6 carbon atoms. Examples of the alkenyl group may be selected from ethenyl or vinyl, prop-1-enyl, prop-2-enyl, 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl, and hexa-1,3-dienyl groups.

The term "alkynyl" refers to a hydrocarbon group selected from linear and branched hydrocarbon group, comprising at least one C≡C triple bond and of 2-18, or 2-12, or 2-6 carbon atoms. Examples of the alkynyl group include ethynyl, 1-propynyl, 2-propynyl (propargyl), l-butynyl, 2-butynyl, and 3-butynyl groups.

The term "cycloalkyl" refers to a hydrocarbon group selected from saturated and partially unsaturated cyclic hydrocarbon groups, comprising monocyclic and polycyclic (e.g., bicyclic and tricyclic) groups. For example, the cycloalkyl group may be of 3-12, or 3-8, or 3-6 carbon atoms. Even further for example, the cycloalkyl group may be a monocyclic group of 3-12, or 3-8, or 3-6 carbon atoms. Examples of the monocyclic cycloalkyl group include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, and cyclododecyl groups. Examples of the bicyclic cycloalkyl groups include those having 7-12 ring atoms arranged as a bicycle ring selected from [4,4], [4,5], [5,5], [5,6] and [6,6] ring systems, or as a bridged bicyclic ring selected from bicyclo[2.2.1]heptane, bicyclo[2.2.2]octane, and bicyclo[3.2.2]nonane. The ring may be saturated or have at least one double bond (i.e. partially unsaturated), but is not fully conjugated, and is not aromatic, as aromatic is defined herein.

The term "aryl" herein refers to a group selected from: 5- and 6-membered carbocyclic aromatic rings, for example, phenyl; bicyclic ring systems such as 7-12 membered bicyclic ring systems wherein at least one ring is carbocyclic and aromatic, selected, for example, from naphthalene, indane, and 1,2,3,4-tetrahydroquinoline; and tricyclic ring systems such as 10-15 membered tricyclic ring systems wherein at least one ring is carbocyclic and aromatic, for example, fluorene.

For example, the aryl group is selected from 5- and 6-membered carbocyclic aromatic rings fused to a 5- to 7-membered cycloalkyl or heterocyclic ring optionally comprising at least one heteroatom selected from N, O, and S, provided that the point of attachment is at the carbocyclic aromatic ring when the carbocyclic aromatic ring is fused with a heterocyclic ring, and the point of attachment can be at the carbocyclic aromatic ring or at the cycloalkyl group when the carbocyclic aromatic ring is fused with a cycloalkyl group. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene.

The term "halogen" or "halo" refers to F, Cl, Br or I.

The term "heteroalkyl" refers to alkyl comprising at least one heteroatom.

The term "heteroaryl" refers to a group selected from:

5- to 7-membered aromatic, monocyclic rings comprising 1, 2, 3 or 4 heteroatoms selected from N, O, and S, with the remaining ring atoms being carbon;

- 8- to 12-membered bicyclic rings comprising 1, 2, 3 or 4 heteroatoms, selected from N, O, and S, with the remaining ring atoms being carbon and wherein at least one ring is aromatic and at least one heteroatom is present in the aromatic ring; and
- 11- to 14-membered tricyclic rings comprising 1, 2, 3 or 4 heteroatoms, selected from N, O, and S, with the remaining ring atoms being carbon and wherein at least one ring is aromatic and at least one heteroatom is present in an aromatic ring.

For example, the heteroaryl group includes a 5- to 7-membered heterocyclic aromatic ring fused to a 5- to 7-membered cycloalkyl ring. For such fused, bicyclic heteroaryl ring systems wherein only one of the rings comprises at least one heteroatom, the point of attachment may be at the heteroaromatic ring or at the cycloalkyl ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1.

Examples of the heteroaryl group include, but are not limited to, (as numbered from the linkage position assigned priority 1) pyridyl (such as 2-pyridyl, 3-pyridyl, or 4-pyridyl), cinnolinyl, pyrazinyl, 2,4-pyrimidinyl, 3,5-pyrimidinyl, 2,4-imidazolyl, imidazopyridinyl, isoxazolyl, oxazolyl, thiazolyl, isothiazolyl, thiadiazolyl, tetrazolyl, thienyl, triazinyl, benzothienyl, furyl, benzofuryl, benzoimidazolyl, indolyl, isoindolyl, indolinyl, phthalazinyl, pyrazinyl, pyridazinyl, pyrrolyl, triazolyl, quinolinyl, isoquinolinyl, pyrazolyl, pyrrolopyridinyl (such as 1H-pyrrolo[2,3-b]pyridin-5-yl), pyrazolopyridinyl (such as 1H-pyrazolo[ 3,4-b]pyridin-5-yl), benzoxazolyl (such as benzo[d]oxazol-6-yl), pteridinyl, purinyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, furazanyl, benzofurazanyl, benzothiophenyl, benzothiazolyl, benzoxazolyl, quinazolinyl, quinoxalinyl, naphthyridinyl, furopyridinyl, benzothiazolyl (such as benzo[d]thiazol-6-yl), indazolyl (such as 1H-indazol-5-yl) and 5,6,7,8-tetrahydroisoquinoline.

The term "heterocyclic" or "heterocycle" or "heterocyclyl" refers to a ring selected from 4- to 12-membered monocyclic, bicyclic and tricyclic, saturated and partially unsaturated rings comprising at least one carbon atoms in addition to 1, 2, 3 or 4 heteroatoms, selected from oxygen, sulfur, and nitrogen. "Heterocycle" also refers to a 5- to 7-membered heterocyclic ring comprising at least one heteroatom selected from N, O, and S fused with 5-, 6-, and/or 7-membered cycloalkyl, carbocyclic aromatic or heteroaromatic ring, provided that the point of attachment is at the heterocyclic ring when the heterocyclic ring is fused with a carbocyclic aromatic or a heteroaromatic ring, and that the point of attachment can be at the cycloalkyl or heterocyclic ring when the heterocyclic ring is fused with cycloalkyl.

"Heterocycle" also refers to an aliphatic spirocyclic ring comprising at least one heteroatom selected from N, O, and S, provided that the point of attachment is at the heterocyclic ring. The rings may be saturated or have at least one double bond (i.e. partially unsaturated). The heterocycle may be substituted with oxo. The point of the attachment may be carbon or heteroatom in the heterocyclic ring. A heterocyle is not a heteroaryl as defined herein.

Examples of the heterocycle include, but not limited to, (as numbered from the linkage position assigned priority 1) 1-pyrrolidinyl, 2-pyrrolidinyl, 2,4-imidazolidinyl, 2,3-pyrazolidinyl, 1-piperidinyl, 2-piperidinyl, 3-piperidinyl, 4-piperidinyl, 2,5-piperazinyl, pyranyl, 2-morpholinyl, 3-morpholinyl, oxiranyl, aziridinyl, thiiranyl, azetidinyl, oxetanyl, thietanyl, 1,2-dithietanyl, 1,3-dithietanyl, dihydropyridinyl, tetrahydropyridinyl, thiomorpholinyl, thioxanyl, piperazinyl, homopiperazinyl, homopiperidinyl, azepanyl, oxepanyl, thiepanyl, 1,4-oxathianyl, 1,4-dioxepanyl, 1,4-oxathiepanyl, 1,4-oxaazepanyl, 1,4-dithiepanyl, 1,4-thiazepanyl and 1,4-diazepane 1,4-dithianyl, 1,4-azathianyl, oxazepinyl, diazepinyl, thiazepinyl, dihydrothienyl, dihydropyranyl, dihydrofuranyl, tetrahydrofuranyl, tetrahydrothienyl, tetrahydropyranyl, tetrahydrothiopyranyl, I-pyrrolinyl, 2-pyrrolinyl, 3-pyrrolinyl, indolinyl, 2H-pyranyl, 4H-pyranyl, 1,4-dioxanyl, 1,3-dioxolanyl, pyrazolinyl, pyrazolidinyl, dithianyl, dithiolanyl, pyrazolidinylimidazolinyl, pyrimidinonyl, 1,1-dioxo-thiomorpholinyl, 3-azabicyco[3.1.0]hexanyl, 3-azabicyclo[4.1.0]heptanyl and azabicyclo[2.2.2]hexanyl. Substituted heterocycle also includes ring systems substituted with one or more oxo moieties, such as piperidinyl N-oxide, morpholinyl-N-oxide, I-oxo-1-thiomorpholinyl and 1,1-dioxo-1-thiomorpholinyl.

The term "fused ring" herein refers to a polycyclic ring system, e.g., a bicyclic or tricyclic ring system, in which two rings share only two ring atoms and one bond in common. Examples of fused rings may comprise a fused bicyclic cycloalkyl ring such as those having from 7 to 12 ring atoms arranged as a bicyclic ring selected from [4,4], [4,5], [5,5], [5,6] and [6,6] ring systems as mentioned above; a fused bicyclic aryl ring such as 7 to 12 membered bicyclic aryl ring systems as mentioned above, a fused tricyclic aryl ring such as 10 to 15 membered tricyclic aryl ring systems mentioned above; a fused bicyclic heteroaryl ring such as 8- to 12-membered bicyclic heteroaryl rings as mentioned above, a fused tricyclic heteroaryl ring such as 11- to 14-membered tricyclic heteroaryl rings as mentioned above; and a fused bicyclic or tricyclic heterocyclyl ring as mentioned above.

In embodiments substituents are selected from optionally substituted heteroatom and optionally substituted, optionally hetero-, optionally cyclic C1-C18 hydrocarbyl, particularly wherein the optionally substituted, optionally hetero-, optionally cyclic C1-C18 hydrocarbyl is optionally-substituted, optionally hetero-, optionally cyclic alkyl, alkenyl or alkynyl, or optionally-substituted, optionally hetero-aryl; and/or the optionally substituted heteroatom is halogen, optionally substituted hydroxyl (such as alkoxy, aryloxy), optionally substituted acyl (such as formyl, alkanoyl, carbamoyl, carboxyl, amido), optionally substituted amino (such as amino, alkylamino, dialkylamino, amido, sulfamidyl), optionally substituted thiol (such as mercapto, alkylthiol, aryl thiol), optionally substituted sulfinyl or sulfonyl (such as alkylsulfinyl, arylsulfinyl, alkyl sulfonyl, arylsulfonyl), nitro, or cyano.

In embodiments, substituents are selected from: halogen, —R', —OR', =O, =NR', =N—OR', —NR'R", —SR', —SiR'R"R'", —OC(O)R'", —C(O)R', —CO2R', —CONR'R", —OC(O)NR'R", —NR"C(O)R', —NR'—C(O)NR"R'", —NR'—SO2NR'", —NR"CO2R', —NH—C(NH2)=NH, —NR'C(NH2)-NH, —NH—C(NH2)=NR', —S(O)R', —SO2R', —SO2NR'R", —NR"SO2R, —CN and —NO2, —N3, —CH(Ph)2, perfluoro(C1-C4)alkoxy and perfluoro(C1-C4)alkyl, in a number ranging from zero to three, with those groups having zero, one or two substituents being particularly preferred. R', R" and R'" each independently refer to hydrogen, unsubstituted (C1-C8)alkyl and heteroalkyl, (C1-C8)alkyl and heteroalkyl substituted with one to three halogens, unsubstituted aryl, aryl substituted with one to three halogens, unsubstituted alkyl, alkoxy or thioalkoxy groups, or aryl-(C1-C4)alkyl groups. When R' and R" are attached to the same nitrogen atom, they can be combined with the nitrogen atom to form a 5-, 6- or 7-membered ring. Hence, —NR'R" includes 1-pyrrolidinyl and 4-morpholinyl, "alkyl" includes groups such as trihaloalkyl (e.g., —CF3 and —CH2CF3), and when the aryl group is 1,2,3,4-tetrahydronaphthalene, it may be substituted with a substituted or unsubstituted (C3-C7)spirocycloalkyl group. The (C3-C7)spirocycloalkyl group may be substituted in the same manner as defined herein for "cycloalkyl".

Preferred substituents are selected from: halogen, —R', —OR', —O, —NR'R", —SR', —SiR'R"R'", —OC(O)R', —C(O)R', —CO2R', —CONR'R", —OC(O)NR'R", —NR"C(O)R', —NR"CO2R', —NR'—SO2NR"R'", —S(O)R', —SO2R', —SO2NR'R", —NR"SO2R, —CN and —NO2, perfluoro(C1-C4)alkoxy and perfluoro(C1-C4)alkyl, where R' and R" are as defined above.

Preferred substituents are disclosed herein and exemplified in the tables, structures, examples, and claims, and may be applied across different compounds of the invention, i.e. substituents of any given compound may be combinatorially used with other compounds.

In particular embodiments applicable substituents are independently substituted or unsubstituted heteroatom, substituted or unsubstituted, 0-3 heteroatom C1-C6 alkyl, substituted or unsubstituted, 0-3 heteroatom C2-C6 alkenyl, substituted or unsubstituted, 0-3 heteroatom C2-C6 alkynyl, or substituted or unsubstituted, 0-3 heteroatom C6-C14 aryl, wherein each heteroatom is independently oxygen, phosphorus, sulfur or nitrogen.

In more particular embodiments, applicable substituents are independently aldehyde, aldimine, alkanoyloxy, alkoxy, alkoxycarbonyl, alkyloxy, alkyl, amine, azo, halogens, carbamoyl, carbonyl, carboxamido, carboxyl, cyanyl, ester, halo, haloformyl, hydroperoxyl, hydroxyl, imine, isocyanide, iscyante, N-tert-butoxycarbonyl, nitrate, nitrile, nitrite, nitro, nitroso, phosphate, phosphono, sulfide, sulfonyl, sulfo, sulfhydryl, thiol, thiocyanyl, trifluoromethyl or trifluromethyl ether (OCF3).

The compounds may contain an asymmetric center and may thus exist as enantiomers. Where the compounds possess two or more asymmetric centers, they may additionally exist as diastereomers. Enantiomers and diastereomers fall within the broader class of stereoisomers. All such possible stereoisomers as substantially pure resolved enantiomers, racemic mixtures thereof, as well as mixtures of diastereomers are intended to be included. All stereoisomers of the compounds and/or pharmaceutically acceptable salts thereof are intended to be included. Unless specifically mentioned otherwise, reference to one isomer applies to any of the possible isomers. Whenever the isomeric composition is unspecified, all possible isomers are included.

The term "substantially pure" means that the target stereoisomer contains no more than 35%, such as no more than 30%, further such as no more than 25%, even further such as no more than 20%, by weight of any other stereoisomer(s). In some embodiments, the term "substantially pure" means that the target stereoisomer contains no more than 10%, for example, no more than 5%, such as no more than 1%, by weight of any other stereoisomer(s).

When compounds contain olefin double bonds, unless specified otherwise, such double bonds are meant to include both E and Z geometric isomers.

Some of the compounds may exist with different points of attachment of hydrogen, referred to as tautomers. For example, compounds including carbonyl —$CH_2C(O)$— groups (keto forms) may undergo tautomerism to form hydroxyl —CH═C(OH)— groups (enol forms). Both keto and enol forms, individually as well as mixtures thereof, are also intended to be included where applicable.

It may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed ("SMB") and preparative thin or thick layer chromatography, as well as techniques of small scale thin layer and flash chromatography. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers can also be separated by use of a chiral HPLC column.

A single stereoisomer, e.g., a substantially pure enantiomer, may be obtained by resolution of the racemic mixture using a method such as formation of diastereomers using optically active resolving agents. Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions.

"Pharmaceutically acceptable salts" include, but are not limited to salts with inorganic acids, selected, for example, from hydrochlorates, phosphates, diphosphates, hydrobromates, sulfates, sulfinates, and nitrates; as well as salts with organic acids, selected, for example, from malates, maleates, fumarates, tartrates, succinates, citrates, lactates, methanesulfonates, p-toluenesulfonates, 2-hydroxyethylsulfonates, benzoates, salicylates, stearates, alkanoates such as acetate, and salts with HOOC—$(CH_2)$n-COOH, wherein n is selected from 0 to 4. Similarly, examples of pharmaceutically acceptable cations include, but are not limited to, sodium, potassium, calcium, aluminum, lithium, and ammonium.

In addition, if a compound is obtained as an acid addition salt, the free base can be obtained by basifying a solution of the acid salt. Conversely, if the product is a free base, an addition salt, such as a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used without undue experimentation to prepare non-toxic pharmaceutically acceptable addition salts.

"Treating," "treat," or "treatment" refers to administering at least one compound and/or at least one stereoisomer thereof, and/or at least one pharmaceutically acceptable salt thereof to a subject in recognized need thereof.

An "effective amount" refers to an amount of at least one compound and/or at least one stereoisomer thereof, and/or at least one pharmaceutically acceptable salt thereof effective to "treat" a disease or disorder in a subject, and that will elicit, to some significant extent, the biological or medical response of a tissue, system, animal or human that is being sought, such as when administered, is sufficient to prevent development of, or alleviate to some extent, one or more of the symptoms of the condition or disorder being treated. The therapeutically effective amount will vary depending on the compound, the disease and its severity and the age, weight, etc., of the mammal to be treated.

The term "at least one substituent" includes, for example, from 1 to 4, such as from 1 to 3, further as 1 or 2, substituents. For example, "at least one substituent $R^{16}$" herein includes from 1 to 4, such as from 1 to 3, further as 1 or 2, substituents selected from the list of $R^{16}$ as described herein.

The subject compounds and stereoisomers thereof, and pharmaceutically acceptable salts thereof may be employed alone or in combination with at least one other therapeutic agent for treatment. In some embodiments, the compounds, stereoisomers thereof, and pharmaceutically acceptable salts thereof can be used in combination with at least one additional therapeutic agent. The compound and/or one pharmaceutically acceptable salt disclosed herein may be administered with the at least one other therapeutic agent in a single dosage form or as a separate dosage form. When administered as a separate dosage form, the at least one other therapeutic agent may be administered prior to, at the same time as, or following administration of the compound and/or one pharmaceutically acceptable salt disclosed herein.

Also provided is a composition comprising a subject compound and stereoisomers thereof, and pharmaceutically acceptable salts thereof, and at least one pharmaceutically acceptable carrier.

The composition comprising a subject compound and stereoisomers thereof, and pharmaceutically acceptable salts thereof can be administered in various known manners, such as orally, topically, rectally, parenterally, by inhalation spray, or via an implanted reservoir, although the most suitable route in any given case will depend on the particular host, and nature and severity of the conditions for which the active ingredient is being administered. The term “parenteral” as used herein includes subcutaneous, intracutaneous, intravenous, intramuscular, intraarticular, intraarterial, intrasynovial, intrasternal, intrathecal, intralesional and intracranial injection or infusion techniques. The compositions disclosed herein may be conveniently presented in unit dosage form and prepared by any of the methods well known in the art.

The subject compounds and stereoisomers thereof, and pharmaceutically acceptable salts thereof can be administered orally in solid dosage forms, such as capsules, tablets, troches, dragées, granules and powders, or in liquid dosage forms, such as elixirs, syrups, emulsions, dispersions, and suspensions. The subject compounds and stereoisomers thereof, and pharmaceutically acceptable salts thereof disclosed herein can also be administered parenterally, in sterile liquid dosage forms, such as dispersions, suspensions or solutions. Other dosages forms that can also be used to administer the subject compounds and stereoisomers thereof, and pharmaceutically acceptable salts thereof disclosed herein as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules containing the compound and/or the at least one pharmaceutically acceptable salt thereof disclosed herein and powdered carriers, such as lactose, starch, cellulose derivatives, magnesium stearate, stearic acid, and the like, can also be used. Similar diluents can be used to make compressed tablets. Both tablets and capsules can be manufactured as sustained release products to provide for continuous release of medication over a period of time. Compressed tablets can be sugar coated or film coated to mask any unpleasant taste and protect the tablet from the atmosphere, or enteric coated for selective disintegration in the gastrointestinal tract.

Liquid dosage forms for oral administration can further comprise at least one agent selected from coloring and flavoring agents to increase patient acceptance.

In general, water, a suitable oil, saline, aqueous dextrose (glucose), and related sugar solutions and glycols such as propylene glycol or polyethylene glycols can be examples of suitable carriers for parenteral solutions. Solutions for parenteral administration may comprise a water soluble salt of the at least one compound describe herein, at least one suitable stabilizing agent, and if necessary, at least one buffer substance. Antioxidizing agents such as sodium bisulfite, sodium sulfite, or ascorbic acid, either alone or combined, can be examples of suitable stabilizing agents. Citric acid and its salts and sodium EDTA can also be used as examples of suitable stabilizing agents. In addition, parenteral solutions can further comprise at least one preservative, selected, for example, from benzalkonium chloride, methyl- and propylparaben, and chlorobutanol.

A pharmaceutically acceptable carrier is, for example, selected from carriers that are compatible with active ingredients of the composition (and in some embodiments, capable of stabilizing the active ingredients) and not deleterious to the subject to be treated. For example, solubilizing agents, such as cyclodextrins (which can form specific, more soluble complexes with the at least one compound and/or at least one pharmaceutically acceptable salt disclosed herein), can be utilized as pharmaceutical excipients for delivery of the active ingredients. Examples of other carriers include colloidal silicon dioxide, magnesium stearate, cellulose, sodium lauryl sulfate, and pigments such as D&C Yellow #10. Suitable pharmaceutically acceptable carriers are described in *Remington's Pharmaceutical Sciences*, A. Osol, a standard reference text in the art.

For administration by inhalation, the subject compounds and stereoisomers thereof, and pharmaceutically acceptable salts thereof may be conveniently delivered in the form of an aerosol spray presentation from pressurized packs or nebulisers. The subject compounds and stereoisomers thereof, and pharmaceutically acceptable salts thereof may also be delivered as powders, which may be formulated and the powder composition may be inhaled with the aid of an insufflation powder inhaler device. One exemplary delivery system for inhalation can be metered dose inhalation (MDI) aerosol, which may be formulated as a suspension or solution of a subject compound and stereoisomers thereof, and pharmaceutically acceptable salts thereof disclosed herein in at least one suitable propellant, selected, for example, from fluorocarbons and hydrocarbons.

For ocular administration, an ophthalmic preparation may be formulated with an appropriate weight percentage of a solution or suspension of the subject compound and stereoisomers thereof, and pharmaceutically acceptable salts thereof in an appropriate ophthalmic vehicle, such that the subject compound and stereoisomers thereof, and at least one pharmaceutically acceptable salts thereof is maintained in contact with the ocular surface for a sufficient time period to allow the compound to penetrate the corneal and internal regions of the eye.

Useful pharmaceutical dosage-forms for administration of the subject compounds and stereoisomers thereof, and pharmaceutically acceptable salts thereof disclosed herein include, but are not limited to, hard and soft gelatin capsules, tablets, parenteral injectables, and oral suspensions.

The dosage administered will be dependent on factors, such as the age, health and weight of the recipient, the extent of disease, type of concurrent treatment, if any, frequency of treatment, and the nature of the effect desired. In general, a daily dosage of the active ingredient can vary, for example, from 0.1 to 2000 milligrams per day. For example, 10-500 milligrams once or multiple times per day may be effective to obtain the desired results.

In some embodiments, a large number of unit capsules can be prepared by filling standard two-piece hard gelatin capsules each with, for example, 100 milligrams of the subject compound and stereoisomers thereof, and pharmaceutically acceptable salt thereof disclosed herein in powder, 150 milligrams of lactose, 50 milligrams of cellulose, and 6 milligrams magnesium stearate.

In some embodiments, a mixture of the compound, stereoisomers thereof, and pharmaceutically acceptable salts thereof a digestible oil such as soybean oil, cottonseed oil or olive oil can be prepared and injected by means of a positive displacement pump into gelatin to form soft gelatin capsules containing 100 milligrams of the active ingredient. The capsules are washed and dried.

In some embodiments, a large number of tablets can be prepared by conventional procedures so that the dosage unit comprises, for example, 100 milligrams of the compound, stereoisomers thereof, and pharmaceutically acceptable salts thereof, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

In some embodiments, a parenteral composition suitable for administration by injection can be prepared by stirring 1.5% by weight of the compound and/or at least an enantiomer, a diastereomer, or pharmaceutically acceptable salt thereof disclosed herein in 10% by volume propylene glycol. The solution is made to the expected volume with water for injection and sterilized.

In some embodiment, an aqueous suspension can be prepared for oral administration. For example, each 5 milliliters of an aqueous suspension comprising 100 milligrams of finely divided compound, stereoisomers thereof, and pharmaceutically acceptable salts thereof, 100 milligrams of sodium carboxymethyl cellulose, 5 milligrams of sodium benzoate, 1.0 grams of sorbitol solution, U.S.P., and 0.025 milliliters of vanillin can be used.

The same dosage forms can generally be used when the compound, stereoisomers thereof, and pharmaceutically acceptable salts thereof are administered stepwise or in conjunction with at least one other therapeutic agent. When drugs are administered in physical combination, the dosage form and administration route should be selected depending on the compatibility of the combined drugs. Thus the term coadministration is understood to include the administration of at least two agents concomitantly or sequentially, or alternatively as a fixed dose combination of the at least two active components.

The compounds, stereoisomers thereof, and pharmaceutically acceptable salt thereof disclosed herein can be administered as the sole active ingredient or in combination with at least one second active ingredient.

The subject compounds are incorporated into pharmaceutical compositions or formulations. The compositions will contain pharmaceutically acceptable diluents and/or carriers, i.e. diluents or carriers that are physiologically compatible and substantially free from pathogenic impurities. Suitable excipients or carriers and methods for preparing administrable compositions are known or apparent to those skilled in the art and are described in more detail in such publications as Remington's Pharmaceutical Science, Mack Publishing Co, NJ (1991). The compositions may also be in the form of controlled release or sustained release compositions as known in the art. For many applications the subject compounds are administered for morning/daytime dosing, with off period at night.

The subject compounds may be used per se, or in the form of their pharmaceutically acceptable salts, such as hydrochlorides, hydrobromides, acetates, sulfates, citrates, carbonates, trifluoroacetates and the like. When compounds contain relatively acidic functionalities, salts can be obtained by addition of the desired base, either neat or in a suitable inert solvent. Examples of pharmaceutically acceptable base addition salts include sodium, potassium, calcium, ammonium, organic amino, or magnesium salts, or the like. When compounds contain relatively basic functionalities, salts can be obtained by addition of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids and the like (see, for example, Berge et al, "Pharmaceutical Salts", Journal of Pharmaceutical Science, 1977, 66, 1-19).

The neutral forms of the compounds may be regenerated by contacting the salt with a base or acid, and isolating the parent compound in the conventional manner. The parent form of the compound differs from the various salt forms in certain physical properties, such as solubility in polar solvents, but otherwise the salts are equivalent to the parent form of the compound for the purposes of this invention.

In addition to salt forms, this invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent. Prodrugs are often useful because, in some situations, they may be easier to administer than the parent drug. They may, for instance, be more bioavailable by oral administration than the parent drug. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the present invention which is administered as an ester (the "prodrug"), but then is metabolically hydrolyzed to the carboxylic acid, the active entity.

Certain compounds of the invention can exist in unsolvated forms as well as solvated forms, including hydrated forms. In general, the solvated forms are equivalent to unsolvated forms and are intended to be encompassed within the scope of the present invention. Certain compounds of the invention may exist in multiple crystalline or amorphous forms. In general, all physical forms are equivalent for the uses contemplated by the present invention and are intended to be within the scope of the invention.

Some of the subject compounds possess asymmetric carbon atoms (optical centers) or double bonds; the racemates, diastereomers, geometric isomers and individual isomers are all intended to be encompassed within the scope of the present invention.

The compounds of the invention may also contain unnatural proportions of atomic isotopes at one or more of the atoms that constitute such compounds, such as deuterium, e.g. $-CD_3$, $CD_2H$ or $CDH_2$ in place of methyl. For example, the compounds may be radiolabeled with radioactive isotopes, such as for example tritium ($^3H$), iodine-125 ($^{125}I$) or carbon-14 ($^{14}C$). All isotopic variations of the compounds of the invention, whether radioactive or not, are intended to be encompassed within the scope of the invention.

The compounds are generally administered in a "therapeutically effective amount", i.e. the amount of the subject compound that will elicit the biological or medical response of a tissue, system, animal or human that is being sought by the researcher, veterinarian, medical doctor or other clinician. The term "therapeutically effective amount" includes that amount of a compound that, when administered, is sufficient to prevent development of, or alleviate to some extent, one or more of the symptoms of the condition or disorder being treated. The therapeutically effective amount will vary depending on the compound, the disease and its severity and the age, weight, etc., of the mammal to be treated.

The contacting is generally effected by administering to the subject an effective amount of one or more compounds having the general formula I (supra), including the various embodiments described above. Generally administration is adjusted to achieve a therapeutic dosage of about 0.1 to 50, preferably 0.5 to 10, more preferably 1 to 10 mg/kg, though optimal dosages are compound specific, and generally empirically determined for each compound.

The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules, lozenges or the like in the case of solid compositions. In such compositions, the mimetic is usually a minor component (from about 0.1 to about 50% by weight or preferably from about 1 to about 40% by weight) with the remainder being various vehicles or carriers and processing aids helpful for forming the desired dosing form. Unit dosage formulations are preferably about of 5, 10, 25, 50, 100, 250, 500, or 1,000 mg per unit. In a particular embodiment, unit dosage forms are packaged in a multipack adapted for sequential use, such as blisterpack comprising sheets of at least 6, 9 or 12 unit dosage forms.

The subject compositions may also be coformulated and/or coadministered with a different compound to treat applicable indications, to inhibit ferroptosis activity, or modulate or inhibit a disease associated with ferroptosis dysregulation, such as neuropathy, ischemia reperfusion injury, acute kidney failure and cancer. In embodiments applicable indications include cancer, neuropathy and neurodegenerative disease of the central or peripheral nervous system, muscular dystrophy, ischemia and ischemia reperfusion injury, kidney disease and failure, degenerative arthritis, retinal necrosis, heart disease, liver, gastrointestinal or pancreatic disease, avascular necrosis, diabetes, cancer-chemo/radiation therapy-induced cell-death and intoxication.

TABLE 1

| Active Compounds: Structures | |
|---|---|
| 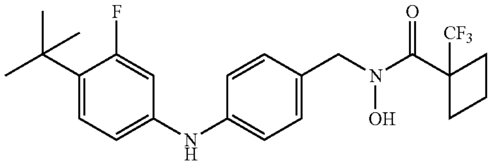 [SMILES: CC(C)(C)c1ccc(Nc2ccc(CN(O)C(=O)C3(C(F)(F)F)CCC3)cc2)cc1F] | 1 |
| 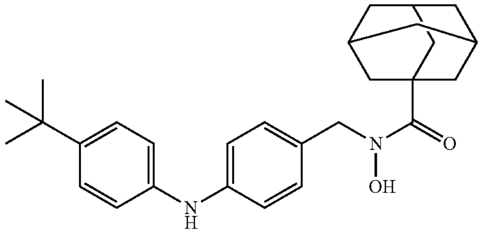 [SMILES: CC(C)(C)c1ccc(Nc2ccc(CN(O)C(=O)C34CC5CC(CC(C5)C3)C4)cc2)cc1] | 2 |
| 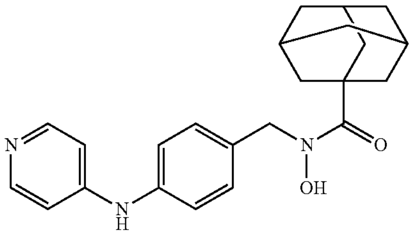 [SMILES: O=C(N(O)Cc1ccc(Nc2ccncc2)cc1)C12CC3CC(CC(C3)C1)C2] | 3 |
| 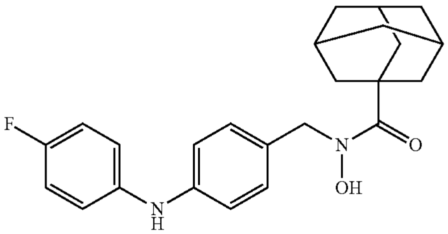 [SMILES: O=C(N(O)Cc1ccc(Nc2ccc(F)cc2)cc1)C12CC3CC(CC(C3)C1)C2] | 4 |

TABLE 1-continued
| Active Compounds: Structures | |
|---|---|
| 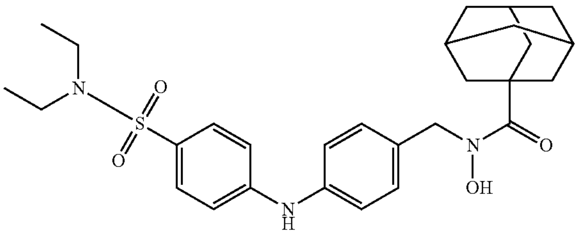 [SMILES: CCN(CC)S(=O)(=O)c1ccc(Nc2ccc(CN(O)C(=O)C34CC5CC(CC(C5)C3)C4)cc2)cc1] | 5 |
| 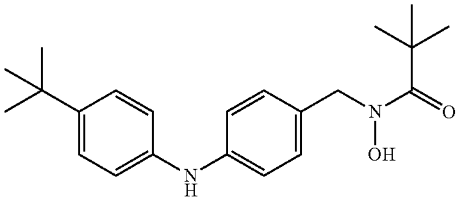 [SMILES: CC(C)(C)C(=O)N(O)Cc1ccc(Nc2ccc(C(C)(C)C)cc2)cc1] | 6 |
| 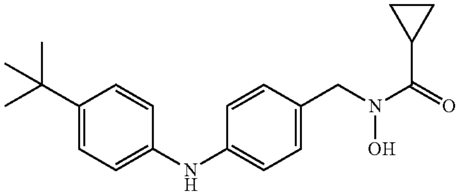 [SMILES: CC(C)(C)c1ccc(Nc2ccc(CN(O)C(=O)C3CC3)cc2)cc1] | 7 |
| 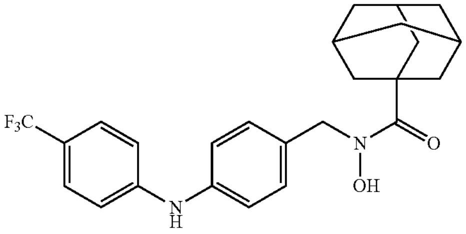 [SMILES: O=C(N(O)Cc1ccc(Nc2ccc(C(F)(F)F)cc2)cc1)C12CC3CC(CC(C3)C1)C2] | 8 |
| 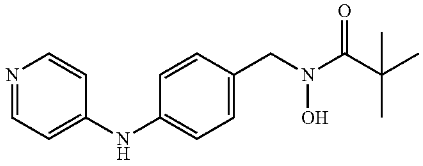 [SMILES: CC(C)(C)C(=O)N(O)Cc1ccc(Nc2ccncc2)cc1] | 9 |
| 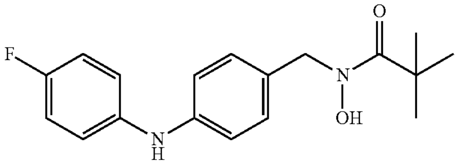 [SMILES: CC(C)(C)C(=O)N(O)Cc1ccc(Nc2ccc(F)cc2)cc1] | 10 |
| 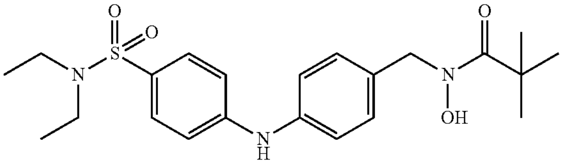 [SMILES: CCN(CC)S(=O)(=O)c1ccc(Nc2ccc(CN(O)C(=O)C(C)(C)C)cc2)cc1] | 11 |
| 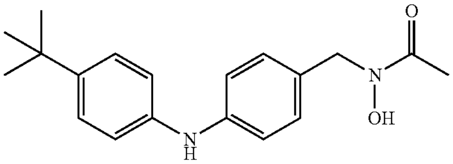 [SMILES: CC(=O)N(O)Cc1ccc(Nc2ccc(C(C)(C)C)cc2)cc1] | 12 |

TABLE 1-continued
| Active Compounds: Structures | |
|---|---|
| 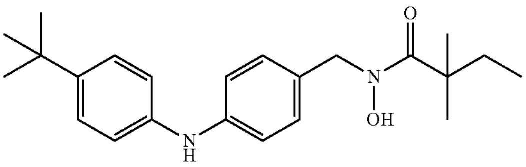 [SMILES: CCC(C)(C)C(=O)N(O)Cc1ccc(Nc2ccc(C(C)(C)C)cc2)cc1] | 13 |
| 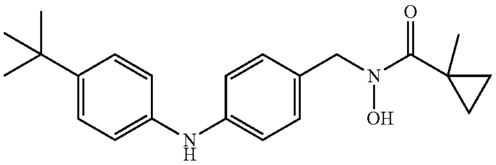 [SMILES: CC1(C(=O)N(O)Cc2ccc(Nc3ccc(C(C)(C)C)cc3)cc2)CC1] | 14 |
| 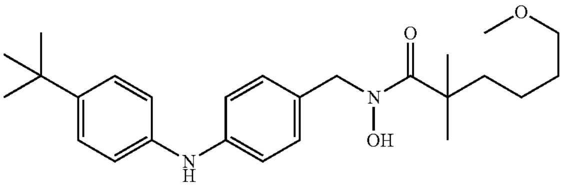 [SMILES: COCCCCC(C)(C)C(=O)N(O)Cc1ccc(Nc2ccc(C(C)(C)C)cc2)cc1] | 15 |
| 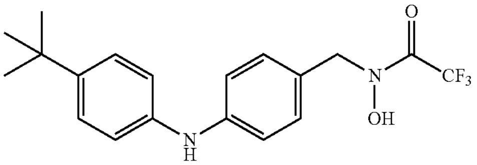 [SMILES: CC(C)(C)c1ccc(Nc2ccc(CN(O)C(=O)C(F)(F)F)cc2)cc1] | 16 |
| 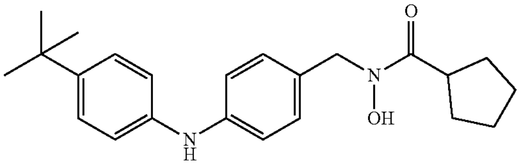 [SMILES: CC(C)(C)c1ccc(Nc2ccc(CN(O)C(=O)C3CCCC3)cc2)cc1] | 17 |
| 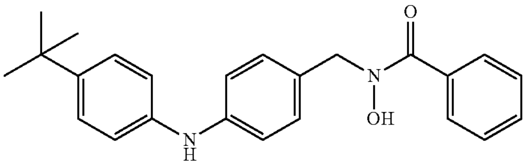 [SMILES: CC(C)(C)c1ccc(Nc2ccc(CN(O)C(=O)c3ccccc3)cc2)cc1] | 18 |
| 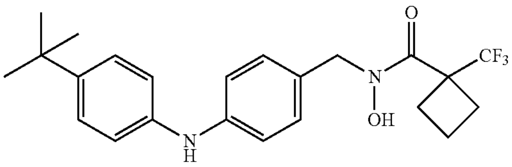 [SMILES: CC(C)(C)c1ccc(Nc2ccc(CN(O)C(=O)C3(C(F)(F)F)CCC3)cc2)cc1] | 19 |
| 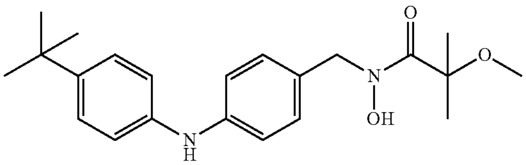 [SMILES: COC(C)(C)C(=O)N(O)Cc1ccc(Nc2ccc(C(C)(C)C)cc2)cc1] | 20 |

TABLE 1-continued
| Active Compounds: Structures | |
|---|---|
| 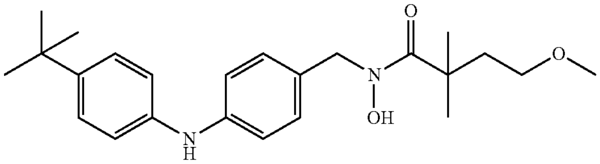 [SMILES: COCCC(C)(C)C(=O)N(O)Cc1ccc(Nc2ccc(C(C)(C)C)cc2)cc1] | 21 |
| 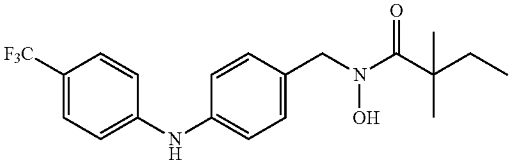 [SMILES: CCC(C)(C)C(=O)N(O)Cc1ccc(Nc2ccc(C(F)(F)F)cc2)cc1] | 22 |
| 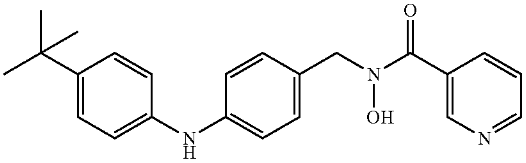 [SMILES: CC(C)(C)c1ccc(Nc2ccc(CN(O)C(=O)c3cccnc3)cc2)cc1] | 23 |
| 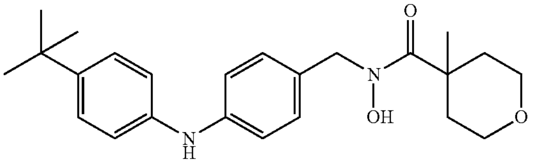 [SMILES: CC1(C(=O)N(O)Cc2ccc(Nc3ccc(C(C)(C)C)cc3)cc2)CCOCC1] | 24 |
| 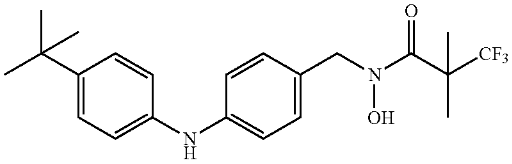 [SMILES: CC(C)(C)c1ccc(Nc2ccc(CN(O)C(=O)C(C)(C)C(F)(F)F)cc2)cc1] | 25 |
| 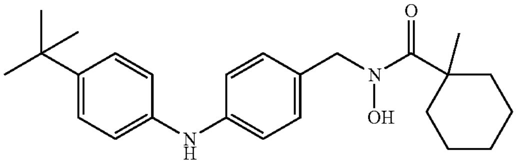 [SMILES: CC1(C(=O)N(O)Cc2ccc(Nc3ccc(C(C)(C)C)cc3)cc2)CCCCC1] | 26 |
| 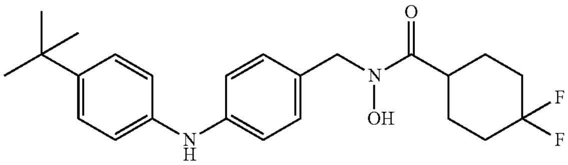 [SMILES: CC(C)(C)c1ccc(Nc2ccc(CN(O)C(=O)C3CCC(F)(F)CC3)cc2)cc1] | 27 |
| 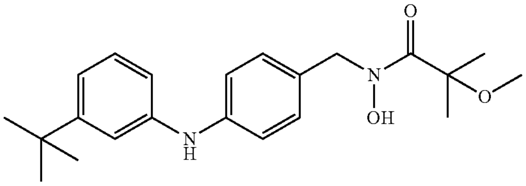 [SMILES: COC(C)(C)C(=O)N(O)Cc1ccc(Nc2cccc(C(C)(C)C)c2)cc1] | 28 |
| 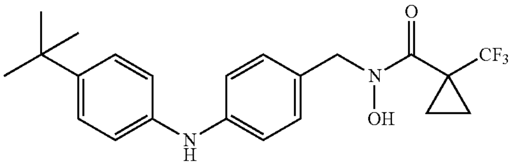 [SMILES: CC(C)(C)c1ccc(Nc2ccc(CN(O)C(=O)C3(C(F)(F)F)CC3)cc2)cc1] | 29 |

TABLE 1-continued
Active Compounds: Structures
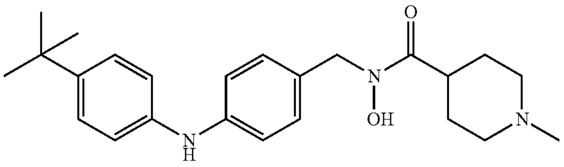 [SMILES: CN1CCC(C(=O)N(O)Cc2ccc(Nc3ccc(C(C)(C)C)cc3)cc2)CC1]
30
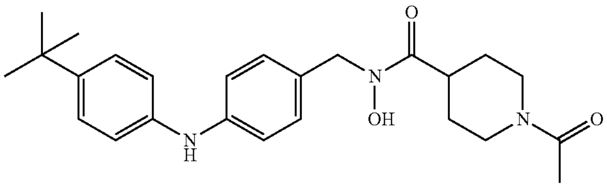 [SMILES: CC(=O)N1CCC(C(=O)N(O)Cc2ccc(Nc3ccc(C(C)(C)C)cc3)cc2)CC1]
31
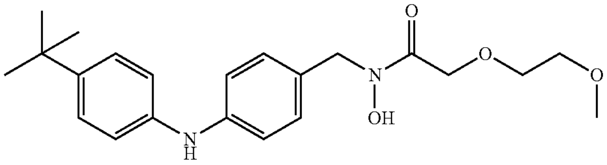 [SMILES: COCCOCC(=O)N(O)Cc1ccc(Nc2ccc(C(C)(C)C)cc2)cc1]
32
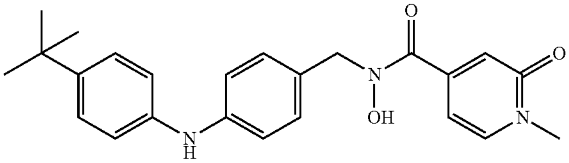
33
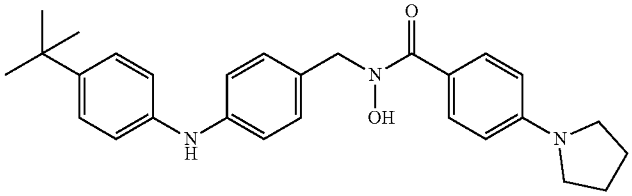 [SMILES: CC(C)(C)c1ccc(Nc2ccc(CN(O)C(=O)c3ccc(N4CCCC4)cc3)cc2)cc1]
34
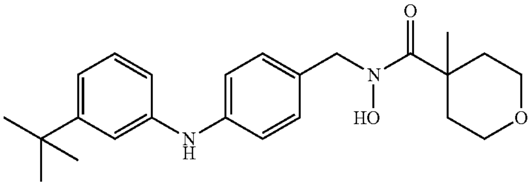 [SMILES: CC1(C(=O)N(O)Cc2ccc(Nc3cccc(C(C)(C)C)c3)cc2)CCOCC1]
35
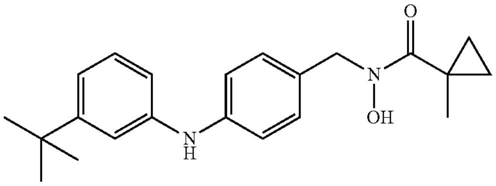 [SMILES: CC1(C(=O)N(O)Cc2ccc(Nc3cccc(C(C)(C)C)c3)cc2)CC1]
36
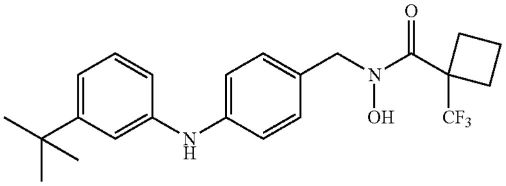 [SMILES: CC(C)(C)c1cccc(Nc2ccc(CN(O)C(=O)C3(C(F)(F)F)CCC3)cc2)c1]
37

TABLE 1-continued
| Active Compounds: Structures | |
|---|---|
| 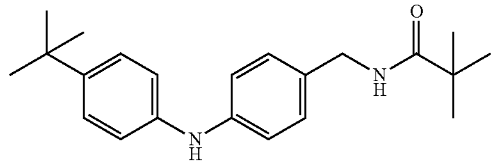 [SMILES: CC(C)(C)C(=O)NCc1ccc(Nc2ccc(C(C)(C)C)cc2)cc1] | 38 |
| 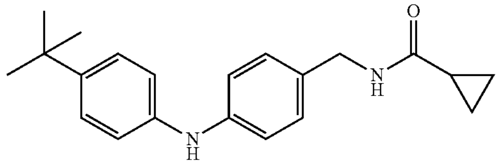 [SMILES: CC(C)(C)c1ccc(Nc2ccc(CNC(=O)C3CC3)cc2)cc1] | 39 |
| 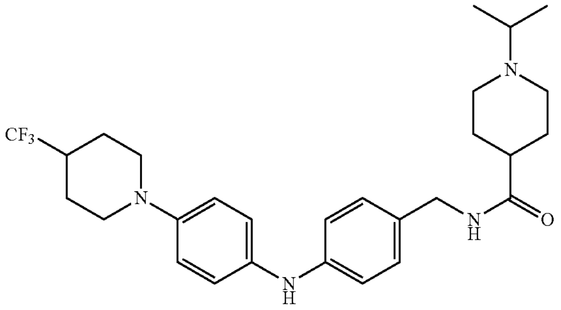 [SMILES: CC(C)N1CCC(C(=O)NCc2ccc(Nc3ccc(N4CCC(C(F)(F)F)CC4)cc3)cc2)CC1] | 40 |
| 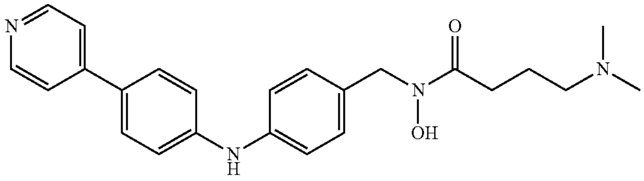 [SMILES: CN(C)CCCC(=O)N(O)Cc1ccc(Nc2ccc(-c3ccncc3)cc2)cc1] | 41 |
| 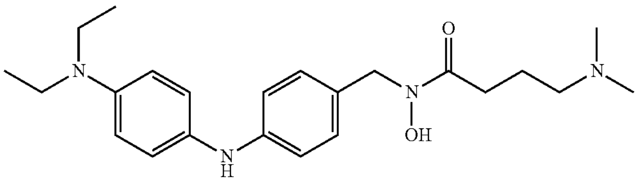 [SMILES: CCN(CC)c1ccc(Nc2ccc(CN(O)C(=O)CCCN(C)C)cc2)cc1] | 42 |
| 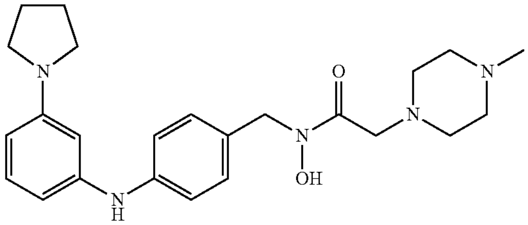 [SMILES: CN1CCN(CC(=O)N(O)Cc2ccc(Nc3cccc(N4CCCC4)c3)cc2)CC1] | 43 |
| 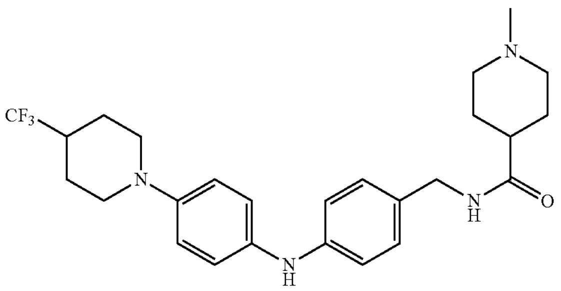 [SMILES: CN1CCC(C(=O)NCc2ccc(Nc3ccc(N4CCC(C(F)(F)F)CC4)cc3)cc2)CC1] | 44 |

TABLE 1-continued
| Active Compounds: Structures | |
|---|---|
| 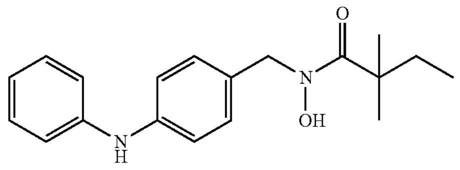 [SMILES: CCC(C)(C)C(=O)N(O)Cc1ccc(Nc2ccccc2)cc1] | 45 |
| 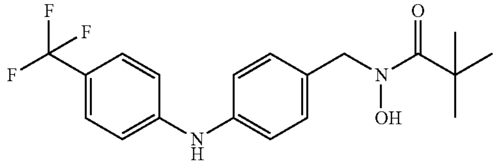 [SMILES: CC(C)(C)C(=O)N(O)Cc1ccc(Nc2ccc(C(F)(F)F)cc2)cc1] | 46 |
| 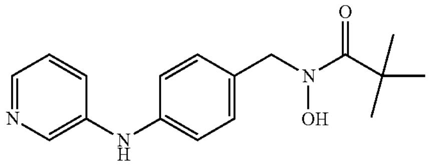 [SMILES: CC(C)(C)C(=O)N(O)Cc1ccc(Nc2cccnc2)cc1] | 47 |
| 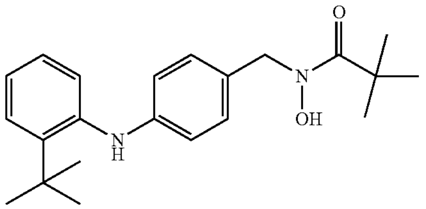 [SMILES: CC(C)(C)C(=O)N(O)Cc1ccc(Nc2ccccc2C(C)(C)C)cc1] | 48 |
| 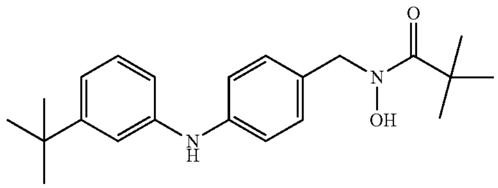 [SMILES: CC(C)(C)C(=O)N(O)Cc1ccc(Nc2cccc(C(C)(C)C)c2)cc1] | 49 |
| 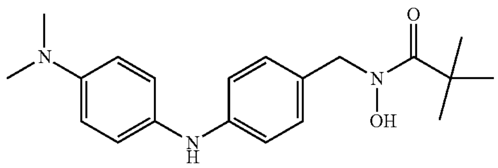 [SMILES: CN(C)c1ccc(Nc2ccc(CN(O)C(=O)C(C)(C)C)cc2)cc1] | 50 |
| 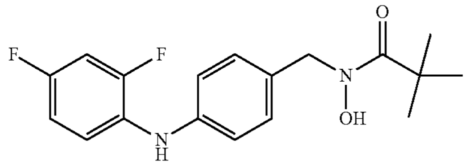 [SMILES: CC(C)(C)C(=O)N(O)Cc1ccc(Nc2ccc(F)cc2F)cc1] | 51 |
| 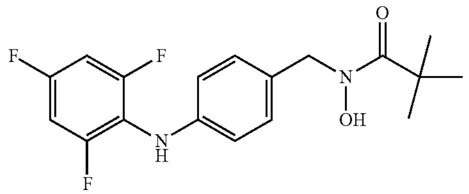 [SMILES: CC(C)(C)C(=O)N(O)Cc1ccc(Nc2c(F)cc(F)cc2F)cc1] | 52 |

TABLE 1-continued
| Active Compounds: Structures |
| --- |
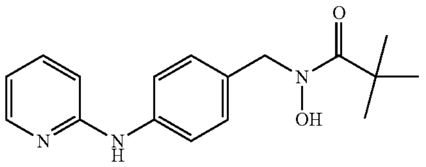 [SMILES: CC(C)(C)C(=O)N(O)Cc1ccc(Nc2ccccn2)cc1]
53
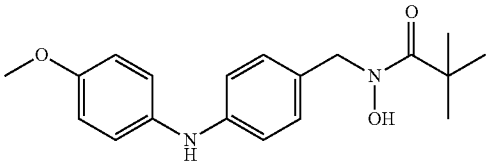 [SMILES: COc1ccc(Nc2ccc(CN(O)C(=O)C(C)(C)C)cc2)cc1]
54
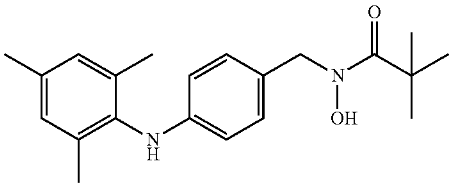 [SMILES: Cc1cc(C)c(Nc2ccc(CN(O)C(=O)C(C)(C)C)cc2)c(C)c1]
55
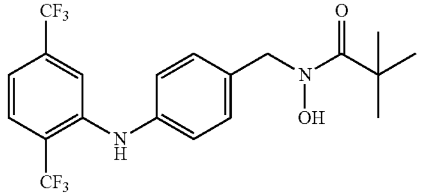 [SMILES: CC(C)(C)C(=O)N(O)Cc1ccc(Nc2cc(C(F)(F)F)ccc2C(F)(F)F)cc1]
56
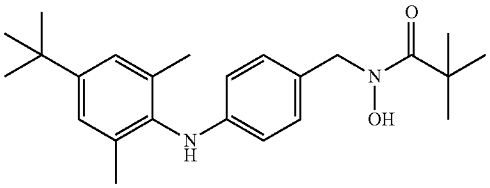 [SMILES: Cc1cc(C(C)(C)C)cc(C)c1Nc1ccc(CN(O)C(=O)C(C)(C)C)cc1]
57
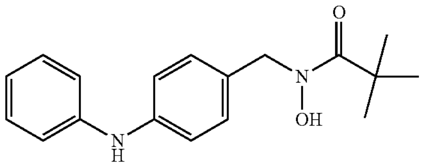 [SMILES: CC(C)(C)C(=O)N(O)Cc1ccc(Nc2ccccc2)cc1]
58
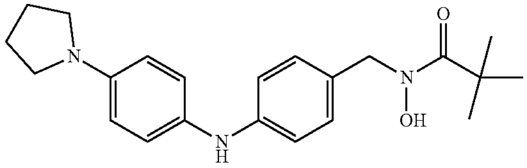 [SMILES: CC(C)(C)C(=O)N(O)Cc1ccc(Nc2ccc(N3CCCC3)cc2)cc1]
59
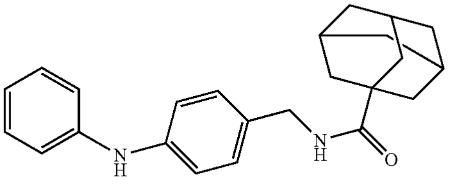 [SMILES: O=C(NCc1ccc(Nc2ccccc2)cc1)C12CC3CC(CC(C3)C1)C2]
60

TABLE 1-continued
| Active Compounds: Structures | |
|---|---|
| 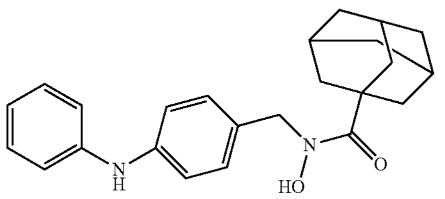 [SMILES: O=C(N(O)Cc1ccc(Nc2ccccc2)cc1)C12CC3CC(CC(C3)C1)C2] | 61 |
| 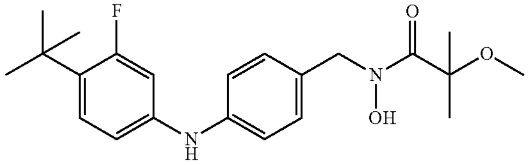 [SMILES: COC(C)(C)C(=O)N(O)Cc1ccc(Nc2ccc(C(C)(C)C)c(F)c2)cc1] | 62 |
| 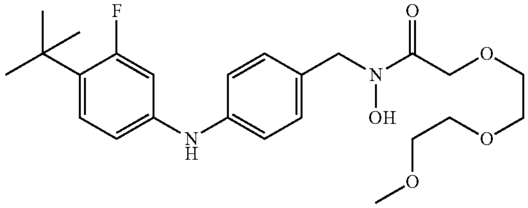 [SMILES: COCCOCCOCC(=O)N(O)Cc1ccc(Nc2ccc(C(C)(C)C)c(F)c2)cc1] | 63 |
| 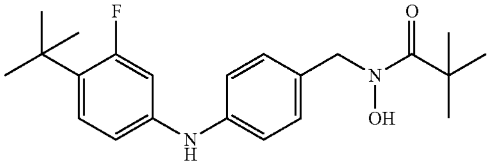 [SMILES: CC(C)(C)C(=O)N(O)Cc1ccc(Nc2ccc(C(C)(C)C)c(F)c2)cc1] | 64 |
| 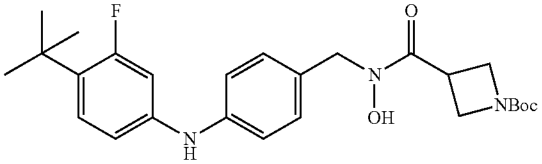 [SMILES: CC(C)(C)OC(=O)N1CC(C(=O)N(O)Cc2ccc(Nc3ccc(C(C)(C)C)c(F)c3)cc2)C1] | 65 |
| 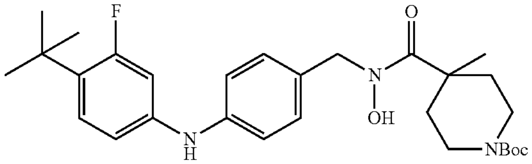 [SMILES: CC(C)(C)OC(=O)N1CCC(C)(C(=O)N(O)Cc2ccc(Nc3ccc(C(C)(C)C)c(F)c3)cc2)CC1] | 66 |
| 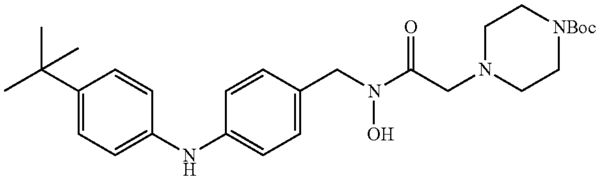 [SMILES: CC(C)(C)OC(=O)N1CCN(CC(=O)N(O)Cc2ccc(Nc3ccc(C(C)(C)C)cc3)cc2)CC1] | 67 |
| 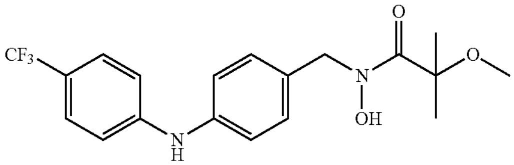 | 68 |

TABLE 1-continued
| Active Compounds: Structures |
| --- |
| 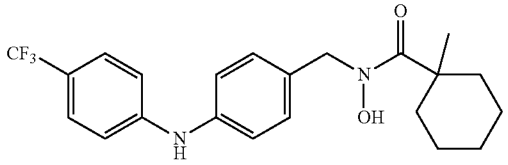 [SMILES: CC1(C(=O)N(O)Cc2ccc(Nc3ccc(C(F)(F)F)cc3)cc2)CCCCC1] 69 |
| 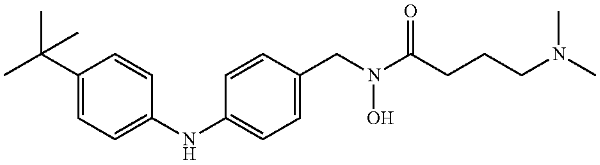 [SMILES: CN(C)CCCC(=O)N(O)Cc1ccc(Nc2ccc(C(C)(C)C)cc2)cc1] 70 |
| 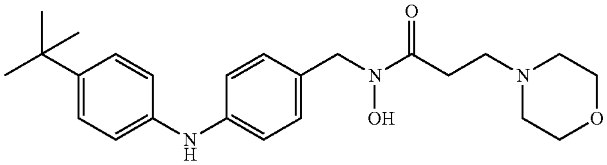 [SMILES: CC(C)(C)c1ccc(Nc2ccc(CN(O)C(=O)CCN3CCOCC3)cc2)cc1] 71 |
| 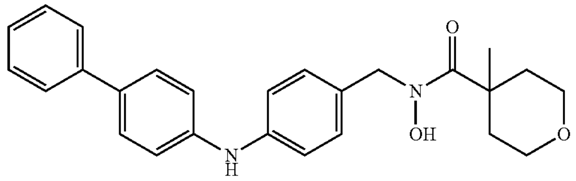 [SMILES: CC1(C(=O)N(O)Cc2ccc(Nc3ccc(-c4ccccc4)cc3)cc2)CCOCC1] 72 |
| 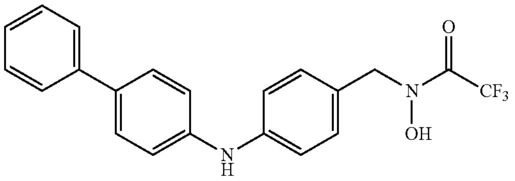 [SMILES: O=C(N(O)Cc1ccc(Nc2ccc(-c3ccccc3)cc2)cc1)C(F)(F)F] 73 |
| 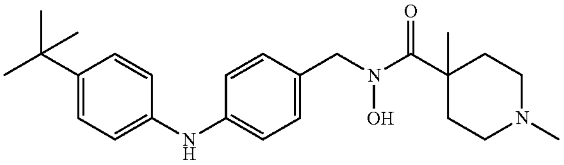 [SMILES: CN1CCC(C)(C(=O)N(O)Cc2ccc(Nc3ccc(C(C)(C)C)cc3)cc2)CC1] 74 |
| 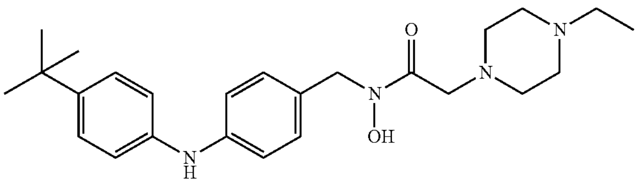 [SMILES: CCN1CCN(CC(=O)N(O)Cc2ccc(Nc3ccc(C(C)(C)C)cc3)cc2)CC1] 75 |
| 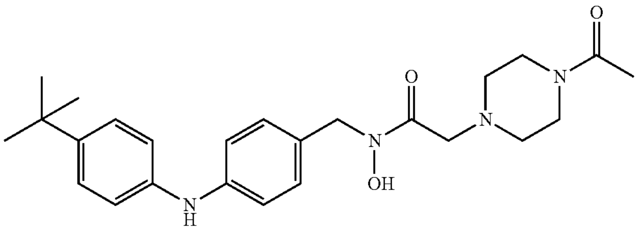 [SMILES: CC(=O)N1CCN(CC(=O)N(O)Cc2ccc(Nc3ccc(C(C)(C)C)cc3)cc2)CC1] 76 |

TABLE 1-continued
| Active Compounds: Structures | |
|---|---|
| 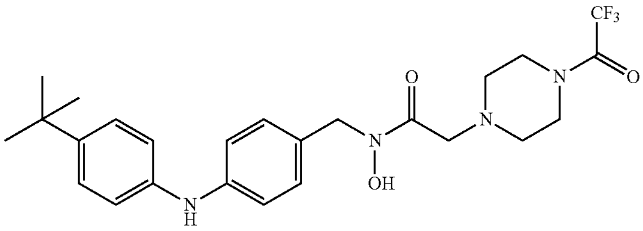 [SMILES: CC(C)(C)c1ccc(Nc2ccc(CN(O)C(=O)CN3CCN(C(=O)C(F)(F)F)CC3)cc2)cc1] | 77 |
| 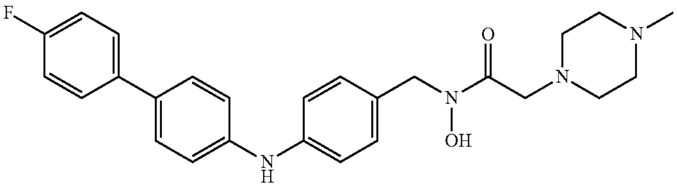 [SMILES: CN1CCN(CC(=O)N(O)Cc2ccc(Nc3ccc(-c4ccc(F)cc4)cc3)cc2)CC1] | 78 |
| 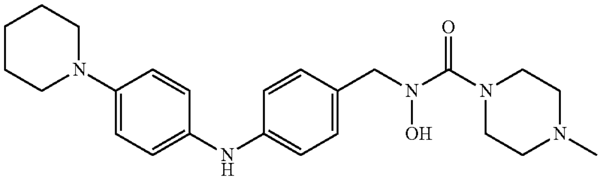 [SMILES: CN1CCN(C(=O)N(O)Cc2ccc(Nc3ccc(N4CCCCC4)cc3)cc2)CC1] | 79 |
| 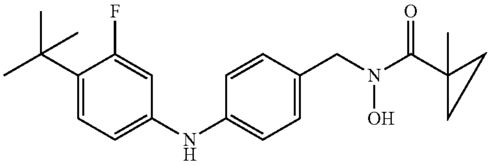 [SMILES: CC1(C(=O)N(O)Cc2ccc(Nc3ccc(C(C)(C)C)c(F)c3)cc2)CC1] | 80 |
| 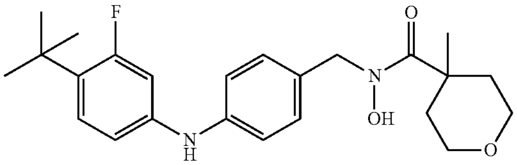 [SMILES: CC1(C(=O)N(O)Cc2ccc(Nc3ccc(C(C)(C)C)c(F)c3)cc2)CCOCC1] | 81 |
| 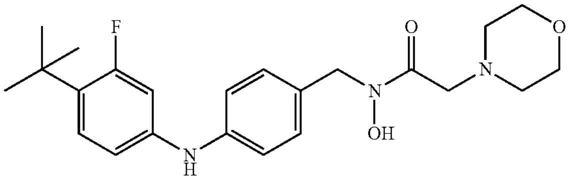 [SMILES: CC(C)(C)c1ccc(Nc2ccc(CN(O)C(=O)CN3CCOCC3)cc2)cc1F] | 82 |
| 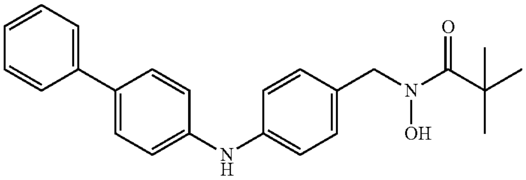 [SMILES: CC(C)(C)C(=O)N(O)Cc1ccc(Nc2ccc(-c3ccccc3)cc2)cc1] | 83 |
| 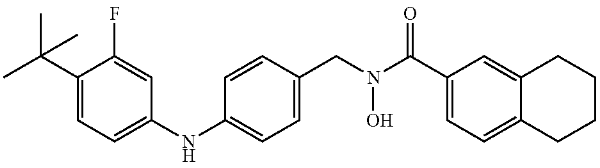 [SMILES: CC(C)(C)c1ccc(Nc2ccc(CN(O)C(=O)c3ccc4c(c3)CCCC4)cc2)cc1F] | 84 |

TABLE 1-continued
Active Compounds: Structures
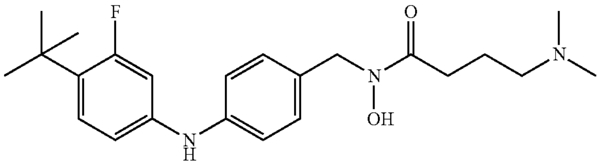 [SMILES: CN(C)CCCC(=O)N(O)Cc1ccc(Nc2ccc(C(C)(C)C)c(F)c2)cc1]
85
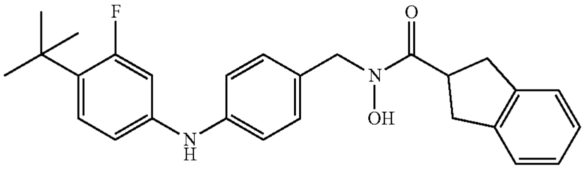 [SMILES: CC(C)(C)c1ccc(Nc2ccc(CN(O)C(=O)C3Cc4ccccc4C3)cc2)cc1F]
86
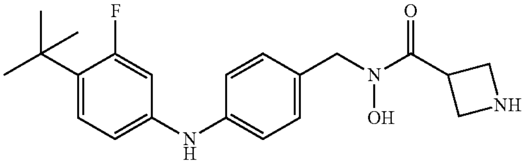 [SMILES: CC(C)(C)c1ccc(Nc2ccc(CN(O)C(=O)C3CNC3)cc2)cc1F]
87
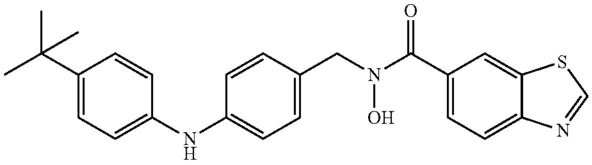 [SMILES: CC(C)(C)c1ccc(Nc2ccc(CN(O)C(=O)c3ccc4ncsc4c3)cc2)cc1]
88
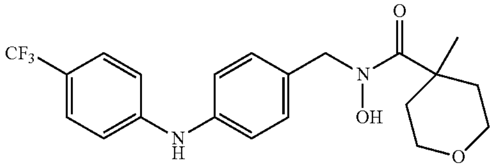 [SMILES: CC1(C(=O)N(O)Cc2ccc(Nc3ccc(C(F)(F)F)cc3)cc2)CCOCC1]
89
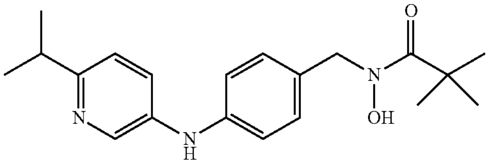 [SMILES: CC(C)c1ccc(Nc2ccc(CN(O)C(=O)C(C)(C)C)cc2)cn1]
90
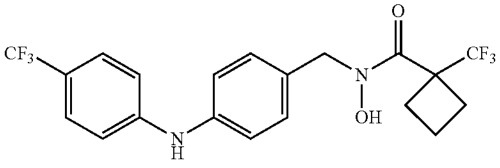 [SMILES: O=C(N(O)Cc1ccc(Nc2ccc(C(F)(F)F)cc2)cc1)C1(C(F)(F)F)CCC1]
91
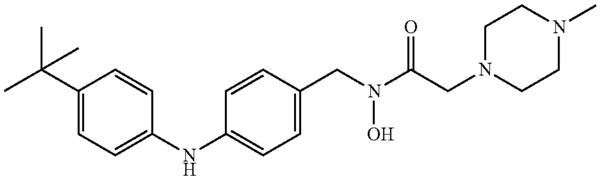 [SMILES: CN1CCN(CC(=O)N(O)Cc2ccc(Nc3ccc(C(C)(C)C)cc3)cc2)CC1]
92

TABLE 1-continued
| Active Compounds: Structures |
| --- |
| 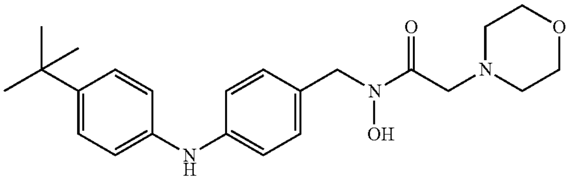 [SMILES: CC(C)(C)c1ccc(Nc2ccc(CN(O)C(=O)CN3CCOCC3)cc2)cc1] 93 |
| 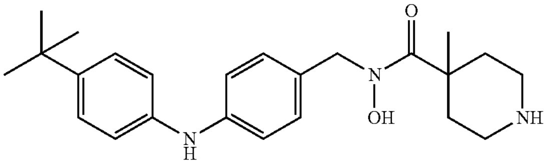 [SMILES: CC1(C(=O)N(O)Cc2ccc(Nc3ccc(C(C)(C)C)cc3)cc2)CCNCC1] 94 |
| 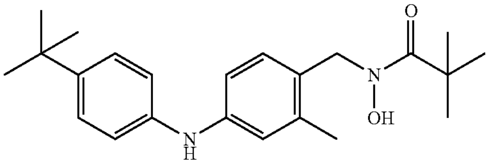 [SMILES: Cc1cc(Nc2ccc(C(C)(C)C)cc2)ccc1CN(O)C(=O)C(C)(C)C] 95 |
| 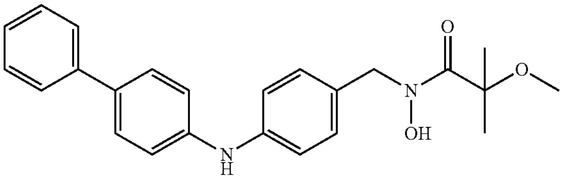 [SMILES: COC(C)(C)C(=O)N(O)Cc1ccc(Nc2ccc(-c3ccccc3)cc2)cc1] 96 |
| 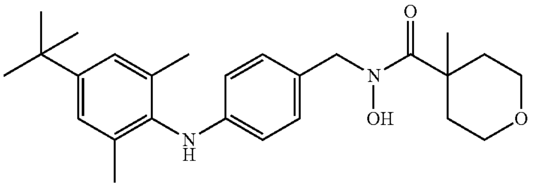 [SMILES: Cc1cc(C(C)(C)C)cc(C)c1Nc1ccc(CN(O)C(=O)C2(C)CCOCC2)cc1] 97 |
| 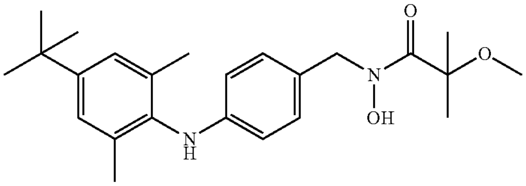 [SMILES: COC(C)(C)C(=O)N(O)Cc1ccc(Nc2c(C)cc(C(C)(C)C)cc2C)cc1] 98 |
| 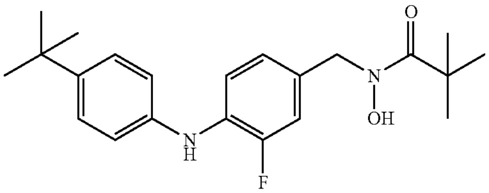 [SMILES: CC(C)(C)C(=O)N(O)Cc1ccc(Nc2ccc(C(C)(C)C)cc2)c(F)c1] 99 |
| 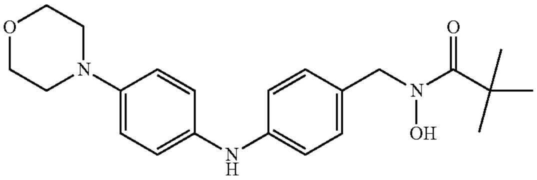 [SMILES: CC(C)(C)C(=O)N(O)Cc1ccc(Nc2ccc(N3CCOCC3)cc2)cc1] 100 |

TABLE 1-continued
| Active Compounds: Structures | |
|---|---|
| 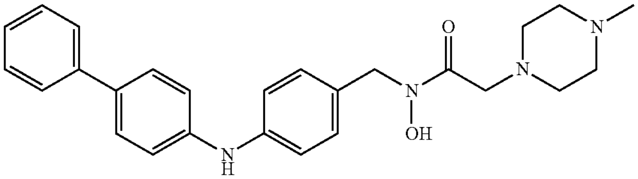 [SMILES: CN1CCN(CC(=O)N(O)Cc2ccc(Nc3ccc(-c4ccccc4)cc3)cc2)CC1] | 101 |
| 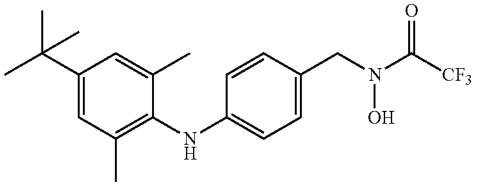 [SMILES: Cc1cc(C(C)(C)C)cc(C)c1Nc1ccc(CN(O)C(=O)C(F)(F)F)cc1] | 102 |
| 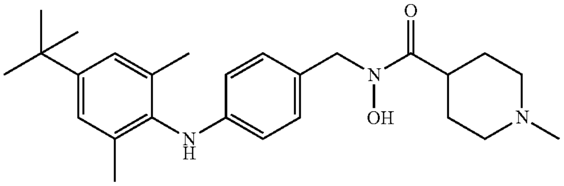 [SMILES: Cc1cc(C(C)(C)C)cc(C)c1Nc1ccc(CN(O)C(=O)C2CCN(C)CC2)cc1] | 103 |
| 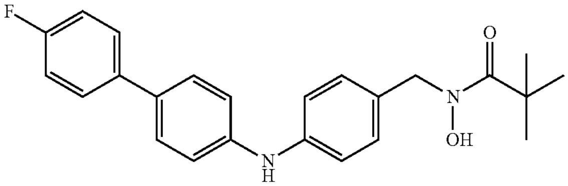 [SMILES: CC(C)(C)C(=O)N(O)Cc1ccc(Nc2ccc(-c3ccc(F)cc3)cc2)cc1] | 104 |
| 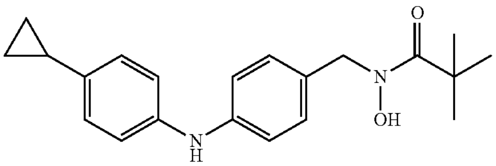 [SMILES: CC(C)(C)C(=O)N(O)Cc1ccc(Nc2ccc(C3CC3)cc2)cc1] | 105 |
| 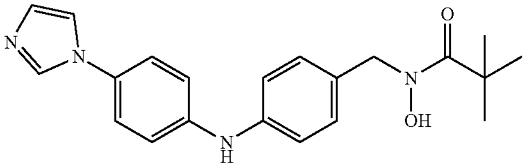 [SMILES: CC(C)(C)C(=O)N(O)Cc1ccc(Nc2ccc(-n3ccnc3)cc2)cc1] | 106 |
| 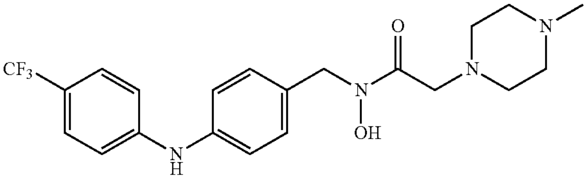 [SMILES: CN1CCN(CC(=O)N(O)Cc2ccc(Nc3ccc(C(F)(F)F)cc3)cc2)CC1] | 107 |
| 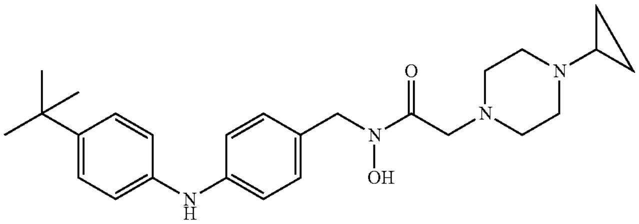 [SMILES: CC(C)(C)c1ccc(Nc2ccc(CN(O)C(=O)CN3CCN(C4CC4)CC3)cc2)cc1] | 108 |

TABLE 1-continued
Active Compounds: Structures
109
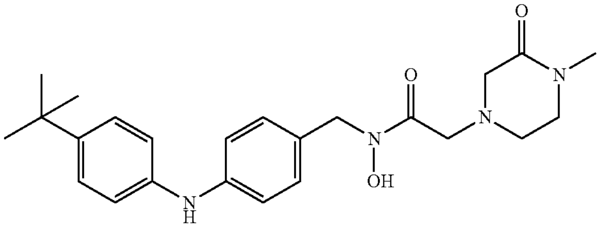 [SMILES: CN1CCN(CC(=O)N(O)Cc2ccc(Nc3ccc(C(C)(C)C)cc3)cc2)CC1=O]
110
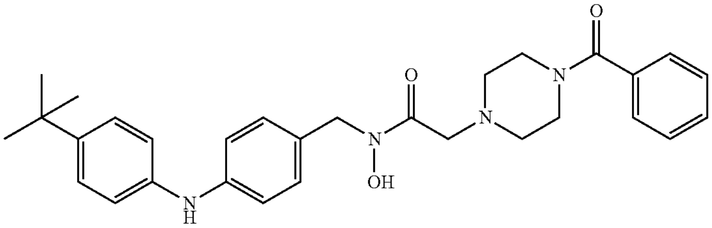 [SMILES: CC(C)(C)c1ccc(Nc2ccc(CN(O)C(=O)CN3CCN(C(=O)c4ccccc4)CC3)cc2)cc1]
111
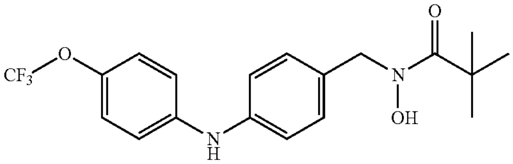 [SMILES: CC(C)(C)C(=O)N(O)Cc1ccc(Nc2ccc(OC(F)(F)F)cc2)cc1]
112
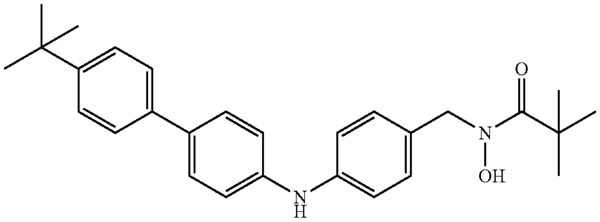 [SMILES: CC(C)(C)C(=O)N(O)Cc1ccc(Nc2ccc(-c3ccc(C(C)(C)C)cc3)cc2)cc1]
113
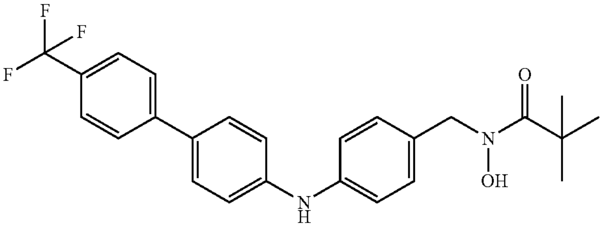 [SMILES: CC(C)(C)C(=O)N(O)Cc1ccc(Nc2ccc(-c3ccc(C(F)(F)F)cc3)cc2)cc1]
114
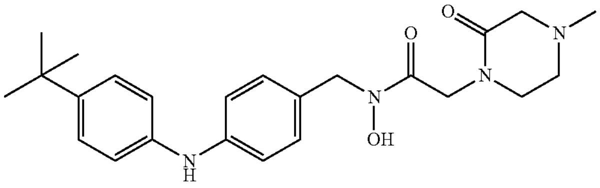 [SMILES: CN1CCN(CC(=O)N(O)Cc2ccc(Nc3ccc(C(C)(C)C)cc3)cc2)C(=O)C1]
115
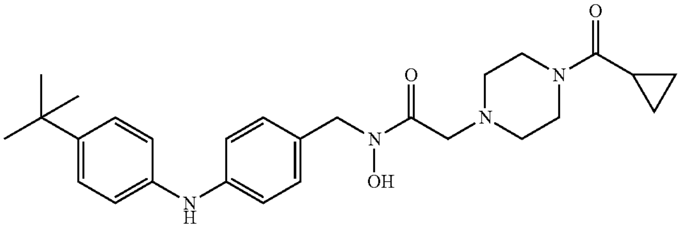 [SMILES: CC(C)(C)c1ccc(Nc2ccc(CN(O)C(=O)CN3CCN(C(=O)C4CC4)CC3)cc2)cc1]

TABLE 1-continued
| Active Compounds: Structures | |
|---|---|
| 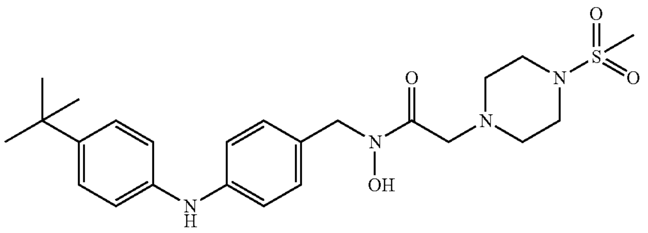 [SMILES: CC(C)(C)c1ccc(Nc2ccc(CN(O)C(=O)CN3CCN(S(C)(=O)=O)CC3)cc2)cc1] | 116 |
| 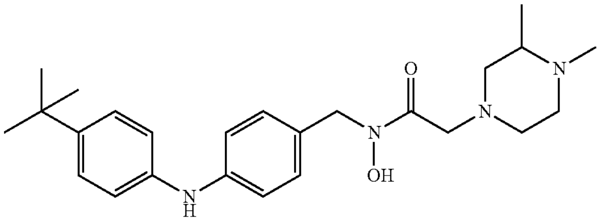 [SMILES: CC1CN(CC(=O)N(O)Cc2ccc(Nc3ccc(C(C)(C)C)cc3)cc2)CCN1C] | 117 |
| 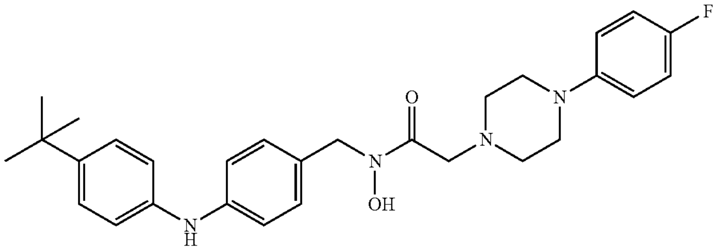 [SMILES: CC(C)(C)c1ccc(Nc2ccc(CN(O)C(=O)CN3CCN(c4ccc(F)cc4)CC3)cc2)cc1] | 118 |
| 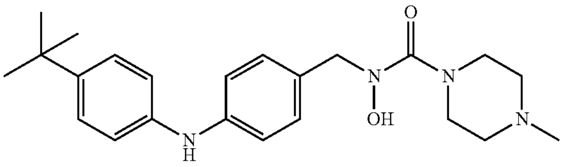 [SMILES: CN1CCN(C(=O)N(O)Cc2ccc(Nc3ccc(C(C)(C)C)cc3)cc2)CC1] | 119 |
| 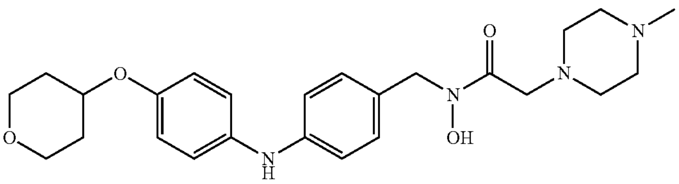 [SMILES: CN1CCN(CC(=O)N(O)Cc2ccc(Nc3ccc(OC4CCOCC4)cc3)cc2)CC1] | 120 |
| 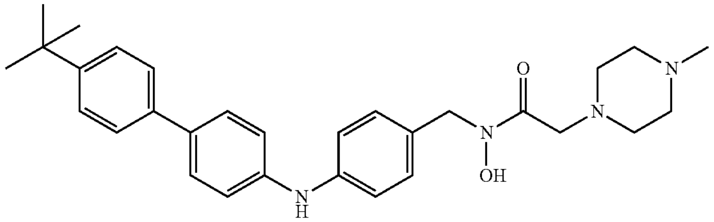 [SMILES: CN1CCN(CC(=O)N(O)Cc2ccc(Nc3ccc(-c4ccc(C(C)(C)C)cc4)cc3)cc2)CC1] | 121 |
| 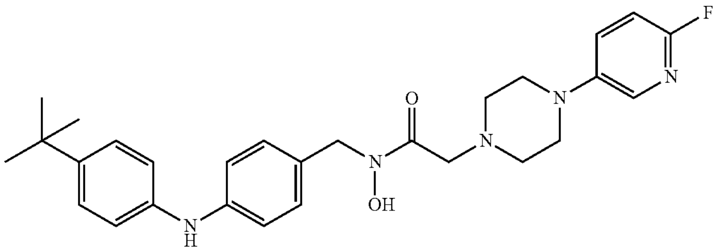 [SMILES: CC(C)(C)c1ccc(Nc2ccc(CN(O)C(=O)CN3CCN(c4ccc(F)nc4)CC3)cc2)cc1] | 122 |

TABLE 1-continued
Active Compounds: Structures
123
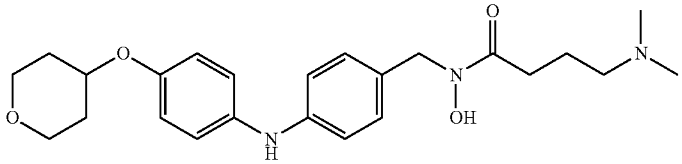 [SMILES: CN(C)CCCC(=O)N(O)Cc1ccc(Nc2ccc(OC3CCOCC3)cc2)cc1]
124
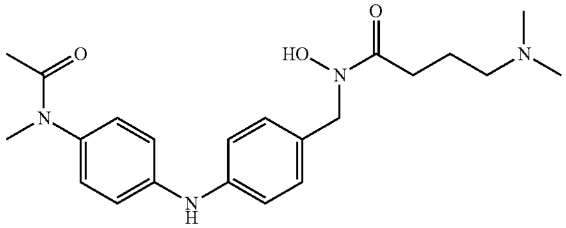
125
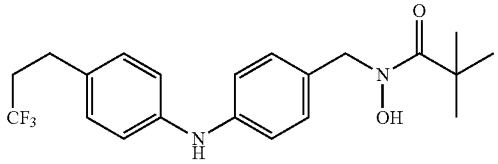 [SMILES: CC(C)(C)C(=O)N(O)Cc1ccc(Nc2ccc(CCC(F)(F)F)cc2)cc1]
126
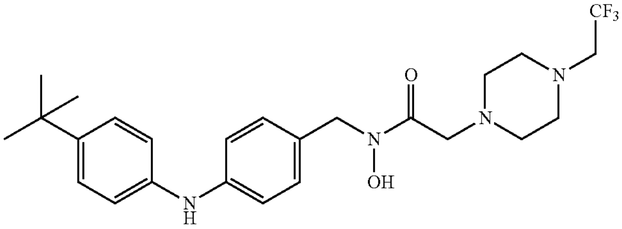 [SMILES: CC(C)(C)c1ccc(Nc2ccc(CN(O)C(=O)CN3CCN(CC(F)(F)F)CC3)cc2)cc1]
127
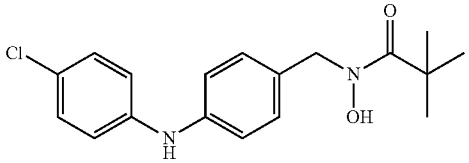 [SMILES: CC(C)(C)C(=O)N(O)Cc1ccc(Nc2ccc(Cl)cc2)cc1]
128
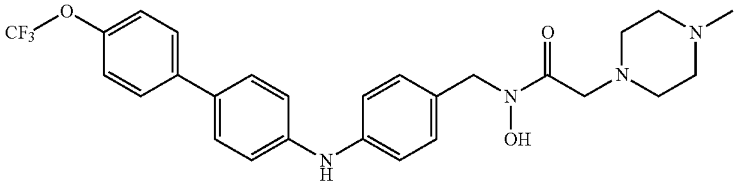 [SMILES: CN1CCN(CC(=O)N(O)Cc2ccc(Nc3ccc(-c4ccc(OC(F)(F)F)cc4)cc3)cc2)CC1]
129
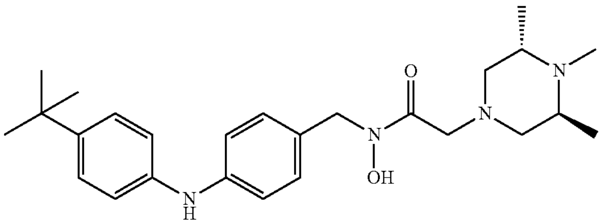 [SMILES: C[C@H]1CN(CC(=O)N(O)Cc2ccc(Nc3ccc(C(C)(C)C)cc3)cc2)C[C@H](C)N1C]
130
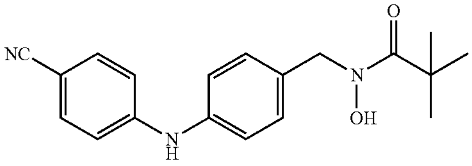 [SMILES: CC(C)(C)C(=O)N(O)Cc1ccc(Nc2ccc(C#N)cc2)cc1]

TABLE 1-continued
| Active Compounds: Structures | |
|---|---|
| 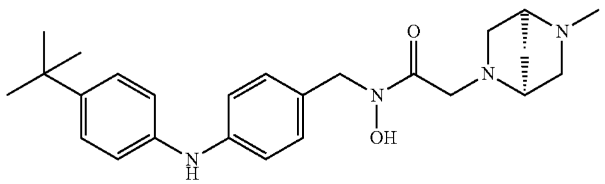 | 131 |
| 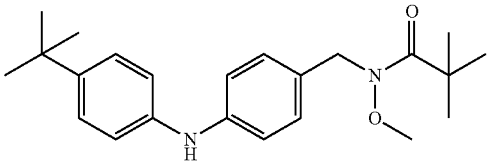 [SMILES: CON(Cc1ccc(Nc2ccc(C(C)(C)C)cc2)cc1)C(=O)C(C)(C)C] | 132 |
| 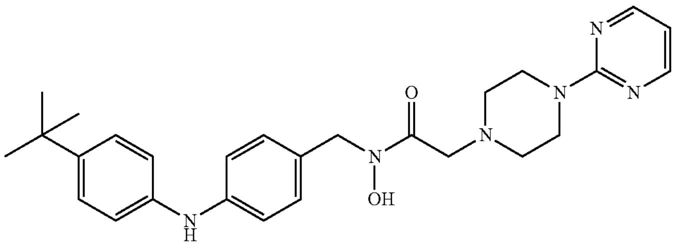 [SMILES: CC(C)(C)c1ccc(Nc2ccc(CN(O)C(=O)CN3CCN(c4ncccn4)CC3)cc2)cc1] | 133 |
| 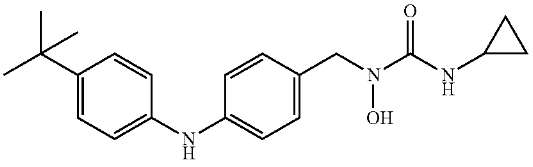 [SMILES: CC(C)(C)c1ccc(Nc2ccc(CN(O)C(=O)NC3CC3)cc2)cc1] | 134 |
| 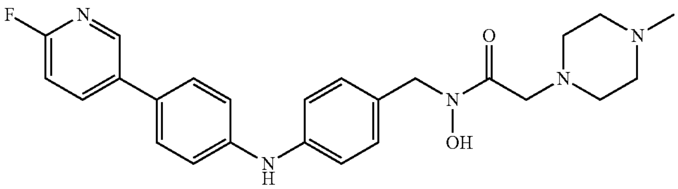 [SMILES: CN1CCN(CC(=O)N(O)Cc2ccc(Nc3ccc(-c4ccc(F)nc4)cc3)cc2)CC1] | 135 |
| 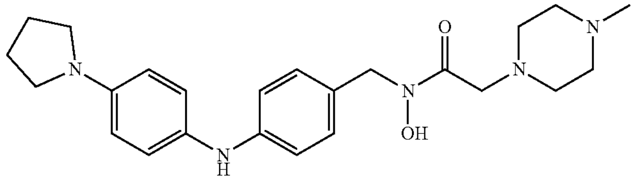 [SMILES: CN1CCN(CC(=O)N(O)Cc2ccc(Nc3ccc(N4CCCC4)cc3)cc2)CC1] | 136 |
| 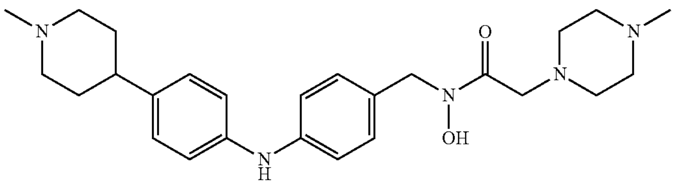 | 137 |
| 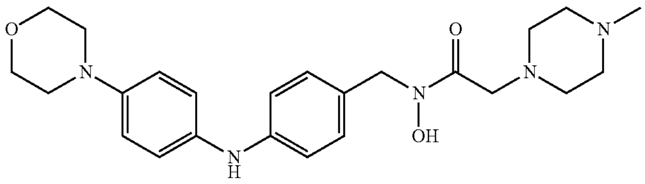 [SMILES: CN1CCN(CC(=O)N(O)Cc2ccc(Nc3ccc(N4CCOCC4)cc3)cc2)CC1] | 138 |

TABLE 1-continued
| Active Compounds: Structures | |
|---|---|
| 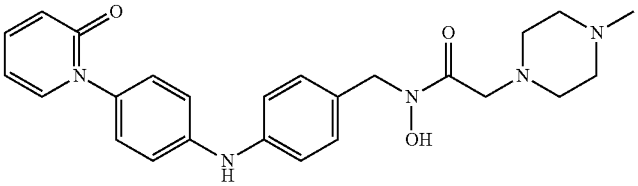 | 139 |
| 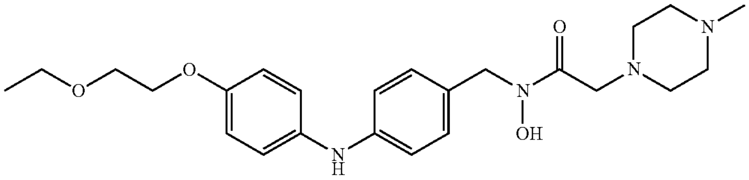 [SMILES: CCOCCOc1ccc(Nc2ccc(CN(O)C(=O)CN3CCN(C)CC3)cc2)cc1] | 140 |
| 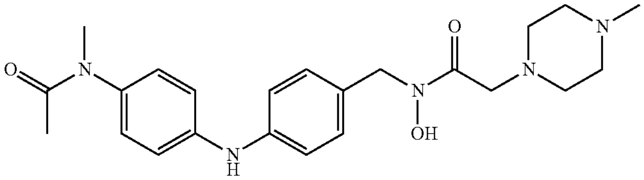 [SMILES: CC(=O)N(C)c1ccc(Nc2ccc(CN(O)C(=O)CN3CCN(C)CC3)cc2)cc1] | 141 |
| 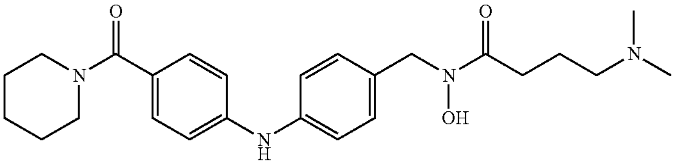 [SMILES: CN(C)CCCC(=O)N(O)Cc1ccc(Nc2ccc(C(=O)N3CCCCC3)cc2)cc1] | 142 |
| 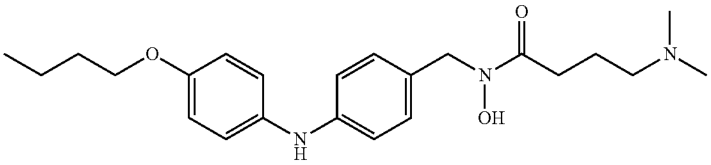 [SMILES: CCCCOc1ccc(Nc2ccc(CN(O)C(=O)CCCN(C)C)cc2)cc1] | 143 |
| 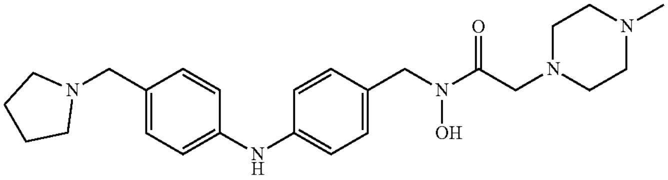 [SMILES: CN1CCN(CC(=O)N(O)Cc2ccc(Nc3ccc(CN4CCCC4)cc3)cc2)CC1] | 144 |
| 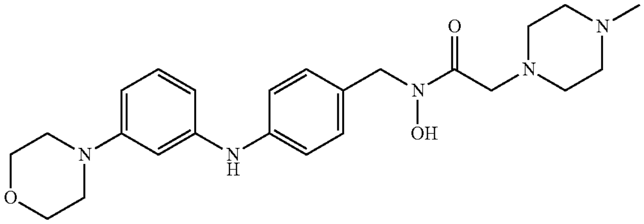 [SMILES: CN1CCN(CC(=O)N(O)Cc2ccc(Nc3cccc(N4CCOCC4)c3)cc2)CC1] | 145 |
| 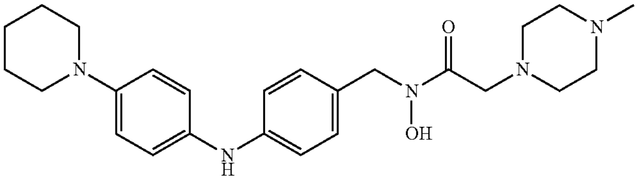 [SMILES: CN1CCN(CC(=O)N(O)Cc2ccc(Nc3ccc(N4CCCCC4)cc3)cc2)CC1] | 146 |

TABLE 1-continued
| Active Compounds: Structures | |
|---|---|
| 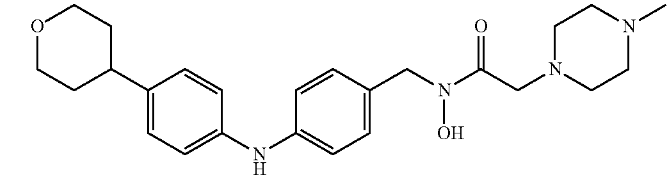 [SMILES: CN1CCN(CC(=O)N(O)Cc2ccc(Nc3ccc(C4CCOCC4)cc3)cc2)CC1] | 147 |
| 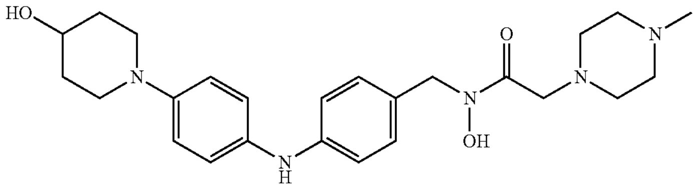 [SMILES: CN1CCN(CC(=O)N(O)Cc2ccc(Nc3ccc(N4CCC(O)CC4)cc3)cc2)CC1] | 148 |
| 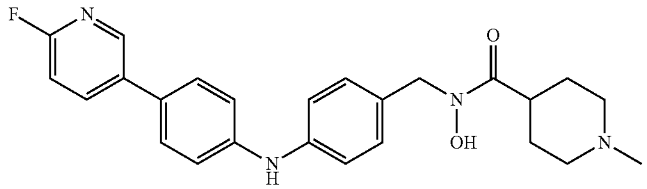 [SMILES: CN1CCC(C(=O)N(O)Cc2ccc(Nc3ccc(-c4ccc(F)nc4)cc3)cc2)CC1] | 149 |
| 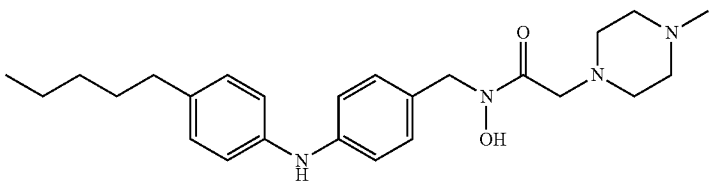 [SMILES: CCCCCc1ccc(Nc2ccc(CN(O)C(=O)CN3CCN(C)CC3)cc2)cc1] | 150 |
| 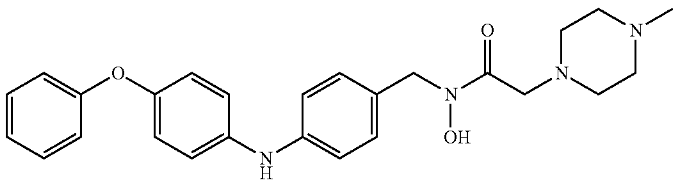 [SMILES: CN1CCN(CC(=O)N(O)Cc2ccc(Nc3ccc(Oc4ccccc4)cc3)cc2)CC1] | 151 |
| 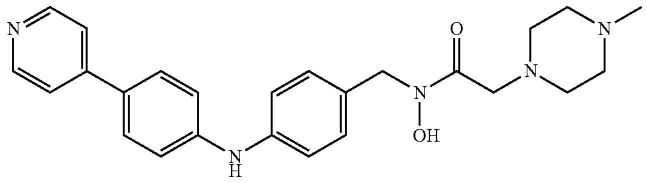 [SMILES: CN1CCN(CC(=O)N(O)Cc2ccc(Nc3ccc(-c4ccncc4)cc3)cc2)CC1] | 152 |
| 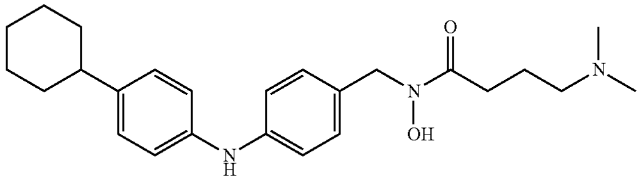 [SMILES: CN(C)CCCC(=O)N(O)Cc1ccc(Nc2ccc(C3CCCCC3)cc2)cc1] | 153 |
| 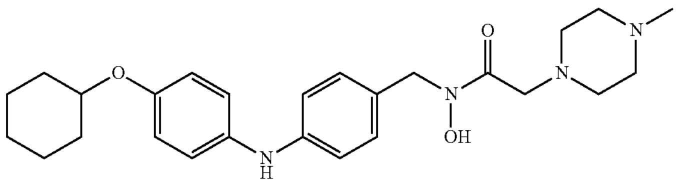 [SMILES: CN1CCN(CC(=O)N(O)Cc2ccc(Nc3ccc(OC4CCCCC4)cc3)cc2)CC1] | 154 |

TABLE 1-continued
| Active Compounds: Structures | |
| --- | --- |
| 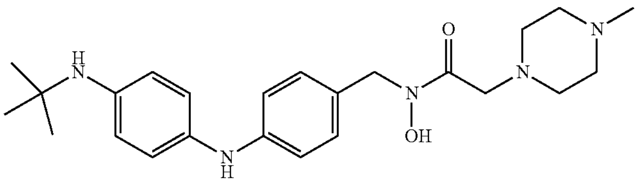 [SMILES: CN1CCN(CC(=O)N(O)Cc2ccc(Nc3ccc(NC(C)(C)C)cc3)cc2)CC1] | 155 |
| 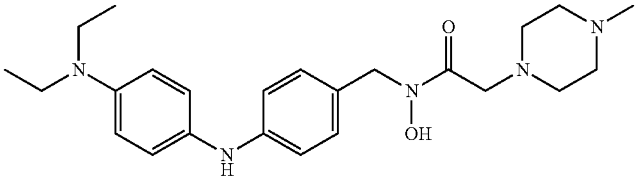 [SMILES: CCN(CC)c1ccc(Nc2ccc(CN(O)C(=O)CN3CCN(C)CC3)cc2)cc1] | 156 |
| 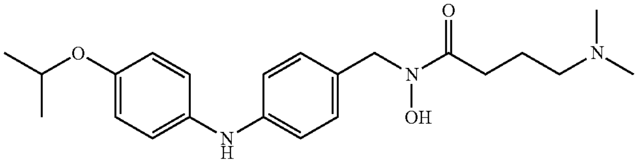 [SMILES: CC(C)Oc1ccc(Nc2ccc(CN(O)C(=O)CCCN(C)C)cc2)cc1] | 157 |
| 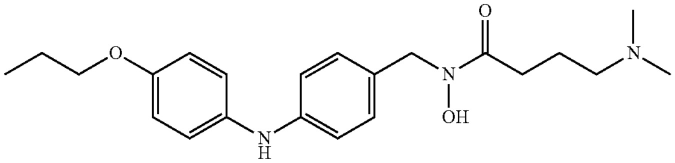 [SMILES: CCCOc1ccc(Nc2ccc(CN(O)C(=O)CCCN(C)C)cc2)cc1] | 158 |
| 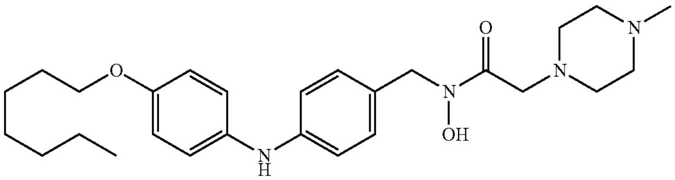 [SMILES: CCCCCCCOc1ccc(Nc2ccc(CN(O)C(=O)CN3CCN(C)CC3)cc2)cc1] | 159 |
| 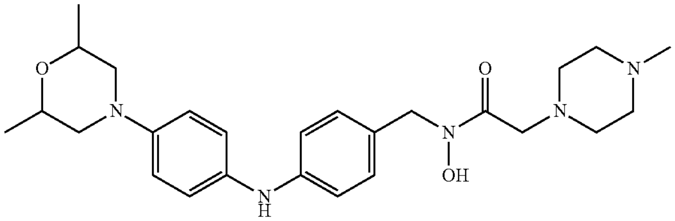 | 160 |
| 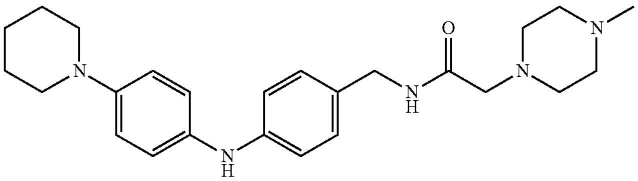 [SMILES: CN1CCN(CC(=O)NCc2ccc(Nc3ccc(N4CCCCC4)cc3)cc2)CC1] | 161 |
| 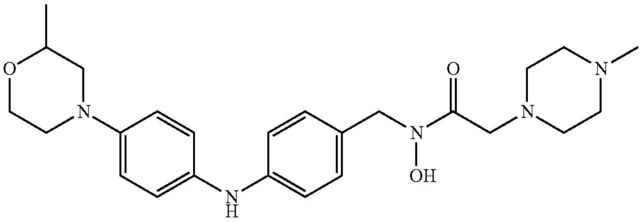 [SMILES: CC1CN(c2ccc(Nc3ccc(CN(O)C(=O)CN4CCN(C)CC4)cc3)cc2)CCO1] | 162 |

TABLE 1-continued
Active Compounds: Structures
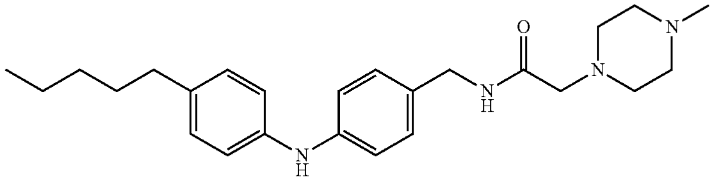 [SMILES: CCCCCc1ccc(Nc2ccc(CNC(=O)CN3CCN(C)CC3)cc2)cc1]
163
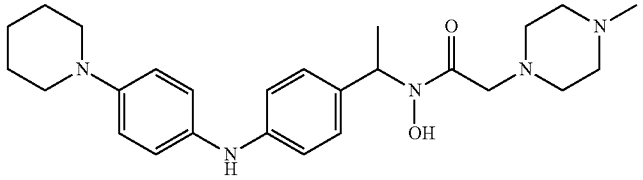 [SMILES: CC(c1ccc(Nc2ccc(N3CCCCC3)cc2)cc1)N(O)C(=O)CN1CCN(C)CC1]
164
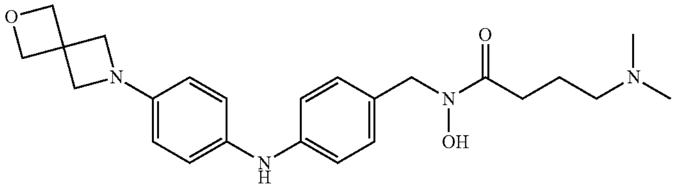 [SMILES: CN(C)CCCC(=O)N(O)Cc1ccc(Nc2ccc(N3CC4(COC4)C3)cc2)cc1]
165
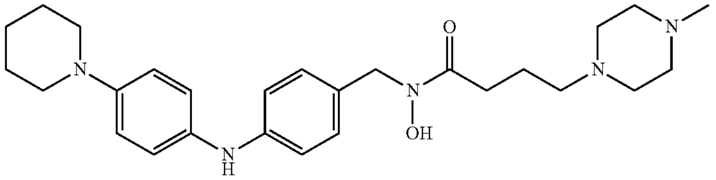 [SMILES: CN1CCN(CCCC(=O)N(O)Cc2ccc(Nc3ccc(N4CCCCC4)cc3)cc2)CC1]
166
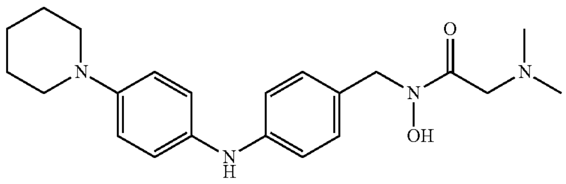 [SMILES: CN(C)CC(=O)N(O)Cc1ccc(Nc2ccc(N3CCCCC3)cc2)cc1]
167
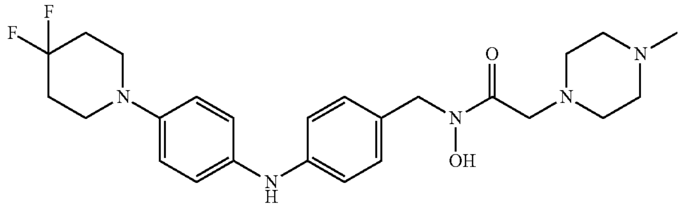 [SMILES: CN1CCN(CC(=O)N(O)Cc2ccc(Nc3ccc(N4CCC(F)(F)CC4)cc3)cc2)CC1]
168
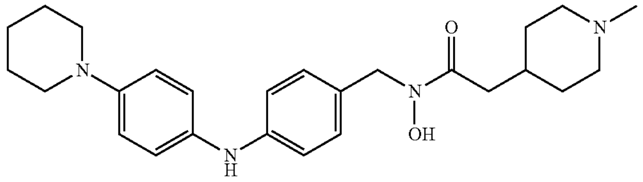 [SMILES: CN1CCC(CC(=O)N(O)Cc2ccc(Nc3ccc(N4CCCCC4)cc3)cc2)CC1]
169
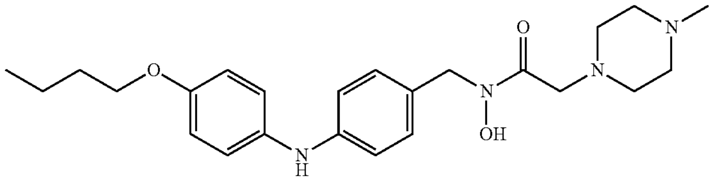 [SMILES: CCCCOc1ccc(Nc2ccc(CN(O)C(=O)CN3CCN(C)CC3)cc2)cc1]
170

TABLE 1-continued
| Active Compounds: Structures | |
|---|---|
| 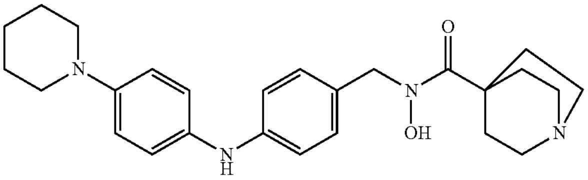 [SMILES: O=C(N(O)Cc1ccc(Nc2ccc(N3CCCCC3)cc2)cc1)C12CCN(CC1)CC2] | 171 |
| 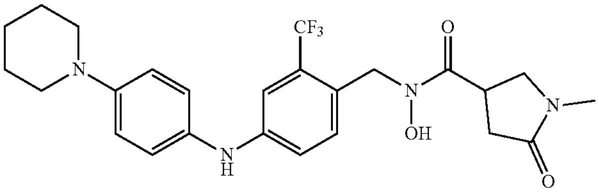 [SMILES: CN1CC(C(=O)N(O)Cc2ccc(Nc3ccc(N4CCCCC4)cc3)cc2C(F)(F)F)CC1=O] | 172 |
| 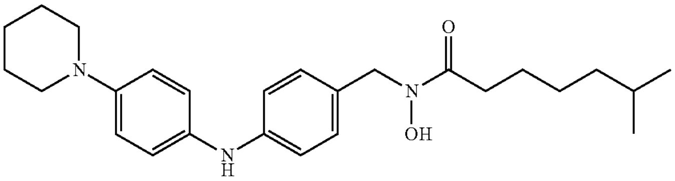 [SMILES: CC(C)CCCCC(=O)N(O)Cc1ccc(Nc2ccc(N3CCCCC3)cc2)cc1] | 173 |
| 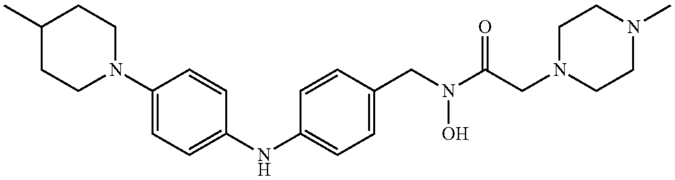 | 174 |
| 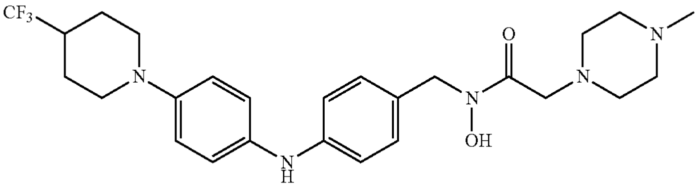 [SMILES: CN1CCN(CC(=O)N(O)Cc2ccc(Nc3ccc(N4CCC(C(F)(F)F)CC4)cc3)cc2)CC1] | 175 |
| 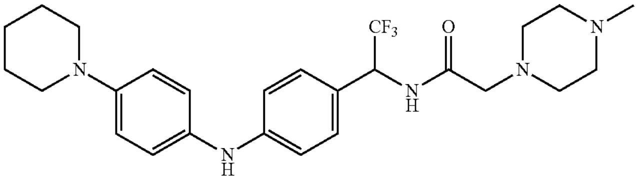 [SMILES: CN1CCN(CC(=O)NC(c2ccc(Nc3ccc(N4CCCCC4)cc3)cc2)C(F)(F)F)CC1] | 176 |
| 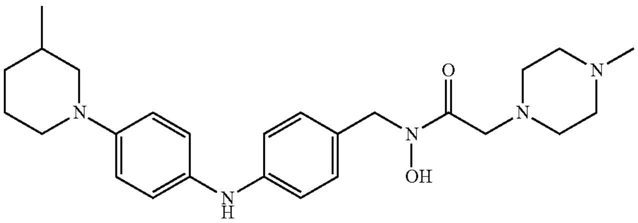 [SMILES: CC1CCCN(c2ccc(Nc3ccc(CN(O)C(=O)CN4CCN(C)CC4)cc3)cc2)C1] | 177 |
| 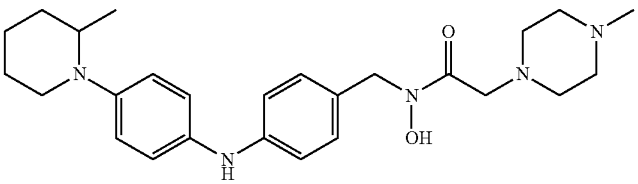 [SMILES: CC1CCCCN1c1ccc(Nc2ccc(CN(O)C(=O)CN3CCN(C)CC3)cc2)cc1] | 178 |

TABLE 1-continued
| Active Compounds: Structures | |
|---|---|
| 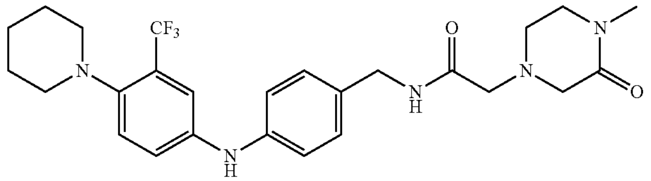 [SMILES: CN1CCN(CC(=O)NCc2ccc(Nc3ccc(N4CCCCC4)c(C(F)(F)F)c3)cc2)CC1=O] | 179 |
| 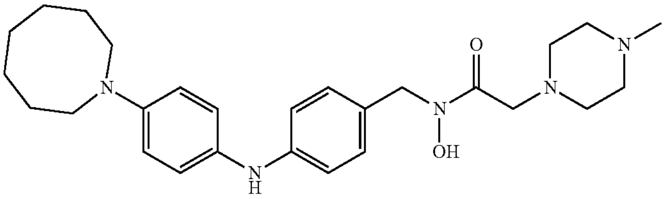 [SMILES: CN1CCN(CC(=O)N(O)Cc2ccc(Nc3ccc(N4CCCCCCC4)cc3)cc2)CC1] | 180 |
| 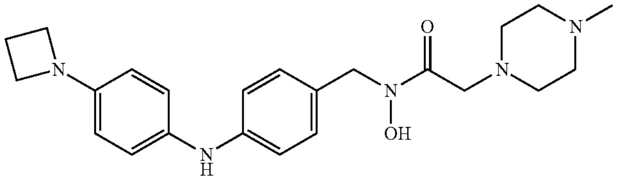 [SMILES: CN1CCN(CC(=O)N(O)Cc2ccc(Nc3ccc(N4CCC4)cc3)cc2)CC1] | 181 |
| 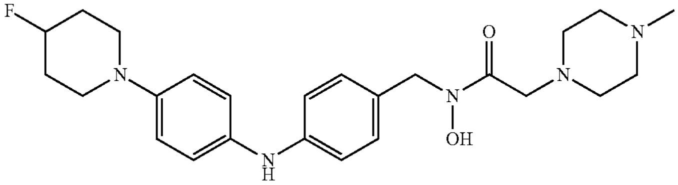 [SMILES: CN1CCN(CC(=O)N(O)Cc2ccc(Nc3ccc(N4CCC(F)CC4)cc3)cc2)CC1] | 182 |
| 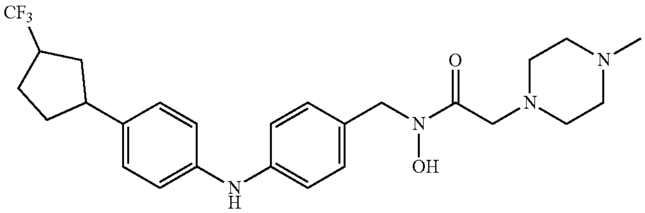 [SMILES: CN1CCN(CC(=O)N(O)Cc2ccc(Nc3ccc(C4CCC(C(F)(F)F)C4)cc3)cc2)CC1] | 183 |
| 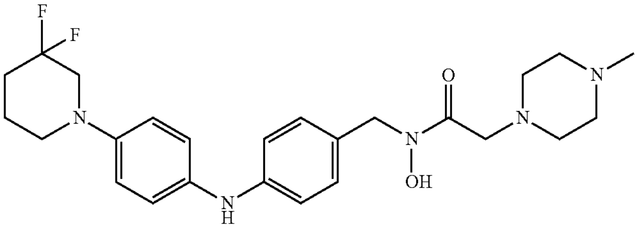 [SMILES: CN1CCN(CC(=O)N(O)Cc2ccc(Nc3ccc(N4CCCC(F)(F)C4)cc3)cc2)CC1] | 184 |
| 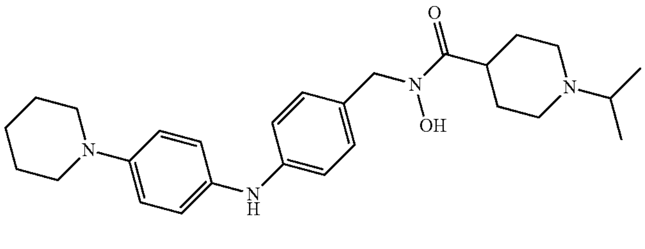 [SMILES: CC(C)N1CCC(C(=O)N(O)Cc2ccc(Nc3ccc(N4CCCCC4)cc3)cc2)CC1] | 185 |

TABLE 1-continued
| Active Compounds: Structures | |
|---|---|
| 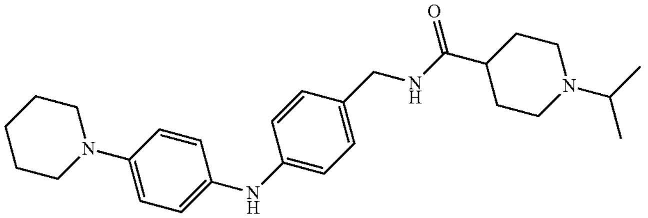 [SMILES: CC(C)N1CCC(C(=O)NCc2ccc(Nc3ccc(N4CCCCC4)cc3)cc2)CC1] | 186 |
| 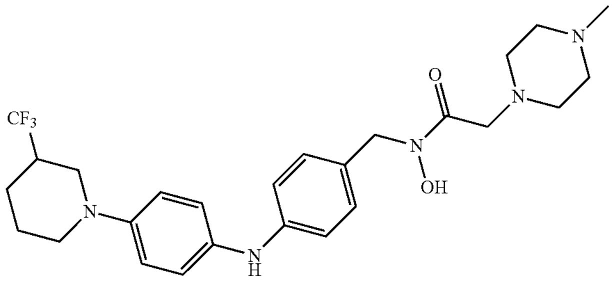 [SMILES: CN1CCN(CC(=O)N(O)Cc2ccc(Nc3ccc(N4CCCC(C(F)(F)F)C4)cc3)cc2)CC1] | 187 |
| 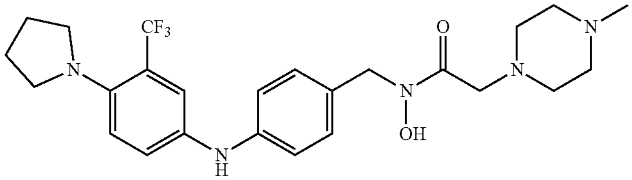 [SMILES: CN1CCN(CC(=O)N(O)Cc2ccc(Nc3ccc(N4CCCC4)c(C(F)(F)F)c3)cc2)CC1] | 188 |
| 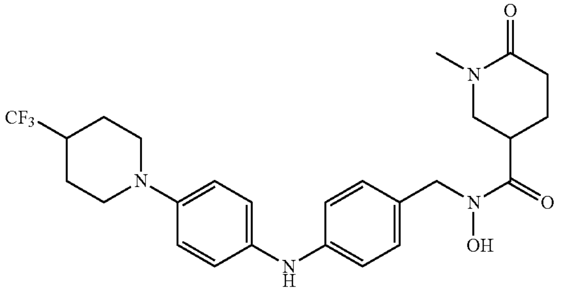 [SMILES: CN1CC(C(=O)N(O)Cc2ccc(Nc3ccc(N4CCC(C(F)(F)F)CC4)cc3)cc2)CCC1=O] | 189 |
| 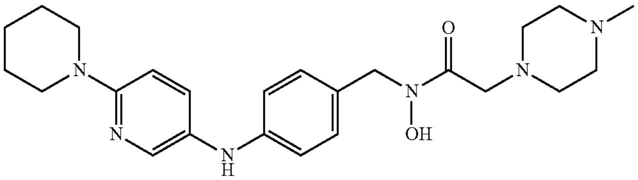 | 190 |
| 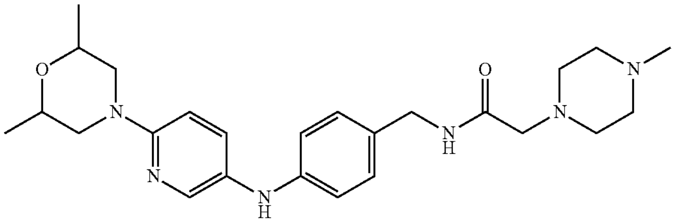 | 191 |

TABLE 1-continued
| Active Compounds: Structures | |
|---|---|
| 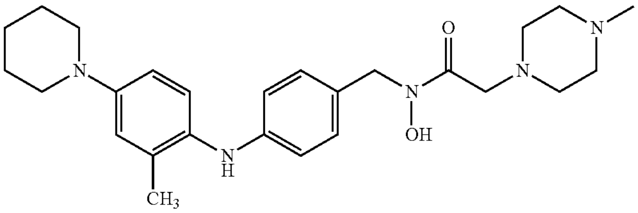 [SMILES: Cc1cc(N2CCCCC2)ccc1Nc1ccc(CN(O)C(=O)CN2CCN(C)CC2)cc1] | 192 |
| 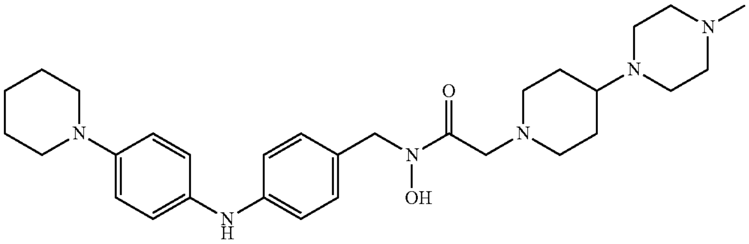 [SMILES: CN1CCN(C2CCN(CC(=O)N(O)Cc3ccc(Nc4ccc(N5CCCCC5)cc4)cc3)CC2)CC1] | 193 |
| 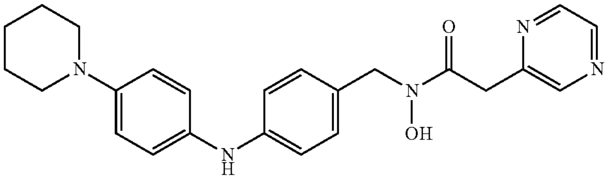 [SMILES: O=C(Cc1cnccn1)N(O)Cc1ccc(Nc2ccc(N3CCCCC3)cc2)cc1] | 194 |
| 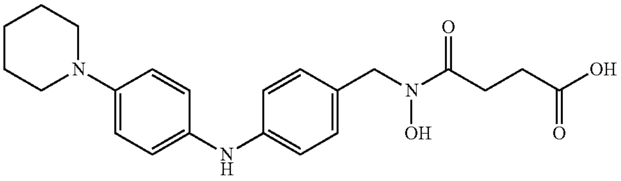 [SMILES: O=C(O)CCC(=O)N(O)Cc1ccc(Nc2ccc(N3CCCCC3)cc2)cc1] | 195 |
| 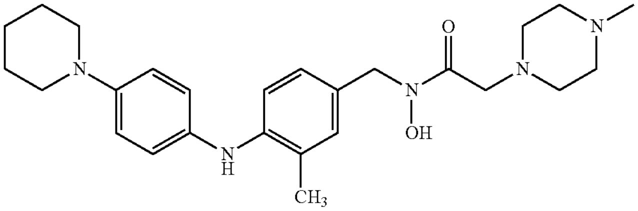 [SMILES: Cc1cc(CN(O)C(=O)CN2CCN(C)CC2)ccc1Nc1ccc(N2CCCCC2)cc1] | 196 |
| 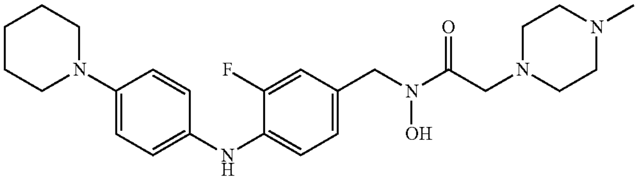 [SMILES: CN1CCN(CC(=O)N(O)Cc2ccc(Nc3ccc(N4CCCCC4)cc3)c(F)c2)CC1] | 197 |
| 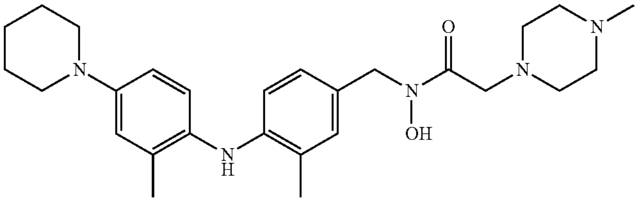 [SMILES: Cc1cc(CN(O)C(=O)CN2CCN(C)CC2)ccc1Nc1ccc(N2CCCCC2)cc1C] | 198 |

TABLE 1-continued
| Active Compounds: Structures |
|---|
| 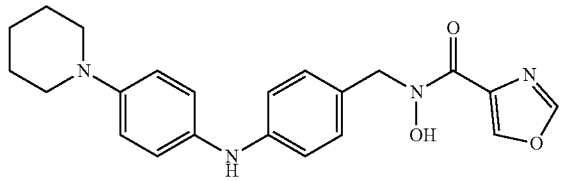 [SMILES: O=C(c1cocn1)N(O)Cc1ccc(Nc2ccc(N3CCCCC3)cc2)cc1] 199 |
| 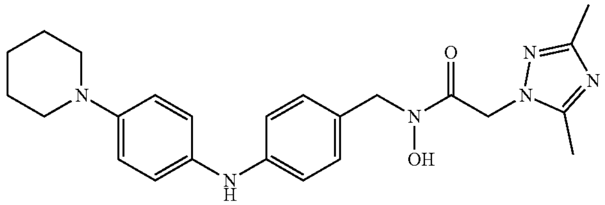 [SMILES: Cc1nc(C)n(CC(=O)N(O)Cc2ccc(Nc3ccc(N4CCCCC4)cc3)cc2)n1] 200 |
| 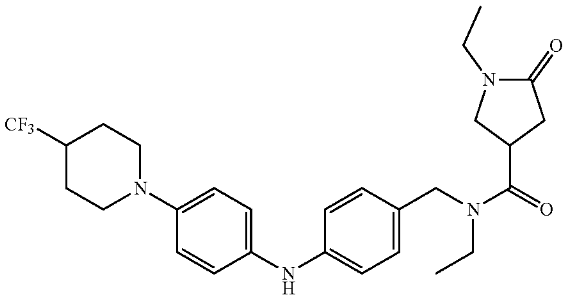 [SMILES: CCN1CC(C(=O)N(CC)Cc2ccc(Nc3ccc(N4CCC(C(F)(F)F)CC4)cc3)cc2)CC1=O] 201 |
| 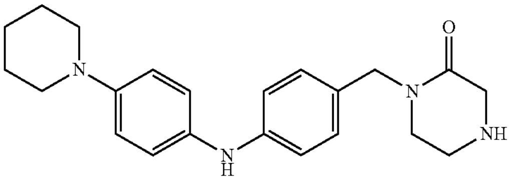 [SMILES: O=C1CNCCN1Cc1ccc(Nc2ccc(N3CCCCC3)cc2)cc1] 202 |
| 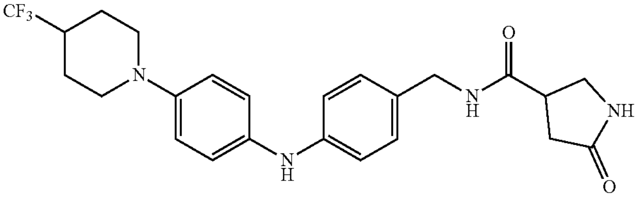 [SMILES: O=C1CC(C(=O)NCc2ccc(Nc3ccc(N4CCC(C(F)(F)F)CC4)cc3)cc2)CN1] 203 |
| 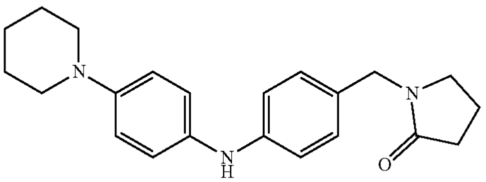 [SMILES: O=C1CCCN1Cc1ccc(Nc2ccc(N3CCCCC3)cc2)cc1] 204 |
| 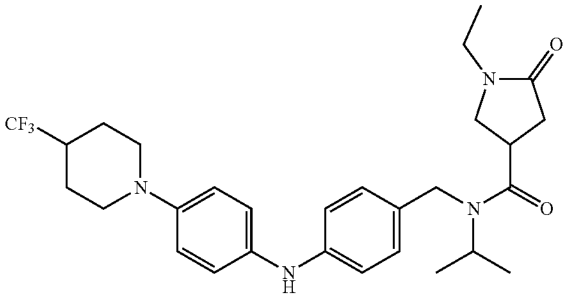 [SMILES: CCN1CC(C(=O)N(Cc2ccc(Nc3ccc(N4CCC(C(F)(F)F)CC4)cc3)cc2)C(C)C)CC1=O] 205 |

TABLE 1-continued
Active Compounds: Structures
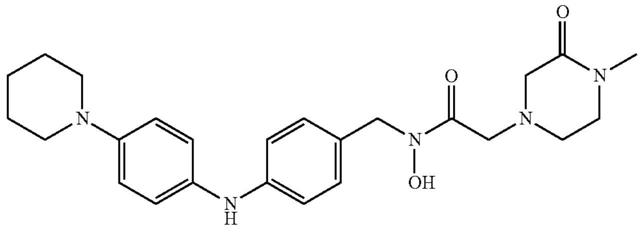 [SMILES: CN1CCN(CC(=O)N(O)Cc2ccc(Nc3ccc(N4CCCCC4)cc3)cc2)CC1=O]
206
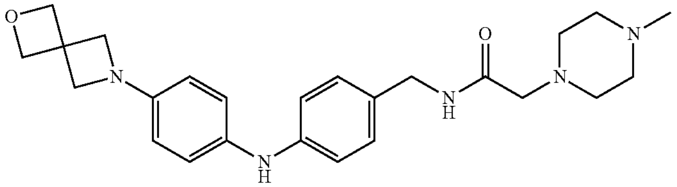 [SMILES: CN1CCN(CC(=O)NCc2ccc(Nc3ccc(N4CC5(COC5)C4)cc3)cc2)CC1]
207
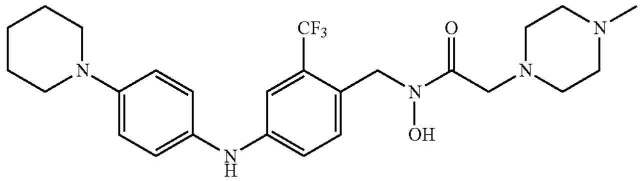
208
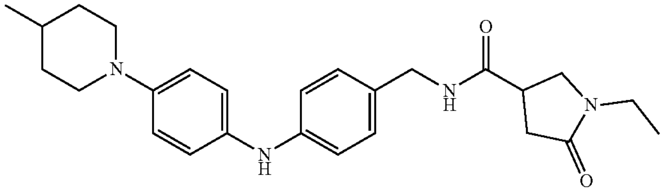 [SMILES: CCN1CC(C(=O)NCc2ccc(Nc3ccc(N4CCC(C)CC4)cc3)cc2)CC1=O]
209
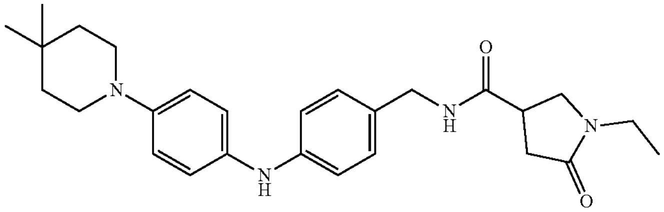 [SMILES: CCN1CC(C(=O)NCc2ccc(Nc3ccc(N4CCC(C)(C)CC4)cc3)cc2)CC1=O]
210
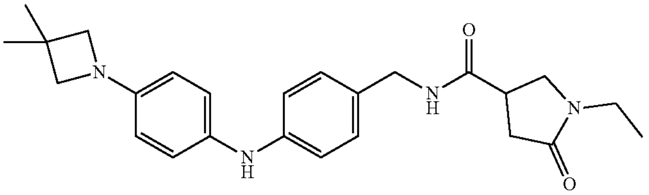 [SMILES: CCN1CC(C(=O)NCc2ccc(Nc3ccc(N4CC(C)(C)C4)cc3)cc2)CC1=O]
211
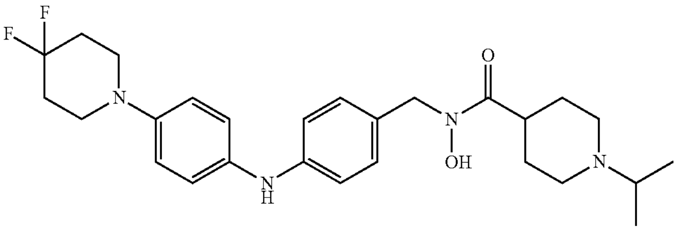 [SMILES: CC(C)N1CCC(C(=O)N(O)Cc2ccc(Nc3ccc(N4CCC(F)(F)CC4)cc3)cc2)CC1]
212

TABLE 1-continued
Active Compounds: Structures
213
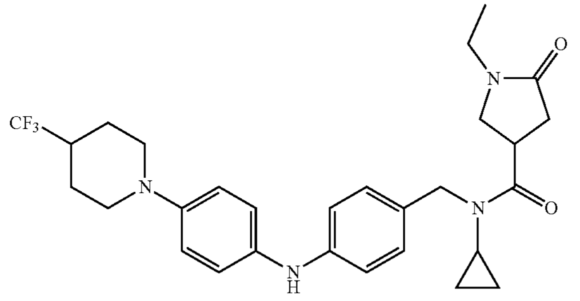 [SMILES: CCN1CC(C(=O)N(Cc2ccc(Nc3ccc(N4CCC(C(F)(F)F)CC4)cc3)cc2)C2CC2)CC1=O]
214
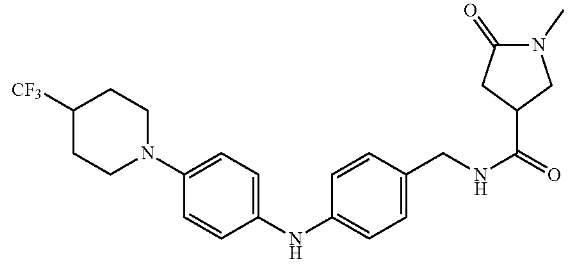 [SMILES: CN1CC(C(=O)NCc2ccc(Nc3ccc(N4CCC(C(F)(F)F)CC4)cc3)cc2)CC1=O]
215
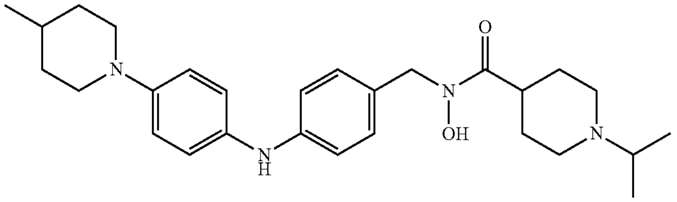 [SMILES: CC1CCN(c2ccc(Nc3ccc(CN(O)C(=O)C4CCN(C(C)C)CC4)cc3)cc2)CC1]
216
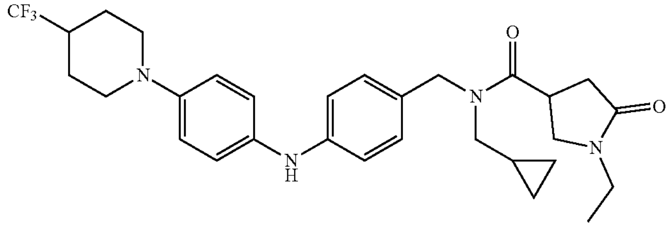 [SMILES: CCN1CC(C(=O)N(Cc2ccc(Nc3ccc(N4CCC(C(F)(F)F)CC4)cc3)cc2)CC2CC2)CC1=O]
217
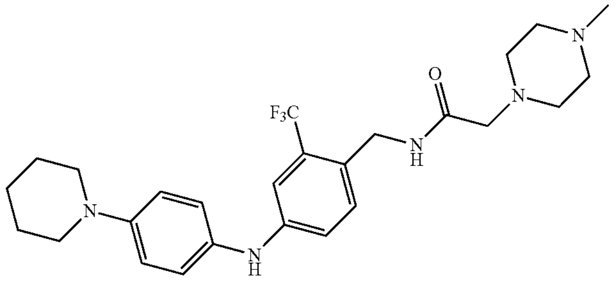 [SMILES: CN1CCN(CC(=O)NCc2ccc(Nc3ccc(N4CCCCC4)cc3)cc2C(F)(F)F)CC1]
218
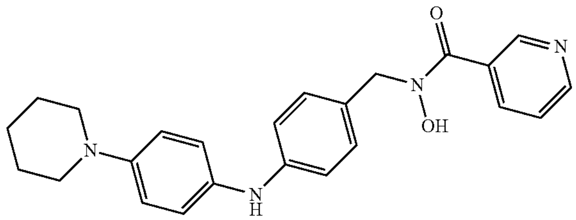 [SMILES: O=C(c1cccnc1)N(O)Cc1ccc(Nc2ccc(N3CCCCC3)cc2)cc1]

TABLE 1-continued
| Active Compounds: Structures | |
|---|---|
| 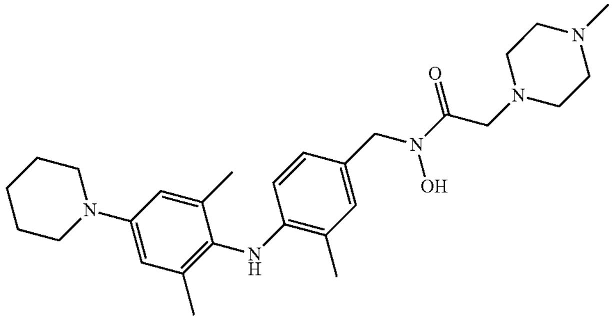 [SMILES: Cc1cc(CN(O)C(=O)CN2CCN(C)CC2)ccc1Nc1c(C)cc(N2CCCCC2)cc1C] | 219 |
| 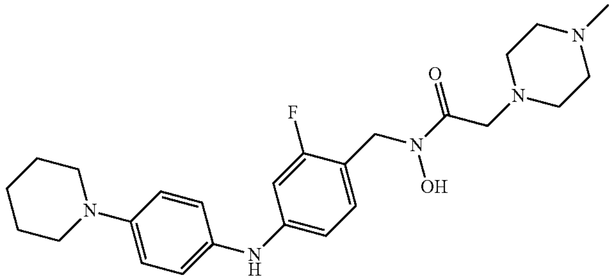 [SMILES: CN1CCN(CC(=O)N(O)Cc2ccc(Nc3ccc(N4CCCCC4)cc3)cc2F)CC1] | 220 |
| 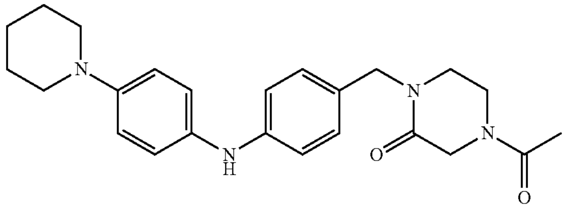 [SMILES: CC(=O)N1CCN(Cc2ccc(Nc3ccc(N4CCCCC4)cc3)cc2)C(=O)C1] | 221 |
| 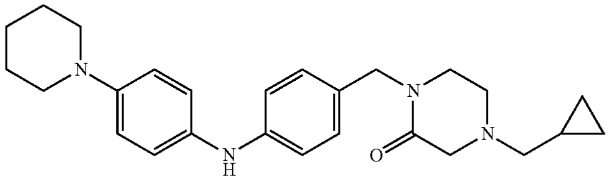 [SMILES: O=C1CN(CC2CC2)CCN1Cc1ccc(Nc2ccc(N3CCCCC3)cc2)cc1] | 222 |
| 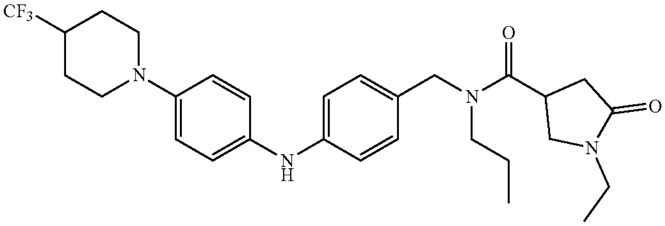 [SMILES: CCCN(Cc1ccc(Nc2ccc(N3CCC(C(F)(F)F)CC3)cc2)cc1)C(=O)C1CC(=O)N(CC)C1] | 223 |
| 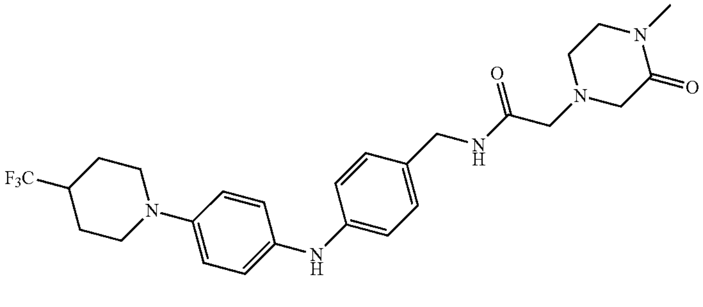 [SMILES: CN1CCN(CC(=O)NCc2ccc(Nc3ccc(N4CCC(C(F)(F)F)CC4)cc3)cc2)CC1=O] | 224 |

TABLE 1-continued
| Active Compounds: Structures |
|---|
| 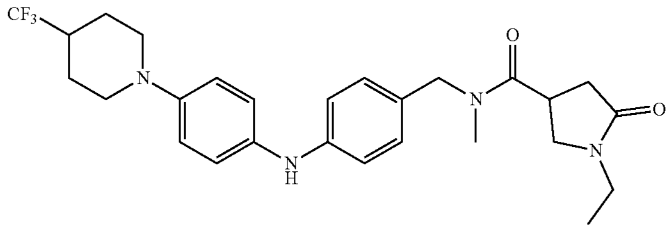 [SMILES: CCN1CC(C(=O)N(C)Cc2ccc(Nc3ccc(N4CCC(C(F)(F)F)CC4)cc3)cc2)CC1=O] 225 |
| 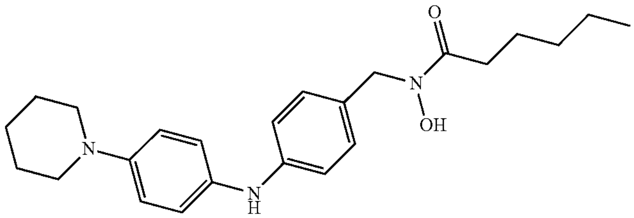 [SMILES: CCCCCC(=O)N(O)Cc1ccc(Nc2ccc(N3CCCCC3)cc2)cc1] 226 |
| 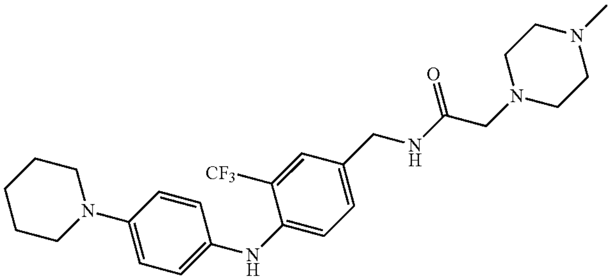 [SMILES: CN1CCN(CC(=O)NCc2ccc(Nc3ccc(N4CCCCC4)cc3)c(C(F)(F)F)c2)CC1] 227 |
| 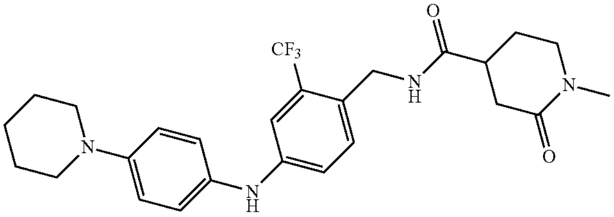 [SMILES: CN1CCC(C(=O)NCc2ccc(Nc3ccc(N4CCCCC4)cc3)cc2C(F)(F)F)CC1=O] 228 |
| 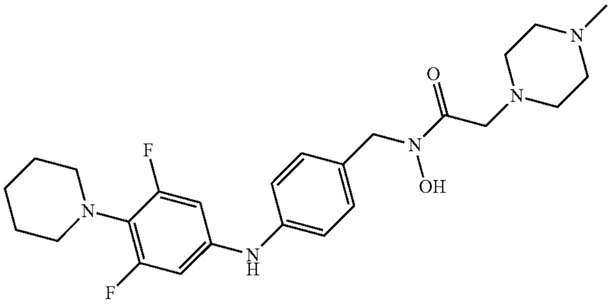 [SMILES: CN1CCN(CC(=O)N(O)Cc2ccc(Nc3cc(F)c(N4CCCCC4)c(F)c3)cc2)CC1] 229 |
| 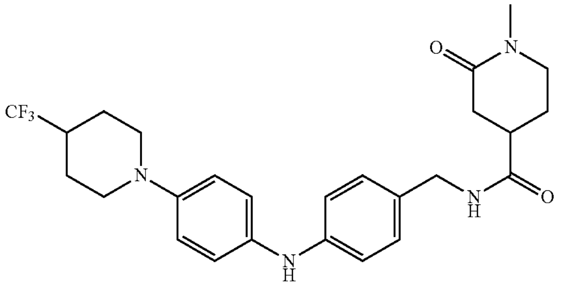 [SMILES: CN1CCC(C(=O)NCc2ccc(Nc3ccc(N4CCC(C(F)(F)F)CC4)cc3)cc2)CC1=O] 230 |

TABLE 1-continued
| Active Compounds: Structures | |
|---|---|
| 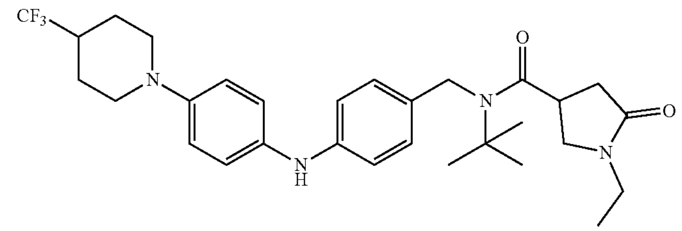 [SMILES: CCN1CC(C(=O)N(Cc2ccc(Nc3ccc(N4CCC(C(F)(F)F)CC4)cc3)cc2)C(C)(C)C)CC1=O] | 231 |
| 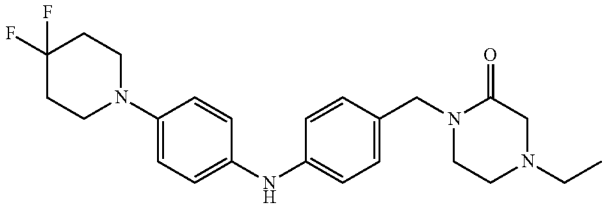 [SMILES: CCN1CCN(Cc2ccc(Nc3ccc(N4CCC(F)(F)CC4)cc3)cc2)C(=O)C1] | 232 |
| 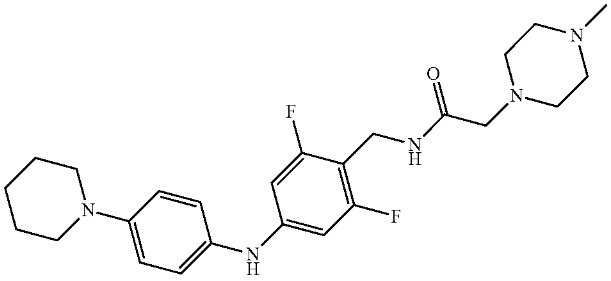 [SMILES: CN1CCN(CC(=O)NCc2c(F)cc(Nc3ccc(N4CCCCC4)cc3)cc2F)CC1] | 233 |
| 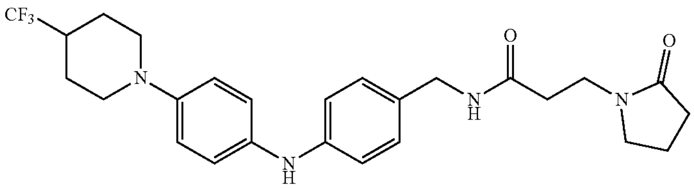 [SMILES: O=C(CCN1CCCC1=O)NCc1ccc(Nc2ccc(N3CCC(C(F)(F)F)CC3)cc2)cc1] | 234 |
| 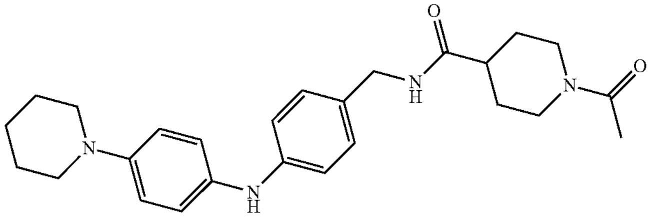 [SMILES: CC(=O)N1CCC(C(=O)NCc2ccc(Nc3ccc(N4CCCCC4)cc3)cc2)CC1] | 235 |
| 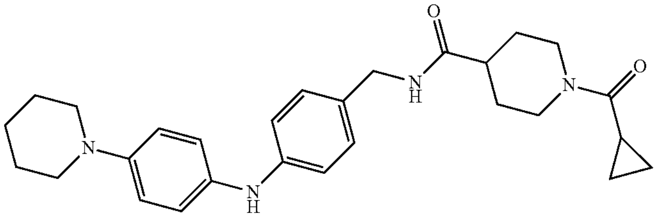 [SMILES: O=C(NCc1ccc(Nc2ccc(N3CCCCC3)cc2)cc1)C1CCN(C(=O)C2CC2)CC1] | 236 |

TABLE 1-continued
| Active Compounds: Structures |
|---|
| 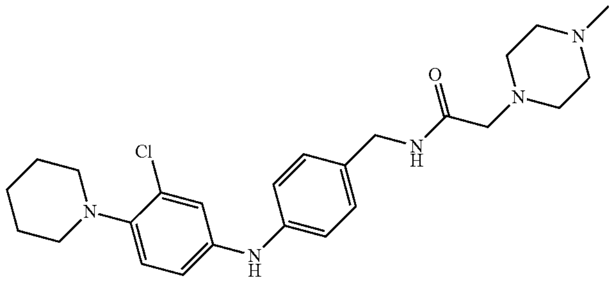 [SMILES: CN1CCN(CC(=O)NCc2ccc(Nc3ccc(N4CCCCC4)c(Cl)c3)cc2)CC1] 237 |
| 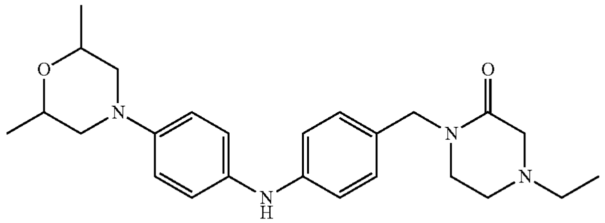 [SMILES: CCN1CCN(Cc2ccc(Nc3ccc(N4CC(C)OC(C)C4)cc3)cc2)C(=O)C1] 238 |
| 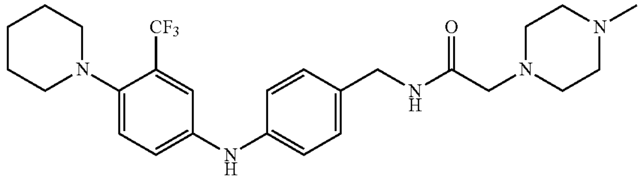 [SMILES: CN1CCN(CC(=O)NCc2ccc(Nc3ccc(N4CCCCC4)c(C(F)(F)F)c3)cc2)CC1] 239 |
| 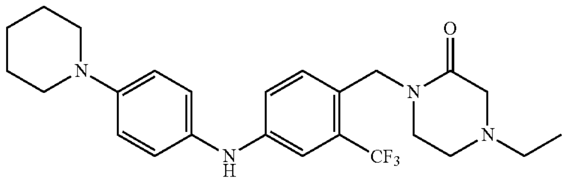 [SMILES: CCN1CCN(Cc2ccc(Nc3ccc(N4CCCCC4)cc3)cc2C(F)(F)F)C(=O)C1] 240 |
| 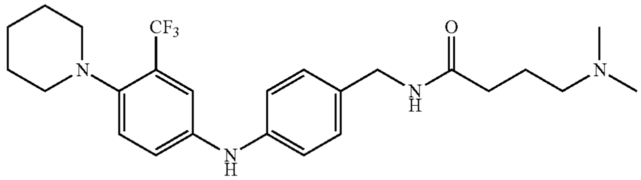 [SMILES: CN(C)CCCC(=O)NCc1ccc(Nc2ccc(N3CCCCC3)c(C(F)(F)F)c2)cc1] 241 |
| 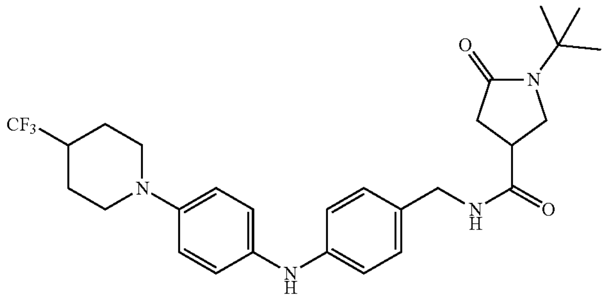 [SMILES: CC(C)(C)N1CC(C(=O)NCc2ccc(Nc3ccc(N4CCC(C(F)(F)F)CC4)cc3)cc2)CC1=O] 242 |

TABLE 1-continued
| Active Compounds: Structures |
|---|
| 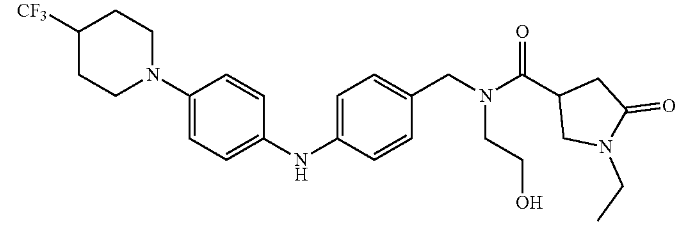 [SMILES: CCN1CC(C(=O)N(CCO)Cc2ccc(Nc3ccc(N4CCC(C(F)(F)F)CC4)cc3)cc2)CC1=O] 243 |
| 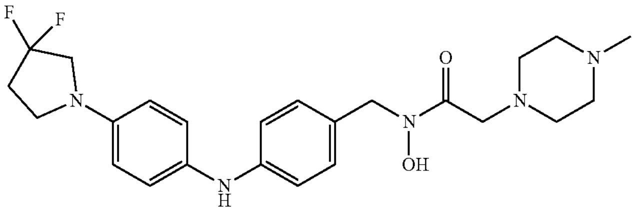 [SMILES: CN1CCN(CC(=O)N(O)Cc2ccc(Nc3ccc(N4CCC(F)(F)C4)cc3)cc2)CC1] 244 |
| 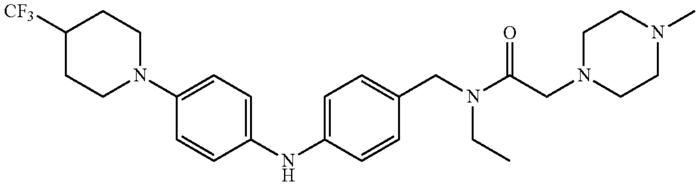 [SMILES: CCN(Cc1ccc(Nc2ccc(N3CCC(C(F)(F)F)CC3)cc2)cc1)C(=O)CN1CCN(C)CC1] 245 |
| 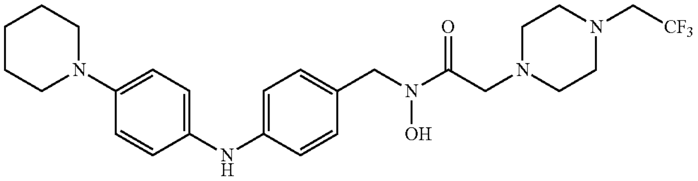 [SMILES: O=C(CN1CCN(CC(F)(F)F)CC1)N(O)Cc1ccc(Nc2ccc(N3CCCCC3)cc2)cc1] 246 |
| 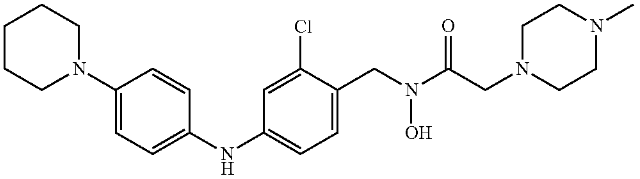 [SMILES: CN1CCN(CC(=O)N(O)Cc2ccc(Nc3ccc(N4CCCCC4)cc3)cc2Cl)CC1] 247 |
| 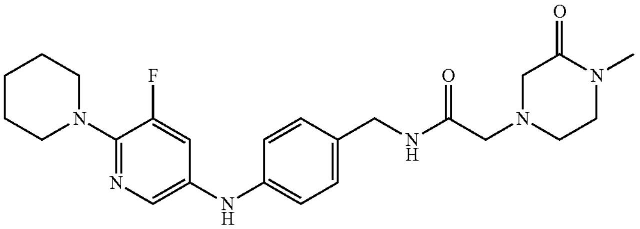 [SMILES: CN1CCN(CC(=O)NCc2ccc(Nc3cnc(N4CCCCC4)c(F)c3)cc2)CC1=O] 248 |
| 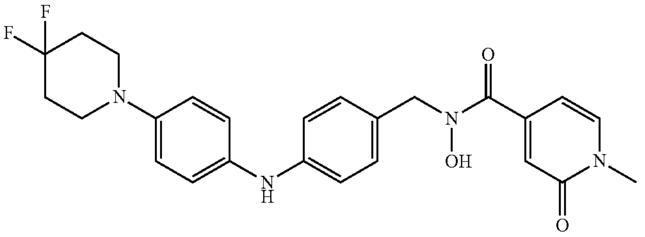 [SMILES: Cn1ccc(C(=O)N(O)Cc2ccc(Nc3ccc(N4CCC(F)(F)CC4)cc3)cc2)cc1=O] 249 |

TABLE 1-continued
| Active Compounds: Structures |
|---|
| 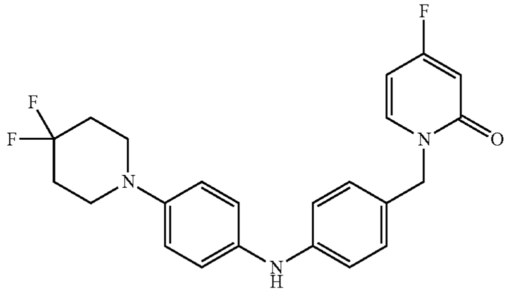 [SMILES: O=c1cc(F)ccn1Cc1ccc(Nc2ccc(N3CCC(F)(F)CC3)cc2)cc1] 250 |
| 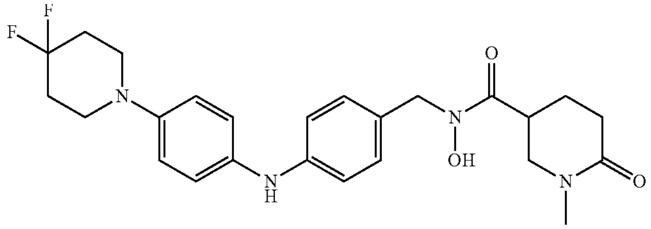 [SMILES: CN1CC(C(=O)N(O)Cc2ccc(Nc3ccc(N4CCC(F)(F)CC4)cc3)cc2)CCC1=O] 251 |
| 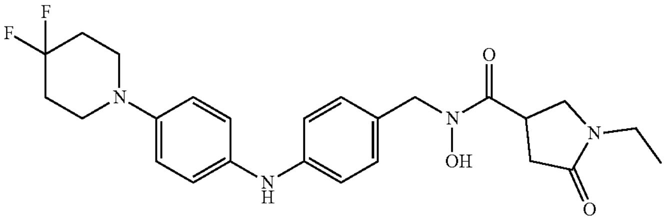 [SMILES: CCN1CC(C(=O)N(O)Cc2ccc(Nc3ccc(N4CCC(F)(F)CC4)cc3)cc2)CC1=O] 252 |
| 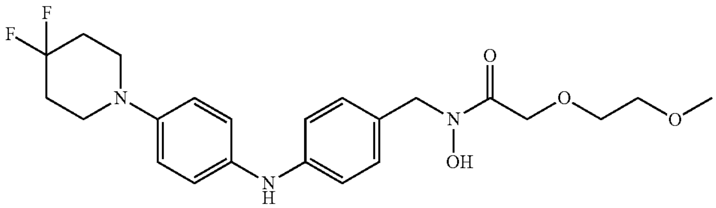 [SMILES: COCCOCC(=O)N(O)Cc1ccc(Nc2ccc(N3CCC(F)(F)CC3)cc2)cc1] 253 |
| 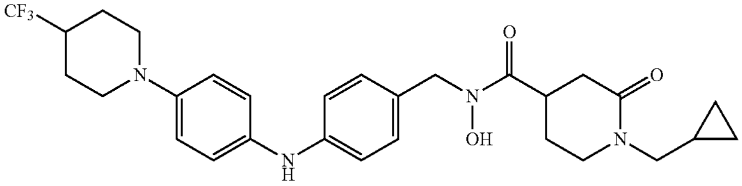 [SMILES: O=C(C1CCN(CC2CC2)C(=O)C1)N(O)Cc1ccc(Nc2ccc(N3CCC(C(F)(F)F)CC3)cc2)cc1] 254 |
| 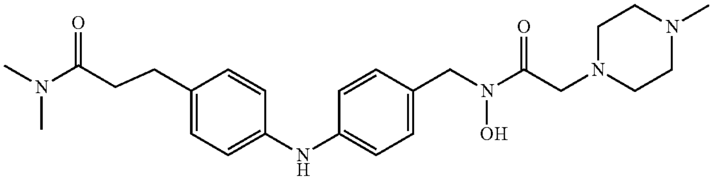 255 |
| 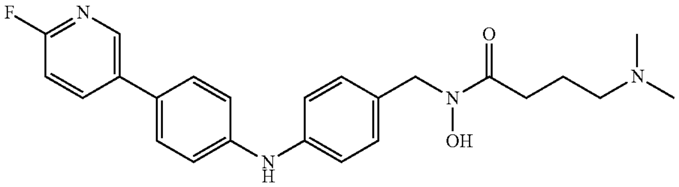 [SMILES: CN(C)CCCC(=O)N(O)Cc1ccc(Nc2ccc(-c3ccc(F)nc3)cc2)cc1] 256 |

TABLE 1-continued
Active Compounds: Structures
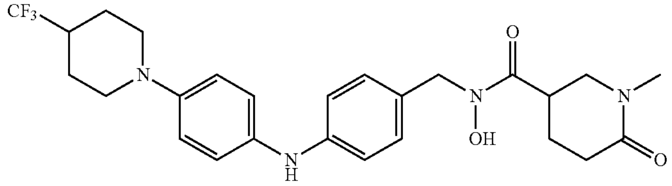 [SMILES: CN1CC(C(=O)N(O)Cc2ccc(Nc3ccc(N4CCC(C(F)(F)F)CC4)cc3)cc2)CCC1=O]
257
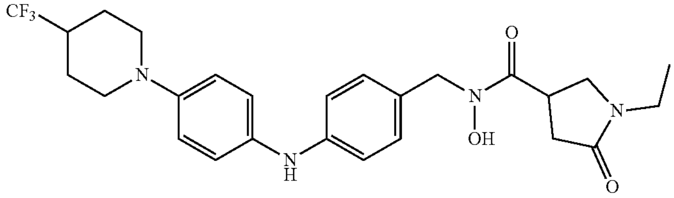 [SMILES: CCN1CC(C(=O)N(O)Cc2ccc(Nc3ccc(N4CCC(C(F)(F)F)CC4)cc3)cc2)CC1=O]
258
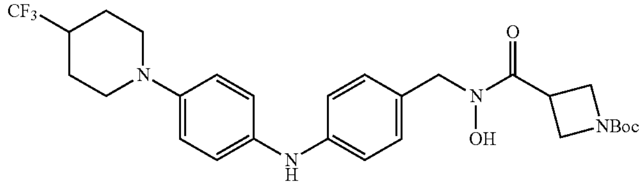 [SMILES: CC(C)(C)OC(=O)N1CC(C(=O)N(O)Cc2ccc(Nc3ccc(N4CCC(C(F)(F)F)CC4)cc3)cc2)C1]
259
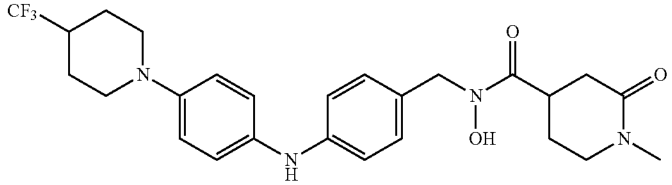 [SMILES: CN1CCC(C(=O)N(O)Cc2ccc(Nc3ccc(N4CCC(C(F)(F)F)CC4)cc3)cc2)CC1=O]
260
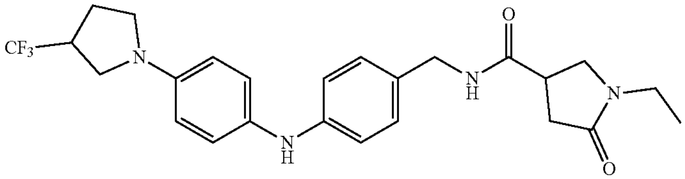 [SMILES: CCN1CC(C(=O)NCc2ccc(Nc3ccc(N4CCC(C(F)(F)F)C4)cc3)cc2)CC1=O]
261
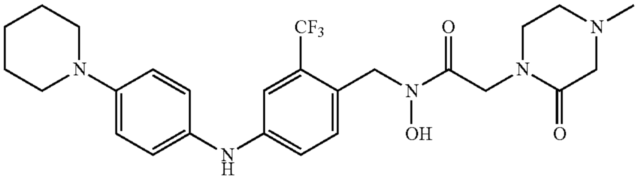 [SMILES: CN1CCN(CC(=O)N(O)Cc2ccc(Nc3ccc(N4CCCCC4)cc3)cc2C(F)(F)F)C(=O)C1]
262
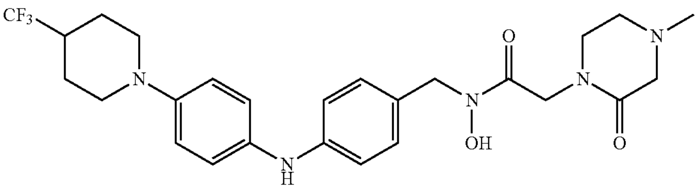 [SMILES: CN1CCN(CC(=O)N(O)Cc2ccc(Nc3ccc(N4CCC(C(F)(F)F)CC4)cc3)cc2)C(=O)C1]
263
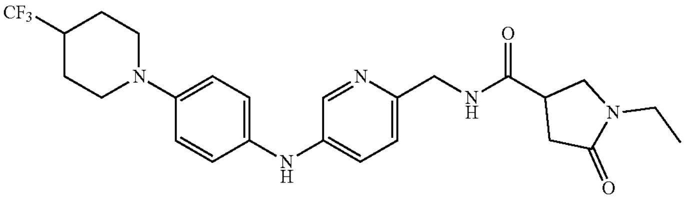 [SMILES: CCN1CC(C(=O)NCc2ccc(Nc3ccc(N4CCC(C(F)(F)F)CC4)cc3)cn2)CC1=O]
264

TABLE 1-continued
Active Compounds: Structures
265
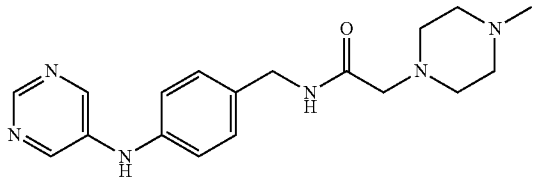 [SMILES: CN1CCN(CC(=O)NCc2ccc(Nc3cncnc3)cc2)CC1]
266
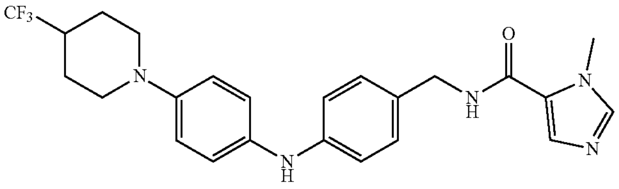 [SMILES: Cn1cncc1C(=O)NCc1ccc(Nc2ccc(N3CCC(C(F)(F)F)CC3)cc2)cc1]
267
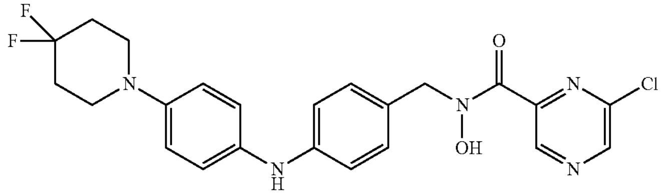 [SMILES: O=C(c1cncc(Cl)n1)N(O)Cc1ccc(Nc2ccc(N3CCC(F)(F)CC3)cc2)cc1]
268
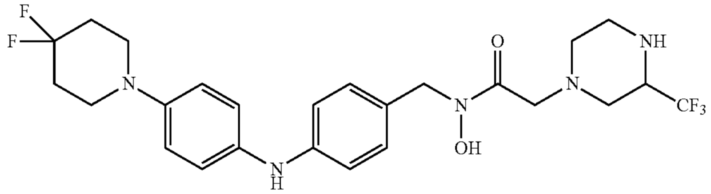 [SMILES: O=C(CN1CCNC(C(F)(F)F)C1)N(O)Cc1ccc(Nc2ccc(N3CCC(F)(F)CC3)cc2)cc1]
269
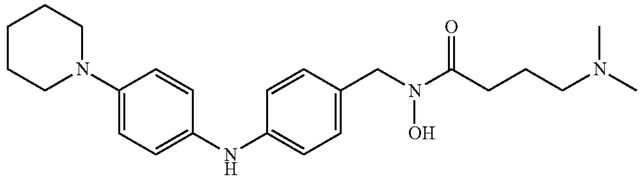 [SMILES: CN(C)CCCC(=O)N(O)Cc1ccc(Nc2ccc(N3CCCCC3)cc2)cc1]
270
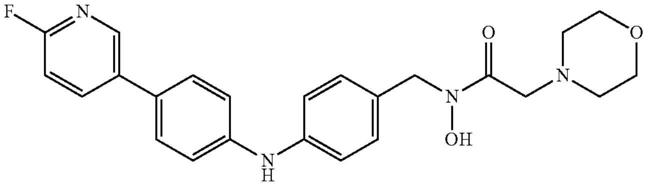 [SMILES: O=C(CN1CCOCC1)N(O)Cc1ccc(Nc2ccc(-c3ccc(F)nc3)cc2)cc1]
271
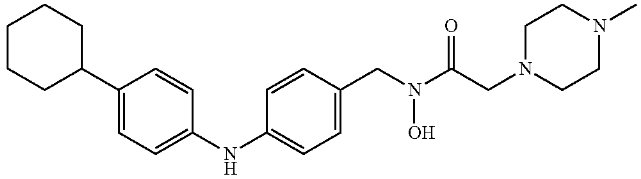
272
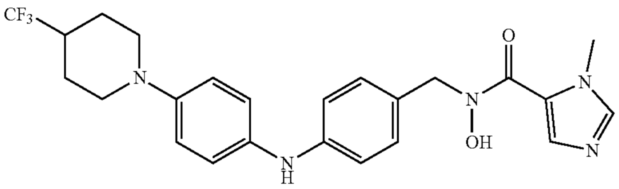 [SMILES: Cn1cncc1C(=O)N(O)Cc1ccc(Nc2ccc(N3CCC(C(F)(F)F)CC3)cc2)cc1]

TABLE 1-continued
| Active Compounds: Structures | |
|---|---|
| 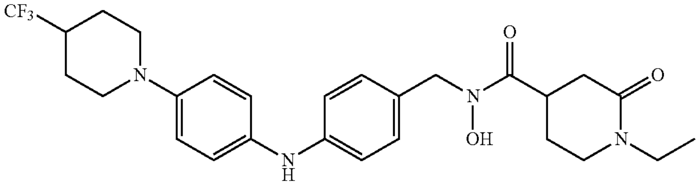 [SMILES: CCN1CCC(C(=O)N(O)Cc2ccc(Nc3ccc(N4CCC(C(F)(F)F)CC4)cc3)cc2)CC1=O] | 273 |
| 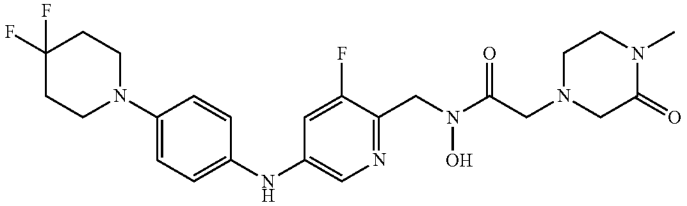 [SMILES: CN1CCN(CC(=O)N(O)Cc2ncc(Nc3ccc(N4CCC(F)(F)CC4)cc3)cc2F)CC1=O] | 274 |
| 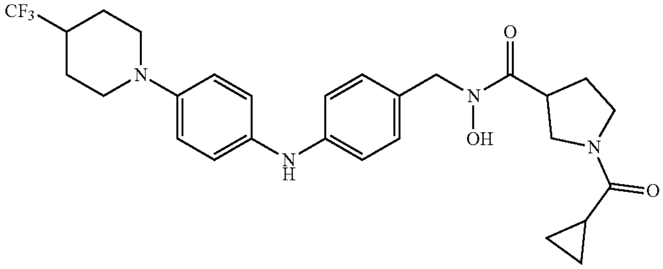 [SMILES: O=C(C1CCN(C(=O)C2CC2)C1)N(O)Cc1ccc(Nc2ccc(N3CCC(C(F)(F)F)CC3)cc2)cc1] | 275 |
| 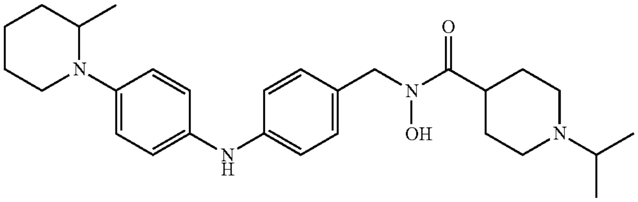 [SMILES: CC(C)N1CCC(C(=O)N(O)Cc2ccc(Nc3ccc(N4CCCCC4C)cc3)cc2)CC1] | 276 |
| 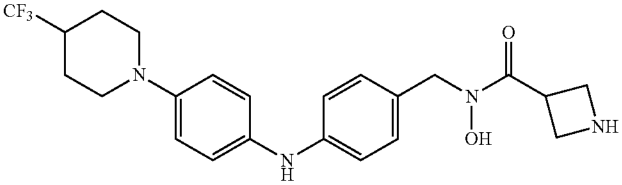 [SMILES: O=C(C1CNC1)N(O)Cc1ccc(Nc2ccc(N3CCC(C(F)(F)F)CC3)cc2)cc1] | 277 |
| 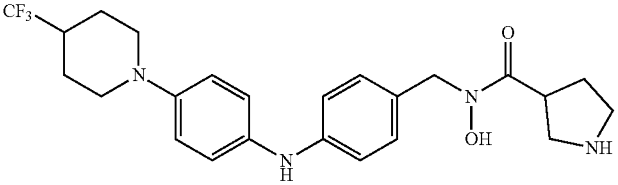 [SMILES: O=C(C1CCNC1)N(O)Cc1ccc(Nc2ccc(N3CCC(C(F)(F)F)CC3)cc2)cc1] | 278 |
| 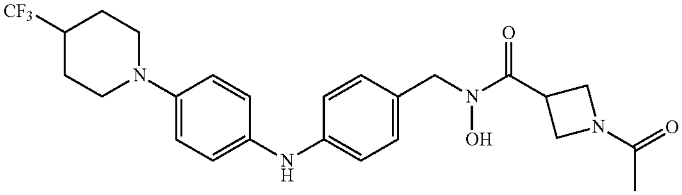 [SMILES: CC(=O)N1CC(C(=O)N(O)Cc2ccc(Nc3ccc(N4CCC(C(F)(F)F)CC4)cc3)cc2)C1] | 279 |

TABLE 1-continued
Active Compounds: Structures
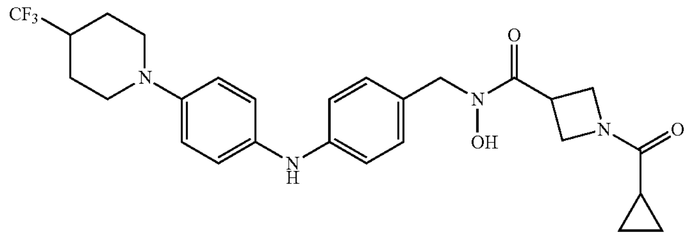 [SMILES: O=C(C1CN(C(=O)C2CC2)C1)N(O)Cc1ccc(Nc2ccc(N3CCC(C(F)(F)F)CC3)cc2)cc1]
280
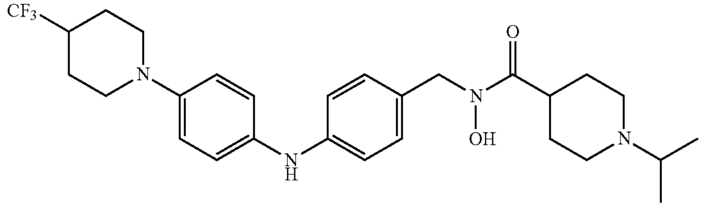 [SMILES: CC(C)N1CCC(C(=O)N(O)Cc2ccc(Nc3ccc(N4CCC(C(F)(F)F)CC4)cc3)cc2)CC1]
281
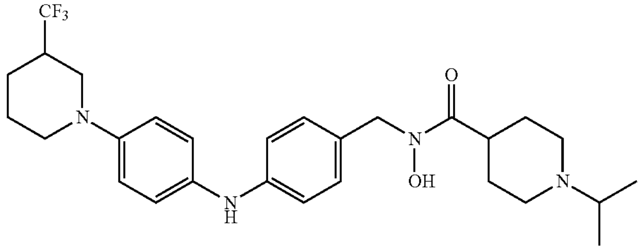 [SMILES: CC(C)N1CCC(C(=O)N(O)Cc2ccc(Nc3ccc(N4CCCC(C(F)(F)F)C4)cc3)cc2)CC1]
282
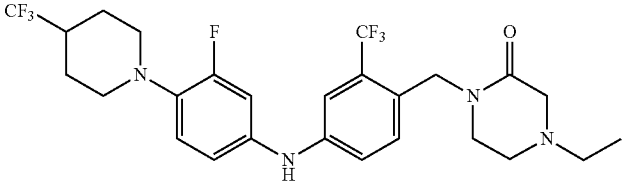 [SMILES: CCN1CCN(Cc2ccc(Nc3ccc(N4CCC(C(F)(F)F)CC4)c(F)c3)cc2C(F)(F)F)C(=O)C1]
283
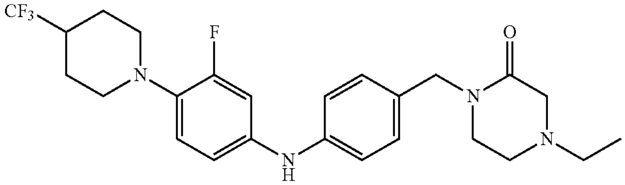 [SMILES: CCN1CCN(Cc2ccc(Nc3ccc(N4CCC(C(F)(F)F)CC4)c(F)c3)cc2)C(=O)C1]
284
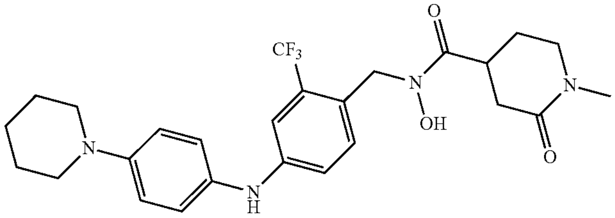 [SMILES: CN1CCC(C(=O)N(O)Cc2ccc(Nc3ccc(N4CCCCC4)cc3)cc2C(F)(F)F)CC1=O]
285
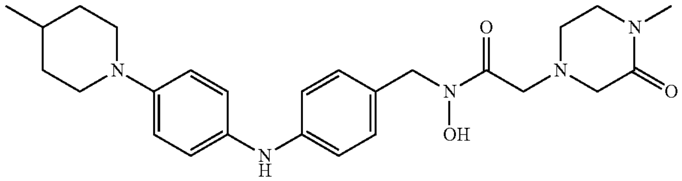 [SMILES: CC1CCN(c2ccc(Nc3ccc(CN(O)C(=O)CN4CCN(C)C(=O)C4)cc3)cc2)CC1]
286

TABLE 1-continued
Active Compounds: Structures
287
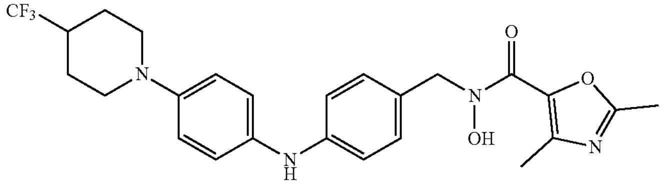 [SMILES: Cc1nc(C)c(C(=O)N(O)Cc2ccc(Nc3ccc(N4CCC(C(F)(F)F)CC4)cc3)cc2)o1]
288
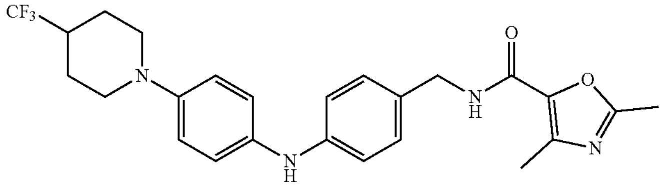 [SMILES: Cc1nc(C)c(C(=O)NCc2ccc(Nc3ccc(N4CCC(C(F)(F)F)CC4)cc3)cc2)o1]
289
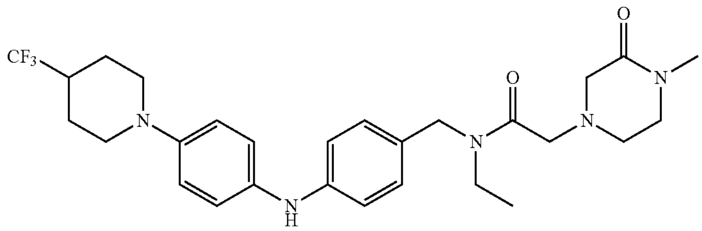 [SMILES: CCN(Cc1ccc(Nc2ccc(N3CCC(C(F)(F)F)CC3)cc2)cc1)C(=O)CN1CCN(C)C(=O)C1]
290
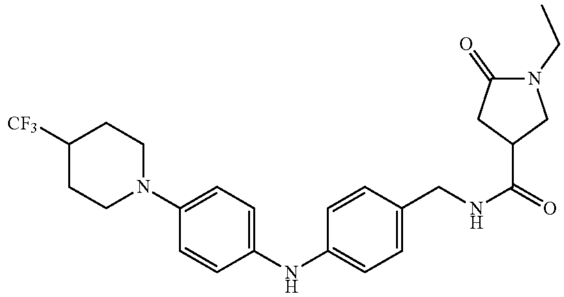 [SMILES: CCN1CC(C(=O)NCc2ccc(Nc3ccc(N4CCC(C(F)(F)F)CC4)cc3)cc2)CC1=O]
291
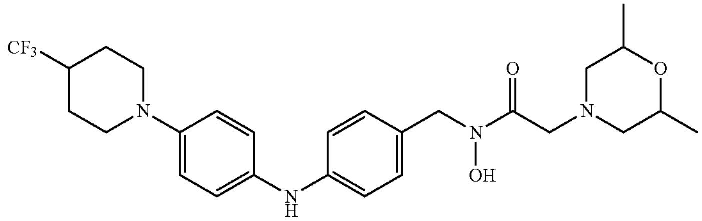 [SMILES: CC1CN(CC(=O)N(O)Cc2ccc(Nc3ccc(N4CCC(C(F)(F)F)CC4)cc3)cc2)CC(C)O1]
292
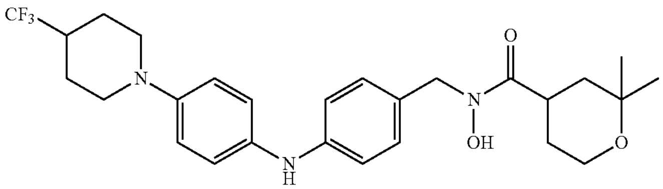 [SMILES: CC1(C)CC(C(=O)N(O)Cc2ccc(Nc3ccc(N4CCC(C(F)(F)F)CC4)cc3)cc2)CCO1]

TABLE 1-continued
| Active Compounds: Structures | |
|---|---|
| 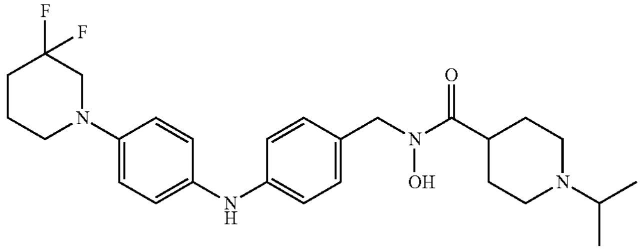 [SMILES: CC(C)N1CCC(C(=O)N(O)Cc2ccc(Nc3ccc(N4CCCC(F)(F)C4)cc3)cc2)CC1] | 293 |
| 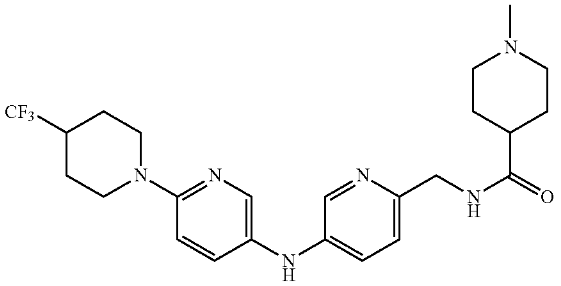 [SMILES: CN1CCC(C(=O)NCc2ccc(Nc3ccc(N4CCC(C(F)(F)F)CC4)nc3)cn2)CC1] | 294 |
| 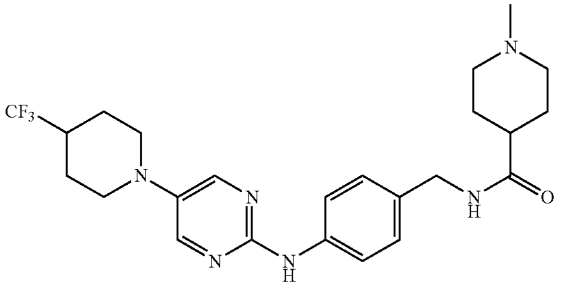 [SMILES: CN1CCC(C(=O)NCc2ccc(Nc3ncc(N4CCC(C(F)(F)F)CC4)cn3)cc2)CC1] | 295 |
| 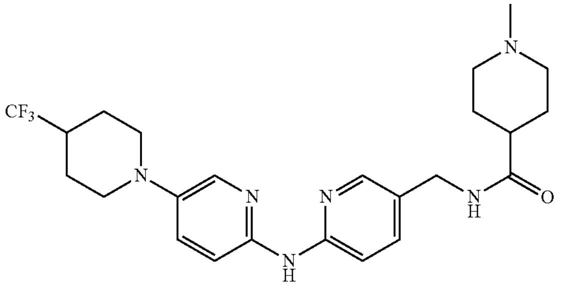 [SMILES: CN1CCC(C(=O)NCc2ccc(Nc3ccc(N4CCC(C(F)(F)F)CC4)cn3)nc2)CC1] | 296 |
| 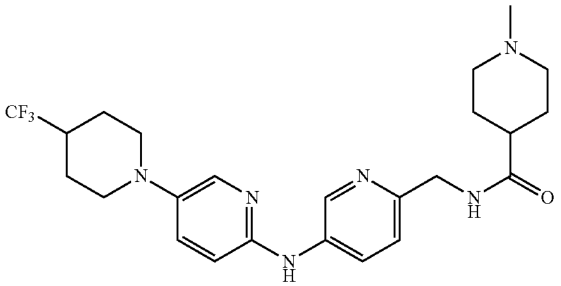 | 297 |

TABLE 1-continued
| Active Compounds: Structures |
| --- |
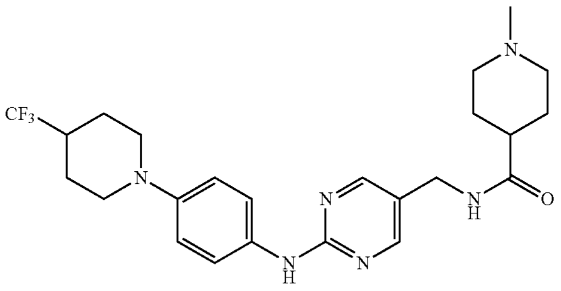 [SMILES: CN1CCC(C(=O)NCc2cnc(Nc3ccc(N4CCC(C(F)(F)F)CC4)cc3)nc2)CC1]
298
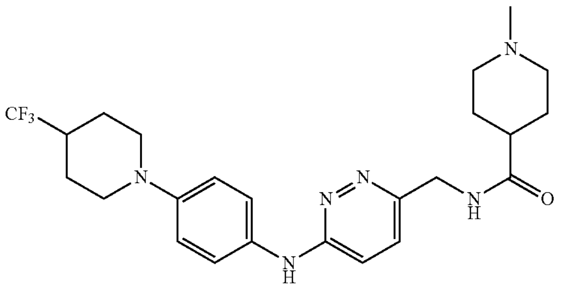 [SMILES: CN1CCC(C(=O)NCc2ccc(Nc3ccc(N4CCC(C(F)(F)F)CC4)cc3)nn2)CC1]
299
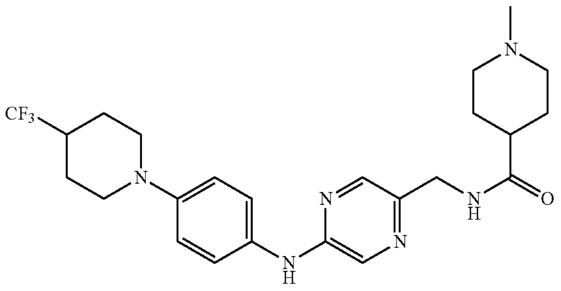 [SMILES: CN1CCC(C(=O)NCc2cnc(Nc3ccc(N4CCC(C(F)(F)F)CC4)cc3)cn2)CC1]
300
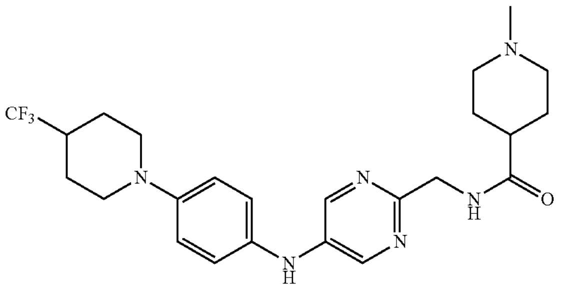 [SMILES: CN1CCC(C(=O)NCc2ncc(Nc3ccc(N4CCC(C(F)(F)F)CC4)cc3)cn2)CC1]
301
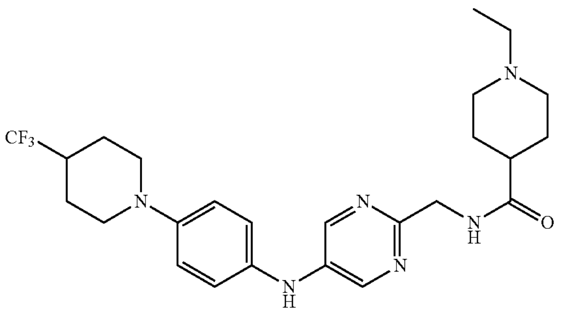 [SMILES: CCN1CCC(C(=O)NCc2ncc(Nc3ccc(N4CCC(C(F)(F)F)CC4)cc3)cn2)CC1]
302

TABLE 1-continued
| Active Compounds: Structures | |
|---|---|
| 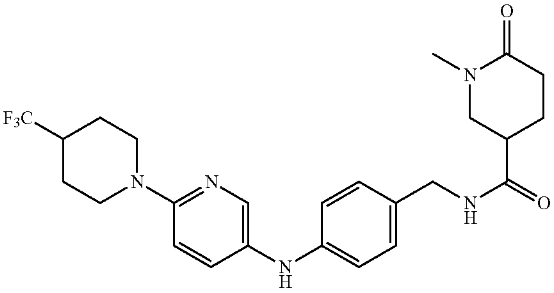 | 303 |
| 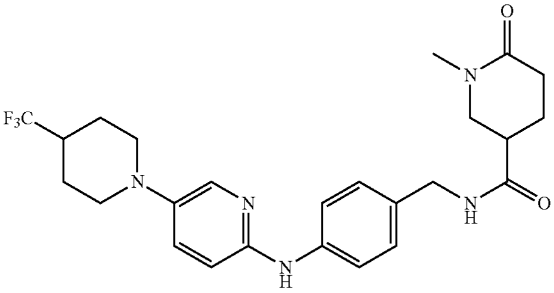 | 304 |
| 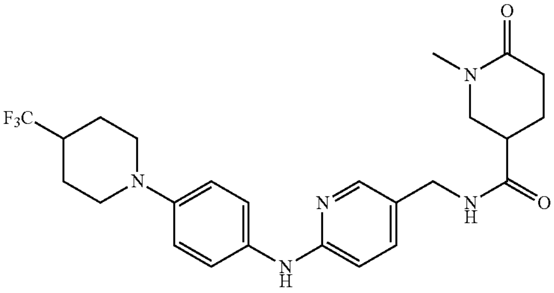 | 305 |
| 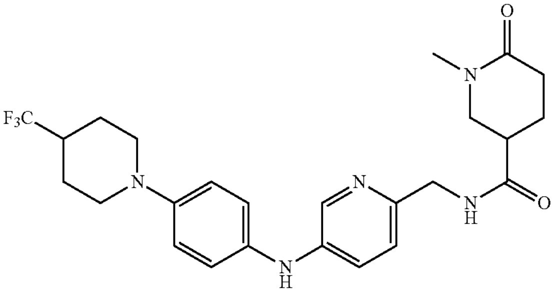 | 306 |
| 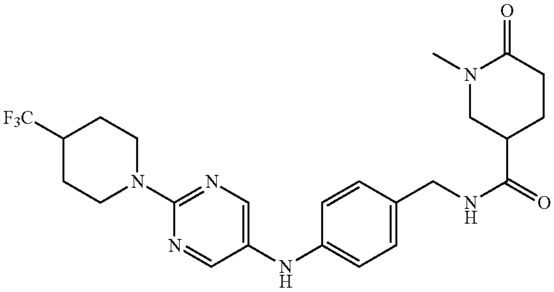 | 307 |

TABLE 1-continued
| Active Compounds: Structures |
| --- |
| 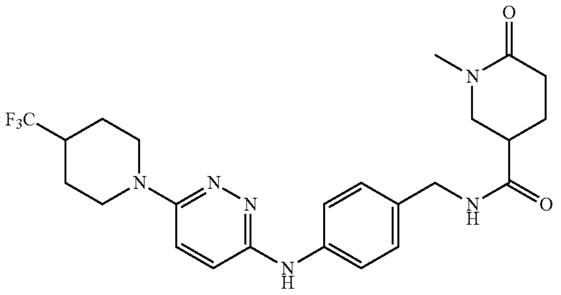 308 |
| 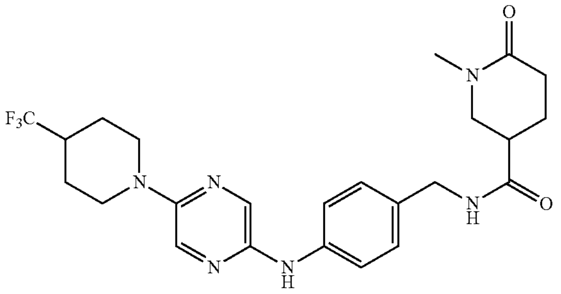 309 |
| 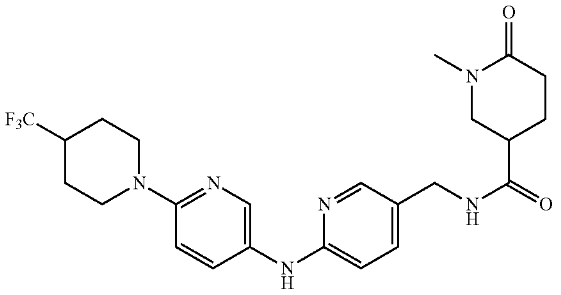 310 |
| 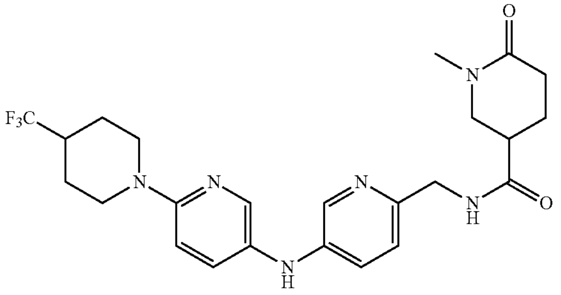 311 |
| 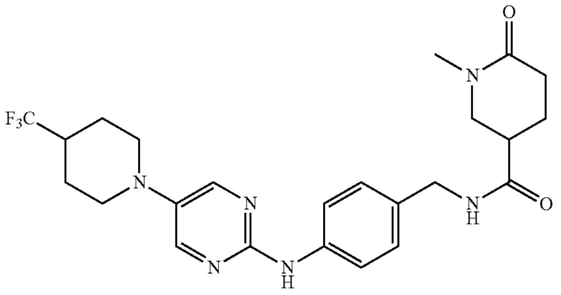 312 |

TABLE 1-continued
Active Compounds: Structures
313
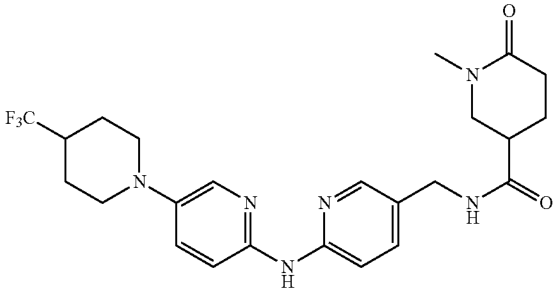
314
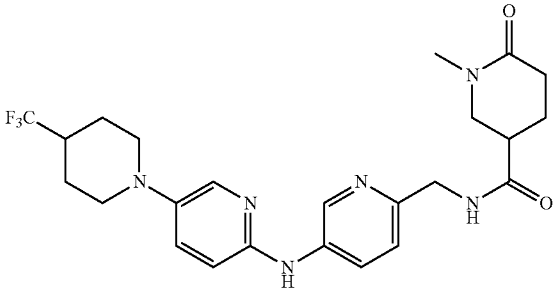
315
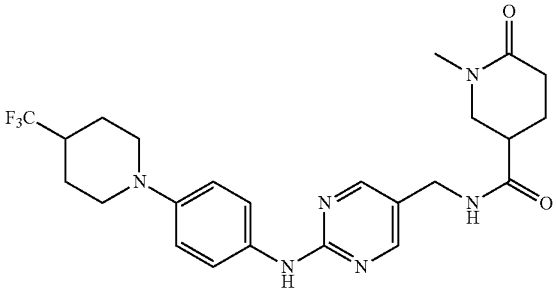
316
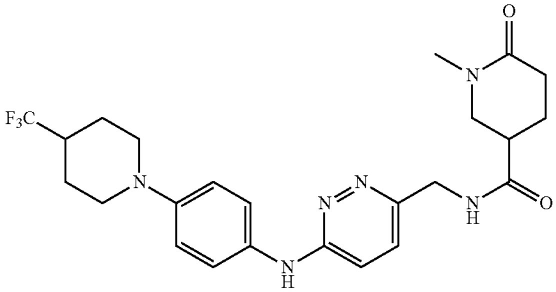
317
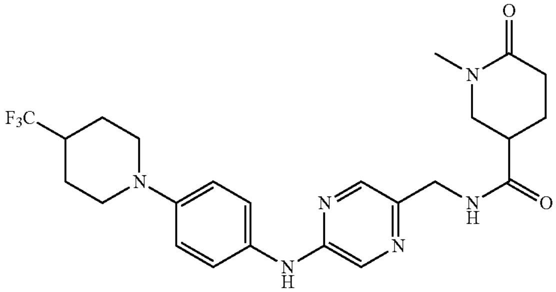

TABLE 1-continued
| Active Compounds: Structures | |
|---|---|
| 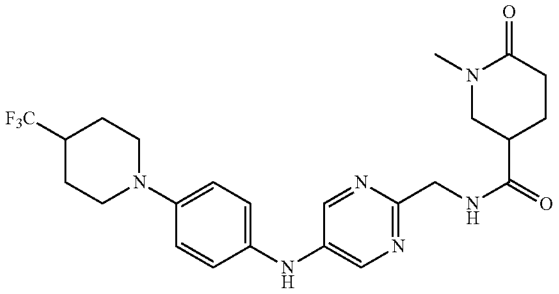 | 318 |
| 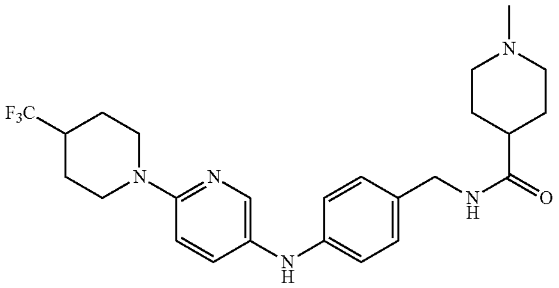 | 319 |
| 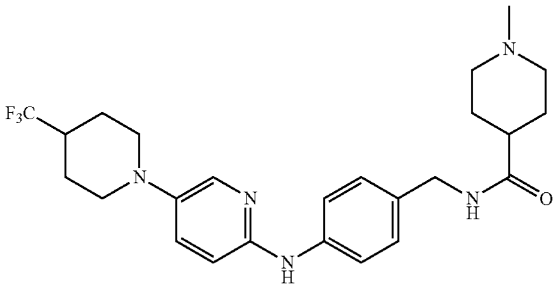 | 320 |
| 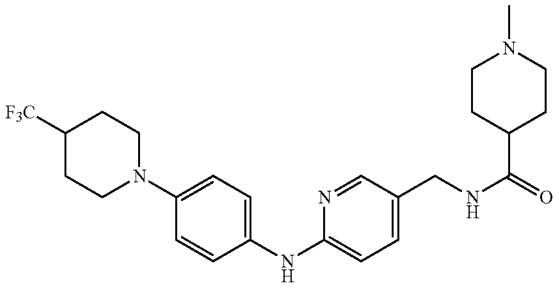 | 321 |
| 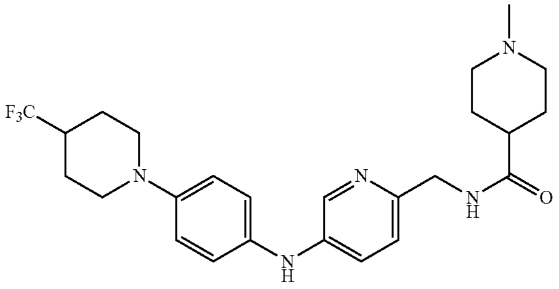 | 322 |

TABLE 1-continued
| Active Compounds: Structures |
| --- |
| 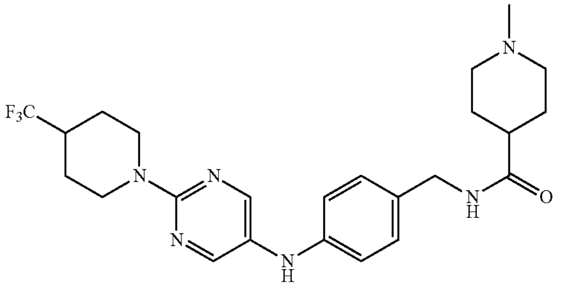 323 |
| 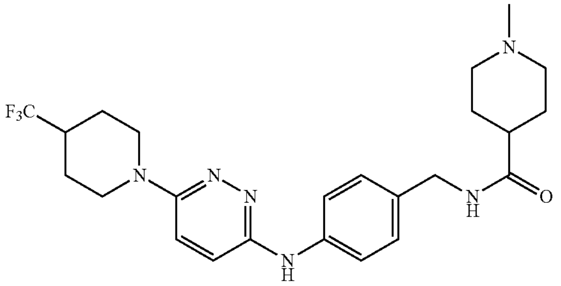 324 |
| 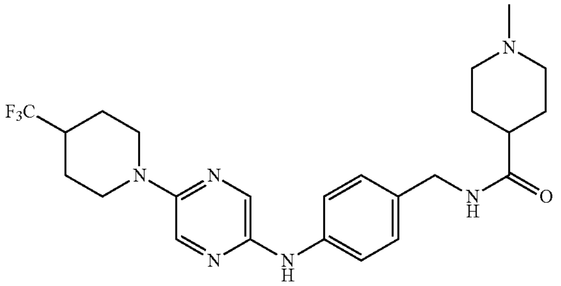 325 |
| 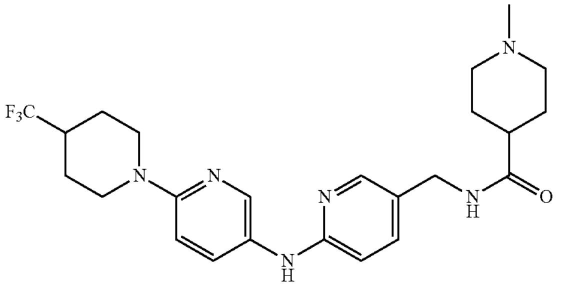 326 |
| 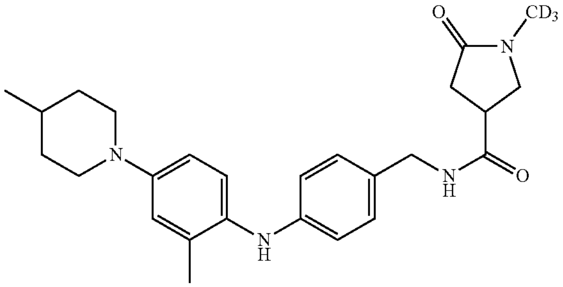 [SMILES: [2H]C([2H])([2H])N1CC(C(=O)NCc2ccc(Nc3ccc(N4CCC(C)CC4)cc3C)cc2)CC1=O] 327 |

TABLE 1-continued
| Active Compounds: Structures | |
|---|---|
| 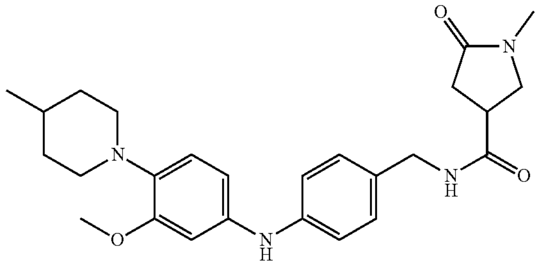 | 328 |
| 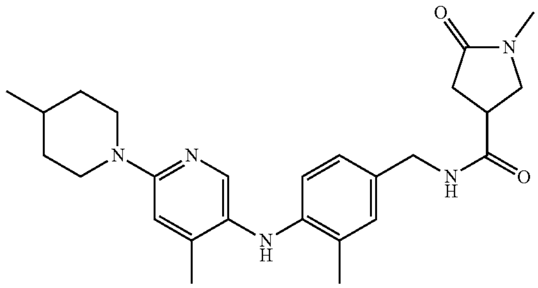 | 329 |
| 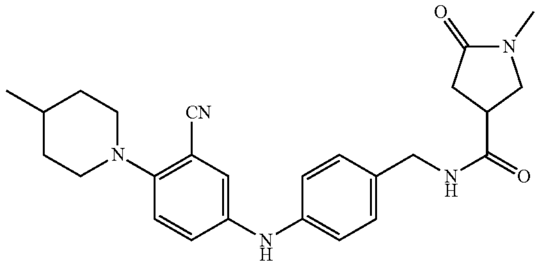 | 330 |
| 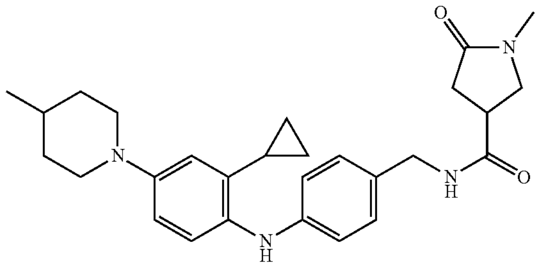 | 331 |
| 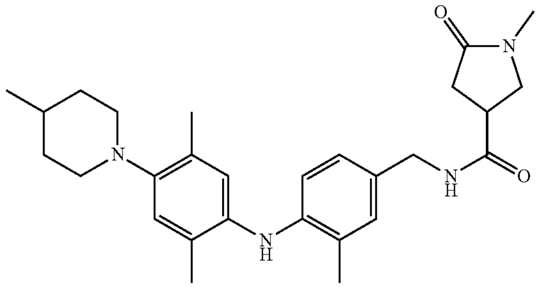 | 332 |

TABLE 1-continued
| Active Compounds: Structures |
|---|
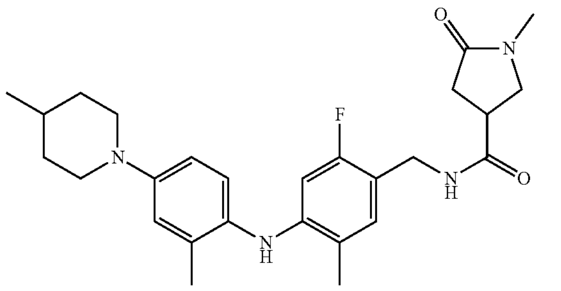
333
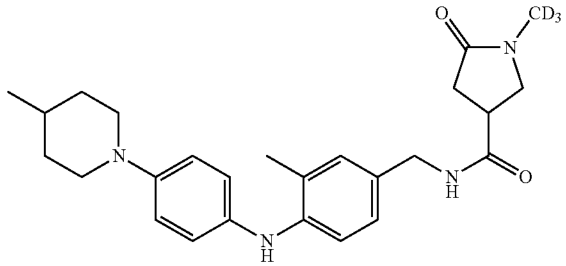 [SMILES: [2H]C([2H])([2H])N1CC(C(=O)NCc2ccc(Nc3ccc(N4CCC(C)CC4)cc3)c(C)c2)CC1=O]
334
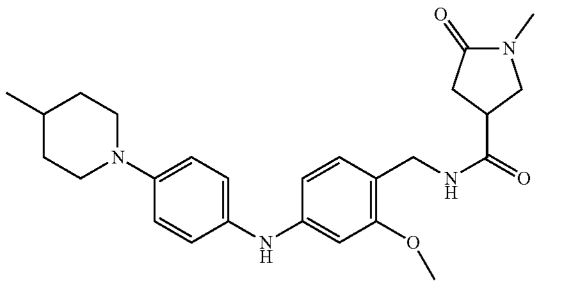
335
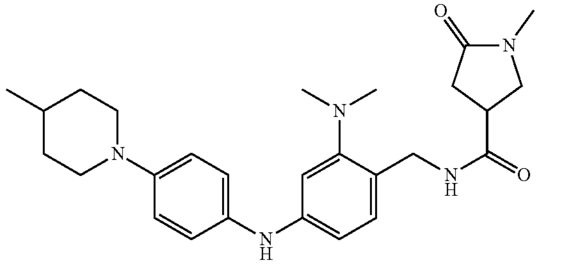
336
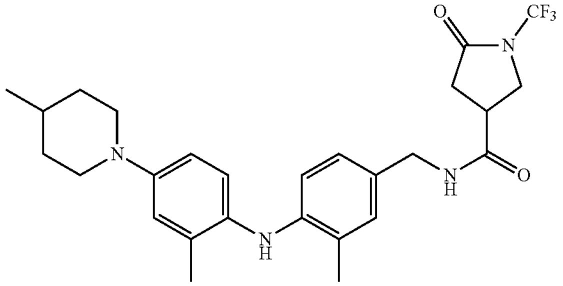 [SMILES: Cc1cc(CNC(=O)C2CC(=O)N(C(F)(F)F)C2)ccc1Nc1ccc(N2CCC(C)CC2)cc1C]
337

TABLE 1-continued
| Active Compounds: Structures | |
|---|---|
| 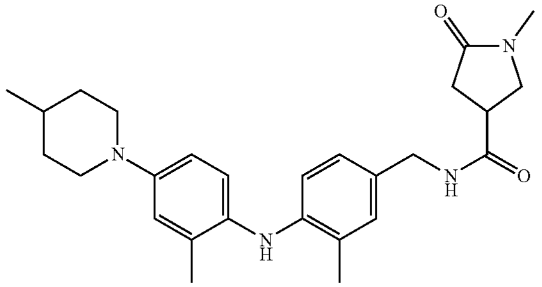 | 338 |
| 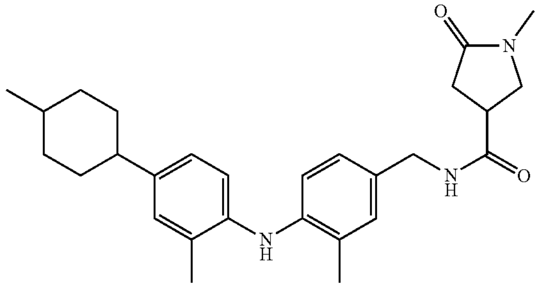 | 339 |
| 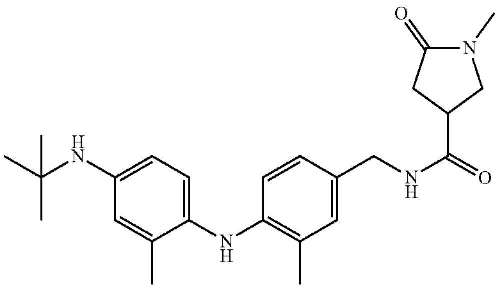 [SMILES: Cc1cc(CNC(=O)C2CC(=O)N(C)C2)ccc1Nc1ccc(NC(C)(C)C)cc1C] | 340 |
| 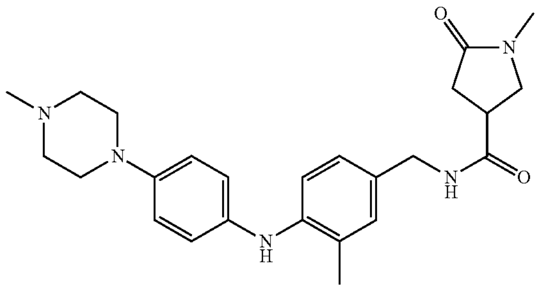 | 341 |
| 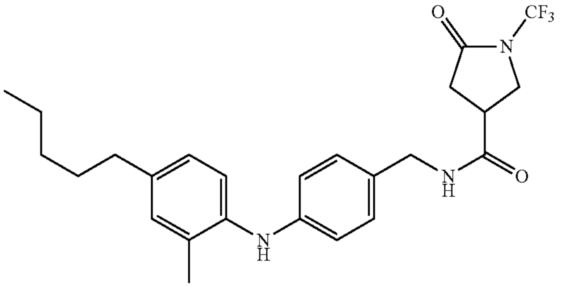 | 342 |

TABLE 1-continued
| Active Compounds: Structures | |
|---|---|
| 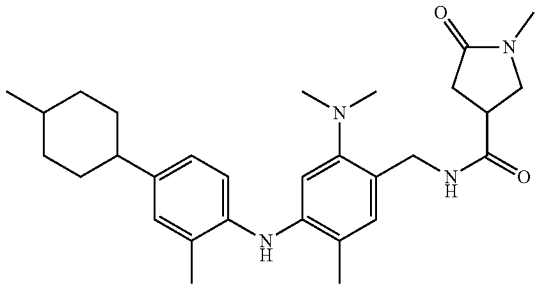 | 343 |
| 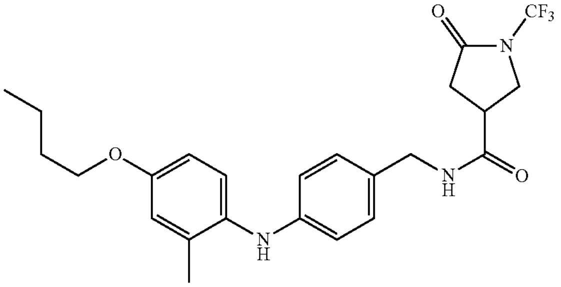 [SMILES: CCCCOc1ccc(Nc2ccc(CNC(=O)C3CC(=O)N(C(F)(F)F)C3)cc2)c(C)c1] | 344 |
| 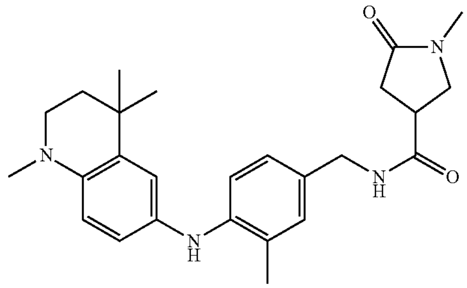 | 345 |
| 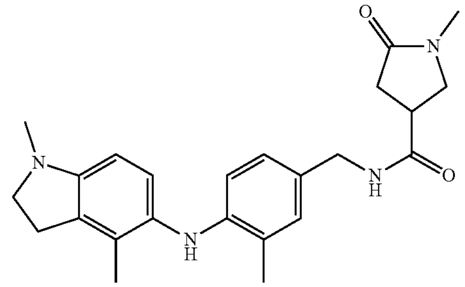 [SMILES: Cc1cc(CNC(=O)C2CC(=O)N(C)C2)ccc1Nc1ccc2c(c1C)CCN2C] | 346 |
| 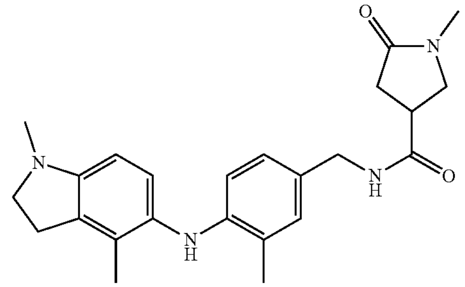 [SMILES: Cc1cc(CNC(=O)C2CC(=O)N(C)C2)ccc1Nc1ccc2c(c1C)CCN2C] | 347 |

TABLE 1-continued
| Active Compounds: Structures | |
|---|---|
| 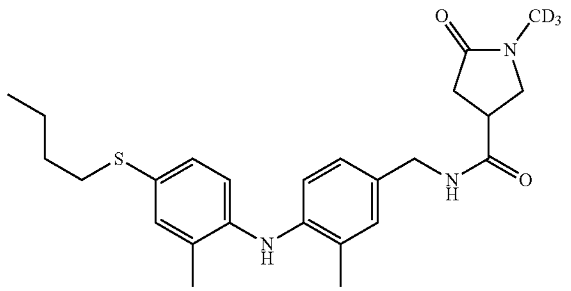 [SMILES: [2H]C([2H])([2H])N1CC(C(=O)NCc2ccc(Nc3ccc(SCCCC)cc3C)c(C)c2)CC1=O] | 348 |
| 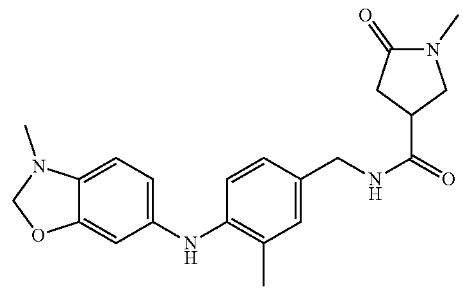 [SMILES: Cc1cc(CNC(=O)C2CC(=O)N(C)C2)ccc1Nc1ccc2c(c1)OCN2C] | 349 |
| 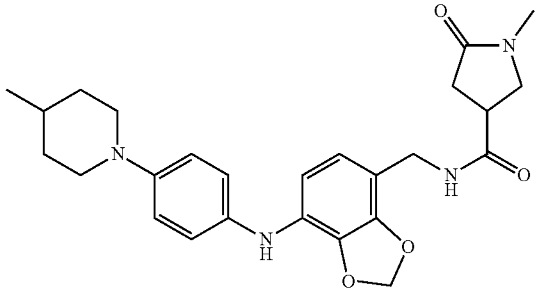 | 350 |
| 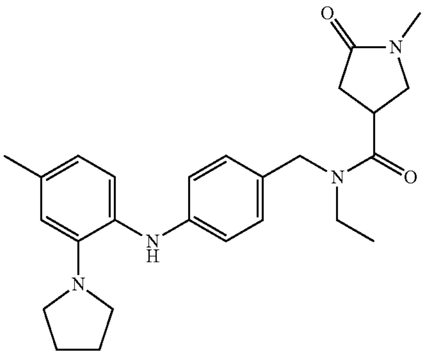 | 351 |
| 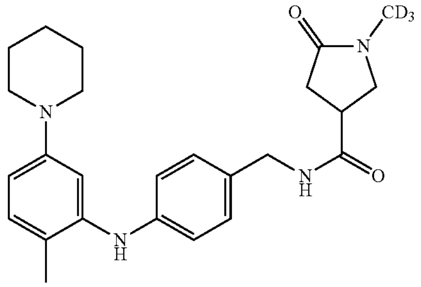 [SMILES: [2H]C([2H])([2H])N1CC(C(=O)NCc2ccc(Nc3cc(N4CCCCC4)ccc3C)cc2)CC1=O] | 352 |

TABLE 1-continued
| Active Compounds: Structures | |
| --- | --- |
| 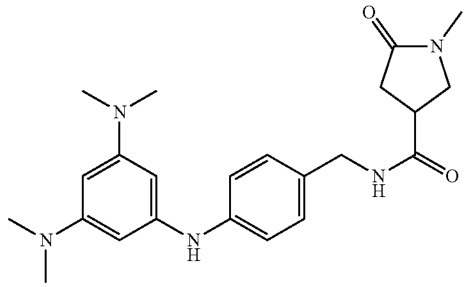 | 353 |
| 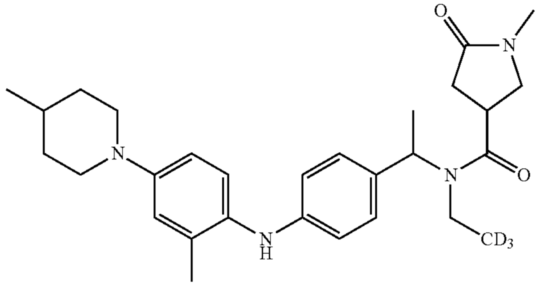 | 354 |
| 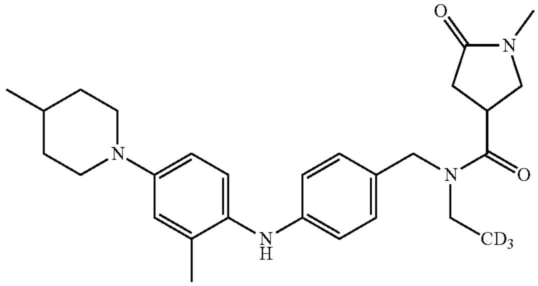 | 355 |
| 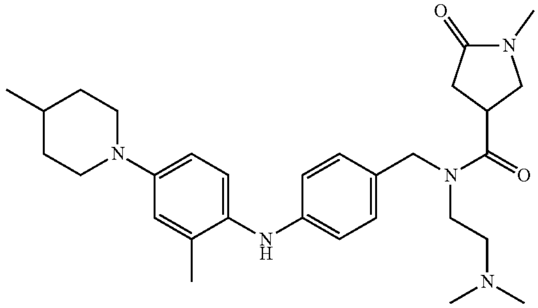 | 356 |
| 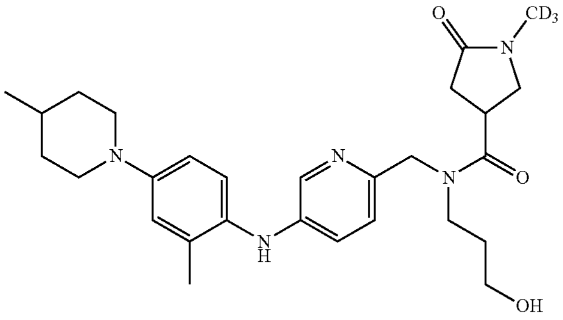 [SMILES: [2H]C([2H])([2H])N1CC(C(=O)N(CCCO)Cc2ccc(Nc3ccc(N4CCC(C)CC4)cc3C)cn2)CC1=O] | 357 |

TABLE 1-continued
| Active Compounds: Structures | |
|---|---|
| 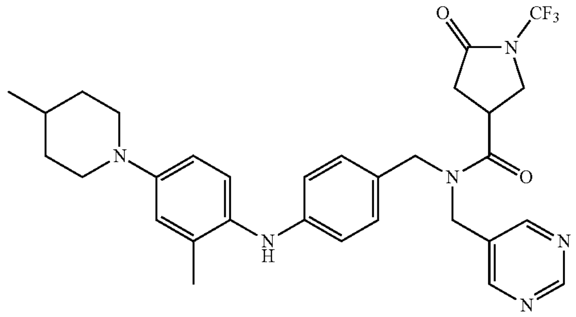 [SMILES: Cc1cc(N2CCC(C)CC2)ccc1Nc1ccc(CN(Cc2cncnc2)C(=O)C2CC(=O)N(C(F)(F)F)C2)cc1] | 358 |
| 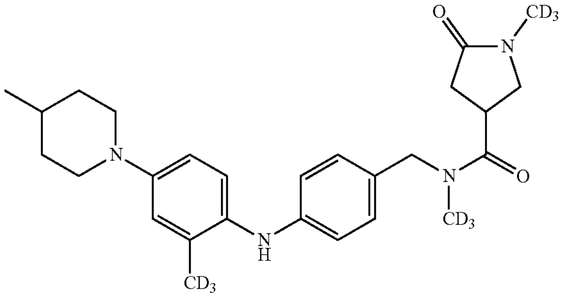 [SMILES: [2H]C([2H])([2H])c1cc(N2CCC(C)CC2)ccc1Nc1ccc(CN(C(=O)C2CC(=O)N(C([2H])([2H])[2H])C2)C([2H])([2H])[2H])cc1] | 359 |
| 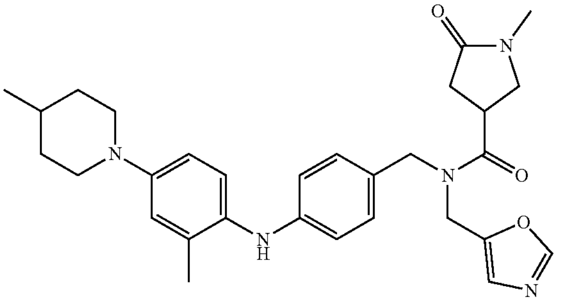 [SMILES: Cc1cc(N2CCC(C)CC2)ccc1Nc1ccc(CN(Cc2cnco2)C(=O)C2CC(=O)N(C)C2)cc1] | 360 |
| 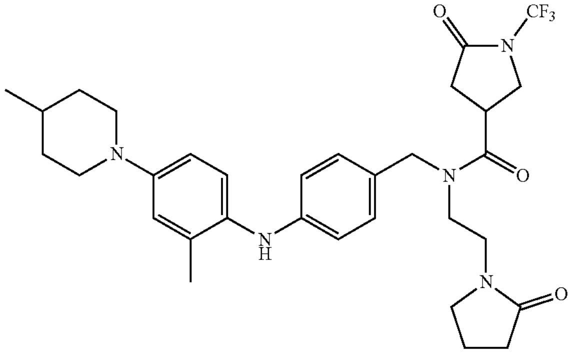 [SMILES: Cc1cc(N2CCC(C)CC2)ccc1Nc1ccc(CN(CCN2CCCC2=O)C(=O)C2CC(=O)N(C(F)(F)F)C2)cc1] | 361 |

TABLE 1-continued
| Active Compounds: Structures | |
|---|---|
| 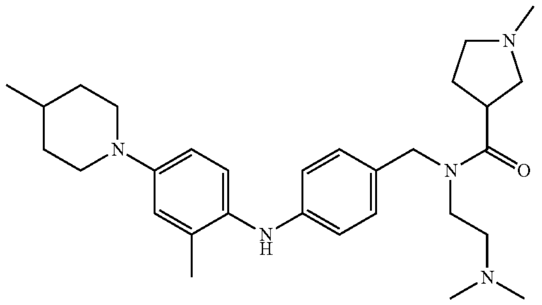 | 362 |
TABLE 2
| Active Compounds: Structures | |
|---|---|
| 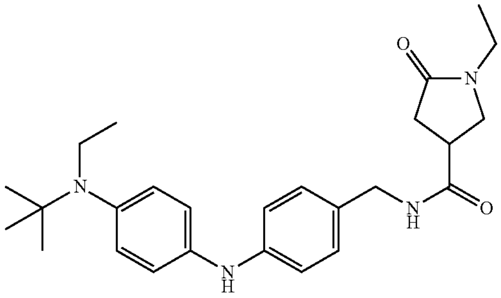 [SMILES: CCN1CC(C(=O)NCc2ccc(Nc3ccc(N(CC)C(C)(C)C)cc3)cc2)CC1=O] | 363 |
| 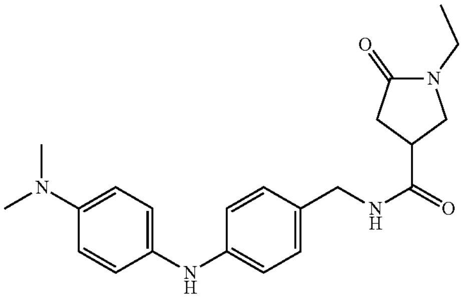 [SMILES: CCN1CC(C(=O)NCc2ccc(Nc3ccc(N(C)C)cc3)cc2)CC1=O] | 364 |
| 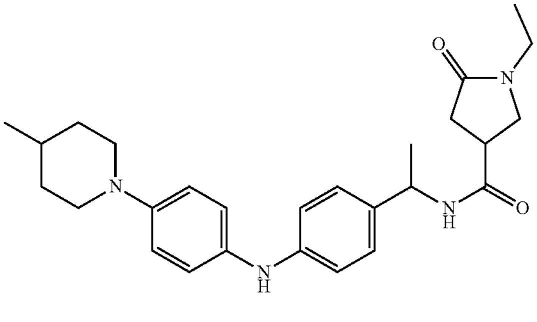 [SMILES: CCN1CC(C(=O)NC(C)c2ccc(Nc3ccc(N4CCC(C)CC4)cc3)cc2)CC1=O] | 365 |

TABLE 2-continued
| Active Compounds: Structures |
| --- |
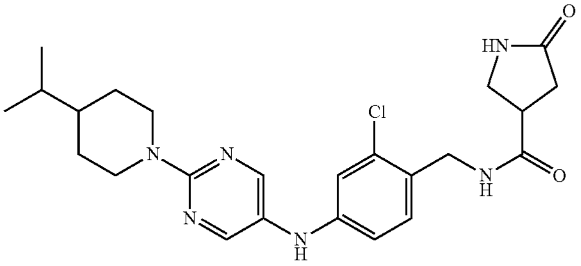
366
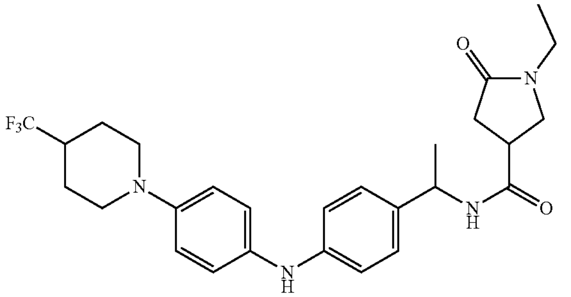 [SMILES: CCN1CC(C(=O)NC(C)c2ccc(Nc3ccc(N4CCC(C(F)(F)F)CC4)cc3)cc2)CC1=O]
367
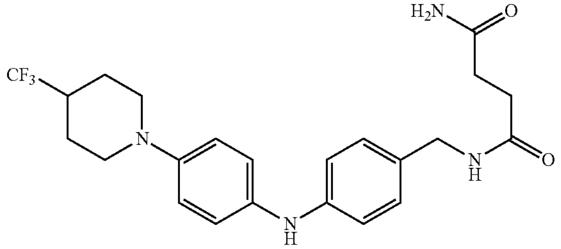 [SMILES: NC(=O)CCC(=O)NCc1ccc(Nc2ccc(N3CCC(C(F)(F)F)CC3)cc2)cc1]
368
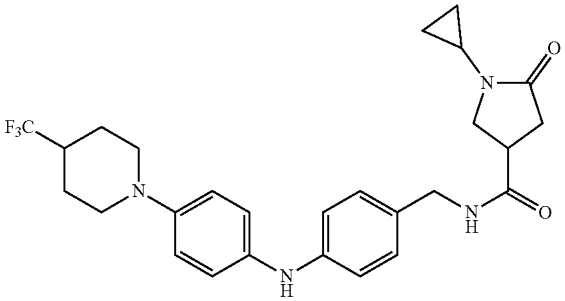 [SMILES: O=C(NCc1ccc(Nc2ccc(N3CCC(C(F)(F)F)CC3)cc2)cc1)C1CC(=O)N(C2CC2)C1]
369
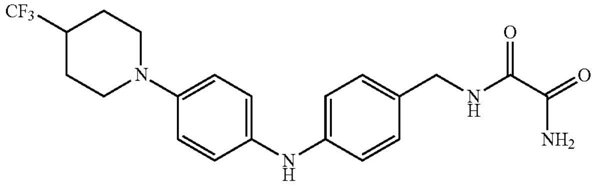 [SMILES: NC(=O)C(=O)NCc1ccc(Nc2ccc(N3CCC(C(F)(F)F)CC3)cc2)cc1]
370
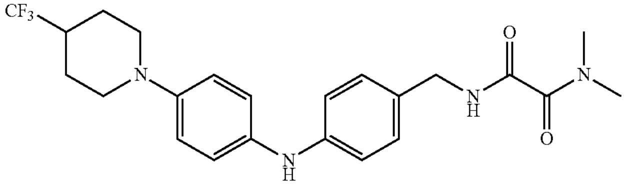 [SMILES: CN(C)C(=O)C(=O)NCc1ccc(Nc2ccc(N3CCC(C(F)(F)F)CC3)cc2)cc1]
371

TABLE 2-continued
| Active Compounds: Structures |
| --- |
372
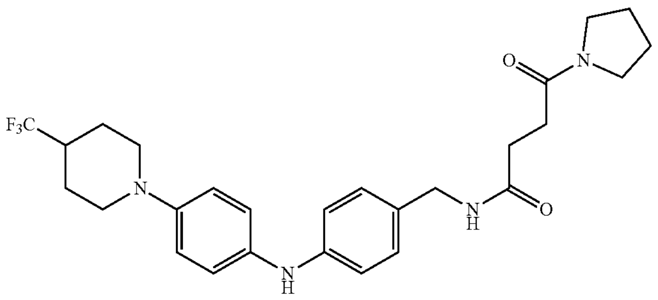 [SMILES: O=C(CCC(=O)N1CCCC1)NCc1ccc(Nc2ccc(N3CCC(C(F)(F)F)CC3)cc2)cc1]
373
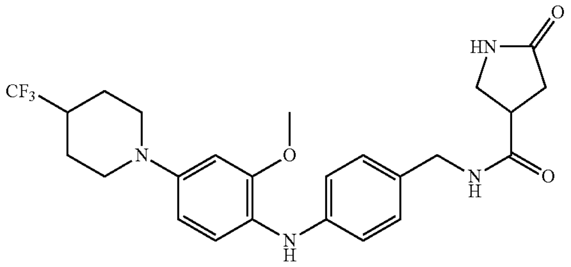 [SMILES: COc1cc(N2CCC(C(F)(F)F)CC2)ccc1Nc1ccc(CNC(=O)C2CNC(=O)C2)cc1]
374
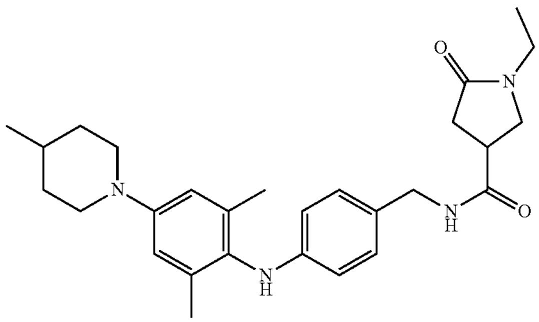 [SMILES: CCN1CC(C(=O)NCc2ccc(Nc3c(C)cc(N4CCC(C)CC4)cc3C)cc2)CC1=O]
375
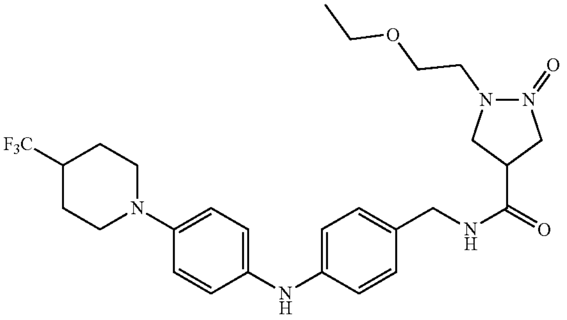
376
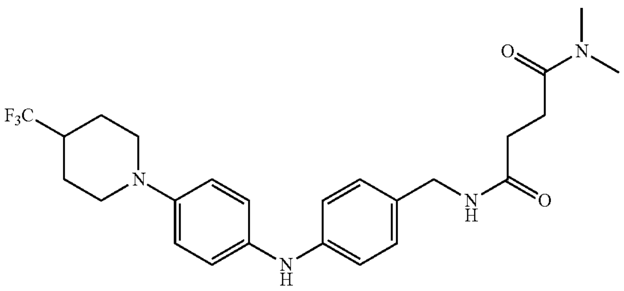 [SMILES: CN(C)C(=O)CCC(=O)NCc1ccc(Nc2ccc(N3CCC(C(F)(F)F)CC3)cc2)cc1]

TABLE 2-continued
| Active Compounds: Structures |
|---|
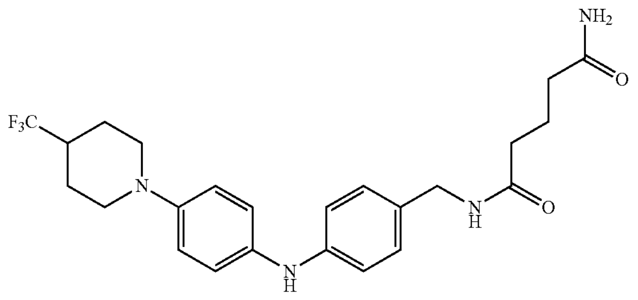 [SMILES: NC(=O)CCCC(=O)NCc1ccc(Nc2ccc(N3CCC(C(F)(F)F)CC3)cc2)cc1]
377
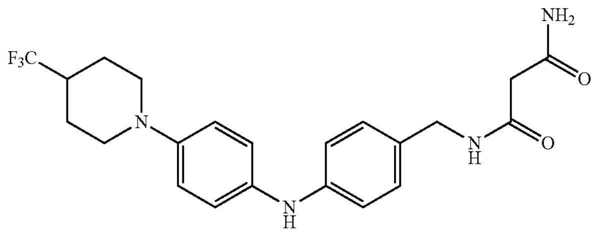 [SMILES: NC(=O)CC(=O)NCc1ccc(Nc2ccc(N3CCC(C(F)(F)F)CC3)cc2)cc1]
378
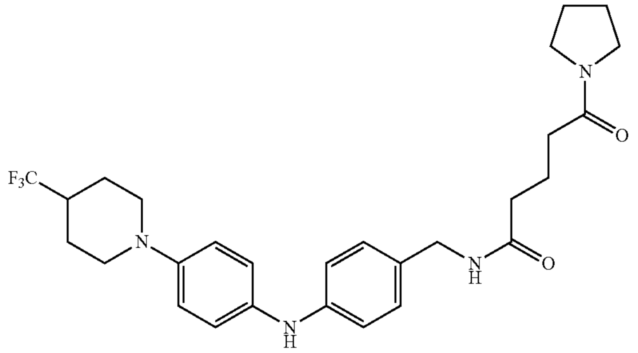 [SMILES: O=C(CCCC(=O)N1CCCC1)NCc1ccc(Nc2ccc(N3CCC(C(F)(F)F)CC3)cc2)cc1]
379
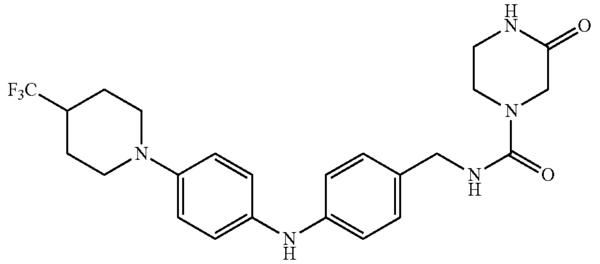 [SMILES: O=C1CN(C(=O)NCc2ccc(Nc3ccc(N4CCC(C(F)(F)F)CC4)cc3)cc2)CCN1]
380
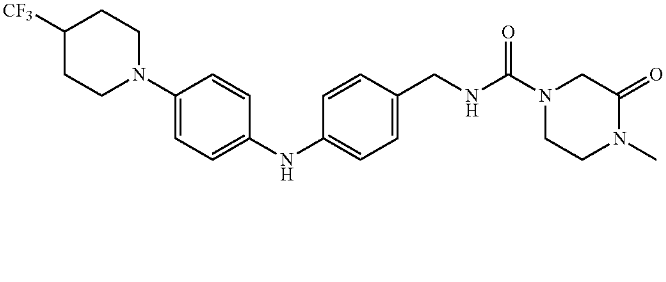 [SMILES: CN1CCN(C(=O)NCc2ccc(Nc3ccc(N4CCC(C(F)(F)F)CC4)cc3)cc2)CC1=O]
381

TABLE 2-continued
| Active Compounds: Structures |
|---|
| 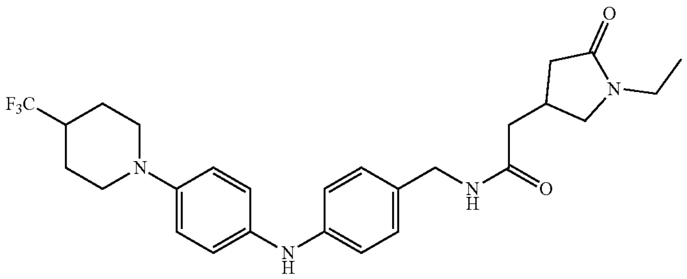 [SMILES: CCN1CC(CC(=O)NCc2ccc(Nc3ccc(N4CCC(C(F)(F)F)CC4)cc3)cc2)CC1=O] 382 |
| 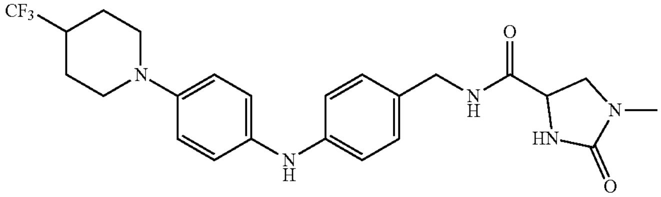 [SMILES: CN1CC(C(=O)NCc2ccc(Nc3ccc(N4CCC(C(F)(F)F)CC4)cc3)cc2)NC1=O] 383 |
| 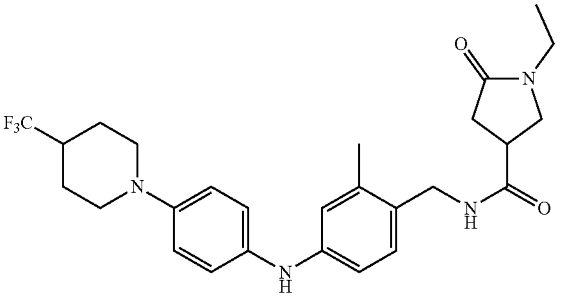 [SMILES: CCN1CC(C(=O)NCc2ccc(Nc3ccc(N4CCC(C(F)(F)F)CC4)cc3)cc2C)CC1=O] 384 |
| 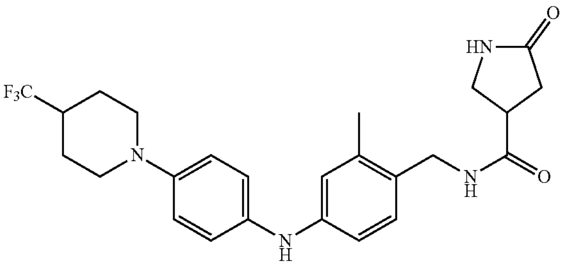 [SMILES: Cc1cc(Nc2ccc(N3CCC(C(F)(F)F)CC3)cc2)ccc1CNC(=O)C1CNC(=O)C1] 385 |
| 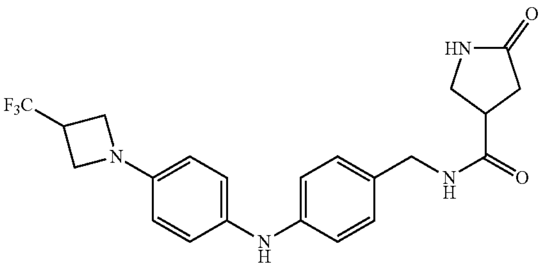 [SMILES: O=C1CC(C(=O)NCc2ccc(Nc3ccc(N4CC(C(F)(F)F)C4)cc3)cc2)CN1] 386 |

TABLE 2-continued
| Active Compounds: Structures |
| --- |
| 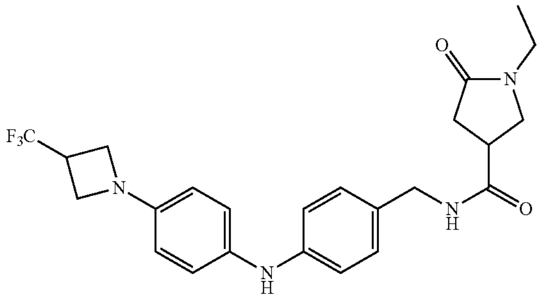 [SMILES: CCN1CC(C(=O)NCc2ccc(Nc3ccc(N4CC(C(F)(F)F)C4)cc3)cc2)CC1=O] 387 |
| 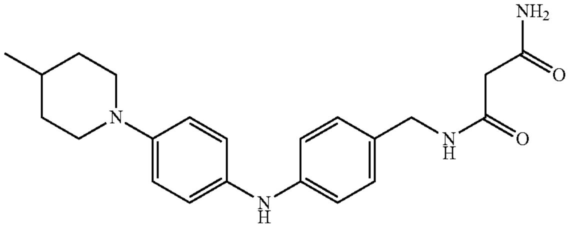 [SMILES: CC1CCN(c2ccc(Nc3ccc(CNC(=O)CC(N)=O)cc3)cc2)CC1] 388 |
| 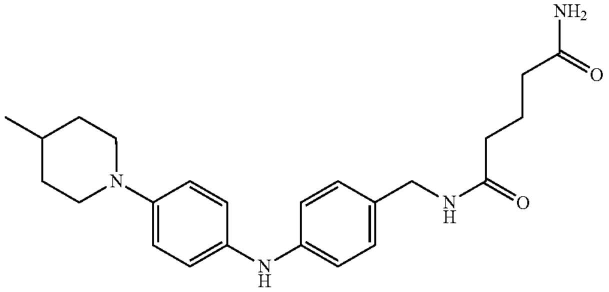 [SMILES: CC1CCN(c2ccc(Nc3ccc(CNC(=O)CCCC(N)=O)cc3)cc2)CC1] 389 |
| 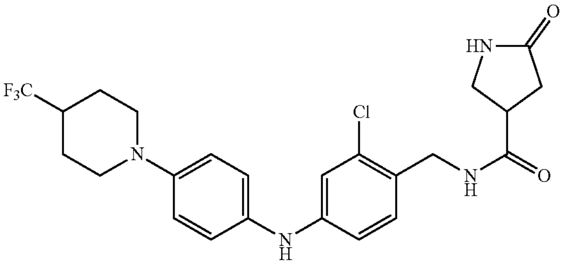 [SMILES: O=C1CC(C(=O)NCc2ccc(Nc3ccc(N4CCC(C(F)(F)F)CC4)cc3)cc2Cl)CN1] 390 |
| 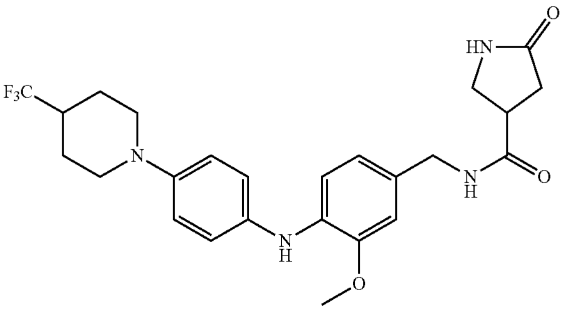 [SMILES: COc1cc(CNC(=O)C2CNC(=O)C2)ccc1Nc1ccc(N2CCC(C(F)(F)F)CC2)cc1] 391 |

TABLE 2-continued
| Active Compounds: Structures |
| --- |
| 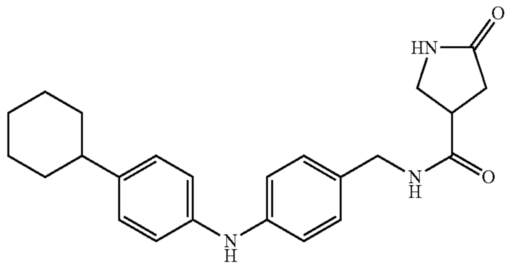 [SMILES: O=C1CC(C(=O)NCc2ccc(Nc3ccc(C4CCCCC4)cc3)cc2)CN1] 392 |
| 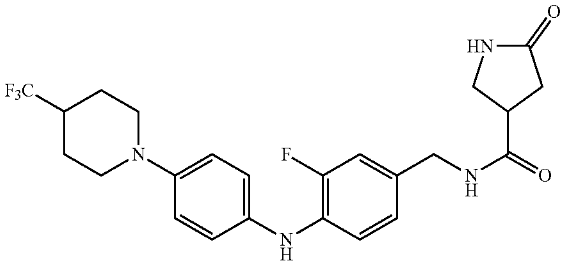 393 |
| 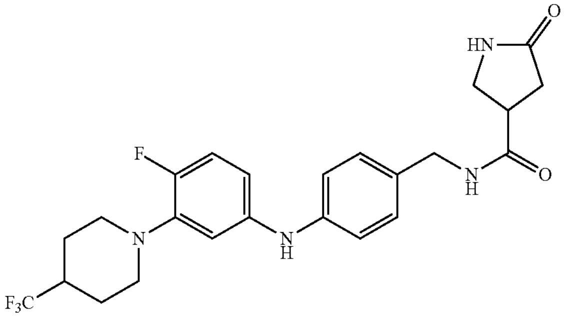 [SMILES: O=C1CC(C(=O)NCc2ccc(Nc3ccc(F)c(N4CCC(C(F)(F)F)CC4)c3)cc2)CN1] 394 |
| 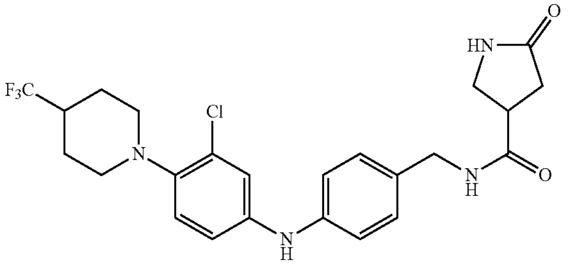 [SMILES: O=C1CC(C(=O)NCc2ccc(Nc3ccc(N4CCC(C(F)(F)F)CC4)c(Cl)c3)cc2)CN1] 395 |
| 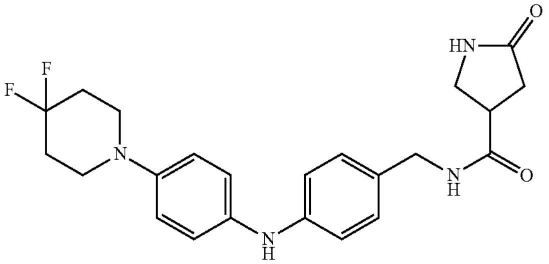 [SMILES: O=C1CC(C(=O)NCc2ccc(Nc3ccc(N4CCC(F)(F)CC4)cc3)cc2)CN1] 396 |

TABLE 2-continued
| Active Compounds: Structures |
|---|
| 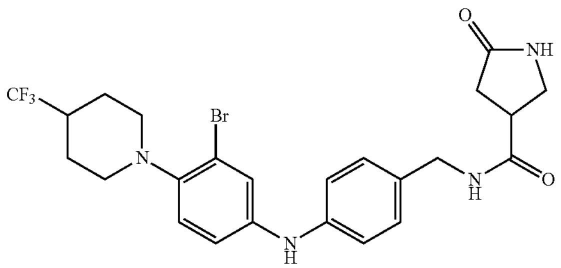 [SMILES: O=C1CC(C(=O)NCc2ccc(Nc3ccc(N4CCC(C(F)(F)F)CC4)c(Br)c3)cc2)CN1] 397 |
| 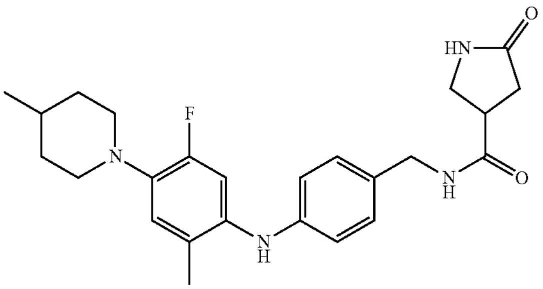 [SMILES: Cc1cc(N2CCC(C)CC2)c(F)cc1Nc1ccc(CNC(=O)C2CNC(=O)C2)cc1] 398 |
| 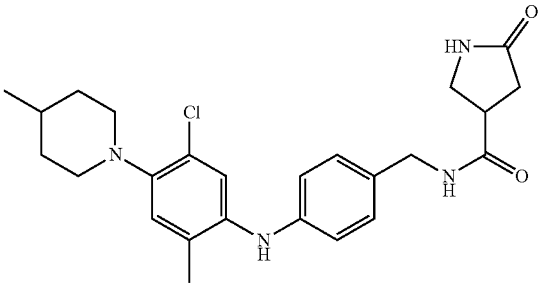 [SMILES: Cc1cc(N2CCC(C)CC2)c(Cl)cc1Nc1ccc(CNC(=O)C2CNC(=O)C2)cc1] 399 |
| 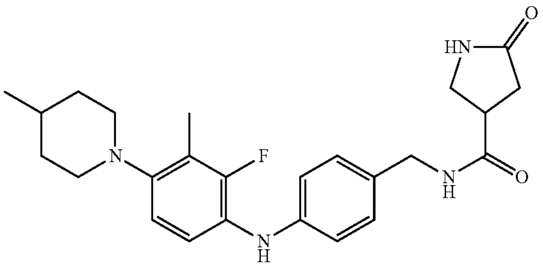 [SMILES: Cc1c(N2CCC(C)CC2)ccc(Nc2ccc(CNC(=O)C3CNC(=O)C3)cc2)c1F] 400 |
| 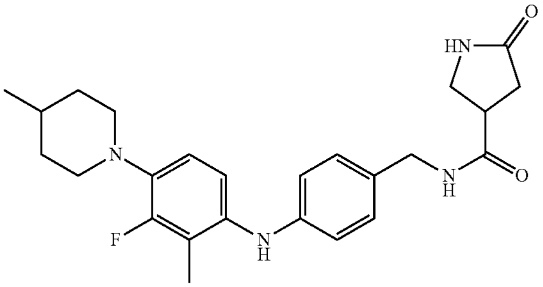 [SMILES: Cc1c(Nc2ccc(CNC(=O)C3CNC(=O)C3)cc2)ccc(N2CCC(C)CC2)c1F] 401 |

TABLE 2-continued
| Active Compounds: Structures | |
| --- | --- |
| 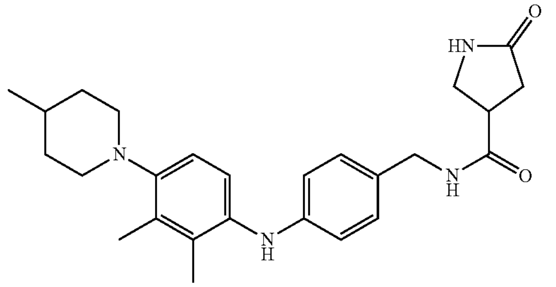 [SMILES: Cc1c(Nc2ccc(CNC(=O)C3CNC(=O)C3)cc2)ccc(N2CCC(C)CC2)c1C] | 402 |
| 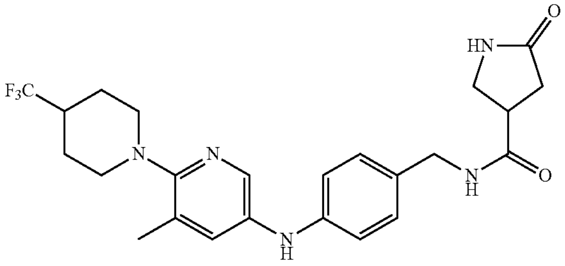 [SMILES: Cc1cc(Nc2ccc(CNC(=O)C3CNC(=O)C3)cc2)cnc1N1CCC(C(F)(F)F)CC1] | 403 |
| 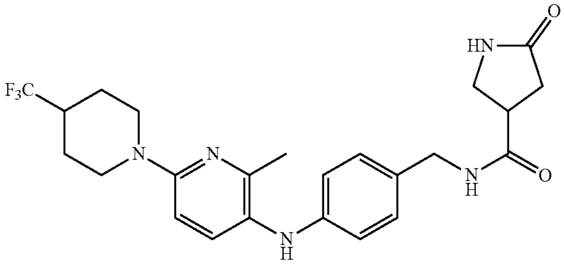 | 404 |
| 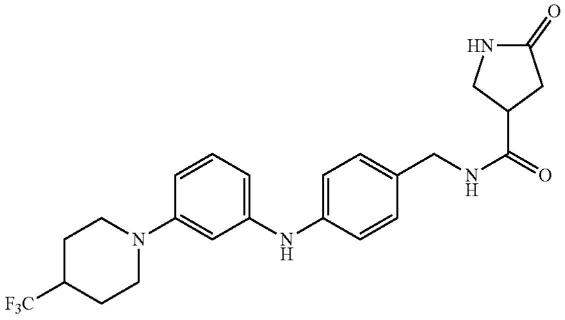 [SMILES: O=C1CC(C(=O)NCc2ccc(Nc3cccc(N4CCC(C(F)(F)F)CC4)c3)cc2)CN1] | 405 |
| 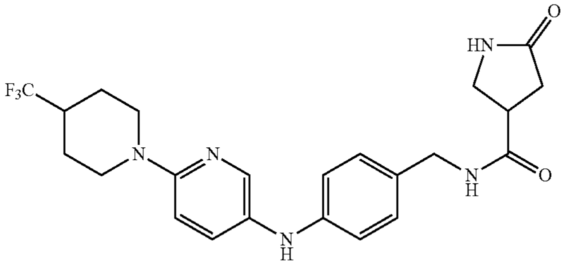 [SMILES: O=C1CC(C(=O)NCc2ccc(Nc3ccc(N4CCC(C(F)(F)F)CC4)nc3)cc2)CN1] | 406 |

TABLE 2-continued
| Active Compounds: Structures |
|---|
| 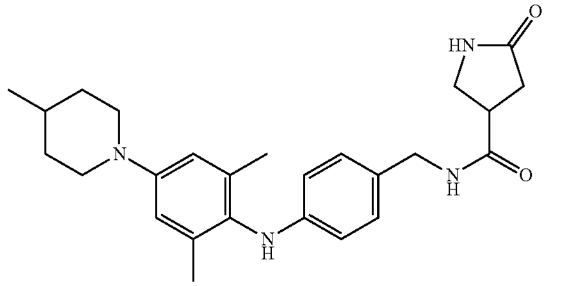 407 |
| 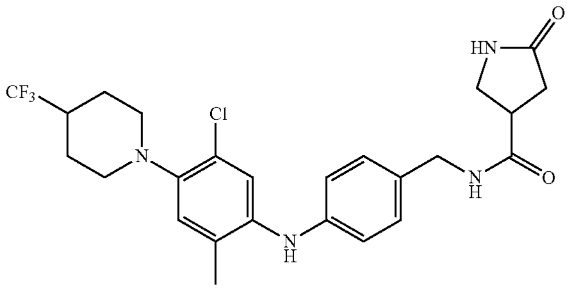 [SMILES: Cc1cc(N2CCC(C(F)(F)F)CC2)c(Cl)cc1Nc1ccc(CNC(=O)C2CNC(=O)C2)cc1] 408 |
| 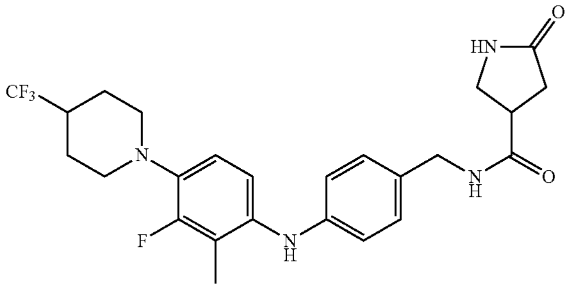 409 |
| 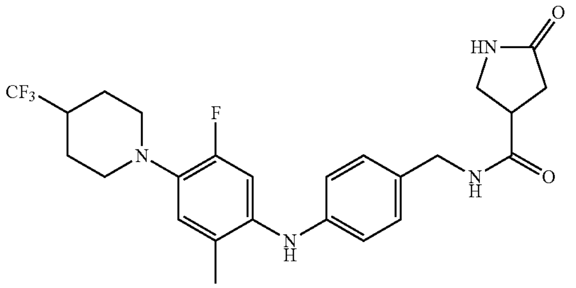 [SMILES: Cc1cc(N2CCC(C(F)(F)F)CC2)c(F)cc1Nc1ccc(CNC(=O)C2CNC(=O)C2)cc1] 410 |
| 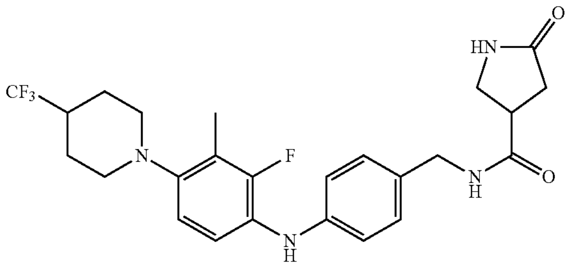 [SMILES: Cc1c(N2CCC(C(F)(F)F)CC2)ccc(Nc2ccc(CNC(=O)C3CNC(=O)C3)cc2)c1F] 411 |

TABLE 2-continued
Active Compounds: Structures
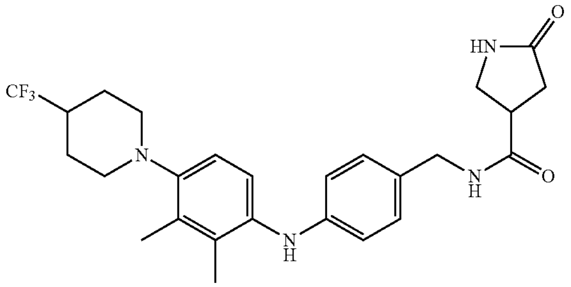 [SMILES: Cc1c(Nc2ccc(CNC(=O)C3CNC(=O)C3)cc2)ccc(N2CCC(C(F)(F)F)CC2)c1C]
412
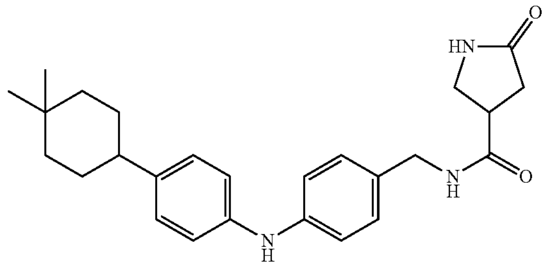 [SMILES: CC1(C)CCC(c2ccc(Nc3ccc(CNC(=O)C4CNC(=O)C4)cc3)cc2)CC1]
413
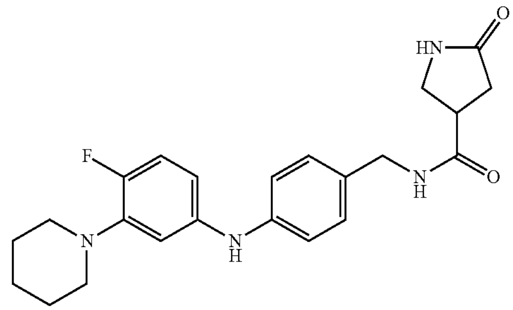 [SMILES: O=C1CC(C(=O)NCc2ccc(Nc3ccc(F)c(N4CCCCC4)c3)cc2)CN1]
414
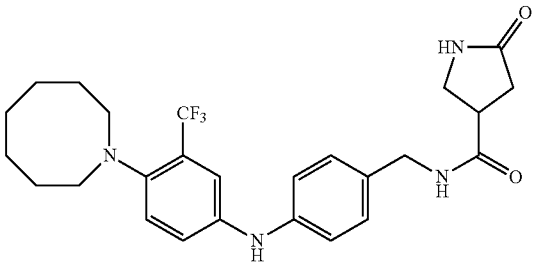 [SMILES: O=C1CC(C(=O)NCc2ccc(Nc3ccc(N4CCCCCCC4)c(C(F)(F)F)c3)cc2)CN1]
415
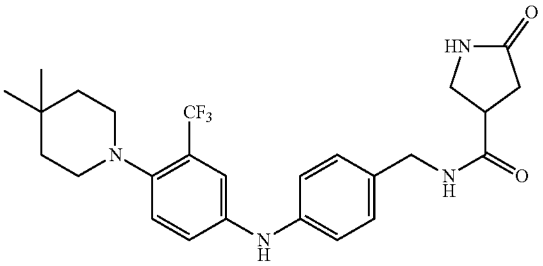 [SMILES: CC1(C)CCN(c2ccc(Nc3ccc(CNC(=O)C4CNC(=O)C4)cc3)cc2C(F)(F)F)CC1]
416

TABLE 2-continued
| Active Compounds: Structures |
| --- |
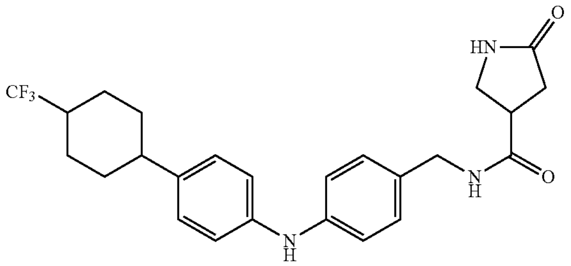 [SMILES: O=C1CC(C(=O)NCc2ccc(Nc3ccc(C4CCC(C(F)(F)F)CC4)cc3)cc2)CN1]
417
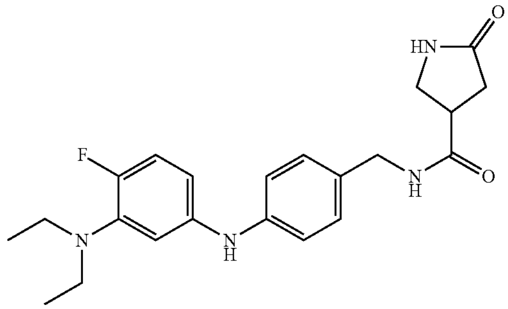 [SMILES: CCN(CC)c1cc(Nc2ccc(CNC(=O)C3CNC(=O)C3)cc2)ccc1F]
418
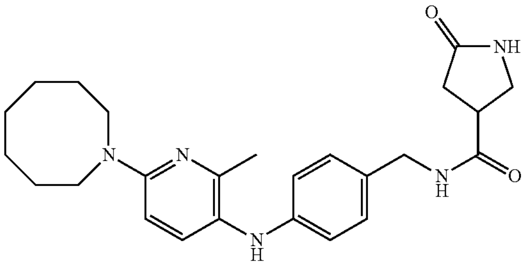 [SMILES: Cc1nc(N2CCCCCCC2)ccc1Nc1ccc(CNC(=O)C2CNC(=O)C2)cc1]
419
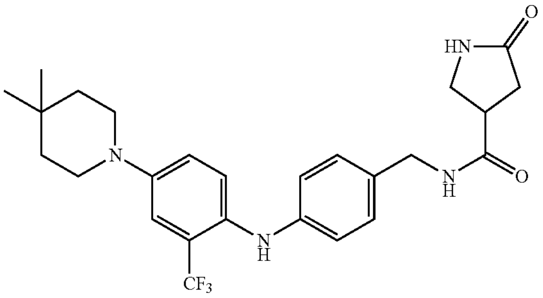 [SMILES: CC1(C)CCN(c2ccc(Nc3ccc(CNC(=O)C4CNC(=O)C4)cc3)c(C(F)(F)F)c2)CC1]
420
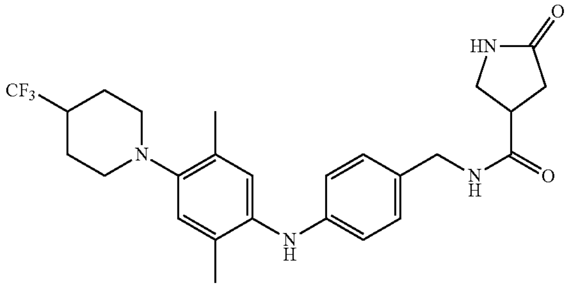 [SMILES: Cc1cc(N2CCC(C(F)(F)F)CC2)c(C)cc1Nc1ccc(CNC(=O)C2CNC(=O)C2)cc1]
421

TABLE 2-continued
| Active Compounds: Structures |
| --- |
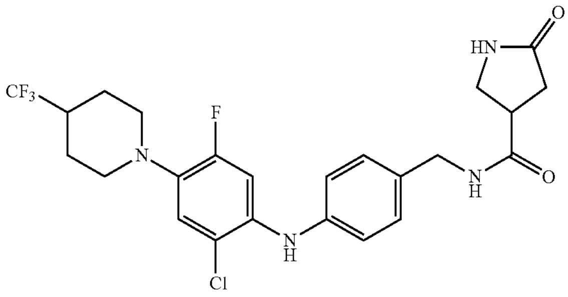 [SMILES: O=C1CC(C(=O)NCc2ccc(Nc3cc(F)c(N4CCC(C(F)(F)F)CC4)cc3Cl)cc2)CN1]
422
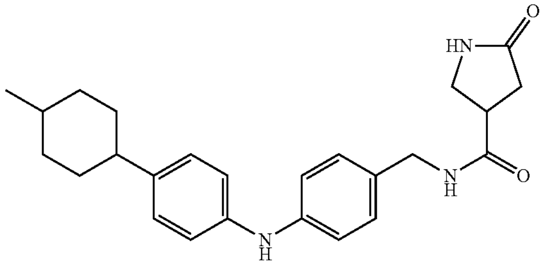 [SMILES: CC1CCC(c2ccc(Nc3ccc(CNC(=O)C4CNC(=O)C4)cc3)cc2)CC1]
423
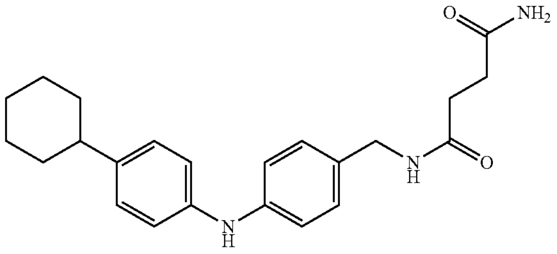 [SMILES: NC(=O)CCC(=O)NCc1ccc(Nc2ccc(C3CCCCC3)cc2)cc1]
424
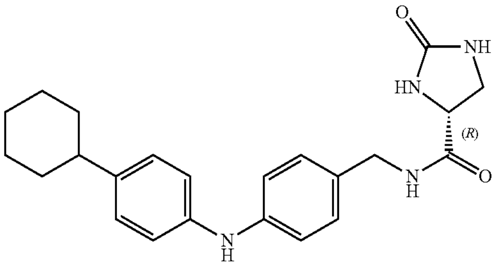
425
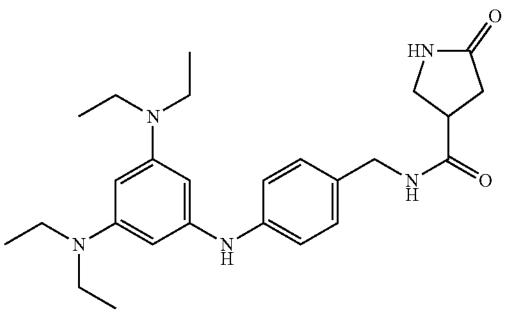 [SMILES: CCN(CC)c1cc(Nc2ccc(CNC(=O)C3CNC(=O)C3)cc2)cc(N(CC)CC)c1]
426

TABLE 2-continued
| Active Compounds: Structures |
|---|
| 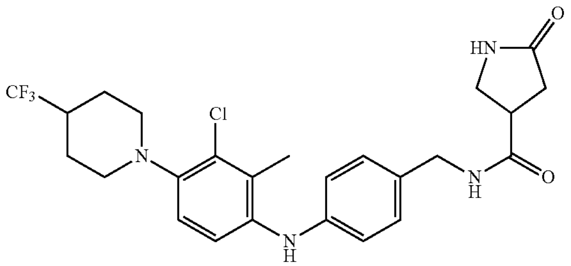 [SMILES: Cc1c(Nc2ccc(CNC(=O)C3CNC(=O)C3)cc2)ccc(N2CCC(C(F)(F)F)CC2)c1Cl] 427 |
| 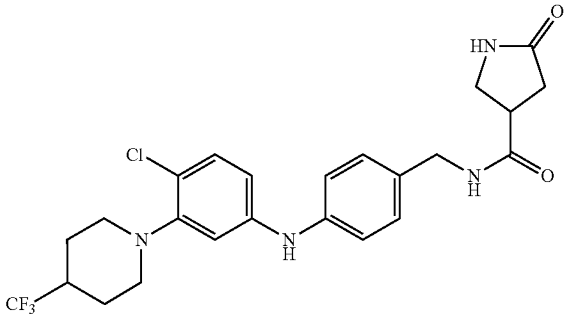 [SMILES: O=C1CC(C(=O)NCc2ccc(Nc3ccc(Cl)c(N4CCC(C(F)(F)F)CC4)c3)cc2)CN1] 428 |
| 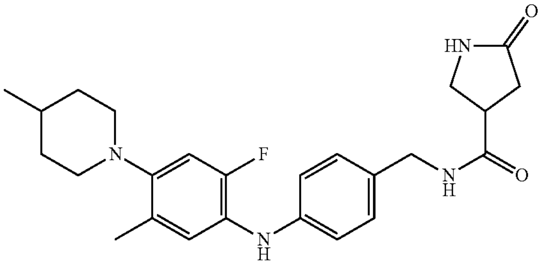 [SMILES: Cc1cc(Nc2ccc(CNC(=O)C3CNC(=O)C3)cc2)c(F)cc1N1CCC(C)CC1] 429 |
| 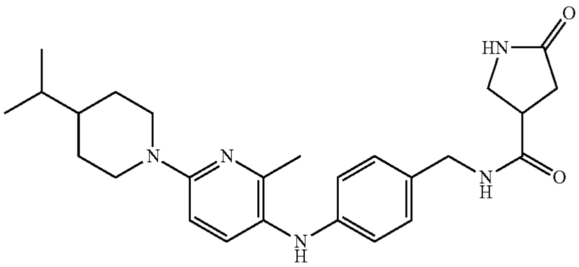 [SMILES: Cc1nc(N2CCC(C(C)C)CC2)ccc1Nc1ccc(CNC(=O)C2CNC(=O)C2)cc1] 430 |
| 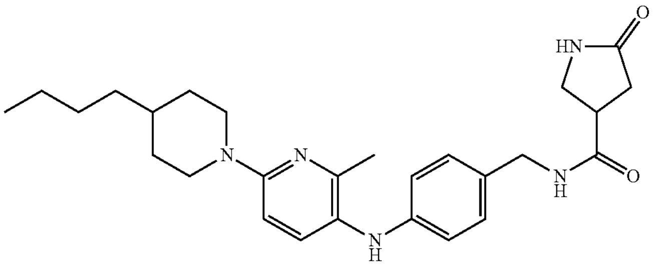 [SMILES: CCCCC1CCN(c2ccc(Nc3ccc(CNC(=O)C4CNC(=O)C4)cc3)c(C)n2)CC1] 431 |

TABLE 2-continued
| Active Compounds: Structures |  |
|---|---|
| 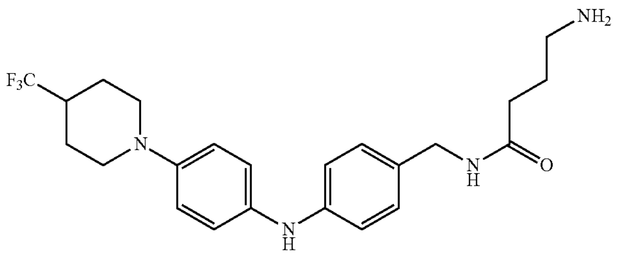 [SMILES: NCCCC(=O)NCc1ccc(Nc2ccc(N3CCC(C(F)(F)F)CC3)cc2)cc1] | 432 |
| 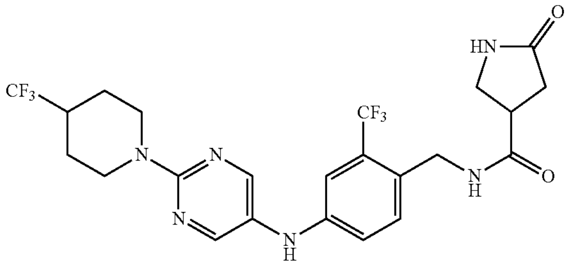 [SMILES: O=C1CC(C(=O)NCc2ccc(Nc3cnc(N4CCC(C(F)(F)F)CC4)nc3)cc2C(F)(F)F)CN1] | 433 |
| 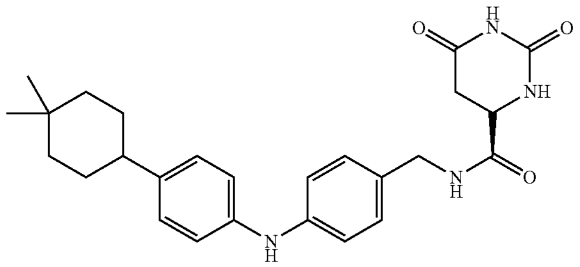 | 434 |
| 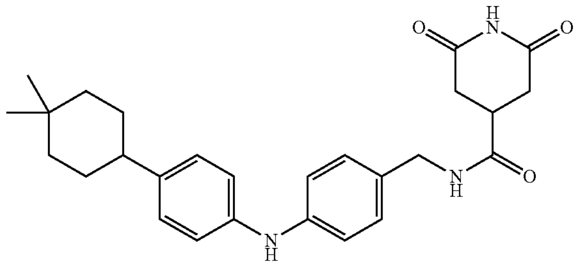 [SMILES: CC1(C)CCC(c2ccc(Nc3ccc(CNC(=O)C4CC(=O)NC(=O)C4)cc3)cc2)CC1] | 435 |
| 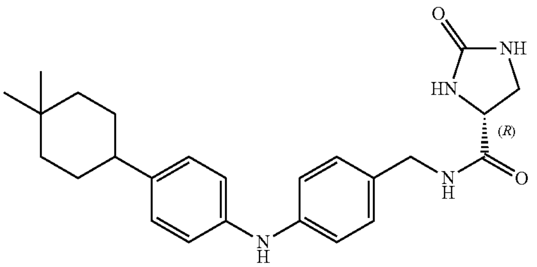 | 436 |

TABLE 2-continued
| Active Compounds: Structures |
| --- |
| 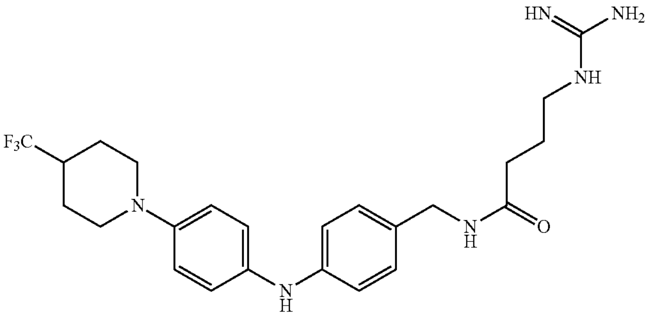 [SMILES: N=C(N)NCCCC(=O)NCc1ccc(Nc2ccc(N3CCC(C(F)(F)F)CC3)cc2)cc1] 437 |
| 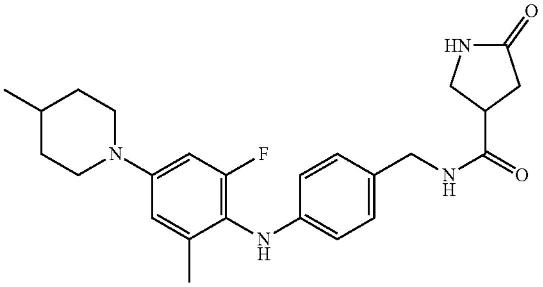 [SMILES: Cc1cc(N2CCC(C)CC2)cc(F)c1Nc1ccc(CNC(=O)C2CNC(=O)C2)cc1] 438 |
| 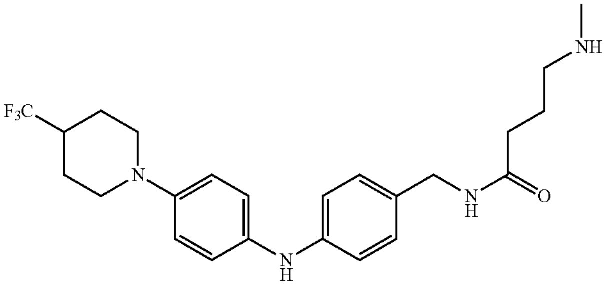 [SMILES: CNCCCC(=O)NCc1ccc(Nc2ccc(N3CCC(C(F)(F)F)CC3)cc2)cc1] 439 |
| 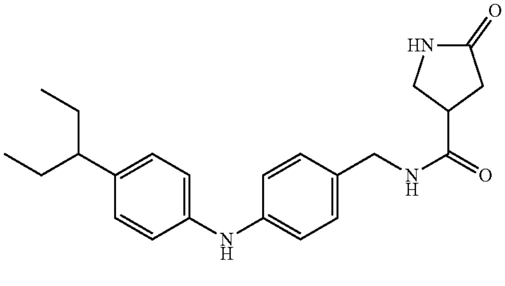 [SMILES: CCC(CC)c1ccc(Nc2ccc(CNC(=O)C3CNC(=O)C3)cc2)cc1] 440 |
| 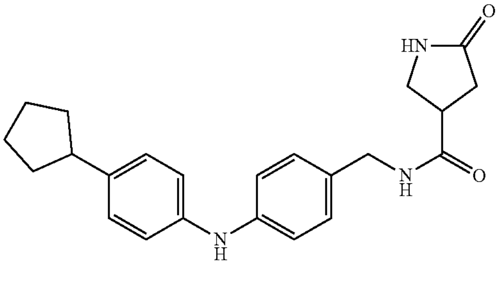 [SMILES: O=C1CC(C(=O)NCc2ccc(Nc3ccc(C4CCCC4)cc3)cc2)CN1] 441 |

TABLE 2-continued
| Active Compounds: Structures | |
|---|---|
| 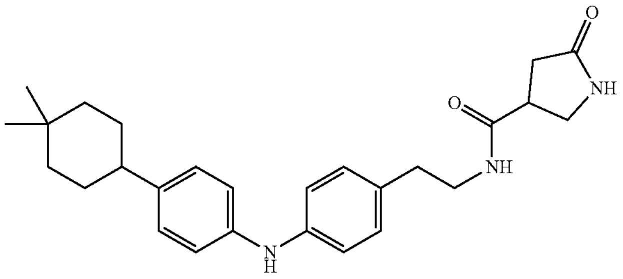 [SMILES: CC1(C)CCC(c2ccc(Nc3ccc(CCNC(=O)C4CNC(=O)C4)cc3)cc2)CC1] | 442 |
| 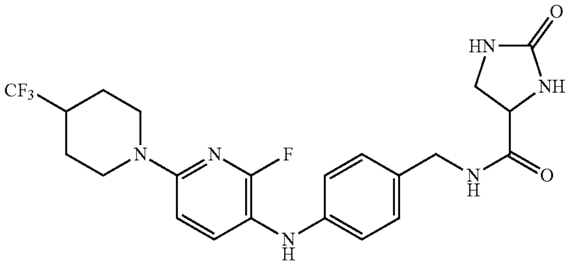 [SMILES: O=C1NCC(C(=O)NCc2ccc(Nc3ccc(N4CCC(C(F)(F)F)CC4)nc3F)cc2)N1] | 443 |
| 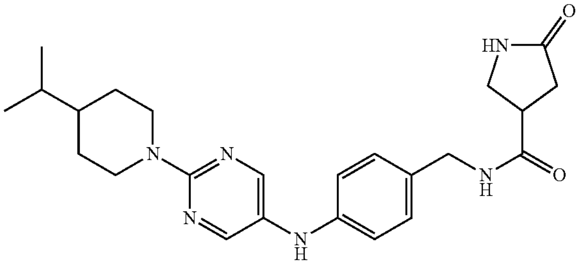 [SMILES: CC(C)C1CCN(c2ncc(Nc3ccc(CNC(=O)C4CNC(=O)C4)cc3)cn2)CC1] | 444 |
| 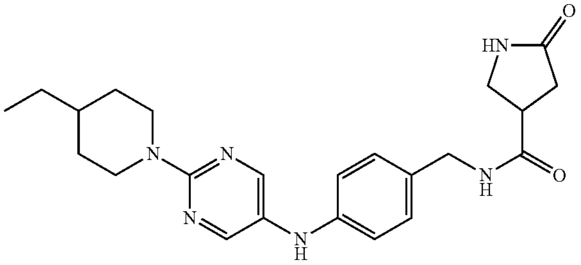 [SMILES: CCC1CCN(c2ncc(Nc3ccc(CNC(=O)C4CNC(=O)C4)cc3)cn2)CC1] | 445 |
| 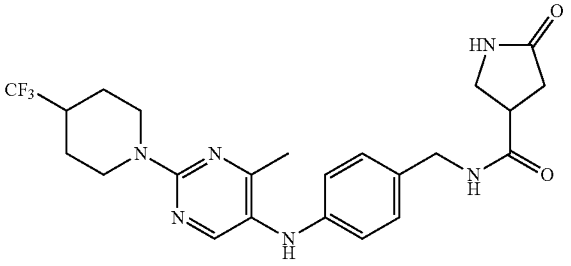 [SMILES: Cc1nc(N2CCC(C(F)(F)F)CC2)ncc1Nc1ccc(CNC(=O)C2CNC(=O)C2)cc1] | 446 |

TABLE 2-continued
| Active Compounds: Structures | |
| --- | --- |
| 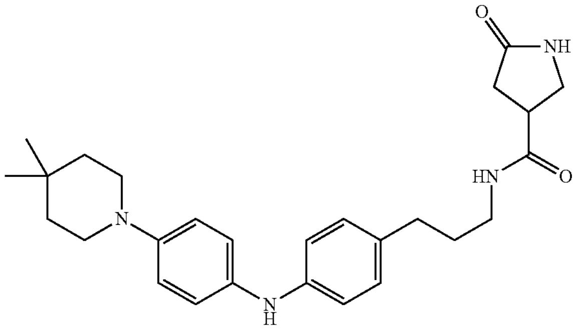 [SMILES: CC1(C)CCN(c2ccc(Nc3ccc(CCCNC(=O)C4CNC(=O)C4)cc3)cc2)CC1] | 447 |
| 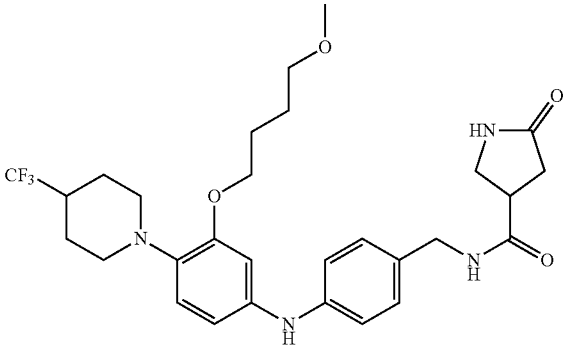 [SMILES: COCCCCOc1cc(Nc2ccc(CNC(=O)C3CNC(=O)C3)cc2)ccc1N1CCC(C(F)(F)F)CC1] | 448 |
| 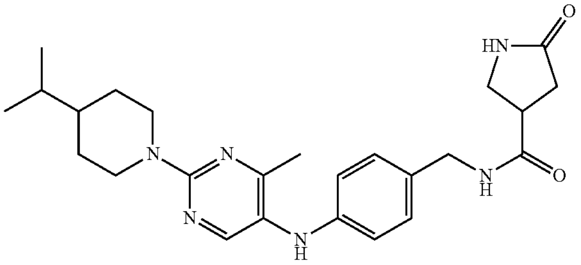 [SMILES: Cc1nc(N2CCC(C(C)C)CC2)ncc1Nc1ccc(CNC(=O)C2CNC(=O)C2)cc1] | 449 |
| 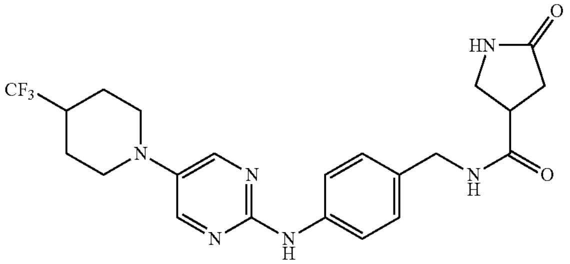 [SMILES: O=C1CC(C(=O)NCc2ccc(Nc3ncc(N4CCC(C(F)(F)F)CC4)cn3)cc2)CN1] | 450 |
| 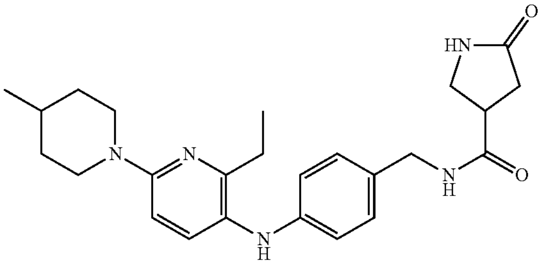 [SMILES: CCc1nc(N2CCC(C)CC2)ccc1Nc1ccc(CNC(=O)C2CNC(=O)C2)cc1] | 451 |

TABLE 2-continued
| Active Compounds: Structures |
| --- |
| 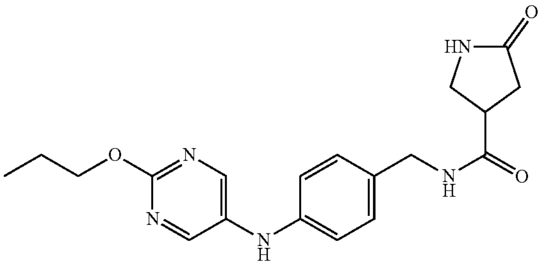 [SMILES: CCCOc1ncc(Nc2ccc(CNC(=O)C3CNC(=O)C3)cc2)cn1] 452 |
| 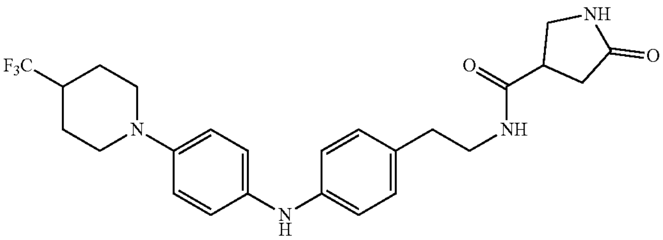 [SMILES: O=C1CC(C(=O)NCCc2ccc(Nc3ccc(N4CCC(C(F)(F)F)CC4)cc3)cc2)CN1] 453 |
| 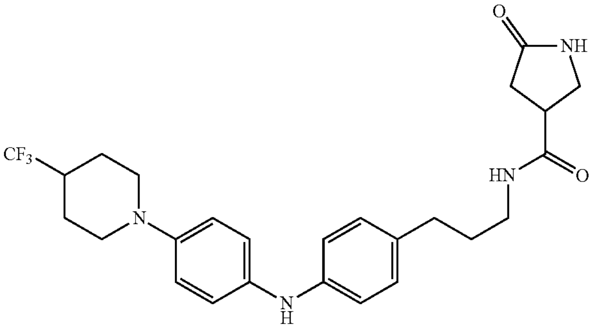 [SMILES: O=C1CC(C(=O)NCCCc2ccc(Nc3ccc(N4CCC(C(F)(F)F)CC4)cc3)cc2)CN1] 454 |
| 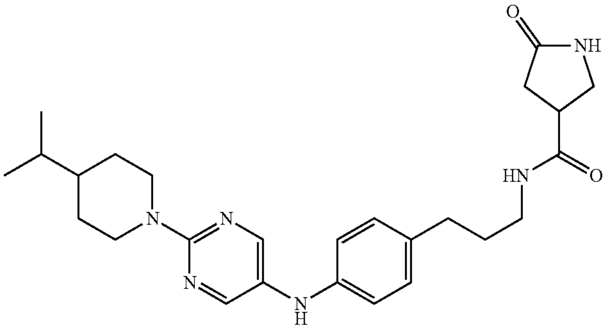 [SMILES: CC(C)C1CCN(c2ncc(Nc3ccc(CCCNC(=O)C4CNC(=O)C4)cc3)cn2)CC1] 455 |
| 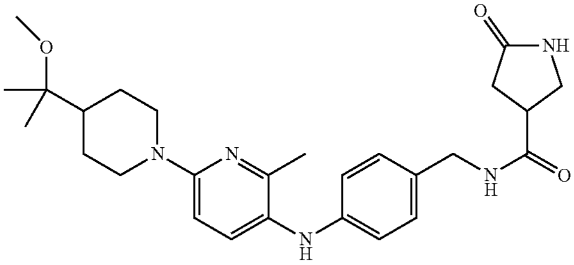 [SMILES: COC(C)(C)C1CCN(c2ccc(Nc3ccc(CNC(=O)C4CNC(=O)C4)cc3)c(C)n2)CC1] 456 |

TABLE 2-continued
| Active Compounds: Structures |
| --- |
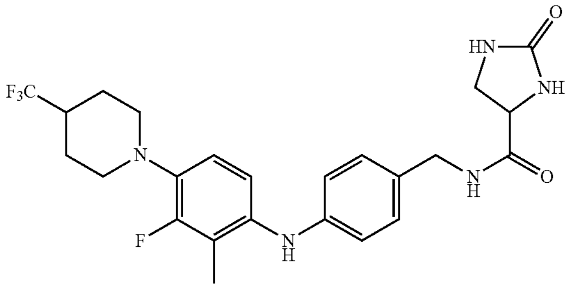 [SMILES: Cc1c(Nc2ccc(CNC(=O)C3CNC(=O)N3)cc2)ccc(N2CCC(C(F)(F)F)CC2)c1F]
457
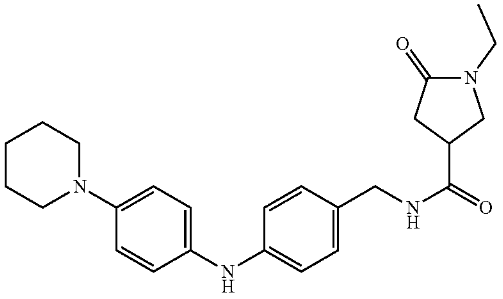 [SMILES: CCN1CC(C(=O)NCc2ccc(Nc3ccc(N4CCCCC4)cc3)cc2)CC1=O]
458
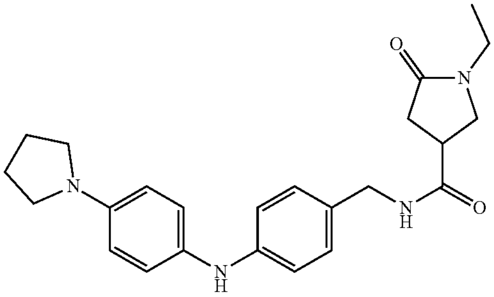 [SMILES: CCN1CC(C(=O)NCc2ccc(Nc3ccc(N4CCCC4)cc3)cc2)CC1=O]
459
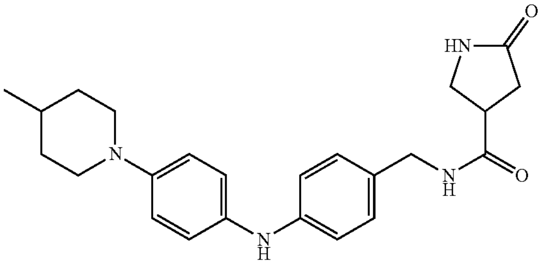 [SMILES: CC1CCN(c2ccc(Nc3ccc(CNC(=O)C4CNC(=O)C4)cc3)cc2)CC1]
460
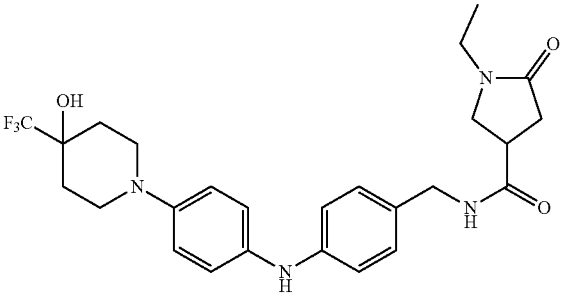 [SMILES: CCN1CC(C(=O)NCc2ccc(Nc3ccc(N4CCC(O)(C(F)(F)F)CC4)cc3)cc2)CC1=O]
461

TABLE 2-continued
| Active Compounds: Structures |
| --- |
| 462 |
| 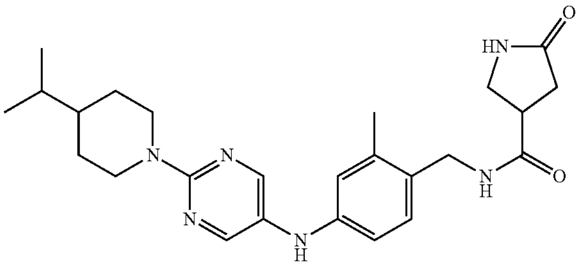 [SMILES: Cc1cc(Nc2cnc(N3CCC(C(C)C)CC3)nc2)ccc1CNC(=O)C1CNC(=O)C1] |
| 463 |
| 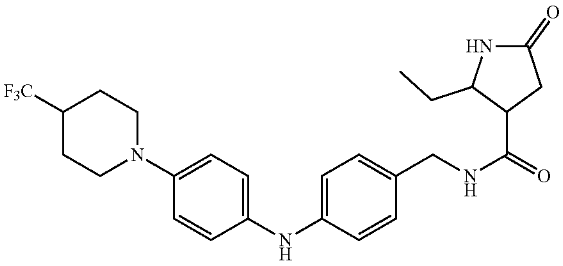 [SMILES: CCC1NC(=O)CC1C(=O)NCc1ccc(Nc2ccc(N3CCC(C(F)(F)F)CC3)cc2)cc1] |
| 464 |
| 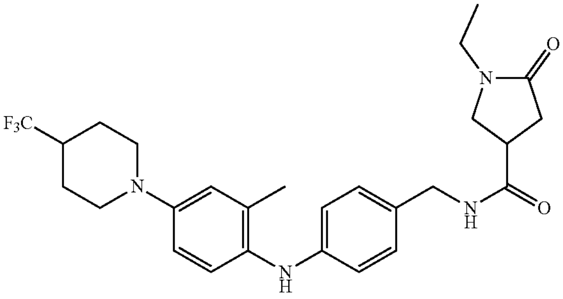 [SMILES: CCN1CC(C(=O)NCc2ccc(Nc3ccc(N4CCC(C(F)(F)F)CC4)cc3C)cc2)CC1=O] |
| 465 |
| 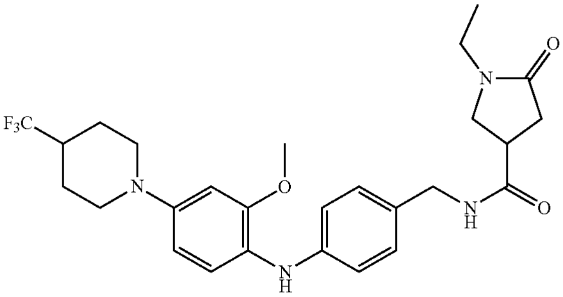 [SMILES: CCN1CC(C(=O)NCc2ccc(Nc3ccc(N4CCC(C(F)(F)F)CC4)cc3OC)cc2)CC1=O] |
| 466 |
| 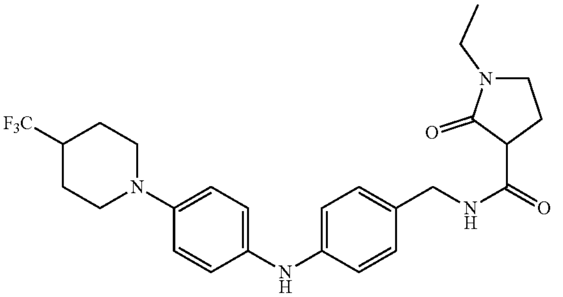 [SMILES: CCN1CCC(C(=O)NCc2ccc(Nc3ccc(N4CCC(C(F)(F)F)CC4)cc3)cc2)C1=O] |

TABLE 2-continued
| Active Compounds: Structures |
| --- |
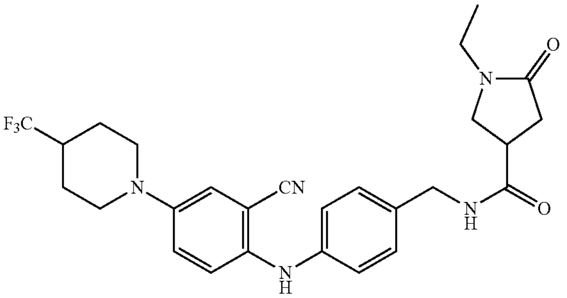 [SMILES: CCN1CC(C(=O)NCc2ccc(Nc3ccc(N4CCC(C(F)(F)F)CC4)cc3C#N)cc2)CC1=O]
467
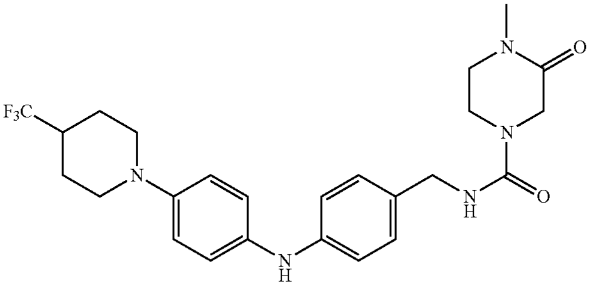 [SMILES: CN1CCN(C(=O)NCc2ccc(Nc3ccc(N4CCC(C(F)(F)F)CC4)cc3)cc2)CC1=O]
468
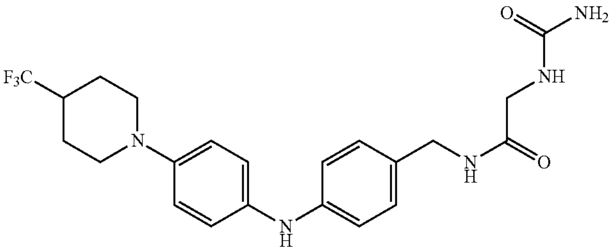 [SMILES: NC(=O)NCC(=O)NCc1ccc(Nc2ccc(N3CCC(C(F)(F)F)CC3)cc2)cc1]
469
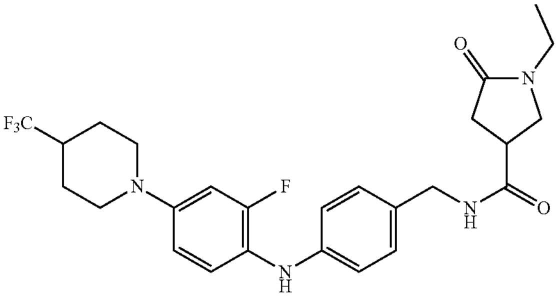 [SMILES: CCN1CC(C(=O)NCc2ccc(Nc3ccc(N4CCC(C(F)(F)F)CC4)cc3F)cc2)CC1=O]
470
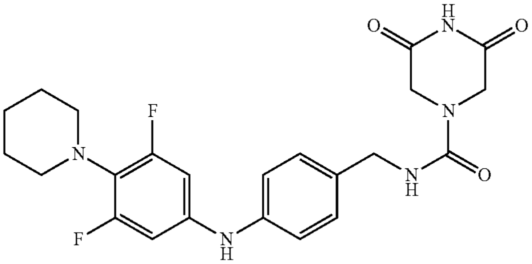 [SMILES: O=C1CN(C(=O)NCc2ccc(Nc3cc(F)c(N4CCCCC4)c(F)c3)cc2)CC(=O)N1]
471

TABLE 2-continued
| Active Compounds: Structures |
| --- |
| 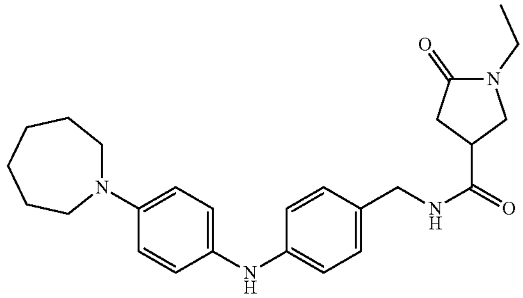 [SMILES: CCN1CC(C(=O)NCc2ccc(Nc3ccc(N4CCCCCC4)cc3)cc2)CC1=O] 472 |
| 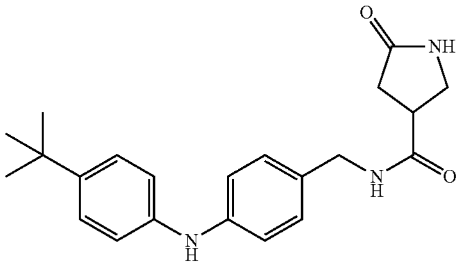 [SMILES: CC(C)(C)c1ccc(Nc2ccc(CNC(=O)C3CNC(=O)C3)cc2)cc1] 473 |
| 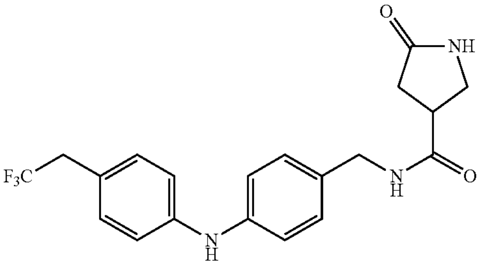 [SMILES: O=C1CC(C(=O)NCc2ccc(Nc3ccc(CC(F)(F)F)cc3)cc2)CN1] 474 |
| 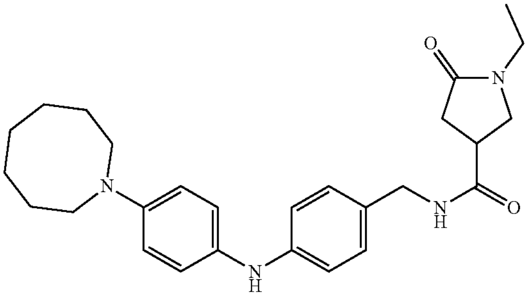 [SMILES: CCN1CC(C(=O)NCc2ccc(Nc3ccc(N4CCCCCCC4)cc3)cc2)CC1=O] 475 |
| 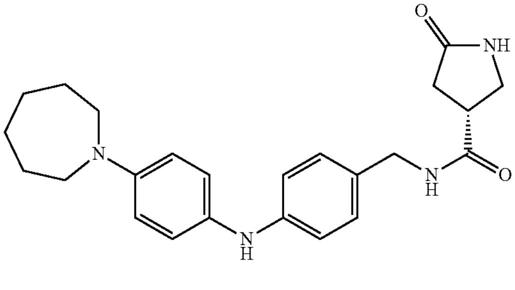 [SMILES: O=C1C[C@@H](C(=O)NCc2ccc(Nc3ccc(N4CCCCCC4)cc3)cc2)CN1] 476 |

TABLE 2-continued
| Active Compounds: Structures |
| --- |
| 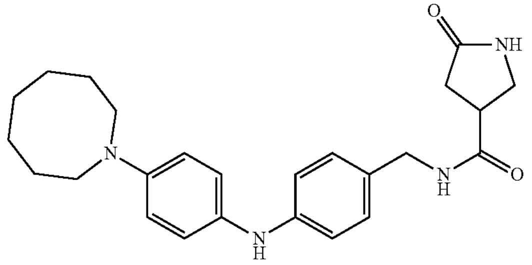 [SMILES: O=C1CC(C(=O)NCc2ccc(Nc3ccc(N4CCCCCCC4)cc3)cc2)CN1] 477 |
| 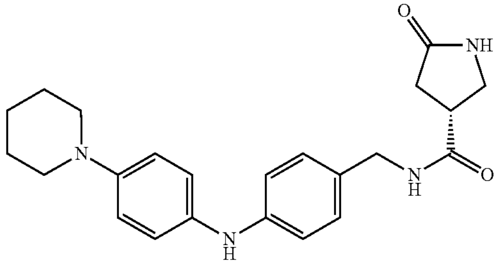 [SMILES: O=C1C[C@@H](C(=O)NCc2ccc(Nc3ccc(N4CCCCC4)cc3)cc2)CN1] 478 |
| 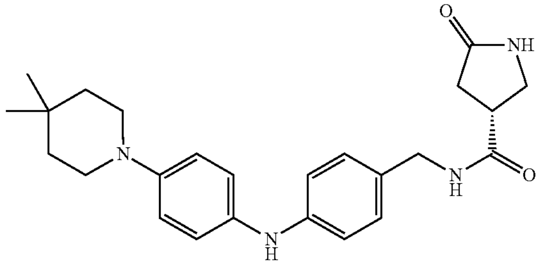 [SMILES: CC1(C)CCN(c2ccc(Nc3ccc(CNC(=O)[C@H]4CNC(=O)C4)cc3)cc2)CC1] 479 |
| 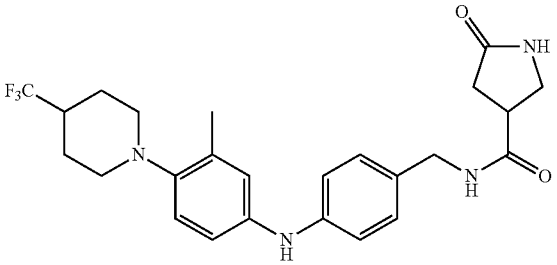 [SMILES: Cc1cc(Nc2ccc(CNC(=O)C3CNC(=O)C3)cc2)ccc1N1CCC(C(F)(F)F)CC1] 480 |
| 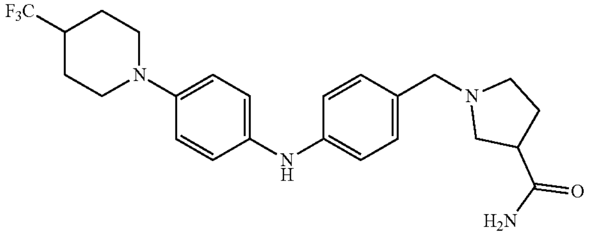 481 |
| 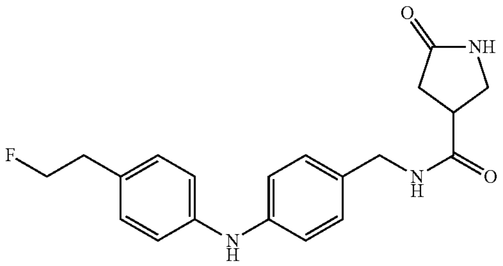 [SMILES: O=C1CC(C(=O)NCc2ccc(Nc3ccc(CCF)cc3)cc2)CN1] 482 |

TABLE 2-continued
| Active Compounds: Structures |
|---|
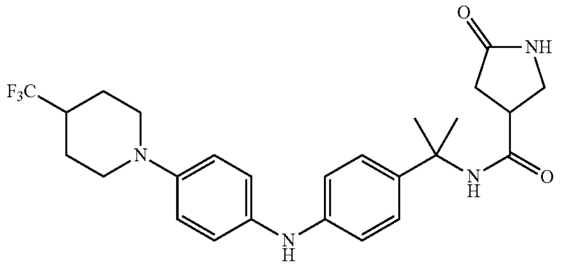 [SMILES: CC(C)(NC(=O)C1CNC(=O)C1)c1ccc(Nc2ccc(N3CCC(C(F)(F)F)CC3)cc2)cc1]
483
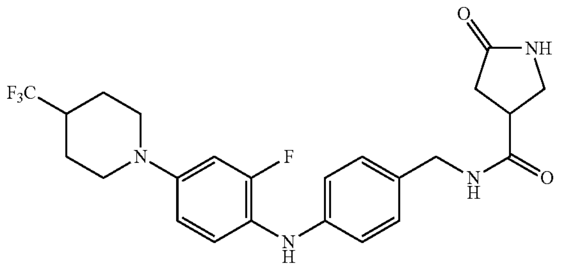 [SMILES: O=C1CC(C(=O)NCc2ccc(Nc3ccc(N4CCC(C(F)(F)F)CC4)cc3F)cc2)CN1]
484
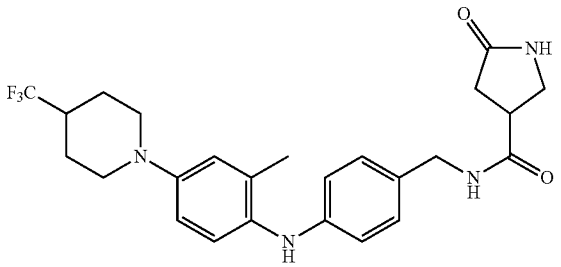 [SMILES: Cc1cc(N2CCC(C(F)(F)F)CC2)ccc1Nc1ccc(CNC(=O)C2CNC(=O)C2)cc1]
485
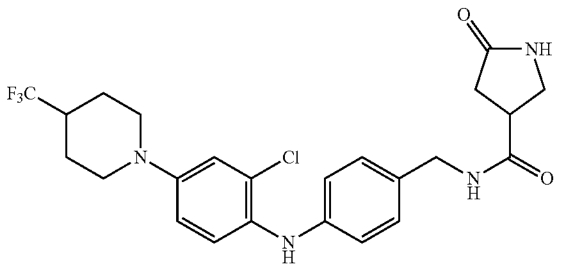 [SMILES: O=C1CC(C(=O)NCc2ccc(Nc3ccc(N4CCC(C(F)(F)F)CC4)cc3Cl)cc2)CN1]
486
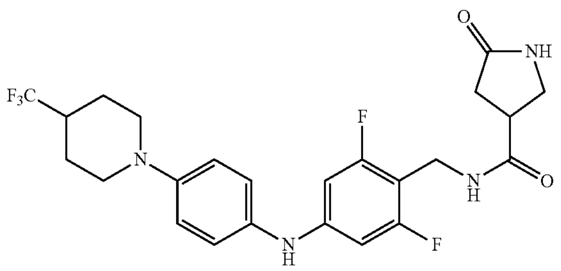 [SMILES: O=C1CC(C(=O)NCc2c(F)cc(Nc3ccc(N4CCC(C(F)(F)F)CC4)cc3)cc2F)CN1]
487

TABLE 2-continued
| Active Compounds: Structures |
| --- |
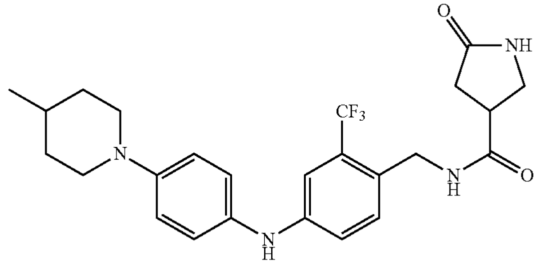 [SMILES: CC1CCN(c2ccc(Nc3ccc(CNC(=O)C4CNC(=O)C4)c(C(F)(F)F)c3)cc2)CC1]
488
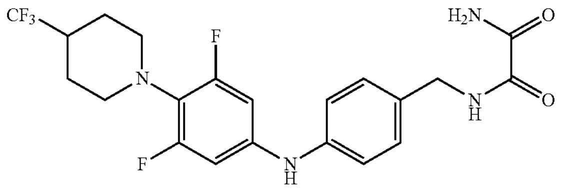 [SMILES: NC(=O)C(=O)NCc1ccc(Nc2cc(F)c(N3CCC(C(F)(F)F)CC3)c(F)c2)cc1]
489
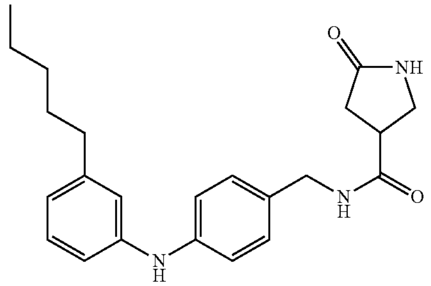 [SMILES: CCCCCc1cccc(Nc2ccc(CNC(=O)C3CNC(=O)C3)cc2)c1]
490
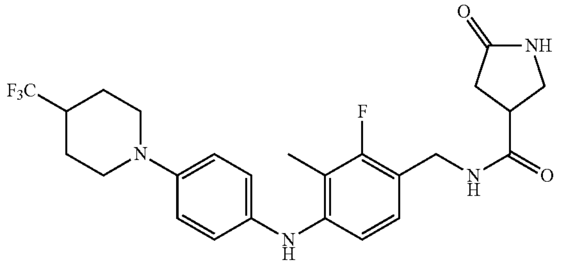 [SMILES: Cc1c(Nc2ccc(N3CCC(C(F)(F)F)CC3)cc2)ccc(CNC(=O)C2CNC(=O)C2)c1F]
491
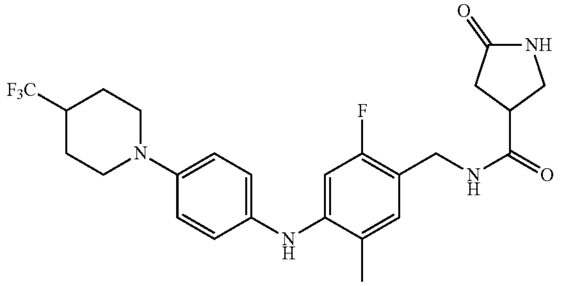 [SMILES: Cc1cc(CNC(=O)C2CNC(=O)C2)c(F)cc1Nc1ccc(N2CCC(C(F)(F)F)CC2)cc1]
492
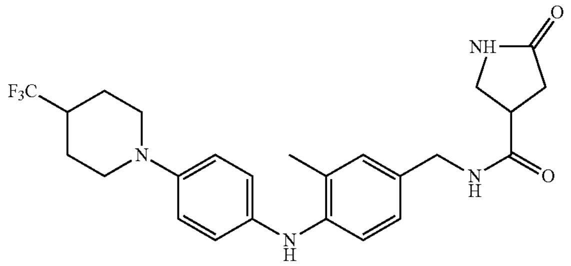 [SMILES: Cc1cc(CNC(=O)C2CNC(=O)C2)ccc1Nc1ccc(N2CCC(C(F)(F)F)CC2)cc1]
493

TABLE 2-continued
| Active Compounds: Structures |
| --- |
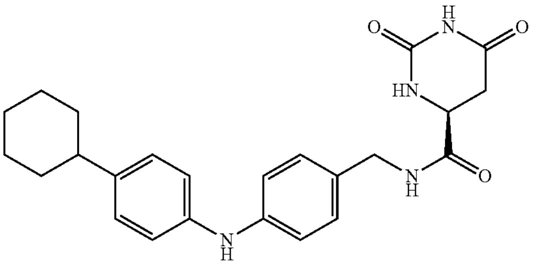 [SMILES: O=C1C[C@@H](C(=O)NCc2ccc(Nc3ccc(C4CCCCC4)cc3)cc2)NC(=O)N1]
494
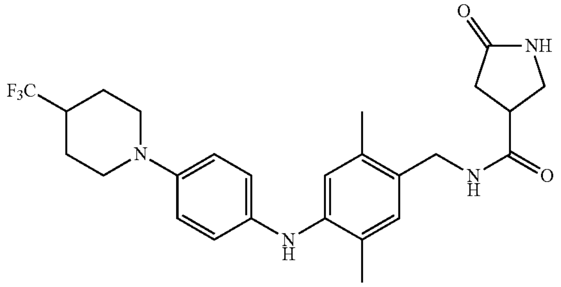 [SMILES: Cc1cc(Nc2ccc(N3CCC(C(F)(F)F)CC3)cc2)c(C)cc1CNC(=O)C1CNC(=O)C1]
495
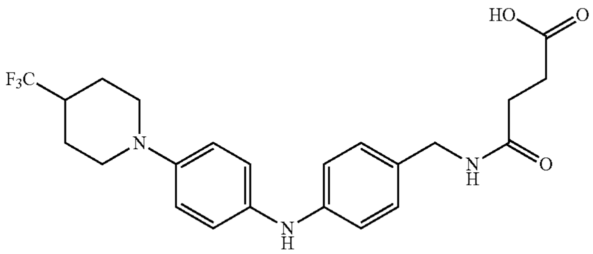 [SMILES: O=C(O)CCC(=O)NCc1ccc(Nc2ccc(N3CCC(C(F)(F)F)CC3)cc2)cc1]
496
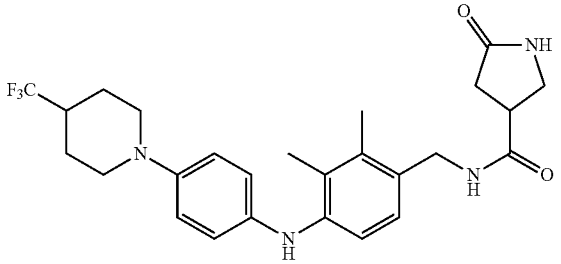 [SMILES: Cc1c(CNC(=O)C2CNC(=O)C2)ccc(Nc2ccc(N3CCC(C(F)(F)F)CC3)cc2)c1C]
497
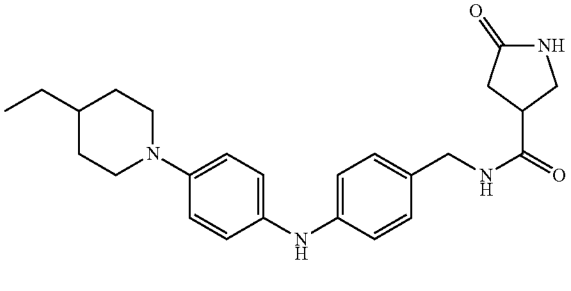 [SMILES: CCC1CCN(c2ccc(Nc3ccc(CNC(=O)C4CNC(=O)C4)cc3)cc2)CC1]
498

TABLE 2-continued
Active Compounds: Structures
499
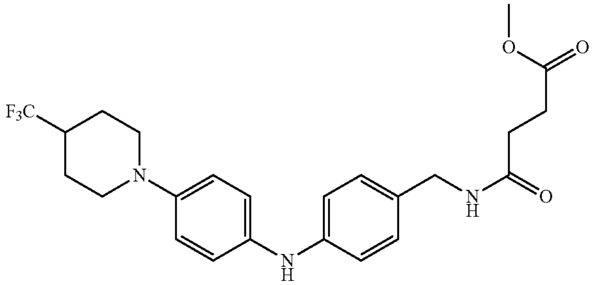 [SMILES: COC(=O)CCC(=O)NCc1ccc(Nc2ccc(N3CCC(C(F)(F)F)CC3)cc2)cc1]
500
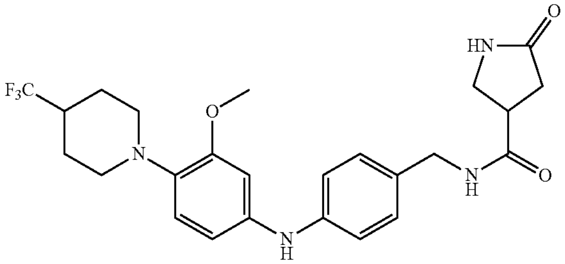 [SMILES: COc1cc(Nc2ccc(CNC(=O)C3CNC(=O)C3)cc2)ccc1N1CCC(C(F)(F)F)CC1]
501
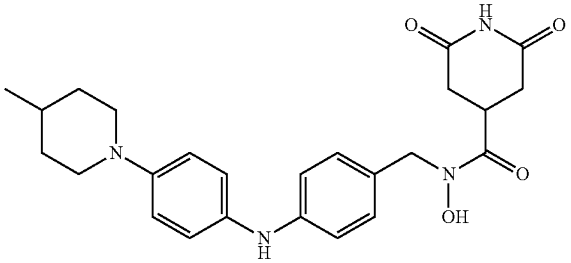 [SMILES: CC1CCN(c2ccc(Nc3ccc(CN(O)C(=O)C4CC(=O)NC(=O)C4)cc3)cc2)CC1]
502
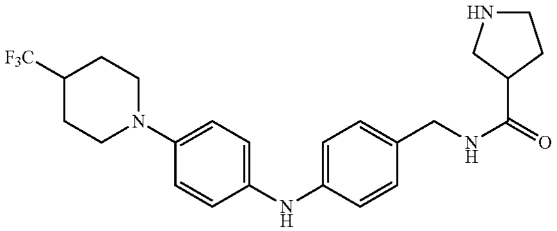 [SMILES: O=C(NCc1ccc(Nc2ccc(N3CCC(C(F)(F)F)CC3)cc2)cc1)C1CCNC1]
503
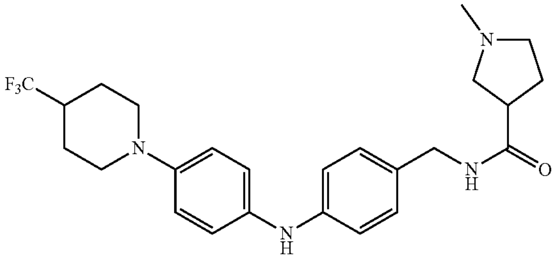 [SMILES: CN1CCC(C(=O)NCc2ccc(Nc3ccc(N4CCC(C(F)(F)F)CC4)cc3)cc2)C1]
504
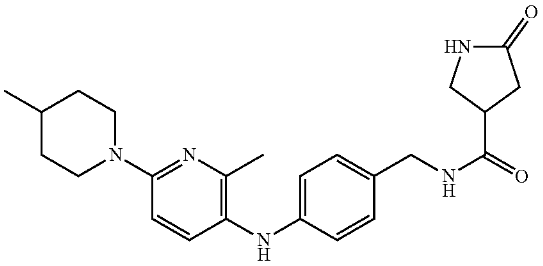 [SMILES: Cc1nc(N2CCC(C)CC2)ccc1Nc1ccc(CNC(=O)C2CNC(=O)C2)cc1]

TABLE 2-continued
Active Compounds: Structures
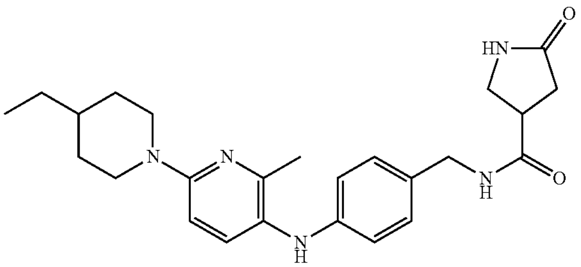 [SMILES: CCC1CCN(c2ccc(Nc3ccc(CNC(=O)C4CNC(=O)C4)cc3)c(C)n2)CC1]
505
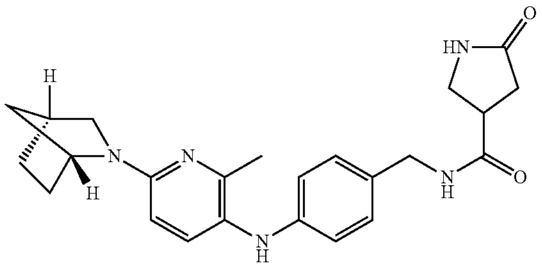 [SMILES: Cc1nc(N2C[C@H]3CC[C@@H]2C3)ccc1Nc1ccc(CNC(=O)C2CNC(=O)C2)cc1]
506
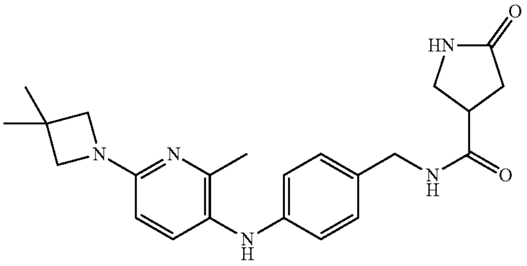 [SMILES: Cc1nc(N2CC(C)(C)C2)ccc1Nc1ccc(CNC(=O)C2CNC(=O)C2)cc1]
507
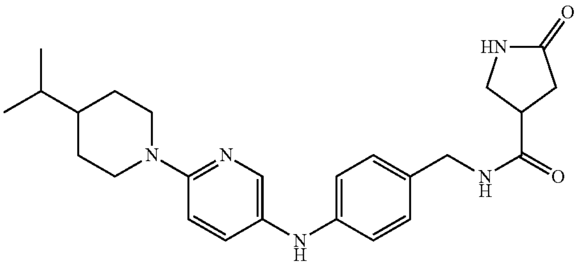 [SMILES: CC(C)C1CCN(c2ccc(Nc3ccc(CNC(=O)C4CNC(=O)C4)cc3)cn2)CC1]
508
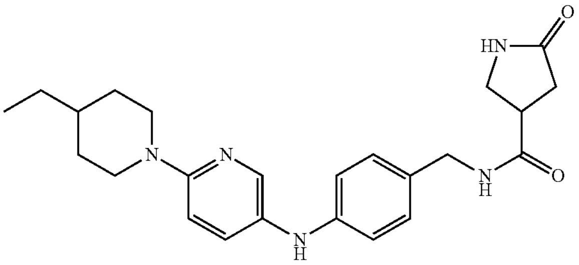 [SMILES: CCC1CCN(c2ccc(Nc3ccc(CNC(=O)C4CNC(=O)C4)cc3)cn2)CC1]
509

TABLE 2-continued
| Active Compounds: Structures |
|---|
| 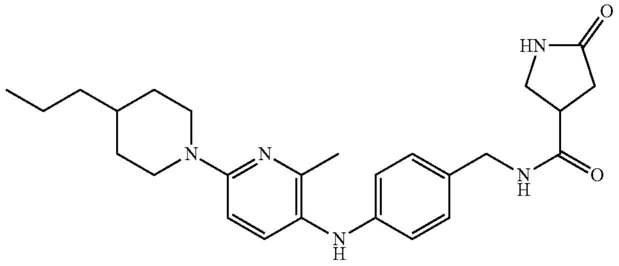 [SMILES: CCCC1CCN(c2ccc(Nc3ccc(CNC(=O)C4CNC(=O)C4)cc3)c(C)n2)CC1] 510 |
| 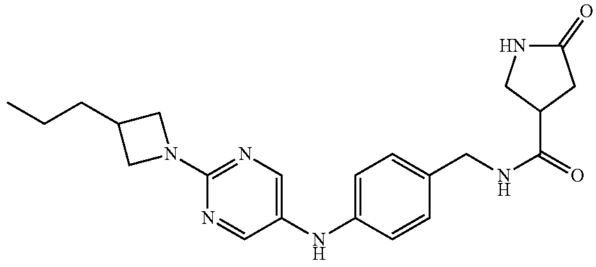 [SMILES: CCCC1CN(c2ncc(Nc3ccc(CNC(=O)C4CNC(=O)C4)cc3)cn2)C1] 511 |
| 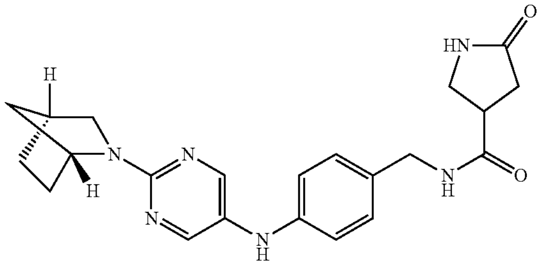 512 |
| 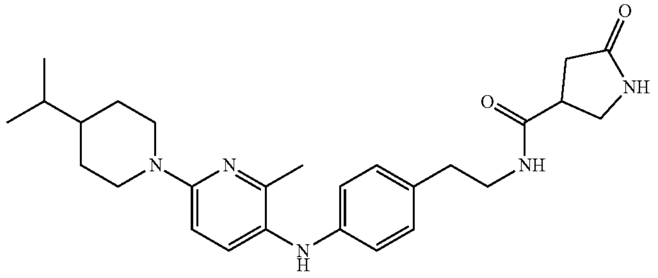 [SMILES: Cc1nc(N2CCC(C(C)C)CC2)ccc1Nc1ccc(CCNC(=O)C2CNC(=O)C2)cc1] 513 |
| 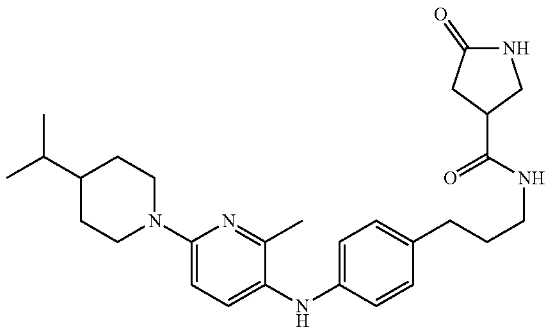 [SMILES: Cc1nc(N2CCC(C(C)C)CC2)ccc1Nc1ccc(CCCNC(=O)C2CNC(=O)C2)cc1] 514 |

TABLE 2-continued
Active Compounds: Structures
515
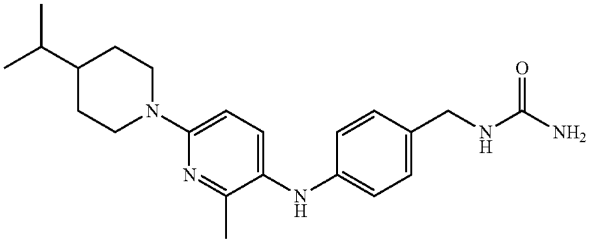 [SMILES: Cc1nc(N2CCC(C(C)C)CC2)ccc1Nc1ccc(CNC(N)=O)cc1]
516
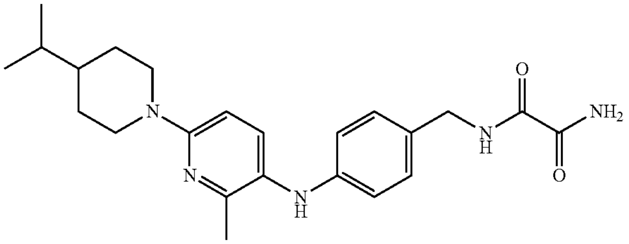 [SMILES: Cc1nc(N2CCC(C(C)C)CC2)ccc1Nc1ccc(CNC(=O)C(N)=O)cc1]
517
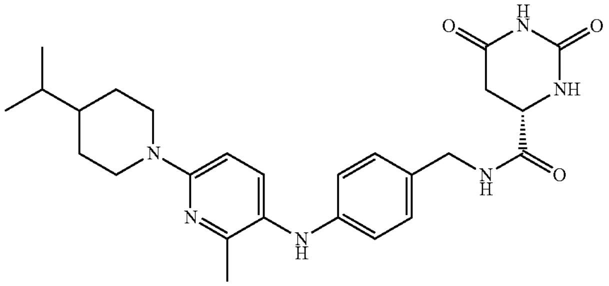 [SMILES: Cc1nc(N2CCC(C(C)C)CC2)ccc1Nc1ccc(CNC(=O)[C@@H]2CC(=O)NC(=O)N2)cc1]
518
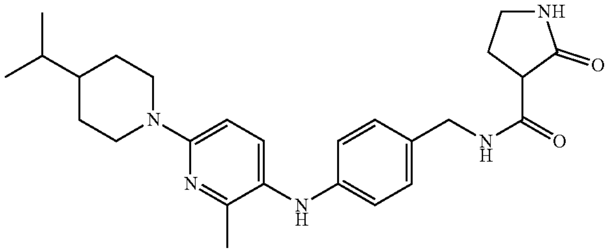 [SMILES: Cc1nc(N2CCC(C(C)C)CC2)ccc1Nc1ccc(CNC(=O)C2CCNC2=O)cc1]
519
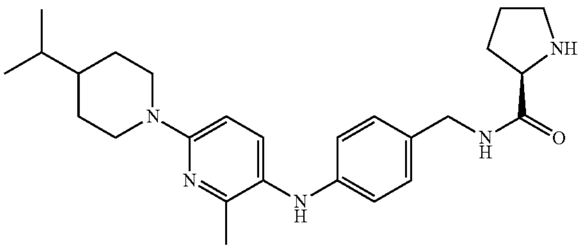 [SMILES: Cc1nc(N2CCC(C(C)C)CC2)ccc1Nc1ccc(CNC(=O)[C@H]2CCCN2)cc1]
520
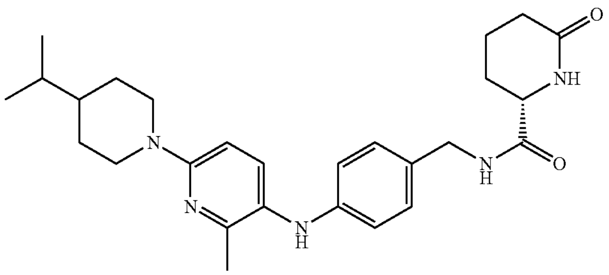 [SMILES: Cc1nc(N2CCC(C(C)C)CC2)ccc1Nc1ccc(CNC(=O)[C@@H]2CCCC(=O)N2)cc1]

TABLE 2-continued
| Active Compounds: Structures |
| --- |
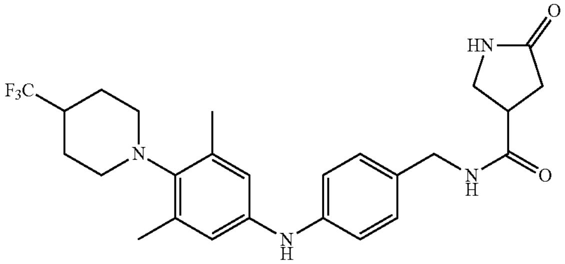 [SMILES: Cc1cc(Nc2ccc(CNC(=O)C3CNC(=O)C3)cc2)cc(C)c1N1CCC(C(F)(F)F)CC1]
521
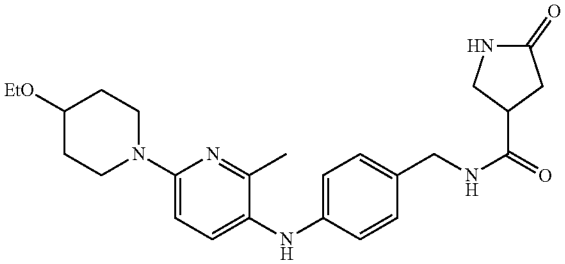 [SMILES: CCOC1CCN(c2ccc(Nc3ccc(CNC(=O)C4CNC(=O)C4)cc3)c(C)n2)CC1]
522
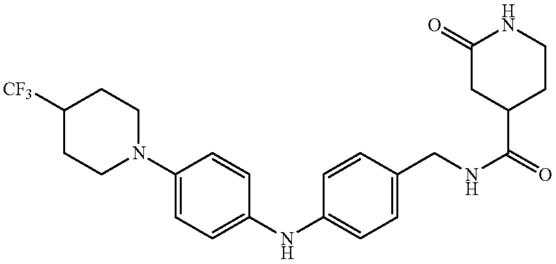 [SMILES: O=C1CC(C(=O)NCc2ccc(Nc3ccc(N4CCC(C(F)(F)F)CC4)cc3)cc2)CCN1]
523
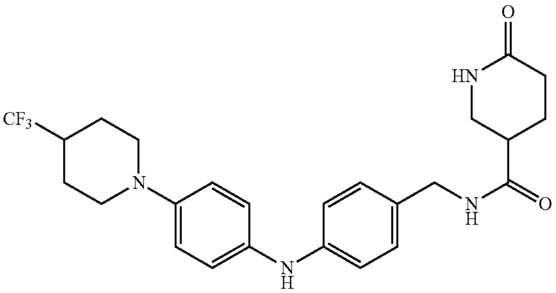 [SMILES: O=C1CCC(C(=O)NCc2ccc(Nc3ccc(N4CCC(C(F)(F)F)CC4)cc3)cc2)CN1]
524
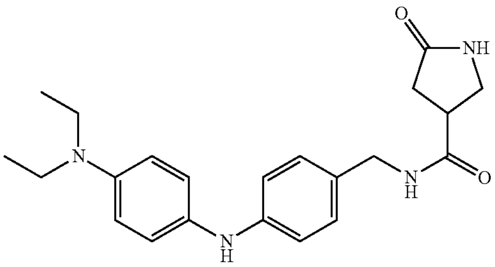 [SMILES: CCN(CC)c1ccc(Nc2ccc(CNC(=O)C3CNC(=O)C3)cc2)cc1]
525

TABLE 2-continued
| Active Compounds: Structures |
| --- |
| 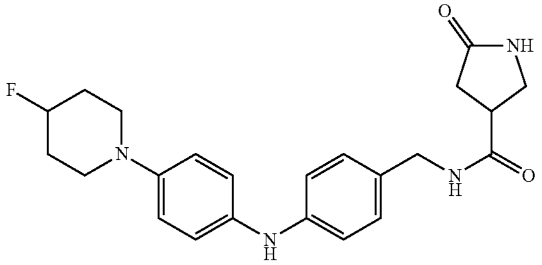 [SMILES: O=C1CC(C(=O)NCc2ccc(Nc3ccc(N4CCC(F)CC4)cc3)cc2)CN1] 526 |
| 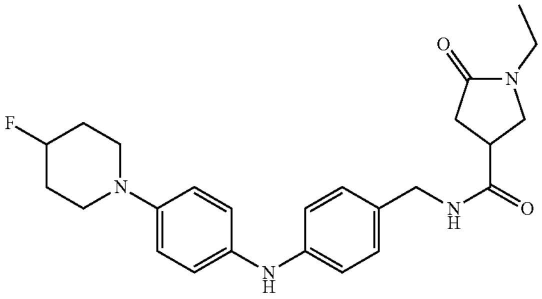 [SMILES: CCN1CC(C(=O)NCc2ccc(Nc3ccc(N4CCC(F)CC4)cc3)cc2)CC1=O] 527 |
| 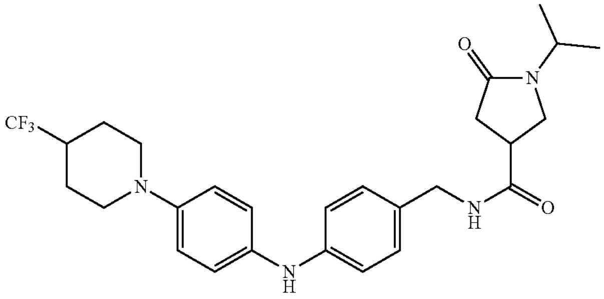 [SMILES: CC(C)N1CC(C(=O)NCc2ccc(Nc3ccc(N4CCC(C(F)(F)F)CC4)cc3)cc2)CC1=O] 528 |
| 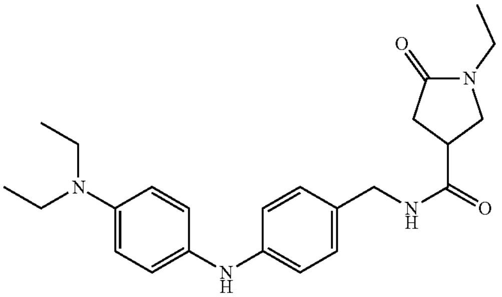 [SMILES: CCN1CC(C(=O)NCc2ccc(Nc3ccc(N(CC)CC)cc3)cc2)CC1=O] 529 |
| 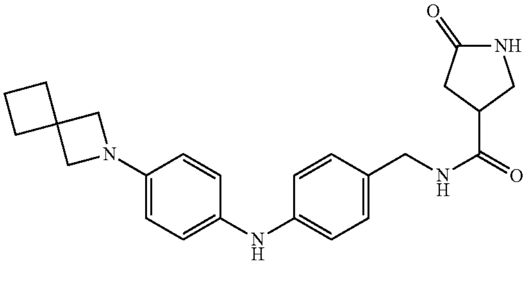 [SMILES: O=C1CC(C(=O)NCc2ccc(Nc3ccc(N4CC5(CCC5)C4)cc3)cc2)CN1] 530 |

TABLE 2-continued
| Active Compounds: Structures |
| --- |
| 531 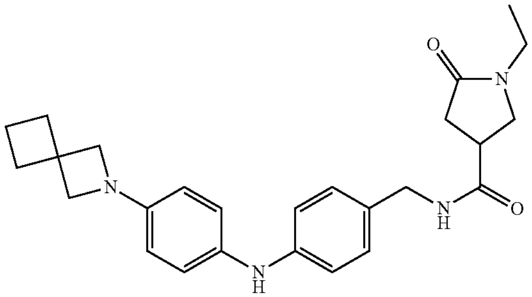 [SMILES: CCN1CC(C(=O)NCc2ccc(Nc3ccc(N4CC5(CCC5)C4)cc3)cc2)CC1=O] |
| 532 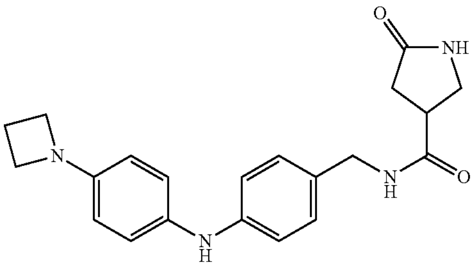 [SMILES: O=C1CC(C(=O)NCc2ccc(Nc3ccc(N4CCC4)cc3)cc2)CN1] |
| 533 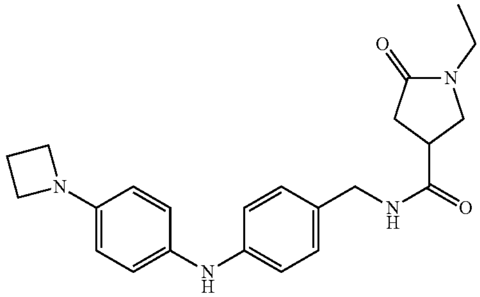 [SMILES: CCN1CC(C(=O)NCc2ccc(Nc3ccc(N4CCC4)cc3)cc2)CC1=O] |
| 534 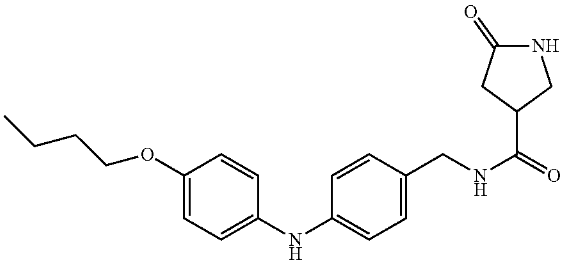 |
| 535 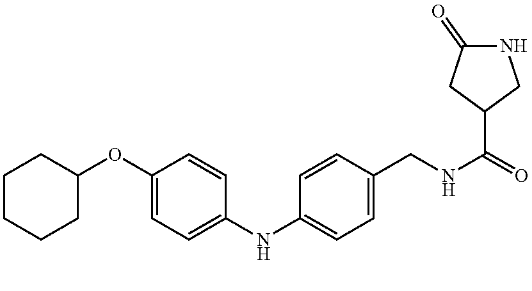 [SMILES: O=C1CC(C(=O)NCc2ccc(Nc3ccc(OC4CCCCC4)cc3)cc2)CN1] |

TABLE 2-continued
| Active Compounds: Structures |
|---|
536
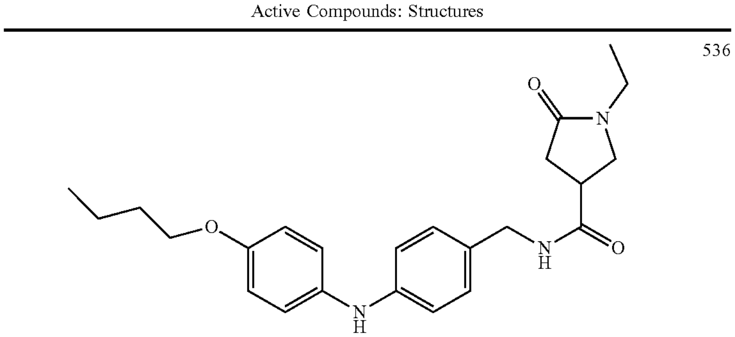
537
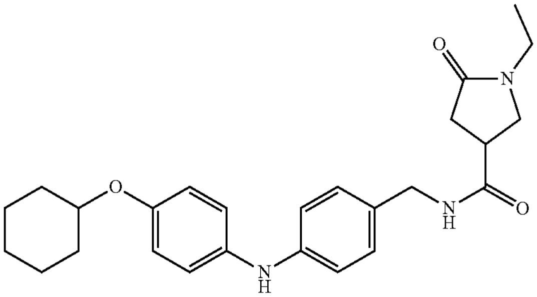 [SMILES: CCN1CC(C(=O)NCc2ccc(Nc3ccc(OC4CCCCC4)cc3)cc2)CC1=O]
538
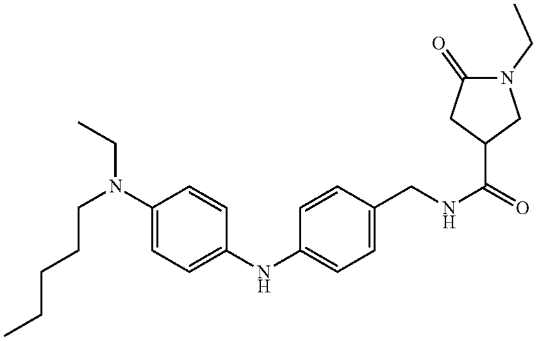 [SMILES: CCCCCN(CC)c1ccc(Nc2ccc(CNC(=O)C3CC(=O)N(CC)C3)cc2)cc1]
539
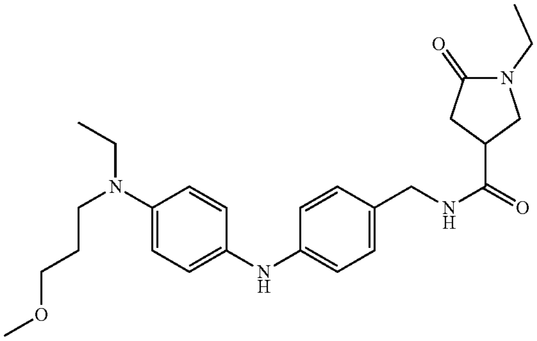 [SMILES: CCN1CC(C(=O)NCc2ccc(Nc3ccc(N(CC)CCCOC)cc3)cc2)CC1=O]
540
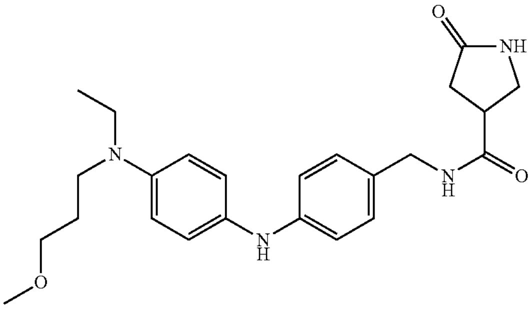 [SMILES: CCN(CCCOC)c1ccc(Nc2ccc(CNC(=O)C3CNC(=O)C3)cc2)cc1]

TABLE 2-continued
| Active Compounds: Structures |
|---|
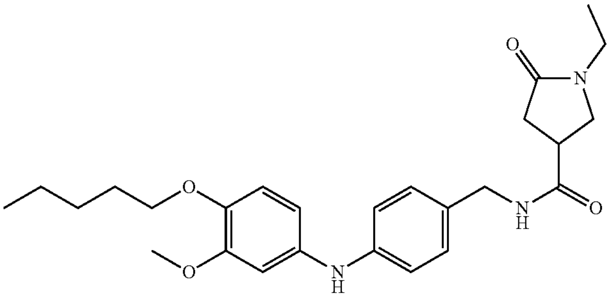 [SMILES: CCCCCOc1ccc(Nc2ccc(CNC(=O)C3CC(=O)N(CC)C3)cc2)cc1OC]
541
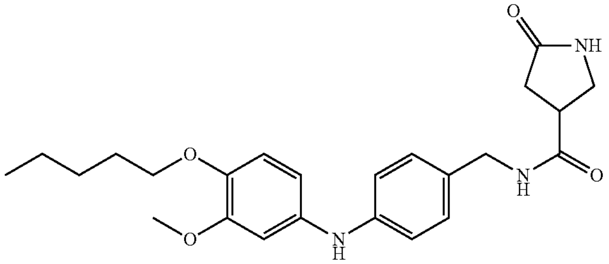 [SMILES: CCCCCOc1ccc(Nc2ccc(CNC(=O)C3CNC(=O)C3)cc2)cc1OC]
542
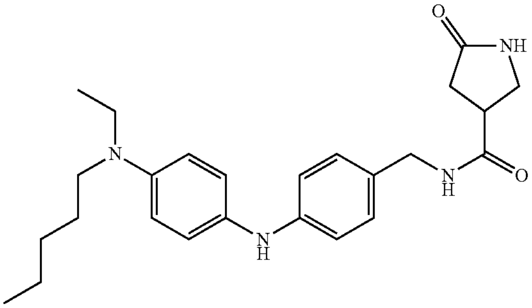 [SMILES: CCCCCN(CC)c1ccc(Nc2ccc(CNC(=O)C3CNC(=O)C3)cc2)cc1]
543
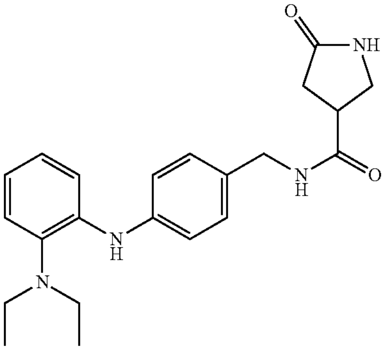 [SMILES: CCN(CC)c1ccccc1Nc1ccc(CNC(=O)C2CNC(=O)C2)cc1]
544

TABLE 2-continued
Active Compounds: Structures
545
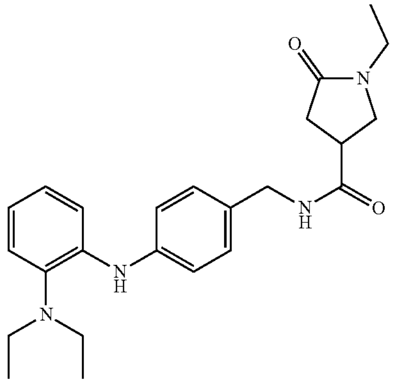 [SMILES: CCN1CC(C(=O)NCc2ccc(Nc3ccccc3N(CC)CC)cc2)CC1=O]
546
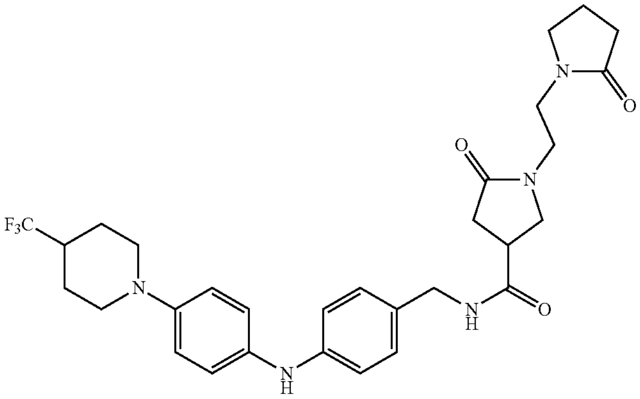 [SMILES: O=C(NCc1ccc(Nc2ccc(N3CCC(C(F)(F)F)CC3)cc2)cc1)C1CC(=O)N(CCN2CCCC2=O)C1]
547
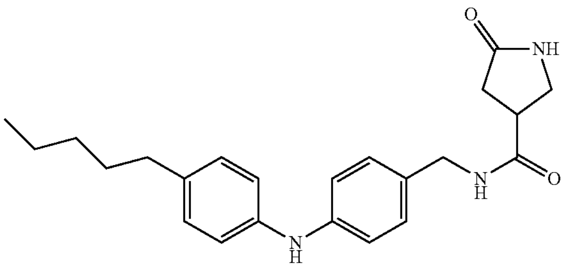 [SMILES: CCCCCc1ccc(Nc2ccc(CNC(=O)C3CNC(=O)C3)cc2)cc1]
548
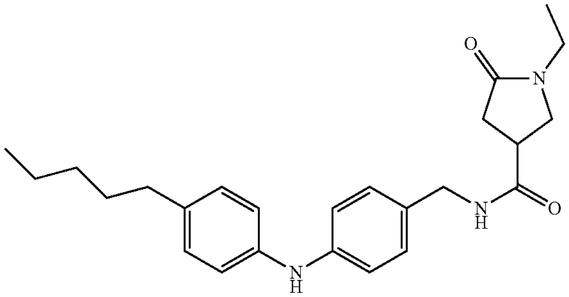

TABLE 2-continued
| Active Compounds: Structures |
| --- |
| 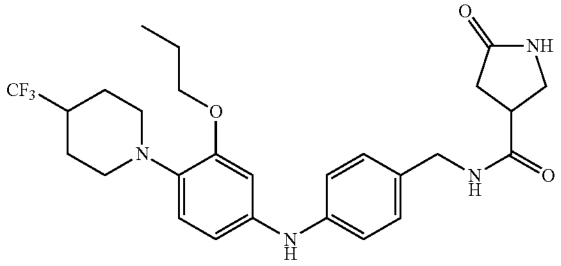 [SMILES: CCCOc1cc(Nc2ccc(CNC(=O)C3CNC(=O)C3)cc2)ccc1N1CCC(C(F)(F)F)CC1] 549 |
| 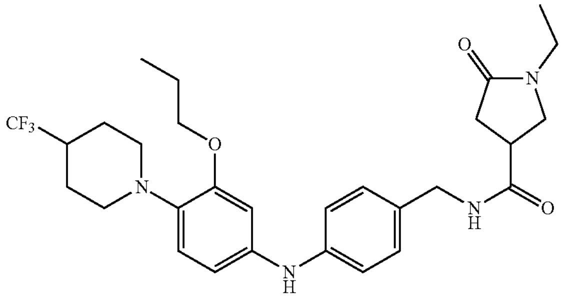 [SMILES: CCCOc1cc(Nc2ccc(CNC(=O)C3CC(=O)N(CC)C3)cc2)ccc1N1CCC(C(F)(F)F)CC1] 550 |
| 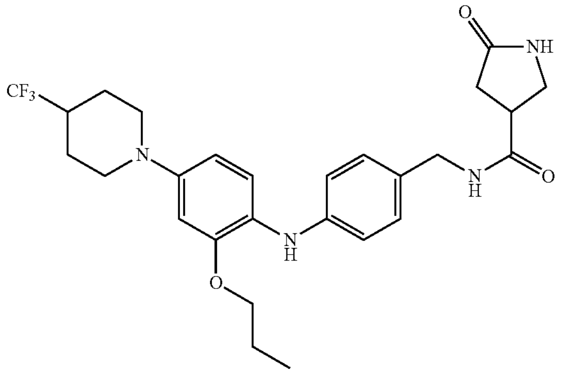 [SMILES: CCCOc1cc(N2CCC(C(F)(F)F)CC2)ccc1Nc1ccc(CNC(=O)C2CNC(=O)C2)cc1] 551 |
| 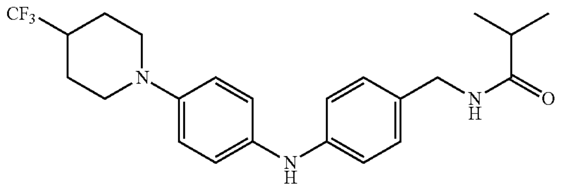 [SMILES: CC(C)C(=O)NCc1ccc(Nc2ccc(N3CCC(C(F)(F)F)CC3)cc2)cc1] 552 |
| 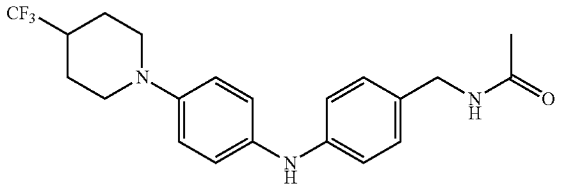 [SMILES: CC(=O)NCc1ccc(Nc2ccc(N3CCC(C(F)(F)F)CC3)cc2)cc1] 553 |

TABLE 2-continued
Active Compounds: Structures
554
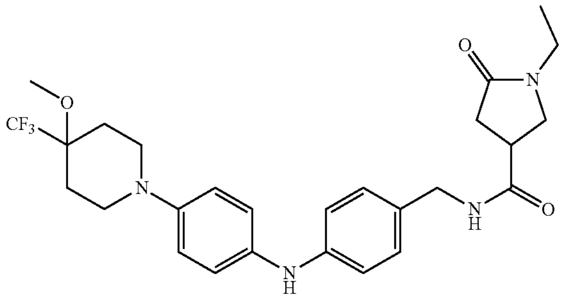 [SMILES: CCN1CC(C(=O)NCc2ccc(Nc3ccc(N4CCC(OC)(C(F)(F)F)CC4)cc3)cc2)CC1=O]
555
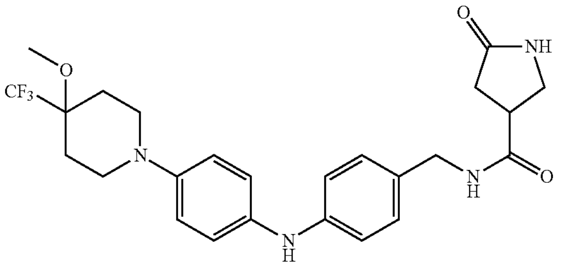 [SMILES: COC1(C(F)(F)F)CCN(c2ccc(Nc3ccc(CNC(=O)C4CNC(=O)C4)cc3)cc2)CC1]
556
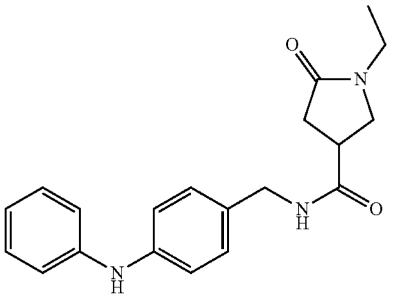 [SMILES: CCN1CC(C(=O)NCc2ccc(Nc3ccccc3)cc2)CC1=O]
557
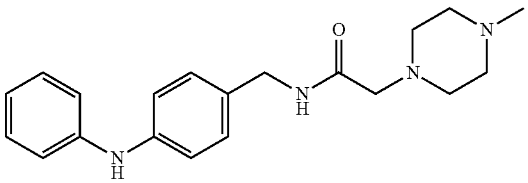 [SMILES: CN1CCN(CC(=O)NCc2ccc(Nc3ccccc3)cc2)CC1]
558
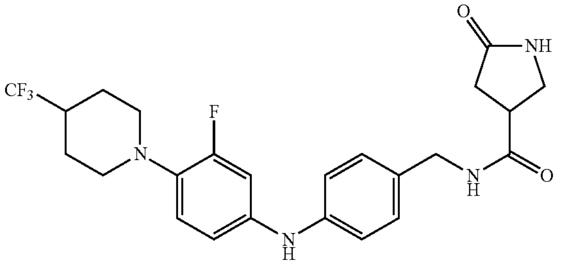 [SMILES: O=C1CC(C(=O)NCc2ccc(Nc3ccc(N4CCC(C(F)(F)F)CC4)c(F)c3)cc2)CN1]

TABLE 2-continued
| Active Compounds: Structures |
| --- |
| 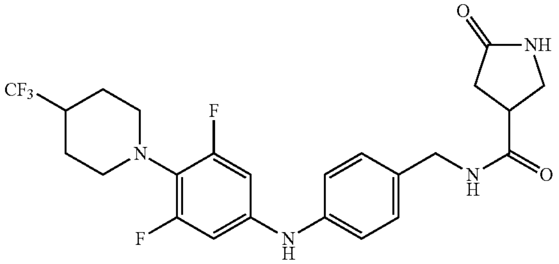 [SMILES: O=C1CC(C(=O)NCc2ccc(Nc3cc(F)c(N4CCC(C(F)(F)F)CC4)c(F)c3)cc2)CN1] 559 |
| 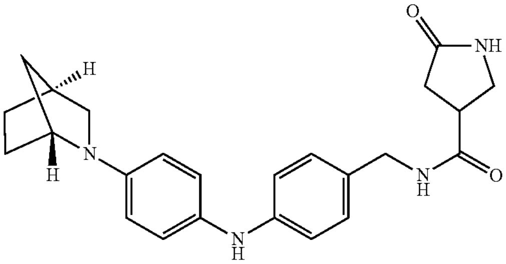 [SMILES: O=C1CC(C(=O)NCc2ccc(Nc3ccc(N4C[C@H]5CC[C@@H]4C5)cc3)cc2)CN1] 560 |
| 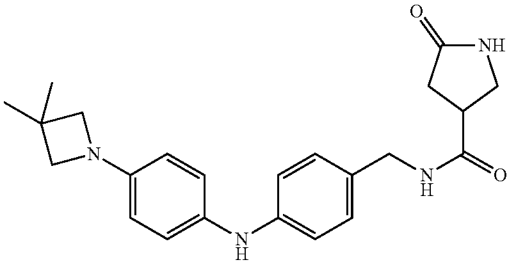 [SMILES: CC1(C)CN(c2ccc(Nc3ccc(CNC(=O)C4CNC(=O)C4)cc3)cc2)C1] 561 |
| 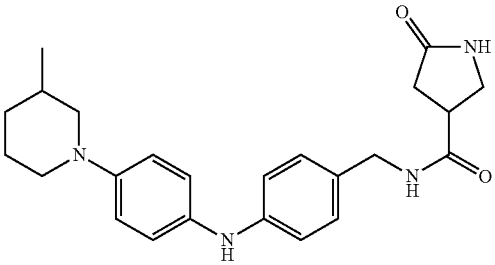 [SMILES: CC1CCCN(c2ccc(Nc3ccc(CNC(=O)C4CNC(=O)C4)cc3)cc2)C1] 562 |
| 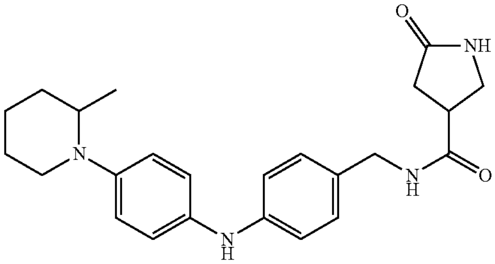 [SMILES: CC1CCCCN1c1ccc(Nc2ccc(CNC(=O)C3CNC(=O)C3)cc2)cc1] 563 |
| 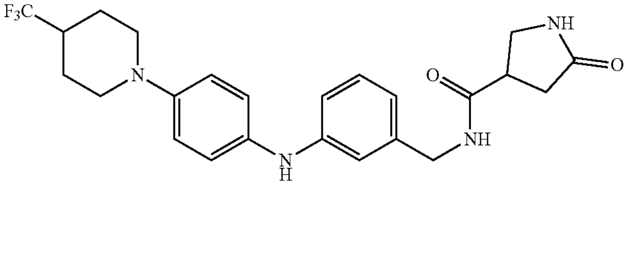 [SMILES: O=C1CC(C(=O)NCc2cccc(Nc3ccc(N4CCC(C(F)(F)F)CC4)cc3)c2)CN1] 564 |

TABLE 2-continued
| Active Compounds: Structures |
| --- |
| 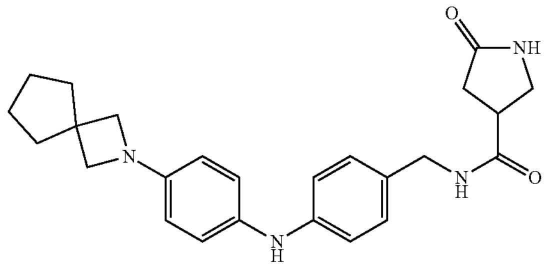 [SMILES: O=C1CC(C(=O)NCc2ccc(Nc3ccc(N4CC5(CCCC5)C4)cc3)cc2)CN1] 565 |
| 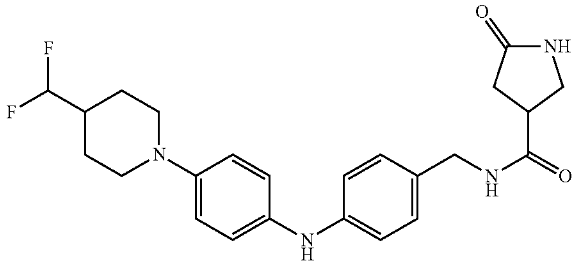 [SMILES: O=C1CC(C(=O)NCc2ccc(Nc3ccc(N4CCC(C(F)F)CC4)cc3)cc2)CN1] 566 |
| 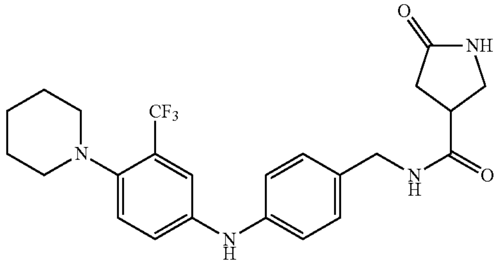 [SMILES: O=C1CC(C(=O)NCc2ccc(Nc3ccc(N4CCCCC4)c(C(F)(F)F)c3)cc2)CN1] 567 |
| 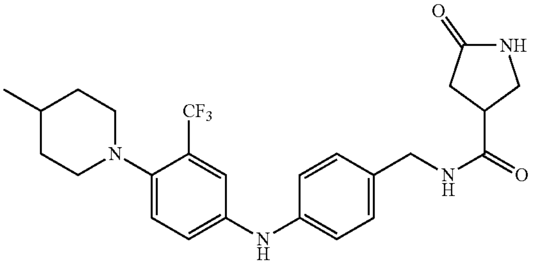 [SMILES: CC1CCN(c2ccc(Nc3ccc(CNC(=O)C4CNC(=O)C4)cc3)cc2C(F)(F)F)CC1] 568 |
| 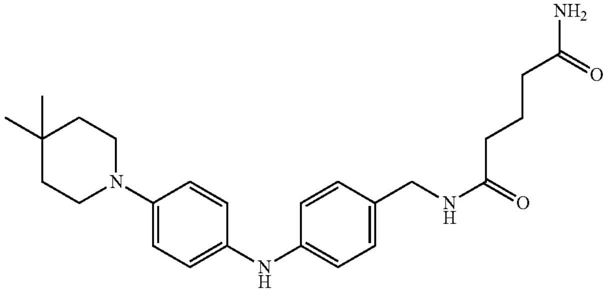 [SMILES: CC1(C)CCN(c2ccc(Nc3ccc(CNC(=O)CCCC(N)=O)cc3)cc2)CC1] 569 |

TABLE 2-continued
Active Compounds: Structures
570
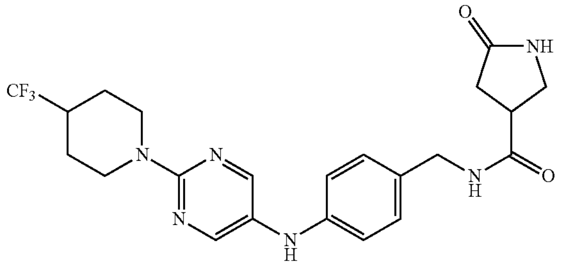 [SMILES: O=C1CC(C(=O)NCc2ccc(Nc3cnc(N4CCC(C(F)(F)F)CC4)nc3)cc2)CN1]
571
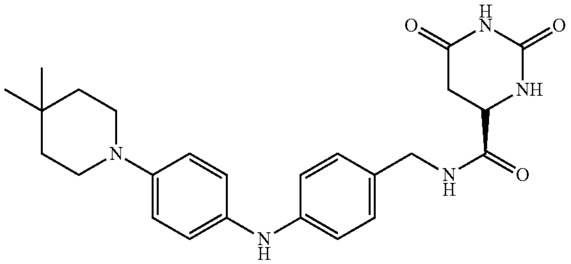
572
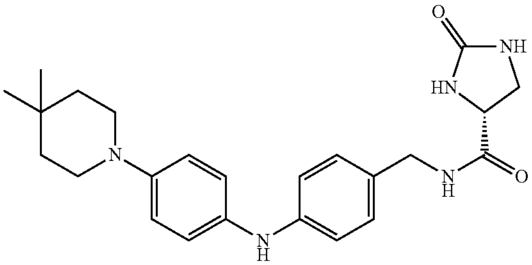 [SMILES: CC1(C)CCN(c2ccc(Nc3ccc(CNC(=O)[C@H]4CNC(=O)N4)cc3)cc2)CC1]
573
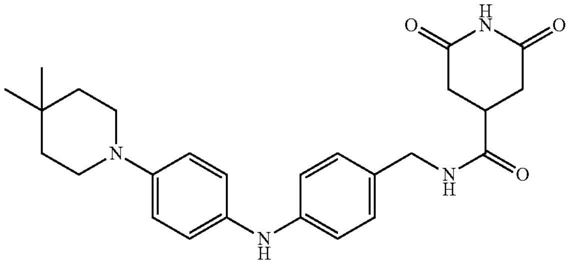 [SMILES: CC1(C)CCN(c2ccc(Nc3ccc(CNC(=O)C4CC(=O)NC(=O)C4)cc3)cc2)CC1]
574
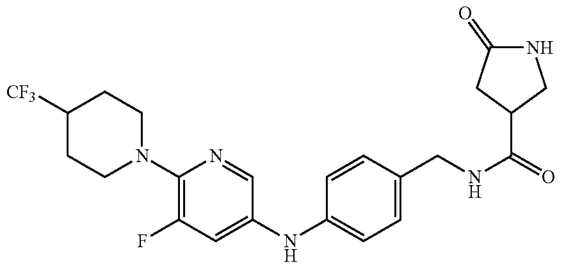 [SMILES: O=C1CC(C(=O)NCc2ccc(Nc3cnc(N4CCC(C(F)(F)F)CC4)c(F)c3)cc2)CN1]

TABLE 2-continued
| Active Compounds: Structures |
| --- |
| 575 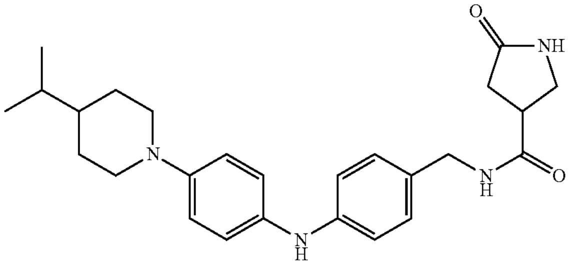 [SMILES: CC(C)C1CCN(c2ccc(Nc3ccc(CNC(=O)C4CNC(=O)C4)cc3)cc2)CC1] |
| 576 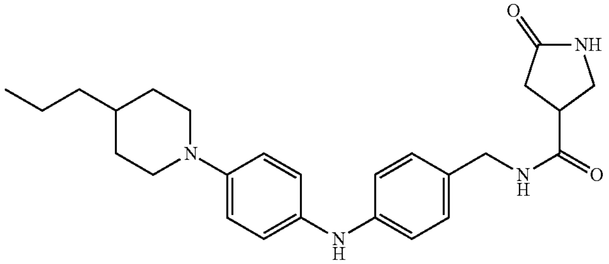 [SMILES: CCCC1CCN(c2ccc(Nc3ccc(CNC(=O)C4CNC(=O)C4)cc3)cc2)CC1] |
| 577 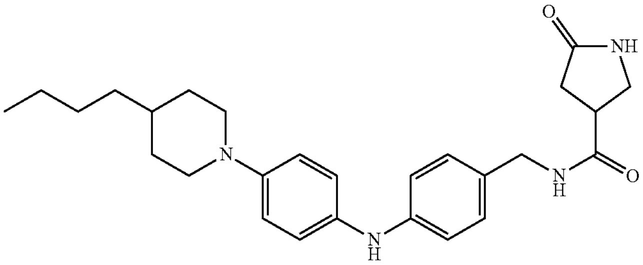 [SMILES: CCCCC1CCN(c2ccc(Nc3ccc(CNC(=O)C4CNC(=O)C4)cc3)cc2)CC1] |
| 578 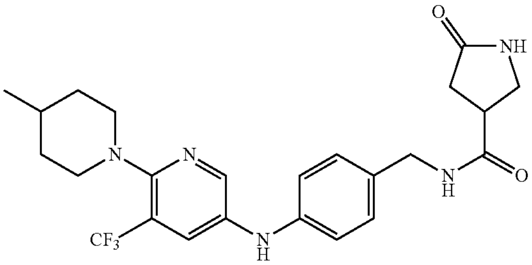 [SMILES: CC1CCN(c2ncc(Nc3ccc(CNC(=O)C4CNC(=O)C4)cc3)cc2C(F)(F)F)CC1] |
| 579 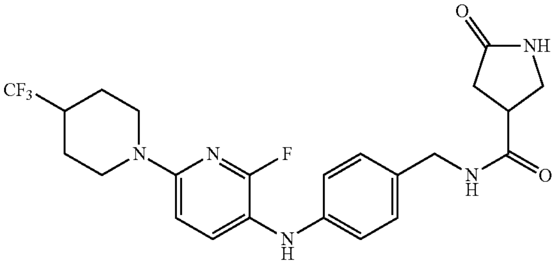 [SMILES: O=C1CC(C(=O)NCc2ccc(Nc3ccc(N4CCC(C(F)(F)F)CC4)nc3F)cc2)CN1] |

TABLE 2-continued
Active Compounds: Structures
580
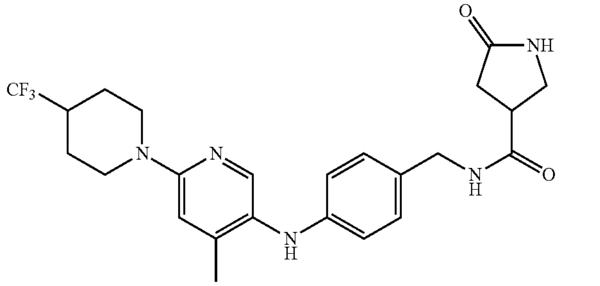 [SMILES: Cc1cc(N2CCC(C(F)(F)F)CC2)ncc1Nc1ccc(CNC(=O)C2CNC(=O)C2)cc1]
581
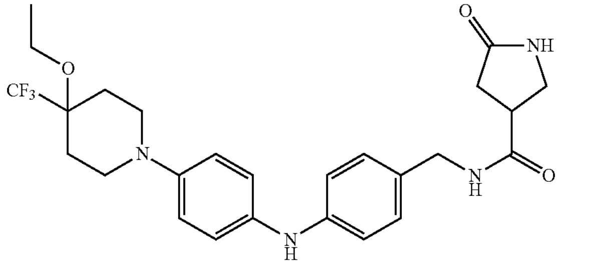 [SMILES: CCOC1(C(F)(F)F)CCN(c2ccc(Nc3ccc(CNC(=O)C4CNC(=O)C4)cc3)cc2)CC1]
582
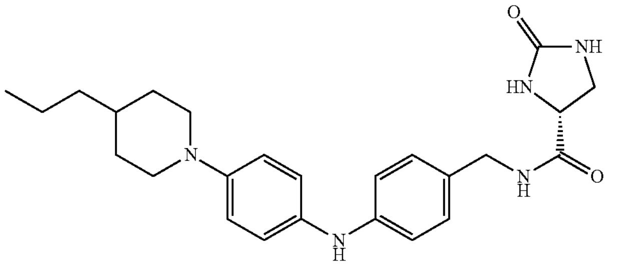 [SMILES: CCCC1CCN(c2ccc(Nc3ccc(CNC(=O)[C@H]4CNC(=O)N4)cc3)cc2)CC1]
583
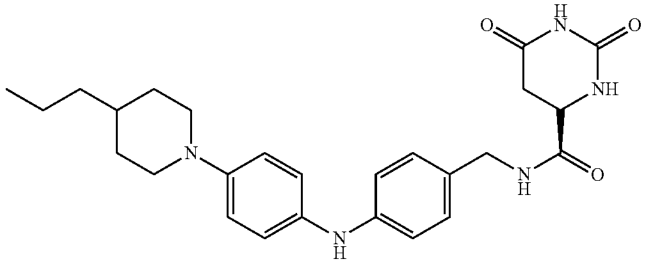
584
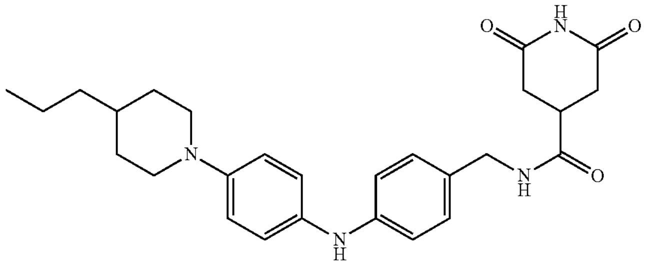 [SMILES: CCCC1CCN(c2ccc(Nc3ccc(CNC(=O)C4CC(=O)NC(=O)C4)cc3)cc2)CC1]
585
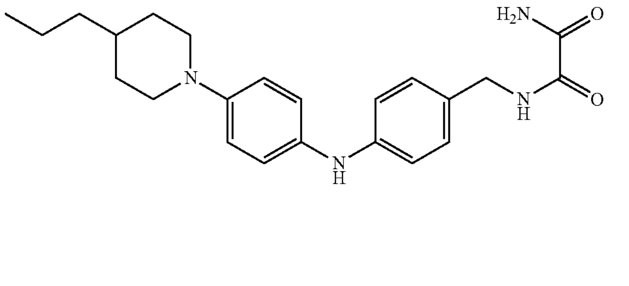 [SMILES: CCCC1CCN(c2ccc(Nc3ccc(CNC(=O)C(N)=O)cc3)cc2)CC1]

TABLE 2-continued
| Active Compounds: Structures |
|---|
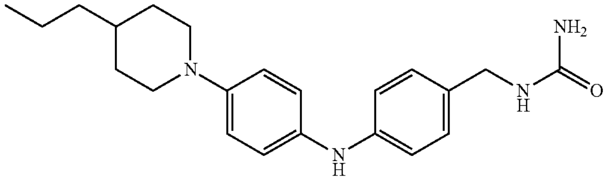 [SMILES: CCCC1CCN(c2ccc(Nc3ccc(CNC(N)=O)cc3)cc2)CC1]
586
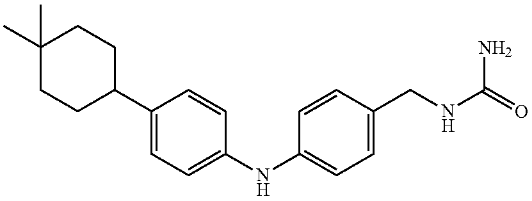 [SMILES: CC1(C)CCC(c2ccc(Nc3ccc(CNC(N)=O)cc3)cc2)CC1]
587
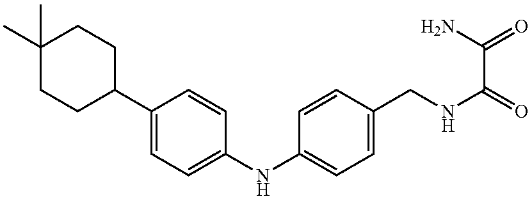 [SMILES: CC1(C)CCC(c2ccc(Nc3ccc(CNC(=O)C(N)=O)cc3)cc2)CC1]
588
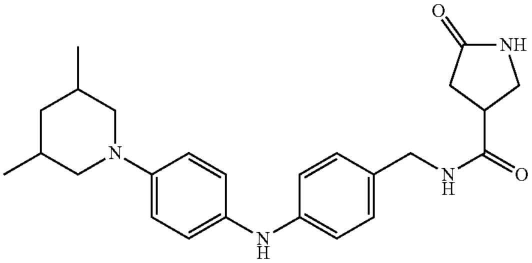 [SMILES: CC1CC(C)CN(c2ccc(Nc3ccc(CNC(=O)C4CNC(=O)C4)cc3)cc2)C1]
589
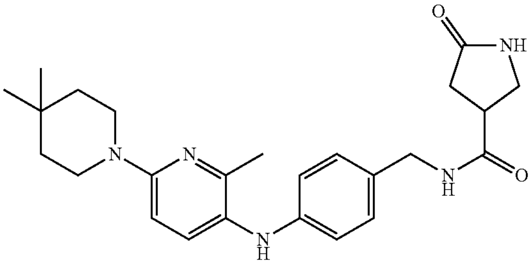 [SMILES: Cc1nc(N2CCC(C)(C)CC2)ccc1Nc1ccc(CNC(=O)C2CNC(=O)C2)cc1]
590
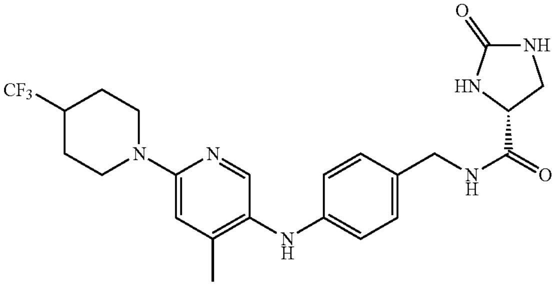 [SMILES: Cc1cc(N2CCC(C(F)(F)F)CC2)ncc1Nc1ccc(CNC(=O)[C@H]2CNC(=O)N2)cc1]
591

TABLE 2-continued
| Active Compounds: Structures |
|---|
| 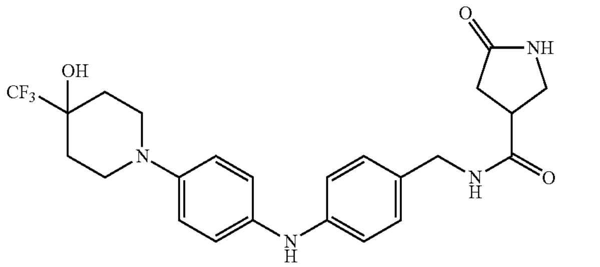 [SMILES: O=C1CC(C(=O)NCc2ccc(Nc3ccc(N4CCC(O)(C(F)(F)F)CC4)cc3)cc2)CN1] 592 |
| 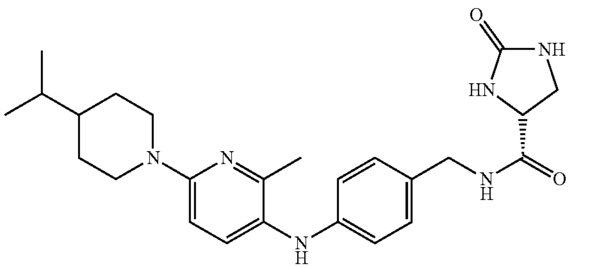 593 |
| 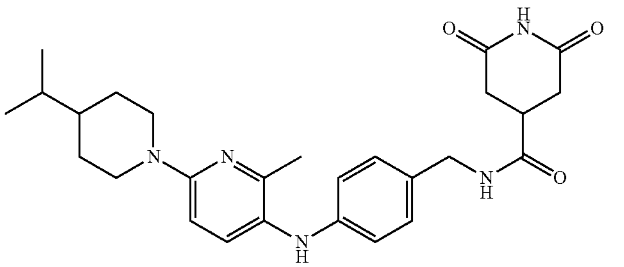 [SMILES: Cc1nc(N2CCC(C(C)C)CC2)ccc1Nc1ccc(CNC(=O)C2CC(=O)NC(=O)C2)cc1] 594 |
| 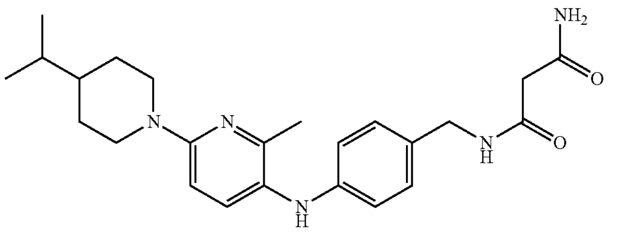 [SMILES: Cc1nc(N2CCC(C(C)C)CC2)ccc1Nc1ccc(CNC(=O)CC(N)=O)cc1] 595 |
| 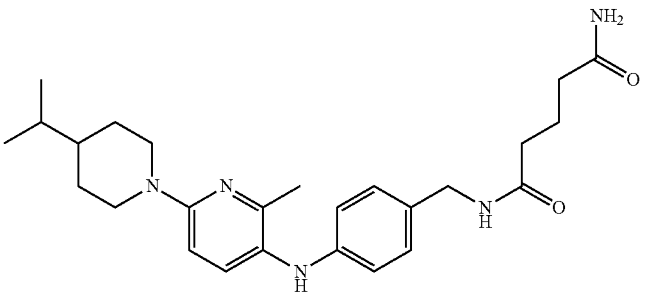 [SMILES: Cc1nc(N2CCC(C(C)C)CC2)ccc1Nc1ccc(CNC(=O)CCCC(N)=O)cc1] 596 |
| 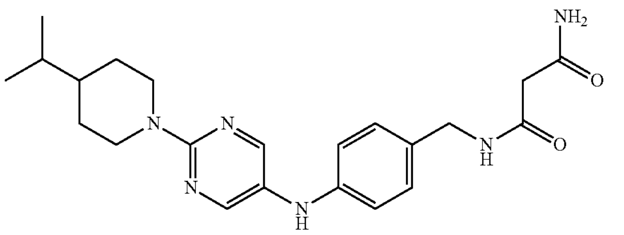 [SMILES: CC(C)C1CCN(c2ncc(Nc3ccc(CNC(=O)CC(N)=O)cc3)cn2)CC1] 597 |

TABLE 2-continued
| Active Compounds: Structures | |
|---|---|
| 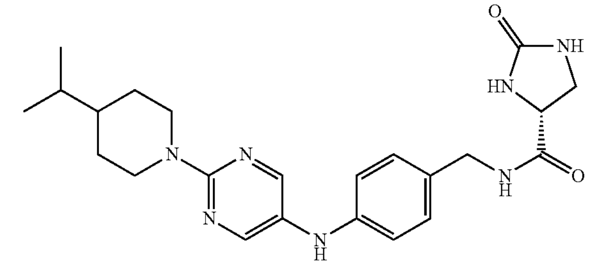 [SMILES: CC(C)C1CCN(c2ncc(Nc3ccc(CNC(=O)[C@H]4CNC(=O)N4)cc3)cn2)CC1] | 598 |
| 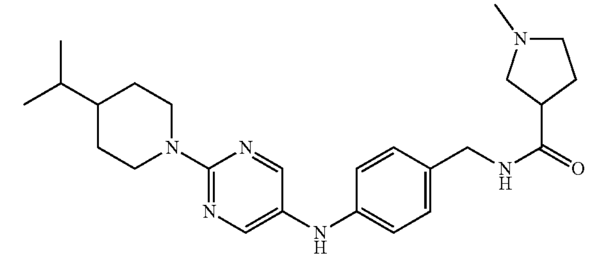 [SMILES: CC(C)C1CCN(c2ncc(Nc3ccc(CNC(=O)C4CCN(C)C4)cc3)cn2)CC1] | 599 |
| 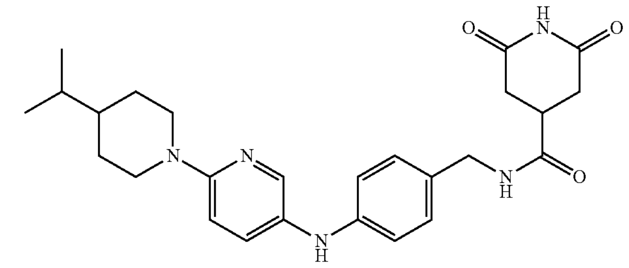 [SMILES: CC(C)C1CCN(c2ccc(Nc3ccc(CNC(=O)C4CC(=O)NC(=O)C4)cc3)cn2)CC1] | 600 |
| 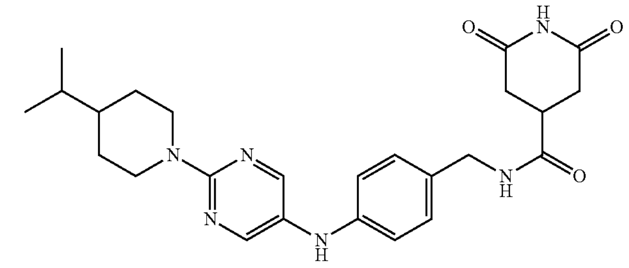 [SMILES: CC(C)C1CCN(c2ncc(Nc3ccc(CNC(=O)C4CC(=O)NC(=O)C4)cc3)cn2)CC1] | 601 |
| 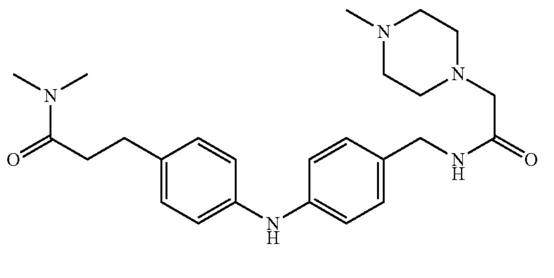 [SMILES: CN1CCN(CC(=O)NCc2ccc(Nc3ccc(CCC(=O)N(C)C)cc3)cc2)CC1] | 602 |
| 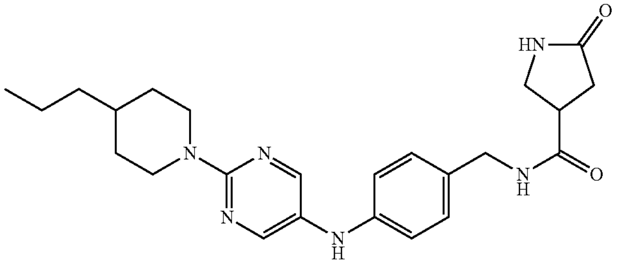 [SMILES: CCCC1CCN(c2ncc(Nc3ccc(CNC(=O)C4CNC(=O)C4)cc3)cn2)CC1] | 603 |

TABLE 2-continued
Active Compounds: Structures
604
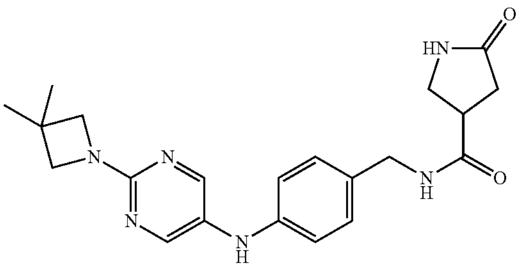 [SMILES: CC1(C)CN(c2ncc(Nc3ccc(CNC(=O)C4CNC(=O)C4)cc3)cn2)C1]
605
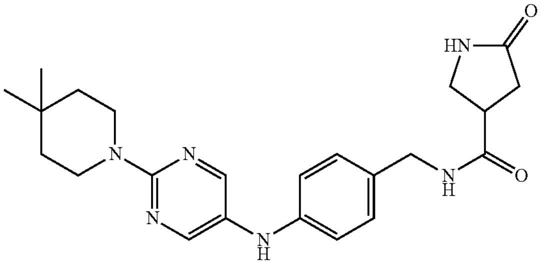 [SMILES: CC1(C)CCN(c2ncc(Nc3ccc(CNC(=O)C4CNC(=O)C4)cc3)cn2)CC1]
606
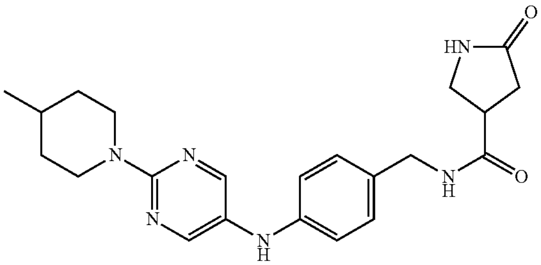 [SMILES: CC1CCN(c2ncc(Nc3ccc(CNC(=O)C4CNC(=O)C4)cc3)cn2)CC1]
607
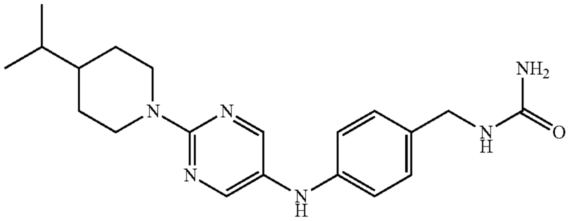 [SMILES: CC(C)C1CCN(c2ncc(Nc3ccc(CNC(N)=O)cc3)cn2)CC1]
608
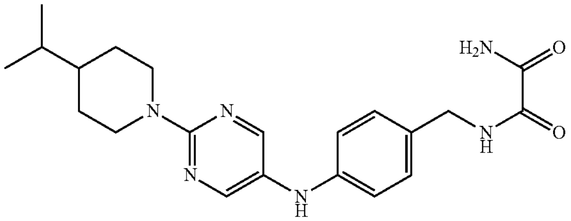 [SMILES: CC(C)C1CCN(c2ncc(Nc3ccc(CNC(=O)C(N)=O)cc3)cn2)CC1]
609
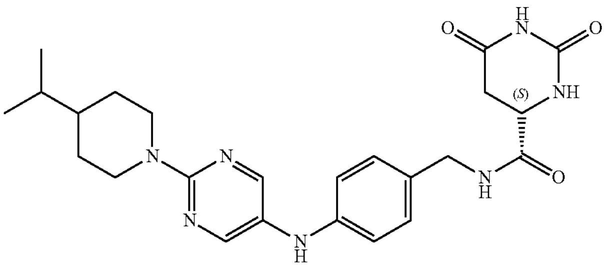

TABLE 2-continued
| Active Compounds: Structures | |
|---|---|
| 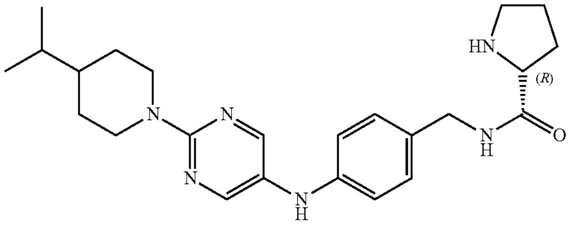 | 610 |
| 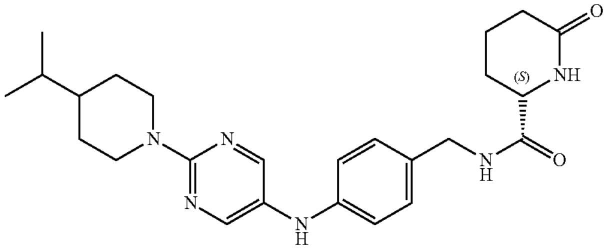 | 611 |
| 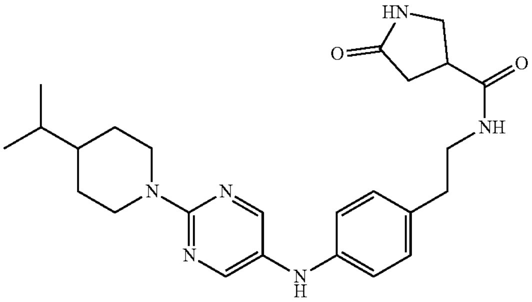 [SMILES: CC(C)C1CCN(c2ncc(Nc3ccc(CCNC(=O)C4CNC(=O)C4)cc3)cn2)CC1] | 612 |
| 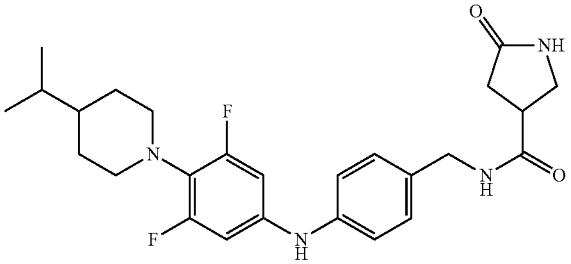 [SMILES: CC(C)C1CCN(c2c(F)cc(Nc3ccc(CNC(=O)C4CNC(=O)C4)cc3)cc2F)CC1] | 613 |
| 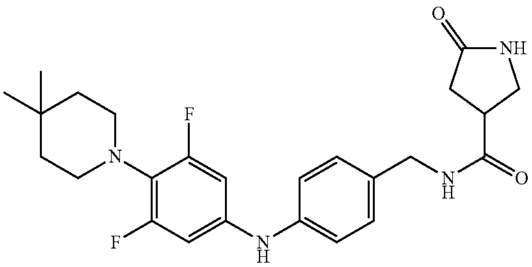 [SMILES: CC1(C)CCN(c2c(F)cc(Nc3ccc(CNC(=O)C4CNC(=O)C4)cc3)cc2F)CC1] | 614 |
| 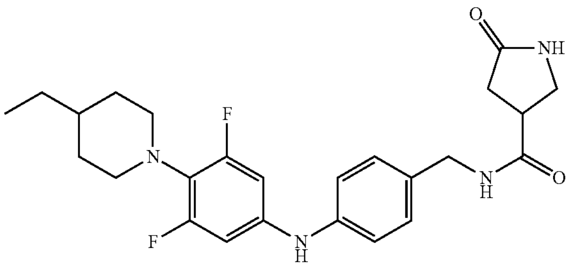 [SMILES: CCC1CCN(c2c(F)cc(Nc3ccc(CNC(=O)C4CNC(=O)C4)cc3)cc2F)CC1] | 615 |

TABLE 2-continued
Active Compounds: Structures
616
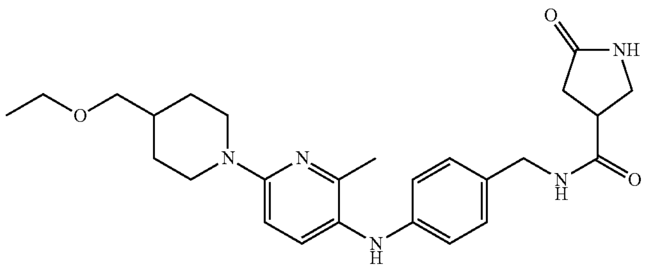 [SMILES: CCOCC1CCN(c2ccc(Nc3ccc(CNC(=O)C4CNC(=O)C4)cc3)c(C)n2)CC1]
617
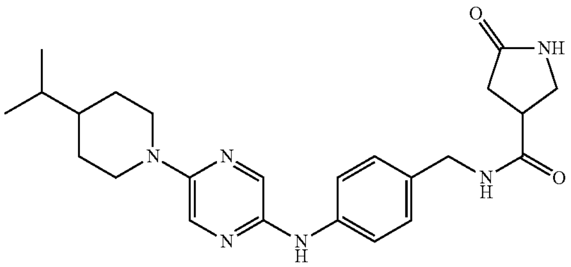 [SMILES: CC(C)C1CCN(c2cnc(Nc3ccc(CNC(=O)C4CNC(=O)C4)cc3)cn2)CC1]
618
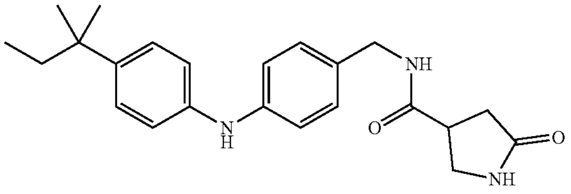 [SMILES: CCC(C)(C)c1ccc(Nc2ccc(CNC(=O)C3CNC(=O)C3)cc2)cc1]
619
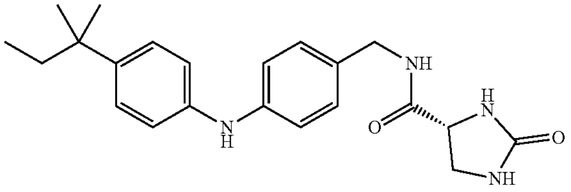 [SMILES: CCC(C)(C)c1ccc(Nc2ccc(CNC(=O)[C@H]3CNC(=O)N3)cc2)cc1]
620
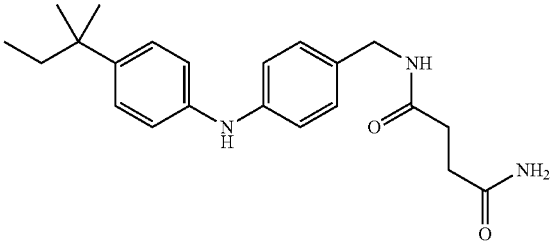 [SMILES: CCC(C)(C)c1ccc(Nc2ccc(CNC(=O)CCC(N)=O)cc2)cc1]
621
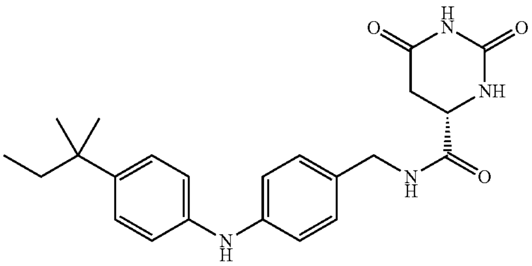 [SMILES: CCC(C)(C)c1ccc(Nc2ccc(CNC(=O)[C@@H]3CC(=O)NC(=O)N3)cc2)cc1]

TABLE 2-continued
| Active Compounds: Structures |
| --- |
| 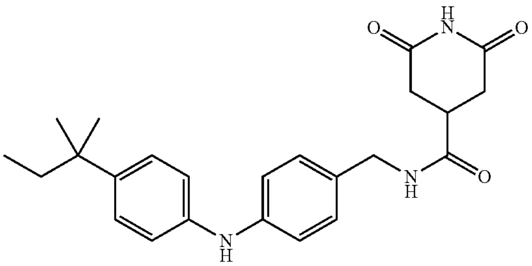 [SMILES: CCC(C)(C)c1ccc(Nc2ccc(CNC(=O)C3CC(=O)NC(=O)C3)cc2)cc1] 622 |
| 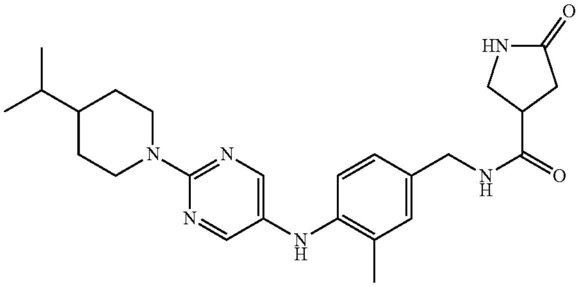 [SMILES: Cc1cc(CNC(=O)C2CNC(=O)C2)ccc1Nc1cnc(N2CCC(C(C)C)CC2)nc1] 623 |
| 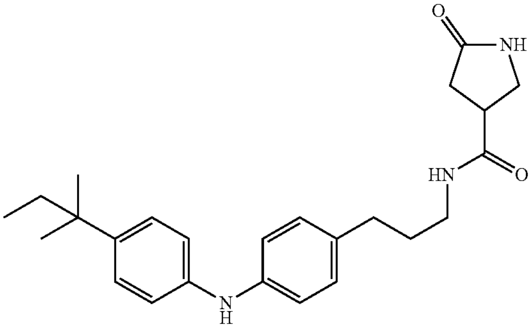 [SMILES: CCC(C)(C)c1ccc(Nc2ccc(CCCNC(=O)C3CNC(=O)C3)cc2)cc1] 624 |
| 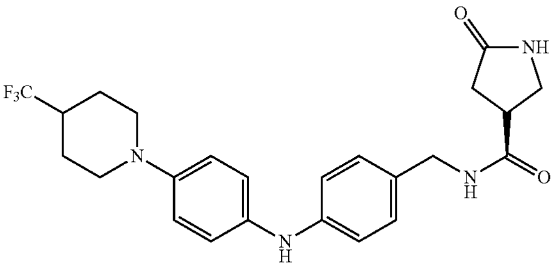 625 |
| 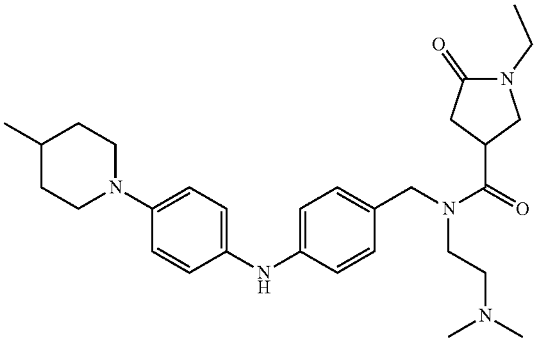 [SMILES: CCN1CC(C(=O)N(CCN(C)C)Cc2ccc(Nc3ccc(N4CCC(C)CC4)cc3)cc2)CC1=O] 626 |

TABLE 2-continued
| Active Compounds: Structures |
| --- |
| 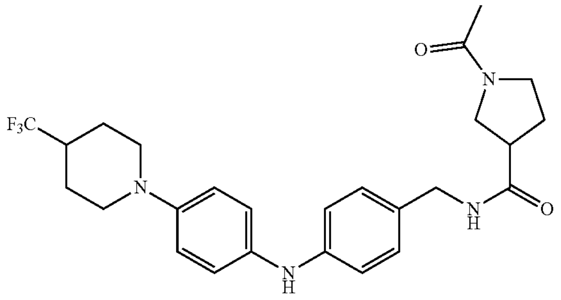 [SMILES: CC(=O)N1CCC(C(=O)NCc2ccc(Nc3ccc(N4CCC(C(F)(F)F)CC4)cc3)cc2)C1] 627 |
| 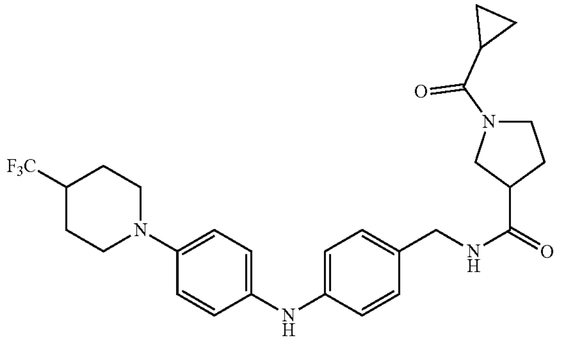 [SMILES: O=C(NCc1ccc(Nc2ccc(N3CCC(C(F)(F)F)CC3)cc2)cc1)C1CCN(C(=O)C2CC2)C1] 628 |
| 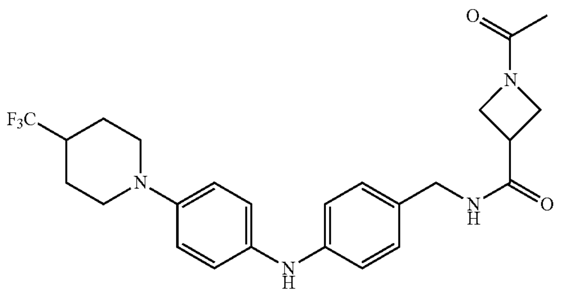 [SMILES: CC(=O)N1CC(C(=O)NCc2ccc(Nc3ccc(N4CCC(C(F)(F)F)CC4)cc3)cc2)C1] 629 |
| 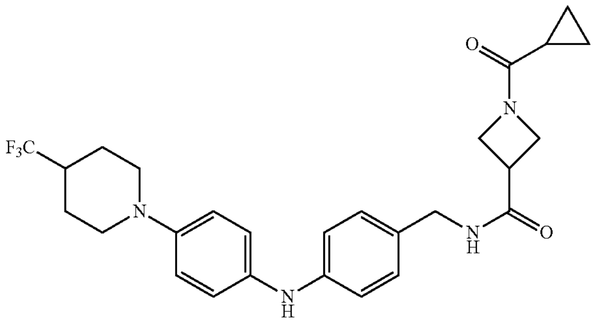 [SMILES: O=C(NCc1ccc(Nc2ccc(N3CCC(C(F)(F)F)CC3)cc2)cc1)C1CN(C(=O)C2CC2)C1] 630 |
| 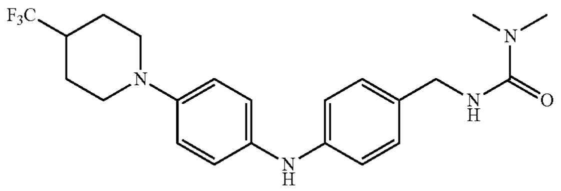 [SMILES: CN(C)C(=O)NCc1ccc(Nc2ccc(N3CCC(C(F)(F)F)CC3)cc2)cc1] 631 |

TABLE 2-continued
| Active Compounds: Structures |
| --- |
| 632 |
| 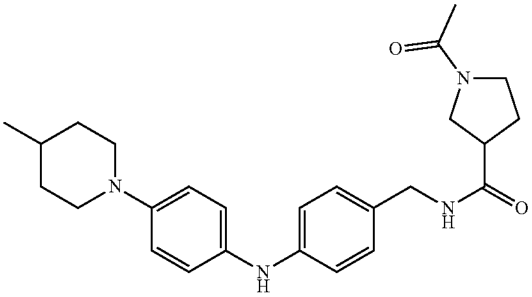 [SMILES: CC(=O)N1CCC(C(=O)NCc2ccc(Nc3ccc(N4CCC(C)CC4)cc3)cc2)C1] |
| 633 |
| 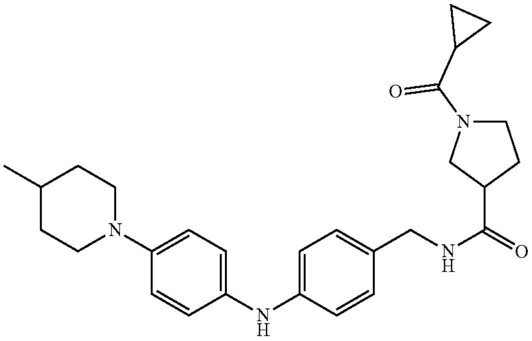 [SMILES: CC1CCN(c2ccc(Nc3ccc(CNC(=O)C4CCN(C(=O)C5CC5)C4)cc3)cc2)CC1] |
| 634 |
| 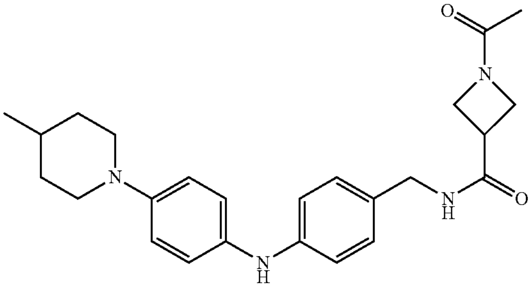 [SMILES: CC(=O)N1CC(C(=O)NCc2ccc(Nc3ccc(N4CCC(C)CC4)cc3)cc2)C1] |
| 635 |
| 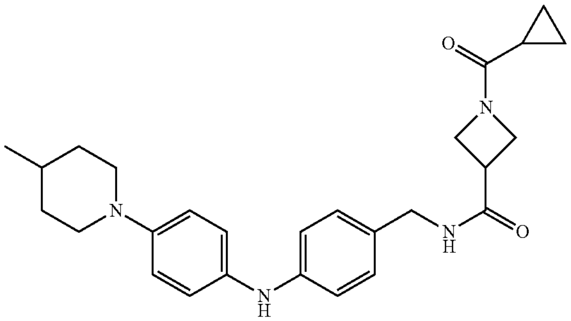 [SMILES: CC1CCN(c2ccc(Nc3ccc(CNC(=O)C4CN(C(=O)C5CC5)C4)cc3)cc2)CC1] |
| 636 |
| 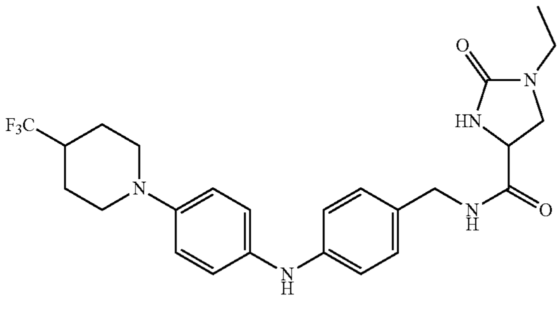 [SMILES: CCN1CC(C(=O)NCc2ccc(Nc3ccc(N4CCC(C(F)(F)F)CC4)cc3)cc2)NC1=O] |

TABLE 2-continued
| Active Compounds: Structures |
|---|
| 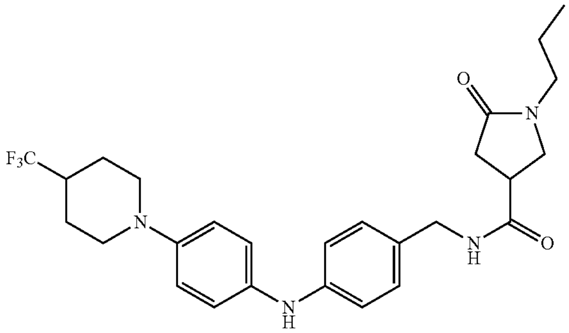 [SMILES: CCCN1CC(C(=O)NCc2ccc(Nc3ccc(N4CCC(C(F)(F)F)CC4)cc3)cc2)CC1=O] 637 |
| 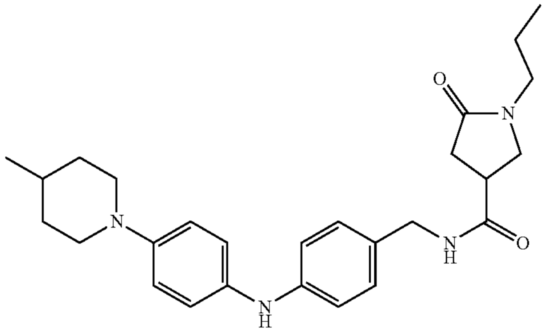 [SMILES: CCCN1CC(C(=O)NCc2ccc(Nc3ccc(N4CCC(C)CC4)cc3)cc2)CC1=O] 638 |
| 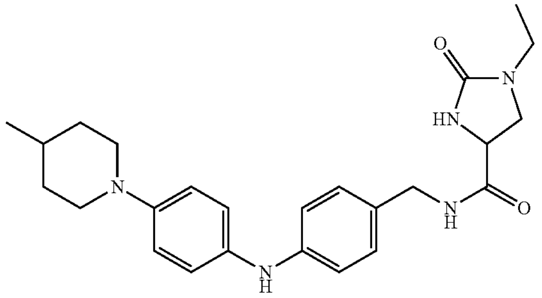 [SMILES: CCN1CC(C(=O)NCc2ccc(Nc3ccc(N4CCC(C)CC4)cc3)cc2)NC1=O] 639 |
| 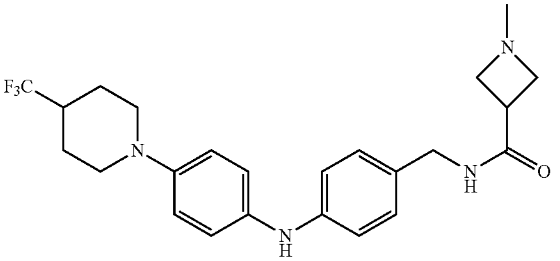 [SMILES: CN1CC(C(=O)NCc2ccc(Nc3ccc(N4CCC(C(F)(F)F)CC4)cc3)cc2)C1] 640 |
| 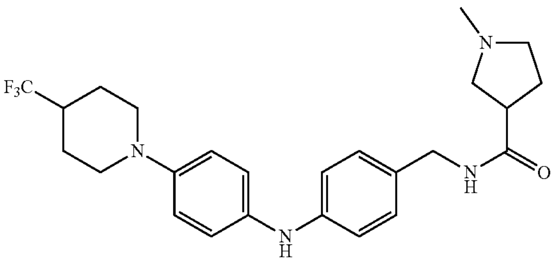 [SMILES: CN1CCC(C(=O)NCc2ccc(Nc3ccc(N4CCC(C(F)(F)F)CC4)cc3)cc2)C1] 641 |

TABLE 2-continued
| Active Compounds: Structures | |
|---|---|
| 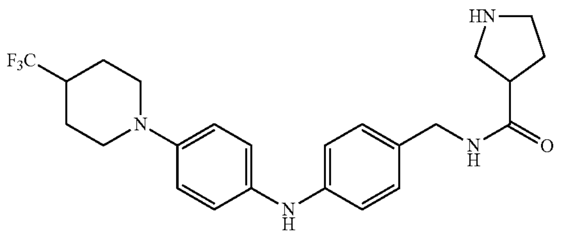 [SMILES: O=C(NCc1ccc(Nc2ccc(N3CCC(C(F)(F)F)CC3)cc2)cc1)C1CCNC1] | 642 |
| 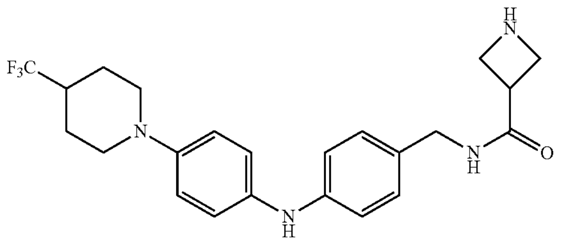 [SMILES: O=C(NCc1ccc(Nc2ccc(N3CCC(C(F)(F)F)CC3)cc2)cc1)C1CNC1] | 643 |
| 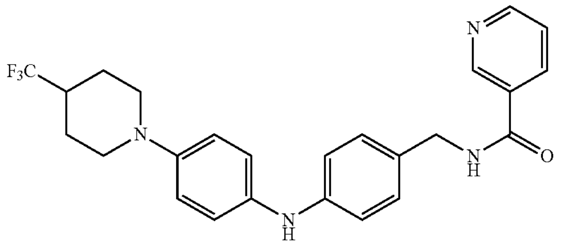 [SMILES: O=C(NCc1ccc(Nc2ccc(N3CCC(C(F)(F)F)CC3)cc2)cc1)c1cccnc1] | 644 |
| 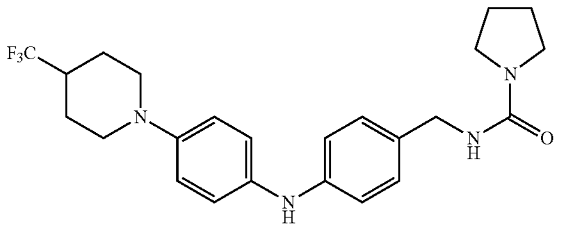 [SMILES: O=C(NCc1ccc(Nc2ccc(N3CCC(C(F)(F)F)CC3)cc2)cc1)N1CCCC1] | 645 |
| 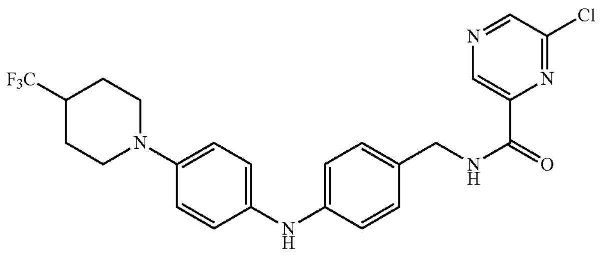 [SMILES: O=C(NCc1ccc(Nc2ccc(N3CCC(C(F)(F)F)CC3)cc2)cc1)c1cncc(Cl)n1] | 646 |
| 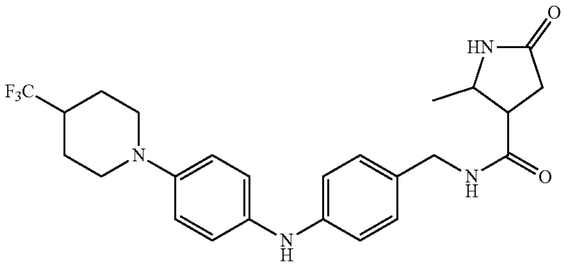 [SMILES: CC1NC(=O)CC1C(=O)NCc1ccc(Nc2ccc(N3CCC(C(F)(F)F)CC3)cc2)cc1] | 647 |

TABLE 2-continued
Active Compounds: Structures
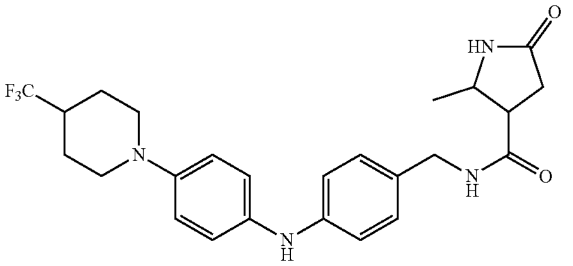 [SMILES: CC1NC(=O)CC1C(=O)NCc1ccc(Nc2ccc(N3CCC(C(F)(F)F)CC3)cc2)cc1]
648
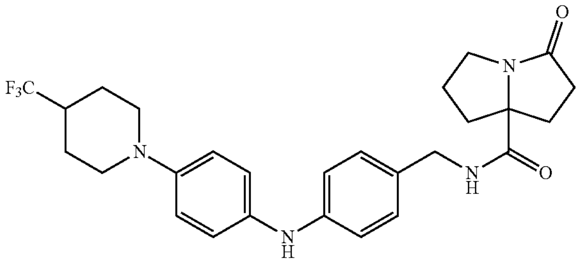 [SMILES: O=C1CCC2(C(=O)NCc3ccc(Nc4ccc(N5CCC(C(F)(F)F)CC5)cc4)cc3)CCCN12]
649
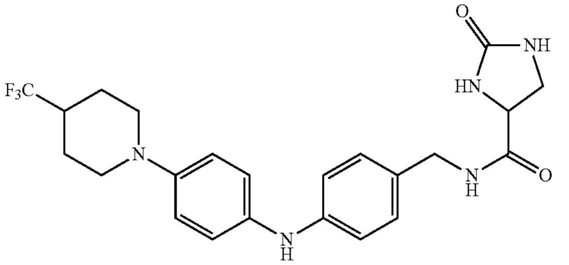 [SMILES: O=C1NCC(C(=O)NCc2ccc(Nc3ccc(N4CCC(C(F)(F)F)CC4)cc3)cc2)N1]
650
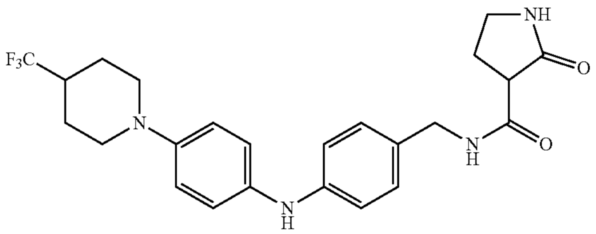 [SMILES: O=C1NCCC1C(=O)NCc1ccc(Nc2ccc(N3CCC(C(F)(F)F)CC3)cc2)cc1]
651
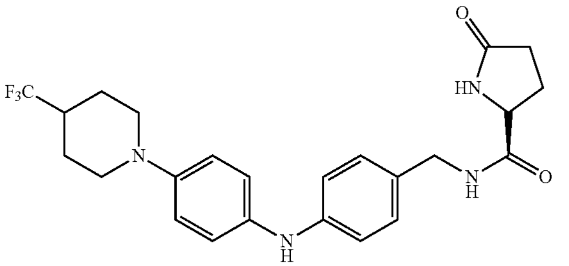
652
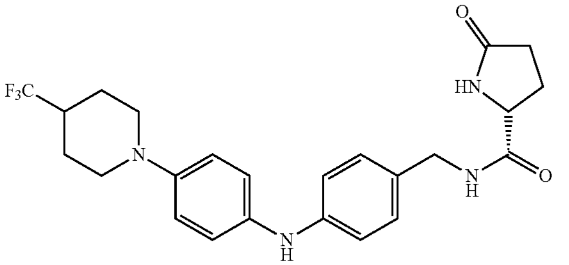
653

TABLE 2-continued
Active Compounds: Structures
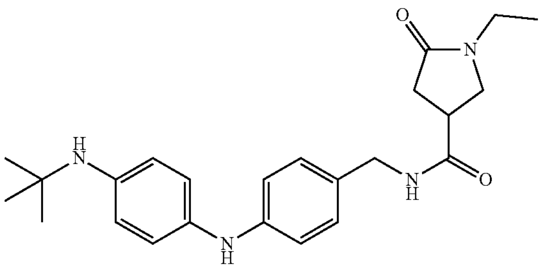 [SMILES: CCN1CC(C(=O)NCc2ccc(Nc3ccc(NC(C)(C)C)cc3)cc2)CC1=O]
654
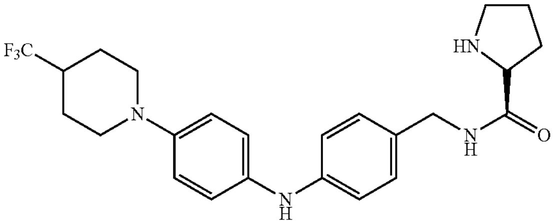
655
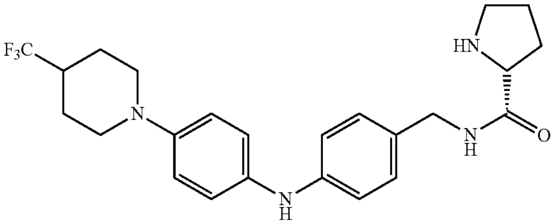
656
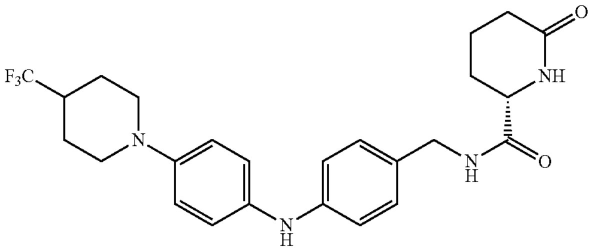 [SMILES: O=C1CCC[C@@H](C(=O)NCc2ccc(Nc3ccc(N4CCC(C(F)(F)F)CC4)cc3)cc2)N1]
657
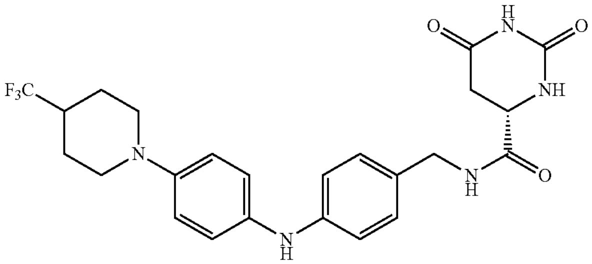 [SMILES: O=C1C[C@@H](C(=O)NCc2ccc(Nc3ccc(N4CCC(C(F)(F)F)CC4)cc3)cc2)NC(=O)N1]
658
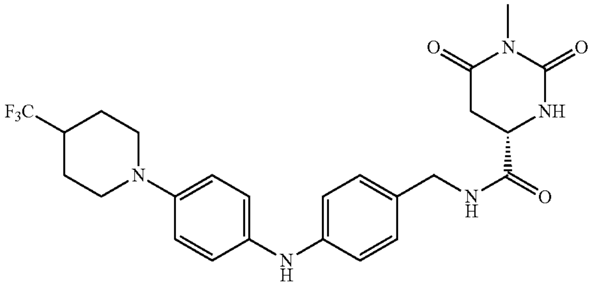 [SMILES: CN1C(=O)C[C@@H](C(=O)NCc2ccc(Nc3ccc(N4CCC(C(F)(F)F)CC4)cc3)cc2)NC1=O]
659

TABLE 2-continued
| Active Compounds: Structures |
| --- |
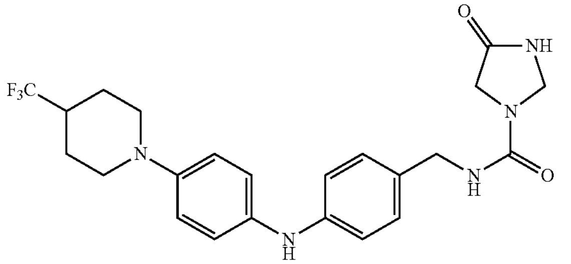 [SMILES: O=C1CN(C(=O)NCc2ccc(Nc3ccc(N4CCC(C(F)(F)F)CC4)cc3)cc2)CN1]
660
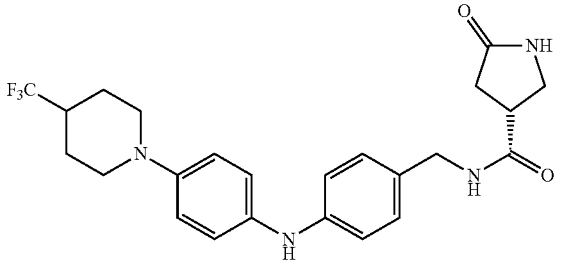
661
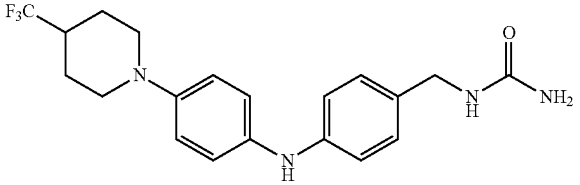 [SMILES: NC(=O)NCc1ccc(Nc2ccc(N3CCC(C(F)(F)F)CC3)cc2)cc1]
662
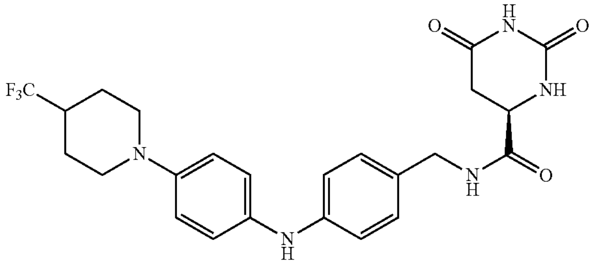 [SMILES: O=C1C[C@H](C(=O)NCc2ccc(Nc3ccc(N4CCC(C(F)(F)F)CC4)cc3)cc2)NC(=O)N1]
663
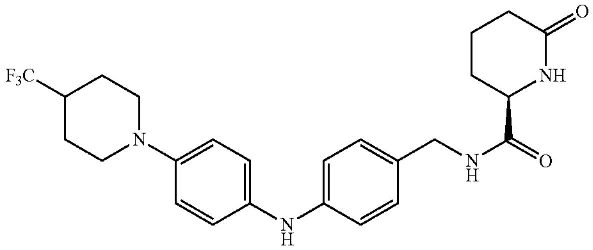 [SMILES: O=C1CCC[C@H](C(=O)NCc2ccc(Nc3ccc(N4CCC(C(F)(F)F)CC4)cc3)cc2)N1]
664
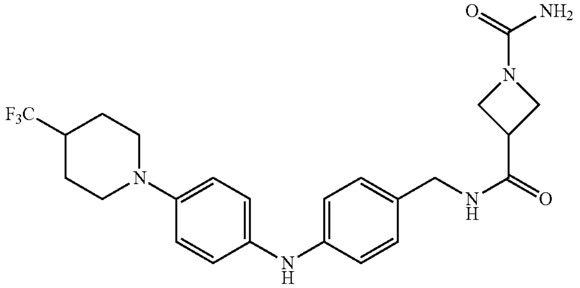 [SMILES: NC(=O)N1CC(C(=O)NCc2ccc(Nc3ccc(N4CCC(C(F)(F)F)CC4)cc3)cc2)C1]
665

TABLE 2-continued
Active Compounds: Structures
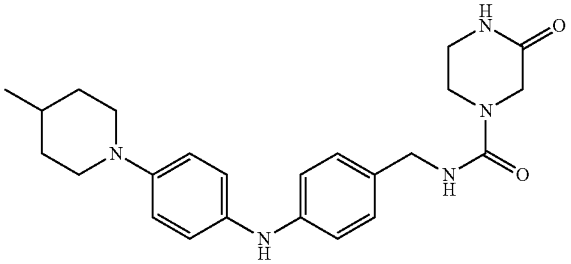 [SMILES: CC1CCN(c2ccc(Nc3ccc(CNC(=O)N4CCNC(=O)C4)cc3)cc2)CC1]
666
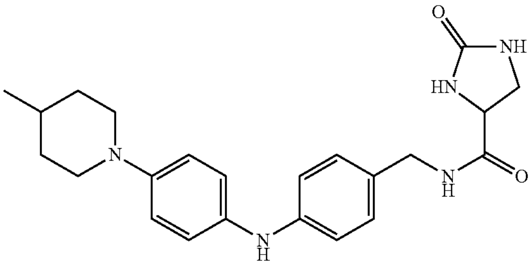 [SMILES: CC1CCN(c2ccc(Nc3ccc(CNC(=O)C4CNC(=O)N4)cc3)cc2)CC1]
667
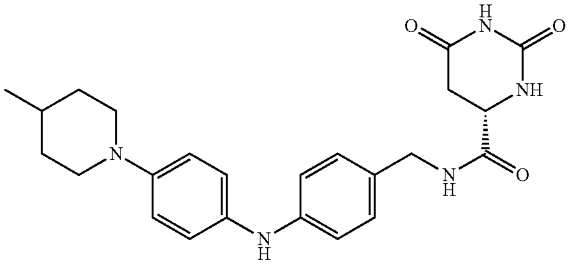 [SMILES: CC1CCN(c2ccc(Nc3ccc(CNC(=O)[C@@H]4CC(=O)NC(=O)N4)cc3)cc2)CC1]
668
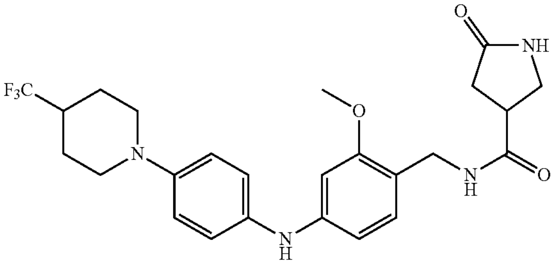 [SMILES: COc1cc(Nc2ccc(N3CCC(C(F)(F)F)CC3)cc2)ccc1CNC(=O)C1CNC(=O)C1]
669
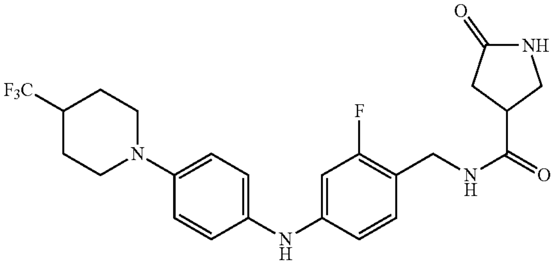 [SMILES: O=C1CC(C(=O)NCc2ccc(Nc3ccc(N4CCC(C(F)(F)F)CC4)cc3)cc2F)CN1]
670
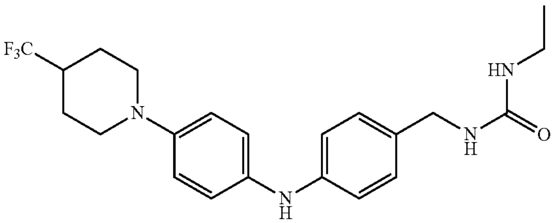 [SMILES: CCNC(=O)NCc1ccc(Nc2ccc(N3CCC(C(F)(F)F)CC3)cc2)cc1]
671

TABLE 2-continued
| Active Compounds: Structures |
|---|
| 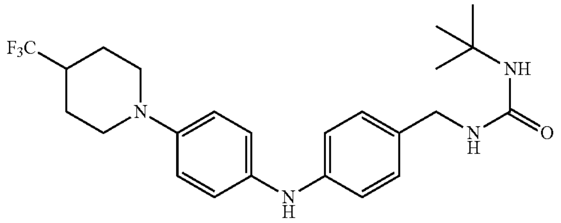 [SMILES: CC(C)(C)NC(=O)NCc1ccc(Nc2ccc(N3CCC(C(F)(F)F)CC3)cc2)cc1] 672 |
| 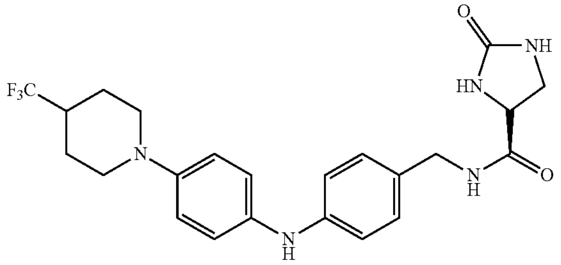 673 |
| 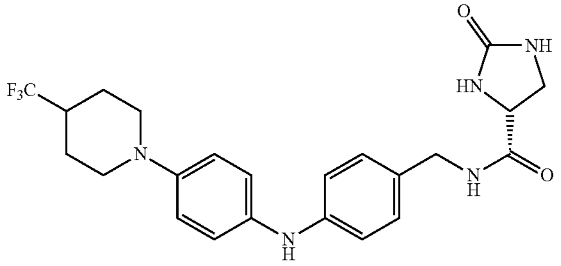 674 |
| 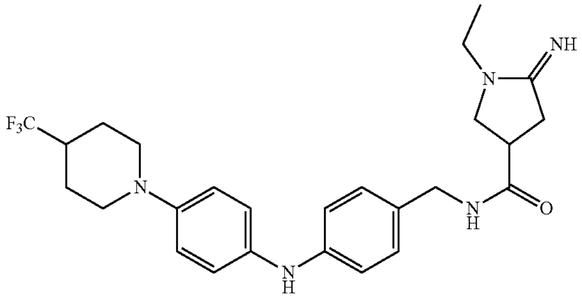 [SMILES: CCN1CC(C(=O)NCc2ccc(Nc3ccc(N4CCC(C(F)(F)F)CC4)cc3)cc2)CC1=N] 675 |
| 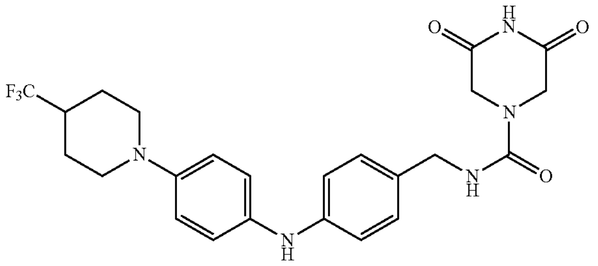 [SMILES: O=C1CN(C(=O)NCc2ccc(Nc3ccc(N4CCC(C(F)(F)F)CC4)cc3)cc2)CC(=O)N1] 676 |

TABLE 2-continued
Active Compounds: Structures
677
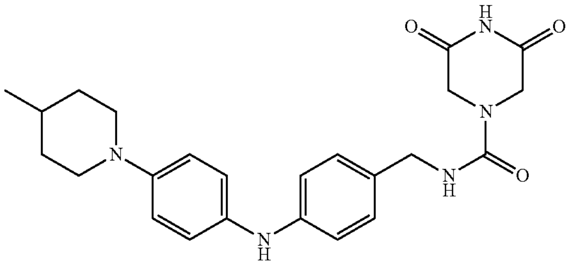 [SMILES: CC1CCN(c2ccc(Nc3ccc(CNC(=O)N4CC(=O)NC(=O)C4)cc3)cc2)CC1]
678
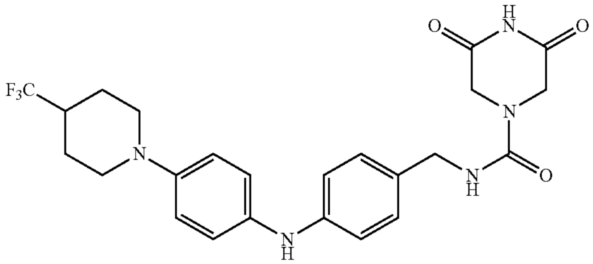 [SMILES: O=C1CN(C(=O)NCc2ccc(Nc3ccc(N4CCC(C(F)(F)F)CC4)cc3)cc2)CC(=O)N1]
679
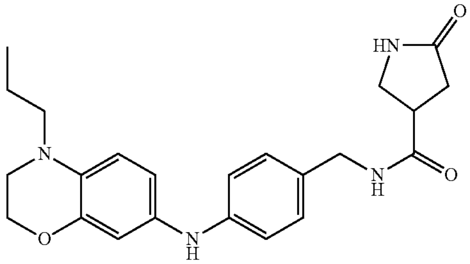 [SMILES: CCCN1CCOc2cc(Nc3ccc(CNC(=O)C4CNC(=O)C4)cc3)ccc21]
680
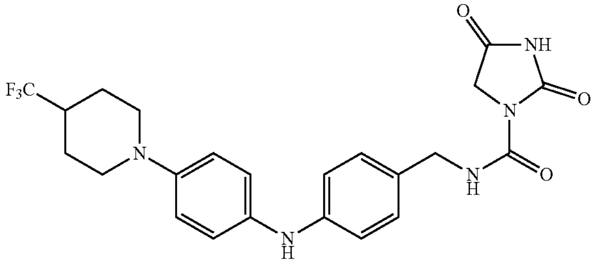 [SMILES: O=C1CN(C(=O)NCc2ccc(Nc3ccc(N4CCC(C(F)(F)F)CC4)cc3)cc2)C(=O)N1]
681
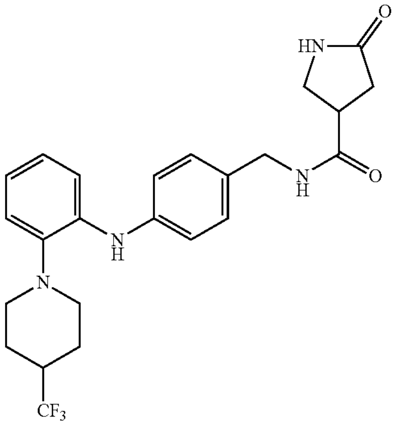 [SMILES: O=C1CC(C(=O)NCc2ccc(Nc3ccccc3N3CCC(C(F)(F)F)CC3)cc2)CN1]

TABLE 2-continued
| Active Compounds: Structures |
| --- |
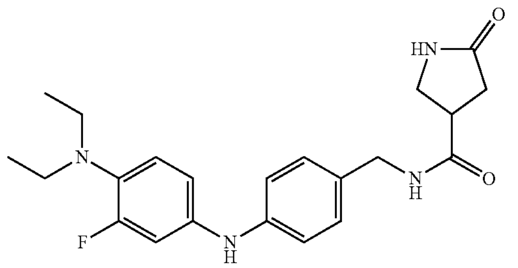 [SMILES: CCN(CC)c1ccc(Nc2ccc(CNC(=O)C3CNC(=O)C3)cc2)cc1F]
682
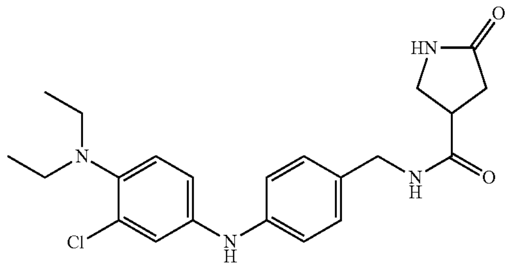 [SMILES: CCN(CC)c1ccc(Nc2ccc(CNC(=O)C3CNC(=O)C3)cc2)cc1Cl]
683
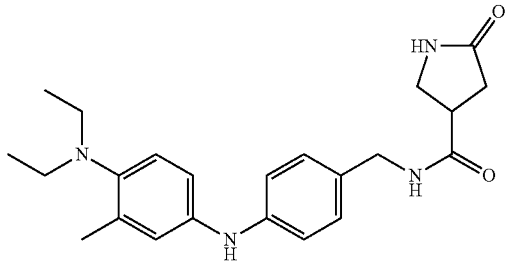 [SMILES: CCN(CC)c1ccc(Nc2ccc(CNC(=O)C3CNC(=O)C3)cc2)cc1C]
684
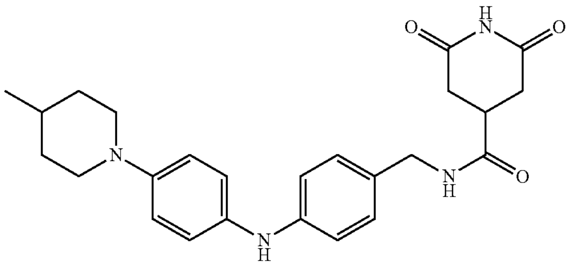 [SMILES: CC1CCN(c2ccc(Nc3ccc(CNC(=O)C4CC(=O)NC(=O)C4)cc3)cc2)CC1]
685
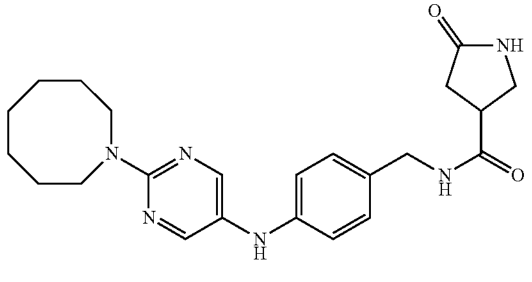 [SMILES: O=C1CC(C(=O)NCc2ccc(Nc3cnc(N4CCCCCCC4)nc3)cc2)CN1]
686

TABLE 2-continued
| Active Compounds: Structures |
| --- |
| 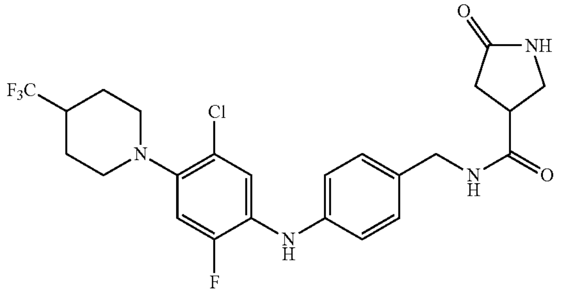 [SMILES: O=C1CC(C(=O)NCc2ccc(Nc3cc(Cl)c(N4CCC(C(F)(F)F)CC4)cc3F)cc2)CN1] 687 |
| 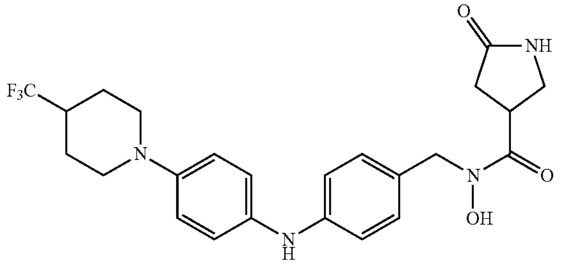 [SMILES: O=C1CC(C(=O)N(O)Cc2ccc(Nc3ccc(N4CCC(C(F)(F)F)CC4)cc3)cc2)CN1] 688 |
| 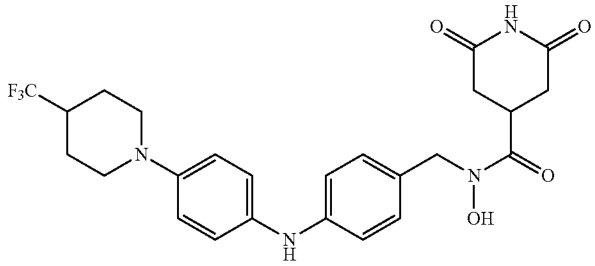 [SMILES: O=C1CC(C(=O)N(O)Cc2ccc(Nc3ccc(N4CCC(C(F)(F)F)CC4)cc3)cc2)CC(=O)N1] 689 |
| 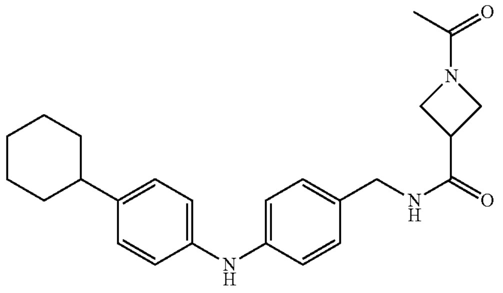 [SMILES: CC(=O)N1CC(C(=O)NCc2ccc(Nc3ccc(C4CCCCC4)cc3)cc2)C1] 690 |
| 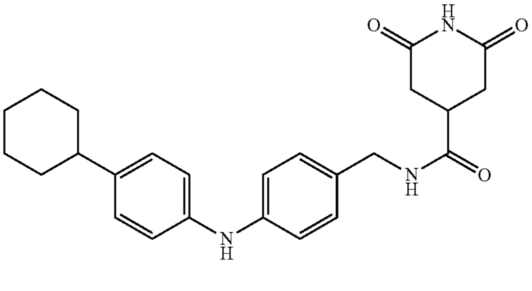 [SMILES: O=C1CC(C(=O)NCc2ccc(Nc3ccc(C4CCCCC4)cc3)cc2)CC(=O)N1] 691 |

TABLE 2-continued
Active Compounds: Structures
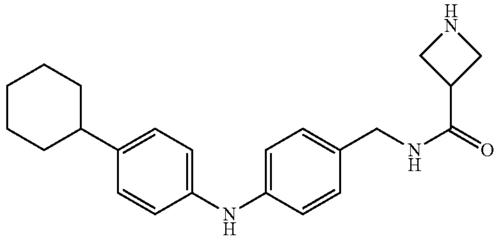 [SMILES: O=C(NCc1ccc(Nc2ccc(C3CCCCC3)cc2)cc1)C1CNC1]
692
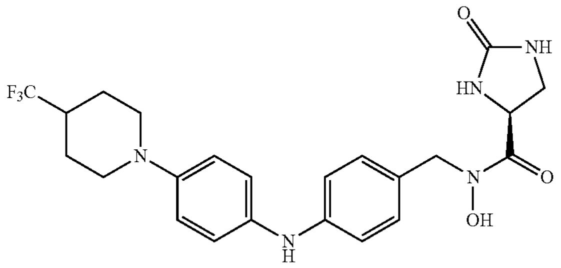 [SMILES: O=C1NC[C@@H](C(=O)N(O)Cc2ccc(Nc3ccc(N4CCC(C(F)(F)F)CC4)cc3)cc2)N1]
693
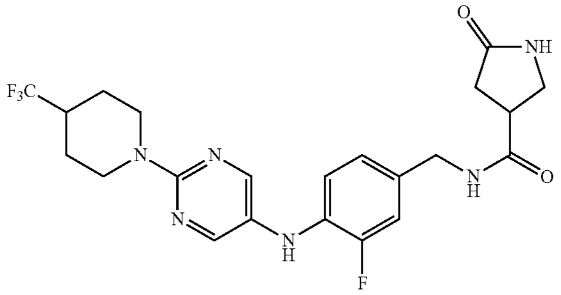 [SMILES: O=C1CC(C(=O)NCc2ccc(Nc3cnc(N4CCC(C(F)(F)F)CC4)nc3)c(F)c2)CN1]
694
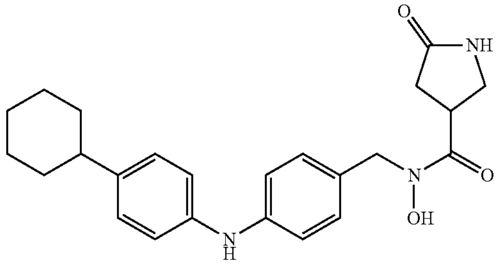 [SMILES: O=C1CC(C(=O)N(O)Cc2ccc(Nc3ccc(C4CCCCC4)cc3)cc2)CN1]
695
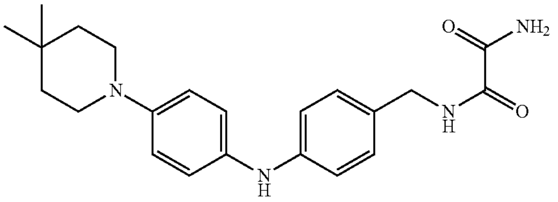 [SMILES: CC1(C)CCN(c2ccc(Nc3ccc(CNC(=O)C(N)=O)cc3)cc2)CC1]
696
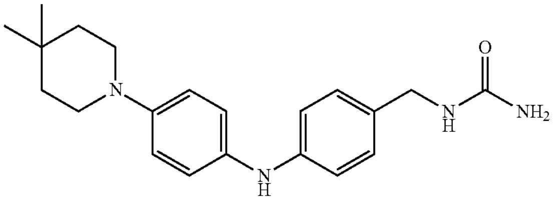 [SMILES: CC1(C)CCN(c2ccc(Nc3ccc(CNC(N)=O)cc3)cc2)CC1]
697

TABLE 2-continued
| Active Compounds: Structures |
| --- |
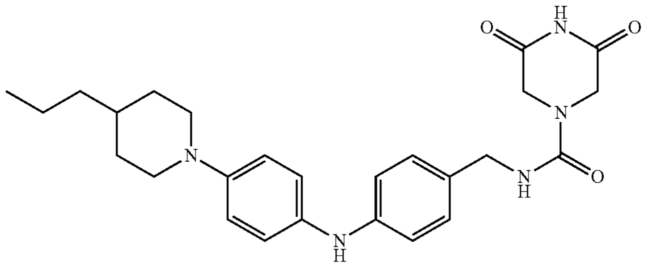 [SMILES: CCCC1CCN(c2ccc(Nc3ccc(CNC(=O)N4CC(=O)NC(=O)C4)cc3)cc2)CC1]
698
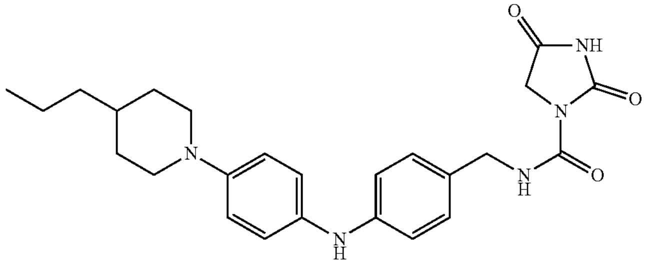 [SMILES: CCCC1CCN(c2ccc(Nc3ccc(CNC(=O)N4CC(=O)NC4=O)cc3)cc2)CC1]
699
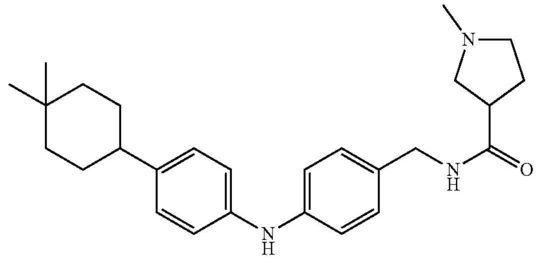 [SMILES: CN1CCC(C(=O)NCc2ccc(Nc3ccc(C4CCC(C)(C)CC4)cc3)cc2)C1]
700
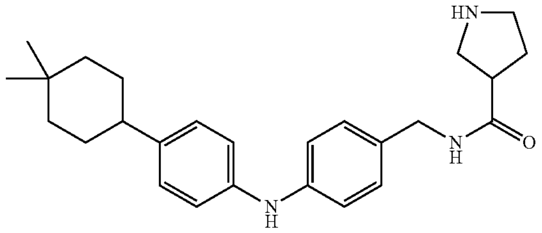 [SMILES: CC1(C)CCC(c2ccc(Nc3ccc(CNC(=O)C4CCNC4)cc3)cc2)CC1]
701
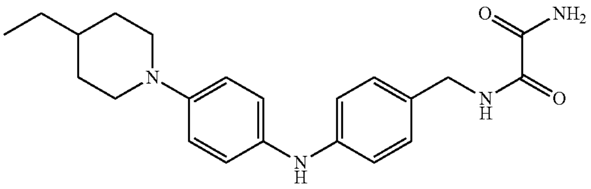 [SMILES: CCC1CCN(c2ccc(Nc3ccc(CNC(=O)C(N)=O)cc3)cc2)CC1]
702
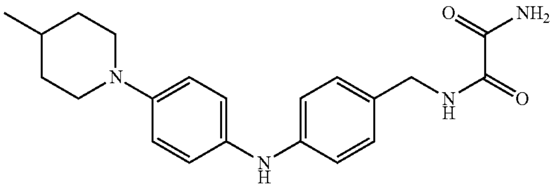 [SMILES: CC1CCN(c2ccc(Nc3ccc(CNC(=O)C(N)=O)cc3)cc2)CC1]
703

TABLE 2-continued
| Active Compounds: Structures | |
|---|---|
| 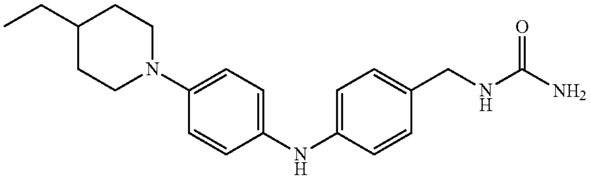 [SMILES: CCC1CCN(c2ccc(Nc3ccc(CNC(N)=O)cc3)cc2)CC1] | 704 |
| 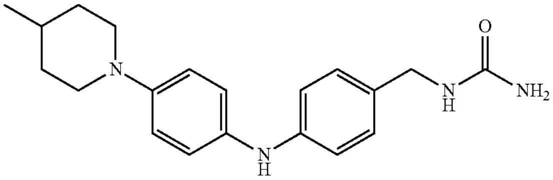 [SMILES: CC1CCN(c2ccc(Nc3ccc(CNC(N)=O)cc3)cc2)CC1] | 705 |
| 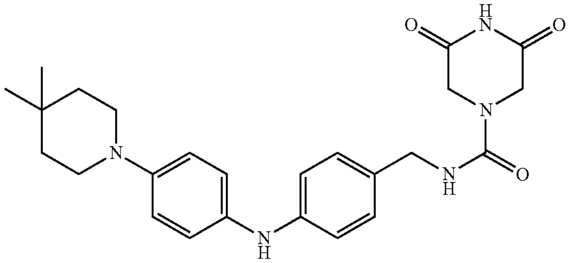 [SMILES: CC1(C)CCN(c2ccc(Nc3ccc(CNC(=O)N4CC(=O)NC(=O)C4)cc3)cc2)CC1] | 706 |
| 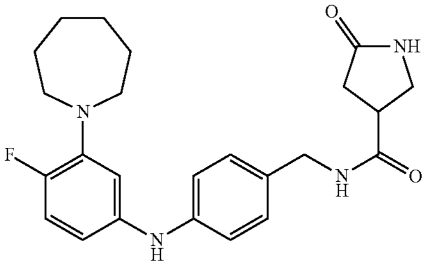 [SMILES: O=C1CC(C(=O)NCc2ccc(Nc3ccc(F)c(N4CCCCCC4)c3)cc2)CN1] | 707 |
| 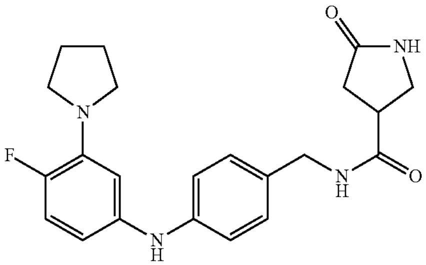 | 708 |
| 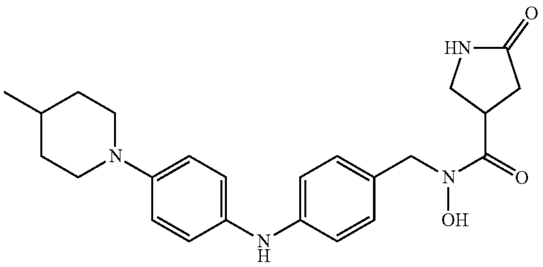 [SMILES: CC1CCN(c2ccc(Nc3ccc(CN(O)C(=O)C4CNC(=O)C4)cc3)cc2)CC1] | 709 |

TABLE 2-continued
| Active Compounds: Structures | |
|---|---|
| 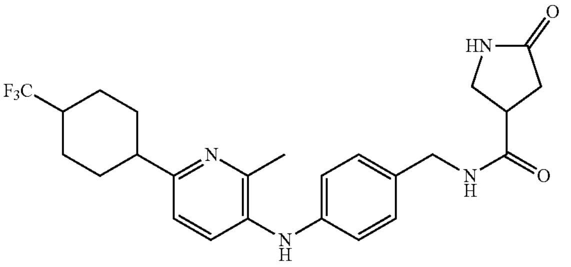 | 710 |
| 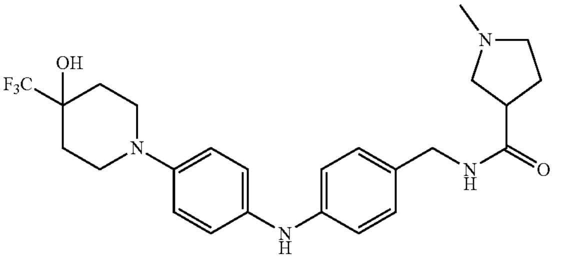 [SMILES: CN1CCC(C(=O)NCc2ccc(Nc3ccc(N4CCC(O)(C(F)(F)F)CC4)cc3)cc2)C1] | 711 |
| 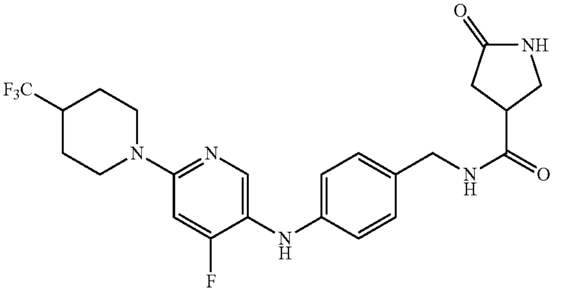 [SMILES: O=C1CC(C(=O)NCc2ccc(Nc3cnc(N4CCC(C(F)(F)F)CC4)cc3F)cc2)CN1] | 712 |
| 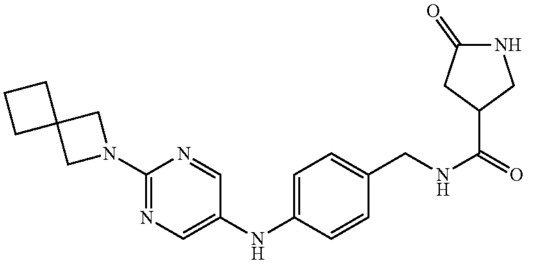 [SMILES: O=C1CC(C(=O)NCc2ccc(Nc3cnc(N4CC5(CCC5)C4)nc3)cc2)CN1] | 713 |
| 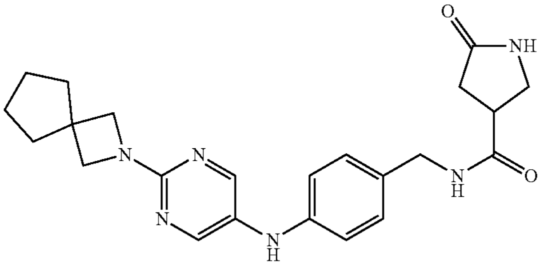 [SMILES: O=C1CC(C(=O)NCc2ccc(Nc3cnc(N4CC5(CCCC5)C4)nc3)cc2)CN1] | 714 |

TABLE 2-continued
Active Compounds: Structures
715
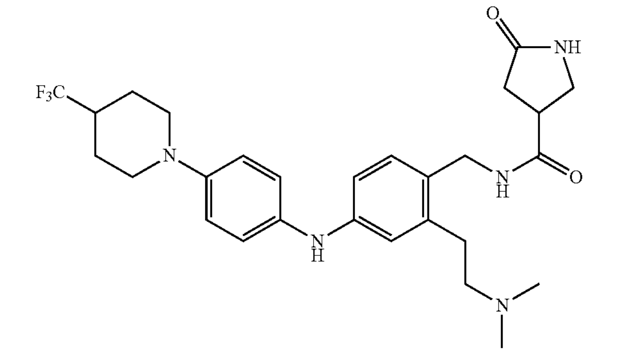 [SMILES: CN(C)CCc1cc(Nc2ccc(N3CCC(C(F)(F)F)CC3)cc2)ccc1CNC(=O)C1CNC(=O)C1]
716
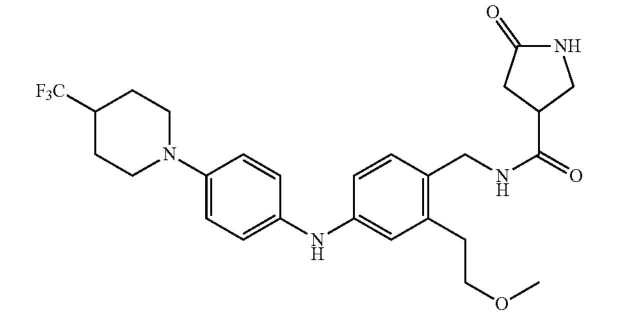 [SMILES: COCCc1cc(Nc2ccc(N3CCC(C(F)(F)F)CC3)cc2)ccc1CNC(=O)C1CNC(=O)C1]
717
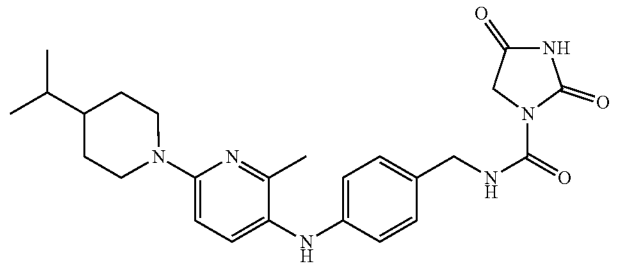 [SMILES: Cc1nc(N2CCC(C(C)C)CC2)ccc1Nc1ccc(CNC(=O)N2CC(=O)NC2=O)cc1]
718
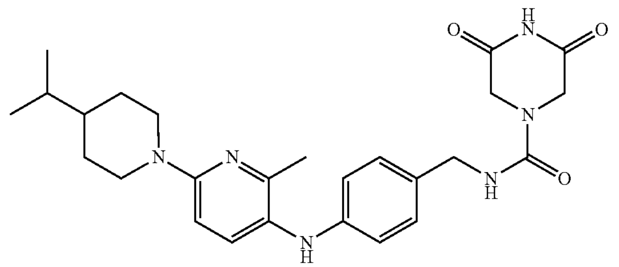 [SMILES: Cc1nc(N2CCC(C(C)C)CC2)ccc1Nc1ccc(CNC(=O)N2CC(=O)NC(=O)C2)cc1]
719
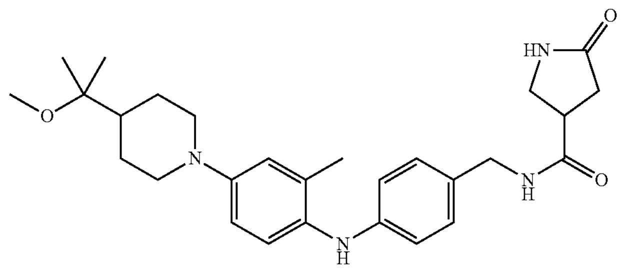 [SMILES: COC(C)(C)C1CCN(c2ccc(Nc3ccc(CNC(=O)C4CNC(=O)C4)cc3)c(C)c2)CC1]

TABLE 2-continued
Active Compounds: Structures
720
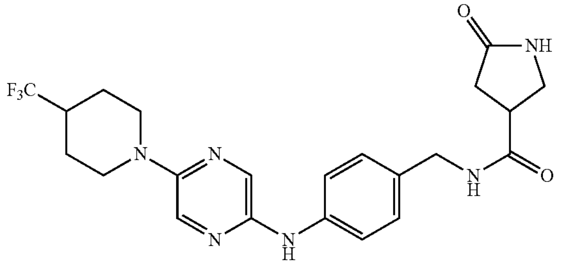 [SMILES: O=C1CC(C(=O)NCc2ccc(Nc3cnc(N4CCC(C(F)(F)F)CC4)cn3)cc2)CN1]
721
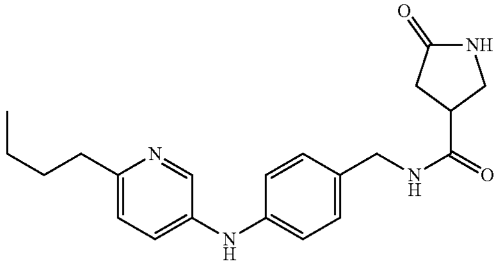 [SMILES: CCCCc1ccc(Nc2ccc(CNC(=O)C3CNC(=O)C3)cc2)cn1]
722
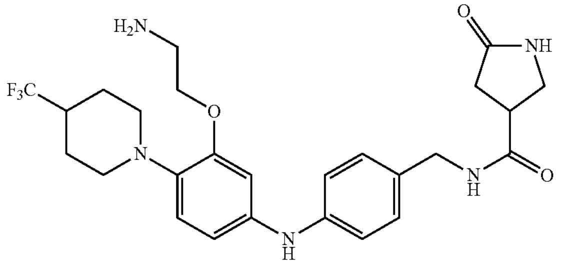 [SMILES: NCCOc1cc(Nc2ccc(CNC(=O)C3CNC(=O)C3)cc2)ccc1N1CCC(C(F)(F)F)CC1]
723
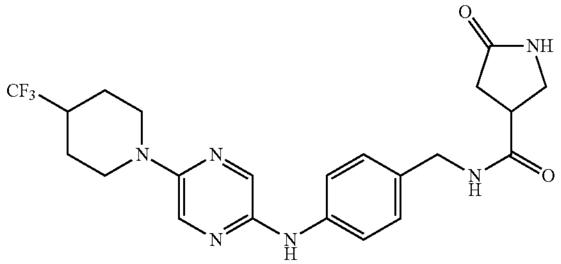 [SMILES: O=C1CC(C(=O)NCc2ccc(Nc3cnc(N4CCC(C(F)(F)F)CC4)cn3)cc2)CN1]
724
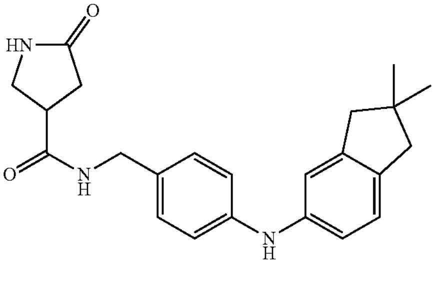 [SMILES: CC1(C)Cc2ccc(Nc3ccc(CNC(=O)C4CNC(=O)C4)cc3)cc2C1]

TABLE 2-continued
| Active Compounds: Structures | |
|---|---|
| 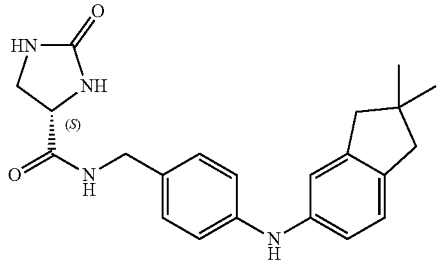 | 725 |
| 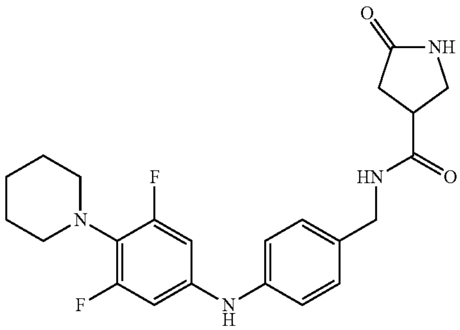 [SMILES: O=C1CC(C(=O)NCc2ccc(Nc3cc(F)c(N4CCCCC4)c(F)c3)cc2)CN1] | 726 |
| 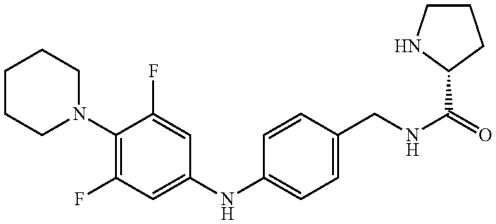 [SMILES: O=C(NCc1ccc(Nc2cc(F)c(N3CCCCC3)c(F)c2)cc1)[C@H]1CCCN1] | 727 |
| 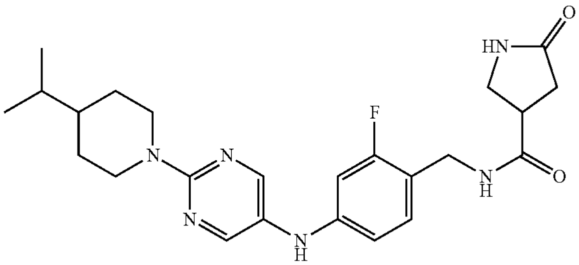 [SMILES: CC(C)C1CCN(c2ncc(Nc3ccc(CNC(=O)C4CNC(=O)C4)c(F)c3)cn2)CC1] | 728 |
| 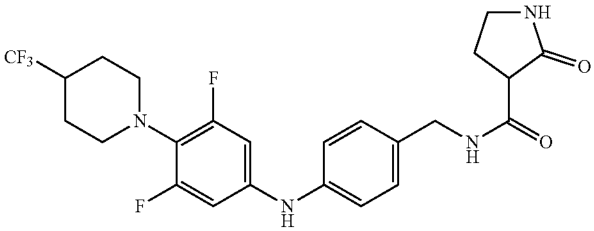 [SMILES: O=C1NCCC1C(=O)NCc1ccc(Nc2cc(F)c(N3CCC(C(F)(F)F)CC3)c(F)c2)cc1] | 729 |

TABLE 2-continued
| Active Compounds: Structures | |
|---|---|
| 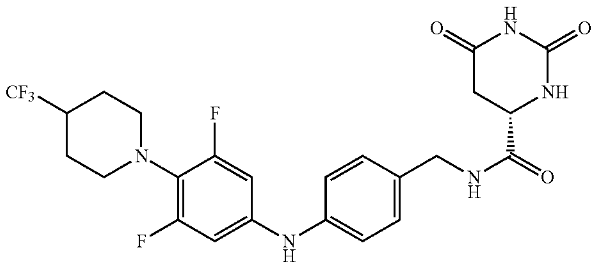 [SMILES: O=C1C[C@@H](C(=O)NCc2ccc(Nc3cc(F)c(N4CCC(C(F)(F)F)CC4)c(F)c3)cc2)NC(=O)N1] | 730 |
| 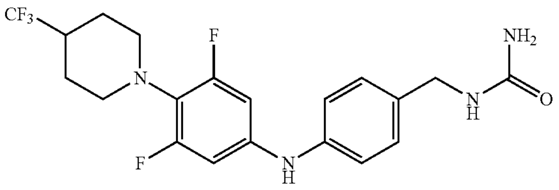 [SMILES: NC(=O)NCc1ccc(Nc2cc(F)c(N3CCC(C(F)(F)F)CC3)c(F)c2)cc1] | 731 |
| 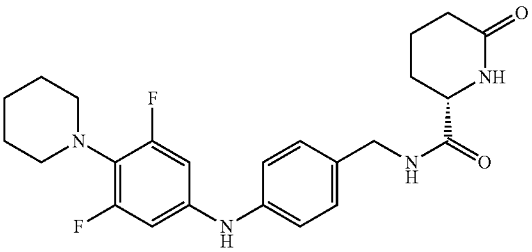 [SMILES: O=C1CCC[C@@H](C(=O)NCc2ccc(Nc3cc(F)c(N4CCCCC4)c(F)c3)cc2)N1] | 732 |
| 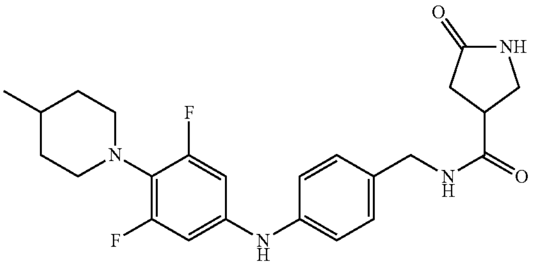 [SMILES: CC1CCN(c2c(F)cc(Nc3ccc(CNC(=O)C4CNC(=O)C4)cc3)cc2F)CC1] | 733 |
Active compounds are demonstrated to inhibit ferroptosis:
TABLE 3
Bioactivity (RSL3-induced HT-1080 cells ferroptosis assay (10% FBS):
| # | | # | | # | | # | |
|---|---|---|---|---|---|---|---|
| 1 | 1-100 nM | 2 | 1-100 nM | 3 | 100-1000 nM | 4 | 1-100 nM |
| 5 | 1-100 nM | 6 | 1-100 nM | 7 | 1-100 nM | 8 | 1-100 nM |
| 9 | 100-1000 nM | 10 | 1-100 nM | 11 | 1-100 nM | 12 | 1-100 nM |
| 13 | 1-100 nM | 14 | 1-100 nM | 15 | 1-100 nM | 16 | 1-100 nM |
| 17 | 1-100 nM | 18 | 1-100 nM | 19 | 1-100 nM | 20 | 1-100 nM |
| 21 | 1-100 nM | 22 | 1-100 nM | 23 | 1-100 nM | 24 | 1-100 nM |
| 25 | 1-100 nM | 26 | 1-100 nM | 27 | 1-100 nM | 28 | 1-100 nM |
| 29 | 1-100 nM | 30 | 1-100 nM | 31 | 1-100 nM | 32 | 1-100 nM |
| 33 | 1-100 nM | 34 | 1-100 nM | 35 | 1-100 nM | 36 | 1-100 nM |
| 37 | 1-100 nM | 38 | 1-100 nM | 39 | 1-100 nM | 40 | 1-100 nM |
| 41 | 1-100 nM | 42 | 1-100 nM | 43 | 1-100 nM | 44 | 1-100 nM |
| 45 | 1-100 nM | 46 | 1-100 nM | 47 | 1-100 nM | 48 | 1-100 nM |
| 49 | 1-100 nM | 50 | 1-100 nM | 51 | 100-1000 nM | 52 | 100-1000 nM |
| 53 | 1-100 nM | 54 | 1-100 nM | 55 | 1-100 nM | 56 | 1-100 nM |
| 57 | 1-100 nM | 58 | 1-100 nM | 59 | 1-100 nM | 60 | 1-100 nM |
| 61 | 1-100 nM | 62 | 1-100 nM | 63 | 1-100 nM | 64 | 1-100 nM |
| 65 | 1-100 nM | 66 | 1-100 nM | 67 | 1-100 nM | 68 | 1-100 nM |

TABLE 3-continued

| Bioactivity (RSL3-induced HT-1080 cells ferroptosis assay (10% FBS): | | | | | | | |
|---|---|---|---|---|---|---|---|
| # | | # | | # | | # | |
| 69 | 1-100 nM | 70 | 1-100 nM | 71 | 1-100 nM | 72 | 1-100 nM |
| 73 | 1-100 nM | 74 | 1-100 nM | 75 | 1-100 nM | 76 | 1-100 nM |
| 77 | 1-100 nM | 78 | 1-100 nM | 79 | 1-100 nM | 80 | 1-100 nM |
| 81 | 1-100 nM | 82 | 1-100 nM | 83 | 1-100 nM | 84 | 1-100 nM |
| 85 | 1-100 nM | 86 | 100-1000 nM | 87 | 1-100 nM | 88 | 1-100 nM |
| 89 | 1-100 nM | 90 | 1-100 nM | 91 | 1-100 nM | 92 | 1-100 nM |
| 93 | 1-100 nM | 94 | 1-100 nM | 95 | 1-100 nM | 96 | 1-100 nM |
| 97 | 1-100 nM | 98 | 1-100 nM | 99 | 1-100 nM | 100 | 1-100 nM |
| 101 | 1-100 nM | 102 | 1-100 nM | 103 | 1-100 nM | 104 | 1-100 nM |
| 105 | 1-100 nM | 106 | 1-100 nM | 107 | 1-100 nM | 108 | 1-100 nM |
| 109 | 1-100 nM | 110 | 1-100 nM | 111 | 1-100 nM | 112 | 1-100 nM |
| 113 | 1-100 nM | 114 | 1-100 nM | 115 | 1-100 nM | 116 | 1-100 nM |
| 117 | 1-100 nM | 118 | 1-100 nM | 119 | 1-100 nM | 120 | 1-100 nM |
| 121 | 1-100 nM | 122 | 1-100 nM | 123 | 1-100 nM | 124 | 100-1000 nM |
| 125 | 1-100 nM | 126 | 1-100 nM | 127 | 1-100 nM | 128 | 1-100 nM |
| 129 | 1-100 nM | 130 | 1-100 nM | 131 | 1-100 nM | 132 | 1-100 nM |
| 133 | 1-100 nM | 134 | 1-100 nM | 135 | 1-100 nM | 136 | 1-100 nM |
| 137 | 100-1000 nM | 138 | 1-100 nM | 139 | 100-1000 nM | 140 | 1-100 nM |
| 141 | 1-100 nM | 142 | 1-100 nM | 143 | 1-100 nM | 144 | 100-1000 nM |
| 145 | 1-100 nM | 146 | 100-1000 nM | 147 | 1-100 nM | 148 | 1-100 nM |
| 149 | 1-100 nM | 150 | 1-100 nM | 151 | 1-100 nM | 152 | 1-100 nM |
| 153 | 1-100 nM | 154 | 1-100 nM | 155 | 1-100 nM | 156 | 1-100 nM |
| 157 | 1-100 nM | 158 | 1-100 nM | 159 | 1-100 nM | 160 | 1-100 nM |
| 161 | 1-100 nM | 162 | 1-100 nM | 163 | 1-100 nM | 164 | 1-100 nM |
| 165 | 1-100 nM | 166 | 1-100 nM | 167 | 1-100 nM | 168 | 1-100 nM |
| 169 | 1-100 nM | 170 | 1-100 nM | 171 | 1-100 nM | 172 | 1-100 nM |
| 173 | 1-100 nM | 174 | 1-100 nM | 175 | 1-100 nM | 176 | 1-100 nM |
| 177 | 1-100 nM | 178 | 1-100 nM | 179 | 1-100 nM | 180- | 1-100 nM |
| 181 | 1-100 nM | 182 | 1-100 nM | 183 | 1-100 nM | 184 | 1-100 nM |
| 185 | 1-100 nM | 186 | 1-100 nM | 187 | 1-100 nM | 188 | 1-100 nM |
| 189 | 1-100 nM | 190 | 100-1000 nM | 191 | 1-100 nM | 192 | 1-100 nM |
| 193 | 1-100 nM | 194 | 1-100 nM | 195 | 1-100 nM | 196 | 1-100 nM |
| 197 | 1-100 nM | 198 | 1-100 nM | 199 | 1-100 nM | 200 | 1-100 nM |
| 201 | 1-100 nM | 202 | 1-100 nM | 203 | 1-100 nM | 204 | 1-100 nM |
| 205 | 1-100 nM | 206 | 1-100 nM | 207 | 1-100 nM | 208 | 1-100 nM |
| 209 | 1-100 nM | 210 | 1-100 nM | 211 | 1-100 nM | 212 | 1-100 nM |
| 213 | 1-100 nM | 214 | 1-100 nM | 215 | 1-100 nM | 216 | 1-100 nM |
| 217 | 1-100 nM | 218 | 1-100 nM | 219 | 1-100 nM | 220 | 1-100 nM |
| 221 | 1-100 nM | 222 | 1-100 nM | 223 | 1-100 nM | 224 | 100-1000 nM |
| 225 | 1-100 nM | 226 | 1-100 nM | 227 | 1-100 nM | 228 | 1-100 nM |
| 229 | 1-100 nM | 230 | 1-100 nM | 231 | 1-100 nM | 232 | 1-100 nM |
| 233 | 1-100 nM | 234 | 1-100 nM | 235 | 1-100 nM | 236 | 1-100 nM |
| 237 | 1-100 nM | 238 | 1-100 nM | 239 | 1-100 nM | 240 | 1-100 nM |
| 241 | 1-100 nM | 242 | 1-100 nM | 243 | 1-100 nM | 244 | 1-100 nM |
| 245 | 1-100 nM | 246 | 1-100 nM | 247 | 1-100 nM | 248 | 1-100 nM |
| 249 | 1-100 nM | 250 | 1-100 nM | 251 | 1-100 nM | 252 | 1-100 nM |
| 253 | 1-100 nM | 254 | 1-100 nM | 255 | 1-100 nM | 256 | 1-100 nM |
| 257 | 1-100 nM | 258 | 1-100 nM | 259 | 1-100 nM | 260 | 1-100 nM |
| 261 | 1-100 nM | 262 | 1-100 nM | 263 | 1-100 nM | 264 | 1-100 nM |
| 265 | 1-100 nM | 266 | 1-100 nM | 267 | 1-100 nM | 268 | 1-100 nM |
| 269 | 1-100 nM | 270 | 1-100 nM | 271 | 1-100 nM | 272 | 1-100 nM |
| 273 | 1-100 nM | 274 | 1-100 nM | 275 | 1-100 nM | 276 | 1-100 nM |
| 277 | 1-100 nM | 278 | 1-100 nM | 279 | 1-100 nM | 280 | 1-100 nM |
| 281 | 1-100 nM | 282 | 1-100 nM | 283 | 1-100 nM | 284 | 1-100 nM |
| 285 | 1-100 nM | 286 | 1-100 nM | 287 | 1-100 nM | 288 | 1-100 nM |
| 289 | 1-100 nM | 290 | 1-100 nM | 291 | 1-100 nM | 292 | 1-100 nM |
| 293 | 1-100 nM | 294 | 1-100 nM | 295 | 1-100 nM | 296 | 1-100 nM |
| 297 | 1-100 nM | 298 | 1-100 nM | 299 | 1-100 nM | 300 | 1-100 nM |
| 301 | 1-100 nM | 302 | 1-100 nM | 303 | 1-100 nM | 304 | 1-100 nM |
| 305 | 1-100 nM | 306 | 1-100 nM | 307 | 1-100 nM | 308 | 1-100 nM |
| 309 | 1-100 nM | 310 | 1-100 nM | 311 | 1-100 nM | 312 | 1-100 nM |
| 313 | 1-100 nM | 314 | 1-100 nM | 315 | 1-100 nM | 316 | 1-100 nM |
| 317 | 1-100 nM | 318 | 1-100 nM | 319 | 1-100 nM | 320 | 1-100 nM |
| 321 | 1-100 nM | 322 | 1-100 nM | 323 | 1-100 nM | 324 | 1-100 nM |
| 325 | 1-100 nM | 326 | 1-100 nM | 327 | 1-100 nM | 328 | 1-100 nM |
| 329 | 1-100 nM | 330 | 1-100 nM | 331 | 1-100 nM | 332 | 1-100 nM |
| 333 | 1-100 nM | 334 | 1-100 nM | 335 | 1-100 nM | 336 | 1-100 nM |
| 337 | 1-100 nM | 338 | 1-100 nM | 339 | 1-100 nM | 340 | 1-100 nM |
| 341 | 1-100 nM | 342 | 1-100 nM | 343 | 1-100 nM | 344 | 1-100 nM |
| 345 | 1-100 nM | 346 | 1-100 nM | 347 | 1-100 nM | 348 | 1-100 nM |
| 349 | 1-100 nM | 350 | 1-100 nM | 351 | 1-100 nM | 352 | 1-100 nM |
| 353 | 1-100 nM | 354 | 1-100 nM | 355 | 1-100 nM | 356 | 1-100 nM |
| 357 | 1-100 nM | 358 | 1-100 nM | 359 | 1-100 nM | 360 | 1-100 nM |
| 361 | 1-100 nM | 362 | 1-100 nM | | | | |

TABLE 4

| Bioactivity (RSL3-induced HT-1080 cells ferroptosis assay (10% FBS): | | | | | | | |
|---|---|---|---|---|---|---|---|
| # | | # | | # | | # | |
| 363 | >1000 nm | 364 | 1-100 nM | 365 | 1-100 nM | 366 | 1-100 nM |
| 367 | 1-100 nM | 368 | 1-100 nM | 369 | 1-100 nM | 370 | 1-100 nM |
| 371 | 1-100 nM | 372 | 1-100 nM | 373 | 1-100 nM | 374 | 100-1000 nM |
| 375 | 1-100 nM | 376 | 1-100 nM | 377 | 1-100 nM | 378 | 1-100 nM |
| 379 | 1-100 nM | 380 | 1-100 nM | 381 | 1-100 nM | 382 | 1-100 nM |
| 383 | 1-100 nM | 384 | 1-100 nM | 385 | 1-100 nM | 386 | 1-100 nM |
| 387 | 1-100 nM | 388 | 1-100 nM | 389 | 1-100 nM | 390 | 1-100 nM |
| 391 | 1-100 nM | 392 | 1-100 nM | 393 | 1-100 nM | 394 | 1-100 nM |
| 395 | 1-100 nM | 396 | 1-100 nM | 397 | 1-100 nM | 398 | 1-100 nM |
| 399 | 1-100 nM | 400 | 1-100 nM | 401 | 1-100 nM | 402 | 1-100 nM |
| 403 | 1-100 nM | 404 | 1-100 nM | 405 | 100-1000 nM | 406 | 1-100 nM |
| 407 | 100-1000 nM | 408 | 100-1000 nM | 409 | 1-100 nM | 410 | 1-100 nM |
| 411 | 1-100 nM | 412 | 1-100 nM | 413 | 1-100 nM | 414 | 100-1000 nM |
| 415 | 1-100 nM | 416 | 1-100 nM | 417 | 1-100 nM | 418 | 100-1000 nM |
| 419 | 1-100 nM | 420 | 1-100 nM | 421 | 1-100 nM | 422 | 100-1000 nM |
| 423 | 1-100 nM | 424 | 1-100 nM | 425 | 1-100 nM | 426 | 100-1000 nM |
| 427 | 1-100 nM | 428 | 100-1000 nM | 429 | 1-100 nM | 430 | 1-100 nM |
| 431 | 1-100 nM | 432 | 1-100 nM | 433 | 100-1000 nM | 434 | 1-100 nM |
| 435 | 1-100 nM | 436 | 1-100 nM | 437 | 1-100 nM | 438 | 100-1000 nM |
| 439 | 1-100 nM | 440 | 1-100 nM | 441 | 1-100 nM | 442 | 1-100 nM |
| 443 | 1-100 nM | 444 | 1-100 nM | 445 | 1-100 nM | 446 | 100-1000 nM |
| 447 | 1-100 nM | 448 | 1-100 nM | 449 | 1-100 nM | 450 | 1-100 nM |
| 451 | 1-100 nM | 452 | >1000 nM | 453 | 1-100 nM | 454 | 1-100 nM |
| 455 | 1-100 nM | 456 | 1-100 nM | 457 | 1-100 nM | 458 | 1-100 nM |
| 459 | 1-100 nM | 460 | 1-100 nM | 461 | 1-100 nM | 462 | 1-100 nM |
| 463 | 1-100 nM | 464 | 1-100 nM | 465 | 1-100 nM | 466 | 1-100 nM |
| 467 | 100-1000 nM | 468 | 1-100 nM | 469 | 1-100 nM | 470 | 1-100 nM |
| 471 | 100-1000 nM | 472 | 1-100 nM | 473 | 100-1000 nM | 474 | >1000 nM |
| 475 | 1-100 nM | 476 | 1-100 nM | 477 | 1-100 nM | 478 | 1-100 nM |
| 479 | 1-100 nM | 480 | 1-100 nM | 481 | 1-100 nM | 482 | >1000 nM |
| 483 | 1-100 nM | 484 | 1-100 nM | 485 | 1-100 nM | 486 | 100-1000 nM: |
| 487 | 1-100 nM | 488 | 1-100 nM | 489 | 100-1000 nM | 490 | 1-100 nM |
| 491 | 1-100 nM | 492 | 1-100 nM | 493 | 1-100 nM | 494 | 1-100 nM |
| 495 | 1-100 nM | 496 | 100-1000 nM | 497 | 1-100 nM | 498 | 1-100 nM |
| 499 | 1-100 nM | 500 | 1-100 nM | 501 | 1-100 nM | 502 | 1-100 nM |
| 503 | 1-100 nM | 504 | 1-100 nM | 505 | 1-100 nM | 506 | 100-1000 nM |
| 507 | 100-1000 nM | 508 | 1-100 nM | 509 | 1-100 nM | 510 | 1-100 nM |
| 511 | 100-1000 nM | 512 | >1000 nM | 513 | 1-100 nM | 514 | 1-100 nM |
| 515 | 1-100 nM | 516 | 1-100 nM | 517 | 1-100 nM | 518 | 1-100 nM |
| 519 | 1-100 nM | 520 | 1-100 nM | 521 | 1-100 nM | 522 | 100-1000 nM |
| 523 | 1-100 nM | 524 | 1-100 nM | 525 | 1-100 nM | 526 | 100-1000 nM |
| 527 | 100-1000 nM | 528 | 1-100 nM | 529 | 1-100 nM | 530 | 1-100 nM |
| 531 | 1-100 nM | 532 | 100-1000 nM | 533 | 100-1000 nM | 534 | 1-100 nM |
| 535 | 1-100 nM | 536 | 1-100 nM | 537 | 1-100 nM | 538 | 1-100 nM |
| 539 | 1-100 nM | 540 | 1-100 nM | 541 | 1-100 nM | 542 | 1-100 nM |
| 543 | 1-100 nM | 544 | >1000 nM | 545 | >1000 nM | 546 | 1-100 nM |
| 547 | 1-100 nM | 548 | 1-100 nM | 549 | 1-100 nM | 550 | 1-100 nM |
| 551 | 1-100 nM | 552 | 1-100 nM | 553 | 1-100 nM | 554 | 1-100 nM |
| 555 | 1-100 nM | 556 | >1000 nM | 557 | 100-1000 nM | 558 | 1-100 nM |
| 559 | 1-100 nM | 560 | 1-100 nM | 561 | 1-100 nM | 562 | 1-100 nM |
| 563 | 1-100 nM | 564 | 1-100 nM | 565 | 1-100 nM | 566 | 1-100 nM |
| 567 | 1-100 nM | 568 | 1-100 nM | 569 | 1-100 nM | 570 | 1-100 nM |
| 571 | 1-100 nM | 572 | 1-100 nM | 573 | 1-100 nM | 574 | 1-100 nM |
| 575 | 1-100 nM | 576 | 1-100 nM | 577 | 1-100 nM | 578 | 100-1000 nM |
| 579 | 1-100 nM | 580 | 100-1000 nM | 581 | 1-100 nM | 582 | 1-100 nM |
| 583 | 1-100 nM | 584 | 1-100 nM | 585 | 1-100 nM | 586 | 1-100 nM |
| 587 | 1-100 nM | 588 | 1-100 nM | 589 | 1-100 nM | 590 | 1-100 nM |
| 591 | 100-1000 nM | 592 | 100-1000 nM | 593 | 1-100 nM | 594 | 1-100 nM |
| 595 | 1-100 nM | 596 | 1-100 nM | 597 | 1-100 nM | 598 | 1-100 nM |
| 599 | 1-100 nM | 600 | 1-100 nM | 601 | 1-100 nM | 602 | >1000 nM |
| 603 | 1-100 nM | 604 | >1000 nM | 605 | 1-100 nM | 606 | 1-100 nM |
| 607 | 1-100 nM | 608 | 1-100 nM | 609 | 1-100 nM | 610 | 1-100 nM |
| 611 | 1-100 nM | 612 | 1-100 nM | 613 | 1-100 nM | 614 | 1-100 nM |
| 615 | 1-100 nM | 616 | 1-100 nM | 617 | 1-100 nM | 618 | 1-100 nM |
| 619 | 1-100 nM | 620 | 1-100 nM | 621 | 1-100 nM | 622 | 1-100 nM |
| 623 | 1-100 nM | 624 | 1-100 nM | 625 | 1-100 nM | 626 | 1-100 nM |
| 627 | 1-100 nM | 628 | 1-100 nM | 629 | 1-100 nM | 630 | 1-100 nM |
| 631 | 1-100 nM | 632 | 1-100 nM | 633 | 1-100 nM | 634 | 1-100 nM |
| 635 | 1-100 nM | 636 | 1-100 nM | 637 | 1-100 nM | 638 | 1-100 nM |
| 639 | 1-100 nM | 640 | 1-100 nM | 641 | 1-100 nM | 642 | 1-100 nM |
| 643 | 1-100 nM | 644 | 1-100 nM | 645 | 1-100 nM | 646 | 1-100 nM |
| 647 | 1-100 nM | 648 | 1-100 nM | 649 | 1-100 nM | 650 | 1-100 nM |
| 651 | 1-100 nM | 652 | 1-100 nM | 653 | 1-100 nM | 654 | 100-1000 nM |
| 655 | 1-100 nM | 656 | 1-100 nM | 657 | 1-100 nM | 658 | 1-100 nM |
| 659 | 1-100 nM | 660 | 1-100 nM | 661 | 1-100 nM | 662 | 1-100 nM |
| 663 | 1-100 nM | 664 | 1-100 nM | 665 | 1-100 nM | 666 | 1-100 nM |

TABLE 4-continued

| Bioactivity (RSL3-induced HT-1080 cells ferroptosis assay (10% FBS): | | | | | | | |
|---|---|---|---|---|---|---|---|
| # | | # | | # | | # | |
| 667 | 1-100 nM | 668 | 1-100 nM | 669 | 1-100 nM | 670 | 1-100 nM |
| 671 | 1-100 nM | 672 | 1-100 nM | 673 | 1-100 nM | 674 | 1-100 nM |
| 675 | 1-100 nM | 676 | 1-100 nM | 677 | 1-100 nM | 678 | 1-100 nM |
| 679 | 1-100 nM | 680 | 1-100 nM | 681 | 100-1000 nM | 682 | 100-1000 nM |
| 683 | 100-1000 nM | 684 | 100-1000 nM | 685 | 1-100 nM | 686 | 1-100 nM |
| 687 | >1000 nM | 688 | 1-100 nM | 689 | 1-100 nM | 690 | 1-100 nM |
| 691 | 1-100 nM | 692 | 1-100 nM | 693 | 1-100 nM | 694 | 100-1000 nM |
| 695 | 1-100 nM | 696 | 1-100 nM | 697 | 1-100 nM | 698 | 1-100 nM |
| 699 | 1-100 nM | 700 | 1-100 nM | 701 | 1-100 nM | 702 | 1-100 nM |
| 703 | 1-100 nM | 704 | 1-100 nM | 705 | 1-100 nM | 706 | 1-100 nM |
| 707 | 100-1000 nM | 708 | 100-1000 nM | 709 | 1-100 nM | 710 | 100-1000 nM |
| 711 | 1-100 nM | 712 | 100-1000 nM | 713 | >1000 nM | 714 | 100-1000 nM |
| 715 | 1-100 nM | 716 | 1-100 nM | 717 | 1-100 nM | 718 | 1-100 nM |
| 719 | 1-100 nM | 720 | 1-100 nM | 721 | >1000 nM | 722 | >1000 nM |
| 723 | 1-100 nM | 724 | 1-100 nM | 725 | 1-100 nM | 726 | 1-100 nM |
| 727 | 1-100 nM | 728 | 1-100 nM | 729 | 1-100 nM | 730 | 1-100 nM |
| 731 | 1-100 nM | 732 | 1-100 nM | 733 | 1-100 nM | | |

Active Compounds Group I: Representative Synthesis

N-(4-((4-(tert-butyl)-3-fluorophenyl)amino)benzyl)-N-hydroxy-1-(trifluoromethyl)cyclobutane-1-carboxamide (1)

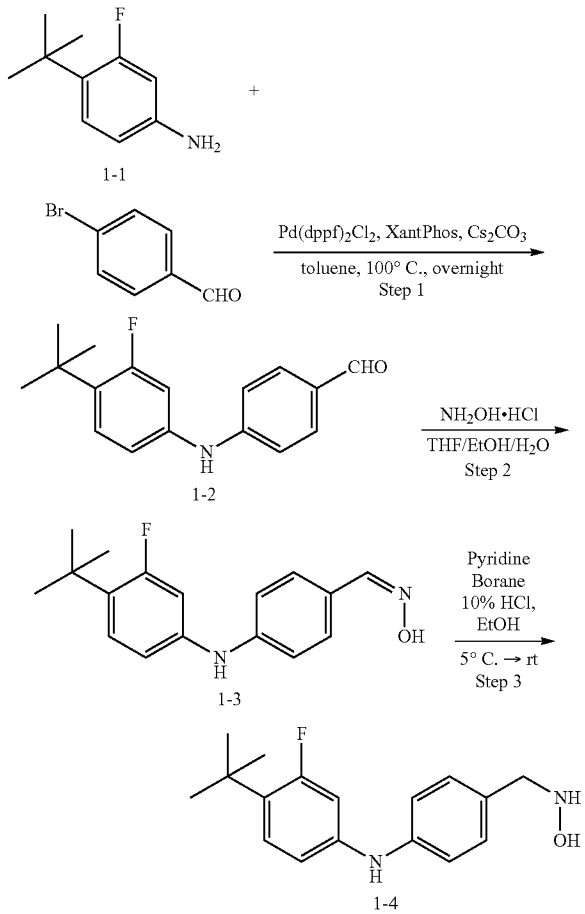

1-1

1-2

1-3

1-4

-continued

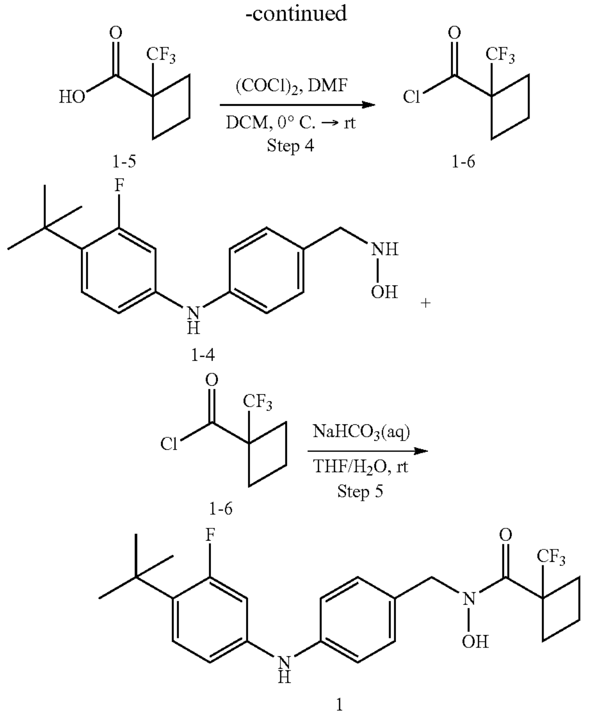

1-5

1-6

1-4

1-6

1

Step 1. 4-(tert-butyl)-3-fluoroaniline (2.17 g, 13 mmol), 4-bromobenzaldehyde (1.85 g, 10 mmol), Pd(dppf)$_2$Cl$_2$ (147 mg, 0.2 mmol), XantPhos (231 mg, 0.4 mmol), and Cs$_2$CO$_3$ (4.89 g, 15 mmol) was dissolved in toluene under an atmosphere of Nitrogen and stirred at 100° C. overnight. After the reaction was completed, the reaction product was cooled to room temperature and diluted with DCM and passed through a plug of silica, after which the solvent was removed under reduced pressure. The residue was purified by silica gel column chromatography (PE/EA=5/1) to give the desired product as yellow solid (1.8 g, 66%). Mass (m/z): 272.3 $[M+H]^+$.

Step 2.

To a solution of 4-((4-(tert-butyl)-3-fluorophenyl)amino) benzaldehyde (928 mg, 3.4 mmol) in THF/H$_2$O/EtOH (2/1/5, 40 mL) was added Hydroxylamine hydrochloride (261 mg, 3.8 mmol). Then the reaction was stirred overnight at rt.

The reaction mixture was concentrated under vacuum. The crude was used directly at next step. (100%). Mass (m/z): 287.2 $[M+H]^+$.

Step 3.

To a solution of (Z)-4-((4-(tert-butyl)-3-fluorophenyl) amino)benzaldehyde oxime (972 mg, 3.4 mmol) in EtOH (40 mL) was added Borane-pyridine (632 mg, 6.8 mmol). Then 10% HCl (6.8 mL) was added dropwise at 0° C. The solution was stirred for 3 hours at rt. The PH of the solution was adjusted to 8-9 with sodium carbonate solution. Then the mixture was extracted by DCM (15 mL×3). The combined organic layers were washed with water (20 mL×3), dried over $Na_2SO_4$ and concentrated under vacuum. The residue was purified by silica gel column chromatography (MeOH/DCM=1/40) to give the desired product as yellow solid (242 mg, 25%). Mass (m/z): 289.3 $[M+H]^+$.

Step 4.

1-(trifluoromethyl)cyclobutane-1-carboxylic acid (25.2 mg, 0.15 mmol) was dissolved in DCM (1 mL). The solution was cooled to 0° C. and then Oxalyl chloride (0.0165 mL, 0.195 mmol) and DMF (0.05 mL) was added. The reaction mixture was stirred for 2 h, concentrated under reduced pressure and re-dissolved in anhydrous $CH_2Cl_2$. The solution was used directly at next step.

Step 5

4-(tert-butyl)-3-fluoro-N-(4-((hydroxyamino)methyl) phenyl)aniline (20 mg, 0.07 mmol) was dissolved in 1.0 ml of $THF/H_2O$ (1:1, v/v) and 1.2 ml of saturated aqueous $NaHCO_3$. The solution was cooled to 0° C. and 1-(trifluoromethyl)cyclobutane-1-carbonyl chloride was added and the mixture was stirred at room temperature for 16 h. The mixture was extracted with EtOAc and the combined organic layer was washed with brine, dried with ($Na_2SO4$) and concentrated in vacuo to give crude product. The residue was purified by prep-TLC (MeOH/DCM=1/10) to give the desired product as white solid (13.9 mg, 45.9%). $^1H$ NMR (400 MHz, Chloroform-d) δ 7.23-7.13 (m, 3H), 7.05 (d, J=8.0 Hz, 2H), 6.81-6.70 (m, 2H), 4.76 (s, 2H), 2.79-2.70 (m, 2H), 2.51 (br m, 2H), 1.36 (m, 9H), 1.30-1.22 (m, 2H). Mass (m/z): 439.2 $[M+H]^+$.

N-(4-((4-(tert-butyl)phenyl)amino)benzyl)-N-hydroxyadamantane-1-carboxamide (2)

2

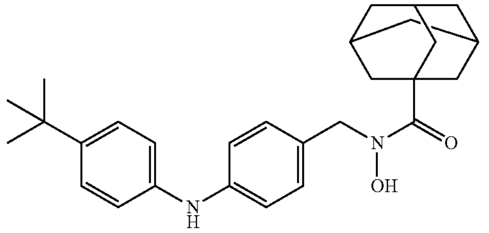

$^1H$ NMR (400 MHz, $CDCl_3$) δ 7.30 (d, J=8.3 Hz, 2H), 7.15 (d, J=8.3 Hz, 2H), 7.02 (t, J=8.1 Hz, 4H), 4.88 (s, 2H), 2.04 (s, 9H), 1.70 (s, 6H), 1.31 (s, 9H). LC-MS (ESI) m/z: 433.2, $[M+H]^+$.

N-hydroxy-N-(4-(pyridin-4-ylamino)benzyl)adamantane-1-carboxamide (3)

3

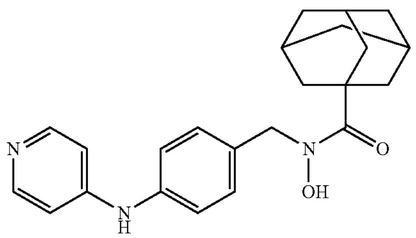

$^1H$ NMR (400 MHz, $CDCl_3$) δ 7.15 (d, J=7.9 Hz, 2H), 7.00 (m, 6H), 4.86 (s, 2H), 2.04 (s, 9H), 1.71 (m, 6H). LC-MS (ESI) m/z: 378.2, $[M+H]^+$.

N-(4-((4-fluorophenyl)amino)benzyl)-N-hydroxyadamantane-1-carboxamide (4)

4

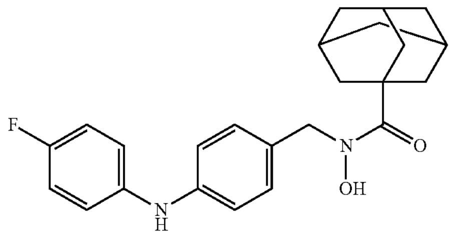

$^1H$ NMR (400 MHz, $CDCl_3$) δ 7.13 (d, J=7.8 Hz, 2H), 7.06-6.88 (m, 6H), 4.84 (s, 2H), 2.02 (s, 9H), 1.73 (m, 6H). LC-MS (ESI) m/z: 395.3, $[M+H]^+$.

N-(4-((4-(N,N-diethylsulfamoyl)phenyl)amino)benzyl)-N-hydroxyadamantane-1-carboxamide (5)

5

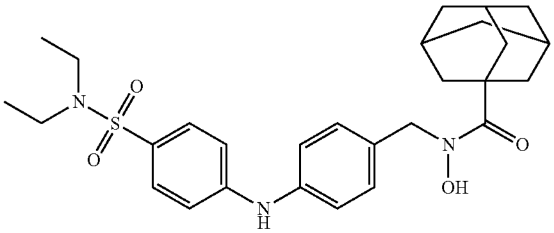

$^1H$ NMR (400 MHz, $CDCl_3$) δ 7.64 (d, J=8.8 Hz, 2H), 7.27-7.22 (m, 2H), 7.14 (d, J=8.4 Hz, 2H), 7.01 (d, J=8.8 Hz, 2H), 4.93 (s, 2H), 3.21 (q, J=7.2 Hz, 4H), 2.05 (s, 9H), 1.73 (s, 6H), 1.30-1.22 (m, 6H). LC-MS (ESI) m/z: 512.3, $[M+H]^+$.

N-(4-((4-(tert-butyl)phenyl)amino)benzyl)-N-hydroxypivalamide (6)

6

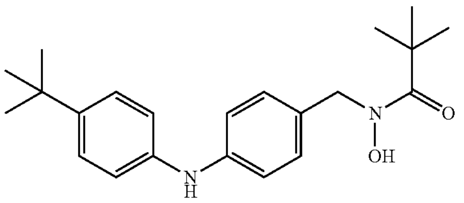

$^1$H NMR (400 MHz, $CDCl_3$) δ 7.31 (d, J=8.7 Hz, 2H), 7.17 (d, J=8.6 Hz, 2H), 7.04 (t, J=8.1 Hz, 4H), 4.83 (s, 2H), 1.38 (s, 9H), 1.25 (s, 9H). LC-MS (ESI) m/z: 355.3, $[M+H]^+$.

N-(4-((4-(tert-butyl)phenyl)amino)benzyl)-N-hydroxycyclopropanecarboxamide (7)

7

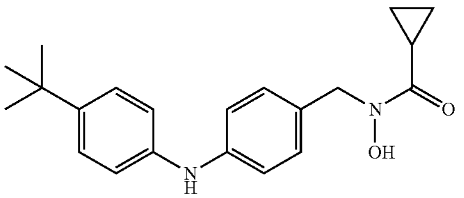

$^1$H NMR (400 MHz, $CDCl_3$) δ 7.30 (d, J=8.3 Hz, 2H), 7.19 (d, J=8.1 Hz, 2H), 7.02 (dd, J=11.8, 8.4 Hz, 4H), 4.83 (s, 2H), 1.89-1.64 (m, 1H), 1.32 (s, 6H), 1.02 (m, 2H), 0.98-0.78 (m, 2H). LC-MS (ESI m/z: 339.3, $[M+H]^+$.

N-hydroxy-N-(4-((4-(trifluoromethyl)phenyl)amino)benzyl)adamantane-1-carboxamide (8)

8

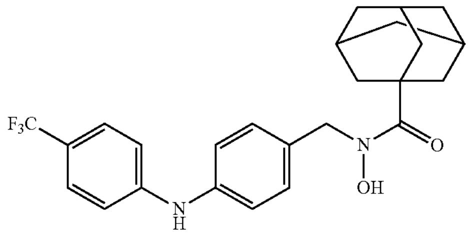

$^1$H NMR (400 MHz, $CDCl_3$) δ 7.46 (d, J=8.2 Hz, 2H), 7.23 (d, J=8.2 Hz, 2H), 7.12 (d, J=8.2 Hz, 2H), 7.04 (d, J=8.2 Hz, 2H), 4.91 (s, 2H), 2.05 (s, 9H), 1.70 (s, 6H). LC-MS (ESI) m/z: 445.3, $[M+H]^+$.

N-hydroxy-N-(4-(pyridin-4-ylamino)benzyl)pivalamide (9)

9

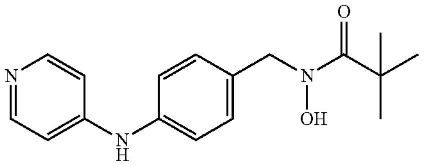

$^1$H NMR (400 MHz, $CDCl_3$) δ 8.28-8.21 (m, 2H), 7.34 (d, J=6.9 Hz, 2H), 7.17 (dd, J=8.4, 1.6 Hz, 2H), 6.86-6.78 (m, 2H), 4.10 (s, 2H), 1.18 (s, 9H). LC-MS (ESI) m/z: 300.3, $[M+H]^+$

N-(4-((4-fluorophenyl)amino)benzyl)-N-hydroxypivalamide (10)

10

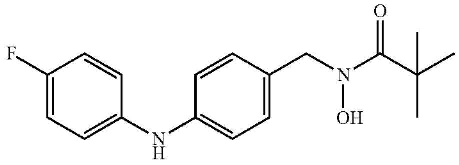

$^1$H NMR (400 MHz, $CDCl_3$) δ 7.15 (d, J=5.8 Hz, 2H), 6.97 (m, 6H), 4.79 (s, 2H), 1.30 (s, 9H). LC-MS (ESI) m/z: 317.3, $[M+H]^+$.

N-(4-((4-(N,N-diethylsulfamoyl)phenyl)amino)benzyl)-N-hydroxypivalamide (11)

11

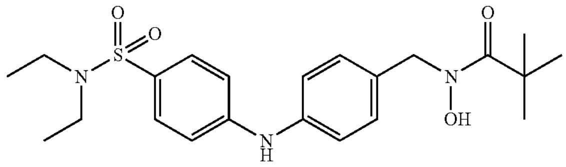

$^1$H NMR (400 MHz, $CDCl_3$) δ 7.54 (d, J=8.2 Hz, 2H), 7.20 (d, J=7.8 Hz, 2H), 7.06 (d, J=7.6 Hz, 2H), 6.95 (d, J=7.8 Hz, 2H), 4.76 (s, 2H), 3.24-3.10 (m, 4H), 1.29 (s, 9H), 1.10 (t, J=7.1 Hz, 6H). LC-MS (ESI) m/z: 434.3, $[M+H]^+$.

N-(4-((4-(tert-butyl)phenyl)amino)benzyl)-N-hydroxyacetamide (12)

12

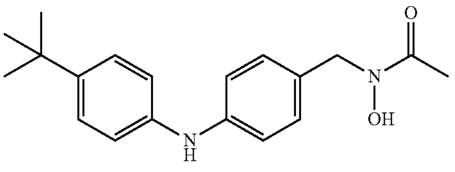

$^1H$ NMR (400 MHz, $CDCl_3$) δ 7.31 (d, J=8.2 Hz, 2H), 7.22-7.13 (m, 2H), 7.03 (m, 4H), 4.73 (s, 2H), 2.18 (s, 3H), 1.31 (s, 9H). LC-MS (ESI) m/z: 313.2. $[M+H]^+$.

N-(4-((4-(tert-butyl)phenyl)amino)benzyl)-N-hydroxy-2,2-dimethylbutanamide (13)

13

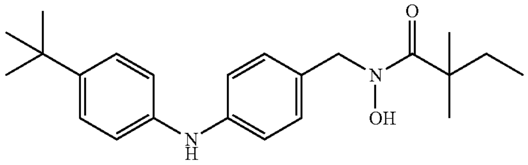

$^1H$ NMR (400 MHz, $CDCl_3$) δ 7.33-7.28 (m, 2H), 7.18 (d, J=8.4 Hz, 2H), 7.07-6.99 (m, 4H), 4.82 (s, 2H), 1.69 (q, J=7.4 Hz, 2H), 1.31 (s, 9H), 1.27 (s, 6H), 0.86 (t, J=7.6 Hz, 3H). LC-MS (ESI) m/z: 369.3, $[M+H]^+$.

N-(4-((4-(tert-butyl)phenyl)amino)benzyl)-N-hydroxy-1-methylcyclopropane-1-carboxamide (14)

14

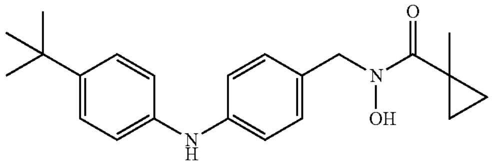

$^1H$ NMR (400 MHz, $CDCl_3$) δ 7.30 (d, J=8.2 Hz, 2H), 7.19 (d, J=8.2 Hz, 2H), 7.03 (dd, J=8.0, 6.2 Hz, 4H), 4.92 (s, 2H), 1.38 (s, 3H), 1.32 (s, 9H), 1.26 (m, 1H), 1.05 (t, J=5.2 Hz, 2H), 0.68 (d, J=5.0 Hz, 2H). LC-MS (ESI) m/z: 353.2, $[M+H]^+$.

N-(4-((4-(tert-butyl)phenyl)amino)benzyl)-N-hydroxy-6-methoxy-2,2-dimethylhexanamide (15)

15

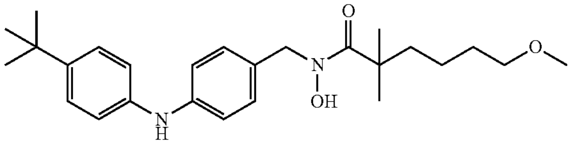

$^1H$ NMR (400 MHz, $CDCl_3$) δ 7.29 (d, J=8.2 Hz, 2H), 7.22 (d, J=8.4 Hz, 2H), 7.02 (m, 4H), 4.76 (s, 2H), 3.34 (t, J=6.0 Hz, 2H), 3.07 (s, 3H), 1.76-1.64 (m, 2H), 1.59-1.45 (m, 2H), 1.43-1.33 (m, 2H), 1.31 (s, 9H), 1.27 (s, 6H). LC-MS (ESI) m/z: 427.2, $[M+H]^+$.

N-(4-((4-(tert-butyl)phenyl)amino)benzyl)-2,2,2-trifluoro-N-hydroxyacetamide (16)

16

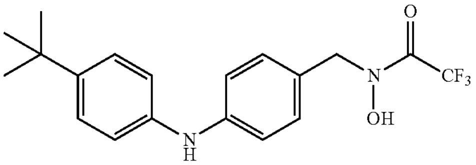

$^1H$ NMR (400 MHz, $CDCl_3$) δ 7.32 (d, J=8.2 Hz, 2H), 7.20 (d, J=8.2 Hz, 2H), 7.05 (d, J=8.6 Hz, 2H), 7.01 (d, J=8.6 Hz, 2H), 4.83 (s, 2H), 1.32 (s, 9H). LC-MS (ESI) m/z: 367.3, $[M+H]^+$.

N-(4-((4-(tert-butyl)phenyl)amino)benzyl)-N-hydroxycyclopentanecarboxamide (17)

17

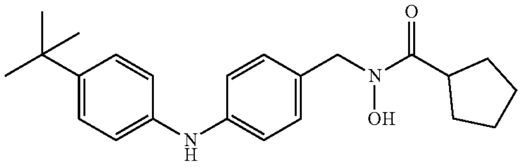

$^1H$ NMR (400 MHz, $CDCl_3$) δ 7.30 (d, J=8.2 Hz, 2H), 7.15 (m, 2H), 7.03 (m, Hz, 4H), 4.78 (s, 2H), 2.90 (m, 1H), 1.83 (m, 6H), 1.58 (m, 2H), 1.32 (s, 9H). LC-MS (ESI) m/z: 367.3, $[M+H]^+$.

N-(4-((4-(tert-butyl)phenyl)amino)benzyl)-N-hydroxybenzamide (18)

18

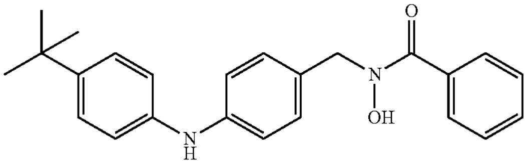

$^1H$ NMR (400 MHz, $CDCl_3$) δ 7.59 (d, J=7.2 Hz, 2H), 7.48 (m, 3H), 7.36-7.29 (m, 2H), 7.12 (d, J=8.3 Hz, 2H), 7.09-6.97 (m, 4H), 4.77 (s, 2H), 1.31 (s, 9H). LC-MS (ESI) m/z: 375.2, $[M+H]^+$.

N-(4-((4-(tert-butyl)phenyl)amino)benzyl)-N-hydroxy-1-(trifluoromethyl)cyclobutane-1-carboxamide (19)

19

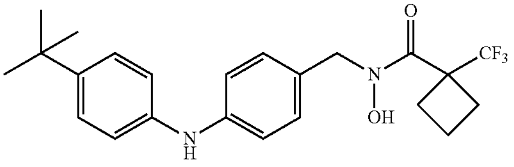

$^1$H NMR (400 MHz, $CDCl_3$) δ 7.31 (d, J=8.2 Hz, 2H), 7.17 (d, J=8.0 Hz, 2H), 7.03 (m, 4H), 4.74 (s, 2H), 2.75 (dd, J=22.4, 10.2 Hz, 2H), 2.51 (m, 2H), 2.19-2.01 (m, 1H), 1.86 (m, 1H), 1.31 (s, 9H). LC-MS (ESI) m/z: 421.4, $[M+H]^+$.

N-(4-((4-(tert-butyl)phenyl)amino)benzyl)-N-hydroxy-2-methoxy-2-methylpropanamide (20)

20

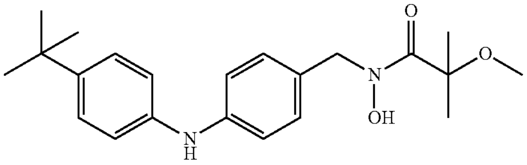

$^1$H NMR (400 MHz, $CDCl_3$) δ 7.30 (d, J=8.2 Hz, 2H), 7.23 (d, J=8.2 Hz, 2H), 7.02 (m, 4H), 5.07 (s, 2H), 3.25 (s, 3H), 1.51 (s, 6H), 1.31 (m, 9H). LC-MS (ESI) m/z: 371.4 $[M+H]^+$.

N-(4-((4-(tert-butyl)phenyl)amino)benzyl)-N-hydroxy-4-methoxy-2,2-dimethylbutanamide (21)

21

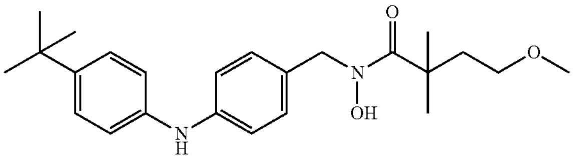

$^1$H NMR (400 MHz, $CDCl_3$) δ 7.30-7.25 (m, 4H), 7.04-6.97 (m, 4H), 4.67 (s, 2H), 3.43-3.34 (m, 2H), 2.89 (s, 3H), 1.31 (s, 9H), 1.29 (s, 6H), 1.26 (m, 2H). LC-MS (ESI) m/z: 399.3, $[M+H]^+$.

N-hydroxy-2,2-dimethyl-N-(4-((4-(trifluoromethyl)phenyl)amino)benzyl)butanamide (22)

22

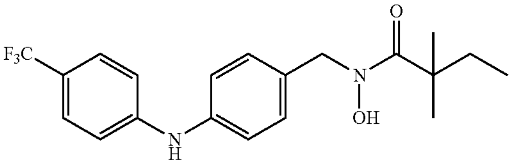

$^1$H NMR (400 MHz, $CDCl_3$) δ 7.47 (d, J=7.8 Hz, 2H), 7.27 (d, J=7.6 Hz, 2H), 7.12 (d, J=7.8 Hz, 2H), 7.04 (d, J=8.0 Hz, 2H), 4.85 (s, 2H), 1.71 (q, J=7.5 Hz, 2H), 1.28 (s, 6H), 0.87 (t, J=7.4 Hz, 3H). LC-MS (ESI) m/z: 381.3, $[M+H]^+$.

N-(4-((4-(tert-butyl)phenyl)amino)benzyl)-N-hydroxynicotinamide (23)

23

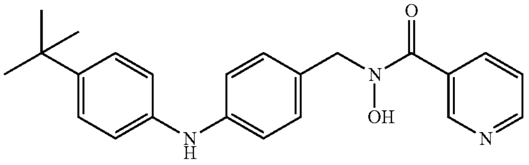

$^1$H NMR (400 MHz, $CDCl_3$) δ 8.34 (br s, 1H), 7.96 (d, J=7.2 Hz, 1H), 7.37-7.18 (m, 6H), 7.00 (dd, J=15.2, 8.4 Hz, 4H), 4.83 (s, 2H), 1.31 (s, 9H). LC-MS (ESI) m/z: 376.3, $[M+H]^+$.

N-(4-((4-(tert-butyl)phenyl)amino)benzyl)-N-hydroxy-4-methyltetrahydro-2H-pyran-4-carboxamide (24)

24

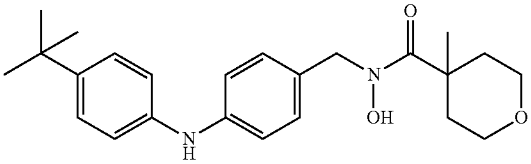

$^1$H NMR (400 MHz, $CDCl_3$) δ 7.30 (d, J=8.0 Hz, 2H), 7.16 (d, J=8.0 Hz, 2H), 7.01 (m, 4H), 4.76 (s, 2H), 3.78-3.65 (m, 2H), 3.60 (t, J=9.6 Hz, 2H), 2.23 (d, J=13.9 Hz, 2H), 1.65-1.48 (m, 2H), 1.31 (s, 12H). LC-MS (ESI) m/z: 397.2, $[M+H]^+$.

N-(4-((4-(tert-butyl)phenyl)amino)benzyl)-3,3,3-trifluoro-N-hydroxy-2,2-dimethylpropanamide (25)

25

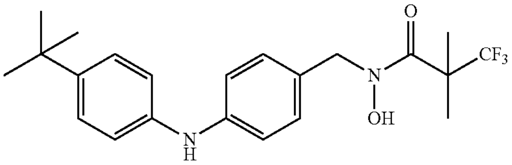

$^1$H NMR (400 MHz, $CDCl_3$) δ 7.32 (d, J=8.0 Hz, 2H), 7.17 (d, J=8.2 Hz, 2H), 7.06 (m, 4H), 4.78 (s, 2H), 1.55 (s, 6H), 1.32 (m, 9H). LC-MS (ESI) m/z: 409.3, $[M+H]^+$.

N-(4-((4-(tert-butyl)phenyl)amino)benzyl)-N-hydroxy-1-methylcyclohexane-1-carboxamide (26)

26

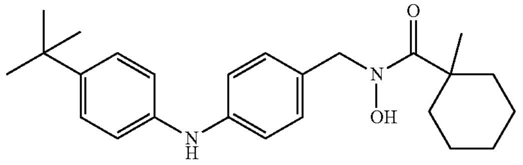

$^1$H NMR (400 MHz, $CDCl_3$) δ 7.30 (d, J=8.4 Hz, 2H), 7.17 (d, J=8.4 Hz, 2H), 7.02 (m, 4H) 4.82 (s, 2H), 2.14 (dd, J=13.4, 5.5 Hz, 2H) 1.59-1.43 (m, 5H), 1.43-1.33 (m, 3H), 1.32 (s, 9H), 1.25 (s, 3H). LC-MS (ESI) m/z: 395.3, $[M+H]^+$.

N-(4-((4-(tert-butyl)phenyl)amino)benzyl)-4,4-difluoro-N-hydroxycyclohexane-1-carboxamide (27)

27

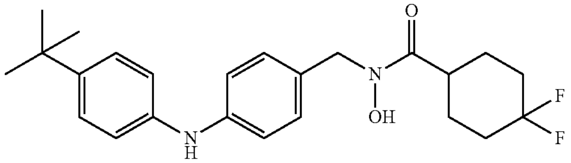

$^1$H NMR (400 MHz, $CDCl_3$) δ 7.31 (d, J=8.0 Hz, 1H), 7.15 (d, J=7.8 Hz, 1H), 7.03 (m, 4H), 4.76 (s, 2H), 2.56 (s, 1H), 2.17 (m, 2H), 1.73 (m, 6H), 1.32 (s, 9H). LC-MS (ESI) m/z: 317.3, $[M+H]^+$.

N-(4-((3-(tert-butyl)phenyl)amino)benzyl)-N-hydroxy-2-methoxy-2-methylpropanamide (28)

28

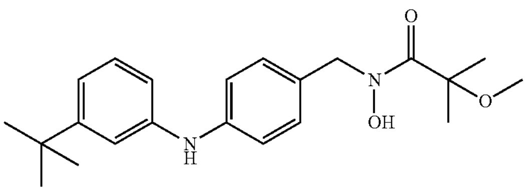

$^1$H NMR (400 MHz, $CDCl_3$) δ 7.25-7.17 (m, 3H), 7.10 (s, 1H), 7.01 (m, 2H), 6.93 (m, 2H), 4.77 (s, 2H), 3.26 (s, 3H), 1.52 (s, 6H), 1.30 (s, 9H). LC-MS (ESI) m/z: 371.3, $[M+H]^+$.

N-(4-((4-(tert-butyl)phenyl)amino)benzyl)-N-hydroxy-1-(trifluoromethyl)cyclopropane-1-carboxamide (29)

29

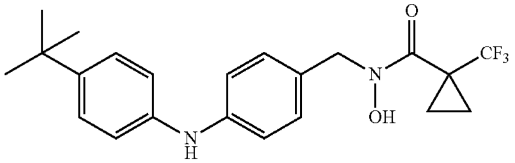

$^1$H NMR (400 MHz, $CDCl_3$) δ 7.31 (d, J=7.8 Hz, 2H), 7.16 (d, J=7.2 Hz, 2H), 7.09-6.95 (m, 4H), 4.91 (s, 2H), 1.37 (m, 2H), 1.32 (s, 9H), 1.29-1.23 (m, 2H). LC-MS (ESI) m/z: 407.3, $[M+H]^+$.

N-(4-((4-(tert-butyl)phenyl)amino)benzyl)-N-hydroxy-1-methylpiperidine-4-carboxamide (30)

30

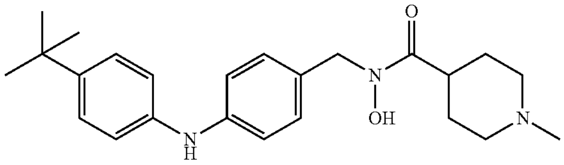

$^1$H NMR (400 MHz, DMSO) δ 7.24 (d, J=8.0 Hz, 2H), 7.08 (d, J=8.0 Hz, 2H), 7.02-6.92 (m, 4H), 4.58 (s, 2H), 3.55-3.22 (m, 2H), 3.01 (m, 3H), 2.70 (s, 3H), 2.07-1.72 (m, 4H), 1.25 (s, 9H). LC-MS (ESI) m/z: 396.3, $[M+H]^+$.

1-acetyl-N-(4-((4-(tert-butyl)phenyl)amino)benzyl)-N-hydroxypiperidine-4-carboxamide (31)

31

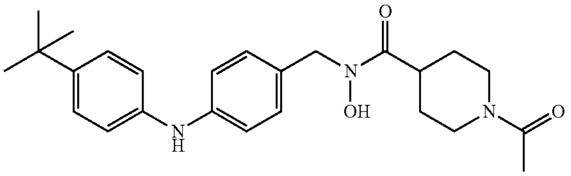

$^1$H NMR (400 MHz, DMSO) δ 7.24 (d, J=8.0 Hz, 2H), 7.08 (d, J=7.8 Hz, 2H), 7.01-6.93 (m, 4H), 4.57 (s, 2H), 4.35 (m, 1H), 3.82 (m, 1H), 3.05 (m, 2H), 2.68-2.51 (m, 1H), 2.00 (s, 3H), 1.70 (m, 2H), 1.63-1.30 (m, 2H), 1.23 (s, 9H). LC-MS (ESI) m/z: 424.3, $[M+H]^+$.

N-(4-((4-(tert-butyl)phenyl)amino)benzyl)-N-hydroxy-2-(2-methoxyethoxy)acetamide (32)

32

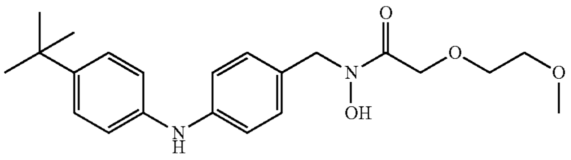

$^1$H NMR (400 MHz, $CDCl_3$) δ 7.29 (d, J=8.4 Hz, 2H), 7.20 (d, J=8.2 Hz, 2H), 7.00 (m, 4H), 4.69 (s, 2H), 4.31 (s, 2H), 3.73-3.60 (m, 2H), 3.59-3.48 (m, 2H), 3.29 (s, 3H), 1.31 (s, 9H). LC-MS (ESI) m/z: 387.2, $[M+H]^+$.

N-(4-((4-(tert-butyl)phenyl)amino)benzyl)-N-hydroxy-1-methyl-2-oxo-1,2-dihydropyridine-4-carboxamide (33)

33

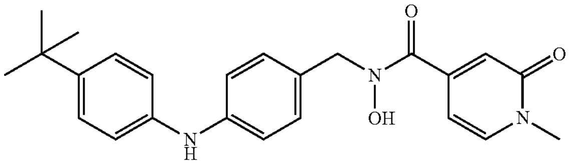

$^1$H NMR (400 MHz, $CDCl_3$) δ 7.26 (m, 6H), 6.99 (m, 4H), 6.63 (s, 1H), 4.81 (s, 2H), 3.41 (s, 3H), 1.31 (s, 9H). LC-MS (ESI) m/z: 406.2, $[M+H]^+$.

N-(4-((4-(tert-butyl)phenyl)amino)benzyl)-N-hydroxy-4-(pyrrolidin-1-yl)benzamide (34)

34

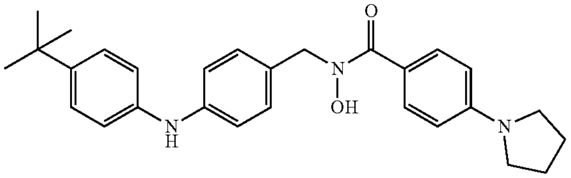

$^1$H NMR (400 MHz, $CDCl_3$) δ 7.54 (d, J=8.0 Hz, 2H), 7.30 (d, J=7.8 Hz, 2H), 7.17 (d, J=7.8 Hz, 2H), 7.08-6.96 (m, 4H), 6.54 (d, J=7.7 Hz, 2H), 4.83 (s, 2H), 3.35 (m, 4H), 2.04 (m, 4H), 1.31 (s, 9H). LC-MS (ESI) m/z: 444.2, $[M+H]^+$.

N-(4-((3-(tert-butyl)phenyl)amino)benzyl)-N-hydroxy-4-methyltetrahydro-2H-pyran-4-carboxamide (35)

35

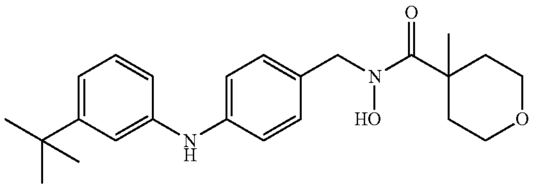

$^1$H NMR (400 MHz, $CDCl_3$) δ 7.25-7.15 (m, 3H), 7.11 (s, 1H), 7.04 (d, J=8.2 Hz, 2H), 7.02-6.89 (m, 2H), 4.81 (s, 2H), 3.84-3.71 (m, 2H), 3.68-3.57 (m, 2H), 2.24 (m, 2H), 1.63-1.53 (m, 2H), 1.31 (s, 9H), 1.25 (s, 3H). LC-MS (ESI) m/z: 397.3, $[M+H]^+$.

N-(4-((3-(tert-butyl)phenyl)amino)benzyl)-N-hydroxy-1-methylcyclopropane-1-carboxamide (36)

36

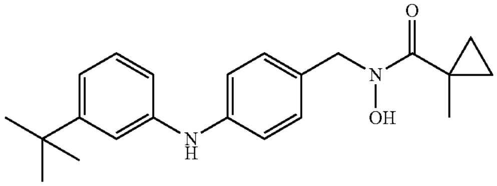

$^1$H NMR (400 MHz, $CDCl_3$) δ 7.22 (m, 3H), 7.11 (s, 1H), 7.03 (m, 2H), 6.94 (d, J=7.8 Hz, 2H), 4.93 (s, 2H), 1.31 (s, 3H), 1.26 (m, 9H), 1.06 (m, 2H), 0.94-0.84 (m, 2H). LC-MS (ESI) m/z: 353.3, $[M+H]^+$

N-(4-((3-(tert-butyl)phenyl)amino)benzyl)-N-hydroxy-1-(trifluoromethyl)cyclobutane-1-carboxamide (37)

37

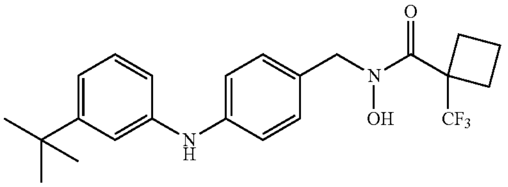

$^1$H NMR (400 MHz, $CDCl_3$) δ 7.20 (m, 3H), 7.11 (s, 1H), 7.03 (t, J=6.8 Hz, 2H), 6.94 (m, 2H), 4.75 (s, 2H), 2.75 (m, 2H), 2.52 (m, 2H), 2.17-2.03 (m, 1H), 1.86 (m, 1H), 1.31 (s, 9H). LC-MS (ESI) m/z: 421.3, $[M+H]^+$

N-(4-((4-(tert-butyl)phenyl)amino)benzyl)pivalamide (38)

38

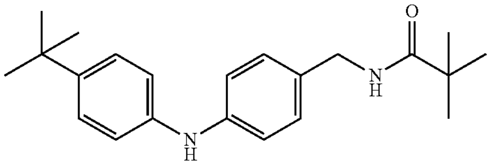

$^1H$ NMR (400 MHz, $CDCl_3$) δ 7.31-7.28 (d, J=8.6 Hz, 2H), 7.14 (d, J=8.4 Hz, 2H), 7.06-6.97 (m, 4H), 4.36 (d, J=5.4 Hz, 2H), 1.32 (s, 9H), 1.23 (s, 9H). LC-MS (ESI) m/z: 339.4, $[M+H]^+$.

N-(4-((4-(tert-butyl)phenyl)amino)benzyl)pivalamide (39)

39

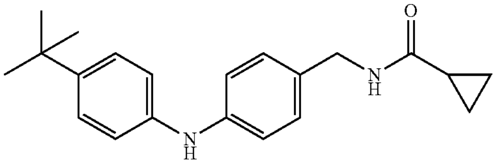

$^1H$ NMR (400 MHz, $CDCl_3$) δ 7.31-7.28 (m, 2H), 7.15 (dd, J=8.6, 2.4 Hz, 2H), 7.04-6.97 (m, 4H), 4.35 (d, J=5.6 Hz, 2H), 1.42-1.33 (m, 1H), 1.32 (s, 9H), 1.02-0.95 (m, 2H), 0.77-0.68 (m, 2H). LC-MS (ESI) m/z: 323.4, $[M+H]^+$.

1-isopropyl-N-(4-((4-(4-(trifluoromethyl)piperidin-1-yl)phenyl)amino)benzyl)piperidine-4-carboxamide (40)

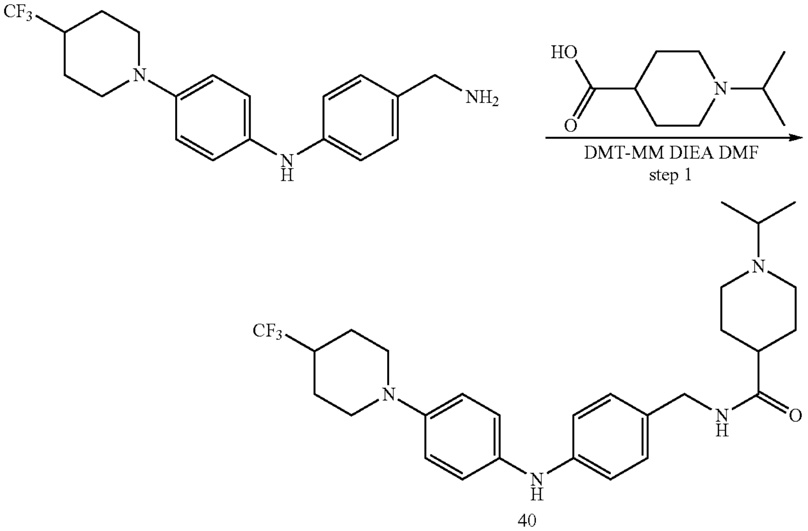

40

The title compound 40 (13.0 mg) was prepared in a yield of 41.01% as a pale blue powder from 4-(aminomethyl)-N-(4-(4-(trifluoromethyl)piperidin-1-yl)phenyl)aniline (30 mg, 0.09 mmol) and 1-isopropylpiperidine-4-carboxylic acid (16 mg, 0.09 mmol). $^1H$ NMR (400 MHz, Methanol-$d_4$) δ 7.25-6.74 (m, 8H), 4.26 (s, 2H), 3.55-3.44 (m, 3H), 3.05 (s, 2H), 2.67 (s, 2H), 2.54 (s, 1H), 2.36-2.18 (m, 1H), 2.16-1.87 (m, 7H), 1.72 (d, J=13.0 Hz, 3H), 1.35 (d, J=6.7 Hz, 6H). LC-MS (m/z) 503.4 $[M+H]^+$.

N-(4-((4-cyclohexylphenyl)amino)benzyl)-N-hydroxy-2-(4-methylpiperazin-1-yl)acetamide (41)

41

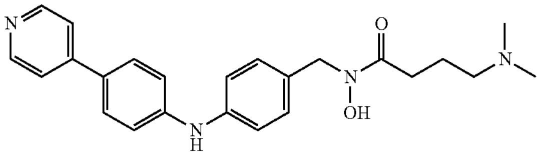

$^1H$ NMR (400 MHz, Methanol-$d_4$) δ 8.63 (d, J=6.4 Hz, 2H), 8.26 (d, J=6.4 Hz, 2H), 7.93 (d, J=8.8 Hz, 2H), 7.32 (d, J=8.4 Hz, 2H), 7.22 (dd, J=8.4, 4.0 Hz, 4H), 4.76 (s, 2H), 3.23-3.12 (m, 2H), 2.91 (s, 6H), 2.69 (t, J=6.8 Hz, 2H), 2.09-1.93 (m, 2H). Mass (m/z): 405.3 $[M+H]^+$.

N-(4-((4-(diethylamino)phenyl)amino)benzyl)-4-(dimethylamino)-N-hydroxybutanamide (42)

42

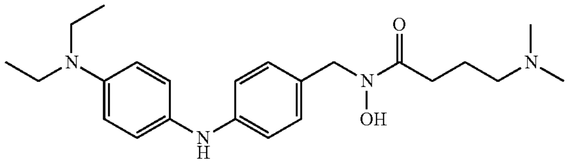

102071 $^1H$ NMR (400 MHz, Methanol-$d_4$) δ 7.34-6.57 (m, 8H), 4.64 (s, 2H), 3.01-2.93 (m, 2H), 2.86-2.80 (m, 4H), 2.72 (s, 6H), 2.63 (t, J=6.8 Hz, 2H), 1.97 (m, 2H), 1.10 (t, J=7.0 Hz, 6H). Mass (m/z): 399.3 $[M+H]^+$.

N-hydroxy-2-(4-methylpiperazin-1-yl)-N-(4-((3-(pyrrolidin-1-yl)phenyl)amino)benzyl)acetamide (43)

43

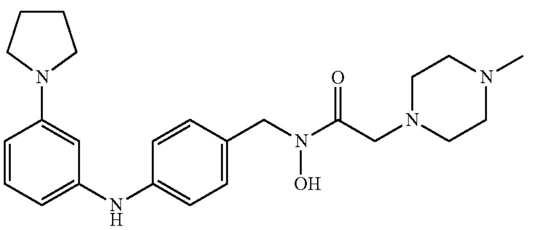

$^1$H NMR (400 MHz, DMSO-$d_6$) δ 7.94 (s, 1H), 7.20-6.92 (m, 5H), 6.37-6.23 (m, 2H), 4.53 (s, 2H), 3.54-3.28 (m, 8H), 3.25 (s, 2H), 3.18 (br m, 4H), 2.29 (br s, 4H), 2.13 (s, 3H), 1.96-1.86 (m, 4H). Mass (m/z): 424.2 $[M+H]^+$.

1-methyl-N-(4-((4-(4-(trifluoromethyl)piperidin-1-yl)phenyl)amino)benzyl)piperidine-4-carboxamide (44)

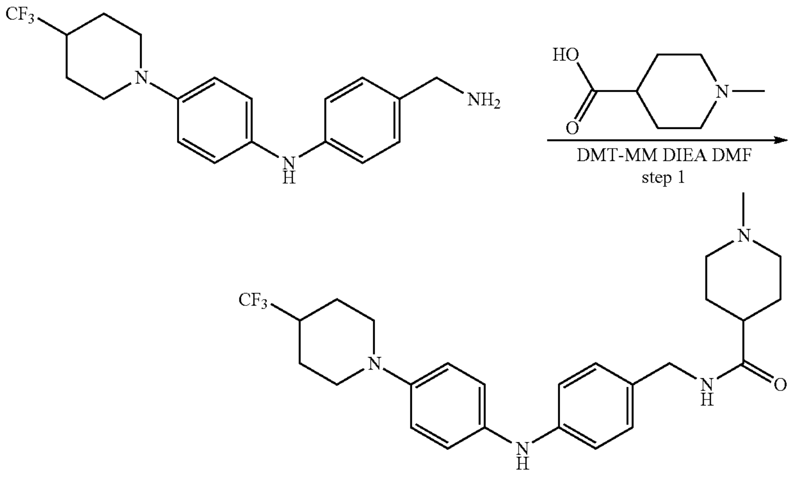

44

The title compound 44 (13.0 mg) was prepared in a yield of 31.90% as a pale yellow powder from 4-(aminomethyl)-N-(4-(4-(trifluoromethyl)piperidin-1-yl)phenyl)aniline (30 mg, 0.09 mmol) and 1-methylpiperidine-4-carboxylic acid (14 mg, 0.09 mmol). $^1$H NMR (400 MHz, Methanol-$d_4$) δ 7.10 (s, 8H), 4.54-3.95 (br, 2H), 3.80-3.51 (m, 1H), 3.52-3.40 (m, 3H), 2.99 (td, J=12.2, 3.6 Hz, 2H), 2.81 (s, 3H), 2.53 (tt, J=10.8, 4.3 Hz, 11H), 2.39-2.16 (m, 1H), 2.13-1.85 (m, 7H), 1.72 (d, J=12.7 Hz, 3H). LC-MS (m/z) 475.7 $[M+H]^+$.

N-hydroxy-2,2-dimethyl-N-(4-(phenylamino)benzyl)butanamide (45)

45

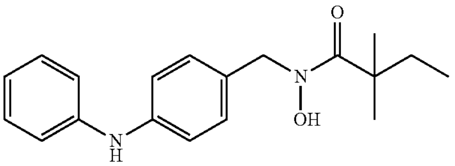

1H NMR (400 MHz, Chloroform-d) δ 7.29-7.12 (m, 4H), 7.07-6.88 (m, 5H), 4.74 (s, 2H), 1.71 (q, J=7.4 Hz, 2H), 1.25 (s, 6H), 0.83 (t, J=7.4 Hz, 3H). Mass (m/z): 313.2 $[M+H]^+$.

N-hydroxy-N-(4-((4-(trifluoromethyl)phenyl)amino)benzyl)pivalamide (46)

46

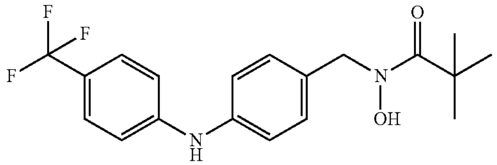

1H NMR (400 MHz, Chloroform-d) δ 7.45 (d, J=8.2 Hz, 2H), 7.23 (d, J=7.8 Hz, 2H), 7.06 (dd, J=27.4, 8.2 Hz, 4H), 4.82 (s, 2H), 1.31 (s, 9H). Mass (m/z): 367.3 $[M+H]^+$.

N-hydroxy-N-(4-(pyridin-2-ylamino)benzyl)pivalamide (47)

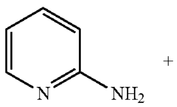

47-1

-continued

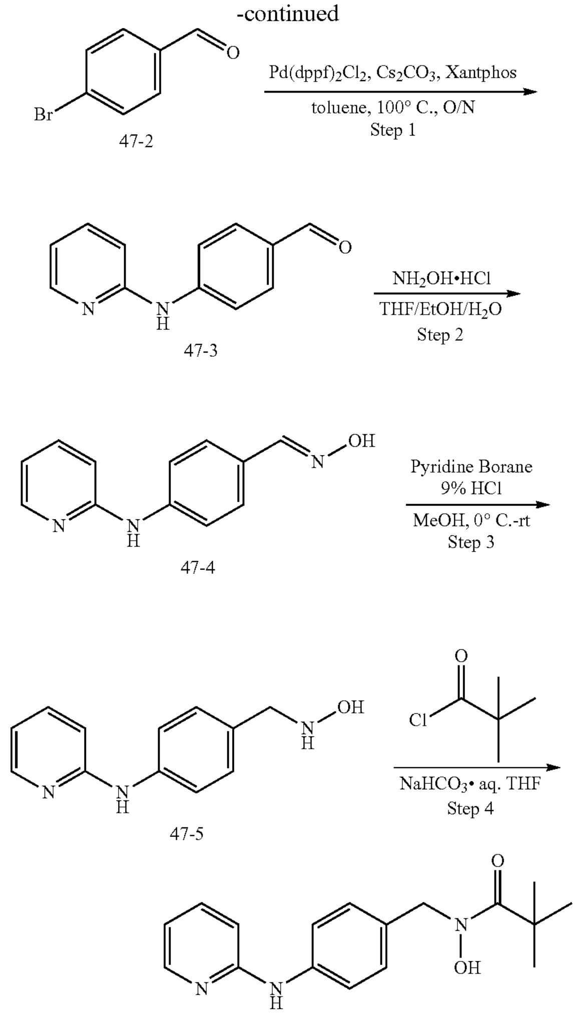

47

Step 1. Preparation of 4-(pyridin-2-ylamino)benzaldehyde (47-3) A mixture of pyridin-2-amine (200 mg, 2.12 mmol), 4-bromobenzaldehyde (433 mg, 2.33 mmol), Pd(dppf)$_2$Cl$_2$ (264 mg, 0.36 mmol), Xantphos (368 mg, 0.637 mmol), $Cs_2CO_3$ (1.73 g, 5.31 mmol) in Toluene (20 mL) was stirred overnight at 100° C. After cooling to rt. 30 ml of water was added. The solid was collected by filtration. Target product was obtained as a yellow solid. (380 mg).

Step 2. Preparation of (E)-4-(pyridin-2-ylamino)benzaldehyde oxime (47-4) The title compound 47-4 (406 mg) was prepared in a total yield of 100% as a crude as a yellow solid from 4-(pyridin-2-ylamino)benzaldehyde (380 mg, 1.91 mmol), Hydroxylamine hydrochloride (146 mg, 2.1 mmol) according to the procedure for 80-3.

Step 3. Preparation of N-(4-((hydroxyamino)methyl)phenyl)pyridin-2-amine (47-5) The title compound 47-5 (105 mg) was prepared in a total yield of 65.4% as a yellow solid from (E)-4-(pyridin-2-ylamino)benzaldehyde oxime (406 mg, 1.91 mmol), Borane-pyridine complex (1.15 ml, 2.1 mmol) and 0.64 mL of 9% HCl according to the procedure for 1.

Step 4. Preparation of N-hydroxy-N-(4-(pyridin-2-ylamino)benzyl)pivalamide (47) The title compound 47 (40 mg) was prepared in a total yield of 45% as a white solid form N-(4-((hydroxyamino)methyl)phenyl)pyridin-2-amine (105 mg, 0.49 mmol), pivaloyl chloride (76 mg, 0.63 mmol) and $NaHCO_3$·aq. (0.6 ml) according to the procedure for 1. 1H NMR (400 MHz, Chloroform-d) δ 11.71 (s, 1H), 7.84-7.73 (m, 2H), 7.32 (d, J=8.0 Hz, 2H), 7.23-7.18 (m, 2H), 7.07 (d, J=9.2 Hz, 1H), 6.83 (t, J=6.6 Hz, 1H), 4.72 (s, 2H), 1.25 (d, J=1.0 Hz, 9H).

N-(4-((2-(tert-butyl)phenyl)amino)benzyl)-N-hydroxypivalamide (48)

48

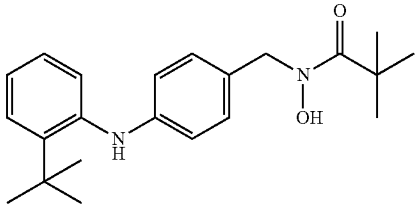

The title compound 48 (50 mg) was prepared in a total yield of 40% as a white solid form 2-(tert-butyl)-N-(4-((hydroxyamino)methyl)phenyl)aniline (94 mg, 0.35 mmol), pivaloyl chloride (55 mg, 0.45 mmol) and $NaHCO_3$·aq. (0.42 ml) according to the procedure for 1. 1H NMR (400 MHz, Chloroform-d) δ 7.41 (dd, J=8.0, 1.6 Hz, 1H), 7.24 (dd, J=8.0, 1.6 Hz, 1H), 7.18-7.04 (m, 4H), 6.77-6.72 (m, 2H), 4.78 (s, 2H), 1.40 (d, J=0.6 Hz, 9H), 1.29 (d, J=0.6 Hz, 9H.

N-(4-((3-(tert-butyl)phenyl)amino)benzyl)-N-hydroxypivalamide (49)

49

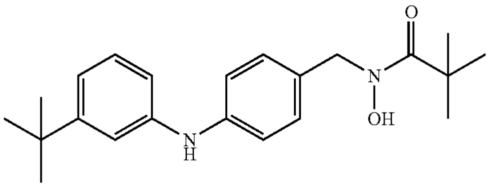

The title compound 49 (50 mg) was prepared in a total yield of 40% as a white solid form 3-(tert-butyl)-N-(4-((hydroxyamino)methyl)phenyl)aniline (69 mg, 0.256 mmol), pivaloyl chloride (40 mg, 0.332 mmol) and $NaHCO_3$·aq. (0.3 ml) according to the procedure for 1. 1H NMR (400 MHz, Chloroform-d) δ 7.21-7.10 (m, 4H), 7.03 (dd, J=14.4, 8.0 Hz, 3H), 6.94 (ddd, J=7.8, 2.4, 1.0 Hz, 1H), 4.79 (s, 2H), 1.29 (d, J=2.6 Hz, 18H).

N-(4-((4-(dimethylamino)phenyl)amino)benzyl)-N-hydroxypivalamide (50)

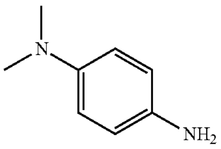

+

50-1

-continued

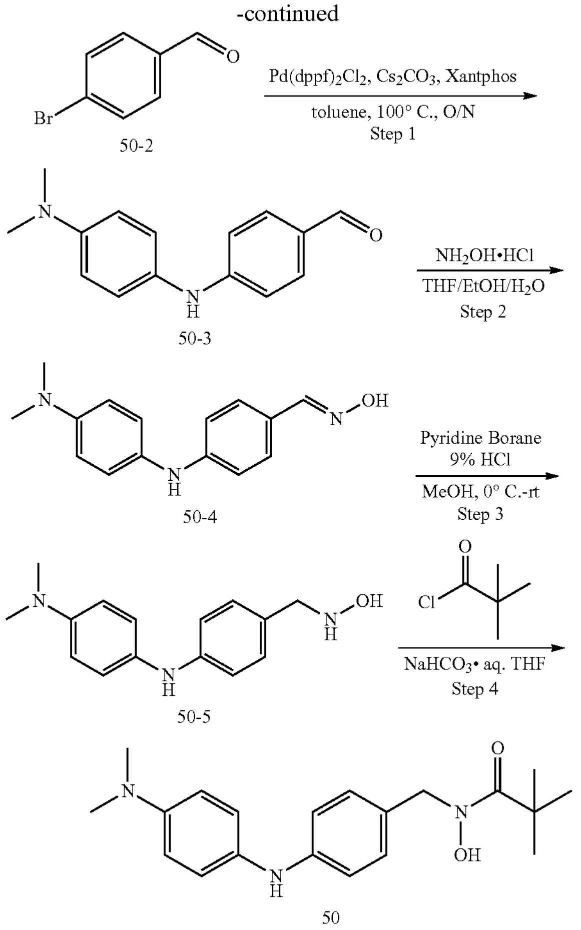

Step 1. Preparation of 4-((4-(dimethylamino)phenyl)amino)benzaldehyde (50-3) A mixture of N1,N1-dimethylbenzene-1,4-diamine (100 mg, 0.73 mmol), 4-bromobenzaldehyde (149 mg, 0.8 mmol), $Pd(dppf)_2Cl_2$ (27 mg, 0.03 mmol). Xantphos (42 mg, 0.07 mmol), $Cs_2CO_3$ (598 mg, 1.83 mmol) in Toluene (15 mL) was stirred overnight at 100° C. After cooling to rt. 30 ml of water was added. The solid was collected by filtration. Target product was obtained as a yellow solid. (110 mg).

Step 2. The title compound 50-4 (130 mg) was prepared in a total yield of 100% as a crude as a yellow solid from 4-((4-(dimethylamino)phenyl)amino)benzaldehyde (110 mg, 0.46 mmol), Hydroxylamine hydrochloride (35 mg, 0.5 mmol) according to the procedure for 1

Step 3. The title compound 50-5 (28 mg) was prepared in a total yield of 65.4% as a yellow solid from (E)-4-((4-(dimethylamino)phenyl)amino)benzaldehyde oxime (130 mg, 0.5 mmol), Borane-pyridine complex (0.3 ml, 2.8 mmol) and 0.93 mL of 9% HCl according to the procedure for 1

Step 4. The title compound 50 (14 mg) was prepared in a total yield of 40% as a white solid form N1-(4-((hydroxyamino)methyl)phenyl)-N4,N4-dimethylbenzene-1,4-diamine (28 mg, 0.11 mmol), pivaloyl chloride (17 mg, 0.14 mmol) and $NaHCO_3$·aq. (0.13 ml) according to the procedure for 1.

N-(4-((2,4-difluorophenyl)amino)benzyl)-N-hydroxypivalamide (51)

51

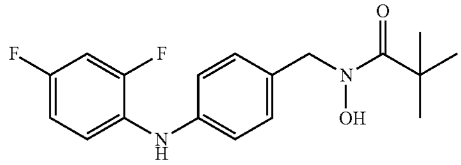

The title compound 51 (28 mg) was prepared in a total yield of 40% as a white solid form 2,4-difluoro-N-(4-((hydroxyamino)methyl)phenyl)aniline (58 mg, 0.23 mmol), pivaloyl chloride (36 mg, 0.3 mmol) and $NaHCO_3$·aq. (0.28 ml) according to the procedure for 1. 1H NMR (400 MHz, Chloroform-d) δ 7.23-7.16 (m, 3H), 6.99-6.94 (m, 2H), 6.87 (ddd, J=11.0, 8.4, 2.8 Hz, 1H), 6.78 (dddd, J=8.8, 7.8, 2.8, 1.6 Hz, 1H), 4.82 (s, 2H), 1.29 (s, 9H).

N-hydroxy-N-(4-((2,4,6-trifluorophenyl)amino)benzyl)pivalamide (52)

52

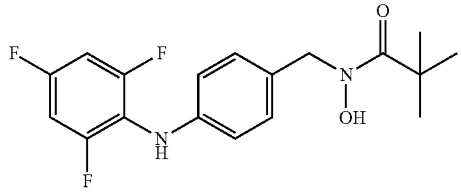

The title compound 52 (42 mg) was prepared in a total yield of 40% as a white solid form 2,4,6-trifluoro-N-(4-((hydroxyamino)methyl)phenyl)aniline (56 mg, 0.207 mmol), pivaloyl chloride (33 mg, 0.27 mmol) and $NaHCO_3$·aq. (0.25 ml) according to the procedure for 1. 1H NMR (400 MHz, Chloroform-d) δ 7.17-7.10 (m, 2H), 6.79-6.71 (m, 2H), 6.70-6.65 (m, 2H), 4.77 (s, 2H), 1.31-1.25 (m, 9H).

N-hydroxy-N-(4-(pyridin-3-ylamino)benzyl)pivalamide (53)

53

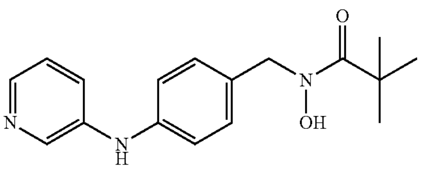

The title compound 53 (35 mg) was prepared in a total yield of 45% as a white solid form N-(4-((hydroxyamino)methyl)phenyl)pyridin-3-amine (93 mg, 0.43 mmol), pivaloyl chloride (68 mg, 0.56 mmol) and NaHCO3·aq. (0.51 ml) according to the procedure for 1. 1H NMR (400 MHz, DMSO-d6) δ 9.64 (s, 1H), 9.06 (s, 1H), 8.35 (s, 1H), 8.15 (s, 1H), 7.86 (dd, J=8.8, 2.4 Hz, 1H), 7.65 (dd, J=8.8, 5.2 Hz, 1H), 7.23-7.12 (m, 4H), 4.62 (s, 2H), 1.18 (d, J=1.0 Hz, 9H).

N-hydroxy-N-(4-((4-methoxyphenyl)amino)benzyl) pivalamide 54)

54

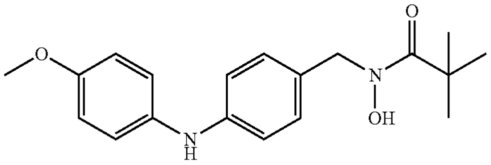

The title compound 54 (23 mg) was prepared in a total yield of 40% as a white solid form 4-((hydroxyamino) methyl)-N-(4-methoxyphenyl)aniline (95 mg, 0.39 mmol), pivaloyl chloride (61 mg, 0.15 mmol) and $NaHCO_3$·aq. (0.47 ml) according to the procedure for 1. 1H NMR (400 MHz, Chloroform-d) δ 7.12 (s, 4H), 6.86 (t, J=10.0 Hz, 4H), 4.79 (s, 2H), 3.78 (s, 3H), 1.29 (d, J=1.6 Hz, 9H). Mass (m/z): 329.4 $[M+H]^+$.

N-hydroxy-N-(4-(mesitylamino)benzyl)pivalamide (55)

55

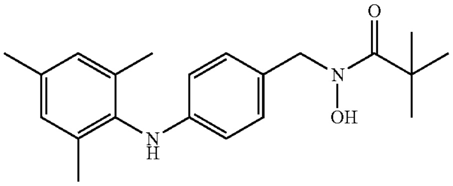

The title compound 55 (50 mg) was prepared in a total yield of 40% as a white solid form N-(4-((hydroxyamino) methyl)phenyl)-2,4,6-trimethylaniline (108 mg, 0.42 mmol), pivaloyl chloride (66 mg, 0.55 mmol) and $NaHCO_3$·aq. (0.5 ml) according to the procedure for 1. 1H NMR (400 MHz, Chloroform-d) δ 7.05 (d, J=8.2 Hz, 2H), 6.92 (s, 2H), 6.48-6.42 (m, 2H), 4.76 (s, 2H), 2.28 (s, 3H), 2.14 (s, 6H), 1.28 (d, J=1.0 Hz, 9H).

N-(4-((2,5-bis(trifluoromethyl)phenyl)amino)benzyl)-N-hydroxypivalamide (56)

56

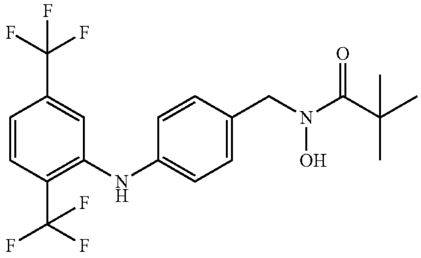

The title compound 56 (40 mg) was prepared in a total yield of 40% as a white solid form N-(4-((hydroxyamino) methyl)phenyl)-2,5-bis(trifluoromethyl)aniline (110 mg, 0.31 mmol), pivaloyl chloride (0.05 ml, 0.41 mmol) and $NaHCO_3$·aq. (0.38 ml) according to the procedure for 1. 1H NMR (400 MHz, Chloroform-d) δ 7.64 (d, J=8.2 Hz, 1H), 7.47 (d, J=1.6 Hz, 1H), 7.31-7.27 (m, 2H), 7.15-7.10 (m, 3H), 4.87 (s, 2H), 1.31 (d, J=0.6 Hz, 9H).

N-(4-((4-(tert-butyl)-2,6-dimethylphenyl)amino) benzyl)-N-hydroxypivalamide (57)

57

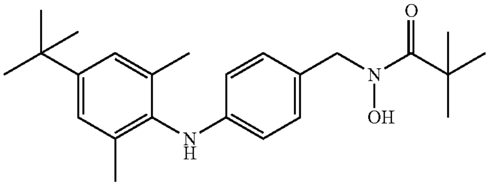

The title compound 57 (43 mg) was prepared in a total yield of 40% as a white solid form 4-(tert-butyl)-N-(4-((hydroxyamino)methyl)phenyl)-2,6-dimethylaniline (150 mg, 0.5 mmol), pivaloyl chloride (0.08 ml, 0.65 mmol) and $NaHCO_3$·aq. (0.6 ml) according to the procedure for 1. 1H NMR (400 MHz, Chloroform-d) δ 7.11-7.03 (m, 4H), 6.50-6.43 (m, 2H), 4.78-4.75 (m, 2H), 2.20-2.16 (m, 6H), 1.31-1.27 (m, 18H). Mass (m/z): 383.6 $[M+H]^+$.

N-hydroxy-N-(4-(phenylamino)benzyl)pivalamide (58)

58

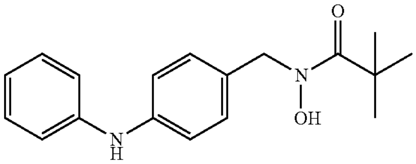

The title compound 58 (7 mg) was prepared in a total yield of 40% as a white solid form 4-((hydroxyamino) methyl)-N-phenylaniline (38 mg, 0.18 mmol), pivaloyl chloride (0.028 ml, 0.23 mmol) and $NaHCO_3$·aq. (0.2 ml) according to the procedure for 1. 1 H NMR (400 MHz, Chloroform-d) δ 7.28-7.22 (m, 2H), 7.17 (d, J=8.0 Hz, 2H), 7.07-7.00 (m, 4H), 6.93 (tt, J=7.4, 1.0 Hz, 1H), 4.81 (s, 2H), 1.31-1.28 (s, 9H).

N-hydroxy-N-(4-((4-(pyrrolidin-1-yl)phenyl)amino) benzyl)pivalamide (59)

59

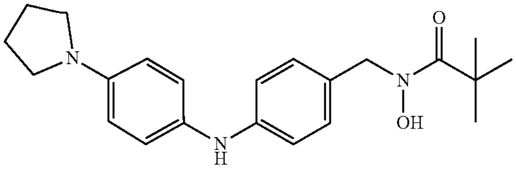

The title compound 59 (10 mg) was prepared in a total yield of 40% as a white solid form 4-((hydroxyamino) methyl)-N-(4-(pyrrolidin-1-yl)phenyl)aniline (15 mg, 0.05 mmol), pivaloyl chloride (0.01 ml, 0.07 mmol) and $NaHCO_3$·aq. (0.06 ml) according to the procedure for 1.

N-(4-(phenylamino)benzyl)adamantane-1-carboxamide (60)

60

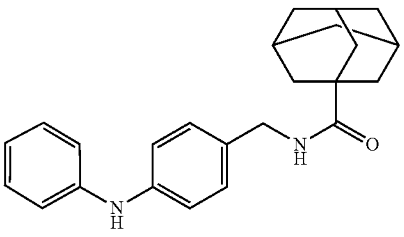

$^1$H NMR (400 MHz, Chloroform-d) δ 7.28-7.21 (m, 2H), 7.13 (d, J=8.4 Hz, 2H), 7.06-7.00 (m, 4H), 6.91 (t, J=7.4 Hz, 1H), 4.34 (s, 2H), 2.03 (s, 3H), 1.86 (d, J=2.8 Hz, 6H). Mass (m/z): 361.3 $[M+H]^+$.

N-hydroxy-N-(4-(phenylamino)benzyl)adamantane-1-carboxamide (61)

61

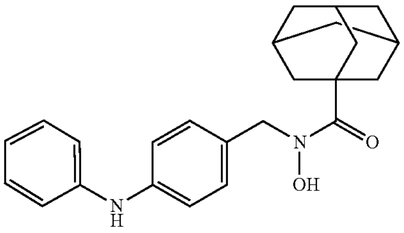

$^1$H NMR (400 MHz, $CDCl_3$) δ 7.30-7.25 (m, 2H), 7.18 (d, J=8.6 Hz, 2H), 7.10-7.03 (m, 4H), 6.95 (m, 1H), 4.91 (s, 2H), 2.05 (s, 9H), 1.71 (s, 6H). LC-MS (ESI) m/z: 377.3. $[M+H]^+$.

N-(4-((4-(tert-butyl)-3-fluorophenyl)amino)benzyl)-N-hydroxy-2-methoxy-2-methylpropanamide (62)

62

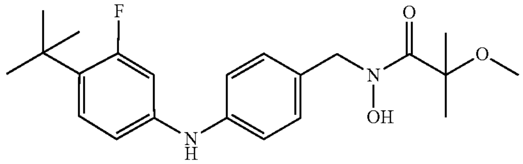

$^1$H NMR (400 MHz, Chloroform-d) δ 7.31-7.15 (m, 3H), 7.04 (d, J=7.8 Hz, 2H), 6.80-6.69 (m, 2H), 4.75 (s, 2H), 3.26 (s, 3H), 1.51 (s, 6H), 1.35 (s, 9H). Mass (m/z): 389.2 $[M+H]^+$.

N-(4-((4-(tert-butyl)-3-fluorophenyl)amino)benzyl)-N-hydroxy-2-(2-(2-methoxyethoxy)ethoxy)acetamide (63)

63

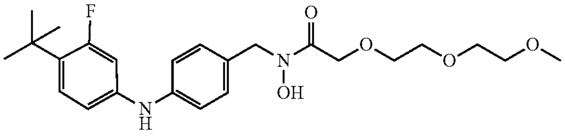

$^1$H NMR (400 MHz, Chloroform-d) δ 7.25-7.21 (m, 2H), 7.18-7.11 (m, 1H), 7.06-7.00 (m, 2H), 6.80-6.64 (m, 2H), 4.73 (s, 2H), 4.36 (s, 2H), 3.80-3.41 (m, 8H), 3.24 (s, 3H), 1.35 (s, 9H). Mass (m/z): 449.2 $[M+H]^+$.

N-(4-((4-(tert-butyl)-3-fluorophenyl)amino)benzyl)-N-hydroxypivalamide (64)

64

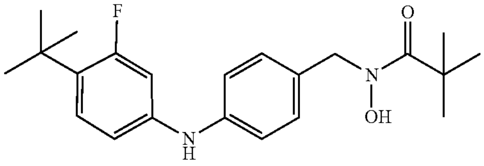

$^1$H NMR (400 MHz, Chloroform-d) δ 7.23-7.11 (m, 3H), 7.09-7.01 (m, 2H), 6.80-6.70 (m, 2H), 4.82 (s, 2H), 1.35 (s, 9H), 1.31 (s, 9H). Mass (m/z): 373.2 $[M+H]^+$.

tert-butyl 3-((4-((4-(tert-butyl)-3-fluorophenyl)amino)benzyl)(hydroxy)carbamoyl)azetidine-1-carboxylate (65)

65

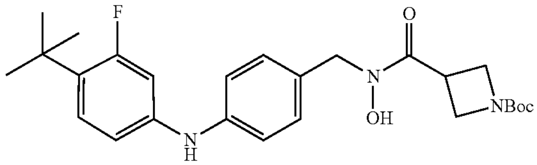

$^1$H NMR (400 MHz, Chloroform-d) δ 7.24-7.09 (m, 3H), 6.99 (d, J=7.8 Hz, 2H), 6.78-6.67 (m, 2H), 4.71 (s, 2H), 4.22-3.91 (m, 4H), 3.77-3.61 (m, 1H), 1.40 (s, 9H), 1.35 (s, 9H). Mass (m/z): 472.3 $[M+H]^+$.

tert-butyl 4-((4-((4-(tert-butyl)-3-fluorophenyl) amino)benzyl)(hydroxy)carbamoyl)-4-methylpiperidine-1-carboxylate (66)

66

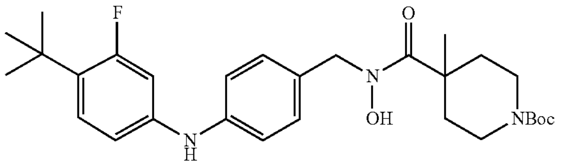

$^1$H NMR (400 MHz, Chloroform-d) δ 7.23-7.12 (m, 3H), 7.06-7.00 (m, 2H), 6.79-6.71 (m, 2H), 4.79 (s, 2H), 3.76-3.61 (m, 2H), 3.18-3.04 (m, 2H), 2.28-2.21 (m, 2H), 2.14-2.00 (m, 2H), 1.44 (s, 9H), 1.35 (s, 9H), 1.30 (s, 3H). Mass (m/z): 514.3 [M+H]$^+$.

tert-butyl 4-(2-((4-((4-(tert-butyl)phenyl)amino)benzyl)(hydroxy)amino)-2-oxoethyl)piperazine-1-carboxylate (67)

67

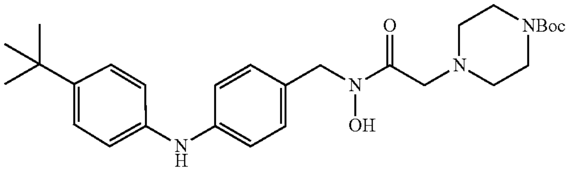

$^1$H NMR (400 MHz, Chloroform-d) δ 7.31-7.15 (m, 4H), 7.06-6.92 (m, 4H), 4.69 (s, 2H), 4.06 (s, 2H), 3.95-2.91 (m, 8H), 1.46 (s, 9H), 1.31 (s, 9H). Mass (m/z): 497.3 [M+H]$^+$.

N-hydroxy-2-methoxy-2-methyl-N-(4-((4-(trifluoromethyl)phenyl)amino)benzyl)propanamide (68)

68

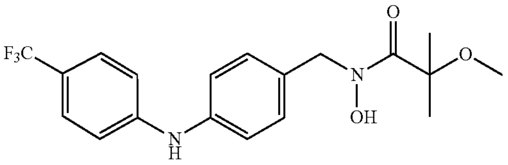

$^1$H NMR (400 MHz, Chloroform-d) δ 7.47 (d, J=8.0 Hz, 2H), 7.31 (d, J=7.8 Hz, 2H), 7.12 (d, J=8.0 Hz, 2H), 7.04 (d, J=8.4 Hz, 2H), 4.80 (s, 2H), 3.27 (s, 3H), 1.52 (s, 6H). Mass (m/z): 383.3 [M+H]$^+$.

N-hydroxy-1-methyl-N-(4-((4-(trifluoromethyl)phenyl)amino)benzyl)cyclohexane-1-carboxamide (69)

69

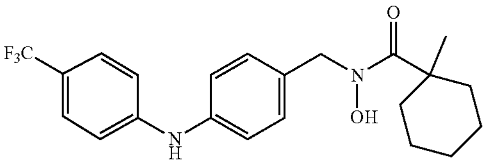

$^1$H NMR (400 MHz, Chloroform-d) δ 7.47 (d, J=8.4 Hz, 2H), 7.30-7.23 (m, 2H), 7.13 (d, J=8.4 Hz, 2H), 7.05 (d, J=8.4 Hz, 2H), 4.89 (s, 2H), 2.16-2.11 (m, 2H), 1.64-1.29 (m, 8H), 1.26 (s, 3H). Mass (m/z): 407.3 [M+H]$^+$.

N-(4-((4-(tert-butyl)phenyl)amino)benzyl)-4-(dimethylamino)-N-hydroxybutanamide (70)

70

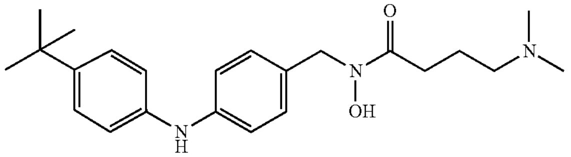

$^1$H NMR (400 MHz, Methanol-$d_4$) δ 7.27 (d, J=8.8 Hz, 2H), 7.18 (d, J=8.4 Hz, 2H), 7.03-6.99 (m, 4H), 4.67 (s, 2H), 3.10-3.06 (m, 2H), 2.82 (s, 6H), 2.67-2.64 (m, 2H), 2.03-1.96 (m, 2H), 1.30 (s, 9H). Mass (m/z): 384.3 [M+H]$^+$.

N-(4-((4-(tert-butyl)phenyl)amino)benzyl)-N-hydroxy-3-morpholinopropanamide (71)

71

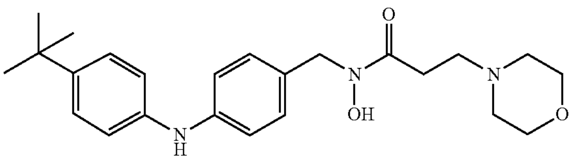

$^1$H NMR (400 MHz, Methanol-$d_4$) δ 7.27 (d, J=8.8 Hz, 2H), 7.18 (d, J=8.4 Hz, 2H), 7.03-6.99 (m, 4H), 4.66 (s, 2H), 3.73-3.55 (m, 4H), 2.84-2.65 (m, 4H), 2.56-2.43 (m, 4H), 1.30 (s, 9H). Mass (m/z): 412.2 [M+H]$^+$.

N-(4-([1,1'-biphenyl]-4-ylamino)benzyl)-N-hydroxy-4-methyltetrahydro-2H-pyran-4-carboxamide (72)

72

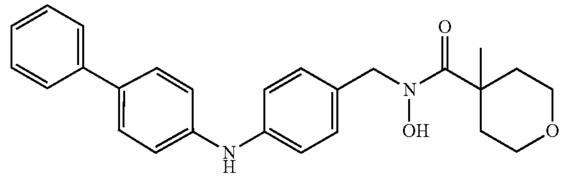

$^1$H NMR (400 MHz, Chloroform-d) δ 7.60-7.47 (m, 4H), 7.45-7.39 (m, 2H), 7.34-7.28 (m, 1H), 7.3-7.11 (m, 6H), 4.83 (s, 2H), 3.83-3.56 (m, 4H), 2.34-2.14 (m, 2H), 1.62-1.55 (m, 2H), 1.33 (s, 3H). Mass (m/z): 417.3 $[M+H]^+$.

N-(4-([1,1'-biphenyl]-4-ylamino)benzyl)-2,2,2-trifluoro-N-hydroxyacetamide (73)

73

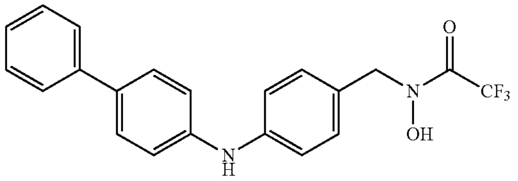

$^1$H NMR (400 MHz, Chloroform-d) δ 7.59-7.52 (m, 4H), 7.46-7.28 (m, 3H), 7.22-7.05 (m, 6H), 4.83 (m, 2H). Mass (m/z): 387.3 $[M+H]^+$.

N-(4-((4-(tert-butyl)phenyl)amino)benzyl)-N-hydroxy-1,4-dimethylpiperidine-4-carboxamide (74)

74

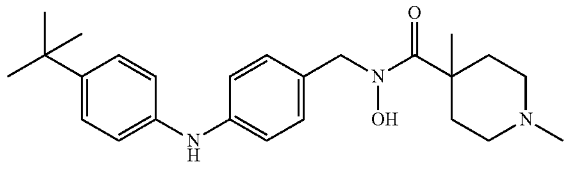

$^1$H NMR (400 MHz, Methanol-$d_4$) δ 7.29-7.25 (m, 2H), 7.19 (d, J=8.4 Hz, 2H), 7.08-6.99 (m, 4H), 4.69 (s, 2H), 3.49-3.36 (m, 2H), 3.13-3.02 (d, J=3.8 Hz, 2H), 2.82 (s, 3H), 2.24-2.12 (m, 4H), 1.34 (s, 3H), 1.30 (s, 9H). Mass (m/z): 410.3 $[M+H]^+$.

N-(4-((4-(tert-butyl)phenyl)amino)benzyl)-2-(4-ethylpiperazin-1-yl)-N-hydroxyacetamide (75)

75

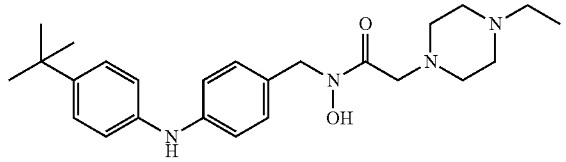

$^1$H NMR (400 MHz, Methanol-$d_4$) δ 7.27 (d, J=8.8 Hz, 2H), 7.18 (d, J=8.4 Hz, 2H), 7.03-6.99 (m, 4H), 4.68 (s, 2H), 4.12 (s, 2H), 3.54 (br s, 8H), 3.26 (t, J=7.2 Hz, 2H), 1.36 (t, J=7.2 Hz, 3H), 1.30 (s, 9H). Mass (m/z): 425.2 $[M+H]^+$.

2-(4-acetylpiperazin-1-yl)-N-(4-((4-(tert-butyl)phenyl)amino)benzyl)-N-hydroxyacetamide (76)

76

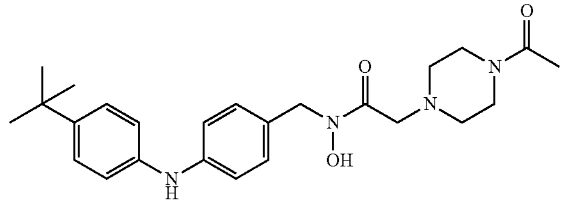

$^1$H NMR (400 MHz, Methanol-$d_4$) δ 7.31-7.24 (m, 2H), 7.22-7.15 (m, 2H), 7.03-6.98 (m, 4H), 4.70 (s, 2H), 4.30 (s, 2H), 3.88 (br s, 41H), 3.44 (br s, 4H), 2.15 (s, 3H), 1.30 (s, 9H). Mass (m/z): 439.3 $[M+H]^+$.

N-(4-((4-(tert-butyl)phenyl)amino)benzyl)-N-hydroxy-2-(4-(2,2,2-trifluoroacetyl)piperazin-1-yl)acetamide (77)

77

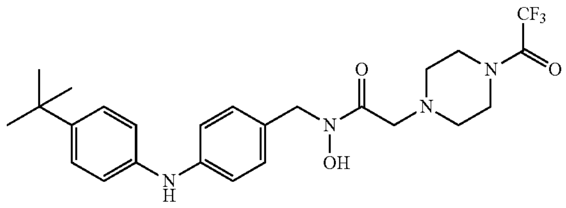

$^1$H NMR (400 MHz, Methanol-$d_4$) δ 7.27 (d, J=8.4 Hz, 2H), 7.19 (d, J=8.4 Hz, 2H), 7.01 (dd, J=8.4, 4.0 Hz, 4H), 4.70 (s, 2H), 4.33 (s, 2H), 4.00 (br s, 4H), 3.54 (br s, 4H), 1.30 (s, 9H). Mass (m/z): 493.2 $[M+H]^+$.

N-(4-((4'-fluoro-[1,1'-biphenyl]-4-yl)amino)benzyl)-N-hydroxy-2-(4-methylpiperazin-1-yl)acetamide (78)

78

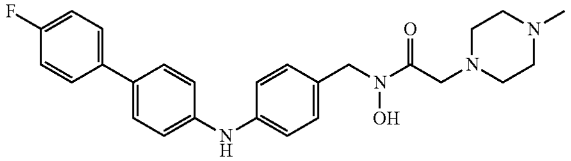

$^1$H NMR (400 MHz, Methanol-$d_4$) δ 7.57 (dd, J=8.8, 5.2 Hz, 2H), 7.46 (d, J=8.4 Hz, 2H), 7.22 (d, J=8.4 Hz, 2H), 7.16-7.07 (m, 6H), 4.70 (s, 2H), 3.81 (s, 2H), 3.39 (br s, 4H), 3.16 (br s, 4H), 2.90 (s, 3H). Mass (m/z): 449.2 $[M+H]^+$.

N-hydroxy-4-methyl-N-(4-((4-(piperidin-1-yl)phenyl)amino)benzyl)piperazine-1-carboxamide (79)

79

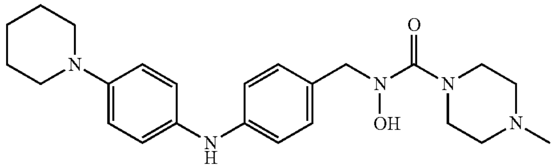

The title compound 79 (13.5 mg) was prepared in a total yield of 33.2% as a white solid. $^1$H NMR (400 MHz, Methanol-$d_4$) δ 7.35-6.67 (m, 8H), 4.60 (s, 2H), 3.73 (br s, 4H), 3.22-3.01 (m, 8H), 2.78 (s, 3H), 2.04-1.77 (m, 4H), 1.75-1.51 (m, 2H). Mass (m/z): 424.3 $[M+H]^+$.

N-(4-((4-(tert-butyl)-3-fluorophenyl)amino)benzyl)-N-hydroxy-1-methylcyclopropane-1-carboxamide (80)

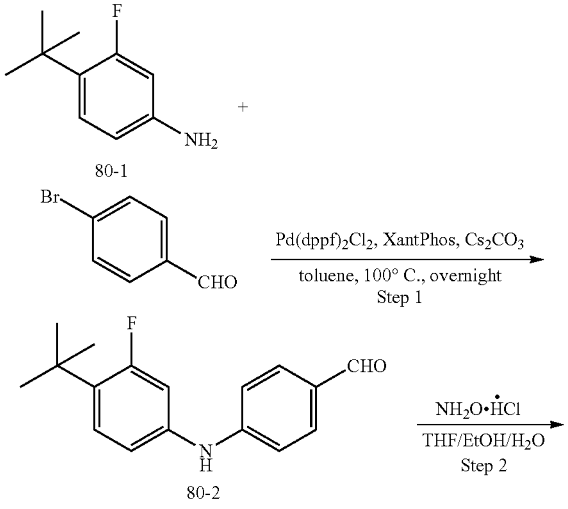

-continued

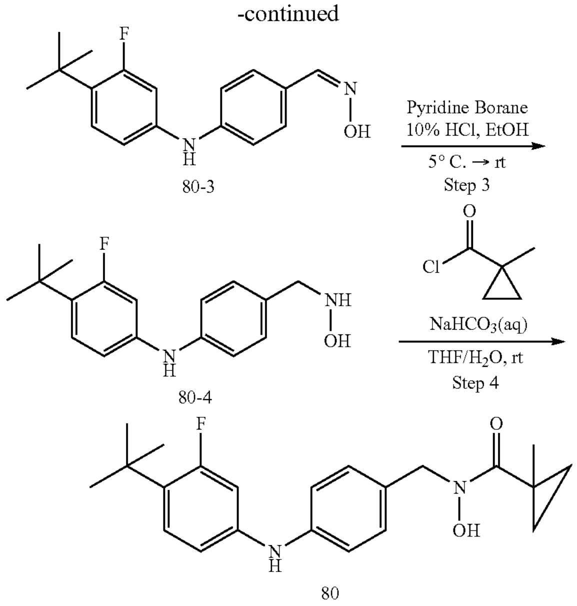

Step 1. 4-(tert-butyl)-3-fluoroaniline (2.17 g, 13 mmol), 4-bromobenzaldehyde (1.85 g, 10 mmol), $Pd(dppf)_2Cl_2$ (147 mg, 0.2 mmol), XantPhos (231 mg, 0.4 mmol), and $Cs_2CO_3$ (4.89 g, 15 mmol) was dissolved in toluene under an atmosphere of Nitrogen and stirred at 100° C. overnight. After the reaction was completed, the reaction product was cooled to room temperature and diluted with DCM and passed through a plug of silica, after which the solvent was removed under reduced pressure. The residue was purified by silica gel column chromatography (PE/EA=5/1) to give the desired product as yellow solid (1.8 g, 66%). Mass (m/z): 272.3 $[M+H]^+$.

Step 2. To a solution of 4-((4-(tert-butyl)-3-fluorophenyl)amino)benzaldehyde (928 mg, 3.4 mmol) in $THF/H_2O/EtOH$ (2/1/5, 40 mL) was added Hydroxylamine hydrochloride (261 mg, 3.8 mmol). Then the reaction was stirred overnight at rt. The reaction mixture was concentrated under vacuum. The crude was used directly at next step. (100%). Mass (m/z): 287.2 $[M+H]^+$.

Step 3. To a solution of (Z)-4-((4-(tert-butyl)-3-fluorophenyl)amino)benzaldehyde oxime (972 mg, 3.4 mmol) in EtOH (40 mL) was added Borane-pyridine (632 mg, 6.8 mmol). Then 10% HCl (6.8 mL) was added dropwise at 0° C. The solution was stirred for 3 hours at it. The PH of the solution was adjusted to 8-9 with sodium carbonate solution. Then the mixture was extracted by DCM (15 mL×3). The combined organic layers were washed with water (20 mL×3), dried over $Na_2SO_4$ and concentrated under vacuum. The residue was purified by silica gel column chromatography (MeOH/DCM-1/40) to give the desired product as yellow solid (242 mg, 25%). Mass (m/z): 289.3 $[M+H]^+$.

Step 4. 4-(tert-butyl)-3-fluoro-N-(4-((hydroxyamino)methyl)phenyl)aniline (20 mg, 0.07 mmol) was dissolved in 1.0 ml of $THF/H_2O$ (1:1, v/v) and 1.2 ml of saturated aqueous $NaHCO_3$. The solution was cooled to 0° C. and 1-methylcyclopropane-1-carbonyl chloride (9.1 mg, 0.077 mmol) was added and the mixture was stirred at room temperature for 16 h. The mixture was extracted with EtOAc and the combined organic layer was washed with brine, dried with (Na2SO4) and concentrated in vacuo to give crude product. The residue was purified by prep-TLC (MeOH/DCM=1/10) to give the desired product as white solid (8.0 mg, 30.9%). $^1$H NMR (400 MHz, Chloroform-d) δ 7.23-7.14 (m, 3H), 7.07 (d, J=8.0 Hz, 2H), 6.78-6.73 (m, 2H), 4.96 (s, 2H), 1.38 (s, 3H), 1.36 (s, 9H), 1.09-1.01 (m, 2H), 0.74-0.66 (m, 1H). Mass (m/z): 371.2 $[M+H]^+$.

N-(4-((4-(tert-butyl)-3-fluorophenyl)amino)benzyl)-N-hydroxy-4-methyltetrahydro-2H-pyran-4-carboxamide (81)

81

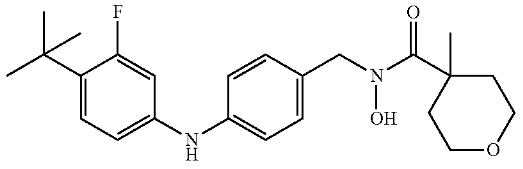

The title compound 81 (8.6 mg) was prepared in a total yield of 29.6% as a white solid from 4-(tert-butyl)-3-fluoro-N-(4-((hydroxyamino)methyl)phenyl)aniline (20 mg, 0.07 mmol), 4-methyltetrahydro-2H-pyran-4-carbonyl chloride (12.5 mg, 0.077 mmol), according to the procedure for compound 80. $^1$H NMR (400 MHz, Chloroform-d) δ 7.21-7.13 (m, 3H), 7.04 (d, J=8.0 Hz, 2H), 6.77-6.72 (m, 2H), 4.81 (s, 2H), 3.81-3.49 (m, 4H), 2.26-2.21 (m, 2H), 1.61-1.53 (m, 2H), 1.35 (s, 9H), 1.32 (s, 3H). Mass (m/z): 415.6 $[M+H]^+$.

N-(4-((4-(tert-butyl)-3-fluorophenyl)amino)benzyl)-N-hydroxy-2-morpholinoacetamide (82)

82

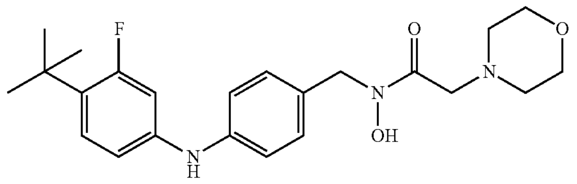

The title compound 82 (11 mg) was prepared in a total yield of 37.8% as a white solid from 4-(tert-butyl)-3-fluoro-N-(4-((hydroxyamino)methyl)phenyl)aniline (20 mg, 0.07 mmol), 2-morpholinoacetyl chloride (12.6 mg, 0.077 mmol), according to the procedure for compound 1. $^1$H NMR (400 MHz, Chloroform-d) 7.21-7.09 (m, 3H), 7.04 (d, J=8.0 Hz, 2H), 6.79-6.66 (m, 2H), 4.68 (s, 2H), 4.16 (s, 2H), 4.07-3.87 (m, 4H), 3.76-3.47 (m, 2H), 3.21-2.93 (m, 2H), 1.35 (s, 9H) Mass (m/z): 416.6 $[M+H]^+$.

N-hydroxy-2-(4-methylpiperazin-1-yl)-N-(4-((4-(1-methylpiperidin-4-yl)phenyl)amino)benzyl)acetamide (83)

83

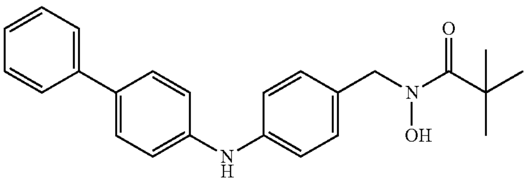

The title compound 83 (16 mg) was prepared in a total yield of 45% as a white solid form N-(4-((hydroxyamino)methyl)phenyl)-[1,1'-biphenyl]-4-amine (30 mg, 0.1 mmol), pivaloyl chloride (16.2 mg, 0.13 mmol) and $NaHCO_3$·aq. (0.13 ml) according to the procedure for 1. 1 H NMR (400 MHz, DMSO-d6) δ 9.57 (s, 1H), 8.30 (s, 1H), 7.63-7.52 (m, 4H), 7.41 (t, J=7.6 Hz, 2H), 7.31-7.23 (m, 1H), 7.17-7.04 (m, 6H), 4.61 (s, 2H), 1.22 (s, 9H).

N-(4-((4-(tert-butyl)-3-fluorophenyl)amino)benzyl)-N-hydroxy-5,6,7,8-tetrahydronaphthalene-2-carboxamide (84)

84

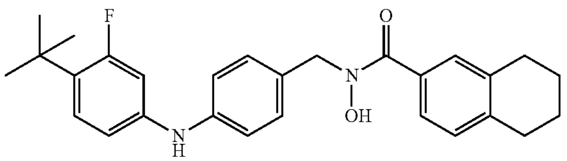

The title compound 84 (30 mg) was prepared in a total yield of 96% as a yellow solid from 4-(tert-butyl)-3-fluoro-N-(4-((hydroxyamino)methyl)phenyl)aniline (20 mg, 0.07 mmol), 5,6,7,8-tetrahydronaphthalene-2-carbonyl chloride (0.077 mmol), according to the procedure for compound 1. $^1$H NMR (400 MHz, Chloroform-d) δ 7.85-7.74 (m, 3H), 7.38-6.96 (m, 6H), 6.79-6.65 (m, 1H), 4.80 (s, 2H), 2.91-2.69 (m, 4H), 1.89-1.71 (m, 4H), 1.35 (s, 9H) Mass (m/z): 447.7 $[M+H]^+$.

N-(4-((4-(tert-butyl)-3-fluorophenyl)amino)benzyl)-4-(dimethylamino)-N-hydroxybutanamide (85)

85

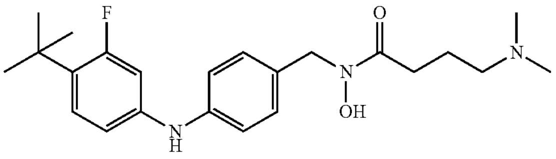

The title compound 85 (2.4 mg) was prepared in a total yield of 8.5% as a white solid from 4-(tert-butyl)-3-fluoro-N-(4-((hydroxyamino)methyl)phenyl)aniline (20 mg, 0.07 mmol), 4-(dimethylamino)butanoyl chloride (0.077 mmol), according to the procedure for compound 1. $^1$H NMR (400 MHz, Chloroform-d) δ 7.20-7.07 (m, 3H), 7.03 (d, J=8.0 Hz, 2H), 6.77-6.64 (m, 2H), 4.73 (s, 2H), 2.54 (t, J=8.0 Hz, 2H), 2.38 (t, J=8.0 Hz, 2H), 2.14 (s, 6H), 1.90-1.63 (m, 2H), 1.35 (s, 9H) Mass (m/z): 402.6 [M+H]$^+$.

N-(4-((4-(tert-butyl)-3-fluorophenyl)amino)benzyl)-N-hydroxy-2,3-dihydro-1H-indene-2-carboxamide (86)

86

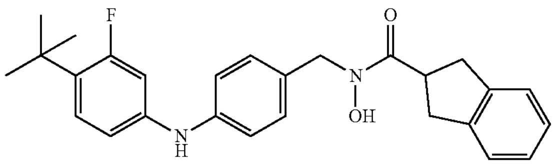

The title compound 86 (32 mg) was prepared in a total yield of 90% as a yellow solid from 4-(tert-butyl)-3-fluoro-N-(4-((hydroxyamino)methyl)phenyl)aniline (20 mg, 0.07 mmol), 2,3-dihydro-1H-indene-2-carbonyl chloride (0.077 mmol), according to the procedure for compound 1. $^1$H NMR (400 MHz, Chloroform-d) δ 7.22-6.90 (m, 9H), 6.77-6.64 (m, 2H), 4.81 (s, 2H), 3.42-2.98 (m, 5H), 1.35 (s, 9H) Mass (m/z): 433.4 [M+H]$^+$.

N-(4-((4-(tert-butyl)-3-fluorophenyl)amino)benzyl)-N-hydroxyazetidine-3-carboxamide (87)

87

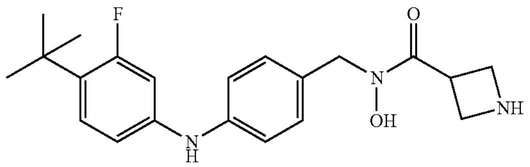

The title compound 87 (4.0 mg) was prepared in a total yield of 15.4% as a white solid from 4-(tert-butyl)-3-fluoro-N-(4-((hydroxyamino)methyl)phenyl)aniline (20 mg, 0.07 mmol), tert-butyl 3-(chlorocarbonyl)azetidine-1-carboxylate (0.077 mmol), according to the procedure for compound 1. $^1$H NMR (400 MHz, Chloroform-d) δ 7.22-7.08 (m, 3H), 7.04-6.93 (m, 3H), 6.79-6.69 (m, 2H), 4.62 (s, 2H), 4.39 (m, 1H), 4.23-3.75 (m, 4H), 1.35 (s, 9H) Mass (m/z): 372.4 [M+H]$^+$.

N-(4-((4-(tert-butyl)phenyl)amino)benzyl)-N-hydroxybenzo[d]thiazole-6-carboxamide (88)

88

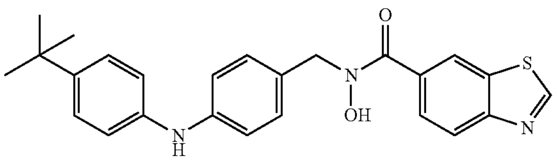

The title compound 88 (4.2 mg) was prepared in a total yield of 13.9% as a white solid from 4-(tert-butyl)-N-(4-((hydroxyamino)methyl)phenyl)aniline (20 mg, 0.074 mmol), benzo[d]thiazole-6-carbonyl chloride (0.077 mmol), according to the procedure for compound 1. $^1$H NMR (400 MHz, Chloroform-d) δ 9.00 (s, 1H), 8.21 (s, 1H), 8.06 (d, J=8.0 Hz, 1H), 7.68 (d, J=8.0 Hz, 1H), 7.29 (d, J=8.0 Hz, 2H), 7.15 (d, J=8.0 Hz, 2H), 7.06-6.96 (m, 4H), 4.81 (s, 2H), 1.30 (s, 9H), 432.3 [M+H]$^+$.

N-hydroxy-4-methyl-N-(4-((4-(trifluoromethyl)phenyl)amino)benzyl)tetrahydro-2H-pyran-4-carboxamide (89)

89

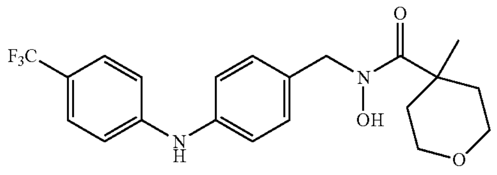

The title compound 89 (5.4 mg) was prepared in a total yield of 13.2% as a yellow solid from 4-((hydroxyamino)methyl)-N-(4-(trifluoromethyl)phenyl)aniline (28 mg, 0.1 mmol), 4-methyltetrahydro-2H-pyran-4-carbonyl chloride (0.11 mmol), according to the procedure for compound 1. $^1$H NMR (400 MHz, Chloroform-d) δ 7.53-7.42 (m, 3H), 7.18-6.99 (m, 5H), 4.86 (s, 2H), 3.82-3.58 (m, 4H), 2.29-2.17 (m, 2H), 1.65-1.53 (m, 2H), 1.34 (s, 3H). Mass (m/z): 408.3 [M+H]$^+$.

N-hydroxy-N-(4-((6-isoproplypyridin-3-yl)amino)benzyl)pivalamide (90)

90

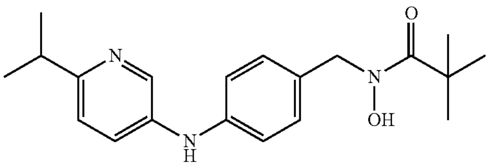

The title compound 90 (12 mg) was prepared in a total yield of 40% as a white solid form N-(4-((hydroxyamino)methyl)phenyl)-6-isopropylpyridin-3-amine (20 mg, 0.08 mmol), pivaloyl chloride (12.3 mg, 0.1 mmol) and $NaHCO_3$·aq. (0.1 ml) according to the procedure for 1. 1H NMR (400 MHz, Methanol-$d_4$) δ 8.08 (s, 1H), 7.98 (dd, J=8.8, 2.4 Hz, 1H), 7.70 (d, J=9.2 Hz, 1H), 7.32 (d, J=8.4 Hz, 2H), 7.22-7.12 (m, 2H), 5.47 (d, J=0.8 Hz, 1H), 4.72 (s, 2H), 1.36 (dd, J=6.8, 0.8 Hz, 6H), 1.27 (s, 9H). Mass (m/z): 342.5 [M+H]$^+$.

N-hydroxy-1-(trifluoromethyl)-N-(4-((4-(trifluoromethyl)phenyl)amino)benzyl)cyclobutane-1-carboxamide (91)

91

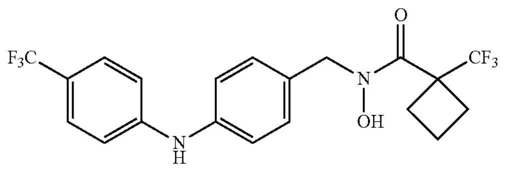

The title compound 91 (7.2 mg) was prepared in a total yield of 23.8% as a yellow solid according to the procedure for compound 80. $^{1}$H NMR (400 MHz, Chloroform-d) δ 1H NMR (400 MHz, Chloroform-d) δ 7.50-7.44 (m, 2H), 7.27-7.22 (m, 2H), 7.17-7.01 (m, 4H), 4.78 (s, 2H), 2.82-2.66 (m, 2H), 2.57-2.45 (m, 2H), 2.17-2.06 (m, 2H). Mass (m/z): 433.2 $[M+H]^+$.

N-(4-((4-(tert-butyl)phenyl)amino)benzyl)-N-hydroxy-2-(4-methylpiperazin-1-yl)acetamide (92)

92

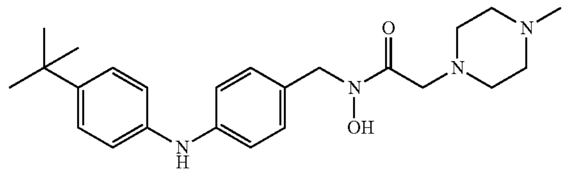

The title compound 92 (10.8 mg) was prepared in a total yield of 26.3% as a yellow solid according to the procedure for compound 80. $^{1}$H NMR (400 MHz, Methanol-$d_4$) δ 7.20 (d, J=8.0 Hz, 2H), 7.11 (d, J=8.0 Hz, 2H), 6.97-6.91 (m, 4H), 4.61 (s, 2H), 3.91 (s, 2H), 3.52-3.11 (m, 8H), 2.87 (s, 3H), 1.23 (s, 9H). Mass (m/z): 411.3 $[M+H]^+$.

N-(4-((4-(tert-butyl)phenyl)amino)benzyl)-N-hydroxy-2-morpholinoacetamide (93)

93

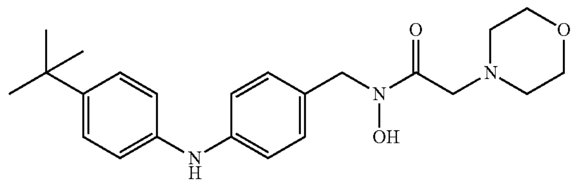

The title compound 93 (14.8 mg) was prepared in a total yield of 50.3% as a yellow solid according to the procedure for compound 80. $^{1}$H NMR (400 MHz, Methanol-$d_4$) δ 7.27 (d, J=8.0 Hz, 2H), 7.18 (d, J=8.0 Hz, 2H), 7.03-6.99 (m, 4H), 4.69 (s, 2H), 4.28 (s, 2H), 4.08-3.78 (m, 4H), 3.66-3.47 (m, 2H), 3.26-3.13 (m, 2H), 1.30 (s, 9H). Mass (m/z): 398.2 $[M+H]^+$.

N-(4-((4-(tert-butyl)phenyl)amino)benzyl)-N-hydroxy-4-methylpiperidine-4-carboxamide (94)

94

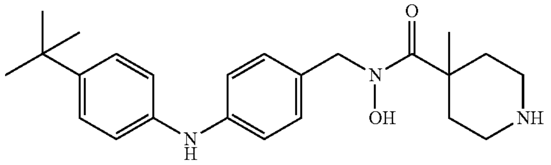

The title compound 94 (3.0 mg) was prepared in a total yield of 20.3% as a yellow solid according to the procedure for compound 80. $^{1}$H NMR (400 MHz, Methanol-$d_4$) δ 7.26 (d, J=8.0 Hz, 2H), 7.11 (d, J=8.0 Hz, 2H), 6.99-6.93 (m, 4H), 4.68 (s, 2H), 3.29-2.92 (m, 4H), 2.64-2.46 (m, 2H), 1.75-1.56 (m, 2H), 1.27 (s, 9H), 1.25 (s, 3H). Mass (m/z): 396.3 $[M+H]^+$ N-(4-((4-(tert-butyl)phenyl)amino)-2-methylbenzyl)-N-hydroxypivalamide (95)

95

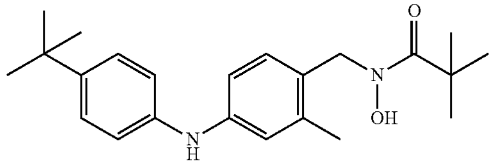

The title compound 95 (17.4 mg) was prepared in a total yield of 47.1% as a yellow solid according to the procedure for compound 80. $^{1}$H NMR (400 MHz, Methanol-$d_4$) δ 7.30 (d, J=8.0 Hz, 2H), 7.09 (d, J=8.0 Hz, 1H), 7.03 (d, J=8.0 Hz, 2H), 6.88-6.83 (m, 2H), 4.82 (s, 2H), 2.25 (s, 3H), 1.32 (s, 9H), 1.30 (s, 9H). Mass (m/z): 369.2 $[M+H]^+$ N-(4-([1,1'-biphenyl]-4-ylamino)benzyl)-N-hydroxy-2-methoxy-2-methylpropanamide (96)

96

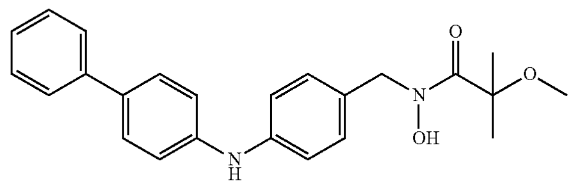

The title compound 96 (26.5 mg) was prepared in a total yield of 61.8% as a white solid according to the procedure for compound 80. $^{1}$H NMR (400 MHz, Chloroform-d) δ 7.51 (d, J=8.0 Hz, 2H), 7.45 (d, J=8.0 Hz, 2H), 7.38-7.34 (m, 2H), 7.25-7.20 (m, 3H), 7.09-7.02 (m, 4H), 4.72 (s, 2H), 3.20 (s, 311), 1.46 (s, 6H). Mass (m/z): 391.4 $[M+H]^+$.

N-(4-((4-(tert-butyl)-2,6-dimethylphenyl)amino) benzyl)-N-hydroxy-4-methyltetrahydro-2H-pyran-4-carboxamide (97)

97

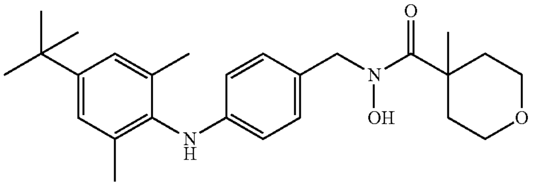

The title compound 97 (28 mg) was prepared in a total yield of 41.8% as a white solid according to the procedure for compound 80. $^1$H NMR (400 MHz, Chloroform-d) δ 7.12 (s, 2H), 7.07 (d, J=8.0 Hz, 2H), 6.46 (d, J=8.0 Hz, 2H), 4.74 (s, 2H), 3.80-3.52 (m, 4H), 2.37-2.10 (m, 8H), 1.58-1.52 (m, 2H), 1.33 (s, 9H), 1.30 (s, 3H). Mass (m/z): 425.2 $[M+H]^+$ N-(4-((4-(tert-butyl)-2,6-dimethylphenyl)amino) benzyl)-N-hydroxy-2-methoxy-2-methylpropanamide (98)

98

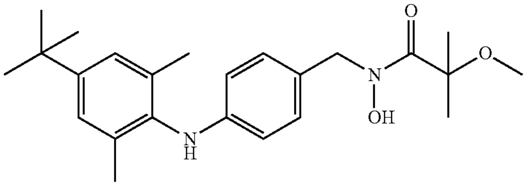

The title compound 98 (21.4 mg) was prepared in a total yield of 53.8% as a white solid according to the procedure for compound 80. $^1$H NMR (400 MHz, Chloroform-d) δ 7.14-7.08 (m, 4H), 6.46 (d, J=8.0 Hz, 2H), 4.64 (s, 2H), 3.23 (s, 3H), 2.19 (s, 6H), 1.49 (s, 6H), 1.32 (s, 9H). Mass (m/z): 399.4 $[M+H]^+$ N-(4-((4-(tert-butyl)phenyl)amino)-3-fluorobenzyl-hydroxypivalamide (99)

99

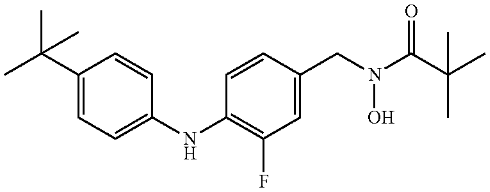

The title compound 99 (25.6 mg) was prepared in a total yield of 70.3% as a white solid according to the procedure for compound 80. $^1$H NMR (400 MHz, Chloroform-d) δ 7.31 (d, J=8.0 Hz, 2H), 7.25-7.20 (m, 1H), 7.06-7.00 (m, 3H), 6.91 (d, J=8.0 Hz, 2H), 4.75 (s, 2H), 1.31 (s, 9H), 1.29 (s, 9H). Mass (m/z): 373.2 $[M+H]^+$ N-hydroxy-N-(4-((4-morpholinophenyl)amino)benzyl)pivalamide (100)

100

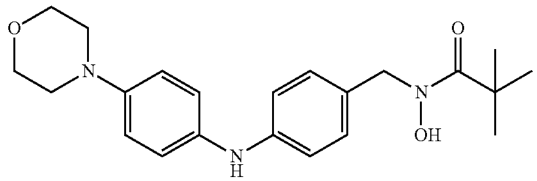

The title compound 100 (13 mg) was prepared in a total yield of 40% as a white solid form 4-((hydroxyamino) methyl)-N-(4-morpholinophenyl)aniline (20 mg, 0.067 mmol), pivaloyl chloride (10 mg, 0.087 mmol) and $NaHCO_3$·aq. (0.08 ml) according to the procedure for 80.

N-(4-([1,1'-biphenyl]-4-ylamino)benzyl)-N-hydroxy-2-(4-methylpiperazin-1-yl)acetamide (101)

101

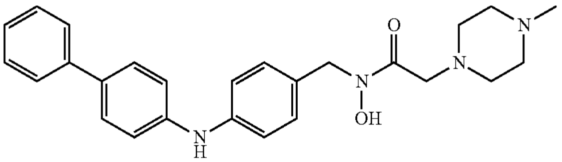

The title compound 101 (2.3 mg) was prepared in a total yield of 9.6% as a white solid according to the procedure for compound 80. $^1$H NMR (400 MHz, Methanol-$d_4$) δ 7.56 (d, J= 8.0 Hz, 2H), 7.50 (d, J=8.4 Hz, 2H), 7.39 (t, J=7.6 Hz, 2H), 7.28-7.21 (m, 3H), 7.16-7.09 (m, 4H), 4.69 (s, 2H), 3.66 (s, 2H), 3.36-3.15 (m, 8H), 2.88 (s, 3H). Mass (m/z): 431.4 $[M+H]^+$ N-(4-((4-(tert-butyl)-2,6-dimethylphenyl)amino) benzyl)-2,2,2-trifluoro-N-hydroxyacetamide (102)

102

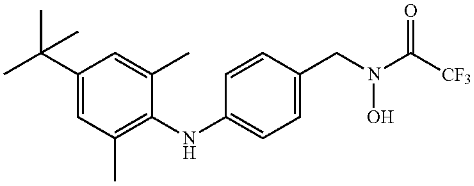

The title compound 102 (30 mg) was prepared in a total yield of 76.1% as a white solid according to the procedure for compound 80. $^1$H NMR (400 MHz, Chloroform-d) δ 7.15-7.08 (m, 4H), 6.48 (d, J=8.4 Hz, 2H), 4.73 (s, 2H), 2.20 (s, 6H), 1.33 (s, 9H). Mass (m/z): 395.3 $[M+H]^+$.

N-(4-((4-(tert-butyl)-2,6-dimethylphenyl)amino)benzyl)-N-hydroxy-1-methylpiperidine-4-carboxamide (103)

103

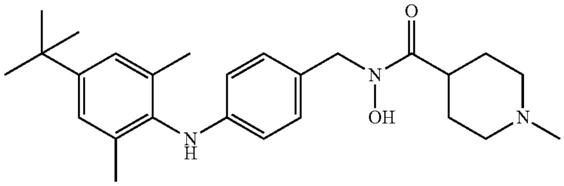

The title compound 103 (3.1 mg) was prepared in a total yield of 12.4% as a white solid according to the procedure for compound 80. $^1$H NMR (400 MHz, Methanol-$d_4$) δ 7.12 (m, 2H), 7.03 (d, J=8.4 Hz, 2H), 6.39 (d, J=8.4 Hz, 2H), 4.61 (s, 2H), 3.56-3.53 (m, 2H), 3.06-3.00 (m, 3H), 2.86 (s, 3H), 2.1 (s, 6H), 2.10-1.85 (m, 4H), 1.31 (s, 9H). Mass (m/z): 424.4 $[M+H]^+$ N-(4-((4'-fluoro-[1,1'-biphenyl]-4-yl)amino)benzyl)-N-hydroxypivalamide (104)

104

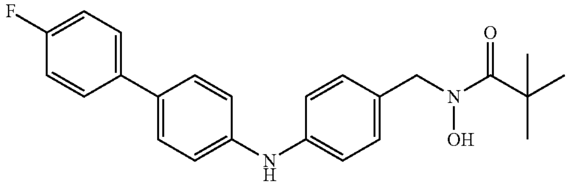

The title compound 104 (19.2 mg) was prepared in a total yield of 48.9% as a white solid according to the procedure for compound 80. $^1$H NMR (400 MHz, Chloroform-d) δ 7.56-7.41 (m, 4H), 7.22 (d, J=8.4 Hz, 2H), 7.14-7.08 (m, 6H), 4.86 (s, 2H), 1.32 (s, 9H). Mass (m/z): 393.1 $[M+H]^+$.

N-(4-((4-cyclopropylphenyl)amino)benzyl)-N-hydroxypivalamide (105)

105

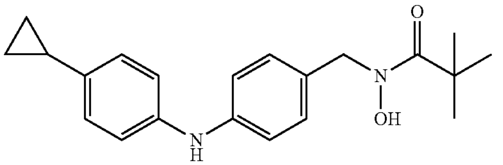

The title compound 105 (10.0 mg) was prepared in a total yield of 29.6% as a white solid according to the procedure for compound 80. $^1$H NMR (400 MHz, Chloroform-d) 67.16 (d, J=8.0 Hz, 2H), 7.03-6.93 (m, 6H), 4.81 (s, 2H), 1.89-1.83 (m, 1H), 1.31 (s, 9H), 0.98-0.88 (m, 2H), 0.65-0.63 (m, 2H). Mass (m/z): 339.4 $[M+H]^+$.

N-(4-((4-(1H-imidazol-1-yl)phenyl)amino)benzyl)-N-hydroxypivalamide (106)

106

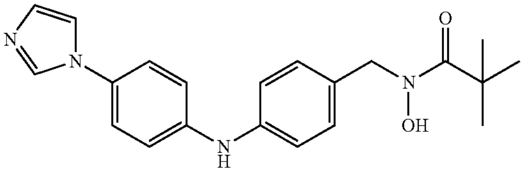

The title compound 106 (13.7 mg) was prepared in a total yield of 37.6% as a white solid according to the procedure for compound 80. $^1$H NMR (400 MHz, Chloroform-d) δ 7.85-7.95 (m, 1H), 7.32-7.18 (m, 6H), 7.14-7.07 (m, 4H), 4.08 (s, 2H), 1.20 (s, 9H). Mass (m/z): 365.4 $[M+H]^+$ N-hydroxy-2-(4-methylpiperazin-1-yl)-N-(4-((4-(trifluoromethyl)phenyl)amino)benzyl)acetamide (107)

107

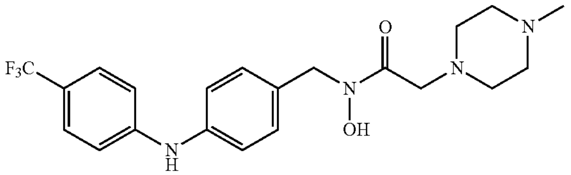

The title compound 107 (13.3 mg) was prepared in a total yield of 35.8% as a white solid according to the procedure for compound 80. $^1$H NMR (400 MHz, Methanol-$d_4$) δ 7.45 (d, J=8.4 Hz, 2H), 7.28 (d, J=8.4 Hz, 2H), 7.16-7.10 (m, 4H), 4.73 (s, 2H), 3.92 (s, 2H), 3.51-3.39 (m, 4H), 3.37-3.22 (m, 4H), 2.93 (s, 3H). Mass (m/z): 423.3 $[M+H]^+$ N-(4-((4-(tert-butyl)phenyl)amino)benzyl)-2-(4-cyclopropylpiperazin-1-yl)-N-hydroxyacetamide (108)

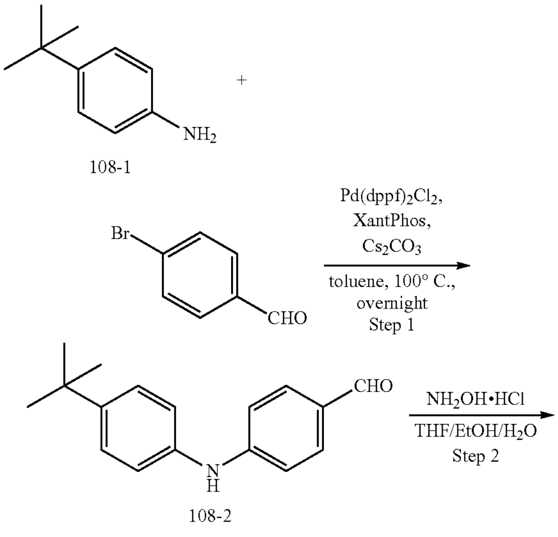

-continued

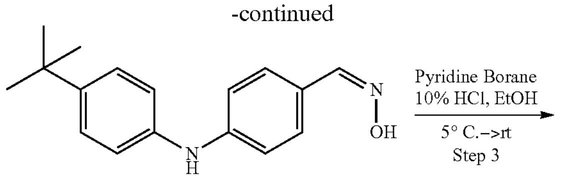

108-3

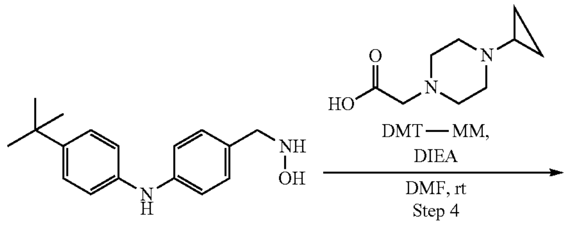

108-4

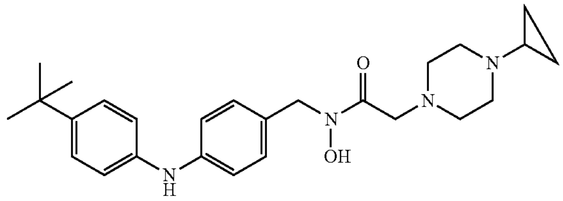

108

Step 1-3. The compound 108-4 (1.45 g) was prepared in a total yield of 27% as a yellow solid according to the procedure for compound 80-4. Mass (m/z): 271.3 $[M+H]^+$.

Step 4. To a solution of 4-(tert-butyl)-N-(4-((hydroxyamino)methyl)phenyl)aniline (54 mg, 0.2 mmol) and 2-(4-cyclopropylpiperazin-1-yl)acetic acid (47.8 mg, 0.26 mmol) in DMF (I ml) was added DIEA (0.045 mL, 0.26 mmol). Followed by the addition of DMT-MM (76.4 mg, 0.26 mmol) then the reaction mixture was stirred for 2 hours at rt. 10 mL of water was added. Then the mixture was extracted by DCM (10 mL×3). The combined organic layers were washed with water (10 mL×3), dried over $Na_2SO_4$ and concentrated under vacuum. The residue was purified by prep-TLC (MeOH/DCM=1/10) to give the desired product as white solid (27.2 mg, 31.1%). $^1H$ NMR (400 MHz, Methanol-$d_4$) δ 7.27 (d, J=8.4 Hz, 2H), 7.18 (d, J=8.4 Hz, 2H), 7.03-6.99 (m, 4H), 4.68 (s, 2H), 4.11 (s, 2H), 3.42-3.30 (m, 4H), 3.23-3.17 (m, 4H), 2.24 (m, 1H), 1.30 (s, 9H), 0.74-0.63 (m, 4H). Mass (m/z): 437.3 $[M+H]^+$.

N-(4-((4-(tert-butyl)phenyl)amino)benzyl)-N-hydroxy-2-(4-methyl-3-oxopiperazin-1-yl)acetamide (109)

109

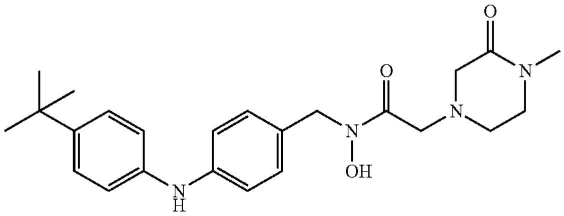

The title compound 109 (5.0 mg) was prepared in a total yield of 16.3% as a white solid according to the procedure for compound 108. $^1H$ NMR (400 MHz, Methanol-$d_4$) δ 7.29-7.24 (m, 2H), 7.19 (d, J=8.0 Hz, 2H), 7.07-7.00 (m, 4H), 4.69 (s, 2H), 4.21 (s, 2H), 3.90 (s, 2H), 3.70-3.48 (m, 4H), 3.02 (s, 3H), 1.31 (s, 9H). Mass (m/z): 425.4 $[M+H]^+$.

2-(4-benzoylpiperazin-1-yl)-N-(4-((4-(tert-butyl) phenyl)amino)benzyl)-N-hydroxyacetamide (110)

110

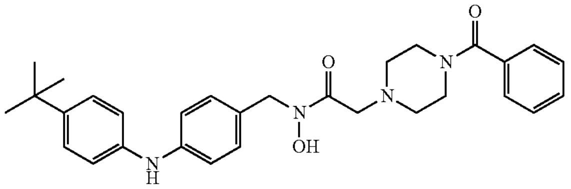

The title compound 110 (7.4 mg) was prepared in a total yield of 49% as a white solid according to the procedure for compound 80. $^1H$ NMR (400 MHz, Methanol-$d_4$) δ 7.53-7.43 (m, 5H), 7.27 (d, J=8.4 Hz, 2H), 7.18 (d, J=8.4 Hz, 2H), 7.03-6.99 (m, 4H), 4.69 (s, 2H), 4.31 (s, 2H), 4.08-3.4 (m, 8H), 1.30 (m, 9H). Mass (m/z): 501.4 $[M+H]^+$.

N-hydroxy-N-(4-((4-(trifluoromethoxy)phenyl) amino)benzyl)pivalamide (111)

111

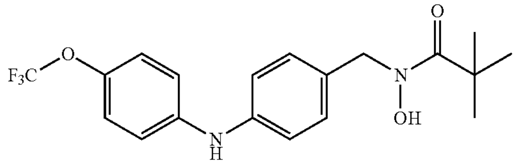

The title compound 111 (28.2 mg) was prepared in a total yield of 73.6% as a white solid according to the procedure for compound 80. $^1H$ NMR (400 MHz, Chloroform-d) δ 7.20 (d, J=8.4 Hz, 2H), 7.11 (d, J=8.4 Hz, 2H), 7.06-7.00 (m, 411), 4.83 (s, 2H), 1.31 (s, 9H). Mass (m/z): 383.1 $[M+H]^+$ N-(4-((4'-(tert-butyl)-[1,1'-biphenyl]-4-yl)amino) benzyl)-N-hydroxypivalamide (112)

112

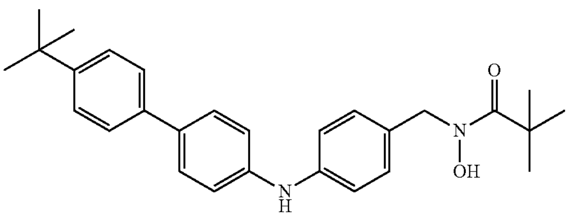

The title compound 112 (14.5 mg) was prepared in a total yield of 33.7% as a white solid according to the procedure for compound 80. $^1H$ NMR (400 MHz, Chloroform-d) δ

7.58-7.41 (m, 6H), 7.21 (d, J=8.4 Hz, 2H), 7.16-7.05 (m, 4H), 4.84 (s, 2H), 1.37 (s, 9H), 1.32 (s, 9H). Mass (m/z): 431.4 $[M+H]^+$ N-hydroxy-N-(4-((4'-(trifluoromethyl)-[1,1'-biphenyl]-4-yl)amino)benzyl)pivalamide (113)

113

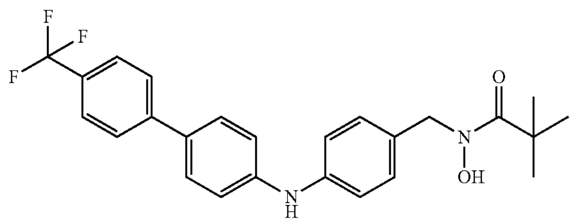

The title compound 113 (7.3 mg) was prepared in a total yield of 27.5% as a white solid according to the procedure for compound 80. $^1H$ NMR (400 MHz, Chloroform-d) δ 7.67-7.74 (m, 4H), 7.53 (d, J=8.4 Hz, 2H), 7.22 (d, J=8.4 Hz, 2H), 7.17-7.09 (m, 4H), 4.87 (s, 2H), 1.33 (s, 9H). Mass (m/z): 443.2 $[M+H]^+$.

N-(4-((4-(tert-butyl)phenyl)amino)benzyl)-N-hydroxy-2-(4-methyl-2-oxopiperazin-1-yl)acetamide (114)

114

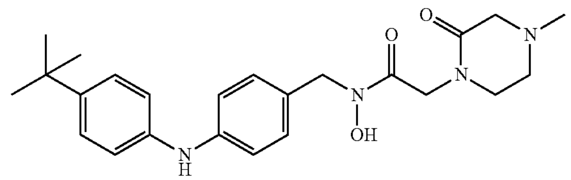

The title compound 114 (5.7 mg) was prepared in a total yield of 13.4% as a white solid according to the procedure for compound 108. $^1H$ NMR (400 MHz, Methanol-$d_4$) δ 7.31-7.24 (m, 2H), 7.20 (d, J=8.4 Hz, 2H), 7.03-7.00 (m, 4H), 4.69 (s, 2H), 4.31 (s, 2H), 4.03-3.90 (m, 2H), 3.84-3.57 (m, 2H), 3.68-3.59 (m, 2H), 3.48 (s, 3H), 1.30 (s, 9H). Mass (m/z): 425.4 $[M+H]^+$.

N-(4-((4-(tert-butyl)phenyl)amino)benzyl)-2-(4-(cyclopropanecarbonyl)piperazin-1-yl)-N-hydroxyacetamide (115)

115

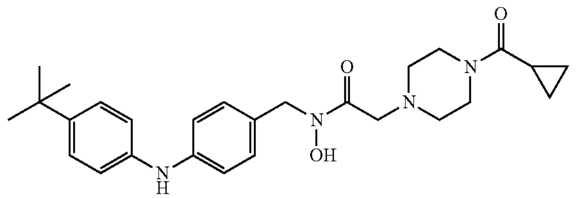

The title compound 115 (11.4 mg) was prepared in a total yield of 81.9% as a white solid according to the procedure for compound 108. $^1H$ NMR (400 MHz, Methanol-$d_4$) δ 7.27 (d, J=8.4 Hz, 2H), 7.19 (d, J=8.4 Hz, 2H), 7.03-7.00 (m, 4H), 4.70 (s, 2H), 4.31 (s, 2H), 4.05 (br s, 4H), 3.48 (br s, 4H), 2.04-1.95 (m, 1H), 1.30 (s, 9H), 0.92-0.87 (m, 4H). Mass (m/z): 465.3 $[M+H]^+$ N-(4-((4-(tert-butyl)phenyl)amino)benzyl)-N-hydroxy-2-(4-(methylsulfonyl)piperazin-1-yl)acetamide (116)

116

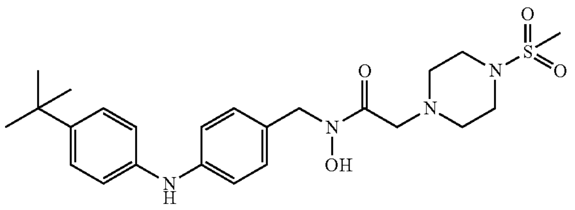

The title compound 116 (20.0 mg) was prepared in a total yield of 42.2% as a white solid according to the procedure for compound 108. $^1H$ NMR (400 MHz, Methanol-$d_4$) δ 7.27 (d, J=8.4 Hz, 2H), 7.19 (d, J=8.4 Hz, 2H), 7.03-7.00 (m, 4H), 4.69 (s, 2H), 4.33 (s, 2H), 3.54 (br s, 8H), 2.97 (s, 3H), 1.30 (s, 9H). Mass (m/z): 475.4 $[M+H]^+$.

N-(4-((4-(tert-butyl)phenyl)amino)benzyl)-2-(3,4-dimethylpiperazin-1-yl)-N-hydroxyacetamide (117)

117

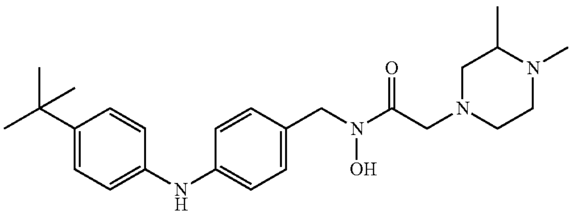

The title compound 117 (17.7 mg) was prepared in a total yield of 42.0% as a white solid according to the procedure for compound 108. $^1H$ NMR (400 MHz, Methanol-$d_4$) δ 7.27 (d, J=8.4 Hz, 2H), 7.17 (d, J=8.4 Hz, 2H), 7.08-6.95 (m, 4H), 4.67 (s, 2H), 3.82 (s, 2H), 3.66-3.33 (m, 7H), 2.91 (s, 3H), 1.38 (d, J=5.6 Hz, 3H), 1.30 (s, 9H). Mass (m/z): 425.3 $[M+H]^+$.

N-(4-((4-(tert-butyl)phenyl)amino)benzyl)-2-(4-(4-fluorophenyl)piperazin-1-yl)-N-hydroxyacetamide (118)

118

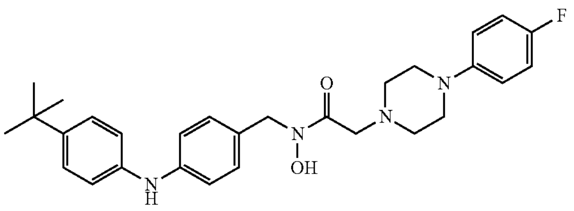

The title compound 118 (9.0 mg) was prepared in a total yield of 30.6% as a white solid according to the procedure for compound 108. $^1$H NMR (400 MHz, Methanol-$d_4$) δ 7.27 (d, J=8.4 Hz, 2H), 7.20 (d, J=8.4 Hz, 2H), 7.07-6.97 (i, 8H), 4.71 (s, 2H), 4.33 (s, 2H), 3.95-2.94 (3, 8H), 1.30 (s, 9H). Mass (m/z): 491.2 [M+H]$^+$.

N-(4-((4-(tert-butyl)phenyl)amino)benzyl)-N-hydroxy-4-methylpiperazine-1-carboxamide (119)

119

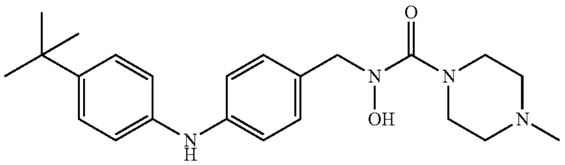

The title compound 119 (13.3 mg) was prepared in a total yield of 33.6% as a white solid according to the procedure for compound 134. $^1$H NMR (400 MHz, Methanol-$d_4$) δ 7.26 (d, J=8.4 Hz, 2H), 7.20 (d, J=8.4 Hz, 2H), 7.03-6.99 (m, 4H), 4.44 (s, 2H), 3.60-3.39 (m, 4H), 3.29-3.16 (m, 4H), 2.91 (s, 3H), 1.30 (s, 9H). Mass (m/z): 397.3 [M+H]$^+$ N-hydroxy-2-(4-methylpiperazin-1-yl)-N-(4-((4-((tetrahydro-2H-pyran-4-yl)oxy)phenyl)amino)benzyl)acetamide 120

120

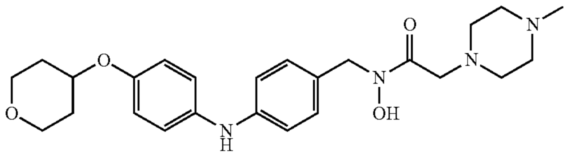

The title compound 120 (13.4 mg) was prepared in a total yield of 6.6% as a white solid according to the procedure for compound 108. $^1$H NMR (400 MHz, Methanol-$d_4$) δ 7.15 (d, J=8.0 Hz, 2H), 7.03 (d, J=8.0 Hz, 2H), 6.97-6.85 (m, 4H), 4.65 (s, 2H), 4.45 (m, 1H), 4.00-3.89 (m, 2H), 3.81 (s, 2H), 3.62-3.53 (m, 2H), 3.39 (br s, 4H), 3.17 (br s, 4H), 2.91 (s, 3H), 2.08-1.94 (m, 2H), 1.77-1.65 (m, 2H). Mass (m/z): 455.3 [M+H]$^+$ N-(4-((4'-(tert-butyl)-[1,1'-biphenyl]-4-yl)amino)benzyl)-N-hydroxy-2-(4-methylpiperazin-1-yl)acetamide (121)

121

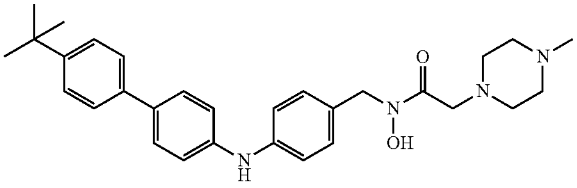

The title compound 121 (13.5 mg) was prepared in a total yield of 27.7% as a white solid according to the procedure for compound 108. $^1$H NMR (400 MHz, Methanol-$d_4$) δ 7.53-7.46 (m, 6H), 7.22 (d, J=8.0 Hz, 2H), 7.14 (d, J=8.4 Hz, 2H), 7.09 (d, J=8.4 Hz, 2H), 4.69 (s, 2H), 3.84 (s, 2H), 3.40 (br s, 4H), 3.20 (br s, 4H), 2.90 (s, 3H), 1.34 (s, 9H). Mass (m/z): 487.3 [M+H]$^+$ N-(4-((4-(tert-butyl)phenyl)amino)benzyl)-2-(4-(6-fluoropyridin-3-yl)piperazin-1-yl)-N-hydroxyacetamide (122)

122

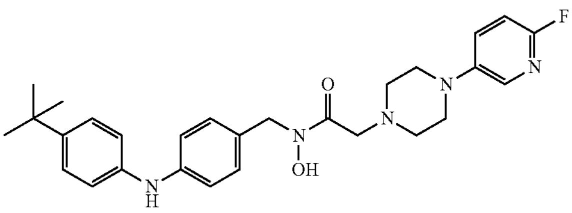

The title compound 122 (2.5 mg) was prepared in a total yield of 8.5% as a white solid according to the procedure for compound 108. $^1$H NMR (400 MHz, Methanol-$d_4$) δ 7.89 (s, 1H), 7.70-7.65 (m, 2H), 7.28 (d, J=8.4 Hz, 2H), 7.20 (d, J=8.4 Hz, 2H), 7.03-7.00 (m, 4H), 4.71 (s, 2H) 4.35 (s, 2H), 3.58 (br s, 8H), 1.30 (s, 9H). Mass (m/z): 492.2 [M+H]$^+$ 4-(dimethylamino)-N-hydroxy-N-(4-((4-((tetrahydro-2H-pyran-4-yl)oxy)phenyl)amino)benzyl)butanamide (123)

123

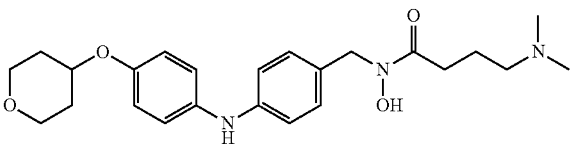

$^1$H NMR (400 MHz, Methanol-$d_4$) δ 7.17 (d, J=8.4 Hz, 2H), 7.02 (d, J=8.8 Hz, 2H), 6.90 (dd, J=13.6, 8.8 Hz, 4H), 4.63 (s, 2H), 4.44 (m, 1H), 4.02-3.88 (m, 2H), 3.59-3.53 (m, 2H), 2.62-2.55 (m, 4H), 2.35 (s, 6H), 2.06-1.85 (m, 4H), 1.77-1.63 (m, 2H). Mass (m/z): 428.2 [M+H]$^+$.

4-(dimethylamino)-N-hydroxy-N-(4-((4-(N-methylacetamido)phenyl)amino)benzyl)butanamide (124)

124

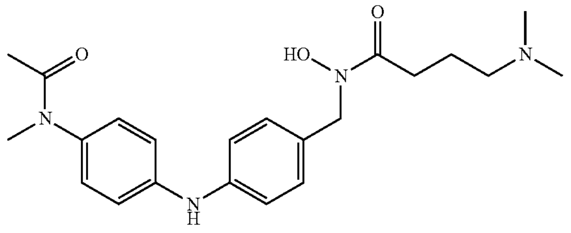

$^1$H NMR (400 MHz, Methanol-$d_4$) δ 7.29-7.20 (m, 2H), 7.14-7.04 (m, 6H), 4.69 (s, 2H), 3.20 (s, 3H), 2.85-2.74 (m, 2H), 2.67-2.57 (m, 2H), 2.53 (s, 6H), 2.02-1.89 (m, 2H), 1.86 (s, 3H). Mass (m/z): 399.2 $[M+H]^+$.

N-hydroxy-N-(4-((4-(2,2,2-trifluoroethoxy)phenyl)amino)benzyl)pivalamide (125)

125

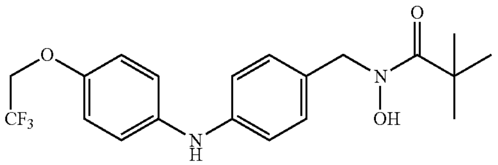

The title compound 125 (35.0 mg) was prepared in a total yield of 88.4% as a white solid according to the procedure for compound 80. $^1$H NMR (400 MHz, Chloroform-d) δ 7.16 (d, J=8.4 Hz, 2H), 7.06 (d, J=8.8 Hz, 2H), 6.93-6.89 (m, 4H), 4.82 (s, 2H), 4.32 (q, J=8.4 Hz, 2H), 1.31 (s, 9H). Mass (m/z): 397.3 $[M+H]^+$ N-(4-((4-(tert-butyl)phenyl)amino)benzyl)-N-hydroxy-2-(4-(2,2,2-trifluoroethyl)piperazin-1-yl)acetamide (126)

126

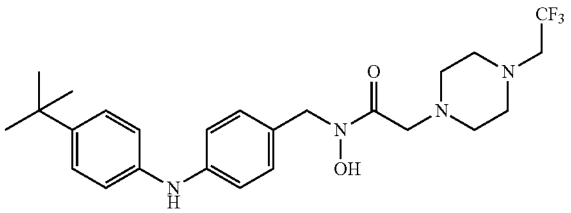

The title compound 126 (29.0 mg) was prepared in a total yield of 73.4% as a white solid according to the procedure for compound 108. $^1$H NMR (400 MHz, Methanol-$d_4$) δ 7.26 (d, J=8.4 Hz, 2H), 7.16 (d, J=8.0 Hz, 2H), 7.03-6.98 (m, 4H), 4.65 (s, 2H), 3.44 (s, 2H), 3.05 (m, 2H), 2.80-2.57 (m, 8H), 1.30 (s, 9H). Mass (m/z): 479.3 $[M+H]^+$ N-(4-((4-chlorophenyl)amino)benzyl)-N-hydroxypivalamide (127)

127

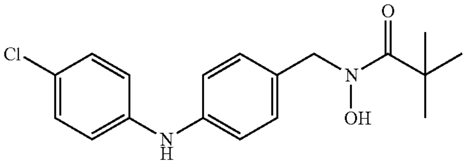

The title compound 127 (33.2 mg) was prepared in a total yield of 98.3% as a white solid according to the procedure for compound 80. $^1$H NMR (400 MHz, Chloroform-d) δ 7.20-7.16 (m, 4H), 6.99-6.94 (m, 4H), 4.78 (s, 2H), 1.30 (s, 9H). Mass (m/z): 333.2 $[M+H]^+$ N-hydroxy-2-(4-methylpiperazin-1-yl)-N-(4-((4'-(trifluoromethoxy)-[1,1'-biphenyl]-4-yl)amino)benzyl)acetamide (128)

128

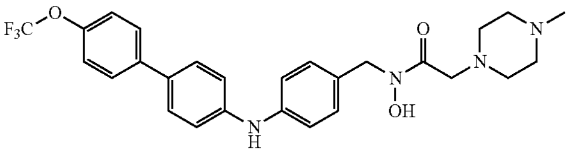

The title compound 128 (23.4 mg) was prepared in a total yield of 45.5% as a white solid according to the procedure for compound 108. $^1$H NMR (400 MHz, Methanol-$d_4$) δ 7.65 (d, J=8.4 Hz, 2H), 7.50 (d, J=8.4 Hz, 2H), 7.34-7.20 (m, 4H), 7.16-7.09 (m, 4H), 4.70 (s, 2H), 3.92 (s, 2H), 3.45 (br s, 4H), 3.29 (br s, 4H), 2.92 (s, 3H). Mass (m/z): 515.3 $[M+H]^+$ N-(4-((4-(tert-butyl)phenyl)amino)benzyl)-N-hydroxy-2-((3S,5R)-3,4,5-trimethylpiperazin-1-yl)acetamide (129)

129

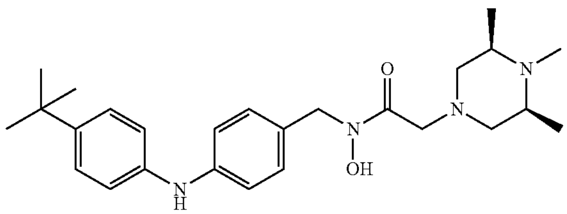

The title compound 129 (25.5 mg) was prepared in a total yield of 90.1% as a white solid according to the procedure for compound 108. $^1$H NMR (400 MHz, Methanol-$d_4$) δ 7.30-7.24 (m, 2H), 7.18 (d, J=8.4 Hz, 2H), 7.04-6.99 (m, 4H), 4.67 (s, 2H), 3.82 (s, 2H), 3.55 (br s, 2H), 3.38 (m, 2H), 2.91 (s, 3H), 2.86 (m, 2H), 1.40 (d, J=6.4 Hz, 6H), 1.30 (s, 9H). Mass (m/z): 439.4 $[M+H]^+$ N-(4-((4-cyanophenyl)amino)benzyl)-N-hydroxypivalamide (130)

130

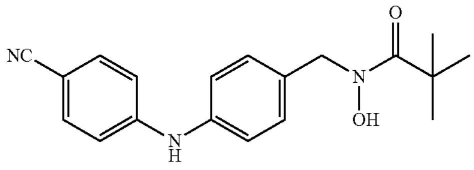

The title compound 130 (10.0 mg) was prepared in a total yield of 30.9% as a white solid according to the procedure for compound 80. $^1$H NMR (400 MHz, Chloroform-d) δ 7.52-7.41 (m, 2H), 7.33-7.22 (m, 2H), 7.18-7.11 (m, 2H), 7.02-6.91 (m, 2H), 4.88 (s, 2H), 1.32 (s, 9H). Mass (m/z): 324.3 [M+H]$^+$ N-(4-((4-(tert-butyl)phenyl)amino)benzyl)-N-hydroxy-2-((1S,4S)-5-methyl-2,5-diazabicyclo[2.2.1]heptan-2-yl)acetamide (131)

131

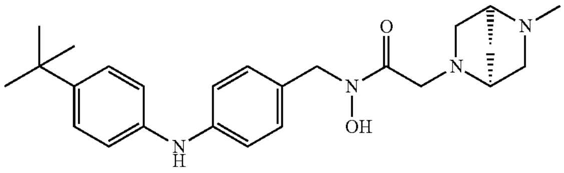

The title compound 131 (10.6 mg) was prepared in a total yield of 39.4% as a white solid according to the procedure for compound 108. $^1$H NMR (400 MHz, Methanol-d$_4$) δ 7.27 (d, J=8.8 Hz, 2H), 7.18 (d, J=8.4 Hz, 2H), 7.03-6.99 (m, 4H), 4.68 (s, 2H), 4.27 (s, 2H), 4.04-3.44 (m, 6H), 3.01 (s, 3H), 2.50 (br s, 2H), 1.30 (s, 9H). Mass (m/z): 423.3 [M+H]$^+$ N-(4-((4-(tert-butyl)phenyl)amino)benzyl)-N-methoxypivalamide (132)

132

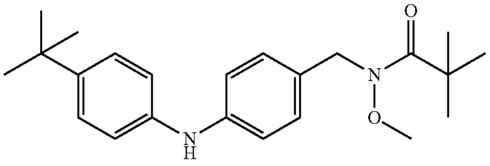

The title compound 132 (32.0 mg) was prepared in a total yield of 86.9% as a white solid according to the procedure for compound 80. $^1$H NMR (400 MHz, Chloroform-d) δ 7.34-7.27 (m, 2H), 7.18 (d, J=8.0 Hz, 2H), 7.04-6.98 (m, 4H), 4.75 (s, 2H), 3.68 (s, 3H), 1.32 (s, 9H), 1.27 (s, 9H). Mass (m/z): 369.3 [M+H]$^+$ N-(4-((4-(tert-butyl)phenyl)amino)benzyl)-N-hydroxy-2-(4-(pyrimidin-2-yl)piperazin-1-yl)acetamide (133)

133

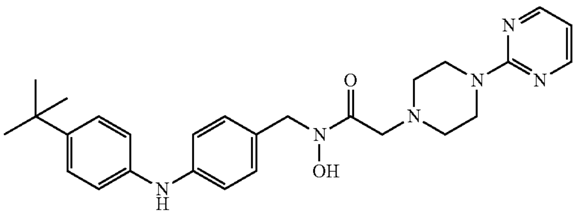

The title compound 133 (38.4 mg) was prepared in a total yield of 45.3% as a white solid according to the procedure for compound 108. $^1$H NMR (400 MHz, Methanol-d$_4$) δ 8.31 (d, J=4.4 Hz, 2H), 7.32-7.08 (m, 4H), 7.08-6.89 (m, 4H), 6.59 (t, J=4.4 Hz, 1H), 4.67 (s, 2H), 3.91 (br s, 4H), 3.69 (s, 2H), 2.86 (br s, 4H), 1.28 (s, 9H). Mass (m/z): 475.2 [M+H]$^+$ 1-(4-((4-(tert-butyl)phenyl)amino)benzyl)-3-cyclopropyl-1-hydroxyurea (134)

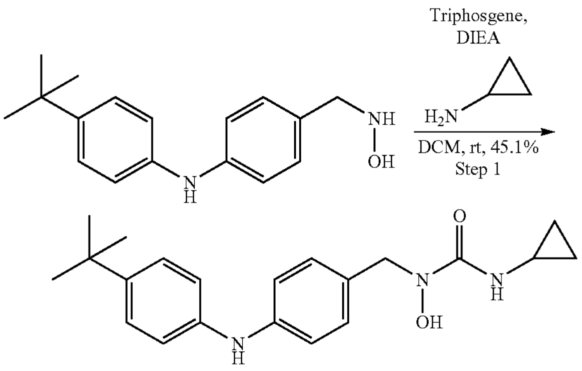

134

To a solution of 4-(tert-butyl)-N-(4-((hydroxyamino)methyl)phenyl)aniline (27.1 mg, 0.1 mmol) in DCM (2 mL) was added triphosgene (29.7 mg, 0.1 mmol) and DIEA (39 mg, 0.3 mmol). After the reaction mixture was stirred for 2 hour. DIEA (39 mg, 0.3 mmol) and cyclopropanamine (5.7 mg, 0.1 mmol) were added. Then the reaction mixture was stirred for 1 hours. The reaction solution was washed with water (3×5 mL), dried over $Na_2SO_4$ and concentrated under vacuum. The residue was purified by prep-TLC (MeOH/DCM=1/10) to give the desired product as yellow solid (21.5 mg, 65.7%). $^1$H NMR (400 MHz, Chloroform-d) δ 7.32-727 (m, 2H), 7.22 (d, J=8.4 Hz, 2H), 7.05-6.95 (m, 4H), 4.57 (s, 2H), 2.63 (m, 1H), 1.31 (s, 9H), 0.76-0.71 (m, 2H), 0.60-0.44 (m, 2H). Mass (m/z): 354.2 [M+H]$^+$ N-(4-((4-(6-fluoropyridin-3-yl)phenyl)amino)benzyl)-N-hydroxy-2-(4-methylpiperazin-1-yl)acetamide (135)

135

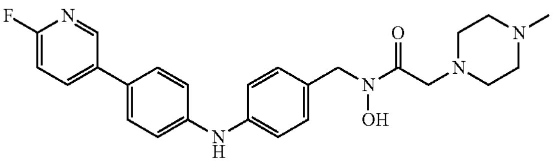

The title compound 135 (12.0 mg) was prepared in a total yield of 26.7% as a white solid according to the procedure for compound 108. $^1$H NMR (400 MHz, Methanol-$d_4$) δ 8.37 (d, J=2.8 Hz, 1H), 8.13 (ddd, J=8.4, 7.6, 2.8 Hz, 1H), 7.50 (d, J=8.4 Hz, 2H), 7.29-7.21 (m, 2H), 7.20-7.14 (m, 2H), 7.13-7.08 (m, 3H), 4.71 (s, 2H), 3.94 (s, 2H), 3.45 (br s, 4H), 3.29 (br s, 4H), 2.93 (s, 3H). Mass (m/z): 450.2 [M+H]$^+$.

N-hydroxy-2-(4-methylpiperazin-1-yl)-N-(4-((4-(pyrrolidin-1-yl)phenyl)amino)benzyl)acetamide (136)

136

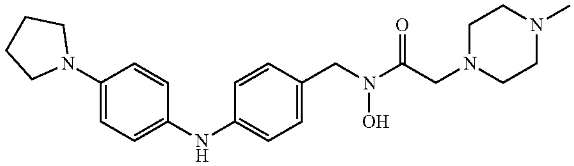

The title compound 136 (5.1 mg) was prepared in a total yield of 13.2% as a white solid according to the procedure for compound 108. $^1$H NMR (400 MHz, Methanol-$d_4$) δ 7.38-6.68 (m, 8H), 4.65 (s, 2H), 3.55 (s, 2H), 3.27-3.15 (m, 4H), 2.89 (br s, 8H), 2.80 (s, 3H), 2.09-1.85 (m, 4H). Mass (m/z): 424.3 [M+H]$^+$ N-hydroxy-2-(4-methylpiperazin-1-yl)-N-(4-((4-(1-methylpiperidin-4-yl)phenyl)amino)benzyl)acetamide (137)

137

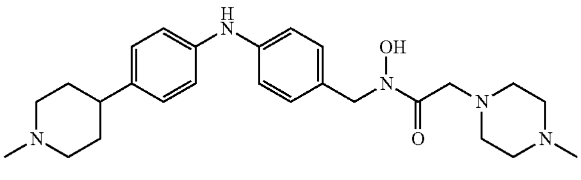

To a solution of 4-((hydroxyamino)methyl)-N-(4-(1-methylpiperidin-4-yl)phenyl)aniline (130 mg, 0.42 mmol), 2-(4-methylpiperazin-1-yl)acetic acid (66 mg, 0.42 mmol) and DIEA (129 mg, 1 mmol) in DMF (1 ml) was added DMT-MM (151 mg, 0.55 mmol). Then the mixture was stirred 3 hours at rt. The reaction was concentrated under vacuum. The residue was purified by perp-TLC to afford the desired product as a white solid. (6 mg, 1.6%). $^1$H NMR (400 MHz, Methanol-$d_4$) δ 7.20-7.16 (m, 2H), 7.15-7.10 (m, 2H), 7.06-6.99 (m, 4H), 4.67 (s, 2H), 3.77 (s, 2H), 3.62-3.56 (m, 2H), 3.41-3.32 (m, 4H), 3.19-3.07 (m, 6H), 2.90 (d, J=5.1 Hz, 6H), 2.82-2.75 (m, 1H), 2.12-2.05 (m, 2H), 1.99-1.86 (m, 2H). Mass (m/z): 452.3 [M+H]$^+$.

N-hydroxy-2-(4-methylpiperazin-1-yl)-N-(4-((4-morpholinophenyl)amino)benzyl)acetamide (138)

138

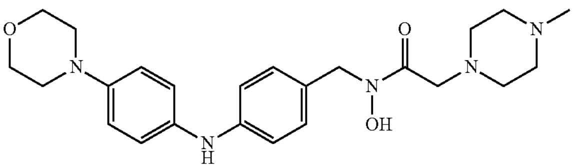

The title compound 138 (38.1 mg) was prepared in a total yield of 86.5% as a white solid according to the procedure for compound 108. $^1$H NMR (400 MHz, Methanol-$d_4$) δ 7.13 (d, J=8.4 Hz, 2H), 7.02 (d, J=8.8 Hz, 2H), 6.93-6.86 (m, 4H), 4.63 (s, 2H), 3.84-3.69 (m, 4H), 3.39 (s, 2H), 3.07-2.91 (m, 4H), 2.75-2.46 (m, 8H), 2.29 (s, 3H). Mass (m/z): 440.2 [M+H]$^+$ N-hydroxy-2-(4-methylpiperazin-1-yl)-N-(4-((4-(2-oxopyridin-1 (2H)-yl)phenyl)amino)benzyl)acetamide (139)

139

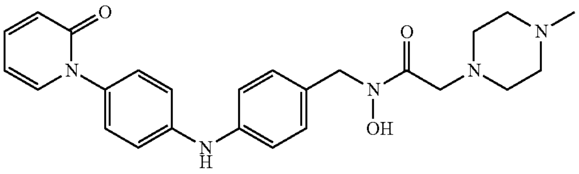

The title compound 139 (5 mg) was prepared in a total yield of 3.4% as a yellow solid form 1-(4-((4-((hydroxyamino)methyl)phenyl)amino)phenyl)pyridin-2 (1H)-one (100 mg, 0.33 mmol), 2-(4-methylpiperazin-1-yl)acetic acid (52 mg, 0.33 mmol) and DMT-MM (118 mg, 0.43 mmol) according to the procedure for 137. $^1$H NMR (400 MHz, Methanol-$d_4$) δ 7.64-7.57 (m, 2H), 7.27-7.10 (m, 8H), 6.63 (dd, J=10.0, 1.4 Hz, 1H), 6.48 (td, J=6.8, 1.4 Hz, 1H), 4.70 (s, 2H), 3.69-3.64 (m, 2H), 3.38-3.32 (m, 4H), 3.08-2.94 (m, 4H), 2.88 (d, J=1.1 Hz, 3H). 448.3 Mass (m/z): [M+H]$^+$ N-hydroxy-N-(4-((4-(2-methoxyethoxy)phenyl)amino)benzyl)-2-(4-methylpiperazin-1-yl)acetamide (140)

140

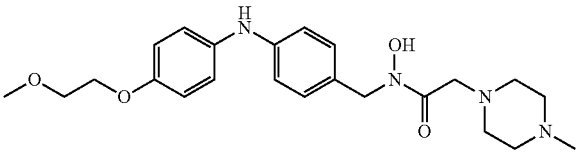

N-hydroxy The title compound 140 (16 mg) was prepared in a total yield of 18.0% as a white solid form 4-((hydroxyamino)methyl)-N-(4-(2-methoxyethoxy)phenyl)aniline (60 mg, 0.21 mmol), 2-(4-methylpiperazin-1-yl)acetic acid (33 mg, 0.21 mmol) and DMT-MM (63 mg, 0.23 mmol) according to the procedure for 137. 1H NMR (400 MHz, Methanol-$d_4$) δ 7.16-7.10 (m, 2H), 7.06-7.01 (m, 2H), 6.92-6.82 (m, 4H), 4.63 (s, 2H), 4.09-4.04 (m, 2H), 3.74-3.70 (m, 2H), 3.55 (s, 2H), 3.42 (s, 3H), 3.24-3.08 (m, 4H), 2.98-2.82 (m, 4H), 2.78 (s, 3H). Mass (m/z): 429.4 [M+H]$^+$.

N-hydroxy-N-(4-((4-(N-methylacetamido)phenyl)amino)benzyl)-2-(4-methylpiperazin-1-yl)acetamide (141)

141

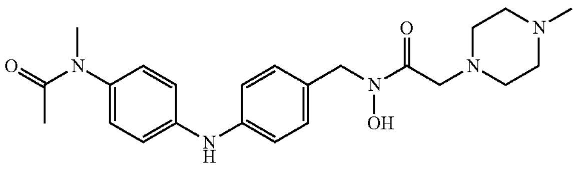

The title compound 141 (10.1 mg) was prepared in a total yield of 23.8% as a white solid according to the procedure for compound 108. $^1$H NMR (400 MHz, Methanol-$d_4$) δ 7.38-7.32 (m, 2H), 7.24-7.17 (m, 6H), 4.80 (s, 2H), 3.92 (s, 2H), 3.50 (br s, 4H), 3.44-3.38 (m, 3H), 3.35-3.18 (br s, 4H), 3.01 (s, 3H), 1.97 (s, 3H). Mass (m/z): 426.3 [M+H]$^+$.

4-(dimethylamino)-N-hydroxy-N-(4-((4-(piperidine-1-carbonyl)phenyl)amino)benzyl)butanamide (142)

142

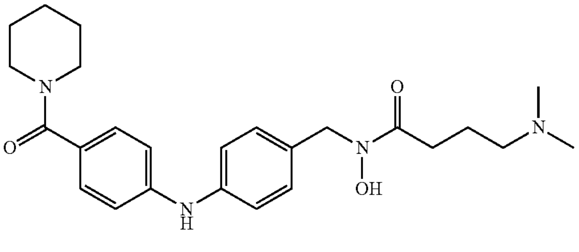

The title compound 142 (8 mg) was prepared in a total yield of 18.32% as a white solid form (4-((4-((hydroxyamino)methyl)phenyl)amino)phenyl)(piperidin-1-yl)methanone (32.5 mg, 0.1 mmol), 4-(dimethylamino)butanoic acid hydrochloride (16.7 mg, 0.1 mmol), DMT-MM (63 mg, 0.23 mmol), DIEA (38.7 mg, 0.3 mmol) and DMF (1 mL) according to the procedure for 137. 1H NMR (400 MHz, Methanol-$d_4$) δ 7.30-7.23 (m, 4H), 7.15-7.05 (m, 4H), 4.71 (s, 2H), 3.65-3.46 (m, 4H), 3.15-3.06 (m, 2H), 2.85 (s, 6H), 2.67 (t, J=6.9 Hz, 2H), 2.05-1.93 (m, 2H), 1.74-1.56 (m, 6H).

Mass (m/z): 439.3 [M+H]$^+$.

N-(4-((4-butoxyphenyl)amino)benzyl)-4-(dimethylamino)-N-hydroxybutanamide (143)

143

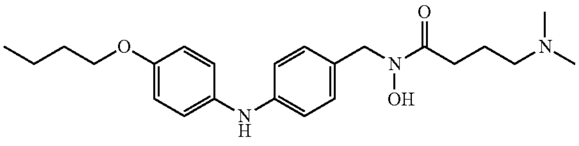

The title compound 143 (5.2 mg) was prepared in a total yield of 13.8% as a white solid according to the procedure for compound 108. $^1$H NMR (400 MHz, Methanol-$d_4$) δ 7.14 (d, J=8.4 Hz, 2H), 7.06-7.00 (m, 2H), 6.92-6.80 (m, 4H), 4.65 (s, 2H), 3.94 (m, 2H), 3.13-3.05 (m, 2H), 2.83 (s, 6H), 2.65 (t, J=6.8 Hz, 2H), 2.07-1.92 (m, 2H), 1.74 (m, 2H), 1.61-1.40 (m, 2H), 0.99 (t, J=7.6, 3H). Mass (m/z): 400.3 [M+H]$^+$.

N-hydroxy-2-(piperazin-1-yl)-N-(4-((4-(pyrrolidin-1-ylmethyl)phenyl)amino)benzyl)acetamide (144)

144

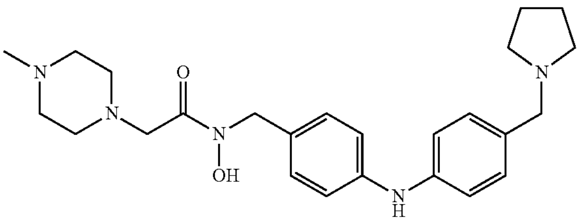

The title compound 144 (19 mg) was prepared in a total yield of 22.5% as a white solid form 4-((hydroxyamino)methyl)-N-(4-(pyrrolidin-1-ylmethyl)phenyl)aniline (52 mg, 0.18 mmol), 2-(4-methylpiperazin-1-yl)acetic acid (28 mg, 0.18 mmol), DMT-MM (53 mg, 0.19 mmol), DIEA (113 mg, 0.88 mmol) and DMF (1 mL) according to the procedure for 137. 1H NMR (400 MHz, Methanol-$d_4$) δ 7.37-7.31 (m, 2H), 7.26-7.21 (m, 2H), 7.13-7.08 (m, 4H), 4.69 (s, 2H), 4.26 (s, 2H), 3.57 (s, 2H), 3.53-3.40 (m, 4H), 3.24-3.07 (m, 6H), 2.87 (s, 3H), 2.77-2.63 (m, 2H), 2.19-2.11 (m, 2H), 2.06-1.96 (m, 2H). Mass (m/z): 439.3 [M+H]$^+$.

N-hydroxy-2-(4-methylpiperazin-1-yl)-N-(4-((3-morpholinophenyl)amino)benzyl) acetamide (145)

145

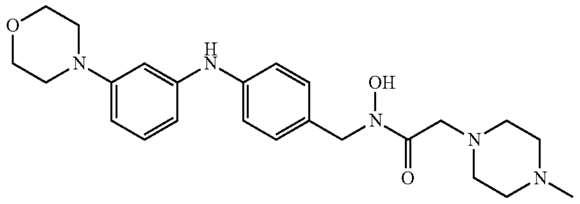

The title compound 145 (14.3 mg) was prepared in a total yield of 16.3% as a white solid form N-(4-((hydroxyamino) methyl)phenyl)-3-morpholinoaniline (60 mg, 0.2 mmol), 2-(4-methylpiperazin-1-yl)acetic acid (32 mg, 0.2 mmol), DMT-MM (61 mg, 0.22 mmol), DIEA (78 mg, 0.6 mmol) and DMF (2 mL) according to the procedure for 137. $^{1}$H NMR (400 MHz, Methanol-$d_4$) δ 7.20-7.16 (m, 2H), 7.10 (t, J=8.1 Hz, 1H), 7.05-7.01 (m, 2H), 6.66 (t, J=2.2 Hz, 11H), 6.63-6.60 (m, 1H), 6.53-6.49 (m, 1H), 4.66 (s, 2H), 3.85-3.78 (m, 4H), 3.57 (s, 2H), 3.27-3.11 (m, 4H), 3.11-3.07 (m, 4H), 2.95-2.69 (m, 7H). Mass (m/z): 440.3 $[M+H]^+$.

N-hydroxy-2-(4-methylpiperazin-1-yl)-N-(4-((4-(piperidin-1-yl)phenyl)amino)benzyl)acetamide (146)

146

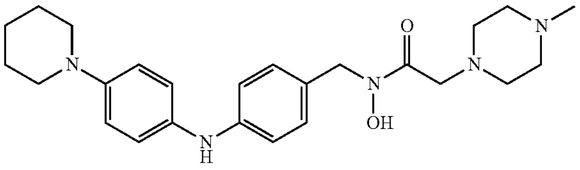

The title compound 146 (5.4 mg) was prepared in a total yield of 24.7% as a white solid according to the procedure for compound 108. $^{1}$H NMR (400 MHz, Methanol-$d_4$) δ 7.51 (d, J=8.8 Hz, 2H), 7.30 (d, J=8.4 Hz, 2H), 7.18-7.13 (m, 4H), 4.76 (s, 2H), 4.51 (s, 2H), 3.80 (br s, 8H), 3.63-3.55 (m, 4H), 3.05 (s, 3H), 2.13-2.00 (m, 4H), 1.98-1.88 (m, 2H). Mass (m/z): 438.2 $[M+H]^+$ N-hydroxy-2-(4-methylpiperazin-1-yl)-N-(4-((4-(tetrahydro-2H-pyran-4-yl)phenyl)amino)benzylacetamide 147

147

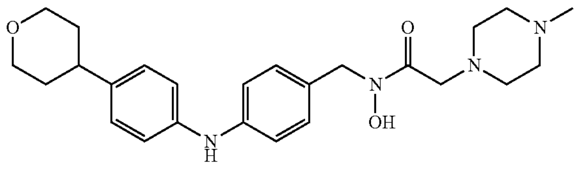

The title compound 147 (13.0 mg) was prepared in a total yield of 29.6% as a white solid form 4-((hydroxyamino) methyl)-N-(4-(tetrahydro-2H-pyran-4-yl)phenyl)aniline (29.8 mg, 0.1 mmol), 2-(4-methylpiperazin-1-yl)acetic acid (15.8 mg, 0.1 mmol), DMT-MM (27.6 mg, 0.1 mmol), DIEA (38.7 mg, 0.3 mmol) and DMF (1 mL) according to the procedure for 137. $^{1}$H NMR (400 MHz, Methanol-$d_4$) δ 7.17 (d, J=8.2 Hz, 2H), 7.12-7.07 (m, 2H), 7.04-6.97 (m, 4H), 4.65 (s, 2H), 4.02 (dt, J=11.1, 3.0 Hz, 2H), 3.58-3.46 (m, 4H), 2.94-2.64 (m, 9H), 2.56 (s, 3H), 1.79-1.65 (m, 4H). Mass (m/z): 439.3 $[M+H]^+$.

N-hydroxy-N-(4-((4-(4-hydroxypiperidin-1-yl)phenyl)amino)benzyl)-2-(4-methylpiperazin-1-yl)acetamide (148)

148

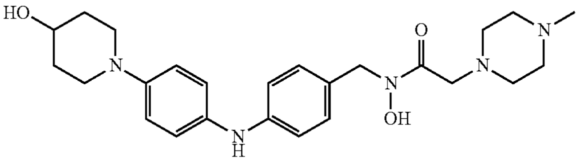

The title compound 148 (2.9 mg) was prepared in a total yield of 16.0% as a white solid according to the procedure for compound 108. $^{1}$H NMR (400 MHz, Methanol-$d_4$) δ 7.51-6.54 (m, 8H), 4.62 (s, 2H), 3.91 (m, 1H), 3.56 (s, 2H), 3.35 (br s, 8H), 3.28-3.21 (m, 2H), 2.99-2.86 (m, 2H), 2.83 (s, 3H), 2.04-1.99 (m, 2H), 1.79-1.68 (m, 2H). Mass (m/z): 454.3 $[M+H]^+$.

N-(4-((4-(6-fluoropyridin-3-yl)phenyl)amino)benzyl)-N-hydroxy-1-methylpiperidine-4-carboxamide (149)

149

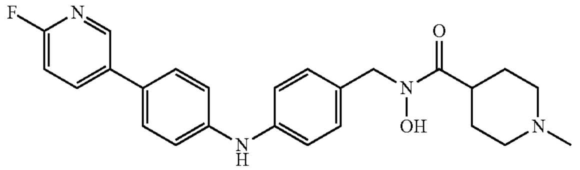

The title compound 149 (5.3 mg) was prepared in a total yield of 24.4% as a white solid according to the procedure for compound 108. $^{1}$H NMR (400 MHz, Methanol-$d_4$) δ 8.38 (d, J=2.8 Hz, 1H), 8.14 (ddd, J=8.3, 7.6, 2.8 Hz, 1H), 7.54-7.47 (m, 2H), 7.27-7.07 (m, 7H), 4.70 (s, 2H), 3.57-3.48 (m, 2H), 3.29-3.20 (m, 1H), 3.17-3.04 (m, 2H), 2.86 (s, 3H), 2.18-1.85 (m, 4H). Mass (m/z): 435.3 $[M+H]^+$ N-hydroxy-2-(4-methylpiperazin-1-yl)-N-(4-((4-pentylphenyl)amino)benzyl) acetamide (150)

150

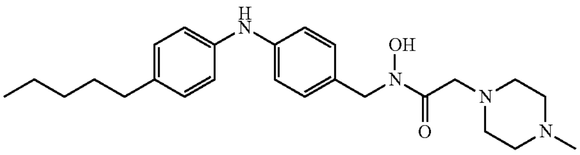

The title compound 150 (20.0 mg) was prepared in a total yield of 23.8% as a white solid form 4-((hydroxyamino)methyl)-N-(4-pentylphenyl)aniline (56.8 mg, 0.2 mmol), 2-(4-methylpiperazin-1-yl)acetic acid (31.6 mg, 0.2 mmol), DMT-MM (60.0 mg, 0.22 mmol), DIEA (76.0 mg, 0.6 mmol) and DMF (1.5 mL) according to the procedure for 137. 1H NMR (400 MHz, Methanol-$d_4$) δ 7.18-7.13 (m, 2H), 7.06-7.01 (m, 2H), 7.01-6.92 (m, 4H), 4.65 (s, 2H), 3.48 (s, 2H), 2.94-2.66 (m, 8H), 2.57-2.44 (m, 5H), 1.63-1.54 (m, 2H), 1.40-1.29 (m, 4H), 0.94-0.85 (m, 3H). Mass (m/z): 425.3 $[M+H]^+$.

N-hydroxy-2-(4-methylpiperazin-1-yl)-N-(4-((4-phenoxyphenyl)amino)benzyl) acetamide (151)

151

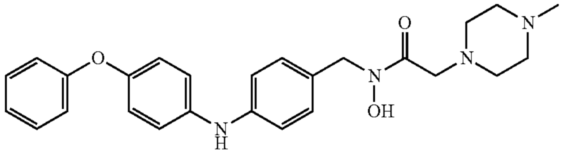

The title compound 151 (30.0 mg) was prepared in a total yield of 42.0% as a white solid form 4-((hydroxyamino)methyl)-N-(4-phenoxyphenyl)aniline (50.0 mg, 0.16 mmol), 2-(4-methylpiperazin-1-yl)acetic acid (25 mg, 0.16 mmol), DMT-MM (49.0 mg, 0.18 mmol), DIEA (62.0 mg, 0.48 mmol) and DMF (2.0 mL) according to the procedure for 137. $^1$H NMR (400 MHz, Methanol-$d_4$) δ 7.33-7.27 (m, 2H), 7.18 (d, J=8.4 Hz, 2H), 7.11-7.06 (m, 2H), 7.05-6.98 (m, 3H), 6.95-6.89 (m, 4H), 4.65 (s, 2H), 3.48 (s, 2H), 2.96-2.72 (m, 2H), 2.55 (s, 3H). Mass (m/z): 447.3 $[M+H]^+$.

N-hydroxy-2-(4-methylpiperazin-1-yl)-N-(4-((4-(pyridin-4-yl)phenyl)amino)benzyl)acetamide (152)

152

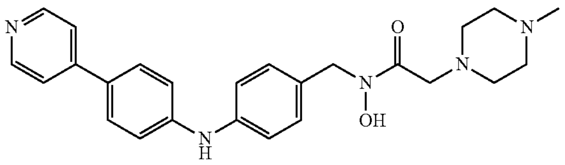

The title compound 152 (5.8 mg) was prepared in a total yield of 23.2% as a white solid according to the procedure for compound 108. $^1$H NMR (400 MHz, Methanol-$d_4$) δ 8.63 (d, J=6.8 Hz, 2H), 8.26 (d, J=72 Hz, 2H), 7.94 (d, J=8.8 Hz, 2H), 7.33 (d, J=8.4 Hz, 2H), 7.24-7.19 (m, 4H), 4.75 (s, 2H), 3.73 (s, 2H), 3.45-3.27 (m, 4H), 3.18-2.97 (m, 4H), 2.90 (s, 3H). Mass (m/z): 432.2 $[M+H]^+$ N-(4-((4-cyclohexylphenyl)amino)benzyl)-4-(dimethylamino)-N-hydroxybutanamide (153)

153

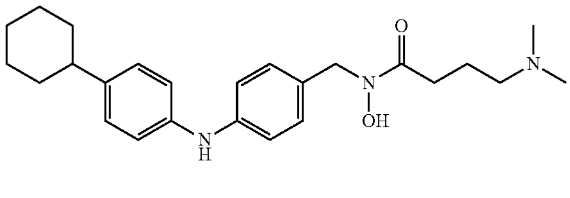

The title compound 153 (12.1 mg) was prepared in a total yield of 29.3% as a white solid according to the procedure for compound 108. $^1$H NMR (400 MHz, Methanol-$d_4$) δ 7.17 (d, J=8.4 Hz, 2H), 7.07 (d, J=8.4 Hz, 2H), 7.03-6.97 (m, 4H), 4.67 (s, 2H), 3.23-3.08 (m, 2H), 2.87 (s, 6H), 2.67 (t, J=6.8 Hz, 2H), 2.50-2.37 (m, 1H), 2.07-1.92 (m, 2H), 1.90-1.78 (m, 4H), 1.49-1.35 (m, 4H), 1.35-1.21 (m, 2H). Mass (m/z): 410.3 $[M+H]^+$ N-(4-((4-(cyclohexyloxy)phenyl)amino)benzyl)-N-hydroxy-2-(4-methylpiperazin-1-yl)acetamide (154)

154

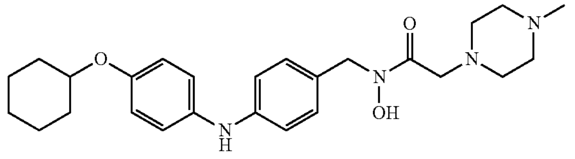

The title compound 154 (14.3 mg) was prepared in a total yield of 19.7% as a yellow solid form 4-(cyclohexyloxy)-N-(4-((hydroxyamino)methyl)phenyl)aniline (50.0 mg, 0.16 mmol), 2-(4-methylpiperazin-1-yl)acetic acid (28 mg, 0.18 mmol), DMT-MM (53 mg, 0.19 mmol), DIEA (62.0 mg, 0.48 mmol) and DMF (1 mL) according to the procedure for 137. $^1$H NMR (400 MHz, Methanol-$d_4$) δ 7.15-7.10 (m, 2H), 7.04-6.98 (m, 2H), 6.91-6.87 (m, 2H), 6.86-6.81 (m, 2H), 4.63 (s, 2H), 4.22-4.16 (m, 2H), 3.56 (s, 2H), 3.28-3.14 (m, 4H), 2.99-2.78 (m, 7H), 2.02-1.92 (m, 2H), 1.86-1.75 (m, 2H), 1.60-1.33 (m, 6H). Mass (m/z): 453.2 $[M+H]^+$.

N-(4-((4-(tert-butylamino)phenyl)amino)benzyl)-N-hydroxy-2-(4-methylpiperazin-1-yl)acetamide (155)

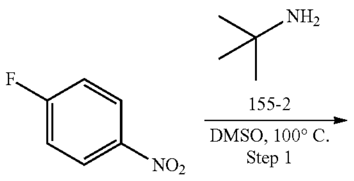

155-1

-continued

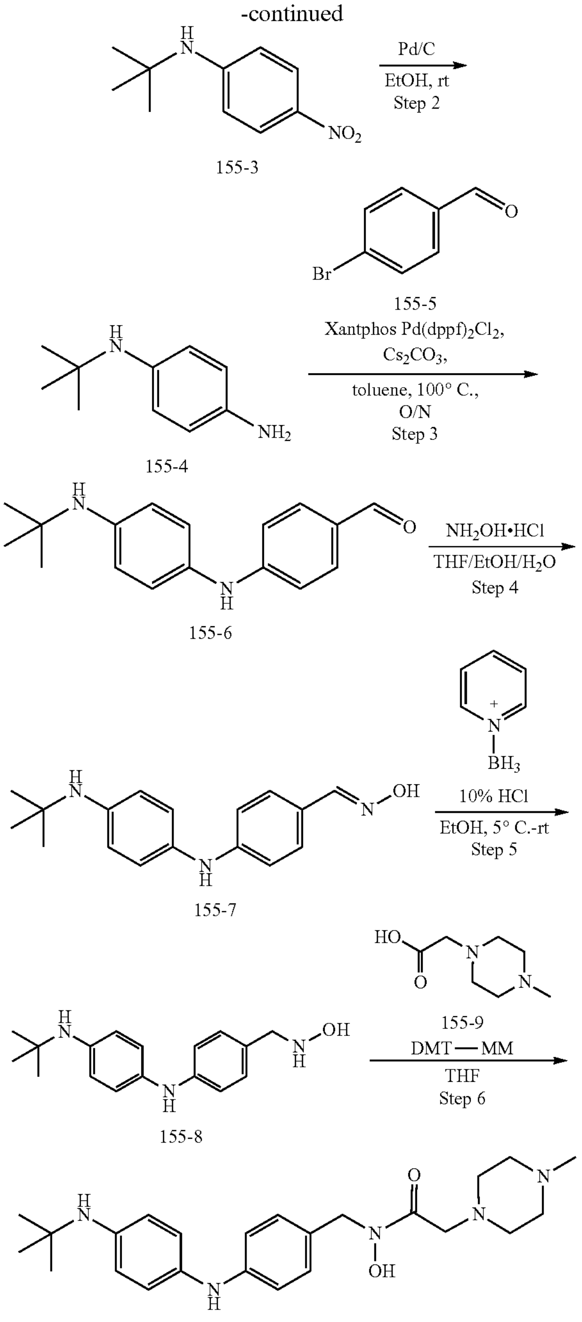

155

Step 1. Preparation of N-(tert-butyl)-4-nitroaniline (155-3) A solution of 1-fluoro-4-nitrobenzene (3 g, 21.3 mg) and 2-methylpropan-2-amine (4.66 g, 63.9 mmol) in DMSO (15 mL) was stirred for 18 hours at 80° C. After cooling to rt. 20 mL of water was added. The resulting solution was extracted with 3×50 mL of ethyl acetate. The organic layers were combined, washed with water (3×100 mL), dried and concentrated under vacuum. The residue was applied on a silica gel column and diluted with ethyl acetate/hexane (1/20-1/5) to desired product as a yellow solid (3.0 g, 72.6%). Mass (m/z): 195.2 $[M+H]^+$.

Step 2. Preparation of N1-(tert-butyl)benzene-1,4-diamine (155-4) To a solution of N-(tert-butyl)-4-nitroaniline (1.5 g, 7.7 mmol) in EtOH (100 mL) was added 10% Pd/C (81.6 mg, 0.08 ml). Then the reaction was stirred overnight at rt under an atmosphere of Hydrogen. Pd/C was filtrated out. The filtrate was concentrated under vacuum to afford the target product as a black oil. (1.11 g, 87.4%). Mass (m/z): 165.2 $[M+H]^+$.

Step 3. Preparation of 4-((4-(tert-butylamino)phenyl)amino)benzaldehyde (155-6) The title compound 155-6 (620 mg) was prepared in a total yield of 59.2% as a yellow solid from $N^1$-(tert-butyl)benzene-1,4-diamine (1.11 g, 6.0 mmol), 4-bromobenzaldehyde (740 mg, 4.0 mmol) $Pd(dppf)_2$ $Cl_2$ (59 mg, 0.08 mmol), Xantphos (93 mg, 0.16 mmol), $Cs_2CO_3$ (1.96 g, 6.0 mmol) according to the procedure for 137-3. Mass (m/z): 269.2 $[M+H]^Y$.

Step 4. Preparation of (E)-4-((4-(tert-butylamino)phenyl)amino)benzaldehyde oxime (155-7) The title compound 155-7 (425 mg) was prepared in a total yield of 100% as a crude as a yellow solid from 4-((4-(tert-butylamino)phenyl)amino)benzaldehyde (404 mg, 1.5 mmol), Hydroxylamine hydrochloride (155 mg, 2.25 mmol) according to the procedure for 137-4. Mass (m/z): 284.2$[M+H]^+$.

Step 5. Preparation of $N^1$-(tert-butyl)-$N^4$-(4-((hydroxyamino)methyl)phenyl)benzene-1,4-diamine (155-8) The title compound 155-8 (130 mg) was prepared in a total yield of 30.6% as a yellow solid from (E)-4-((4-(tert-butylamino)phenyl)amino)benzaldehyde oxime (425 mg, 1.5 mmol), Borane-pyridine complex (279 mg, 3.0 mmol) and 5 mL of 10% HCl according to the procedure for 137-5. Mass (m/z): 307.2 $[M+H]^+$.

Step 6. Preparation of N-(4-((4-(tert-butylamino)phenyl)amino)benzyl)-N-hydroxy-2-(4-methylpiperazin-1-yl)acetamide (155) The title compound 155 (20.0 mg) was prepared in a total yield of 20.0% as a yellow solid form $N^1$-(tert-butyl)-$N^4$-(4-((hydroxyamino)methyl)phenyl)benzene-1,4-diamine (69 mg, 0.24 mmol), 2-(4-methylpiperazin-1-yl)acetic acid (38 mg, 0.24 mmol), DMT-MM (73 mg, 0.26 mmol), DIEA (93 mg, 0.72 mmol) and DMF (1.0 mL) according to the procedure for 137. $^1H$ NMR (400 MHz, Methanol-$d_4$) δ 7.24-7.16 (m, 2H), 7.09-6.96 (m, 6H), 4.66 (s, 2H), 3.47 (s, 2H), 2.86-2.64 (m, 8H), 2.50 (s, 3H), 1.27 (s, 9H). Mass (m/z): 426.3 $[M+H]^+$.

N-(4-((4-(diethylamino)phenyl)amino)benzyl)-N-hydroxy-2-(4-methylpiperazin-1-yl)acetamide (156)

156

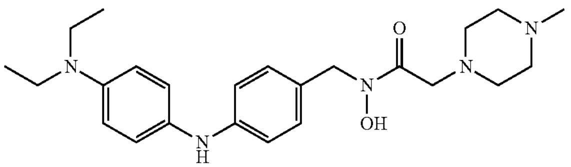

The title compound 156 (15.9 mg) was prepared in a total yield of 37.4% as a white solid according to the procedure for compound 108. $^1H$ NMR (400 MHz, Methanol-$d_4$) δ 7.34-6.58 (m, 8H), 4.64 (s, 2H), 3.40 (s, 2H), 3.35 (m, 4H), 2.81-2.44 (m, 8H), 2.33 (s, 3H), 1.10 (t, J=6.8 Hz, 6H). Mass (m/z): 426.3 $[M+H]^+$ 4-(dimethylamino)-N-hydroxy-N-(4-((4-isopropoxyphenyl)amino)benzyl)butanamide (157)

157

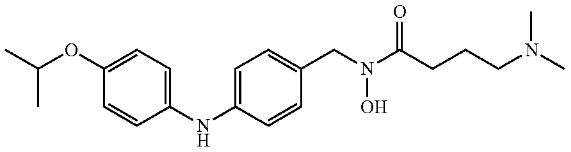

The title compound 157 (10.3 mg) was prepared in a total yield of 13.4% as a yellow solid form 4-((hydroxyamino)methyl)-N-(4-isopropoxyphenyl)aniline (54 mg, 0.2 mmol), 4-(dimethylamino)butanoic acid hydrochloride (37 mg, 0.22 mmol), DMT-MM (66 mg, 0.24 mmol), DIEA (77 mg, 0.6 mmol) and DMF (1.0 mL) according to the procedure for 137. $^1$H NMR (400 MHz, Methanol-$d_4$) δ 7.20-7.10 (m, 2H), 7.06-6.98 (m, 2H), 6.94-6.80 (m, 4H), 4.65 (s, 2H), 4.48 (p, J=6.2 Hz, 1H), 3.09-3.01 (m, 2H), 2.79 (s, 6H), 2.64 (t, J=7.0 Hz, 2H), 2.03-1.95 (m, 2H), 1.28 (d, J=6.0 Hz, 6H). Mass (m/z): 386.3 $[M+H]^+$.

4-(dimethylamino)-N-hydroxy-N-(4-((4-propoxyphenyl)amino)benzyl)butanamide (158)

158

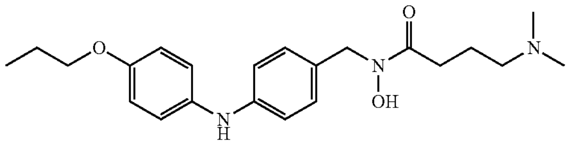

The title compound 158 (23.5 mg) was prepared in a total yield of 60.9% as a white solid according to the procedure for compound 108. $^1$H NMR (400 MHz, Methanol-$d_4$) δ 7.17 (d, J=8.4 Hz, 2H), 7.01 (d, J=8.8 Hz, 2H), 6.89 (d, J=8.4 Hz, 2H), 6.83 (d, J=8.8 Hz, 2H), 4.62 (s, 2H), 3.88 (t, J=6.4 Hz, 2H), 2.54 (t, J=7.2 Hz, 2H), 2.38 (t, J=7.2 Hz, 2H), 2.14 (s, 6H), 1.91-1.72 (m, 4H), 1.03 (t, J=7.2 Hz, 3H). Mass (m/z): 386.1 $[M+H]^+$.

N-(4-((4-(heptyloxy)phenyl)amino)benzyl)-N-hydroxy-2-(4-methylpiperazin-1-yl)acetamide (159)

159

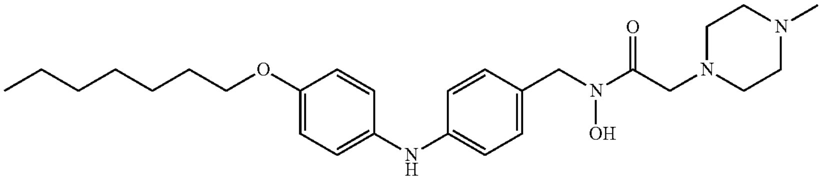

The title compound 159 (11.6 mg) was prepared in a total yield of 24.8% as a white solid according to the procedure for compound 108. $^1$H NMR (400 MHz, Methanol-$d_4$) δ 7.13 (d, J=8.4 Hz, 2H), 7.03 (d, J=8.8 Hz, 2H), 6.89 (d, J=8.4 Hz, 2H), 6.83 (d, J=8.8 Hz, 2H), 4.64 (s, 2H), 3.93 (t, J=6.4 Hz, 21H), 3.57 (s, 2H), 3.26 (br s, 4H), 2.92 (br s, 4H), 2.84 (s, 3H), 1.81-1.69 (m, 2H), 1.57-1.18 (m, 8H), 0.96-0.84 (m, 3H). Mass (m/z): 469.3 $[M+H]^+$ N-(4-((4-(2,6-dimethylmorpholino)phenyl)amino)benzyl)-N-hydroxy-2-(4-methylpiperazin-1-yl)acetamide (160)

160

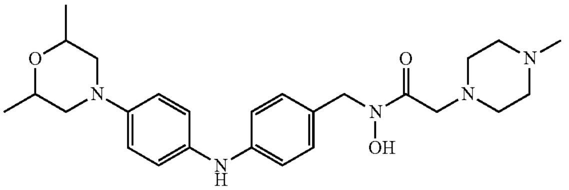

The title compound 160 (9.1 mg) was prepared in a total yield of 19.4% as a white solid according to the procedure for compound 108. $^1$H NMR (400 MHz, DMSO-$d_6$) δ 7.05 (d, J=8.0 Hz, 2H), 6.97 (d, J=8.8 Hz, 2H), 6.86 (m, 4H), 4.52 (s, 2H), 3.68 (m, 2H), 3.51-3.21 (m, 6H), 2.94-2.61 (m, 8H), 2.49 (s, 3H), 1.13 (d, J=6.4 Hz, 6H). Mass (m/z): 468.2 $[M+H]^+$.

2-(4-methylpiperazin-1-yl)-N-(4-((4-(piperidin-1-yl)phenyl)amino)benzyl)acetamide (161)

161

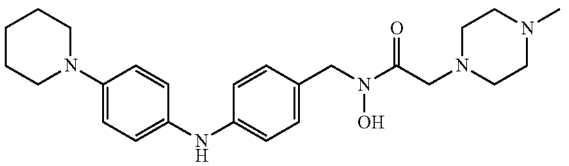

The title compound 161 (4.1 mg) was prepared in a total yield of 19.5% as a white solid according to the procedure for compound 163. $^1$H NMR (400 MHz, Methanol-$d_4$) δ 7.25-6.91 (m, 8H), 4.30 (s, 2H), 3.07 (s, 2H), 3.04 (br s, 4H), 2.59 (br s, 8H), 2.35 (s, 3H), 1.77-1.71 (m, 4H), 1.64-1.51 (m, 2H). Mass (m/z): 422.2 $[M+H]^+$.

N-hydroxy-N-(4-((4-(2-methylmorpholino)phenyl) amino)benzyl)-2-(4-methylpiperazin-1-yl)acetamide (162)

162

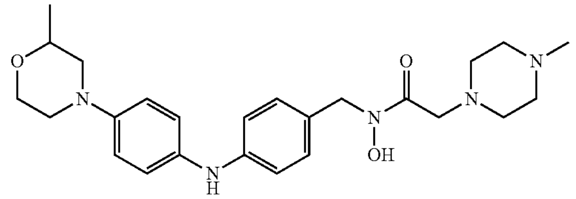

The title compound 162 (37.6 mg) was prepared in a total yield of 41.5% as a white solid according to the procedure for compound 108. $^1$H NMR (400 MHz, Methanol-$d_4$) δ 7.13 (d, J=8.0 Hz, 2H), 7.03 (d, J=8.4 Hz, 2H), 6.97-6.84 (m, 4H), 4.63 (s, 2H), 3.93 (m, 1H), 3.82-3.66 (m, 2H), 3.47 (s, 2H), 3.39-3.28 (m, 4H), 2.80 (br m, 8H), 2.53 (s, 3H), 1.19 (d, J=6.4 Hz, 3H). Mass (m/z): 454.1 $[M+H]^+$ 2-(4-methylpiperazin-1-yl)-N-(4-((4-pentylphenyl) amino)benzyl)acetamide (163)

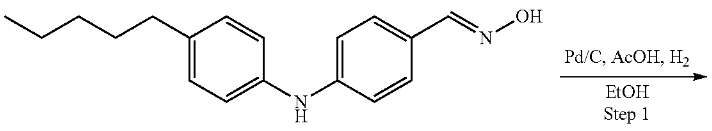

150-4

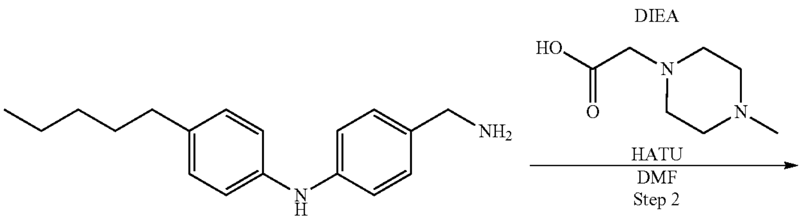

163-1

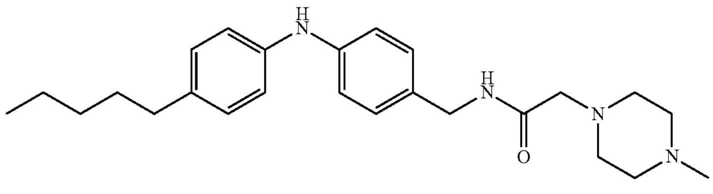

163

Step 1. Preparation of 4-(aminomethyl)-N-(4-pentylphenyl)aniline (163-1): To a solution of (E)-4-((4-pentylphenyl) amino)benzaldehyde oxime (423 mg, 1.5 mmol) in EtOH (20 mL) was added 10% Pd/C (16 mg, 0.015 ml) and AcOH (0.5 mL). Then the reaction was stirred overnight at rt under an atmosphere of Hydrogen. Pd/C was filtrated out. The PH of the filtration was adjusted to 8-9 with sodium carbonate solution. Then the mixture was extracted by DCM (20 mL×3). The combined organic layers were washed with brine (20 mL×3), dried over $Na_2SO_4$ and concentrated to give the desired product as yellow solid. (190 mg, 47.3%). 252.3 $[M-NH2]^+$.

Step 2. Preparation of 2-(4-methylpiperazin-1-yl)-N-(4-((4-pentylphenyl)amino)benzyl)acetamide (163) To a solution of 4-(aminomethyl)-N-(4-pentylphenyl)aniline (53.4 mg, 0.2 mmol) and 2-(4-methylpiperazin-1-yl)acetic acid (34.8 mg, 0.22 mmol) in DMF (1 ml) was added DIEA (77.4 mg, 0.6 mmol). Followed by the addition of HATU (83.6 mg, 0.22 mmol) then the reaction mixture was stirred for 2 hours at rt. 10 mL of water was added. Then the mixture was extracted by DCM (10 mL×3). The combined organic layers were washed with water (10 mL×3), dried over $Na_2SO_4$ and concentrated under vacuum. The residue was purified by prep-TLC (MeOH/DCM=1/10) to give the desired product as white solid (38.1 mg, 46.7%). $^1$H NMR (400 MHz, Methanol-$d_4$) δ 7.14-7.11 (m, 2H), 7.05-7.01 (m, 2H), 7.00-6.95 (m, 4H), 4.31 (s, 2H), 3.11 (s, 2H), 2.91-2.77 (m, 4H), 2.73-2.59 (m, 4H), 2.55-2.50 (m, 5H), 1.63-1.55 (m, 2H), 1.38-1.28 (m, 4H), 0.90 (t, J=7.0 Hz, 3H). Mass (m/z): 409.4 $[M+H]^+$.

N-hydroxy-2-(4-methylpiperazin-1-yl)-N-(1-(4-((4-(piperidin-1-yl)phenyl)amino)phenyl)ethyl)acetamide (164)

164

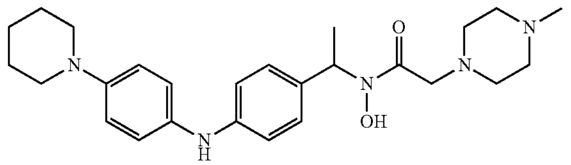

The title compound 164 (6.4 mg) was prepared in a total yield of 8.8% as a yellow solid form 4-(1-(hydroxyamino)ethyl)-N-(4-(piperidin-1-yl)phenyl)aniline (50 mg, 0.16 mmol), 4-(dimethylamino)butanoic acid hydrochloride (25 mg, 0.16 mmol). DMT-MM (44 mg, 0.16 mmol), DIEA (62 mg, 0.48 mmol) and DMF (1.0 mL) according to the procedure for 137. $^1$H NMR (400 MHz, Methanol-$d_4$) δ 8.25-5.75 (m, 8H), 4.64-4.52 (m, 1H), 3.52 (s, 2H), 3.29-3.09 (m, 6H), 3.01-2.75 (m, 9H), 1.99-1.56 (m, 6H), 1.52 (d, J=7.0 Hz, 3H). Mass (m/z): 226.7 [M/2+H]J.

N-(4-((4-(2-oxa-6-azaspiro[3.3]heptan-6-yl)phenyl)amino)benzyl)-4-(dimethylamino)-N-hydroxybutanamide (165)

165

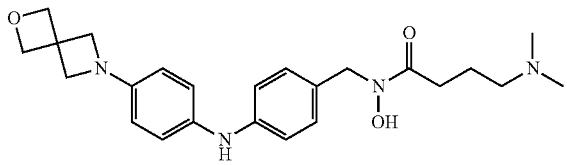

The title compound 165 (15.1 mg) was prepared in a total yield of 52.3% as a white solid according to the procedure for compound 108. $^1$H NMR (400 MHz, Methanol-$d_4$) δ 7.15 (d, J=8.4 Hz, 2H), 6.98 (d, J=8.4 Hz, 2H), 6.84 (d, J=8.8 Hz, 2H), 6.49 (d, J=8.8 Hz, 2H), 4.83 (s, 4H), 4.61 (s, 2H), 3.95 (s, 4H), 2.53 (t, J=6.8 Hz, 2H), 2.32 (t, J=6.8 Hz, 2H), 2.08 (s, 6H), 1.87 (p, J=6.8 Hz, 2H). Mass (m/z): 425.3 $[M+H]^+$ N-hydroxy-4-(4-methylpiperazin-1-yl)-N-(4-((4-(piperidin-1-yl)phenyl)amino)benzyl)butanamide (166)

166

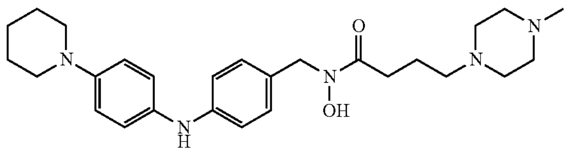

The title compound 166 (7.4 mg) was prepared in a total yield of 31.8% as a white solid according to the procedure for compound 108. $^1$H NMR (400 MHz, Methanol-$d_4$) δ 7.19 (d, J=8.0 Hz, 2H), 7.07-6.86 (m, 6H), 4.63 (s, 2H), 3.21-2.88 (m, 4H), 2.75-2.01 (m, 15H), 1.95-1.85 (m, 2H), 1.81-1.69 (m, 4H), 1.63-1.54 (m, 2H). Mass (m/z): 466.2 $[M+H]^+$ 2-(dimethylamino)-N-hydroxy-N-(4-((4-(piperidin-1-yl)phenyl)amino)benzyl)acetamide (167)

167

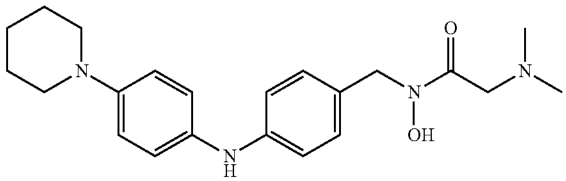

The title compound 167 (11.1 mg) was prepared in a total yield of 58.1% as a white solid according to the procedure for compound 108. $^1$H NMR (400 MHz, Methanol-$d_4$) δ 7.15 (d, J=8.0 Hz, 2H), 7.02-6.74 (m, 6H), 4.67 (s, 2H), 3.94 (s, 2H), 3.05 (br s, 4H), 2.75 (s, 6H), 1.77-1.72 (m, 4H), 1.63-1.54 (m, 2H). Mass (m/z): 383.2 $[M+H]^+$ N-(4-((4-(4,4-difluoropiperidin-1-yl)phenyl)amino)benzyl)-N-hydroxy-2-(4-methylpiperazin-1-yl)acetamide

168

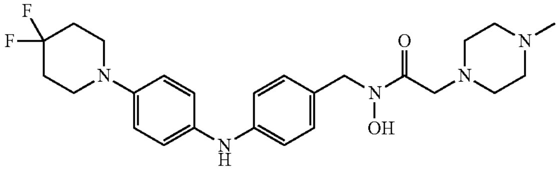

The title compound 168 (15.0 mg) was prepared in a total yield of 35.5% as a white solid from 4-(4,4-difluoropiperidin-1-yl)-N-(4-((hydroxyamino)methyl)phenyl)aniline (30 mg, 0.090 mmol) and 2-(4-methylpiperazin-1-yl)acetic acid (18 mg, 0.117 mmol) according to the procedure for 174. 1H NMR (400 MHz, Methanol-$d_4$) δ $^1$H NMR (400 MHz, Methanol-$d_4$) δ 7.13 (d, J=8.0 Hz, 2H), 7.02 (d, J=8.4 Hz, 2H), 6.93 (t, J=10.0 Hz, 4H), 4.63 (s, 2H), 3.47 (s, 2H), 3.22 (s, 4H), 2.80 (d, J=36.8 Hz, 8H), 2.53 (s, 3H), 2.08 (tt, J=13.6, 5.7 Hz, 5H). Mass (m/z): 574.3 $[M+H]^+$.

N-hydroxy-2-(1-methylpiperidin-4-yl)-N-(4-((4-(piperidin-1-yl)phenyl)amino)benzyl)acetamide (169)

169

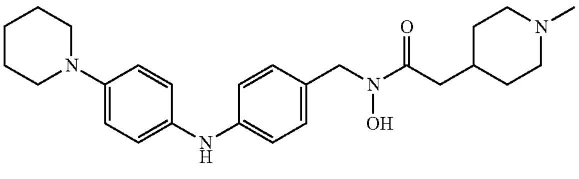

The title compound 169 (12.0 mg) was prepared in a total yield of 55.0% as a white solid according to the procedure for compound 108. $^1$H NMR (400 MHz, Methanol-$d_4$) δ 7.31-6.77 (m, 8H), 4.63 (s, 2H), 3.56-3.39 (m, 4H), 3.11-2.93 (m, 4H), 2.84 (s, 3H), 2.52 (d, J=6.8 Hz, 2H), 2.11 (br s, 1H), 1.99-1.55 (m, 10H). Mass (m/z): 437.2 $[M+H]^+$ N-(4-((4-butoxyphenyl)amino)benzyl)-N-hydroxy-2-(4-methylpiperazin-1-yl)acetamide (170)

170

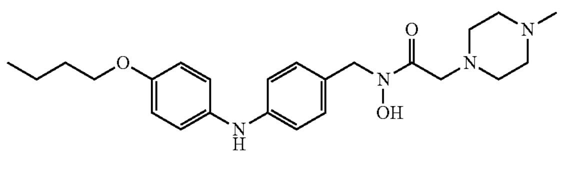

$^1$H NMR (400 MHz, Methanol-$d_4$) δ 7.13 (d, J=8.4 Hz, 2H), 7.03 (d, J=8.8 Hz, 2H), 6.93-6.79 (m, 4H), 4.64 (s, 2H), 3.94 (t, J=6.4 Hz, 2H), 3.57 (s, 2H), 3.24 (br s, 4H), 2.90 (br s, 4H), 2.83 (s, 3H), 1.82-1.66 (m, 2H), 1.57-1.42 (m, 2H), 0.99 (t, J=7.2 Hz, 3H). Mass (m/z): 427.3 $[M+H]^+$.

N-hydroxy-N-(4-((4-(piperidin-1-yl)phenyl)amino)benzyl)quinuclidine-4-carboxamide (171)

171

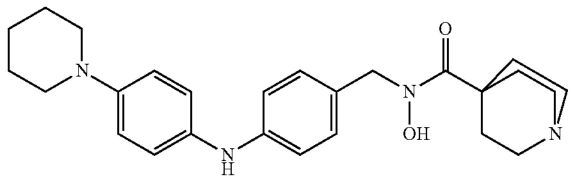

The title compound 171 (15.4 mg) was prepared in a total yield of 25.2% as a white solid according to the procedure for compound 108. $^1$H NMR (400 MHz, Methanol-$d_4$) δ 7.37-6.73 (m, 8H), 4.64 (s, 2H), 3.49-3.34 (m, 6H), 3.26-3.07 (m, 4H), 2.37-2.25 (m, 6H), 2.04-1.51 (m, 6H). Mass (m/z): 435.3 $[M+H]^+$ N-hydroxy-1-methyl-5-oxo-N-(4-((4-(piperidin-1-yl)phenyl)amino)-2-(trifluoromethyl)benzyl)pyrrolidine-3-carboxamide (172)

172

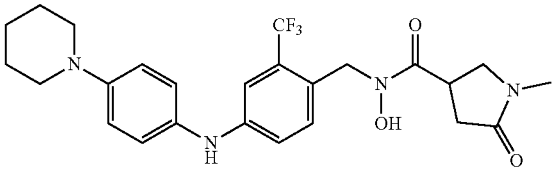

To a solution of 4-((hydroxyamino)methyl)-N-(4-(piperidin-1-yl)phenyl)-3-(trifluoromethyl)aniline (36.5 mg, 0.1 mmol), 1-methyl-5-oxopyrrolidine-3-carboxylic acid (21.6 mg, 0.15 mmol) and DIEA (38.7 mg, 0.3 mmol) in DMF (1 ml) was added DMT-MM (33.1 mg, 0.12 mmol) then the reaction mixture was stirred for 3 hours at rt. 5 ml of water was added. Then the mixture was extracted by DCM (5 mL×3). The combined organic layers were washed with water (10 mL×3), dried over $Na_2SO_4$ and concentrated under vacuum. The residue was purified by prep-TLC (MeOH/DCM=1/10) to give the desired product as yellow solid (16.4 mg, 33.5%). $^1$H NMR (400 MHz, Methanol-$d_4$) δ 7.25-7.18 (m, 2H), 7.13-6.99 (m, 5H), 4.86 (s, 2H), 3.86-3.78 (m, 1H), 3.70 (t, J=9.6 Hz, 1H), 3.62-3.55 (m, 1H), 3.14-3.06 (m, 4H), 2.84 (s, 3H), 2.66 (t, J=7.7 Hz, 2H), 1.79-1.71 (m, 4H), 1.62-1.55 (m, 2H). Mass (m/z): 491.3 $[M+H]^+$ 5-(dimethylamino)-N-hydroxy-N-(4-((4-(piperidin-1-yl)phenyl)amino)benzyl)pentanamide (173)

173

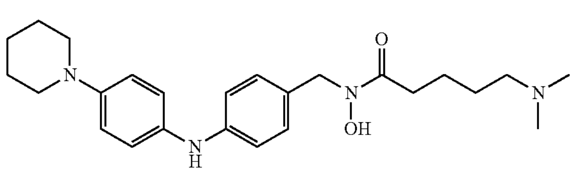

The title compound 173 (21.1 mg) was prepared in a total yield of 51.2% as a white solid according to the procedure for compound 108. $^1$H NMR (400 MHz, Methanol-$d_4$) δ 7.37-6.65 (m, 8H), 4.67 (s, 2H), 3.19-3.03 (m, 4H), 2.87 (m, 2H), 2.84 (s, 6H), 2.70-2.50 (m, 2H), 1.90-1.42 (m, 10H). Mass (m/z): 425.2 $[M+H]^+$ N-hydroxy-2-(4-methylpiperazin-1-yl)-N-(4-((4-(4-methylpiperidin-1-yl)phenyl)amino)benzyl)acetamide (174)

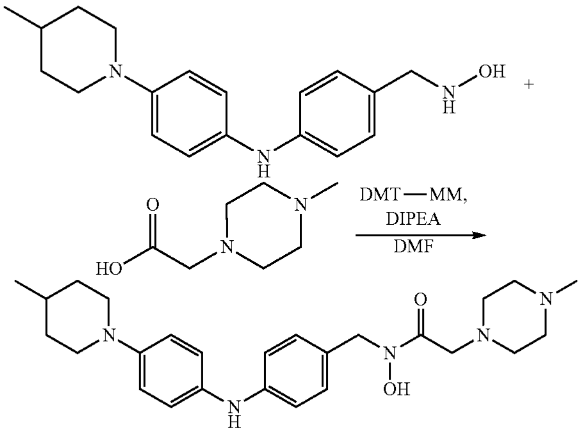

174

To a solution of 4-((hydroxyamino)methyl)-N-(4-(4-methylpiperidin-1-yl)phenyl)aniline (30 mg, 0.096 mmol) and 2-(4-methylpiperazin-1-yl)acetic acid (20 mg, 0.125 mmol) in DMF (3 mL) was added DMT-MM (37 mg, 0.125 mmol) and DIPEA (16 mg, 0.125 mmol), then the mixture was stirred at room temperature for 2 h. The mixture was extracted by EA (25 mL×3). The combined organic layers were washed with brine (15 mL×3), dried over Na2SO4 and concentrated to give the crude product, which was purified by TLC (MeOH/DCM=1:8) to give the desired product as white solid (13.2 mg, 30.0%). $^1$H NMR (400 MHz, Methanol-$d_4$) δ 7.20-6.81 (m, 8H), 4.64 (s, 2H), 3.46 (s, 2H), 2.80 (d, J=36.0 Hz, 9H), 2.52 (s, 3H), 1.76 (s, 2H), 1.55-1.26 (m, 5H), 0.99 (d, J=6.4 Hz, 3H). Mass (m/z): 452.3 [M+H]$^+$.

N-hydroxy-2-(4-methylpiperazin-1-yl)-N-(4-((4-(4-(trifluoromethyl)piperidin-1-yl)phenyl)amino)benzyl)acetamide (175)

175

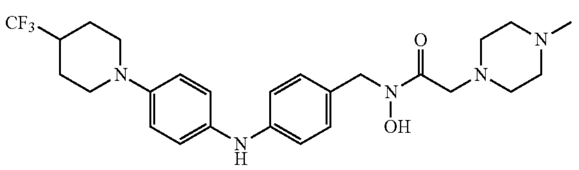

The title compound 175 (16.3 mg) was prepared in a total yield of 39.2% as a white solid from 4-((hydroxyamino)methyl)-N-(4-(4-(trifluoromethyl)piperidin-1-yl)phenyl)aniline (30 mg, 0.082 mmol) and 2-(4-methylpiperazin-1-yl)acetic acid (17 mg, 0.107 mmol) according to the procedure for 174. $^1$H NMR (400 MHz, Methanol-$d_4$) δ 7.43-6.70 (m, 8H), 4.65 (s, 2H), 3.58-3.50 (m, 2H), 3.28-3.12 (m, 4H), 2.96-2.83 (m, 3H), 2.80 (d, J=2.0 Hz, 3H), 2.35-2.14 (m, 2H), 2.01 (s, 2H), 1.72 (s, 3H). Mass (m/z): 506.3 [M+H]$^+$.

2-(4-methylpiperazin-1-yl)-N-(2,2,2-trifluoro-1-(4-((4-(piperidin-1-yl)phenyl)amino)phenyl)ethyl)acetamide (176)

176

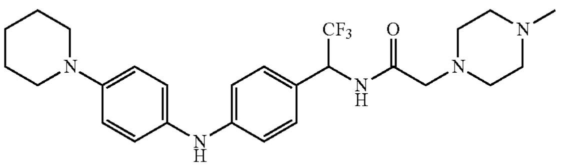

The title compound 176 (8.0 mg) was prepared in a total yield of 23.5% as a yellow solid from 4-(1-amino-2,2,2-trifluoroethyl)-N-(4-(piperidin-1-yl)phenyl)aniline (25 mg, 0.07 mmol), 2-(4-methylpiperazin-1-yl)acetic acid (12.5 mg, 0.08 mmol), DIEA (27 mg, 0.21 mmol) and HATU (30.4 mg, 0.08 mmol) according to the procedure for 163. 1H NMR (400 MHz, Methanol-$d_4$) δ 7.31-7.20 (m, 2H), 7.15-6.88 (m, 6H), 5.63-5.54 (m, 1H), 3.34 (s, 2H), 3.23-3.05 (m, 8H), 2.87-2.70 (m, 7H), 1.81-1.72 (m, 4H), 1.64-1.56 (m, 2H). Mass (m/z): 490.3 [M+H]$^+$.

N-hydroxy-2-(4-methylpiperazin-1-yl)-N-(4-((4-(3-methylpiperidin-1-yl)phenyl)amino)benzyl)acetamide (177)

177

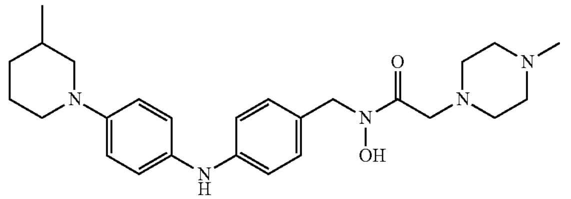

The title compound 177 (28.3 mg) was prepared in a total yield of 61.9% as a white solid according to the procedure for compound 108. $^1$H NMR (400 MHz, Methanol-$d_4$) δ 7.26-6.77 (m, 8H), 4.64 (s, 2H), 3.54-3.39 (m, 6H), 2.78 (br s, 8H), 2.49 (s, 3H), 1.88-1.54 (m, 5H), 0.96 (d, J=6.8 Hz, 3H). Mass (m/z): 452.4 [M+H]$^+$.

N-hydroxy-2-(4-methylpiperazin-1-yl)-N-(4-((4-(2-methylpiperidin-1-yl)phenyl)amino)benzyl)acetamide (178)

178

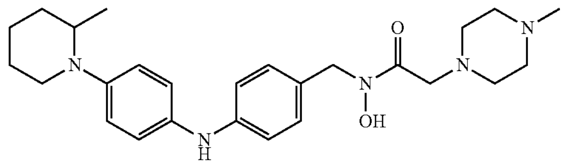

The title compound 178 (34.2 mg) was prepared in a total yield of 75.7% as a white solid according to the procedure for compound 108. $^1$H NMR (400 MHz, Methanol-$d_4$) δ 7.12 (d, J=8.0 Hz, 2H), 7.04-6.89 (m, 6H), 4.61 (s, 2H), 3.38 (s, 2H), 3.06-2.80 (m, 3H), 2.60 (br s, 8H), 2.30 (s, 3H), 1.88-1.42 (m, 6H), 0.86 (d, J=6.4 Hz, 3H). Mass (m/z): 452.4 [M+H]$^+$ 2-(4-methyl-3-oxopiperazin-1-yl)-N-(4-((4-(piperidin-1-yl)-3-(trifluoromethyl)phenyl)amino)benzyl)acetamide (179)

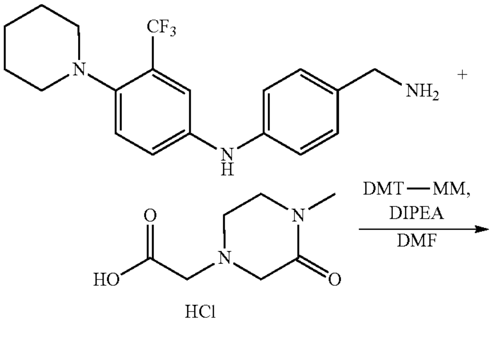

-continued

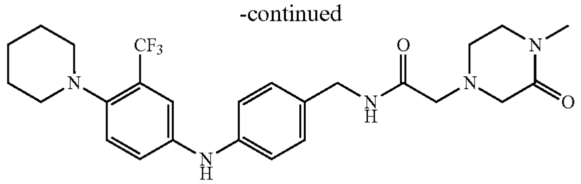

179

To a solution of N-(4-(aminomethyl)phenyl)-4-(piperidin-1-yl)-3-(trifluoromethyl)aniline (30 mg, 0.086 mmol) and 2-(4-methyl-3-oxopiperazin-1-yl)acetic acid hydrochloride (20 mg, 0.112 mmol) in DMF (3 mL) was added DMT-MM (33 mg, 0.112 mmol) and DIPEA (15 mg, 0.112 mmol), then the mixture was stirred at mom temperature for 2 h. The mixture was extracted by EA (25 mL×3). The combined organic layers were washed with brine (15 mL×3), dried over Na2SO4 and concentrated to give the crude product, which was purified by TLC (MeOH/DCM=1:10) to give the desired product as white solid (41.2 mg, 89.1%). $^1$H NMR (400 MHz, Methanol-$d_4$) δ 7.30 (d, J=8.5 Hz, 1H), 7.25-7.16 (m, 4H), 7.04-6.99 (m, 2H), 4.33 (s, 2H), 3.38 (dd, J=6.3, 4.7 Hz, 2H), 3.19 (s, 2H), 3.15 (s, 2H), 2.92 (s, 3H), 2.77 (q, J=5.4 Hz, 6H), 1.65 (p, J=5.6 Hz, 4H), 1.58-1.49 (m, 2H). Mass (m/z): 504.3 [M+H]$^+$.

N-(4-((4-(azocan-1-yl)phenyl)amino)benzyl)-N-hydroxy-2-(4-methylpiperazin-1-yl)acetamide (180)

180

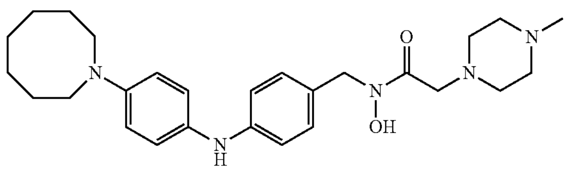

The title compound 180 (16.1 mg) was prepared in a total yield of 34.6% as a white solid according to the procedure for compound 108. $^1$H NMR (400 MHz, Methanol-$d_4$) δ 7.35-6.49 (m, 8H), 4.62 (s, 2H), 3.47 (s, 2H), 3.25-3.17 (m, 4H), 2.95 (br s, 4H), 2.78 (br s, 4H), 2.60 (s, 3H), 1.81-1.66 (m, 4H), 1.64-1.49 (m, 6H). Mass (m/z): 466.2 [M+H]$^+$ N-(4-((4-(azetidin-1-yl)phenyl)amino)benzyl)-N-hydroxy-2-(4-methylpiperazin-1-yl)acetamide (181)

181

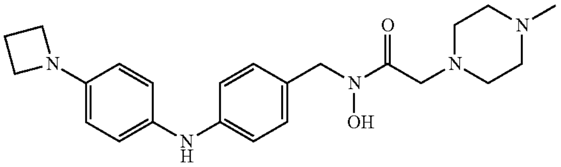

The title compound 181 (9.1 mg) was prepared in a total yield of 20.0% as a yellow solid form 4-(azetidin-1-yl)-N-(4-((hydroxyamino)methyl)phenyl)aniline (26.9 mg, 0.1 mmol), 4-(dimethylamino)butanoic acid hydrochloride (15.8 mg, 0.1 mmol), DMT-MM (26.7 mg, 0.1 mmol), DIEA (38.7 mg, 0.3 mmol) and DMF (1.0 mL) according to the procedure for 137. $^1$H NMR (400 MHz, Methanol-$d_4$) δ 6.99-6.94 (m, 8H), 4.63 (s, 2H), 3.54 (s, 2H), 3.28-3.01 (m, 6H), 2.99-2.61 (m, 7H), 2.38-2.27 (m, 2H). Mass (m/z): 410.3 [M+H]$^+$.

N-(4-((4-(4-fluoropiperidin-1-yl)phenyl)amino)benzyl)-N-hydroxy-2-(4-methylpiperazin-1-yl)acetamide (182)

182

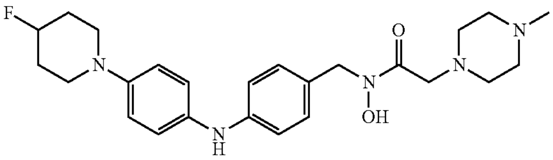

To a solution of 4-(4-fluoropiperidin-1-yl)-N-(4-((hydroxyamino)methyl)phenyl)aniline (30 mg, 0.095 mmol) and 2-(4-methylpiperazin-1-yl)acetic acid (20 mg, 0.124 mmol) in DMF (3 mL) was added DMT-MM (37 mg, 0.125 mmol) and DIPEA (16 mg, 0.125 mmol), then the mixture was stirred at room temperature for 2 h. The mixture was extracted by EA (25 mL×3). The combined organic layers were washed with brine (15 mL×3), dried over Na2SO4 and concentrated to give the crude product, which was purified by TLC (MeOH/DCM=1:8) to give the desired product as white solid (8.1 mg, 29%). 1H NMR (400 MHz, Methanol-$d_4$) δ 7.14 (d, J=8.0 Hz, 2H), 6.98 (d, J=34.2 Hz, 6H), 4.64 (s, 2H), 3.51-3.45 (m, 2H), 3.29-3.19 (m, 2H), 3.06 (d, J=8.6 Hz, 2H), 2.83 (d, J=45.6 Hz, 10H), 2.55 (s, 3H), 2.12-1.87 (m, 6H). Mass (m/z): 456.3 [M+H]$^+$.

N-hydroxy-2-(4-methylpiperazin-1-yl)-N-(4-((4-(3-(trifluoromethyl)pyrrolidin-1-yl)phenyl)amino)benzyl)acetamide (183)

183

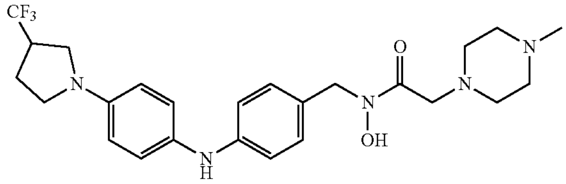

The tide compound 183 (25.1 mg) was prepared in a total yield of 60% as a white green from 4-((hydroxyamino)methyl)-N-(4-(3-(trifluoromethyl)pyrrolidin-1-yl)phenyl)aniline (30 mg, 0.086 mmol) and 2-(4-methylpiperazin-1-yl)acetic acid (18 mg, 0.111 mmol) according to the procedure for 182. $^1$H NMR (400 MHz, Methanol-$d_4$) δ 7.54-6.58 (m, 8H), 4.63 (s, 2H), 3.77-3.57 (m, 2H), 3.55-3.47 (m, 2H), 3.02 (s, 4H), 2.83 (s, 4H), 2.66 (s, 3H), 2.36-2.06 (m, 3H), 1.35-1.23 (m, 2H). Mass (m/z): 492.3 [M+H]$^+$.

N-(4-((4-(3,3-difluoropiperidin-1-yl)phenyl)amino)benzyl)-N-hydroxy-2-(4-methylpiperazin-1-yl)acetamide (184)

184

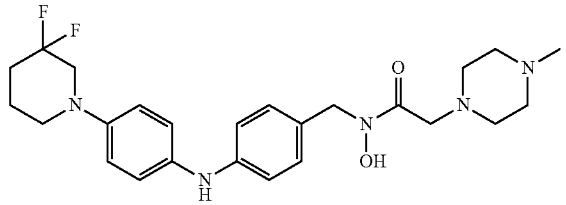

The title compound 184 (10.0 mg) was prepared in a total yield of 21.1% as a yellow solid form 4-(3,3-difluoropiperidin-1-yl)-N-(4-((hydroxyamino)methyl)phenyl)aniline (33.3 mg, 0.1 mmol), 4-(dimethylamino)butanoic acid hydrochloride (15.8 mg, 0.1 mmol), DMT-MM (26.7 mg, 0.1 mmol), DIEA (38.7 mg, 0.3 mmol) and DMF (1.0 mL) according to the procedure for 137. $^{1}$H NMR (400 MHz, Methanol-$d_4$) δ 7.16-7.11 (m, 2H), 7.06-6.94 (m, 2H), 6.98-6.89 (m, 4H), 4.64 (s, 2H), 3.54 (s, 2H), 3.25 (t, J=11.4 Hz, 2H), 2.03-1.95 (m, 6H), 2.92-2.80 (m, 4H), 2.74 (s, 3H), 2.03-1.95 (m, 2H), 1.92-1.83 (m, 2H). Mass (m/z): 237.7 $[M/2+H]^+$.

N-hydroxy-1-isopropyl-N-(4-((4-(piperidin-1-yl)phenyl)amino)benzyl)piperidine-4-carboxamide (185)

185

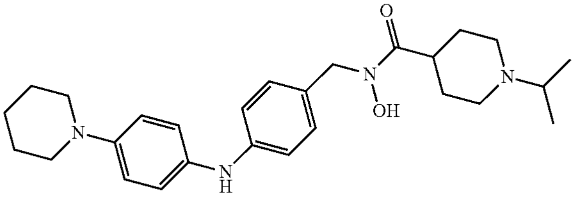

The title compound 185 (12.3 mg) was prepared in a total yield of 40.7% as a white solid according to the procedure for compound 108. $^{1}$H NMR (400 MHz, Methanol-$d_4$) δ 7.28-6.77 (m, 8H), 4.66 (s, 2H), 3.55-3.43 (m, 4H), 3.30-3.20 (m, 1H), 3.18-3.04 (m, 4H), 2.22-1.88 (m, 5H), 1.87-1.71 (m, 4H), 1.67-1.52 (m, 2H), 1.35 (d, J=6.8 Hz, 6H). Mass (m/z): 451.3 $[M+H]^+$ 1-isopropyl-N-(4-((4-(piperidin-1-yl)phenyl)amino)benzyl)piperidine-4-carboxamide (186)

186

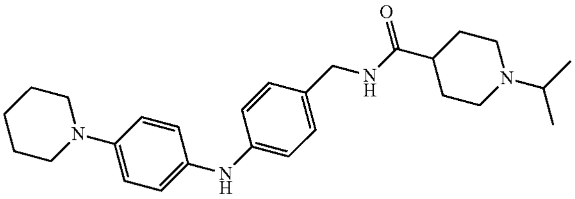

The title compound 186 (16.1 mg) was prepared in a total yield of 43.1% as a white solid according to the procedure for compound 163. $^{1}$H NMR (400 MHz, Methanol-$d_4$) δ 7.26-6.78 (m, 8H), 4.26 (s, 2H), 3.61-3.40 (m, 4H), 3.23-2.87 (m, 5H), 2.57 (m, 1H), 2.16-1.91 (m, 4H), 1.74 (br s, 4H), 1.59 (br s, 2H), 1.35 (d, J=6.8 Hz, 6H). Mass (m/z): 435.3 $[M+H]^+$ N-hydroxy-2-(4-methylpiperazin-1-yl)-N-(4-((4-(3-(trifluoromethyl)piperidin-1-yl)phenyl)amino)benzyl)acetamide (187)

187

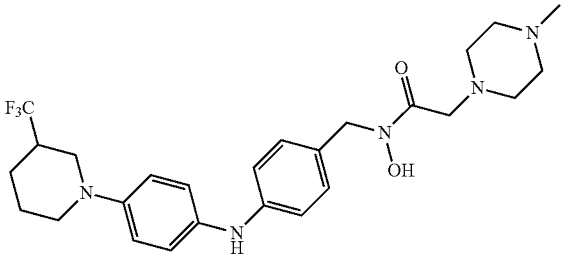

The title compound 187 (16.5 mg) was prepared in a total yield of 32.7% as a white solid according to the procedure for compound 108. $^{1}$H NMR (400 MHz, Methanol-$d_4$) δ 7.14 (d, J=8.4 Hz, 2H), 7.03 (d, J=8.4 Hz, 2H), 6.93 (d, J=8.0 Hz, 4H), 4.64 (s, 2H), 3.63 (m, 1H), 3.55-3.38 (s, 2H), 2.97-2.49 (m, 12H), 2.45 (s, 3H), 2.08-1.82 (m, 2H), 1.79-1.36 (m, 2H). Mass (m/z): 506.3 $[M+H]^+$ N-hydroxy-2-(4-methylpiperazin-1-yl)-N-(4-((4-(pyrrolidin-1-yl)-3-(trifluoromethyl)phenyl)amino)benzyl)acetamide (188)

188

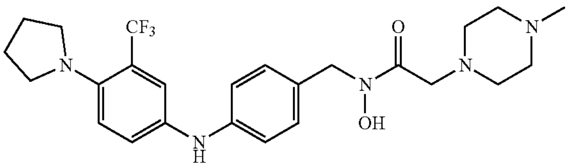

The title compound 188 (13.5 mg) was prepared in a total yield of 22.1% as a white solid according to the procedure for compound 108. $^1$H NMR (400 MHz, Methanol-$d_4$) δ 7.28-7.17 (m, 5H), 6.98 (d, J=8.4 Hz, 2H), 4.67 (s, 2H), 3.51 (s, 2H), 3.17-3.05 (m, 4H), 2.98 (br s, 4H), 2.82 (br s, 4H), 2.63 (s, 3H), 1.96-1.87 (n, 4H). Mass (m/z): 492.2 $[M+H]^+$ 1-methyl-6-oxo-N-(4-((4-(4-(trifluoromethyl)piperidin-1-yl)phenyl)amino)benzyl)piperidine-3-carboxamide (189)

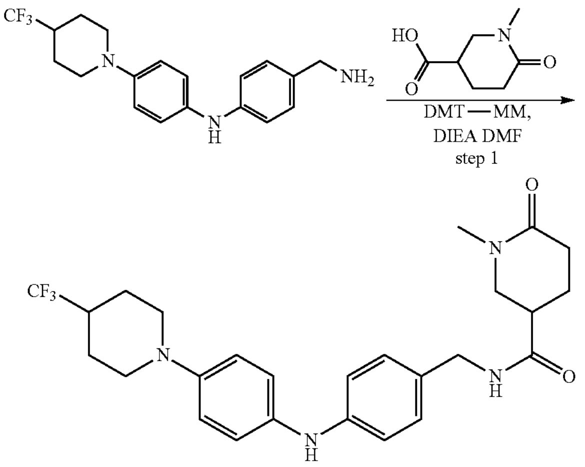

189

Step 1. The title compound 189 (18.3 mg) was prepared in a yield of 43.63% as a pale yellow powder from 4-(aminomethyl)-N-(4-(4-(trifluoromethyl)piperidin-1-yl)phenyl) aniline (30 mg, 0.09 mmol) and 1-methyl-6-oxopiperidine-3-carboxylic acid (15 mg, 0.09 mmol). $^1$H NMR (400 MHz, Methanol-$d_4$) δ 7.02 (d, J=63.1 Hz, 8H), 4.27 (s, 2H), 3.54 (dd, J=12.4, 9.7 Hz, 3H), 3.40 (ddd, J=12.4, 5.4, 1.3 Hz, 1H), 2.93 (s, 3H), 2.77 (tdd, J=9.7, 5.4, 4.3 Hz, 1H), 2.49-2.16 (m, 4H), 2.07-1.90 (m, 4H), 1.72 (d, J=13.5 Hz, 2H). LC-MS (m/z) 489.3 $[M+H]^+$.

N-hydroxy-2-(4-methylpiperazin-1-yl)-N-(4-((6-(piperidin-1-yl)pyridin-3-yl)amino)benzyl)acetamide (190)

190

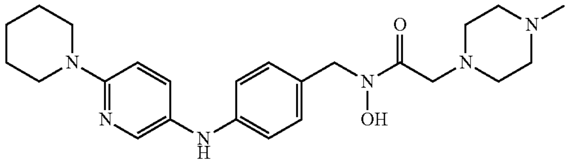

The title compound 190 (22.1 mg) was prepared in a total yield of 50.4% as a white solid according to the procedure for compound 108. $^1$H NMR (400 MHz, Methanol-$d_4$) δ 7.93 (s, 1H), 7.42 (d, J=8.8 Hz, 1H), 7.14 (d, J=8.4 Hz, 2H), 6.86-6.79 (m, 3H), 4.63 (s, 2H), 3.47 (s, 2H), 3.45-3.38 (m, 4H), 2.86 (br s, 4H), 2.76 (br s, 4H), 2.54 (s, 3H), 1.72-1.65 (m, 6H). Mass (m/z): 439.3 $[M+H]^+$ N-(4-((4-(2,6-dimethylmorpholino)phenyl)amino)benzyl)-2-(4-methylpiperazin-1-yl)acetamide (191)

191

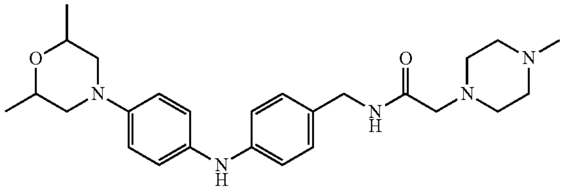

The title compound 191 (31.4 mg) was prepared in a total yield of 72.3% as a white solid according to the procedure for compound 163. $^1$H NMR (400 MHz, Methanol-$d_4$) δ 7.09 (d, J=8.4 Hz, 2H), 7.02 (d, J=8.4 Hz, 2H), 6.96-6.79 (m, 4H), 4.29 (s, 2H), 3.84-3.73 (m, 2H), 3.43-3.33 (m, 2H), 3.06 (s, 2H), 2.77-2.48 (m, 10H), 2.36 (s, 3H), 1.20 (d, J=6.4 Hz, 6H). Mass (m/z): 452.3 $[M+H]^+$ N-hydroxy-N-(4-((2-methyl-4-(piperidin-1-yl)phenyl)amino)benzyl)-2-(4-methylpiperazin-1-yl)acetamide (192)

192

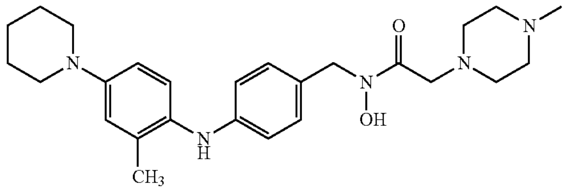

The title compound 192 (20.1 mg) was prepared in a total yield of 56.3% as a white solid according to the procedure for compound 108. $^1$H NMR (400 MHz, Methanol-$d_4$) δ 7.19-6.52 (m, 7H), 4.61 (s, 2H), 3.41 (s, 2H), 3.07 (br s, 4H), 2.63 (br s, 8H), 2.36 (s, 3H), 2.17 (s, 3H), 1.79-1.68 (m, 4H), 1.63-1.52 (m, 2H). Mass (m/z): 452.3 $[M+H]^+$ N-hydroxy-2-(4-(4-methylpiperazin-1-yl)piperidin-1-yl)-N-(4-((4-(piperidin-1-yl)phenyl)amino)benzyl) acetamide (193)

193

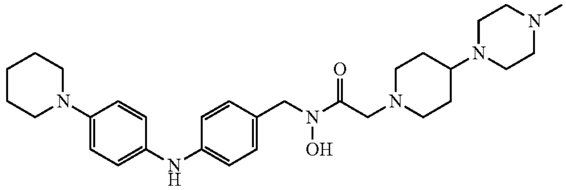

The title compound 193 (10.4 mg) was prepared in a total yield of 21.7% as a white solid according to the procedure for compound 108. $^1$H NMR (400 MHz, Methanol-$d_4$) δ 7.30-6.69 (m, 8H), 4.65 (s, 2H), 3.64 (s, 2H), 3.29-3.19 (m, 4H), 3.15-2.69 (m, 13H), 2.56 (s, 3H), 2.01-1.91 (m, 2H), 1.81-1.67 (m, 6H), 1.59 (s, 2H). Mass (m/z): 521.4 $[M+H]^+$ N-hydroxy-N-(4-((4-(piperidin-1-yl)phenyl)amino)benzyl)-2-(pyrazin-2-yl)acetamide (194)

194

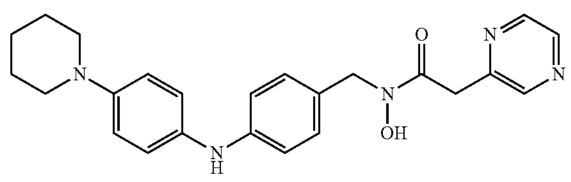

The title compound 194 (15.9 mg) was prepared in a total yield of 31.8% as a white solid according to the procedure for compound 108. $^1H$ NMR (400 MHz, Methanol-$d_4$) δ 8.58-8.53 (m, 2H), 8.48-8.46 (m, 1H), 7.48-6.78 (m, 8H), 4.73 (s, 2H), 4.09 (s, 2H), 3.29-3.19 (m, 4H), 1.80 (br s, 4H), 1.63 (br s, 2H). Mass (m/z): 418.3 [M+H]~

4-(hydroxy(4-((4-(piperidin-1-yl)phenyl)amino)benzyl)amino)-4-oxobutanoic acid (195)

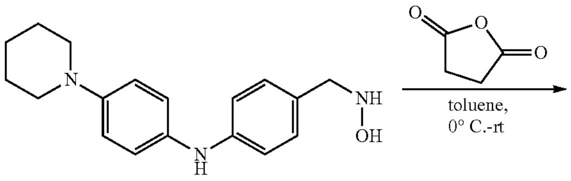

108-4

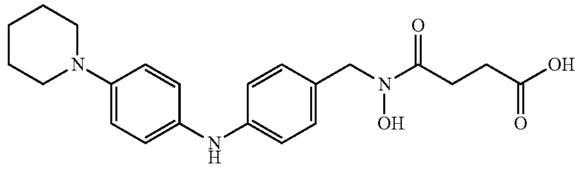

195

To a solution of 4-((hydroxyamino)methyl)-N-(4-(piperidin-1-yl)phenyl)aniline (59.4 mg, 0.2 mmol) in toluene (1 ml) was added dihydrofuran-2,5-dione (20.0 mg, 0.2 mmol) at 0° C. Then the reaction was stirred for 3 hours. After completion, the reaction solution was concentrated and purified by prep-TLC (MeOH/DCM=1/10) to give the desired product as white solid (18.2 mg, 23.1%). $^1H$ NMR (400 MHz, Methanol-$d_4$) δ 7.32-6.77 (m, 8H), 4.66 (s, 2H), 3.28-2.91 (m, 411), 2.77 (t, J=6.8 Hz, 2H), 2.58 (t, J=6.8 Hz, 2H), 1.89-1.70 (m, 4H), 1.61 (br s, 2H). Mass (m/z): 398.3 $[M+H]^+$ N-hydroxy-N-(3-methyl-4-((4-(piperidin-1-yl)phenyl)amino)benzyl)-2-(4-methylpiperazin-1-yl)acetamide (196)

196

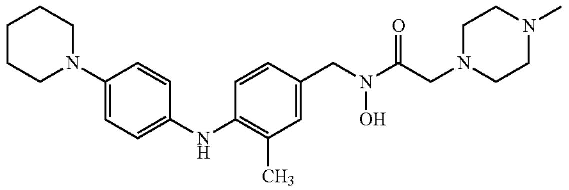

The title compound 1% (26.5 mg) was prepared in a total yield of 52.5% as a white solid according to the procedure for compound 108. $^1H$ NMR (400 MHz, Methanol-$d_4$) δ 7.15-6.85 (m, 7H), 4.63 (s, 2H), 3.40 (s, 2H), 3.00 (br s, 4H), 2.60 (br s, 8H), 2.31 (s, 3H), 2.21 (s, 3H), 1.79-1.68 (m, 4H), 1.63-1.52 (m, 2H). Mass (m/z): 452.3$[M+H]^+$ N-(3-fluoro-4-((4-(piperidin-1-yl)phenyl)amino)benzyl)-N-hydroxy-2-(4-methylpiperazin-1-yl)acetamide (197)

197

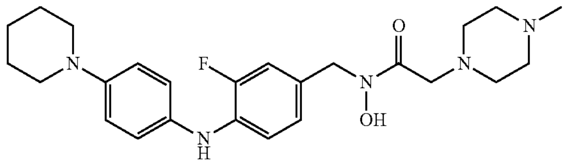

The title compound 197 (20.6 mg) was prepared in a total yield of 41.7% as a white solid according to the procedure for compound 108. $^1H$ NMR (400 MHz, Methanol-$d_4$) δ 7.12-6.88 (m, 7H), 4.65 (s, 2H), 3.47 (s, 2H), 3.13-3.02 (m, 4H), 2.77 (br s, 8H), 2.49 (s, 3H), 1.76-1.69 (m, 4H), 1.60-1.54 (m, 2H). Mass (m/z): 456.2$[M+H]^+$ N-hydroxy-N-(3-methyl-4-((2-methyl-4-(piperidin-1-yl)phenyl)amino)benzyl)-2-(4-methylpiperazin-1-yl)acetamide (198)

198

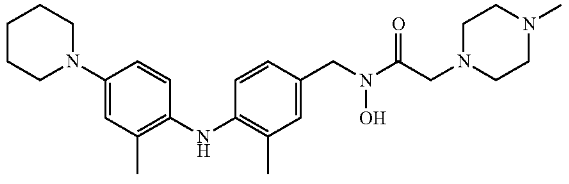

The title compound 198 (10.2 mg) was prepared in a total yield of 21.9% as a yellow solid form 4-((hydroxyamino)methyl)-2-methyl-N-(2-methyl-4-(piperidin-1-yl)phenyl)aniline (32.5 mg, 0.1 mmol), 4-(dimethylamino)butanoic acid hydrochloride (15.8 mg, 0.1 mmol), DMT-MM (26.7 mg, 0.1 mmol), DIEA (38.7 mg, 0.3 mmol) and DMF (1.0 mL) according to the procedure for 137. $^1$H NMR (400 MHz, Methanol-$d_4$) δ 7.07 (s, 1H), 6.96-6.81 (m, 4H), 6.41 (d, J=8.2 Hz, 1H), 4.62 (s, 2H), 3.52 (s, 2H), 3.14-2.99 (m, 8H), 2.90-2.76 (m, 4H), 2.69 (s, 3H), 2.22 (s, 3H), 2.15 (s, 3H), 1.78-1.69 (m, 4H), 1.62-1.54 (m, 4H). Mass (m/z): 233.7 $[M/2+H]^+$.

N-hydroxy-N-(4-((4-(piperidin-1-yl)phenyl)amino)benzyl)oxazole-4-carboxamide (199)

199

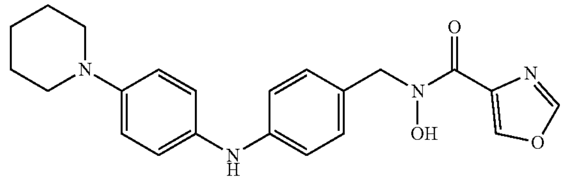

The title compound 199 (12.5 mg) was prepared in a total yield of 37.4% as a white solid according to the procedure for compound 108. $^1$H NMR (400 MHz, Methanol-$d_4$) δ 8.49 (s, 1H), 8.25 (s, 1H), 7.47-6.77 (m, 8H), 4.62 (s, 2H), 3.25-2.90 (m, 4H), 1.77 (br s, 4H), 1.60 (br s, 2H). Mass (m/z): 393.2$[M+H]^+$ 2-(3,5-dimethyl-1H-1,2,4-triazol-1-yl)-N-hydroxy-N-(4-((4-(piperidin-1-yl)phenyl)amino)benzyl)acetamide (200)

200

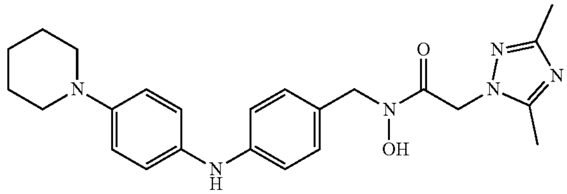

The title compound 200 (10.2 mg) was prepared in a total yield of 25.1% as a white solid according to the procedure for compound 108. $^1$H NMR (400 MHz, Methanol-$d_4$) δ 7.44-6.78 (m, 8H), 5.12 (s, 2H), 4.67 (s, 2H), 3.26-2.87 (m, 4H), 2.35 (s, 3H), 2.28 (s, 3H), 1.79 (br s, 4H), 1.62 (br s, 2H). Mass (m/z): 435.3$[M+H]^+$ N,1-diethyl-5-oxo-N-(4-((4-(4-(trifluoromethyl)piperidin-1-yl)phenyl)amino)benzyl)pyrrolidine-3-carboxamide (201)

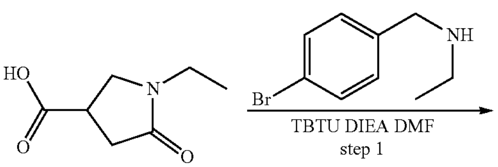

-continued

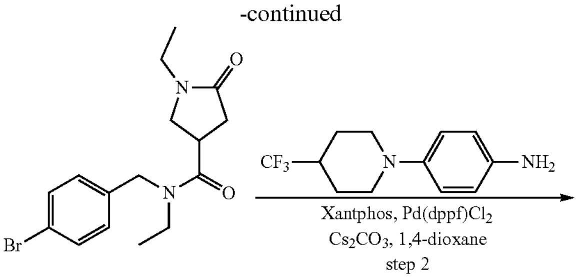

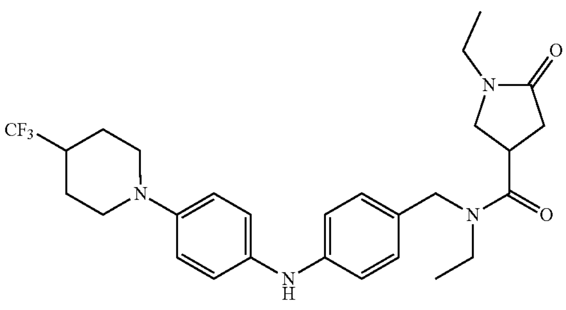

201

Step 1. The intermediate N-(4-bromobenzyl)-N,1-diethyl-5-oxopyrrolidine-3-carboxamide (467 mg) was prepared in a yield of 56.61% as a brown oil from 1-ethyl-5-oxopyrrolidine-3-carboxylic acid (367 mg, 2.34 mmol) and N-(4-bromobenzyl)ethanamine (500 mg, 2.34 mmol), according to the procedure for intermediate. LC-MS (m/z) 353.2, 355.1 $[M+H]^+$.

Step 2. The title compound 201 (5.9 mg) was prepared in a yield of 5.58% as a pale yellow powder from 4-(4-(trifluoromethyl)piperidin-1-yl)aniline (50 mg, 0.20 mmol) and N-(4-bromobenzyl)-N,1-diethyl-5-oxopyrrolidine-3-carboxamide (72 mg, 0.20 mmol). $^1$H NMR (400 MHz, Methanol-$d_4$) δ 7.67-6.72 (m, 8H), 3.81-3.51 (m, 6H), 3.51-3.34 (in, 5H), 2.77-2.44 (m, 4H), 1.30 (d, J=3.8 Hz, 2H), 1.25-1.05 (m, 9H). LC-MS (m/z) 517.6 $[M+H]^+$.

1-(4-((4-(piperidin-1-yl)phenyl)amino)benzyl)piperazin-2-one (202)

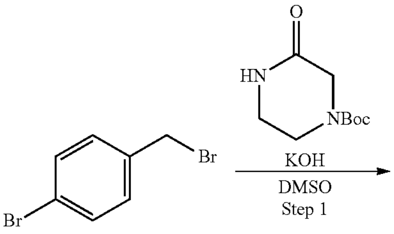

202-1

-continued

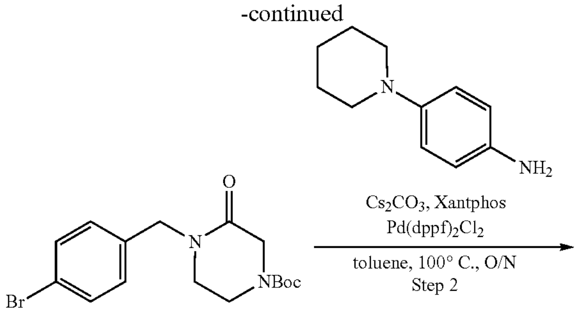

202-2

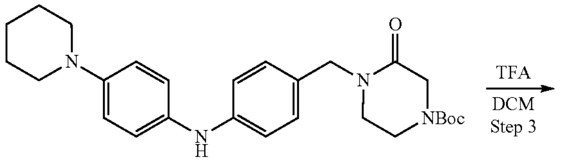

202-3

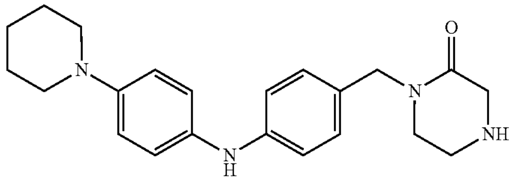

202

Step 1. Preparation of tert-butyl 4-(4-bromobenzyl)-3-oxopiperazine-1-carboxylate (202-2) To a solution of 1-bromo-4-(bromomethyl)benzene (992 mg, 4.0 mmol) and tert-butyl 3-oxopiperazine-1-carboxylate (800 mg, 4.0 mmol) in DMSO (10.0 mL) was added KOH (828 mg, 6.0 mmol). Then the mixture was stirred overnight at rt. After cooling to rt. 20 mL of water was added. The resulting solution was extracted with 3×20 mL of ethyl acetate. The organic layers were combined, washed with water (3×30 mL), dried and concentrated under vacuum to afford the desired product as a yellow oil. (500 mg, 34.0%). Mass (m/z): 313.1[M+H]$^+$.

Step 2. Preparation of tert-butyl 3-oxo-4-(4-((4-(piperidin-1-yl)phenyl)amino)benzyl)piperazine-1-carboxylate (202-3) The title compound 202-3 (173 mg) was prepared in a total yield of 27.6% as a yellow oil from 4-(piperidin-1-yl)aniline (310 mg, 1.77 mmol), tert-butyl 4-(4-bromobenzyl)-3-oxopiperazine-1-carboxylate (500 mg, 1.36 mmol), $Pd(dppf)_2Cl_2$ (20 mg, 0.03 mmol), Xantphos (32 mg, 0.05 mmol), $Cs_2CO_3$ (665 mg, 2.04 mmol) according to the procedure for 137-3. Mass (m/z): 465.4 [M+H]$^+$.

Step 3. Preparation of 1-(4-((4-(piperidin-1-yl)phenyl)amino)benzyl)piperazin-2-one (202) To a solution of tert-butyl tert-butyl 3-oxo-4-(4-((4-(piperidin-1-yl)phenyl)amino)benzyl)piperazine-1-carboxylate (162 mg, 0.35 mmol) in DCM (2 mL) was added TFA (2 mL). Then the reaction was stirred for 30 mins at rt. The reaction solution was concentrated under vacuum, 10 ml was added. The pH value of the solution was adjusted to 8 with $Na_2CO_3$. The resulting solution was extracted with 3×10 mL of ethyl DCM. The organic layers were combined, washed with water (3×10 mL), dried and concentrated under vacuum. The residue was purified by perp-TLC (MeOH/DCM=1/5) to afford the desired product as a yellow solid. (74.0 mg, 61.2%). $^1$H NMR (400 MHz, Methanol-$d_4$) δ 7.11 (d, J=8.1 Hz, 2H), 7.05-6.84 (m, 6H), 4.50 (s, 2H), 3.50 (s, 2H), 3.30-3.28 (m, 3H), 3.15-2.89 (m, 6H), 1.79-1.70 (m, 4H), 1.63-1.53 (m, 2H). Mass (m/z): 365.3[M+H]$^+$.

5-oxo-N-(4-((4-(4-(trifluoromethyl)piperidin-1-yl)phenyl)amino)benzyl) pyrrolidine-3-carboxamide (203)

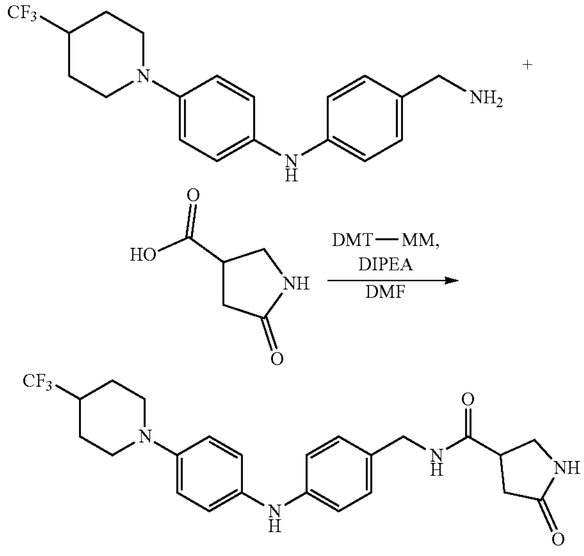

203

To a solution of 4-(aminomethyl)-N-(4-(4-(trifluoromethyl)piperidin-1-yl)phenyl)aniline (105 mg, 0.302 mmol) and 5-oxopyrrolidine-3-carboxylic acid (30 mg, 0.233 mmol) in DMF (3 mL) was added DMT-MM (89 mg, 0.302 mmol) and DIPEA (39 mg, 0.302 mmol), then the mixture was stirred at room temperature for 2 h. The mixture was extracted by EA (25 mL×3). The combined organic layers were washed with brine (15 mL×3), dried over Na2SO4 and concentrated to give the crude product, which was purified by TLC (MeOH/DCM=1:10) to give the desired product as white solid (56.7 mg, 53.0%). $^1$H NMR (400 MHz, DMSO-$d_6$) δ 8.34 (t, J=5.6 Hz, 1H), 7.76 (s, 1H), 7.56 (s, 1H), 7.04-7.00 (m, 2H), 6.97-6.92 (m, 2H), 6.90-6.84 (m, 4H), 4.13 (d, J=5.6 Hz, 2H), 3.59 (d, J=12.0 Hz, 2H), 3.25-3.10 (m, 2H), 2.60 (td, J=12.4, 2.4 Hz, 2H), 2.45-2.36 (m, 1H), 2.27 (dd, J=8.4, 5.0 Hz, 2H), 1.91-1.80 (m, 2H), 1.55 (qd, J=12.4, 4.0 Hz, 2H). Mass (m/z): 461.3 [M+H]$^+$.

1-(4-((4-(piperidin-1-yl)phenyl)amino)benzyl)pyrrolidin-2-one (204)

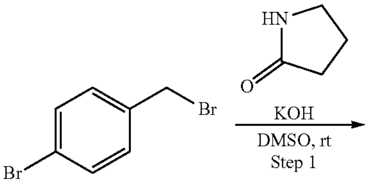

204-1

-continued

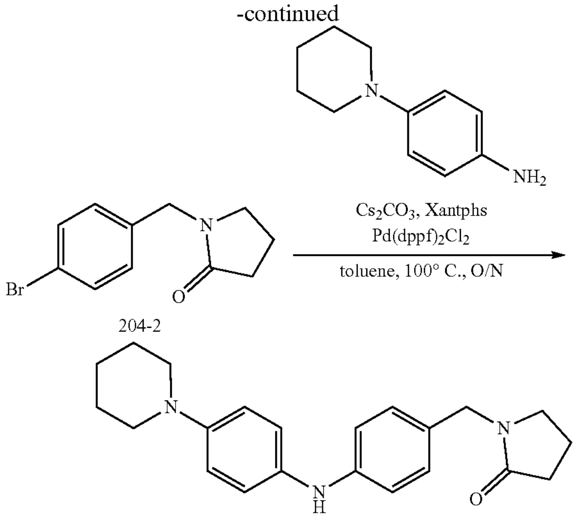

204-2

204

Step 1. Preparation of 1-(4-bromobenzyl)pyrrolidin-2-one (204-2) To a solution of 1-bromo-4-(bromomethyl)benzene (992 mg, 4.0 mmol) and pyrrolidin-2-one (744 mg, 4.0 mmol) in DMSO (10.0 mL) was added KOH (828 mg, 6.0 mmol). Then the mixture was stirred overnight at rt. After cooling to rt. 20 mL of water was added. The resulting solution was extracted with 3×20 mL of ethyl acetate. The organic layers were combined, washed with water (3×30 mL), dried and concentrated under vacuum to afford the desired product as a yellow oil. (460 mg, 45.5%). Mass (m/z): 254.1[M+H]$^+$.

Step 2. Preparation of 1-(4-((4-(piperidin-1-yl)phenyl) amino)benzyl)pyrrolidin-2-one (204) The title compound 304 (40.1 mg) was prepared in a total yield of 22.9% as a yellow oil from 4-(piperidin-1-yl)aniline (176 mg, 1.0 mmol), 1-(4-bromobenzyl)pyrrolidin-2-one (121 mg, 0.5 mmol), $Pd(dppf)_2Cl_2$ (7.3 mg, 0.01 mmol), Xantphos (11.6 mg, 0.02 mmol), $Cs_2CO_3$ (244 mg, 0.75 mmol) according to the procedure for 137-3. $^1$H NMR (400 MHz, Chloroform-d) δ 7.65-6.32 (brm, 8H), 4.70-4.10 (brs, 2H), 3.28-3.23 (m, 2H), 2.42 (t, J=8.0 Hz, 2H), 2.02-1.92 (m, 2H), 1.89-1.65 (m, 4H), 1.62-1.53 (m, 2H). Mass (m/z): 350.3 [M+H]$^+$.

1-ethyl-N-isopropyl-5-oxo-N-(4-((4-(4-(trifluoromethyl)piperidin-1-yl)phenyl)amino)benzyl)pyrrolidine-3-carboxamide (205)

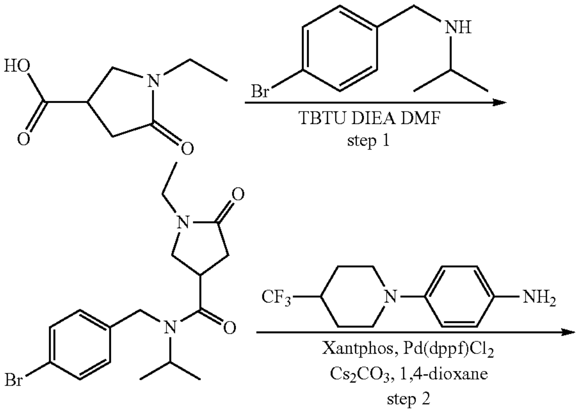

-continued

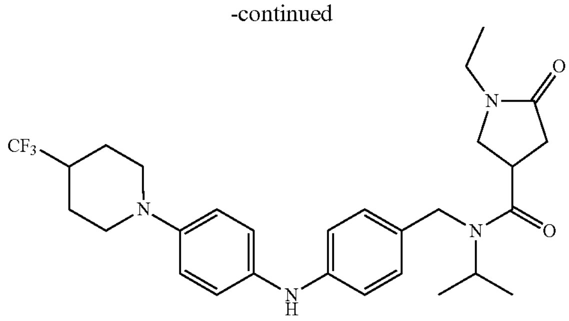

205

Step 1. The intermediate N-(4-bromobenzyl)-1-ethyl-N-isopropyl-5-oxopyrrolidine-3-carboxamide (150 mg) was prepared in a yield of 93.17% as a brown oil from 1-ethyl-5-oxopyrrolidine-3-carboxylic acid (69 mg, 0.44 mmol) and N-(4-bromobenzyl)cyclopropanamine (100 mg, 0.44 mmol), according to the procedure for intermediate. LC-MS (m/z) 367.2, 369.2 [M+H]$^+$.

Step 2. The title compound 205 (14 mg) was prepared in a yield of 6.44% as a blue powder from 4-(4-(trifluoromethyl)piperidin-1-yl)aniline (100 mg, 0.41 mmol) and N-(4-bromobenzyl)-1-ethyl-N-isopropyl-5-oxopyrrolidine-3-carboxamide (150 mg, 0.41 mmol). $^1$H NMR (400 MHz, DMSO-$d_6$) δ 7.06-6.78 (m, 8H), 4.54 (q, J=6.8 Hz, 1H), 4.42 (s, 1H), 4.36 (d, J=6.4 Hz, 1H), 4.28-4.15 (m, 1H), 3.66-3.55 (m, 3H), 3.47 (q, J=4.3 Hz, 1H), 3.26-3.10 (m, 3H), 2.62 (t, J=12.4 Hz, 2H), 2.36-2.28 (m, 1H), 1.88 (d, J=12.7 Hz, 2H), 1.57 (qd, J=12.5, 4.1 Hz, 2H), 1.09 (dd, J=6.6, 1.7 Hz, 3H), 1.07-1.00 (m, 5H), 0.96 (t, J=7.2 Hz, 2H). LC-MS (m/z) 531.5 [M+H]$^+$.

N-hydroxy-2-(4-methyl-3-oxopiperazin-1-yl)-N-(4-((4-(piperidin-1-yl)phenyl)amino)benzyl)acetamide (206)

206

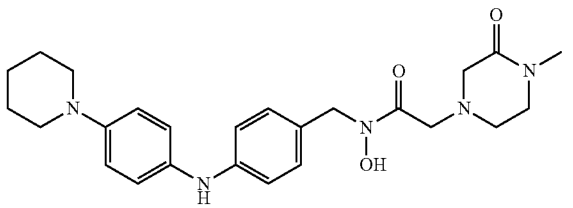

The title compound 206 (5.6 mg) was prepared in a total yield of 21.6% as a white solid according to the procedure for compound 108. $^1$H NMR (400 MHz, Methanol-$d_4$) δ 7.52-6.55 (m, 8H), 4.65 (s, 2H), 3.50 (s, 2H), 3.39-3.23 (m, 8H), 2.94 (s, 3H), 2.88 (m, 2H), 1.75 (br s, 4H), 1.59 ((br s, 2H). Mass (m/z): 452.3[M+H]$^+$.

N-(4-((4-(2-oxa-6-azaspiro[3.3]heptan-6-yl)phenyl) amino)benzyl)-2-(4-methylpiperazin-1-yl)acetamide (207)

207

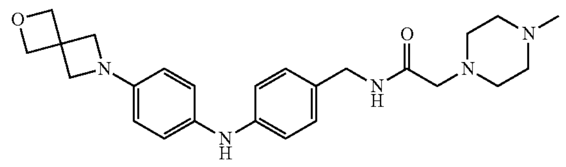

The title compound 207 (21.8 mg) was prepared in a total yield of 50.7% as a white solid according to the procedure for compound 163. $^{1}$H NMR (400 MHz, Methanol-$d_4$) δ 7.12-6.40 (m, 8H), 4.81 (s, 411), 4.28 (s, 2H), 3.95 (s, 4H), 3.08 (s, 2H), 2.66 (br s, 8H), 2.43 (s, 3H). Mass (m/z): 436.2[M+H]$^+$.

N-hydroxy-2-(4-methylpiperazin-1-yl)-N-(4-((4-(piperidin-1-yl)phenyl)amino)-2-(trifluoromethyl) benzyl)acetamide (208)

208

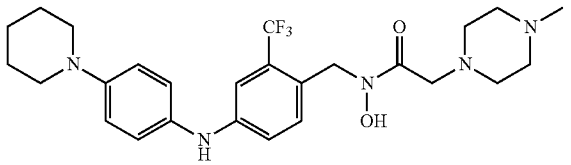

The title compound 208 (28.2 mg) was prepared in a total yield of 58.4% as a white solid according to the procedure for compound 108. $^{1}$H NMR (400 MHz, Methanol-$d_4$) δ 7.27-7.17 (m, 2H), 7.15-6.94 (m, 5H), 4.85 (s, 2H), 3.52 (s, 2H), 3.12-3.02 (m, 4H), 2.93-2.64 (m, 8H), 2.52 (s, 3H), 1.77-1.69 (m, 4H), 1.65-1.51 (m, 2H). Mass (m/z): 506.3 [M+H]$^+$.

1-ethyl-N-(4-((4-(4-methylpiperidin-1-yl)phenyl) amino)benzyl)-5-oxopyrrolidine-3-carboxamide (209)

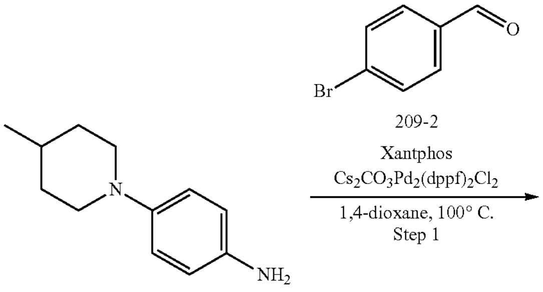

209-1

-continued

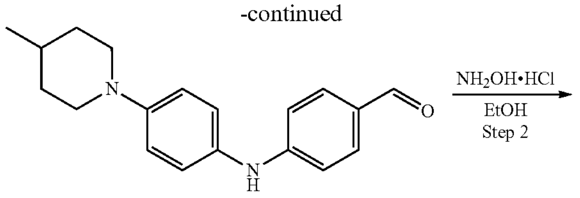

209-3

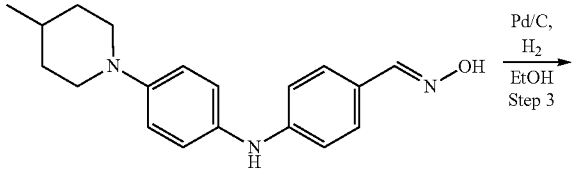

209-4

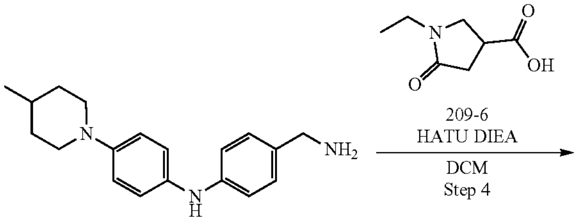

209-5

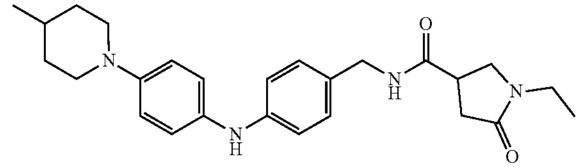

209

Step 1. A mixture of 1,4-dioxane 4-(4-methylpiperidin-1-yl)aniline (375 mg, 2.0 mmol), 4-bromobenzaldehyde (281 mg, 1.5 mmol), Pd(dppf)$_2$Cl$_2$ (22 mg, 0.03 mmol), Xantphos (35 mg, 0.06 mmol), Cs2CO3 (734 mg, 2.3 mmol) (5 mL) was stirred overnight at 110° C. After cooling to rt. 5 ml of water was added. Then the mixture was extracted by DCM (5 mL×3). The combined organic layers were washed with water (10 mL×3), dried over Na2SO4 and concentrated under vacuum. The residue was purified by prep-TLC (MeOH/DCM=1/10) to give the desired product as yellow solid. (490 mg, 86.0%). Mass (m/z): 295.3 [M+H]$^+$ Step 2. To a solution of 4-((4-(4-methylpiperidin-1-yl) phenyl)amino)benzaldehyde (490 mg, 5 mmol) in EtOH (20 mL) was added Hydroxylamine hydrochloride (230 mg, 3.34). Then the reaction was stirred overnight at rt. The reaction mixture was concentrated under vacuum. The crude was used directly at next step. (100%). Mass (m/z): 310.3 [M+H]$^+$.

Step 3. To a solution of (E)-4-((4-(4-methylpiperidin-1-yl)phenyl)amino)benzaldehyde oxime (516 mg, 1.67 mmol) in EtOH (20 mL) was added 10% Pd/C (18 mg, 16.7 ummol) and AcOH (0.5 mL). Then the reaction was stirred overnight at rt under an atmosphere of Hydrogen. Pd/C was filtrated out. The PH of the filtration was adjusted to 8-9 with sodium carbonate solution. Then the mixture was extracted by DCM (20 mL×3). The combined organic layers were washed with brine (20 mL×3), dried over $Na_2SO_4$ and concentrated to give the desired product as yellow solid. (120 mg, 24.3%). 296.3 [M+H]$^+$.

Step 4. To a solution of 4-(aminomethyl)-N-(4-(4-methylpiperidin-1-yl)phenyl)aniline (29.6 mg, 0.1 mmol) and 1-ethyl-5-oxopyrrolidine-3-carboxylic acid (15.7 mg, 0.1 mmol) in DCM (1 ml) was added DIEA (38.7 mg, 0.3 mmol). Followed by the addition of HATU (38 mg, 0.1 mmol) then the reaction mixture was stirred for 2 hours at rt. 5 mL of water was added. Then the mixture was extracted by DCM (5 mL×3). The combined organic layers were washed with water (10 mL×3), dried over $Na_2SO_4$ and concentrated under vacuum. The residue was purified by prep-TLC (MeOH/DCM=1/5) to give the desired product as white solid (16.9 mg, 28.9/o). $^1$H NMR (400 MHz, Methanol-$d_4$) δ 7.45-7.38 (m, 2H), 7.25-7.19 (m, 2H), 7.16-7.07 (m, 4H), 4.87 (s, 1H) 4.39-4.26 (m, 2H), 3.69-3.52 (m, 4H), 3.34-3.32 (m, 2H), 3.28-3.16 (m, 2H), 2.61 (d, J=8.5 Hz, 2H), 2.08-2.00 (m, 2H), 1.92-1.82 (m, 1H), 1.71-1.61 (m, 2H), 1.18-1.02 (m, 6H). Mass (m/z): 435.4[M+H]$^+$.

N-(4-((4-(4,4-dimethylpiperidin-1-yl)phenyl)amino) benzyl)-1-ethyl-5-oxopyrrolidine-3-carboxamide (210)

210

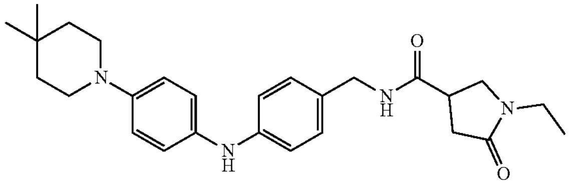

The title compound 210 (26.4 mg) was prepared in a total yield of 58.9% as a yellow solid from 4-(aminomethyl)-N-(4-(4,4-dimethylpiperidin-1-yl)phenyl)aniline (31 mg, 0.1 mmol), 1-ethyl-5-oxopyrrolidine-3-carboxylic acid (15.7 mg, 0.1 mmol), DIEA (38.7 mg, 0.3 mmol), HATU (38 mg, 0.1 mmol) according to the procedure for 209. $^1$H NMR (400 MHz, Methanol-d4) δ 7.49-7.43 (m, 2H), 7.26-7.19 (m, 2H), 7.18-7.09 (m, 4H), 4.87 (s, 1H), 4.39-4.27 (m, 2H), 3.69-3.49 (m, 4H), 3.36-3.32 (m, 1H), 3.27-3.16 (m, 2H), 2.61 (d, J=8.5 Hz, 2H), 1.91-1.75 (m, 4H), 1.23-1.06 (m, 9H). Mass (m/z): 449.4 [M+H]$^+$.

N-(4-((4-(3,3-dimethylazetidin-1-yl)phenyl)amino) benzyl)-1-ethyl-5-oxopyrrolidine-3-carboxamide (211)

211

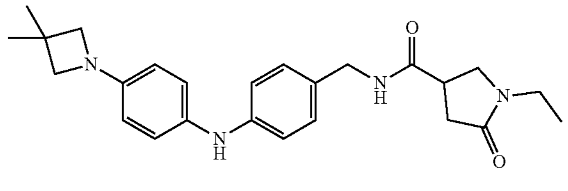

The title compound 211 (5.7 mg) was prepared in a total yield of 6.8% as a yellow solid from 4-(aminomethyl)-N-(4-(3,3-dimethylazetidin-1-yl)phenyl)aniline (56.2 mg, 0.2 mmol), 1-ethyl-5-oxopyrrolidine-3-carboxylic acid (31.4 mg, 0.2 mmol), DIEA (77.4 mg, 0.6 mmol), HATU (76 mg, 0.2 mmol) according to the procedure for 209. $^1$H NMR (400 MHz, Methanol-$d_4$) δ 7.49-7.43 (m, 2H), 7.26-7.19 (m, 2H), 7.18-7.09 (m, 4H), 4.87 (s, 1H), δ 3.69-3.51 (m, 3H), 3.37-3.31 (m, 4H), 3.27-3.16 (m, 2H), 2.61 (d, J=8.4 Hz, 2H), 1.47 (s, 6H), 1.11 (d, J=7.2 Hz, 3H). Mass (m/z): 421.4 [M+H]$^+$.

N-(4-((4-(4,4-difluoropiperidin-1-yl)phenyl)amino) benzyl)-N-hydroxy-1-isopropylpiperidine-4-carboxamide (212)

212

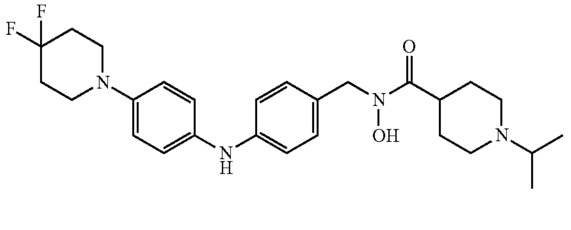

The title compound 212 (21.8 mg) was prepared in a total yield of 49.8% as a white solid from 4-(4,4-difluoropiperidin-1-yl)-N-(4-((hydroxyamino)methyl)phenyl)aniline (30 mg, 0.090 mmol) and 1-isopropylpiperidine-4-carboxylic acid hydrochloride (25 mg, 0.117 mmol) according to the procedure for 174. $^1$H NMR (400 MHz, Methanol-$d_4$) δ 7.20-6.85 (m, 8H), 4.65 (s, 2H), 3.55-3.43 (m, 4H), 3.14 (d, J=31.6 Hz, 4H), 2.09 (tt, J=13.6, 5.7 Hz, 7H), 1.96 (s, 2H), 1.36 (s, 3H), 1.34 (s, 3H). Mass (m/z): 487.4 [M+H]$^+$.

N-cyclopropyl-1-ethyl-5-oxo-N-(4-((4-(4-(trifluoromethyl)piperidin-1-yl)phenyl)amino)benzyl)pyrrolidine-3-carboxamide (213)

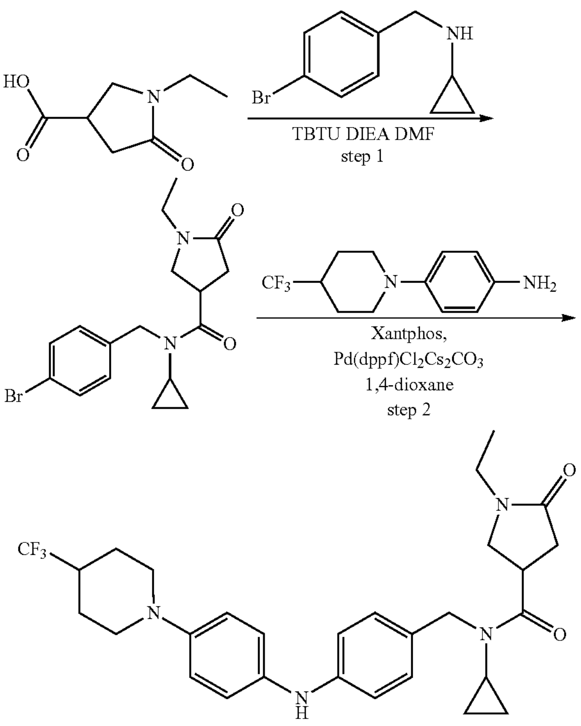

213

Step 1. To a solution of N-(4-bromobenzyl)cyclopropanamine (200 mg, 0.88 mmol, 1.0 equivs) and 1-ethyl-5- oxopyrrolidine-3-carboxylic acid (139 mg, 0.89 mmol 1.1 equivs) in super dry N,N-dimethylformamide (10 mL), 2-(1H-benzo[d][1,2,3]triazol-1-yl)-1,1,3,3-tetramethylisouronium tetrafluoroborate (340 mg, 1.06 mmol, 1.5 equivs) and N-ethyl-N-isopropylpropan-2-amine (438 mmL, 2.65 mmol, 3.0 equivs) was added under argon atmosphere at room temperature and stirred for overnight. The reaction was diluted with water (10 mL) and extracted with dichloromethane (5 mL) 3 times. The organic layer was combined and washed with water, sat·$NH_4Cl$(aq), and brine respectively. Then dried over $MgSO_4$, filtered, and concentrated under reduced pressure. The residue N-(4-bromobenzyl)-N-cyclopropyl-1-ethyl-5 -oxopyrrolidine-3-carboxamide (275 mg) was used in next step directly without further purification after concentrated and dry in vacuo. LC-MS (m/z) 365.2, 367.1 $[M+H]^+$.

Step 2. To a solution of 4-(4-(trifluoromethyl)piperidin-1-yl)aniline (100 mg, 0.41 mmol, 1.0 equivs) and N-(4-bromobenzyl)-N-cyclopropyl-1-ethyl-5-oxopyrrolidine-3-carboxamide (150 mg, 0.41 mmol, 1.0 equivs) in 1,4-dioxane (10 mL) was added (9,9-dimethyl-9H-xanthene-4,5-diyl)bis(diphenylphosphane) (18.95 mg, 0.032 mmol, 0.08 equivs) and [1,1'-Bis(diphenylphosphino)ferrocene]dichloropalladium(II) (11.98 mg, 0.016 mmol, 0.04 equivs) and cesium carbonate (200.0 mg, 0.64 mmol, 1.5 equivs) respectively under argon atmosphere. The resulting mixture was heated to 100° C. and stirred for overnight at the same temperature. The reaction was diluted with water (10 mL) and extracted with ethyl acetate (5 mL) 3 times. The organic layer was combined and washed with water, sat·$NaHCO_3$ (aq), and brine respectively. Then dried over $MgSO_4$, filtered, and concentrated under reduced pressure. The residue was purified by silica gel column chromatography (petroleum ether/AcOEt, 1/6) to give 108.2 mg of N-cyclopropyl-1-ethyl-5-oxo-N-(4-((4-(4-(trifluoromethyl)piperidin-1-yl)phenyl)amino)benzyl)pyrrolidine-3-carboxamide 299 in a yield of 50.00% as a blue solid. $^1H$ NMR (400 MHz, Methanol-$d_4$) δ 7.48-7.41 (m, 2H), 7.14 (d, J=8.3 Hz, 2H), 7.11-6.80 (m, 4H), 4.58 (s, 2H), 4.08 (dtt, J=12.8, 9.1, 6.8 Hz, 2H), 3.67 (q, J=9.3 Hz, 2H), 3.55 (ddd, J=9.7, 5.7, 4.0 Hz, 2H), 2.75-2.50 (m, 5H), 2.23 (dtd, J=15.9, 7.8, 3.8 Hz, 1H), 1.97-1.84 (m, 1H), 1.70 (td, J=12.9, 12.5, 4.2 Hz, 1H), 1.10 (td, J=7.2, 1.7 Hz, 4H), 0.96-0.74 (m, 6H). LC-MS (m/z) 529.4 $[M+H]^+$.

1-methyl-5-oxo-N-(4-((4-(4-(trifluoromethyl)piperidin-1-yl)phenyl)amino)benzyl)pyrrolidine-3-carboxamide (214)

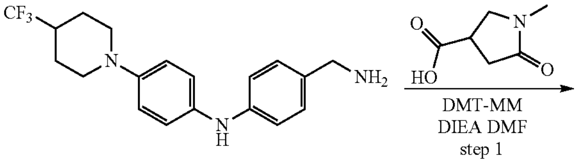

-continued

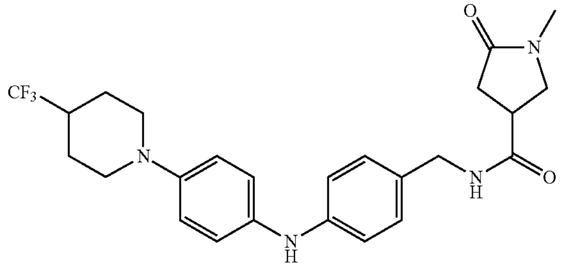

214

The title compound 214 (14.2 mg) was prepared in a yield of 26.14% as a pale blue solid from 4-(aminomethyl)-N-(4-(4-(trifluoromethyl)piperidin-1-yl)phenyl)aniline (40 mg, 0.11 mmol) and 1-methyl-5-oxopyrrolidine-3-carboxylic acid hydrochloride (31 mg, 0.17 mmol), according to the procedure for compound 276. $^1H$ NMR (400 MHz, DMSO-$d_6$) δ 8.40 (t, J=5.7 Hz, 1H), 7.78 (s, 1H), 7.10-7.01 (m, 2H), 7.00-6.94 (m, 2H), 6.93-6.83 (m, 4H), 4.15 (d, J=5.6 Hz, 2H), 3.61 (d, J=12.1 Hz, 2H), 3.49 (dd, J=9.6, 9.0 Hz, 1H), 3.36 (dd, J=6.6, 3.0 Hz, 1H), 3.31 (s, 1H), 3.21-3.05 (m, 1H), 2.69 (d, J=0.8 Hz, 3H), 2.62 (td, J=13.8, 12.3, 3.3 Hz, 2H), 2.43-2.37 (m, 2H), 1.88 (d, J=12.7 Hz, 2H), 1.58 (td, J=12.5, 4.0 Hz, 2H). LC-MS (m/z) 475.4 $[M+H]^+$.

N-hydroxy-1-isopropyl-N-(4-((4-(4-methylpiperidin-1-yl)phenyl)amino)benzyl)piperidine-4-carboxamide (215)

215

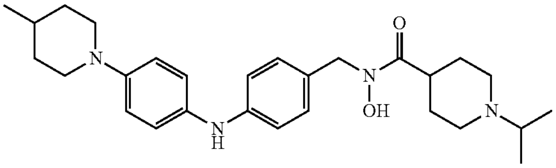

The title compound 215 (23.2 mg) was prepared in a total yield of 51.9% as a white solid from 4-((hydroxyamino)methyl)-N-(4-(4-methylpiperidin-1-yl)phenyl)aniline (30 mg, 0.096 mmol) and 1-isopropylpiperidine-4-carboxylic acid hydrochloride (26 mg, 0.125 mmol) according to the procedure for 174. $^1H$ NMR (400 MHz, Methanol-$d_4$) δ 7.37-6.85 (m, 8H), 4.65 (s, 2H), 3.53-3.41 (m, 4H), 3.27-3.19 (m, 11H), 3.10 (t, J=12.4 Hz, 3H), 2.15-1.93 (m, 5H), 1.77 (s, 3H), 1.57-1.44 (m, 2H), 1.35 (s, 3H), 1.33 (s, 3H), 0.99 (d, J=6.4 Hz, 3H). Mass (m/z): 465.4 $[M+H]^+$.

N-(cyclopropylmethyl)-1-ethyl-5-oxo-N-(4-((4-(4-(trifluoromethyl)piperidin-1-yl)phenyl)amino)benzyl)pyrrolidine-3-carboxamide (216)

216

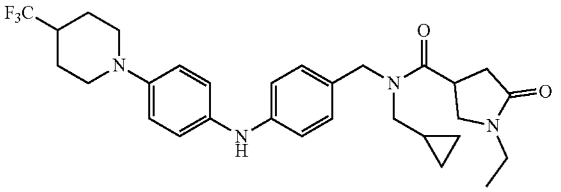

$^1$H NMR (400 MHz, Methanol-$d_4$) δ 7.23-6.68 (m, 8H), 4.61 (s, 2H), 3.77-3.12 (m, 10H), 2.72-2.40 (m, 31H), 2.31-2.13 (m, 1H), 1.98-1.87 (m, 2H), 1.74-1.63 (m, 2H), 1.09 (dt, J=18.2, 7.4 Hz, 3H), 0.99-0.87 (m, 1H), 0.57-0.43 (m, 2H), 0.23-0.17 (m, 2H). Mass (m/z): 543.3 [M+H]$^+$.

2-(4-methylpiperazin-1-yl)-N-(4-((4-(piperidin-1-yl)phenyl)amino)-2-(trifluoromethyl)benzyl)acetamide (217)

217

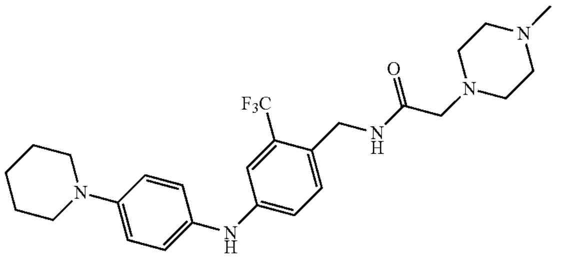

The title compound 217 (20.2 mg) was prepared in a total yield of 35.4% as a white solid according to the procedure for compound 163. $^1$H NMR (400 MHz, Methanol-$d_4$) δ 7.52- 6.99 (m, 711), 4.61 (s, 2H), 3.44 (s, 2H), 3.27-3.12 (m, 4H), 3.05-2.74 (m, 8H), 2.52 (s, 3H), 1.87 (br s, 4H), 1.72 (br s, 2H). Mass (m/z): 490.3[M+H]$^+$.

N-hydroxy-N-(4-((4-(piperidin-1-yl)phenyl)amino)benzyl)nicotinamide (218)

218

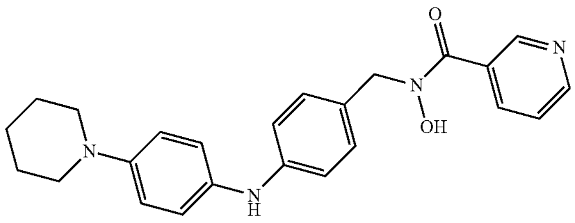

The title compound 218 (15.2 mg) was prepared in a total yield of 41.7% as a white solid according to the procedure for compound 108. $^1$H NMR (400 MHz, Methanol-$d_4$) δ 8.83 (s, 1H), 8.66-8.51 (m, 1H), 8.13 (d, J=8.0 Hz, 1H), 7.50 (dd, J=8.0, 4.8 Hz, 1H), 7.40-6.77 (m, 8H), 4.72 (s, 2H), 3.29-2.97 (m, 4H), 1.86 (br s, 4H), 1.67 (br s, 2H). Mass (m/z): 403.2[M+H]$^+$.

N-(4-((2,6-dimethyl-4-(piperidin-1-yl)phenyl)amino)-3-methylbenzyl)-N-hydroxy-2-(4-methylpiperazin-1-yl)acetamide (219)

219

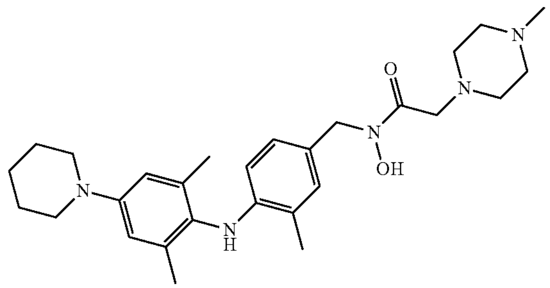

The title compound 219 (16.8 mg) was prepared in a total yield of 43.9% as a white solid according to the procedure for compound 108. $^1$H NMR (400 MHz, Methanol-$d_4$) δ 7.04 (s, 1H), 6.92-6.75 (m, 3H), 5.92 (d, J=8.0, 1H), 4.58 (s, 2H), 3.53 (s, 2H), 3.27-2.88 (br m, 12H), 2.77 (s, 3H), 2.29 (s, 3H), 2.11 (s, 6H), 1.86-1.68 (m, 4H), 1.67-1.53 (m, 2H). Mass (m/z): 480.2[M+H]$^+$.

N-(2-fluoro-4-((4-(piperidin-1-yl)phenyl)amino)benzyl)-N-hydroxy-2-(4-methylpiperazin-1-yl)acetamide (220)

220

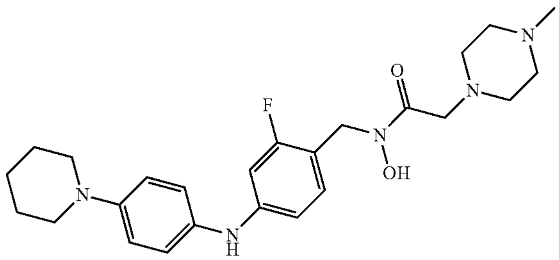

The title compound 220 (20.1 mg) was prepared in a total yield of 48.7% as a white solid according to the procedure for compound 108. $^1$H NMR (400 MHz, Methanol-$d_4$) δ 7.22-6.86 (m, 51H), 6.72-6.58 (m, 2H), 4.70 (s, 2H), 3.47 (s, 2H), 3.06 (br s, 4H), 2.83 (br m, 8H), 2.56 (s, 3H), 1.81-1.67 (m, 4H), 1.64-1.51 (m, 2H). Mass (m/z): 456.3[M+H]$^+$.

4-acetyl-1-(4-((4-(piperidin-1-yl)phenyl)amino)benzyl)piperazin-2-one (221)

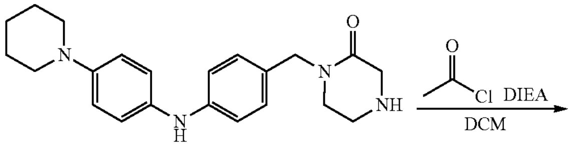

-continued

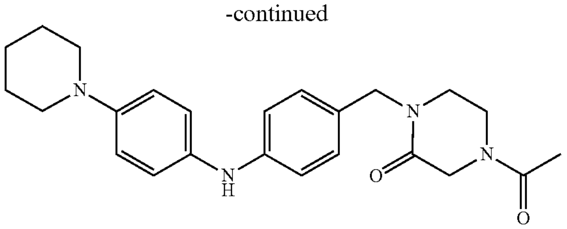

221

To a solution of 1-(4-((4-(piperidin-1-yl)phenyl)amino)benzyl)piperazin-2-one (36.5 mg, 0.1 mmol) and DIEA (38.7 mg, 0.3 mmol) in DCM (2 mL) was added dropwise acetyl chloride (15.7 mg, 0.2 mmol) at 0° C. Then the reaction was stirred for 2 hours at 0° C. The reaction solution was washed with water (3×5 mL), dried over $Na_2SO_4$ and concentrated under vacuum. The residue was purified by prep-TLC (MeOH/DCM=1/10) to afford the desired product as a yellow solid. $^1H$ NMR (400 MHz, Methanol-$d_4$) δ 7.27-6.72 (m, 8H), 4.52 (s, 2H), 4.22 (d, J=15.0 Hz, 2H), 3.71 (q, J=5.2 Hz, 2H), 3.41-3.32 (m, 2H), 3.25-2.82 (m, 4H), 2.10 (s, 3H), 1.76 (p, J=5.6 Hz, 4H), 1.65-1.51 (m, 2H). Mass (m/z): 407.3$[M+H]^+$ 4-(cyclopropylmethyl)-1-(4-((4-(piperidin-1-yl)phenyl)amino)benzyl)piperazin-2-one (222)

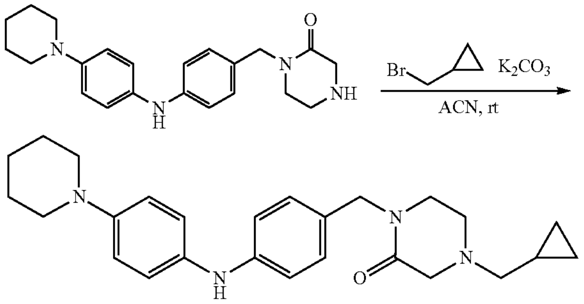

222

To a mixture of 1-(4-((4-(piperidin-1-yl)phenyl)amino)benzyl)piperazin-2-one (18.2 mg, 0.05 mmol) and $K_2CO_3$ (10.4 mg, 0.75 mmol) in ACN (2.0 mL) was added (bromomethyl)cyclopropane (8.1 mg, 0.6 mmol). Then the reaction was stirred overnight at rt. 10 ml of water was added. The resulting solution was extracted with 3×10 mL of ethyl DCM. The organic layers were combined, washed with water (3×10 mL), dried and concentrated under vacuum. The residue was purified by perp-TLC (MeOH/DCM=1/20) to afford the desired product as a yellow solid. (7.0 mg, 33.4%). $^1H$ NMR (400 MHz, Methanol-$d_4$) δ 7.37-6.56 (m, 8H), 4.52 (s, 2H), 3.34-3.31 (m, 2H), 3.28-2.90 (m, 4H), 2.84-2.76 (m, 2H), 2.35 (d, J=6.8 Hz, 2H), 1.86-1.74 (m, 4H), 1.69-1.52 (m, 2H), 0.97-0.86 (m, 1H), 0.56 (d, J=8.1 Hz, 2H), 0.17 (q, J=4.7 Hz, 2H). Mass (m/z): 419.3$[M+H]^+$.

1-ethyl-5-oxo-N-propyl-N-(4-((4-(4-(trifluoromethyl)piperidin-1-yl)phenyl)amino)benzyl)pyrrolidine-3-carboxamide (223)

223

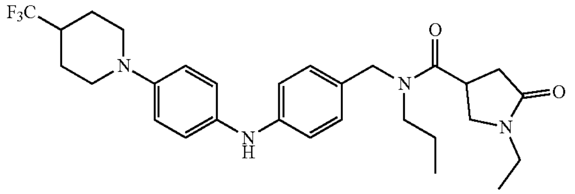

1H NMR (400 MHz, Methanol-$d_4$) δ 7.04-6.97 (m, 8H), 4.51 (s, 2H), 3.77-3.12 (m, 10H), 2.70-2.40 (m, 3H), 2.35-2.09 (m, 1H), 1.92 (d, J=12.7 Hz, 2H), 1.80-1.46 (m, 4H), 1.09 (dt, J=17.6, 7.4 Hz, 3H), 0.87 (dt, J=9.8, 7.4 Hz, 3H). Mass (m/z): 531.2 $[M+H]^+$.

2-(4-methyl-3-oxopiperazin-1-yl)-N-(4-((4-(4-(trifluoromethyl)piperidin-1-yl)phenyl)amino)benzyl)acetamide (224)

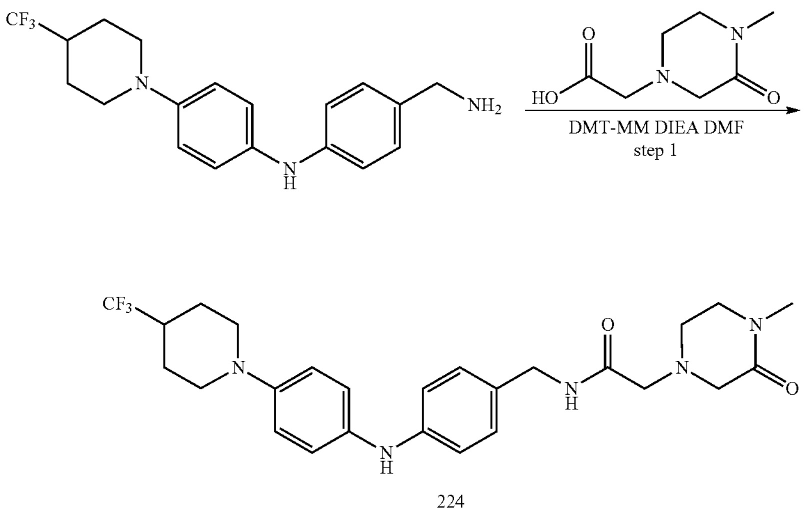

224

The title compound 224 (18.4 mg) was prepared in a yield of 12.77% as a pale blue solid from 4-(aminomethyl)-N-(4-(4-(trifluoromethyl)piperidin-1-yl)phenyl)aniline (100 mg, 0.29 mmol) and 2-(4-methyl-3-oxopiperazin-1-yl)acetic acid (66 mg, 0.31 mmol). $^1$H NMR (400 MHz, DMSO-$d_6$) δ 8.29 (t, J=5.8 Hz, 1H), 7.78 (s, 1H), 7.25-6.63 (m, 8H), 4.14 (s, 2H), 3.61 (s, 2H), 3.28-3.21 (m, 2H), 2.79 (s, 3H), 2.73-2.56 (m, 4H), 2.34-2.26 (m, 2H), 1.92 (ddd, J=13.1, 5.8, 2.8 Hz, 3H), 1.77 (dddd, J=13.3, 10.5, 8.4, 7.2 Hz, 1H), 1.57 (s, 2H). LC-MS (m/z) 504.4 [M+H]$^+$.

1-ethyl-N-methyl-5-oxo-N-(4-((4-(4-(trifluoromethyl)piperidin-1-yl)phenyl)amino)benzyl)pyrrolidine-3-carboxamide (225)

225

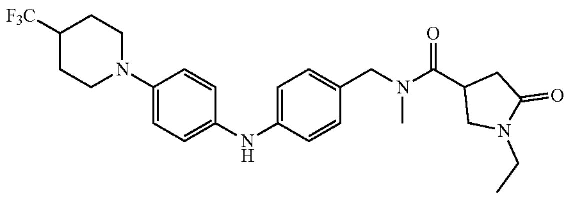

$^1$H NMR (400 MHz, Methanol-$d_4$) δ 7.41-6.55 (m, 8H), 4.48 (s, 2H), 3.75-3.43 (m, 4H), 3.39-3.17 (m, 4H), 2.92 (s, 3H), 2.68-2.45 (m, 3H), 2.21 (br m, 1H), 1.93 (br m, 2H), 1.68 (br m, 2H), 1.08 (t, J=7.4 Hz, 3H). Mass (m/z): 503.3 [M+H]$^+$.

N-hydroxy-N-(4-((4-(piperidin-1-yl)phenyl)amino)benzyl)hexanamide (226)

226

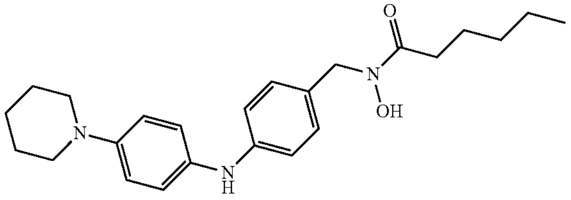

The title compound 226 (11.3 mg) was prepared in a total yield of 38.4% as a white solid according to the procedure for compound 108. $^1$H NMR (400 MHz, Methanol-$d_4$) δ 7.43-6.64 (m, 8H), 4.75 (s, 2H), 3.03 (br s, 4H), 2.38 (t, J=7.4 Hz, 2H), 1.73 (br, 4H), 1.60-1.16 (m, 8H), 1.04-0.81 (m, 3H). Mass (m/z): 396.3[M+H]$^+$.

2-(4-methylpiperazin-1-yl)-N-(4-((4-(piperidin-1-yl)phenyl)amino)-3-(trifluoromethyl)benzyl)acetamide (227)

227

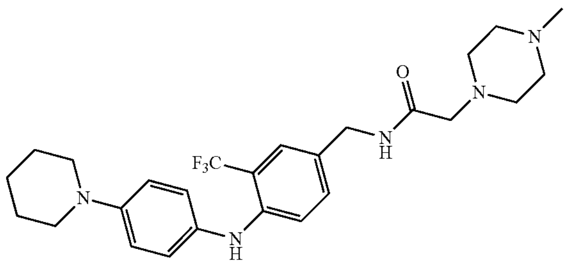

The title compound 227 (15.9 mg) was prepared in a total yield of 56.9% as a white solid according to the procedure for compound 163. $^1$H NMR (400 MHz, Methanol-$d_4$) δ 7.47 (s, 1H), 7.27 (d, J=8.0 Hz, 1H), 7.05-6.89 (m, 5H), 4.34 (s, 2H), 3.15 (s, 2H), 3.10-2.75 (br m, 12H), 2.66 (s, 3H), 1.74 (br s, 4H), 1.60 (br s, 2H). Mass (m/z): 490.3[M+H]$^+$.

1-methyl-2-oxo-N-(4-((4-(piperidin-1-yl)phenyl)amino)-2-(trifluoromethyl)benzyl)piperidine-4-carboxamide (228)

228

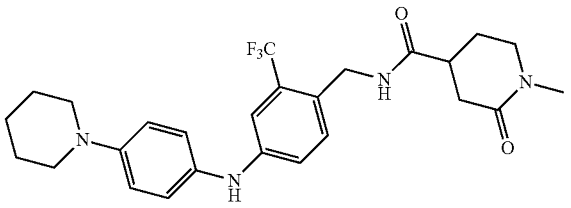

The title compound 228 (21.2 mg) was prepared in a total yield of 47.5% as a white solid according to the procedure for compound 163. $^1$H NMR (400 MHz, Methanol-$d_4$) δ 7.46-6.87 (m, 7H), 4.44 (s, 2H), 3.39-3.37 (m, 2H), 3.19 (br s, 4H), 2.93 (s, 3H), 2.81 (m, 1H), 2.57-2.40 (m, 2H), 2.11-1.89 (m, 2H), 1.81 (br s, 4H), 1.64 (br s, 2H). Mass (m/z): 489.3[M+H]$^+$.

N-(4-((3,5-difluoro-4-(piperidin-1-yl)phenyl)amino)benzyl)-N-hydroxy-2-(4-methylpiperazin-1-yl)acetamide (229)

229

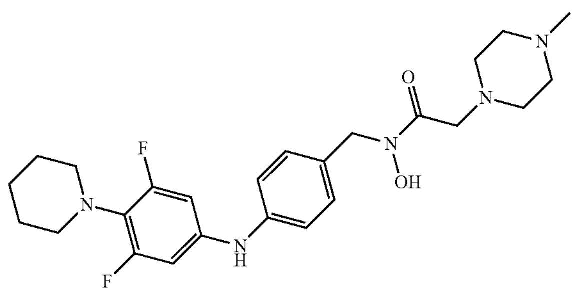

The title compound 229 (11.9 mg) was prepared in a total yield of 27.1% as a white solid according to the procedure for compound 108. $^1$H NMR (400 MHz, Methanol-$d_4$) δ 7.23 (d, J=8.4 Hz, 2H), 7.05 (d, J=8.4 Hz, 2H), 6.53 (d, J=11.6 Hz, 2H), 4.68 (s, 2H), 3.45 (s, 2H), 3.07-2.95 (m, 4H), 2.72 (br s, 8H), 2.43 (s, 3H), 1.69-1.62 (m, 4H), 1.57-1.50 (m, 2H). Mass (m/z): 474.2[M+H]$^+$.

1-methyl-2-oxo-N-(4-((4-(4-(trifluoromethyl)piperidin-1-yl)phenyl)amino)benzyl)piperidine-4-carboxamide (230)

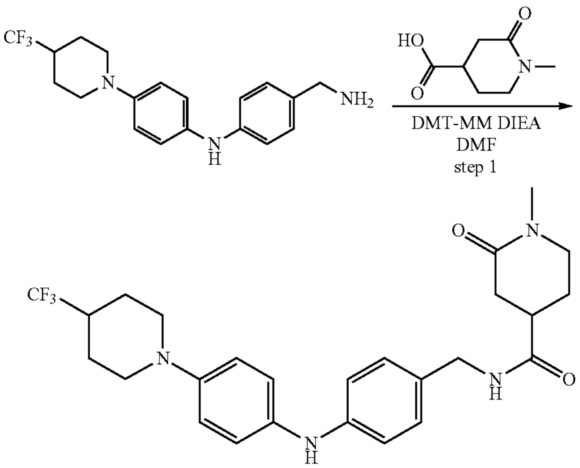

230

To a solution of 4-(aminomethyl)-N-(4-(4-(trifluoromethyl)piperidin-1-yl)phenyl)aniline (100 mg, 0.29 mmol, 1.0 equivs) and 1-methyl-2-oxopiperidine-4-carboxylic acid (49 mg, 0.31 mmol, 1.1 equivs) in super dry N,N-dimethylformamide (5 mL), 4-(4,6-dimethoxy-1,3,5-triazin-2-yl)-4-methylmorpholin-4-ium chloride (87 mg, 0.31 mmol, 1.1 equivs) and N-ethyl-N-isopropylpropan-2-amine (142 mmL, 0.86 mmol, 3.0 equivs) were added respectively at room temperature. The resulting solution was stirred for overnight at room temperature. The reaction mixture was added into water (25 mL) drop by drop with stirring. The precipitate was filtered, cake was wash with water 3 times and dry in vacuo. The residue was purified by silica gel column chromatography (petroleum ether/AcOEt, 1/5) to give 1-methyl-2-oxo-N-(4-((4-(4-(trifluoromethyl)piperidin-1-yl)phenyl)amino)benzyl)piperidine-4-carboxamide 296 as pale blue solid in a yield of 31.32%. $^1$H NMR (400 MHz, DMSO-$d_6$) δ 8.24 (d, J=6.8 Hz, 1H), 7.77 (s, 1H), 7.05 (d, J=8.0 Hz, 2H), 6.97 (d, J=8.2 Hz, 2H), 6.89 (d, J=9.7 Hz, 4H), 4.16 (d, J=5.8 Hz, 2H), 3.61 (d, J=12.1 Hz, 2H), 3.28 (t, J=5.5 Hz, 2H), 3.06 (d, J=8.5 Hz, 4H), 2.81 (s, 3H), 2.71 (t, J=5.5 Hz, 2H), 2.63 (q, J=12.1, 10.1 Hz, 2H), 1.88 (d, J=12.4 Hz, 2H), 1.57 (d, J=12.8 Hz, 2H). LC-MS (m/z) 489.4 [M+H]$^+$.

N-(tert-butyl)-1-ethyl-5-oxo-N-(4-((4-(4-(trifluoromethyl)piperidin-1-yl)phenyl)amino)benzyl)pyrrolidine-3-carboxamide (231)

231

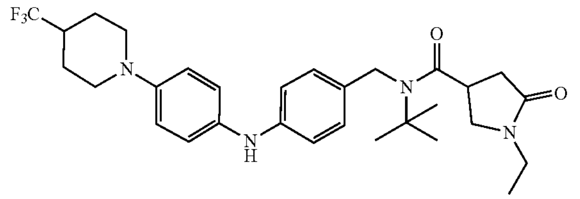

$^1$H NMR (400 MHz, Methanol-$d_4$) δ 7.25-6.72 (m, 8H), 4.62 (s, 2H), 3.79-3.37 (m, 5H), 3.27-3.13 (m, 3H), 2.55 (m, 3H), 2.38-2.19 (m, 1H), 1.99 (br m, 2H), 1.73 (br m, 2H), 1.46 (s, 9H), 1.10 (t, J=7.3 Hz, 3H). Mass (m/z): 545.3 [M+H]$^+$.

1-(4-((4-(4,4-difluoropiperidin-1-yl)phenyl)amino)benzyl)-4-ethylpiperazin-2-one (232)

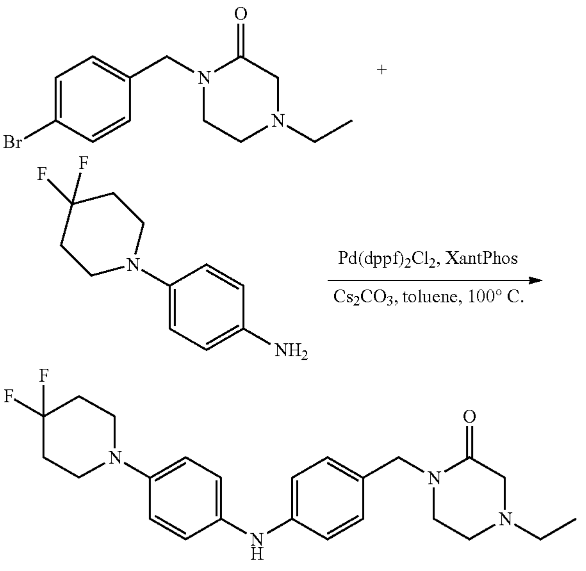

232

A mixture of 1-(4-bromobenzyl)-4-ethylpiperazin-2-one (91 mg, 0.307 mmol), 4-(4,4-difluoropiperidin-1-yl)aniline (50 mg, 0.236 mmol), Pd2(dppf)2Cl2 (4 mg, 0.005 mmol), Xantphos (6 mg, 0.010 mmol), Cs2CO3 (116 mg, 0.354 mmol) and Tol (5 mL) was stirred at 100° C. for 16 h. The mixture was concentrated and purified by prep-HPLC to give the desired product as white solid (10.0 mg, 9.9%). $^1$H NMR (400 MHz, Methanol-$d_4$) δ 7.29-7.11 (m, 8H), 4.82-4.75 (m, 2H), 4.07 (s, 2H), 3.55 (td, J=21.4, 20.6, 10.4 Hz, 6H), 3.34 (td, J=7.4, 1.4 Hz, 2H), 2.87 (s, 2H), 2.07-1.94 (m, 2H), 1.88-1.74 (m, 2H), 1.38 (td, J=7.3, 1.4 Hz, 3H). Mass (m/z): 429.3 [M+H]$^+$.

N-(2,6-difluoro-4-((4-(piperidin-1-yl)phenyl)amino)benzyl)-2-(4-methylpiperazin-1-yl)acetamide (233)

233

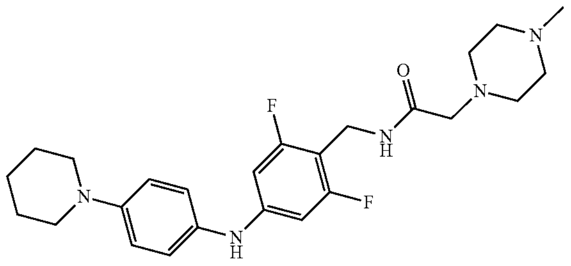

The title compound 233 (20.7 mg) was prepared in a total yield of 46.1% as a white solid according to the procedure for compound 163. $^1$H NMR (400 MHz, Methanol-$d_4$) δ 7.55 (d, J=8.8 Hz, 2H), 7.27 (d, J=8.8 Hz, 2H), 6.69 (d, J=9.6 Hz, 2H), 4.42 (s, 2H), 3.45 (s, 2H), 3.21 (br s, 4H), 2.89 (br in, 8H), 2.41 (s, 3H), 1.74-1.48 (m, 6H). Mass (m/z): 458.3[M+H]$^+$.

3-(2-oxopyrrolidin-1-yl)-N-(4-((4-(4-(trifluoromethyl)piperidin-1-yl)phenyl)amino)benzyl)propanamide (234)

234

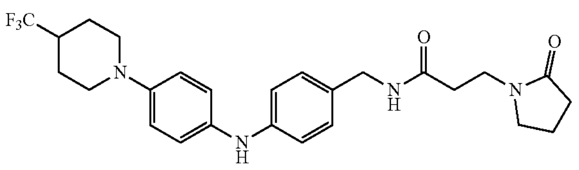

$^1$H NMR (400 MHz, Methanol-$d_4$) δ 7.12-6.93 (m, 8H), 4.23 (s, 2H), 3.66-3.52 (m, 4H), 3.38 (t, J=6.8 Hz, 2H), 2.70 (br m, 2H), 2.43 (t, J=6.8 Hz, 2H), 2.31-2.26 (m, 3H), 2.07-1.82 (m, 4H), 1.79-1.68 (m, 2H). Mass (m/z): 4902 [M+H]$^+$.

1-acetyl-N-(4-((4-(piperidin-1-yl)phenyl)amino)benzyl)piperidine-4-carboxamide (235)

235

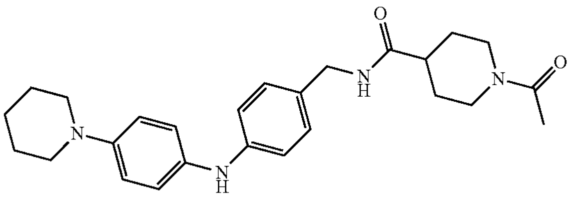

The title compound 235 (4.2 mg) was prepared in a total yield of 30.8% as a white solid according to the procedure for compound 163. $^1$H NMR (400 MHz, Methanol-$d_4$) δ 7.45-6.85 (m, 8H), 4.26 (s, 2H), 3.60-3.39 (m, 4H), 3.25-2.87 (m, 4H), 2.49 (m, 1H), 2.10 (s, 3H), 1.98-1.47 (m, 10H). Mass (m/z): 435.3[M+H]$^+$.

1-(cyclopropanecarbonyl)-N-(4-((4-(piperidin-1-yl)phenyl)amino)benzyl)piperidine-4-carboxamide (236)

236

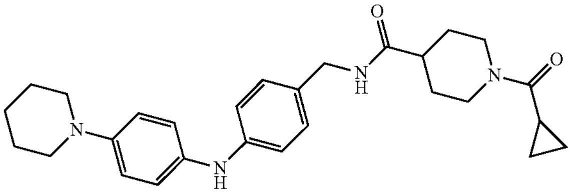

The title compound 236 (5.1 mg) was prepared in a total yield of 35.1% as a white solid according to the procedure for compound 163. $^1$H NMR (400 MHz, Methanol-$d_4$) δ 7.47-6.76 (m, 8H), 4.27 (s, 2H), 3.35 (br s, 4H), 3.26-2.62 (m, 4H), 2.52 (m, 1H), 1.98-1.47 (m, 11H), 0.94-0.74 (m, 4H). Mass (m/z): 461.3[M+H]$^+$ N-(4-((3-chloro-4-(piperidin-1-yl)phenyl)amino)benzyl)-2-(4-methylpiperazin-1-yl)acetamide (237)

237

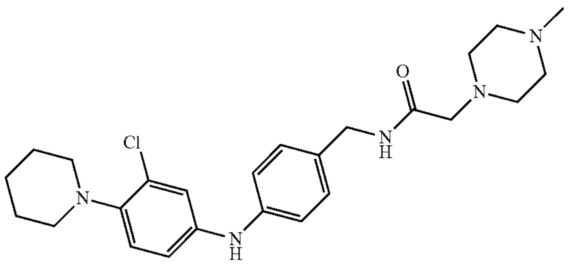

The title compound 237 (20.7 mg) was prepared in a total yield of 48.3% as a white solid according to the procedure for compound 163. $^1$H NMR (400 MHz, Methanol-$d_4$) δ 7.16 (d, J=8.4 Hz, 2H), 7.07 (s, 1H), 7.03-6.93 (m, 4H), 4.32

(s, 2H), 3.11 (s, 2H), 2.88 (br m, 4H), 2.73 (br m, 8H), 2.50 (s, 3H), 1.81-1.64 (m, 4H), 1.57 (br s, 2H). Mass (m/z): 456.2[M+H]$^+$ 1-(4-((4-(2,6-dimethylmorpholino)phenyl)amino) benzyl)-4-ethylpiperazin-2-one (238)

238

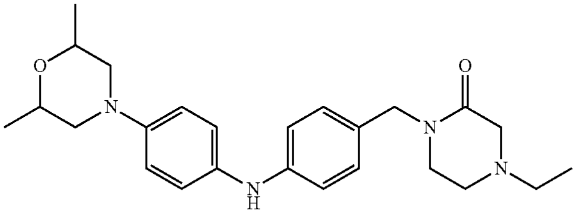

The title compound 238 (11.3 mg) was prepared in a total yield of 26.7% as a white solid according to the procedure for compound 202. $^1$H NMR (400 MHz, Methanol-d$_4$) δ 7.46-6.65 (m, 8H), 4.53 (s, 2H), 3.79 (m, 2H), 3.24 (s, 2H), 3.05 (br m, 4H), 2.78-2.71 (m, 4H), 2.55 (q, J=7.2 Hz, 2H), 1.22 (d, J=6.2 Hz, 6H), 1.12 (t, J=7.2 Hz, 3H). Mass (m/z): 423.3[M+H]$^+$ 2-(4-methylpiperazin-1-yl)-N-(4-((4-(piperidin-1-yl)-3-(trifluoromethyl)phenyl)amino)benzyl)acetamide (239)

239

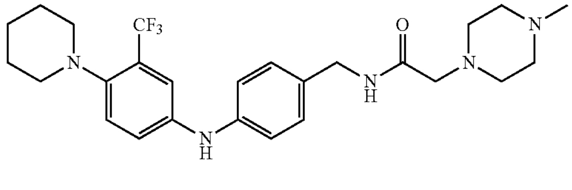

The title compound 239 (12.5 mg) was prepared in a total yield of 25.5% as a yellow solid form N-(4-(aminomethyl) phenyl)-4-(piperidin-1-yl)-3-(trifluoromethyl)aniline (34.9 mg, 0.1 mmol), 4-(dimethylamino)butanoic acid hydrochloride (19.0 mg, 0.12 mmol), HATU (45.6 mg, 0.12 mmol), DIEA (38.7 mg, 0.3 mmol) and DMF (1.0 mL) according to the procedure for 163. $^1$H NMR (400 MHz, Methanol-d$_4$) δ 7.79-7.72 (m, 2H), 7.14-7.02 (m, 2H), 6.71-6.62 (m, 2H), 4.17-4.09 (m, 1H), 3.55-3.45 (m, 2H), 3.18-3.09 (m, 2H), 3.05 (d, J=7.9 Hz, 4H), 2.85 (s, 3H), 2.18 (d, J=12.2 Hz, 2H), 1.% (q, J=12.8 Hz, 2H), 1.70-1.61 (m, 2H), 1.51-1.40 (m, 1H), 1.38-1.26 (m, 2H), 0.97 (d, J=6.4 Hz, 3H). Mass (m/z): 490.4 [M+H]$^+$.

4-ethyl-1-(4-((4-(piperidin-1-yl)phenyl)amino)-2-(trifluoromethyl)benzyl)piperazin-2-one (240)

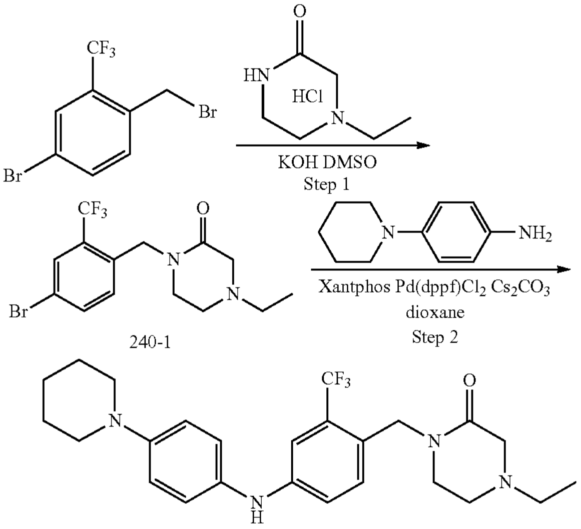

240

Step 1. 1-(4-bromo-2-(trifluoromethyl)benzyl)-4-ethylpiperazin-2-one (240-1)(530 mg) was prepared in a yield of 92.28% as a pale yellow oil from 4-bromo-1-(bromomethyl)-2-(trifluoromethyl)benzene (500 mg, 1.57 mmol) and 4-ethylpiperazin-2-one hydrochloride (259 mg, 1.57 mmol), according to the procedure for compound 1-(3-bromo-5-fluorobenzyl)-4-ethylpiperazin-2-one (241-1). LC-MS (m/z) 365.2, 367.2 [M+H]$^+$.

Step 2. The title compound 240 (40.1 mg) was prepared in a yield of 63.6% as a pale yellow solid from 1-(4-bromo-2-(trifluoromethyl)benzyl)-4-ethylpiperazin-2-one (240-1) (50 mg, 0.14 mmol) and 4-(piperidin-1-yl)aniline (29 mg, 0.16 mmol), according to the procedure for compound 253. $^1$H NMR (400 MHz, Chloroform-d) δ 7.17 (d, J=8.5 Hz, 1H), 7.10 (s, 1H), 7.02 (s, 2H), 6.95 (d, J=18.1 Hz, 3H), 5.69 (s, 1H), 4.70 (s, 2H), 3.24 (s, 2H), 3.23-3.19 (m, 2H), 3.11 (s, 4H), 2.66-2.60 (m, 2H), 2.47 (q, J=7.2 Hz, 2H), 1.72 (p, J=5.5 Hz, 4H), 1.57 (p, J=5.8 Hz, 2H), 1.10 (t, J=7.2 Hz, 3H). LC-MS (m/z) 461.4 [M+H]$^+$.

4-(dimethylamino)-N-(4-((4-(piperidin-1-yl)-3-(trifluoromethyl)phenyl)amino)benzyl)butanamide (241)

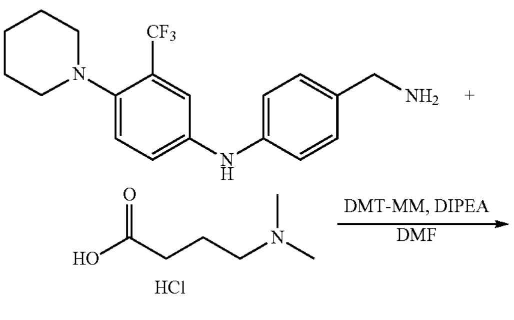

-continued

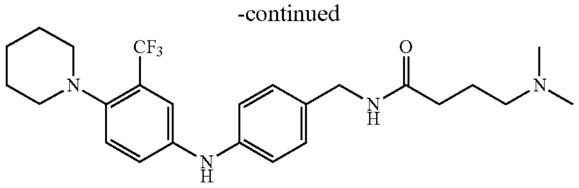

241

The title compound 241 (32.0 mg) was prepared in a total yield of 76.1% as a white solid from N-(4-(aminomethyl) phenyl)-4-(piperidin-1-yl)-3-(trifluoromethyl)aniline (30 mg, 0.086 mmol) and 4-(dimethylamino)butanoic acid hydrochloride (19 mg, 0.122 mmol) according to the procedure for 179. $^1$H NMR (400 MHz, Methanol-$d_4$) δ 7.30 (d, J=8.6 Hz, 1H), 7.26-7.15 (m, 4H), 7.06-6.98 (m, 2H), 4.28 (s, 2H), 2.85-2.74 (m, 6H), 2.61 (d, J=1.0 Hz, 6H), 2.38-2.31 (m, 2H), 1.92 (p, J=7.2 Hz, 2H), 1.65 (p, J=5.6 Hz, 4H), 1.53 (q, J=6.1 Hz, 2H). Mass (m/z): 463.3 $[M+H]^+$.

1-(tert-butyl)-5-oxo-N-(4-((4-(4-(trifluoromethyl) piperidin-1-yl)phenyl)amino)benzyl)pyrrolidine-3-carboxamide (242)

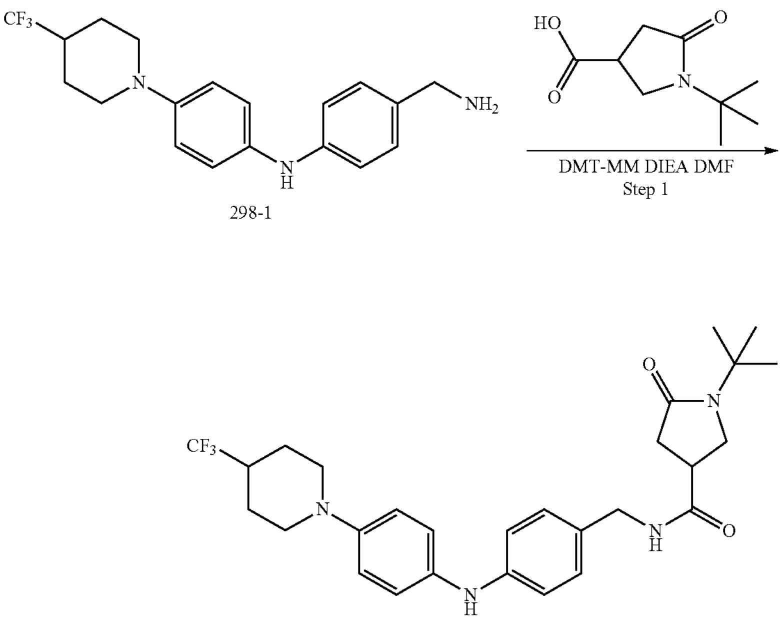

The title compound 242 (97.2 mug) was prepared in a yield of 69.74% as a white solid from 4-(aminomethyl)-N-(4-(4-(trifluoromethyl)piperidin-1-yl)phenyl)aniline (100 mg, 0.29 mmol) and 1-(tert-butyl)-5-oxopyrrolidine-3-carboxylic acid (58 mug, 0.31 mmol). $^1$H NMR (400 MHz, DMSO-$d_6$) δ 8.37 (t, J=5.8 Hz, 1H), 7.78 (s, 1H), 7.04 (d, J=8.5 Hz, 2H), 6.99-6.94 (mu, 2H), 6.91-6.84 (m, 4H), 4.15 (d, J=5.7 Hz, 2H), 3.60 (t, J=9.3 Hz, 3H), 3.45-3.40 (m, 2H), 3.07-2.96 (m, 1H), 2.66-2.57 (m, 2H), 2.38 (dd, J=8.9, 3.8 Hz, 2H), 1.87 (d, J=12.6 Hz, 2H), 1.56 (qd, J=12.5, 4.1 Hz, 2H), 1.30 (s, 9H). LC-MS (m/z) 517.4 $[M+H]^+$.

1-ethyl-N-(2-hydroxyethyl)-5-oxo-N-(4-((4-(4-(trifluoromethyl)piperidin-1-yl)phenyl)amino)benzyl) pyrrolidine-3-carboxamide (243)

243

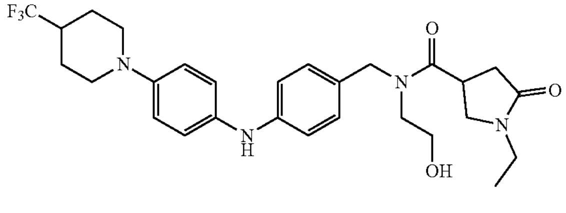

$^1$H NMR (400 MHz, Methanol-$d_4$) δ 7.32-6.68 (m, 8H), 4.64 (s, 2H), 3.81-3.17 (m, 12H), 2.73-2.44 (m, 3H), 2.26 (br m, 1H), 1.96 (br m, 2H), 1.71 (br m, 2H), 1.10 (dt, J=15.0, 7.4 Hz, 3H). Mass (m/z): 533.4 $[M+H]^+$.

N-hydroxy-2-(4-methylpiperazin-1-yl)-N-(4-((4-(3-(trifluoromethyl)pyrrolidin-1-yl)phenyl)amino)benzyl)acetamide (244)

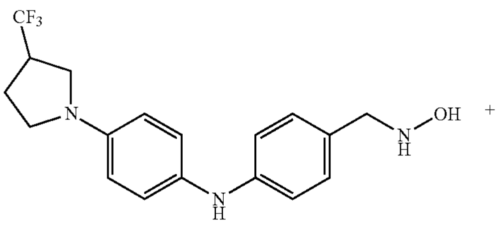

-continued

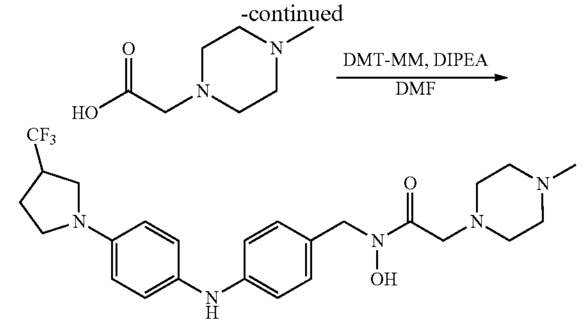

244

The title compound 244 (24.6 mg) was prepared in a total yield of 57.1% as a white solid from 4-((hydroxyamino) methyl)-N-(4-(3-(trifluoromethyl)pyrrolidin-1-yl)phenyl) aniline (30 mg, 0.094 mmol) and 2-(4-methylpiperazin-1-yl)acetic acid (19 mg, 0.122 mmol) according to the procedure for 179. $^1$H NMR (400 MHz, Methanol-$d_4$) δ 7.48-7.36 (m, 1H), 7.10 (s, 2H), 6.91-6.55 (m, 5H), 4.63 (s, 2H), 3.54 (s, 2H), 3.17 (d, J=10.4 Hz, 4H), 2.88 (s, 3H), 2.77 (s, 4H), 2.46 (d, J=16.1 Hz, 3H). Mass (m/z): 460.3 $[M+H]^+$.

N-ethyl-2-(4-methylpiperazin-1-yl)-N-(4-((4-(4-(trifluoromethyl)piperidin-1-yl)phenyl)amino)benzyl)acetamide (245)

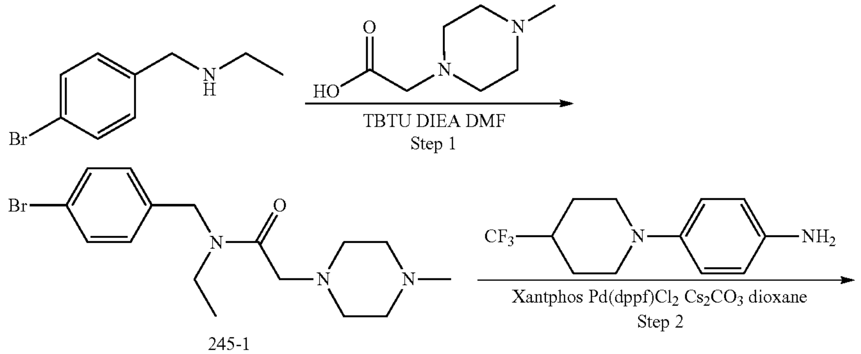

245-1

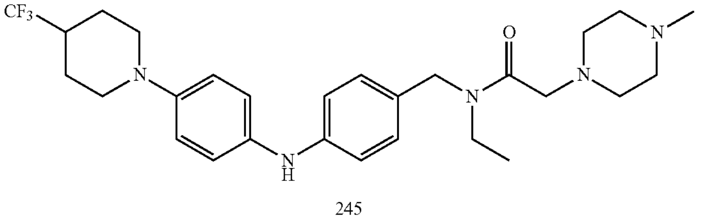

245

Step 1. N-(4-bromobenzyl)-N-ethyl-2-(4-methylpiperazin-1-yl)acetamide (245-1) was prepared as a colorless oil from N-(4-bromobenzyl)ethanamine (500 mg, 2.34 mmol) and 2-(4 -methylpiperazin-1-yl)acetic acid (406 mg, 2.57 mmol), according to the procedure for N-(4-bromobenzyl)-N-ethyl-2-(4-methyl-3-oxopiperazin-1-yl)acetamide (289-1). The residue was used in next step directly without further purification after concentrated and dry in vacuo. LC-MS (m/z) 354.2, 356.1 $[M+H]^+$.

Step 2. The title compound 245 (56.2 mg) was prepared in a yield of 26.52% as a blue solid from 4-(4-(trifluoromethyl)piperidin-1-yl)aniline (100 mg, 0.41 mmol) and N-(4-bromobenzyl)-N-ethyl-2-(4-methylpiperazin-1-yl)acetamide (145 mg, 0.41 mmol). $^1$H NMR (400 MHz, Methanol-$d_4$) δ 7.56-7.51 (m, 1H), 7.49-7.44 (m, 1H), 7.22-7.16 (m, 2H), 7.05 (dt, J=13.2, 7.2 Hz, 2H), 6.96 (d, J=8.4 Hz, 2H), 4.55 (s, 2H), 3.62 (d, J=12.0 Hz, 2H), 3.44-3.34 (m, 6H), 2.66 (s, 2H), 2.40 (d, J=1.9 Hz, 4H), 2.01-1.94 (m, 2H), 1.73 (qd, J=12.5, 4.1 Hz, 2H), 1.24 (t, J=7.1 Hz, 2H), 1.21-1.15 (m, 4H), 1.08 (td, J=7.0, 4.3 Hz, 3H). LC-MS (m/z) 518.4 $[M+H]^+$.

N-hydroxy-N-(4-((4-(piperidin-1-yl)phenyl)amino)benzyl)-2-(4-(2,2,2-trifluoroethyl)piperazin-1-yl)acetamide (246)

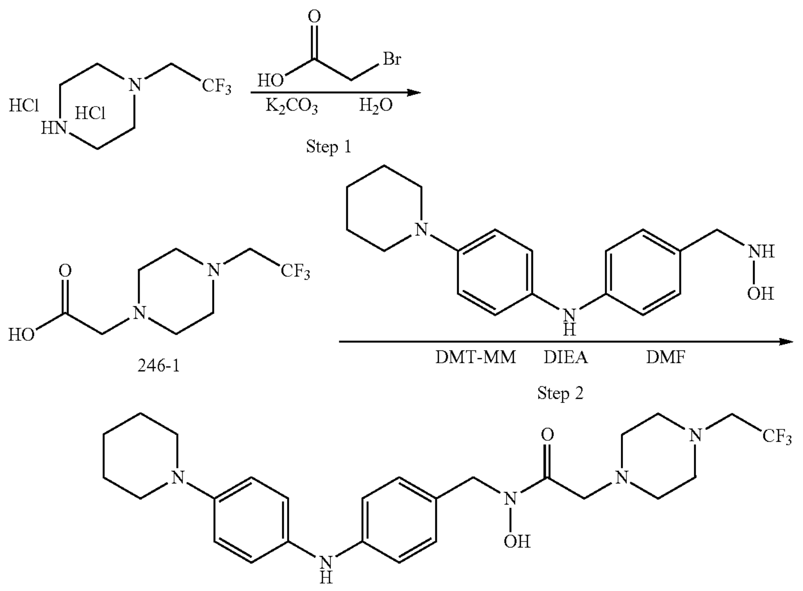

246-1

246

Step 1. To a solution of 1-(2,2,2-trifluoroethyl)piperazine dihydrochloride (300 mg, 1.24 mmol, 1.0 equivs) in water (5 mL) was added 2-bromoacetic acid (190 mg, 1.37 mmol, 1.1 equivs) and potassium carbonate (516 mg, 3.73 mmol, 3.0 equivs) respectively slowly at 0° C. with ice-water bath. The reaction allowed to warm to room temperature and stirred for overnight. The reaction mixture was acidized by 1N hydrochloride to pH=4, then extracted with dichloromethane (5 mL) 3 times. The organic layer was combined and dried over $MgSO_4$, filtered, and concentrated under reduced pressure. The residue 2-(4-(2,2,2-trifluoroethyl)piperazin-1-yl)acetic acid (246-1) was used in next step directly without further purification after concentrated and dry in vacuo. LC-MS (m/z) 227.4 $[M+H]^+$.

Step 2. The title compound 246 (14.9 mg) was prepared in a yield of 17.53% as a brown solid from 2-(4-(2,2,2-trifluoroethyl)piperazin-1-yl)acetic acid (246-1) (46 mg, 0.16 mmol) and 4-((hydroxyamino)methyl)-N-(4-(piperidin-1-yl)phenyl)aniline (50 mg, 0.17 mmol), according to the procedure for compound 290. $^1H$ NMR (400 MHz, Chloroform-d) δ 7.35-7.11 (br, 2H), 7.10-6.65 (br, 6H), 5.89-5.17 (br, 1H), 4.70 (s, 2H), 3.35 (s, 2H), 3.29-3.00 (br, 3H), 2.95 (q, J=9.5 Hz, 3H), 2.76-2.51 (m, 8H), 1.82-1.61 (m, 4H), 1.57 (s, 2H). LC-MS (m/z) 506.7 $[M+H]^+$.

N-(2-chloro-4-((5-(piperidin-1-yl)pyridin-2-yl)amino)benzyl)-N-hydroxy-2-(4-methylpiperazin-1-yl)acetamide (247)

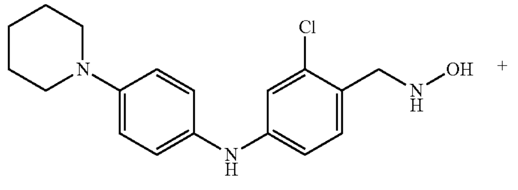

-continued

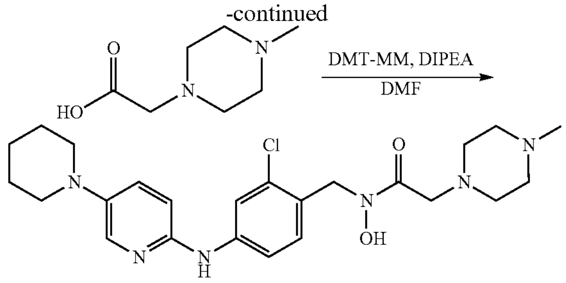

247

The title compound 247 (17.9 mg) was prepared in a total yield of 42.3% as a white solid from N-(3-chloro-4-((hydroxyamino)methyl)phenyl)-5-(piperidin-1-yl)pyridin-2-amine (30 mg, 0.090 mmol) and 2-(4-methylpiperazin-1-yl)acetic acid (19 mg, 0.117 mmol) according to the procedure for 179. $^1H$ NMR (400 MHz, Methanol-$d_4$) δ 7.18-6.90 (m, 7H), 4.78 (s, 2H), 3.56 (s, 2H), 3.11 (d, J=22.2 Hz, 8H), 2.88 (s, 3H), 2.75 (s, 3H), 1.75 (p, J=5.6 Hz, 4H), 1.59 (s, 3H). Mass (m/z): 473.3 $[M+H]^+$.

N-(4-((5-fluoro-6-(piperidin-1-yl)pyridin-3-yl)amino)benzyl)-2-(4-methyl-3-oxopiperazin-1-yl)acetamide (248)

248

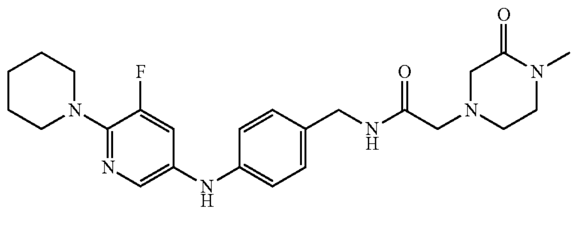

The title compound 248 (16.9 mg) was prepared in a total yield of 41.2% as a white solid according to the procedure for compound 163. $^1$H NMR (400 MHz, Methanol-$d_4$) δ 7.80 (s, 1H), 7.24-7.13 (m, 3H), 6.95 (d, J=8.4 Hz, 2H), 4.32 (s, 2H), 3.38 (m, 2H), 3.25-3.17 (m, 6H), 3.15 (s, 2H), 2.93 (s, 3H), 2.82-2.76 (m, 2H), 1.78-1.55 (m, 6H). Mass (m/z): 455.2[M+H]$^+$ N-(4-((4-(4,4-difluoropiperidin-1-yl)phenyl)amino)benzyl)-N-hydroxy-1-methyl-2-oxo-1,2-dihydropyridine-4-carboxamide (249)

249

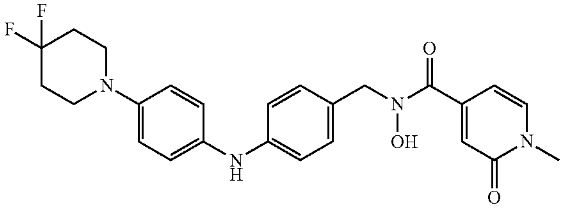

The title compound 249 (10.1 mg) was prepared in a total yield of 33.4% as a white solid according to the procedure for compound 108. $^1$H NMR (400 MHz, Methanol-$d_4$) δ 7.65 (d, J=6.4 Hz, 1H), 7.31-6.82 (m, 8H), 6.67 (s, 1H), 6.55-6.38 (m, 1H), 4.74 (s, 2H), 3.55 (s, 3H), 3.30-3.06 (m, 4H), 2.13-2.03 (m, 4H). Mass (m/z): 469.3[M+H]$^+$.

1-(4-((4-(4,4-difluoropiperidin-1-yl)phenyl)amino)benzyl)-4-fluoropyridin-2 (1H)-one (250)

250

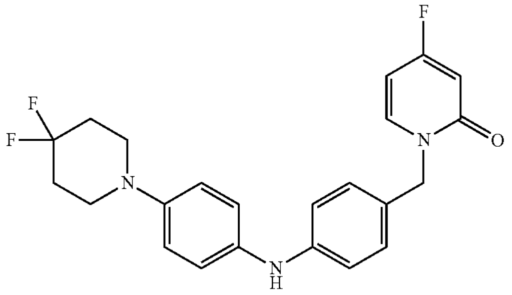

The title compound 250 (20.1 mg) was prepared in a total yield of 48.4% as a white solid according to the procedure for compound 202. $^1$H NMR (400 MHz, Methanol-$d_4$) δ 7.86-7.68 (m, 1H), 7.28-6.56 (m, 8H), 6.35-6.17 (m, 2H), 4.15 (s, 2H), 3.27-3.06 (m, 4H), 2.14-2.03 (m, 4H). Mass (m/z): 414.3[M+H]$^+$ N-(4-((4-(4,4-difluoropiperidin-1-yl)phenyl)amino)benzyl)-N-hydroxy-1-methyl-6-oxopiperidine-3-carboxamide (251)

251

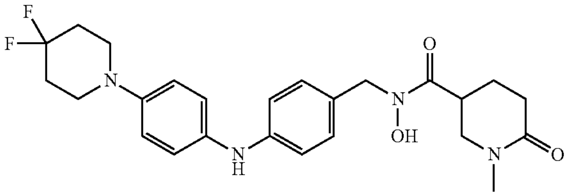

The title compound 251 (9.9 mg) was prepared in a total yield of 23.5% as a white solid from 4-(4,4-difluoropiperidin-1-yl)-N-(4-((hydroxyamino)methyl)phenyl)aniline (30 mg, 0.090 mmol) and 1-methyl-6-oxopiperidine-3-carboxylic acid (18.5 mg, 0.117 mmol) according to the procedure for 174. $^1$H NMR (400 MHz, Methanol-$d_4$) δ 7.83-6.43 (m, 8H), 4.65 (s, 2H), 3.80-3.74 (m, 1H), 3.73-3.66 (m, 1H), 3.56 (dd, J=9.8, 5.2 Hz, 1H), 3.30 (dq, J=3.2, 1.6 Hz, 7H), 2.67-2.60 (m, 2H), 2.40 (s, 4H), 1.11 (td, J=7.2, 0.6 Hz, 3H). Mass (m/z): 473.3 [M+H]$^+$.

N-(4-((4-(4,4-difluoropiperidin-1-yl)phenyl)amino)benzyl)-1-ethyl-N-hydroxy-5-oxopyrrolidine-3-carboxamide (252)

252

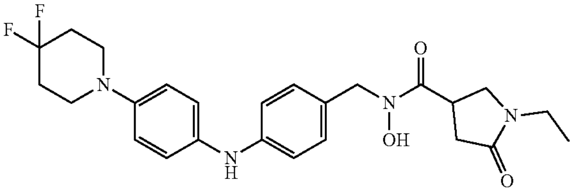

The tide compound 251 (7.0 mg) was prepared in a total yield of 17% as a white solid from 4-(4,4-difluoropiperidin-1-yl)-N-(4-((hydroxyamino)methyl)phenyl)aniline (30 mg, 0.090 mmol) and 1-ethyl-5-oxopyrrolidine-3-carboxylic acid (18.5 mg, 0.117 mmol) according to the procedure for 174. $^1$H NMR (400 MHz, Methanol-$d_4$) δ 7.74-6.73 (m, 8H), 4.65 (s, 2H), 3.49 (ddd, J=22.8, 13.5, 9.6 Hz, 5H), 2.94 (s, 4H), 2.42-2.34 (m, 4H), 2.03 (d, J=0.4 Hz, 2H), 2.00-1.91 (m, 2H). Mass (m/z): 473.3 [M+H]$^+$.

N-(4-((4-(4,4-difluoropiperidin-1-yl)phenyl)amino)benzyl)-N-hydroxy-2-(2-methoxyethoxy)acetamide (253)

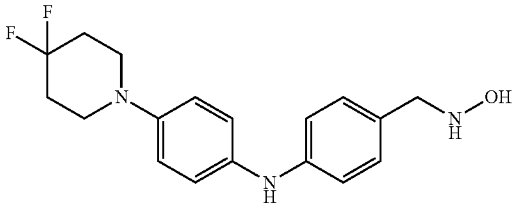

+

-continued

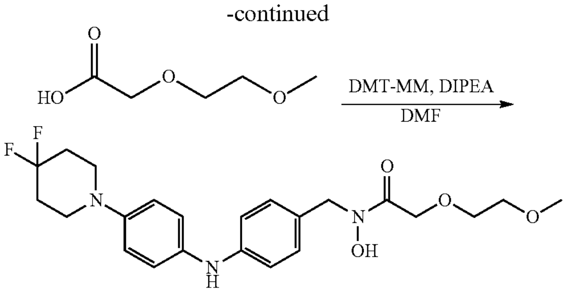

253

The title compound 253 (8.2 mg) was prepared in a total yield of 10.2% as a white solid from 4-(4,4-difluoropiperidin-1-yl)-N-(4-((hydroxyamino)methyl)phenyl)aniline (30 mg, 0.090 mmol) and 2-(2-methoxyethoxy)acetic acid (16 mg, 0.117 mmol) according to the procedure for 179. $^1$H NMR (400 MHz, Methanol-$d_4$) δ 7.29-7.11 (m, 8H), 4.37 (s, 2H), 3.72-3.67 (m, 2H), 3.60-3.55 (m, 2H), 3.36 (d, J=0.5 Hz, 3H), 2.41 (s, 4H), 1.78-1.55 (m, 6). Mass (m/z): 450.3 $[M+H]^+$.

1-(cyclopropylmethyl)-N-hydroxy-2-oxo-N-(4-((4-(4-(trifluoromethyl)piperidin-1-yl)phenyl)amino)benzyl)piperidine-4-carboxamide 254

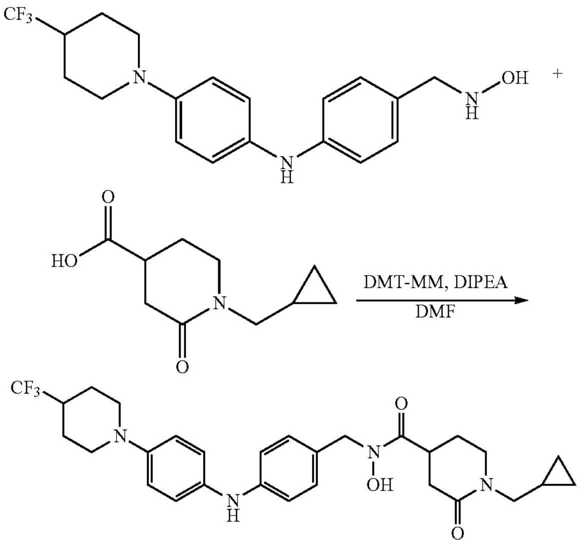

254

The title compound 254 (11.6 mg) was prepared in a total yield of 26.4% as a white solid from 4-((hydroxyamino)methyl)-N-(4-(4-(trifluoromethyl)piperidin-1-yl)phenyl)aniline (30 mg, 0.082 mmol) and 1-(Cyclopropylmethyl)-2-oxopiperidine-4-carboxylic acid (21 mg, 0.107 mmol) according to the procedure for 179. $^1$H NMR (400 MHz, Methanol-$d_4$) δ 7.18-6.81 (m, 8H), 4.65 (q, J=16.0, 15.4 Hz, 2H), 3.68-3.38 (m, 5H), 3.22 (dd, J=13.8, 6.9 Hz, 1H), 2.65 (s, 2H), 2.49 (d, J=7.3 Hz, 2H), 2.25 (dtt, J=16.1, 7.7, 4.0 Hz, 1H), 2.05 (t, J=7.4 Hz, 1H), 2.01-1.89 (m, 3H), 1.71 (qd, J=12.6, 3.9 Hz, 2H), 1.29 (d, J=3.9 Hz, 1H), 1.05-0.98 (m, 1H), 0.50 (ddd, J=8.2, 4.1, 2.3 Hz, 2H), 0.29-0.17 (m, 2H). Mass (n/z): 545.3 $[M+H]^+$.

3-(4-((4-((N-hydroxy-2-(4-methylpiperazin-1-yl)acetamido)methyl)phenyl)amino)phenyl)-N,N-dimethylpropanamide (255)

255

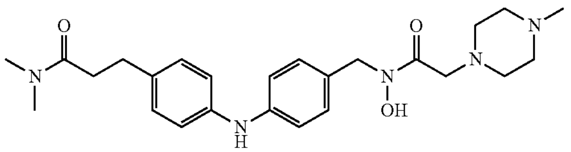

1H NMR (400 MHz, Methanol-$d_4$) δ 7.17 (d, J=8.4 Hz, 2H), 7.09 (d, J=8.4 Hz, 2H), 7.00 (d, J=8.4 Hz, 4H), 4.65 (s, 2H), 3.48 (s, 2H), 2.96 (s, 3H), 2.91 (s, 3H), 2.89-2.68 (m, 10H), 2.63 (t, J=8.4 Hz, 2H), 2.53 (s, 3H). Mass (m/z): 454.3 $[M+H]^+$.

4-(dimethylamino)-N-(4-((4-(6-fluoropyridin-3-yl)phenyl)amino)benzyl)-N-hydroxybutanamide (256)

256

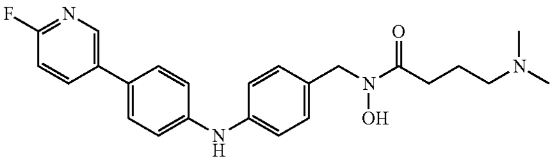

1H NMR (400 MHz, Methanol-$d_4$) δ 8.37 (s, 1H), 8.13 (m, 1H), 7.50 (d, J=8.8 Hz, 2H), 7.30-7.22 (m, 2H), 7.20-7.06 (m, 5H), 4.70 (s, 2H), 2.82 (t, J=7.4 Hz, 2H), 2.68-2.59 (m, 2H), 2.56 (s, 6H), 2.06-1.88 (m, 2H). Mass (m/z): 423.3 $[M+H]^+$.

N-hydroxy-1-methyl-6-oxo-N-(4-((4-(4-(trifluoromethyl)piperidin-1-yl)phenyl)amino)benzyl)piperidine-3-carboxamide (257)

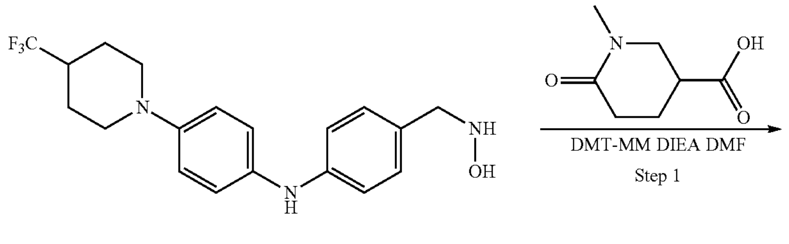

-continued

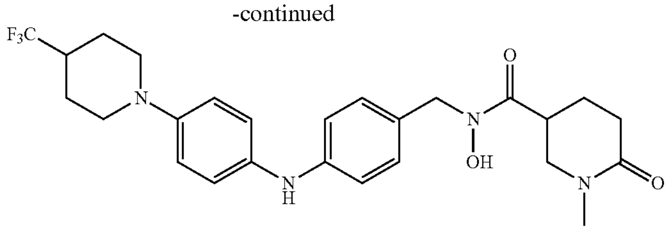

257

Step 1. The title compound 257 (10.5 mg) was prepared in a yield of 38.02% as a pale yellow powder from 4-((hydroxyamino)methyl)-N-(4-(4-(trifluoromethyl)piperidin-1-yl)phenyl)aniline (20 mg, 0.054 mmol) and 1-methyl-6-oxopiperidine-3-carboxylic acid (10.3 mg, 0.066 mmol), according to the procedure for compound 290. $^{1}H$ NMR (400 MHz, Methanol-$d_4$) δ 7.81-6.16 (m, 8H), 4.81-4.42 (br, 2H), 3.55-3.38 (m, 4H), 2.93 (s, 3H), 2.42-2.20 (m, 4H), 2.12-1.85 (m, 5H), 1.72 (s, 3H). LC-MS (m/z) 505.4 $[M+H]^{+}$.

N-hydroxy-1-methyl-6-oxo-N-(4-((4-(4-(trifluoromethyl)piperidin-1-yl)phenyl)amino)benzyl)piperidine-3-carboxamide 258

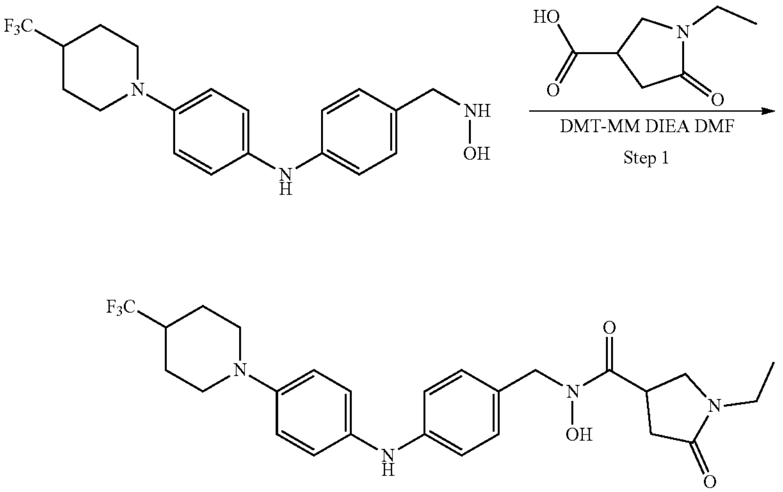

258

The title compound 258 (19.9 mg) was prepared in a yield of 72.06% as a pale yellow solid from 4-((hydroxyamino)methyl)-N-(4-(4-trifluoromethyl)piperidin-1-yl)phenyl)aniline (20 mg, 0.054 mmol) and 1-ethyl-5-oxopyrrolidine-3-carboxylic acid (9.4 mg, 0.066 mmol), according to the procedure for compound 290. $^{1}H$ NMR (400 MHz, Methanol-$d_4$) δ 7.37-7.10 (br, 3H), 7.076.55 (br, 5H), 4.66 (s, 2H), 3.81-3.47 (m, 5H), 2.83-2.42 (m, 4H), 2.34-2.20 (m, 1H), 2.06-1.86 (m, J=24.3 Hz, 3H), 1.84-1.55 (m, 2H), 1.34-1.27 (m, 1H), 1.10 (t, J=7.2 Hz, 3H). LC-MS (m/z) 491.2 $[M+H]^{+}$.

tert-butyl3-(hydroxy(4-((4-(4-(trifluoromethyl)piperidin-1-yl)phenyl)amino)benzyl)carbamoyl)azetidine-1-carboxylate (259)

259

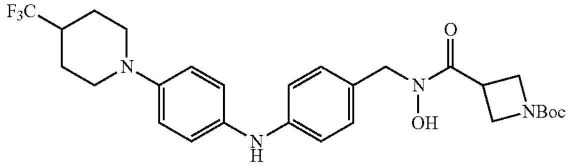

The title compound 259 (164.1 mg) was prepared in a total yield of 46.9% as a white solid according to the procedure for compound 108. $^{1}H$ NMR (400 MHz, Methanol-$d_4$) δ7.27-6.79 (m, 8H), 4.67 (s, 2H), 4.05 (br m, 4H), 3.25-3.16 (m, 4H), 2.31-2.17 (m, 2H), 2.02-1.85 (m, 2H), 1.76-1.72 (m, 2H), 1.45 (s, 9H). Mass (m/z): 549.3$[M+H]^{+}$ N-hydroxy-1-methyl-2-oxo-N-(4-((4-(4-(trifluoromethyl)piperidin-1-yl)phenyl)amino)benzyl)piperidine-4-carboxamide (260)

260

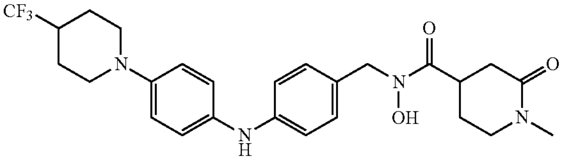

The title compound 260 (36.6 mg) was prepared in a total yield of 40.4% as a yellow solid form 4-((hydroxyamino)methyl)-N-(4-(4-(trifluoromethyl)piperidin-1-yl)phenyl)aniline (55.0 mg, 0.15 mmol), 1-methyl-2-oxopiperidine-4-carboxylic acid (28.0 mg, 0.18 mmol), DMT-MM (48.0 mg, 0.18 mmol), DIEA (58.0 mg, 0.45 mmol) and DMF (1.0 mL) according to the procedure for 137. $^1$H NMR (400 MHz, Methanol-$d_4$) δ 7.34-6.41 (m, 8H), 4.64 (s, 2H), 3.74-3.31 (m, 6H), 2.92 (s, 3H), 2.47 (d, J=7.3 Hz, 2H), 2.32-2.19 (m, 1H), 2.09-1.88 (m, 4H), 1.79-1.64 (m, 2H). Mass (m/z): 505.3 [M/2+H]$^+$.

1-ethyl-5-oxo-N-(4-((4-(3-(trifluoromethyl)pyrrolidin-1-yl)phenyl)amino)benzyl)pyrrolidine-3-carboxamide (261)

261

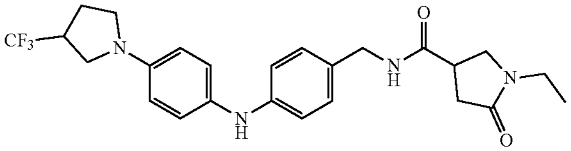

The title compound 261 (9.4 mg) was prepared in a total yield of 32.9% as a blue solid from 4-(aminomethyl)-N-(4-(3-(trifluoromethyl)pyrrolidin-1-yl)phenyl)aniline (20 mg, 0.06 mmol), 1-ethyl-5-oxopyrrolidine-3-carboxylic acid (11.8 mg, 0.08 mmol), DIEA (23.2 mg, 0.18 mmol), HATU (30.4 mg, 0.08 mmol) according to the procedure for 209. $^1$H NMR (400 MHz, Methanol-$d_4$) δ 7.49-7.43 (m, 2H), 7.26-7.19 (m, 2H), 7.18-7.09 (m, 4H), 4.87 (s, 1H), 4.39-4.27 (m, 2H), 3.71-3.49 (m, 3H), 3.46-3.32 (m, 4H), 3.22-3.11 (m, 2H), 2.60 (d, J=8.1 Hz, 2H), 1.41-1.25 (m, 3H), 1.16-1.07 (m, 3H). Mass (m/z): 475.3 [M+H]$^+$.

N-hydroxy-2-(4-methyl-3-oxopiperazin-1-yl)-N-(4-((4-(piperidin-1-yl)phenyl)amino)-2-(trifluoromethyl)benzyl)acetamide (262)

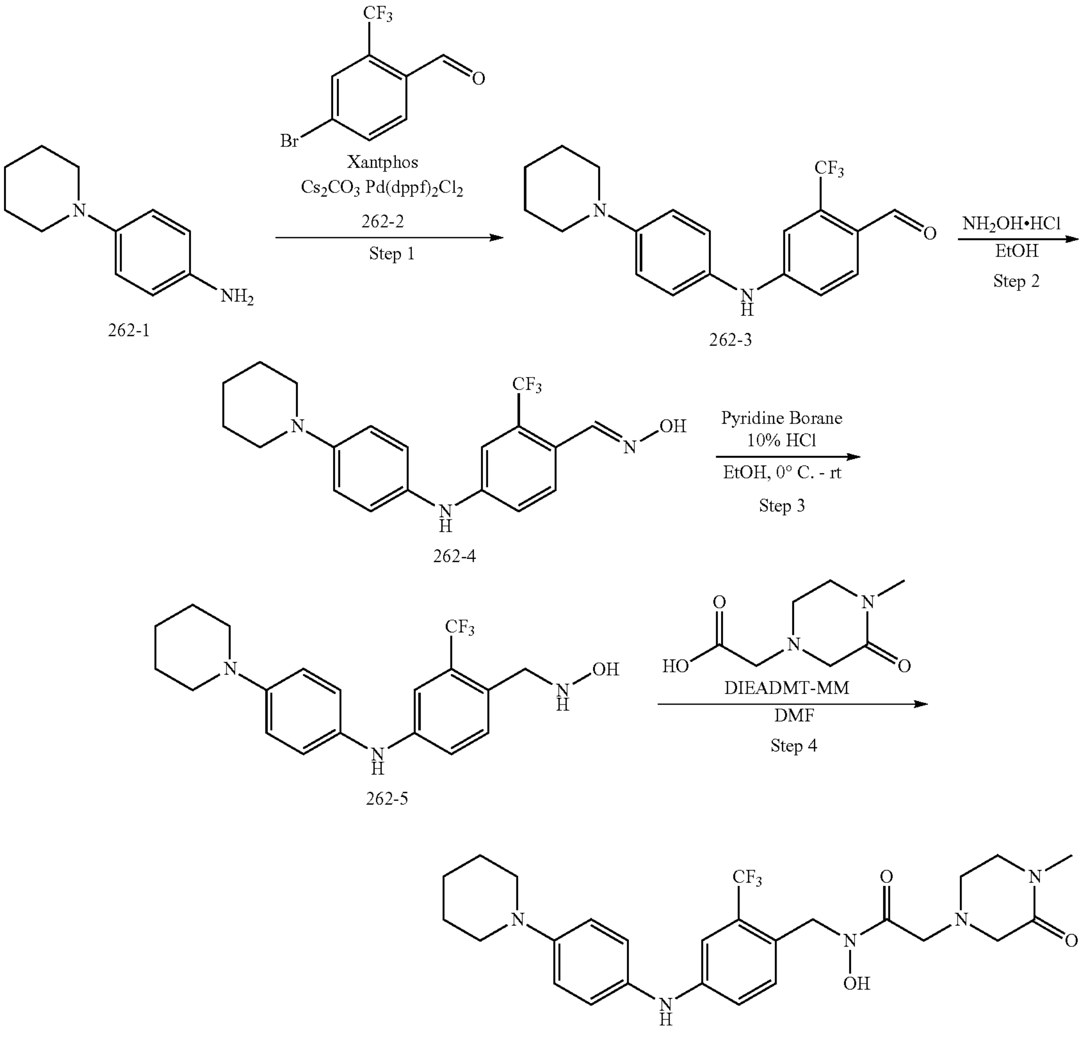

262

Step 1. The title compound 262-3 (2.1 g) was prepared in a total yield of 60.3% as a yellow oil from 4-(piperidin-1-yl)aniline (1.76 g, 10.0 mmol), 4-bromo-2-(trifluoromethyl) benzaldehyde (2.53 g, 10.0 mmol), Pd(dppf)$_2$Cl$_2$ (73.1 mg, 0.2 mmol), Xantphos (231.6 mg, 0.4 mmol), $Cs_2CO_3$ (4.89 g, 15 mmol) according to the procedure for 137-3. Mass (m/z): 349.3 $[M+H]^+$.

Step 2. The title compound 262-4 (1.4 g) was prepared in a total yield of 64.0% as a yellow solid from 4-((4-(piperidin-1-yl)phenyl)amino)-2-(trifluoromethyl)benzaldehyde (2.1 g, 6.03 mmol), Hydroxylamine hydrochloride (625 mg, 9.05 mmol) according to the procedure for 137-4. Mass (m/z): 364.2$[M+H]^+$.

Step 3. The title compound 262-5 (720 mg) was prepared in a total yield of 50.0% as a yellow solid from (E)-4-((4-(piperidin-1-yl)phenyl)amino)-2-(trifluoromethyl)benzaldehyde oxime (720 mg, 2.0 mmol), Borane-pyridine complex (370 mg, 0.4 mmol) and 15 mL of 10% HCl according to the procedure for 137-5. Mass (m/z): 366.2 $[M+H]^+$.

Step 4. The title compound 262 (30.0 mg) was prepared in a total yield of 38.5% as a yellow solid form 4-((hydroxyamino)methyl)-N-(4-(piperidin-1-yl)phenyl)-3-(trifluoromethyl)aniline (55 mg, 0.15 mmol), 2-(4-methyl-3-oxopiperazin-1-yl)acetic acid hydrochloride (41 mg, 0.20 mmol), DMT-MM (65 mg, 0.23 mmol), DIEA (58 mg, 0.45 mmol) and DMF (1.0 mL) according to the procedure for 137. $^1$H NMR (400 MHz, Methanol-d$_4$) δ 7.30-7.03 (m, 7H), 4.88-4.85 (m, 7H), 4.41 (s, 2H), 3.49-3.43 (m, 2H), 3.19 (s, 2H), 3.17-3.09 (m, 4H), 2.81 (t, J=5.5 Hz, 2H), 2.39 (s, 3H), 1.78 (p, J=5.9 Hz, 4H), 1.64-1.54 (m, 7H). Mass (m/z): 520.3 $[M+H]^+$.

N-hydroxy-2-(4-methyl-2-oxopiperazin-1-yl)-N-(4-((4-(4-(trifluoromethyl)piperidin-1-yl)phenyl)amino) benzyl)acetamide (263)

263

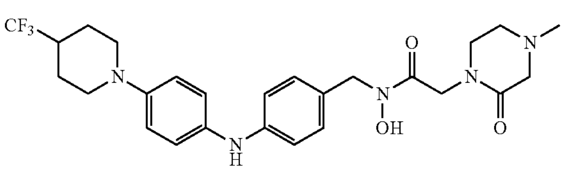

The title compound 263 (19.0 mg) was prepared in a total yield of 24.4% as a yellow solid form 4-((hydroxyamino) methyl)-N-(4-(4-(trifluoromethyl)piperidin-1-yl)phenyl) aniline (55 mg, 0.15 mmol), 2-(4-methyl-3-oxopiperazin-1-yl)acetic acid hydrochloride (41 mg, 0.20 mmol), DMT-MM (65 mg, 0.23 mmol), DIEA (58 mg, 0.45 mmol) and DMF (1.0 mL) according to the procedure for 137. $^1$H NMR (400 MHz, Methanol-d$_4$) δ 7.17-6.87 (m, 8H), 4.64 (s, 2H), 4.35 (s, 2H), 3.66-3.52 (m, 2H), 3.47-3.38 (m, 2H), 3.20-3.15 (m, 2H), 2.80 (t, J=5.4 Hz, 2H), 2.73-2.57 (m, 2H), 2.39 (d, J=s, 3H), 2.31-2.21 (m, 1H), 2.00-1.90 (m, 2H), 1.78-1.66 (m, 2H). Mass (m/z): 260.7 $[M/2+H]^+$.

1-ethyl-5-oxo-N-((5-((4-(4-(trifluoromethyl)piperidin-1-yl)phenyl)amino)pyridin-2-yl)methyl)pyrrolidine-3-carboxamide (264)

264

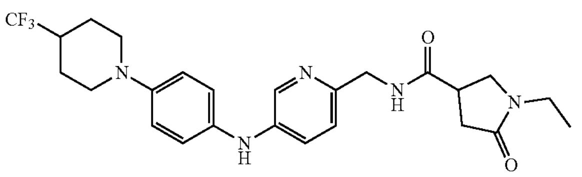

The title compound 264 (23.6 mg) was prepared in a total yield of 48.2% as a blue solid from 6-(aminomethyl)-N-(4-(4-(trifluoromethyl)piperidin-1-yl)phenyl)pyridin-3-amine (35 mg, 0.1 mmol), 1-ethyl-5-oxopyrrolidine-3-carboxylic acid (15.7 mg, 0.1 mmol), DIEA (38.7 mg, 0.3 mmol), HATU (38.0 mg, 0.1 mmol) according to the procedure for 209. $^1$H NMR (400 MHz, Methanol-d$_4$) δ 8.27-8.09 (m, 1H), 7.99-7.86 (m, 1H), 7.71-7.54 (m, 1H), 7.46-7.13 (m, 4H), 4.81 (s, 2H), 4.60-4.43 (m, 2H), 3.83-3.55 (m, 4H), 3.29-3.19 (m, 4H), 2.67-2.48 (m, 3H), 2.22-2.07 (m, 2H), 1.98-1.81 (m, 2H), 1.11 (t, J=7.3 Hz, 3H). Mass (m/z): 490.3 $[M+H]^+$.

2-(4-methylpiperazin-1-yl)-N-(4-(pyrimidin-5-ylamino)benzyl)acetamide (265)

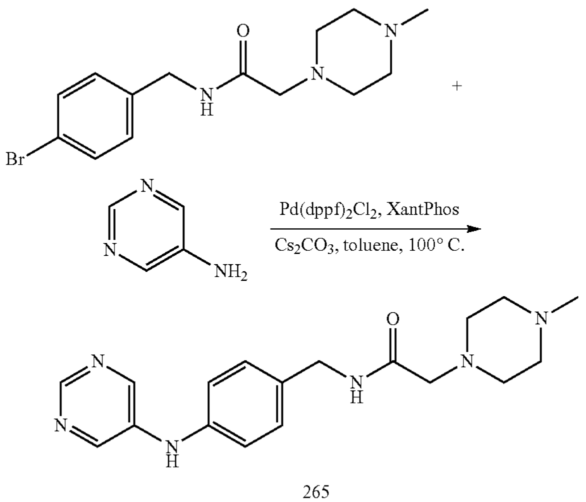

265

The title compound 265 (6.7 mg) was prepared in a total yield of 12.9% as a white solid from N-(4-bromobenzyl)-2-(4-methylpiperazin-1-yl)acetamide (50 mg, 0.153 mmol) and pyrimidin-5-amine (22 mg, 0.230 mmol) according to the procedure for 232. $^1$H NMR (400 MHz, Methanol-d$_4$) δ 8.55 (d, J=0.5 Hz, 1H), 8.51-8.47 (m, 2H), 7.31-7.24 (m, 2H), 7.16-7.08 (m, 2H), 4.37 (s, 2H), 3.10 (s, 2H), 2.64 (d, J=15.7 Hz, 8H), 2.39 (s, 3H). Mass (m/z): 341.3 $[M+H]^+$.

1-methyl-N-(4-((4-(4-(trifluoromethyl)piperidin-1-yl)phenyl)amino)benzyl)-1H-Imidazole-5-carboxamide (266)

266

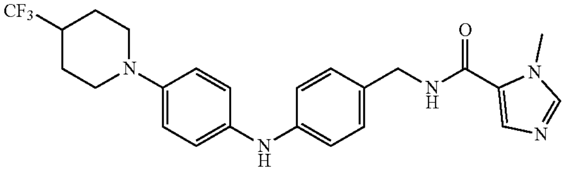

The title compound 266 (12.8 mg) was prepared in a total yield of 32.6% as a white solid from 4-(aminomethyl)-N-(4-(4-(trifluoromethyl)piperidin-1-yl)phenyl)aniline (30 mg, 0.086 mmol) and 1-methyl-1H-imidazole-5-carboxylic acid (14 mg, 0.112 mmol) according to the procedure for 203. $^{1}$H NMR (400 MHz, DMSO-$d_6$) δ 8.69 (t, J=6.0 Hz, 1H), 7.78 (s, 1H), 7.71 (s, 1H), 7.59 (d, J=1.2 Hz, 1H), 7.08 (d, J=8.4 Hz, 2H), 6.98-6.93 (m, 2H), 6.89-6.83 (m, 4H), 4.27 (d, J=6.0 Hz, 2H), 3.80 (s, 3H), 3.61-3.55 (m, 2H), 2.59 (td, J=12.4, 2.4 Hz, 2H), 1.88-1.82 (m, 2H), 1.54 (qd, J=12.6, 4.0 Hz, 3H). Mass (m/z): 458.3 $[M+H]^+$.

6-chloro-N-(4-((4-(4,4-difluoropiperidin-1-yl)phenyl)amino)benzyl)-N-hydroxypyrazine-2-carboxamide (267)

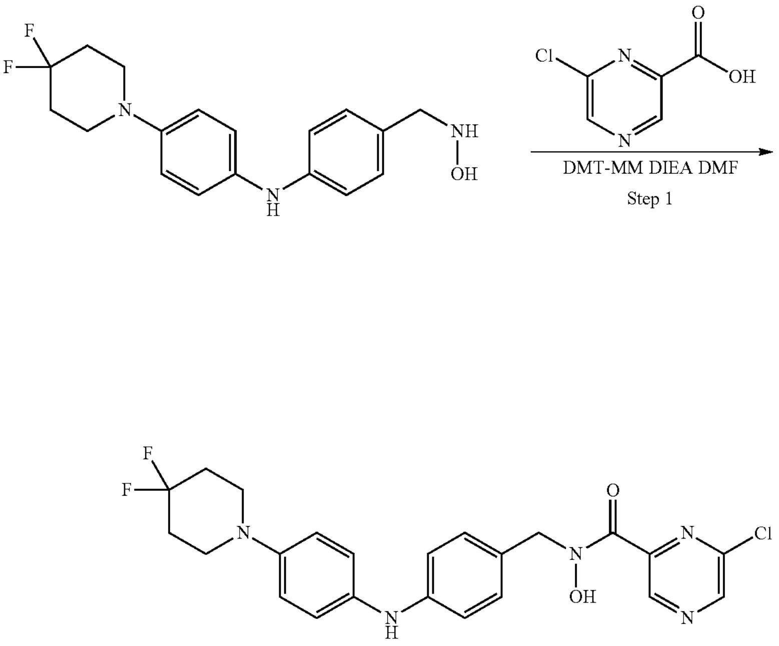

267

The title compound 267 (11.4 mg) was prepared in a yield of 4.01% as a pink powder from 4-(4,4-difluoropiperidin-1-yl)-N-(4-((hydroxyamino)methyl)phenyl)aniline (200 mg, 0.60 mmol) and 6-chloropyrazine-2-carboxylic acid (105 mg, 0.66 mmol), according to the procedure for compound 290. $^{1}$H NMR (400 MHz, Methanol-$d_4$) δ 7.38-7.24 (m, 2H), 7.11 (d, J=8.4 Hz, 3H), 7.02 (t, J=9.0 Hz, 5H), 5.01 (s, 2H), 4.11-3.97 (m, 4H), 2.18 (q, J=14.2, 11.8 Hz, 4H). $^{19}$F NMR (376 MHz, Methanol-$d_4$) δ −99.35. LC-MS (m/z) 474.2 $[M+H]^+$.

N-(4-((4-(4,4-difluoropiperidin-1-yl)phenyl)amino)benzyl)-N-hydroxy-2-(3-(trifluoromethyl)piperazin-1-yl)acetamide (268)

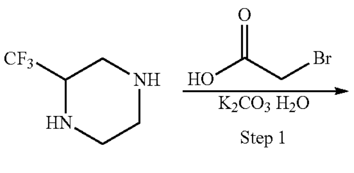

-continued

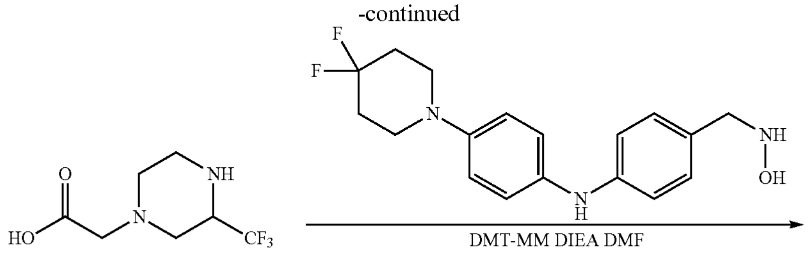

268-1

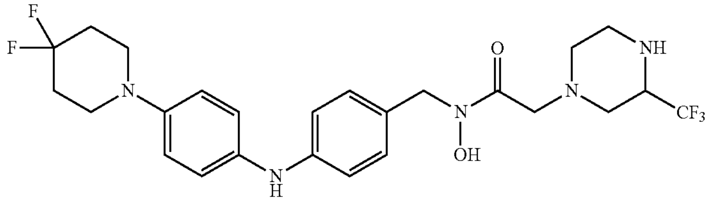

268

Step 1. 2-(3-(trifluoromethyl)piperazin-1-yl)acetic acid (268-1) (190 mg) was prepared as a yellow powder from 2-(trifluoromethyl)piperazine (150 mg, 0.97 mmol) and 2-bromoacetic acid (162 mg, 1.17 mmol), according to the procedure for 2-(4-(2,2,2-trifluoroethyl)piperazin-1-yl)acetic acid (246-1). The residue was used in next step directly without further purification after concentrated and dry in vacuo. LC-MS (m/z) 213.4 $[M+H]^+$.

Step 2 The title compound 268 (22.0 mg) was prepared in a yield of 34.26% as a white powder from 4-(4,4-difluoropiperidin-1-yl)-N-(4-((hydroxyamino)methyl)phenyl)aniline (40 mg, 0.12 mmol) and 2-(3-(trifluoromethyl)piperazin-1-yl)acetic acid (268-1) (31 g, 0.14 mmol), according to the procedure for compound 290. $^1$H NMR (400 MHz, Methanol-$d_4$) δ 7.23 (d, J=7.8 Hz, 2H), 7.12 (d, J=8.3 Hz, 2H), 7.03 (t, J=8.9 Hz, 4H), 4.73 (s, 2H), 3.58 (d, J=17.6 Hz, 3H), 3.20 (d, J=11.1 Hz, 1H), 3.07 (d, J=2.6 Hz, 2H), 3.05-2.97 (d, J=24.0 Hz, 2H), 2.94 (d, J=2.6 Hz, 2H), 2.44-2.26 (m, 2H), 2.24-2.09 (m, 4H). LC-MS (m/z) 578.4 $[M+H]^+$.

4-(dimethylamino)-N-hydroxy-N-(4-((4-(piperidin-1-yl)phenyl)amino)benzyl)butanamide (269)

269

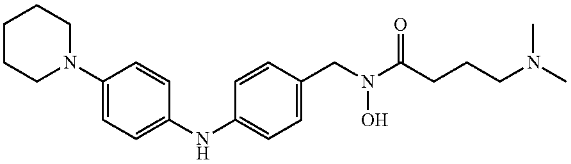

$^1$H NMR (400 MHz, Methanol-$d_4$) δ 7.30-6.79 (m, 8H), 4.66 (s, 2H), 3.06 (br m, 4H), 3.04-2.96 (m, 2H), 2.75 (s, 6H), 2.64 (t, J=6.8 Hz, 2H), 2.04-1.94 (m, 2H), 1.74 (br s, 4H), 1.59 (br s, 2H). Mass (m/z): 411.3 $[M+H]^+$.

N-(4-((4-(6-fluoropyridin-3-yl)phenyl)amino)benzyl)-N-hydroxy-2-morpholinoacetamide (270)

270

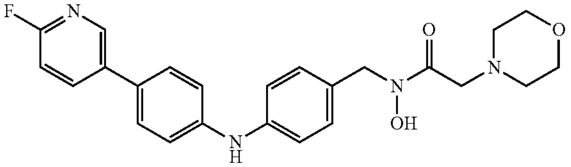

$^1$H NMR (400 MHz, Methanol-$d_4$) δ 8.39 (s, 1H), 8.14 (m, 1H), 7.51 (d, J=8.6 Hz, 2H), 7.26 (d, J=8.4 Hz, 2H), 7.21-7.08 (m, 5H), 4.73 (s, 2H), 4.29 (s, 2H), 3.96 (br s, 4H), 3.41 (br s, 4H). Mass (m/z): 437.3 $[M+H]^+$.

N-(4-((4-cyclohexylphenyl)amino)benzyl)-N-hydroxy-2-(4-methylpiperazin-1-yl)acetamide (271)

271

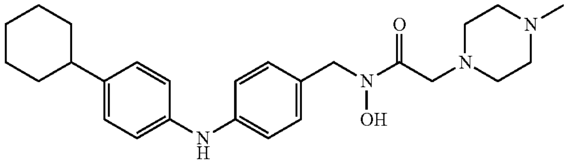

$^1$H NMR (400 MHz, Methanol-$d_4$) δ 7.16 (d, J=8.4 Hz, 2H), 7.08 (d, J=8.4 Hz, 2H), 6.99 (dd, J=8.4, 3.2 Hz, 4H), 4.65 (s, 2H), 3.56 (s, 2H), 3.19 (br s, 4H), 2.89 (br s, 4H), 2.79 (s, 3H), 2.52-2.34 (m, 1H), 1.91-1.67 (m, 6H), 1.49-1.34 (m, 4H). Mass (m/z): 437.3 $[M+H]^+$.

N-hydroxy-1-methyl-N-(4-((4-(4-(trifluoromethyl) piperidin-1-yl)phenyl)amino)benzyl)-1H-imidazole-5-carboxamide (272)

272

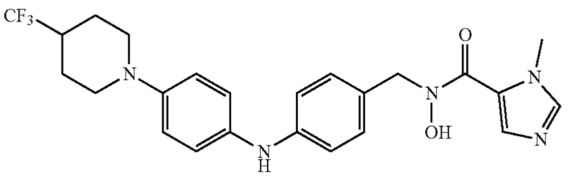

The tide compound 272 (20.1 mg) was prepared in a total yield of 51.7% as a white solid from 4-((hydroxyamino) methyl)-N-(4-(4-(trifluoromethyl)piperidin-1-yl)phenyl) aniline (30 mg, 0.082 mmol) and 1-methyl-1H-imidazole-5-carboxylic acid (14 mg, 0.107 mmol) according to the procedure for 174. $^1$H NMR (400 MHz, Methanol-$d_4$) δ 7.70 (d, J=10.0 Hz, 2H), 7.18 (d, J=8.0 Hz, 2H), 7.04-6.89 (m, 6H), 4.77 (s, 2H), 3.89 (s, 3H), 3.57 (d, J=11.2 Hz, 2H), 2.70-2.54 (m, 2H), 2.24 (ddd, J=12.4, 8.2, 4.0 Hz, 1H), 1.98-1.91 (m, 2H), 1.69 (dd, J=12.4, 4.0 Hz, 2H). Mass (m/z): 474.3 [M+H]$^+$.

1-ethyl-N-hydroxy-2-oxo-N-(4-((4-(4-(trifluoromethyl)piperidin-1-yl)phenyl)amino)benzyl)piperidine-4-carboxamide (273)

273

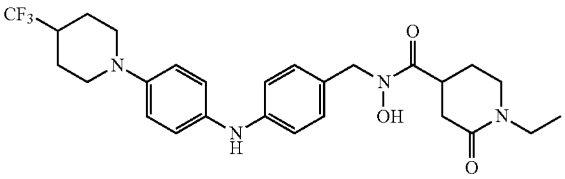

The title compound 273 (14.5 mg) was prepared in a total yield of 34.0% as a white solid from 4-((hydroxyamino) methyl)-N-(4-(4-(trifluoromethyl)piperidin-1-yl)phenyl) aniline (30 mg, 0.082 mmol) and 1-ethyl-2-oxopiperidine-4-carboxylic acid (14 mg, 0.107 mmol) according to the procedure for 174. $^1$H NMR (400 MHz, Methanol-$d_4$) δ 7.16-6.88 (m, 8H), 4.73-4.52 (m, 2H), 3.61 (s, 2H), 3.46-3.33 (m, 5H), 2.70 (d, J=29.6 Hz, 2H), 2.47 (d, J=8.0 Hz, 1H), 2.27 (dtd, J=12.4, 8.4, 4.0 Hz, 1H), 2.06-1.90 (m, 4H), 1.75-1.65 (m, 2H), 1.11 (td, J=7.2, 1.6 Hz, 3H). Mass (m/z): 519.4 [M+H]$^+$.

N-((5-((4-(4,4-difluoropiperidin-1-yl)phenyl)amino)-3-fluoropyridin-2-yl)methyl)-N-hydroxy-2-(4-methyl-3-oxopiperazin-1-yl)acetamide (274)

274

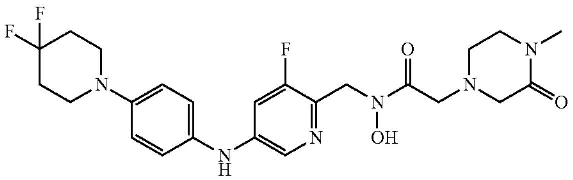

The title compound 274 (11.6 mg) was prepared in a total yield of 26.9% as a white solid from N-(4-(4,4-difluoropiperidin-1-yl)phenyl)-5-fluoro-6-((hydroxyamino)methyl) pyridin-3-amine (30 mg, 0.085 mmol) and 2-(4-methyl-3-oxopiperazin-1-yl)acetic acid hydrochloride (23 mg, 0.111 mmol) according to the procedure for 174. $^1$H NMR (400 MHz, Methanol-$d_4$) δ 7.13-6.98 (m, 6H), 4.54 (d, J=17.2 Hz, 2H), 3.54 (d, J=2.6 Hz, 2H), 3.40 (s, 2H), 3.35 (d, J=2.6 Hz, 3H), 2.95 (d, J=2.6 Hz, 3H), 2.92-2.85 (m, 2H), 2.15-2.02 (m, 5H), 1.35-1.27 (m, 2H). Mass (m/z): 507.3 [M+H]$^+$.

1-(cyclopropanecarbonyl)-N-hydroxy-N-(4-((4-(4-(trifluoromethyl)piperidin-1-yl)phenyl)amino)benzyl)pyrrolidine-3-carboxamide (275)

275

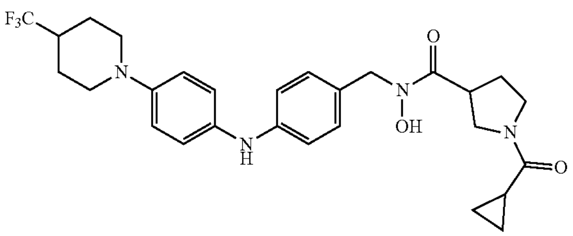

The title compound 275 (13.1 mg) was prepared in a total yield of 22.3% as a white solid according to the procedure for compound 108. $^1$H NMR (400 MHz, Methanol-$d_4$) δ 7.47-6.58 (m, 8H), 4.67 (s, 2H), 3.96-3.79 (m, 2H), 3.75-3.66 (m, 2H), 3.65-3.50 (m, 4H), 3.41 (m, 1H), 2.40-2.11 (m, 3H), 2.11-1.88 (m, 2H), 1.84-1.65 (m, 3H), 0.99-0.73 (m, 4H). Mass (m/z): 531.3[M+H]$^+$ N-hydroxy-1-isopropyl-N-(4-((4-(2-methylpiperidin-1-yl)phenyl)amino)benzyl) piperidine-4-carboxamide (276)

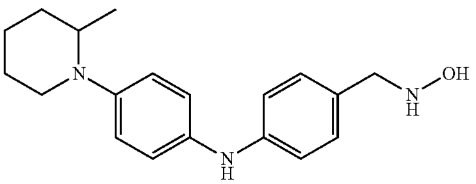

+

-continued

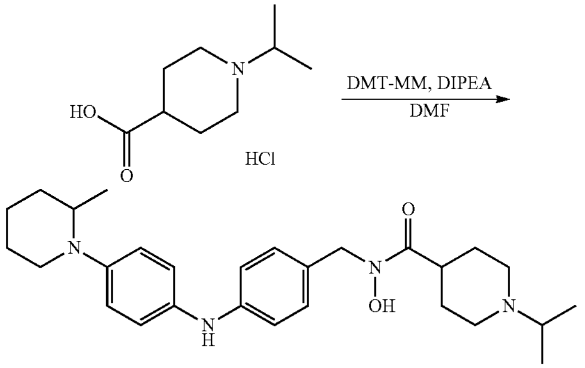

276

The title compound 276 (13.5 mg) was prepared in a total yield of 30.3% as a white solid from 4-((hydroxyamino) methyl)-N-(4-(2-methylpiperidin-1-yl)phenyl)aniline (30 mg, 0.096 mmol) and 1-isopropylpiperidine-4-carboxylic acid (26 mg, 0.125 mmol) according to the procedure for 179. $^1$H NMR (400 MHz, Methanol-$d_4$) δ 7.17 (s, 8H), 4.67 (s, 2H), 3.48 (dd, J=11.5, 5.3 Hz, 3H), 3.25 (dd, J=9.3, 5.2 Hz, 1H), 3.14-3.00 (m, 3H), 2.17-1.71 (m, 10H), 1.59 (s, 2H), 1.34 (d, J=6.6 Hz, 6H), 0.95 (d, J=6.2 Hz, 3H). Mass (n/z): 465.3 $[M+H]^+$.

N-hydroxy-N-(4-((4-(4-(trifluoromethyl)piperidin-1-yl)phenyl)amino)benzyl)azetidine-3-carboxamide (277)

277

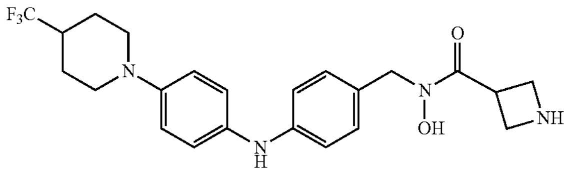

The title compound 277 (86.1 mg) was prepared in a total yield of 42.8% as a white solid according to the procedure for compound 108. $^1$H NMR (400 MHz, Methanol-$d_4$) δ 7.21-6.86 (m, 8H), 4.63 (s, 2H), 4.32-4.13 (m, 4H), 3.27-3.18 (m, 41H), 2.37-2.19 (m, 211), 2.03-1.91 (m, 2H), 1.81-1.63 (m, 2H). Mass (m/z): 449.3 $[M+H]^+$ N-hydroxy-N-(4-((4-(4-(trifluoromethyl)piperidin-1-yl)phenyl)amino)benzyl)pyrrolidine-3-carboxamide (278)

278

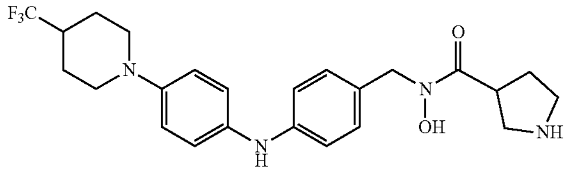

The title compound 278 (90.1 mg) was prepared in a total yield of 44.5% as a white solid according to the procedure for compound 108. $^1$H NMR (400 MHz, Methanol-$d_4$) δ 7.23-6.81 (m, 8H), 4.64 (s, 2H), 3.88-3.70 (m, 2H), 3.70-3.38 (m, 6H), 2.43-2.19 (m, 3H), 2.19-2.07 (m, 1H), 1.99-1.93 (m, 2H), 1.78-1.65 (m, 2H). Mass (m/z): 463.2 $[M+H]^+$.

1-acetyl-N-hydroxy-N-(4-((4-(4-(trifluoromethyl)piperidin-1-yl)phenyl)amino)benzyl)azetidine-3-carboxamide (279)

279

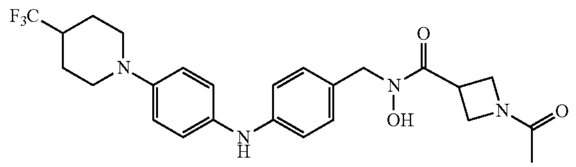

The title compound 279 (15.1 mg) was prepared in a total yield of 31.6% as a white solid according to the procedure for compound 108. $^1$H NMR (400 MHz, Methanol-$d_4$) δ 7.33-6.68 (m, 8H), 4.67 (s, 2H), 4.40-4.27 (m, 2H), 4.18-3.99 (m, 2H), 3.83-3.46 (m, 4H), 2.39-2.20 (m, 2H), 2.10-1.91 (m, 2H), 1.85 (s, 3H), 1.81-1.64 (m, 2H). Mass (m/z): 491.3 $[M+H]^+$ 1-(cyclopropanecarbonyl)-N-hydroxy-N-(4-((4-(4-(trifluoromethyl)piperidin-1-yl)phenyl)amino)benzyl)azetidine-3-carboxamide (280)

280

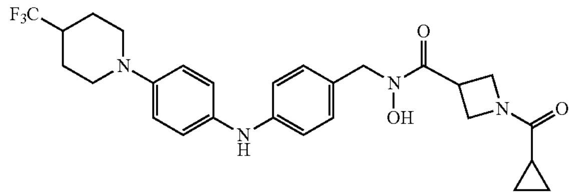

The title compound 280 (17.5 mg) was prepared in a total yield of 32.7% as a white solid according to the procedure for compound 108. $^1$H NMR (400 MHz, Methanol-$d_4$) δ 7.51-6.47 (m, 8H), 4.66 (s, 2H), 4.50-4.38 (m, 2H), 4.16-4.02 (m, 2H), 3.90-3.81 (m, 4H), 2.39-2.18 (m, 2H), 1.98 (br s, 2H), 1.72 (br s, 2H), 1.60-1.50 (m, 1H), 0.91-0.74 (m, 4H). Mass (m/z): 517.3 $[M+H]^+$ N-hydroxy-1-isopropyl-N-(4-((4-(4-(trifluoromethyl)piperidin-1-yl)phenyl)amino)benzyl)piperidine-4-carboxamide (281)

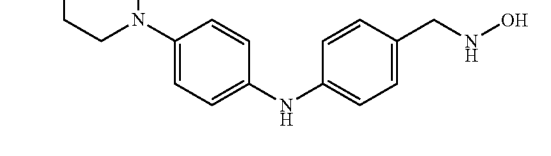

+

-continued

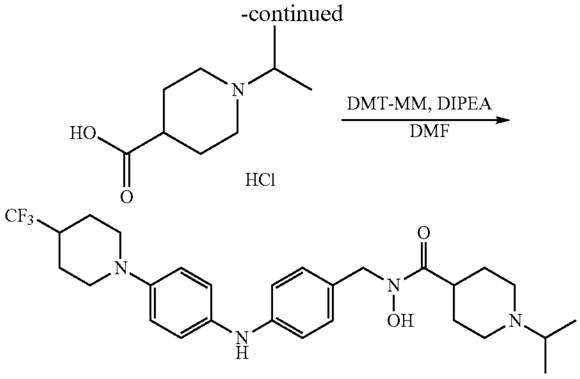

281

The title compound 281 (14.0 mg) was prepared in a total yield of 32.9% as a white solid from 4-((hydroxyamino)methyl)-N-(4-(4-(trifluoromethyl)piperidin-1-yl)phenyl)aniline (30 mg, 0.082 mmol) and 1-isopropylpiperidine-4-carboxylic acid hydrochloride (22 mg, 0.107 mmol) according to the procedure for 179. $^1$H NMR (400 MHz, Methanol-$d_4$) δ 7.12 (s, 8H), 4.65 (s, 2H), 4.26 (s, 1H), 3.53-3.44 (m, 31H), 3.17-3.04 (m, 2H), 2.66 (d, J=63.8 Hz, 2H), 2.27 (dq, J=8.4, 5.0, 4.4 Hz, 1H), 2.04 (dd, J=54.4, 9.9 Hz, 6H), 1.71 (d, J=12.0 Hz, 2H), 1.40-1.37 (m, 2H), 1.37-1.34 (m, 6H). Mass (m/z): 519.3 $[M+H]^+$.

N-hydroxy-1-isopropyl-N-(4-((4-(3-(trifluoromethyl)piperidin-1-yl)phenyl)amino)benzyl)piperidine-4-carboxamide (282)

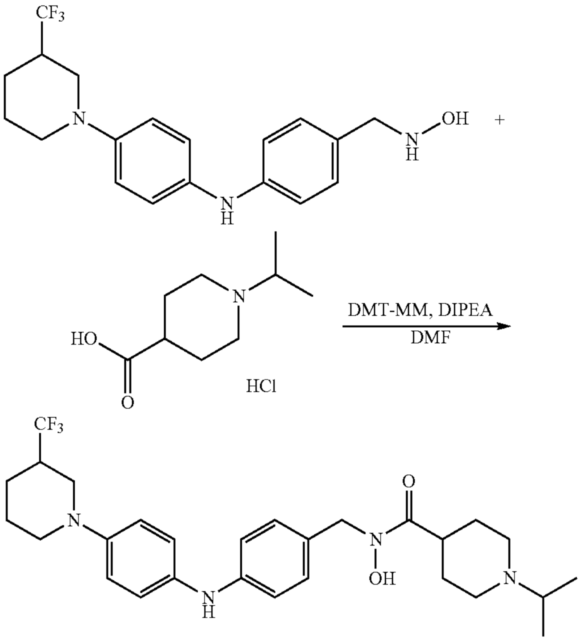

282

The title compound 282 (19.6 mg) was prepared in a total yield of 45.7% as a white solid from 4-((hydroxyamino)methyl)-N-(4-(3-(trifluoromethyl)piperidin-1-yl)phenyl)aniline (30 mg, 0.082 mmol) and 1-isopropylpiperidine-4-carboxylic acid hydrochloride (22 mg, 0.107 mmol) according to the procedure for 179. $^1$H NMR (400 MHz, Methanol-$d_4$) δ 7.17-6.81 (m, 8H), 4.65 (s, 2H), 3.50-3.43 (m, 3H), 3.10 (t, J=13.0 Hz, 2H), 2.52 (d, J=9.7 Hz, 4H), 2.00 (ddd, J=51.6, 24.7, 13.0 Hz, 7H), 1.72 (tdd, J=12.9, 8.7, 4.0 Hz, 1H), 1.38-1.36 (m, 2H), 1.34 (d, J=6.7 Hz, 6H). Mass (m/z): 519.3 $[M+H]^+$.

4-ethyl-1-(4-((3-fluoro-4-(4-(trifluoromethyl)piperidin-1-yl)phenyl)amino)-2-(trifluoromethyl)benzyl)piperazin-2-one (283)

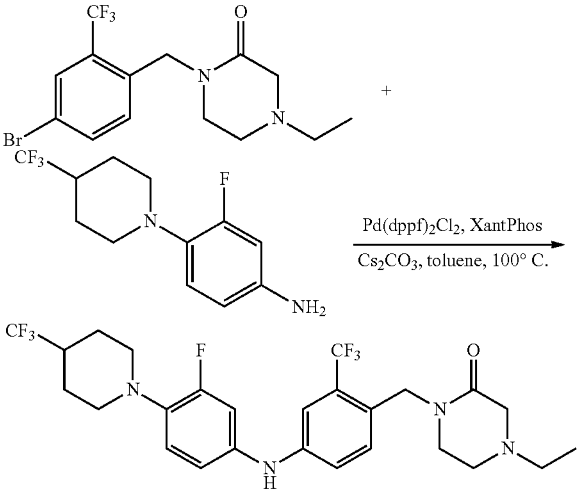

283

The title compound 283 (6.1 mg) was prepared in a total yield of 12% as a white solid from 1-(4-bromo-2-(trifluoromethyl)benzyl)-4-ethylpiperazin-2-one (50 mg, 0.137 mmol) and 3-fluoro-4-(4-(trifluoromethyl)piperidin-1-yl)aniline (47 mg, 0.178 mmol) according to the procedure for 232. $^1$H NMR (400 MHz, Methanol-$d_4$) δ 7.29 (d, J=10.1 Hz, 3H), 7.11 (s, 1H), 6.89 (s, 2H), 4.82-4.75 (m, 2H), 4.07 (s, 2H), 3.55 (td, J=21.4, 20.6, 10.4 Hz, 6H), 3.34 (td, J= 7.4, 1.4 Hz, 2H), 2.87 (s, 2H), 2.40-2.32 (m, 1H), 2.07-1.94 (m, 2H), 1.88-1.74 (m, 2H), 1.38 (td, J=7.3, 1.4 Hz, 3H). Mass (m/z): 547.3 $[M+H]^+$.

4-ethyl-1-(4-((3-fluoro-4-(4-(trifluoromethyl)piperidin-1-yl)phenyl)amino)benzyl) piperazin-2-one (284)

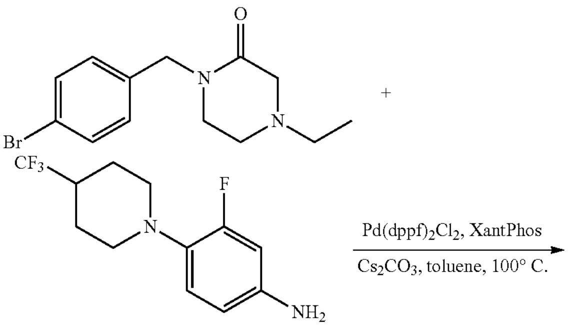

-continued

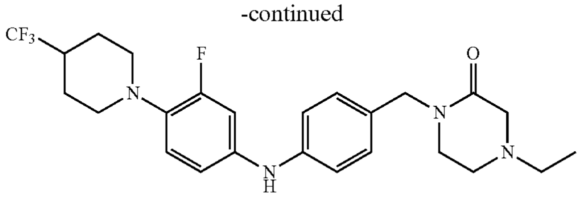

284

The title compound 284 (2.9 mg) was prepared in a total yield of 3.7% as a white solid from 1-(4-bromobenzyl)-4-ethylpiperazin-2-one (50 mg, 0.168 mmol) and 3-fluoro-4-(4-(trifluoromethyl)piperidin-1-yl)aniline (57 mg, 0.218 mmol) according to the procedure for 232.

$^1$H NMR (400 MHz, Methanol-$d_4$) δ 7.29 (d, J=10.1 Hz, 3H), 7.11 (s, 2H), 6.89 (s, 2H), 4.82-4.75 (m, 2H), 4.07 (s, 2H), 3.55 (td, J=21.4, 20.6, 10.4 Hz, 6H), 3.34 (td, J=7.4, 1.4 Hz, 2H), 2.87 (s, 2H), 2.40-2.32 (m, 1H), 2.07-1.94 (m, 2H), 1.88-1.74 (m, 2H), 1.38 (td, J=7.3, 1.4 Hz, 3H). Mass (m/z): 479.3 $[M+H]^+$.

N-hydroxy-1-methyl-2-oxo-N-(4-((4-(piperidin-1-yl)phenyl)amino)-2-(trifluoromethyl)benzyl)piperidine-4-carboxamide (285)

285

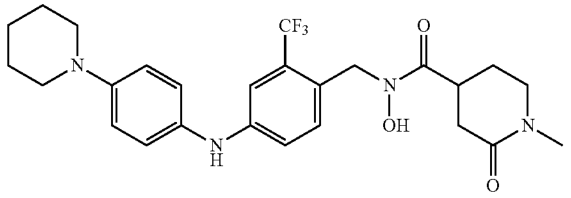

The title compound 285 (13.4 mg) was prepared in a total yield of 17.7% as a yellow solid form 4-((hydroxyamino)methyl)-N-(4-(piperidin-1-yl)phenyl)-3-(trifluoromethyl)aniline (55 mg, 0.15 mmol), 1-methyl-2-oxopiperidine-4-carboxylic acid (28 mg, 0.18 mmol), DMT-MM (48 mg, 0.18 mmol), DIEA (58 mg, 0.45 mmol) and DMF (1.0 mL) according to the procedure for 137. $^1$H NMR (400 MHz, Methanol-$d_4$) δ 7.53-7.47 (m, 2H), 7.41-7.32 (m, 3H), 7.27-7.19 (m, 2H), 4.86 (s, 2H), 3.64-3.57 (m, 4H), 3.42-3.38 (m, 1H), 3.28-3.22 (m, 2H), 2.94 (s, 3H), 2.53-2.50 (m, 2H), 2.11-1.97 (m, 6H). Mass (m/z): 505.3 $[M+H]^+$.

N-hydroxy-2-(4-methyl-3-oxopiperazin-1-yl)-N-(4-((4-(4-methylpiperidin-1-yl)phenyl)amino)benzyl)acetamide (286)

286

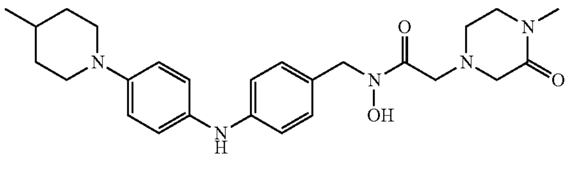

The title compound 286 (24.5 mg) was prepared in a total yield of 31.0% as a yellow solid form 4-((hydroxyamino)methyl)-N-(4-(4-methylpiperidin-1-yl)phenyl)aniline (54 mg, 0.17 mmol), 2-(4-methyl-3-oxopiperazin-1-yl)acetic acid hydrochloride (42 mg, 0.20 mmol), DMT-MM (55 mg, 0.20 mmol), DIEA (66 mg, 0.51 mmol) and DMF (1.0 mL) according to the procedure for 137. 1H NMR (400 MHz, Methanol-d4) δ 7.21-6.87 (m, 8H), 4.63 (s, 2H), 3.56-3.43 (m, 4H), 3.39 (t, J=5.3 Hz, 2H), 3.29-3.26 (m, 2H), 2.94 (s, 3H), 2.87 (t, J=5.2 Hz, 2H), 2.79-2.54 (m, 2H), 1.84-1.73 (m, 2H), 1.56-1.47 (m, 1H), 1.44-1.32 (m, 2H), 0.99 (d, J=6.4 Hz, 3H). Mass (m/z): 466.2 $[M+H]^+$.

N-hydroxy-2,4-dimethyl-N-(4-((4-(4-(trifluormethyl)piperidin-1-yl)phenyl)amino)benzyl)oxazole-5-carboxamide (287)

287

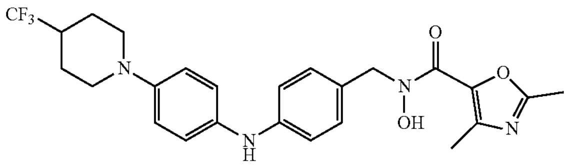

The title compound 287 (15.0 mg) was prepared in a total yield of 37.4% as a white solid from 4-((hydroxyamino)methyl)-N-(4-(4-(trifluoromethyl)piperidin-1-yl)phenyl)aniline (30 mg, 0.082 mmol) and 2,4-dimethyloxazole-5-carboxylic acid (15 mg, 0.107 mmol) according to the procedure for 174. $^1$H NMR (400 MHz, Methanol-$d_4$) δ 7.06 (d, J=89.8 Hz, 8H), 3.99 (d, J=2.6 Hz, 2H), 2.48 (d, J=2.6 Hz, 2H), 2.39 (dd, J=6.4, 2.7 Hz, 3H), 2.29 (dd, J=10.8, 2.6 Hz, 5H), 1.98 (d, J=20.6 Hz, 3H), 1.75-1.64 (m, 2H). Mass (m/z): 489.3 $[M+H]^+$.

2,4-dimethyl-N-(4-((4-(4-(trifluoromethyl)piperidin-1-yl)phenyl)amino)benzyl) oxazole-5-carboxamide (288)

288

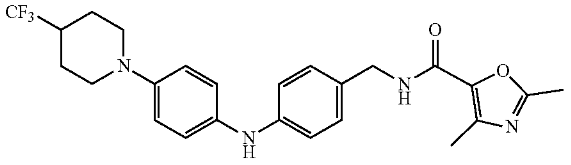

The title compound 288 (8.8 mg) was prepared in a total yield of 21.7% as a white solid from 4-(aminomethyl)-N-(4-(4-(trifluoromethyl)piperidin-1-yl)phenyl)aniline (30 mg, 0.086 mmol) and 2,4-dimethyloxazole-5-carboxylic acid (16 mg, 0.112 mmol) according to the procedure for 203. $^1$H NMR (400 MHz, DMSO-$d_6$) δ 8.69 (t, J=6.0 Hz, 1H), 7.78 (s, 1H), 7.08 (d, J=8.4 Hz, 2H), 6.98-6.93 (m, 2H), 6.89-6.83 (m, 4H), 4.27 (d, J=6.0 Hz, 2H), 3.61-3.55 (m, 2H), 2.59 (td, J=12.4, 2.4 Hz, 2H), 2.40 (s, 3H), 2.29 (s, 3H), 1.88-1.82 (m, 2H), 1.54 (qd, J=12.6, 4.0 Hz, 3H). Mass (m/z): 473.3 $[M+H]^+$.

N-ethyl-2-(4-methyl-3-oxopiperazin-1-yl)-N-(4-((4-(4-(trifluoromethyl)piperidin-1-yl)phenyl)amino)benzyl)acetamide (289)

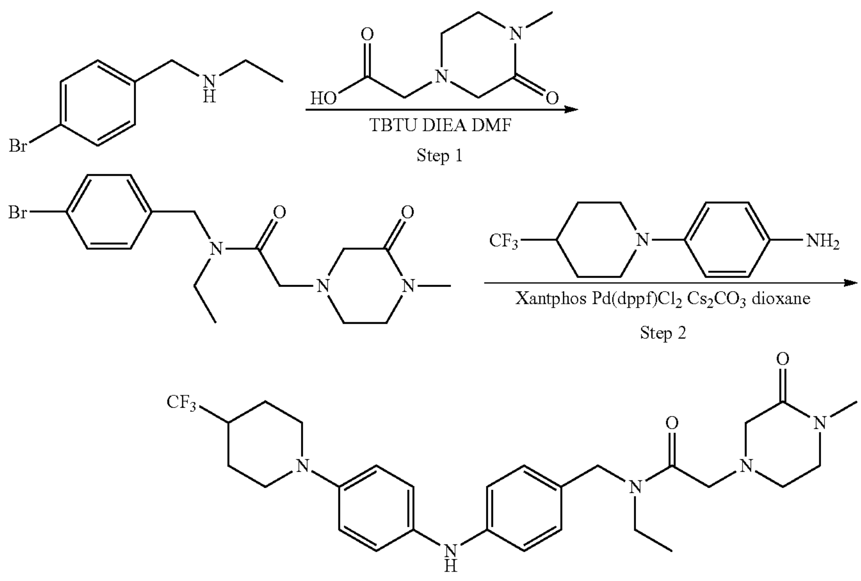

289

Step 1. To a solution of N-(4-bromobenzyl)ethanamine (200 mg, 0.93 mmol, 1.0 equivs) and 2-(4-methyl-3-oxopiperazin-1-yl)acetic acid (177 mg, 1.03 mmol, 1.1 equivs) in super dry N,N-dimethylformamide (5 mL), 2-(1H-benzo[d][1,2,3]triazol-1-yl)-1,1,3,3-tetramethylisouronium tetrafluoroborate (390 mg, 1.21 mmol, 1.3 equivs) and N-ethyl-N-isopropylpropan-2-amine (463 mmL, 2.80 mmol, 3.0 equivs) was added under argon atmosphere at room temperature and stirred for overnight. The reaction was diluted with water (10 mL) and extracted with dichloromethane (5 mL) 3 times. The organic layer was combined and washed with water, sat·$NH_4Cl$(aq), and brine respectively. Then dried over $MgSO_4$, filtered, and concentrated under reduced pressure. The residue N-(4-bromobenzyl)-N-ethyl-2-(4-methyl-3-oxopiperazin-1-yl)acetamide (289-1) was used in next step directly without further purification after concentrated and dry in vacuo. LC-MS (n/z) 368.2, 370.1 $[M+H]^+$.

Step 2. The title compound 289 (38.2 mg) was prepared in a yield of 17.55% as a white powder from 4-(4-(trifluoromethyl)piperidin-1-yl)aniline (100 mg, 0.41 mmol) and N-(4-bromobenzyl)-N-ethyl-2-(4-methyl-3-oxopiperazin-1-yl)acetamide (151 mg, 0.41 mmol), according to the procedure for compound 253. $^1$H NMR (400 MHz, Chloroform-d) 7.30-6.37 (br, 8H), 4.76 (s, 3H), 4.65-4.19 (br, 3H), 3.75-3.32 (m, 3H), 2.75 (dd, J=6.3, 4.8 Hz, 2H), 2.69 (dd, J=6.2, 4.8 Hz, 2H), 2.24-2.09 (m, 2H), 1.94-1.78 (m, 3H), 1.60 (d, J=13.1 Hz, 3H), 1.09-1.02 (m, 3H), 0.97 (t, J=7.1 Hz, 3H). LC-MS (m/z) 532.5 $[M+H]^+$.

1-ethyl-5-oxo-N-(4-((4-(4-(trifluoromethyl)piperidin-1-yl)phenyl)amino)benzyl)pyrrolidine-3-carboxamide (290)

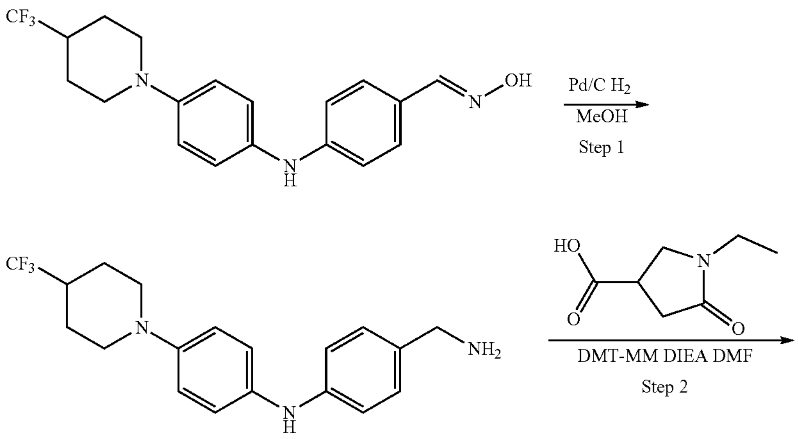

290-1

-continued

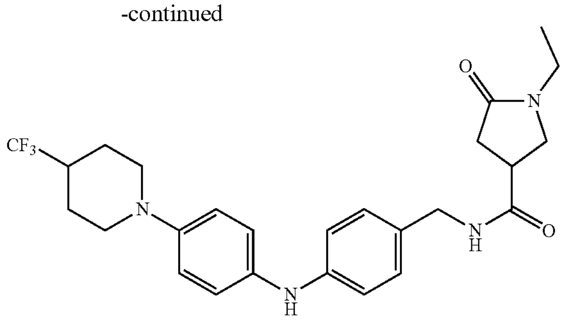

290

Step 1. To a solution of (E)-4-((4-(4-(trifluoromethyl)piperidin-1-yl)phenyl)amino)benzaldehyde oxime (900 mg, 2.48 mmol) in methanol (100 mL), Palladium on activated carbon (100 mg, 10%) was added under argon atmosphere, acetic acid (1.5 mL) was added dropwise. The flask was evacuated and flushed three times with hydrogen. The mixture was stirred at room temperature under an atmosphere of hydrogen (balloon) for overnight. The completion reaction mixture was filtered with celite, the filtrate was concentrated and the residue 4-(aminomethyl)-N-(4-(4-(trifluoromethyl)piperidin-1-yl)phenyl)aniline (290-1) was used in next step directly without further purification after concentrated and dry in vacuo. LC-MS (m/z) 350.2 $[M+H]^+$.

Step 2. To a solution of 4-(aminomethyl)-N-(4-(4-(trifluoromethyl)piperidin-1-yl)phenyl)aniline (290-1) (100 mg, 0.29 mmol, 1.0 equivs) and 1-ethyl-5-oxopyrrolidine-3-carboxylic acid (49 mg, 0.31 mmol, 1.1 equivs) in super dry N,N-dimethylformamide (5 mL), 4-(4,6-dimethoxy-1,3,5-triazin-2-yl)-4-methylmorpholin-4-ium chloride (87 mg, 0.31 mmol, 1.1 equivs) and N-ethyl-N-isopropylpropan-2-amine (142 mmL, 0.86 mmol, 3.0 equivs) were added respectively at room temperature. The resulting solution was stirred for overnight at room temperature. The reaction mixture was added into water (25 mL) drop by drop with stirring. The precipitate was filtered, cake was wash with water 3 times and dry in vacuo. 1-ethyl-5-oxo-N-(4-((4-(4-(trifluoromethyl)piperidin-1-yl)phenyl)amino)benzyl)pyrrolidine-3-carboxamide (290) was obtained as pale white solid in a yield of 79.38%. $^1H$ NMR (400 MHz, DMSO-$d_6$) δ 8.41 (t, J=5.8 Hz, 1H), 7.79 (s, 1H), 7.08-7.02 (m, 2H), 6.99-6.94 (m, 2H), 6.92-6.85 (m, 4H), 4.16 (d, J=5.7 Hz, 2H), 3.62 (d, J=12.3 Hz, 2H), 3.51 (dd, J=9.6, 8.9 Hz, 1H), 3.34 (d, J=3.7 Hz, 2H), 3.19 (qd, J=7.3, 1.7 Hz, 2H), 3.15-3.08 (m, 1H), 2.62 (td, J=12.1, 2.3 Hz, 2H), 2.41 (dt, J=8.2, 2.4 Hz, 2H), 1.88 (d, J=12.8 Hz, 2H), 1.59 (td, J=12.5, 4.1 Hz, 2H), 1.00 (t, J=7.2 Hz, 3H). LC-MS (m/z) 389.3 $[M+H]^+$.

2-(2,6-dimethylmorpholino)-N-hydroxy-N-(4-((4-(4-(trifluoromethyl)piperidin-1-yl)phenyl)amino)benzyl)acetamide (291)

291

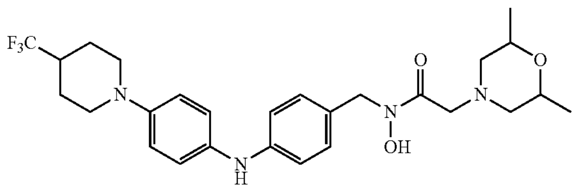

The title compound 291 (31.4 mg) was prepared in a total yield of 55.9% as a white solid according to the procedure for compound 108. $^1H$ NMR (400 MHz, Methanol-$d_4$) δ 7.25-6.82 (m, 8H), 4.63 (s, 2H), 3.80-3.51 (m, 4H), 3.38 (s, 2H), 3.22-3.15 (m, 2H), 2.89-2.83 (m, 2H), 2.71-2.58 (m, 2H), 2.23 (m, 1H), 2.00-1.71 (m, 4H), 1.10 (d, J=6.4 Hz, 6H). Mass (m/z): 521.3 $[M+H]^+$ N-hydroxy-2,2-dimethyl-N-(4-((4-(4-(trifluoromethyl)piperidin-1-yl)phenyl)amino)benzyl)tetrahydro-2H-pyran-4-carboxamide (292)

292

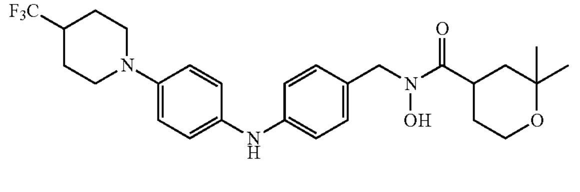

The title compound 292 (10.1 mg) was prepared in a total yield of 21.8% as a white solid according to the procedure for compound 108. $^1H$ NMR (400 MHz, Methanol-$d_4$) δ 7.49-6.56 (m, 8H), 4.63 (s, 2H), 3.80-3.66 (m, 2H), 3.46-3.34 (m, 2H), 2.99-2.86 (m, 2H), 2.39-2.15 (m, 2H), 2.03-1.91 (m, 2H), 1.83-1.57 (m, 6H), 1.24 (s, 3H), 1.21 (s, 3H). Mass (m/z): 506.2 $[M+H]^+$ N-(4-((4-(3,3-difluoropiperidin-1-yl)phenyl)amino) benzyl)-N-hydroxy-1-isopropylpiperidine-4-carboxamide (293)

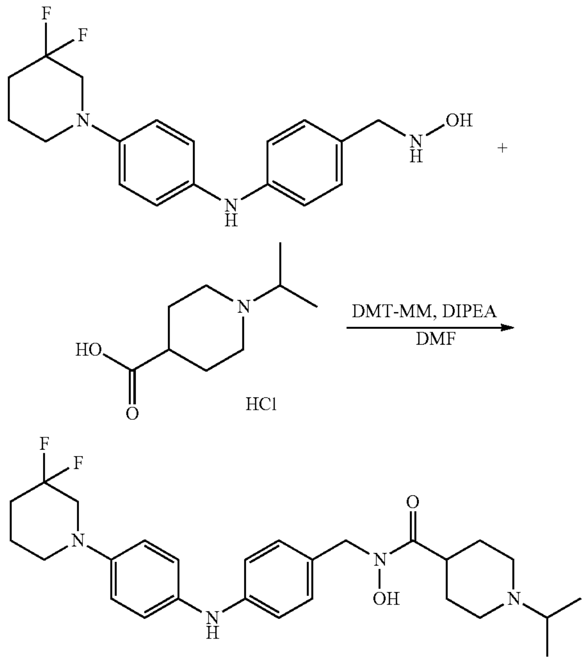

293

The title compound 293 (19.0 mg) was prepared in a total yield of 43.2% as a white solid from 4-(3,3-difluoropiperidin-1-yl)-N-(4-((hydroxyamino)methyl)phenyl) aniline (30 mg, 0.090 mmol) and 1-isopropylpiperidine-4-carboxylic acid hydrochloride (24 mg, 0.117 mmol) according to the procedure for 179. $^1$H NMR (400 MHz, Methanol-$d_4$) δ 7.17-6.87 (m, 8H), 4.65 (s, 2H), 3.50-3.43 (m, 3H), 3.28-3.00 (m, 7H), 2.16-1.82 (m, 9H), 1.34 (d, J=6.6 Hz, 6H). Mass (m/z): 487.3 $[M+H]^+$.

Compound 294-302 are prepared according to the method of scheme 1

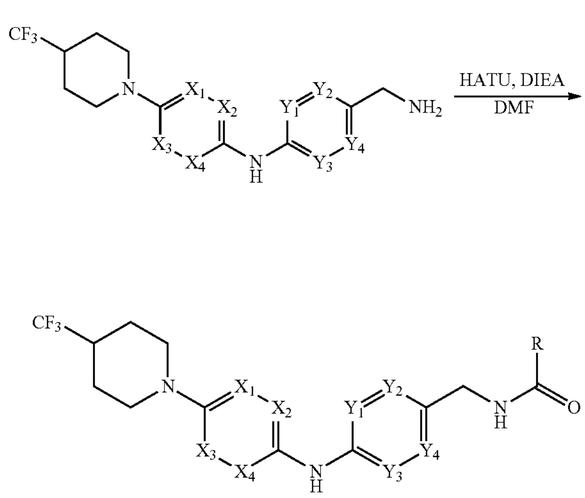

-continued

294

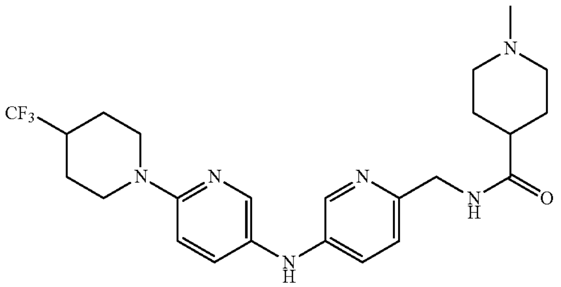

295

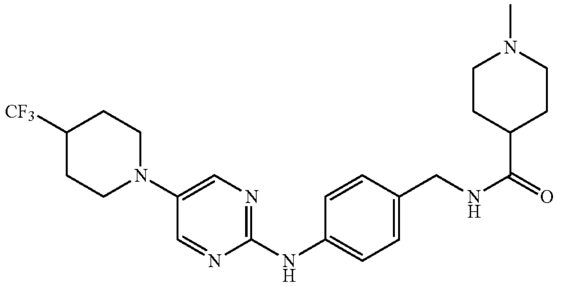

296

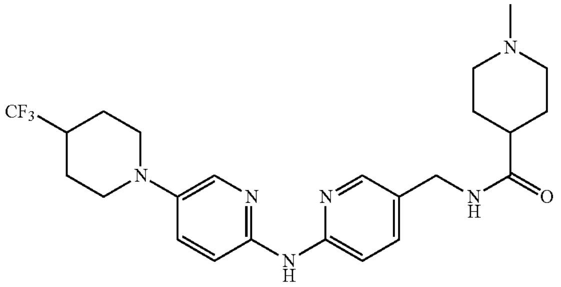

297

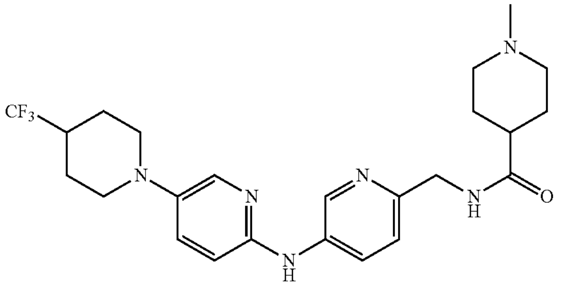

298

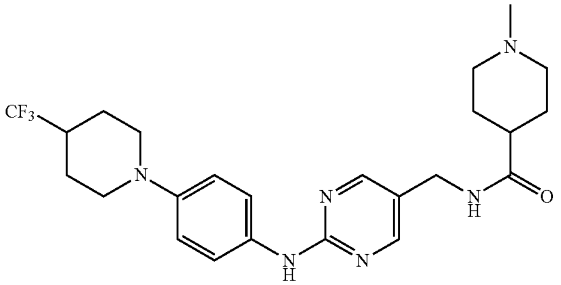

-continued
299
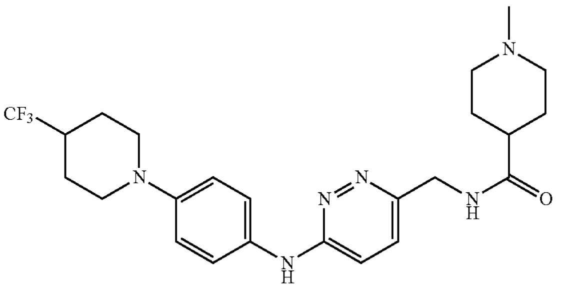
300
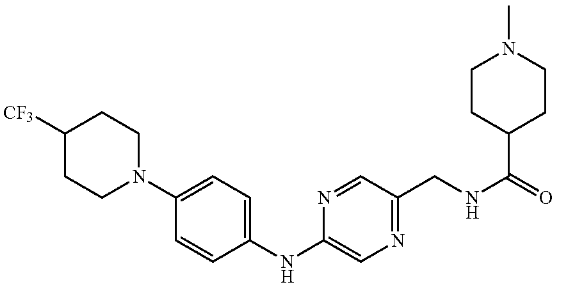
301
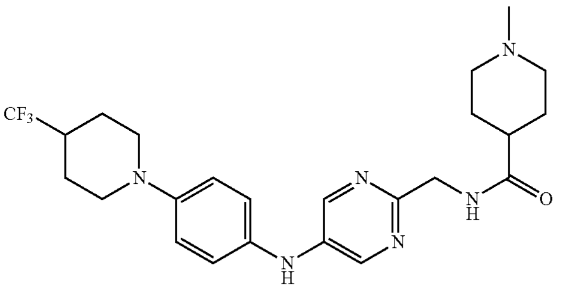
302
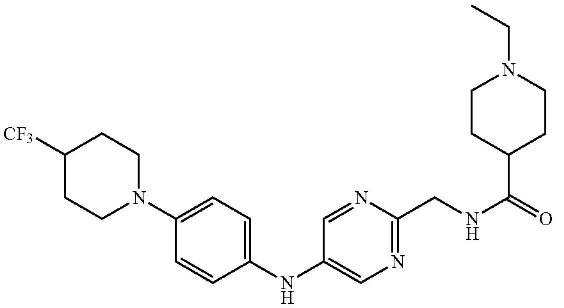
Compound 303-314 are prepared according to the method of scheme 2
Scheme 2
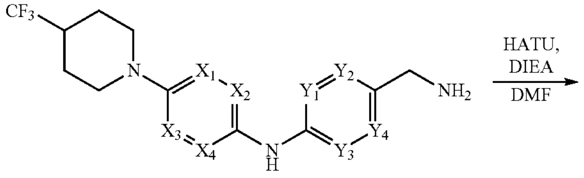
-continued
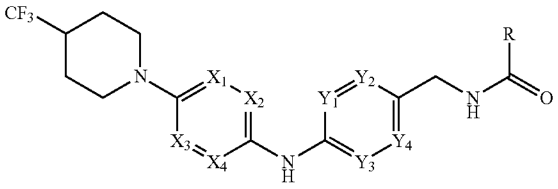
303
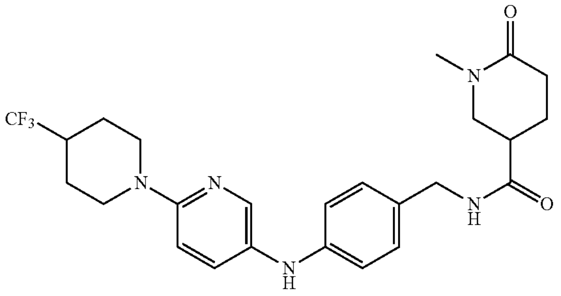
304
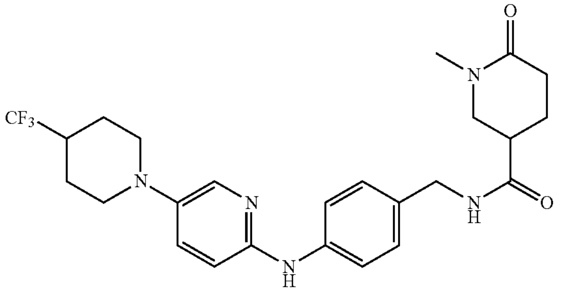
305
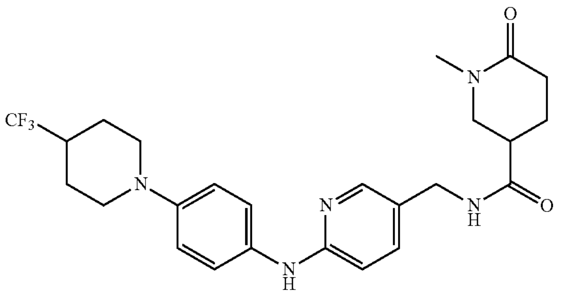
306
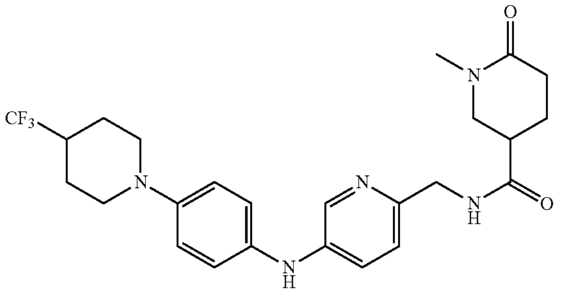

307
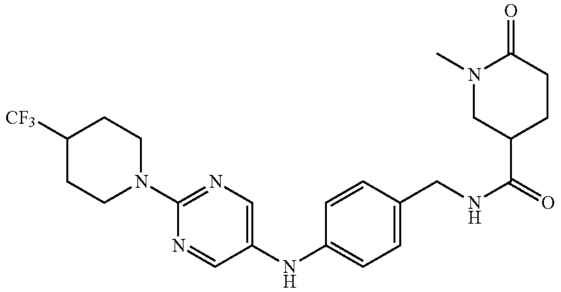
308
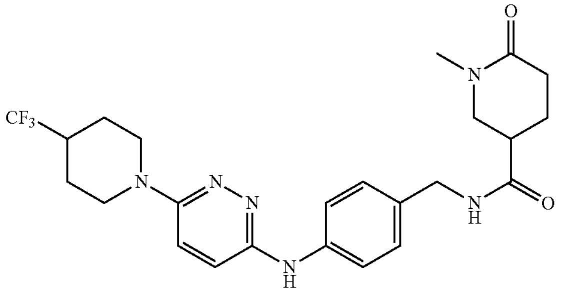
309
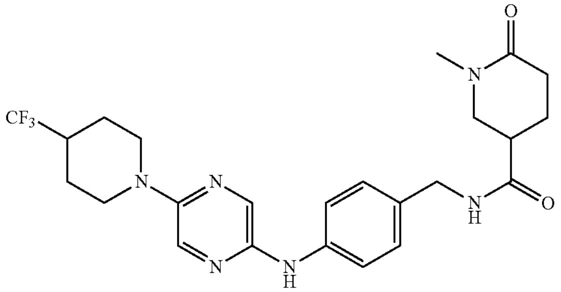
310
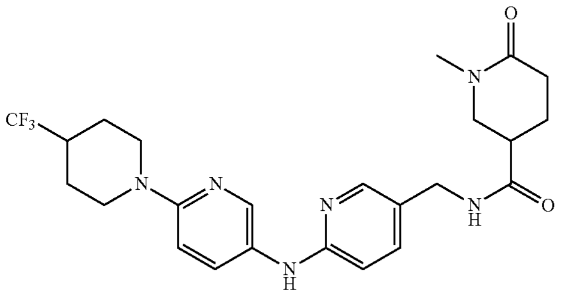
311
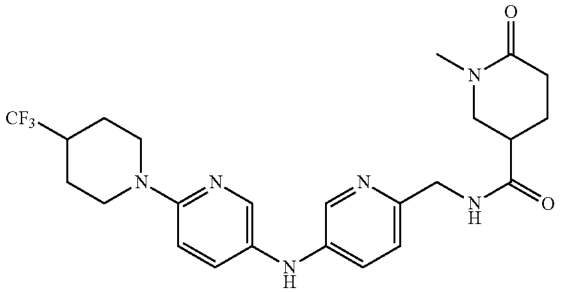
312
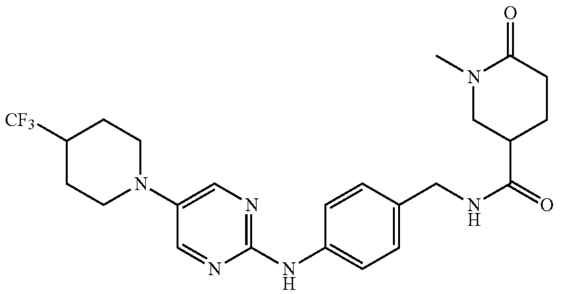
313
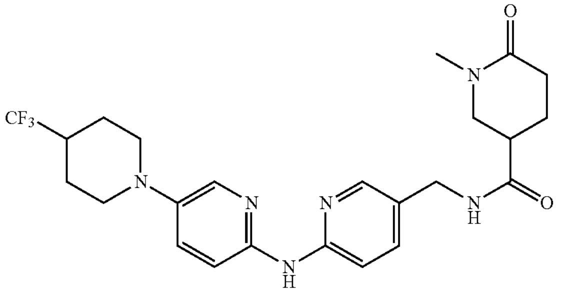
314
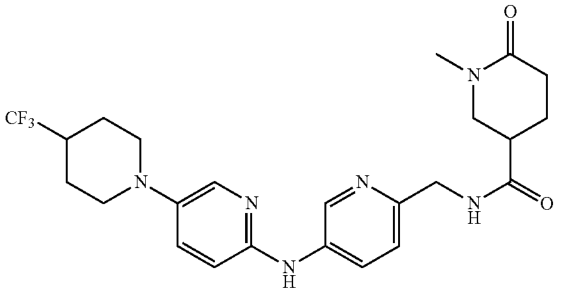
Compound 315-326 are prepared according to the method of scheme 3
Scheme 3
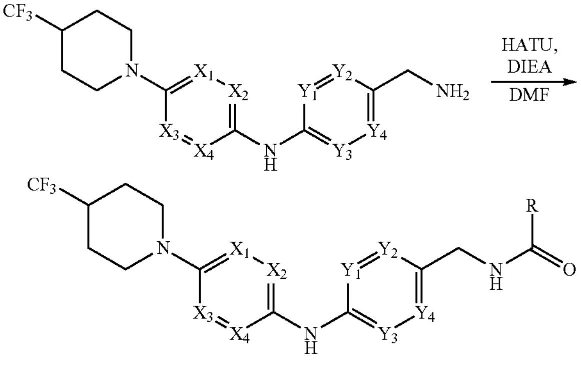

315
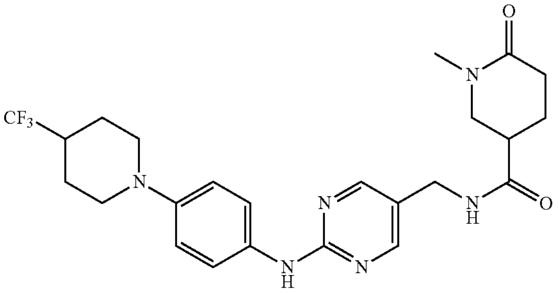
316
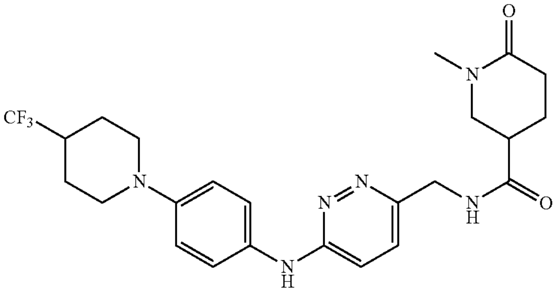
317
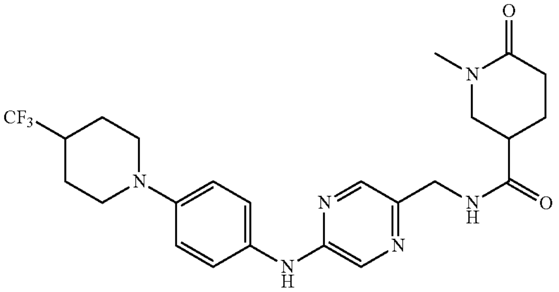
318
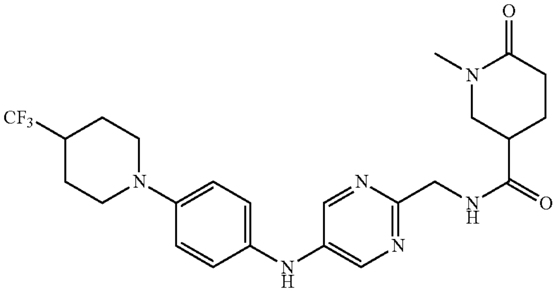
319
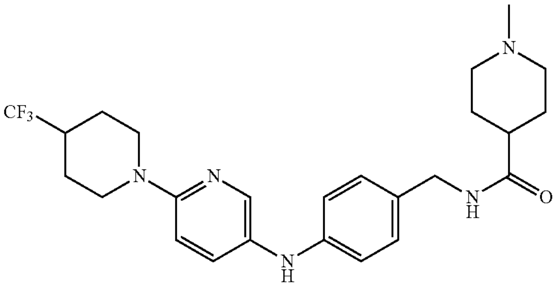
320
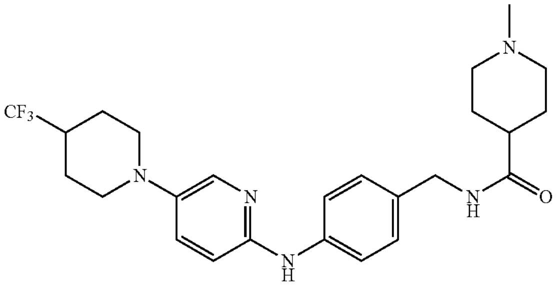
321
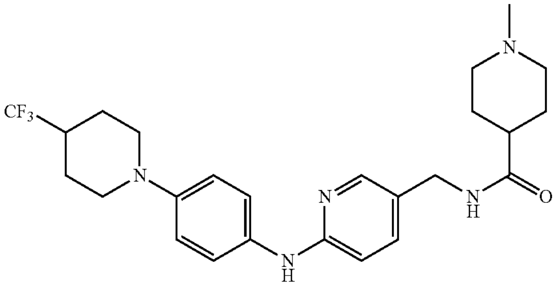
322
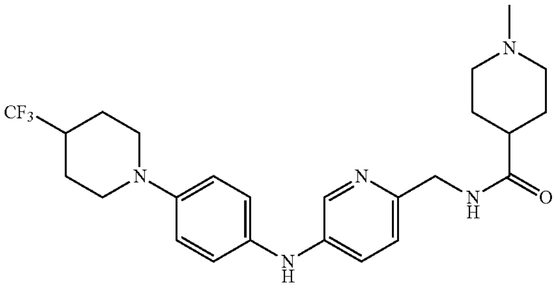
323
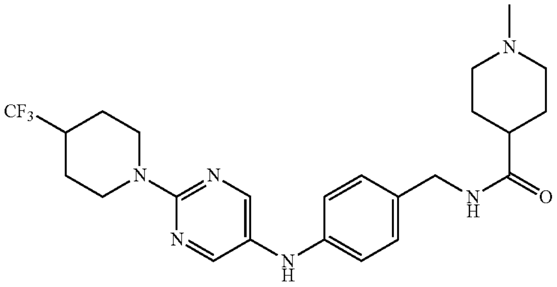
324
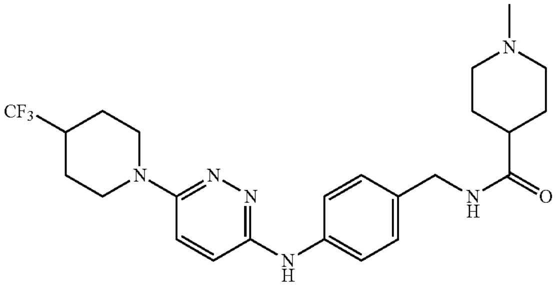

-continued
325
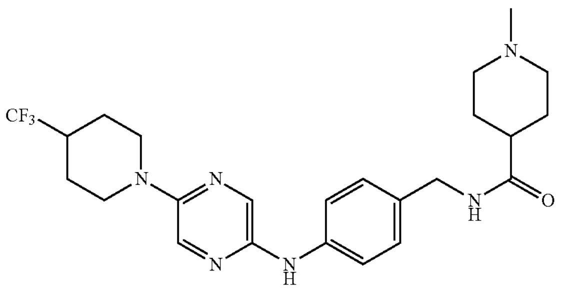
326
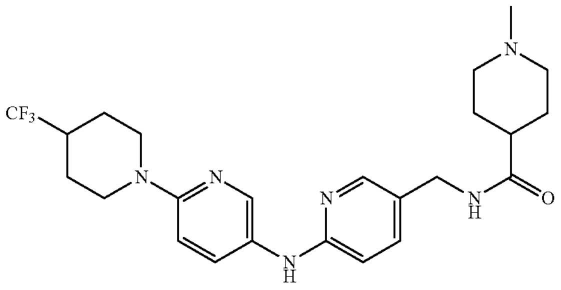
Compound 327-338 are prepared according to the method of scheme 4
Scheme 4
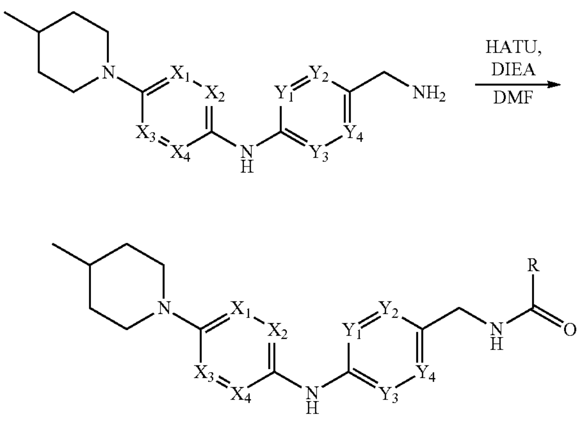
327
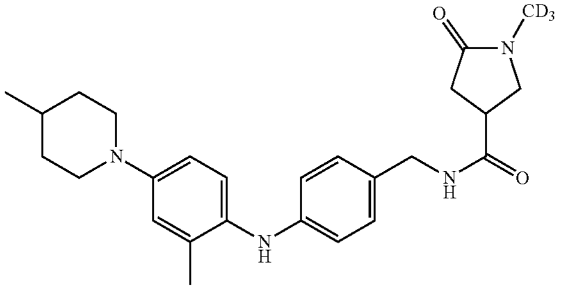
-continued
328
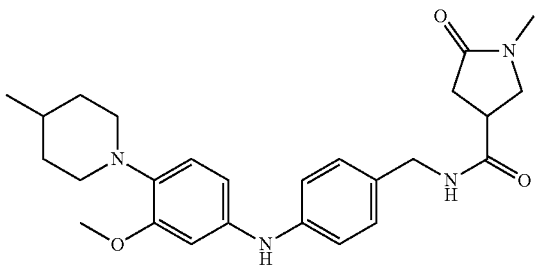
329
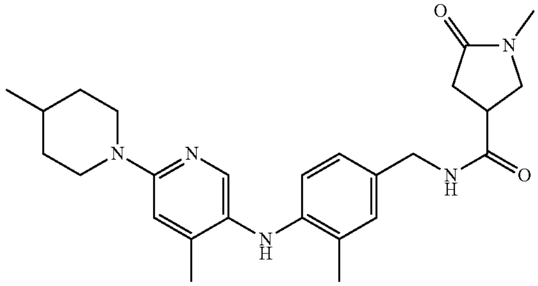
330
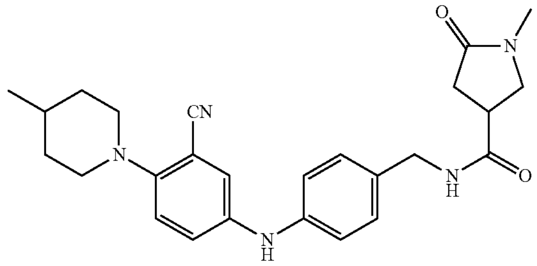
331
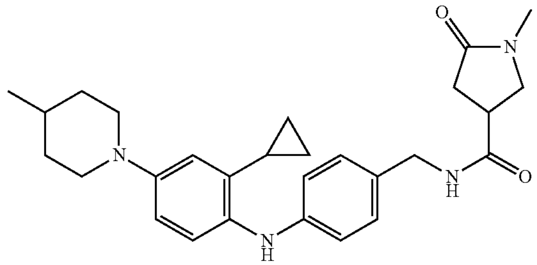
332
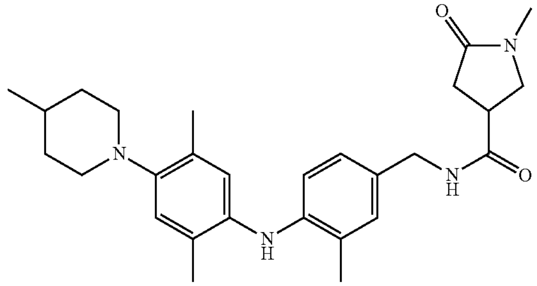

-continued
333
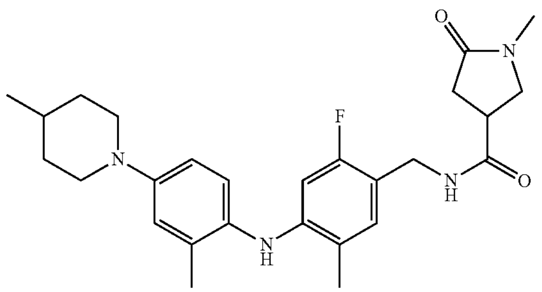
334
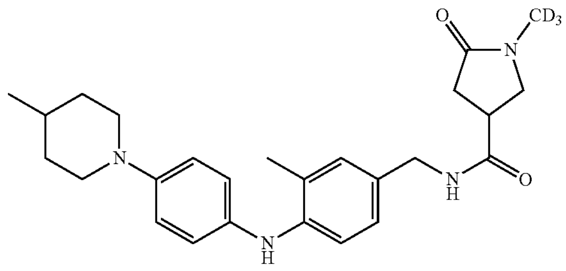
335
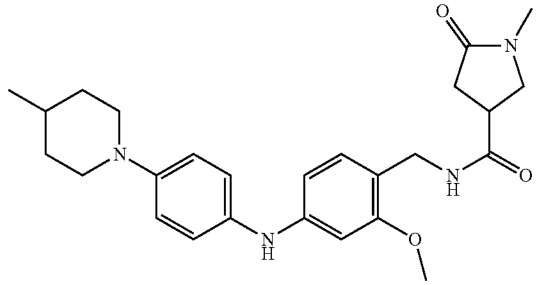
336
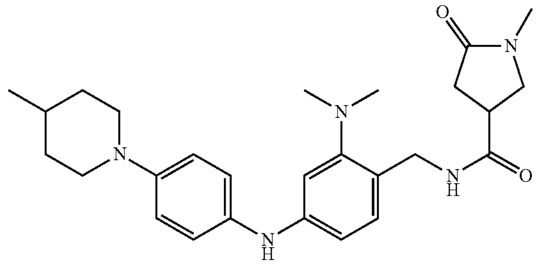
337
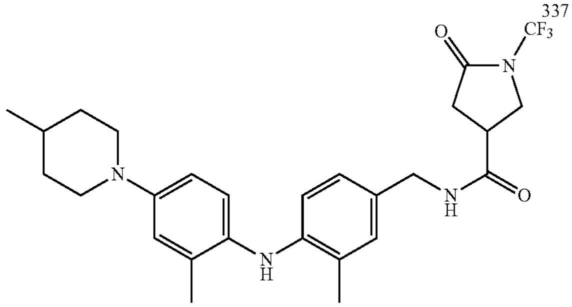
-continued
338
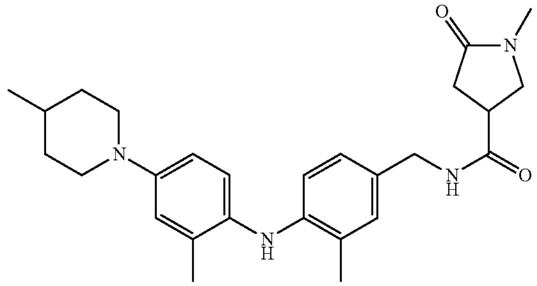
Compound 339-350 are prepared according to the method of scheme 5
Scheme 5
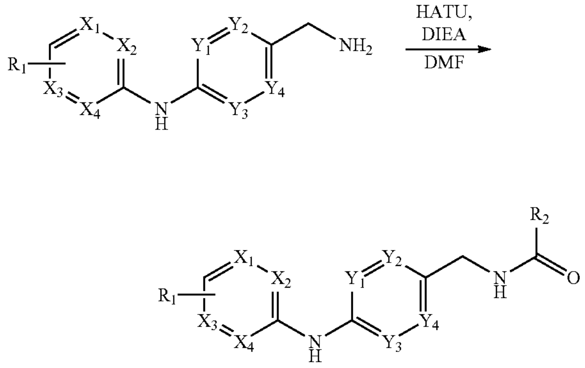
339
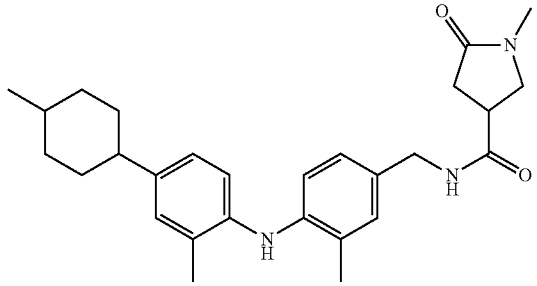
340
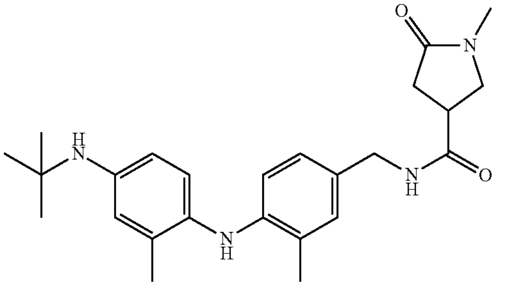

-continued
341
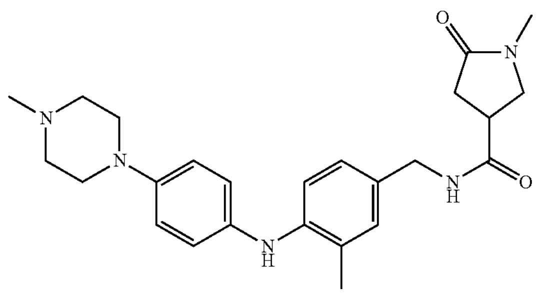
342
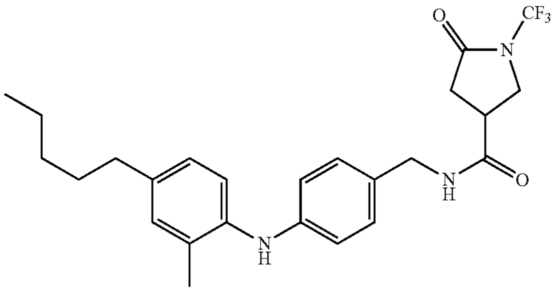
343
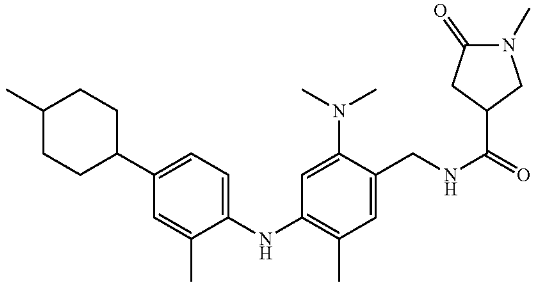
344
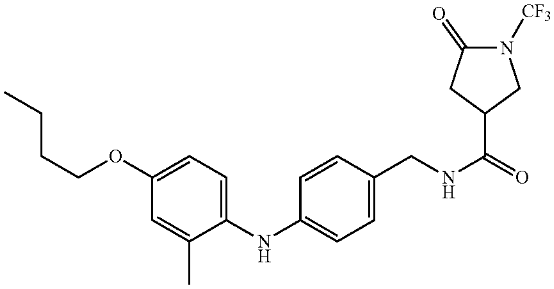
345
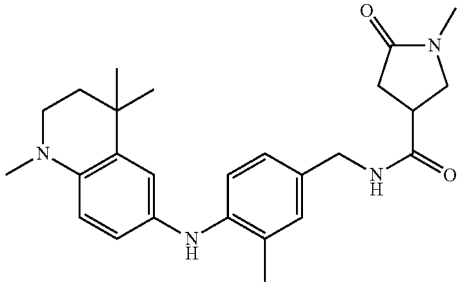
-continued
346
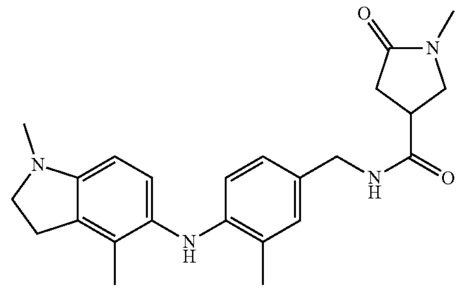
347
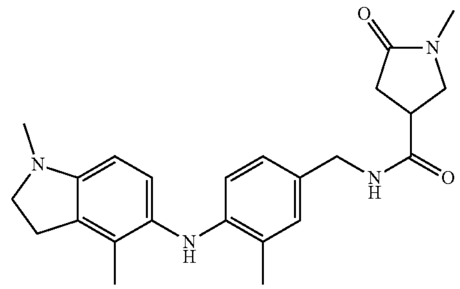
348
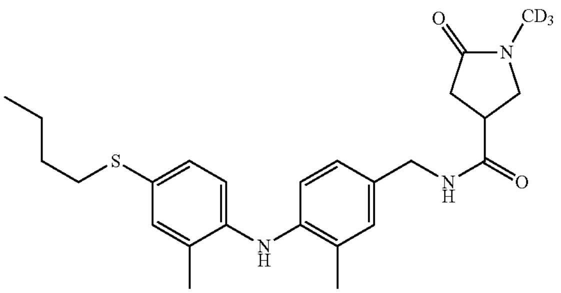
349
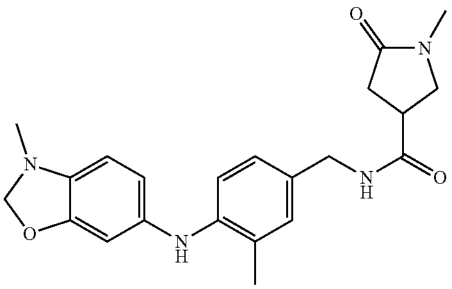
350
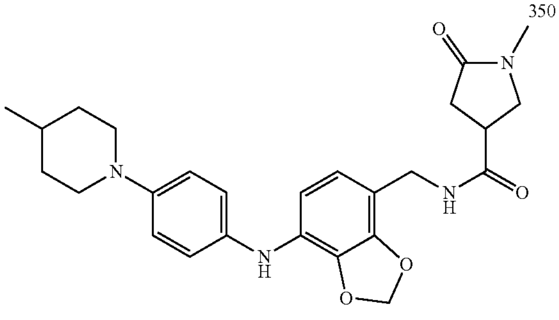

Compound 351-362 are prepared according to the method of scheme 6
Scheme 6
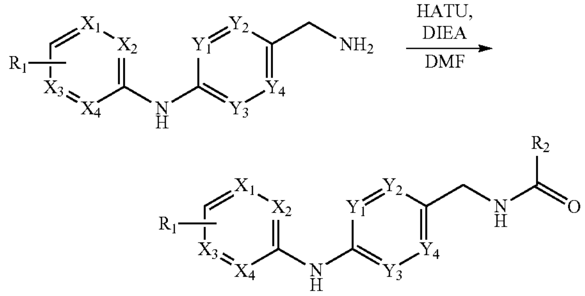
351
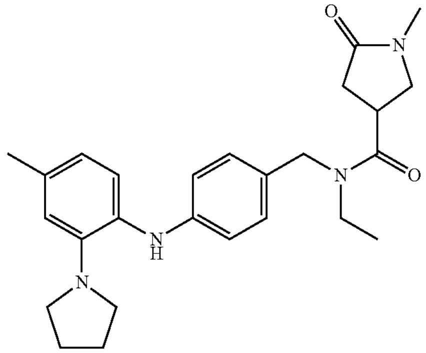
352
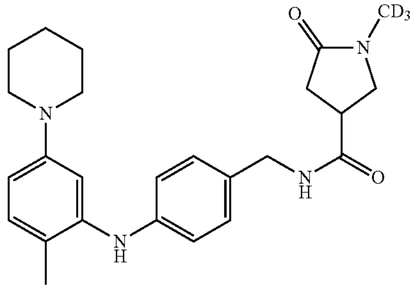
353
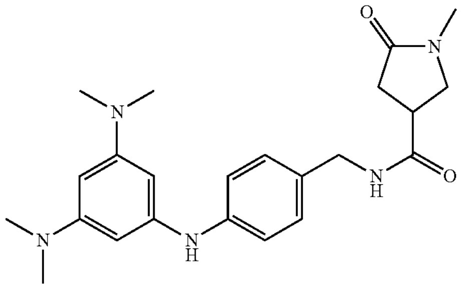
354
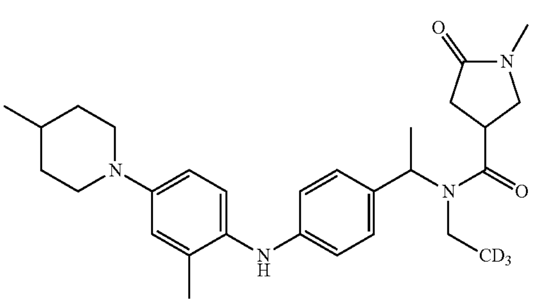
-continued
355
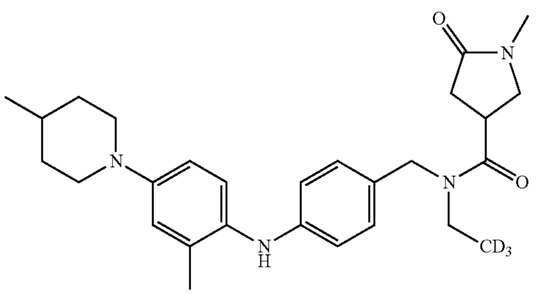
356
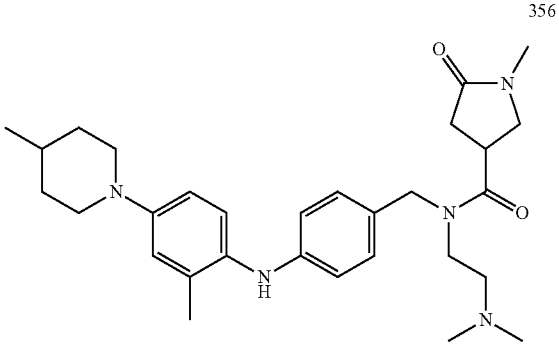
357
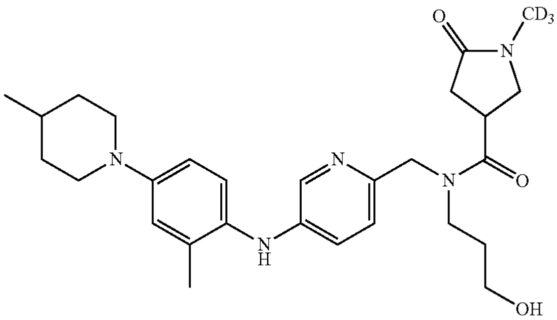
358
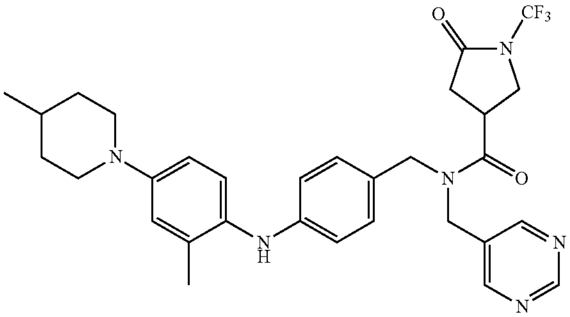
359
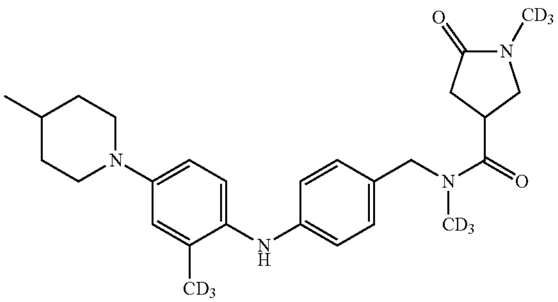

-continued

360

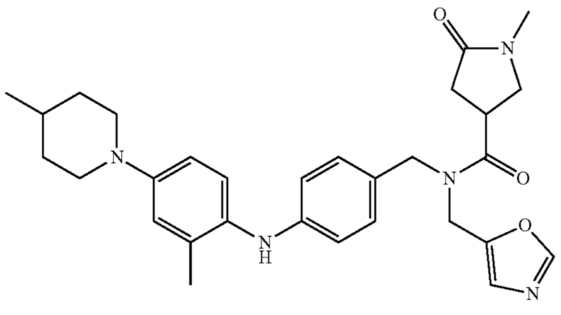

361

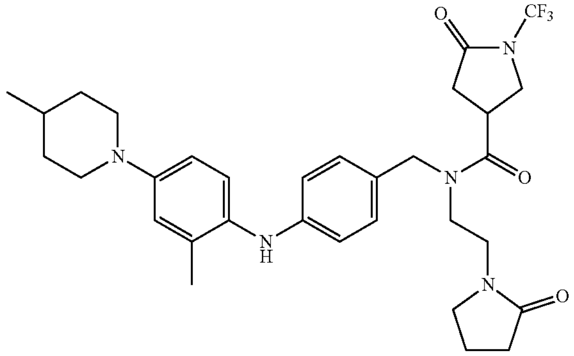

362

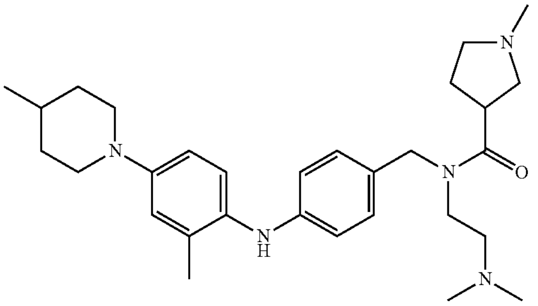

Active Compounds Group II: Representative Synthesis

N-(4-((4-(tert-butyl(ethyl)amino)phenyl)amino)benzyl)1-ethyl-5-oxopyrrolidine-3-carboxamide (363)

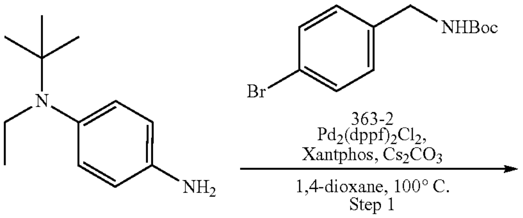

363-1

-continued

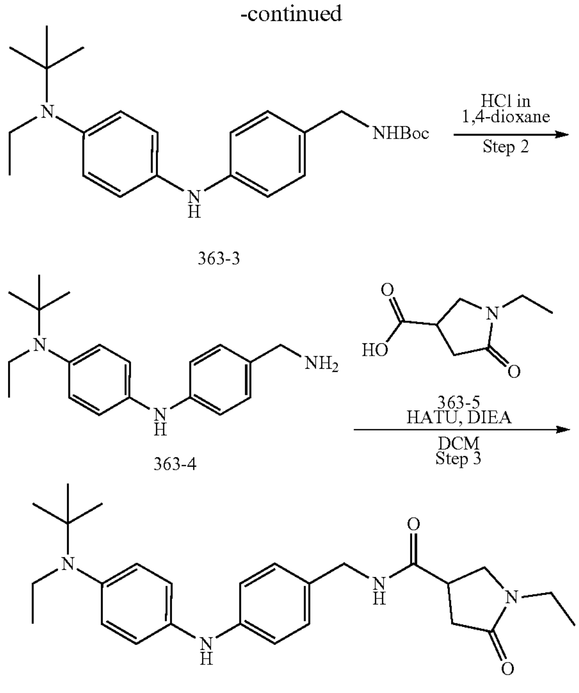

363

Step 1. Preparation of tert-butyl (4-((4-(tert-butyl(ethyl)amino)phenyl)amino)benzyl)carbamate (363-3). A mixture of N1-(tert-butyl)-N1-ethylbenzene-1,4-diamine (192 mg, 1.0 mmol), tert-butyl (4-bromobenzyl)carbamate (220 mg, 0.77 mmol), $Pd(dppf)_2Cl_2$ (14.6 mg, 0.02 umol), Xantphos (23.2 mg, 0.04 mmol), $Cs_2CO_3$ (489 mg, 1.5 mmol) in 1,4-dioxane (10 mL) was stirred overnight at 100° C. After cooling to rt. 15 mL of water was added. Then the mixture was extracted by DCM (15 mL×3). The combined organic layers were washed with water (20 mL×3), dried over $Na_2SO_4$ and concentrated under vacuum. The residue was purified by prep-TLC (EA) to give the desired product as yellow solid (204 mg, 67.8%). Mass (m/z): 398.4 $[M+H]^+$ Step 2. Preparation of $N^1$-(4-(aminomethyl)phenyl)-N4-(tert-butyl)-N4-ethylbenzene-1,4-diamine (363-4). A solution of tert-butyl (4-((4-(tert-butyl(ethyl)amino)phenyl)amino)benzyl)carbamate (204 mg, 0.51 mmol) in 10 mL of a solution of HCl in 1,4-dioxane was stirred for 30 mins at rt and concentrated. 5 ml water was added. The PH of the filtration was adjusted to 8-9 with sodium carbonate solution. Then the mixture was extracted by DCM (5 mL×3). The combined organic layers were washed with water (10 mL), dried over Na2SO4 and concentrated. The residue was purified by perp-TLC (MeOH/DCM=1/5) to afford the desired product as a yellow solid. Mass (m/z): 298.3 $[M+H]^+$.

Step 3. Preparation of N-(4-((4-(tert-butyl(ethyl)amino)phenyl)amino)benzyl)-1-ethyl-5-oxopyrrolidine-3-carboxamide (363). To a solution of 1-ethyl-5-oxopyrrolidine-3-carboxylic acid (31.4 mg, 0.2 mmol) in DCM (5 ml) was added HATU (76.0 mg, 0.2 mmol). Then the reaction mixture was stirred for 1 hour at rt. $N^1$-(4-(aminomethyl)phenyl)-N4-(tert-butyl)-N4-ethylbenzene-1,4-diamine (59.4 mg, 0.2 mmol) and DIEA (77.4 mg, 0.6 mmol) were added. Then the reaction mixture was stirred for 3 hours at rt. 5 mL of water was added. Then the mixture was extracted by DCM (5 mL×3). The combined organic layers were washed with water (10 mL×3), dried over $Na_2SO_4$ and concentrated under vacuum. The residue was purified by prep-TLC (MeOH/DCM=1/15) to give the desired product as white solid (13.2 mg, 15.0%).

$^1$H NMR (300 MHz, Methanol-$d_4$) δ 7.33-7.04 (m, 9H), 4.33 (d, J=5.0 Hz, 2H), 3.77-3.54 (m, 5H), 3.27-3.18 (m, 2H), 2.62 (d, J=8.2 Hz, 2H), 1.41 (s, 9H), 1.13 (t, J=7.2 Hz, 3H), 1.07 (t, J=7.0 Hz, 3H). Mass (m/z): 437.4$[M+H]^+$.

N-(4-((4-(dimethylamino)phenyl)amino)benzyl)-1-ethyl-5-oxopyrrolidine-3-carboxamide (364)

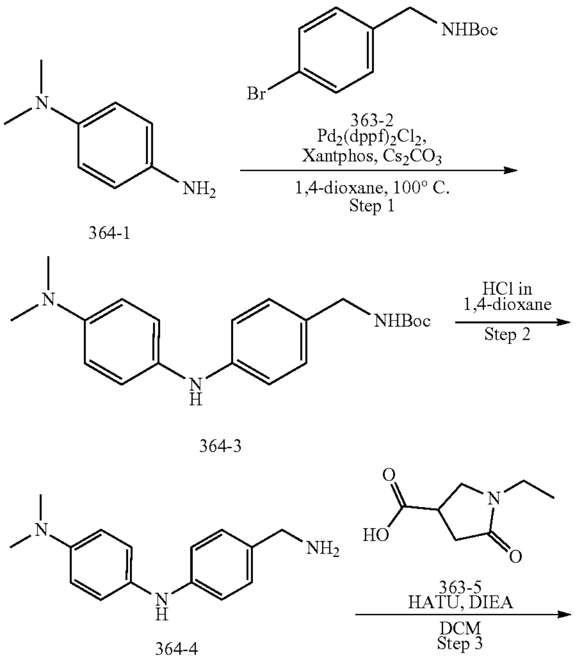

364-1

364-3

364-4

-continued

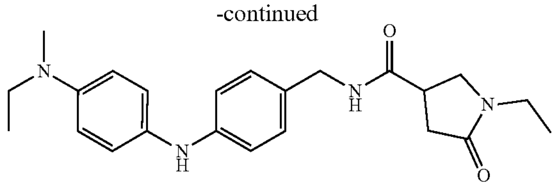

364

Step 1. Preparation of tert-butyl (4-((4-(dimethylamino) phenyl)amino)benzyl)carbamate (364-3). The title compound 364-3 (160 mg) was prepared in a total yield of 46.9% as a yellow solid from $N^1$,$N^1$-dimethylbenzene-1,4-diamine (204 mg, 1.5 mmol), tert-butyl (4-bromobenzyl)carbamate (286 mg, 1.0 mmol), $Pd(dppf)_2Cl_2$ (14.6 mg, 0.02 mmol), Xantphos (23.2 mg, 0.04 mmol), $Cs_2CO_3$ (489 mg, 1.5 mmol) according to the procedure for 363. Mass (m/z): 342.3 $[M+H]^+$.

Step 2. Preparation of $N^1$-(4-(aminomethyl)phenyl)-N4, N4-dimethylbenzene-1,4-diamine (364-4). The title compound 364-4 (147 mg) was prepared in a total yield of 100% as a yellow solid from tert-butyl (4-((4-(dimethylamino) phenyl)amino)benzyl)carbamate (160 mg, 0.47 mmol). HCl in 1,4-dioxane (5.0 mL) according to the procedure for 363-4. Mass (m/z): 242.3 $[M+H]^+$.

Step 3. Preparation of N-(4-((4-(dimethylamino)phenyl) amino)benzyl)-1-ethyl-5-oxopyrrolidine-3-carboxamide (364). The title compound 364 (21.6 mg) was prepared in a total yield of 28.4% as a yellow solid from $N^1$-(4-(aminomethyl)phenyl)-$N^4$,$N^4$-dimethylbenzene-1,4-diamine (48.4 mg, 0.2 mmol), 1-methylpiperazine (31.4 mg, 0.2 mmol), DIEA (77.4 mg, 0.6 mmol) and HATU (76.0 mg, 0.02 mmol) according to the procedure for 363. $^1$H NMR (400 MHz, Methanol-$d_4$) 7.51-6.83 (m, 8H), 4.41 (d, J=5.0 Hz, 2H), 3.78-3.52 (m, 4H), 3.30 (s, 6H), 3.28-3.15 (m, 2H), 2.60 (d, J=8.4 Hz, 2H), 1.13 (t, J=7.2 Hz, 3H). Mass (m/z): 381.3 $[M+H]^+$.

1-ethyl-N-(1-(4-((4-(4-methylpiperidin-1-yl)phenyl) amino)phenyl)ethyl)-5-oxopyrrolidine-3-carboxamide (365)

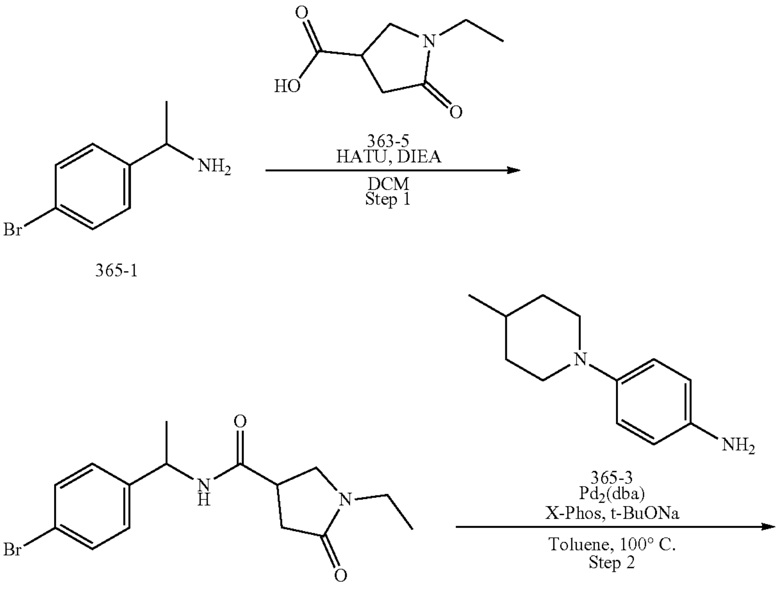

365-1

365-2

-continued

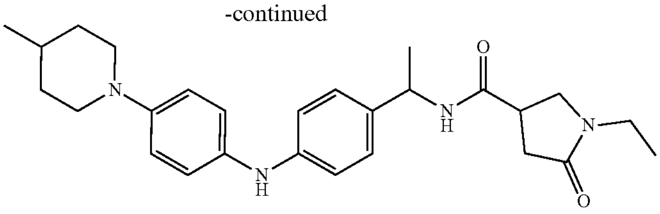

365

Step 1. Preparation of N-(1-(4-bromophenyl)ethyl)-1-ethyl-5-oxopyrrolidine-3-carboxamide (365-2). The title compound (365-2 (560 mg) was prepared in a total yield of 82.8% as a white solid from 1-(4-bromophenyl)ethan-1-amine (400 mg, 2.0 mmol), 1-methylpiperazine (345 mg, 2.2 mmol), DIEA (774 mg, 6.0 mmol) and HATU (836 mg, 2.2 mmol) according to the procedure for 363. Mass (m/z): 339.1 $[M+H]^+$.

Step 2. Preparation of 1-ethyl-N-(1-(4-((4-(4-methylpiperidin-1-yl)phenyl)amino)phenyl)ethyl)-5-oxopyrrolidine-3-carboxamide (365). The title compound 365 (4.2 mg) was prepared in a total yield of 3.8% as a gray solid from N-(1-(4-bromophenyl)ethyl)-1-ethyl-5-oxopyrrolidine-3-carboxamide (84.5 mg, 0.25 mmol), 4-(4-methylpiperidin-1-yl)aniline (63 mg, 0.33 mmol), $Pd_2(dba)_3$ (2.3 mg, 2.5 umol), X-Phos (5.9 mg, 12.5 umol), t-BuONa (36 mg, 0.38 mmol) according to the procedure for 363-3. $^1H$ NMR (400 MHz, Methanol-$d_4$) δ 7.24-6.84 (m, 8H), 4.99-4.92 (m, 1H), 3.71-3.44 (m, 4H), 3.37-3.34 (m, 2H), 3.25-3.17 (m, 1H), 2.73-2.50 (m, 4H), 1.86-1.73 (m, 2H), 1.56-1.48 (m, 1H), 1.47-1.36 (m, 5H), 1.13 (dt, J=13.0, 7.3 Hz, 3H), 1.02 (d, J=6.2 Hz, 3H). Mass (m/z): 449.4 $[M+H]^+$.

N-(2-chloro-4-((2-(4-isopropylpiperidin-1-yl)pyrimidin-5-yl)amino)benzyl)-5-oxopyrrolidine-3-carboxamide (366)

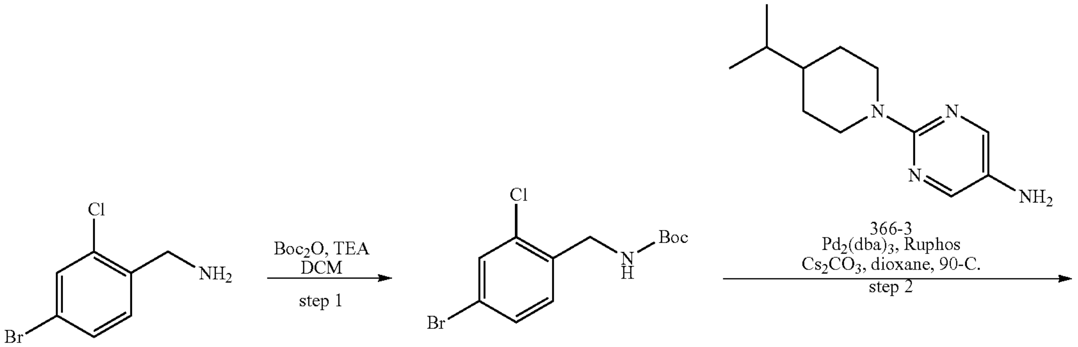

366-1

366-2

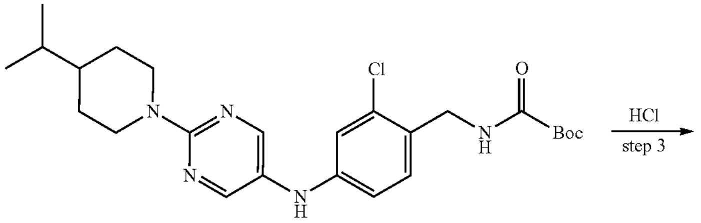

366-4

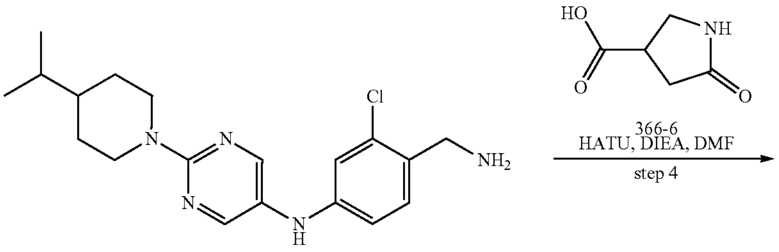

366-4

-continued

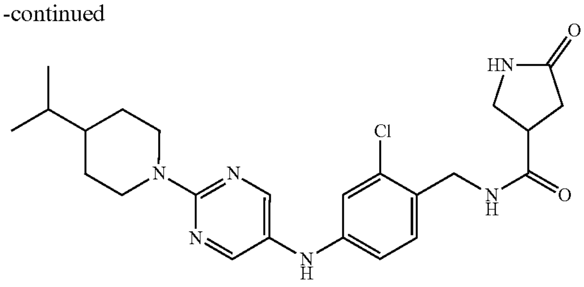

366

Step 1. Preparation of tert-butyl (4-bromo-2-chlorobenzyl)carbamate. To a solution of compound 366-1 (600 mg, 2.72 mmol) in DCM (20 mL) was added $Boc_2O$ (891 mg, 4.08 mmol) and TEA (551 mg, 5.44 mmol) at 25° C. Then the mixture was stirred at room temperature overnight. The mixture was poured into $H_2O$ and extracted with DCM (50 mL*3), the organic layer was washed with brine, dried over $Na_2SO_4$, filtered and concentrated, the residue was purified by silica gel chromatography with EA/PE (20:1) to give tert-butyl (4-bromo-2-chlorobenzyl)carbamate 366-2 (854 mg, 97% yield) as a yellow oil. MS (ESI) m/z 264.0, 266.0 $[M+H]^+$.

Step 2. Preparation of tert-butyl (2-chloro-4-((2-(4-isopropylpiperidin-1-yl)pyrimidin-5-yl)amino)benzyl)carbamate. To a mixture solution of compound 366-2 (400 mg, 1.25 mmol), compound 366-3 (275 mg, 1.25 mmol) and dicyclohexyl (2',6'-diisopropoxybiphenyl-2-yl)phosphine (116 mg, 0.25 mmol) in dioxane (20 mL) under nitrogen was added $Cs_2CO_3$ (610 mg, 1.87 mmol) and tris(dibenzylideneacetone)dipalladium (114 mg, 0.12 mmol). The reaction mixture was stirred at 90° C. for 16 hrs. Then the mixture was filtered and concentrated. The residue was purified by pre-TLC to afford to give tert-butyl (2-chloro-4-((2-(4-isopropylpiperidin-1-yl)pyrimidin-5-yl)amino)benzyl)carbamate 366-4 (351 mg, 61% yield) as a yellow solid. MS (ESI) m/z 460.2 $[M+H]^+$.

Step 3. Preparation of N-(4-(aminomethyl)-3-chlorophenyl)-2-(4-Isopropylpiperidin-1-yl)pyrimidin-5-amine. To a solution of compound 366-4 (351 mg, 0.76 mmol) in DCM (5 mL) was added 4 N HCl in dioxane (5 mL) at room temperature. Then the mixture was stirred at room temperature rt overnight. LCMS showed the reaction was completed. The mixture was filtered and dried to give N-(4-(aminomethyl)-3-chlorophenyl)-2-(4-isopropylpiperidin-1-yl)pyrimidin-5-amine 366-5 (253 mg, 92% yield) as a brown solid. MS (ESI) m/z 360.2 $[M+H]^+$.

Step 4. Preparation of N-(2-chloro-4-((2-(4-isopropylpiperidin-1-yl)pyrimidin-5-yl)amino)benzyl)-5-oxopyrrolidine-3-carboxamide (SIR-00005284). To a stirred solution of compound 366-5 (253 mg, 0.70 mmol), 5-oxopyrrolidine-3-carboxylic acid 366-6 (91 mg, 0.70 mmol) in DMF (10 mL) under nitrogen was added N,N,N',N'-Tetramethyl-O-(7-azabenzotriazol-1-yl)uronium (321 mg, 0.84 mmol) and DIEA (136 mg, 1.05 mmol). The reaction mixture was stirred at room temperature for 16 hrs. The mixture was poured into $H_2O$ (10 mL) and extracted with EA (20 mL*3), the organic layer was washed with brine, dried over $Na_2SO_4$, filtered and concentrated, the residue was purified by prep-HPLC to give 366 (93 mg) as a white solid. MS (ESI) m/z 471.2 $[M+H]^+$. $^1H$ NMR (400 MHz, $CD_3OD$) δ 8.19 (s, 2H), 7.15 (d, J=8.4 Hz, 1H), 6.76 (d, J=2.4 Hz, 1H), 6.66 (dd, J=8.4, 2.4 Hz, 1H), 4.76-4.65 (m, 2H), 4.35 (s, 2H), 3.62-3.53 (m, 1H), 3.51-3.45 (m, 1H), 2.88-2.77 (m, 2H), 2.61-2.44 (m, 2H), 1.81-1.70 (m, 2H), 1.53-1.43 (m, 1H), 1.38-1.28 (m, 2H), 1.27-1.14 (m, 2H), 0.93 (d, J=6.8 Hz, 6H).

1-ethyl-5-oxo-N-(1-(4-((4-(4-(trifluoromethyl)piperidin-1-yl)phenyl)amino)phenyl)ethyl)pyrrolidine-3-carboxamide (367)

367

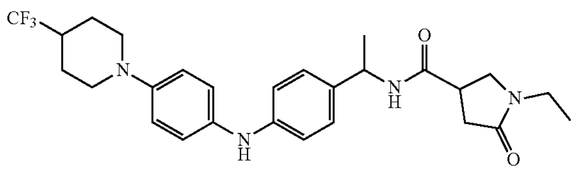

The title compound 367 (4.1 mg) was prepared in a total yield of 6.5% as a yellow solid from N-(1-(4-bromophenyl)ethyl)-1-ethyl-5-oxopyrrolidine-3-carboxamide (42.3 mg, 0.125 mmol), 4-(4-(trifluoromethyl)piperidin-1-yl)aniline (40 mg, 0.16 mmol), $Pd_2(dba)_3$ (1.1 mg, 1.6 umol), X-Phos (3.0 mg, 6.2 umol), t-BuONa (18 mg, 0.19 mmol) according to the procedure for 363-3. $^1H$ NMR (400 MHz, Methanol-$d_4$) δ 7.16 (d, J=8.2 Hz, 2H), 7.04 (d, J=8.5 Hz, 2H), 7.00-6.89 (m, 4H), 4.97-4.92 (m, 1H), 3.66-3.61 (m, 2H), 3.53-3.44 (m, 1H), 3.30-3.14 (m, 2H), 2.75-2.59 (m, 4H), 2.34-2.24 (m, 1H), 2.03-1.94 (m, 2H), 1.75 (qd, J=12.5, 4.0 Hz, 2H), 1.49-1.40 (m, 3H), 1.11 (t, J=7.3 Hz, 3H). Mass (m/z): 503.3 $[M+H]^+$.

N'-(4-((4-(4-(trifluoromethyl)piperidin-1-yl)phenyl) amino)benzyl)succinamide (368)

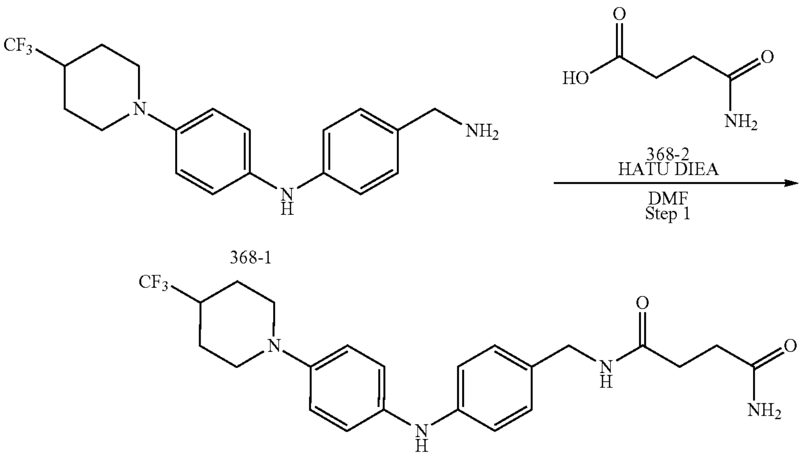

368-1

368

The title compound 368 (11.2 mg) was prepared in a total yield of 16.7% as a light yellow solid from 4-(aminomethyl)-N-(4-(4-(trifluoromethyl)piperidin-1-yl)phenyl)aniline (52 mg, 0.15 mmol), 4-amino-4-oxobutanoic acid (18 mg, 0.15 mmol), DIEA (58 mg, 0.45 mmol) and HATU (57 mg, 0.15 mmol) according to the procedure for 363. $^1$H NMR (400 MHz, Methanol-$d_4$) δ 7.09-6.76 (m, 8H), 4.16 (s, 2H), 3.58-3.45 (m, 2H), 2.64-2.49 (m, 2H), 2.45-2.38 (m, 4H), 2.24-2.12 (m, 2H), 1.92-1.83 (m, 2H), 1.64 (qd, J=12.9, 3.7 Hz, 2H). Mass (m/z): 449.3 $[M+H]^+$.

1-cyclopropyl-5-oxo-N-(4-((4-(4-(trifluoromethyl) piperidin-1-yl)phenyl)amino)benzyl)pyrrolidine-3-carboxamide (369)

The title compound 369 (10.6 mg) was prepared in a total yield of 14.1% as a yellow solid from 4-(aminomethyl)-N-(4-(4-(trifluoromethyl)piperidin-1-yl)phenyl)aniline (52 mg, 0.15 mmol), 1-cyclopropyl-5-oxopyrrolidine-3-carboxylic acid (25 mg, 0.15 mmol), DIEA (58 mg, 0.45 mmol) and HATU (57 mg, 0.15 mmol) according to the procedure for 363. $^1$H NMR (400 MHz, Methanol-$d_4$) δ 7.07-6.74 (m, 8H), 4.15 (s, 2H), 3.55-3.36 (m, 4H), 3.10-2.99 (m, 1H) 2.61-2.44 (m, 5H), 2.26-2.12 (m, 1H), 1.91-1.81 (m, 2H), 1.62 (qd, J=12.5, 4.1 Hz, 2H), 0.67-0.60 (m, 4H). Mass (m/z): 501.3 $[M+H]^+$.

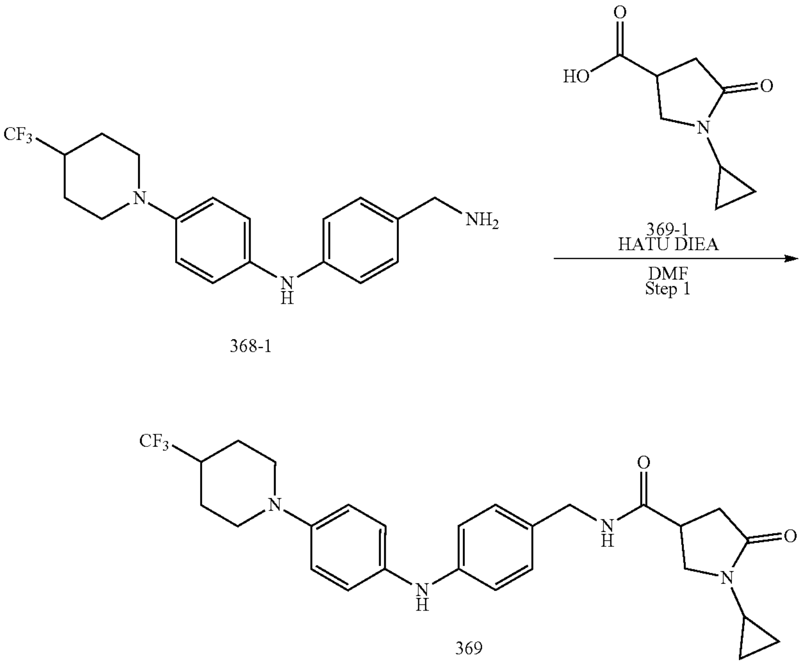

368-1

369

N'-(4-((4-(4-(trifluoromethyl)piperidin-1-yl)phenyl)amino)benzyl)oxalamide (370)

370

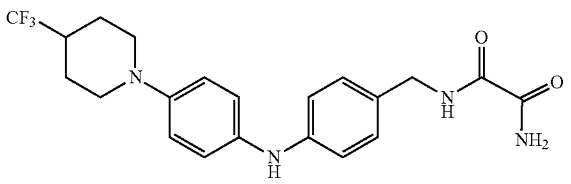

The title compound 370 (10.3 mg) was prepared in a total yield of 16.3% as a yellow solid from 4-(aminomethyl)-N-(4-(4-(trifluoromethyl)piperidin-1-yl)phenyl)aniline (52 mg, 0.15 mmol), 2-amino-2-oxoacetic acid (13.4 mg, 0.15 mmol), DIEA (58 mg, 0.45 mmol) and HATU (57 mg, 0.15 mmol) according to the procedure for 363. $^1$H NMR (400 MHz, Methanol-$d_4$) δ 7.63-6.47 (m, 8H), 4.34 (s, 2H), 3.79-3.33 (m, 2H), 2.85-2.42 (m, 2H), 2.34-2.24 (m, 1H), 2.05-1.91 (m, 2H), 1.78-1.63 (m, 2H). Mass (m/z): 421.3 $[M+H]^+$.

N',N'-dimethyl-N2-(4-((4-(4-(trifluoromethyl)piperidin-1-yl)phenyl)amino)benzyl)oxalamide (371)

371

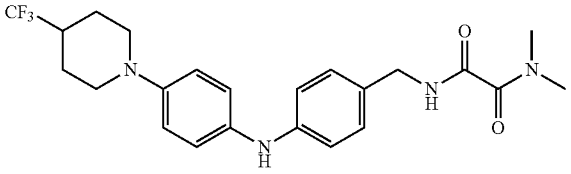

The title compound 371 (16.4 mg) was prepared in a total yield of 24.4% as a light yellow solid from 4-(aminomethyl)-N-(4-(4-(trifluoromethyl)piperidin-1-yl)phenyl)aniline (52.0 mg, 0.15 mmol), 2-(dimethylamino)-2-oxoacetic acid (17.6 mg, 0.15 mmol), DIEA (58 mg, 0.45 mmol) and HATU (57 mg, 0.15 mmol) according to the procedure for 363. $^1$H NMR (400 MHz, Methanol-$d_4$) δ 7.05 (d, J=8.3 Hz, 2H), 6.94 (d, J=8.8 Hz, 2H), 6.85 (dd, J=11.4, 8.5 Hz, 4H), 4.24 (s, 2H), 3.55-3.49 (m, 2H), 2.98 (s, 3H), 2.87 (s, 3H), 2.61-2.54 (m, 2H), 2.22-2.14 (m, 1H), 1.91-1.85 (m, 2H), 1.63 (qd, J=12.5, 4.1 Hz, 2H). Mass (m/z): 449.3 $[M+H]^+$.

4-oxo-4-(pyrrolidin-1-yl)-N-(4-((4-(4-(trifluoromethyl)piperidin-1-yl)phenyl)amino)benzyl)butanamide (372)

372

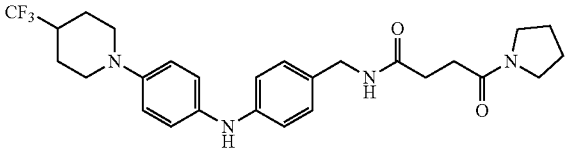

The title compound 372 (16.4 mg) was prepared in a total yield of 24.4% as a light yellow solid from 4-(aminomethyl)-N-(4-(4-(trifluoromethyl)piperidin-1-yl)phenyl)aniline (70.0 mg, 0.2 mmol), 4-oxo-4-(pyrolidin-1-yl)butanoic acid (41.0 mg, 0.24 mmol), DIEA (77.4 mg, 0.6 mmol) and HATU (91.2 mg, 0.24 mmol) according to the procedure for 363. $^1$H NMR (400 MHz, Methanol-$d_4$) δ 7.03-6.80 (m, 8H), 4.15 (s, 2H), 3.55-3.46 (m, 2H), 3.41 (t, J=6.8 Hz, 2H), 3.29 (t, J=6.9 Hz, 2H), 2.59-2.39 (m, 6H), 2.21-2.13 (m, 1H), 1.90-1.83 (m, 4H), 1.81-1.75 (m, 2H), 1.63 (qd, J=12.5, 4.0 Hz, 2H). Mass (m/z): 503.4 $[M+H]^+$.

N-(4-((2-methoxy-4-(4-(trifluoromethyl)piperidin-1-yl)phenyl)amino)benzyl)-5-oxopyrrolidine-3-carboxamide (373)

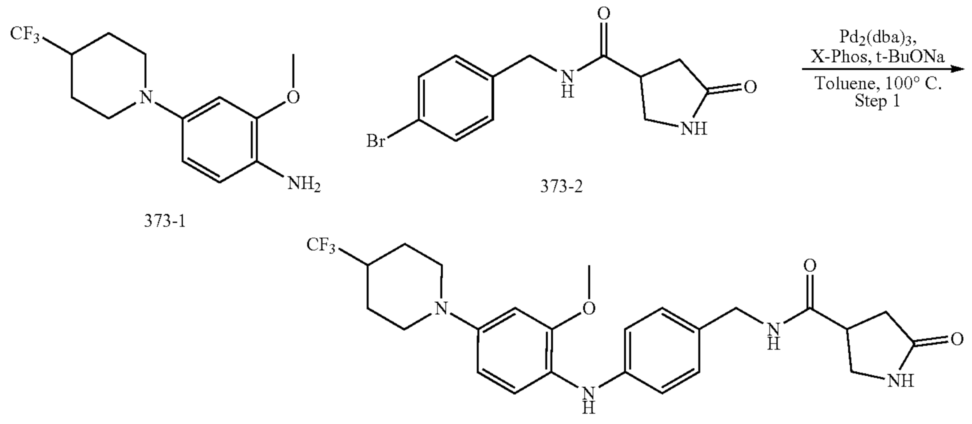

373-1 373-2

373

The title compound 373 (4.2 mg) was prepared in a total yield of 3.4% as a yellow solid from N-(4-bromobenzyl)-5-oxopyrrolidine-3-carboxamide (74 mg, 0.25 mmol), 2-methoxy-4-(4-(trifluoromethyl)piperidin-1-yl)aniline (89 mg, 0.33 mmol), $Pd_2(dba)_3$ (2.0 mg, 2.5 umol), X-Phos (6.0 mg, 12.5 umol), t-BuONa (36.0 mg, 0.38 mmol) according to the procedure for 363-3.

$^1$H NMR (400 MHz, Methanol-$d_4$) δ 7.48-6.01 (m, 7H), 4.18 (s, 2H), 3.73 (s, 3H), 3.64-3.29 (m, 5H), 2.80-2.30 (m, 4H), 2.25-2.12 (m, 1H), 1.96-1.82 (m, 2H), 1.72-1.57 (m, 2H). Mass (m/z): 591.3 $[M+H]^+$.

N-(4-((2,6-dimethyl-4-(4-methylpiperidin-1-yl)phenyl)amino)benzyl)-1-ethyl-5-oxopyrrolidine-3-carboxamide (374)

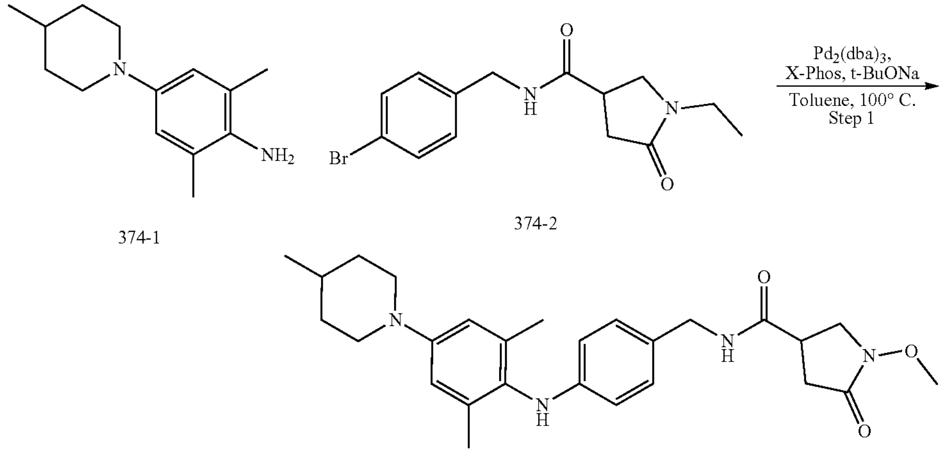

374-1

374-2

374

The title compound 374 (35.1 mg) was prepared in a total yield of 30.4% as a white solid from N-(4-bromobenzyl)-1-ethyl-5-oxopyrrolidine-3-carboxamide (81.0 mg, 0.25 mmol), 2,6-dimethyl-4-(4-methylpiperidin-1-yl)aniline (72 mg, 0.33 mmol), $Pd_2(dba)_3$ (2.0 mg, 2.5 umol), X-Phos (6.0 mg, 12.5 umol), t-BuONa (36.0 mg, 0.38 mmol) according to the procedure for 363-3. $^1$H NMR (400 MHz, Methanol-$d_4$) δ 7.02 (d, J=8.4 Hz, 2H), 6.81 (s, 2H), 6.39 (d, J=8.4 Hz, 2H), 4.23 (s, 2H), 3.68-3.52 (m, 4H), 3.39-3.33 (m, 2H), 3.24-3.13 (m, 2H), 2.78-2.56 (m, 4H), 2.15 (s, 6H), 1.84-1.73 (m, 2H), 1.60-1.49 (m, 1H), 1.44-1.34 (m, 2H), 1.13 (t, J=7.3 Hz, 3H), 1.02 (d, J=6.4 Hz, 3H). Mass (m/z): 463.4 $[M+H]^+$.

1-(2-ethoxyethyl)-5-oxo-N-(4-((4-(4-(trifluoromethyl)piperidin-1-yl)phenyl)amino)benzyl)pyrrolidine-3-carboxamide (375)

375

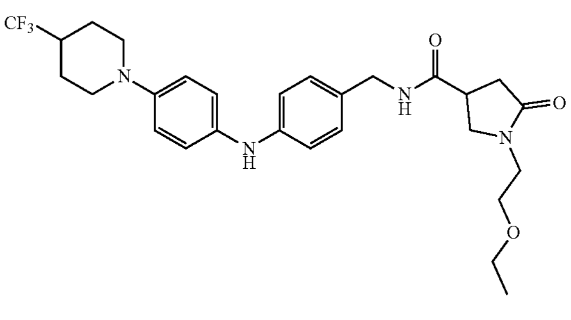

The title compound 375 (11.0 mg) was prepared in a total yield of 11.4% as a light yellow solid from 4-(aminomethyl)-N-(4-(4-(trifluoromethyl)piperidin-1-yl)phenyl)aniline hydrochloride salt (77.0 mg, 0.2 mmol), 1-(2-ethoxyethyl)-5-oxopyrrolidine-3-carboxylic acid (40.2 mg, 0.2 mmol), DIEA (77.9 mg, 0.6 mmol) and HATU (76.0 mg, 0.2 mmol) according to the procedure for 363. $^1$H NMR (400 MHz, Methanol-$d_4$) δ 7.93-5.89 (m, 8H), 4.30 (s, 2H), 3.67-3.59 (m, 2H), 3.53 (dd, J=10.0, 6.3 Hz, 1H), 3.47-3.29 (m, 8H), 3.15-3.07 (m, 2H), 2.57-2.46 (m, 2H), 2.27-2.10 (m, 1H), 2.04-1.80 (m, 2H), 1.72-1.51 (m, 2H), 1.06 (t, J=7.0 Hz, 3H). Mass (m/z): 533.4 $[M+H]^+$.

N1,N1-dimethyl-N'-(4-((4-(4-(trifluoromethyl)piperidin-1-yl)phenyl)amino)benzyl)succinimide (376)

376

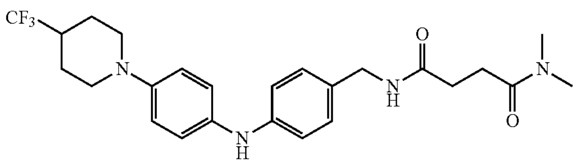

The title compound 376 (15.9 mg) was prepared in a total yield of 22.3% as a light yellow solid from 4-(aminomethyl)-N-(4-(4-(trifluoromethyl)piperidin-1-yl)phenyl)aniline hydrochloride salt (60.3 mg, 0.15 mmol), 4-(dimethylamino)-4-oxobutanoic acid (21.8 mg, 0.15 mmol), DIEA (58.0 mg, 0.45 mmol) and HATU (57 mg, 0.15 mmol) according to the procedure for 363. $^1$H NMR (400 MHz, Methanol-$d_4$) δ 7.13 (d, J=7.9 Hz, 2H), 7.07-6.88 (m, 6H), 4.27 (s, 2H), 3.68-3.56 (m, 2H), 3.09 (s, 3H), 2.94 (s, 3H), 2.78-2.63 (m, 4H), 2.53 (t, J=6.9 Hz, 2H) 2.34-2.21 (m, 11H), 2.03-1.95 (m, 2H), 1.75 (qd, J=12.6, 4.1 Hz, 2H). Mass (m/z): 477.4 $[M+H]^+$.

N'-(4-((4-(4-(trifluoromethyl)piperidin-1-yl)phenyl)amino)benzyl)glutaramide (377)

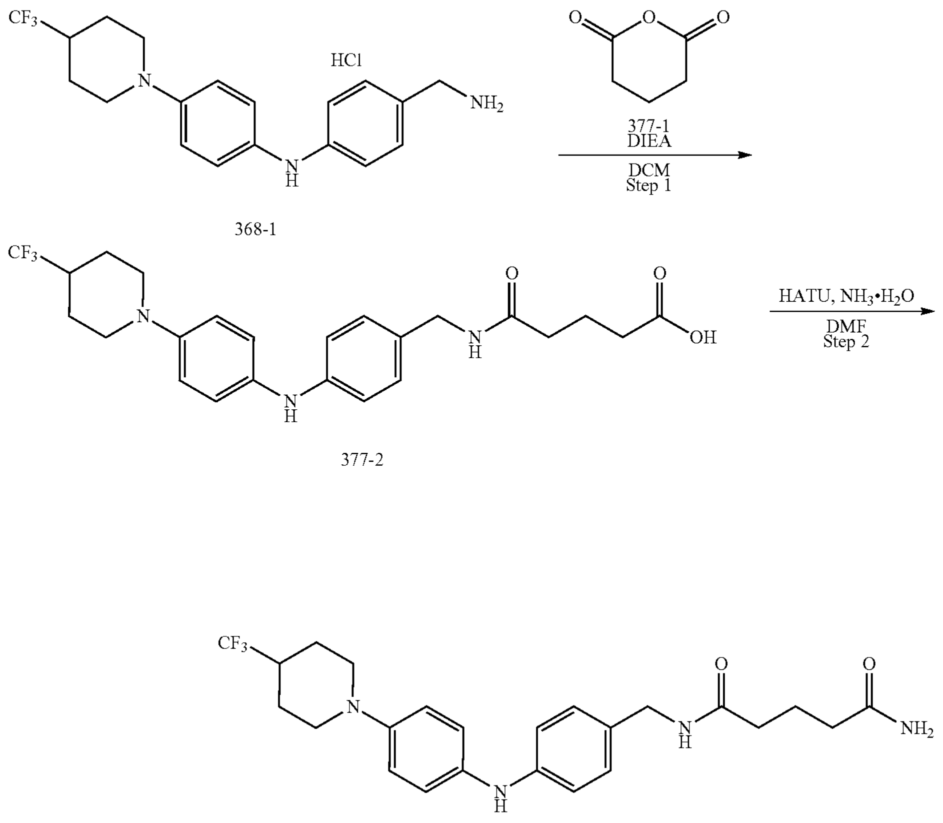

368-1

377-2

377

Step 1. Preparation of 5-oxo-5-((4-((4-(4-(trifluoromethyl)piperidin-1-yl)phenyl)amino)benzyl)amino)pentanoic acid (377-2). To a solution of 4-(aminomethyl)-N-(4-(4-(trifluoromethyl)piperidin-1-yl)phenyl)aniline hydrochloride salt (115 mg, 3.0 mmol) in DCM (10.0 mL) was added DIEA (1.16 g, 9 mmol). Followed by the addition of dihydro-2H-pyran-2,6(3H)-dione (410.8 mg, 3.6 mmol) then the reaction was stirred for 2 hours at rt. The solution was washed with 2×10 mL of water, dried over $Na_2SO_4$ and concentrated under vacuum. The residue was purified by prep-TLC (MeOH/DCM=1/10) to afford the desired product as a yellow solid. (42 mg, 30.2%). Mass (m/z): 464.3 $[M+H]^+$.

Step 2. Preparation of N'-(4-((4-(4-(trifluoromethyl)piperidin-1-yl)phenyl)amino)benzyl)glutaramide (377). To a solution of 5-oxo-5-((4-((4-(4-(trifluoromethyl)piperidin-1-yl)phenyl)amino)benzyl)amino)pentanoic acid (42 mg, 0.09 mmol) in DMF (1.0 mL) was added HATU (41 mg, 0.11 mmol). Then the reaction was stirred for 5 hours at rt. $NH_3 \cdot H_2O$ (0.2 mL) was added. Then the mixture was stirred overnight at rt. 5 mL water was added. The resulting solution was extracted with 3×5 mL EA. The organic layers were combined, washed with 3×10 mL of water, dried over $Na_2SO_4$ and concentrated under vacuum. The residue was purified by prep-TLC (MeOH/DCM=1/20) to afford the desired product as a yellow solid. (6.5 mg, 15.5%). $^1H$ NMR (400 MHz, Methanol-$d_4$) δ 7.22-6.86 (m, 8H), 4.27 (s, 2H), 3.72-3.55 (m, 211), 2.77-2.61 (m, 2H), 2.30-2.24 (m, 4H), 2.08-1.86 (m, 5H), 1.80-1.69 (m, 2H). Mass (m/z): 463.3 $[M+H]^+$.

N'-(4-((4-(4-(trifluoromethyl)piperidin-1-yl)phenyl)amino)benzyl)malonamide (378)

378

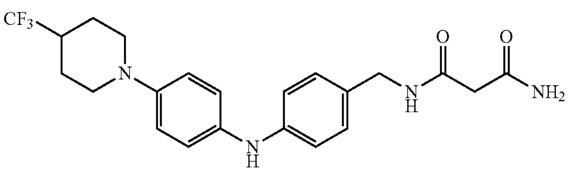

The title compound 378 (5.3 mg) was prepared in a total yield of 6.1% as a light yellow solid from 4-(aminomethyl)-N-(4-(4-(trifluoromethyl)piperidin-1-yl)phenyl)aniline hydrochloride salt (77.1 mg, 0.2 mmol), 3-amino-3-oxopropanoic acid (33.8 mg, 0.24 mmol), DIEA (77.4 mg, 0.6 mmol) and HATU (91.2 mg, 0.24 mmol) according to the procedure for 363. $^1H$ NMR (400 MHz, Methanol-$d_4$) δ 7.12-6.69 (m, 8H), 4.20 (s, 2H), 3.67-359 (m, 1H), 3.57-3.43 (m, 2H), 3.17-3.10 (m, 1H), 2.65-2.44 (m, 2H), 2.23-2.12 (m, 1H), 1.94-1.84 (m, 2H), 1.70-1.60 (m, 2H). Mass (m/z): 435.3 $[M+H]^+$.

5-oxo-5-(pyrrolidin-1-yl)-N-(4-((4-(4-(trifluoromethyl)piperidin-1-yl)phenyl)amino)benzyl)pentanamide (379)

379

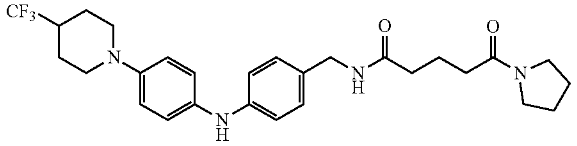

The title compound 379 (17.7 mg) was prepared in a total yield of 17.2% as a light yellow solid from 4-(aminomethyl)-N-(4-(4-(trifluoromethyl)piperidin-1-yl)phenyl)aniline hydrochloride salt (77.1 mg, 0.2 mmol), 5-oxo-5-(pyrrolidin-1-yl)pentanoic acid (37.0 mg, 0.2 mmol), DIEA (77.4 mg, 0.6 mmol) and HATU (76.0 mg, 0.2 mmol) according to the procedure for 363. $^1$H NMR (400 MHz, Methanol-$d_4$) δ 8.09-5.94 (m, 8H), 4.16 (s, 2H), 3.26 (q, J=7.1 Hz, 4H), 2.23-2.09 (m, 5H), 1.94-1.69 (m, 8H), 1.68-1.53 (m, 2H). Mass (m/z): 517.4 [M+H]$^+$.

3-oxo-N-(4-((4-(4-(trifluoromethyl)piperidin-1-yl)phenyl)amino)benzyl)piperazine-1-carboxamide (380)

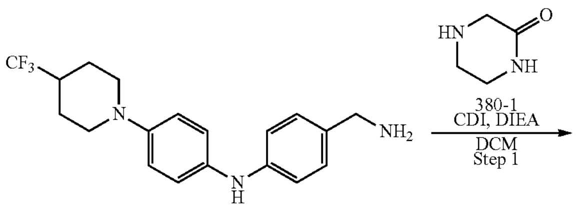

368-1

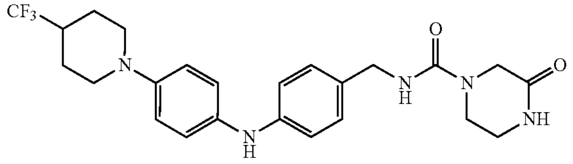

380

To a solution of 4-(aminomethyl)-N-(4-(4-(trifluoromethyl)piperidin-1-yl)phenyl)aniline (34.9 mg, 0.1 mmol) in DCM (10 mL) was added CDI (17.8 mg, 0.11 mmol). Then the reaction was stirred for 1 hour at rt, piperazin-2-one (11.0 mg, 0.11 mmol) and DIEA (38.7 mg, 0.3 mmol) were added. Then the reaction was stirred for 3 hours at rt. Then the solution was washed with 3×10 mL of water, dried over $Na_2SO_4$ and concentrated under vacuum. The residue was purified by prep-TLC (MeOH/DCM=1/15) to afford the desired product as a light yellow solid. (26.7 mg, 56.2%). $^1$H NMR (400 MHz, Methanol-$d_4$) δ 7.50-6.40 (m, 8H), 4.30 (s, 2H), 4.05 (s, 2H), 3.84-3.47 (m, 4H), 3.36 (d, J=5.6 Hz, 2H), 2.99-2.45 (m, 2H), 2.36-2.22 (m, 1H), 2.09-1.89 (m, 2H), 1.83-1.66 (m, 2H). Mass (m/z): 476.3 [M+H]$^+$.

4-methyl-3-oxo-N-(4-((4-(4-(trifluoromethyl)piperidin-1-yl)phenyl)amino)benzyl)piperazine-1-carboxamide (381)

381

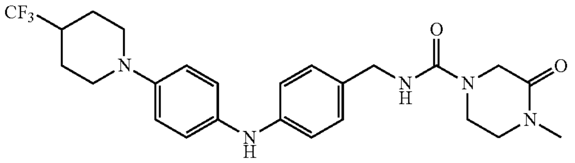

The title compound 381 (9.8 mg) was prepared in a total yield of 20.0% as a blue solid from 4-(aminomethyl)-N-(4-(4-(trifluoromethyl)piperidin-1-yl)phenyl)aniline (34.9 mg, 0.1 mmol), 1-methylpiperazin-2-one (12.5 mg, 0.11 mmol), CDI (17.8 mg, 0.11 mmol) and DIEA (38.7 mg, 0.3 mmol) according to the procedure for 380. $^1$H NMR (400 MHz, Methanol-$d_4$) δ 7.77-6.65 (m, 8H), 4.37 (s, 2H), 4.06 (s, 2H), 3.99-3.36 (m, 8H), 3.03-2.97 (m, 3H), 2.88-2.69 (m, 1H), 2.42-1.74 (m, 4H). Mass (m/z): 490.3 [M+H]$^+$.

2-(1-ethyl-5-oxopyrrolidin-3-yl)-N-(4-((4-(4-(trifluoromethyl)piperidin-1-yl)phenyl)amino)benzyl)acetamide (382)

382

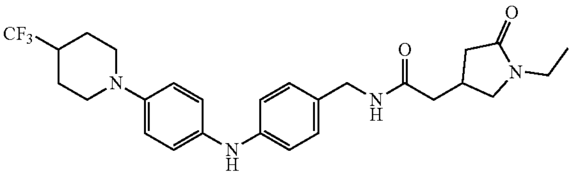

The title compound 382 (20.6 mg) was prepared in a total yield of 41.0% as a light yellow solid from 4-(aminomethyl)-N-(4-(4-(trifluoromethyl)piperidin-1-yl)phenyl)aniline (34.9 mg, 0.1 mmol), 2-(1-ethyl-5-oxopyrrolidin-3-yl)acetic acid (17.1 mg, 0.1 mmol), DIEA (38.7 mg, 0.3 mmol) and HATU (38.0 mg, 0.1 mmol) according to the procedure for 363. $^1$H NMR (400 MHz, Methanol-$d_4$) δ 7.17-7.09 (m, 2H), 7.08-6.87 (m, 6H), 4.27 (s, 2H), 3.68-3.57 (m, 3H), 3.32-3.27 (m, 2H), 3.19 (dd, J=10.1, 6.0 Hz, 1H), 2.83-2.75 (m, 1H), 2.73-2.61 (m, 2H), 2.56 (dd, J=16.9, 8.8 Hz, 1H), 2.39 (d, J=7.5 Hz, 2H), 2.32-2.23 (m, 1H), 2.18-2.10 (m, 1H), 2.04-1.91 (m, 2H), 1.81-1.70 (m, 2H), 1.12 (t, J=7.3 Hz, 3H). Mass (m/z): 503.3 [M+H]$^+$.

1-methyl-2-oxo-N-(4-((4-(4-(trifluoromethyl)piperidin-1-yl)phenyl)amino)benzyl)imidazolidine-4-carboxamide (383)

383

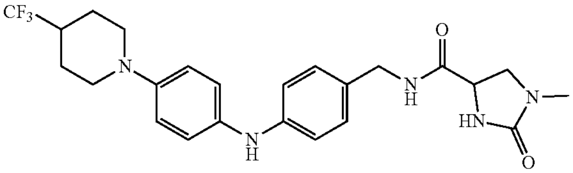

The title compound 383 (15.6 mg) was prepared in a total yield of 32.8% as a white solid from 4-(aminomethyl)-N-(4-(4-(trifluoromethyl)piperidin-1-yl)phenyl)aniline (34.9 mg, 0.1 mmol), 1-methyl-2-oxoimidazolidine-4-carboxylic acid (14.3 mg, 0.1 mmol), DIEA (38.7 mg, 0.3 mmol) and HATU (38.0 mg, 0.1 mmol) according to the procedure for 363. $^{1}$H NMR (400 MHz, Methanol-$d_4$) δ 7.03 (d, J=8.4 Hz, 2H), 6.94 (d, J=8.9 Hz, 2H), 6.86 (dd, J=12.0, 8.6 Hz, 4H), 4.22 (s, 2H), 4.04 (dd, J=9.9, 7.2 Hz, 1H), 3.58-3.49 (m, 3H), 2.64 (s, 3H), 2.58 (t, J=12.1 Hz, 2H), 2.25-2.16 (m, 1H), 1.92-1.86 (m, 2H), 1.64 (qd, J=12.5, 4.1 Hz, 2H). Mass (m/z): 476.3 $[M+H]^+$.

1-ethyl-N-(2-methyl-4-((4-(4-(trifluoromethyl)piperidin-1-yl)phenyl)amino)benzyl)-5-oxopyrrolidine-3-carboxamide (384)

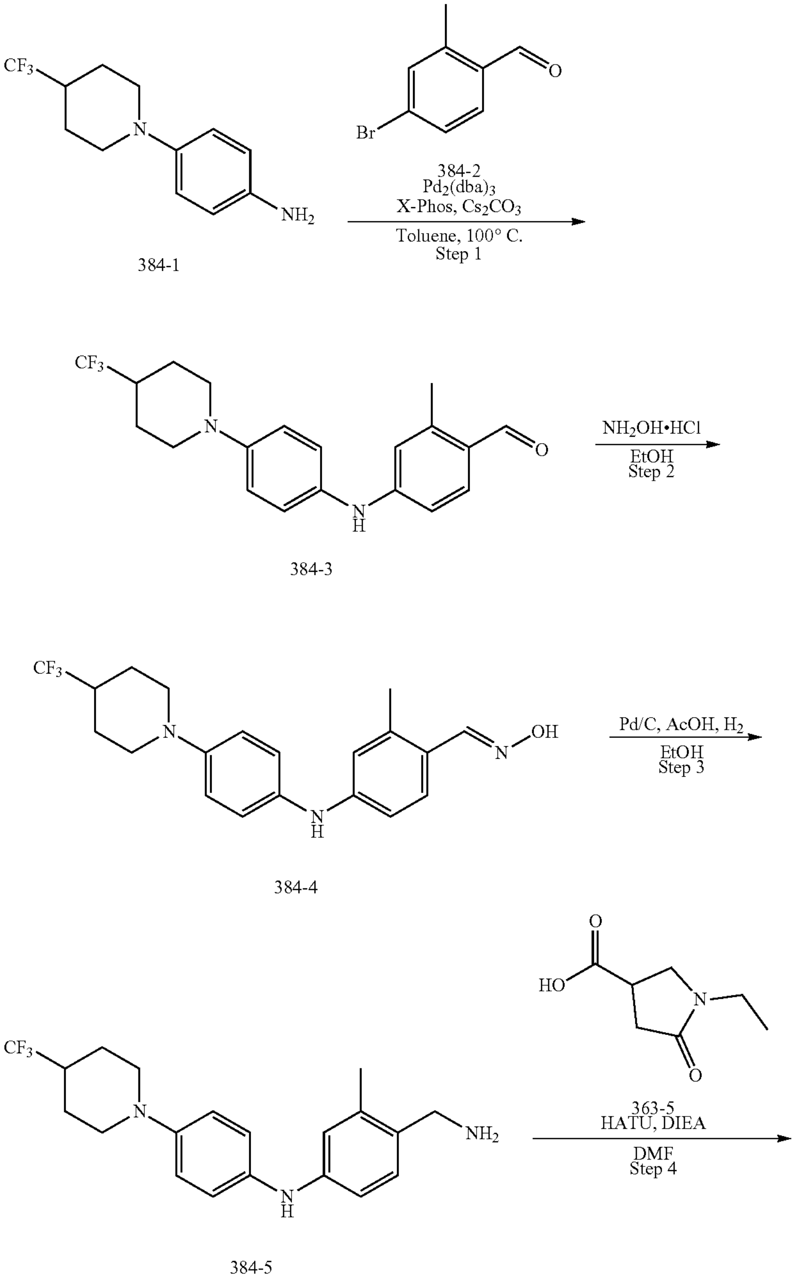

-continued

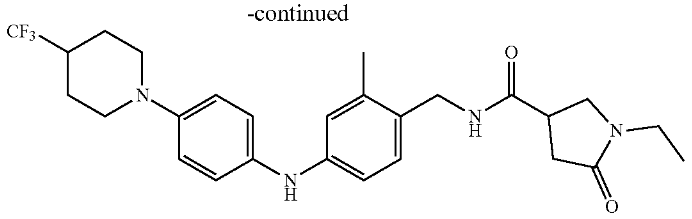

384

Step 1. Preparation of 2-methyl-4-((4-(4-(trifluoromethyl)piperidin-1-yl)phenyl)amino)benzaldehyde (384-3). The title compound 384-3 (1.22 g) was prepared in a total yield of 77.7% as a yellow oil from 4-bromo-2-methylbenzaldehyde (995 mg, 5 mmol), 4-(4-(trifluoromethyl)piperidin-1-yl)aniline (1.06 g, 4.34 mmol), $Pd_2(dba)_3$ (46 mg, 50 umol), X-Phos (119 mg, 0.25 mol), $Cs_2CO_3$ (2.72 g, 7.5 mmol) according to the procedure for 363-3. Mass (m/z): 363.3 $[M+H]^+$.

Step 2. Preparation of (E)-2-methyl-4-((4-(4-(trifluoromethyl)piperidin-1-yl)phenyl)amino)benzaldehyde oxime (384-4). To a solution of 2-methyl-4-((4-(4-(trifluoromethyl)piperidin-1-yl)phenyl)amino)benzaldehyde (1.22 g, 3.36 mmol) in a solution of EtOH (20 mL) was added Hydroxylamine hydrochloride (318 mg, 5 mmol). Then the reaction was stirred overnight at rt. The reaction mixture was concentrated under vacuum. The residue was applied on a silica gel column and eluted with ethyl acetate/hexane (0-1/1) to afford the crude product as a yellow oil. (1.01 g, 79.5%). Mass (m/z): 378.2 $[M+H]^+$.

Step 3. Preparation of 4-(aminomethyl)-3-methyl-N-(4-(4-(trifluoromethyl)piperidin-1-yl)phenyl)aniline (384-5). To a solution of (E)-2-methyl-4-((4-(4-(trifluoromethyl)piperidin-1-yl)phenyl)amino)benzaldehyde oxime (500 mg, 1.32 mmol) in EtOH (20 mL) was added 10% Pd/C (16 mg, 0.015 ml) and AcOH (0.5 mL). Then the reaction was stirred overnight at rt under an atmosphere of Hydrogen. Pd/C was filtrated out. The PH of the filtration was adjusted to 8-9 with sodium carbonate solution. Then the mixture was extracted by DCM (20 mL×3). The combined organic layers were washed with brine (20 mL×3), dried over $Na_2SO_4$ and concentrated to give the desired product as yellow solid. (190 mg, 40.0%). 364.2 $[M+H]^+$.

Step 4. Preparation of 1-ethyl-N-(2-methyl-4-((4-(4-(trifluoromethyl)piperidin-1-yl)phenyl)amino)benzyl)-5-oxopyrrolidine-3-carboxamide (384). The title compound 384 (17.9 mg) was prepared in a total yield of 35.7% as a white powder from 4-(aminomethyl)-3-methyl-N-(4-(4-(trifluoromethyl)piperidin-1-yl)phenyl)aniline (36.3 mg, 0.1 mmol), 1-ethyl-5-oxopyrrolidine-3-carboxylic acid (15.7 mg, 0.1 mmol), DIEA (38.7 mg, 0.3 mmol) and HATU (38.0 mg, 0.1 mmol) according to the procedure for 363. $^1H$ NMR (400 MHz, Methanol-$d_4$) δ 7.09-6.56 (m, 8H), 4.21 (s, 2H), 3.59-3.45 (m, 4H), 3.29-3.23 (m, 4H), 3.16-3.08 (m, 1H), 2.67-2.47 (m, 4H), 2.22-2.12 (m, 4H), 1.93-1.84 (m, 2H), 1.70-1.60 (m, 2H), 1.04 (t, J=7.3 Hz, 3H). Mass (m/z): 503.3 $[M+H]^+$.

N-(2-methyl-4-((4-(4-(trifluoromethyl)piperidin-1-yl)phenyl)amino)benzyl)-5-oxopyrrolidine-3-carboxamide (385)

385

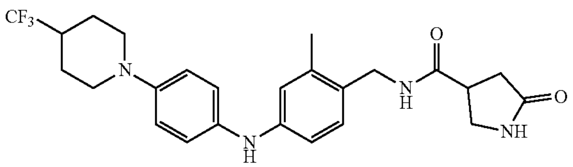

The title compound 385 (17.7 mg) was prepared in a total yield of 37.3% as a white powder from 4-(aminomethyl)-3-methyl-N-(4-(4-(trifluoromethyl)piperidin-1-yl)phenyl)aniline (36.3 mg, 0.1 mmol), 5-oxopyrrolidine-3-carboxylic acid (12.8 mg, 0.1 mmol), DIEA (38.7 mg, 0.3 mmol) and HATU (38.0 mg, 0.1 mmol) according to the procedure for 363. $^1H$ NMR (400 MHz, Methanol-$d_4$) δ 6.98-6.91 (m, 3H), 6.89-6.84 (m, 2H), 6.73-6.67 (m, 2H), 4.21 (s, 2H), 3.57-3.37 (m, 5H), 2.65-2.35 (m, 6H), 2.23-2.12 (m, 4H), 1.93-1.84 (m, 2H), 1.70-1.58 (m, 2H). Mass (m/z): 475.3 $[M+H]^+$.

5-oxo-N-(4-((4-(3-(trifluoromethyl)azetidin-1-yl)phenyl)amino)benzyl)pyrrolidine-3-carboxamide (386)

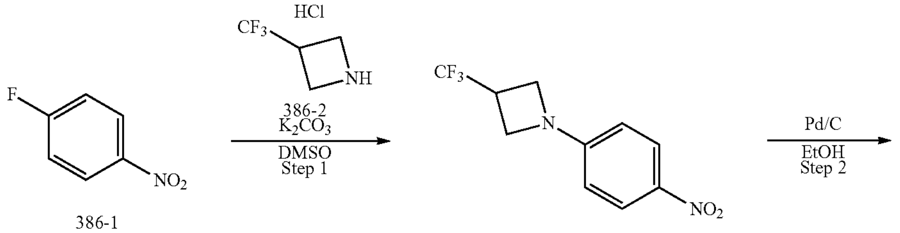

386-1

386-3

-continued

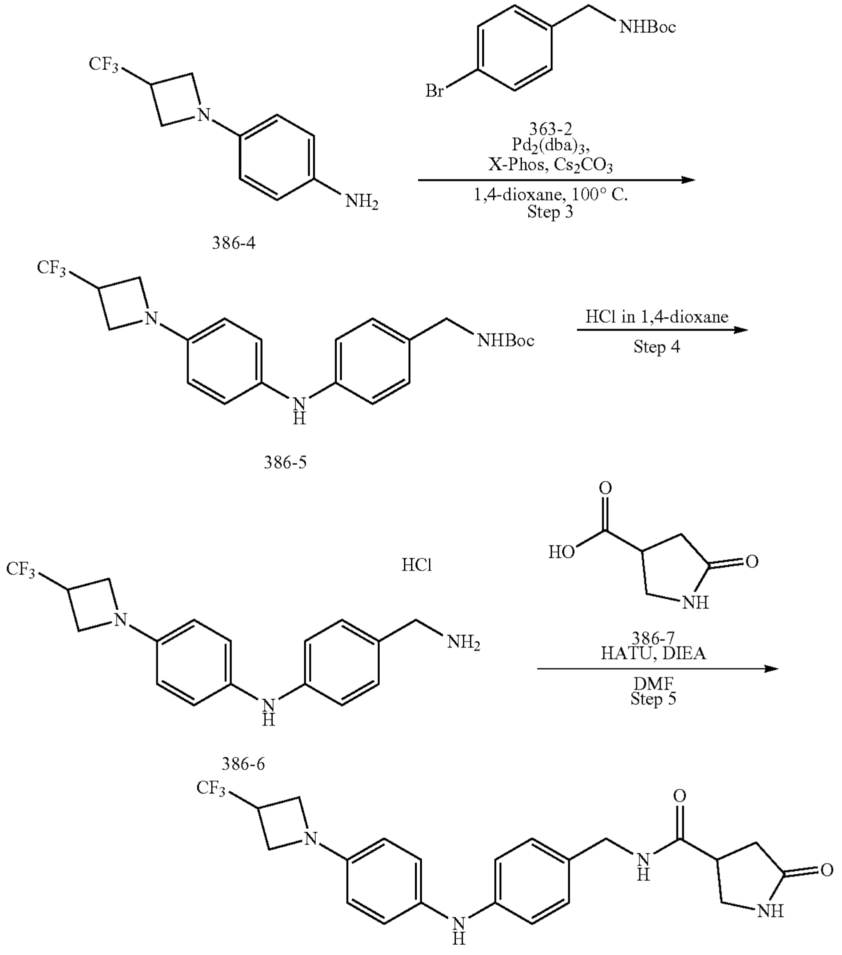

386-4

386-5

386-6

386

Step 1. Preparation of 1-(4-nitrophenyl)-3-(trifluoromethyl)azetidine (386-3). A solution of 1-fluoro-4-nitrobenzene (241 mg, 1.71 mmol), 3-(trifluoromethyl)azetidine hydrochloride (250 mg, 1.55 mmol) and $K_2CO_3$ (320 mg, 2.32 mmol) in DMSO (5 mL) was stirred for 18 hours at 80° C. After cooling to rt. 10 mL of water was added. The resulting solution was extracted with 3×10 mL of ethyl acetate. The organic layers were combined, washed with water (3×15 mL), dried and concentrated under vacuum. The residue was purified by prep-TLC (EA/PE=1/10) to afford the desired product as a yellow solid (275 mg, 72.2%). Mass (m/z): 247.1 $[M+H]^+$.

Step 2. Preparation of 4-(3-(trifluoromethyl)azetidin-1-yl) aniline (386-4). To a solution of 1-(4-nitrophenyl)-3-(trifluoromethyl)azetidine (135 mg, 0.55 mmol) in EtOH (10 mL) was added 10% Pd/C (5.8 mg, 5.5 umol). Then the reaction was stirred overnight at rt under an atmosphere of Hydrogen. Pd/C was filtrated out. The filtrate was concentrated under vacuum to afford the target product as a yellow oil. (99 mg, 83.2%). Mass (m/z): 217.2 $[M+H]^+$.

Step 3. Preparation of tert-butyl (4-((4-(3-(trifluoromethyl)azetidin-1-yl)phenyl)amino)benzyl)carbamate (386-5). The title compound 386-5 (116 mg) was prepared in a total yield of 72.5% as a yellow solid from tert-butyl (4-bromobenzyl)carbamate (109 mg, 0.38 mmol), 4-(3-(trifluoromethyl)azetidin-1-yl)aniline (99 mg, 0.46 mmol), $Pd_2(dba)_3$ (3.5 mg, 3.8 umol), X-Phos (9.0 mg, 19 umol), $Cs_2CO_3$ (206 mg, 0.57 mmol) according to the procedure for 363-3. Mass (m/z): 422.3 $[M+H]^+$.

Step 4. Preparation of 4-(aminomethyl)-N-(4-(3-(trifluoromethyl)azetidin-1-yl)phenyl)aniline hydrochloride (386-6). The title compound 386-6 (98 mg) was prepared in a total yield of 100% as a yellow solid from tert-butyl (4-((4-(3-(trifluoromethyl)azetidin-1-yl)phenyl)amino)benzyl)carbamate (116 mg, 0.28 mmol), HCl in 1,4-dioxane (5.0 mL) according to the procedure for 363-4. Mass (m/z): 322.3 $[M+H]^+$.

Step 5. Preparation of 5-oxo-N-(4-((4-(3-(trifluoromethyl)azetidin-1-yl)phenyl)amino)benzyl)pyrrolidine-3-carboxamide (386). The title compound 386 (3.0 mg) was prepared in a total yield of 5.0% as a dark blue powder from 4-(aminomethyl)-N-(4-(3-(trifluoromethyl)azetidin-1-yl) phenyl)aniline hydrochloride (49 mg, 0.14 mmol), 5-oxopyrrolidine-3-carboxylic acid (18 mg, 0.14 mmol), DIEA (53.4 mg, 0.41 mmol) and HATU (52 mg, 0.14 mmol) according to the procedure for 363. 1H NMR (400 MHz, Methanol-$d_4$) δ 8.16-6.48 (m, 8H), 4.87 (s, 2H), 3.62-3.56 (m, 1H), 3.53-3.46 (m, 1H), 3.37-3.34 (m, 2H), 3.27-3.19 (m, 1H), 2.64-2.46 (m, 2H), 2.25-2.17 (m, 1H), 2.07-2.02 (m, 1H), 1.66-1.57 (m, 1H). Mass (m/z): 433.3 $[M+H]^+$.

1-ethyl-5-oxo-N-(4-((4-(3-(trifluoromethyl)azetidin-1-yl)phenyl)amino)benzyl)pyrrolidine-3-carboxamide (387)

387

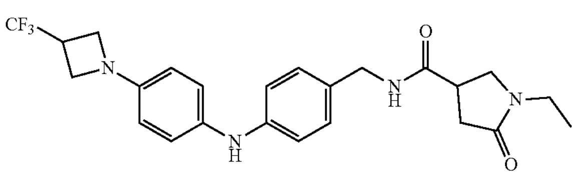

The title compound 387 (4.1 mg) was prepared in a total yield of 6.5% as a dark blue powder from 4-(aminomethyl)-N-(4-(3-(trifluoromethyl)azetidin-1-yl)phenyl)aniline hydrochloride (49 mg, 0.14 mmol), 1-ethyl-5-oxopyrrolidine-3-carboxylic acid (21.8 mg, 0.14 mmol), DIEA (53.4 mg, 0.41 mmol) and HATU (52 mg, 0.14 mmol) according to the procedure for 363. $^1$H NMR (400 MHz, Methanol-$d_4$) δ 7.79-6.15 (m, 8H), 4.77 (s, 2H), 3.59-3.45 (m, 2H), 3.29-3.23 (m, 4H), 3.14-3.05 (m, 1H), 2.52 (d, J=8.4 Hz, 2H), 2.01-1.83 (m, 11H), 1.04 (t, J=7.3 Hz, 3H). Mass (m/z): 461.3 [M+H]$^+$.

N$^1$-(4-((4-(4-methylpiperidin-1-yl)phenyl)amino)benzyl)malonamide (388)

388

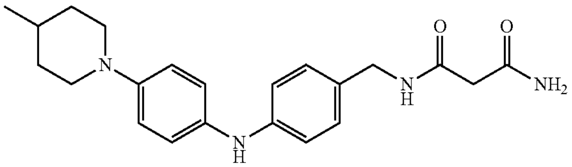

The title compound 388 (15.3 mg) was prepared in a total yield of 20.1% as a dark blue powder from 4-(aminomethyl)-N-(4-(4-methylpiperidin-1-yl)phenyl)aniline (59 mg, 0.2 mmol), 3-amino-3-oxopropanoic acid (30.9 mg, 0.3 mmol), DIEA (77.4 mg, 0.6 mmol) and HATU (91.2 mg, 0.24 mmol) according to the procedure for 363. $^1$H NMR (400 MHz, Methanol-$d_4$) δ 7.35 (d, J=8.6 Hz, 2H), 7.18 (d, J=8.0 Hz, 2H), 7.04 (dd, J=13.4, 8.3 Hz, 4H), 4.27 (s, 2H), 3.57-3.43 (m, 4H), 3.23 (s, 2H), 2.01-1.92 (m, 2H), 1.86-1.74 (m, 11H), 1.64-1.49 (m, 2H), 1.01 (d, J=6.4 Hz, 3H). Mass (m/z): 381.3 [M+H]$^+$.

N'-(4-((4-(4-methylpiperidin-1-yl)phenyl)amino)benzyl)glutaramide (389)

389

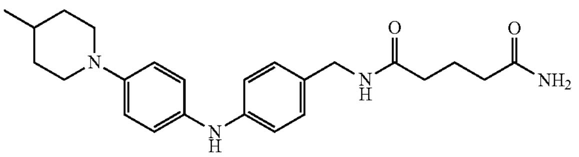

The title compound 389 (15.3 mg) was prepared in a total yield of 20.1% as a dark blue powder from 4-(aminomethyl)-N-(4-(4-methylpiperidin-1-yl)phenyl)aniline (59 mg, 0.2 mmol), 3-amino-3-oxopropanoic acid (39.3 mg, 0.3 mmol), DIEA (77.4 mg, 0.6 mmol) and HATU (91.2 mg, 0.24 mmol) according to the procedure for 363. $^1$H NMR (400 MHz, Methanol-$d_4$) δ 7.36 (d, J=8.6 Hz, 2H), 7.14 (d, J=8.0 Hz, 2H), 7.04 (dd, J=12.6, 8.4 Hz, 4H), 4.23 (s, 2H), 3.58-3.45 (m, 4H), 2.22-2.13 (m, 4H), 1.99-1.91 (m, 4H), 1.88-1.71 (m, 3H), 1.65-1.51 (m, 2H), 1.01 (d, J=6.4 Hz, 3H). Mass (m/z): 409.3 [M+H]$^+$.

N-(2-chloro-4-((4-(4-(trifluoromethyl)piperidin-1-yl)phenyl)amino)benzyl)-5-oxopyrrolidine-3-carboxamide (390)

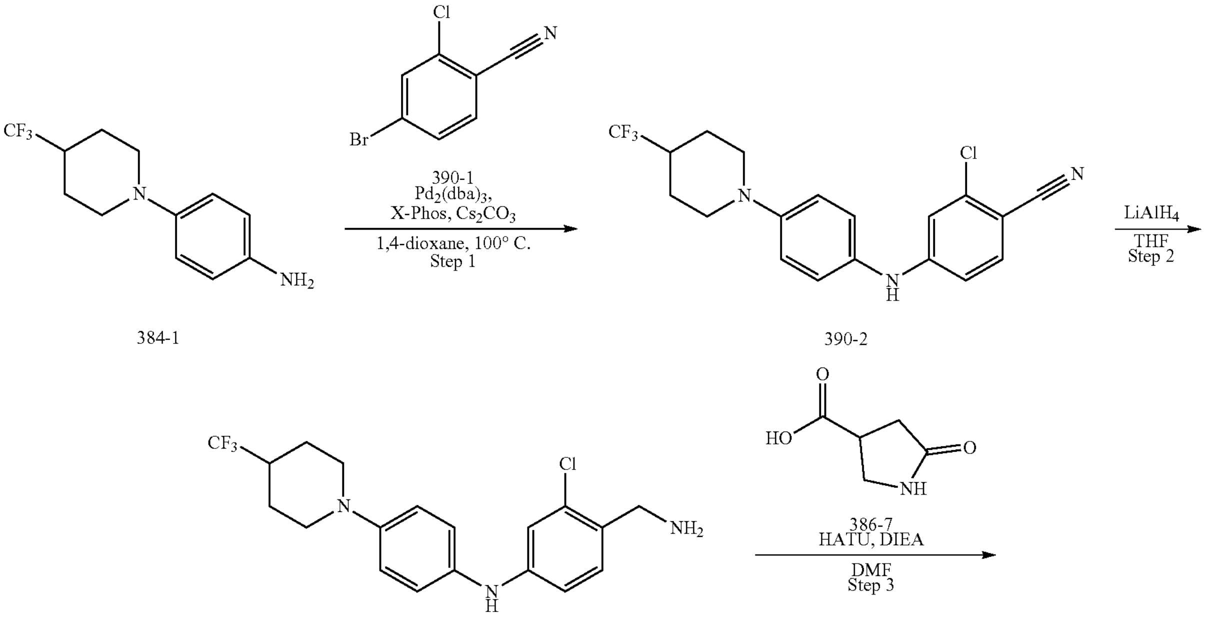

384-1

390-2

390-3

-continued

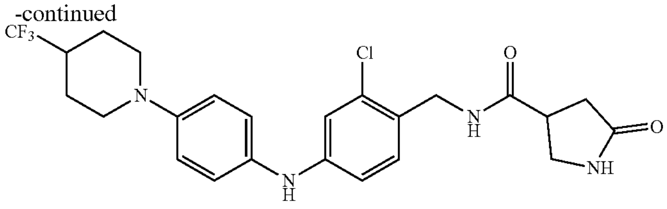

390

Step 1. Preparation of 2-chloro-4-((4-(4-(trifluoromethyl)piperidin-1-yl)phenyl)amino)benzonitrile (390-2). The title compound 390-2 (1.26 g) was prepared in a total yield of 82.9% as a gray solid from 4-bromo-2-chlorobenzonitrile (860 mg, 4 mmol), 4-(4-(trifluoromethyl)piperidin-1-yl)aniline (1.27 g, 5.2 mmol), $Pd_2$(dba), (36.6 mg, 0.04 mmol), X-Phos (95.4 mg, 0.2 mmol), $Cs_2CO_1$ (1.96 g, 6 mmol) according to the procedure for 363-3. Mass (m/z): 380.2 $[M+H]^+$.

Step 2. Preparation of 4-(aminomethyl)-3-chloro-N-(4-(4-(trifluoromethyl)piperidin-1-yl)phenyl)aniline (390-3). To a solution of 2-chloro-4-((4-(4-(trifluoromethyl)piperidin-1-yl)phenyl)amino)benzonitrile (379 mg, 1 mmol) in THF (20 mL) was added $LiAlH_4$ (380 mg, 10 mmol). Then the reaction was refluxed overnight at rt. 20 mL of water was added at 0° C. The resulting solution was extracted with 3×20 mL of ethyl acetate. The organic layers were combined, washed with water (3×50 mL), dried and concentrated under vacuum. The residue was purified by prep-TLC (MeOH/DCM-1/15) to afford the desired product as a yellow solid (50 mg, 13.0%). Mass (m/z): 384.2 $[M+H]^+$.

Step 3. Preparation of N-(2-chloro-4-((4-(4-(trifluoromethyl)piperidin-1-yl)phenyl)amino)benzyl)-5-oxopyrrolidine-3-carboxamide (390). The title compound 390 (40.9 mg) was prepared in a total yield of 63.9% as a dark blue powder from 4-(aminomethyl)-3-chloro-N-(4-(4-(trifluoromethyl)piperidin-1-yl)phenyl)aniline (50 mg, 0.13 mmol), 5-oxopyrrolidine-3-carboxylic acid (33.0 mg, 0.26 mmol), DIEA (50.0 mg, 0.40 mmol) and HATU (59 mg, 0.16 mmol) according to the procedure for 363. $^1$H NMR (400 MHz, Methanol-$d_4$) δ 7.98-6.52 (m, 7H), 4.33 (s, 2H), 3.88-3.37 (m, 4H), 3.31-3.25 (m, 1H), 2.78-2.37 (m, 4H), 2.35-1.43 (m, 5H). Mass (m/z): 495.3 $[M+H]^+$.

N-(3-methoxy-4-((4-(4-(trifluoromethyl)piperidin-1-yl)phenyl)amino)benzyl)-5-oxopyrrolidine-3-carboxamide (391)

391

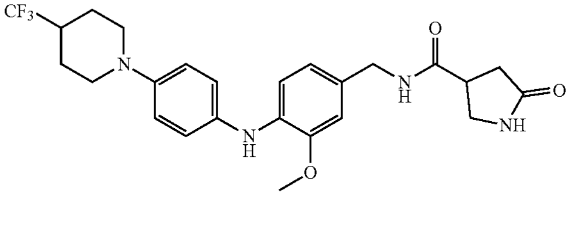

The title compound 391 (12.8 mg) was prepared in a total yield of 26.1% as a white powder from 4-(aminomethyl)-2-methoxy-N-(4-(4-(trifluoromethyl)piperidin-1-yl)phenyl)aniline (37.9 mg, 0.1 mmol), 5-oxopyrrolidine-3-carboxylic acid (12.8 mg, 0.1 mmol), DIE A (38.7 mg, 0.1 mmol) and HATU (38.0 mg, 0.1 mmol) according to the procedure for 363. H NMR (400 MHz, Methanol-$d_4$) δ 7.52-6.34 (m, 7H), 4.23 (s, 2H), 3.80 (s, 3H), 3.61-3.38 (m, 3H), 3.26-3.23 (m, 1H), 3.22-3.20 (m, 1H), 2.79-2.35 (m, 4H), 2.25-2.16 (m, 1H), 2.00-1.79 (m, 2H), 1.73-1.55 (m, 21H). Mass (m/z): 491.3 $[M+H]^+$.

N-(4-((4-cyclohexylphenyl)amino)benzyl)-5-oxopyrrolidine-3-carboxamide (392)

392

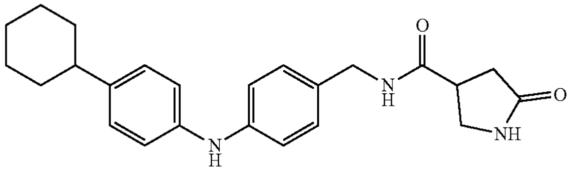

The title compound 392 (9.3 mg) was prepared in a total yield of 9.5% as a light yellow solid from N-(4-bromobenzyl)-5-oxopyrrolidine-3-carboxamide (74 mg, 0.25 mmol), 4-cyclohexylaniline (58 mg, 0.33 mmol), $Pd_2(dba)_3$ (2.3 mg, 2.5 umol), X-Phos (6.0 mg, 12.5 umol), $Cs_2CO_3$ (122 mg, 0.38 mmol) according to the procedure for 363-3. $^1$H NMR (400 MHz, DMSO-$d_6$) δ 8.33 (t, J=5.6 Hz, 1H), 7.93 (s, 1H), 7.52 (s, 1H), 7.04-6.97 (m, 4H), 6.93-6.87 (m, 4H), 4.10 (d, J=5.6 Hz, 2H), 3.33 (t, J=8.8 Hz, 1H), 3.20-3.10 (m, 2H), 2.37-2.29 (m, 1H), 2.23 (dd, J=8.4, 4.2 Hz, 2H), 1.74-1.67 (m, 4H), 1.66-1.58 (m, 4H), 1.33-1.24 (m, 4H). Mass (m/z): 392.3 $[M+H]^+$.

N-(3-fluoro-4-((4-(4-(trifluoromethyl)piperidin-1-yl)phenyl)amino)benzyl)-5-oxopyrrolidine-3-carboxamide (393)

vacuum. The residue was purified by prep-TLC (MeOH/DCM=1/5) to afford the target product as a yellow solid. (220 mg, 60.0%). Mass (m/z): 368.1 $[M+H]^+$.

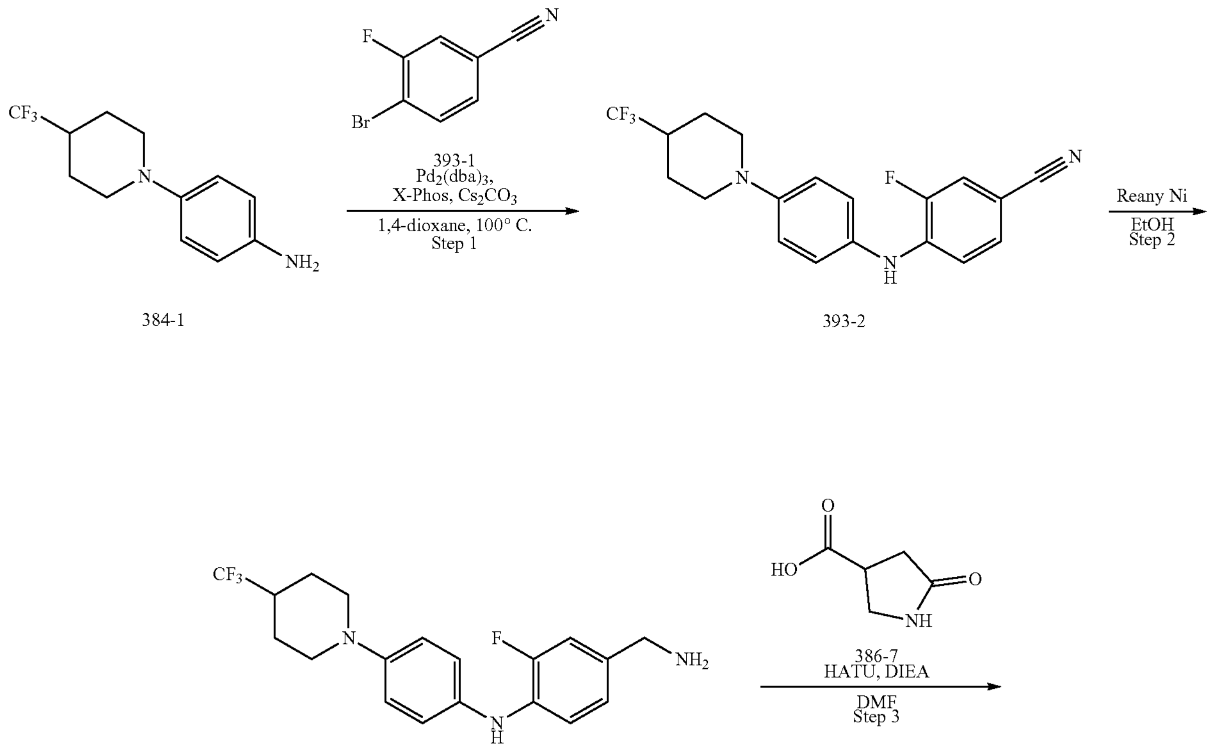

384-1

393-2

393-3

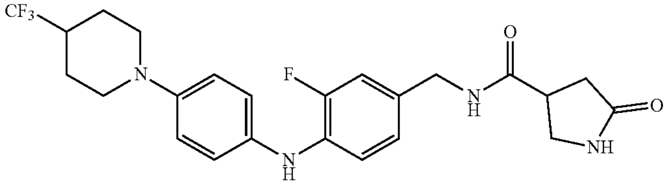

393

Step 1. Preparation of 3-fluoro-4-((4-(4-(trifluoromethyl)piperidin-1-yl)phenyl)amino)benzonitrile (393-2). The title compound 393-2 (1.56 g) was prepared in a total yield of 85.7% as a gray solid from 4-bromo-3-fluorobenzonitrile (1.0 g, 5 mmol), 4-(4-(trifluoromethyl)piperidin-1-yl)aniline (1.59 g, 6.5 mmol), $Pd_2(dba)_3$ (46 mg, 0.05 mmol), X-Phos (119 mg, 0.25 mmol), $Cs_2CO_3$ (2.45 g, 7.5 mmol) according to the procedure for 363-3. Mass (m/z): 364.2 $[M+H]^+$.

Step 2. Preparation of 4-(aminomethyl)-2-fluoro-N-(4-(4-(trifluoromethyl)piperidin-1-yl)phenyl)aniline (393-3). To a solution of 3-fluoro-4-((4-(4-(trifluoromethyl)piperidin-1-yl)phenyl)amino)benzonitrile (363 mg, 1 mmol) in EtOH (10 mL) was added Raney Ni. Then the reaction was stirred overnight at rt under an atmosphere of Hydrogen. Raney Ni was filtrated out. The filtrate was concentrated under Step 3. Preparation of N-(3-fluoro-4-((4-(4-(trifluoromethyl)piperidin-1-yl)phenyl)amino)benzyl)-5-oxopyrrolidine-3-carboxamide (393). The title compound 393 (28.0 mg) was prepared in a total yield of 43.1% as a white powder from 4-(aminomethyl)-2-fluoro-N-(4-(4-(trifluoromethyl)piperidin-1-yl)phenyl)aniline (50 mg, 0.14 mmol), 5-oxopyrrolidine-3-carboxylic acid (35.0 mg, 0.27 mmol), DIEA (52.6 mg, 0.41 mol) and HATU (62 mg, 0.16 mmol) according to the procedure for 363. $^1H$ NMR (400 MHz, DMSO-$d_6$) δ 8.47 (t, J=5.8 Hz, 1H), 7.59 (s, 1H), 7.55 (s, 1H), 7.08-7.00 (m, 2H), 6.97-6.88 (m, 5H), 4.19 (d, J=5.6 Hz, 2H), 3.66-3.60 (m, 2H), 3.42-3.39 (m, 1H), 3.28-3.17 (m, 2H), 2.63 (t, J=12.1 Hz, 2H), 2.47-2.37 (m, 11), 2.33-2.28 (m, 2H), 1.91-1.85 (m, 2H), 1.62-1.52 (m, 2H). Mass (m/z): 479.3 $[M+H]^+$.

N-(4-((4-fluoro-3-(4-(trifluoromethyl)piperidin-1-yl)phenyl)amino)benzyl)-5-oxopyrrolidine-3-carboxamide (394)

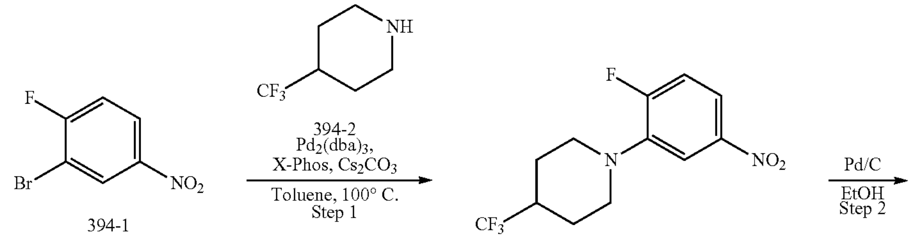

394-1

394-3

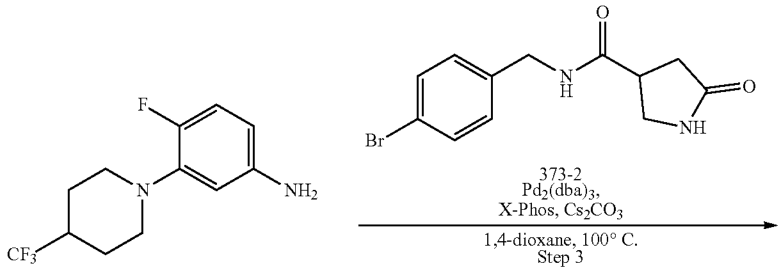

394-4

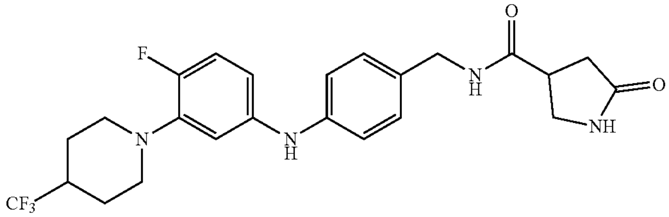

394

Step 1. Preparation of 1-(2-fluoro-5-nitrophenyl)-4-(trifluoromethyl)piperidine (394-3). The title compound 394-3 (570 mg) was prepared in a total yield of 39.0% as a yellow solid from 2-bromo-1-fluoro-4-nitrobenzene (1.1 g, 5 mmol), 4-(trifluoromethyl)piperidine (995 mg, 6.5 mmol), $Pd_2(dba)_3$ (46 mg, 0.05 mmol), X-Phos (119 mg, 0.25 mmol), $Cs_2CO_3$ (2.45 g, 7.5 mmol) according to the procedure for 363-3.

Step 2. Preparation of 4-fluoro-3-(4-(trifluoromethyl)piperidin-1-yl)aniline (394-4). To a solution of 1-(2-fluoro-5-nitrophenyl)-4-(trifluoromethyl)piperidine (570 mg, 1.92 mmol) in EtOH (10 mL) was added 10% Pd/C (20.6 mg, 20 umol). Then the reaction was stirred overnight at rt under an atmosphere of Hydrogen. Pd/C was filtrated out. The filtrate was concentrated under vacuum. The residue was purified by prep-TLC (MeOH/DCM=1/5) to afford the target product as a yellow oil. (390 mg, 76.3%). Mass (m/z): 263.2 $[M+H]^+$.

Step 3. Preparation of N-(4-((4-fluoro-3-(4-(trifluoromethyl)piperidin-1-yl)phenyl)amino)benzyl)-5-oxopyrrolidine-3-carboxamide (394). The title compound 394 (5.0 mg) was prepared in a total yield of 5.0% as a white powder from N-(4-bromobenzyl)-5-oxopyrrolidine-3-carboxamide (74 mg, 0.25 mmol), 1-(2-fluoro-5-nitrophenyl)-4-(trifluoromethyl)piperidine (87 mg, 0.33 mmol), $Pd_2(dba)_3$ (2.3 mg, 2.5 umol), X-Phos (6.0 mg, 12.5 umol), $Cs_2CO_3$ (122 mg, 0.38 mmol) according to the procedure for 363-3. $^1H$ NMR (400 MHz, DMSO-d6) δ 8.40 (t, J=5.8 Hz, 1H), 8.03 (s, 1H), 7.59 (s, 1H), 7.10 (d, J=8.5 Hz, 2H), 7.03-6.93 (m, 3H), 6.71-6.58 (m, 2H), 4.18 (d, J=5.7 Hz, 2H), 3.45-3.37 (m, 3H), 3.27-3.15 (m, 2H), 2.70-2.62 (m, 2H), 2.48-2.41 (m, 2H), 2.34-2.28 (m, 2H), 1.94-1.84 (m, 2H), 1.60 (qd, J=12.6, 4.0 Hz, 2H). Mass (m/z): 479.3 $[M+H]^+$.

N-(4-((3-chloro-4-(4-(trifluoromethyl)piperidin-1-yl) phenyl)amino)benzyl-5-oxopyrrolidine-3-carboxamide (395)

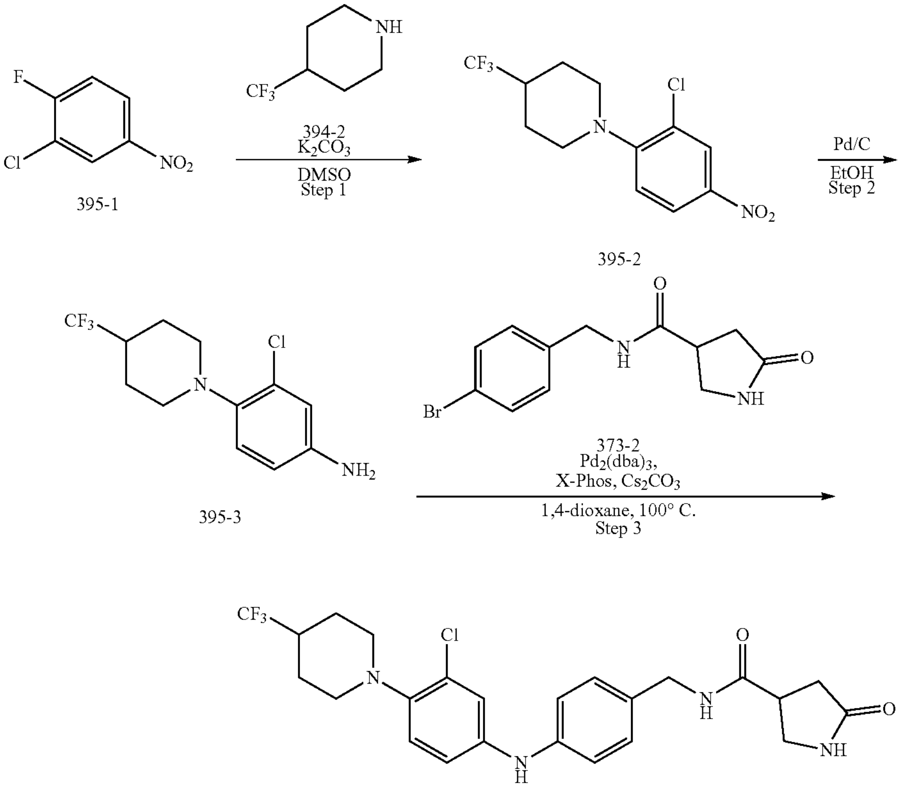

395-1

395-2

395-3

395

Step 1. Preparation of N-(4-bromobenzyl)-5-oxopyrrolidine-3-carboxamide (395-2). The title compound 395-2 (616 mg) was prepared in a total yield of 50.0% as a yellow solid from 2-chloro-1-fluoro-4-nitrobenzene (700 mg, 4.0 mmol), 4-(trifluoromethyl)piperidine (612 mg, 4.0 mmol) and $K_2CO_3$ (828 mg, 6.0 mmol) according to the procedure for 386-3.

Step 2. Preparation of 3-chloro-4-(4-(trifluoromethyl)piperidin-1-yl)aniline (395-3). The title compound 395-3 (500 mg) was prepared in a total yield of 89.9% as a yellow solid from 1-(2-chloro-4-nitrophenyl)-4-(trifluoromethyl)piperidine (616 mg, 2.0 mmol) in EtOH (20 mL) and 10% Pd/C (21.2 mg, 0.02 mmol) according to the procedure for 386-4. Mass (m/z): 279.3 $[M+H]^+$.

Step 3. Preparation of N-(4-((3-chloro-4-(4-(trifluoromethyl)piperidin-1-yl)phenyl)amino)benzyl)-5-oxopyrrolidine-3-carboxamide (395). The title compound 395 (30.0 mg) was prepared in a total yield of 24.3% as a white powder from N-(4-bromobenzyl)-5-oxopyrrolidine-3-carboxamide (74 mg, 0.25 mmol), 3-chloro-4-(4-(trifluoromethyl)piperidin-1-yl)aniline (92 mg, 0.33 mmol), $Pd_2(dba)_3$ (2.5 mg, 2.5 umol), X-Phos (6.0 mg, 12.5 umol), $Cs_2CO_3$ (122 mg, 0.38 mmol) according to the procedure for 363-3. $^1$H NMR (400 MHz, DMSO-d6) δ 8.41 (t. J=5.8 Hz, 1H), 8.13 (s, 1H), 7.59 (s, 11H), 7.15-7.10 (m, 2H), 7.08-7.03 (m, 2H), 7.00-6.95 (m, 3H), 4.19 (d, J=5.7 Hz, 2H), 3.29-3.15 (m, 5H), 2.70-2.60 (m, 2H), 2.47-2.38 (m, 1H), 2.31 (dd, J=8.4, 3.4 Hz, 2H), 1.95-1.86 (m, 2H), 1.61 (qd, J=12.3, 4.0 Hz, 2H). Mass (m/z): 495.3 $[M+H]^+$.

N-(4-((4-(4,4-difluoropiperidin-1-yl)phenyl)amino) benzyl)-5-oxopyrrolidine-3-carboxamide (396)

396

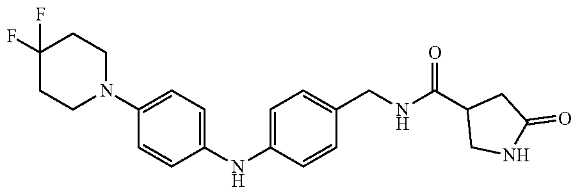

The title compound 396 (36.2 mg) was prepared in a total yield of 33.8% as a white powder from N-(4-bromobenzyl)-5-oxopyrrolidine-3-carboxamide (74 mg, 0.25 mmol), 4-(4,4-difluoropiperidin-1-yl)aniline (70 mg, 0.33 mmol), $Pd_2$(dba), (2.3 mg, 2.5 umol), X-Phos (6.0 mg, 12.5 umol), $Cs_2CO_3$ (122 mg, 0.38 mmol) according to the procedure for 363-3. $^1$H NMR (400 MHz, DMSO-$d_6$) δ 8.37 (t, J=5.8 Hz, 1H), 7.82 (s, 1H), 7.58 (s, 1H), 7.06 (d, J=8.1 Hz, 2H) 6.96 (q, J=8.8 Hz, 4H), 6.89 (d, J=8.1 Hz, 2H), 4.16 (d, J=5.6 Hz, 2H), 3.40 (t, J=8.7 Hz, 1H), 3.28-3.13 (m, 6H), 2.35-2.24 (m, 2H), 2.13-2.00 (m, 4H). Mass (m/z): 429.3 $[M+H]^+$.

N-(4-((3-bromo-4-(4-(trifluoromethyl)piperidin-1-yl)phenyl)amino)benzyl)-5-oxopyrrolidine-3-carboxamide (397)

EtOH (20 mL) and 10% Pd/C (21.2 mg, 0.02 mmol) according to the procedure for 386-4. Mass (m/z): 323.1 [M+H]+.

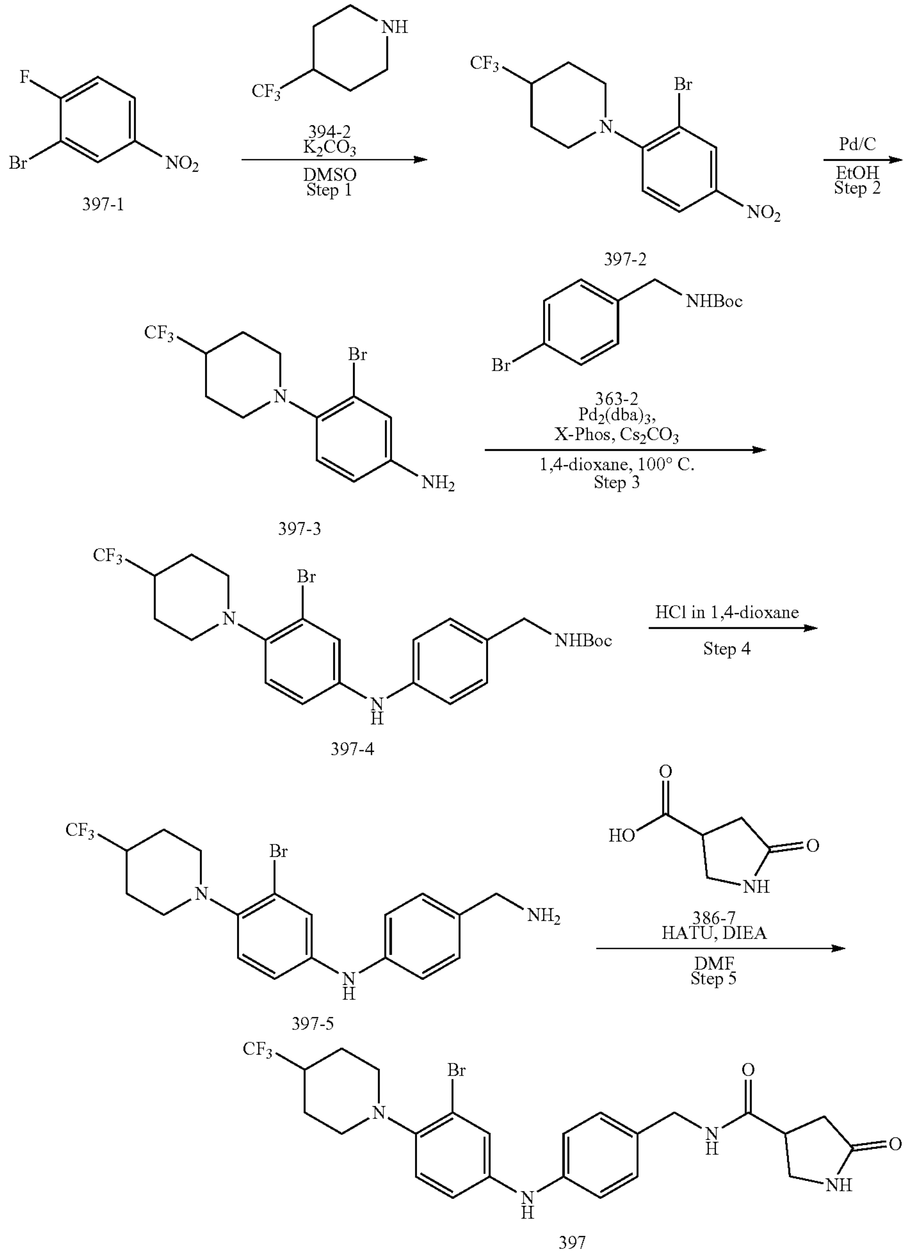

397-1, 397-2, 397-3, 397-4, 397-5, 397

Step 1. Preparation of 1-(2-bromo-4-nitrophenyl)-4-(trifluoromethyl)piperidine (397-2). The title compound 397-2 (2.38 g) was prepared in a total yield of 67.6% as a yellow solid from 2-bromo-1-fluoro-4-nitrobenzene (2.19 g, 10 mmol), 4-(trifluoromethyl)piperidine (1.53 g, 10 mmol) and $K_2CO_3$ (2.07 g, 15 mmol) according to the procedure for 386-3.

Step 2. Preparation of 3-bromo-4-(4-(trifluoromethyl)piperidin-1-yl)aniline (397-3). The title compound 397-3 (315 mg) was prepared in a total yield of 48.9% as a yellow solid from 4-(trifluoromethyl)piperidine (704 mg, 2.0 mmol) in Step 3. Preparation of tert-butyl (4-((3-bromo-4-(4-(trifluoromethyl)piperidin-1-yl)phenyl)amino)benzyl)carbamate (397-4). The title compound 397-4 (102 mg) was prepared in a total yield of 38.6% as a yellow solid from tert-butyl (4-bromobenzyl)carbamate (143 mg, 0.5 mmol), 3-bromo-4-(4-(trifluoromethyl)piperidin-1-yl)aniline (209 mg, 0.65 mmol), $Pd_2(dba)_3$ (4.6 mg, 5.0 umol), X-Phos (11.9 mg, 25 umol), $Cs_2CO_3$ (245 mg, 0.75 mmol) according to the procedure for 363-3. Mass (m/z): 528.3 [M+H]+.

Step 4. Preparation of N-(4-(aminomethyl)phenyl)-3-bromo-4-(4-(trifluoromethyl)piperidin-1-yl)aniline (397-5). The title compound 397-5 (32.9 mg) was prepared in a total yield of 39.8% as a yellow solid from tert-butyl (4-((3- bromo-4-(4-(trifluoromethyl)piperidin-1-yl)phenyl)amino) benzyl)carbamate (102 mg, 0.19 mmol), HCl in 1,4-dioxane (5.0 mL) according to the procedure for 363-4. Mass (m/z): 428.1 [M+H]$^+$.

Step 5. Preparation of N-(4-((3-bromo-4-(4-(trifluoromethyl)piperidin-1-yl)phenyl)amino)benzyl)-5-oxopyrrolidine-3-carboxamide (397). The title compound 397 (9.0 mg) was prepared in a total yield of 27.3% as a light yellow solid from N-(4-(aminomethyl)phenyl)-3-bromo-4-(4-(trifluoromethyl)piperidin-1-yl)aniline (32.9 mg, 77 umol), 5-oxopyrrolidine-3-carboxylic acid (11.9 mg, 92 umol), DIEA (30.0 mg, 0.23 mmol) and HATU (35.1 mg, 92 umol) according to the procedure for 363. $^1$H NMR (400 MHz, DMSO-d$_6$) δ 8.34 (t, J=5.8 Hz, 1H), 8.07 (s, 1H), 7.52 (s, 1H), 7.16 (d, J=2.4 Hz, 1H), 7.09-7.02 (m, 2H), 7.01-6.89 (m, 4H), 4.12 (d, J=5.7 Hz, 2H), 3.24-3.08 (m, 5H), 2.61-2.52 (m, 2H), 2.37-2.26 (m, 11H), 2.24 (dd, J=8.4, 3.2 Hz, 2H), 1.86-1.80 (m, 2H), 1.54 (qd, J=12.4, 4.0 Hz, 2H). Mass (m/z): 539.3 [M+H]$^+$.

N-(4-((5-fluoro-2-methyl-4-(4-methylpiperidin-1-yl) phenyl)amino)benzyl)-5-oxopyrrolidine-3-carboxamide (398)

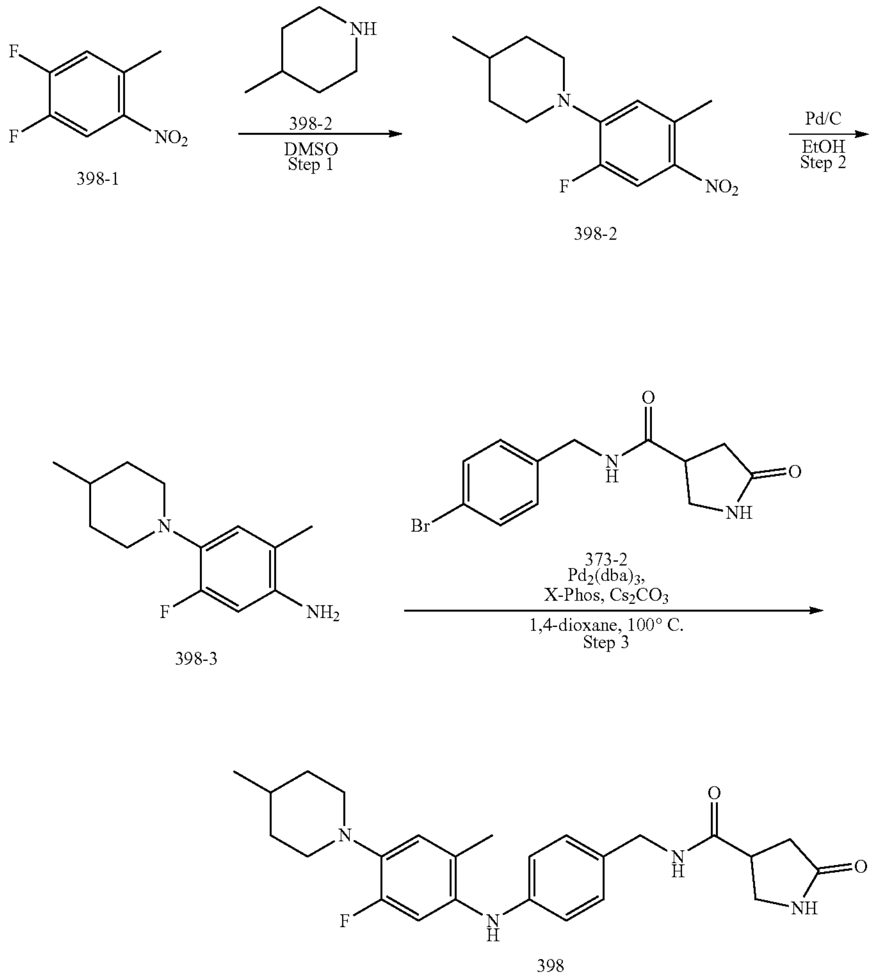

Step 1. Preparation of 1-(2-fluoro-5-methyl-4-nitrophenyl)-4-methylpiperidine (398-3). The title compound 398-3 (1.27 g) was prepared in a total yield of 88.2% as a yellow solid from 1,2-difluoro-4-methyl-5-nitrobenzene (1.0 g, 5.7 mmol), 4-methylpiperidine (1.72 g, 17.3 mmol) according to the procedure for 386-3.

Step 2. Preparation of 5-fluoro-2-methyl-4-(4-methylpiperidin-1-yl)aniline (398-4). The title compound 398-4 (1.16 g) was prepared in a total yield of 100% as a yellow solid from 1-(2 -fluoro-5-methyl-4-nitrophenyl)-4-methylpiperidine (1.27 g, 5.0 mmol) in EtOH (20 mL) and 10% Pd/C (53 mg, 0.05 mmol) according to the procedure for 386-4. Mass (m/z): 223.2 [M+H]$^+$.

Step 3. Preparation of N-(4-((5-fluoro-2-methyl-4-(4-methylpiperidin-1-yl)phenyl)amino)benzyl)-5-oxopyrrolidine-3-carboxamide (398). The title compound 398 (22.1 mg) was prepared in a total yield of 20.2% as a white powder from N-(4-bromobenzyl)-5-oxopyrrolidine-3-carboxamide (74 mg, 0.25 mmol), 5-fluoro-2-methyl-4-(4-methylpiperidin-1-yl)aniline (74 mg, 0.33 mmol), $Pd_2(dba)_3$ (2.5 mg, 2.5 umol), X-Phos (6.0 mg, 12.5 umol), $Cs_2CO_3$ (122 mg, 0.38 mmol) according to the procedure for 363-3. $^1$H NMR (400 MHz, DMSO-d$_6$) δ 8.40 (t, J=5.8 Hz, 1H), 7.59 (s, 1H), 7.45 (s, 1H), 7.18-7.02 (m, 3H), 6.94-6.77 (m, 3H), 4.19 (d, J=5.6 Hz, 2H), 3.44-3.14 (m, 5H), 3.03-2.73 (m, 2H), 2.33-2.26 (m, 2H), 2.15 (s, 3H), 1.80-1.69 (m, 2H), 1.60-1.50 (m, 1H), 1.46-1.34 (m, 2H), 0.96 (d, J=6.4 Hz, 3H). Mass (m/z): 439.4 [M+H]$^+$.

N-(4-((5-chloro-2-methyl-4-(4-methylpiperidin-1-yl) phenyl)amino)benzyl)-5-oxopyrrolidine-3-carboxamide (399)

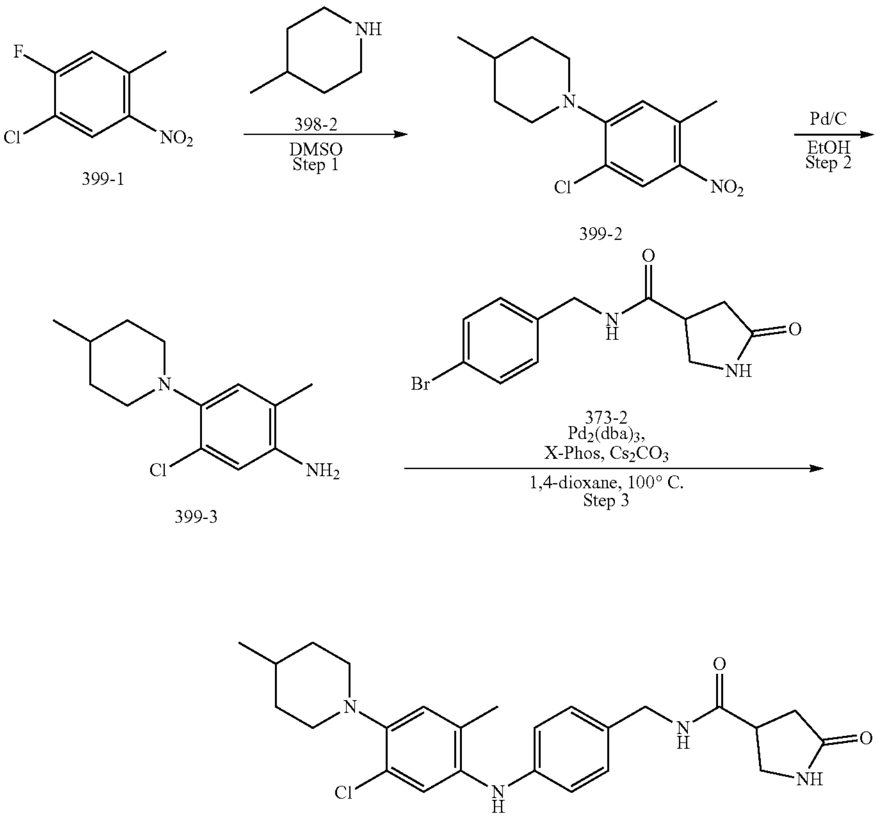

399-1

399-2

399-3

399

Step 1. Preparation of 1-(2-chloro-5-methyl-4-nitrophenyl)-4-methylpiperidine (399-2). The title compound 399-2 (1.35 g) was prepared in a total yield of 88.2% as a yellow solid from 1-chloro-2-fluoro-4-methyl-5-nitrobenzene (1.08 g, 5.7 mmol), 4-methylpiperidine (1.72 g, 17.3 mmol) according to the procedure for 386-3.

Step 2. Preparation of 5-chloro-2-methyl-4-(4-methylpiperidin-1-yl)aniline (399-3). The title compound 399-3 (1.19 g) was prepared in a total yield of 100% as a yellow solid from 1-(2-chloro-5-methyl-4-nitrophenyl)-4-methylpiperidine (1.35 g, 5.0 mmol) in EtOH (20 mL) and 10% Pd/C (53 mg, 0.05 mmol) according to the procedure for 386-4. Mass (m/z): 239.2 $[M+H]^+$.

Step 3. Preparation of N-(4-((5-chloro-2-methyl-4-(4-methylpiperidin-1-yl)phenyl)amino)benzyl)-5-oxopyrrolidine-3-carboxamide (399). The title compound 399 (21.0 mg) was prepared in a total yield of 18.5% as a white powder from N-(4-bromobenzyl)-5-oxopyrrolidine-3-carboxamide (74 mg, 0.25 mmol), 5-chloro-2-methyl-4-(4-methylpiperidin-1-yl)aniline (79 mg, 0.33 mmol), $Pd_2(dba)_3$ (2.5 mg, 2.5 umol), X-Phos (6.0 mg, 12.5 umol), $Cs_2CO_3$ (122 mg, 0.38 mmol) according to the procedure for 363-3. $^1H$ NMR (400 MHz, DMSO-$d_6$) δ 8.37 (t, J=5.8 Hz, 1H), 7.59 (s, 1H), 7.36 (s, 1H), 7.13-6.98 (m, 4H), 6.83-6.73 (m, 2H), 4.17 (d, J=5.6 Hz, 2H), 3.40 (t, J=8.9 Hz, 1H), 3.28-3.14 (m, 4H), 2.70-2.57 (m, 2H), 2.35-2.25 (m, 2H), 2.15 (s, 3H), 1.76-1.67 (m, 1H), 1.54-1.45 (m, 1H), 1.37-1.26 (m, 2H), 0.97 (d, J=6.4 Hz, 3H). Mass (m/z): 455.4 $[M+H]^+$.

N-(4-((2-fluoro-3-methyl-4-(4-methylpiperidin-1-yl) phenyl)amino)benzyl)-5-oxopyrrolidine-3-carboxamide (400)

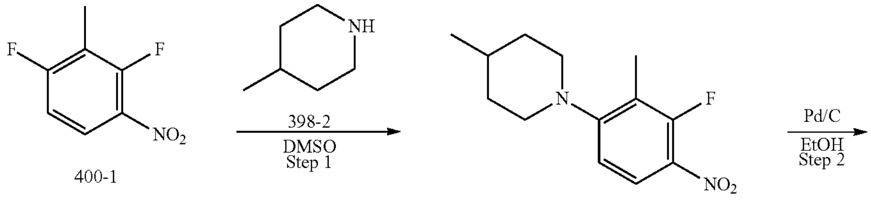

400-1

400-2

-continued

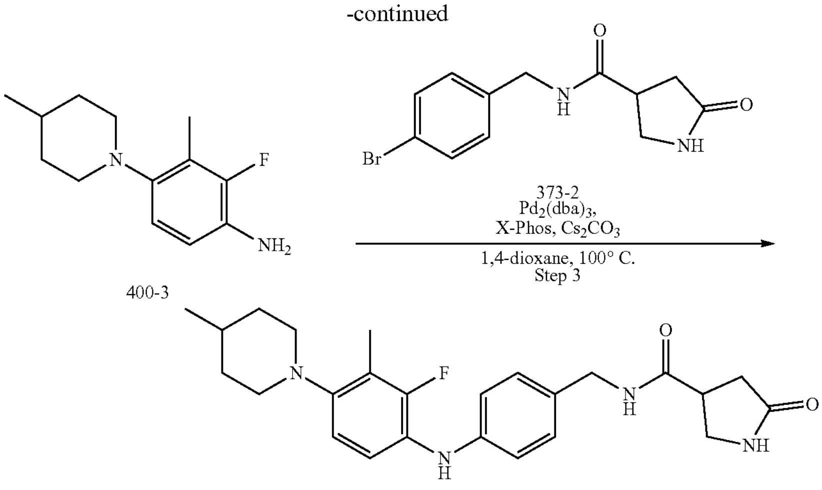

400-3

400

Step 1. Preparation of 1-(3-fluoro-2-methyl-4-nitrophenyl)-4-methylpiperidine (400-2). A solution of 1,3-difluoro-2-methyl-4-nitrobenzene (1 g, 5.7 mmol), 4-methylpiperidine (1.72 g, 17.3 mmol) in DMSO (10 mL) was stirred overnight at rt. 10 mL of water was added dropwise. The precipitates were collected by filtrated to afford the desired product as a yellow solid (1.20 g, 83.3%). Mass (m/z): 253.2 $[M+H]^+$.

Step 2. Preparation of 5-chloro-2-methyl-4-(4-methylpiperidin-1-yl)aniline (400-3). The title compound 400-3 (1.1 g) was prepared in a total yield of 100% as a yellow solid from 2-fluoro-3-methyl-4-(4-methylpiperidin-1-yl)aniline (1.20 g, 4.8 mmol) in EtOH (20 mL) and 10% Pd/C (53 mg, 0.05 mmol) according to the procedure for 386-4. Mass (m/z): 239.2 $[M+H]^+$.

Step 3. Preparation of N-(4-((2-fluoro-3-methyl-4-(4-methylpiperidin-1-yl)phenyl)amino)benzyl)-5-oxopyrrolidine-3-carboxamide (400). The title compound 400 (17.2 mg) was prepared in a total yield of 15.7% as a white powder from N-(4-bromobenzyl)-5-oxopyrrolidine-3-carboxamide (74 mg, 0.25 mmol), 2-fluoro-3-methyl-4-(4-methylpiperidin-1-yl)aniline (74 mg, 0.33 mmol), $Pd_2(dba)_3$ (2.5 mg, 2.5 umol), X-Phos (6.0 mg, 12.5 umol), $Cs_2CO_3$ (122 mg, 0.38 mmol) according to the procedure for 363-3. $^1H$ NMR (400 MHz, DMSO-$d_6$) δ 8.38 (t, J=5.8 Hz, 1H), 7.59 (s, 1H), 7.10-7.00 (m, 3H), 6.92-6.80 (m, 3H), 4.17 (d, J=5.6 Hz, 2H), 3.40 (t, J=8.8 Hz, 1H), 3.29-2.93 (m, 6H), 2.33-2.28 (m, 2H), 2.23-2.15 (m, 3H), 1.78-1.70 (m, 2H), 1.56-1.47 (m, 1H), 1.42-1.30 (m, 2H), 0.97 (d, J=6.4 Hz, 3H). Mass (m/z): 439.3 $[M+H]^+$.

N-(4-((3-fluoro-2-methyl-4-(4-methylpiperidin-1-yl)phenyl)amino)benzyl)-5-oxopyrrolidine-3-carboxamide (401)

401

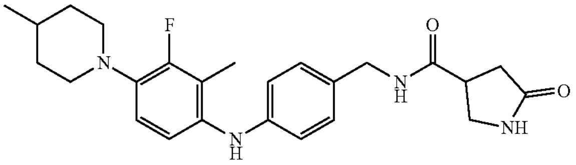

The title compound 401 (11.7 mg) was prepared in a total yield of 10.7% as a white powder from N-(4-bromobenzyl)-5-oxopyrrolidine-3-carboxamide (74 mg, 0.25 mmol), 3-fluoro-2-methyl-4-(4-methylpiperidin-1-yl)aniline (74 mg, 0.33 mmol), $Pd_2(dba)_3$ (2.5 mg, 2.5 umol), X-Phos (6.0 mg, 12.5 umol), $Cs_2CO_3$ (122 mg, 0.38 mmol) according to the procedure for 398. $^1H$ NMR (400 MHz, DMSO-$d_6$) δ 8.39 (t, J=5.8 Hz, 1H), 7.59 (s, 1H), 7.51 (s, 1H), 7.08 (d, J=8.2 Hz, 2H), 7.04-6.95 (m, 11H), 6.89 (d, J=8.6 Hz, 11H), 6.83-6.72 (m, 2H), 4.17 (d, J=5.6 Hz, 2H), 3.41-3.11 (m, 5H), 3.00-2.73 (m, 2H), 2.33-2.27 (m, 2H), 2.08 (s, 3H), 1.79-1.69 (m, 2H), 1.60-1.50 (m, 1H), 1.46-1.32 (m, 2H), 0.97 (d, J=6.4 Hz, 3H). Mass (m/z): 439.3 $[M+H]^+$.

N-(4-((2,3-dimethyl-4-(4-methylpiperidin-1-yl)phenyl)amino)benzyl)-5-oxopyrrolidine-3-carboxamide (402)

402

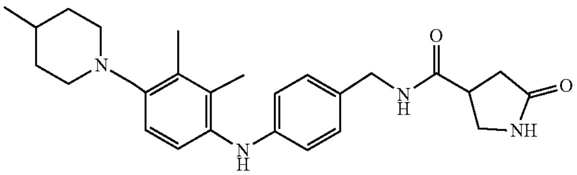

The title compound 402 (11.1 mg) was prepared in a total yield of 10.2% as a yellow powder from N-(4-bromobenzyl)-5-oxopyrrolidine-3-carboxamide (74 mg, 0.25 mmol), 2,3-dimethyl-4-(4-methylpiperidin-1-yl)aniline (73 mg, 0.33 mmol), $Pd_2(dba)_3$ (2.5 mg, 2.5 umol), X-Phos (6.0 mg, 12.5 umol), $Cs_2CO_3$ (122 mg, 0.38 mmol) according to the procedure for 398. H NMR (400 MHz, DMSO-$d_6$) δ 8.33 (t, J=5.7 Hz, 1H), 7.58 (s, 1H), 7.30 (s, 1H), 7.01-6.96 (m, 2H), 6.92 (d, J=8.5 Hz, 1H), 6.87 (d, J=8.6 Hz, 1H), 6.63-6.53 (m, 2H), 4.13 (d, J=5.4 Hz, 2H), 3.39 (t, J=8.9 Hz, 1H), 3.25-3.16 (m, 2H), 2.96-2.89 (m, 2H), 2.59-2.52 (m, 2H), 2.29 (dd, J=8.4, 5.1 Hz, 2H), 2.19 (s, 3H), 2.05 (s, 3H), 1.74-1.67 (m, 2H), 1.50-1.43 (m, 1H), 1.28-1.36 (m, 2H), 0.97 (d, J=6.4 Hz, 3H). Mass (m/z): 435.4 $[M+H]^+$.

N-(4-((5-methyl-6-(4-(trifluoromethyl)piperidin-1-yl)pyridin-3-yl)amino)benzyl)-5-oxopyrrolidine-3-carboxamide (403)

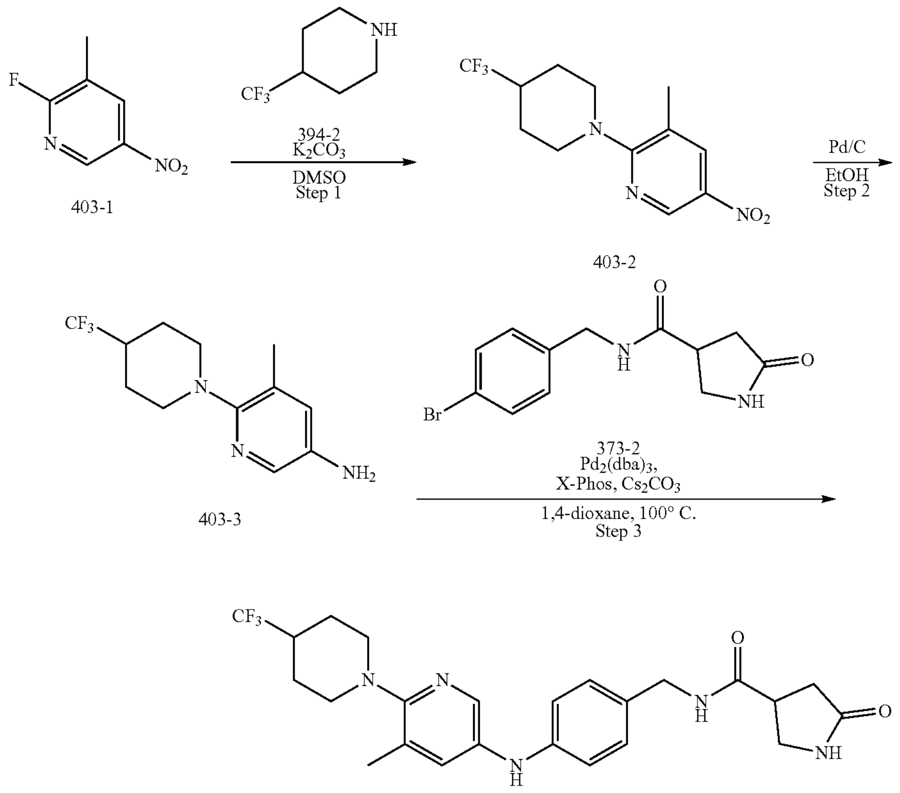

403-1

403-2

403-3

403

Step 1. Preparation of 4-(trifluoromethyl)piperidine (403-2). The title compound 403-2 (959 mg) was prepared in a total yield of 83.1% as a yellow solid from 2-fluoro-3-methyl-5-nitropyridine (624 mg, 4 mmol), 4-(trifluoromethyl)piperidine (734 mg, 4.8 mmol) and $K_2CO_3$ (828 mg, 6 mmol) according to the procedure for 386-3.

Step 2. Preparation of 5-methyl-6-(4-(trifluoromethyl)piperidin-1-yl)pyridin-3-amine (403-3). The title compound 403-3 (390 mg) was prepared in a total yield of 72.5% as a purple solid from 3-methyl-5-nitro-2-(4-(trifluoromethyl)piperidin-1-yl)pyridine (578 mg, 2 mmol) in EtOH (20 mL) and 10% Pd/C (22 mg, 0.02 mmol) according to the procedure for 3864. Mass (m/z): 260.3 $[M+H]^+$.

Step 3. Preparation of N-(4-((5-methyl-6-(4-(trifluoromethyl)piperidin-1-yl)pyridin-3-yl)amino)benzyl)-5-oxopyrrolidine-3-carboxamide (403). The title compound 403 (25.2 mg) was prepared in a total yield of 21.2% as a light yellow powder from N-(4-bromobenzyl)-5-oxopyrrolidine-3-carboxamide (74 mg, 0.25 mmol), 5-methyl-6-(4-(trifluoromethyl)piperidin-1-yl)pyridin-3-amine (86 mg, 0.33 mmol), $Pd_2(dba)$; (2.5 mg, 2.5 umol), X-Phos (6.0 mg, 12.5 umol), $Cs_2CO_3$ (122 mg, 0.38 mmol) according to the procedure for 363-3. $^1H$ NMR (400 MHz, DMSO-$d_6$) δ 8.51 (s, 1H), 8.10 (s, 1H), 7.98 (d, J=2.7 Hz, 1H), 7.66 (s, 1H), 7.36 (d, J=2.7 Hz, 1H), 7.20-7.13 (m, 2H), 7.04-6.97 (m, 2H), 4.24 (d, J=5.7 Hz, 2H), 3.49 (d, J=8.6 Hz, 1H), 3.39-3.19 (m, 4H), 2.79 (t, J=12.2 Hz, 2H), 2.55-2.45 (m, 1H), 2.39-2.32 (m, 2H), 1.99-1.91 (m, 2H), 1.67 (qd, J=12.4, 4.0 Hz, 2H). Mass (m/z): 476.3 $[M+H]^+$.

N-(4-((2-methyl-6-(4-(trifluoromethyl)piperidin-1-yl)pyridin-3-yl)amino)benzyl)-5-oxopyrrolidine-3-carboxamide (404)

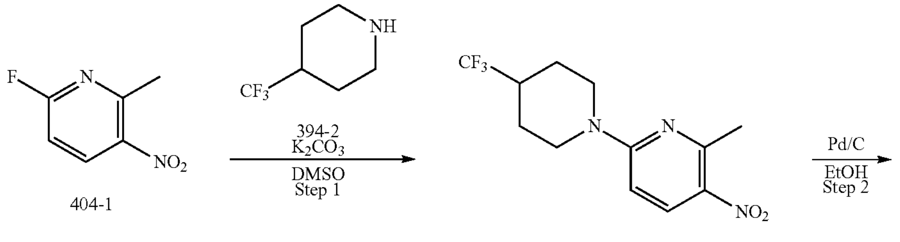

404-1

404-2

-continued

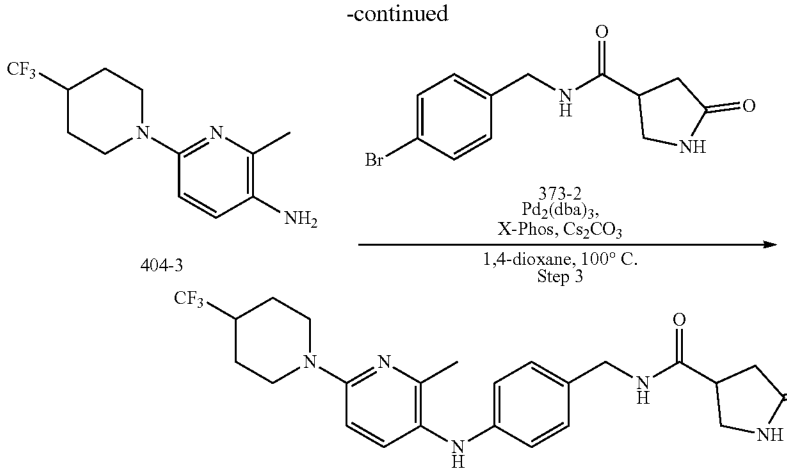

404-3

404

Step 1. Preparation of 2-methyl-3-nitro-6-(4-(trifluoromethyl)piperidin-1-yl)pyridine (404-2). The title compound 404-2 (1.03 g) was prepared in a total yield of 89.0% as a yellow solid from 6-fluoro-2-methyl-3-nitropyridine (624 mg, 4 mmol), 4-(trifluoromethyl)piperidine (734 mg, 4.8 mmol) and $K_2CO_3$ (828 mg, 6 mmol) according to the procedure for 386-3.

Step 2. Preparation of 2-methyl-6-(4-(trifluoromethyl) piperidin-1-yl)pyridin-3-amine (404-3). The title compound 404-3 (406 mg) was prepared in a total yield of 78.3% as a yellow oil from 2-methyl-3-nitro-6-(4-(trifluoromethyl)piperidin-1-yl)pyridine (578 mg, 2 mmol) in EtOH (20 mL) and 10% Pd/C (21 mg, 0.02 mmol) according to the procedure for 386-4. Mass (m/z): 260.2 $[M+H]^+$.

Step 3. Preparation of N-(4-((2-methyl-6-(4-(trifluoromethyl)piperidin-1-yl)pyridin-3-yl)amino)benzyl)-5-oxopyrrolidine-3-carboxamide (404). The title compound 404 (18.6 mg) was prepared in a total yield of 15.6% as a light yellow powder from N-(4-bromobenzyl)-5-oxopyrrolidine-3-carboxamide (74 mg, 0.25 mmol), 2-methyl-6-(4-(trifluoromethyl)piperidin-1-yl)pyridin-3-amine (86 mg, 0.33 mmol), $Pd_2(dba)_3$ (2.5 mg, 2.5 umol), X-Phos (6.0 mg, 12.5 umol), $Cs_2CO_3$ (122 mg, 0.38 mmol) according to the procedure for 363-3. $^1H$ NMR (400 MHz, DMSO-$d_6$) δ 8.33 (t, J=5.7 Hz, 1H), 7.58 (s, 1H), 7.32 (d, J=8.2 Hz, 1H), 7.25 (s, 1H), 7.02-6.95 (m, 2H), 6.72 (d, J=8.1 Hz, 111), 6.57-6.49 (m, 2H), 4.38-4.30 (m, 2H), 4.13 (d, J=5.7 Hz, 2H), 3.39 (t, J=8.8 Hz, 311), 3.25-3.15 (m, 2H), 2.83-2.74 (m, 2H), 2.61-2.53 (m, 1H), 2.29 (dd, J=8.5, 4.5 Hz, 2H), 2.23 (s, 311), 1.91-1.83 (m, 2H), 1.45 (qd, J=12.4, 3.9 Hz, 2H). Mass (m/z): 476.4 $[M+H]^+$.

5-oxo-N-(4-((3-(4-(trifluoromethyl)piperidin-1-yl) phenyl)amino)benzyl)pyrrolidine-3-carboxamide (405)

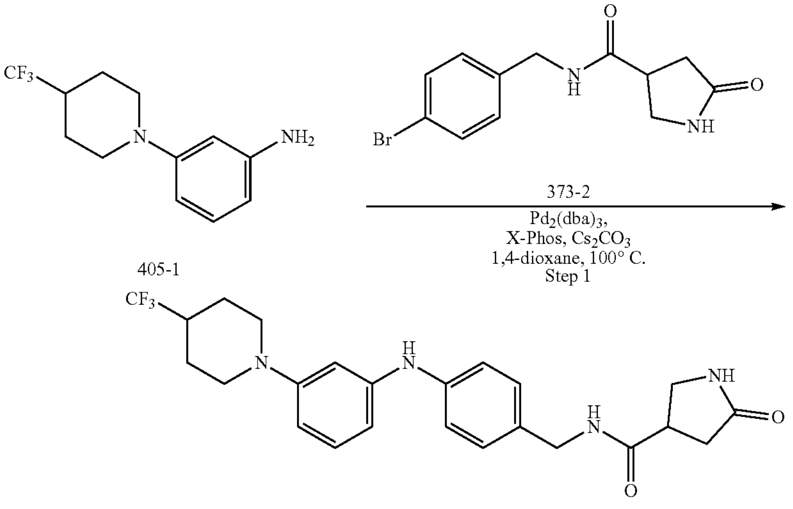

405-1

405

The title compound 405 (4.6 mg) was prepared in a total yield of 9.8% as a light yellow powder from N-(4-bromobenzyl)-5-oxopyrrolidine-3-carboxamide (30 mg, 0.10 mmol), 3-(4-(trifluoromethyl)piperidin-1-yl)aniline (30 mg, 0.12 mmol), $Pd_2(dba)_3$ (0.9 mg, 1.0 umol), X-Phos (2.4 mg, 5.0 umol), $Cs_2CO_3$ (50 mg, 0.15 mmol) according to the procedure for 363-3. $^1H$ NMR (400 MHz, DMSO-$d_6$) δ 8.40 (t, J=5.6 Hz, 1H), 8.01 (s, 1H), 7.59 (s, 11H), 7.12-7.00 (m, 4H), 6.59 (s, 1H), 6.54-6.50 (m, 1H), 6.47-6.43 (m, 1H), 4.19 (d, J=5.7 Hz, 2H), 3.73-3.67 (m, 2H), 3.41 (t, J=8.8 Hz, 1H), 3.26-3.19 (m, 2H), 2.74-2.66 (m, 2H), 2.34-2.27 (m, 2H), 1.90-1.84 (m, 2H), 1.59-1.52 (m, 211). Mass (m/z): 461.3 $[M+H]^+$.

5-oxo-N-(4-((6-(4-(trifluoromethyl)piperidin-1-yl)pyridin-3-yl)amino)benzyl)pyrrolidine-3-carboxamide (406)

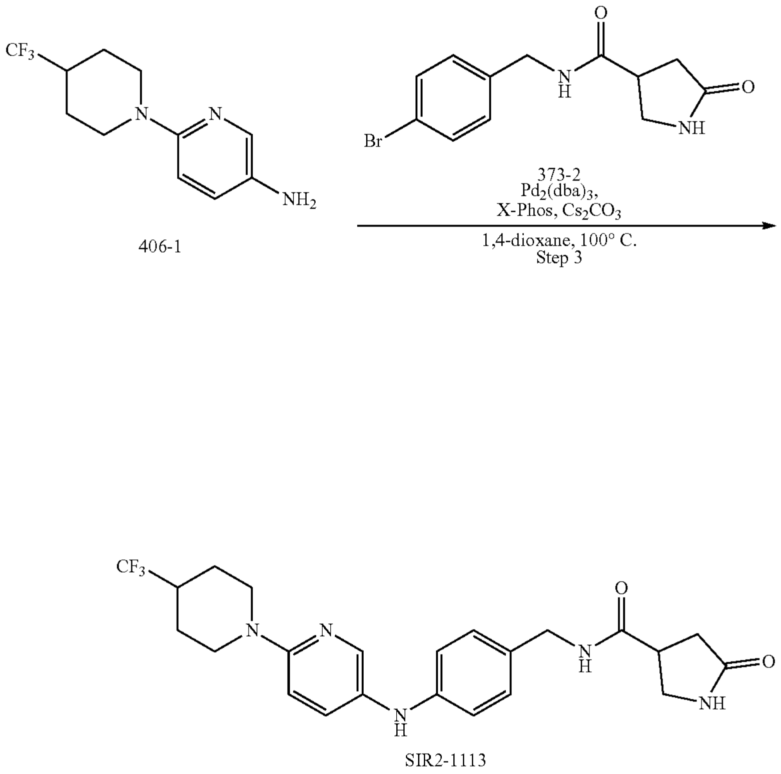

The title compound 406 (72.4 mg) was prepared in a total yield of 31.5% as a purple powder from N-(4-bromobenzyl)-5-oxopyrrolidine-3-carboxamide (74 mg, 0.25 mmol), 2,3-dimethyl-4-(4-methylpiperidin-1-yl)aniline (73 mg, 0.33 mmol), $Pd_2(dba)_3$ (2.5 mg, 2.5 umol), X-Phos (6.0 mg, 12.5 umol), $Cs_2CO_3$ (122 mg, 0.38 mmol) according to the procedure for 363-3.

$^1H$ NMR (300 MHz, DMSO-$d_6$) δ 8.33 (t, J=5.8 Hz, 1H), 7.94 (d, J=2.8 Hz, 1H), 7.71 (s, 1H), 7.56 (s, 11H), 7.35 (dd, J=8.9, 2.8 Hz, 1H), 7.06-6.97 (m, 2H), 6.84 (d, J=9.0 Hz, 11H), 6.80-6.73 (m, 2H), 4.32-4.21 (m, 2H), 4.13 (d, J=5.7 Hz, 2H), 3.39 (t, J=8.6 Hz, 1H), 3.26-3.14 (m, 2H), 2.76 (td, J=12.5, 2.2 Hz, 2H), 2.61-2.52 (m, 1H), 2.33-2.21 (m, 2H), 1.90-1.80 (m, 2H), 1.44 (qd, J=12.5, 4.2 Hz, 2H). Mass (m/z): 435.4 $[M+H]^+$.

N-(4-((2,6-dimethyl-4-(4-methylpiperidin-1-yl)phenyl)amino)benzyl)-5-oxopyrrolidine-3-carboxamide (407)

407

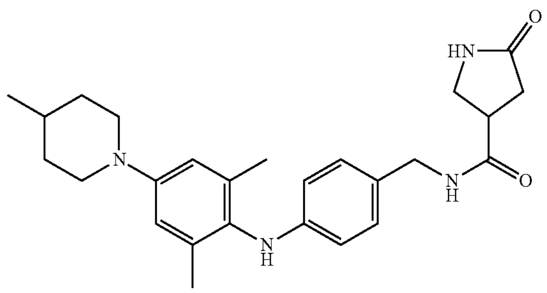

The title compound 407 (8.6 mg) was prepared in a total yield of 13.7% as a light yellow solid from N-(4-(aminomethyl)phenyl)-2,6-dimethyl-4-(4-methylpiperidin-1-yl)aniline (53 mg, 0.16 mmol), 5-oxopyrrolidine-3-carboxylic acid (25.4 mg, 0.20 mmol), DIEA (62 mg, 0.48 mmol) and HATU (76 mg, 0.20 mmol) according to the procedure for 397. $^1H$ NMR (400 MHz, DMSO-$d_6$) δ 8.32 (t, J=5.5 Hz, 1H), 7.58 (s, 1H), 7.35-7.10 (m, 3H), 6.97 (d, J=8.4 Hz, 2H), 6.34 (d, J=8.2 Hz, 2H), 4.13-4.09 (m, 2H), 3.63-3.58 (m, 2H), 3.37 (d, J=8.9 Hz, 1H), 3.24-3.16 (m, 2H), 2.28 (dd, J=8.5, 4.2 Hz, 2H), 2.11 (s, 6H), 1.86-1.77 (m, 2H), 1.68-1.60 (m, 1H), 1.47-1.33 (m, 2H), 0.98 (d, J=6.4 Hz, 3H). Mass (m/z): 435.3 $[M+H]^+$.

N-(4-((5-chloro-2-methyl-4-(4-(trifluoromethyl)piperidin-1-yl)phenyl)amino)benzyl)-5-oxopyrrolidine-3-carboxamide (408)

408

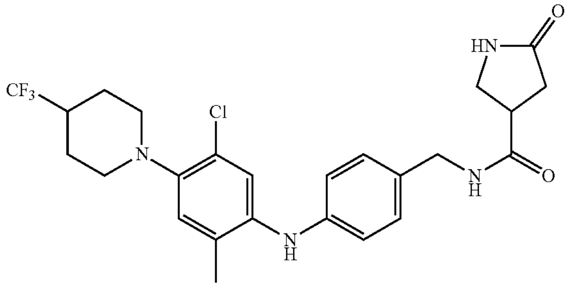

The title compound 408 (30.8 mg) was prepared in a total yield of 18.2% as a yellow powder from N-(4-bromobenzyl)-5-oxopyrrolidine-3-carboxamide (99 mg, 0.33 mmol), 5-chloro-2-methyl-4-(4-(trifluoromethyl)piperidin-1-yl)aniline (126 mg, 0.43 mmol), $Pd_2$(dba), (3.0 mg, 3.3 umol), X-Phos (7.9 mg, 16.5 umol), $Cs_2CO_3$ (163 mg, 0.50 mmol) according to the procedure for 404. $^1$H NMR (400 MHz, DMSO-$d_6$) δ 8.38 (t, J=5.8 Hz, 1H), 7.59 (s, 1H), 7.37 (s, 1H), 7.12-7.05 (m, 3H), 7.01 (s, 1H), 6.82-6.76 (m, 2H), 4.17 (d, J=5.6 Hz, 2H), 3.40 (t, J=8.8 Hz, 1H), 3.28-3.13 (m, 4H), 2.70-2.63 (m, 2H), 2.32-2.26 (m, 2H), 2.15 (s, 3H), 1.94-1.87 (m, 2H), 1.67-1.57 (m, 2H). Mass (m/z): 509.3 $[M+H]^+$.

N-(4-((3-fluoro-2-methyl-4-(4-(trifluoromethyl)piperidin-1-yl)phenyl)amino)benzyl)-5-oxopyrrolidine-3-carboxamide (409)

409

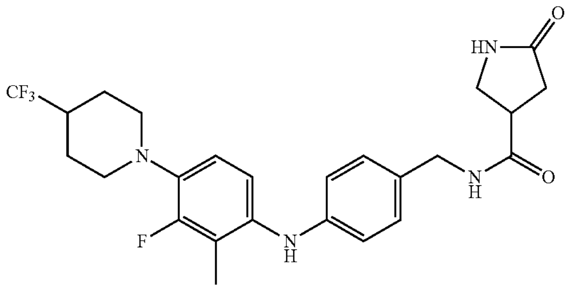

The title compound 409 (13.1 mg) was prepared in a total yield of 8.0% as a yellow powder from N-(4-bromobenzyl)-5-oxopyrrolidine-3-carboxamide (99 mg, 0.33 mmol), 3-fluoro-2-methyl-4-(4-(trifluoromethyl)piperidin-1-yl)aniline (119 mg, 0.43 mmol), $Pd_2(dba)_3$ (3.0 mg, 3.3 umol), X-Phos (7.9 mg, 16.5 umol), $Cs_2CO_3$ (163 mg, 0.50 mmol) according to the procedure for 404. $^1$H NMR (400 MHz, DMSO-$d_6$) δ 8.38 (t, J=5.8 Hz, 1H), 7.59 (s, 1H), 7.43 (s, 1H), 7.08-7.01 (m, 2H), 6.91-6.81 (m, 2H), 6.75-6.68 (m, 2H), 4.15 (d, J=5.7 Hz, 2H), 3.43-3.39 (m, 1H), 3.34-3.30 (m, 2H), 3.26-3.14 (m, 2H), 2.70-2.61 (m, 2H), 2.48-2.40 (m, 1H), 2.33-2.24 (m, 2H), 2.06 (d, J=2.5 Hz, 3H), 1.93-1.86 (m, 2H), 1.61 (qd, J=12.5, 4.2 Hz, 2H). Mass (m/z): 493.3 $[M+H]^+$.

N-(4-((5-fluoro-2-methyl-4-(4-(trifluoromethyl)piperidin-1-yl)phenyl)amino)benzyl)-5-oxopyrrolidine-3-carboxamide (410)

410

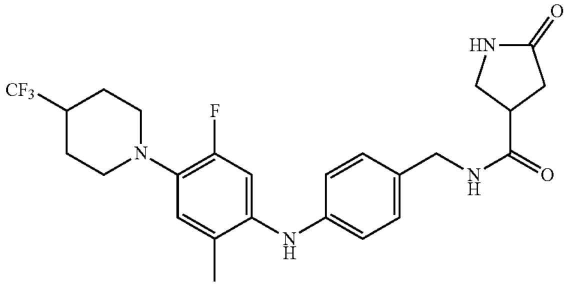

The title compound 410 (28.9 mg) was prepared in a total yield of 17.6% as a yellow powder from N-(4-bromobenzyl)-5-oxopyrrolidine-3-carboxamide (99 mg, 0.33 mmol), 5-fluoro-2-methyl-4-(4-(trifluoromethyl)piperidin-1-yl)aniline (119 mg, 0.43 mmol), $Pd_2(dba)_3$ (3.0 mg, 3.3 umol), X-Phos (7.9 mg, 16.5 umol), $Cs_2CO_3$ (163 mg, 0.50 mmol) according to the procedure for 404. $^1$H NMR (400 MHz, DMSO-$d_6$) δ 8.38 (t, J=5.8 Hz, 1H), 7.59 (s, 1H), 7.34 (s, 1H), 7.09-7.03 (m, 2H), 6.90 (d, J=9.8 Hz, 1H), 6.83 (d, J=14.0 Hz, 1H), 6.79-6.76 (m, 2H), 4.16 (d, J=5.7 Hz, 2H), 3.40 (t, J=8.9 Hz, 1H), 3.34-3.30 (m, 2H), 3.25-3.13 (m, 2H), 2.72-2.63 (m, 2H), 2.43 (dp, J=12.2, 4.2, 3.8 Hz, 1H), 2.34-2.23 (m, 2H), 2.13 (s, 3H), 1.94-1.86 (m, 2H), 1.61 (qd, J=12.4, 4.0 Hz, 2H). Mass (m/z): 493.3 $[M+H]^+$.

N-(4-((2-fluoro-3-methyl-4-(4-(trifluoromethyl)piperidin-1-yl)phenyl)amino)benzyl)-5-oxopyrrolidine-3-carboxamide (411)

411

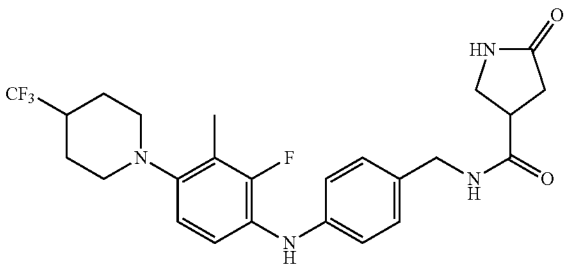

The title compound 411 (38.5 mg) was prepared in a total yield of 23.8% as a white powder from N-(4-bromobenzyl)-5-oxopyrrolidine-3-carboxamide (99 mg, 0.33 mmol), 2-fluoro-3-methyl-4-(4-(rifluoromethyl)piperidin-1-yl)aniline (119 mg, 0.43 mmol), $Pd_2(dba)_3$ (3.0 mg, 3.3 umol), X-Phos (7.9 mg, 16.5 umol), $Cs_2CO_3$ (163 mg, 0.50 mmol) according to the procedure for 404. $^1$H NMR (400 MHz, DMSO-$d_6$) δ 8.37 (t, J=5.7 Hz, 1H), 7.65 (s, 1H), 7.58 (s, 1H), 7.08-7.02 (m, 3H), 6.86-6.77 (m, 3H), 4.16 (d, J=5.7 Hz, 2H), 3.40 (t, J=8.8 Hz, 1H), 3.25-3.04 (m, 4H), 2.67-2.58 (m, 2H), 2.46-2.36 (m, 1H), 2.32-2.24 (m, 2H), 2.16 (d, J=2.7 Hz, 3H), 1.94-1.86 (m, 2H), 1.63 (qd, J=12.4, 3.9 Hz, 2H). Mass (m/z): 493.3 $[M+H]^+$.

N-(4-((2,3-dimethyl-4-(4-(trifluoromethyl)piperidin-1-yl)phenyl)amino)benzyl)-5-oxopyrrolidine-3-carboxamide (412)

412

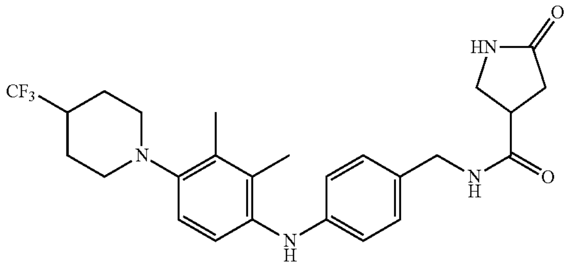

The title compound 412 (10.6 mg) was prepared in a total yield of 6.6% as a white powder from N-(4-bromobenzyl)-5-oxopyrrolidine-3-carboxamide (99 mg, 0.33 mmol), 2,3-dimethyl-4-(4-(trifluoromethyl)piperidin-1-yl)aniline (107 mg, 0.40 mmol), $Pd_2(dba)_3$ (3.0 mg, 3.3 umol), X-Phos (7.9 mg, 16.5 umol), $Cs_2CO_3$ (163 mg, 0.50 mmol) according to the procedure for 404. $^1H$ NMR (400 MHz, DMSO-$d_6$) δ 8.34 (t, J=5.7 Hz, 1H), 7.58 (s, 1H), 7.34 (s, 1H), 7.01-6.97 (m, 2H), 6.95 (d, J=8.2 Hz, 1H), 6.89 (d, J=8.8 Hz, 1H), 6.64-6.57 (m, 2H), 4.13 (d, J=5.7 Hz, 2H), 3.39 (t, J=8.8 Hz, 1H), 3.25-3.15 (m, 2H), 3.10-3.02 (m, 2H), 2.69-2.59 (m, 3H), 2.48-2.36 (m, 1H), 2.33-2.25 (m, 2H), 2.20 (s, 3H), 2.06 (s, 3H), 1.94-1.86 (m, 2H), 1.71-1.60 (m, 2H). Mass (m/z): 489.4 $[M+H]^+$.

N-(4-((4-(4,4-dimethylcyclohexyl)phenyl)amino)benzyl)-5-oxopyrrolidine-3-carboxamide (413)

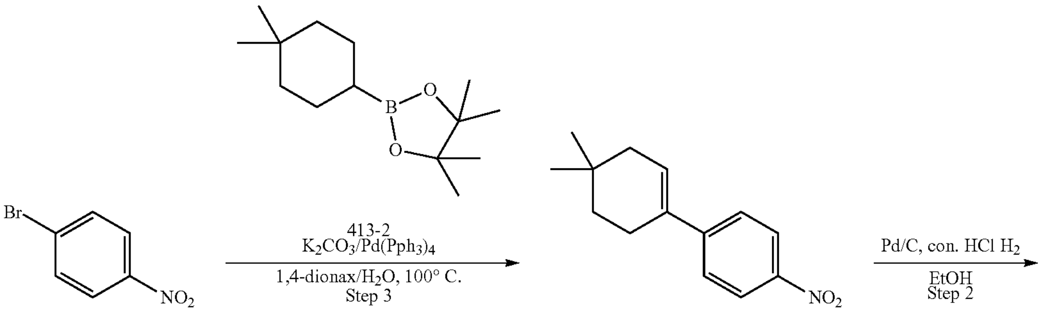

413-1

413-3

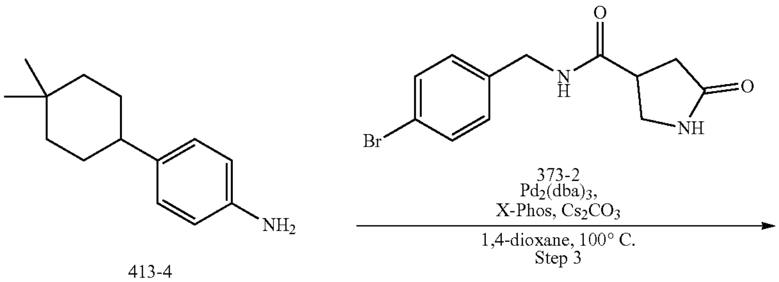

413-4

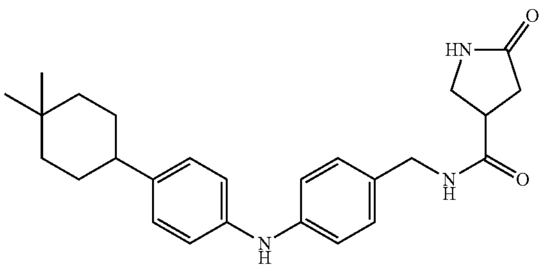

413

Step 1. Preparation of 4,4-dimethyl-4'-nitro-2,3,4,5-tetrahydro-1,1'-biphenyl (413-3). To a mixture of 1-bromo-4-nitrobenzene (6.06 g, 30 mmol), 2-(4,4-dimethylcyclohex-1-en-1-yl)-4,4,5,5-tetramethyl-1,3,2-dioxaborolane (8.52 g, 36 mmol) and $Pd(PPh_3)_4$ (690 mg, 0.6 mmol) in 100 m L of 1,4-dioxane and 20 mL of water was added $K_2CO_3$ (6.24 g, 45 mmol). After stirring overnight at 110° C. under Ar, the reaction was cooled to room temperature (RT). The mixture was treated with EtOAc (100 mL), washed with H2O (3×200 mL) and brine (200 mL). The organic layer was dried (Na2SO4) and concentrated in vacuo. The residue was purified by flash chromatography on silica gel (0-10% EtOAc/hexane) to give desired product as a Light-yellow oil. (6.5 g, 94.0%).

Step 2. Preparation of 4-(4,4-dimethylcyclohexyl)aniline (413-4). To a solution of 4,4-dimethyl-4'-nitro-2,3,4,5-tetrahydro-1,1'-biphenyl (2.5 g, 10.8 mmol) in THF (50 mL) was added 10% Pd/C (114.7 mg, 0.11 ml) and 1.0 mL of con·HCl. Then the reaction was stirred overnight at 60° C. under an atmosphere of Hydrogen. The reaction was cooled to room temperature (RT). Pd/C was filtrated out. The filtrate was concentrated under vacuum, 50 ml water was added, The PH of the solution was adjusted to 8-9 with sodium carbonate solution. Then the mixture was extracted by DCM (50 mL×3). The combined organic layers were washed with water (100 mL), dried over Na2SO4 and concentrated to afford the desired product as a yellow solid (1.8 g, 81.8%). Mass (m/z): 204.3 $[M+H]^+$.

Step 3. Preparation of N-(4-((4-(4,4-dimethylcyclohexyl)phenyl)amino)benzyl)-5-oxopyrrolidine-3-carboxamide (413). The title compound 413 (33.5 mg) was prepared in a total yield of 32.2% as a white powder from N-(4-bromobenzyl)-5-oxopyrrolidine-3-carboxamide (73.5 mg, 0.25 mmol), 4-(4,4-dimethylcyclohexyl)aniline (58 mg, 0.29 mmol), $Pd_2(dba)_3$ (2.3 mg, 2.5 umol), X-Phos (5.9 mg, 12.4 umol), $Cs_2CO_3$ (121 mg, 0.37 mmol) according to the procedure for 404. $^1H$ NMR (400 MHz, DMSO-$d_6$) δ 8.39 (t, J=5.7 Hz, 1H), 8.00 (s, 1H), 7.59 (s, 1H), 7.11-7.04 (m, 4H), 7.06-6.92 (m, 4H), 4.17 (d, J=5.7 Hz, 2H), 3.40 (t, J=8.8 Hz, 1H), 3.25-3.12 (m, 2H), 2.32-2.28 (m, 2H), 1.63-1.53 (m, 4H), 1.47-1.41 (m, 2H), 1.34-1.24 (m, 2H), 0.95 (d, J=10.0 Hz, 6H). Mass (m/z): 420.4 $[M+H]^+$.

N-(4-((4-fluoro-3-(piperidin-1-yl)phenyl)amino)benzyl)-5-oxopyrrolidine-3-carboxamide (414)

414

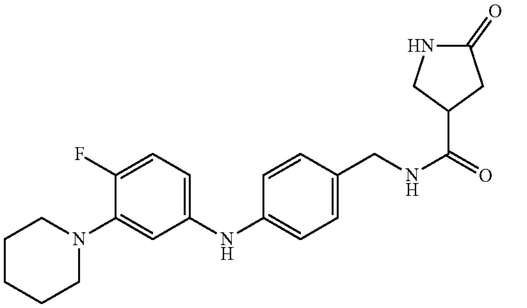

The title compound 414 (57.8 mg) was prepared in a total yield of 37.1% as a yellow powder from N-(4-bromobenzyl)-5-oxopyrrolidine-3-carboxamide (112 mg, 0.38 mmol), 4-fluoro-3-(piperidin-1-yl)aniline (90 mg, 0.46 mmol), $Pd_2(dba)_3$ (3.5 mg, 3.8 umol), X-Phos (9.1 mg, 19 umol), $Cs_2CO_3$ (186 mg, 0.57 mmol) according to the procedure for 404. $^1H$ NMR (400 MHz, DMSO-$d_6$) δ 8.39 (t, J=5.7 Hz, 1H), 7.99 (s, 1H), 7.59 (s, 1H), 7.12-7.06 (m, 2H), 6.99-6.91 (m, 3H), 6.61-6.55 (m, 1H), 6.58 (ddt, J=7.8, 3.7, 2.7 Hz, 1H), 4.17 (d, J=5.7 Hz, 2H), 3.40 (t, J=8.7 Hz, 1H), 3.27-3.15 (m, 2H), 2.95-2.87 (m, 4H), 2.33-2.25 (m, 2H), 1.67-1.60 (m, 4H), 1.54-1.47 (m, 2H). Mass (m/z): 411.3 $[M+H]^+$.

N-(4-((4-(azocan-1-yl)-3-(trifluoromethyl)phenyl)amino)benzyl)-5-oxopyrrolidine-3-carboxamide (415)

415

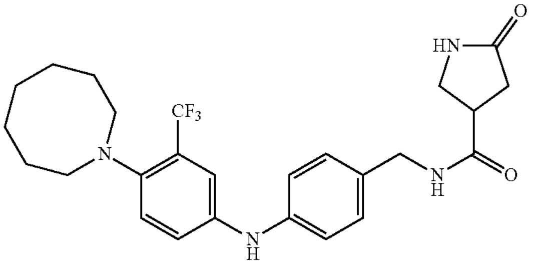

The title compound 415 (63.6 mg) was prepared in a total yield of 39.1% as a yellow powder from N-(4-bromobenzyl)-5-oxopyrrolidine-3-carboxamide (99 mg, 0.33 mmol), 4-(azocan-1-yl)-3-(trifluoromethyl)aniline (117 mg, 0.43 mmol), $Pd_2(dba)_3$ (3.0 mg, 3.3 umol), X-Phos (7.9 mg, 16.5 umol), $Cs_2CO_3$ (163 mg, 0.5 mmol) according to the procedure for 404. $^1H$ NMR (400 MHz, DMSO-$d_6$) δ 8.43 (t, J=5.8 Hz, 1H), 8.36 (s, 1H), 7.59 (s, 1H), 7.37 (d, J=8.8 Hz, 11H), 7.28 (dd, J=8.7, 2.7 Hz, 1H), 7.19 (d, J=2.7 Hz, 1H), 7.16-7.12 (m, 2H), 7.07-7.01 (m, 2H), 4.20 (d, J=5.7 Hz, 2H), 3.41 (t, J=8.8 Hz, 1H), 3.27-3.16 (m, 2H), 3.00-2.85 (m, 4H), 2.34-2.26 (m, 2H), 1.72-1.55 (m, 10H). Mass (m/z): 489.3 $[M+H]^+$.

N-(4-((4-(4,4-dimethylpiperidin-1-yl)-3-(trifluoromethyl)phenyl)amino)benzyl)-5-oxopyrrolidine-3-carboxamide (416)

416

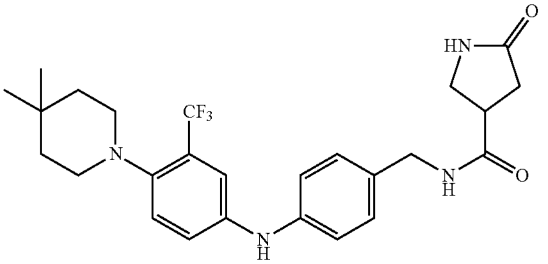

The title compound 416 (54.1 mg) was prepared in a total yield of 33.3% as a white powder from N-(4-bromobenzyl)-5-oxopyrrolidine-3-carboxamide (99 mg, 0.33 mmol), 4-(4,4-dimethylpiperidin-1-yl)-3-(trifluoromethyl)aniline (117 mg, 0.43 mmol), $Pd_2(dba)_3$ (3.0 mg, 3.3 umol), X-Phos (7.9 mg, 16.5 umol), $Cs_2CO_3$ (163 mg, 0.5 mmol) according to the procedure for 404. $^1$H NMR (400 MHz, DMSO-$d_6$) δ 8.42 (t, J=5.8 Hz, 1H), 8.34 (s, 11H), 7.59 (s, 1H), 7.49 (d, J=8.7 Hz, 1H), 7.26 (dd, J=8.6, 2.7 Hz, 1H), 7.21 (d, J=2.7 Hz, 1H), 7.18-7.10 (m, 2H), 7.05-7.00 (m, 2H), 4.20 (d, J=5.7 Hz, 2H), 3.44-3.38 (m, 1H), 3.27-3.16 (m, 2H), 2.80-2.69 (m, 4H), 2.30 (dd, J=8.4, 3.4 Hz, 2H), 1.46-1.36 (m, 4H), 0.98 (s, 6H). Mass (m/z): 489.3 [M+H]$^+$.

5-oxo-N-(4-((4-(4-(trifluoromethyl)cyclohexyl)phenyl)amino)benzyl)pyrrolidine-3-carboxamide (417)

417

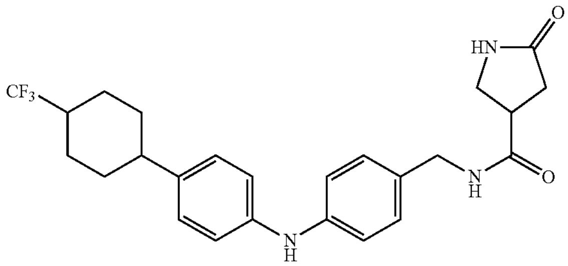

The title compound 417 (9.6 mg) was prepared in a total yield of 8.4% as a white powder from N-(4-bromobenzyl)-5-oxopyrrolidine-3-carboxamide (74 mg, 0.25 mmol), 4-(4-(trifluoromethyl)cyclohexyl)aniline (73 mg, 0.30 mmol), $Pd_2(dba)_3$ (2.3 mg, 2.5 umol), X-Phos (5.9 mg, 12.4 umol), $Cs_2CO_3$ (121 mg, 0.37 mmol) according to the procedure for 413. $^1$H NMR (400 MHz, DMSO-$d_6$) δ 8.39 (t, J=5.7 Hz, 1H), 8.04 (s, 1H), 7.59 (s, 1H), 7.16-7.05 (m, 4H), 7.03-6.92 (m, 4H), 4.17 (d, J=5.6 Hz, 2H), 3.40 (t, J=8.8 Hz, 1H), 3.27-3.15 (m, 2H), 2.69-2.64 (m, 1H), 2.35-2.26 (m, 2H), 1.87-1.67 (m, 8H). Mass (m/z): 460.3 [M+H]$^+$.

N-(4-((3-(diethylamino)-4-fluorophenyl)amino)benzyl)-5-oxopyrrolidine-3-carboxamide (418)

418

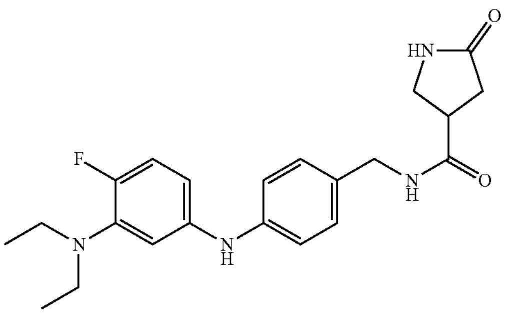

The title compound 418 (9.0 mg) was prepared in a total yield of 6.8% as a white solid from N-(4-bromobenzyl)-5-oxopyrrolidine-3-carboxamide (99 mg, 0.33 mmol), 4-(4-(trifluoromethyl)cyclohexyl)aniline (73 mg, 0.30 mmol), $Pd_2(dba)_3$ (3.0 mg, 3.3 umol), X-Phos (7.9 mg, 16.5 umol), $Cs_2CO_3$ (163 mg, 0.50 mmol) according to the procedure for 404. $^1$H NMR (400 MHz, DMSO-$d_6$) δ 8.41 (t, J=5.9 Hz, 1H), 8.11 (s, 1H), 7.59 (s, 1H), 7.15-6.94 (m, 5H), 6.83-6.56 (m, 2H), 4.18 (d, J=5.7 Hz, 2H), 3.41 (t, J=8.8 Hz, 1H), 3.32-3.16 (m, 6H), 2.34-2.25 (m, 2H), 1.04 (t, J=7.0 Hz, 6H). Mass (m/z): 399.3 [M+H]$^+$.

N-(4-((6-(azepan-1-yl)-2-methylpyridin-3-yl)amino)benzyl)-5-oxopyrrolidine-3-carboxamide (419)

419

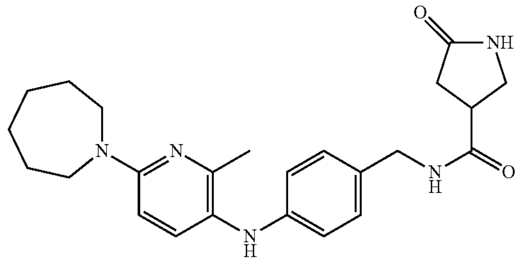

The title compound 419 (16.1 mg) was prepared in a total yield of 11.5% as a yellow powder from N-(4-bromobenzyl)-5-oxopyrrolidine-3-carboxamide (99 mg, 0.33 mmol), 6-(azepan-1-yl)-2-methylpyridin-3-amine (88 mg, 0.43 mmol), $Pd_2(dba)_3$ (3.0 mg, 3.3 umol), X-Phos (7.9 mg, 16.5 umol), $Cs_2CO_3$ (163 mg, 0.50 mmol) according to the procedure for 404. $^1$H NMR (400 MHz, DMSO-$d_6$) δ 8.35 (s, 1H), 7.58 (s, 1H), 7.27-7.08 (m, 2H), 7.04-6.93 (m, 2H), 6.56-6.28 (m, 3H), 4.12 (d, J=5.7 Hz, 2H), 3.71-3.50 (m, 4H), 3.41-3.37 (m, 1H), 3.25-3.13 (m, 2H), 2.32-2.24 (m, 2H), 2.22-2.13 (m, 2H), 1.80-1.67 (m, 4H), 1.56-1.45 (m, 4H). Mass (m/z): 422.3 [M+H]$^+$.

N-(4-((4-(4,4-dimethylpiperidin-1-yl)-2-(trifluoromethyl)phenyl)amino)benzyl)-5-oxopyrrolidine-3-carboxamide (420)

420

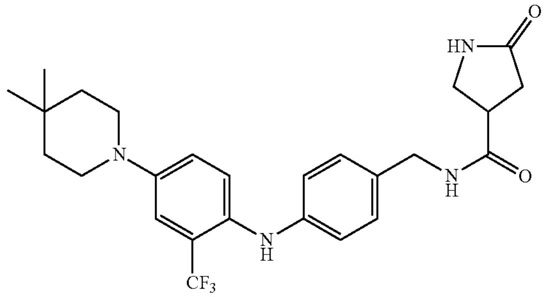

The title compound 420 (9.2 mg) was prepared in a total yield of 18.8% as a light yellow solid from N-(4-(aminomethyl)phenyl)-4-(4,4-dimethylpiperidin-1-yl)-2-(trifluoromethyl)aniline (37.7 mg, 0.1 mmol), 5-oxopyrrolidine-3-carboxylic acid (15.5 mg, 0.12 mmol), DIEA (38.7 mg, 0.3 mmol) and HATU (45.6 mg, 0.12 mmol) according to the procedure for 397. $^1$H NMR (400 MHz, DMSO-$d_6$) δ 8.34 (t, =5.7 Hz, 1H), 7.57 (s, 1H), 7.21-7.11 (m, 4H), 7.02-6.97 (m, 2H), 6.67-6.61 (m, 2H), 4.13 (d, J=5.6 Hz, 2H), 3.39 (t, J=8.9 Hz, 1H), 3.25-3.13 (m, 6H), 2.34-2.25 (m, 2H), 1.48-1.40 (m, 4H), 0.96 (s, 6H). Mass (m/z): 489.3 [M+H]$^+$.

N-(4-((2,5-dimethyl-4-(4-(trifluoromethyl)piperidin-1-yl)phenyl)amino)benzyl)-5-oxopyrrolidine-3-carboxamide (421)

421

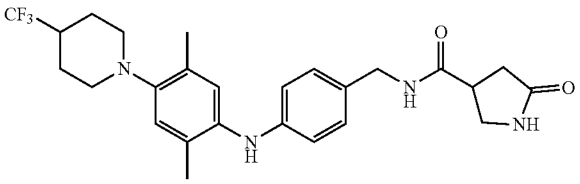

The title compound 421 (17.0 mg) was prepared in a total yield of 10.4% as a light yellow powder from N-(4-bromobenzyl)-5-oxopyrrolidine-3-carboxamide (99 mg, 0.33 mmol), 2,5-dimethyl-4-(4-(trifluoromethyl)piperidin-1-yl) aniline (117 mg, 0.43 mmol), $Pd_2(dba)_3$ (3.3 mg, 3.3 umol), X-Phos (7.9 mg, 16.5 umol), $Cs_2CO_3$ (163 mg, 0.50 mmol) according to the procedure for 394. $^1$H NMR (400 MHz, DMSO-$d_6$) δ 8.34 (t, J=5.7 Hz, 1H), 7.57 (s, 1H), 7.20 (s, 1H), 7.05-6.98 (m, 2H), 6.92 (s, 1H), 6.86 (s, 1H), 6.71-6.64 (m, 2H), 4.14 (d, J=5.7 Hz, 2H), 3.44-3.36 (m, 1H), 3.27-3.14 (m, 2H), 3.10-3.00 (m, 2H), 2.67-2.59 (m, 2H), 2.47-2.37 (m, 1H), 2.33-2.25 (m, 2H), 2.14 (s, 3H), 2.10 (s, 3H), 1.93-1.83 (m, 2H), 1.61 (qd, J=12.3, 4.0 Hz, 2H). Mass (m/z): 489.3 $[M+H]^+$.

N-(4-((2-chloro-5-fluoro-4-(4-(trifluoromethyl)piperidin-1-yl)phenyl)amino)benzyl)-5-oxopyrrolidine-3-carboxamide (422)

422

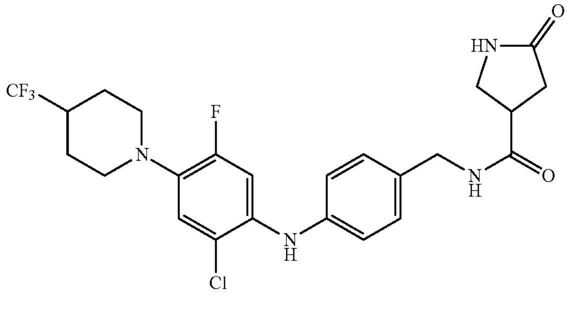

The title compound 422 (10.1 mg) was prepared in a total yield of 24.5% as a light yellow solid from N-(4-(aminomethyl)phenyl)-2-chloro-5-fluoro-4-(4-(trifluoromethyl)piperidin-1-yl)aniline (31 mg, 0.1 mmol), 5-oxopyrrolidine-3-carboxylic acid (12.9 mg, 0.1 mmol), DIEA (31.2 mg, 0.24 mmol) and HATU (38 mg, 0.1 mmol) according to the procedure for 397. $^1$H NMR (400 MHz, DMSO-$d_6$) δ 8.41 (t, J=5.8 Hz, 1H), 7.62 (s, 1H), 7.58 (s, 1H), 7.15-7.07 (m, 3H), 6.99-6.92 (m, 3H), 4.19 (d, J=5.7 Hz, 2H), 3.41 (t, J=8.8 Hz, 1H), 3.27-3.14 (m, 2H), 2.74-2.64 (m, 2H), 2.46-2.39 (m, 1H), 2.33-2.26 (m, 2H), 1.93-1.85 (m, 2H), 1.59 (qd, J=12.3, 3.7 Hz, 2H). Mass (m/z): 513.3 $[M+H]^+$.

N-(4-((4-(4-methylcyclohexyl)phenyl)amino)benzyl)-5-oxopyrrolidine-3-carboxamide (423)

423

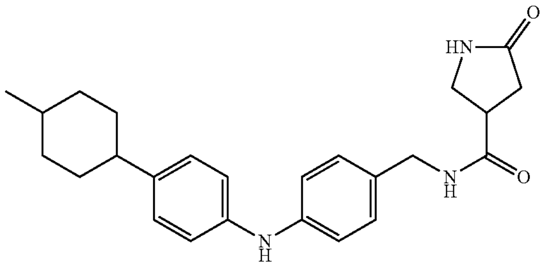

The title compound 423 (4.1 mg) was prepared in a total yield of 10.0% as a white solid from 4-(aminomethyl)-N-(4-(4-methylcyclohexyl)phenyl)aniline (21.6 mg, 74 umol), 5-oxopyrrolidine-3-carboxylic acid (11.4 mg, 88 umol), DIEA (28.6 mg, 0.22 mmol) and HATU (33.4 mg, 88 umol) according to the procedure for 413. $^1$H NMR (400 MHz, DMSO-$d_6$) δ 8.38 (t, J=5.8 Hz, 1H), 7.99 (s, 1H), 7.58 (s, 1H), 7.13-7.07 (m, 4H), 7.01-6.94 (m, 4H), 4.17 (d, J=5.8 Hz, 2H), 3.40 (t, J=8.8 Hz, 1H), 3.26-3.16 (m, 2H), 2.46-2.40 (m, 1H), 2.33-2.27 (m, 2H), 1.93-1.85 (m, 1H), 1.69-1.45 (m, 9H), 1.00 (d, J=7.1 Hz, 3H). Mass (m/z): 406.3 $[M+H]^+$.

$N^1$-(4-((4-cyclohexylphenyl)amino)benzyl)succinamide (424)

424

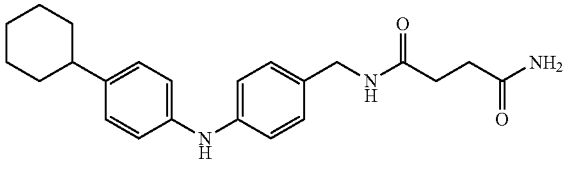

The title compound 424 (17.1 mg) was prepared in a total yield of 45.1% as a white powder from 4-(aminomethyl)-N-(4-cyclohexylphenyl)aniline (28.0 mg, 0.1 mmol), 4-amino-4-oxobutanoic acid (14 mg, 0.2 mmol), DIEA (38.7 mg, 0.3 mmol) and HATU (38.7 mg, 0.3 mmol) according to the procedure for 413. $^1$H NMR (400 MHz, DMSO-$d_6$) δ 8.21 (t, J=5.8 Hz, 1H), 7.96 (s, 1H), 7.28 (s, 1H), 7.11-7.04 (m, 4H), 6.98-6.91 (m, 4H), 6.74 (s, 1H), 4.14 (d, J=5.8 Hz, 2H), 2.45-2.24 (m, 6H), 1.83-1.66 (m, 6H), 1.39-1.29 (m, 4H). Mass (m/z): 380.3 $[M+H]^+$.

(R)—N-(4-((4-cyclohexylphenyl)amino)benzyl)-2-oxoimidazolidine-4-carboxamide (425)

425

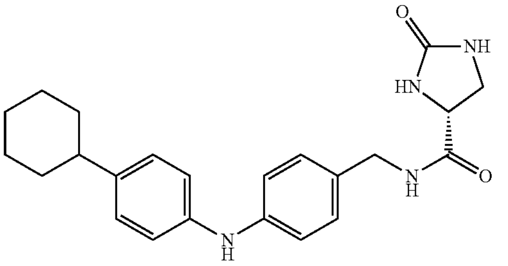

The title compound 425 (9.9 mg) was prepared in a total yield of 15.3% as a white solid from 4-(aminomethyl)-N-(4-cyclohexylphenyl)aniline (28.0 mg, 0.1 mmol), (R)-2-oxoimidazolidine-4-carboxylic acid (15.6 mg, 0.12 mmol), DIEA (38.7 mg, 0.3 mmol) and HATU (45.6 mg, 0.12 mmol) according to the procedure for 413. $^1$H NMR (400 MHz, DMSO-$d_6$) δ 8.29 (t, J=5.9 Hz, 1H), 7.98 (s, 1H), 7.13-7.03 (m, 4H), 7.01-6.91 (m, 4H), 6.54 (s, 5H), 6.32 (s, 1H), 4.21-4.16 (m, 2H), 4.13-4.05 (m, 1H), 3.59-3.52 (m, 1H), 3.24-3.19 (m, 1H), 2.44-2.34 (m, 1H), 1.82-1.65 (m, 5H), 1.41-1.09 (m, 6H). Mass (m/z): 393.3 $[M+H]^+$.

N-(4-((3,5-bis(diethylamino)phenyl)amino)benzyl)-5-oxopyrrolidine-3-carboxamide (426)

426

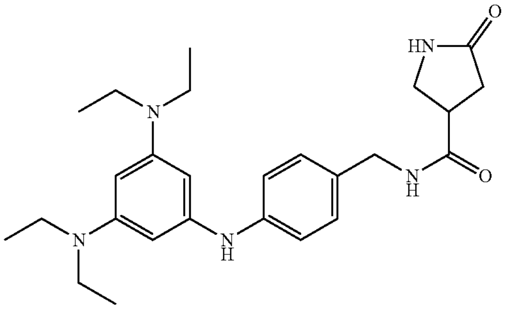

The title compound 426 (15.7 mg) was prepared in a total yield of 20.0% as a green solid from N'-(4-(aminomethyl)phenyl)-$N^3$,$N^3$,$N^5$,$N^5$-tetraethylbenzene-1,3,5-triamine (60.6 mg, 0.18 mmol), 5-oxopyrrolidine-3-carboxylic acid (27.6 mg, 0.21 mmol), DIEA (69 mg, 0.53 mmol) and HATU (81.3 mg, 0.21 mmol) according to the procedure for 397. Mass (m/z): 452.3 $[M+H]^+$.

N-(4-((3-chloro-2-methyl-4-(4-(trifluoromethyl)piperidin-1-yl)phenyl)amino)benzyl)-5-oxopyrrolidine-3-carboxamide (427)

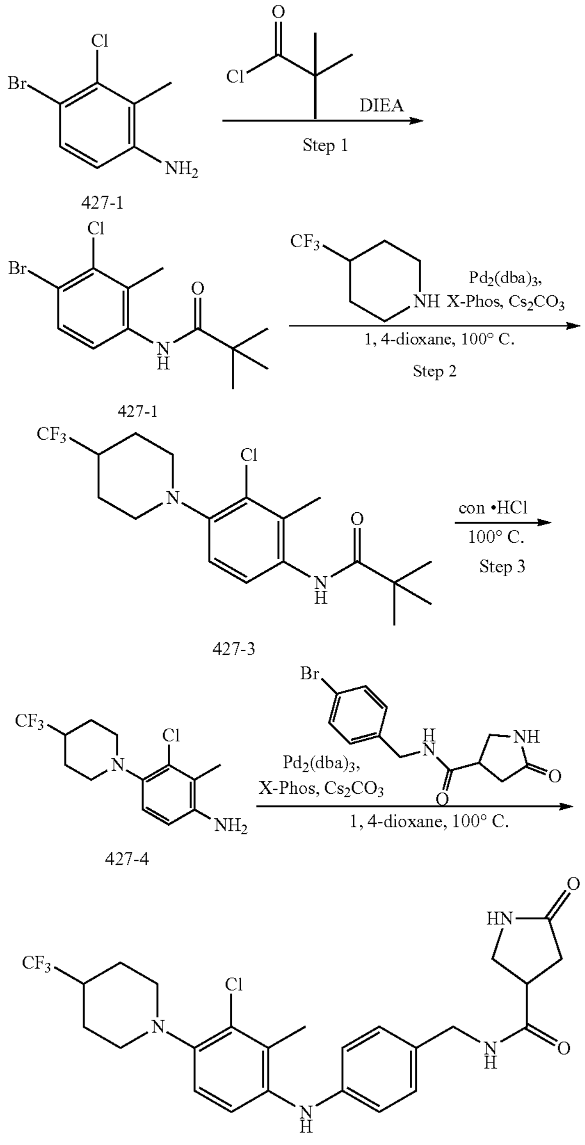

427

Step 1. Preparation of N-(4-bromo-3-chloro-2-methylphenyl)pivalamide (427-2). To a solution of 4-bromo-3-chloro-2-methylaniline (4.36 g, 20 mmol) and DIEA (3.87 g, 30 mmol) in DCM (30 mL) was added dropwise pivaloyl chloride (2.88 g, 24 mmol) at 0'C. Then the mixture was stirred overnight at rt. The solution was washed with $H_2O$ (3×50 mL) and brine (50 mL). The organic layer was dried ($Na_2SO_4$) and concentrated in vacuo. The residue was purified by flash chromatography on silica gel (0-10% EtOAc/hexane) to give desired product as a Light-yellow oil. (5.6 g, 92.4%). Mass (m/z): 304.2 $[M+H]^+$.

Step 2. Preparation of N-(3-chloro-2-methyl-4-(4-(trifluoromethyl)piperidin-1-yl)phenyl)pivalamide (427-3). The title compound 427-3 (545 mg) was prepared in a total yield of 29.0% as a yellow solid from N-(4-bromo-3-chloro-2- methylphenyl)pivalamide (1.52 g, 5 mmol), 4-(trifluoromethyl)piperidine (765 mg, 5.0 mmol), $Pd_2(dba)_3$ (91.5 mg, 0.05 mmol), X-Phos (119 mg, 0.25 mmol), $Cs_2CO_3$ (2.45 g, 7.5 mmol) according to the procedure for 394-3.

Step 3. Preparation of 3-chloro-2-methyl-4-(4-(trifluoromethyl)piperidin-1-yl)aniline (427-4). In a pressure tube, a solution of N-(3-chloro-2-methyl-4-(4-(trifluoromethyl) piperidin-1-yl)phenyl)pivalamide (545 mg, 1.45 mmol) in 10 mL of con·HCl was stirred overnight at 100'C. Then the solution was concentrated, 10 ml water was added. The PH of the filtration was adjusted to 8-9 with sodium carbonate solution. Then the mixture was extracted by DCM (10 mL×3). The combined organic layers were washed with water (15 mL), dried over Na2SO4 and concentrated. The residue was purified by perp-TLC (EA/PE-1/2) to afford the desired product as a yellow solid. (87.6 mg, 20.7%). Mass (m/z): 293.3 $[M+H]^+$.

Step 3. Preparation of N-(4-((3-chloro-2-methyl-4-(4-(trifluoromethyl)piperidin-1-yl)phenyl)amino)benzyl)-5-oxopyrrolidine-3-carboxamide (427). The title compound 427 (19.3 mg) was prepared in a total yield of 15.2% as a white solid from N-(4-bromobenzyl)-5-oxopyrrolidine-3-carboxamide (74 mg, 0.25 mmol), 3-chloro-2-methyl-4-(4-(trifluoromethyl)piperidin-1-yl)aniline (87.6 mg, 0.3 mmol), $Pd_2(dba)_3$ (2.3 mg, 2.5 umol), X-Phos (6.0 mg, 12.5 umol), $Cs_2CO_3$ (122 mg, 0.38 mmol) according to the procedure for 404. $^1H$ NMR (400 MHz, DMSO-$d_6$) δ 8.38 (t, J=5.7 Hz, 1H), 7.58 (s, 1H), 7.52 (s, 1H), 7.09-6.96 (m, 4H), 6.71-6.64 (m, 2H), 4.15 (d, J=5.7 Hz, 2H), 3.42-3.36 (m, 1H), 3.28-3.14 (m, 4H), 2.69-2.61 (m, 2H), 2.47-2.39 (m, 1H), 2.34-2.25 (m, 2H), 2.21 (s, 3H), 1.95-1.87 (m, 2H), 1.63 (qd, J=12.4, 4.0 Hz, 2H). Mass (m/z): 509.3 $[M+H]^+$.

N-(4-((4-chloro-3-(4-(trifluoromethyl)piperidin-1-yl) phenyl)amino)benzyl)-5-oxopyrrolidine-3-carboxamide (428)

428

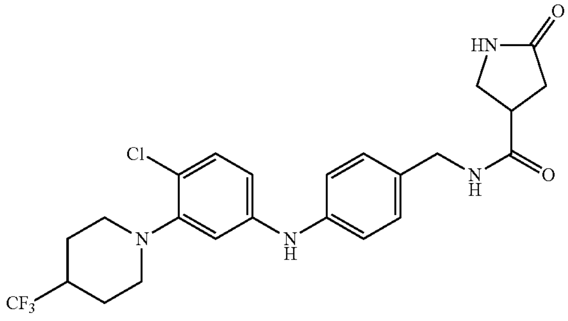

The title compound 428 (4.6 mg) was prepared in a total yield of 10.3% as a white solid from N-(4-(aminomethyl) phenyl)-4-chloro-3-(4-(trifluoromethyl)piperidin-1-yl)aniline (35 mg, 0.09 mmol), 5-oxopyrrolidine-3-carboxylic acid (14.0 mg, 0.11 mmol), DIEA (34.8 mg, 0.27 mmol) and HATU (41.8 mg, 0.11 mmol) according to the procedure for 397. $^1H$ NMR (400 MHz, DMSO-$d_6$) δ 8.42 (t, J=5.8 Hz, 1H), 8.26 (s, 1H), 7.59 (s, 1H), 7.20 (d, J=8.6 Hz, 1H), 7.16-7.10 (m, 2H), 7.06-6.99 (m, 2H), 6.77 (d, J=2.6 Hz, 1H), 6.70 (dd, J=8.6, 2.6 Hz, 1H), 4.20 (d, J=5.7 Hz, 2H), 3.44-3.39 (m, 1H), 3.26-3.17 (m, 2H), 2.65-2.57 (m, 2H), 2.47-2.40 (m, 1H), 2.34-2.27 (m, 2H), 1.94-1.88 (m, 2H), 1.61 (qd, J=12.1, 3.6 Hz, 2H). Mass (m/z): 495.2 $[M+H]^+$.

N-(4-((2-fluoro-5-methyl-4-(4-methylpiperidin-1-yl) phenyl)amino)benzyl)-5-oxopyrrolidine-3-carboxamide (429)

429

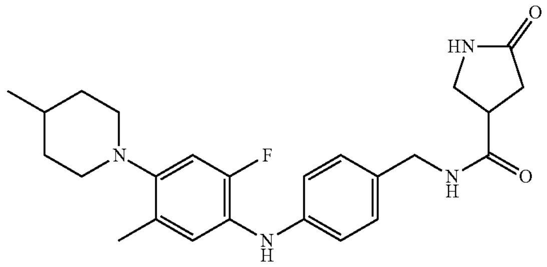

The title compound 429 (19.3 mg) was prepared in a total yield of 15.2% as a white solid from N-(4-bromobenzyl)-5-oxopyrrolidine-3-carboxamide (111 mg, 0.38 mmol), 2-fluoro-5-methyl-4-(4-methylpiperidin-1-yl)aniline (100 mg, 0.45 mmol), $Pd_2(dba)_3$ (3.5 mg, 3.8 umol), X-Phos (9.7 mg, 19 umol), $Cs_2CO_3$ (186 mg, 0.57 mmol) according to the procedure for 404. $^1H$ NMR (400 MHz, DMSO-$d_6$) δ 8.36 (t, J=5.7 Hz, 1H), 7.60 (s, 1H), 7.58 (s, 111), 7.06-6.99 (m, 3H), 6.86 (d, J=13.1 Hz, 1H), 6.80-6.75 (m, 2H), 4.15 (d, J=5.7 Hz, 2H), 3.43-3.36 (m, 1H), 3.26-3.15 (m, 2H), 3.02-2.94 (m, 2H), 2.57-2.52 (m, 2H), 2.32-2.24 (m, 2H), 2.15 (s, 3H), 1.69 (d, J=12.4 Hz, 2H), 1.51-1.41 (m, 1H), 1.33-1.23 (m, 2H), 0.96 (d, J=6.5 Hz, 3H). Mass (m/z): 439.3 $[M+H]^+$.

N-(4-((6-(4-isopropylpiperidin-1-yl)-2-methylpyridin-3-yl)amino)benzyl)-5-oxopyrrolidine-3-carboxamide (430)

430

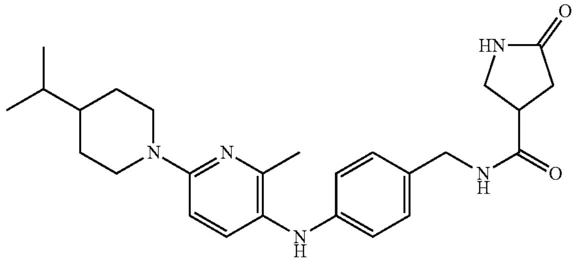

The title compound 430 (19.3 mg) was prepared in a total yield of 15.2% as a white solid from N-(4-bromobenzyl)-5-oxopyrrolidine-3-carboxamide (98 mg, 0.33 mmol), 6-(4-isopropylpiperidin-1-yl)-2-methylpyridin-3-amino (92 mg, 0.40 mmol), $Pd_2(dba)_3$ (3.0 mg, 3.3 umol), X-Phos (7.9 mg, 16.5 umol), $Cs_2CO_3$ (163 mg, 0.50 mmol) according to the procedure for 404. $^1H$ NMR (400 MHz, DMSO-$d_6$) δ 8.31 (t, J=5.7 Hz, 1H), 7.57 (s, 1H), 7.25 (d, J=8.7 Hz, 11H), 7.19 (s, 11H), 7.01-6.93 (m, 2H), 6.63 (d, J=8.8 Hz, 1H), 6.54-6.46 (m, 2H), 4.32-4.23 (m, 2H), 4.11 (d, J=5.7 Hz, 2H), 3.40-3.34 (m, 1H), 3.25-3.12 (m, 2H), 2.70-2.60 (m, 2H), 2.34-2.21 (m, 2H), 2.19 (s, 3H), 1.74-1.65 (m, 2H), 1.48-1.38 (m, 1H), 1.27-1.10 (m, 4H), 0.88 (d, J=6.7 Hz, 6H). Mass (m/z): 450.3 $[M+H]^+$.

N-(4-((6-(4-butylpiperidin-1-yl)-2-methylpyridin-3-yl)amino)benzyl)-5-oxopyrrolidine-3-carboxamide (431)

431

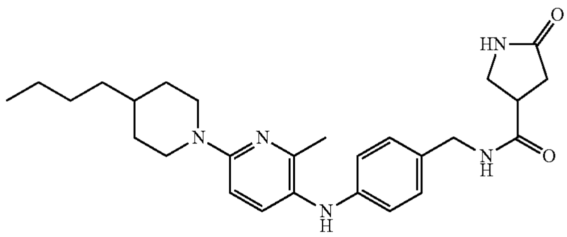

The title compound 431 (22.9 mg) was prepared in a total yield of 14.9% as a white solid from N-(4-bromobenzyl)-5-oxopyrrolidine-3-carboxamide (98 mg, 0.33 mmol), 6-(4-butylpiperidin-1-yl)-2-methylpyridin-3-amine (99 mg, 0.40 mmol), $Pd_2(dba)_3$ (3.0 mg, 3.3 umol), X-Phos (7.9 mg, 16.5 umol), $Cs_2CO_3$ (163 mg, 0.50 mmol) according to the procedure for 404. $^1$H NMR (400 MHz, DMSO-$d_6$) δ 8.31 (t, J=5.6 Hz, 1H), 7.57 (s, 1H), 7.24 (d, J=8.7 Hz, 1H), 7.19 (s, 1H), 7.01-6.94 (m, 2H), 6.63 (d, J=8.8 Hz, 1H), 6.52-6.47 (m, 2H), 4.26-4.18 (m, 2H), 4.13-4.08 (m, 2H), 3.41-3.37 (m, 1H), 3.24-3.15 (m, 2H), 2.72-2.63 (m, 2H), 2.57-2.52 (m, 1H), 2.33-2.26 (m, 2H), 2.19 (s, 3H), 1.74-1.68 (m, 2H), 1.45-1.38 (m, 1H), 1.31-1.21 (m, 6H), 1.14-1.05 (m, 2H), 0.90-0.85 (m, 3H). Mass (m/z): 4564.4 $[M+H]^+$.

4-amino-N-(4-((4-(4-(trifluoromethyl)piperidin-1-yl)phenyl)amino)benzyl)butanamide (432)

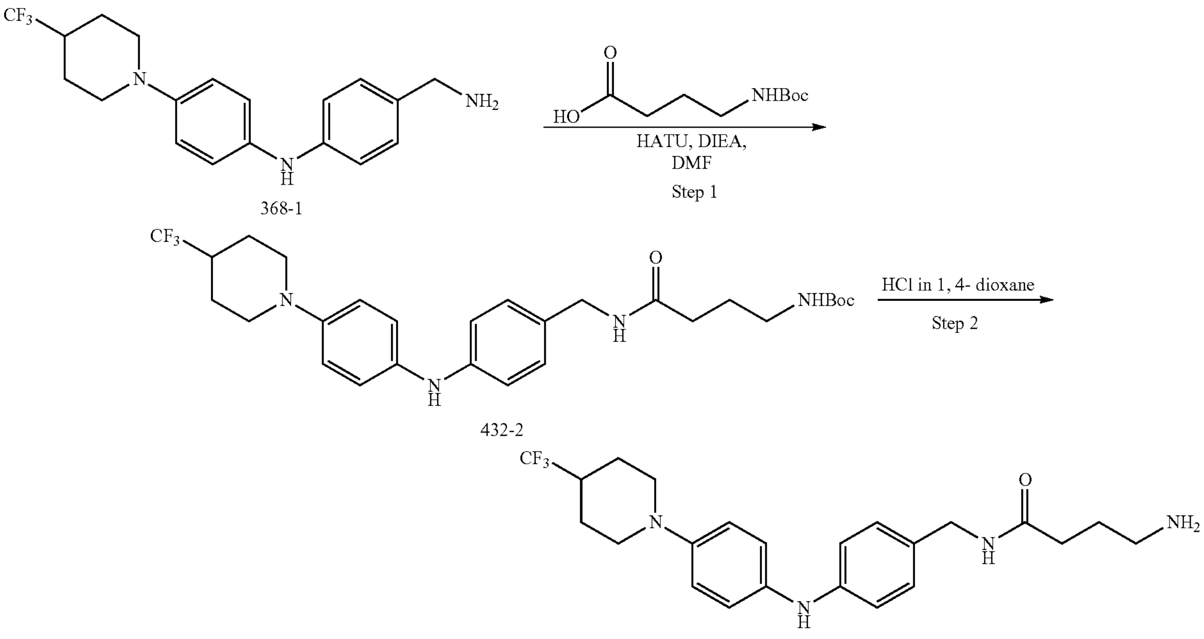

368-1

432-2

432

Step 1. Preparation of tert-butyl (4-oxo-4-((4-((4-(4-(trifluoromethyl)piperidin-1-yl)phenyl)amino)benzyl)amino)butyl)carbamate (432-2). The title compound 432-2 (110 mg) was prepared in a total yield of 68.8% as a blue solid from 4-(aminomethyl)-N-(4-(4-(trifluoromethyl)piperidin-1-yl)phenyl)aniline (116 mg, 0.3 mmol), 4-((tert-butoxycarbonyl)amino)butanoic acid (73 mg, 0.0.36 mmol), DIEA (116 mg, 0.3 mmol) and HATU (137 mg, 0.36 mmol) according to the procedure for 397. Mass (m/z): 535.4 $[M+H]^+$.

Step 2. Preparation of 4-amino-N-(4-((4-(4-(trifluoromethyl)piperidin-1-yl)phenyl)amino)benzyl)butanamide (432). The title compound 432 (45.2 mg) was prepared in a total yield of 52.0% as a gray solid from tert-butyl (4-oxo-4-((4-((4-(4-(trifluoromethyl)piperidin-1-yl)phenyl)amino)benzyl)amino)butyl)carbamate (110 mg, 0.20 mmol), HCl in 1,4-dioxane (10.0 mL) according to the procedure for 363-4. $^1$H NMR (300 MHz, DMSO-$d_6$) δ 8.33 (t, J=5.8 Hz, 1H), 7.92 (s, 1H), 7.42 (s, 1H), 7.24-6.83 (m, 8H), 4.26-4.06 (m, 2H), 3.70-3.51 (m, 2H), 2.83-2.73 (m, 2H), 2.70-2.54 (m, 2H), 2.45-2.35 (m, 1H), 2.22 (t, J=7.2 Hz, 2H), 1.95-1.74 (m, 4H), 1.65-1.51 (m, 2H). Mass (m/z): 435.2 $[M+H]^+$.

5-oxo-N-(2-(trifluoromethyl)-4-((2-(4-(trifluoromethyl)piperidin-1-yl)pyrimidin-5-yl)amino)benzyl)pyrrolidine-3-carboxamide (433)

433

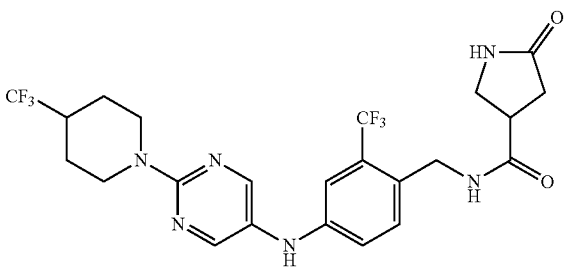

The title compound 433 (6.2 mg) was prepared in a total yield of 16.7% as a white solid from N-(4-(aminomethyl)-3-(trifluoromethyl)phenyl-2-(4-(trifluoromethyl)piperidin-1-yl)pyrimidin-5-amine (31 mg, 0.07 mmol), 5-oxopyrrolidine-3-carboxylic acid (11.5 mg, 0.09 mmol), DIEA (28.6 mg, 0.22 mmol) and HATU (33.7 mg, 0.09 mmol) according to the procedure for 397. $^1$H NMR (400 MHz, DMSO-$d_6$) δ 8.41 (t, J=5.5 Hz, 1H), 8.29 (s, 2H), 8.07 (s, 1H), 7.59 (s, 1H), 7.24 (d, J=8.6 Hz, 1H), 7.02 (d, J=2.5 Hz, 1H), 6.97 (dd, J=8.3, 2.4 Hz, 1H), 4.72 (d, J=13.4 Hz, 2H), 4.30 (d, J=5.6 Hz, 2H), 3.44-3.37 (m, 2H), 3.25-3.20 (m, 2H), 2.96-2.87 (m, 3H), 2.31-2.27 (m, 2H), 1.91-1.85 (m, 2H), 1.43-1.35 (m, 3H). Mass (m/z): 531.3 $[M+H]^+$.

(S)—N-(4-((4-(4,4-dimethylcyclohexyl)phenyl)amino)benzyl)-2,6-dioxohexahydropyrimidine-4-carboxamide (434)

434

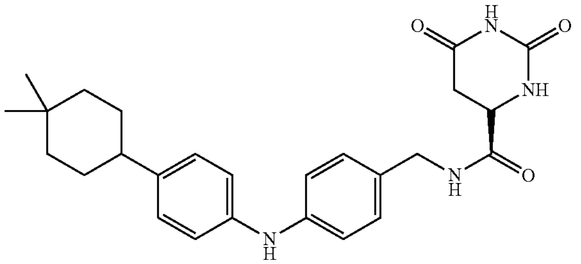

The title compound 434 (6.1 mg) was prepared in a total yield of 13.6% as a white solid from 4-(aminomethyl)-N-(4-(4,4-dimethylcyclohexyl)phenyl)aniline (25 mg, 0.08 mmol), (S)-2,6-dioxohexahydropyrimidine-4-carboxylic acid (15.8 mg, 0.1 mmol), DIEA (38.7 mg, 0.3 mmol) and HATU (38.0 mg, 0.1 mmol) according to the procedure for 413. $^1$H NMR (400 MHz, DMSO-$d_6$) δ 10.03 (s, 1H), 8.47 (t, J=5.7 Hz, 1H), 8.02 (s, 1H), 7.63 (s, 1H), 7.15-7.05 (m, 4H), 6.99-6.92 (m, 4H), 4.20-4.12 (m, 2H), 4.01 (dt, J=73, 3.5 Hz, 1H), 2.85 (dd, J=16.6, 7.2 Hz, 1H), 2.38-2.27 (m, 2H), 1.64-1.52 (m, 2H), 1.46-1.40 (m, 2H), 1.34-1.24 (m, 2H), 0.95 (d, J=10.0 Hz, 6H). Mass (m/z): 449.3 $[M+H]^+$.

N-(4-((4-(4,4-dimethylcyclohexyl)phenyl)amino)benzyl)-2,6-dioxopiperidine-4-carboxamide (435)

435

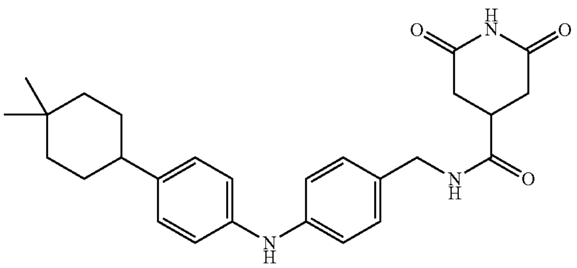

The title compound 435 (19.6 mg) was prepared in a total yield of 54.7% as a light yellow solid from 4-(aminomethyl)-N-(4-(4,4-dimethylcyclohexyl)phenyl)aniline (25 mg, 0.08 mmol), 2,6-dioxopiperidine-4-carboxylic acid (15.7 mg, 0.1 mmol), DIEA (38.7 mg, 0.3 mmol) and HATU (38.0 mg, 0.1 mmol) according to the procedure for 413. $^1$H NMR (300 MHz, DMSO-$d_6$) δ 10.66 (s, 1H), 8.43 (t, J=5.7 Hz, 1H), 7.98 (s, 1H), 7.13-7.02 (m, 4H), 6.98-6.92 (m, 4H), 4.15 (d, J=5.7 Hz, 2H), 2.89-3.10 (m, 1H), 2.63-2.53 (m, 4H), 2.36-2.27 (m, 1H), 1.62-1.51 (m, 4H), 1.47-1.40 (m, 2H), 1.34-1.27 (m, 2H), 0.94 (d, J=7.5 Hz, 6H). Mass (m/z): 448.3 [M+H]j.

(R)—N-(4-((4-(4,4-dimethylcyclohexyl)phenyl)amino)benzyl)-2-oxoimidazolidine-4-carboxamide (436)

436

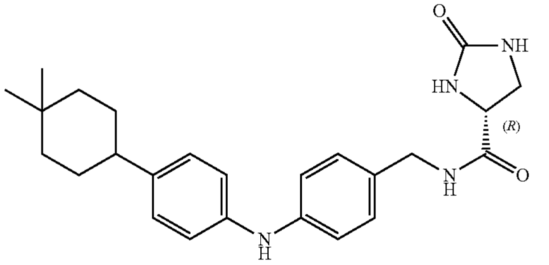

The title compound 436 (12.6 mg) was prepared in a total yield of 37.5% as a light yellow solid from 4-(aminomethyl)-N-(4-(4,4-dimethylcyclohexyl)phenyl)aniline (25 mg, 0.08 mmol), (R)-2-oxoimidazolidine-4-carboxylic acid (13.0 mg, 0.1 mmol), DIEA (38.7 mg, 0.3 mmol) and HATU (38.0 mg, 0.1 mmol) according to the procedure for 413. $^1$H NMR (300 MHz, DMSO-$d_6$) δ 8.28 (t, J=5.7 Hz, 1H), 7.97 (s, 1H), 7.12-7.05 (m, 4H), 6.99-6.92 (m, 4H), 6.53 (s, 1H), 6.30 (s, 1H), 4.18 (d, J=5.8 Hz, 2H), 4.09 (dd, J=9.7, 6.1 Hz, 2H), 3.54 (t, J= 9.3 Hz, 1H), 3.27-3.18 (m, 2H), 1.58-1.35 (m, 8H), 0.94 (d, J=7.5 Hz, 6H). Mass (m/z): 421.3 $[M+H]^+$.

4-guanidino-N-(4-((4-(4-(trifluoromethyl)piperidin-1-yl)phenyl)amino)benzyl)butanamide (437)

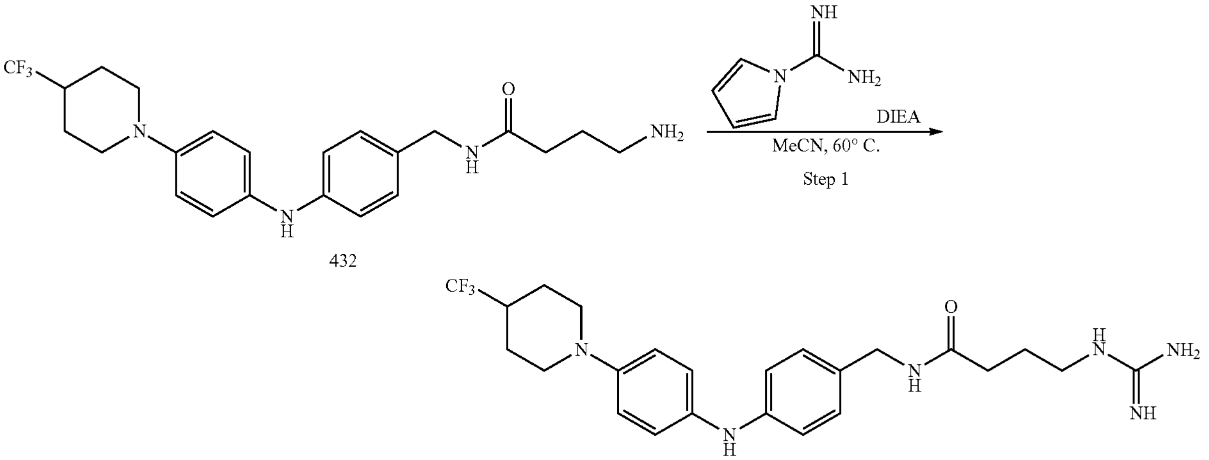

432

437

To a solution of 4-amino-N-(4-((4-(4-(trifluoromethyl) piperidin-1-yl)phenyl)amino)benzyl)butanamide (33.6 mg, 7.7 umol) and DIEA (29.8 mg, 23.1 ummol) in MeCN (3.0 mL) was added 1H-pyrrole-1-carboximidamide (10.1 mg, 9.3 ummol). Then the mixture was stirred for 16 hours at 60'C. After cooling to rt. The solid was collected by filtration and washed with 5 mL of MeCN to afford the desired product as a white solid. (16.5 mg, 45.1%). $^1$H NMR (400 MHz, DMSO-$d_6$) δ 8.32 (t, J=5.8 Hz, 1H), 7.80 (s, 1H), 7.70 (s, 1H), 7.35 (s, 3H), 7.07-7.02 (m, 2H), 6.99-6.94 (m, 2H), 6.91-6.85 (m, 4H), 4.14 (d, J=5.7 Hz, 2H), 3.66-3.57 (m, 2H), 3.10 (q, J=6.7 Hz, 2H), 2.62 (td, J=12.2, 2.4 Hz, 2H), 2.45-2.37 (m, 11H), 2.18 (t, J=7.3 Hz, 2H), 1.92-1.83 (m, 2H), 1.71 (p, J=7.3 Hz, 2H), 1.57 (qd, J=12.4, 4.1 Hz, 2H). Mass (m/z): 477.3 [M+H]$^+$.

N-(4-((2-fluoro-6-methyl-4-(4-methylpiperidin-1-yl) phenyl)amino)benzyl)-5-oxopyrrolidine-3-carboxamide (438)

438

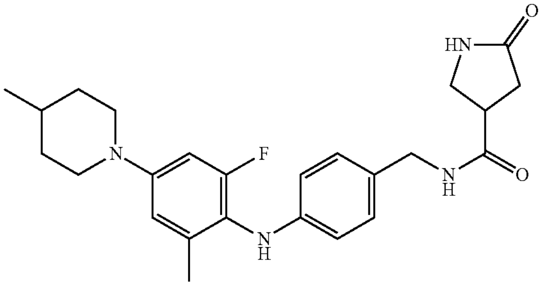

The title compound 438 (5.9 mg) was prepared in a total yield of 4.0% as a white solid from N-(4-bromobenzyl)-5-oxopyrrolidine-3-carboxamide (99 mg, 0.33 mmol), 2-fluoro-6-methyl-4-(4-methylpiperidin-1-yl)aniline (95 mg, 0.43 mmol), $Pd_2(dba)_3$ (3.0 mg, 3.3 umol), X-Phos (7.9 mg, 16.5 umol), $Cs_2CO_3$ (163 mg, 0.50 mmol) according to the procedure for 427. $^1$H NMR (400 MHz, DMSO-$d_6$) δ 8.30 (t, J=5.6 Hz, 11H), 7.56 (s, 11H), 7.10 (s, 11H), 7.00-6.91 (m, 2H), 6.67 (d, J=2.9 Hz, 1H), 6.63 (dd, J=13.5, 2.7 Hz, 1H), 6.43-6.35 (m, 2H), 4.10 (d, J=5.6 Hz, 2H), 3.73-3.61 (m, 2H), 3.38 (t, J=8.9 Hz, 11H), 3.24-3.14 (m, 2H), 2.69-2.62 (m, 2H), 2.30-2.22 (m, 2H), 2.10 (s, 3H), 1.71-1.65 (m, 2H), 1.54-1.47 (m, 1H), 1.25-1.18 (m, 2H), 0.94 (d, J=6.5 Hz, 3H). Mass (m/z): 439.4 [M+H]$^+$.

4-(methylamino)-N-(4-((4-(4-(trifluoromethyl)piperidin-1-yl)phenyl)amino)benzyl)butanamide (439)

439

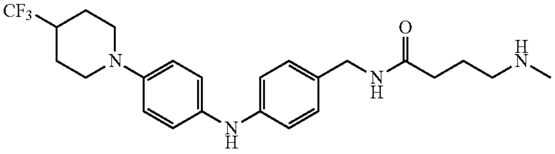

The title compound 439 (4.0 mg) was prepared in a total yield of 31.5% as a gray solid from tert-butyl methyl(4-oxo-4-((4-((4-(4-(trifluoromethyl)piperidin-1-yl)phenyl)amino) benzyl)amino)butyl)carbamate (15.6 mg, 2.8 umol), HCl in 1,4-dioxane (3.0 mL) according to the procedure for 363-4. $^1$H NMR (400 MHz, DMSO-$d_6$) δ 8.59 (s, 2H), 8.34 (s, 1H), 7.80 (s, 1H), 7.10-6.79 (m, 8H), 4.21-4.08 (m, 2H), 3.67-3.55 (m, 2H), 2.90-2.83 (m, 2H), 2.65-2.58 (m, 1H), 2.54 (t, J=4.6 Hz, 2H), 2.23 (t, J=7.2 Hz, 2H), 1.92-1.77 (m, 4H), 1.63-1.49 (m, 2H). Mass (m/z): 449.3 [M+H]$^+$.

5-oxo-N-(4-((4-(pentan-3-yl)phenyl)amino)benzyl) pyrrolidine-3-carboxamide (440)

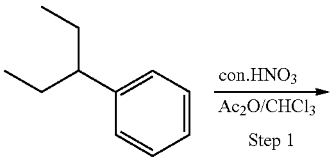

440-1

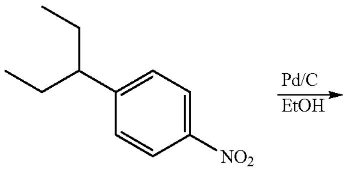

440-2

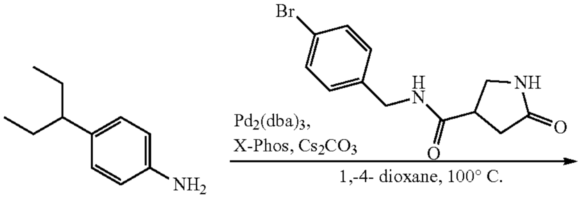

440-3

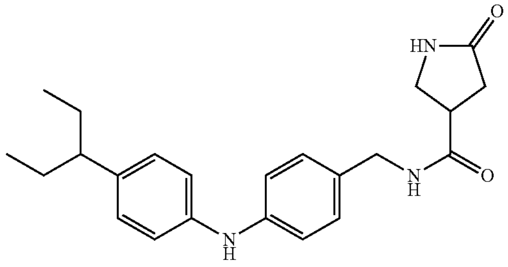

440

Step 1. 1-nitro-4-(pentan-3-yl)benzene (440-2). To a stirred solution of pentan-3-ylbenzene (444 mg, 3.0 mol) in acetic anhydride (2.0 mL) and $CHCl_3$ (5.0 mL) at −5° C. was added con. $HNO_3$ (0.3 mL) slowly. The reaction was maintained at 0° C. for 1 hour and then room temperature for 18 hours. Water (10 mL) was added. The reaction was extracted with EtOAc (3×10 mL), dried over $Na_2SO_4$ and concentrated in vacuum. The residue was purified by prep-TLC (DCM/PE=1/10) to afford the title compound (482 mg, 83.2%).

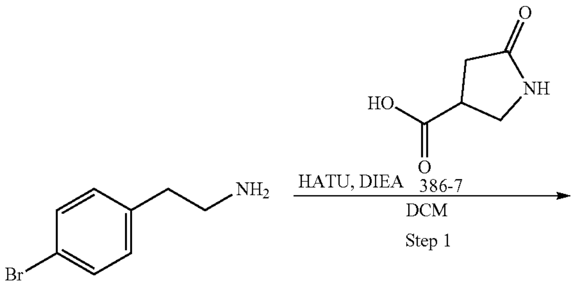

442-1

Step 2. Preparation of 4-(pentan-3-yl)aniline (440-3). The title compound 440-3 (390 mg) was prepared in a total yield of 72.5% as a purple solid from 1-nitro-4-(pentan-3-yl) benzene (578 mg, 2 mmol) in EtOH (20 mL) and 10/u Pd/C (22 mg, 0.02 mmol) according to the procedure for 386-4. Mass (m/z): 164.2 $[M+H]^+$.

Step 3. Preparation of 5-oxo-N-(4-((4-(pentan-3-yl)phenyl)amino)benzyl)pyrrolidine-3-carboxamide (440). The title compound 440 (29.5 mg) was prepared in a total yield of 23.4% as a light-yellow solid from N-(4-bromobenzyl)-5-oxopyrrolidine-3-carboxamide (99 mg, 0.33 mmol), 4-(pentan-3-yl)aniline (70 mg, 0.43 mmol), $Pd_2(dba)_3$ (3.0 mg, 3.3 umol), X-Phos (7.9 mg, 16.5 umol), $Cs_2CO_3$ (163 mg, 0.50 mmol) according to the procedure for 427. $^1H$ NMR (400 MHz, DMSO-$d_6$) δ 8.39 (t, J=5.8 Hz, 1H), 8.00 (s, 11H), 7.58 (s, 11H), 7.11-7.06 (m, 2H), 7.04-6.95 (m, 6H), 4.18 (d, J=5.7 Hz, 2H), 3.40 (t, J=8.7 Hz, 1H), 3.26-3.11 (m, 2H), 2.31 (td, J=8.9, 4.4 Hz, 2H), 2.20 (dt, J=9.6, 5.1 Hz, 1H), 1.68-1.55 (m, 2H), 1.51-1.40 (m, 2H), 0.72 (t, J=7.3 Hz, 6H). Mass (m/z): 439.4 $[M+H]^+$.

N-(4-((4-cyclopentylphenyl)amino)benzyl)-5-oxopyrrolidine-3-carboxamide (441)

441

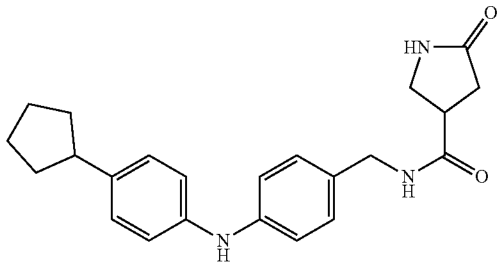

The title compound 441 (20.5 mg) was prepared in a total yield of 27.2% as a white solid from 4-(aminomethyl)-N-(4-cyclopentylphenyl)aniline hydrochloride (60 mg, 0.2 mmol), 5-oxopyrrolidine-3-carboxylic acid (31 mg, 0.24 mmol), DIEA (77.4 mg, 0.6 mmol) and HATU (91.2 mg, 0.24 mmol) according to the procedure for 413. $^1H$ NMR (400 MHz, DMSO-$d_6$) δ 8.39 (t, J=5.8 Hz, 1H), 8.00 (s, 1H), 7.58 (s, 1H), 7.13-7.06 (m, 4H), 7.00-6.93 (m, 4H), 4.17 (d, J=5.7 Hz, 2H), 3.40 (t, J=8.9 Hz, 1H), 3.26-3.14 (m, 2H), 2.90-2.80 (m, 1H), 2.33-2.25 (m, 2H), 2.02-1.92 (m, 2H), 1.79-1.69 (m, 2H), 1.67-1.57 (m, 2H), 1.53-1.41 (m, 2H). Mass (m/z): 378.3 $[M+H]^+$.

N-(4-((4-(4,4-dimethylcyclohexyl)phenyl)amino) phenethyl)-5-oxopyrrolidine-3-carboxamide (442)

-continued

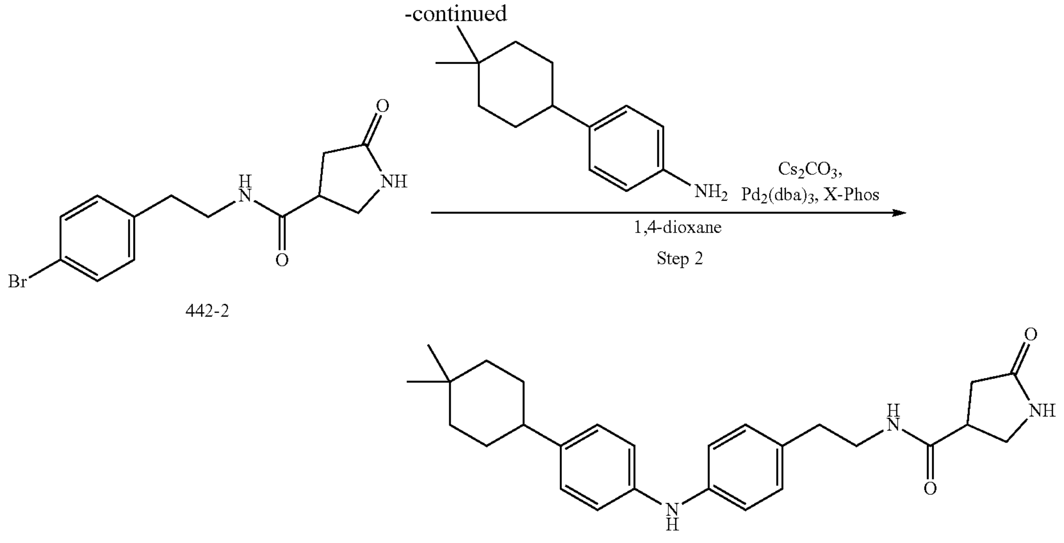

442-2

442

Step 1. Preparation of N-(4-bromophenethyl)-5-oxopyrrolidine-3-carboxamide (442-2). To a solution of 1-ethyl-5-oxopyrrolidine-3-carboxylic acid (568 mg, 4.4 mmol) in DCM (20 ml) was added HATU (1.67 mg, 4.4 mmol). Then the reaction mixture was stirred for 1 hour at rt. 2-(4-bromophenyl)ethan-1-amine (800 mg, 4.0 mmol) and DIEA (1.55 mg, 12.0 mmol) were added. Then the reaction mixture was stirred for 3 hours at rt. 5 mL of water was added. Then the mixture was extracted by DCM (5 mL×3). The precipitates were collected by filtrated to afford the desired product as a white solid (1.14 g, 91.9%). Mass (m/z): 311.1 $[M+H]^+$.

Step 2. Preparation of N-(4-((4-(4,4-dimethylcyclohexyl)phenyl)amino)phenethyl)-5-oxopyrrolidine-3-carboxamide (442). The title compound 442 (14.0 mg) was prepared in a total yield of 12.9% as a white solid from N-(4-bromophenethyl)-5-oxopyrrolidine-3-carboxamide (78 mg, 0.25 mmol), 4-(4,4-dimethylcyclohexyl)aniline (61 mg, 0.3 mmol), $Pd_2(dba)_3$ (2.3 mg, 2.5 umol), X-Phos (6.0 mg, 12.5 umol), $Cs_2CO_3$ (122 mg, 0.40 mmol) according to the procedure for 427. $^1H$ NMR (400 MHz, DMSO-$d_6$) δ 8.05 (t, J=5.6 Hz, 1H), 7.92 (s, 1H), 7.56 (s, 1H), 7.11-7.07 (m, 2H), 7.04-7.01 (m, 2H), 6.98-6.92 (m, 4H), 3.38-3.35 (m, 1H), 3.27-3.10 (m, 4H), 2.61 (t, J=7.3 Hz, 2H), 2.46 (s, 1H), 2.34-2.21 (m, 4H), 1.62-1.50 (m, 4H), 1.47-1.39 (m, 2H), 1.34-1.24 (m, 2H), 0.95 (d, J=10.1 Hz, 6H). Mass (m/z): 434.3 $[M+H]^+$.

N-(4-((2-fluoro-6-(4-(trifluoromethyl)piperidin-1-yl)pyridin-3-yl)amino)benzyl)-2-oxoimidazolidine-4-carboxamide (443)

443

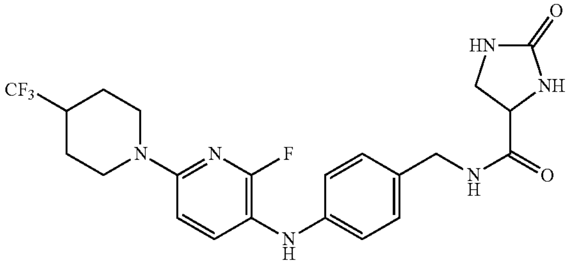

The title compound 443 (4.8 mg) was prepared in a total yield of 8.3% as a light white solid from N-(4-(aminomethyl)phenyl)-2-fluoro-6-(4-(trifluoromethyl)piperidin-1-yl)pyridin-3-amine hydrochloride (50 mg, 0.12 mmol), 2-oxoimidazolidine-4-carboxylic acid (18.6 mg, 0.14 mmol), DIEA (46.0 mg, 0.36 mmol) and HATU (55.0 mg, 0.14 mmol) according to the procedure for 397. $^1H$ NMR (400 MHz, DMSO-$d_6$) δ 8.25 (t, J=5.9 Hz, 1H), 7.55 (dd, J=10.7, 8.5 Hz, 1H), 7.46 (s, 1H), 7.06-7.01 (m, 2H), 6.73 (dd, J=7.9, 1.5 Hz, 1H), 6.64-6.59 (m, 2H), 6.55-6.49 (m, 1H), 6.31 (s, 1H), 4.28-4.20 (m, 2H), 4.18-4.11 (m, 2H), 4.08 (dd, J=9.7, 6.2 Hz, 1H), 3.55 (d, J=9.3 Hz, 1H), 3.20 (dd, J=8.9, 6.2 Hz, 1H), 2.84 (td, J=12.8, 2.1 Hz, 2H), 2.64-2.58 (m, 11H), 1.92-1.81 (m, 2H), 1.43 (qd, J=13.0, 12.2, 3.5 Hz, 2H). Mass (m/z): 481.3 $[M+H]^+$.

N-(4-((2-(4-isopropylpiperidin-1-yl)pyrimidin-5-yl)amino)benzyl)-5-oxopyrrolidine-3-carboxamide (444)

444

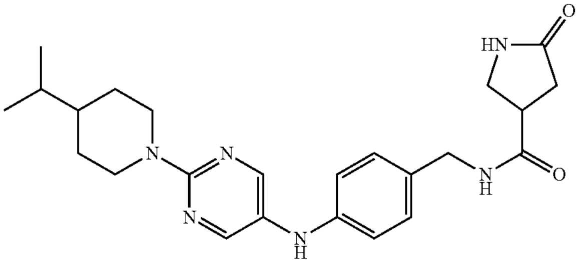

The title compound 444 (40.0 mg) was prepared in a total yield of 36.7% as a white solid from N-(4-bromobenzyl)-5-oxopyrrolidine-3-carboxamide (74 mg, 0.25 mmol), 2-(4-isopropylpiperidin-1-yl)pyrimidin-5-amine (73 mg, 0.33 mmol), $Pd_2(dba)_3$ (2.3 mg, 2.5 umol), X-Phos (6.0 mg, 12.5 umol), $Cs_2CO_3$ (122 mg, 0.38 mmol) according to the procedure for 427.

$^1H$ NMR (400 MHz, DMSO-$d_6$) δ 8.37 (t, J=5.8 Hz, 1H), 8.21 (s, 2H), 7.62 (s, 1H), 7.58 (s, 1H), 7.06-7.00 (m, 2H), 6.74-6.68 (m, 2H), 4.67-4.59 (m, 2H), 4.13 (d, J=5.7 Hz, 2H), 3.39 (t, J=8.6 Hz, 1H), 3.25-3.11 (m, 2H), 2.75 (td, J=12.8, 2.5 Hz, 2H), 2.32-2.20 (m, 2H), 1.73-1.62 (m, 2H), 1.47-1.36 (m, 1H), 1.31-1.22 (m, 1H), 1.10 (qd, J=12.4, 4.1 Hz, 2H), 0.87 (d, J=6.7 Hz, 6H). Mass (m/z): 437.4 $[M+H]^+$.

N-(4-((2-(4-ethylpiperidin-1-yl)pyrimidin-5-yl)amino)benzyl)-5-oxopyrrolidine-3-carboxamide (445)

445

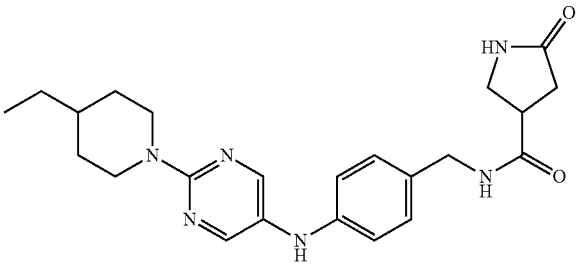

The title compound 445 (23.2 mg) was prepared in a total yield of 22.0% as a light yellow solid from N-(4-bromobenzyl)-5-oxopyrrolidine-3-carboxamide (74 mg, 0.25 mmol), 2-(4-ethylpiperidin-1-yl)pyrimidin-5-amine (68 mg, 0.33 mmol), $Pd_2(dba)_3$ (2.3 mg, 2.5 umol), X-Phos (6.0 mg, 12.5 umol), $Cs_2CO_3$ (122 mg, 0.38 mmol) according to the procedure for 427. $^1H$ NMR (400 MHz, DMSO-$d_6$) δ 8.35 (t, J=5.8 Hz, 1H), 8.21 (s, 2H), 7.61 (s, 1H), 7.58 (s, 1H), 7.06-6.98 (m, 2H), 6.76-6.67 (m, 2H), 4.64-4.54 (m, 2H), 4.13 (d, J=5.7 Hz, 2H), 3.42-3.36 (m, 1H), 3.24-3.13 (m, 2H), 2.81 (td, J=12.8, 2.7 Hz, 2H), 2.32-2.22 (m, 2H), 1.75-1.69 (m, 2H), 1.40 (s, 1H), 1.25 (p, J=7.3 Hz, 2H), 1.08-0.99 (m, 2H), 0.89 (t, J=7.4 Hz, 3H). Mass (m/z): 423.4 $[M+H]^+$.

N-(4-((4-methyl-2-(4-(trifluoromethyl)piperidin-1-yl)pyrimidin-5-yl)amino)benzyl)-5-oxopyrrolidine-3-carboxamide (446)

446

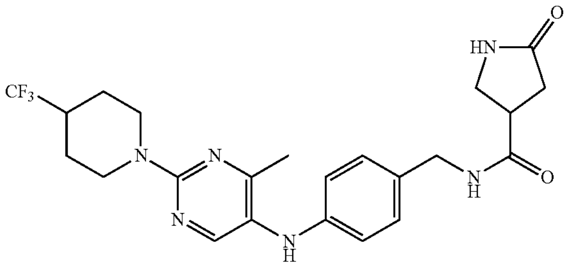

The title compound 446 (4.1 mg) was prepared in a total yield of 15.1% as a white powder from N-(4-(aminomethyl)phenyl)-4-methyl-2-(4-(trifluoromethyl)piperidin-1-yl)pyrimidin-5-amino (21 mg, 57 umol), 5-oxopyrrolidine-3-carboxylic acid (8.9 mg, 69 umol), DIEA (22.0 mg, 0.17 mmol) and HATU (26 mg, 69 umol) according to the procedure for 413.

$^1H$ NMR (400 MHz, DMSO-$d_6$) δ 8.33 (t, J=5.6 Hz, 11H), 8.09 (s, 1H), 7.57 (s, 1H), 7.29 (s, 11H), 7.03-6.96 (m, 2H), 6.52-6.46 (m, 2H), 4.80-4.68 (m, 2H), 4.12 (d, J=5.7 Hz, 2H), 3.43-3.36 (m, 1H), 3.23-3.12 (m, 2H), 2.92-2.84 (m, 2H), 2.65-2.56 (m, 1H), 2.32-2.26 (m, 2H), 2.18 (s, 3H), 1.92-1.83 (m, 2H), 1.38 (qd, J=12.6, 4.3 Hz, 2H). Mass (m/z): 477.3 $[M+H]^+$.

N-(3-(4-((4-(4,4-dimethylcyclohexyl)phenyl)amino)phenyl)propyl)-5-oxopyrrolidine-3-carboxamide (447)

447

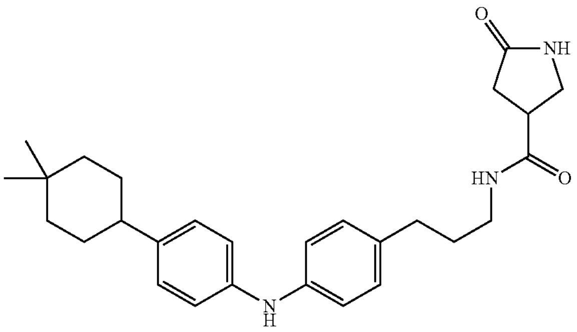

The title compound 447 (6.8 mg) was prepared in a total yield of 16.3% as a white solid from N-(3-(4-bromophenyl)propyl)-5-oxopyrrolidine-3-carboxamide (32.4 mg, 0.1 mmol), 4-(4,4-dimethylcyclohexyl)aniline (24.5 mg, 0.12 mmol), $Pd_2$(dba); (1.8 mg, 2 umol), X-Phos (4.8 mg, 10 umol), $Cs_2CO_3$ (99 mg, 0.3 mmol) according to the procedure for 442. $^1H$ NMR (400 MHz, DMSO-$d_6$) δ 8.01 (t, J=5.5 Hz, 1H), 7.90 (s, 1H), 7.57 (s, 1H), 7.11-7.06 (m, 2H), 7.06-7.00 (m, 2H), 6.98-6.91 (m, 4H), 3.41-3.37 (m, 1H), 3.23-3.04 (m, 4H), 2.49-2.44 (m, 2H), 2.35-2.23 (m, 3H), 1.68-1.39 (m, 8H), 1.33-1.21 (m, 2H), 0.95 (d, J=10.1 Hz, 6H). Mass (m/z): 448.4 $[M+H]^+$.

N-(4-((3-(4-methoxybutoxy)-4-(4-(trifluoromethyl)piperidin-1-yl)phenyl)amino)benzyl)-5-oxopyrrolidine-3-carboxamide (448)

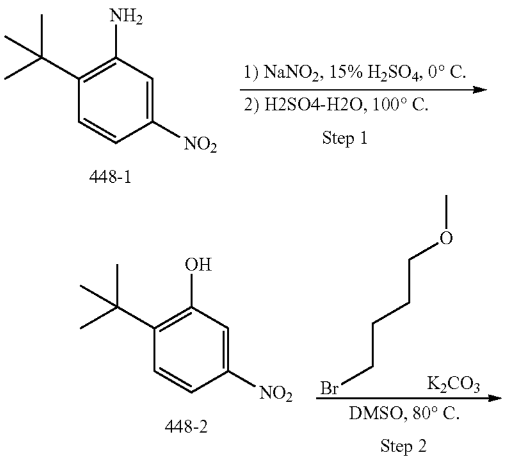

-continued

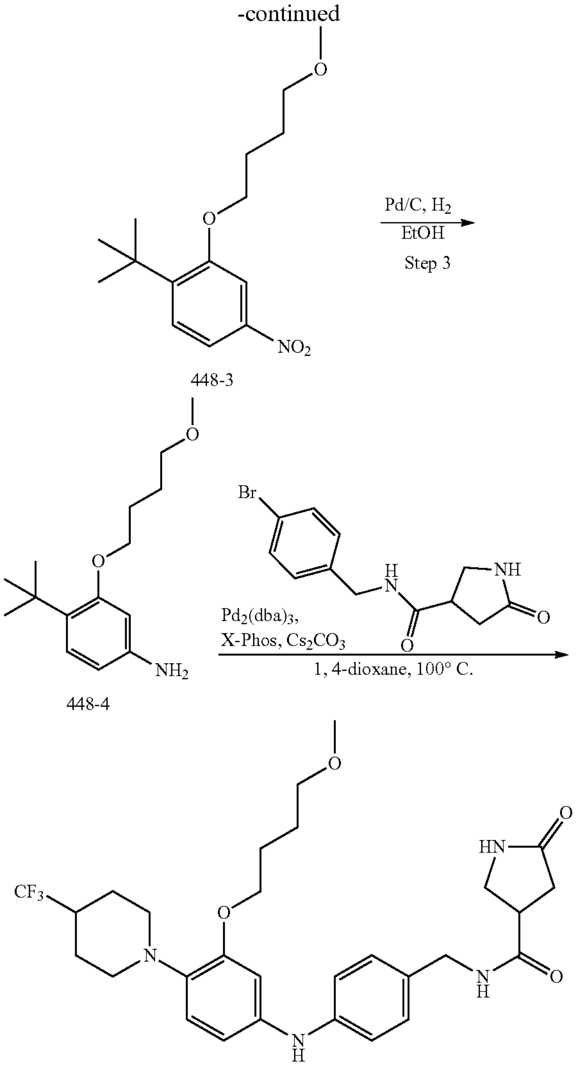

448-3

448-4

448

Step 1. Preparation of 2-(tert-butyl)-5-nitrophenol (448-2). To a mixture of 2-tert-butyl-5-nitroaniline (582 g, 3.0 mmol) in 10 mL of 15% $H_2SO_4$ was added dropwise a solution of $NaNO_2$ (217 mg, 3.15 mmol) in water (3 mL) at 0° C. The resulting mixture was stirred at 0-5° C. for 20 min. Then the solution was added dropwise to a solution of 5 mL of $H_2SO_4$—$H_2O$ (V/V=1/2) stirred at 100° C. The resulting mixture was stirred at 100° C. for 20 min. After cooling to rt, and extracted by DCM (20 mL×3). The combined organic layers were washed with water (20 mL), dried over $Na_2SO_4$ and concentrated. The residue was purified by prep-TLC (DCM/PE=1/3) to afford the title compound as a yellow oil (300 mg, 51.5%).

Mass (m/z): 194.0 $[M-H]^+$.

Step 2. Preparation of 1-(tert-butyl)-2-(4-methoxybutoxy)-4-nitrobenzene (448-3). To a mixture of 2-(tert-butyl)-5-nitrophenol (150 mg, 0.77 mmol). KI (12.8 mg, 77 ummol) and $K_2CO_3$ (212 mg, 1.54 mmol) in DMSO (2.0 mL) was added 1-bromo-4-methoxybutane (190 mg, 1.15 mmol). Then the mixture was stirred overnight at 80° C. After cooling to rt, 5 mL was added, and extracted by DCM (10 mL×3). The combined organic layers were washed with water (10 mL×3), dried over $Na_2SO_4$ and concentrated to afford the title compound as a crude as a yellow oil (216 mg, 100%).

Step 3. Preparation of 4-(tert-butyl)-3-(4-methoxybutoxy)aniline (448-4). The title compound 448-4 (193 mg) was prepared in a total yield of 100% as a Yellow solid from 1-(tert-butyl)-2-(4-methoxybutoxy)-4-nitrobenzene (216 mg, 0.77 mmol) and 10% Pd/C (81.6 mg, 77 umol) according to the procedure for 386-4. Mass (m/z): 252.4 $[M+H]^+$.

Step 4. Preparation of N-(4-((3-(4-methoxybutoxy)-4-(4-(trifluoromethyl)piperidin-1-yl)phenyl)amino)benzyl)-5-oxopyrrolidine-3-carboxamide (448). The title compound 448 (9.2 mg) was prepared in a total yield of 8.2% as a white solid from N-(4-bromobenzyl)-5-oxopyrrolidine-3-carboxamide (59.2 mg, 0.2 mmol), 4-(tert-butyl)-3-(4-methoxybutoxy)aniline (83 mg, 0.24 mmol), $Pd_2(dba)$; (1.8 mg, 2 umol), X-Phos (4.8 mg, 10 umol), $Cs_2CO_3$ (99 mg, 0.3 mmol) according to the procedure for 442. $^1H$ NMR (400 MHz, DMSO-$d_6$) δ 8.43 (s, 1H), 7.60 (s, 1H), 7.22-6.92 (m, 5H), 6.73-6.60 (m, 2H), 4.19 (d, J=4.8 Hz, 2H), 4.02-3.96 (m, 2H), 3.85-3.67 (m, 4H), 3.56-3.45 (m, 2H), 3.41-3.36 (m, 3H), 3.29-3.17 (m, 5H), 2.62-2.54 (m, 1H), 2.33-2.28 (m, 2H), 2.08-1.93 (m, 2H), 1.86-1.79 (m, 2H), 1.72-1.64 (m, 2H).

N-(4-((2-(4-isopropylpiperidin-1-yl)-4-methylpyrimidin-5-yl)amino)benzyl)-5-oxopyrrolidine-3-carboxamide (449)

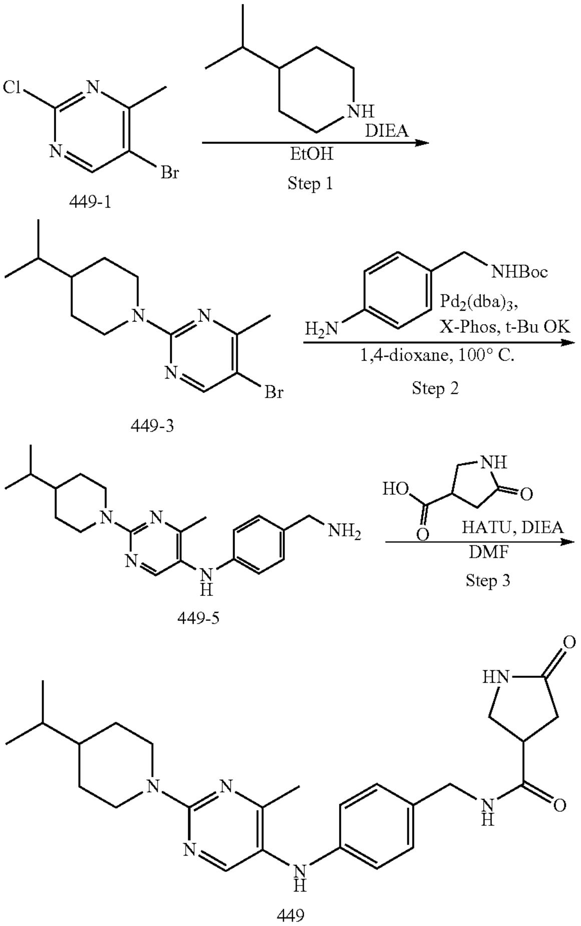

449-1

449-3

449-5

449

Step 1. Preparation of 5-bromo-2-(4-isopropylpiperidin-1-yl)-4-methylpyrimidine (449-3). A solution of 4-isopropylpiperidine (254 mg, 2.0 mmol), 5-bromo-2-chloro-4-methylpyrimidine (414 mg, 2.0 mmol) and DIEA (774 mg, 6.0 mmol) in EtOH (10 mL) was stirred for 18 hours at 100° C. After cooling to rt. 20 mL of water was added. The precipitates were collected by filtrated to afford the desired product as a white solid (414 mg, 69.5%).

Mass (m/z): 298.1 $[M+H]^+$.

Step 2. Preparation of N-(4-(aminomethyl)phenyl)-2-(4-isopropylpiperidin-1-yl)-4-methylpyrimidin-5-amine (449-5). The title compound 449-5 (16.3 mg) was prepared in a total yield of 14.4% as yellow solid from 5-bromo-2-(4-isopropylpiperidin-1-yl)-4-methylpyrimidine (100 mg, 0.33 mmol), tert-butyl (4-aminobenzyl)carbamate (111 mg, 0.50 mmol), $Pd_2(dba)_3$ (3.0 mg, 3.3 umol), X-Phos (7.9 mg, 16.5 umol), t-BuOK (56 mg, 0.50 mmol) according to the procedure for 427. Mass (m/z): 340.3 $[M+H]^+$.

Step 3. Preparation of N-(4-((2-(4-isopropylpiperidin-1-yl)-4-methylpyrimidin-5-yl)amino)benzyl)-5-oxopyrrolidine-3-carboxamide (449) The title compound 449 (3.4 mg) was prepared in a total yield of 15.2% as a gray solid from N-(4-(aminomethyl)phenyl)-2-(4-isopropylpiperidin-1-yl)-4-methylpyrimidin-5-amine (16.3 mg, 0.05 mmol), 5-oxopyrrolidine-3-carboxylic acid (7.8 mg, 0.06 mmol), DIEA (19.4 mg, 0.15 mmol) and HATU (20.9 mg, 0.06 mmol) according to the procedure for 413. $^1H$ NMR (400 MHz, DMSO-$d_6$) δ 8.30 (t, J=5.7 Hz, 1H), 8.01 (s, 1H), 7.54 (s, 1H), 7.22 (s, 1H), 6.97-6.93 (m, 2H), 6.46-6.40 (m, 2H), 4.70-4.64 (m, 2H), 4.08 (d, J=5.7 Hz, 2H), 3.37-3.33 (m, 1H), 3.20-3.09 (m, 2H), 2.75-2.67 (m, 2H), 2.27-2.20 (m, 2H), 2.12 (s, 3H), 1.69-1.63 (m, 2H), 1.44-1.36 (m, 1H), 1.24 (d, J=6.1 Hz, 1H), 1.14-0.99 (m, 2H), 0.84 (d, J=6.8 Hz, 6H). Mass (m/z): 451.1 [M+H]1.

5-oxo-N-(4-((5-(4-(trifluoromethyl)piperidin-1-yl) pyrimidin-2-yl)amino)benzyl)pyrrolidine-3-carboxamide (450)

450

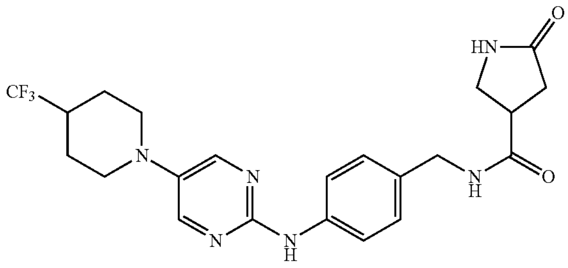

The title compound 450 (10.2 mg) was prepared in a total yield of 12.3% as a white powder from N-(4-(aminomethyl) phenyl)-5-(4-(trifluoromethyl)piperidin-1-yl)pyrimidin-2-amine (53.7 mg, 0.15 mmol), 5-oxopyrrolidine-3-carboxylic acid (23.2 mg, 0.18 mmol), DIEA (58 mg, 0.45 mmol) and HATU (57 mg, 0.15 mmol) according to the procedure for 413. $^1H$ NMR (400 MHz, DMSO-$d_6$) δ 8.33 (t, J=5.8 Hz, 1H), 8.22 (s, 2H), 7.65 (s, 1H), 7.54 (s, 1H), 7.03-6.98 (m, 2H), 6.73-6.69 (m, 2H), 4.69-4.61 (m, 2H), 4.10 (d, J=5.8 Hz, 2H), 3.35 (t, J=8.7 Hz, 1H), 3.20-3.09 (m, 2H), 2.85 (td, J=12.9, 2.6 Hz, 2H), 2.61-2.55 (m, 1H), 2.25 (dd, J=8.4, 3.4 Hz, 2H), 1.88-1.77 (m, 2H), 1.39-1.28 (m, 2H). Mass (m/z): 463.3 $[M+H]^+$.

N-(4-((2-ethyl-6-(4-methylpiperidin-1-yl)pyridin-3-yl)amino)benzyl)-5-oxopyrrolidine-3-carboxamide (451)

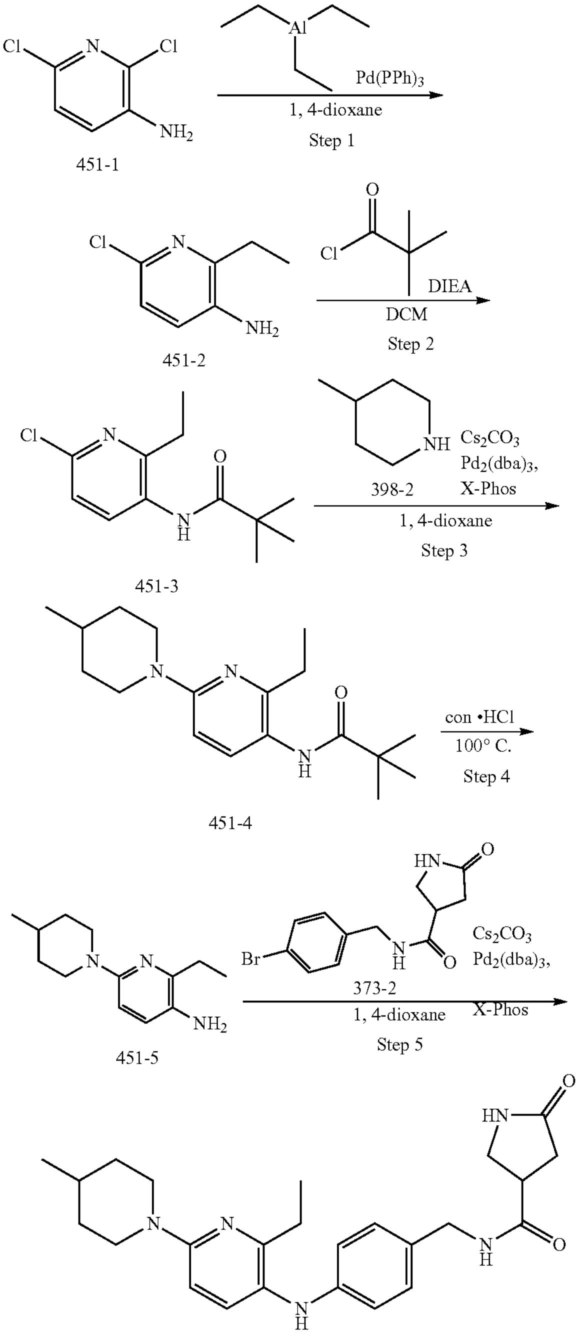

451

Step 1. Preparation of 6-chloro-2-ethylpyridin-3-amine (451-2). To a solution of 2,6-dichloropyridin-3-amine (1.63 g, 10 mmol) in 1,4-dioxane (25 ml) was added tetrakis (triphenylphosphine)palladium(0) (231 mg, 0.2 mmol) and triethylaluminum (2.2 mL, 2M in hexane, 10.4 mmol) at room temperature, and the mixture was stirred for 3 hours at 100° C. The mixture was quenched with 2 M HCl aqueous solution after cooling, and then it was separated between the aqueous and organic phases. The aqueous phase was extracted with EtOAc. The combined organic phases were dried over magnesium sulfate and concentrated. The crude product was purified by silica gel column chromatography, eluding with hexane/EtOAc (2:1), to give the title compound (25 mg, 16.0%). 157.3 $[M+H]^+$.

Step 2. Preparation of N-(6-chloro-2-ethylpyridin-3-yl) pivalamide (451-3). To a solution of 6-chloro-2-ethylpyridin-3-amine (250 mg, 1.59 mmol) and DIEA (410 mg, 3.18 mmol) in DCM (20 mL) was added dropwise pivaloyl chloride (289 mg, 2.39 mmol) at 0° C. Then the mixture was stirred overnight at rt. The solution was washed with $H_2O$ (3×20 mL) and brine (20 mL). The organic layer was dried ($Na_2SO_4$) and concentrated in vacuo. The residue was purified by flash chromatography on silica gel (0-10% EtOAc/hexane) to give desired product as a Light-yellow oil. (300 mg, 78.9%). Mass (m/z): 241.2 $[M+H]^+$.

Step 3. Preparation of N-(2-ethyl-6-(4-methylpiperidin-1-yl)pyridin-3-yl)pivalamide (451-4). The title compound 451-4 (330 mg) was prepared in a total yield of 87.3% as a yellow solid from N-(6-chloro-2-ethylpyridin-3-yl)pivalamide (300 mg, 1.25 mmol), 4-methylpiperidine (186 mg, 1.9 mmol), $Pd_2(dba)_3$ (11.4 mg, 12.5 umol), X-Phos (29.8 mg, 62.5 mmol), $Cs_2CO_3$ (611 mg, 1.08 mmol) according to the procedure for 394-3.

Step 4. Preparation of 2-ethyl-6-(4-methylpiperidin-1-yl) pyridin-3-amine (451-5). In a pressure tube, a solution of N-(2-ethyl-6-(4-methylpiperidin-1-yl)pyridin-3-yl)pivalamide (330 mg, 1.09 mmol) in 10 mL of con·HCl was stirred overnight at 100'C. Then the solution was concentrated. 10 ml water was added. The PH of the filtration was adjusted to 8-9 with sodium carbonate solution. Then the mixture was extracted by DCM (10 mL×3). The combined organic layers were washed with water (15 mL), dried over $Na_2SO_4$ and concentrated. The residue was purified by perp-TLC (EA/PE=1/2) to afford the desired product as a yellow solid. (230 mg, 98.2%). Mass (m/z): 220.3 $[M+H]^+$.

Step 5. Preparation of N-(4-((2-ethyl-6-(4-methylpiperidin-1-yl)pyridin-3-yl)amino)benzyl)-5-oxopyrrolidine-3-carboxamide (451). The title compound 451 (15.5 mg) was prepared in a total yield of 10.7% as a white solid from N-(4-bromobenzyl)-5-oxopyrrolidine-3-carboxamide (97 mg, 0.33 mmol), 2-ethyl-6-(4-methylpiperidin-1-yl)pyridin-3-amine (87 mg, 0.4 mmol), $Pd_2(dba)_3$ (3.0 mg, 3.3 umol), X-Phos (7.9 mg, 16.5 umol), $Cs_2CO_3$ (163 mg, 0.50 mmol) according to the procedure for 404. $^1H$ NMR (400 MHz, DMSO-$d_6$) δ 8.33 (t, J=5.7 Hz, 1H), 7.57 (s, 1H), 7.33 (s, 1H), 7.07 (s, 1H), 7.01-6.91 (m, 2H), 6.64 (s, 1H), 6.52-6.46 (m, 2H), 4.28-4.20 (m, 2H), 4.11 (d, J=5.7 Hz, 2H), 3.41-3.35 (m, 2H), 3.25-3.14 (m, 2H), 2.78-2.67 (m, 2H), 2.58-2.53 (m, 2H), 2.28 (dd, J=8.4, 5.2 Hz, 2H), 1.71-1.63 (m, 2H), 1.61-1.51 (m, 1H), 1.17-1.07 (m, 5H), 0.93 (d, J=6.5 Hz, 3H). Mass (m/z): 436.4 $[M+H]^+$.

5-oxo-N-(4-((2-propoxypyrimidin-5-yl)amino)benzyl)pyrrolidine-3-carboxamide (452)

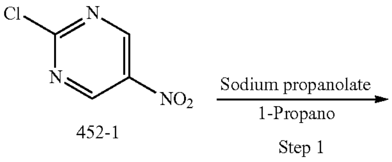

452-1

-continued

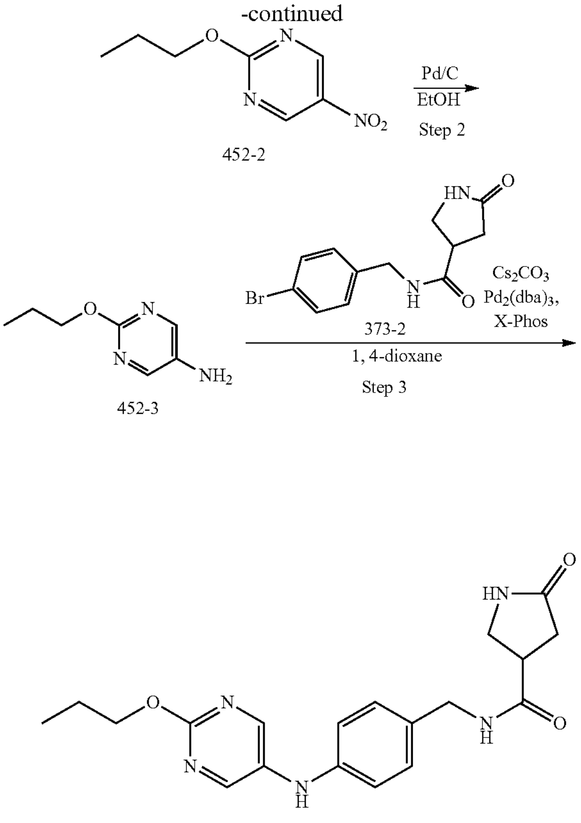

452-2

373-2

452-3

452

Step 1. Preparation of 5-nitro-2-propoxypyrimidine (452-2). To a solution of 2-chloro-5-nitropyrimidine (474 mg, 3 mmol) in 1-Propano (10 mL) was added Sodium propanolate (492 mg, 6 mmol). Then the mixture was stirred for 2 hours at 80'C. After cooling to rt. 15 ml of water was added. Then the mixture was extracted by DCM (15 mL×3). The combined organic layers were washed with water (20 mL×3), dried over $Na_2SO4$ and concentrated under vacuum. The residue was purified by prep-TLC (EA/PE=1/10) to give the desired product as yellow solid (80 mg, 14.6%). Mass (m/z): 184.1 $[M+H]^+$ Step 2. Preparation of 2-propoxypyrimidin-5-amine (452-3). The title compound 452-3 (60 mg) was prepared in a total yield of 92.3% as a Yellow solid from 5-nitro-2-propoxypyrimidine (80 mg, 0.43 mmol) and 10% Pd/C (4.6 mg, 4.3 umol) according to the procedure for 386-4. Mass (m/z): 154.1 $[M+H]^+$.

Step 3. Preparation of 5-oxo-N-(4-((2-propoxypyrimidin-5-yl)amino)benzyl)pyrrolidine-3-carboxamide (452). The title compound 452 (23.3 mg) was prepared in a total yield of 17.5% as a white solid from N-(4-bromobenzyl)-5-oxopyrrolidine-3-carboxamide (107 mg, 0.36 mmol), 2-propoxypyrimidin-5-amine (60 mg, 0.4 mmol), $Pd_2(dba)_3$ (3.3 mg, 3.6 umol), X-Phos (8.6 mg, 18 umol), $Cs_2CO_3$ (176 mg, 0.54 mmol) according to the procedure for 442. $^1H$ NMR (400 MHz, DMSO-$d_6$) δ 8.43 (s, 1H), 7.60 (s, 1H), 7.22-6.92 (m, 5H), 6.73-6.60 (m, 2H), 4.19 (d, J=4.8 Hz, 2H), 4.02-3.96 (m, 2H), 3.85-3.67 (m, 4H), 3.56-3.45 (m, 2H), 3.41-3.36 (m, 3H), 3.29-3.17 (m, 5H), 2.62-2.54 (m, 1H), 2.33-2.28 (m, 2H), 2.08-1.93 (m, 2H), 1.86-1.79 (m, 2H), 1.72-1.64 (m, 2H). Mass (m/z): 370.2 $[M+H]^+$.

5-oxo-N-(4-((4-(4-(trifluoromethyl)piperidin-1-yl)phenyl)amino)phenethyl)pyrrolidine-3-carboxamide (453)

453

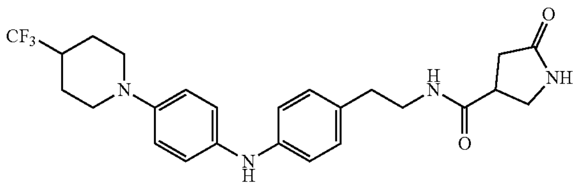

The title compound 453 (17.5 mg) was prepared in a total yield of 18.5% as a white solid from N-(4-bromophenethyl)-5-oxopyrrolidine-3-carboxamide (62 mg, 0.2 mmol), 4-(4-(trifluoromethyl)piperidin-1-yl)aniline (63 mg, 0.26 mmol), $Pd_2(dba)_3$ (1.8 mg, 2.0 umol), X-Phos (4.8 mg, 10 umol), $Cs_2CO_3$ (98 mg, 0.3 mmol) according to the procedure for 442. $^1H$ NMR (400 MHz, DMSO-$d_6$) δ 7.98 (t, J=5.6 Hz, 1H), 7.66 (s, 1H), 7.51 (s, 1H), 6.97-6.90 (m, 4H), 6.87-6.80 (m, 4H), 3.60-3.54 (m, 2H), 3.34-3.29 (m, 1H), 3.21-3.13 (m, 3H), 3.10-3.03 (m, 1H), 2.56 (td, J=7.6, 6.7, 3.4 Hz, 4H), 2.42-2.33 (m, 11H), 2.21 (dd, J=8.5, 3.1 Hz, 2H), 1.88-1.81 (m, 2H), 1.54 (qd, J=12.4, 4.0 Hz, 2H). Mass (m/z): 475.2 $[M+H]^+$.

5-oxo-N-(3-(4-((4-(4-(trifluoromethyl)piperidin-1-yl)phenyl)amino)phenyl)propyl)pyrrolidine-3-carboxamide (454)

447

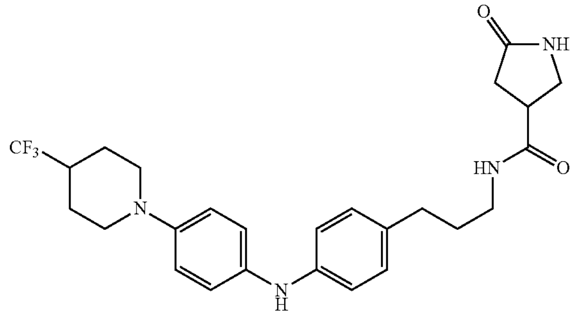

The title compound 454 (8.8 mg) was prepared in a total yield of 10.6% as a white solid from N-(3-(4-bromophenyl)propyl)-5-oxopyrrolidine-3-carboxamide (50 mg, 0.15 mmol), 4-(4-(trifluoromethyl)piperidin-1-yl)aniline (41.1 mg, 0.17 mmol), $Pd_2(dba)_3$ (1.8 mg, 2.0 umol), X-Phos (4.8 mg, 10 umol), $Cs_2CO_3$ (83 mg, 0.26 mmol) according to the procedure for 442. $^1H$ NMR (400 MHz, DMSO-$d_6$) δ 7.95 (t, J=5.6 Hz, 1H), 7.65 (s, 1H), 7.53 (s, 1H), 6.97-6.89 (m, 4H), 6.86-6.80 (m, 4H), 3.60-3.53 (m, 2H), 3.35 (t, J=8.7 Hz, 1H), 3.20-3.15 (m, 1H), 3.11-2.99 (m, 3H), 2.62-2.54 (m, 3H), 2.44-2.37 (m, 4H), 2.26-2.21 (m, 2H), 1.88-1.82 (m, 2H), 1.65-1.46 (m, 4H). Mass (m/z): 489.2 $[M+H]^+$.

N-(3-(4-((2-(4-isopropylpiperidin-1-yl)pyrimidin-5-yl)amino)phenyl)propyl)-5-oxopyrrolidine-3-carboxamide (455)

455

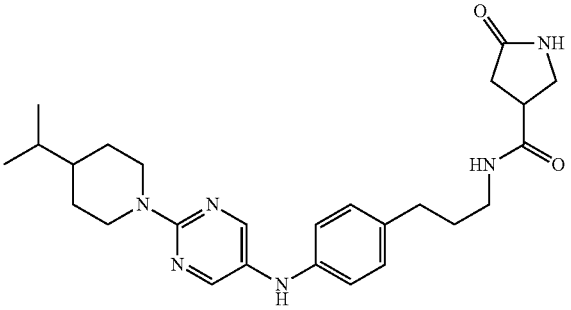

The title compound 455 (7.8 mg) was prepared in a total yield of 9.9% as a white solid from N-(3-(4-bromophenyl)propyl)-5-oxopyrrolidine-3-carboxamide (50 mg, 0.15 mmol), 2-(4-isopropylpiperidin-1-yl)pyrimidin-5-amine (37.4 mg, 0.17 mmol), $Pd_2(dba)_3$ (1.8 mg, 2.0 umol), X-Phos (4.8 mg, 10 umol), $Cs_2CO_3$ (83 mg, 0.26 mmol) according to the procedure for 442. $^1H$ NMR (400 MHz, DMSO-$d_6$) δ 7.95 (t, J=5.6 Hz, 1H), 7.65 (s, 1H), 7.53 (s, 1H), 6.97-6.89 (m, 4H), 6.86-6.80 (m, 4H), 3.60-3.53 (m, 2H), 3.35 (t, J=8.7 Hz, 1H), 3.20-3.15 (m, 1H), 3.11-2.99 (m, 3H), 2.62-2.54 (m, 3H), 2.44-2.37 (m, 4H), 2.26-2.21 (m, 2H), 1.88-1.82 (m, 2H), 1.65-1.46 (m, 4H). Mass (m/z): 465.2 $[M+H]^+$.

N-(4-((6-(4-(2-methoxypropan-2-yl)piperidin-1-yl)-2-methylpyridin-3-yl)amino)benzyl)-5-oxopyrrolidine-3-carboxamide (456)

456

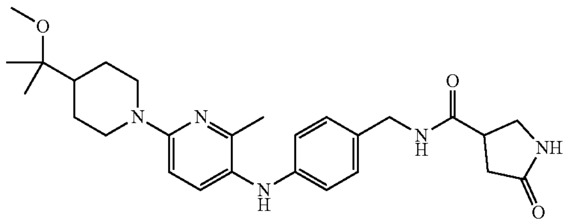

The title compound 456 (22.0 mg) was prepared in a total yield of 18.3% as a light yellow solid from N-(4-bromobenzyl)-5-oxopyrrolidine-3-carboxamide (74 mg, 0.25 mmol), 6-(4-(2-methoxypropan-2-yl)piperidin-1-yl)-2-methylpyridin-3-amine (87 mg, 0.33 mmol), $Pd_2(dba)_3$ (2.3 mg, 2.5 umol), X-Phos (6.0 mg, 12.5 umol), $Cs_2CO_3$ (122 mg, 0.38 mmol) according to the procedure for 427. $^1H$ NMR (400 MHz, DMSO-$d_6$) δ 8.27 (t, J=5.7 Hz, 1H), 7.52 (s, 1H), 7.21 (d, J=8.7 Hz, 1H), 7.14 (s, 1H), 6.97-6.90 (m, 2H), 6.59 (d, J=8.8 Hz, 1H), 6.49-6.44 (m, 2H), 4.32-4.23 (m, 2H), 4.08 (d, J=5.6 Hz, 2H), 3.39-3.31 (m, 1H), 3.23-3.10 (m, 2H), 3.06 (s, 3H), 2.62-2.54 (m, 2H), 2.24 (dd, J=8.4, 5.2 Hz, 2H), 2.16 (s, 3H), 1.69-1.62 (m, 2H), 1.60-1.52 (m, 2H), 1.20 (td, J=12.9, 4.3 Hz, 2H), 1.02 (s, 6H). Mass (m/z): 480.3 $[M+H]^+$.

N-(4-((3-fluoro-2-methyl-4-(4-(trifluoromethyl)piperidin-1-yl)phenyl)amino)benzyl)-2-oxoimidazolidine-4-carboxamide (457)

457

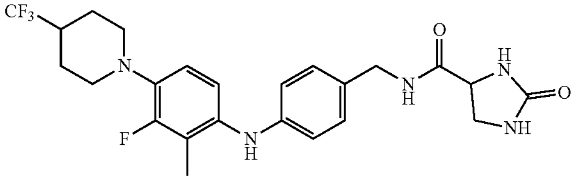

The title compound 457 (31.0 mg) was prepared in a total yield of 31.4% as a light blue solid from N-(4-(aminomethyl)phenyl)-3-fluoro-2-methyl-4-(4-(trifluoromethyl)piperidin-1-yl)aniline hydrochloride (81.4 mg, 0.2 mmol), 2-oxoimidazolidine-4-carboxylic acid (52 mg, 0.4 mmol), DIEA (77.4 mg, 0.6 mmol) and HATU (91.2 mg, 0.24 mmol) according to the procedure for 413. $^1$H NMR (400 MHz, DMSO-$d_6$) δ 826 (t, J=5.8 Hz, 1H), 7.40 (s, 1H), 7.05 (d, J=8.5 Hz, 2H), 6.90-6.80 (m, 2H), 6.75-6.68 (m, 2H), 6.53 (s, 1H), 6.30 (s, 1H), 4.16 (s, 2H), 4.11-4.04 (m, 2H), 3.57-3.49 (m, 1H), 3.35 (s, 2H), 3.24-3.17 (m, 2H), 2.71-2.63 (m, 2H), 2.45 (s, 1H), 2.05 (d, J=2.7 Hz, 3H), 1.93-1.87 (m, 2H), 1.61 (qd, J=12.3, 4.1 Hz, 2H). Mass (m/z): 494.2 $[M+H]^+$.

1-ethyl-5-oxo-N-(4-((4-(piperidin-1-yl)phenyl)amino)benzyl)pyrrolidine-3-carboxamide (458)

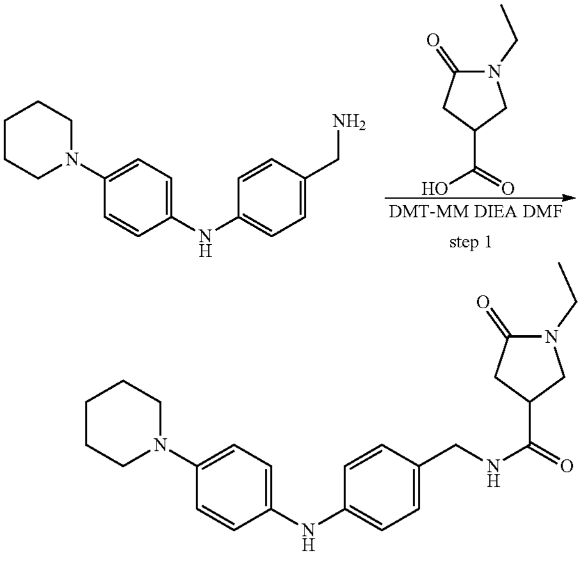

458

Step 1. Preparation of 1-ethyl-5-oxo-N-(4-((4-(piperidin-1-yl)phenyl)amino)benzyl)pyrrolidine-3-carboxamide (458). To a solution of 1-ethyl-5-oxopyrrolidine-3-carboxylic acid (39 mg, 0.25 mmol) and DMT-MM (69 mg, 0.25 mmol) in super dry N,N-dimethylfromamide (5 mL), 4-(aminomethyl)-N-(4-(piperidin-1-yl)phenyl)aniline (70 mmL, 0.25 mmol) and N-ethyl-N-isopropylpropan-2-amine (75 mg, 0.75 mmol) was added, The resulting solution was stirred for overnight at room temperature. The reaction mixture was added into water (15 mL) drop by drop with stirring. The precipitate was filtered, cake was wash with water 3 times and dry in vacuo. The residue was purified by perp-TLC to give desired product 458 (36.2 mg) as pale blue powder a yield of 34.60%. $^1$H NMR (400 MHz, DMSO-$d_6$) δ 10.89 (s, 1H), 8.49 (t, J=6.0 Hz, 1H), 7.47 (s, 2H), 7.12 (dd, J=28.8, 10.1 Hz, 6H), 4.21 (s, 3H), 3.51 (t, J=9.2 Hz, 4H), 3.37 (dd, J=9.5, 6.3 Hz, 11H), 3.25-3.06 (m, 3H), 2.41 (dd, J=8.5, 4.0 Hz, 2H), 1.87 (s, 4H), 1.54 (s, 2H), 1.00 (t, J=7.2 Hz, 3H). Mass (m/z): 421.4 $[M+H]^+$.

1-ethyl-5-oxo-N-(4-((4-(pyrrolidin-1-yl)phenyl)amino)benzyl)pyrrolidine-3-carboxamide (459)

459

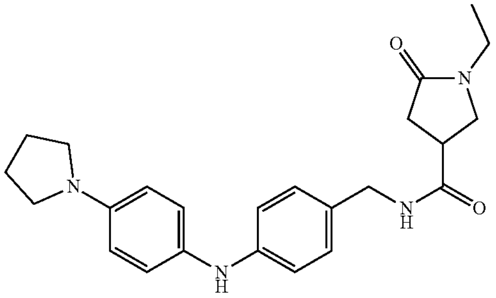

The title compound 459 (30.0 mg) was prepared in a yield of 28.19% as a pale blue powder from 4-(aminomethyl)-N-(4-(pyrrolidin-1-yl)phenyl)aniline (70 mg, 0.26 mmol) and 1-ethyl-5-oxopyrrolidine-3-carboxylic acid (41 mg, 0.26 mmol) according to the procedure for 458. $^1$H NMR (400 MHz, DMSO-$d_6$) δ 8.42 (s, 1H), 7.56-6.45 (m, 7H), 4.79 (s, 3H), 3.51 (t, J=9.2 Hz, 1H), 3.36 (dd, J=9.5, 6.3 Hz, 2H), 3.19 (qd, J=7.3, 1.6 Hz, 4H), 3.16-3.07 (m, 2H), 2.41 (dd, J=8.5, 1.7 Hz, 2H), 2.25-1.82 (br, 3H), 1.00 (t, J=7.2 Hz, 3H). Mass (m/z): 407.3 $[M+H]^+$.

N-(4-((4-(4-methylpiperidin-1-yl)phenyl)amino)benzyl)-5-oxopyrrolidine-3-carboxamide (460)

460

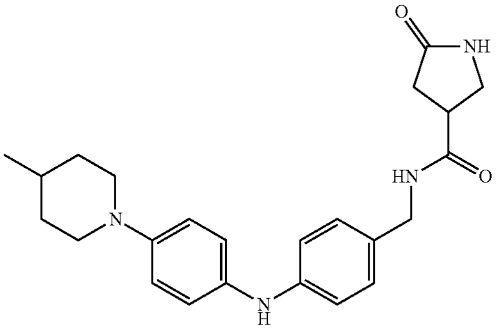

The title compound 460 (25.7 mg) was prepared in a yield of 19.66% as a pale light gray powder from 4-(aminomethyl)-N-(4-(4-methylpiperidin-1-yl)phenyl)aniline (95 mg, 0.32 mmol) and 5-oxopyrrolidine-3-carboxylic acid (46 mg, 0.35 mmol) according to the procedure for 458.1H NMR (400 MHz, DMSO-d6) δ 8.37 (s, 1H), 7.58 (s, 1H), 7.34-6.45 (m, 6H), 4.16 (s, 2H), 3.64-3.36 (m, 4H), 3.20 (ddt, J=23.6, 15.6, 7.2 Hz, 2H), 2.29 (dd, J=8.4, 4.3 Hz, 2H), 1.69 (s, 2H), 1.44 (s, 2H), 1.19 (d, J=35.5 Hz, 2H), 0.94 (d, J=6.1 Hz, 3H). Mass (m/z): 407.3 $[M+H]^+$.

1-ethyl-N-(4-((4-(4-hydroxy-4-(trifluoromethyl)piperidin-1-yl)phenyl)amino)benzyl)-5-oxopyrrolidine-3-carboxamide (461)

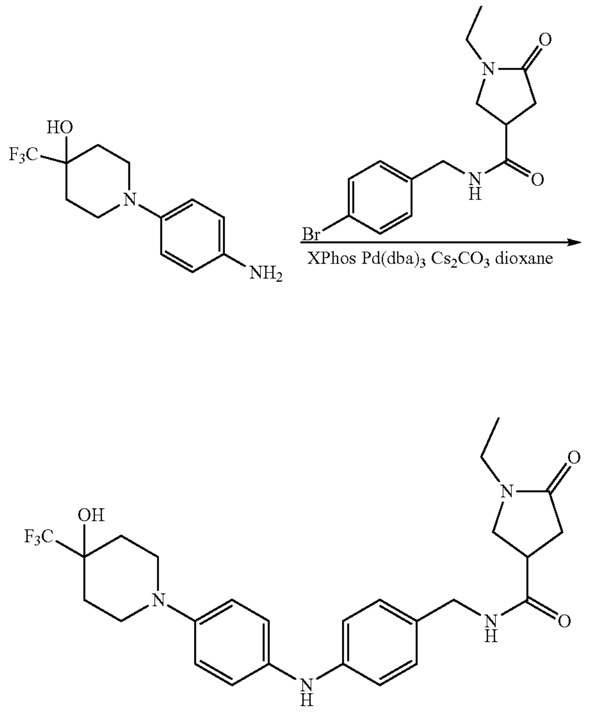

461

To a solution of 1-(4-aminophenyl)-4-(trifluoromethyl)piperidin-4-ol (50 mg, 0.15 mmol, 1.0 equivs) and N-(4-bromobenzyl)-1-ethyl-5-oxopyrrolidine-3-carboxamide (40 mg, 0.15 mmol, 1.0 equivs) in super dry 1,4-dioxane (5 mL) was added dicyclohexyl(2',4',6'-triisopropyl-[1,1'-biphenyl]-2-yl)phosphane (7.12 mg, 0.012 mmol, 0.08 equivs) and Tris(Dibenzylidenacetone)palladium (O) (4.5 mg, 0.006 mmol, 0.04 equivs) and cesium carbonate (75 mg, 0.23 mmol, 1.5 equivs) respectively under argon atmosphere. The resulting mixture was heated to 110° C. and stirred for overnight at the same temperature. The reaction was diluted with water (20 mL) and extracted with ethyl acetate (5 mL) 3 times. The organic layer was combined and washed with water, sat·$NaHCO_3$(aq), and brine respectively. Then dried over $MgSO_4$, filtered, and the filtrate concentrated under reduced pressure. The residue was purified by perp-TLC to give desired product 461 (9.5 mg) as pale floralwhite powder a yield of 12.25%.

$^1$H NMR (400 MHz, DMSO-$d_6$) δ 8.35 (t, J=6.2 Hz, 1H), 7.77 (s, 1H), 7.11 (d, J=8.3 Hz, 2H), 7.01-6.93 (m, 2H), 6.93-6.83 (m, 4H), 5.93 (s, 1H), 5.76 (s, 1H), 4.35 (d, J=5.9 Hz, 2H), 3.82 (d, J=10.3 Hz, 6H), 3.44 (d, J=12.1 Hz, 2H), 2.86 (td, J=12.2, 2.9 Hz, 2H), 1.77 (ddd, J=23.5, 15.3, 12.3 Hz, 4H). Mass (m/z): 505.3 $[M+H]^+$.

N-(4-((2-(4-isopropylpiperidin-1-yl)pyrimidin-5-yl)amino)-2-methylbenzyl)-5-oxopyrrolidine-3-carboxamide (462)

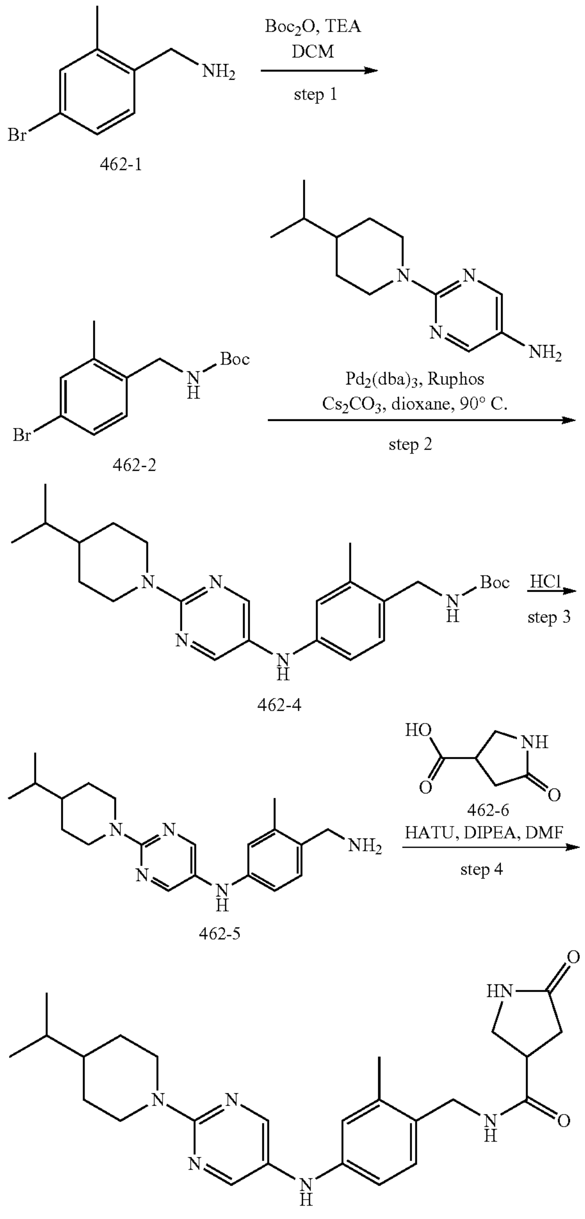

462

Step 1. Preparation of tert-butyl (4-bromo-2-methylbenzyl)carbamate. To a solution of compound 462-1 (600 mg, 3.00 mmol) in DCM (20 mL) was added $Boc_2O$ (982 mg, 4.50 mmol) and TEA (607 mg, 6.00 mmol) at 25° C. Then the mixture was stirred at room temperature overnight. The mixture was poured into $H_2O$ and extracted with DCM (50 mL*3), the organic layer was washed with brine, dried over $Na_2SO_4$, filtered and concentrated, the residue was purified by silica gel chromatography with EA/PE (20:1) to give tert-butyl (4-bromo-2-methylbenzyl)carbamate 462-2 (745 mg, 83% yield) as a yellow oil. MS (ESI) m/z 322.0, 324.1 $[M+H]^+$.

Step 2. Preparation of tert-butyl (4-((2-(4-isopropylpiperidin-1-yl)pyrimidin-5-yl)amino)-2-methylbenzyl)carbamate. To a mixture solution of compound 462-2 (300 mg, 1.00 mmol), compound 462-3 (220 mg, 1.00 mmol) and dicyclohexyl (2',6'-diisopropoxybiphenyl-2-yl)phosphine (93 mg, 0.20 mmol) in dioxane (15 mL) under nitrogen was added $Cs_2CO_3$ (488 mg, 1.50 mmol) and tris(dibenzylideneacetone)dipalladium (92 mg, 0.10 mmol). The reaction mixture was stirred at 90° C. for 16 hrs. Then the mixture was filtered and concentrated. The residue was purified by pre-TLC to afford to give tert-butyl (4-((2-(4-isopropylpiperidin-1-yl)pyrimidin-5-yl)amino)-2-methylbenzyl)carbamate 462-4 (283 mg, 64% yield) as a yellow solid. MS (ESI) m/z 440.1 $[M+H]^+$.

Step 3. Preparation of N-(4-(aminomethyl)-3-methylphenyl)-2-(4-isopropylpiperidin-1-yl)pyrimidin-5-amine. To a solution of compound 462-4 (283 mg, 0.64 mmol) in DCM (5 mL) was added 4 N HCl in dioxane (5 mL) at room temperature. Then the mixture was stirred at room temperature rt for overnight. LCMS showed the reaction was completed. The mixture was filtered and dried to give N-(4-(aminomethyl)-3-methylphenyl)-2-(4-isopropylpiperidin-1-yl)pyrimidin-5-amine 462-5 (165 mg, 76% yield) as a brown solid. MS (ESI) m/z 340.2 [M+H]t.

Step 4. Preparation of N-(4-((2-(4-isopropylpiperidin-1-yl)pyrimidin-5-yl)amino)-2-methylbenzyl)-5-oxopyrrolidine-3-carboxamide (462). To a stirred solution of compound 462-5 (165 mg, 0.49 mmol), 5-oxopyrrolidine-3-carboxylic acid 462-6 (63 mg, 0.49 mmol) in DMF (5 mL) under nitrogen was added N,N,N',N'-Tetramethyl-O-(7-azabenzotriazol-1-yl)uronium (222 mg, 0.58 mmol) and DIEA (94 mg, 0.73 mmol). The reaction mixture was stirred at room temperature for 16 hrs. The mixture was poured into $H_2O$ (10 m L) and extracted with EA (20 mL*3), the organic layer was washed with brine, dried over $Na_2SO_4$, filtered and concentrated, the residue was purified by prep-H PLC to give 462 (10 mg) as a white solid. MS (ESI) m/z 451.3 $[M+H]^+$. H NMR (400 MHz, $CD_3OD$) δ 8.28 (s, 2H), 7.12 (d, J=8.1 Hz, 1H), 6.83-6.71 (m, 2H), 4.55 (d, J=12.7 Hz, 2H), 4.38-4.24 (m, 2H), 3.57 (dd, J=9.8, 8.9 Hz, 1H), 3.49 (dd, J=9.9, 6.4 Hz, 1H), 3.13-2.97 (m, 2H), 2.61-2.46 (m, 2H), 2.27 (s, 3H), 1.86 (d, J=13.0 Hz, 2H), 1.55-1.45 (m, 1H), 1.46-1.24 (m, 5H), 0.94 (d, J=6.7 Hz, 6H).

2-ethyl-5-oxo-N-(4-((4-(4-(trifluoromethyl)piperidin-1-yl)phenyl)amino)benzyl)pyrrolidine-3-carboxamide (463)

463

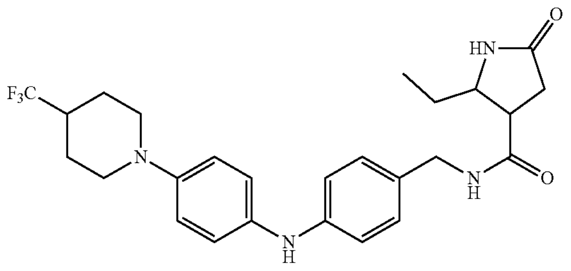

The title compound 463 (6.5 mg) was prepared in a yield of 4.65% as a pale gray powder from 4-(aminomethyl)-N-(4-(4-(trifluoromethyl)piperidin-1-yl)phenyl)aniline (100 mg, 0.29 mmol) and 2-ethyl-5-oxopyrrolidine-3-carboxylic acid (49 mg, 0.31 mmol) according to the procedure for 458. $^1H$ NMR (400 MHz, DMSO-d6) δ 8.47 (s, 1H), 7.84 (s, 1H), 7.35-6.84 (m, 7H), 4.18 (s, 2H), 3.72 (s, 1H), 3.49 (q, J=6.0 Hz, 2H), 2.81-2.68 (m, 1H), 2.40-2.21 (m, 3H), 2.04 (d, J=26.4 Hz, 2H), 1.76 (s, 2H), 1.53-1.36 (m, 2H), 1.25 (dd, J=10.7, 4.6 Hz, 2H), 0.85 (t, J=7.4 Hz, 3H). Mass (m/z): 489.4 $[M+H]^+$.

1-ethyl-N-(4-((2-methyl-4-(4-(trifluoromethyl)piperidin-1-yl)phenyl)amino)benzyl)-5-oxopyrrolidine-3-carboxamide (464)

464

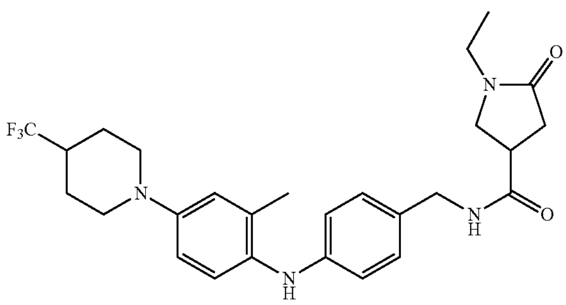

The title compound 464 (31.1 mg) was prepared in a yield of 31.97% as a white powder from 2-methyl-4-(4-(trifluoromethyl)piperidin-1-yl)aniline (50 mg, 0.19 mmol) and N-(4-bromobenzyl)-1-ethyl-5-oxopyrrolidine-3-carboxamide (63 mg, 0.19 mmol) according to the procedure for 461. $^1H$ NMR (400 MHz, DMSO-$d_6$) δ 8.30 (t, J=6.3 Hz, 1H), 7.14 (s, 1H), 7.09-7.02 (m, 2H), 6.97 (d, J=8.6 Hz, 1H), 6.84 (d, J=2.8 Hz, 1H), 6.74 (dd, J=8.7, 2.9 Hz, 1H), 6.63-6.54 (m, 2H), 4.32 (d, J=6.1 Hz, 2H), 3.81 (d, J=10.9 Hz, 6H), 3.76-3.59 (m, 2H), 3.30 (s, 3H), 2.70-2.58 (m, 2H), 2.49-2.37 (m, 2H), 2.11 (s, 3H), 1.88 (d, J=12.6 Hz, 2H), 1.56 (qd, J=12.5, 4.1 Hz, 2H). Mass (m/z): 503.3 $[M+H]^+$.

1-ethyl-N-(4-((2-methoxy-4-(4-(trifluoromethyl)piperidin-1-yl)phenyl)amino)benzyl)-5-oxopyrrolidine-3-carboxamide (465)

465

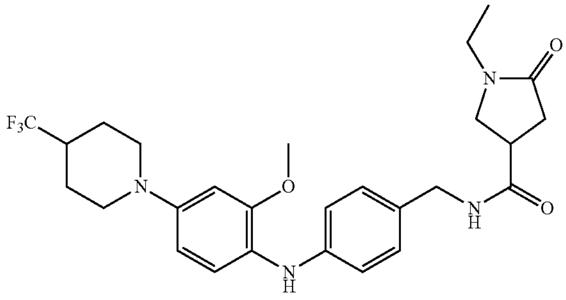

The title compound 465 (29.5 mg) was prepared in a yield of 31.2% as a white powder from 2-methoxy-4-(4-(trifluoromethyl)piperidin-1-yl)aniline (50 mg, 0.18 mmol) and N-(4-bromobenzyl)-1-ethyl-5-oxopyrrolidine-3-carboxamide (59 mg, 0.18 mmol) according to the procedure for 461. $^1H$ NMR (400 MHz, DMSO-$d_6$) δ 8.32 (t, J=6.3 Hz, 1H), 7.10-6.97 (m, 4H), 6.74 (dd, J=8.6, 1.9 Hz, 2H), 6.65 (d, J=2.6 Hz, 1H), 6.46 (dd, J=8.6, 2.6 Hz, 1H), 4.33 (d, J=5.8 Hz, 2H), 3.82 (d, J=10.7 Hz, 6H), 3.76 (s, 3H), 3.70 (d, J=12.3 Hz, 2H), 3.34-3.31 (m, 3H), 2.66 (td, J=12.3, 2.4 Hz, 2H), 2.44 (ddd, J=12.3, 8.4, 3.7 Hz, 2H), 1.95-1.83 (m, 2H), 1.58 (qd, J=12.5, 4.1 Hz, 2H). Mass (m/z): 519.3 $[M+H]^+$.

1-ethyl-2-oxo-N-(4-((4-(4-(trifluoromethyl)piperidin-1-yl)phenyl)amino)benzyl)pyrrolidine-3-carboxamide (466)

466

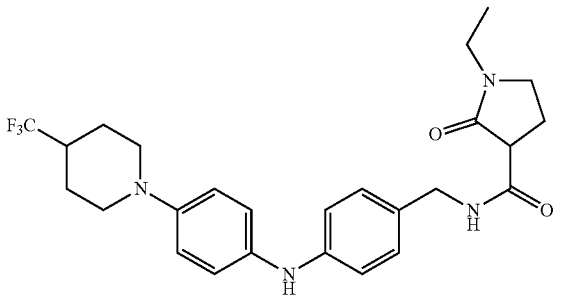

The title compound 466 (12.3 mg) was prepared in a yield of 17.6% as a white powder from 4-(aminomethyl)-N-(4-(4-(trifluoromethyl)piperidin-1-yl)phenyl)aniline (50 mg, 0.14 mmol) and 1-ethyl-2-oxopyrrolidine-3-carboxylic acid (27 mg, 0.17 mmol) according to the procedure for 458. $^1$H NMR (400 MHz, DMSO-$d_6$) δ 8.01-7.90 (m, 1H), 7.77 (s, 1H), 7.04 (d, J=8.4 Hz, 2H), 6.97 (d, J=8.9 Hz, 2H), 6.93-6.80 (m, 4H), 4.22-4.09 (m, 2H), 3.62 (d, J=12.3 Hz, 2H), 3.34 (s, 2H), 3.20-3.08 (m, 2H), 2.70-2.57 (m, 2H), 2.41 (td, J=8.6, 4.1 Hz, 1H), 1.89 (ddd, J=12.4, 7.5, 5.3 Hz, 3H), 1.81 (dd, J=13.8, 7.2 Hz, 1H), 1.69-1.48 (m, 3H), 0.80 (t, J=7.4 Hz, 3H). Mass (m/z): 489.3 $[M+H]^+$.

N-(4-((2-cyano-4-(4-(trifluoromethyl)piperidin-1-yl)phenyl)amino)benzyl)-1-ethyl-5-oxopyrrolidine-3-carboxamide (467)

467

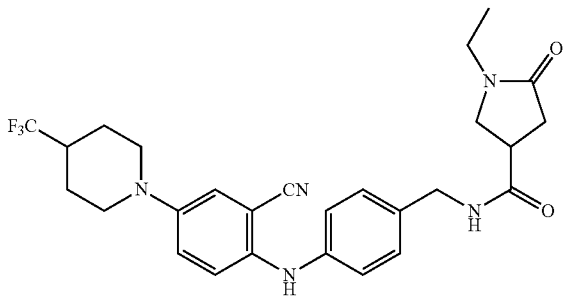

The title compound 467 (60.2 mg) was prepared in a yield of 63.13% as a white powder from 2-amino-5-(4-(trifluoromethyl)piperidin-1-yl)benzonitrile (50 mg, 0.18 mmol) and N-(4-bromobenzyl)-1-ethyl-5-oxopyrrolidine-3-carboxamide (60 mg, 0.18 mmol) according to the procedure for 461. $^1$H NMR (400 MHz, DMSO-$d_6$) δ 8.44 (t, J=5.8 Hz, 1H), 8.04 (s, 1H), 7.24 (d, J=8.2 Hz, 2H), 7.19-7.13 (m, 1H), 7.11-7.06 (m, 2H), 6.90-6.82 (m, 2H), 4.23-4.11 (m, 2H), 3.73 (d, J=12.2 Hz, 2H), 3.50 (4, J=9.2 Hz, 1H), 3.39-3.34 (m, 1H), 3.30 (s, 1H), 3.18 (qd, J=7.2, 1.6 Hz, 2H), 3.14-3.06 (m, 1H), 2.69 (td, J=12.4, 2.5 Hz, 2H), 2.43-2.36 (m, 2H), 1.91-1.80 (m, 2H), 1.54 (qd, J=12.6, 4.1 Hz, 2H), 1.00 (t, J=7.2 Hz, 3H). Mass (m/z): 514.3 $[M+H]^+$.

4-methyl-3-oxo-N-(4-((4-(4-(trifluoromethyl)piperidin-1-yl)phenyl)amino)benzyl)piperazine-1-carboxamide (468)

468

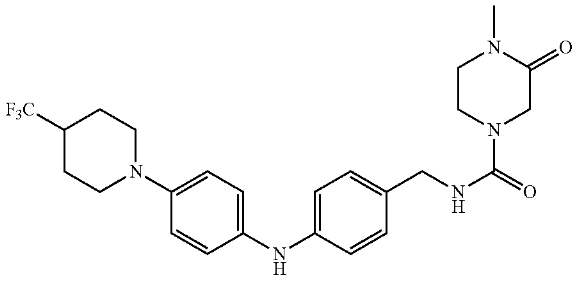

The title compound 468 (9.0 mg) was prepared in a yield of 7.09% as a light pink powder from 4-(aminomethyl)-N-(4-(4-(trifluoromethyl)piperidin-1-yl)phenyl)aniline (100 mg, 0.49 mmol) and 4-methyl-3-oxopiperazine-1-carboxylic acid (49 mg, 0.53 mmol) according to the procedure for 458. $^1$H NMR (400 MHz, Methanol-$d_4$) δ 7.16 (s, 3H), 6.93 (s, 5H), 4.48 (s, 2H), 3.60 (s, 1H), 3.54 (t, J=6.7 Hz, 2H), 2.66 (s, 2H), 2.33-2.20 (m, 2H), 2.15-2.07 (m, 2H), 1.97 (d, J=12.6 Hz, 2H), 1.72 (d, J=12.7 Hz, 2H), 1.52 (q, J=7.0 Hz, 2H), 1.49-1.37 (m, 1H), 0.97-0.83 (m, 3H). Mass (m/z): 489.3 $[M+H]^+$.

N-(4-((4-(4-(trifluoromethyl)piperidin-1-yl)phenyl)amino)benzyl)-2-ureidoacetamide (469)

469

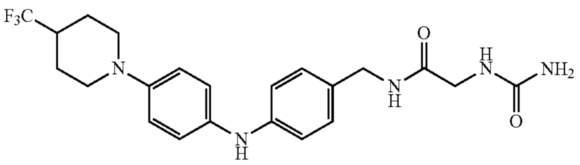

The title compound 469 (2.3 mg) was prepared in a yield of 3.58% as a pale gray powder from 4-(aminomethyl)-N-(4-(4-(trifluoromethyl)piperidin-1-yl)phenyl)aniline (50 mg, 0.14 mmol) and carbamoylglycine (18 mg, 0.15 mmol) according to the procedure for 458. $^1$H NMR (400 MHz, DMSO-$d_6$) δ 8.16 (t, J=5.9 Hz, 1H), 7.77 (s, 1H), 7.05 (d, J=8.4 Hz, 2H), 6.96 (d, J=8.9 Hz, 2H), 6.87 (t, J=8.6 Hz, 4H), 6.16 (s, 1H), 5.64 (s, 2H), 5.32 (t, J=4.8 Hz, 1H), 4.15 (d, J=5.9 Hz, 2H), 3.62 (d, J=5.7 Hz, 4H), 2.62 (t, J=11.9 Hz, 2H), 2.00 (q, J=7.0, 6.5 Hz, 1H), 1.88 (d, J=12.6 Hz, 2H), 1.63-1.54 (m, 2H). Mass (m/z): 450.2 $[M+H]^+$.

1-ethyl-N-(4-((2-fluoro-4-(4-(trifluoromethyl)piperidin-1-yl)phenyl)amino)benzyl)-5-oxopyrrolidine-3-carboxamide (470)

470

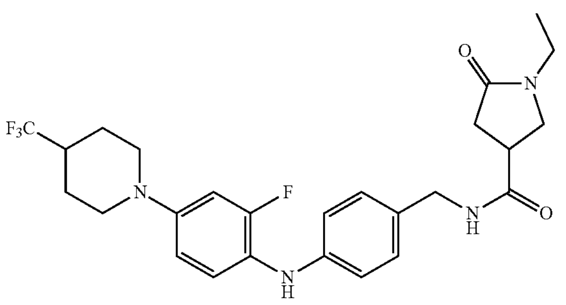

The title compound 470 (45.4 mg) was prepared in a yield of 46.60% as a pale gray powder from 2-fluoro-4-(4-(trifluoromethyl)piperidin-1-yl)aniline (50 mg, 0.19 mmol) and N-(4-bromobenzyl)-1-ethyl-5-oxopyrrolidine-3-carboxamide (68 mg, 0.21 mmol) according to the procedure for 461. $^1H$ NMR (400 MHz, DMSO-$d_6$) δ 8.39 (t, J=5.7 Hz, 1H), 7.50 (s, 1H), 7.09 (dd, J=9.8, 8.8 Hz, 1H), 7.05-6.99 (m, 2H), 6.85 (dd, J=14.3, 2.7 Hz, 1H), 6.76-6.71 (m, 1H), 6.71-6.66 (m, 2H), 4.14 (d, J=5.6 Hz, 2H), 3.73 (d, J=12.3 Hz, 2H), 3.49 (t, J=9.2 Hz, 1H), 3.38-3.33 (m, 2H), 3.18 (qd, J=7.2, 1.4 Hz, 2H), 3.13-3.04 (m, 1H), 2.68 (td, J=12.5, 2.6 Hz, 2H), 2.42-2.37 (m, 2H), 1.92-1.79 (m, 2H), 1.54 (qd, J=12.5, 4.2 Hz, 2H), 0.99 (t, J=7.2 Hz, 3H). Mass (m/z): 507.3 $[M+H]^+$.

N-(4-((3,5-difluoro-4-(piperidin-1-yl)phenyl)amino)benzyl)-3,5-dioxopiperazine-1-carboxamide (471)

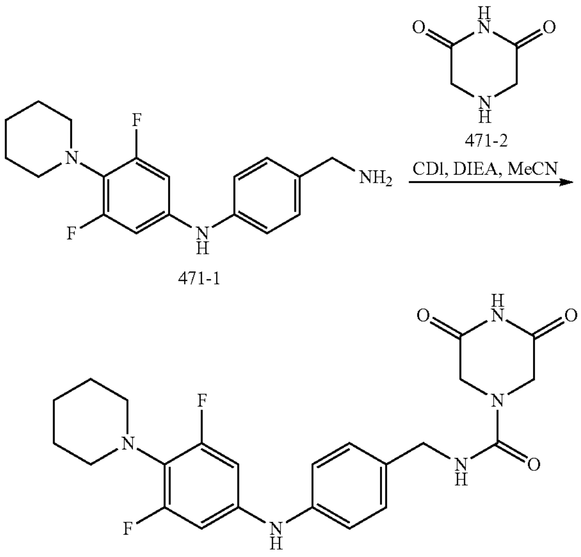

471

Preparation of N-(4-((3,5-difluoro-4-(piperidin-1-yl)phenyl)amino)benzyl)-3,5-dioxopiperazine-1-carboxamide (471). A mixture solution of N-(4-(aminomethyl)phenyl)-3,5-difluoro-4-(piperidin-1-yl)aniline (50 mg, 0.14 mmol), CDI (46 mg, 0.28 mmol) and TEA (43 mg, 0.42 mmol) in MeCN (10 mL) was stirred at rt for 2 hrs. Then piperazine-2,6-dione (19 mg, 0.17 mmol) was added into the mixture and stirred overnight at rt. The solvent was removed under vacuo, the residue was diluted with EA (20 mL), washed with water (10 mL×3), dried with $Na_2SO_4$, filtered and evaporated. The residue was purified by prep-HPLC to give 471 (6.3 mg, 11.96%). Mass (m/z): 457.7 $[M+H]^+$. $^1H$ NMR (400 MHz, $CD_3OD$) δ 7.20-7.16 (m, 2H), 7.03-6.98 (m, 2H), 6.52-6.44 (m, 2H), 4.27 (s, 2H), 3.28 (dt, J=3.3, 1.6 Hz, 4H), 3.02-2.96 (m, 4H), 1.66-1.58 (m, 4H), 1.56-1.48 (m, 2H).

N-(4-((4-(azepan-1-yl)phenyl)amino)benzyl)-1-ethyl-5-oxopyrrolidine-3-carboxamide (472)

472

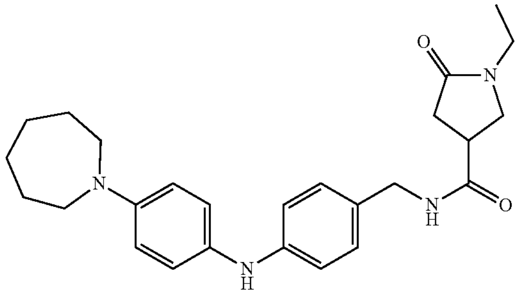

The title compound 472 (86.3 mg) was prepared in a yield of 75.58% as a pale olive solid from 4-(azepan-1-yl)aniline (50 mg, 0.26 mmol) and N-(4-bromobenzyl)-1-ethyl-5-oxopyrrolidine-3-carboxamide (94 mg, 0.28 mmol) according to the procedure for 461. $^1H$ NMR (400 MHz, DMSO-$d_6$) δ 8.40 (s, 2H), 7.42-6.56 (m, 6H), 4.12 (s, 3H), 3.50 (t, J=9.2 Hz, 1H), 3.17 (s, 10H), 2.40 (d, J=8.5 Hz, 2H), 1.58 (d, J=85.1 Hz, 5H), 1.00 (t, J=7.2 Hz, 3H). Mass (m/z): 435.4 $[M+H]^+$.

N-(4-((4-(tert-butyl)phenyl)amino)benzyl)-5-oxopyrrolidine-3-carboxamide (473)

473

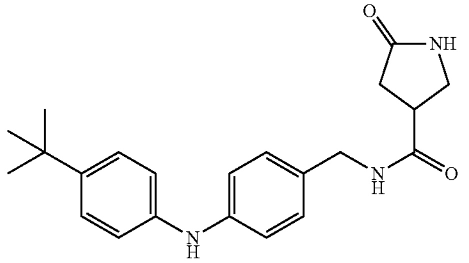

The title compound 473 (15.5 mg) was prepared in a yield of 12.60% as a dimgray powder from 4-(tert-butyl)aniline (50 mg, 0.34 mmol) and N-(4-bromobenzyl)-5-oxopyrrolidine-3-carboxamide (100 mg, 0.34 mmol) according to the procedure for 461. $^1H$ NMR (400 MHz, DMSO-$d_6$) δ 8.39 (t, J=5.8 Hz, 1H), 8.01 (s, 1H), 7.58 (s, 1H), 7.30-7.18 (m, 2H), 7.09 (d, J=8.5 Hz, 2H), 7.04-6.93 (m, 4H), 4.17 (d, J=5.7 Hz, 2H), 3.17 (dd, J=15.4, 8.1 Hz, 1H), 2.30 (dd, J=8.4, 4.2 Hz, 3H), 2.00 (q, J=7.0, 6.5 Hz, 1H), 1.25 (s, 9H). Mass (m/z): 366.3 [M+H]+.

5-oxo-N-(4-((4-(2,2,2-trifluoroethyl)phenyl)amino) benzyl)pyrrolidine-3-carboxamide (474)

474

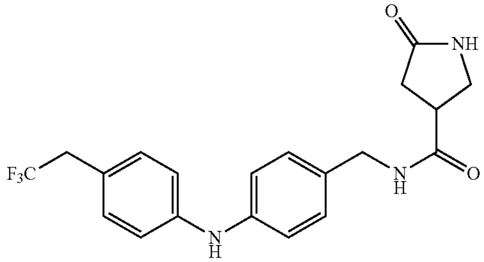

The title compound 474 (34.5 mg) was prepared in a yield of 26.19% as a pale yellow powder from 4-(2,2,2-trifluoroethyl)aniline (59 mg, 0.34 mmol) and N-(4-bromobenzyl)-5-oxopyrrolidine-3-carboxamide (100 mg, 0.34 mmol) according to the procedure for 461. $^1$H NMR (400 MHz, DMSO-$d_6$) δ 8.42 (s, 1H), 8.22 (s, 1H), 7.58 (s, 1H), 7.17 (d, J=8.2 Hz, 2H), 7.14-7.09 (m, 2H), 7.06-6.99 (m, 4H), 4.19 (d, J=5.8 Hz, 2H), 3.49 (q, J=11.6 Hz, 2H), 3.40 (t, J=8.7 Hz, 1H), 3.21 (ddt, J=23.4, 15.5, 7.2 Hz, 2H), 2.35-2.25 (m, 2H). Mass (m/z): 366.3 [M+H]+. Mass (m/z): 392.2 [M+H]+.

N-(4-((4-(azocan-1-yl)phenyl)amino)benzyl)-1-ethyl-5-oxopyrrolidine-3-carboxamide (475)

475

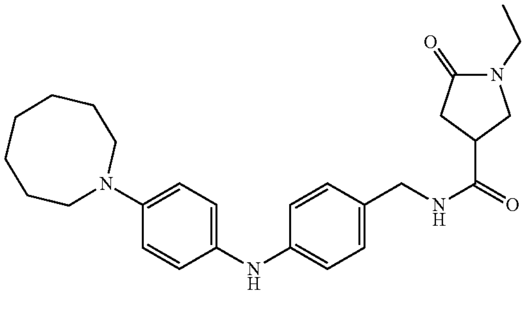

The title compound 475 (143.7 mg) was prepared in a yield of 65.45% as a gray solid from 4-(azocan-1-yl)aniline (100 mg, 0.49 mmol) and N-(4-bromobenzyl)-1-ethyl-5-oxopyrrolidine-3-carboxamide (191 mg, 0.59 mmol) according to the procedure for 461. $^1$H NMR (400 MHz, DMSO-$d_6$) δ 8.36 (t, J=5.6 Hz, 1H), 7.59-6.35 (m, 8H), 4.12 (s, 2H), 3.49 (t, J=9.2 Hz, 2H), 3.43-3.33 (m, 4H), 3.17 (qd, J=7.2, 1.5 Hz, 2H), 3.13-3.05 (m, 1H), 2.39 (d, J=8.6 Hz, 2H), 1.66 (s, 5H), 1.49 (s, 5H), 0.99 (t, J=7.2 Hz, 3H). Mass (m/z): 449.3 [M+H]+.

(R)—N-(4-((4-(azepan-1-yl)phenyl)amino)benzyl)-5-oxopyrrolidine-3-carboxamide (476)

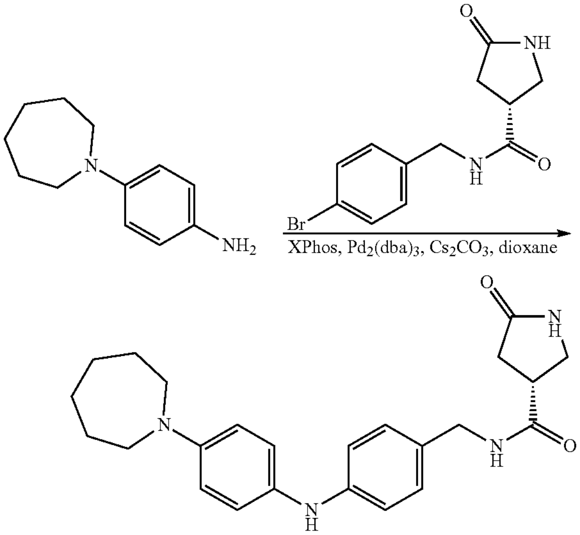

476

The title compound 476 (23.7 mg) was prepared in a yield of 16.59% as a gray powder from 4-(azepan-1-yl)aniline (64 mg, 0.34 mmol) and N-(4-bromobenzyl)-5-oxopyrrolidine-3-carboxamide (100 mg, 0.34 mmol) according to the procedure for 461. $^1$H NMR (400 MHz, DMSO-$d_6$) δ 8.33 (s, 1H), 7.57 (s, 1H), 7.54-7.47 (m, 1H), 7.20 (d, J=8.4 Hz, 1H), 6.90 (s, 5H), 4.23 (t, J=5.8 Hz, 1H), 3.29-3.03 (m, 5H), 2.33-2.25 (m, 3H), 2.03-1.92 (m, 2H), 1.88-1.33 (m, 7H), 0.88-0.78 (m, 1H). Mass (m/z): 407.3 [M+H]+.

N-(4-((4-(azocan-1-yl)phenyl)amino)benzyl)-5-oxopyrrolidine-3-carboxamide (477)

477

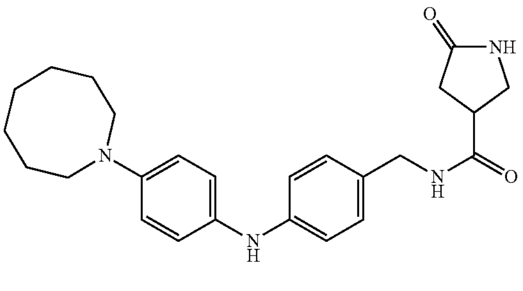

The title compound 477 (28.3 mg) was prepared in a yield of 20.00% as a gray powder from 4-(azocan-1-yl)aniline (69 mg, 0.34 mmol) and N-(4-bromobenzyl)-5-oxopyrrolidine-3-carboxamide (100 mg, 0.34 mmol) according to the procedure for 461. $^1$H NMR (400 MHz, DMSO-$d_6$) δ 8.32 (s, 1H), 7.56 (s, 1H), 6.99 (s, 7H), 4.25-4.10 (m, 2H), 3.30-3.05 (m, 2H), 2.27 (dd, J=8.4, 5.2 Hz, 3H), 1.99 (q, J=7.2 Hz, 1H), 1.84-1.33 (m, 11H), 0.89-0.76 (m, 2H). Mass (m/z): 421.3 [M+H]+.

(R)-5-oxo-N-(4-((4-(piperidin-1-yl)phenyl)amino)benzyl)pyrrolidine-3-carboxamide (478)

478

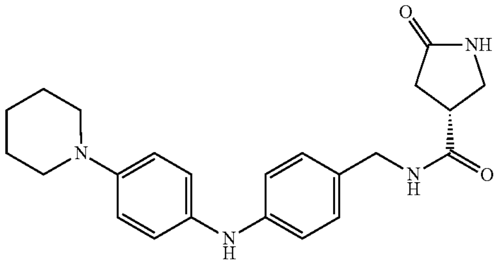

The title compound 478 (27.5 mg) was prepared in a yield of 20.82% as a dimgray powder from 4-(piperidin-1-yl)aniline (59 mg, 0.34 mmol) and (R)—N-(4-bromobenzyl)-5-oxopyrrolidine-3-carboxamide (100 mg, 0.34 mmol) according to the procedure for 461. $^1$H NMR (400 MHz, DMSO-d$_6$) δ 8.36 (s, 1H), 7.74 (s, 1H), 7.57 (s, 1H), 7.03 (s, 2H), 6.95 (s, 2H), 6.86 (s, 3H), 4.14 (s, 2H), 3.39 (t, J=8.8 Hz, 2H), 3.27-3.11 (m, 3H), 3.00 (s, 4H), 2.32-2.24 (m, 2H), 1.98 (p, J=7.0, 6.5 Hz, 1H), 1.50 (s, 3H). Mass (m/z): 393.3 [M+H]$^+$.

(R)—N-(4-((4-(4,4-dimethylpiperidin-1-yl)phenyl)amino)benzyl)-5-oxopyrrolidine-3-carboxamide (479)

479

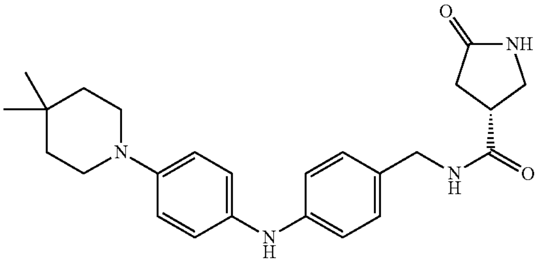

The title compound 479 (16.8 mg) was prepared in a yield of 11.87% as a gray powder from 4-(4,4-dimethylpiperidin-1-yl)aniline (69 mg, 0.34 mmol) and (R)—N-(4-bromobenzyl)-5-oxopyrrolidine-3-carboxamide (100 mg, 0.34 mmol) according to the procedure for 461. $^1$H NMR (400 MHz, DMSO-d$_6$) δ 8.35 (s, 1H), 7.72 (s, 1H), 7.57 (s, 1H), 7.02 (s, 2H), 6.94 (s, 2H), 6.86 (s, 4H), 4.14 (s, 2H), 3.40 (d, J=7.6 Hz, 2H), 3.27-3.11 (m, 2H), 3.02 (s, 3H), 2.34-2.25 (m, 4H), 1.99 (q, J=7.0, 6.4 Hz, 2H), 0.94 (s, 6H). Mass (m/z): 421.3 [M+H]$^+$.

N-(4-((3-methyl-4-(4-(trifluoromethyl)piperidin-1-yl)phenyl)amino)benzyl)-5-oxopyrrolidine-3-carboxamide (480)

480

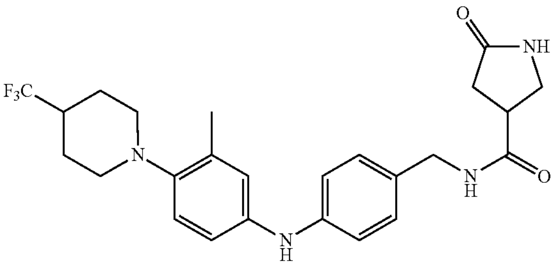

The title compound 480 (30.2 mg) was prepared in a yield of 16.44% as a white powder from 3-methyl-4-(4-(trifluoromethyl)piperidin-1-yl)aniline (115 mg, 0.39 mmol) and N-(4-bromobenzyl)-5-oxopyrrolidine-3-carboxamide (100 mg, 0.39 mmol) according to the procedure for 461. $^1$H NMR (400 MHz, DMSO-d$_6$) δ 8.37 (t, J=5.7 Hz, 1H), 7.88 (s, 1H), 7.58 (s, 1H), 7.13-7.02 (m, 2H), 6.99-6.90 (m, 3H), 6.90-6.81 (m, 2H), 4.16 (d, J=5.7 Hz, 2H), 3.03 (d, J=11.3 Hz, 2H), 2.72-2.56 (m, 3H), 2.45-2.25 (m, 3H), 2.19 (s, 3H), 2.06-1.93 (m, 1H), 1.95-1.84 (m, 2H), 1.60 (d, J=12.5 Hz, 2H), 1.45 (s, 1H). Mass (m/z): 476.3 [M+H]$^+$.

1-(4-((4-(4-(trifluoromethyl)piperidin-1-yl)phenyl)amino)benzyl)pyrrolidine-3-carboxamide (481)

481

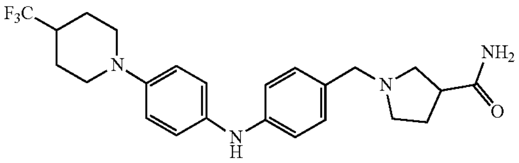

The title compound 481 (3.8 mg) was prepared in a yield of 5.74% as a white powder from 4-(4-(trifluoromethyl)piperidin-1-yl)aniline (36 mg, 0.15 mmol) and 1-(4-bromobenzyl)pyrrolidine-3-carboxamide (42 mg, 0.15 mmol) according to the procedure for 461. $^1$H NMR (400 MHz, Methanol-d$_4$) δ 7.39 (s, 4H), 7.19 (d, J=24.9 Hz, 4H), 4.31 (d, J=33.8 Hz, 2H), 3.73 (s, 2H), 3.62 (s, 2H), 3.45 (d, J=11.3 Hz, 3H), 2.59 (d, J=48.1 Hz, 2H), 2.31 (s, 1H), 2.12 (s, 3H), 2.09-1.90 (m, 31H). Mass (m/z): 447.4 [M+H]$^+$.

N-(4-((4-(2-fluoroethyl)phenyl)amino)benzyl)-5-oxopyrrolidine-3-carboxamide (482)

482

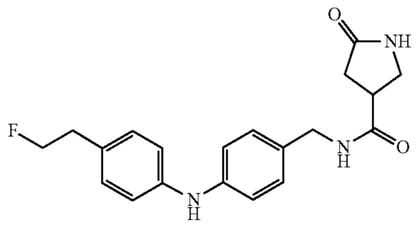

The title compound 482 (8.4 mg) was prepared in a yield of 3.29% as a white powder from 4-(2-fluoroethyl)aniline (100 mg, 0.72 mmol) and N-(4-bromobenzyl)-5-oxopyrrolidine-3-carboxamide (213 mg, 0.72 mmol) according to the procedure for 461. $^1$H NMR (400 MHz, Methanol-$d_4$) δ 7.17-7.07 (m, 4H), 7.05-6.97 (m, 4H), 4.61 (t, J=6.6 Hz, 1H), 4.49 (t, J=6.6 Hz, 1H), 4.28 (s, 2H), 3.58 (dd, J=9.9, 8.8 Hz, 1H), 3.49 (dd, J=9.9, 6.5 Hz, 11H), 2.94 (t, J=6.6 Hz, 1H), 2.88 (t, J=6.6 Hz, 1H), 2.54 (qd, J=17.0, 8.6 Hz, 2H), 1.31 (dt, J=7.4, 3.3 Hz, 1H). Mass (m/z): 356.2 $[M+H]^+$.

5-oxo-N-(2-(4-((4-(4-(trifluoromethyl)piperidin-1-yl)phenyl)amino)phenyl)propan-2-yl)pyrrolidine-3-carboxamide (483)

483

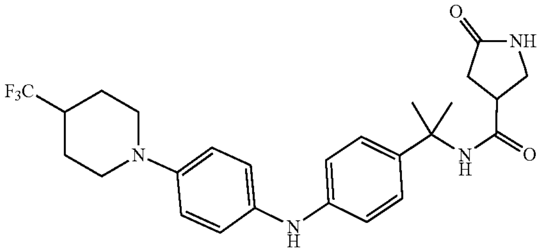

The title compound 483 (9.7 mg) was prepared in a yield of 9.7% as a pale blue powder from 4-(4-(trifluoromethyl)piperidin-1-yl)aniline (67 mg, 0.20 mmol) and N-(2-(4-bromophenyl)propan-2-yl)-5-oxopyrrolidine-3-carboxamide (50 mg, 0.20 mmol) according to the procedure for 461. $^1$H NMR (400 MHz, DMSO-$d_6$) δ 8.20-7.99 (m, 1H), 7.53 (s, 1H), 7.31-6.70 (m, 7H), 3.42 (d, J=8.5 Hz, 3H), 3.29-3.12 (m, 3H), 2.55 (s, 2H), 2.28-2.20 (m, 2H), 1.71 (s, 2H), 1.53 (s, 6H). Mass (m/z): 489.3 $[M+H]^+$.

N-(4-((2-fluoro-4-(4-(trifluoromethyl)piperidin-1-yl)phenyl)amino)benzyl)-5-oxopyrrolidine-3-carboxamide (484)

484

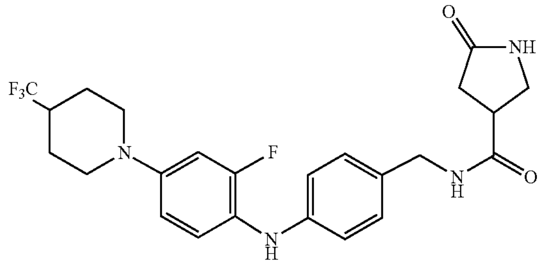

The title compound 484 (6.4 mg) was prepared in a yield of 7.95% as a gray powder from 2-fluoro-4-(4-(trifluoromethyl)piperidin-1-yl)aniline (50 mg, 0.17 mmol) and N-(4-bromobenzyl)-5-oxopyrrolidine-3-carboxamide (44 mg, 0.17 mmol) according to the procedure for 461. $^1$H NMR (400 MHz, DMSO-$d_6$) δ 8.35 (t, J=5.7 Hz, 1H), 7.58 (s, 2H), 7.11 (t, J=9.2 Hz, 1H), 7.03 (d, J=8.3 Hz, 2H), 6.88 (d, J=14.2 Hz, 1H), 6.76 (d, J=8.8 Hz, 11H), 6.71 (d, J=8.1 Hz, 2H), 4.15 (d, J=5.6 Hz, 2H), 3.39 (d, J=8.8 Hz, 2H), 3.31-3.08 (m, 2H), 2.72 (t, J=12.6 Hz, 3H), 2.36-2.22 (m, 3H), 1.89 (d, J=12.6 Hz, 2H), 1.55 (tt, J=12.4, 6.4 Hz, 2H). Mass (m/z): 479.3 $[M+H]^+$.

N-(4-((2-methyl-4-(4-(trifluoromethyl)piperidin-1-yl)phenyl)amino)benzyl)-5-oxopyrrolidine-3-carboxamide (485)

485

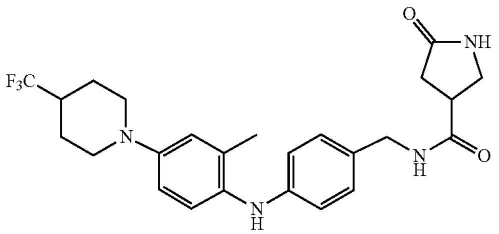

The title compound 485 (4.5 mg) was prepared in a yield of 5.64% as a gray powder from 2-methyl-4-(4-(trifluoromethyl)piperidin-1-yl)aniline (50 mg, 0.17 mmol) and N-(4-bromobenzyl)-5-oxopyrrolidine-3-carboxamide (43 mg, 0.17 mmol) according to the procedure for 461. $^1$H NMR (400 MHz, DMSO-$d_6$) δ 8.35 (s, 1H), 7.58 (s, 1H), 7.22 (s, 1H), 7.15-6.78 (m, 5H), 6.67 (s, 2H), 4.14 (d, J=5.5 Hz, 2H), 3.40 (t, J=8.8 Hz, 2H), 3.28-3.04 (m, 3H), 2.29 (dd, J=8.4, 4.1 Hz, 2H), 2.15 (s, 3H), 2.00 (p, J=7.1 Hz, 3H), 1.64 (s, 2H), 1.47 (d, J=8.0 Hz, 1H), 1.18 (t, J=7.3 Hz, 1H), 0.90-0.82 (m, 2H). Mass (m/z): 475.3 $[M+H]^+$.

N-(4-((2-chloro-4-(4-(trifluoromethyl)piperidin-1-yl) phenyl)amino)benzyl)-5-oxopyrrolidine-3-carboxamide (486)

486

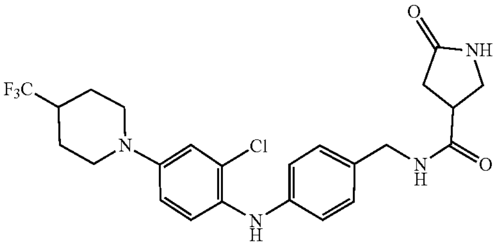

The title compound 486 (9.5 mg) was prepared in a yield of 5.70% as a gray powder from 2-chloro-4-(4-(trifluoromethyl)piperidin-1-yl)aniline (100 mg, 0.34 mmol) and N-(4-bromobenzyl)-5-oxopyrrolidine-3-carboxamide (93 mg, 0.34 mmol) according to the procedure for 461. $^{1}$H NMR (400 MHz, Pyridine-$d_5$) δ 9.27 (d, J=6.1 Hz, 1H), 8.53 (d, J=9.4 Hz, 1H), 8.06 (s, 1H), 7.49-7.37 (m, 3H), 7.24 (d, J=2.8 Hz, 1H), 7.20-7.16 (m, 2H), 6.96 (dd, J=8.9, 2.8 Hz, 1H), 4.76-4.62 (m, 2H), 3.93 (dd, J=9.3, 6.5 Hz, 1H), 3.74-3.48 (m, 4H), 3.15 (dd, J=16.5, 7.8 Hz, 1H), 2.72 (dd, J=16.5, 9.5 Hz, 1H), 2.56 (td, J=12.3, 2.5 Hz, 2H), 2.19 (dtt, J=12.6, 8.2, 4.2 Hz, 1H), 1.83 (d, J=12.9 Hz, 2H), 1.65 (qd, J=12.5, 4.2 Hz, 2H). Mass (m/z): 495.6 [M+H]$^+$.

N-(2,6-difluoro-4-((4-(4-(trifluoromethyl)piperidin-1-yl)phenyl)amino)benzyl)-5-oxopyrrolidine-3-carboxamide (487)

487

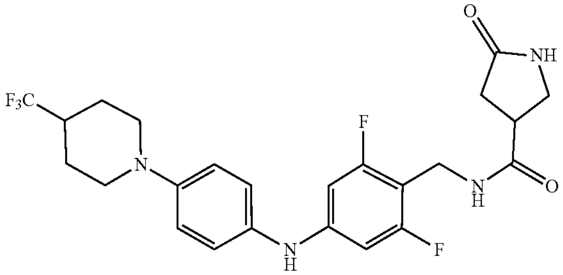

The title compound 487 (9.3 mg) was prepared in a yield of 7.22% as a pale blue powder from 4-(aminomethyl)-3,5-difluoro-N-(4-(4-(trifluoromethyl)piperidin-1-yl)phenyl) aniline (100 mg, 0.26 mmol) and 5-oxopyrrolidine-3-carboxylic acid (40 mg, 0.31 mmol) according to the procedure for 458. $^{1}$H NMR (400 MHz, DMSO-$d_6$) δ 8.51 (s, 1H), 8.26 (t, J=5.1 Hz, 1H), 7.56 (s, 1H), 7.09 (s, 4H), 6.50 (d, J=10.1 Hz, 2H), 4.23-4.14 (m, 2H), 3.68 (d, J=12.0 Hz, 2H), 3.35 (t, J=8.8 Hz, 1H), 3.23-3.01 (m, 3H), 2.95 (s, 2H), 2.30-2.11 (m, 2H), 1.96 (d, J=13.1 Hz, 2H), 1.67 (d, J=12.8 Hz, 2H). Mass (m/z): 497.3 [M+H]$^+$.

N-(4-((4-(4-methylpiperidin-1-yl)phenyl)amino)-2-(trifluoromethyl)benzyl)-5-oxopyrrolidine-3-carboxamide (488)

488

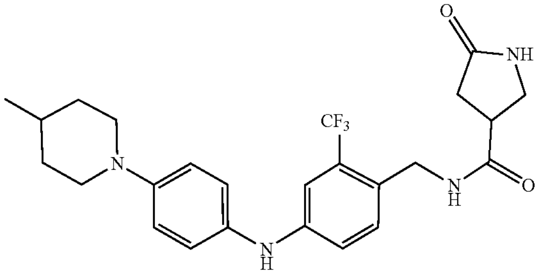

The title compound 488 (52.0 mg) was prepared in a yield of 79.65% as a gray white powder from 4-(aminomethyl)-N-(4-(4-methylpiperidin-1-yl)phenyl)-3-(trifluoromethyl) aniline (50 mg, 0.14 mmol) and 5-oxopyrrolidine-3-carboxylic acid (35 mg, 0.27 mmol) according to the procedure for 458. $^{1}$H NMR (400 MHz, DMSO-$d_6$) δ 8.41 (t, J=5.6 Hz, 1H), 8.16 (s, 1H), 7.60 (s, 1H), 7.24 (d, J=8.5 Hz, 1H), 7.13 (d, J=2.4 Hz, 1H), 7.09 (dd, J=8.4, 2.4 Hz, 1H), 6.99 (d, J=8.5 Hz, 2H), 6.90 (d, J=8.6 Hz, 2H), 4.30 (d, J=5.4 Hz, 2H), 3.55 (dt, J=12.5, 3.5 Hz, 2H), 3.40 (q, J=6.5, 5.2 Hz, 1H), 3.28-3.14 (m, 2H), 2.67-2.52 (m, 2H), 2.37-2.21 (m, 2H), 1.73-1.61 (m, 2H), 1.57-1.37 (m, 1H), 1.34-1.13 (m, 2H), 0.93 (d, J=6.5 Hz, 3H). Mass (m/z): 475.3 [M+H]$^+$.

N1-(4-((3,5-difluoro-4-(4-(trifluoromethyl)piperidin-1-yl)phenyl)amino)benzyl) oxalamide 489

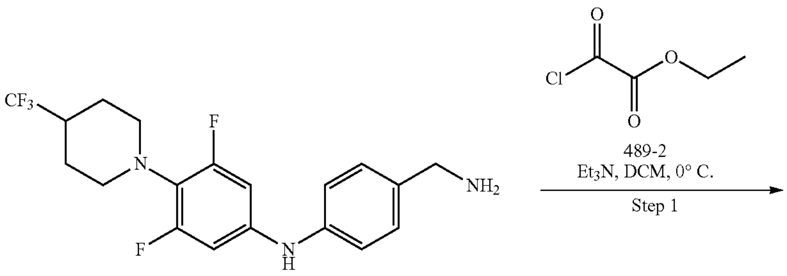

489-1

-continued

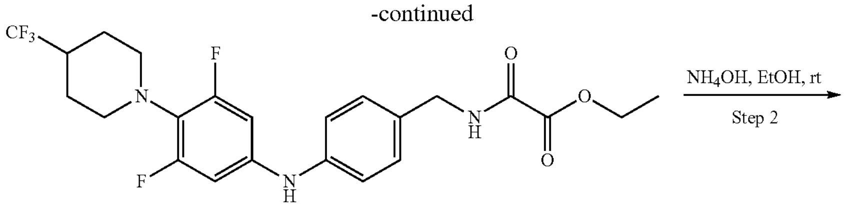

489-3

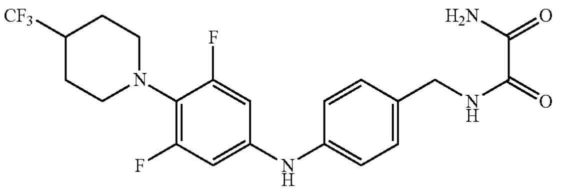

489

Step 1. Preparation of ethyl 2-((4-((3,5-difluoro-4-(4-(trifluoromethyl)piperidin-1-yl)phenyl)amino)benzyl)amino)-2-oxoacetate (489-3): A mixture of N-(4-(aminomethyl)phenyl)-3,5-difluoro-4-(4-(trifluoromethyl)piperidin-1-yl)aniline (0.2 g, 0.52 mmol) and $Et_3N$ (0.16 g, 1.56 mmol) was stirred in DCM (10 mL) at 0° C. for 0.5 h. The ethyl 2-chloro-2-oxoacetate was dissolved in DCM (5 mL) and then dropped into the stirred mixture solution at 25° C. then stirred at rt overnight. The mixture was diluted with DCM (100 mL) and washed with water (100 mL×3). The organic phase was concentrated and evaporated to give ethyl 2-((4-((3,5-difluoro-4-(4 -(trifluoromethyl)piperidin-1-yl)phenyl)amino)benzyl)amino)-2-oxoacetate 489-3 as a colorless oil (0.2 g, 78.8%). Mass (m/z): 486.1 $[M+H]^+$.

Step 2. Preparation of N1-(4-((3,5-difluoro-4-(4-(trifluoromethyl)piperidin-1-yl)phenyl)amino)benzyl) oxalamide (489): To a solution of 2-((4-((3,5-difluoro-4-(4-(trifluoromethyl)piperidin-1-yl) phenyl) amino) benzyl)amino)-2-oxoacetate (0.2 g, 0.41 mmol) and $NH_4OH$ (0.5 mL, 13 mmol) in THF (10 mL) was stirred at 25° C. for 2 hrs. The mixture was diluted with EA (100 mL) and wash with water (100 mL×2), the organic phase was removed under vacuum and the residue was purified by perp-HPLC (column-Xbridge-C18 150×21.2 mm, Sum; Mobile phase: ACN-H2O (0.1% FA), 40%-60%) to afford 489 as white solid. (38.3 mg, 18.5%). Mass (m/z): 456.6 $[M+H]^+$. $^1H$ NMR (400 MHz, DMSO-$d_6$) δ 9.16 (t, J=8.0 Hz, 1H), 8.40 (s, 1H), 8.07 (s, 1H), 7.80 (s, 1H), 7.19 (d, J=8.4 Hz, 2H), 7.04 (d, J=8.4 Hz, 2H), 6.58 (d, J=11.6 Hz, 2H), 4.24 (d, J=4.0 Hz, 2H), 3.05 (s, 4H), 2.43-2.37 (m, 1H), 1.83 (d, J=10.8 Hz, 2H), 1.59-1.49 (m, 2H).

5-oxo-N-(4-((3-pentylphenyl amino)benzyl)pyrrolidine-3-carboxamide (490)

490

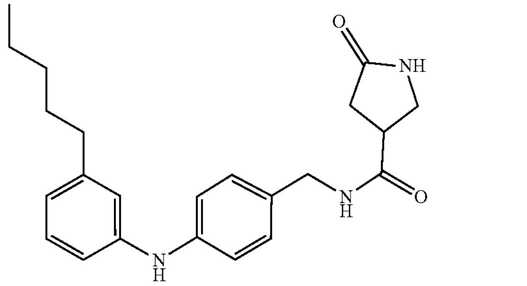

The title compound 490 (9.5 mg) was prepared in a yield of 16.83% as a white powder from 3-pentylaniline (55 mg, 0.34 mmol) and N-(4-bromobenzyl)-5-oxopyrrolidine-3-carboxamide (100 mg, 0.34 mmol) according to the procedure for 461. $^1H$ NMR (400 MHz, DMSO-$d_6$) δ 8.39 (t, J=5.8 Hz, 1H), 8.05 (s, 1H), 7.58 (s, 1H), 7.10 (dt, J=8.6, 3.8 Hz, 3H), 7.04-6.95 (m, 2H), 6.84 (dq, J=4.2, 1.6 Hz, 2H), 6.62 (dt, J=7.5, 1.3 Hz, 1H), 4.18 (d, J=5.7 Hz, 2H), 3.45-3.36 (m, 1H), 3.28-3.11 (m, 2H), 2.47 (d, J=7.7 Hz, 2H), 2.37-2.22 (m, 2H), 1.54 (p, J=7.4 Hz, 2H), 1.28 (qdt, J=12.0, 7.8, 4.5 Hz, 4H), 0.93-0.79 (m, 3H). Mass (m/z): 380.5 $[M+H]^+$.

N-(2-fluoro-3-methyl-4-((4-(4-(trifluoromethyl)piperidin-1-yl)phenyl)amino)benzyl)-5-oxopyrrolidine-3-carboxamide (491)

491

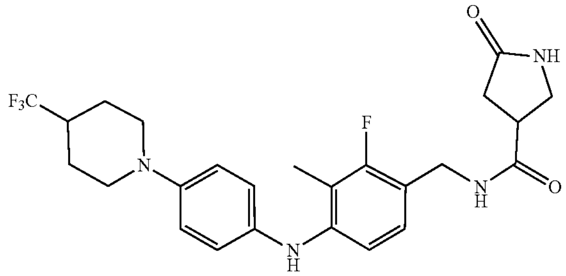

The title compound 491 (49.6 mg) was prepared in a yield of 37.95% as a rosybrown powder from 4-(aminomethyl)-3-fluoro-2-methyl-N-(4-(4-(trifluoromethyl)piperidin-1-yl)phenyl)aniline (100 mg, 0.26 mmol) and 5-oxopyrrolidine-3-carboxylic acid (37 mg, 0.29 mmol) according to the procedure for 458. $^1H$ NMR (400 MHz, DMSO-$d_6$) δ 8.36 (s, 1H), 7.69 (d, J=18.6 Hz, 1H), 7.58 (s, 1H), 7.19 (s, 1H), 6.90 (s, 4H), 6.71 (d, J=8.0 Hz, 1H), 4.20 (s, 2H), 3.63 (d, J=11.8 Hz, 2H), 3.20 (s, 2H), 2.62 (t, J=12.3 Hz, 2H), 2.27 (d, J=8.3 Hz, 2H), 2.09 (s, 2H), 1.88 (d, J=12.3 Hz, 2H), 1.56 (d, J=13.0 Hz, 2H), 1.37 (s, 1H), 1.23 (s, 1H), 0.91 (s, 1H). Mass (m/z): 493.6 $[M+H]^+$.

N-(2-fluoro-5-methyl-4-((4-(4-(trifluoromethyl)piperidin-1-yl)phenyl)amino)benzyl)-5-oxopyrrolidine-3-carboxamide (492)

492

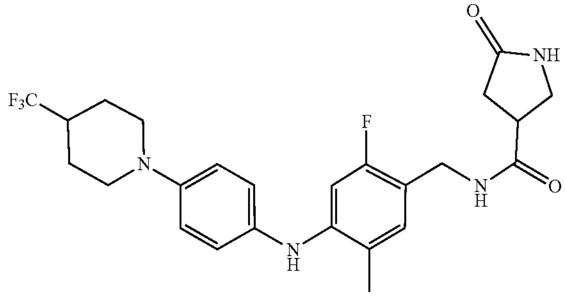

The title compound 492 (23.5 mg) was prepared in a yield of 18.20% as a dimgray powder from 4-(aminomethyl)-5-fluoro-2-methyl-N-(4-(4-(trifluoromethyl)piperidin-1-yl)phenyl)aniline (100 mg, 0.26 mmol) and 5-oxopyrrolidine-3-carboxylic acid (37 mg, 0.29 mmol) according to the procedure for 458. $^1H$ NMR (400 MHz, DMSO-$d_6$) δ 8.33 (t, J=5.5 Hz, 1H), 7.57 (s, 1H), 7.12 (s, 1H), 7.04-6.85 (m, 5H), 6.56 (d, J=12.7 Hz, 1H), 4.15 (d, J=5.5 Hz, 2H), 3.66 (d, J=12.1 Hz, 2H), 3.38 (t, J=8.5 Hz, 2H), 3.26-3.08 (m, 2H), 2.64 (td, J=12.4, 2.5 Hz, 2H), 2.43 (tt, J=8.6, 3.7 Hz, 2H), 2.27 (dd, J=8.4, 2.4 Hz, 2H), 1.88 (d, J=12.6 Hz, 2H), 1.58 (pd, J=13.6, 12.5, 5.6 Hz, 3H). Mass (m/z): 493.3 $[M+H]^+$.

N-(3-methyl-4-((4-(4-(trifluoromethyl)piperidin-1-yl)phenyl)amino)benzyl)-5-oxopyrrolidine-3-carboxamide (493)

493

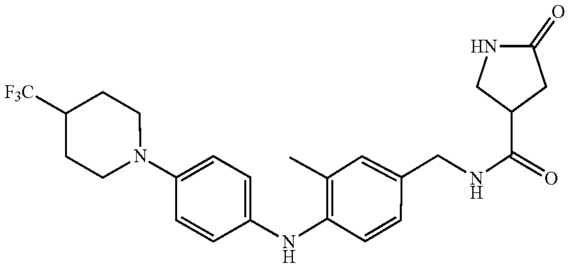

The title compound 493 (28.8 mg) was prepared in a yield of 11.02% as a gray powder from 4-(4-(trifluoromethyl)piperidin-1-yl)aniline (134 mg, 0.55 mmol) and N-(4-bromo-3-methylbenzyl)-5-oxopyrrolidine-3-carboxamide (180 mg, 0.58 mmol) according to the procedure for 461. $^1H$ NMR (400 MHz, DMSO-$d_6$) δ 8.41 (s, 1H), 7.58 (s, 1H), 7.27-6.91 (m, 5H), 6.84 (d, J=8.4 Hz, 2H), 4.30-4.13 (m, 2H), 3.67-3.56 (m, 2H), 3.40 (t, J=8.7 Hz, 2H), 3.30-3.12 (m, 3H), 2.72-2.51 (br, 1H), 2.29 (dd, J=8.4, 1.7 Hz, 2H), 2.15 (s, 3H), 2.00 (s, 2H), 1.76 (s, 2H). Mass (m/z): 475.6 $[M+H]^+$.

(S)—N-(4-((4-cyclohexylphenyl)amino)benzyl)-2,6-dioxohexahydropyrimidine-4-carboxamide (494)

494

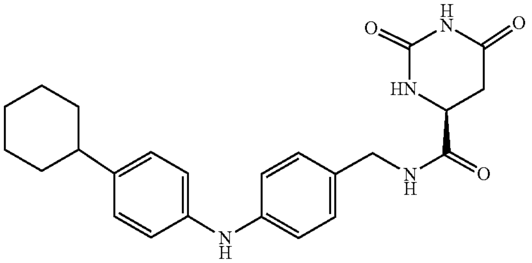

The title compound 494 (31.1 mg) was prepared in a yield of 69.13% as a offwhite powder from 4-(aminomethyl)-N-(4-cyclohexylphenyl)aniline (30 mg, 0.11 mmol) and (S)-2,6-dioxohexahydropyrimidine-4-carboxylic acid (61 mg, 0.16 mmol) according to the procedure for 458. $^1H$ NMR (400 MHz, DMSO-$d_6$) δ 10.03 (d, J=1.8 Hz, 1H), 8.43 (t, J=5.7 Hz, 1H), 8.00 (s, 1H), 7.62 (d, J=3.4 Hz, 1H), 7.12-7.02 (m, 4H), 7.00-6.88 (m, 4H), 4.25-4.09 (m, 2H), 4.00 (dt, J=7.1, 3.5 Hz, 11H), 3.61 (s, 1H), 3.13 (s, 1H), 2.96-2.78 (m, 1H), 2.42 (d, J=23.3 Hz, 1H), 1.76 (d, J=8.8 Hz, 4H), 1.69 (d, J=12.8 Hz, 1H), 1.35 (dd, J=11.5, 8.5 Hz, 4H). Mass (m/z): 421.5 $[M+H]^+$.

N-(2,5-dimethyl-4-((4-(4-(trifluoromethyl)piperidin-1-yl)phenyl)amino)benzyl)-5-oxopyrrolidine-3-carboxamide (495)

495

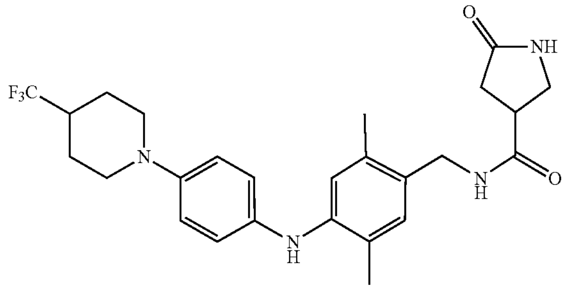

The title compound 495 (37.2 mg) was prepared in a yield of 43.55% as a pale gray powder from 4-(aminomethyl)-2,5-dimethyl-N-(4-(4-(trifluoromethyl)piperidin-1-yl)phenyl)aniline (66 mg, 0.17 mmol) and 5-oxopyrrolidine-3-carboxylic acid (34 mg, 0.26 mmol) according to the procedure for 458. $^1$H NMR (400 MHz, DMSO-$d_6$) δ 8.26 (t, J=5.4 Hz, 1H), 7.58 (s, 1H), 6.93 (d, J=1.6 Hz, 2H), 6.89-6.82 (m, 4H), 6.79 (s, 1H), 4.13 (d, J=5.4 Hz, 2H), 3.59 (d, J=12.3 Hz, 2H), 3.29-3.14 (m, 2H), 2.60 (td, J=12.3, 2.5 Hz, 2H), 2.40 (dq, J=12.4, 3.8 Hz, 1H), 2.35-2.20 (m, 3H), 2.11 (d, J=5.3 Hz, 6H), 1.87 (d, J=12.6 Hz, 2H), 1.56 (qd, J=12.5, 4.1 Hz, 2H). Mass (m/z): 489.4 $[M+H]^+$.

4-oxo-4-((4-((4-(4-(trifluoromethyl)piperidin-1-yl)phenyl)amino)benzyl)amino)butanoic acid (496)

496

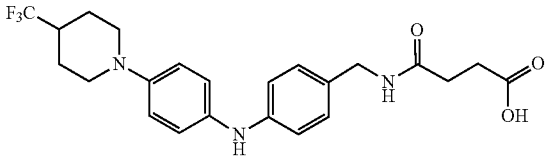

To a solution of 4-(aminomethyl)-N-(4-(4-(trifluoromethyl)piperidin-1-yl)phenyl)aniline hydrochloride (100 mg, 0.26 mmol) in toluene (5 mL), dihydrofuran-2,5-dione (26 mg, 0.26 mmol) and triethylamine (26 mg, 0.26 mmol) was added, The resulting solution was stirred for overnight at room temperature. The reaction mixture was added into water (15 mL) drop by drop with stirring. The precipitate was filtered, cake was wash with water 3 times and dry in vacuo. The residue was purified by perp-TLC to give desired product 496 (36.2 mg) as pale gray powder a yield of 31.25%. $^1$H NMR (400 MHz, DMSO-$d_6$) δ 11.22-12.33 (br, 1H), 8.24 (t, J=5.8 Hz, 1H), 7.77 (s, 1H), 7.09-7.00 (m, 2H), 7.00-6.93 (m, 2H), 6.92-6.81 (m, 4H), 4.13 (d, J=5.8 Hz, 2H), 3.61 (d, J=11.9 Hz, 2H), 2.62 (td, J=12.4, 2.5 Hz, 2H), 2.48-2.40 (m, 3H), 2.35 (td, J=6.7, 1.3 Hz, 2H), 1.94-1.83 (m, 2H), 1.57 (qd, J=12.5, 4.1 Hz, 2H). Mass (m/z): 450.3 $[M+H]^4$.

N-(2,3-dimethyl-4-((4-(4-(trifluoromethyl)piperidin-1-yl)phenyl)amino)benzyl)-5-oxopyrrolidine-3-carboxamide (497)

497

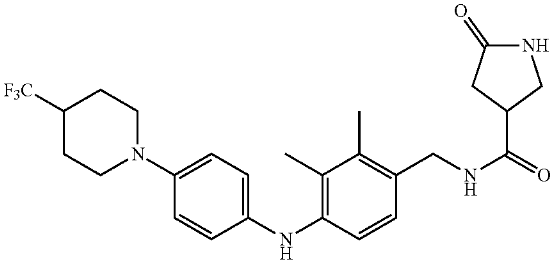

The title compound 497 (11.2 mg) was prepared in a yield of 43.55% as a offwhite powder from 4-(aminomethyl)-2,3-dimethyl-N-(4-(4-(trifluoromethyl)piperidin-1-yl)phenyl)aniline (30 mg, 0.08 mmol) and 5-oxopyrrolidine-3-carboxylic acid (16 mg, 0.12 mmol) according to the procedure for 458. $^1$H NMR (400 MHz, DMSO-$d_6$) δ 8.23 (d, J=5.3 Hz, 1H), 7.56 (d, J=10.9 Hz, 1H), 7.22 (s, 1H), 7.04 (s, 1H), 6.92 (d, J=8.2 Hz, 1H), 6.87-6.80 (m, 2H), 6.74 (d, J=8.9 Hz, 1H), 6.67 (s, 1H), 4.20 (d, J=5.8 Hz, 2H), 3.55 (d, J=11.4 Hz, 1H), 3.30-3.09 (m, 2H), 2.28 (dd, J=8.4, 5.9 Hz, 2H), 2.04-1.93 (m, 5H), 1.92-1.81 (m, 2H), 1.64-1.51 (m, 2H), 1.45 (d, J=7.0 Hz, 3H), 0.84 (t, J=6.7 Hz, 4H). Mass (m/z): 489.3 $[M+H]^+$.

N-(4-((4-(4-ethylpiperidin-1-yl)phenyl)amino)benzyl)-5-oxopyrrolidine-3-carboxamide (498)

498

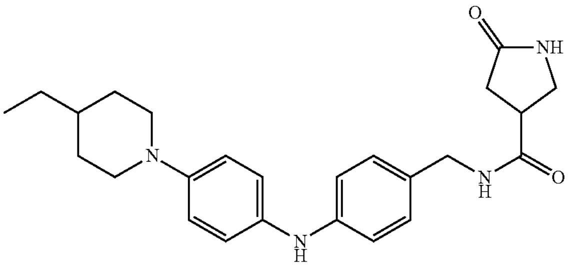

The title compound 498 (41.4 mg) was prepared in a yield of 20.11% as a white powder from 4-(4-ethylpiperidin-1-yl)aniline (152 mg, 0.51 mmol) and N-(4-bromobenzyl)-5-oxopyrrolidine-3-carboxamide (100 mg, 0.49 mmol) according to the procedure for 461. $^1$H NMR (400 MHz, DMSO-$d_6$) δ 8.35 (t, J=5.7 Hz, 1H), 7.74 (s, 1H), 7.58 (s, 1H), 7.08-6.99 (m, 2H), 6.99-6.91 (m, 2H), 6.90-6.81 (m, 4H), 4.14 (d, J=5.7 Hz, 2H), 3.52 (d, J=11.5 Hz, 2H), 3.43-3.36 (m, 1H), 3.28-3.20 (m, 1H), 3.20-3.12 (m, 1H), 2.35-2.22 (m, 2H), 1.74 (d, J=8.9 Hz, 2H), 1.25 (d, J=15.1 Hz, 7H), 0.89 (t, J=7.2 Hz, 3H). Mass (m/z): 421.4 $[M+H]^+$.

Methyl-4-oxo-4-((4-((4-(4-(trifluoromethyl)piperidin-1-yl)phenyl)amino)benzyl)amino)butanoate (499)

499

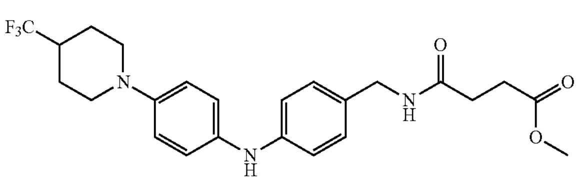

The title compound 499 (45.3 mg) was prepared in a yield of 37.71% as a offwhite powder from 4-(aminomethyl)-N-(4-(4-(trifluoromethyl)piperidin-1-yl)phenyl)aniline hydrochloride (100 mg, 0.26 mmol) and 4-methoxy-4-oxobutanoic acid (41 mg, 0.31 mmol) according to the procedure for 458. $^1$H NMR (400 MHz, DMSO-d$_6$) δ 8.26 (t, J=5.8 Hz, 1H), 7.78 (s, 1H), 7.08-7.00 (m, 2H), 7.00-6.94 (m, 2H), 6.88 (ddd, J=8.6, 6.0, 2.5 Hz, 4H), 4.13 (d, J=5.8 Hz, 2H), 3.65-3.58 (m, 2H), 3.57 (s, 3H), 2.67-2.56 (m, 2H), 2.54 (s, 2H), 2.40 (t, J=6.7 Hz, 3H), 1.87 (d, J=12.6 Hz, 2H), 1.57 (qd, J=12.5, 4.1 Hz, 2H). Mass (m/z): 464.4 [M+H]$^+$.

N-(4-((3-methoxy-4-(4-(trifluoromethyl)piperidin-1-yl)phenyl)amino)benzyl)-5-oxopyrrolidine-3-carboxamide (500)

500

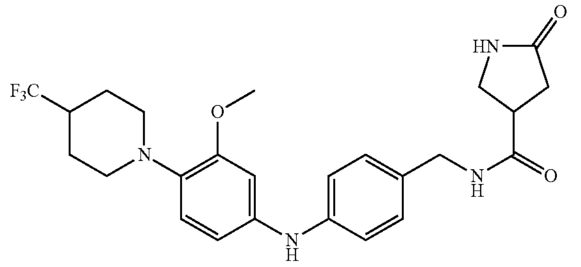

The title compound 500 (53.2 mg) was prepared in a yield of 66.86% as a pale gray powder from 3-methoxy-4-(4-(trifluoromethyl)piperidin-1-yl)aniline (100 mg, 0.36 mmol) and N-(4-bromobenzyl)-5-oxopyrrolidine-3-carboxamide (113 mg, 0.38 mmol) according to the procedure for 461. $^1$H NMR (400 MHz, DMSO-d$_6$) δ 8.46 (t, J=5.8 Hz, 1H), 7.60 (s, 1H), 7.32 (d, J=8.7 Hz, 1H), 7.16 (d, J=8.1 Hz, 2H), 7.09 (d, J=8.1 Hz, 2H), 6.84-6.73 (m, 1H), 6.68 (d, J=8.5 Hz, 1H), 4.21 (d, J=5.9 Hz, 2H), 3.87 (s, 3H), 3.51 (d, J=25.7 Hz, 3H), 3.47-3.36 (m, 2H), 3.32-3.12 (m, 2H), 2.30 (dd, J=8.4, 1.7 Hz, 2H), 2.01 (d, J=23.0 Hz, 4H). Mass (m/z): 491.4 [M+H]$^+$.

N-hydroxy-N-(4-((4-(4-methylpiperidin-1-yl)phenyl)amino)benzyl)-2,6-dioxopiperidine-4-carboxamide (501)

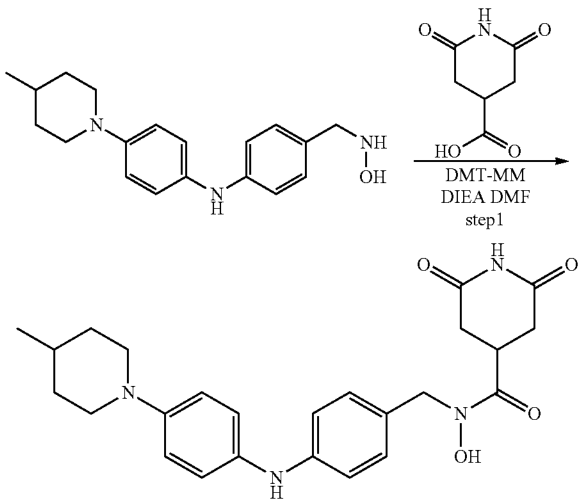

501

The title compound 501 (29.8 mg) was prepared in a yield of 20.60% as a pale blue powder from 4-((hydroxyamino)methyl)-N-(4-(4-methylpiperidin-1-yl)phenyl)aniline (100 mg, 0.32 mmol) and 2,6-dioxopiperidine-4-carboxylic acid (60 mg, 0.39 mmol) according to the procedure for 458. $^1$H NMR (300 MHz, DMSO-d$_6$) δ 10.66 (s, 1H), 10.04 (s, 1H), 8.53 (s, 1H), 7.47 (d, J=8.5 Hz, 1H), 7.08 (dt, J=16.0, 8.7 Hz, 5H), 4.59 (s, 2H), 3.95 (s, 2H), 3.64-3.37 (m, 4H), 2.62 (qd, J=16.7, 5.7 Hz, 3H), 1.89 (d, J=14.1 Hz, 2H), 1.55 (s, 2H), 0.98 (d, J=6.2 Hz, 3H). Mass (m/z): 451.3 [M+H]$^+$.

N-(4-((4-(4-(trifluoromethyl)piperidin-1-yl)phenyl)amino)benzyl)pyrrolidine-3-carboxamide (502)

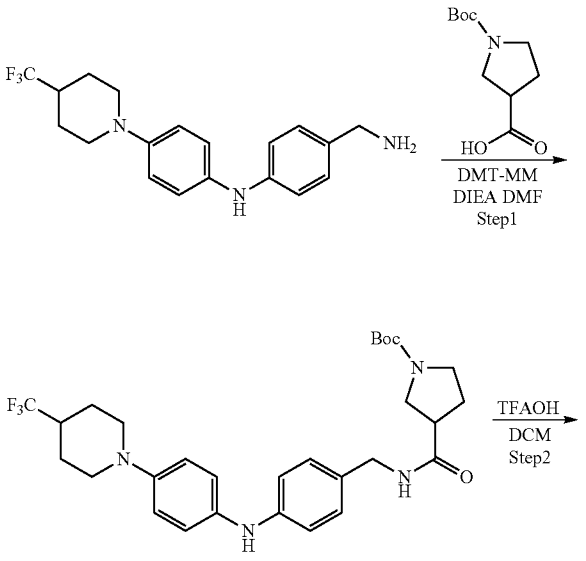

-continued

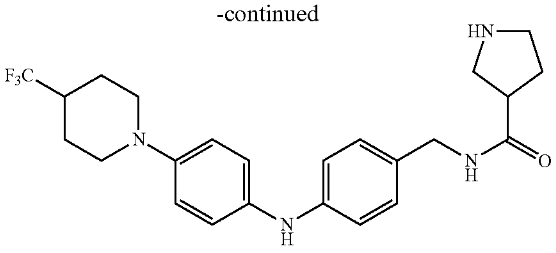

502

Step 1. Preparation of tert-butyl 3-((4-((4-(4-(trifluoromethyl)piperidin-1-yl)phenyl)amino)benzyl)carbamoyl)pyrrolidine-1-carboxylate. The intermediate tert-butyl 3-((4-((4-(4-(trifluoromethyl)piperidin-1-yl)phenyl)amino)benzyl)carbamoyl)pyrrolidine-1-carboxylate (151 mg) was prepared in a yield of 47.94% as a pale gray powder from 4-(aminomethyl)-N-(4-(4-(trifluoromethyl)piperidin-1-yl)phenyl)aniline (200 mg, 0.57 mmol) and 1-(tert-butoxycarbonyl)pyrrolidine-3-carboxylic acid (123 mg, 0.57 mmol) according to the procedure for 458.

Step 2. Preparation of N-(4-((4-(4-(trifluoromethyl)piperidin-1-yl)phenyl)amino)benzyl)pyrrolidine-3-carboxamide (502). To a solution of tert-butyl 3-((4-((4-(4-(trifluoromethyl)piperidin-1-yl)phenyl)amino)benzyl)carbamoyl)pyrrolidine-1 -carboxylate (100 mg, 0.18 mmol) in DCM (5 mL), TFAOH (2 mL) was added, The resulting solution was stirred for overnight at room temperature. The reaction mixture was added into water (15 mL) and extracted with ethyl acetate (5 mL) 3 times. The organic layer was combined and washed with water, sat·$NaHCO_3$(aq), and brine respectively. Then dried over $MgSO_4$, filtered, and the filtrate concentrated under reduced pressure. The residue was purified by perp-TLC to give desired product 502 (35.2 mg) as pale white powder a yield of 40.09%. $^1$H NMR (400 MHz, DMSO-$d_6$) δ 9.17 (s, 2H), 8.59 (t, J=5.8 Hz, 1H), 7.82 (s, 1H), 7.10-7.02 (m, 2H), 7.00-6.94 (m, 2H), 6.88 (dd, J=8.8, 3.3 Hz, 4H), 4.16 (d, J=5.6 Hz, 2H), 3.61 (d, J=11.7 Hz, 2H), 3.33-3.28 (in, 1H), 3.27-3.02 (m, 4H), 2.62 (td, J=12.3, 2.4 Hz, 2H), 2.42 (ddt, J=12.4, 8.7, 4.3 Hz, 1H), 2.21-2.08 (m, 1H), 2.02-1.92 (m, 11H), 1.91-1.83 (m, 2H), 1.57 (qd, J=12.4, 4.0 Hz, 2H). Mass (m/z): 447.6 [M+H]$^+$.

1-methyl-N-(4-((4-(4-(trifluoromethyl)piperidin-1-yl)phenyl)amino)benzyl)pyrrolidine-3-carboxamide (503)

503

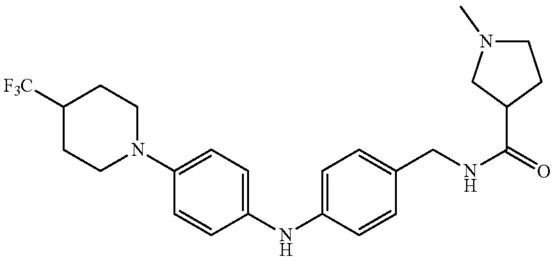

The title compound 503 (22.4 mg) was prepared in a yield of 18.77% as a white powder from 4-(aminomethyl)-N-(4-(4-(trifluoromethyl)piperidin-1-yl)phenyl)aniline hydrochloride (100 mg, 0.26 mmol) and 1-methylpyrrolidine-3-carboxylic acid (40 mg, 0.31 mmol) according to the procedure for 458. $^1$H NMR (300 MHz, DMSO-$d_6$) δ 8.57 (t, J=5.7 Hz, 11H), 7.80 (s, 1H), 7.04 (d, J=8.4 Hz, 2H), 7.00-6.92 (m, 2H), 6.87 (dd, J=8.9, 3.1 Hz, 4H), 4.16 (d, J=5.6 Hz, 2H), 3.61 (d, J=12.0 Hz, 2H), 3.29-3.11 (m, 3H), 2.80 (s, 3H), 2.62 (t, J=12.1 Hz, 2H), 2.42 (dd, J=8.4, 4.0 Hz, 1H), 2.22 (d, J=9.3 Hz, 1H), 2.03 (d, J=16.5 Hz, 2H), 1.88 (d, J=12.6 Hz, 2H), 1.57 (qd, J=12.4.4.0 Hz, 3H). Mass (m/z): 461.2 [M+H]$^+$.

N-(4-((2-methyl-6 (4-methylpiperidin-1-yl)pyridin-3-yl)amino)benzyl)-5-oxopyrrolidine-3-carboxamide (504)

504

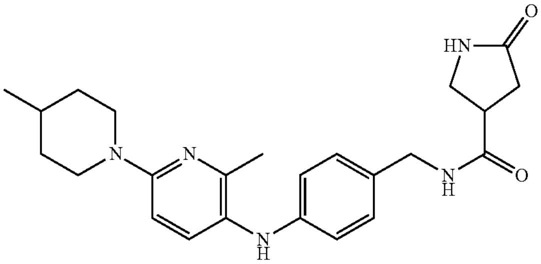

The title compound 504 (40.3 mg) was prepared in a yield of 39.25% as a pale yellow powder from 2-methyl-6-(4-methylpiperidin-1-yl)pyridin-3-amine (50 mg, 0.24 mmol) and N-(4-bromobenzyl)-5-oxopyrrolidine-3-carboxamide (70 mg, 0.24 mmol) according to the procedure for 461. $^1$H NMR (400 MHz, DMSO-$d_6$) δ 8.32 (t, J=5.7 Hz, 1H), 7.57 (s, 1H), 7.29-7.16 (m, 2H), 7.01-6.93 (m, 2H), 6.64 (d, J=8.8 Hz, 1H), 6.54-6.45 (m, 2H), 4.27-4.17 (m, 2H), 4.11 (d, J=5.7 Hz, 2H), 3.44-3.35 (m, 1H), 3.26-3.14 (m, 2H), 2.71 (t, J=12.5 Hz, 2H), 2.36-2.24 (m, 2H), 2.19 (s, 3H), 1.67 (d, J=12.9 Hz, 2H), 1.61-1.49 (m, 1H), 1.11 (qd, J=12.4, 4.1 Hz, 2H), 0.93 (d, J=6.5 Hz, 3H). Mass (m/z): 422.4 [M+H]$^+$.

N-(4-((6-(4-ethylpiperidin-1-yl)-2-methylpyridin-3-yl)amino)benzyl)-5-oxopyrrolidine-3-carboxamide (505)

505

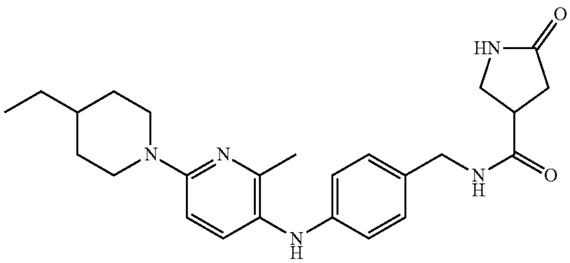

The title compound 505 (41.0 mg) was prepared in a yield of 41.29% as a pale yellow powder from 6-(4-ethylpiperidin-1-yl)-2-methylpyridin-3-amine (50 mg, 0.23 mmol) and N-(4-bromobenzyl)-5-oxopyrrolidine-3-carboxamide (68 mg, 0.23 mmol) according to the procedure for 461. $^1$H NMR (400 MHz, DMSO-$d_6$) δ 8.33 (t, J=5.7 Hz, 1H), 7.57

(s, 1H), 7.26 (d, J=8.6 Hz, 1H), 7.21 (s, 1H), 7.03-6.94 (m, 2H), 6.64 (d, J=8.9 Hz, 1H), 6.54-6.46 (m, 2H), 4.30-4.18 (m, 2H), 4.11 (d, J=5.7 Hz, 2H), 3.38 (t, J=8.6 Hz, 1H), 3.26-3.08 (m, 2H), 2.69 (t, J=12.2 Hz, 2H), 2.34-2.23 (m, 2H), 2.20 (s, 3H), 1.77-1.66 (m, 2H), 1.33 (s, 1H), 1.25 (p, J=7.2 Hz, 2H), 1.09 (qd, J=12.2, 3.9 Hz, 2H), 0.89 (t, J=7.4 Hz, 3H). Mass (m/z): 436.4 $[M+H]^+$.

N-(4-((6-((1R,4S)-2-azabicyclo[2.2.1]heptan-2-yl)-2-methylpyridin-3-yl)amino)benzyl)-5-oxopyrrolidine-3-carboxamide (506)

506

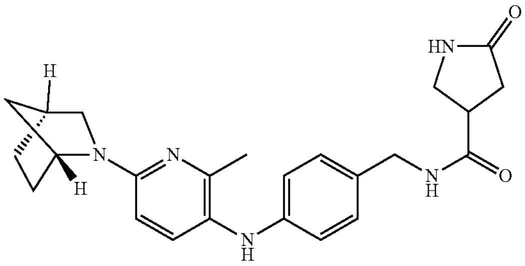

The title compound 506 (9.0 mg) was prepared in a yield of 8.78% as a pale yellow powder from 6-((1R,4S)-2-azabicyclo[2.2.1]heptan-2-yl)-2-methylpyridin-3-amine (51 mg, 0.25 mmol) and N-(4-bromobenzyl)-5-oxopyrrolidine-3-carboxamide (75 mg, 0.25 mmol) according to the procedure for 461. $^1$H NMR (400 MHz, DMSO-$d_6$) δ 12.26 (s, 1H), 8.38 (t, J=5.8 Hz, 1H), 7.71 (s, 1H), 7.60 (s, 1H), 7.54 (s, 1H), 7.05 (d, J=8.4 Hz, 2H), 6.93 (s, 1H), 6.58 (d, J=8.4 Hz, 2H), 4.69 (s, 1H), 4.15 (dd, J=5.9, 3.6 Hz, 2H), 3.56 (s, 1H), 3.39 (d, J=8.8 Hz, 1H), 3.26-3.11 (m, 3H), 2.76 (s, 1H), 2.35 (s, 3H), 2.32-2.27 (m, 2H), 1.76 (d, J=8.8 Hz, 3H), 1.69-1.58 (m, 2H), 1.46 (s, 1H). Mass (m/z): 420.3 $[M+H]^+$.

N-(4-((6-(3,3-dimethylazetidin-1-yl)-2-methylpyridin-3-yl)amino)benzyl)-5-oxopyrrolidine-3-carboxamide (507)

507

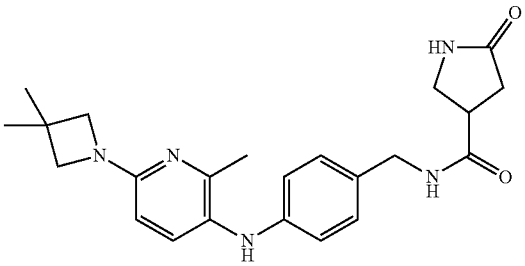

The title compound 507 (15.0 mg) was prepared in a yield of 14.58% as a pale yellow powder from 6-(3,3-dimethylazetidin-1-yl)-2-methylpyridin-3-amine (48 mg, 0.25 mmol) and N-(4-bromobenzyl)-5-oxopyrrolidine-3-carboxamide (75 mg, 0.25 mmol) according to the procedure for 461. $^1$H NMR (400 MHz, DMSO-$d_6$) δ 8.32 (t, J=5.7 Hz, 1H), 7.56 (s, 1H), 7.24 (d, J=8.5 Hz, 1H), 7.19 (s, 1H), 7.00-6.93 (m, 2H), 6.50-6.42 (m, 2H), 6.20 (d, J=8.5 Hz, 1H), 4.10 (d, J=5.7 Hz, 2H), 3.59 (s, 4H), 3.24-3.12 (m, 3H), 2.27 (dd, J=8.4, 4.9 Hz, 2H), 2.17 (s, 3H), 1.26 (s, 6H). Mass (m/z): 408.2 $[M+H]^+$.

N-(4-((6-(4-isopropylpiperidin-1-yl)pyridin-3-yl)amino)benzyl)-5-oxopyrrolidine-3-carboxamide (508)

508

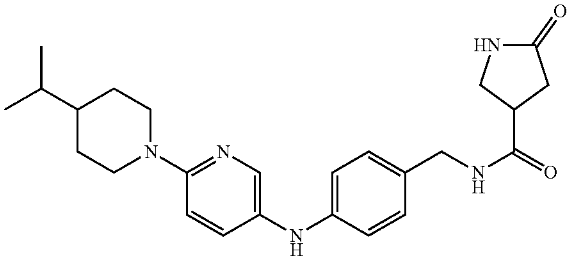

The title compound 508 (50.3 mg) was prepared in a yield of 68.63% as a pale yellow powder from 6-(4-isopropylpiperidin-1-yl)pyridin-3-amine (37 mg, 0.17 mmol) and N-(4-bromobenzyl)-5-oxopyrrolidine-3-carboxamide (50 mg, 0.17 mmol) according to the procedure for 461. $^1$H NMR (400 MHz, DMSO-$d_6$) δ 8.35 (t, J=5.7 Hz, 1H), 7.93 (d, J=2.8 Hz, 1H), 7.67 (s, 1H), 7.57 (s, 1H), 7.33 (dd, J=9.0, 2.8 Hz, 1H), 7.07-6.97 (m, 2H), 6.83-6.71 (m, 3H), 4.20 (d, J=12.9 Hz, 2H), 4.13 (d, J=5.7 Hz, 2H), 3.41-3.36 (m, 1H), 3.26-3.12 (m, 2H), 2.63 (t, J=11.8 Hz, 2H), 2.34-2.22 (m, 2H), 1.69 (d, J=10.4 Hz, 2H), 1.49-1.35 (m, 11H), 1.29-1.10 (m, 4H), 0.87 (d, J=6.8 Hz, 6H). Mass (m/z): 436.7 $[M+H]^+$.

N-(4-((6-(4-ethylpiperidin-1-yl)pyridin-3-yl)amino)benzyl)-5-oxopyrrolidine-3-carboxamide (509)

509

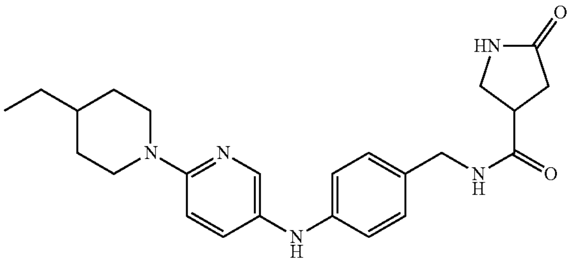

The title compound 509 (17.9 mg) was prepared in a yield of 25.24% as a pale yellow powder from 6-(4-ethylpiperidin-1-yl)pyridin-3-amine (35 mg, 0.17 mmol) and N-(4-bromobenzyl)-5-oxopyrrolidine-3-carboxamide (50 mg, 0.17 mmol) according to the procedure for 461. $^1$H NMR (400 MHz, DMSO-$d_6$) δ 8.36 (t, J=5.8 Hz, 1H), 7.94 (d, J=2.8 Hz, 1H), 7.67 (s, 1H), 7.58 (s, 1H), 7.33 (dd, J=9.0, 2.9 Hz, 1H), 7.06-7.00 (m, 2H), 6.82-6.74 (m, 3H), 4.23-4.09 (m, 4H), 3.39 (t, J=8.9 Hz, 1H), 3.27-3.11 (m, 2H), 2.68 (td, J=12.5, 2.5 Hz, 2H), 2.33-2.24 (m, 2H), 2.00 (q, J=6.9, 6.5 Hz, 11H), 1.72 (d, J=12.5 Hz, 2H), 1.17-1.02 (m, 3H), 0.89 (t, J=7.4 Hz, 4H). Mass (m/z): 422.6 $[M+H]^+$.

N-(4-((2-methyl-6-(4-propylpiperidin-1-yl)pyridin-3-yl)amino)benzyl)-5-oxopyrrolidine-3-carboxamide (510)

510

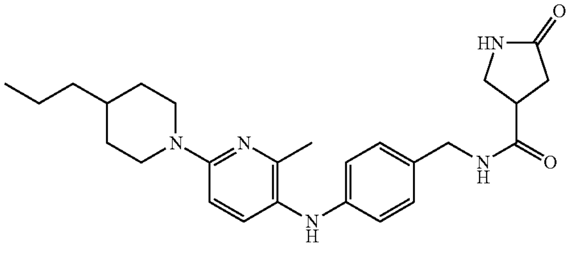

The title compound 510 (28.5 mg) was prepared in a yield of 29.59% as a white powder from 2-methyl-6-(4-propylpiperidin-1-yl)pyridin-3-amine (63 mg, 0.21 mmol) and N-(4-bromobenzyl)-5-oxopyrrolidine-3-carboxamide (50 mg, 0.21 mmol) according to the procedure for 461. $^{1}H$ NMR (400 MHz, DMSO-$d_6$) δ 8.32 (t, J=5.6 Hz, 1H), 7.57 (s, 1H), 7.24 (d, J=8.7 Hz, 11H), 7.19 (s, 11H), 6.98 (d, J=8.4 Hz, 2H), 6.62 (d, J=8.8 Hz, 1H), 6.53-6.46 (m, 2H), 4.22 (d, J=12.8 Hz, 2H), 4.11 (d, J=5.6 Hz, 2H), 3.39 (d, J=8.7 Hz, 2H), 3.26-3.10 (m, 3H), 2.74-2.62 (m, 2H), 2.36-2.21 (m, 3H), 1.99 (dt, J=13.2, 7.3 Hz, 11H), 1.71 (d, J=12.3 Hz, 2H), 1.51-1.37 (m, 1H), 1.32 (p, J=7.3 Hz, 3H), 1.09 (qd, J=12.5, 4.0 Hz, 2H), 0.88 (t, J=7.2 Hz, 4H). Mass (m/z): 450.4 $[M+H]^+$.

5-oxo-N-(4-((2-(3-propylazetidin-1-yl)pyrimidin-5-yl)amino)benzyl)pyrrolidine-3-carboxamide (511)

511

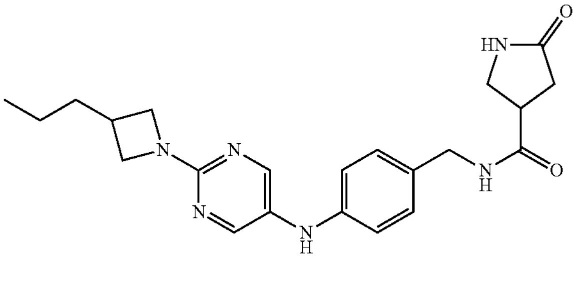

The title compound 511 (14.7 mg) was prepared in a yield of 11.53% as a yellow powder from 2-(3-propylazetidin-1-yl)pyrimidin-5-amine (60 mg, 0.31 mmol) and N-(4-bromobenzyl)-5-oxopyrrolidine-3-carboxamide (97 mg, 0.32 mmol) according to the procedure for 461. $^{1}H$ NMR (400 MHz, DMSO-$d_6$) δ 8.37 (t, J=5.7 Hz, 1H), 7.67-7.55 (m, 2H), 7.35-7.25 (m, 2H), 7.08-7.02 (m, 2H), 6.76-6.66 (m, 2H), 4.14 (d, J=5.8 Hz, 2H), 3.63 (dd, J=8.5, 5.7 Hz, 2H), 2.70-2.62 (m, 1H), 2.37-2.25 (m, 3H), 1.66-1.48 (m, 3H), 0.98-0.81 (m, 5H). Mass (m/z): 409.3 $[M+H]^+$.

N-(4-((2-((1R,4S)-2-azabicyclo[2.2.1]heptan-2-yl)pyrimidin-5-yl)amino)benzyl)-5-oxopyrrolidine-3-carboxamide (512)

512

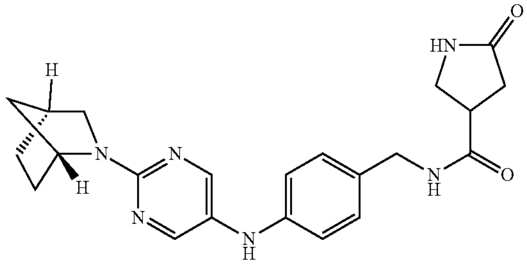

The title compound 512 (34.8 mg) was prepared in a yield of 32.57% as a yellow powder from 2-((1R,4S)-2-azabicyclo[2.2.1]heptan-2-yl)pyrimidin-5-amine (50 mg, 0.26 mmol) and N-(4-bromobenzyl)-5-oxopyrrolidine-3-carboxamide (78 mg, 0.26 mmol) according to the procedure for 461. $^{1}H$ NMR (400 MHz, DMSO-$d_6$) δ 8.34 (t, J=5.8 Hz, 1H), 8.16 (s, 2H), 7.57 (s, 1H), 7.53 (s, 1H), 7.06-6.97 (m, 2H), 6.71-6.64 (m, 2H), 4.54 (s, 1H), 4.12 (d, J=5.7 Hz, 2H), 3.41-3.36 (m, 2H), 3.25-3.08 (m, 3H), 2.60 (s, 1H), 2.33-2.19 (m, 2H), 1.73-1.60 (m, 3H), 1.59-1.52 (m, 1H), 1.46 (dq, J=9.3, 1.5 Hz, 1H), 1.36 (ddd, J=9.4, 7.3, 2.2 Hz, 1H). Mass (m/z): 407.2 $[M+H]^+$ N-(4-((6-(4-isopropylpiperidin-1-yl)-2-methylpyridin-3-yl)amino)phenethyl)-5-oxopyrrolidine-3-carboxamide (513)

513

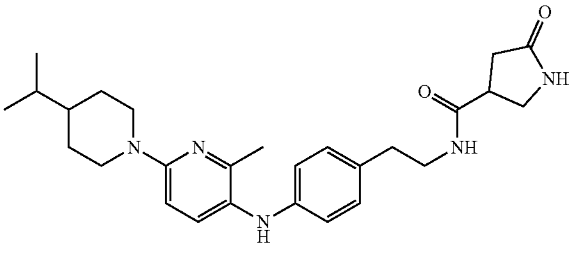

The title compound 513 (18.5 mg) was prepared in a yield of 22.65% as a yellow powder from 6-(4-isopropylpiperidin-1-yl)-2-methylpyridin-3-amine (40 mg, 0.17 mmol) and N-(4-bromophenethyl)-5-oxopyrrolidine-3-carboxamide (50 mg, 0.17 mmol) according to the procedure for 461. $^{1}H$ NMR (400 MHz, DMSO-$d_6$) δ 8.09-7.98 (m, 2H), 7.55 (s, 2H), 6.92 (d, J=8.4 Hz, 2H), 6.63 (d, J=8.7 Hz, 1H), 6.50 (d, J=8.4 Hz, 2H), 4.28 (d, J=12.6 Hz, 2H), 3.24-3.15 (m, 4H), 2.70 (d, J=6.9 Hz, 3H), 2.28-2.22 (m, 4H), 2.21 (s, 3H), 2.01 (dd, J=14.6, 6.9 Hz, 1H), 1.71 (d, J=11.2 Hz, 2H), 1.52-1.39 (m, 2H), 0.89 (d, J=6.8 Hz, 7H). Mass (m/z): 464.3 $[M+H]^+$ N-(3-(4-((6-(4-isopropylpiperidin-1-yl)-2-methylpyridin-3-yl)amino)phenyl)propyl)-5-oxopyrrolidine-3-carboxamide (514)

514

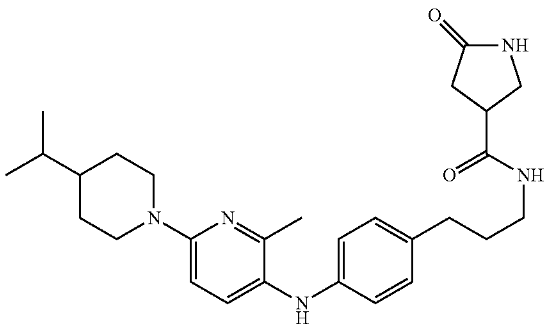

The title compound 514 (16 mg) was prepared in a yield of 19.54% as a yellow powder from 6-(4-isopropylpiperidin-1-yl)-2-methylpyridin-3-amine (40 mg, 0.17 mmol) and N-(3-(4-bromophenyl)propyl)-5-oxopyrrolidine-3-carboxamide (50 mg, 0.17 mmol) according to the procedure for 461. $^1$H NMR (400 MHz, DMSO-$d_6$) δ 7.97 (t, J=5.5 Hz, 1H), 7.55 (s, 1H), 7.26 (d, J=8.7 Hz, 1H), 7.05 (s, 1H), 6.95-6.89 (m, 2H), 6.62 (d, J=8.8 Hz, 1H), 6.53-6.46 (m, 2H), 4.27 (d, J=12.8 Hz, 2H), 3.42-3.35 (m, 1H), 3.20 (dd, J=9.3, 6.5 Hz, 1H), 3.16-3.09 (m, 1H), 3.04 (q, J=6.7 Hz, 2H), 2.63 (t, J=12.1 Hz, 2H), 2.42 (t, J=7.6 Hz, 2H), 2.26 (dd, J=8.5, 2.0 Hz, 2H), 2.20 (s, 3H), 1.70 (d, J=11.1 Hz, 2H), 1.63 (p, J=7.2 Hz, 2H), 1.42 (dt, J=13.0, 6.5 Hz, 1H), 1.26-1.10 (m, 3H), 0.88 (d, J=6.8 Hz, 6H). Mass (m/z): 478.6 $[M+H]^+$.

1-(4-((6-(4-isopropylpiperidin-1-yl)-2-methylpyridin-3-yl)amino)benzyl)urea (515)

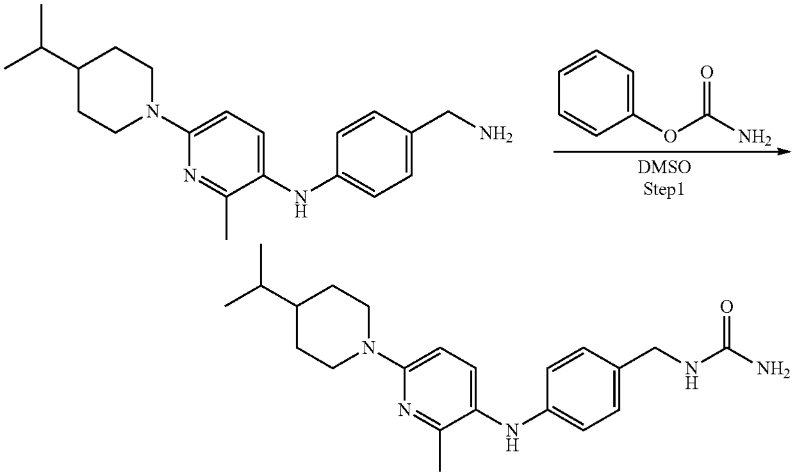

515

To a solution of N-(4-(aminomethyl)phenyl)-6-(4-isopropylpiperidin-1-yl)-2-methylpyridin-3-amine (30 mg, 0.09 mmol) in DMSO (5 mL), phenyl carbamate (24 mg, 0.18 mmol) was added, The resulting solution was stirred for overnight at room temperature. The reaction mixture was added into water (15 mL) and extracted with ethyl acetate (5 mL) 3 times. The organic layer was combined and washed with water, sat·$NaHCO_3$(aq), and brine respectively. Then dried over $MgSO_4$, filtered, and the filtrate concentrated under reduced pressure. The residue was purified by perp-TLC to give desired product 515 (9.4 mg) as pale white powder a yield of 27.80%. $^1$H NMR (400 MHz, DMSO-$d_6$) δ 7.24 (d, J=8.8 Hz, 1H), 7.13 (s, 1H), 7.00-6.94 (m, 2H), 6.62 (d, J=8.8 Hz, 1H), 6.53-6.44 (m, 2H), 6.17 (t, J=5.8 Hz, 1H), 4.27 (d, J=12.8 Hz, 2H), 3.99 (d, J=5.8 Hz, 2H), 2.61 (d, J=12.0 Hz, 2H), 2.19 (s, 3H), 1.69 (d, J=11.2 Hz, 2H), 1.42 (dq, J=13.1, 6.8 Hz, 1H), 1.26-1.07 (m, 3H), 0.87 (d, J=6.8 Hz, 6H). Mass (m/z): 381.2 $[M+H]^+$ N1-(4-((6-(4-isopropylpiperidin-1-yl)-2-methylpyridin-3-yl)amino)benzyl)oxalamide (516)

516

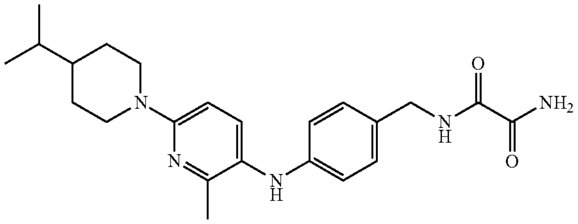

The title compound 516 (7.1 mg) was prepared in a yield of 19.56% as a yellow powder from N-(4-(aminomethyl)phenyl)-6-(4-isopropylpiperidin-1-yl)-2-methylpyridin-3-amine (30 mg, 0.09 mmol) and 2-amino-2-oxoacetic acid (50 mg, 0.15 mmol) according to the procedure for 458. $^1$H NMR (400 MHz, DMSO-$d_6$) δ 9.00 (s, 1H), 8.04 (s, 1H), 7.76 (s, 1H), 7.24 (d, J=8.8 Hz, 1H), 7.16 (d, J=6.7 Hz, 1H), 6.98 (dd, J=11.7, 8.5 Hz, 2H), 6.61 (d, J=9.0 Hz, 1H), 6.48 (dd, J=8.5, 3.2 Hz, 2H), 4.27 (d, J=13.2 Hz, 2H), 4.13 (d, J=6.5 Hz, 1H), 2.61 (d, J=11.9 Hz, 3H), 1.99 (q, J=6.8, 6.1 Hz, 3H), 1.69 (d, J=11.2 Hz, 3H), 1.42 (dd, J=13.2, 6.7 Hz, 3H), 0.87 (d, J=6.7 Hz, 6H). Mass (m/z): 410.5 $[M+H]^+$.

(S)—N-(4-((6-(4-isopropylpiperidin-1-yl)-2-methylpyridin-3-yl)amino)benzyl)-2,6-dioxohexahydropyrimidine-4-carboxamide (517)

517

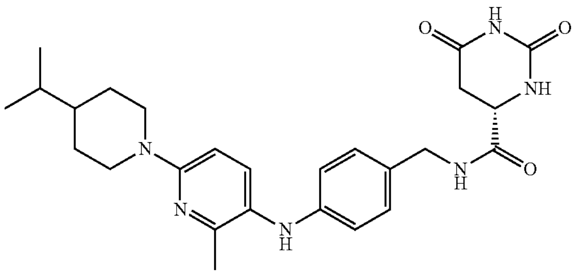

The title compound 517 (6.5 mg) was prepared in a yield of 15.32% as a yellow powder from N-(4-(aminomethyl)phenyl)-6-(4-isopropylpiperidin-1-yl)-2-methylpyridin-3-amine (30 mg, 0.09 mmol) and (S)-2,6-dioxohexahydropyrimidine-4-carboxylic acid (21 mg, 0.15 mmol) according to the procedure for 458. $^1$H NMR (400 MHz, DMSO-$d_6$) δ 10.01 (s, 1H), 8.35 (t, J=5.6 Hz, 1H), 7.59 (s, 1H), 7.26 (d, J=8.7 Hz, 1H), 7.20 (s, 1H), 6.98 (d, J=8.5 Hz, 2H), 6.64 (d, J=8.8 Hz, 1H), 6.50 (d, J=8.5 Hz, 2H), 4.29 (d, J=13.0 Hz, 2H), 4.12 (d, J=5.6 Hz, 2H), 3.99 (dt, J=7.1, 3.4 Hz, 11H), 2.88-2.81 (m, 1H), 2.63 (d, J=11.9 Hz, 2H), 2.20 (s, 3H), 1.71 (d, J=11.4 Hz, 2H), 1.48-1.39 (m, 11H), 1.22-1.12 (m, 4H), 0.89 (d, J=6.8 Hz, 6H). Mass (m/z): 479.3 [M+H]$^+$ N-(4-((6-(4-isopropylpiperidin-1-yl)-2-methylpyridin-3-yl)amino)benzyl)-2-oxopyrrolidine-3-carboxamide (518)

518

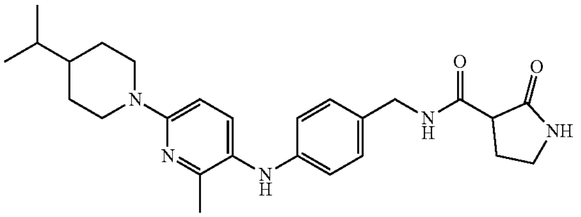

The title compound 518 (11.5 mg) was prepared in a yield of 28.86% as a yellow powder from N-(4-aminomethyl)phenyl)-6-(4-isopropylpiperidin-1-yl)-2-methylpyridin-3-amine (30 mg, 0.09 mmol) and 2-oxopyrrolidine-3-carboxylic acid (17 mg, 0.15 mmol) according to the procedure for 458. $^1$H NMR (400 MHz, DMSO-$d_6$) δ 8.31 (s, 1H), 7.79 (s, 1H), 7.23 (d, J=34.0 Hz, 2H), 7.01 (d, J=8.2 Hz, 2H), 6.65 (s, 1H), 6.50 (d, J=8.1 Hz, 2H), 4.26 (d, J=12.9 Hz, 2H), 4.16-4.05 (m, 2H), 3.61 (dtd, J=13.2, 6.6, 4.1 Hz, 2H), 3.24 (td, J=8.9, 4.0 Hz, 2H), 3.13 (qd, J=7.3, 4.2 Hz, 3H), 2.28-2.09 (m, 5H), 1.70 (d, J=11.4 Hz, 2H), 1.48-1.36 (m, 2H), 0.87 (d, J=6.8 Hz, 6H). Mass (m/z): 450.3 [M+H]$^+$.

(R)—N-(4-((6-(4-isopropylpiperidin-1-yl)-2-methylpyridin-3-yl)amino)benzyl)pyrrolidine-2-carboxamide (519)

519

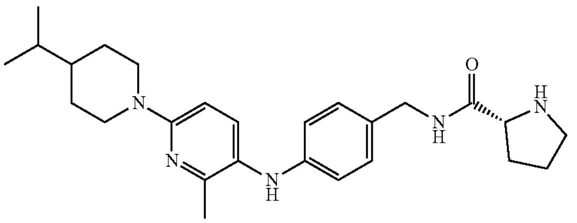

The title compound 519 (6.8 mg) was prepared in a yield of 17.61% as a yellow powder from N-(4-(aminomethyl)phenyl)-6-(4-isopropylpiperidin-1-yl)-2-methylpyridin-3-amine (30 mg, 0.09 mmol) and (R)-2-oxopyrrolidine-3-carboxylic acid (15 mg, 0.15 mmol) according to the procedure for 458. $^1$H NMR (400 MHz, DMSO-$d_6$) δ 8.02 (s, 1H), 7.35 (s, 1H), 7.26 (d, J=8.9 Hz, 1H), 7.09 (d, J=8.3 Hz, 2H), 6.65 (d, J=8.8 Hz, 1H), 6.55 (d, J=8.3 Hz, 2H), 4.30 (d, J=12.9 Hz, 2H), 4.18 (d, J=5.4 Hz, 2H), 2.64 (d, J=11.8 Hz, 2H), 2.19 (s, 3H), 2.04-1.95 (m, 1H), 1.71 (d, J=11.6 Hz, 2H), 1.51-1.39 (m, 1H), 1.33-1.23 (m, 6H), 1.23-1.10 (m, 3H), 0.89 (d, J=6.8 Hz, 6H). Mass (m/z): 436.4 [M+H]$^+$ (S)—N-(4-((6-(4-isopropylpiperidin-1-yl)-2-methylpyridin-3-yl)amino)benzyl)-6-oxopiperidine-2-carboxamide (520)

520

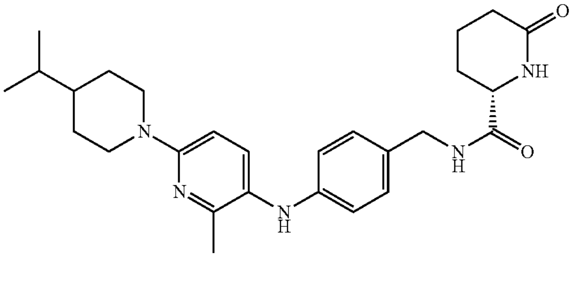

The title compound 520 (12.4 mg) was prepared in a yield of 30.18% as a yellow powder from N-(4-(aminomethyl)phenyl)-6-(4-isopropylpiperidin-1-yl)-2-methylpyridin-3-amine (30 mg, 0.09 mmol) and (S)-2-oxopyrrolidine-3-carboxylic acid (19 mg, 0.15 mmol) according to the procedure for 458. $^1$H NMR (400 MHz, DMSO-$d_6$) δ 8.25 (t, J=5.9 Hz, 1H), 7.47 (d, J=2.6 Hz, 1H), 7.24 (d, J=8.8 Hz, 1H), 7.16 (s, 1H), 7.02-6.96 (m, 2H), 6.62 (d, J=8.8 Hz, 1H), 6.51-6.45 (m, 2H), 4.27 (d, J=12.8 Hz, 2H), 4.12 (qd, J=14.6, 5.8 Hz, 2H), 3.86 (td, J=5.6, 2.7 Hz, 1H), 2.61 (d, J=11.9 Hz, 2H), 2.18 (s, 3H), 2.11 (t, J=6.5 Hz, 2H), 1.84 (dq, J=9.5, 5.1, 4.7 Hz, 1H), 1.68 (ddd, J=12.9, 8.6, 4.8 Hz, 4H), 1.63-1.51 (m, 1H), 1.46-1.36 (m, 1H), 1.20-1.07 (m, 3H), 0.87 (d, J=6.7 Hz, 6H). Mass (m/z): 464.5 [M+H]$^+$ N-(4-((3,5-dimethyl-4-(4-(trifluoromethyl)piperidin-1-yl)phenyl)amino)benzyl)-5-oxopyrrolidine-3-carboxamide (521)

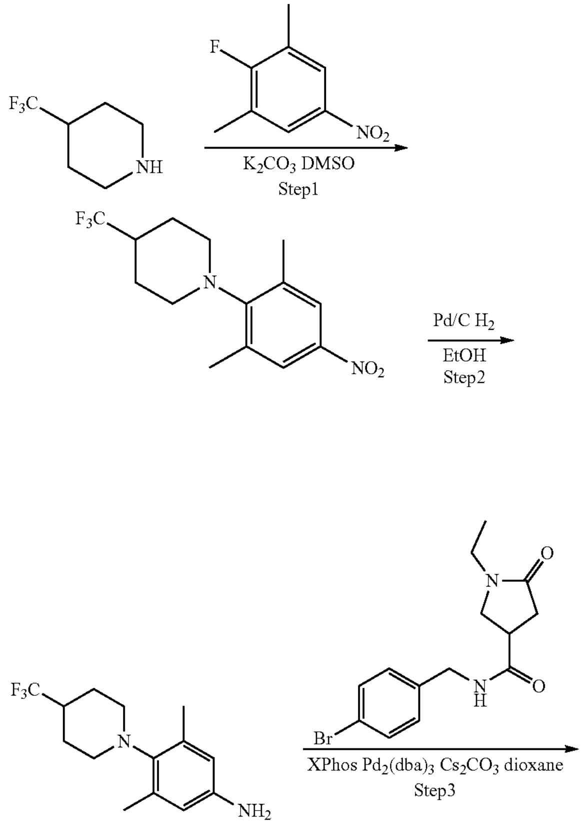

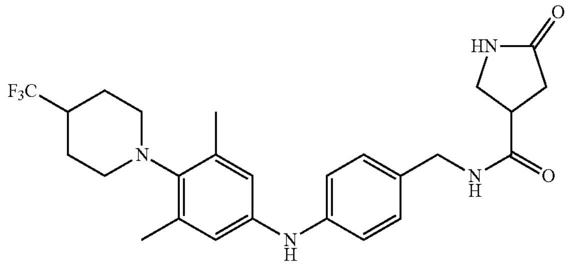

521

Step 1. Preparation of 1-(2,6-dimethyl-4-nitrophenyl)-4-(trifluoromethyl)piperidine. To a solution of 4-(trifluoromethyl)piperidine (2.0 g, 13.06 mmol) and 2-fluoro-1,3-dimethyl-5-nitrobenzene (2.21 g, 13.06 mmol) in DMF (30 mL), $K_2CO_3$ (5.11 g, 15.67 mmol) was added, The resulting solution was stirred for overnight at 165° C. with microwave. The reaction mixture was added into water (150 mL) drop by drop with stirring. The precipitate was filtered, cake was wash with water 3 times and dry in vacuo. The residue was purified by silica gel column chromatography (petroleum ether/AcOEt, 10/1) to give 1.3 g of 1-(2,6-dimethyl-4-nitrophenyl)-4-(trifluoromethyl)piperidine as pale yellow solid in a in a yield of 32.93%. Mass (m/z): 303.5 $[M+H]^+$ Step 2. Preparation of 3,5-dimethyl-4-(4-(trifluoromethyl)piperidin-1-yl)aniline. To a solution of 1-(2,6-dimethyl-4-nitrophenyl)-4-(trifluoromethyl)piperidine (1.3 g, 4.3 mmol) in ethanol (50 mL), a suspension of palladium on carbon (130 mg, 0.1 equivs) was added under argon atmosphere. Hydrogen was bubbled for 10 min with balloon. The resulting mixture was stirred for overnight at the same temperature under hydrogen atmosphere. The completion reaction mixture was bubbled by argon with balloon afterwards added celite, filtered with celite, the cake was washed with ethanol. The filtrate was concentrated under reduced pressure. The residue was purified by silica gel column chromatography (petroleum ether/AcOEt, 1/1 to 0/1) to give 920 mg of 3,5-dimethyl-4-(4-(trifluoromethyl)piperidin-1-yl)aniline as brown oil in a yield of 78.56%. Mass (m/z): 273.3 $[M+H]^+$.

Step 3. Preparation of N-(4-((3,5-dimethyl-4-(4-(trifluoromethyl)piperidin-1-yl)phenyl)amino)benzyl)-5-oxopyrrolidine-3-carboxamide (521). The title compound 521 (7.4 mg) was prepared in a yield of 5.89% as a white powder from 3,5-dimethyl-4-(4-(trifluoromethyl)piperidin-1-yl)aniline (70 mg, 0.26 mmol) and N-(4-bromobenzyl)-5 -oxopyrrolidine-3-carboxamide (84 mg, 0.28 mmol) according to the procedure for 461. $^1$H NMR (400 MHz, DMSO-$d_6$) δ 8.37 (t, J=5.8 Hz, 1H), 7.86 (s, 1H), 7.58 (s, 1H), 7.09 (d, J=8.6 Hz, 2H), 7.01-6.94 (m, 2H), 6.72 (d, J=2.6 Hz, 1H), 6.61 (d, J=2.7 Hz, 1H), 4.18 (d, J=5.7 Hz, 2H), 3.44-3.38 (m, 1H), 3.30-3.22 (m, 2H), 3.21-3.12 (m, 3H), 2.90 (d, J=11.7 Hz, 2H), 2.31 (dd, J=8.4, 4.3 Hz, 2H), 2.20 (d, J=10.3 Hz, 6H), 1.82 (d, J=12.1 Hz, 2H), 1.56 (qd, J=12.0, 4.2 Hz, 2H). Mass (m/z): 489.3 $[M+H]^+$ N-(4-((6-(4-ethoxypiperidin-1-yl)-2-methylpyridin-3-yl)amino)benzyl)-5-oxopyrrolidine-3-carboxamide (522)

522

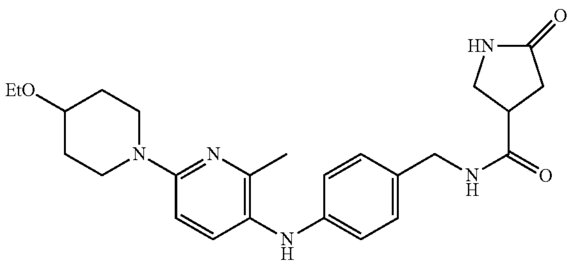

The title compound 522 (18.5 mg) was prepared in a yield of 18.84% as a yellow powder from 6-(4-ethoxypiperidin-1-yl)-2-methylpyridin-3-amine (70 mg, 0.30 mmol) and N-(4-bromobenzyl)-5-oxopyrrolidine-3-carboxamide (88 mg, 0.30 mmol) according to the procedure for 461. $^1$H NMR (400 MHz, DMSO-$d_6$) δ 8.31 (t, J=5.7 Hz, 1H), 7.57 (s, 11H), 7.26 (d, J=8.7 Hz, 1H), 7.20 (s, 1H), 7.01-6.93 (m, 2H), 6.66 (d, J=8.7 Hz, 1H), 6.54-6.47 (m, 2H), 4.12 (d, J=5.7 Hz, 2H), 3.95 (dt, J=12.8, 4.3 Hz, 2H), 3.49 (q, J=7.0 Hz, 3H), 3.39 (t, J=9.0 Hz, 1H), 3.26-3.19 (m, 1H), 3.18-3.13 (m, 1H), 3.02 (ddd, J=13.1, 10.1, 3.0 Hz, 2H), 2.28 (dd, J=8.4, 5.2 Hz, 2H), 2.20 (s, 3H), 1.94-1.83 (m, 2H), 1.41 (dtd, J=13.0, 9.4, 3.9 Hz, 2H), 1.12 (t, J=7.0 Hz, 3H). Mass (m/z): 452.4 $[M+H]^+$ 2-oxo-N-(4-((4-(4-(trifluoromethyl)piperidin-1-yl) phenyl)amino)benzyl) piperidine-4-carboxamide (523)

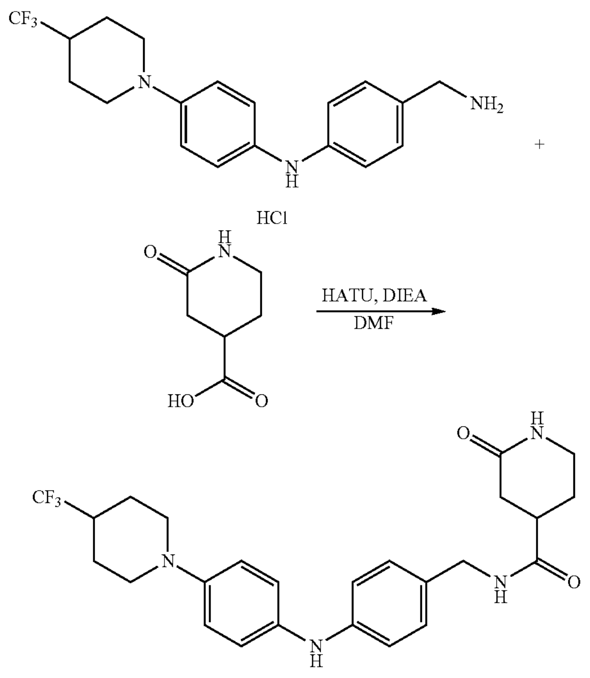

DMF

523

To a solution of 4-(aminomethyl)-N-(4-(4-(trifluoromethyl)piperidin-1-yl)phenyl) aniline hydrochloride (50 mg, 0.145 mmol) and 2-oxopiperidine-4-carboxylic acid (27 mg, 0.188 mmol) in DMF (3 mL) was added HATU (72 mg, 0.188 mmol) and DIEA (25 mg, 0.188 mmol), then the mixture was stirred at room temperature for 2 h. The mixture was extracted by EA (25 mL×3). The combined organic layers were washed with brine (15 mL×3), dried over Na2SO4 and concentrated to give the crude product, which was purified by prep-HPLC to give the desired product as white solid (32.8 mg, 47.7%). $^1$H NMR (400 MHz, DMSO-$d_6$) δ 8.29 (t, J=5.6 Hz, 1H), 7.76 (s, 1H), 7.41 (s, 1H), 6.97 (d, J=8.4 Hz, 2H), 6.93-6.88 (m, 2H), 6.82 (dd, J=8.8, 2.4 Hz, 4H), 4.15-4.00 (m, 2H), 3.54 (d, J=12.0 Hz, 2H), 3.05 (tdd, J=16.4, 9.5, 4.2 Hz, 2H), 2.65-2.50 (m, 4H), 2.36 (dtd, J=12.4, 8.4, 3.6 Hz, 1H), 2.24-2.10 (m, 2H), 1.80 (td, J=11.1, 8.4, 3.5 Hz, 3H), 1.53 (tdd, J=25.2, 12.8, 4.8 Hz, 3H). Mass (m/z): 475.3 [M+H]$^+$.

6-oxo-N-(4-((4-(4-(trifluoromethyl)piperidin-1-yl) phenyl)amino)benzyl) piperidine-3-carboxamide (524)

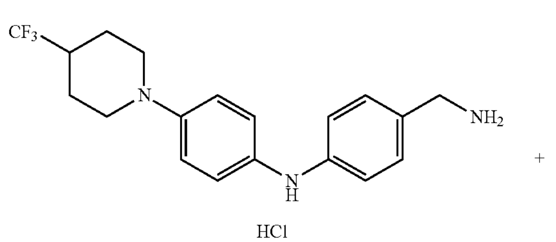

-continued

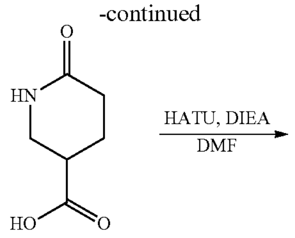

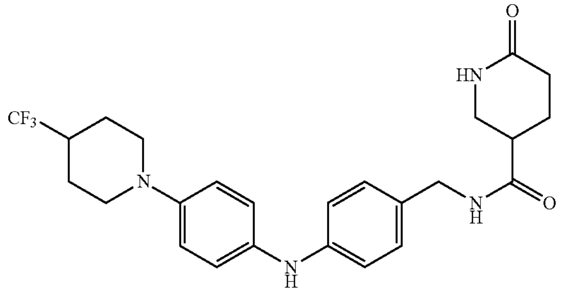

524

The title compound 524 (24.6 mg) was prepared in a total yield of 35.8% as a white solid from 4-(aminomethyl)-N-(4-(4-(trifluoromethyl)piperidin-1-yl)phenyl) aniline hydrochloride (50 mg, 0.145 mmol), 6-oxopiperidine-3-carboxylic acid (27 mg, 0.188 mmol), HATU (72 mg, 0.188 mmol), DIEA (25 mg, 0.188 mmol) and DMF (3 mL) according to the procedure for 523. $^1$H NMR (400 MHz, DMSO-$d_6$) δ 8.37 (t, J=5.6 Hz, 1H), 7.80 (s, 1H), 7.45 (d, J=10.0 Hz, 1H), 7.04 (d, J=8.4 Hz, 2H), 7.00-6.94 (m, 2H), 6.92-6.85 (m, 4H), 4.21-4.09 (m, 2H), 3.62 (d, J=12.4 Hz, 2H), 3.25-3.19 (m, 2H), 2.68-2.57 (m, 3H), 2.43 (dd, J=8.4, 4.0 Hz, 1H), 2.17 (ddd, J=13.2, 10.4, 6.4 Hz, 2H), 1.88 (dd, J=11.2, 5.2 Hz, 3H), 1.84-1.77 (m, 1H), 1.57 (qd, J=12.4, 4.0 Hz, 2H). Mass (m/z): 475.3 [M+H]$^+$.

N-(4-((4-(diethylamino)phenyl)amino)benzyl)-5-oxopyrrolidine-3-carboxamide (525)

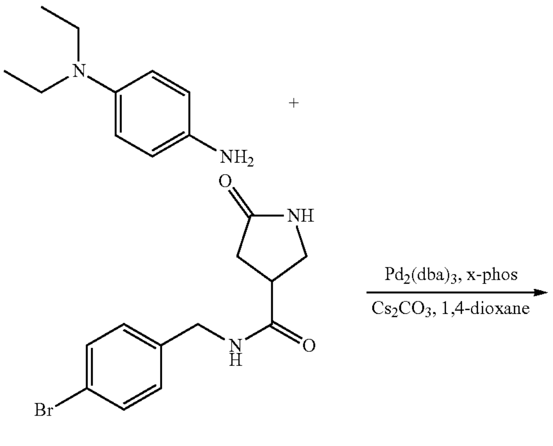

-continued

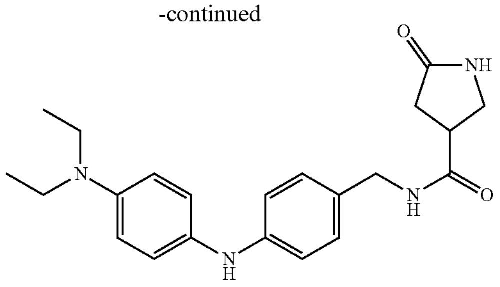

525

To a solution of N1,N1-diethylbenzene-1,4-diamine (33 mg, 0.202 mmol) and N-(4-bromobenzyl)-5-oxopyrrolidine-3-carboxamide (50 mg, 0.168 mmol), in 1,4-dioxane (5 mL) was added Pd2(dba)$_3$ (2 mg, 0.002 mmol), x-phos (6 mg, 0.01 mmol) and $Cs_2CO_3$ (83 mg, 0.252 mmol), then the mixture was stirred at 110° C. for 16 h. The mixture was extracted by EA (25 mL×3). The combined organic layers were washed with brine (15 mL×3), dried over Na2SO4 and concentrated to give the crude product, which was purified by TLC (MeOH/DCM=1/15) to give the desired product as light green solid (11.7 mg, 18.3%). 1H NMR (400 MHz, DMSO-d6) δ 8.34 (t, J=5.6 Hz, 1H), 7.57 (d, J=5.6 Hz, 2H), 7.01 (d, J=8.0 Hz, 2H), 6.94 (d, J=8.4 Hz, 2H), 6.78 (d, J=8.0 Hz, 2H), 6.65 (d, J=8.4 Hz, 2H), 4.13 (d, J=5.6 Hz, 2H), 3.40 (s, 1H), 3.31-3.12 (m, 6H), 2.29 (dd, J=8.4, 5.0 Hz, 2H), 1.06 (t, J=7.2 Hz, 6H). Mass (m/z): 381.3 $[M+H]^+$.

N-(4-((4-(4-fluoropiperidin-1-yl)phenyl)amino)benzyl)-5-oxopyrrolidine-3-carboxamide (526)

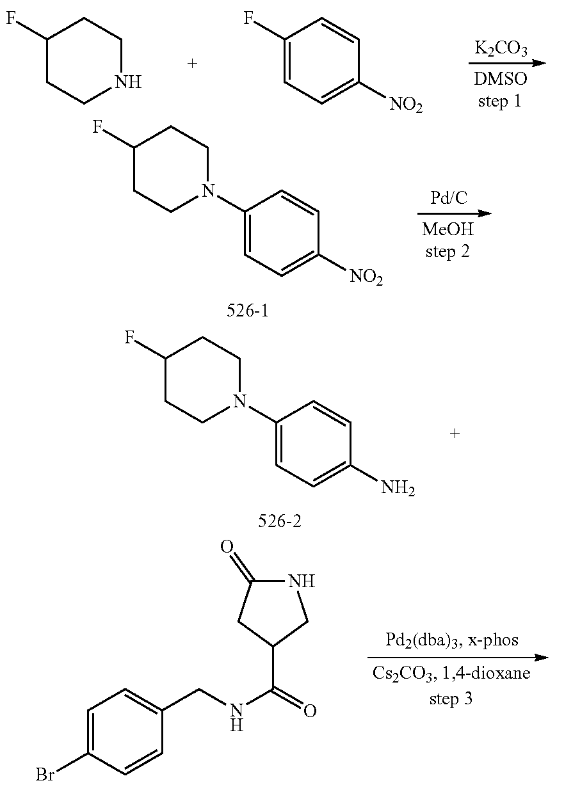

-continued

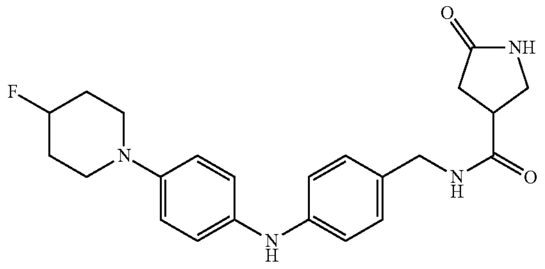

526

Step 1. 4-fluoro-1-(4-nitrophenyl)piperidine: (526-1). To a solution of 4-fluoropiperidine (357 mg, 2.55 mmol) and 1-fluoro-4-nitrobenzene (300 mg, 2.13 mmol) in DMSO (5 mL) was added K2CO3 (440 mg, 3.20 mmol). Then the reaction was stirred overnight at 80° C. The mixture was extracted by EA (25 mL×3). The combined organic layers were washed with brine (15 mL×3), dried over Na2SO4 and concentrated to give the crude product, which was purified by silica gel chromatography (EA/PE=1:3) to give the desired product as a yellow solid (454 mg, 95%). Mass (m/z): 225.2 $[M+H]^+$.

Step 2. 4-(4-fluoropiperidin-1-yl)aniline: (526-2). To a solution of 4-fluoro-1-(4-nitrophenyl)piperidine (454 mg, 2.03 mmol) in MeOH (10 mL) was added Pd/C (50 mg). The solution was stirred for 3 hours at room temperature under $H_2$. The reaction mixture was filtered and concentrated under vacuum to afford the desired product as a purple solid. (310 mg, 79%). Mass (m/z): 195.3 $[M+H]^+$.

Step 3. N-(4-((4-(4-fluoropiperidin-1-yl)phenyl)amino)benzyl)-5-oxopyrrolidine-3-carboxamide: (526). The title compound 526 (18.9 mg) was prepared in a total yield of 27.4% as a white solid from 4-(4-fluoropiperidin-1-yl)aniline (39 mg, 0.202 mmol), N-(4-bromobenzyl)-5-oxopyrrolidine-3-carboxamide (50 mg, 0.168 mmol), $Pd_2(dba)_3$ (2 ng, 0.002 mmol), x-phos (6 mg, 0.01 mmol) and $Cs_2CO_3$ (83 mg, 0.252 mmol) and 1,4-dioxane (5 mL) according to the procedure for 525. $^1H$ NMR (400 MHz, DMSO-$d_6$) δ 8.45 (dt, J=71.2, 5.6 Hz, 1H), 7.59 (d, J=5.6 Hz, 1H), 7.55-7.49 (m, 1H), 7.24-7.18 (m, 1H), 7.05 (d, J=8.4 Hz, 1H), 6.99-6.94 (m, 1H), 6.93-6.83 (m, 2H), 4.81 (dtt, J=49.2, 7.2, 3.6 Hz, 1H), 4.25 (d, J=5.6 Hz, 1H), 4.15 (d, J=5.6 Hz, 1H), 3.45-3.37 (m, 1H), 3.29-3.12 (m, 3H), 3.00 (ddd, J=12.0, 7.6, 3.6 Hz, 1H), 2.37-2.26 (m, 2H), 2.04-1.92 (m, 11H), 1.81 (dqd, J=14.8, 7.6, 4.0 Hz, 1H). Mass (m/z): 411.3 $[M+H]^+$.

1-ethyl-N-(4-((4-(4-fluoropiperidin-1-yl)phenyl)amino)benzyl)-5-oxopyrrolidine-3-carboxamide (527)

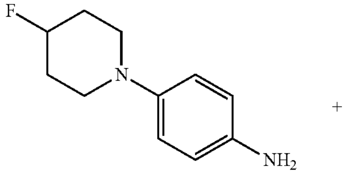

+

-continued

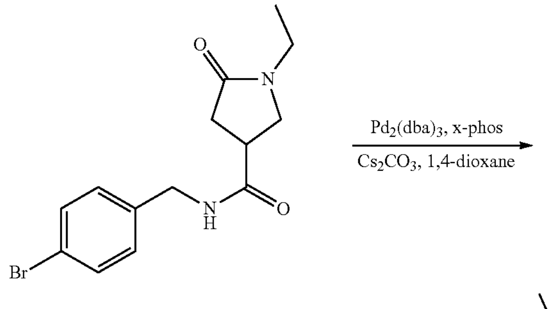

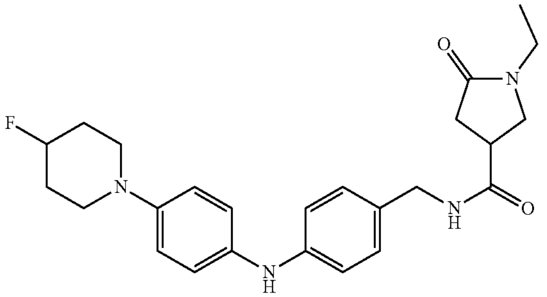

527

The title compound 527 (43.1 mg) was prepared in a total yield of 63.8% as a light green solid from 4-(4-fluoropiperidin-1-yl)aniline (36 mg, 0.185 mmol), N-(4-bromobenzyl)-1-ethyl-5-oxopyrrolidine-3-carboxamide (50 mg, 0.154 mmol), $Pd_2(dba)_3$ (2 mg, 0.002 mmol), x-phos (6 mg, 0.01 mmol) and $Cs_2CO_3$ (76 mg, 0.231 mmol) and 1,4-dioxane (5 mL) according to the procedure for 525. $^1H$ NMR (400 MHz, DMSO-$d_6$) δ 8.46 (t, J=5.6 Hz, 1H), 7.81 (s, 1H), 7.09-7.02 (m, 2H), 6.99-6.95 (m, 2H), 6.92-6.86 (m, 4H), 4.81 (dtt, J=49.2, 7.2, 3.6 Hz, 1H), 4.16 (d, J=5.6 Hz, 2H), 3.51 (t, J=9.2 Hz, 1H), 3.34 (d, J=4.0 Hz, 1H), 3.26-3.10 (m, 5H), 2.99 (ddd, J=12.0, 7.6, 3.6 Hz, 2H), 2.41 (d, J=8.4 Hz, 2H), 2.06-1.89 (m, 2H), 1.87-1.73 (m, 2H), 1.00 (t, J=7.2 Hz, 3H). Mass (m/z): 439.3 $[M+H]^+$.

1-isopropyl-5-oxo-N-(4-((4-(4-(trifluoromethyl)piperidin-1-yl)phenyl)amino)benzyl)pyrrolidine-3-carboxamide (528)

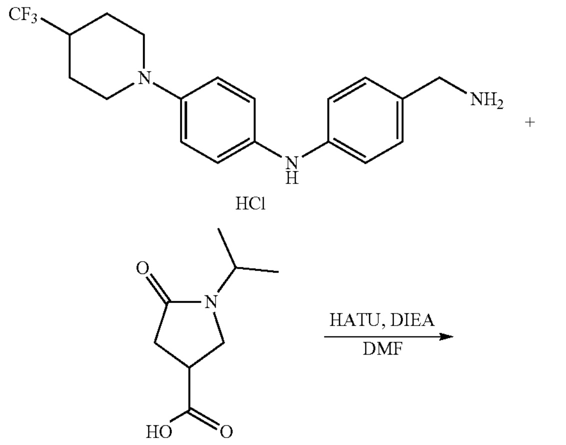

-continued

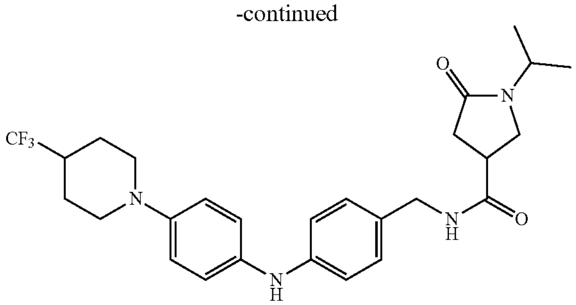

528

The title compound 528 (17.3 mg) was prepared in a total yield of 22.0% as a blue solid from 4-(aminomethyl)-N-(4-(4-(trifluoromethyl)piperidin-1-yl)phenyl) aniline hydrochloride (50 mg, 0.145 mmol), 1-isopropyl-5-oxopyrrolidine-3-carboxylic acid (32 mg, 0.188 mmol), HATU (72 mg, 0.188 mmol), DIEA (25 mg, 0.188 mmol) and DMF (3 mL) according to the procedure for 523. $^1H$ NMR (400 MHz, DMSO-$d_6$) δ 8.41 (t, J=5.6 Hz, 1H), 7.83 (s, 1H), 7.17-6.63 (m, 8H), 4.12 (p, J=6.8 Hz, 2H), 3.62 (s, 2H), 3.47 (t, J=9.2 Hz, 3H), 3.30 (dd, J=9.6, 6.4 Hz, 3H), 3.08 (td, J=8.4, 6.4 Hz, 1H), 2.41 (d, J=8.4 Hz, 2H), 2.01-1.81 (m, 2H), 1.66-1.44 (m, 2H), 1.05 (t, J=6.4 Hz, 6H). Mass (m/z): 503.3 $[M+H]^+$.

N-(4-((4-(diethylamino)phenyl)amino)benzyl)-1-ethyl-5-oxopyrrolidine-3-carboxamide (529)

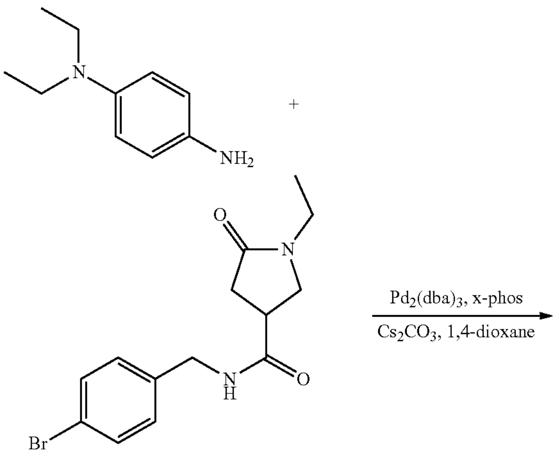

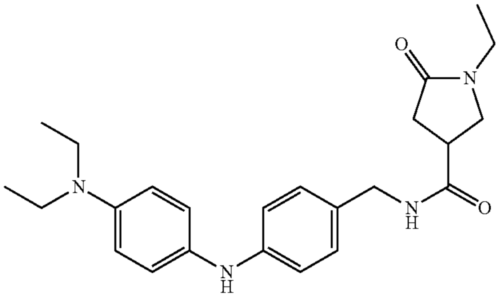

529

The title compound 529 (23.4 mg) was prepared in a total yield of 37.3% as a blue solid from N1,N1-diethylbenzene-1,4-diamine (30 mg, 0.185 mmol), N-(4-bromobenzyl)-1- ethyl-5-oxopyrrolidin-3-carboxamide (50 mg, 0.154 mmol), $Pd_2$(dba). (2 mg, 0.002 mmol), x-phos (6 mg, 0.01 mmol) and $Cs_2CO_3$ (76 mg, 0.231 mmol) and 1,4-dioxane (5 mL) according to the procedure for 525. $^1$H NMR (400 MHz, DMSO-$d_6$) δ 11.47 (s, 1H), 8.52 (s, 2H), 7.57-6.93 (m, 8H), 4.22 (s, 2H), 3.53 (t, J=9.2 Hz, 3H), 3.38 (dd, J=9.6, 6.3 Hz, 2H), 3.26-3.08 (m, 4H), 2.42 (dd, J=8.4, 2.4 Hz, 2H), 1.01 (t, J=7.2 Hz, 9H). Mass (n/z): 409.3 [M+H]$^+$.

N-(4-((4-(2-azaspiro[3.3]heptan-2-yl)phenyl)amino) benzyl)-5-oxopyrrolidine-3-carboxamide (530)

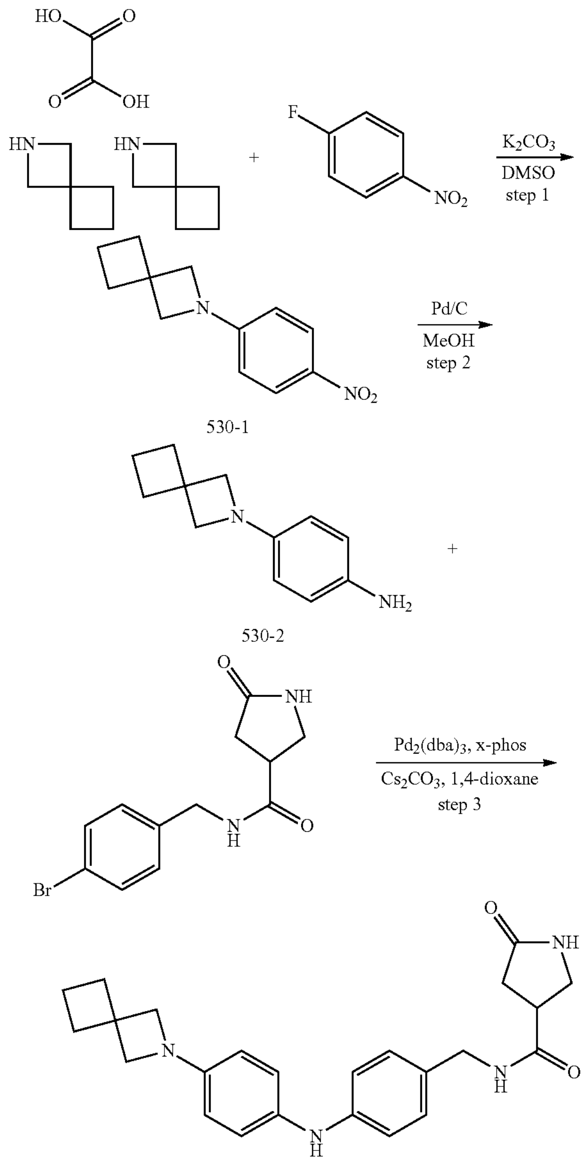

530

Step 1. 2-(4-nitrophenyl)-2-azaspiro[3.3]heptane: (530-1). The title compound 530-1 (1 g) was prepared in a total yield of 97.7% as a yellow solid from 2-azaspiro[3.3] heptane hemioxalate (800 mg, 2.817 mmol) and 1-fluoro-4-nitrobenzene (662 mg, 4.695 mmol) according to the procedure for 526-1. Mass (m/z): 219.2 [M+H]$^+$.

Step 2. 4-(2-azaspiro[3.3]heptan-2-yl)aniline: (530-2). The title compound 530-2 (836 mg) was prepared in a total yield of 96% as a purple solid from 2-(4-nitrophenyl)-2-azaspiro[3.3]heptane (1 g, 4.587 mmol) according to the procedure for 526-2. Mass (m/z): 189.3 [M+H]$^+$.

Step 3. 4-((4-((1R,4S)-2-azabicyclo[2.2.1]heptan-2-yl) phenyl)amino)benzaldehyde (530). The title compound 530 (10.1 mg) was prepared in a total yield of 14.9% as a white solid from 4-(2-azaspiro[3.3]heptan-2-yl)aniline (38 mg, 0.202 mmol), N-(4-bromobenzyl)-5-oxopyrrolidine-3-carboxamide (50 mg, 0.168 mmol), $Pd_2(dba)_3$ (2 mg, 0.002 mmol), x-phos (6 mg, 0.01 mmol) and $Cs_2CO_3$ (83 mg, 0.252 mmol) and 1,4-dioxane (5 mL) according to the procedure for 525. $^1$H NMR (400 MHz, DMSO-$d_6$) δ 8.34 (t, J=5.6 Hz, 1H), 7.59 (d, J=13.6 Hz, 2H), 7.01 (d, J=8.4 Hz, 2H), 6.97-6.88 (m, 2H), 6.78 (d, J=8.4 Hz, 2H), 6.42-6.30 (m, 2H), 4.13 (d, J=5.6 Hz, 2H), 3.70 (s, 4H), 3.41 (d, J=9.2 Hz, 1H), 3.26-3.17 (m, 2H), 2.29 (dd, J=8.4, 4.4 Hz, 2H), 2.16 (t, J=7.6 Hz, 4H), 1.82 (p, J=7.6 Hz, 2H). Mass (m/z): 405.3 [M+H]$^+$.

N-(4-((4-(2-azaspiro[3.3]heptan-2-yl)phenyl)amino) benzyl)-1-ethyl-5-oxopyrrolidine-3-carboxamide (531)

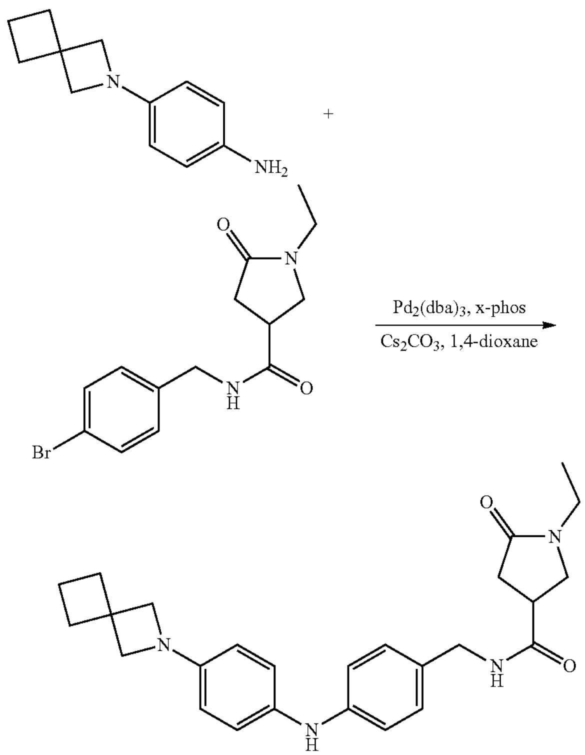

531

The title compound 531 (52.4 mg) was prepared in a total yield of 78.8% as a brown solid from 4-(2-azaspiro[3.3] heptan-2-yl)aniline (38 mg, 0.185 mmol), N-(4-bromobenzyl)-1-ethyl-5-oxopyrrolidine-3-carboxamide (50 mg, 0.154 mmol), $Pd_2(dba)_3$ (2 mg, 0.002 mmol), x-phos (6 mg, 0.01 mmol) and $Cs_2CO_3$ (76 mg, 0.231 mmol) and 1,4-dioxane (5 mL) according to the procedure for 525. $^1$H NMR (400 MHz, DMSO-$d_6$) δ 8.39 (t, J=5.6 Hz, 1H), 7.62 (s, 1H), 7.04-6.98 (m, 2H), 6.96-6.90 (m, 2H), 6.82-6.76 (m, 2H), 6.40-6.34 (m, 2H), 4.14 (d, J=5.6 Hz, 2H), 3.70 (s, 4H), 3.50 (t, J=9.2 Hz, 1H), 3.37 (d, J=6.4 Hz, 1H), 3.23-3.05 (m, 3H), 2.44-2.36 (m, 2H), 2.16 (t, J=7.6 Hz, 4H), 1.87-1.77 (m, 2H), 1.00 (t, J=7.2 Hz, 3H). Mass (m/z): 433.3 $[M+H]^+$.

N-(4-((4-(azetidin-1-yl)phenyl)amino)benzyl)-5-oxopyrrolidine-3-carboxamide (532)

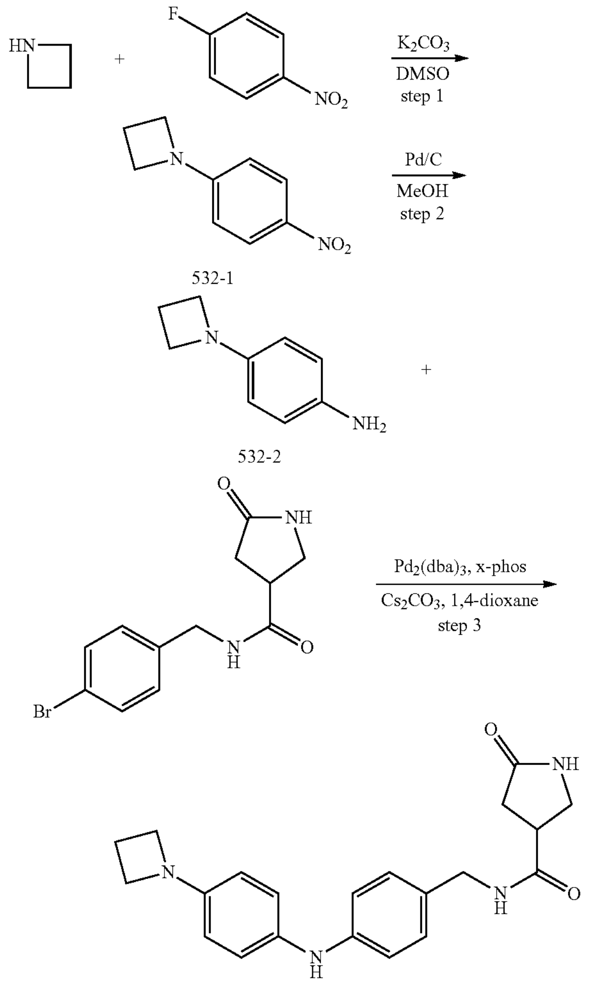

532-1
532-2
532

Step 1. 1-(4-nitrophenyl)azetidine: (532-1). The title compound 532-1 (995 mg) was prepared in a total yield of 79% as a yellow solid from 1-fluoro-4-nitrobenzene (1 g, 7.09 mmol) and azetidine (445 mg, 7.80 mmol) according to the procedure for 526-1. Mass (m/z): 279.2 $[M+H]^+$.

Step 2. 4-(azetidin-1-yl)aniline: (532-2). The title compound 532-2 (788 mg) was prepared in a total yield of 95% as a purple solid from 1-(4-nitrophenyl)azetidine (995 g, 5.59 mmol) according to the procedure for 526-2. Mass (m/z): 149.3 $[M+H]^+$.

Step 3. N-(4-((4-(azetidin-1-yl)phenyl)amino)benzyl)-5-oxopyrrolidine-3-carboxamide: (532). The title compound 532 (12.7 mg) was prepared in a total yield of 20.8% as a brown solid from 4-(azetidin-1-yl)aniline (30 mg, 0.202 mmol), N-(4-bromobenzyl)-5-oxopyrrolidine-3-carboxamide (50 mg, 0.168 mmol), $Pd_2(dba)_3$ (2 mg, 0.002 mmol), x-phos (6 mg, 0.01 mmol) and $Cs_2CO_3$ (83 mg, 0.252 mmol) and 1,4-dioxane (5 mL) according to the procedure for 525. $^1H$ NMR (300 MHz, DMSO-$d_6$) δ 8.33 (d, J=5.7 Hz, 1H), 7.57 (s, 2H), 7.09-6.64 (m, 8H), 6.36 (s, 1H), 4.12 (s, 2H), 3.72 (s, 3H), 3.40 (d, J=8.4 Hz, 2H), 3.27-3.10 (m, 3H), 2.33-2.23 (m, 3H). Mass (m/z): 365.3 $[M+H]^+$.

N-(4-((4-(azetidin-1-yl)phenyl)amino)benzyl)-1-ethyl-5-oxopyrrolidine-3-carboxamide (533)

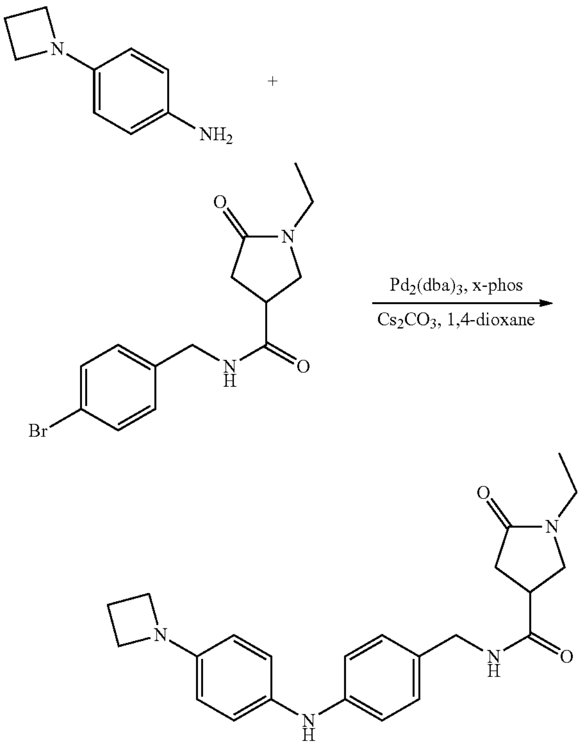

533

The title compound 533 (26.6 mg) was prepared in a total yield of 44.0% as a blue solid from 4-(azetidin-1-yl)aniline (27 mg, 0.185 mmol), N-(4-bromobenzyl)-1-ethyl-5-oxopyrrolidine-3-carboxamide (50 mg, 0.154 mmol), $Pd_2(dba)_3$ (2 mg, 0.002 mmol), x-phos (6 mg, 0.01 mmol) and $Cs_2CO_3$ (76 mg, 0.231 mmol) and 1,4-dioxane (5 mL) according to the procedure for 525. $^1H$ NMR (300 MHz, DMSO-$d_6$) δ 8.33 (d, J=5.7 Hz, 1H), 7.57 (s, 2H), 7.09-6.64 (m, 8H), 4.24 (s, 3H), 3.51 (td, J=9.0, 1.8 Hz, 2H), 3.41-3.32 (m, 2H), 3.23-3.09 (m, 5H), 2.44-2.37 (m, 3H), 1.00 (t, J=7.2 Hz, 3H). Mass (m/z): 393.3 $[M+H]^+$.

N-(4-((4-butoxyphenyl)amino)benzyl)-5-oxopyrrolidine-3-carboxamide (534)

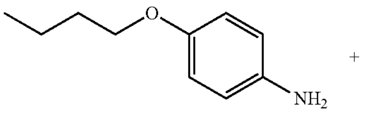

-continued

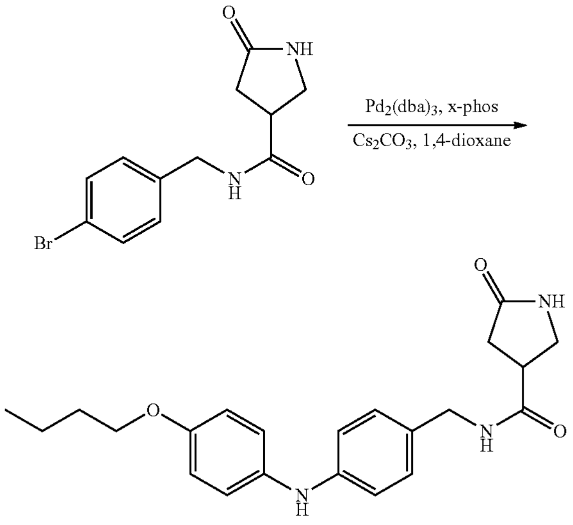

534

The title compound 534 (3.7 mg) was prepared in a total yield of 5.8% as a white solid from 4-butoxyaniline (33 mg, 0.202 mmol), N-(4-bromobenzyl)-5-oxopyrrolidine-3-carboxamide (50 mg, 0.168 mmol), $Pd_2(dba)_3$ (2 mg, 0.002 mmol), x-phos (6 mg, 0.01 mmol) and $Cs_2CO_3$ (83 mg, 0.252 mmol) and 1,4-dioxane (5 mL) according to the procedure for 525. $^1H$ NMR (400 MHz, DMSO-$d_6$) δ 8.41 (d, J=6.0 Hz, 1H), 7.83 (d, J=2.4 Hz, 1H), 7.59 (s, 1H), 7.07-7.03 (m, 2H), 7.02-6.96 (m, 2H), 6.90-6.81 (m, 411), 4.15 (d, J=5.6 Hz, 2H), 3.90 (t, J=6.4 Hz, 2H), 3.40 (t, J=8.4 Hz, 1H), 3.27-3.14 (m, 2H), 2.35-2.24 (m, 2H), 1.67 (dq, J=8.4, 6.4 Hz, 2H), 1.48-1.38 (m, 2H), 0.93 (t, J=7.4 Hz, 3H). Mass (m/z): 382.3 $[M+H]^+$.

N-(4-((4-(cyclohexyloxy)phenyl)amino)benzyl)-5-oxopyrrolidine-3-carboxamide (535)

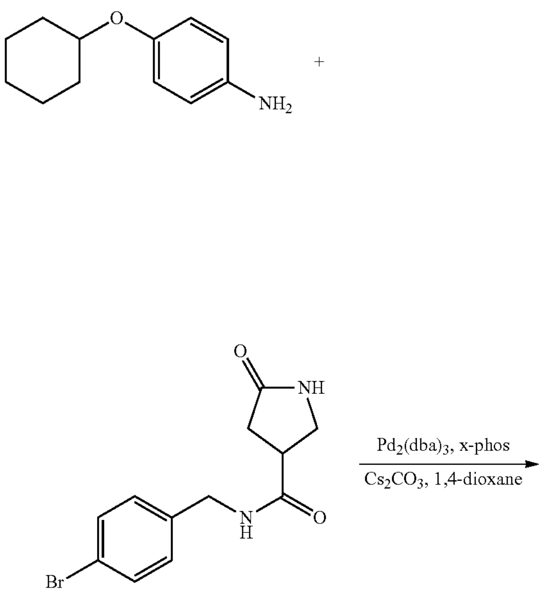

-continued

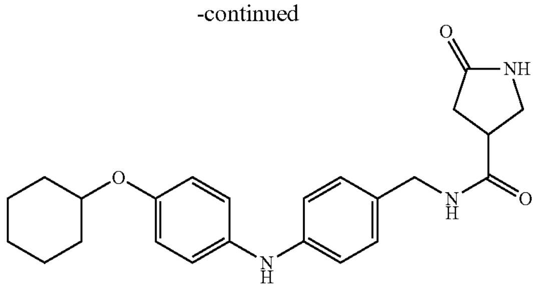

535

The title compound 535 (37.7 mg) was prepared in a total yield of 55.1% as a white solid from 4-(cyclohexyloxy) aniline (39 mg, 0.202 mmol), N-(4-bromobenzyl)-5-oxopyrrolidine-3-carboxamide (50 mg, 0.168 mmol), $Pd_2(dba)_3$ (2 mg, 0.002 mmol), x-phos (6 mg, 0.01 mmol) and $Cs_2CO_3$ (83 mg, 0.252 mmol) and 1,4-dioxane (5 mL) according to the procedure for 525. $^1H$ NMR (400 MHz, DMSO-$d_6$) δ 8.53 (d, J=5.6 Hz, 1H), 7.92 (t, J=2.0 Hz, 1H), 7.61 (s, 1H), 7.08-7.02 (m, 2H), 7.02-6.95 (m, 2H), 6.93-6.86 (m, 2H), 6.86-6.79 (m, 2H), 4.16 (dd, J=12.8, 4.8 Hz, 3H), 3.27-3.16 (m, 2H), 2.33-2.25 (m, 2H), 1.90 (dt, J=8.4, 4.0 Hz, 2H), 1.70 (dd, J=10.4, 6.0 Hz, 2H), 1.55-1.48 (m, 1H), 1.43-1.21 (m, 6H). Mass (m/z): 408.3 $[M+H]^+$.

N-(4-((4-butoxyphenyl)amino)benzyl)-1-ethyl-5-oxopyrrolidine-3-carboxamide (536)

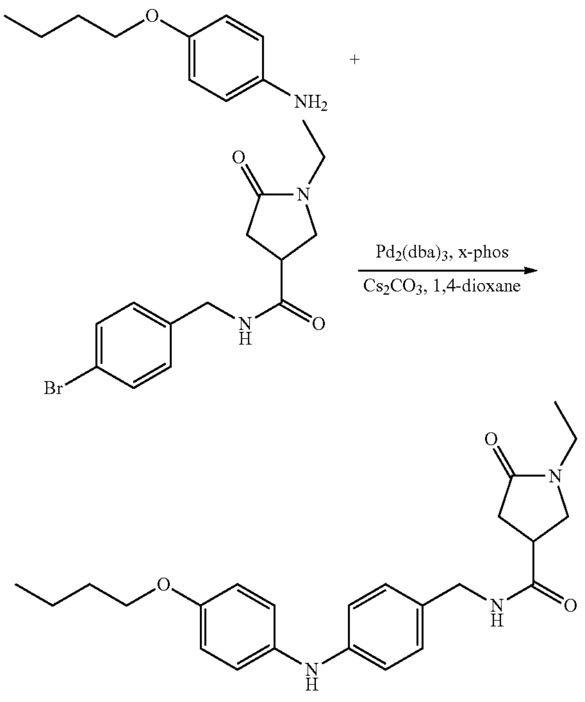

536

The title compound 536 (12.0 mg) was prepared in a total yield of 19.0% as a white solid from 4-butoxyaniline (31 mg, 0.185 mmol), N-(4-bromobenzyl)-1-ethyl-5-oxopyrrolidine-3-carboxamide (50 mg, 0.154 mmol), $Pd_2(dba)_3$ (2 mg, 0.002 mmol), x-phos (6 mg, 0.01 mmol) and $Cs_2CO_3$ (76 mg, 0.231 mmol) and 1,4-dioxane (5 mL) according to the procedure for 525. $^1$H NMR (400 MHz, DMSO-$d_6$) δ 8.43 (t, J=5.6 Hz, 1H), 7.81 (s, 1H), 7.08-7.03 (m, 211), 7.02-6.97 (m, 2H), 6.90-6.82 (m, 4H), 4.16 (d, J=5.6 Hz, 2H), 3.90 (t, J=6.4 Hz, 2H), 3.51 (t, J=9.2 Hz, 1H), 3.36 (dd, J=9.6, 6.4 Hz, 1H), 3.19 (qd, J=7.2, 1.6 Hz, 2H), 3.15-3.08 (m, 1H), 2.41 (d, J=8.4 Hz, 2H), 1.67 (dq, J=8.4, 6.4 Hz, 2H), 1.49-1.37 (m, 2H), 1.03-0.90 (m, 8H). Mass (m/z): 410.3 [M+H]$^+$.

N-(4-((4-(cyclohexyloxy)phenyl)amino)benzyl)-1-ethyl-5-oxopyrrolidine-3-carboxamide (537)

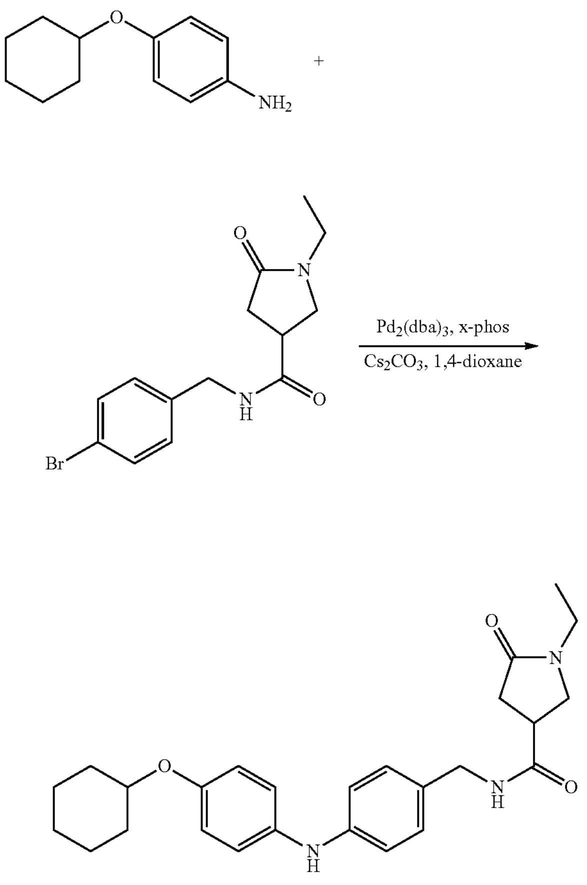

537

The title compound 537 (17.6 mg) was prepared in a total yield of 26.3% as a white solid from 4-(cyclohexyloxy) aniline (35 mg, 0.185 mmol). N-(4-bromobenzyl)-1-ethyl-5-oxopyrrolidine-3-carboxamide (50 mg, 0.154 mmol), Pd$_2$(dba)$_3$ (2 mg, 0.002 mmol), x-phos (6 mg, 0.01 mmol) and $Cs_2CO_3$ (76 mg, 0.231 mmol) and 1,4-dioxane (5 mL) according to the procedure for 525. $^1$H NMR (300 MHz, DMSO-$d_6$) δ 8.40 (t, J=5.7 Hz, 1H), 7.80 (s, 1H), 7.04 (d, J=8.4 Hz, 2H), 7.00-6.93 (m, 2H), 6.90-6.79 (m, 4H), 4.16 (t, J=5.4 Hz, 3H), 3.50 (t, J=9.3 Hz, 1H), 3.36 (dd, J=9.6, 6.3 Hz, 1H), 3.22-3.08 (m, 3H), 2.40 (d, J=8.4 Hz, 2H), 1.90 (d, J=8.1 Hz, 2H), 1.71 (d, J=6.9 Hz, 2H), 1.56-1.48 (m, 1H), 1.46-1.22 (m, 6H), 1.00 (t, J=7.2 Hz, 3H). Mass (m/z): 436.3 [M+H]$^+$.

1-ethyl-N-(4-((4-(ethyl(pentyl)amino)phenyl)amino)benzyl)-5-oxopyrrolidine-3-carboxamide (538)

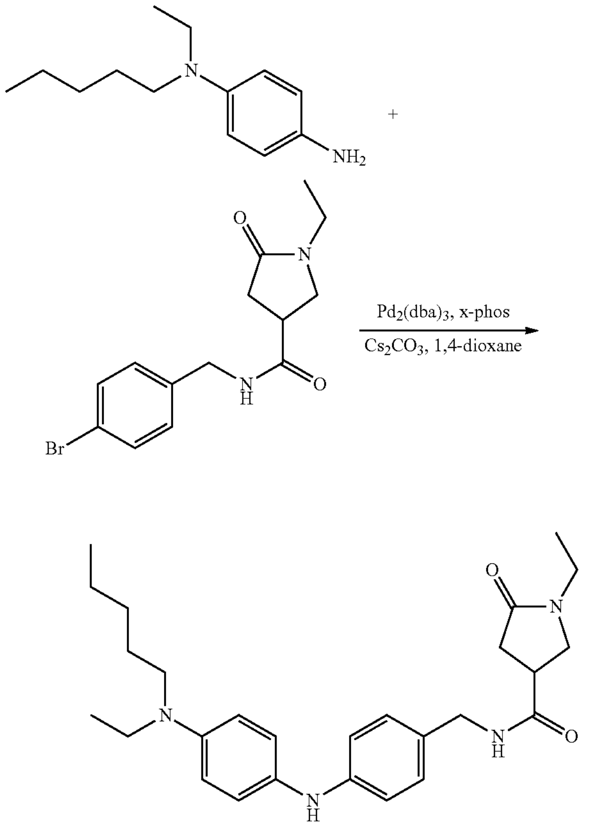

538

The title compound 538 (44.2 mg) was prepared in a total yield of 63.8% as a blue solid from N1-ethyl-N1-pentylbenzene-1,4-diamine (38 mg, 0.185 mmol), N-(4-bromobenzyl)-1-ethyl-5-oxopyrrolidine-3-carboxamide (50 mg, 0.154 mmol), Pd$_2$(dba), (2 mg, 0.002 mmol), x-phos (6 mg, 0.01 mmol) and $Cs_2CO_3$ (76 mg, 0.231 mmol) and 1,4-dioxane (5 mL) according to the procedure for 525. $^1$H NMR (400 MHz, DMSO-$d_6$) δ 8.51 (t, J=6.0 Hz, 2H), 7.43 (s, 2H), 7.12 (s, 6H), 4.22 (s, 2H), 3.53 (t, J=9.2 Hz, 2H), 3.41-3.36 (m, 1H), 3.17 (ddd, J=16.4, 8.0, 2.0 Hz, 3H), 2.42 (dd, J=8.4, 2.4 Hz, 2H), 1.48 (s, 1H), 1.26-1.19 (m, 4H), 1.01 (t, J=7.2 Hz, 6H), 0.84-0.77 (m, 3H). Mass (m/z): 451.3 [M+H]$^+$.

1-ethyl-N-(4-((4-(ethyl(3-methoxypropyl)amino)phenyl)amino)benzyl)-5-oxopyrrolidine-3-carboxamide (539)

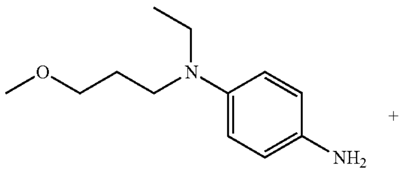

-continued

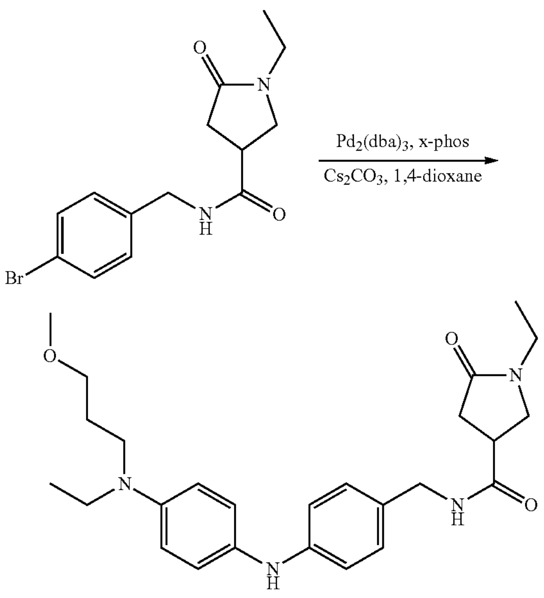

539

The title compound 539 (49.2 mg) was prepared in a total yield of 70.7% as a blue solid from N1-ethyl-N1-(3-methoxypropyl)benzene-1,4-diamine (39 mg, 0.185 mmol), N-(4-bromobenzyl)-1-ethyl-5-oxopyrrolidine-3-carboxamide (50 mg, 0.154 mmol), $Pd_2(dba)_3$ (2 mg, 0.002 mmol), x-phos (6 mg, 0.01 mmol) and $Cs_2CO_3$ (76 mg, 0.231 mmol) and 1,4-dioxane (5 mL) according to the procedure for 525. $^1$H NMR (300 MHz, DMSO-$d_6$) δ 8.49 (s, 2H), 7.50-6.97 (m, 8H), 4.13 (s, 4H), 3.52 (t, J=9.3 Hz, 3H), 3.37 (dd, J=9.6, 6.3 Hz, 2H), 3.20 (s, 1H), 3.18 (s, 3H), 3.18-3.10 (m, 3H), 2.42 (dd, J=8.4, 1.2 Hz, 2H), 1.01 (t, J=7.2 Hz, 6H). Mass (m/z): 453.3 $[M+H]^+$.

N-(4-((4-(ethyl(3-methoxypropyl)amino)phenyl)amino)benzyl)-5-oxopyrrolidine-3-carboxamide (540)

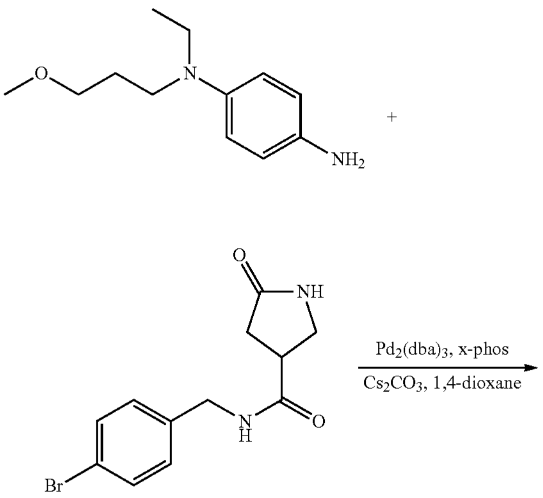

-continued

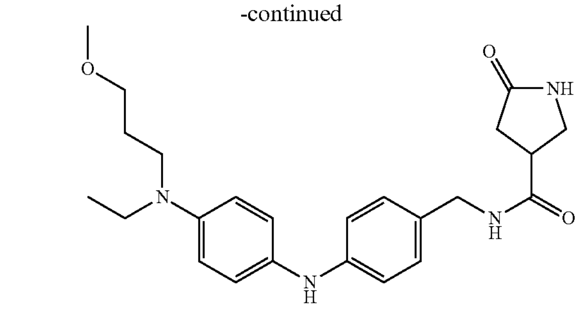

540

The title compound 540 (10.7 mg) was prepared in a total yield of 15.0% as a black solid from N1-ethyl-N1-(3-methoxypropyl)benzene-1,4-diamine (42 mg, 0.202 mmol), N-(4-bromobenzyl)-5-oxopyrrolidine-3-carboxamide (50 mg, 0.168 mmol), $Pd_2(dba)_3$ (2 mg, 0.002 mmol), x-phos (6 mg, 0.01 mmol) and $Cs_2CO_3$ (83 mg, 0.252 mmol) and 1,4-dioxane (5 mL) according to the procedure for 525. $^1$H NMR (300 MHz, DMSO-$d_6$) δ 8.49 (s, 2H), 7.50-6.97 (m, 8H), 4.13 (s, 2H), 3.52 (t, J=9.3 Hz, 3H), 3.37 (dd, J=9.6, 6.3 Hz, 2H), 3.20 (s, 1H), 3.18 (s, 3H), 3.18-3.10 (m, 3H), 2.42 (dd, J=8.4, 1.2 Hz, 2H). Mass (m/z): 425.3 $[M+H]^+$.

1-ethyl-N-(4-((3-methoxy-4-(pentyloxy)phenyl)amino)benzyl)-5-oxopyrrolidine-3-carboxamide (541)

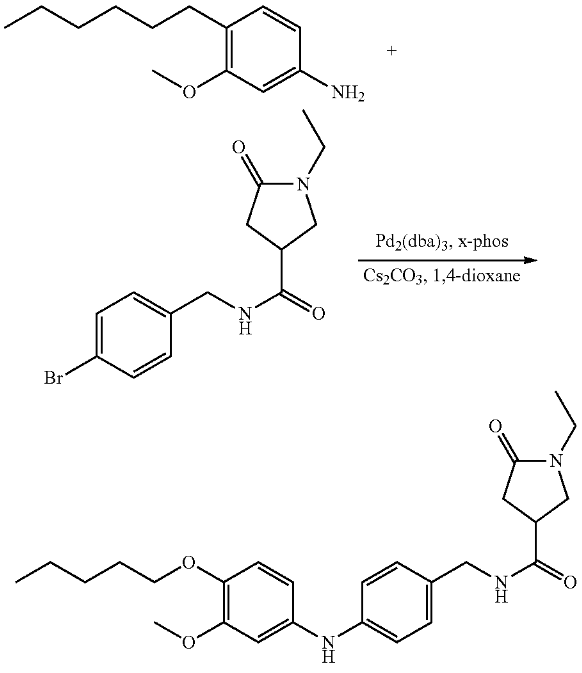

541

The title compound 541 (45.3 mg) was prepared in a total yield of 64.9% as a white solid from 3-methoxy-4-(pentyloxy)aniline (39 mg, 0.185 mmol), N-(4-bromobenzyl)-1-ethyl-5-oxopyrrolidine-3-carboxamide (50 mg, 0.154 mmol), $Pd_2(dba)_3$ (2 mg, 0.002 mmol), x-phos (6 mg, 0.01 mmol) and $Cs_2CO_3$ (76 mg, 0.231 mmol) and 1,4-dioxane (5 mL) according to the procedure for 525. $^1$H NMR (300 MHz, DMSO-$d_6$) δ 8.40 (t, J=5.7 Hz, 1H), 7.84 (s, 1H), 7.09-7.02 (m, 2H), 6.95-6.89 (m, 2H), 6.82 (d, J=8.7 Hz, 1H), 6.66 (d, J=2.4 Hz, 1H), 6.56 (dd, J=8.4, 2.4 Hz, 1H), 4.16 (d, J=5.7 Hz, 2H), 3.86 (t, J=6.6 Hz, 2H), 3.71 (s, 3H), 3.51 (t, J=9.3 Hz, 1H), 3.35 (d, J=6.3 Hz, 1H), 3.23-3.08 (m, 3H), 2.41 (d, J=8.6 Hz, 2H), 1.74-1.61 (m, 2H), 1.46-1.28 (m, 4H), 1.01 (t, J=7.2 Hz, 3H), 0.93-0.85 (m, 3H). Mass (m/z): 454.3 [M+H]$^+$.

N-(4-((3-methoxy-4-(pentyloxy)phenyl)amino)benzyl)-5-oxopyrrolidine-3-carboxamide (542)

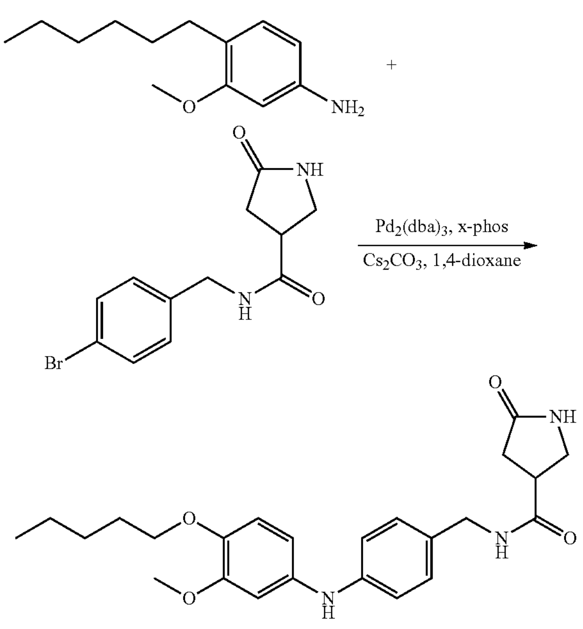

542

The title compound 542 (25.1 mg) was prepared in a total yield of 35.2% as a white solid from 3-methoxy-4-(pentyloxy)aniline (42 mg, 0.202 mmol), N-(4-bromobenzyl)-5-oxopyrrolidine-3-carboxamide (50 mg, 0.168 mmol), $Pd_2(dba)_3$ (2 mg, 0.002 mmol), x-phos (6 mg, 0.01 mmol) and $Cs_2CO_3$ (83 mg, 0.252 mmol) and 1,4-dioxane (5 mL) according to the procedure for 525. $^1$H NMR (300 MHz, DMSO-$d_6$) δ 8.35 (t, J=5.7 Hz, 1H), 7.84 (s, 1H), 7.56 (s, 1H), 7.05 (d, J=8.4 Hz, 2H), 6.94-6.88 (m, 2H), 6.82 (d, J=8.4 Hz, 1H), 6.66 (d, J=2.4 Hz, 1H), 6.56 (dd, J=8.4, 2.4 Hz, 1H), 4.16 (d, J=5.7 Hz, 2H), 3.86 (t, J=6.6 Hz, 2H), 3.71 (s, 3H), 3.38 (d, J=8.4 Hz, 1H), 3.28-3.14 (m, 2H), 2.30 (dd, J=8.4, 2.6 Hz, 2H), 1.66 (q, J=6.9 Hz, 2H), 1.37 (ddt, J=12.0, 8.7, 4.5 Hz, 4H), 0.94-0.85 (m, 3H). Mass (m/z): 426.3 [M+H]$^+$.

N-(4-((4-(ethyl(pentyl)amino)phenyl)amino)benzyl)-5-oxopyrrolidine-3-carboxamide (543)

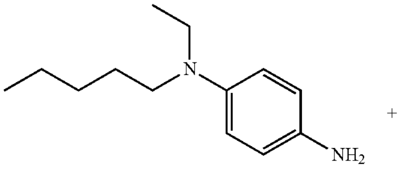

-continued

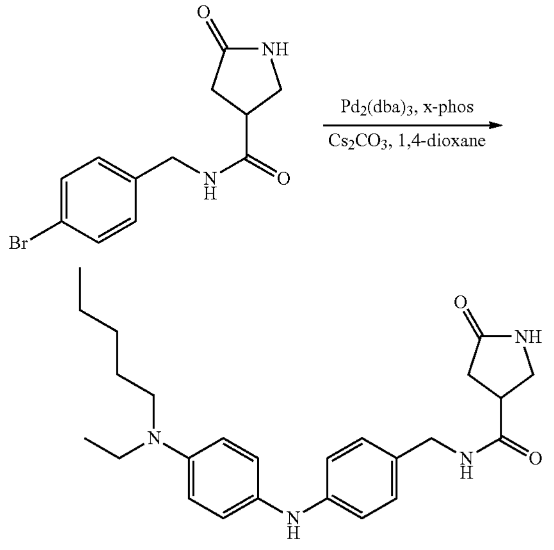

543

The title compound 543 (6.5 mg) was prepared in a total yield of 9.2% as a blue solid from N1-ethyl-N1-pentylbenzene-1,4-diamine (43 mg, 0.202 mmol), N-(4-bromobenzyl)-5-oxopyrrolidine-3-carboxamide (50 mg, 0.168 mmol), $Pd_2(dba)_3$ (2 mg, 0.002 mmol), x-phos (6 mg, 0.01 mmol) and $Cs_2CO_3$ (83 mg, 0.252 mmol) and 1,4-dioxane (5 mL) according to the procedure for 525. $^1$H NMR (300 MHz, DMSO-$d_6$) δ 8.32 (t, J=5.7 Hz, 1H), 7.54 (d, J=6.3 Hz, 2H), 6.95 (dd, J=21.3, 8.2 Hz, 4H), 6.76 (d, J=8.1 Hz, 2H), 6.61 (d, J=8.6 Hz, 2H), 4.12 (d, J=5.7 Hz, 2H), 3.28-3.12 (m, 6H), 2.29 (dd, J=8.4, 3.2 Hz, 2H), 1.49 (s, 3H), 1.30 (d, J=3.3 Hz, 3H), 1.05 (t, J=6.9 Hz, 3H), 0.90-0.86 (m, 3H). Mass (m/z): 423.3 [M+H]$^+$.

N-(4-((2-(diethylamino)phenyl)amino)benzyl)-5-oxopyrrolidine-3-carboxamide (544)

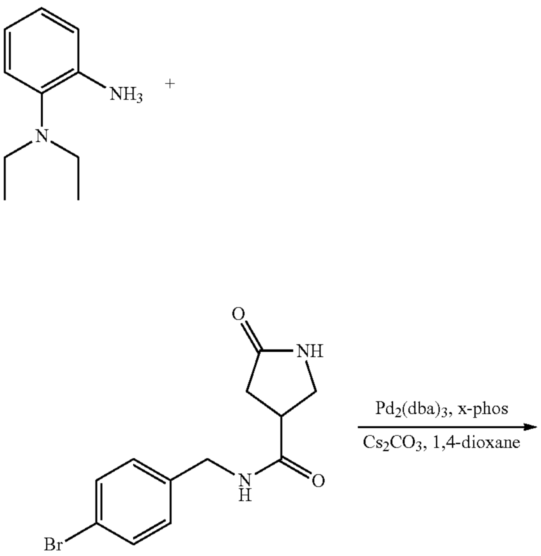

-continued

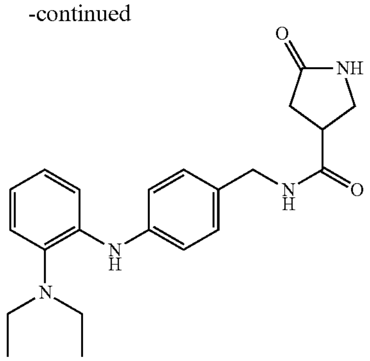

544

The title compound 544 (15.0 mg) was prepared in a total yield of 23.5% as a orange solid from N1,N1-diethylbenzene-1,2-diamine (33 mg, 0.202 mmol), N-(4-bromobenzyl)-5-oxopyrrolidine-3-carboxamide (50 mg, 0.168 mmol), $Pd_2(dba)_3$ (2 mg, 0.002 mmol), x-phos (6 mg, 0.01 mmol) and $Cs_2CO_3$ (83 mg, 0.252 mmol) and 1,4-dioxane (5 mL) according to the procedure for 525. $^1H$ NMR (300 MHz, DMSO-$d_6$) δ 8.40 (t, J=5.7 Hz, 1H), 7.56 (s, 1H), 7.21 (s, 2H), 7.10 (d, J=8.4 Hz, 2H), 7.02 (s, 3H), 4.18 (d, J=5.7 Hz, 2H), 3.44-3.36 (m, 3H), 3.29-3.13 (m, 4H), 2.30 (dd, J=8.4, 2.3 Hz, 2H), 0.94 (t, J=7.2 Hz, 6H). Mass (m/z): 381.3 $[M+H]^+$.

N-(4-((2-(diethylamino)phenyl)amino)benzyl)-1-ethyl-5-oxopyrrolidine-3-carboxamide (545)

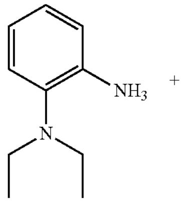

+

-continued

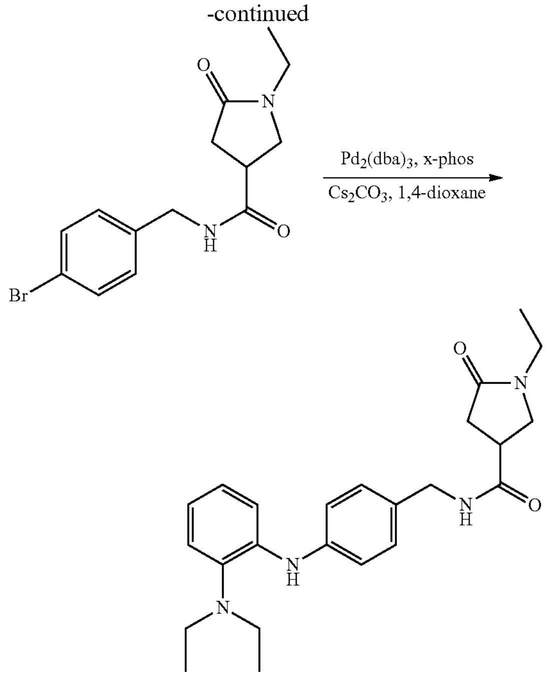

545

The title compound 545 (46.1 mg) was prepared in a total yield of 73.4% as a yellow solid from N1,N1-diethylbenzene-1,2-diamine (30 mg, 0.185 mmol), N-(4-bromobenzyl)-1-ethyl-5-oxopyrrolidine-3-carboxamide (50 mg, 0.154 mmol), $Pd_2(dba)_3$ (2 mg, 0.002 mmol), x-phos (6 mg, 0.01 mmol) and $Cs_2CO_3$ (76 mg, 0.231 mmol) and 1,4-dioxane (5 mL) according to the procedure for 525. $^1H$ NMR (300 MHz, DMSO-$d_6$) δ 8.46 (t, J=5.7 Hz, 1H), 7.60 (s, 1H), 7.32 (s, 2H), 7.22 (s, 1H), 7.13-7.06 (m, 2H), 6.85 (d, J=8.1 Hz, 2H), 4.19 (d, J=5.7 Hz, 2H), 3.51 (t, J=9.3 Hz, 2H), 3.36 (dd, J=9.6, 6.3 Hz, 3H), 3.16 (ddt, J=12.9, 8.7, 6.3 Hz, 4H), 2.41 (dd, J=8.4, 1.3 Hz, 2H), 0.99 (td, J=7.1, 5.7 Hz, 9H). Mass (m/z): 409.3 $[M+H]^+$.

5-oxo-1-(2-(2-oxopyrrolidin-1-yl)ethyl)-N-(4-((4-(4-(trifluoromethyl)piperidin-1-yl)phenyl)amino)benzyl)pyrrolidine-3-carboxamide (546)

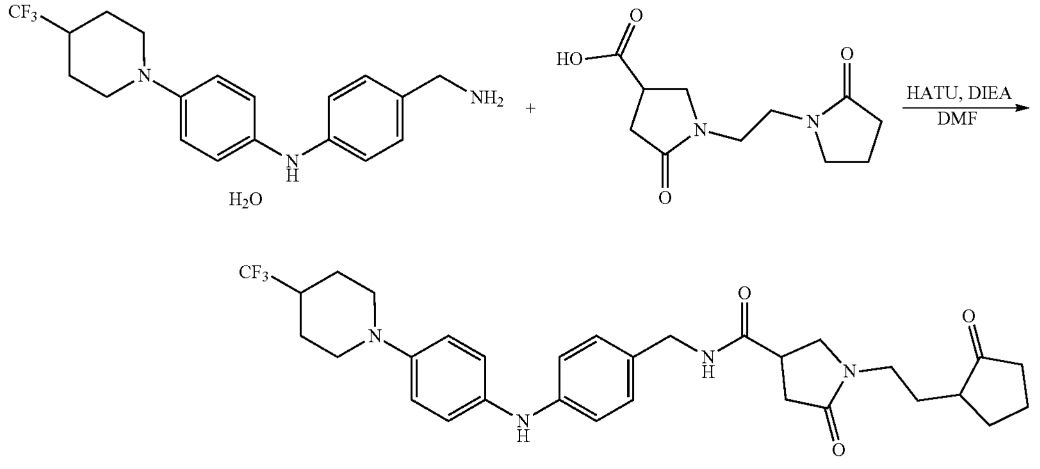

546

The title compound 546 (16.2 mg) was prepared in a total yield of 19.6% as a blue solid from 4-(aminomethyl)-N-(4-(4-(trifluoromethyl)piperidin-1-yl)phenyl) aniline hydrochloride (50 mg, 0.145 mmol), 5-oxo-1-(2-(2-oxopyrrolidin-1-yl)ethyl) pyrrolidine-3-carboxylic acid (45 mg, 0.188 mmol), HATU (72 mg, 0.188 mmol), DIEA (25 mg, 0.188 mmol) and DMF (3 mL) according to the procedure for 523. $^1$H NMR (400 MHz, DMSO-$d_6$) δ 8.41 (d, J=6.0 Hz, 1H), 7.05 (s, 8H), 4.17 (s, 2H), 3.75-3.68 (m, 4H), 3.58 (s, 2H), 3.45-3.34 (m, 5H), 3.33-3.25 (m, 2H), 3.21 (qd, J=8.8, 8.0, 3.6 Hz, 2H), 3.10-3.03 (m, 1H), 2.38 (dd, J=8.4, 3.2 Hz, 2H), 2.15 (td, J=7.6, 2.8 Hz, 2H), 1.86 (td, J=8.0, 6.0 Hz, 2H). Mass (m/z): 572.3 $[M+H]^+$.

5-oxo-N-(4-((4-pentylphenyl)amino)benzyl)pyrrolidine-3-carboxamide (547)

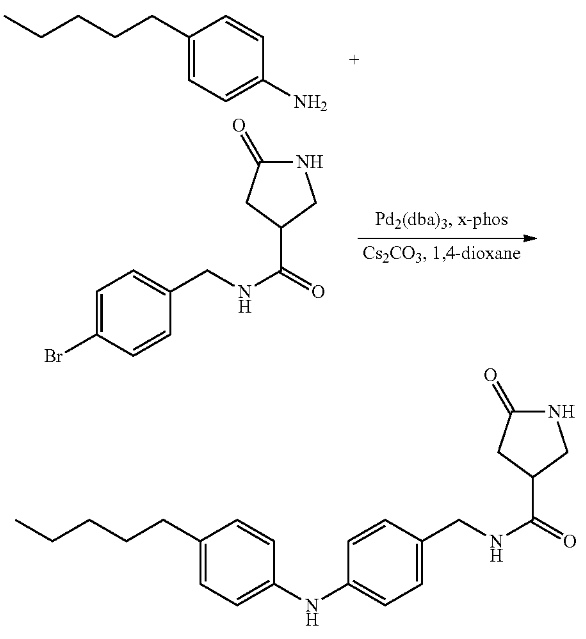

547

The title compound 547 (9.0 mg) was prepared in a total yield of 14.1% as a white solid from 4-pentylaniline (33 mg, 0.202 mmol), N-(4-bromobenzyl)-5-oxopyrrolidine-3-carboxamide (50 mg, 0.168 mmol), $Pd_2(dba)_3$ (2 mg, 0.002 mmol), x-phos (6 mg, 0.01 mmol) and $Cs_2CO_3$ (83 mg, 0.252 mmol) and 1,4-dioxane (5 mL) according to the procedure for 525. $^1$H NMR (400 MHz, DMSO-$d_6$) δ 8.40 (t, J=5.6 Hz, 1H), 8.00 (s, 1H), 7.59 (s, 1H), 7.09 (d, J=8.0 Hz, 2H), 7.04 (d, J=8.0 Hz, 2H), 6.97 (dd, J=8.0, 5.2 Hz, 4H), 4.17 (d, J=5.6 Hz, 2H), 3.39 (d, J=8.8 Hz, 1H), 3.28-3.15 (m, 2H), 2.46 (d, J=7.6 Hz, 1H), 2.30 (dd, J=8.4, 4.4 Hz, 2H), 1.53 (p, J=7.6 Hz, 2H), 1.32-1.22 (m, 5H), 0.86 (t, J=6.8 Hz, 3H). Mass (m/z): 380.3 $[M+H]^+$.

1-ethyl-5-oxo-N-(4-((4-pentylphenyl)amino)benzyl) pyrrolidine-3-carboxamide (548)

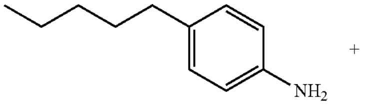

-continued

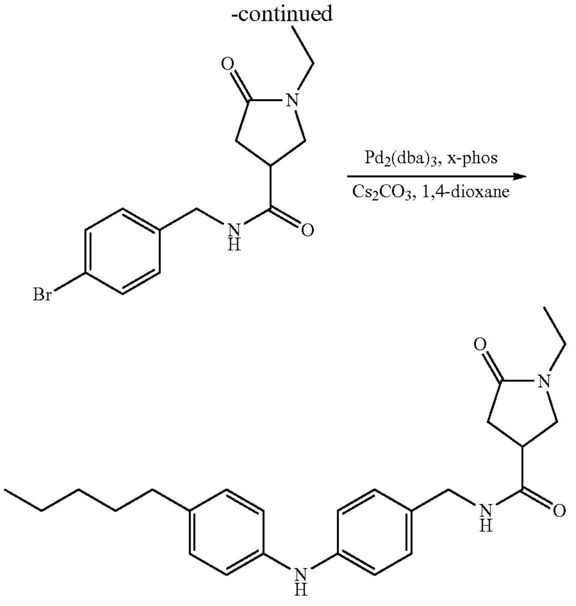

548

The title compound 548 (12.4 mg) was prepared in a total yield of 19.8% as a white solid from 4-pentylaniline (30 mg, 0.185 mmol), N-(4-bromobenzyl)-1-ethyl-5-oxopyrrolidine-3-carboxamide (50 mg, 0.154 mmol), $Pd_2(dba)_3$ (2 mg, 0.002 mmol), x-phos (6 mg, 0.01 mmol) and $Cs_2CO_3$ (76 mg, 0.231 mmol) and 1,4-dioxane (5 mL) according to the procedure for 525. $^1$H NMR (400 MHz, DMSO-$d_6$) δ 8.45 (t, J=5.6 Hz, 1H), 8.00 (s, 1H), 7.09 (d, J=8.4 Hz, 2H), 7.04 (d, J=8.4 Hz, 2H), 6.97 (dd, J=8.4, 5.6 Hz, 4H), 4.18 (d, J=5.6 Hz, 2H), 3.51 (t, J=9.2 Hz, 1H), 3.38 (d, J=6.4 Hz, 1H), 3.22-3.09 (m, 3H), 2.48 (s, 1H), 2.41 (d, J=8.4 Hz, 2H), 1.53 (p, J=7.2 Hz, 2H), 1.28 (ddt, J=14.4, 9.2, 5.2 Hz, 5H), 1.00 (t, J=7.2 Hz, 3H), 0.86 (t, J=6.8 Hz, 3H). Mass (m/z): 408.3 $[M+H]^+$.

5-oxo-N-(4-((3-propoxy-4-(4-(trifluoromethyl)piperidin-1-yl)phenyl)amino)benzyl)pyrrolidine-3-carboxamide (549)

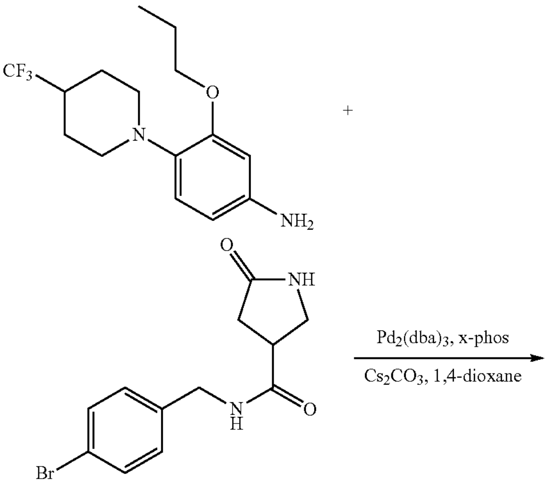

-continued

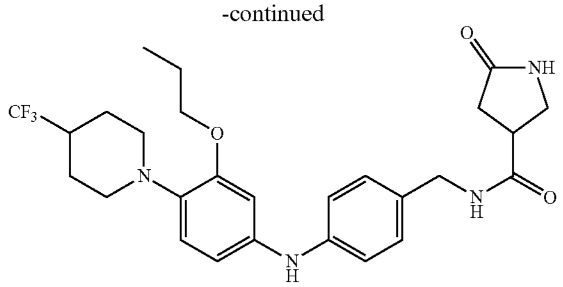

549

The title compound 549 (12.4 mg) was prepared in a total yield of 14.3% as a white solid from 3-propoxy-4-(4-(trifluoromethyl)piperidin-1-yl)aniline (61 mg, 0.202 mmol), N-(4-bromobenzyl)-5-oxopyrrolidine-3-carboxamide (50 mg, 0.168 mmol), $Pd_2(dba)_3$ (2 mg, 0.002 mmol), x-phos (6 mg, 0.01 mmol) and $Cs_2CO_3$ (83 mg, 0.252 mmol) and 1,4-dioxane (5 mL) according to the procedure for 525. $^1H$ NMR (400 MHz, DMSO-$d_6$) δ 8.54 (s, 1H), 7.97 (s, 1H), 7.08 (d, J=8.0 Hz, 2H), 6.96 (d, J=8.4 Hz, 2H), 6.78 (d, J=8.4 Hz, 1H), 6.66-6.57 (m, 2H), 4.17 (d, J=5.6 Hz, 2H), 3.85 (t, J=6.0 Hz, 2H), 3.52 (t, J=9.2 Hz, 1H), 3.18 (tt, J=10.4, 5.2 Hz, 3H), 2.54 (s, 1H), 2.41 (d, J=8.4 Hz, 3H), 1.87 (d, J=12.4 Hz, 2H), 1.59 (qd, J=12.4, 4.0 Hz, 2H). Mass (m/z): 520.3 $[M+H]^+$.

1-ethyl-5-oxo-N-(4-((3-propoxy-4-(4-(trifluoromethyl)piperidin-1-yl)phenyl)amino)benzyl)pyrrolidine-3-carboxamide (550)

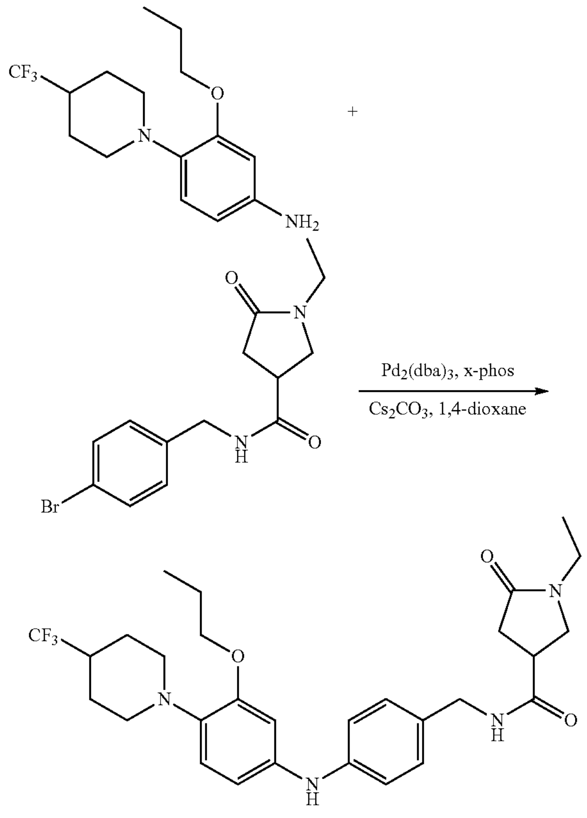

550

The title compound 550 (35.1 mg) was prepared in a total yield of 41.7% as a brown solid from 3-propoxy-4-(4-(trifluoromethyl)piperidin-1-yl)aniline (56 mg, 0.185 mmol), N-(4-bromobenzyl)-1-ethyl-5-oxopyrrolidine-3-carboxamide (50 mg, 0.154 mmol), $Pd_2(dba)_3$ (2 mg, 0.002 mmol), x-phos (6 mg, 0.01 mmol) and $Cs_2CO_3$ (76 mg, 0.231 mmol) and 1,4-dioxane (5 mL) according to the procedure for 525. $^1H$ NMR (400 MHz, DMSO-$d_6$) δ 8.54 (s, 1H), 7.97 (s, 1H), 7.08 (d, J=8.4 Hz, 2H), 6.96 (d, J=8.4 Hz, 2H), 6.78 (d, J=8.4 Hz, 1H), 6.63 (d, J=2.4 Hz, 1H), 6.59 (dd, J=8.4, 2.4 Hz, 1H), 4.17 (d, J=5.6 Hz, 2H), 3.85 (t, J=6.0 Hz, 2H), 3.52 (t, J=9.2 Hz, 1H), 3.18 (tt, J=10.4, 5.2 Hz, 3H), 2.54 (s, 1H), 2.41 (d, J=8.4 Hz, 3H), 1.87 (d, J=12.4 Hz, 2H), 1.75 (q, J=6.8 Hz, 2H), 1.58 (tt, J=12.4, 6.1 Hz, 2H), 1.01 (td, J=7.2, 5.2 Hz, 6H). Mass (m/z): 547.3 $[M+H]^+$.

5-oxo-N-(4-((2-propoxy-4-(4-(trifluoromethyl)piperidin-1-yl)phenyl)amino)benzyl)pyrrolidine-3-carboxamide (551)

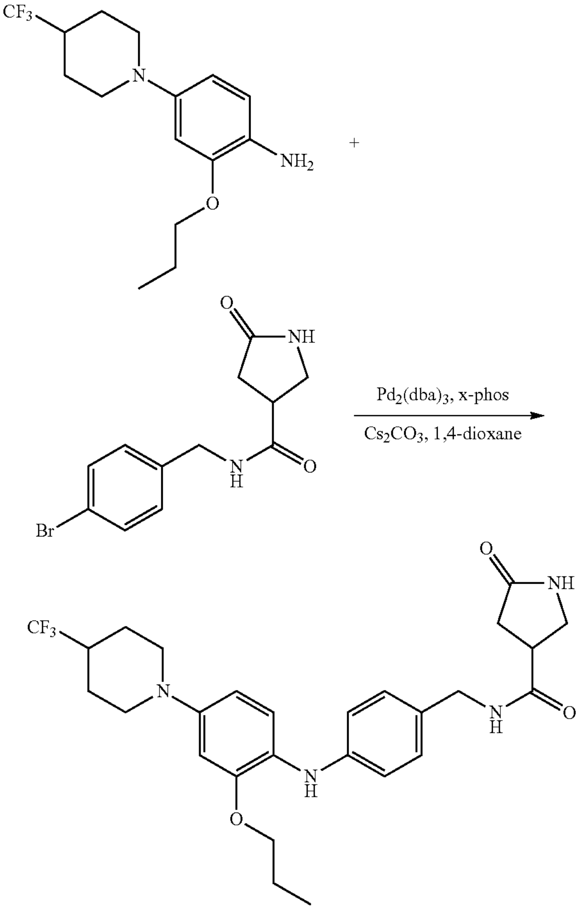

551

The title compound 551 (15.4 mg) was prepared in a total yield of 17.7% as a blue solid from 2-propoxy-4-(4-(trifluoromethyl)piperidin-1-yl)aniline (61 mg, 0.202 mmol), N-(4-bromobenzyl)-5-oxopyrrolidine-3-carboxamide (50 mg, 0.168 mmol), $Pd_2(dba)_3$ (2 mg, 0.002 mmol), x-phos (6 mg, 0.01 mmol) and $Cs_2CO_3$ (83 mg, 0.252 mmol) and 1,4-dioxane (5 mL) according to the procedure for 525. $^1H$ NMR (400 MHz, DMSO-$d_6$) δ 8.38 (s, 1H), 7.58 (s, 1H), 7.23-6.56 (m, 7H), 4.10 (d, J=5.6 Hz, 5H), 3.40 (t, J=8.8 Hz, 2H), 3.27-3.13 (m, 3H), 2.89 (s, 1H), 2.29 (dd, J=8.4, 3.6 Hz, 211), 2.00 (dd, J=16.0, 8.4 Hz, 211), 1.69 (s, 3H), 0.92 (t, J=7.4 Hz, 3H). Mass (m/z): 519.3 $[M+H]^+$.

N-(4-((4-(4-(trifluoromethyl)piperidin-1-yl)phenyl)amino)benzyl)isobutyramide (552)

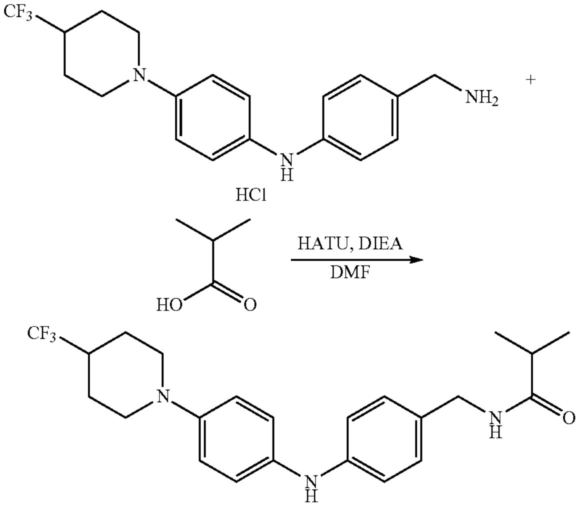

552

The title compound 552 (28.6 mg) was prepared in a total yield of 47.0% as a white solid from 4-(aminomethyl)-N-(4-(4-(trifluoromethyl)piperidin-1-yl)phenyl) aniline hydrochloride (50 mg, 0.145 mmol), isobutyric acid (17 mg, 0.188 mmol), HATU (72 mg, 0.188 mmol), DIEA (25 mg, 0.188 mmol) and DMF (3 mL) according to the procedure for 523. $^1$H NMR (400 MHz, DMSO-$d_6$) δ 8.13 (t, J=5.6 Hz, 1H), 7.79 (s, 1H), 7.06-7.00 (m, 2H), 6.99-6.94 (m, 2H), 6.91-6.84 (m, 4H), 4.12 (d, J=5.6 Hz, 2H), 3.61 (d, J=12.4 Hz, 2H), 2.67-2.57 (m, 2H), 2.42-2.37 (m, 1H), 1.88 (d, J=12.8 Hz, 2H), 1.57 (qd, J=12.8, 4.2 Hz, 3H), 1.01 (d, J=6.8 Hz, 6H). Mass (m/z): 420.3 $[M+H]^+$.

N-(4-((4-(4-(trifluoromethyl)piperidin-1-yl)phenyl)amino)benzyl)acetamide (553)

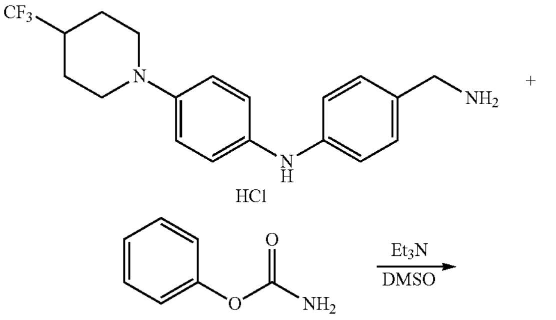

-continued

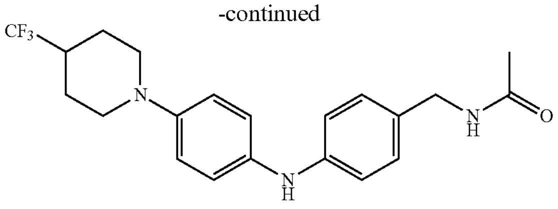

553

To a solution of 4-(aminomethyl)-N-(4-(4-(trifluoromethyl)piperidin-1-yl)phenyl) aniline hydrochloride (50 mg, 0.145 mmol) and phenyl carbamate (26 mg, 0.188 mmol) in DMSO (3 mL) was added $Et_3N$ (43 mg, 0.435 mmol), then the mixture was stirred at room temperature for 2 h. The mixture was extracted by EA (25 mL×3). The combined organic layers were washed with brine (15 mL×3), dried over Na2SO4 and concentrated to give the crude product, which was purified by prep-HPLC to give the desired product as white solid (29.0 mg, 51.1%). $^1$H NMR (400 MHz, DMSO-$d_6$) δ 8.20 (t, J=5.6 Hz, 1H), 7.78 (s, 1H), 7.07-7.02 (m, 2H), 7.00-6.94 (m, 2H), 6.91-6.85 (m, 4H), 4.11 (d, J=5.6 Hz, 2H), 3.61 (d, J=12.0 Hz, 2H), 2.62 (td, J=12.4, 2.4 Hz, 2H), 2.42 (dp, J=12.4, 4.4, 3.6 Hz, 1H), 1.88 (d, J=12.8 Hz, 2H), 1.84 (s, 3H), 1.57 (qd, J=12.4, 4.0 Hz, 3H). Mass (m/z): 392.3 $[M+H]^+$.

1-ethyl-N-(4-((4-(4-methoxy-4-(trifluoromethyl)piperidin-1-yl)phenyl)amino)benzyl)-5-oxopyrrolidine-3-carboxamide (554)

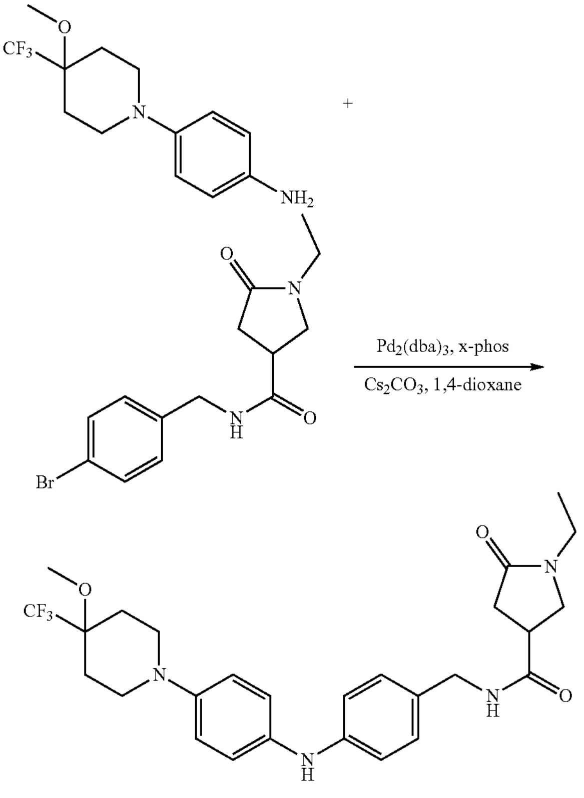

554

The title compound 554 (31.3 mg) was prepared in a total yield of 39.2% as a blue solid from 4-(4-methoxy-4-(trifluoromethyl)piperidin-1-yl)aniline (51 mg, 0.185 mmol), N-(4-bromobenzyl)-1-ethyl-5-oxopyrrolidine-3-carboxamide (50 mg, 0.154 mmol), $Pd_2(dba)_3$ (2 mg, 0.002 mmol), x-phos (6 mg, 0.01 mmol) and $Cs_2CO_3$ (76 mg, 0.231 mmol) and 1,4-dioxane (5 mL) according to the procedure for 525.1H NMR (400 MHz, DMSO-$d_6$) δ 8.46 (t, J=5.9 Hz, 1H), 7.08 (s, 8H), 3.52 (t, J=9.2 Hz, 2H), 3.87-3.82 (m, 3H), 3.46-3.32 (m, 5H), 3.22-3.07 (m, 4H), 3.00 (s, 1H), 2.41 (dd, J=8.5, 1.4 Hz, 2H), 2.17-1.86 (m, 3H), 1.00 (t, J=7.2 Hz, 3H). Mass (m/z): 519.3 $[M+H]^+$.

N-(4-((4-(4-hydroxy-4-(trifluoromethyl)piperidin-1-yl)phenyl)amino)benzyl)-5-oxopyrrolidine-3-carboxamide (555)

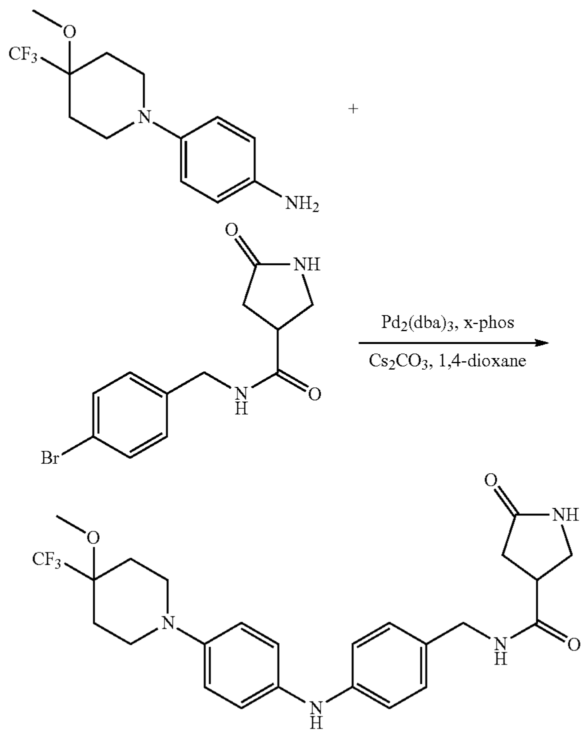

555

The title compound 555 (14.7 mg) was prepared in a total yield of 17.9% as a blue solid from 1-(4-aminophenyl)-4-(trifluoromethyl)piperidin-4-ol (55 mg, 0.202 mmol), N-(4-bromobenzyl)-5-oxopyrrolidine-3-carboxamide (50 mg, 0.168 mmol), $Pd_2(dba)_3$ (2 mg, 0.002 mmol), x-phos (6 mg, 0.01 mmol) and $Cs_2CO_3$ (83 mg, 0.252 mmol) and 1,4-dioxane (5 mL) according to the procedure for 525. $^1$H NMR (400 MHz, DMSO-$d_6$) δ 8.42 (t, J=5.8 Hz, 1H), 7.59 (s, 1H), 7.21-6.84 (m, 8H), 4.17 (s, 2H), 3.87-3.82 (m, 3H), 3.49 (s, 2H), 3.28-3.13 (m, 3H), 2.99 (s, 2H), 2.30 (dd, J=8.3, 3.9 Hz, 2H), 2.03 (dd, J=25.4, 9.2 Hz, 4H). Mass (m/z): 491.3 $[M+H]^+$.

1-ethyl-5-oxo-N-(4-(phenylamino)benzyl)pyrrolidine-3-carboxamide (556)

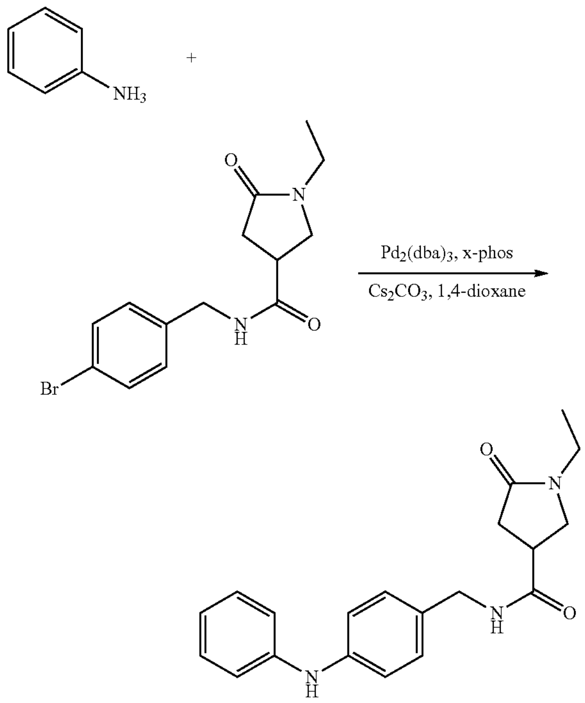

556

The title compound 556 (34.1 mg) was prepared in a total yield of 62.1% as a white solid from anilinel (17 mg, 0.185 mmol), N-(4-bromobenzyl)-1-ethyl-5-oxopyrrolidine-3-carboxamide (50 mg, 0.154 mmol), $Pd_2(dba)_3$ (2 mg, 0.002 mmol), x-phos (6 mg, 0.01 mmol) and $Cs_2CO_3$ (76 mg, 0.231 mmol) and 1,4-dioxane (5 mL) according to the procedure for 525. $^1$H NMR (400 MHz, DMSO-$d_6$) δ 8.46 (t, J=5.6 Hz, 1H), 8.13 (s, 1H), 7.25-7.17 (m, 2H), 7.15-7.09 (m, 2H), 7.06-7.00 (m, 4H), 6.79 (t, J=7.2, 1.1 Hz, 1H), 4.20 (d, J=5.6 Hz, 2H), 3.52 (t, J=9.2 Hz, 1H), 3.40-3.36 (m, 1H), 3.25-3.08 (m, 3H), 2.45-2.38 (m, 2H), 1.01 (t, J=7.2 Hz, 3H). Mass (m/z): 338.3 $[M+H]^+$.

2-(4-methylpiperazin-1-yl)-N-(4-(phenylamino)benzyl)acetamide (557)

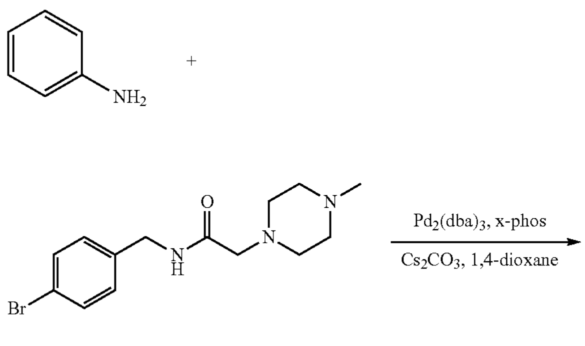

-continued

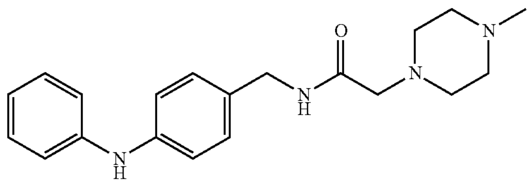

557

The title compound 557 (40.5 mg) was prepared in a total yield of 78.3% as a white solid from anilinel (17 mg, 0.184 mmol), N-(4-bromobenzyl)-2-(4-methylpiperazin-1-yl)acetamide (50 mg, 0.153 mmol), $Pd_2(dba)_3$ (2 mg, 0.002 mmol), x-phos (6 mg, 0.01 mmol) and $Cs_2CO_3$ (75 mg, 0.229 mmol) and 1,4-dioxane (5 mL) according to the procedure for 525. $^1H$ NMR (400 MHz, DMSO-$d_6$) δ 8.31-8.19 (m, 2H), 7.24-7.17 (m, 2H), 7.16-7.09 (m, 2H), 7.04 (td, J=6.8, 1.6 Hz, 4H), 6.79 (tt, J=7.2, 1.2 Hz, 1H), 4.21 (d, J=6.0 Hz, 2H), 3.02 (s, 2H), 2.81-2.53 (m, 8H), 2.41 (s, 3H). Mass (m/z): 339.3 $[M+H]^+$.

N-(4-((3-fluoro-4-(4-(trifluoromethyl)piperidin-1-yl) phenyl)amino)benzyl)-5-oxopyrrolidine-3-carboxamide (558)

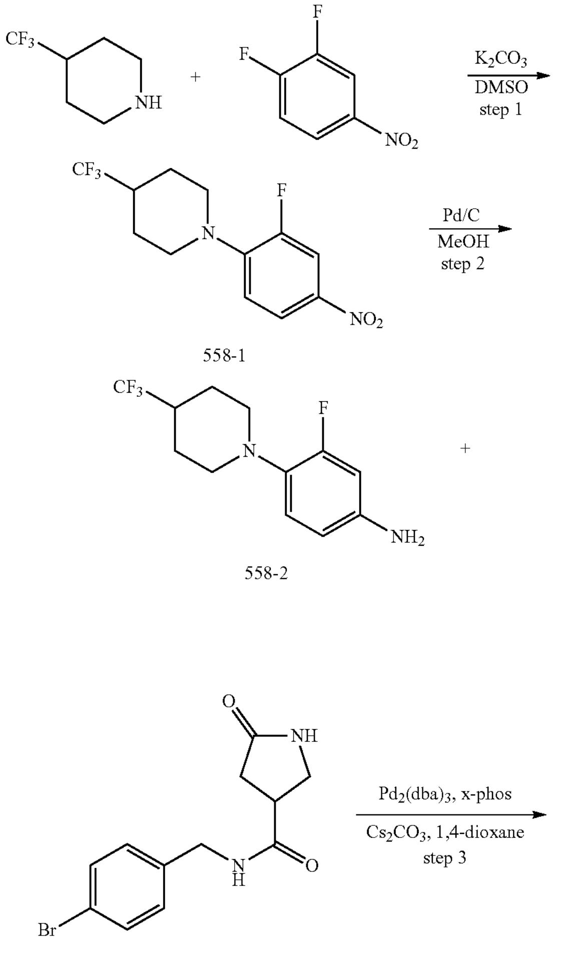

558-1

558-2

-continued

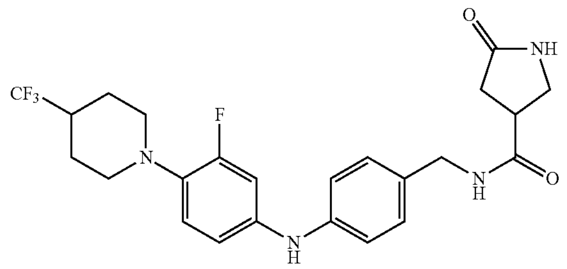

558

Step 1. 1-(2-fluoro-4-nitrophenyl)-4-(trifluoromethyl)piperidine: (558-1). The title compound 558-1 (3.4 g) was prepared in a total yield of 93% as a yellow solid from 4-(trifluoromethyl)piperidine (1.9 g, 12.5 mmol) and 1,2-difluoro-4-nitrobenzene (1.8 g, 11.3 mmol) according to the procedure for 526-1. Mass (m/z): 293.2 $[M+H]^+$.

Step 2. 3-fluoro-4-(4-(trifluoromethyl)piperidin-1-yl)aniline: (558-2). The title compound 558-2 (2.9 g) was prepared in a total yield of 92% as a purple solid from 1-(2-fluoro-4-nitrophenyl)-4-(trifluoromethyl)piperidine (3.4 g, 12.0 mmol) according to the procedure for 526-2. Mass (m/z): 263.3 $[M+H]^+$.

Step 3. N-(4-((3-fluoro-4-(4-(trifluoromethyl)piperidin-1-yl)phenyl)amino)benzyl)-5-oxopyrrolidine-3-carboxamide: (558). The title compound 558 (53.7 mg) was prepared in a total yield of 66.9% as a white solid from 3-fluoro-4-(4-(trifluoromethyl)piperidin-1-yl)aniline (53 mg, 0.202 mmol), N-(4-bromobenzyl)-5-oxopyrrolidine-3-carboxamide (50 mg, 0.168 mmol), $Pd_2(dba)_3$ (2 mg, 0.002 mmol), x-phos (6 mg, 0.01 mmol) and $Cs_2CO_3$ (83 mg, 0.252 mmol) and 1,4-dioxane (5 mL) according to the procedure for 525$^1H$ NMR (400 MHz, DMSO-$d_6$) δ 8.52 (s, 1H), 8.21 (d, J=2.4 Hz, 1H), 7.60 (s, 1H), 7.14-7.08 (m, 2H), 7.02-6.91 (m, 3H), 6.83-6.76 (m, 2H), 4.18 (d, J=5.6 Hz, 2H), 3.31-3.17 (m, 4H), 2.70-2.59 (m, 2H), 2.47-2.37 (m, 1H), 2.33-2.27 (m, 2H), 1.93-1.84 (m, 2H), 1.60 (qd, J=12.4, 4.0 Hz, 2H). Mass (m/z): 479.3 $[M+H]^+$.

N-(4-((3,5-difluoro-4-(4-(trifluoromethyl)piperidin-1-yl)phenyl)amino)benzyl)-5-oxopyrrolidine-3-carboxamide (559)

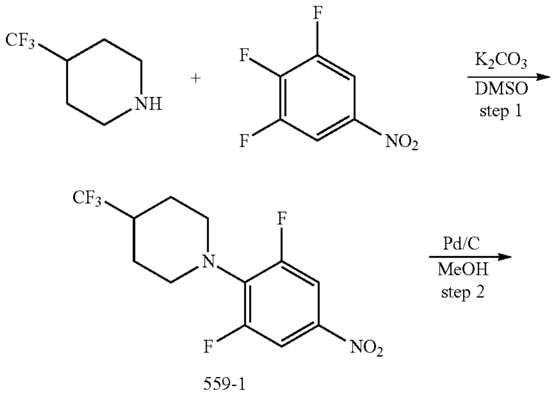

559-1

-continued

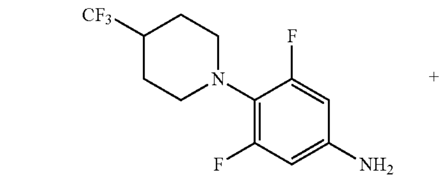

559-2

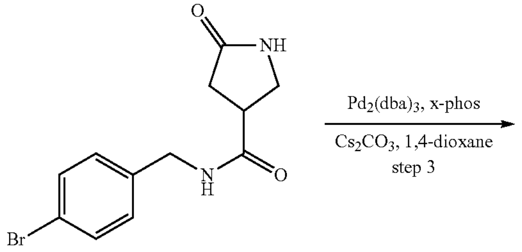

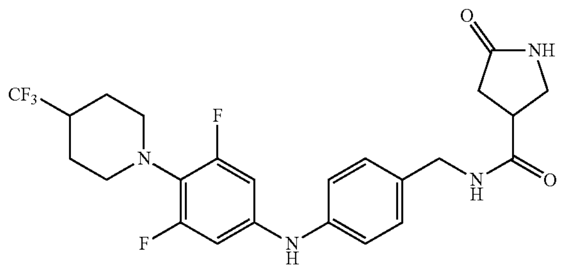

559

Step 1. 1-(2,6-difluoro-4-nitrophenyl)-4-(trifluoromethyl)piperidine: (559-1). The title compound 559-1 (1.5 g) was prepared in a total yield of 96.4% as a yellow solid from 4-(trifluoromethyl)piperidine (0.95 g, 5.6 mmol) and 1,2,3-trifluoro-5-nitrobenzene (1 g, 6.2 mmol) according to the procedure for 526-1. Mass (m/z): 311.2 $[M+H]^+$.

Step 2. 3,5-difluoro-4-(4-(trifluoromethyl)piperidin-1-yl)aniline: (559-2). The title compound 559-2 (1.3 g) was prepared in a total yield of 96% as a purple solid from 1-(2,6-difluoro-4-nitrophenyl)-4-(trifluoromethyl)piperidine (1.5 g, 4.8 mmol) according to the procedure for 526-2. Mass (m/z): 281.3 $[M+H]^+$.

Step 3. N-(4-((3,5-difluoro-4-(4-(trifluoromethyl)piperidin-1-yl)phenyl)amino)benzyl)-5-oxopyrrolidine-3-carboxamide: (559). The title compound 559 (24.9 mg) was prepared in a total yield of 29.9% as a white solid from 3,5-difluoro-4-(4-(trifluoromethyl)piperidin-1-yl)aniline (57 mg, 0.202 mmol), N-(4-bromobenzyl)-5-oxopyrrolidine-3-carboxamide (50 mg, 0.168 mmol), $Pd_2(dba)$; (2 mg, 0.002 mmol), x-phos (6 mg, 0.01 mmol) and $Cs_2CO_3$ (83 mg, 0.252 mmol) and 1,4-dioxane (5 mL) according to the procedure for 525. $^1H$ NMR (400 MHz, DMSO-$d_6$) δ 8.44 (d, J=4.8 Hz, 2H), 7.59 (s, 1H), 7.19-7.14 (m, 2H), 7.08-7.01 (m, 2H), 6.62-6.53 (m, 2H), 4.21 (d, J=5.6 Hz, 2H), 3.45-3.38 (m, 1H), 3.29-3.14 (m, 2H), 3.03 (d, J=14.0 Hz, 4H), 2.41 (dq, J=8.4, 4.8, 4.4 Hz, 1H), 2.31 (dd, J=8.4, 3.2 Hz, 2H), 1.88-1.78 (m, 2H), 1.54 (qd, J=12.0, 5.2 Hz, 2H). Mass (m/z): 497.3 [M+H]J.

N-(4-((4-((1R,4S)-2-azabicyclo[2.2.1]heptan-2-yl)phenyl)amino)benzyl)-5-oxopyrrolidine-3-carboxamide (560)

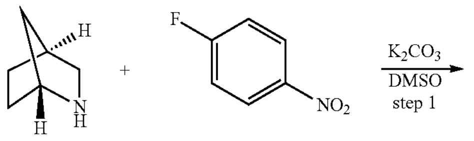

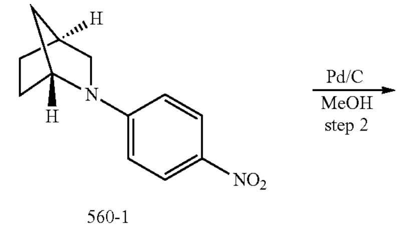

560-1

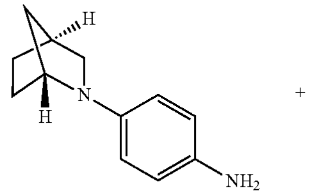

560-2

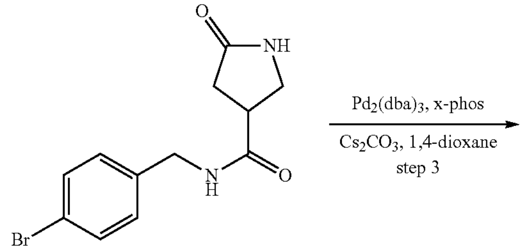

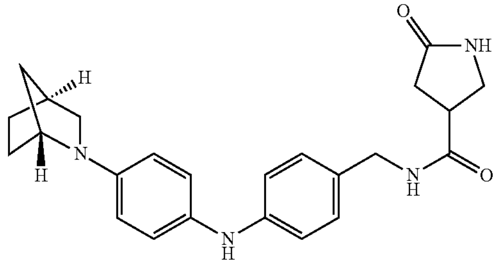

560

Step 1. (1R,4S)-2-(4-nitrophenyl)-2-azabicyclo[2.2.1]heptane (560-1). The title compound 560-1 (970 mg) was prepared in a total yield of 92% as a yellow solid from (1R,4S)-2-azabicyclo[2.2.1]heptane (500 mg, 5.155 mmol) and 4-bromobenzaldehyde (606 mg, 4.296 mmol) according to the procedure for 526-1. Mass (m/z): 219.2 $[M+H]^+$.

Step 2. 4-((1R,4S)-2-azabicyclo[2.2.1]heptan-2-yl)aniline: (560-2). The title compound 560-2 (906 mg) was prepared in a total yield of 90% as a purple solid from (1R,4S)-2-(4-nitrophenyl)-2-azabicyclo[2.2.1]heptane (970 mg, 4.450 mmol) according to the procedure for 526-2. Mass (m/z): 189.3 $[M+H]^+$.

Step 3. N-(4-((4-((1R,4S)-2-azabicyclo[2.2.1]heptan-2-yl)phenyl)amino)benzyl)-5-oxopyrrolidine-3-carboxamide (560-3). The title compound 560 (4.2 mg) was prepared in a total yield of 6.2% as a blue solid from 4-((1R,4S)-2- azabicyclo[2.2.1]heptan-2-yl)aniline (38 mg, 0.202 mmol), N-(4-bromobenzyl)-5-oxopyrrolidine-3-carboxamide (50 mg, 0.168 mmol), $Pd_2(dba)_3$ (2 mg, 0.002 mmol), x-phos (6 mg, 0.01 mmol) and $Cs_2CO_A$ (83 mg, 0.252 mmol) and 1,4-dioxane (5 mL) according to the procedure for 525. $^1$H NMR (400 MHz, DMSO-$d_6$) δ 8.51 (s, 1H), 8.35 (s, 2H), 7.58 (s, 3H), 7.35-7.30 (m, 2H), 7.25 (dd, J=7.2, 2.8 Hz, 3H), 4.28 (d, J=6.0 Hz, 2H), 2.33-2.26 (m, 6H), 2.00 (q, J=6.8, 6.4 Hz, 2H), 1.65 (s, 4H). Mass (m/z): 405.3 $[M+H]^+$.

N-(4-((4-(3,3-dimethylazetidin-1-yl)phenyl)amino) benzyl)-5-oxopyrrolidine-3-carboxamide (561)

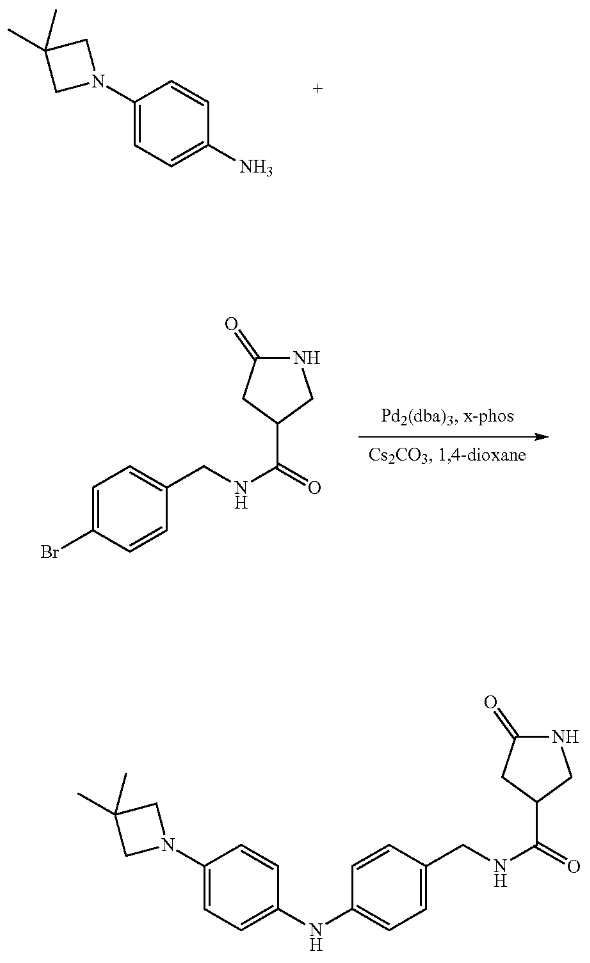

561

The title compound 561 (10.0 mg) was prepared in a total yield of 15.2% as a blue solid from 4-(3,3-dimethylazetidin-1-yl)aniline (36 mg, 0.202 mmol), N-(4-bromobenzyl)-5-oxopyrrolidine-3-carboxamide (50 mg, 0.168 mmol), $Pd_2(dba)_3$ (2 mg, 0.002 mmol), x-phos (6 mg, 0.01 mmol) and $Cs_2CO_3$ (83 mg, 0.252 mmol) and 1,4-dioxane (5 mL) according to the procedure for 525.1H NMR (400 MHz, DMSO-$d_6$) δ 8.38 (s, 2H), 7.59 (s, 2H), 7.41-6.75 (m, 8H), 4.27-4.16 (m, 2H), 3.40 (t, J=8.8 Hz, 2H), 3.27-3.12 (m, 4H), 2.30 (dd, J=8.4, 3.6 Hz, 3H), 1.31 (d, J=2.0 Hz, 6H). Mass (m/z): 393.3 $[M+H]^+$.

N-(4-((4-(3-methylpiperidin-1-yl)phenyl)amino) benzyl)-5-oxopyrrolidine-3-carboxamide (562)

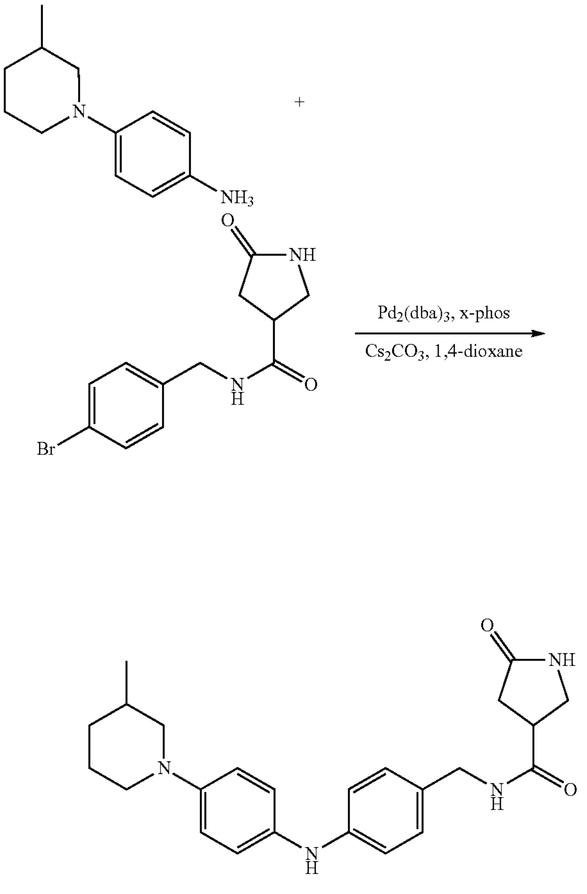

562

The title compound 562 (14.7 mg) was prepared in a total yield of 21.6% as a green solid from 4-(3-methylpiperidin-1-yl)aniline (39 mg, 0.202 mmol), N-(4-bromobenzyl)-5-oxopyrrolidine-3-carboxamide (50 mg, 0.168 mmol), $Pd_2(dba)_3$ (2 mg, 0.002 mmol), x-phos (6 mg, 0.01 mmol) and $Cs_2CO_3$ (83 mg, 0.252 mmol) and 1,4-dioxane (5 mL) according to the procedure for 525. $^1$H NMR (400 MHz, DMSO-$d_6$) δ 8.44 (t, J=5.6 Hz, 2H), 7.60 (s, 2H), 7.22-6.98 (m, 8H), 3.42 (d, J=8.8 Hz, 4H), 3.23 (dt, J=15.2, 7.2 Hz, 4H), 2.30 (dd, J=8.4, 3.2 Hz, 3H), 1.95-1.77 (m, 3H), 0.92 (s, 3H). Mass (m/z): 407.3 $[M+H]^+$.

N-(4-((4-(2-methylpiperidin-1-yl)phenyl)amino) benzyl)-5-oxopyrrolidine-3-carboxamide (563)

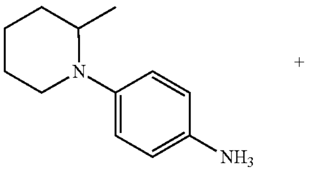

-continued

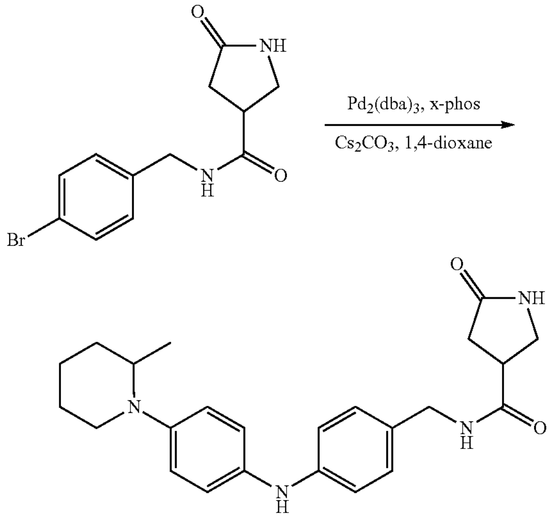

563

The title compound 563 (19.1 mg) was prepared in a total yield of 27.9% as a white solid from 4-(2-methylpiperidin-1-yl)aniline (39 mg, 0.202 mmol), N-(4-bromobenzyl)-5-oxopyrrolidine-3-carboxamide (50 mg, 0.168 mmol), $Pd_2(dba)_3$ (2 mg, 0.002 mmol), x-phos (6 mg, 0.01 mmol) and $Cs_2CO_3$ (83 mg, 0.252 mmol) and 1,4-dioxane (5 mL) according to the procedure for 525. $^1$H NMR (400 MHz, DMSO-$d_6$) δ 10.67 (s, 1H), 8.57-8.42 (m, 2H), 7.60 (s, 1H), 7.50 (d, J=8.4 Hz, 2H), 7.20-7.05 (m, 6H), 4.22 (dd, J=6.0, 2.0 Hz, 2H), 3.57-3.38 (m, 4H), 3.30-3.17 (m, 2H), 2.34-2.28 (m, 2H), 2.02 (t, J=6.8 Hz, 1H), 1.93-1.77 (m, 3H), 1.73-1.62 (m, 2H), 0.97 (d, J=6.4 Hz, 3H). Mass (m/z): 407.3 $[M+H]^+$.

5-oxo-N-(3-((4-(4-(trifluoromethyl)piperidin-1-yl)phenyl)amino)benzyl) pyrrolidine-3-carboxamide (564)

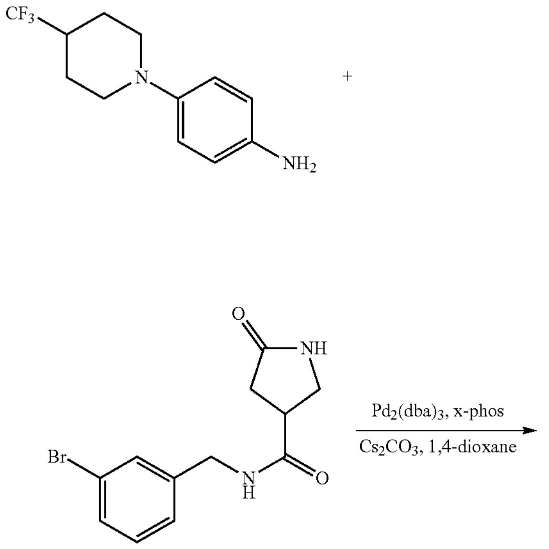

-continued

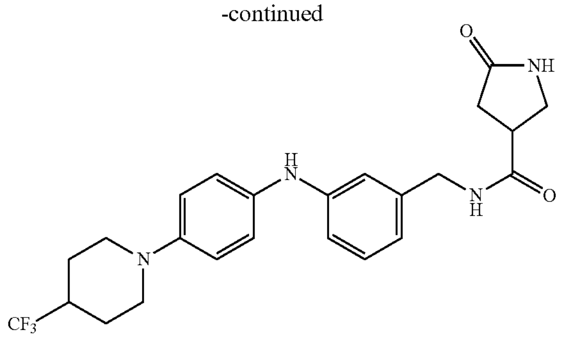

564

The title compound 564 (22.5 mg) was prepared in a total yield of 29.1% as a brown solid from 4-(4-(trifluoromethyl)piperidin-1-yl)aniline (49 mg, 0.202 mmol), N-(3-bromobenzyl)-5-oxopyrrolidine-3-carboxamide (50 mg, 0.168 mmol), $Pd_2(dba)_3$ (2 mg, 0.002 mmol), x-phos (6 mg, 0.01 mmol) and $Cs_2CO_3$ (83 mg, 0.252 mmol) and 1,4-dioxane (5 mL) according to the procedure for 525. $^1$H NMR (400 MHz, DMSO-$d_6$) δ 8.60 (s, 1H), 7.95 (s, 1H), 7.68 (s, 1H), 7.16 (t, J=7.6 Hz, 1H), 7.05 (d, J=8.4 Hz, 2H), 6.96 (d, J=8.4 Hz, 2H), 6.90-6.82 (m, 2H), 6.64 (d, J=7.6 Hz, 1H), 4.24 (d, J=5.6 Hz, 2H), 3.70 (d, J=12.0 Hz, 2H), 3.47 (d, J=16.8 Hz, 1H), 3.35-3.25 (m, 2H), 2.69 (t, J=12.0 Hz, 2H), 2.50 (d, J=8.4 Hz, 1H), 2.40-2.34 (m, 2H), 1.95 (d, J=12.4 Hz, 2H), 1.73-1.55 (m, 2H). Mass (m/z): 461.3 $[M+H]^+$.

N-(4-((4-(2-azaspiro[3.4]octan-2-yl)phenyl)amino)benzyl)-5-oxopyrrolidine-3-carboxamide (565)

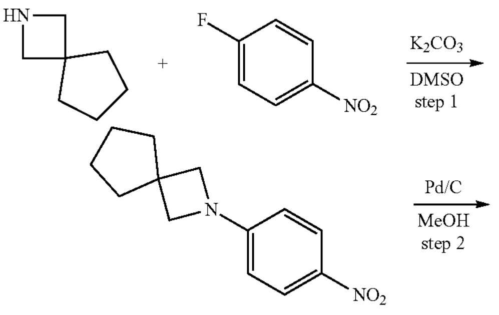

565-1

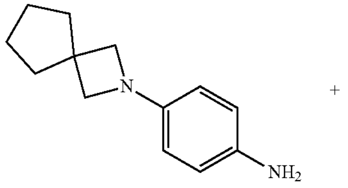

565-2

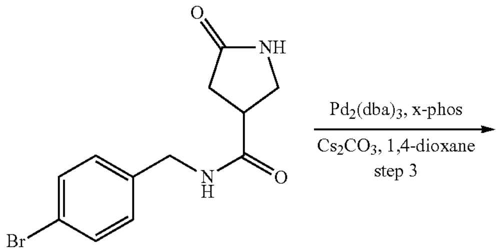

-continued

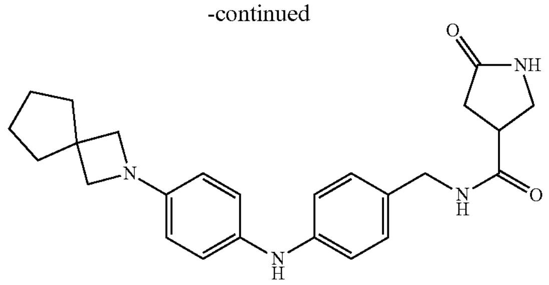

565

Step 1. 2-(4-nitrophenyl)-2-azaspiro[3.4]octane: (565-1). The title compound 565-1 (510 mg) was prepared in a total yield of 98% as a yellow solid from 2-azaspiro[3.4]octane (250 mg, 2.252 mmol) and 1-fluoro-4-nitrobenzene (265 mg, 1.877 mmol) according to the procedure for 526-1. Mass (m/z): 233.2 $[M+H]^+$.

Step 2. 4-(2-azaspiro[3.4]octan-2-yl)aniline: (565-2). The title compound 565-2 (290 mg) was prepared in a total yield of 65% as a purple solid from 2-(4-nitrophenyl)-2-azaspiro[3.4]octane (510 mg, 2.198 mmol) according to the procedure for 526-2. Mass (m/z): 203.3 $[M+H]^+$.

Step 3. N-(4-((4-(2-azaspiro[3.4]octan-2-yl)phenyl)amino)benzyl)-5-oxopyrrolidine-3-carboxamide (565). The title compound 565 (21.5 mg) was prepared in a total yield of 30.6% as a white solid from 4-(2-azaspiro[3.4]octan-2-yl)aniline (41 mg, 0.202 mmol), N-(4-bromobenzyl)-5-oxopyrrolidine-3-carboxamide (50 mg, 0.168 mmol), $Pd_2(dba)_3$ (2 mg, 0.002 mmol), x-phos (6 mg, 0.01 mmol) and $Cs_2CO_3$ (83 mg, 0.252 mmol) and 1,4-dioxane (5 mL) according to the procedure for 525. $^1H$ NMR (400 MHz, DMSO-$d_6$) δ 8.33 (s, 1H), 7.54 (d, J=18.8 Hz, 2H), 6.90 (dd, J=31.2, 8.4 Hz, 4H), 6.72 (d, J=8.0 Hz, 2H), 6.31 (d, J=8.0 Hz, 2H), 4.06 (d, J=5.6 Hz, 2H), 3.53 (s, 4H), 3.21-3.06 (m, 3H), 2.22 (dd, J=8.4, 5.2 Hz, 2H), 1.71 (td, J=6.0, 4.8, 2.8 Hz, 4H), 1.55-1.47 (m, 4H). Mass (m/z): 419.3 $[M+H]^+$.

N-(4-((4-(4-(difluoromethyl)piperidin-1-yl)phenyl)amino)benzyl)-5-oxopyrrolidine-3-carboxamide (566)

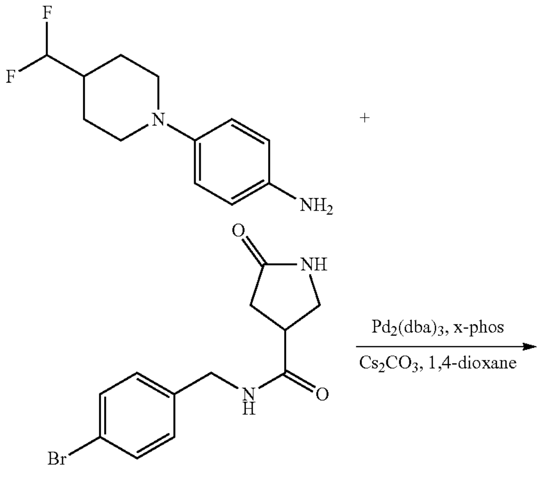

-continued

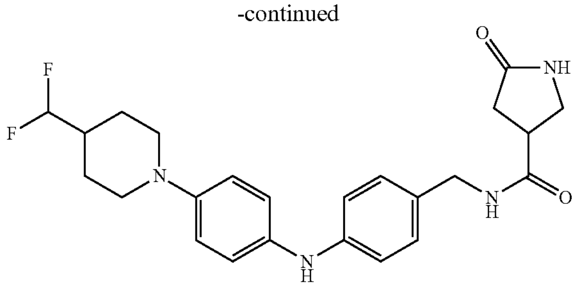

566

The title compound 566 (20.1 mg) was prepared in a total yield of 27.1% as a brown solid from 4-(4-(difluoromethyl)piperidin-1-yl)aniline (46 mg, 0.202 mmol), N-(4-bromobenzyl)-5-oxopyrrolidine-3-carboxamide (50 mg, 0.168 mmol), $Pd_2(dba)_3$ (2 mg, 0.002 mmol), x-phos (6 mg, 0.01 mmol) and $Cs_2CO_3$ (83 mg, 0.252 mmol) and 1,4-dioxane (5 mL) according to the procedure for 525. $^1H$ NMR (400 MHz, DMSO-$d_6$) δ 8.36 (s, 1H), 7.75 (s, 1H), 7.53 (s, 1H), 7.05-6.69 (m, 8H), 4.08 (d, J=5.6 Hz, 2H), 3.52 (d, J=11.6 Hz, 2H), 3.33 (t, J=8.4 Hz, 1H), 3.20-3.09 (m, 2H), 2.50 (d, J=11.6 Hz, 2H), 2.27-2.19 (m, 2H), 1.84 (s, 1H), 1.69 (d, J=12.4 Hz, 2H), 1.41 (d, J=12.4 Hz, 2H). Mass (m/z): 443.3 $[M+H]^+$.

5-oxo-N-(4-((4-(piperidin-1-yl)-3-(trifluoromethyl)phenyl)amino)benzyl) pyrrolidine-3-carboxamide (567)

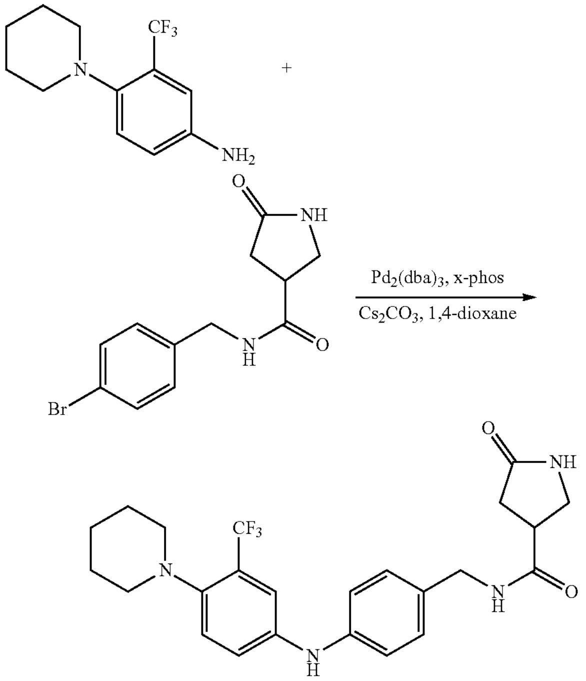

567

The title compound 567 (26.5 mg) was prepared in a total yield of 34.3% as a white solid from 4-(piperidin-1-yl)-3-(trifluoromethyl)aniline (50 mg, 0.202 mmol), N-(4-bromobenzyl)-5-oxopyrrolidine-3-carboxamide (50 mg, 0.168 mmol), $Pd_2(dba)_3$ (2 mg, 0.002 mmol), x-phos (6 mg, 0.01 mmol) and $Cs_2CO_3$ (83 mg, 0.252 mmol) and 1,4-dioxane (5 mL) according to the procedure for 525. $^1H$ NMR (400 MHz, DMSO-$d_6$) δ 8.51 (t, J=5.6 Hz, 1H), 8.44 (s, 1H), 7.61 (s, 1H), 7.39 (d, J=8.8 Hz, 1H), 7.27 (dd, J=8.8, 2.8 Hz, 1H), 7.23 (d, J=2.8 Hz, 1H), 7.17-7.12 (m, 2H), 7.06-7.00 (m, 2H), 4.20 (d, J=5.6 Hz, 2H), 3.46-3.39 (m, 1H), 3.30-3.16 (m, 2H), 2.73 (t, J=5.2 Hz, 4H), 2.31 (dd, J=8.4, 4.4 Hz, 2H), 1.59 (p, J=5.2 Hz, 4H), 1.49 (s, 2H). Mass (m/z): 461.3 [M+H]1.

N-(4-((4-(4-methylpiperidin-1-yl)-3-(trifluoromethyl)phenyl)amino)benzyl)-5-oxopyrrolidine-3-carboxamide (568)

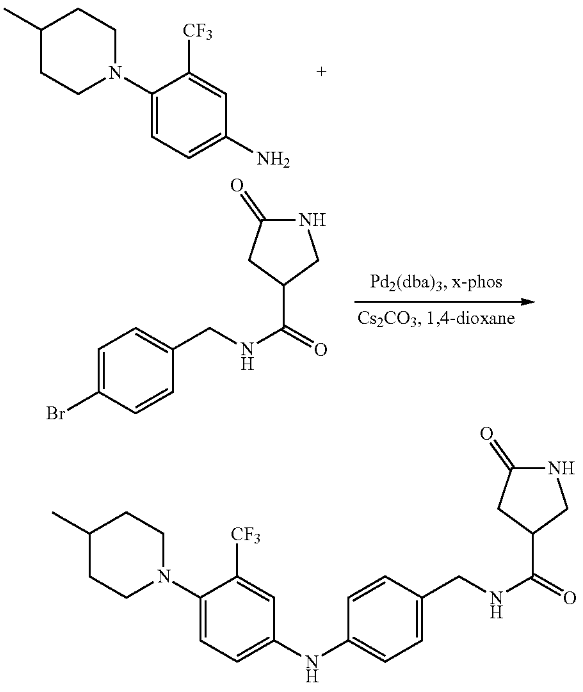

568

The title compound 568 (13.3 mg) was prepared in a total yield of 16.7% as a white solid from 4-(4-methylpiperidin-1-yl)-3-(trifluoromethyl)aniline (52 mg, 0.202 mmol), N-(4-bromobenzyl)-5-oxopyrrolidine-3-carboxamide (50 mg, 0.168 mmol), $Pd_2(dba)_3$ (2 mg, 0.002 mmol), x-phos (6 mg, 0.01 mmol) and $Cs_2CO_3$ (83 mg, 0.252 mmol) and 1,4-dioxane (5 mL) according to the procedure for 525. $^1H$ NMR (400 MHz, DMSO-$d_6$) δ 8.42 (t, J=5.6 Hz, 1H), 8.34 (s, 11H), 7.59 (s, 1H), 7.40 (d, J=8.8 Hz, 11H), 7.26 (dd, J=8.8, 2.8 Hz, 1H), 7.21 (d, J=2.8 Hz, 1H), 7.18-7.12 (m, 2H), 7.06-7.00 (m, 2H), 4.20 (d, J=5.6 Hz, 2H), 3.41 (t, J=8.8 Hz, 3H), 3.30-3.12 (m, 3H), 2.82 (d, J=11.2 Hz, 2H), 2.67 (td, J=11.6, 2.0 Hz, 211), 2.30 (dd, J=8.4, 3.2 Hz, 2H), 1.70-1.60 (m, 211), 1.44 (q, J=7.2, 6.4 Hz, 1H), 1.30-1.19 (m, 3H), 0.95 (d, J=6.4 Hz, 3H). Mass (m/z): 475.3 $[M+H]^+$.

N1-(4-((4-(4,4-dimethylpiperidin-1-yl)phenyl)amino)benzyl)glutaramide (569)

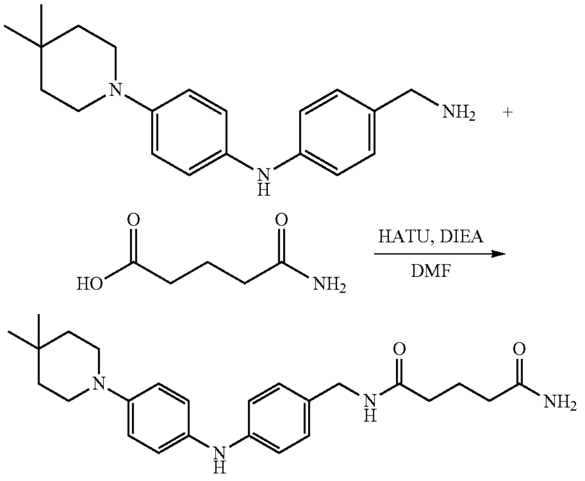

569

The title compound 569 (19.9 mg) was prepared in a total yield of 29.1% as a blue solid from 4-(aminomethyl)-N-(4-(4,4-dimethylpiperidin-1-yl)phenyl)aniline (50 mg, 0.162 mmol), 5-amino-5-oxopentanoic acid (28 mg, 0.210 mmol), HATU (80 mg, 0.210 mmol), DIEA (27 mg, 0.210 mmol) and DMF (3 mL) according to the procedure for 523. $^1H$ NMR (400 MHz, DMSO-$d_6$) δ 8.46 (s, 1H), 8.27 (t, J=6.0 Hz, 11H), 7.53 (s, 2H), 7.27 (s, 1H), 7.16 (d, J=8.0 Hz, 2H), 7.07 (dd, J=15.6, 8.0 Hz, 4H), 6.74 (s, 1H), 4.19 (d, J=5.6 Hz, 4H), 2.13 (t, J=7.6 Hz, 211), 2.05 (t, J=7.6 Hz, 2H), 1.72 (p, J=7.6 Hz, 4H), 1.07 (s, 6H). Mass (m/z): 423.3 $[M+H]^+$.

5-oxo-N-(4-((2-(4-(trifluoromethyl)piperidin-1-yl)pyrimidin-5-yl)amino)benzyl) pyrrolidine-3-carboxamide (570)

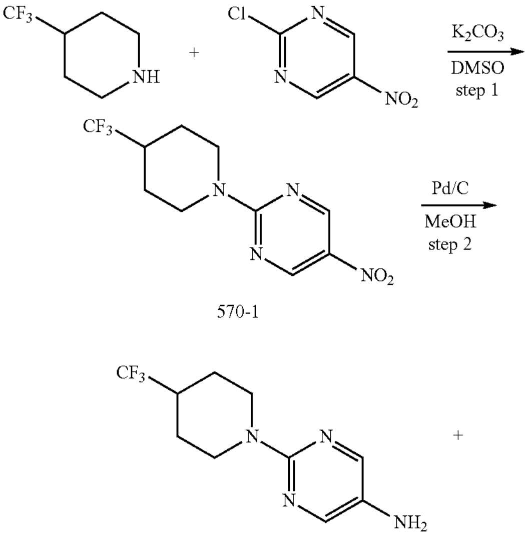

570-1

-continued

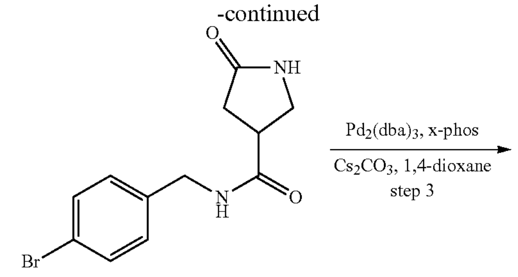

570-2

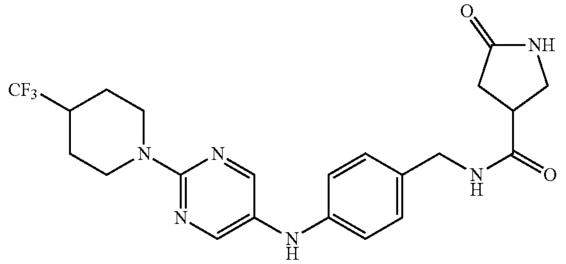

570

Step 1. 5-nitro-2-(4-(trifluoromethyl)piperidin-1-yl)pyrimidine: (570-1). The title compound 570-1 (1.6 g) was prepared in a total yield of 86.4% as a yellow solid from 4-(trifluoromethyl)piperidine (1.1 g, 7.382 mmol) and 2-chloro-5-nitropyrimidine (1 g, 6.711 mmol) according to the procedure for 526-1. Mass (m/z): 277.2 $[M+H]^+$.

Step 2. 2-(4-(trifluoromethyl)piperidin-1-yl)pyrimidin-5-amine: (570-2). The title compound 570-2 (1.2 g) was prepared in a total yield of 84% as a purple solid from 5-nitro-2-(4-(trifluoromethyl)piperidin-1-yl)pyrimidine (1.6 g, 5.80 mmol) according to the procedure for 526-2. Mass (m/z): 247.3 $[M+H]^+$.

Step 3. 5-oxo-N-(4-((2-(4-(trifluoromethyl)piperidin-1-yl)pyrimidin-5-yl)amino)benzyl)pyrrolidine-3-carboxamide (570). The title compound 570 (18.6 mg) was prepared in a total yield of 24.0% as a yellow solid from 2-(4-(trifluoromethyl)piperidin-1-yl)pyrimidin-5-amine (52 mg, 0.202 mmol). N-(4-bromobenzyl)-5-oxopyrrolidine-3-carboxamide (50 mg, 0.168 mmol), $Pd_2(dba)_3$ (2 mg, 0.002 mmol), x-phos (6 mg, 0.01 mmol) and $Cs_2CO_3$ (83 mg, 0.252 mmol) and 1,4-dioxane (5 mL) according to the procedure for 525. $^1$H NMR (400 MHz, DMSO-$d_6$) δ 8.37 (t, J=6.0 Hz, 1H), 8.26 (s, 2H), 7.58 (s, 1H), 7.07-7.00 (m, 2H), 6.78-6.71 (m, 2H), 4.69 (d, J=13.2 Hz, 2H), 4.14 (d, J=5.6 Hz, 2H), 3.39 (t, J=8.8 Hz, 1H), 3.28-3.10 (m, 2H), 2.89 (td, J=12.8, 2.6 Hz, 2H), 2.62 (ddd, J=12.4, 8.4, 3.6 Hz, 1H), 2.29 (dd, J=8.4, 3.42 Hz, 2H), 1.95-1.79 (m, 2H), 1.38 (qd, J=12.4, 4.4 Hz, 2H). Mass (m/z): 463.3 $[M+H]^+$.

(S)—N-(4-((4-(4,4-dimethylpiperidin-1-yl)phenyl)amino)benzyl)-2,6-dioxohexahydropyrimidine-4-carboxamide (571)

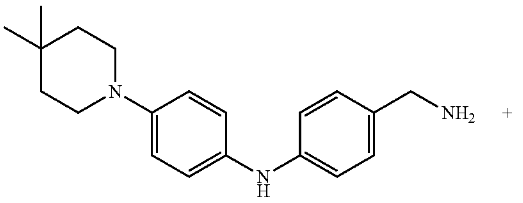

+

-continued

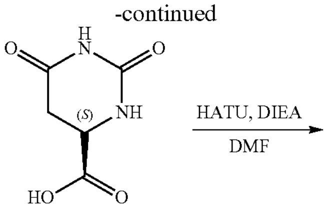

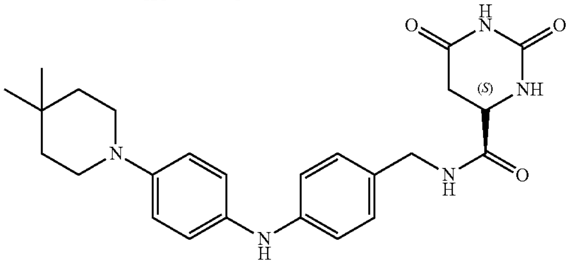

571

The title compound 571 (7.1 mg) was prepared in a total yield of 9.8% as a blue solid from 4-(aminomethyl)-N-(4-(4,4-dimethylpiperidin-1-yl)phenyl)aniline (50 mg, 0.162 mmol), (S)-2,6-dioxohexahydropyrimidine-4-carboxylic acid (33 mg, 0.210 mmol), HATU (80 mg, 0.210 mmol), DIEA (27 mg, 0.210 mmol) and DMF (3 mL) according to the procedure for 523. $^1$H NMR (400 MHz, DMSO-$d_6$) δ 10.05 (d, J=1.6 Hz, 1H), 8.50 (s, 2H), 7.64 (t, J=2.4 Hz, 1H), 7.52 (s, 1H), 7.29-6.92 (m, 7H), 4.21 (s, 2H), 4.01 (dt, J=7.2, 3.6 Hz, 2H), 3.54-3.35 (m, 3H), 3.10 (qd, J=7.2, 4.8 Hz, 1H), 2.87 (dd, J=16.4, 7.2 Hz, 11H), 1.66 (s, 4H), 1.14-0.99 (m, 6H). Mass (m/z): 450.3 $[M+H]^+$.

(R)—N-(4-((4-(4,4-dimethylpiperidin-1-yl)phenyl)amino)benzyl)-2-oxoimidazolidine-4-carboxamide (572)

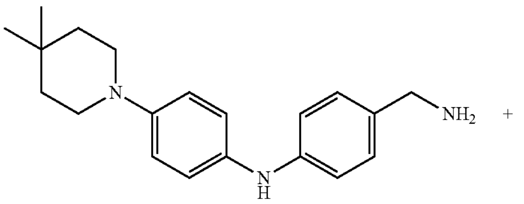

+

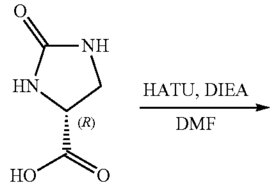

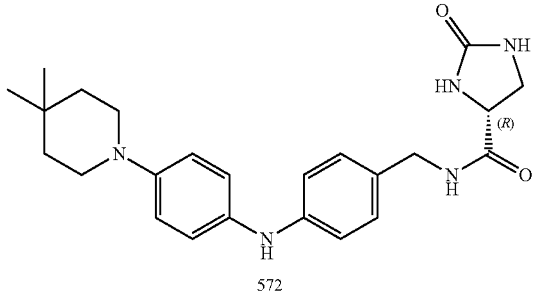

572

The title compound 572 (43.2 mg) was prepared in a total yield of 63.3% as a blue solid from 4-(aminomethyl)-N-(4-(4,4-dimethylpiperidin-1-yl)phenyl)aniline (50 mg, 0.162 mmol), (R)-2-oxoimidazolidine-4-carboxylic acid (27 mg, 0.210 mmol), HATU (80 mg, 0.210 mmol), DIEA (27 mg, 0.210 mmol) and DMF (3 mL) according to the procedure for 523.1H NMR (400 MHz, DMSO-$d_6$) δ 8.47 (s, 1H), 8.38 (t, J=6.0 Hz, 1H), 7.53 (s, 2H), 7.18 (d, J=8.0 Hz, 2H), 7.08 (dd, J=16.0, 8.4 Hz, 4H), 6.57 (s, 1H), 6.35 (s, 1H), 4.23 (d, J=5.4 Hz, 2H), 4.11 (dd, J=9.6, 6.2 Hz, 2H), 3.56 (t, J=9.6 Hz, 2H), 3.22 (dd, J=889, 6.2 Hz, 1H), 3.10 (qd, J=7.2, 4.8 Hz, 3H), 1.69 (s, 3H), 1.07 (s, 6H). Mass (m/z): 422.3 $[M+H]^+$.

N-(4-((4-(4,4-dimethylpiperidin-1-yl)phenyl)amino) benzyl)-2,6-dioxopiperidine-4-carboxamide (573)

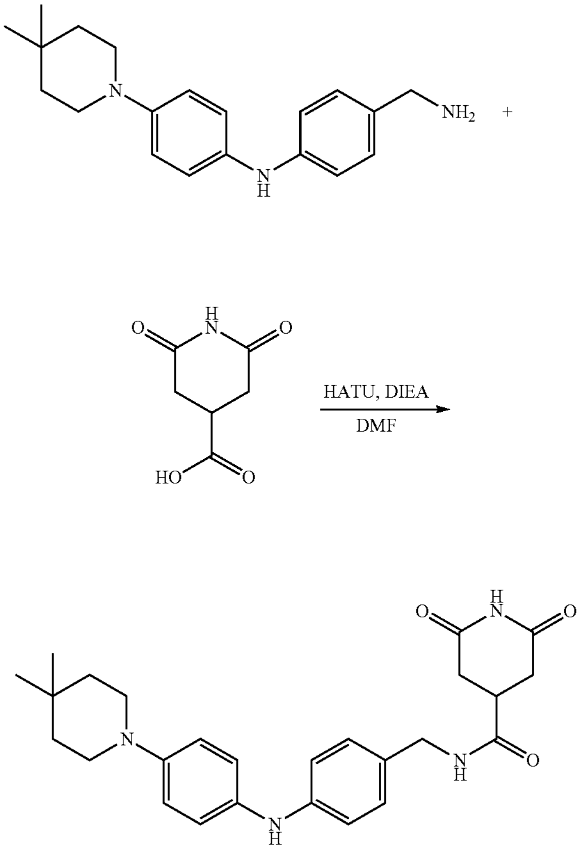

573

The title compound 573 (7.0 mg) was prepared in a total yield of 9.6% as a blue solid from 4-(aminomethyl)-N-(4-(4,4-dimethylpiperidin-1-yl)phenyl)aniline (50 mg, 0.162 mmol), 2,6-dioxopiperidine-4-carboxylic acid (33 mg, 0.210 mmol), HATU (80 mg, 0.210 mmol), DIEA (27 mg, 0.210 mmol) and DMF (3 mL) according to the procedure for 523. $^1$H NMR (400 MHz, DMSO-$d_6$) δ 10.70 (s, 1H), 8.50 (s, 1H), 7.52 (s, 1H), 7.10 (d, J=19.6 Hz, 8H), 4.19 (s, 2H), 3.47-3.27 (m, 5H), 3.03-2.95 (m, 1H), 2.61 (qd, J=16.8, 6.2 Hz, 5H), 1.62 (s, 3H), 1.05 (s, 6H). Mass (m/z): 449.3 $[M+H]^+$.

N-(4-((5-fluoro-6-(4-(trifluoromethyl)piperidin-1-yl) pyridin-3-yl)amino)benzyl)-5-oxopyrrolidine-3-carboxamide (574)

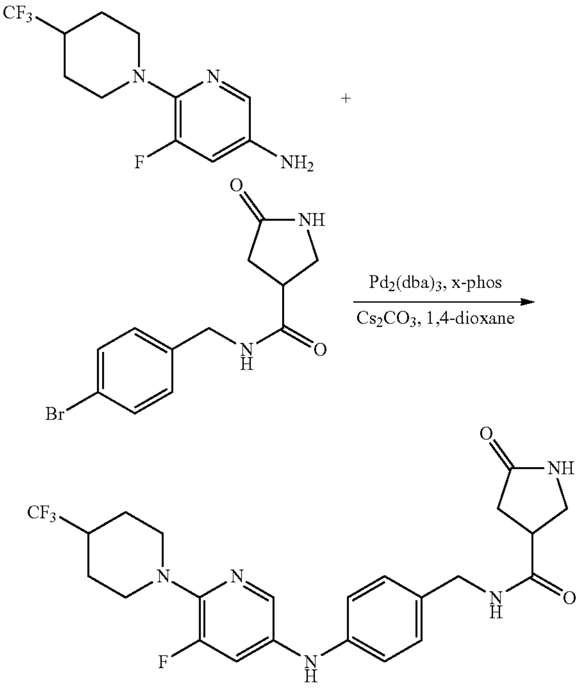

574

The title compound 574 (8.1 mg) was prepared in a total yield of 10.1% as a white solid from 5-fluoro-6-(4-(trifluoromethyl)piperidin-1-yl)pyridin-3-amine (53 mg, 0.202 mmol), N-(4-bromobenzyl)-5-oxopyrrolidine-3-carboxamide (50 mg, 0.168 mmol), $Pd_2(dba)_3$ (2 mg, 0.002 mmol), x-phos (6 mg, 0.01 mmol) and $Cs_2CO_3$ (83 mg, 0.252 mmol) and 1,4-dioxane (5 mL) according to the procedure for 525. $^1$H NMR (400 MHz, DMSO-$d_6$) δ 8.45 (t, J=5.6 Hz, 1H), 8.20 (s, 1H), 7.87 (dd, J=2.4, 1.0 Hz, 1H), 7.59 (s, 1H), 7.28 (dd, J=14.4, 2.4 Hz, 1H), 7.14-7.08 (m, 2H), 6.98-6.92 (m, 2H), 4.18 (d, J=5.6 Hz, 2H), 3.77 (d, J=12.4 Hz, 2H), 3.28-3.12 (m, 2H), 2.81 (td, J=12.8, 2.4 Hz, 2H), 2.30 (dd, J=8.4, 3.6 Hz, 2H), 1.95-1.81 (m, 2H), 1.57 (qd, J=12.4, 4.0 Hz, 2H). Mass (m/z): 480.3 $[M+H]^+$.

N-(4-((4-(4-isopropylpiperidin-1-yl)phenyl)amino) benzyl)-5-oxopyrrolidine-3-carboxamide (575)

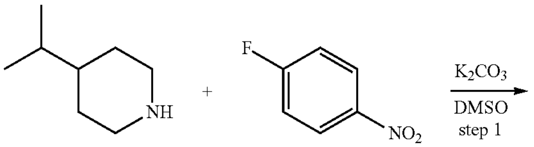

-continued

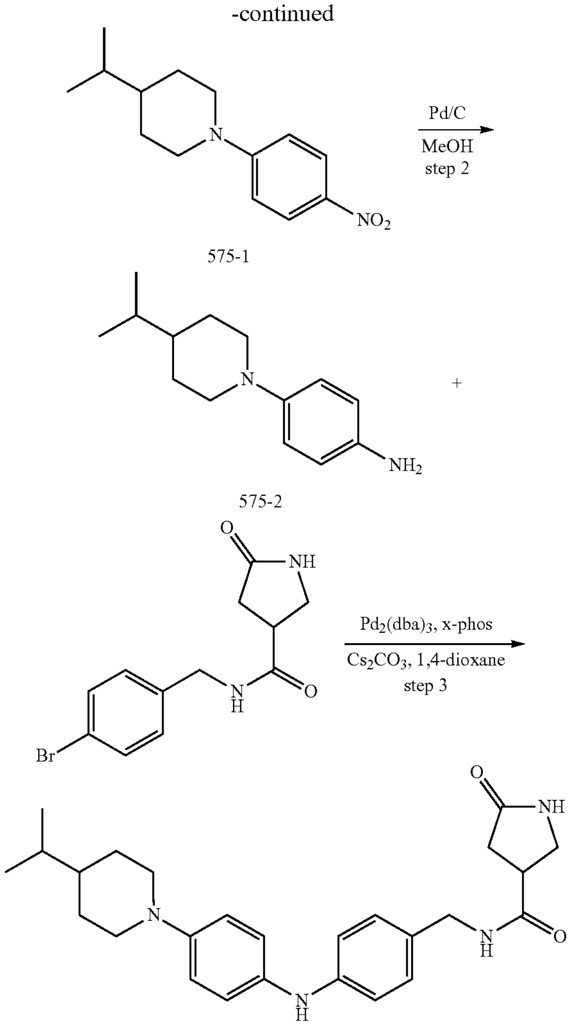

575-1

575-2

575

Step 1. 4-isopropyl-1-(4-nitrophenyl)piperidine: (575-1). The title compound 575-1 (485 mg) was prepared in a total yield of 92% as a yellow solid from 4-isopropylpiperidine (297 mg, 2.340 mmol) and 1-fluoro-4-nitrobenzene (300 mg, 2.128 mmol) according to the procedure for 526-1. Mass (m/z): 249.2 $[M+H]^+$.

Step 2. 4-(4-isopropylpiperidin-1-yl)aniline: (575-2). The title compound 575-2 (405 mg) was prepared in a total yield of 95.1% as a purple solid from 4-isopropyl-1-(4-nitrophenyl)piperidine (485 mg, 1.956 mmol) according to the procedure for 526-2. Mass (m/z): 219.3 $[M+H]^+$.

Step 3. N-(4-((4-(4-isopropylpiperidin-1-yl)phenyl)amino)benzyl)-5-oxopyrrolidine-3-carboxamide (575). The title compound 575 (14.5 mg) was prepared in a total yield of 19.9% as a brown solid from 4-(4-isopropylpiperidin-1-yl)aniline (44 mg, 0.202 mmol), N-(4-bromobenzyl)-5-oxopyrrolidine-3-carboxamide (50 mg, 0.168 mmol), $Pd_2(dba)_3$ (2 mg, 0.002 mmol), x-phos (6 mg, 0.01 mmol) and $Cs_2CO_3$ (83 mg, 0.252 mmol) and 1,4-dioxane (5 mL) according to the procedure for 525. $^1$H NMR (400 MHz, DMSO-$d_6$) δ 8.83 (s, 1H), 8.39 (t, J=5.6 Hz, 1H), 7.88 (dd, J=9.6, 1.6 Hz, 2H), 7.58 (s, 1H), 7.50-7.37 (m, 4H), 7.13-7.07 (m, 2H), 4.18 (d, J=5.6 Hz, 2H), 4.15-4.08 (m, 2H), 3.40 (t, J=8.4 Hz, 1H), 3.28-3.15 (m, 2H), 2.62 (d, J=12.0 Hz, 2H), 2.34-2.26 (m, 2H), 1.77-1.67 (m, 2H), 1.48-1.37 (m, 1H), 0.87 (d, J=6.8 Hz, 6H). Mass (m/z): 435.3 $[M+H]^+$.

5-oxo-N-(4-((4-(4-propylpiperidin-1-yl)phenyl)amino)benzyl)pyrrolidine-3-carboxamide (576)

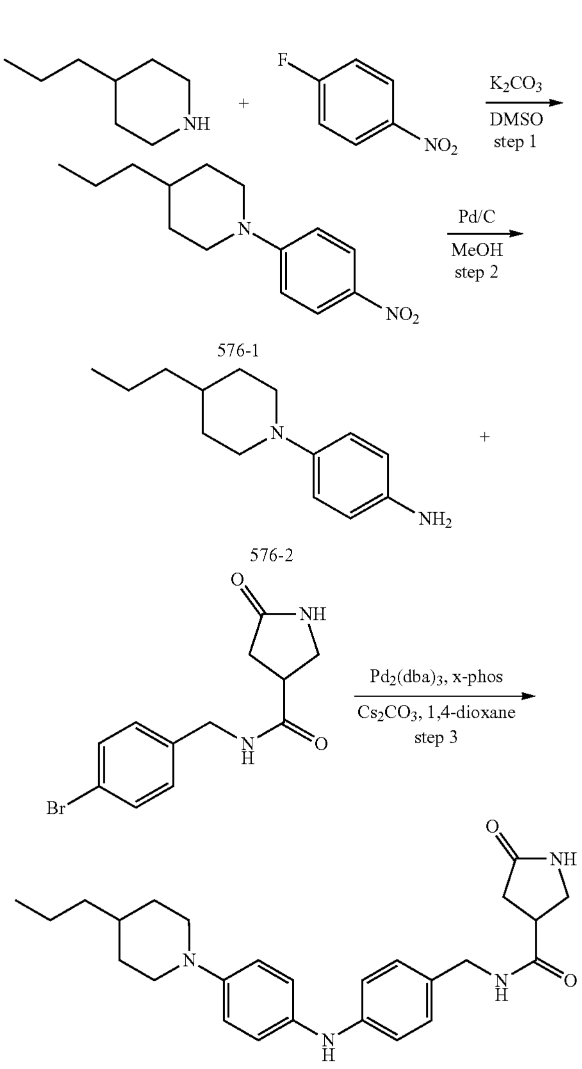

576-1

576-2

576

Step 1. 1-(4-nitrophenyl)-4-propylpiperidine: (576-1). The title compound 576-1 (410 mg) was prepared in a total yield of 93% as a yellow solid from 4-propylpiperidine (247 mg, 1.950 mmol) and 1-fluoro-4-nitrobenzene (250 mg, 1.773 mmol) according to the procedure for 526-1. Mass (m/z): 249.2 $[M+H]^+$.

Step 2. 4-(4-propylpiperidin-1-yl)aniline: (576-2). The title compound 576-2 (350 mg) was prepared in a total yield of 95.1% as a purple solid from 1-(4-nitrophenyl)-4-propylpiperidine (410 mg, 1.653 mmol) according to the procedure for 526-2. Mass (m/z): 219.3 $[M+H]^+$.

Step 3. 5-oxo-N-(4-((4-(4-propylpiperidin-1-yl)phenyl)amino)benzyl)pyrrolidine-3-carboxamide (576). The title compound 576 (27.9 mg) was prepared in a total yield of 38.3% as a brown solid from 4-(4-propylpiperidin-1-yl)aniline (44 mg, 0.202 mmol), N-(4-bromobenzyl)-5-oxopyrrolidine-3-carboxamide (50 mg, 0.168 mmol), $Pd_2(dba)_3$ (2 mg, 0.002 mmol), x-phos (6 mg, 0.01 mmol) and $Cs_2CO_3$ (83 mg, 0.252 mmol) and 1,4-dioxane (5 mL) according to the procedure for 525.1H NMR (400 MHz, DMSO-$d_6$) δ 8.39 (s, 1H), 7.76 (s, 1H), 7.59 (s, 1H), 7.12-6.79 (m, 8H), 4.15 (s, 2H), 3.50 (s, 2H), 3.40 (t, J=8.6 Hz, 1H), 3.26-3.17 (m, 2H), 2.29 (dd, J=8.4, 4.8 Hz, 2H), 1.73 (s, 2H), 1.39-1.28 (m, 3H), 1.23 (t, J=7.2 Hz, 4H), 0.89 (t, J=7.2 Hz, 3H). Mass (m/z): 435.3 $[M+H]^+$.

N-(4-((4-(4-butylpiperidin-1-yl)phenyl)amino)benzyl)-5-oxopyrrolidine-3-carboxamide (577)

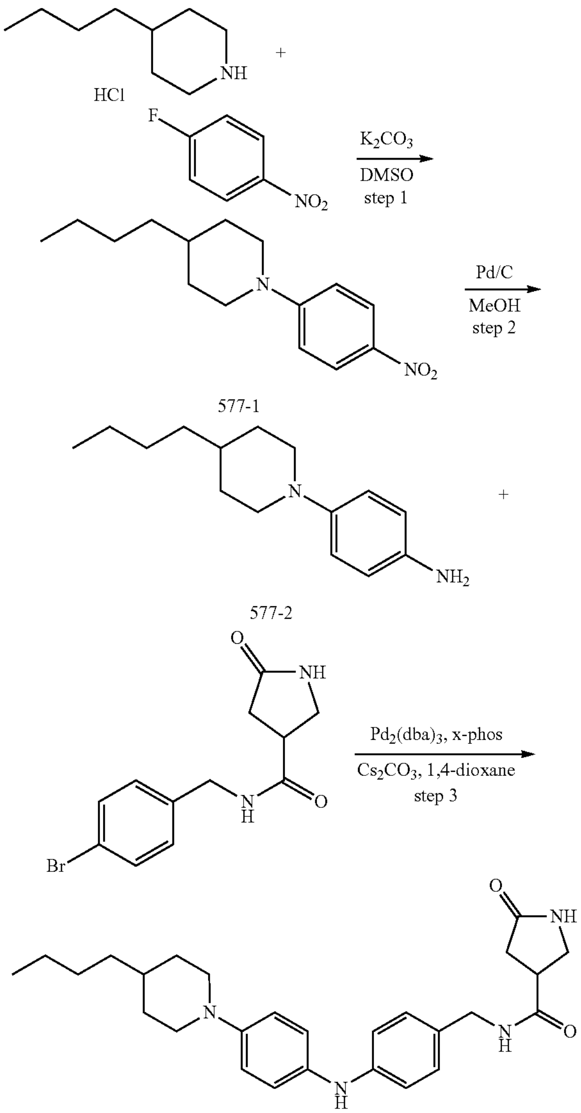

577

Step 1. 4-butyl-1-(4-nitrophenyl)piperidine: (577-1). The title compound 577-1 (620 mg) was prepared in a total yield of 92.7% as a yellow solid from 4-butylpiperidine hydrochloride (500 mg, 2.809 mmol) and 1-fluoro-4-nitrobenzene (360 mg, 2.554 mmol) according to the procedure for 526-1. Mass (m/z): 263.2 $[M+H]^+$.

Step 2. 4-butyl-1-(4-nitrophenyl)piperidine: (577-2). The title compound 577-2 (505 mg) was prepared in a total yield of 92% as a purple solid from 4-butyl-1-(4-nitrophenyl)piperidine (620 mg, 2.366 mmol) according to the procedure for 526-2. Mass (m/z): 233.3 $[M+H]^+$.

Step 3. N-(4-((4-(4-butylpiperidin-1-yl)phenyl)amino)benzyl)-5-oxopyrrolidine-3-carboxamide (577). The title compound 577 (33.9 mg) was prepared in a total yield of 44.5% as a brown solid from 4-(4-butylpiperidin-1-yl)aniline (45 mg, 0.202 mmol), N-(4-bromobenzyl)-5-oxopyrrolidine-3-carboxamide (50 mg, 0.168 mmol), $Pd_2(dba)_3$ (2 mg, 0.002 mmol), x-phos (6 mg, 0.01 mmol) and $Cs_2CO_3$ (83 mg, 0.252 mmol) and 1,4-dioxane (5 mL) according to the procedure for 525. $^1H$ NMR (400 MHz, DMSO-$d_6$) δ 8.46 (s, 1H), 7.83 (d, J=27.0 Hz, 1H), 7.60 (s, 1H), 7.14-6.75 (m, 8H), 4.15 (s, 2H), 3.40 (d, J=16.8 Hz, 11H), 3.26-3.16 (m, 2H), 2.29 (dd, J=8.4, 5.5 Hz, 2H), 1.74 (s, 2H), 1.36-1.20 (m, 9H), 0.91-0.86 (m, 3H). Mass (m/z): 449.3 $[M+H]^+$.

N-(4-((6-(4-methylpiperidin-1-yl)-5-(trifluoromethyl)pyridin-3-yl)amino)benzyl)-5-oxopyrrolidine-3-carboxamide (578)

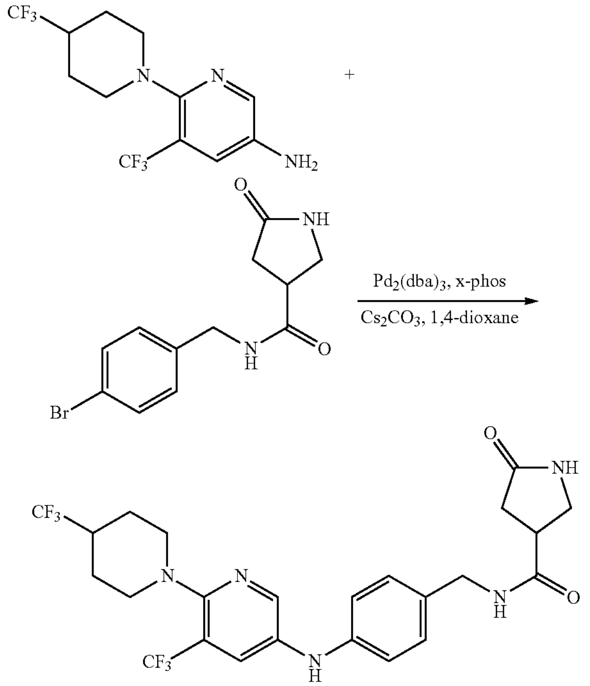

578

The title compound 578 (20.5 mg) was prepared in a total yield of 25.7% as a off-white solid from 6-(4-methylpiperidin-1-yl)-5-(trifluoromethyl)pyridin-3-amine (52 mg, 0.202 mmol), N-(4-bromobenzyl)-5-oxopyrrolidine-3-carboxamide (50 mg, 0.168 mmol), $Pd_2(dba)_3$ (2 mg, 0.002 mmol), x-phos (6 mg, 0.01 mmol) and $Cs_2CO_3$ (83 mg, 0.252 mmol) and 1,4-dioxane (5 mL) according to the procedure for 525. $^1H$ NMR (400 MHz, DMSO-$d_6$) δ 8.44 (d, J=4.4 Hz, 2H), 8.34 (d, J=2.8 Hz, 1H), 7.62-7.55 (m, 2H), 7.19-7.14 (m, 2H), 7.07-7.00 (m, 2H), 4.21 (d, J=5.6 Hz, 2H), 3.45-3.37 (m, 1H), 3.28-3.15 (m, 2H), 3.08 (d, J=11.6 Hz, 2H), 2.85-2.74 (m, 2H), 2.30 (dd, J=8.4, 3.2 Hz, 2H), 1.68 (d, J=12.4 Hz, 2H), 1.47 (dt, J=10.8, 5.2 Hz, 1H), 1.25 (qd, J=12.4, 3.6 Hz, 2H), 0.95 (d, J=6.4 Hz, 3H). Mass (m/z): 476.3 $[M+H]^+$.

N-(4-((2-fluoro-(4-(trifluoromethyl)piperidin-1-yl) pyridin-3-yl)amino)benzyl)-5-oxopyrrolidine-3-carboxamide (579)

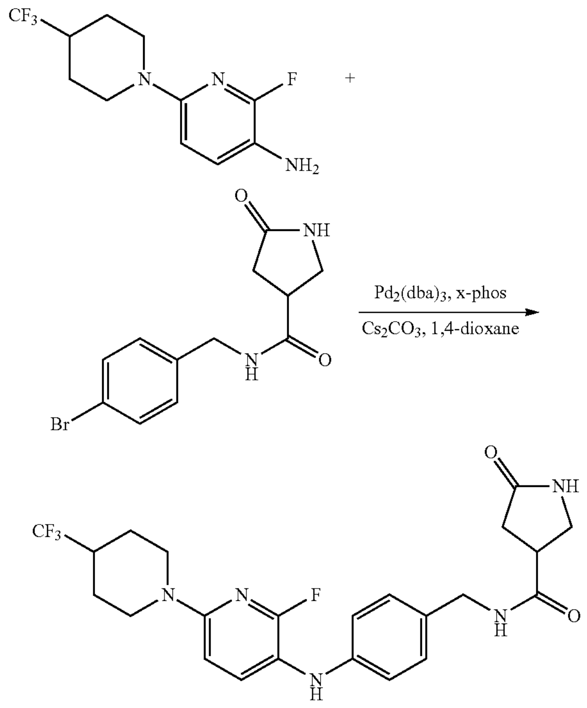

579

The title compound 579 (3.4 mg) was prepared in a total yield of 4.2% as a off-white solid from 2-fluoro-6-(4-(trifluoromethyl)piperidin-1-yl)pyridin-3-amine (52 mg, 0.202 mmol), N-(4-bromobenzyl)-5-oxopyrrolidine-3-carboxamide (50 mg, 0.168 mmol), $Pd_2(dba)_3$ (2 mg, 0.002 mmol), x-phos (6 mg, 0.01 mmol) and $Cs_2CO_3$ (83 mg, 0.252 mmol) and 1,4-dioxane (5 mL) according to the procedure for 525. $^1H$ NMR (400 MHz, DMSO-$d_6$) δ 8.34 (t, J=5.6 Hz, 1H), 7.59-7.50 (m, 2H), 7.46 (s, 1H), 7.05-6.98 (m, 2H), 6.73 (dd, J=8.4, 1.2 Hz, 1H), 6.66-6.60 (m, 2H), 4.29-4.19 (m, 2H), 4.14 (d, J=5.6 Hz, 2H), 3.39 (t, J=9.2 Hz, 11H), 3.26-3.13 (m, 2H), 2.88-2.78 (m, 2H), 2.65-2.55 (m, 1H), 2.30 (td, J=8.8, 4.4 Hz, 2H), 1.88 (d, J=12.8 Hz, 2H), 1.43 (qd, J=12.4, 4.0 Hz, 2H). Mass (m/z): 480.3 $[M+H]^+$.

N-(4-((4-methyl-6-(4-(trifluoromethyl)piperidin-1-yl)pyridin-3-yl)amino)benzyl)-5-oxopyrrolidine-3-carboxamide (580)

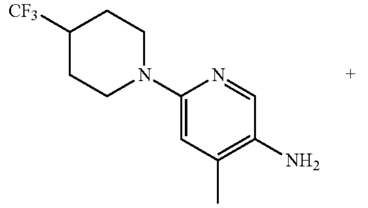

-continued

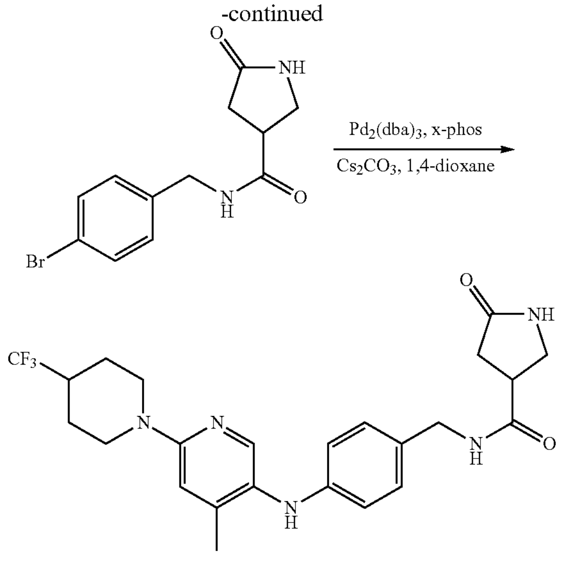

580

The title compound 580 (10.5 mg) was prepared in a total yield of 13.2% as a yellow solid from 4-methyl-6-(4-(trifluoromethyl)piperidin-1-yl)pyridin-3-amino(52 mg, 0.202 mmol), N-(4-bromobenzyl)-5-oxopyrrolidine-3-carboxamide (50 mg, 0.168 mmol), Pd2(dba)$_3$ (2 mg, 0.002 mmol), x-phos (6 mg, 0.01 mmol) and $Cs_2CO_3$ (83 mg, 0.252 mmol) and 1,4-dioxane (5 mL) according to the procedure for 525. $^1H$ NMR (400 MHz, DMSO-$d_6$) δ 8.40 (t, J=5.6 Hz, 1H), 7.73 (s, 1H), 7.59 (s, 2H), 7.27 (s, 1H), 7.10-7.02 (m, 2H), 6.75-6.63 (m, 2H), 4.24 (d, J=13.6 Hz, 3H), 4.16 (dd, J=5.6, 1.6 Hz, 2H), 3.27-3.15 (m, 2H), 3.09 (t, J=12.8 Hz, 2H), 2.69 (dq, J=16.4, 6.8, 5.2 Hz, 1H), 2.31-2.27 (m, 2H), 2.23 (s, 3H), 1.93 (dd, J=13.6, 3.6 Hz, 2H), 1.53 (qd, J=12.8, 4.0 Hz, 2H). Mass (m/z): 476.3 $[M+H]^+$.

N-(4-((4-(4-ethoxy-4-(trifluoromethyl)piperidin-1-yl)phenyl)amino)benzyl)-5-oxopyrrolidine-3-carboxamide (581)

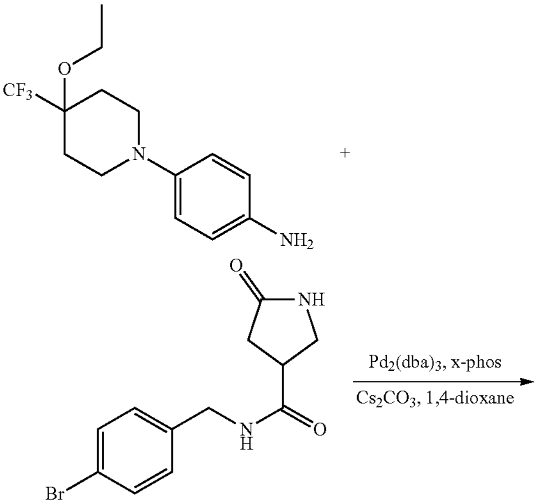

-continued

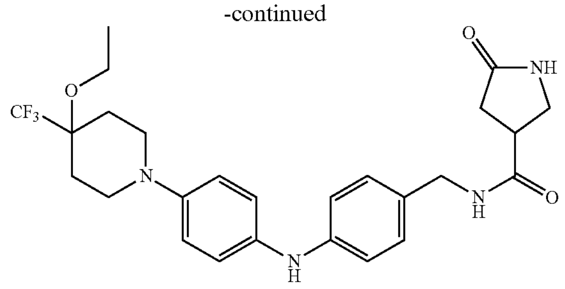

581

The title compound 581 (6.1 mg) was prepared in a total yield of 7.2% as a blue solid from 4-(4-ethoxy-4-(trifluoromethyl)piperidin-1-yl)aniline (58 mg, 0.202 mmol), N-(4-bromobenzyl)-5-oxopyrrolidine-3-carboxamide (50 mg, 0.168 mmol), $Pd_2(dba)_3$ (2 mg, 0.002 mmol), x-phos (6 mg, 0.01 mmol) and $Cs_2CO_3$ (83 mg, 0.252 mmol) and 1,4-dioxane (5 mL) according to the procedure for 525. $^1$H NMR (400 MHz, DMSO-$d_6$) δ 8.39 (s, 1H), 7.59 (s, 1H), 7.22-6.82 (m, 8H), 4.17 (s, 2H), 3.65 (d, J=7.2 Hz, 3H), 3.50 (s, 1H), 3.40 (t. J=8.8 Hz, 1H), 3.26-3.12 (m, 3H), 2.98 (s, 1H), 2.30 (dd, J=8.4, 3.2 Hz, 2H), 2.15-1.89 (m, 4H), 1.18 (t, J=6.8 Hz, 3H). Mass (m/z): 505.3 [M+H]$^+$.

(R)-2-oxo-N-(4-((4-(4-propylpiperidin-1-yl)phenyl)amino)benzyl)imidazolidine-4-carboxamide (582)

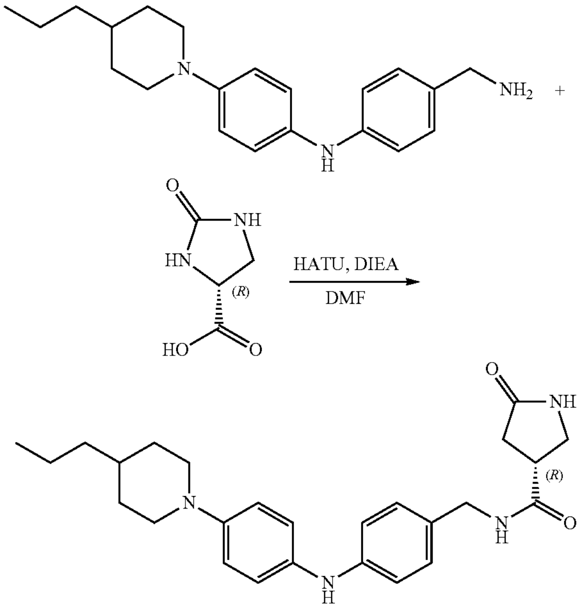

582

The title compound 582 (35.2 mg) was prepared in a total yield of 52.3% as a white solid from 4-(anilinomethyl)-N-(4-(4-propylpiperidin-1-yl)phenyl)aniline (50 mg, 0.155 mmol), (R)-2-oxoimidazolidine-4-carboxylic acid (26 mg, 0.201 mmol), HATU (76 mg, 0.201 mmol), DIEA (26 mg, 0.201 mmol) and DMF (3 mL) according to the procedure for 523. $^1$H NMR (400 MHz, DMSO-$d_6$) δ 8.40 (s, 1H), 7.81 (s, 1H), 7.23-6.76 (m, 8H), 6.60 (s, 1H), 6.33 (s, 1H), 4.24-4.08 (m, 3H), 3.54 (t, J=9.2 Hz, 3H), 3.23 (dd, J=8.8, 6.4 Hz, 1H), 1.73 (s, 3H), 1.37-1.18 (m, 7H), 0.89 (t, J=7.2 Hz, 3H). Mass (m/z): 436.3 [M+H]$^+$.

(S)-2,6-dioxo-N-(4-((4-(4-propylpiperidin-1-yl)phenyl)amino)benzyl) hexahydropyrimidine-4-carboxamide (583)

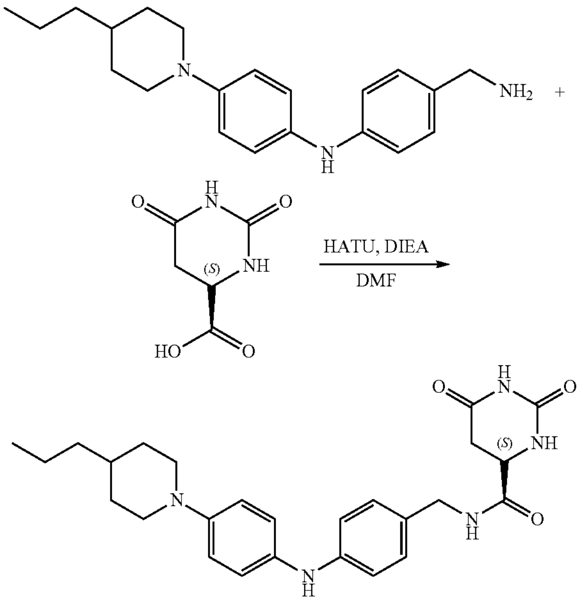

583

The title compound 583 (2.0 mg) was prepared in a total yield of 2.8% as a white solid from 4-(aminomethyl)-N-(4-(4-propylpiperidin-1-yl)phenyl)aniline (50 mg, 0.155 mmol), (S)-2,6-dioxohexahydropyrimidine-4-carboxylic acid (32 mg, 0.201 mmol), HATU (76 mg, 0.201 mmol), DIEA (26 mg, 0.201 mmol) and DMF (3 mL) according to the procedure for 523. $^1$H NMR (400 MHz, DMSO-d6) δ 10.04 (d, J=1.4 Hz, 1H), 8.47 (s, 1H), 7.63 (d, J=3.2 Hz, 1H), 7.28-6.91 (m, 8H), 4.20 (s, 2H), 4.01 (dt, J=7.2, 3.6 Hz, 1H), 3.51 (s, 3H), 2.86 (dd, J=16.4, 7.2 Hz, 2H), 2.03-1.83 (m, 4H), 1.33 (dd, J=9.2, 5.6 Hz, 3H), 0.90 (t, J=7.2 Hz, 3H). 1H NMR (400 MHz, DMSO-d6) δ 8.29 (t, J=5.6 Hz, 1H), 7.76 (s, 1H), 7.41 (s, 1H), 6.97 (d, J=8.4 Hz, 2H), 6.93-6.88 (m, 2H), 6.82 (dd, J=8.8, 2.4 Hz, 4H), 4.15-4.00 (m, 2H), 3.54 (d, J=12.0 Hz, 2H), 3.05 (tdd, J=16.4, 9.5, 4.2 Hz, 2H), 2.65-2.50 (m, 4H), 2.36 (dtd, J=12.4, 8.4, 3.6 Hz, 1H), 2.24-2.10 (m, 2H), 1.80 (td, J=11.1, 8.4, 3.5 Hz, 3H), 1.53 (tdd, J=25.2, 12.8, 4.8 Hz, 3H). Mass (m/z): 464.3 [M+H]$^+$.

2,6-dioxo-N-(4-((4-(4-propylpiperidin-1-yl)phenyl)amino)benzyl)piperidine-4-carboxamide (584)

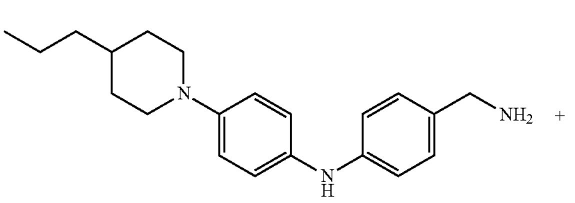

-continued

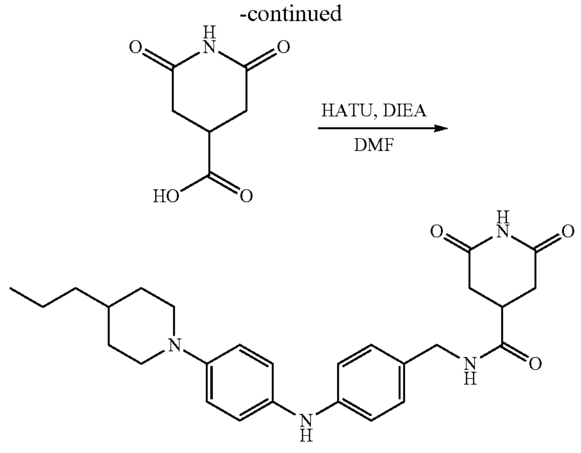

584

The title compound 584 (18.5 mg) was prepared in a total yield of 25.8% as a red solid from 4-(aminomethyl)-N-(4-(4-propylpiperidin-1-yl)phenyl)aniline (50 mg, 0.155 mmol), 2,6-dioxopiperidine-4-carboxylic acid (32 mg, 0.201 mmol), HATU (76 mg, 0.201 mmol), DIEA (26 mg, 0.201 mmol) and DMF (3 mL) according to the procedure for 523. $^1$H NMR (400 MHz, DMSO-$d_6$) δ 10.69 (s, 1H), 8.64 (s, 2H), 7.73 (s, 2H), 7.12 (dd, J=16.0, 9.2 Hz, 6H), 4.19 (d, J=5.6 Hz, 2H), 3.03 (ddd, J=7.2, 5.2, 2.0 Hz, 1H), 2.69-2.55 (m, 4H), 1.85 (s, 4H), 1.66 (s, 1H), 1.43-1.16 (m, 7H), 0.90 (t, J=7.2 Hz, 3H). Mass (m/z): 463.3 [M+H]$^+$.

N1-(4-((4-(4-propylpiperidin-1-yl)phenyl)amino)benzyl)oxalamide (585)

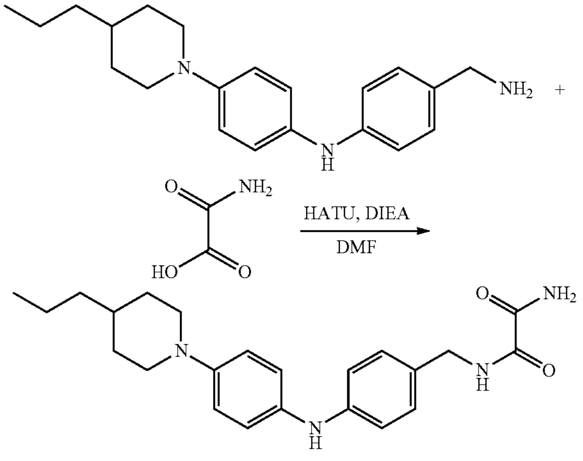

585

The title compound 585 (19.7 mg) was prepared in a total yield of 32.2% as a white solid from 4-(aminomethyl)-N-(4-(4-propylpiperidin-1-yl)phenyl)aniline (50 mg, 0.155 mmol), 2-amino-2-oxoacetic acid (18 mg, 0.201 mmol), HATU (76 mg, 0.201 mmol), DIEA (26 mg, 0.201 mmol) and DMF (3 mL) according to the procedure for 523. $^1$H NMR (400 MHz, DMSO-$d_6$) δ 9.17 (s, 1H), 8.57 (s, 1H), 8.09 (s, 1H), 7.84-7.80 (m, 1H), 7.70 (s, 1H), 7.13 (d, J=36.4 Hz, 7H), 4.23 (d, J=6.4 Hz, 2H), 3.59-3.48 (m, 3H), 1.95-1.56 (m, 6H), 1.33 (td, J=8.8, 7.2, 5.2 Hz, 4H), 0.90 (t, J=7.2 Hz, 3H). Mass (m/z): 395.3 [M+H]$^+$.

1-(4-((4-(4-propylpiperidin-1-yl)phenyl)amino)benzyl)urea (586)

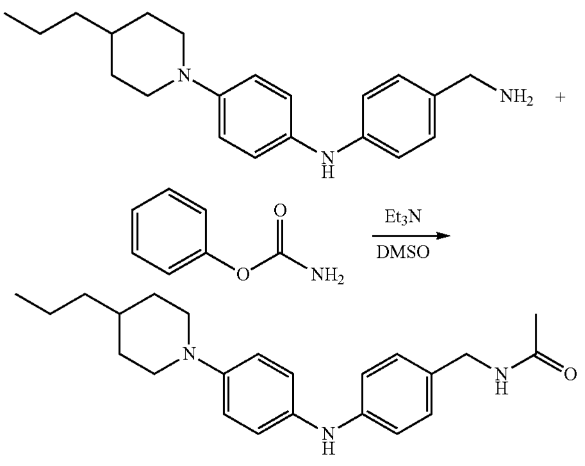

586

The title compound 586 (12.9 mg) was prepared in a total yield of 22.7% as a white solid from 4-(aminomethyl)-N-(4-(4-propylpiperidin-1-yl)phenyl)aniline (50 mg, 0.155 mmol), phenyl carbamate (28 mg, 0.201 mmol), $Et_3N$ (46 mg, 0.465 mmol) and DMSO (3 mL) according to the procedure for 553. $^1$H NMR (400 MHz, DMSO-$d_6$) δ 7.74 (s, 1H), 7.23-6.70 (m, 8H), 6.58-6.38 (m, 1H), 5.56 (s, 2H), 4.09 (s, 2H), 3.51 (s, 3H), 1.83 (s, 3H), 1.40-1.17 (m, 6H), 0.89 (t, J=7.2 Hz, 3H). Mass (m/z): 367.3 [M+H]$^+$.

N-(4-((4-(4,4-dimethylcyclohexyl)phenyl)amino)benzyl)acetamide (587)

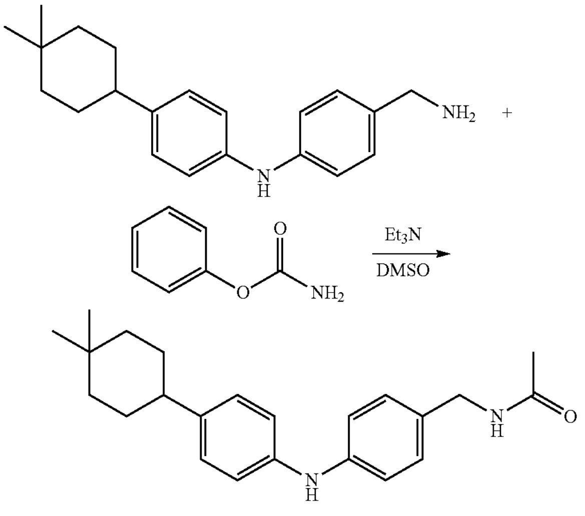

587

The title compound 587 (13.0 mg) was prepared in a total yield of 22.8% as a yellow solid from 4-(aminomethyl)-N-(4-(4,4-dimethylcyclohexyl)phenyl)aniline (50 mg, 0.162 mmol), phenyl carbamate (29 mg, 0.210 mmol), $Et_3N$ (48 mg, 0.486 mmol) and DMSO (3 mL) according to the procedure for 553. $^1$H NMR (400 MHz, DMSO-$d_6$) δ 8.01 (d, J=2.0 Hz, 1H), 7.09 (dd, J=8.4, 1.6 Hz, 4H), 6.97 (dq, J=9.2, 2.4 Hz, 4H), 6.49-6.32 (m, 1H), 5.52 (s, 2H), 4.06 (d, J=6.0 Hz, 2H), 2.31 (tt, J=10.0, 50 Hz, 1H), 1.60-1.54 (m, 3H), 1.43 (dd, J=8.8, 6.0 Hz, 2H), 1.30 (td, J=12.4, 5.6 Hz, 2H), 0.94 (d, J=10.0 Hz, 6H). Mass (m/z): 352.3 $[M+H]^+$.

N1-(4-((4-(4,4-dimethylcyclohexyl)phenyl)amino)benzyl)oxalamide (588)

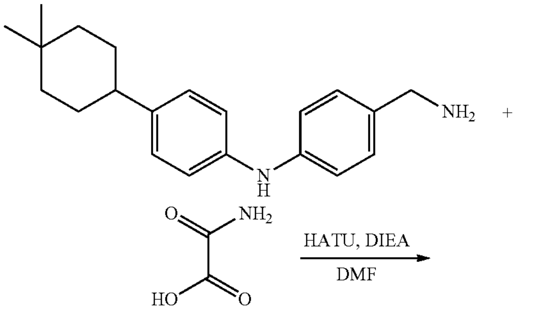

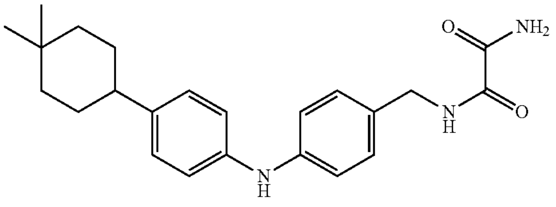

588

The title compound 588 (6.9 mg) was prepared in a total yield of 11.2% as a white solid from 4-(aminomethyl)-N-(4-(4,4-dimethylcyclohexyl)phenyl)aniline (50 mg, 0.162 mmol), 2-amino-2-oxoacetic acid (19 mg, 0.210 mmol), HATU (80 mg, 0.210 mmol), DIEA (27 mg, 0.210 mmol) and DMF (3 mL) according to the procedure for 523. $^1$H NMR (400 MHz, DMSO-$d_6$) δ 9.10 (t, J=6.4 Hz, 1H), 8.07 (s, 1H), 7.99 (s, 1H), 7.79 (s, 1H), 7.10 (dd, J=8.4, 6.0 Hz, 4H), 6.96 (dd, J=8.4, 4.0 Hz, 4H), 4.20 (d, J=6.4 Hz, 2H), 2.31 (tt, J=10.4, 5.2 Hz, 5H), 1.61-1.54 (m, 3H), 1.44 (d, J=12.8 Hz, 2H), 1.30 (td, J=12.4, 5.2 Hz, 2H), 0.94 (d, J=10.0 Hz, 6H). Mass (m/z): 380.3 $[M+H]^+$.

N-(4-((4-(3,5-dimethylpiperidin-1-yl)phenyl)amino)benzyl)-5-oxopyrrolidine-3-carboxamide (589)

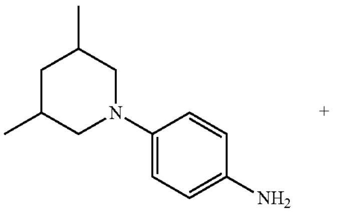

-continued

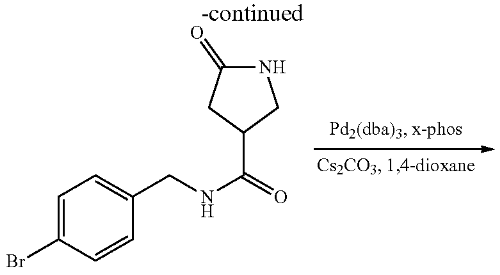

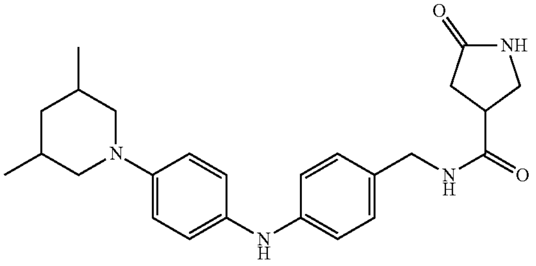

589

The title compound 589 (6.8 mg) was prepared in a total yield of 9.6% as a white solid from 4-(3,5-dimethylpiperidin-1-yl)aniline (41 mg, 0.202 mmol), N-(4-bromobenzyl)-5-oxopyrrolidine-3-carboxamide (50 mg, 0.168 mmol), $Pd_2(dba)_3$ (2 mg, 0.002 mmol), x-phos (6 mg, 0.01 mmol) and $Cs_2CO_3$ (83 mg, 0.252 mmol) and 1,4-dioxane (5 mL) according to the procedure for 525. $^1$H NMR (400 MHz, DMSO-$d_6$) δ 8.45 (d, J=7.2 Hz, 1H), 7.60 (s, 1H), 7.47 (s, 1H), 7.12 (d, J=33.2 Hz, 5H), 4.21 (s, 2H), 3.42 (t, J=8.8 Hz, 3H), 3.30-3.13 (m, 3H), 3.02 (s, 2H), 2.36-2.27 (m, 2H), 2.13-1.96 (m, 2H), 1.79 (s, 1H), 0.93 (s, 6H). Mass (m/z): 421.3 $[M+H]^+$.

N-(4-((6-(4,4-dimethylpiperidin-1-yl)-2-methylpyridin-3-yl)amino)benzyl)-5-oxopyrrolidine-3-carboxamide (590)

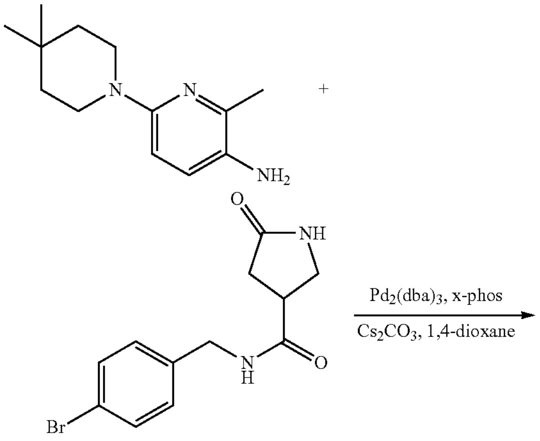

-continued

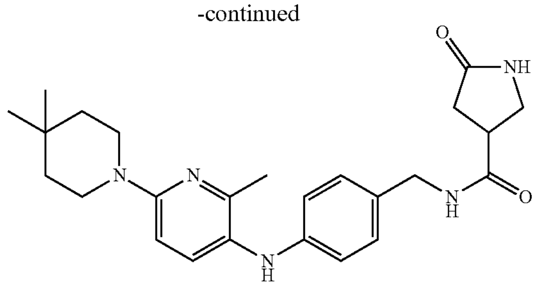

590

The title compound 590 (4.5 mg) was prepared in a total yield of 6.2% as a blue solid from 6-(4,4-dimethylpiperidin-1-yl)-2-methylpyridin-3-amine (44 mg, 0.202 mmol), N-(4-bromobenzyl)-5-oxopyrrolidine-3-carboxamide (50 mg, 0.168 mmol), $Pd_2(dba)_3$ (2 mg, 0.002 mmol), x-phos (6 mg, 0.01 mmol) and $Cs_2CO_3$ (83 mg, 0.252 mmol) and 1,4-dioxane (5 mL) according to the procedure for 525.1H NMR (400 MHz, DMSO-$d_6$) δ 8.35 (t, J=5.6 Hz, 1H), 7.59 (s, 1H), 7.41 (d, J=35.2 Hz, 2H), 7.01 (d, J=8.0 Hz, 2H), 6.92-6.81 (m, 1H), 6.55 (d, J=8.0 Hz, 2H), 4.13 (d, J=5.6 Hz, 2H), 3.52 (s, 5H), 3.26-3.13 (m, 3H), 2.28 (qd, J=8.0, 7.6, 2.4 Hz, 5H), 1.41 (t, J=5.6 Hz, 4H), 0.98 (s, 6H). Mass (m/z): 436.3 $[M+H]^+$.

(R)—N-(4-((4-methyl-6-(4-(trifluromethyl)piperidin-1-yl)pyridin-3-yl)amino)benzyl)-2-oxoimidazolidine-4-carboxamide (591)

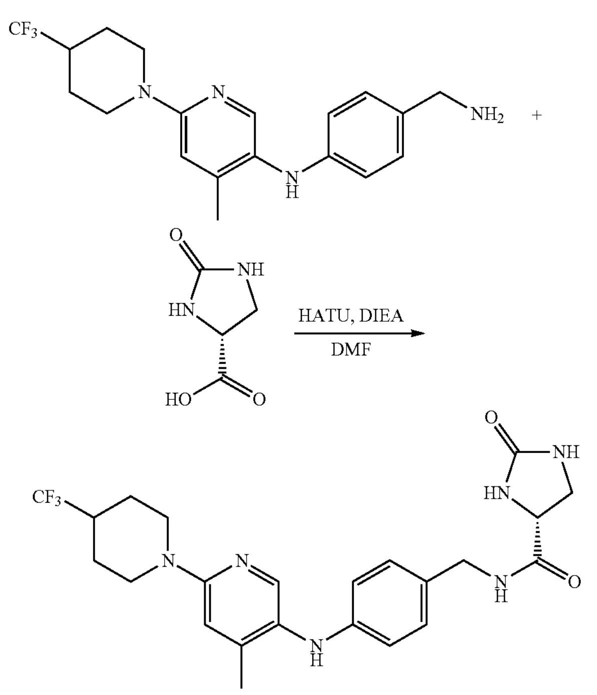

591

The title compound 591 (7.0 mg) was prepared in a total yield of 10.7% as a white solid from N-(4-(aminomethyl) phenyl)-4-methyl-6-(4-(trifluoromethyl) piperidin-1-yl) pyridin-3-amine (50 mg, 0.137 mmol), (R)-2-oxoimidazolidine-4-carboxylic acid (23 mg, 0.179 mmol), HATU (68 mg, 0.179 mmol), DIEA (23 mg, 0.179 mmol) and DMF (3 mL) according to the procedure for 523. $^1$H NMR (400 MHz, DMSO-$d_6$) δ 8.25 (t, J=5.6 Hz, 1H), 7.87 (s, 1H), 7.26 (s, 1H), 7.04-6.97 (m, 2H), 6.81 (s, 1H), 6.54 (s, 1H), 6.52-6.47 (m, 2H), 6.31 (s, 1H), 4.35 (d, J=13.2 Hz, 2H), 4.13 (d, J=5.6 Hz, 2H), 4.08 (ddd, J=9.6, 6.0, 1.6 Hz, 1H), 3.21 (ddd, J=8.8, 6.0, 1.2 Hz, 1H), 2.79 (t, J=12.0 Hz, 2H), 2.57 (dt, J=7.6, 3.6 Hz, 1H), 2.08 (s, 3H), 1.86 (d, J=12.8 Hz, 2H), 1.43 (qd, J=12.4, 4.0 Hz, 2H), 1.28 (dd, J=12.0, 6.8 Hz, 1H). Mass (m/z): 477.3 $[M+H]^+$.

N-(4-((4-(4-hydroxy-4-(trifluoromethyl)piperidin-1-yl)phenyl)amino)benzyl)-5-oxopyrrolidine-3-carboxamide (592)

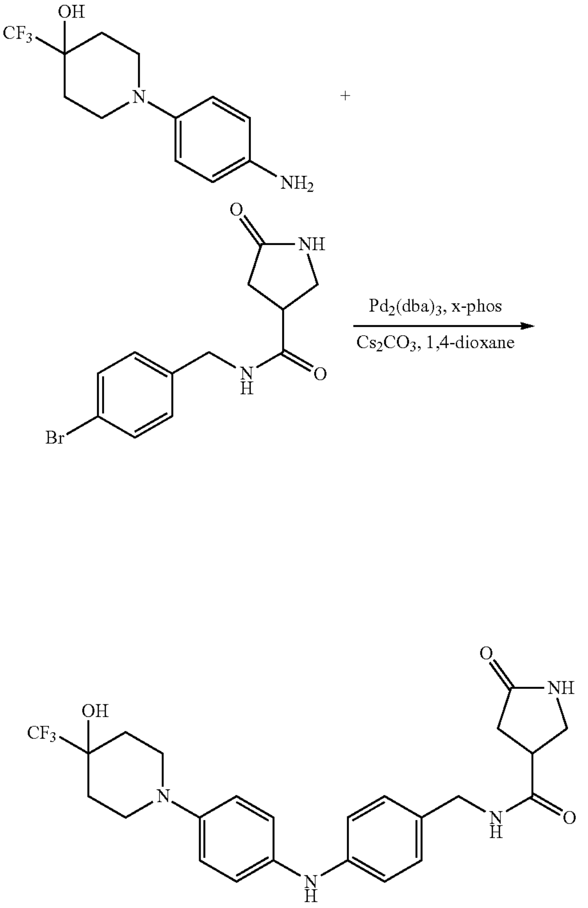

592

The title compound 592 (15.3 mg) was prepared in a total yield of 19.1% as a blue solid from 1-(4-aminophenyl)-4-(trifluoromethyl)piperidin-4-ol (53 mg, 0.202 mmol), N-(4-bromobenzyl)-5-oxopyrrolidine-3-carboxamide (50 mg, 0.168 mmol), $Pd_2(dba)_3$ (2 mg, 0.002 mmol), x-phos (6 mg, 0.01 mmol) and $Cs_2CO_3$ (83 mg, 0.252 mmol) and 1,4-dioxane (5 mL) according to the procedure for 525. $^1$H NMR (400 MHz, DMSO-$d_6$) δ 8.41 (t, J=5.6 Hz, 1H), 7.60 (s, 1H), 7.09 (s, 8H), 4.18 (s, 2H), 3.40 (d, J=8.8 Hz, 2H), 3.28-3.13 (m, 4H), 2.30 (dd, J=8.4, 2.4 Hz, 2H), 2.00 (q, J=7.2, 6.4 Hz, 2H), 1.87 (s, 2H). Mass (m/z): 477.3 $[M+H]^+$.

(R)—N-(4-((6-(4-isopropylpiperidin-1-yl)-2-methylpyridin-3-yl)amino)benzyl)-2-oxoimidazolidine-4-carboxamide (593)

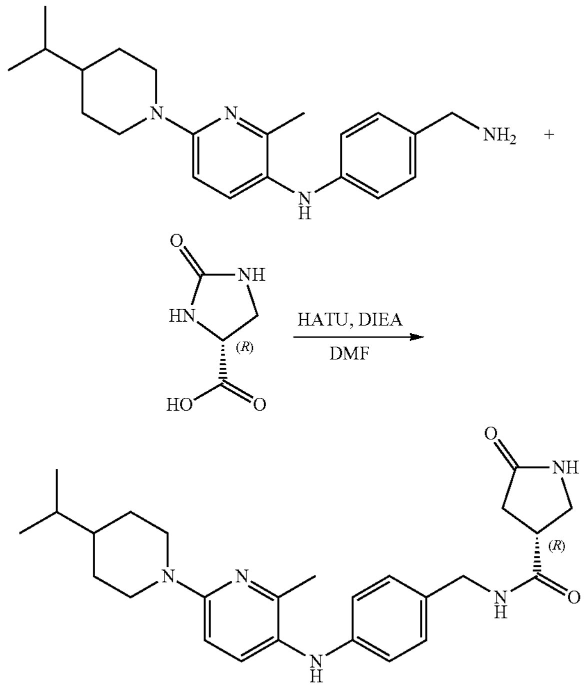

593

The title compound 593 (19.8 mg) was prepared in a total yield of 29.7% as a white solid from N-(4-(aminomethyl)phenyl)-6-(4-isopropylpiperidin-1-yl)-2-methylpyridin-3-amine (50 mg, 0.148 mmol), (R)-2-oxoimidazolidine-4-carboxylic acid (25 mg, 0.192 mmol), HATU (73 mg, 0.192 mmol), DIEA (25 mg, 0.192 mmol) and DMF (3 mL) according to the procedure for 523. $^1$H NMR (400 MHz, DMSO-$d_6$) δ 8.23 (t, J=6.0 Hz, 1H), 7.33-7.18 (m, 2H), 7.01 (d, J=8.0 Hz, 2H), 6.51 (d, J=10.0 Hz, 3H), 6.31 (s, 1H), 4.27 (d, J=12.8 Hz, 2H), 4.13 (d, J=5.6 Hz, 2H), 4.08 (dd, J=9.6, 6.0 Hz, 1H), 3.53 (t, J=9.2 Hz, 1H), 3.20 (dd, J=8.8, 6.0 Hz, 1H), 2.21 (s, 2H), 1.71 (d, J=11.2 Hz, 2H), 1.46-1.40 (m, 1H), 1.31-1.21 (m, 5H), 0.88 (d, J=6.8 Hz, 6H). Mass (m/z): 451.3 [M+H]$^+$.

N-(4-((6-(4-isopropylpiperidin-1-yl)-2-methylpyridin-3-yl)amino)benzyl)-2,6-dioxopiperidine-4-carboxamide (594)

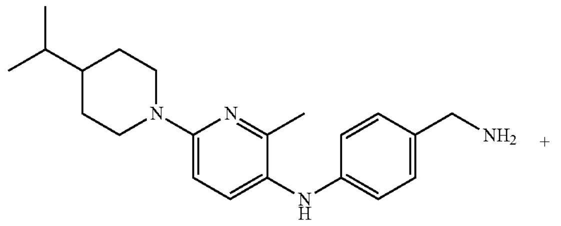

-continued

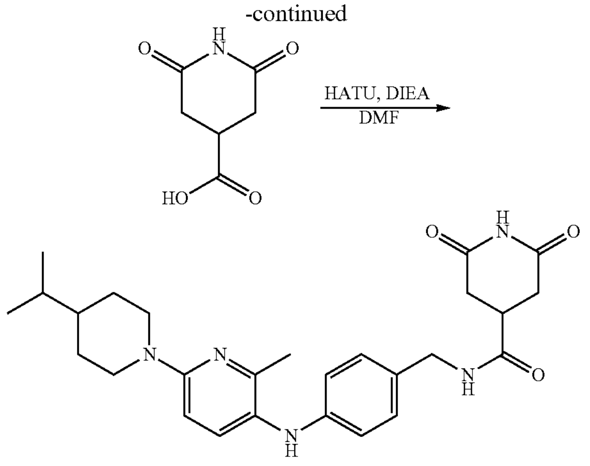

594

The title compound 594 (4.9 mg) was prepared in a total yield of 6.9% as a yellow solid from N-(4-(aminomethyl)phenyl)-6-(4-isopropylpiperidin-1-yl)-2-methylpyridin-3-amine (50 mg, 0.148 mmol), 2,6-dioxopiperidine-4-carboxylic acid (30 mg, 0.192 mmol), HATU (73 mg, 0.192 mmol), DIEA (25 mg, 0.192 mmol) and DMF (3 mL) according to the procedure for 523. $^1$H NMR (400 MHz, DMSO-$d_6$) δ 10.68 (s, 1H), 8.42 (t, J=5.6 Hz, 1H), 7.50 (d, J=40.8 Hz, 2H), 7.01 (d, J=8.0 Hz, 2H), 6.58 (d, J=8.0 Hz, 2H), 4.23 (d, J=13.2 Hz, 2H), 4.12 (d, J=5.6 Hz, 2H), 3.01-2.84 (m, 3H), 2.68-2.53 (m, 4H), 2.30 (s, 3H), 1.75 (d, J=12.4 Hz, 2H), 1.45 (dq, J=13.2, 6.4 Hz, 1H), 1.33-1.17 (m, 3H), 0.88 (d, J=6.8 Hz, 6H). Mass (m/z): 478.3 [M+H]$^+$.

N1-(4-((6-(4-isopropylpiperidin-1-yl)-2-methylpyridin-3-yl)amino)benzyl) malonamide (595)

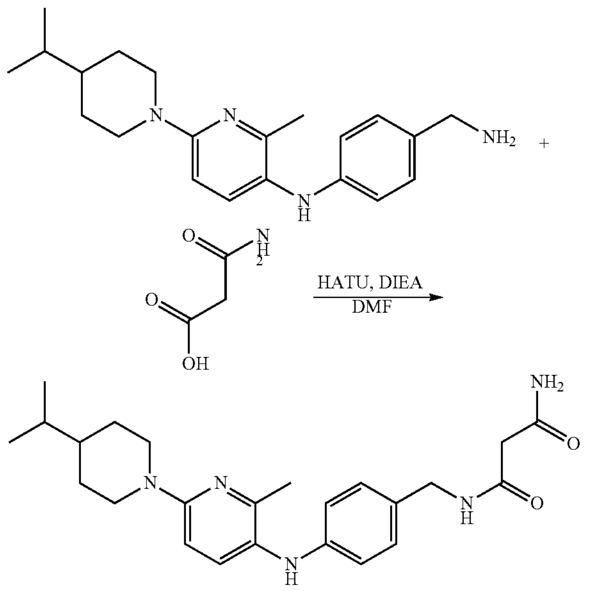

595

The title compound 595 (10.2 mg) was prepared in a total yield of 16.3% as a yellow solid from N-(4-(aminomethyl)phenyl)-6-(4-isopropylpiperidin-1-yl)-2-methylpyridin-3- amine (50 mg, 0.148 mmol), 3-amino-3-oxopropanoic acid (20 mg, 0.192 mmol), HATU (73 mg, 0.192 mmol), DIEA (25 mg, 0.192 mmol) and DMF (3 mL) according to the procedure for 523. $^{1}$H NMR (400 MHz, DMSO-$d_6$) δ 8.34 (t, J=5.6 Hz, 1H), 7.60 (s, 1H), 7.45 (s, 1H), 7.06 (d, J=8.4 Hz, 4H), 6.60 (d, J=8.0 Hz, 2H), 4.22 (d, J=13.2 Hz, 2H), 4.15 (d, J=5.6 Hz, 2H), 2.92 (s, 2H), 2.32 (s, 3H), 1.76 (d, J=12.4 Hz, 2H), 1.46 (dt, J=13.2, 6.5 Hz, 1H), 1.34-1.17 (m, 5H), 0.88 (d, J=6.8 Hz, 6H). Mass (m/z): 424.3 [M+H]$^+$.

N1-(4-((6-(4-isopropylpiperidin-1-yl)-2-methylpyridin-3-yl)amino)benzyl) glutaramide (596)

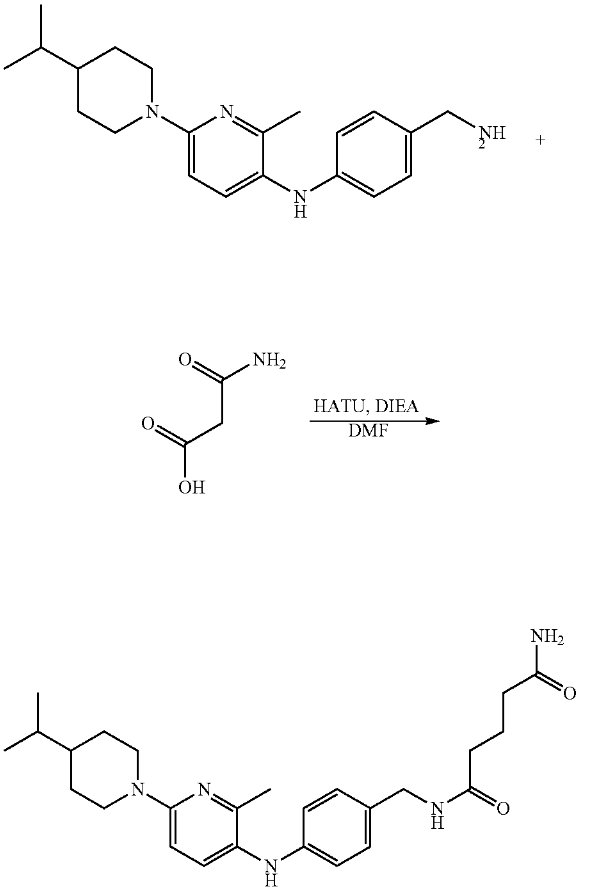

596

The title compound 5% (13.8 mg) was prepared in a total yield of 20.7% as a yellow solid from N-(4-(aminomethyl) phenyl)-6-(4-isopropylpiperidin-1-yl)-2-methylpyridin-3-amine (50 mg, 0.148 mmol), 5-amino-5-oxopentanoic acid (25 mg, 0.192 mmol), HATU (73 mg, 0.192 mmol), DIEA (25 mg, 0.192 mmol) and DMF (3 mL) according to the procedure for 523.1H NMR (400 MHz, DMSO-$d_6$) δ 8.19 (t, J=6.0 Hz, 1H), 7.74-7.41 (m, 2H), 7.26 (s, 1H), 7.04 (d, J=8.4 Hz, 3H), 6.73 (s, 1H), 6.61 (d, J=8.0 Hz, 2H), 4.21 (d, J=13.2 Hz, 2H), 4.12 (d, J=5.6 Hz, 2H), 2.98 (q, J=12.0, 11.2 Hz, 2H), 2.34 (s, 3H), 2.07 (dt, J=24.4, 7.6 Hz, 4H), 1.72 (ddd, J=22.4, 15.6, 9.6 Hz, 4H), 1.46 (dq, J=13.2, 6.4 Hz, 1H), 1.37-1.16 (m, 4H), 0.89 (d, J=6.8 Hz, 6H). Mass (m/z): 452.3 [M+H]$^+$.

N1-(4-((2-(4-isopropylpiperidin-1-yl)pyrimidin-5-yl) amino)benzyl)malonamide (597)

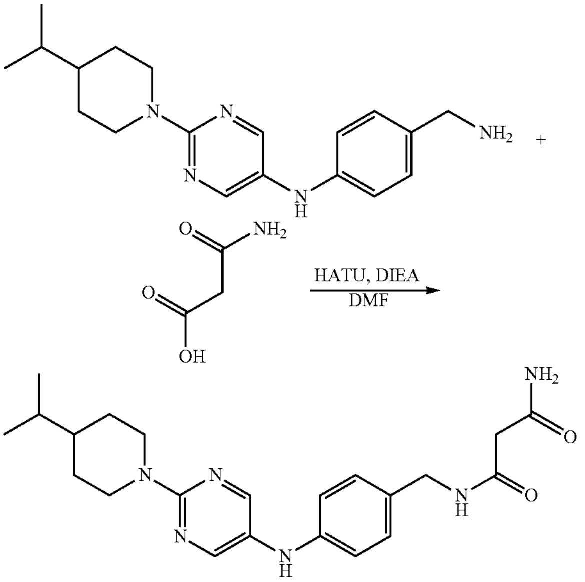

597

The title compound 597 (9.7 mg) was prepared in a total yield of 20.7% as a white solid from N-(4-(aminomethyl) phenyl)-2-(4-isopropylpiperidin-1-yl)pyrimidin-5-amine (50 mg, 0.154 mmol), 3-amino-3-oxopropanoic acid (21 mg, 0.200 mmol), HATU (76 mg, 0.200 mmol), DIEA (26 mg, 0.200 mmol) and DMF (3 mL) according to the procedure for 523. $^{1}$H NMR (400 MHz, DMSO-$d_6$) δ 8.58-8.29 (m, 1H), 8.18 (s, 1H), 7.62 (s, 1H), 7.50-7.45 (m, 2H), 722-7.19 (m, 1H), 7.05-6.97 (m, 3H), 6.69-6.66 (m, 1H), 4.60 (d, J=13.2 Hz, 2H), 4.24-4.06 (m, 3H), 3.01 (d, J=14.0 Hz, 3H), 2.75-2.69 (m, 1H), 1.66 (d, J=12.4 Hz, 2H), 1.43-1.35 (m, 1H), 1.08 (td, J=12.0, 4.0 Hz, 2H), 0.83 (d, J=6.8 Hz, 6H). Mass (m/z): 411.3 [M+H]$^+$.

(R)—N-(4-((2-(4-isopropylpiperidin-1-yl)pyrimidin-5-yl)amino)benzyl)-2-oxoimidazolidine-4-carboxamide (598)

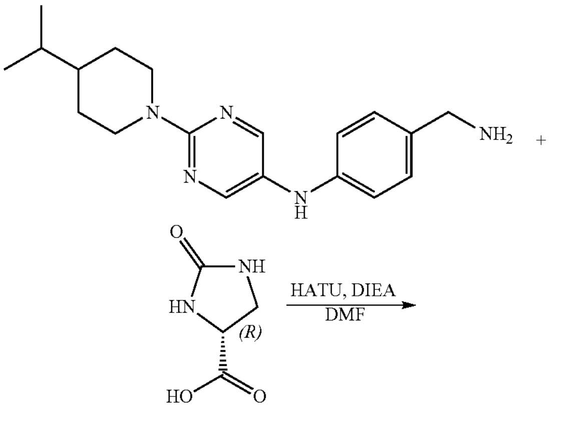

-continued

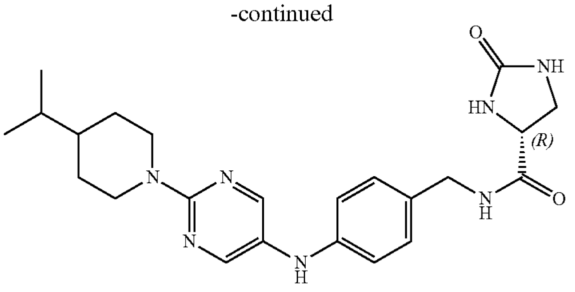

598

The title compound 598 (21.5 mg) was prepared in a total yield of 31.9% as a yellow solid from N-(4-(aminomethyl) phenyl)-2-(4-isopropylpiperidin-1-yl)pyrimidin-5-amine (50 mg, 0.154 mmol), (R)-2-oxoimidazolidine-4-carboxylic acid (26 mg, 0.200 mmol), HATU (76 mg, 0.200 mmol), DIEA (26 mg, 0.200 mmol) and DMF (3 mL) according to the procedure for 523. $^{1}$H NMR (400 MHz, DMSO-$d_6$) δ 8.18 (s, 1H), 7.50-7.45 (m, 1H), 7.06-6.93 (m, 2H), 6.70-6.65 (m, 1H), 6.57 (d, J=17.6 Hz, 1H), 6.30 (d, J=12.4 Hz, 1H), 4.60 (d, J=13.2 Hz, 2H), 4.21 (d, J=6.0 Hz, 1H), 4.14-4.01 (m, 3H), 3.52-3.48 (m, 1H), 3.17 (ddt, J=7.4, 6.0, 3.2 Hz, 1H), 2.71 (td, J=12.8, 2.4 Hz, 2H), 1.65 (d, J=12.4 Hz, 2H), 1.42-1.36 (m, 1H), 1.12-1.02 (m, 2H), 0.83 (d, J=6.8 Hz, 6H). Mass (m/z): 438.3 [M+H]$^+$.

N-(4-((2-(4-isopropylpiperidin-1-yl)pyrimidin-5-yl) amino)benzyl)-1-methylpyrrolidine-3-carboxamide (599)

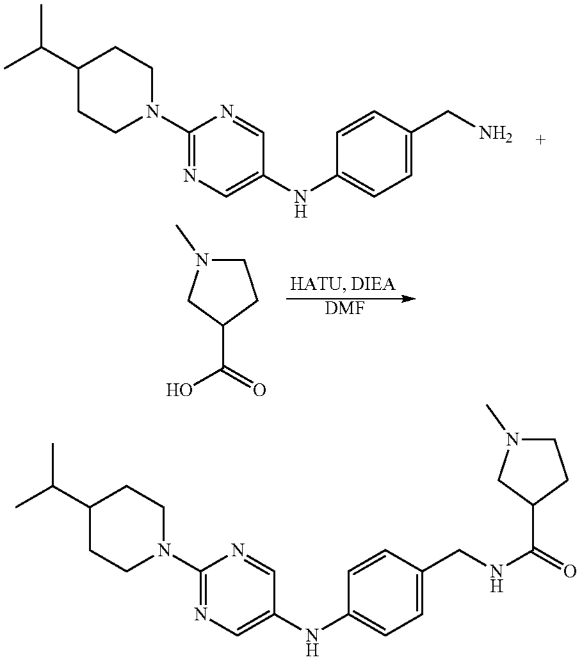

599

The title compound 599 (16.3 mg) was prepared in a total yield of 24.3% as a yellow solid from N-(4-(aminomethyl) phenyl)-2-(4-isopropylpiperidin-1-yl)pyrimidin-5-amine (50 mg, 0.154 mmol), 1-methylpyrrolidine-3-carboxylic acid (26 mg, 0.200 mmol), HATU (76 mg, 0.200 mmol), DIEA (26 mg, 0.200 mmol) and DMF (3 mL) according to the procedure for 523.1H NMR (400 MHz, DMSO-$d_6$) δ 8.76-8.48 (m, 2H), 8.18 (s, 2H), 7.51-7.43 (m, 2H), 7.19-7.15 (m, 2H), 7.02-6.96 (m, 2H), 6.71-6.63 (m, 2H), 4.66-4.58 (m, 2H), 4.20 (d, J=6.0 Hz, 2H), 4.10 (d, J=6.0 Hz, 2H), 3.10 (d, J=18.4 Hz, 4H), 2.99 (d, J=8.0 Hz, 2H), 2.90 (s, 2H), 2.71 (td, J=12.8, 2.4 Hz, 2H), 2.59 (d, J=7.6 Hz, 6H), 2.09 (dq, J=13.2, 7.2, 6.4 Hz, 2H), 2.01-1.91 (m, 3H), 1.69-1.63 (m, 2H), 1.42-1.35 (m, 1H), 1.28-1.21 (m, 2H), 1.12-1.01 (m, 3H), 0.84 (s, 3H), 0.82 (s, 3H). Mass (m/z): 437.3 [M+H]$^+$.

N-(4-((2-(4-isopropylpiperidin-1-yl)pyrimidin-5-yl) amino)benzyl)-2,6-dioxopiperidine-4-carboxamide (600)

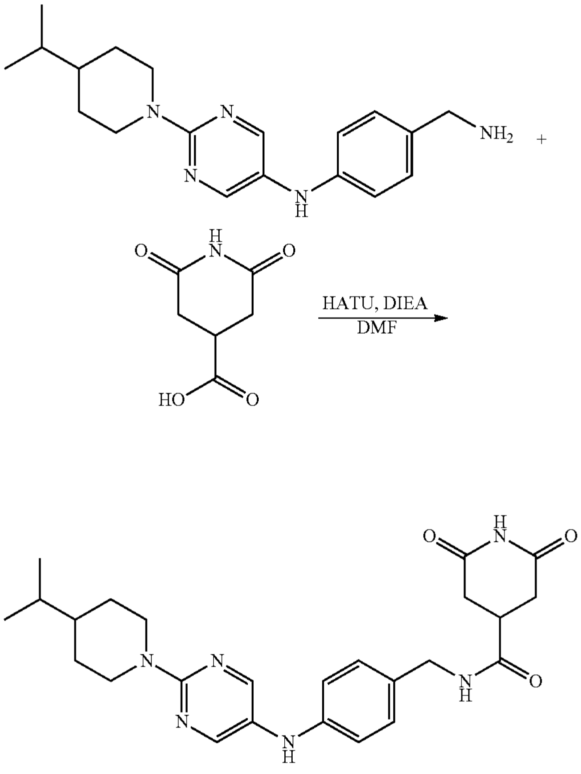

600

The title compound 600 (2.7 mg) was prepared in a total yield of 3.8% as a yellow solid from N-(4-(aminomethyl) phenyl)-2-(4-isopropylpiperidin-1-yl)pyrimidin-5-amine (50 mg, 0.154 mmol), 2,6-dioxopiperidine-4-carboxylic acid (31 mg, 0.200 mmol), HATU (76 mg, 0.200 mmol), DIEA (26 mg, 0.200 mmol) and DMF (3 mL) according to the procedure for 523.1H NMR (400 MHz, DMSO-$d_6$) δ 10.68 (s, 1H), 8.42 (t, J=6.0 Hz, 1H), 8.21 (s, 2H), 7.05-6.98 (m, 2H), 6.75-6.67 (m, 2H), 4.64 (d, J=12.8 Hz, 2H), 4.12 (d, J=5.6 Hz, 2H), 2.96 (dt, J=7.2, 5.2 Hz, 1H), 2.81-2.71 (m, 2H), 2.59 (dd, J=12.8, 6.0 Hz, 3H), 1.99 (p. J=7.2, 6.4 Hz, 2H), 1.69 (d, J=12.8 Hz, 2H), 1.43 (dq, J=13.2, 6.6 Hz, 2H), 1.27 (d, J=11.6 Hz, 2H), 1.10 (qd, J=12.0, 4.0 Hz, 3H), 0.87 (d, J=6.8 Hz, 6H). Mass (m/z): 465.3 [M+H]$^+$.

N-(4-((2-(4-isopropylpiperidin-1-yl)pyrimidin-5-yl)amino)benzyl)-2,6-dioxopiperidine-4-carboxamide (601)

601

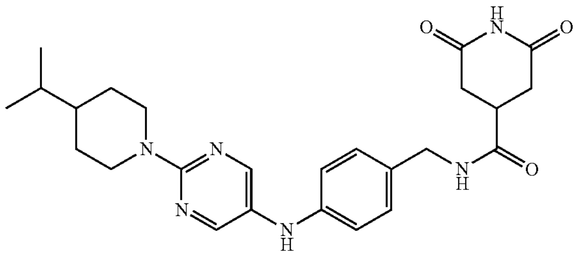

The title compound 601 (3.2 mg) was prepared in a total yield of 4.5% as a yellow solid from N-(4-(aminomethyl)phenyl)-2-(4-isopropylpiperidin-1-yl)pyrimidin-5-amine (50 mg, 0.154 mmol), 2,6-dioxopiperidine-4-carboxylic acid (31 mg, 0.200 mmol), HATU (76 mg, 0.200 mmol), DIEA (26 mg, 0.200 mmol) and DMF (3 mL) according to the procedure for 523. $^1$H NMR (400 MHz, DMSO-$d_6$) δ 8.17 (s, 2H), 7.38 (s, 1H), 7.08-6.96 (m, 2H), 6.92-6.83 (m, 1H), 6.68-6.58 (m, 2H), 4.60 (dt, J=13.2, 2.4 Hz, 2H), 4.43-4.29 (m, 2H), 3.05-2.96 (m, 1H), 2.75-2.66 (m, 2H), 2.53-2.49 (m, 2H), 2.39 (dd, J=17.6, 5.1 Hz, 1H), 1.96 (q, J=6.8, 6.4 Hz, 1H), 1.70-1.62 (m, 2H), 1.43-1.35 (m, 1H), 1.25 (d, J=6.8 Hz, 1H), 1.06 (qd, J=12.8, 12.4, 4.4 Hz, 2H), 0.83 (d, J=6.8 Hz, 6H). Mass (m/z): 465.3 [M+H]$^+$.

N,N-dimethyl-3-(4-((4-((2-(4-methylpiperazin-1-yl)acetamido)methyl)phenyl)amino)phenyl)propanamide (602)

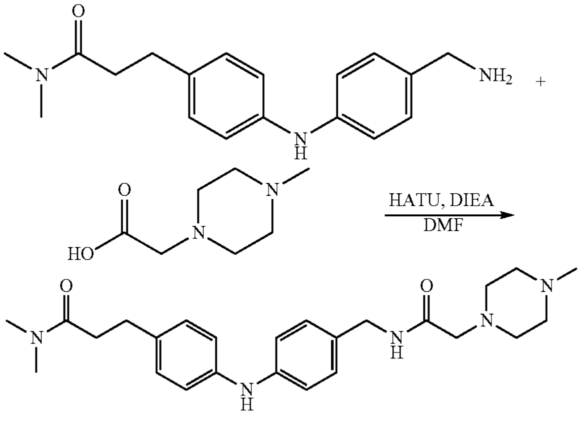

602

The title compound 602 (16.1 mg) was prepared in a total yield of 21.9% as a yellow solid from 3-(4-((4-(aminomethyl)phenyl)amino)phenyl)-N,N-dimethylpropanamide (50 mg, 0.168 mmol), 2-(4-methylpiperazin-1-yl)acetic acid (31 mg, 0.218 mmol), HATU (83 mg, 0.218 mmol), DIEA (28 mg, 0.218 mmol) and DMF (3 mL) according to the procedure for 523. $^1$H NMR (400 MHz, DMSO-$d_6$) δ 8.18 (t, J=6.0 Hz, 1H), 8.09-8.04 (m, 1H), 7.08-7.01 (m, 4H), 6.93 (dd, J=8.8, 2.7 Hz, 4H), 4.15 (d, J=6.0 Hz, 2H), 2.96 (s, 2H), 2.89 (s, 3H), 2.77 (s, 3H), 2.65 (q, J=5.6, 4.0 Hz, 4H), 2.56-2.49 (m, 4H), 2.33 (s, 3H). Mass (m/z): 438.3 [M+H]$^+$.

5-oxo-N-(4-((2-(4-propylpiperidin-1-yl)pyrimidin-5-yl)amino)benzyl)pyrrolidine-3-carboxamide (603)

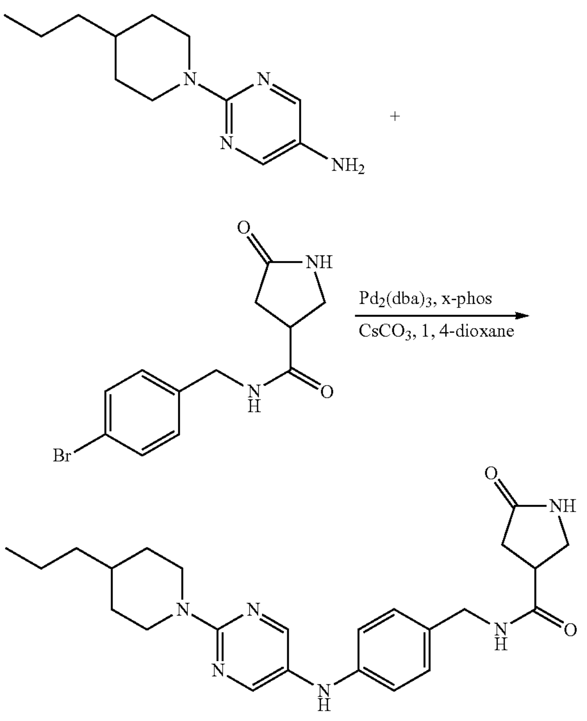

603

The title compound 603 (28.7 mg) was prepared in a total yield of 39.2% as a white solid from 2-(4-propylpiperidin-1-yl)pyrimidin-5-amine (44 mg, 0.202 mmol), N-(4-bromobenzyl)-5-oxopyrrolidine-3-carboxamide (50 mg, 0.168 mmol), $Pd_2(dba)_3$ (2 mg, 0.002 mmol), x-phos (6 mg, 0.01 mmol) and $Cs_2CO_3$ (83 mg, 0.252 mmol) and 1,4-dioxane (5 mL) according to the procedure for 525. $^1$H NMR (400 MHz, DMSO-$d_6$) δ 8.38 (t, J=6.0 Hz, 1H), 8.17 (s, 2H), 7.63 (s, 1H), 7.55 (s, 1H), 7.01-6.96 (m, 2H), 6.71-6.64 (m, 2H), 4.59-4.47 (m, 2H), 4.09 (d, J=5.6 Hz, 2H), 3.39-3.32 (m, 1H), 3.23-3.13 (m, 2H), 2.77 (td, J=12.8, 2.8 Hz, 2H), 2.28-2.22 (m, 2H), 1.66 (dd, J=13.6, 3.2 Hz, 2H), 1.46 (ddp, J=11.2, 6.8, 3.6 Hz, 1H), 1.33-1.23 (m, 2H), 1.22-1.13 (m, 2H), 1.06-0.92 (m, 2H), 0.84 (t, J=7.2 Hz, 3H). Mass (m/z): 437.3 [M+H]$^+$.

N-(4-((2-(3,3-dimethylazetidin-1-yl)pyrimidin-5-yl)amino)benzyl)-5-oxopyrrolidine-3-carboxamide (604)

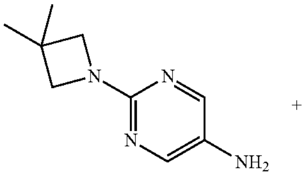

-continued

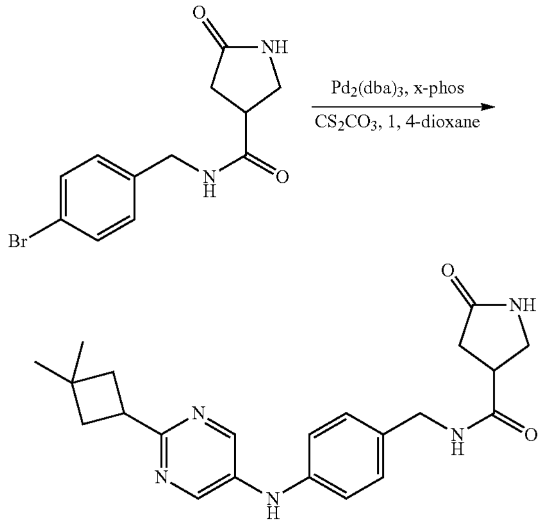

604

The title compound 604 (21.4 mg) was prepared in a total yield of 32.4% as a yellow solid from 2-(3,3-dimethylcyclobutyl)pyrimidin-5-amine (36 mg, 0.202 mmol), N-(4-bromobenzyl)-5-oxopyrrolidine-3-carboxamide (50 mg, 0.168 mmol), $Pd_2(dba)_3$ (2 mg, 0.002 mmol), x-phos (6 mg, 0.01 mmol) and $Cs_2CO_3$ (83 mg, 0.252 mmol) and 1,4-dioxane (5 mL) according to the procedure for 525. $^1$H NMR (400 MHz, DMSO-$d_6$) δ 8.42 (d, J=6.2 Hz, 1H), 8.17 (s, 2H), 7.71 (s, 1H), 7.56 (s, 1H), 7.02-6.96 (m, 2H), 6.71-6.66 (m, 2H), 4.09 (d, J=5.8 Hz, 2H), 3.66 (s, 4H), 3.22-3.12 (m, 2H), 2.50-2.47 (m, 1H), 2.28-2.20 (m, 2H), 1.24 (s, 6H). Mass (m/z): 395.3 $[M+H]^+$.

N-(4-((2-(4,4-dimethylpiperidin-1-yl)pyrimidin-5-yl)amino)benzyl)-5-oxopyrrolidine-3-carboxamide (605)

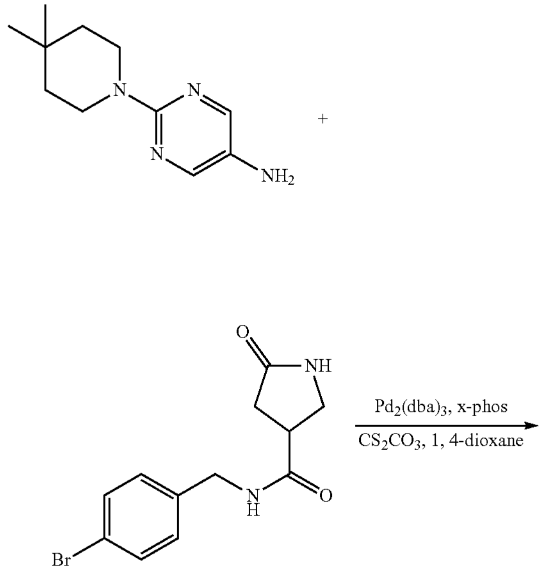

-continued

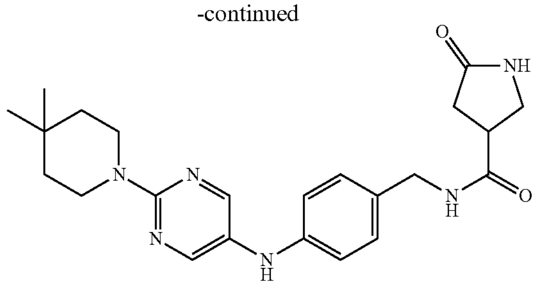

605

The title compound 605 (2.1 mg) was prepared in a total yield of 2.9% as a yellow solid from 2-(4,4-dimethylpiperidin-1-yl)pyrimidin-5-amine (42 mg, 0.202 mmol), N-(4-bromobenzyl)-5-oxopyrrolidine-3-carboxamide (50 mg, 0.168 mmol), $Pd_2$(dba) (2 mg, 0.002 mmol), x-phos (6 mg, 0.01 mmol) and $Cs_2CO_3$ (83 mg, 0.252 mmol) and, 4-dioxane (5 mL) according to the procedure for 525. $^1$H NMR (400 MHz, DMSO-d) δ 8.32 (t, J=6.0 Hz, 1H), 8.18 (s, 2H), 7.54 (s, 1H), 7.02-6.97 (m, 2H), 6.71-6.64 (m, 2H), 4.10 (d, J=5.6 Hz, 2H), 3.68-3.64 (m, 4H), 3.35 (t, J=9.2 Hz, 2H), 3.22-3.06 (m, 3H), 2.26 (td, J=9.2, 3.6 Hz, 3H), 1.95 (p, J=7.2, 6.4 Hz, 1H), 1.32-1.27 (m, 4H), 0.94 (s, 6H). Mass (m/z): 423.3 $[M+H]^+$.

N-(4-((2-(4-methylpiperidin-1-yl)pyrimidin-5-yl)amino)benzyl)-5-oxopyrrolidine-3-carboxamide (606)

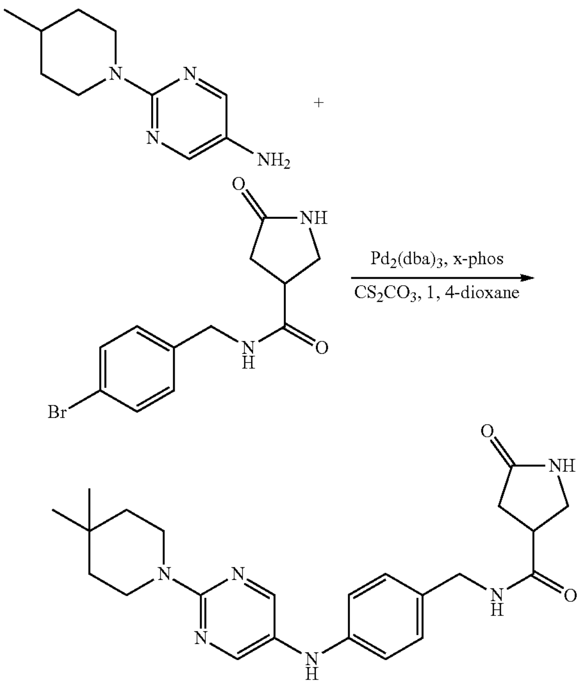

606

The title compound 606 (11.9 mg) was prepared in a total yield of 17.4% as a yellow solid from 2-(4-methylpiperidin-1-yl)pyrimidin-5-amine (39 mg, 0.202 mmol), N-(4-bromobenzyl)-5-oxopyrrolidine-3-carboxamide (50 mg, 0.168 mmol), $Pd_2(dba)_3$ (2 mg, 0.002 mmol), x-phos (6 mg, 0.01 mmol) and $Cs_2CO_3$ (83 mg, 0.252 mmol) and 1,4-dioxane (5 mL) according to the procedure for 525. $^1H$ NMR (400 MHz, Ethanol-$d_6$) δ 8.35 (t, J=6.0 Hz, 1H), 8.21 (s, 2H), 7.57 (s, 1H), 7.05-6.99 (m, 2H), 6.74-6.69 (m, 2H), 4.55 (dq, J=12.4, 2.6, 2.4 Hz, 2H), 4.13 (d, J=5.6 Hz, 4H), 3.44-3.33 (m, 1H), 3.25-3.11 (m, 2H), 2.89-2.77 (m, 2H), 2.28 (dd, J=8.4, 3.6 Hz, 2H), 1.63 (ddt, J=14.4, 10.4, 3.9 Hz, 3H), 1.11-1.00 (m, 2H), 0.92 (d, J=6.4 Hz, 3H). Mass (m/z): 409.3 $[M+H]^+$.

1-(4-((2-(4-isopropylpiperidin-1-yl)pyrimidin-5-yl)amino)benzyl)urea (607)

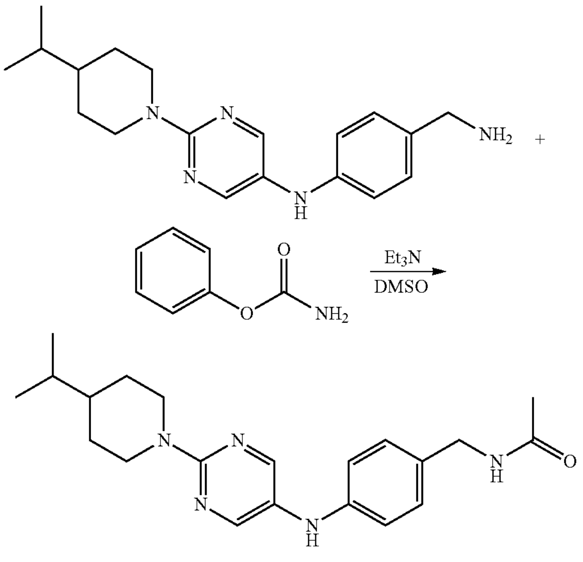

606

The title compound 607 (15.9 mg) was prepared in a total yield of 28.1% as a yellow solid from N-(4-(aminomethyl)phenyl)-2-(4-isopropylpiperidin-1-yl) pyrimidin-5-amine (50 mg, 0.154 mmol)phenyl carbamate (27 mg, 0.200 mmol), $Et_3N$ (46 mg, 0.462 mmol) and DMSO (3 mL) according to the procedure for 553. $^1H$ NMR (400 MHz, DMSO-$d_6$) δ 8.21 (s, 2H), 7.61 (s, 1H), 7.06-7.00 (m, 2H), 6.75-6.69 (m, 2H), 6.28 (t, J=6.0 Hz, 1H), 5.46 (s, 2H), 4.64 (dt, J=12.8, 2.5 Hz, 2H), 4.03 (d, J=6.0 Hz, 2H), 2.75 (td, J=12.8, 2.4 Hz, 2H), 1.74-1.64 (m, 2H), 1.44 (dt, J=13.2, 6.7 Hz, 1H), 1.28 (dq, J=5.6, 3.2 Hz, 1H), 1.12 (td, J=12.4, 4.4 Hz, 2H), 0.87 (d, J=6.8 Hz, 6H). Mass (m/z): 369.3 $[M+H]^+$.

N1-(4-((2-(4-isopropylpiperidin-1-yl)pyrimidin-5-yl)amino)benzyl)oxalamide (608)

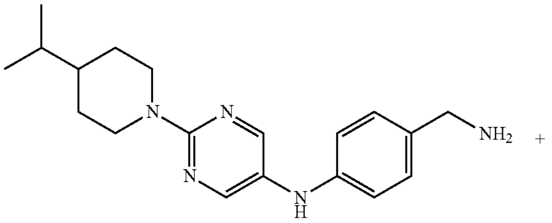

-continued

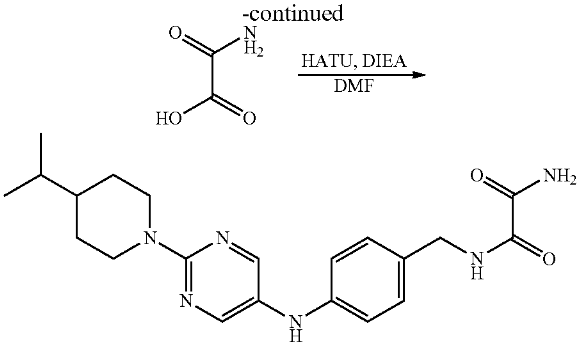

608

The title compound 608 (31.5 mg) was prepared in a total yield of 57.6% as a yellow solid from N-(4-(aminomethyl)phenyl)-2-(4-isopropylpiperidin-1-yl) pyrimidin-5-amine (50 mg, 0.154 mmol), 2-amino-2-oxoacetic acid (18 mg, 0.200 mmol), HATU (76 mg, 0.200 mmol), DIEA (26 mg, 0.200 mmol) and DMF (3 mL) according to the procedure for 523. $^1H$ NMR (400 MHz, DMSO-$d_6$) δ 9.06 (t, J=6.4 Hz, 1H), 8.22 (s, 2H), 8.05 (s, 1H), 7.78 (d, J=16.0 Hz, 2H), 7.09-7.02 (m, 2H), 6.75-6.68 (m, 2H), 4.69-4.60 (m, 2H), 4.17 (d, J=6.4 Hz, 2H), 2.75 (td, J= 12.8, 2.4 Hz, 2H), 1.74-1.64 (m, 2H), 1.46-1.39 (m, 1H), 1.10 (qd, J=12.4, 4.0 Hz, 3H), 0.87 (d, J=6.8 Hz, 6H). Mass (m/z): 397.3 $[M+H]^+$.

(S)—N-(4-((2-(4-isopropylpiperidin-1-yl)pyrimidin-5-yl)amino)benzyl)-2,6-dioxohexahydropyrimidine-4-carboxamide (609)

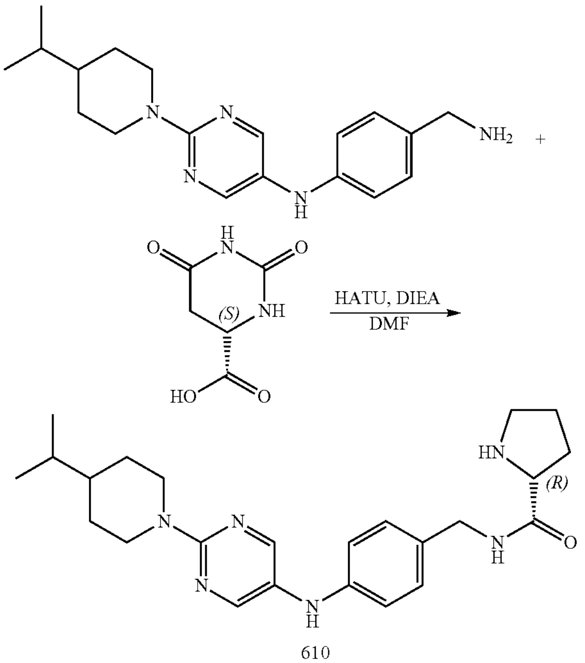

610

The title compound 609 (20.9 mg) was prepared in a total yield of 29.2% as a yellow solid from N-(4-(aminomethyl)phenyl)-2-(4-isopropylpiperidin-1-yl) pyrimidin-5-amine (50 mg, 0.154 mmol), (S)-2,6-dioxohexahydropyrimidine-4-carboxylic acid (32 mg, 0.200 mmol), HATU (76 mg, 0.200 mmol), DIEA (26 mg, 0.200 mmol) and DMF (3 mL) according to the procedure for 523. $^1$H NMR (400 MHz, DMSO-$d_6$) δ 10.00 (s, 1H), 8.45 (t, J=5.6 Hz, 1H), 8.22 (s, 2H), 7.66 (s, 1H), 7.62 (d, J=3.6 Hz, 1H), 7.06-6.98 (m, 2H), 6.75-6.68 (m, 2H), 4.64 (d, J=13.2 Hz, 2H), 4.13 (d, J=5.6 Hz, 2H), 4.00 (dt, J=7.2, 3.6 Hz, 1H), 2.83 (dd, J=16.8, 7.2 Hz, 1H), 2.75 (td, J=12.8, 2.4 Hz, 2H), 1.69 (d, J=12.8 Hz, 2H), 1.42 (dt, J=13.2, 6.6 Hz, 1H), 1.30-1.27 (m, 1H), 1.11 (qd, J=12.4, 4.2 Hz, 3H), 0.87 (d, J=6.8 Hz, 6H). Mass (m/z): 466.3 [M+H]$^+$.

(R)—N-(4-((2-(4-isopropylpiperidin-1-yl)pyrimidin-5-yl)amino)benzyl) pyrrolidine-2-carboxamide (610)

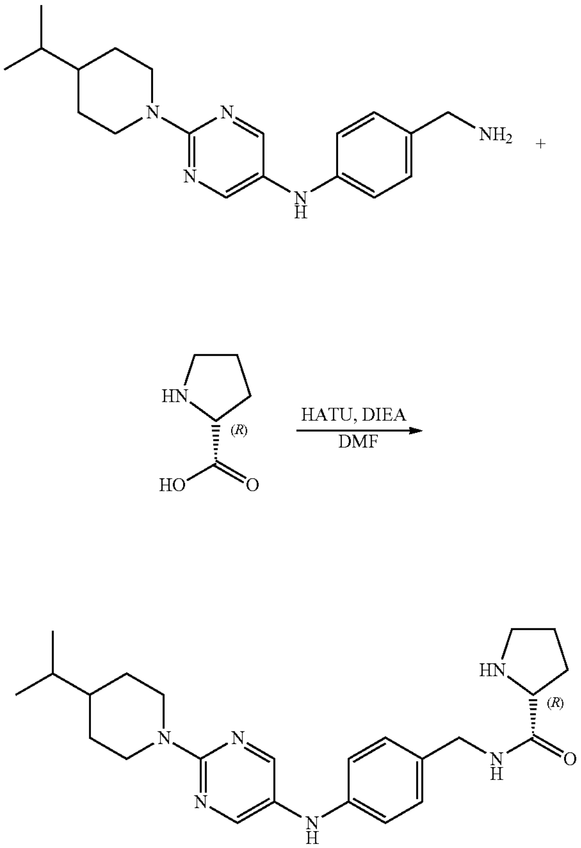

610

The title compound 610 (24.3 mg) was prepared in a total yield of 37.4% as a yellow solid from N-(4-(aminomethyl) phenyl)-2-(4-isopropylpiperidin-1-yl) pyrimidin-5-amine (50 mg, 0.154 mmol), D-proline (23 mg, 0.200 mmol), HATU (76 mg, 0.200 mmol), DIEA (26 mg, 0.200 mmol) and DMF (3 mL) according to the procedure for 523. $^1$H NMR (400 MHz, DMSO-$d_6$) δ 8.33 (s, 1H), 8.23 (d, J=6.8 Hz, 2H), 7.92 (s, 1H), 7.17-7.10 (m, 2H), 6.75 (dd, J=21.2, 8.4 Hz, 2H), 4.64 (d, J=12.8 Hz, 2H), 4.19 (s, 2H), 2.80-2.72 (m, 3H), 2.69 (s, 2H), 1.69 (d, J=12.4 Hz, 2H), 1.43 (td, J=12.8, 6.0 Hz, 2H), 1.29 (s, 1H), 1.11 (tt, J=12.4, 6.0 Hz, 3H), 0.87 (d, J=6.8 Hz, 6H). Mass (m/z): 423.3 [M+H]$^+$.

(S)—N-(4-((2-(4-isopropylpiperidin-1-yl)pyrimidin-5-yl)amino)benzyl)-6-oxopiperidine-2-carboxamide (611)

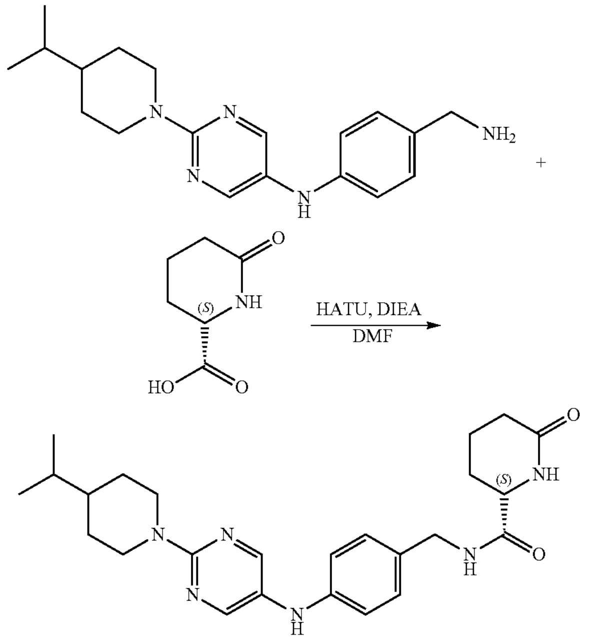

611

The title compound 611 (40.3 mg) was prepared in a total yield of 58.2% as a yellow solid from N-(4-(aminomethyl) phenyl)-2-(4-isopropylpiperidin-1-yl) pyrimidin-5-amine (50 mg, 0.154 mmol), (S)-6-oxopiperidine-2-carboxylic acid (29 mg, 0.200 mmol), HATU (76 mg, 0.200 mmol), DIEA (26 mg, 0.200 mmol) and DMF (3 mL) according to the procedure for 523. $^1$H NMR (400 MHz, DMSO-$d_6$) δ 8.36 (t, J=6.0 Hz, 1H), 8.22 (s, 2H), 7.68 (s, 1H), 7.50 (d, J=2.4 Hz, 1H), 7.08-7.01 (m, 2H), 6.75-6.68 (m, 2H), 4.64 (d, J=13.2 Hz, 2H), 4.15 (qd, J=14.4, 5.6 Hz, 2H), 3.89 (td, J=5.6, 2.8 Hz, 1H), 2.75 (td, J=11.6, 10.4, 2.8 Hz, 2H), 2.12 (t, J=6.4 Hz, 2H), 1.85 (ddd, J=13.2, 6.0, 3.6 Hz, 1H), 1.75-1.64 (m, 4H), 1.60 (td, J=6.8, 6.0, 3.6 Hz, 1H), 1.42 (dt, J=11.6, 6.0 Hz, 1H), 1.34-1.26 (m, 2H), 1.10 (qd, J=12.4, 4.0 Hz, 2H), 0.87 (d, J=6.8 Hz, 6H). Mass (m/z): 451.3 [M+H]$^+$.

N-(4-((2-(4-isopropylpiperidin-1-yl)pyrimidin-5-yl) amino)phenethyl)-5-oxopyrrolidine-3-carboxamide (612)

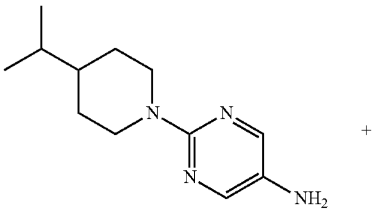

-continued

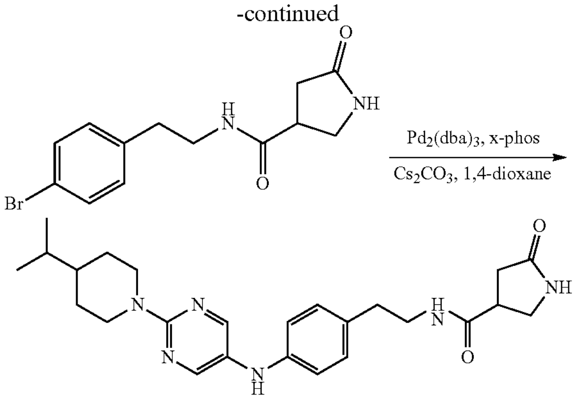

612

The title compound 612 (24.4 mg) was prepared in a total yield of 33.7% as a yellow solid from 2-(4-isopropylpiperidin-1-yl)pyrimidin-5-amine (42 mg, 0.193 mmol), N-(4-bromophenethyl)-5-oxopyrrolidine-3-carboxamide (50 mg, 0.161 mmol), $Pd_2(dba)_3$ (2 mg, 0.002 mmol), x-phos (6 mg, 0.01 mmol) and $Cs_2CO_3$ (79 mg, 0.242 mmol) and 1,4-dioxane (5 mL) according to the procedure for 525. $^1$H NMR (400 MHz, DMSO-$d_6$) δ 8.21 (s, 2H), 8.07 (t, J=5.6 Hz, 1H), 7.58 (s, 1H), 7.55 (s, 1H), 6.99-6.94 (m, 2H), 6.72-6.68 (m, 2H), 4.69-4.59 (m, 2H), 3.19 (h, J=6.8 Hz, 3H), 3.14-3.08 (m, 11H), 2.75 (td, J=13.2, 2.8 Hz, 2H), 2.57 (t, J=7.6 Hz, 2H), 2.27-2.21 (m, 2H), 1.73-1.65 (m, 2H), 1.44 (dt, J=13.2, 6.8 Hz, 1H), 1.12 (td, J=12.4, 4.0 Hz, 2H), 0.87 (d, J=6.8 Hz, 6H). Mass (m/z): 451.3 [M+H]$^+$.

N-(4-((3,5-difluoro-4-(4-isopropylpiperidin-1-yl) phenyl)amino)benzyl)-5-oxopyrrolidine-3-carboxamide (613)

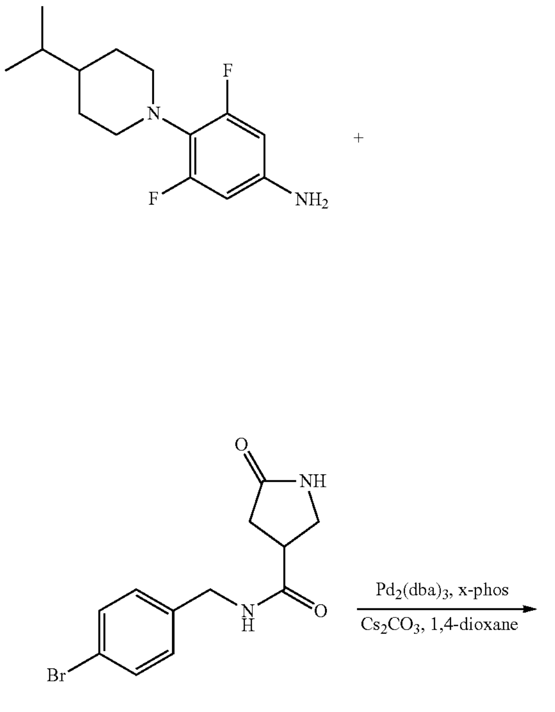

-continued

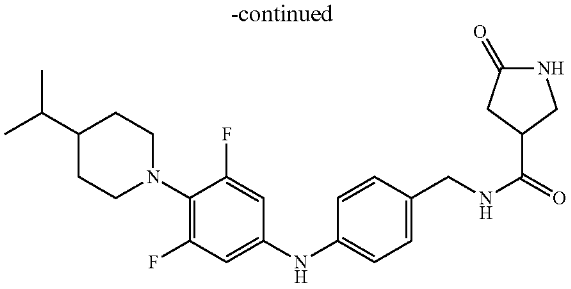

613

The title compound 613 (7.0 mg) was prepared in a total yield of 8.9% as a white solid from 3,5-difluoro-4-(4-isopropylpiperidin-1-yl)aniline (51 mg, 0.202 mmol). N-(4-bromobenzyl)-5-oxopyrrolidine-3-carboxamide (50 mg, 0.168 mmol), $Pd_2(dba)_3$ (2 mg, 0.002 mmol), x-phos (6 mg, 0.01 mmol) and $Cs_2CO_3$ (83 mg, 0.252 mmol) and 1,4-dioxane (5 mL) according to the procedure for 525. $^1$H NMR (400 MHz, DMSO-$d_6$) δ 8.39 (t, J=5.6 Hz, 1H), 8.34 (s, 11H), 7.55 (s, 11H), 7.15-7.10 (m, 2H), 7.03-6.98 (m, 2H), 6.56-6.49 (m, 2H), 4.17 (d, J=5.6 Hz, 2H), 3.40-3.33 (m, 1H), 3.24-3.13 (m, 2H), 3.01-2.86 (m, 4H), 2.27 (dd, J=8.4, 3.2 Hz, 2H), 1.60 (d, J=12.4 Hz, 2H), 1.41 (dt, J=13.2, 6.4 Hz, 1H), 1.30-1.20 (m, 3H), 1.12-0.99 (m, 1H), 0.84 (d, J=6.8 Hz, 6H). Mass (m/z): 471.3 [M+H]$^+$.

N-(4-((4-(4,4-dimethylpiperidin-1-yl)-3,5-difluorophenyl)amino)benzyl)-5-oxopyrrolidine-3-carboxamide (614)

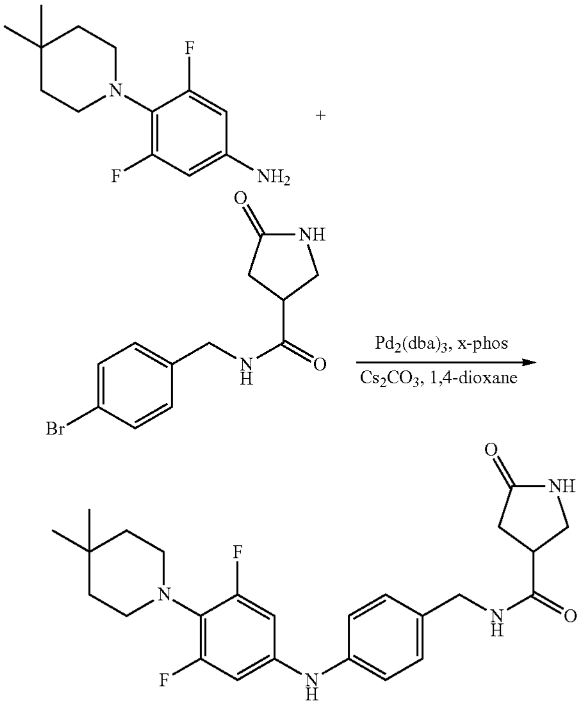

614

The title compound 614 (6.8 mg) was prepared in a total yield of 8.9% as a white solid from 3,4-(4,4-dimethylpiperidin-1-yl)-3,5-difluoroaniline (48 mg, 0.202 mmol), N-(4- bromobenzyl)-5-oxopyrrolidine-3-carboxamide (50 mg, 0.168 mmol), $Pd_2(dba)_3$ (2 mg, 0.002 mmol), x-phos (6 mg, 0.01 mmol) and $Cs_2CO_3$ (83 mg, 0.252 mmol) and 1,4-dioxane (5 mL) according to the procedure for 525. $^1H$ NMR (400 MHz, DMSO-$d_6$) δ 8.38 (t, J=5.6 Hz, 1H), 8.33 (s, 1H), 7.54 (s, 1H), 7.13 (d, J=8.4 Hz, 2H), 7.03-6.98 (m, 2H), 6.57-6.48 (m, 2H), 4.17 (d, J=5.8 Hz, 2H), 3.37 (d, J=17.6 Hz, 1H), 3.25-3.11 (m, 2H), 2.91 (t, J=5.6 Hz, 4H), 2.27 (dd, J=8.4, 3.6 Hz, 2H), 1.41-1.34 (m, 4H), 0.92 (s, 6H). Mass (m/z): 457.3 $[M+H]^+$.

N-(4-((4-(4-ethylpiperidin-1-yl)-3,5-difluorophenyl) amino)benzyl)-5-oxopyrrolidine-3-carboxamide (615)

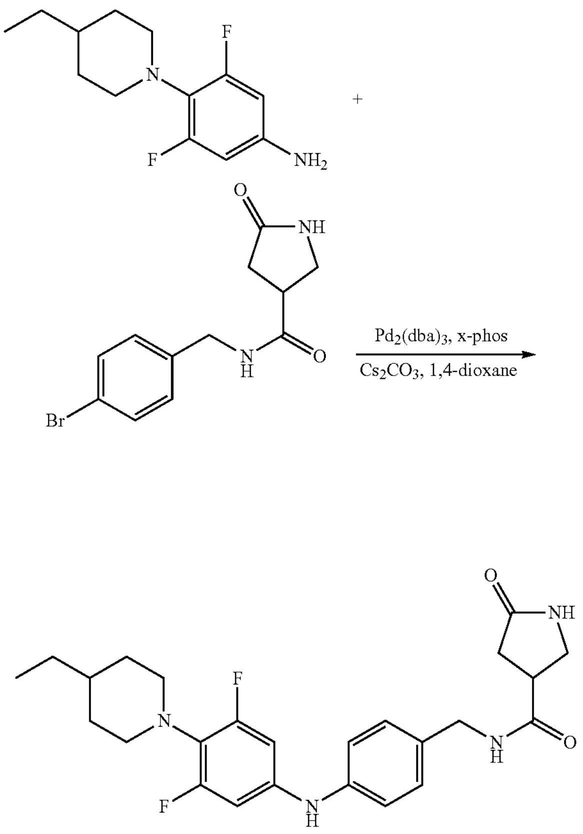

615

The title compound 625 (3.2 mg) was prepared in a total yield of 4.2% as a white solid from 4-(4-ethylpiperidin-1-yl)-3,5-difluoroaniline (48 mg, 0.202 mmol), N-(4-bromobenzyl)-5-oxopyrrolidine-3-carboxamide (50 mg, 0.168 mmol), $Pd_2(dba)_3$ (2 mg, 0.002 mmol), x-phos (6 mg, 0.01 mmol) and $Cs_2CO_3$ (83 mg, 0.252 mmol) and 1,4-dioxane (5 mL) according to the procedure for 525. $^1H$ NMR (400 MHz, DMSO-$d_6$) δ 8.39 (t, J=6.0 Hz, 1H), 8.33 (s, 1H), 7.55 (s, 1H), 7.15-7.09 (m, 2H), 7.04-6.97 (m, 2H), 6.57-6.48 (m, 2H), 4.17 (d, J=6.0 Hz, 2H), 3.42-3.35 (m, 1H), 3.24-3.12 (m, 2H), 2.92 (d, J=14.0 Hz, 4H), 2.52-2.48 (m, 2H), 2.27 (dd, J=8.4, 3.2 Hz, 2H), 1.64 (d, J=8.4 Hz, 2H), 1.23 (d, J=7.2 Hz, 3H), 0.84 (t, J=7.2 Hz, 3H). Mass (m/z): 457.3 $[M+H]^+$.

N-(4-((6-(4-(ethoxymethyl)piperidin-1-yl)-2-methylpyridin-3-yl)amino)benzyl)-5-oxopyrrolidine-3-carboxamide (616)

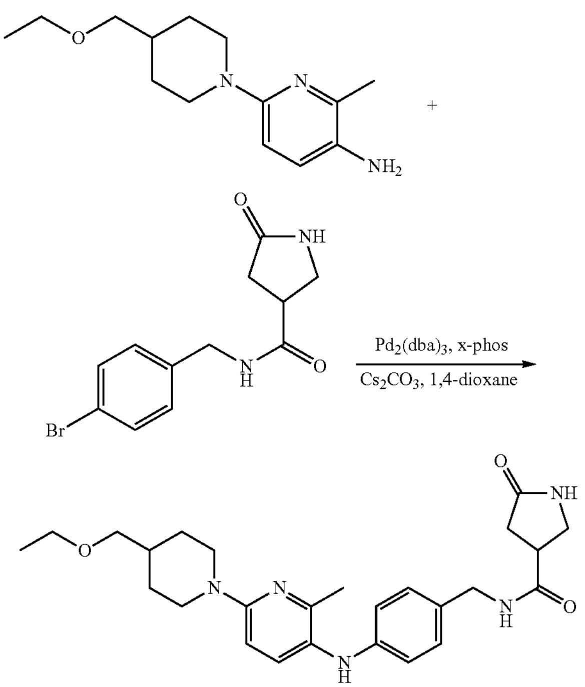

616

The title compound 616 (6.7 mg) was prepared in a total yield of 8.6% as a white solid from 6-(4-(ethoxymethyl) piperidin-1-yl)-2-methylpyridin-3-amine (50 mg, 0.202 mmol), N-(4-bromobenzyl)-5-oxopyrrolidine-3-carboxamide (50 mg, 0.168 mmol), $Pd_2(dba)_3$ (2 mg, 0.002 mmol), x-phos (6 mg, 0.01 mmol) and $Cs_2CO_3$ (83 mg, 0.252 mmol) and 1,4-dioxane (5 mL) according to the procedure for 525. $^1H$ NMR (400 MHz, DMSO-$d_6$) δ 8.31 (t, J=5.6 Hz, 1H), 7.57 (s, 1H), 7.25 (d, J=8.8 Hz, 1H), 7.19 (s, 1H), 7.01-6.95 (m, 2H), 6.63 (d, J=8.8 Hz, 1H), 6.53-6.47 (m, 2H), 4.23 (d, J=12.8 Hz, 2H), 4.11 (d, J=5.6 Hz, 2H), 3.46-3.37 (m, 3H), 3.28-3.12 (m, 4H), 2.72 (dd, J=12.8, 2.4 Hz, 2H), 2.28 (dd, J=8.4, 5.2 Hz, 2H), 2.19 (s, 3H), 1.72 (dd, J=12.0, 3.2 Hz, 3H), 1.22-1.13 (m, 2H), 1.11 (t, J=7.2 Hz, 3H). Mass (m/z): 466.3 $[M+H]^+$.

N-(4-((5-(4-isopropylpiperidin-1-yl)pyrazin-2-yl) amino)benzyl)-5-oxopyrrolidine-3-carboxamide (617)

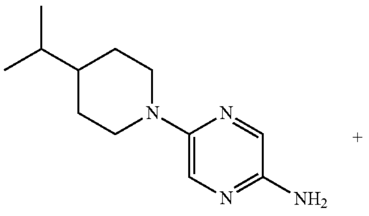

-continued

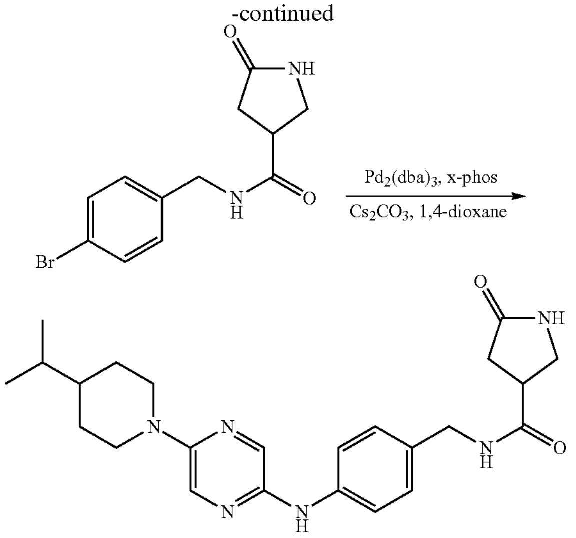

617

The title compound 617 (9.2 mg) was prepared in a total yield of 12.6% as a yellow solid from 5-(4-isopropylpiperidin-1-yl)pyrazin-2-amino (44 mg, 0.202 mmol), N-(4-bromobenzyl)-5-oxopyrrolidine-3-carboxamide (50 mg, 0.168 mmol), $Pd_2(dba)_3$ (2 mg, 0.002 mmol), x-phos (6 mg, 0.01 mmol) and $Cs_2CO_3$ (83 mg, 0.252 mmol) and 1,4-dioxane (5 mL) according to the procedure for 525. $^1H$ NMR (400 MHz, DMSO-$d_6$) δ 8.83 (s, 1H), 8.39 (t, J=5.6 Hz, 1H), 7.88 (dd, J=9.6, 1.6 Hz, 2H), 7.58 (s, 1H), 7.48-7.41 (m, 2H), 7.13-7.07 (m, 2H), 4.18 (d, J=5.6 Hz, 2H), 4.15-4.08 (m, 2H), 3.40 (t, J=8.4 Hz, 1H), 3.28-3.15 (m, 2H), 2.62 (d, J=12.0 Hz, 2H), 2.34-2.26 (m, 2H), 1.77-1.67 (m, 2H), 1.48-1.37 (m, 1H), 0.87 (d, J=6.8 Hz, 6H). Mass (m/z): 437.3 $[M+H]^+$.

5-oxo-N-(4-((4-(tert-pentyl)phenyl)amino)benzyl) pyrrolidine-3-carboxamide (618)

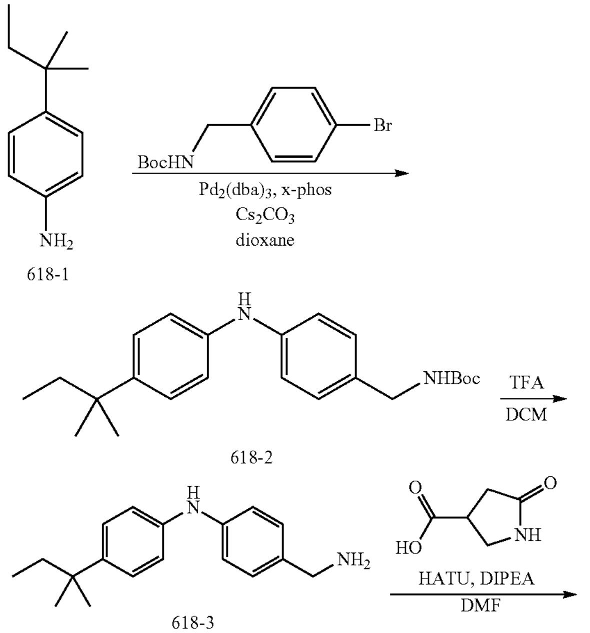

618-1

618-2

618-3

-continued

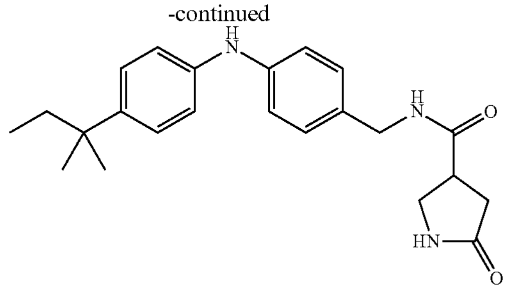

618

Step 1. tert-butyl (4-((4-(tert-pentyl)phenyl)amino)benzyl)carbamate (618-2). To a solution of 4-(tert-pentyl)aniline (600 mg, 3.68 mmol) and tert-butyl (4-bromobenzyl) carbamate (1.05 g, 3.68 mmol) in dioxane (15 mL) was added $Pd_2$(dba), (168 mg, 0.184 mmol), X-phos (176 mg, 0.368 mmol) and $Cs_2CO_3$ (1.8 g, 5.52 mmol) under nitrogen atmosphere. Then the mixture was stirred at 100° C. overnight. The mixture was extracted by EA (25 mL×3). The combined organic layers were washed with brine (15 mL×3), dried over Na2SO4 and concentrated to give the crude product, which was purified by column chromatography (PE/EA-4:1) to give the desired product as white solid (800 mg, 59.1%). Mass (m/z): 369.3 $[M+H]^+$.

Step 2. 4-(aminomethyl)-N-(4-(tert-pentyl)phenyl)aniline (618-3). To a solution of tert-butyl (4-((4-(tert-pentyl)phenyl)amino)benzyl)carbamate (800 mg, 2.17 mmol) in DCM (15 mL) was added 2,2,2-trifluoracetic acid (5 mL). Then the mixture was stirred at room temperature for 0.5 h. The mixture was extracted by EA (25 mL×3). The combined organic layers were washed with brine (15 mL×3), dried over Na2SO4 and concentrated to give the crude product as yellow oil. Mass (m/z): 269.3 $[M+H]^+$.

Step 3. 5-oxo-N-(4-((4-(tert-pentyl)phenyl)amino)benzyl)pyrrolidine-3-carboxamide (618). To a solution of 5-oxopyrrolidine-3-carboxylic acid (29 mg, 0.223 mmol) HATU (102 mg, 0.268 mmol) and DIPEA (58 mg, 0.446 mmol) in DMF (3 mL) was added 618-3 (60 mg, 0.223 mmol). The mixture was stirred at room temperature overnight. Then the mixture was extracted by EA (25 mL×3). The combined organic layers were washed with brine (15 mL×3), dried over Na2SO4 and concentrated to give the crude product, which was purified by pre-HPLC to give the desired product as white solid (20.3 mg, 24.0%). 1H NMR (400 MHz, DMSO-d6) δ 8.35 (t, J=5.7 Hz, 1H), 7.97 (s, 1H), 7.55 (s, 1H), 7.18-7.10 (m, 2H), 7.08-7.03 (m, 2H), 7.00-6.90 (m, 4H), 4.14 (d, J=5.7 Hz, 2H), 3.23-3.17 (m, 1H), 2.35-2.20 (m, 2H), 1.53 (q, J=7.5 Hz, 2H), 1.17 (s, 6H), 0.60 (t, J=7.4 Hz, 3H). Mass (m/z): 380.2 $[M+H]^+$.

(R)-2-oxo-N-(4-((4-(tert-pentyl)phenyl)amino)benzyl)imidazolidine-4-carboxamide (619)

619

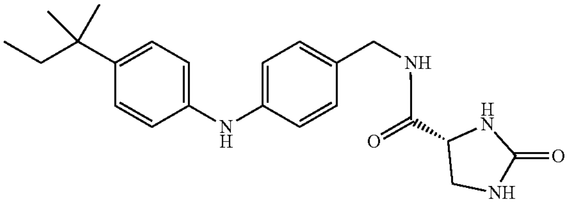

The title compound 619 (17.7 mg) was prepared in a total yield of 20.8% as a white solid from (R)-2-oxoimidazolidine-4-carboxylic acid (29 mg, 0.223 mmol), HATU (102 mg, 0.268 mmol) and DIPEA (58 mg, 0.446 mmol) according to the procedure for SIR-00004702. $^1$H NMR (400 MHz, DMSO-d6) δ 8.26 (t, J=5.9 Hz, 1H), 7.97 (s, 1H), 7.20-7.02 (m, 4H), 6.99-6.88 (m, 4H), 6.51 (s, 1H), 6.28 (s, 1H), 4.15 (d, J=5.8 Hz, 2H), 4.06 (ddd, J=9.8, 6.2, 1.8 Hz, 1H), 3.51 (ddd, J=9.8, 8.9, 1.1 Hz, 1H), 3.19 (ddd, J=8.9, 6.2, 1.3 Hz, 1H), 1.53 (q, J=7.4 Hz, 2H), 1.17 (s, 6H), 0.60 (t, J=7.4 Hz, 3H). Mass (m/z): 381.2 $[M+H]^+$.

N$^1$-(4-((4-(tert-pentyl)phenyl)amino)benzyl)succinamide (620)

620

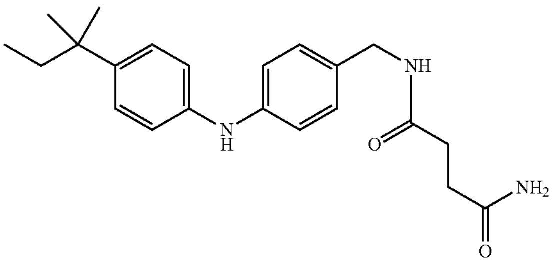

The title compound 620 (6.5 mg) was prepared in a total yield of 7.1% as a white solid from 4-amino-4-oxobutanoic acid (26.1 mg, 0.223 mmol), HATU (102 mg, 0.268 mmol) and DIPEA (58 mg, 0.446 mmol) according to the procedure for SIR-00004702. $^1$H NMR (400 MHz, DMSO-d6) δ 8.18 (t. J=5.9 Hz, 1H), 7.95 (s, 1H), 7.25 (s, 1H), 7.18-7.10 (m, 2H), 7.08-7.01 (m, 2H), 6.98-6.88 (m, 4H), 6.71 (s, 1H), 4.11 (d, J=5.8 Hz, 2H), 2.30-2.27 (m, 4H), 1.53 (q, J=7.4 Hz, 2H), 1.17 (s, 6H), 0.60 (t, J=7.4 Hz, 3H). Mass (m/z): 368.3 $[M+H]^+$.

(S)-2,6-dioxo-N-(4-((4-(tert-pentyl)phenyl)amino)benzyl)hexahydropyrimidine-4-carboxamide (621)

621

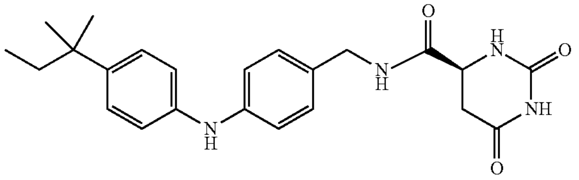

The title compound 621 (20.5 mg) was prepared in a total yield of 22.5% as a white solid from (S)-2,6-dioxohexahydropyrimidine-4-carboxylic acid (35.2 mg, 0.223 mmol), HATU (102 mg, 0.268 mmol) and DIPEA (58 mg, 0.446 mmol) according to the procedure for SIR-00004702. $^1$H NMR (400 MHz, DMSO-d6) δ 10.02 (d, J=1.8 Hz, 11H), 8.42 (t, J=5.7 Hz, 1H), 8.01 (s, 1H), 7.61 (d, J=3.0 Hz, 1H), 7.25-7.13 (m, 2H), 7.12-7.06 (m, 2H), 7.03-6.92 (m, 411), 4.17 (dd, J=6.1, 1.7 Hz, 2H), 4.00 (dt, J=7.2, 3.5 Hz, 1H), 2.85 (dd, J=16.6, 7.2 Hz, 111), 1.57 (q, J=7.4 Hz, 2H), 1.21 (s, 6H), 0.63 (t, J=7.4 Hz, 3H). Mass (m/z): 409.2 $[M+H]^+$.

2,6-dioxo-N-(4-((4-(tert-pentyl)phenyl)amino)benzyl)piperidine-4-carboxamide (622)

622

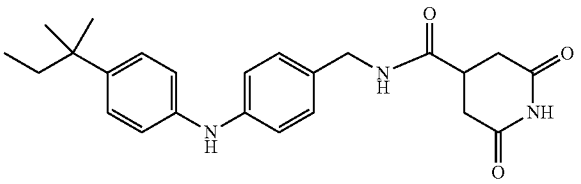

The title compound 622 (25.7 mg) was prepared in a total yield of 28.3% as a white solid from 2,6-dioxopiperidine-4-carboxylic acid (35 mg, 0.223 mmol), HATU (102 mg, 0.268 mmol) and DIPEA (58 mg, 0.446 mmol) according to the procedure for SIR-00004702. $^1$H NMR (400 MHz, DMSO-d6) δ 7.98 (s, 1H), 7.38 (s, 1H), 7.16-7.12 (m, 2H), 7.10-7.06 (m, 2H), 6.97-6.93 (m, 2H), 6.93-6.87 (m, 3H), 4.48-4.32 (m, 2H), 3.08-2.98 (m, 1H), 2.78 (dd, J=17.8, 9.2 Hz, 1H), 2.53-2.50 (m, 2H), 2.43 (d, J=4.9 Hz, 1H), 1.53 (q, J=7.4 Hz, 2H), 1.17 (s, 6H), 0.59 (t, J=7.4 Hz, 3H). Mass (m/z): 408.3 $[M+H]^+$.

N-(4-((2-(4-isopropylpiperidin-1-yl)pyrimidin-5-yl)amino)-3-methylbenzyl)-5-oxopyrrolidine-3-carboxamide (623)

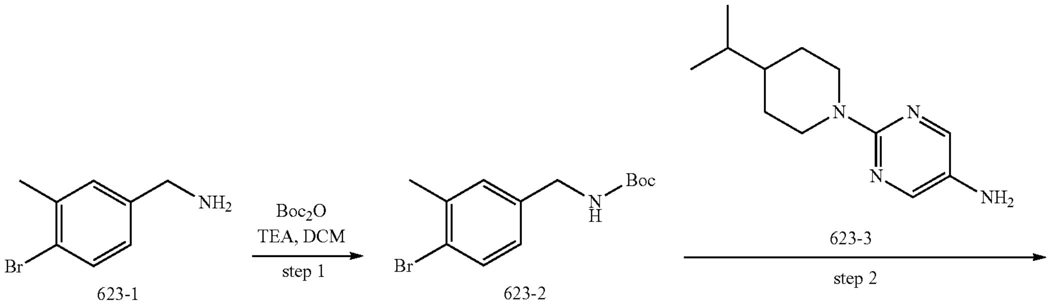

-continued

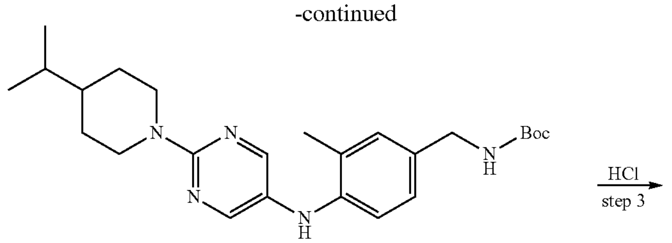

623-4

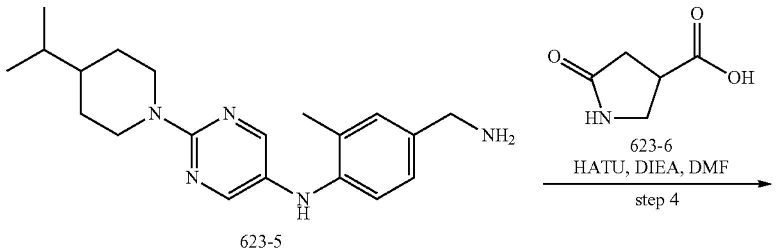

623-5

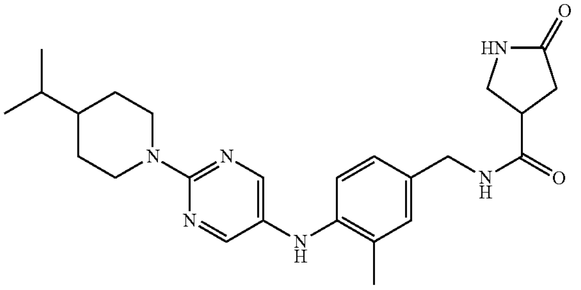

623

Step 1. Preparation of tert-butyl (4-bromo-3-methylbenzyl)carbamate (623-2): A mixture solution of (4-bromo-3-methylphenyl)methanamine (0.2 g, 1.0 mmol), $Boc_2O$ (0.26 g, 1.2 mmol), triethylamine (0.30 g, 3.0 mmol) in DCM (20 mL) was stirred at 25° C. for 3 hrs. The mixture was diluted with DCM (100 mL) and washed with water (100 mL×3). The organic phase was concentrated and purified by flash, eluting with PE/EA=10:1 to give tert-butyl (4-bromo-3-methylbenzyl)carbamate as a yellow oil (0.26 g, 87.8%). Mass (m/z): 243.8 $[M+H]^+$.

Step 2. Preparation of tert-butyl (4-((2-(4-isopropylpiperidin-1-yl)pyrimidin-5-yl)amino)-3-methylbenzyl)carbamate (623-4): To a solution of tert-butyl (4-bromo-3-methylbenzyl)carbamate (0.26 g, 0.87 mmol), 2-(4-isopropylpiperidin-1-yl)pyrimidin-5-amine (3) (0.23 g, 1.04 mmol), Ruphos (81 mg, 0.17 mmol), $Pd2(dba)_3$ (80 mg, 0.34 mmol) and $Cs_2CO_3$ (0.85 g, 2.60 mmol) in 1,4-dioxane (20 mL)) was stirred at 100° C. under $N_2$ atmosphere for 12 hrs. The mixture was concentrated and purified by combiflash, eluting with PE/EA=10:1 to 1:1 to give tert-butyl (4-((2-(4-isopropylpiperidin-1-yl)pyrimidin-5-yl)amino)-3-methylbenzyl)carbamate as a yellow solid (0.45 g, 88.7%). Mass (m/z): 440.3 $[M+H]^+$.

Step 3. Preparation of N-(4-(aminomethyl)-2-methylphenyl)-2-(4-isopropylpiperidin-1-yl)pyrimidin-5-amine (623-5): A solution of tert-butyl (4-((2-(4-isopropylpiperidin-1-yl)pyrimidin-5-yl)amino)-3-methylbenzyl)carbamate (0.45 g, 0.92 mmol) in 4 N HCl in dioxane (10 mL) was stirred at 25° C. for 2 hrs. Quenching with saturated $NaHCO_3$ (30 mL), extracted with EA (50 mL*3), the organic phase was concentrated under vacuum to afford N-(4 -(aminomethyl)-2-methylphenyl)-2-(4-isopropylpiperidin-1-yl)pyrimidin-5-amine 623-5 as yellow oil. (0.35 g, 94.5%). Mass (m/z): 339.2 $[M+H]^+$.

Step 4. Preparation of N-(4-((2-(4-isopropylpiperidin-1-yl)pyrimidin-5-yl)amino)-3-methylbenzyl)-5-oxopyrrolidine-3-carboxamide (623): A mixture solution of N-(4-(aminomethyl)-2-methylphenyl)-2-(4-isopropylpiperidin-1-yl)pyrimidin-5-amine (0.1 g, 0.3 mmol), 5-oxopyrrolidine-3-carboxylic acid (6) (0.04 g, 0.33 mmol), DIEA (0.12 g, 0.9 mmol), HATU (0.13 g, 0.33 mmol) in DMF (10 mL) was stirred at 25° C. for 3 hrs. The mixture was removed under vacuum and the residue was purified by perp-HPLC (column-Xbridge-C18 150×21.2 mm, Sum; Mobile phase: ACN-H2O (0.1% FA), 40%-60%) to afford 623 as yellow solid. (106.5 mg, 74.9%). Mass (m/z): 451.2 $[M+H]^+$. $^1H$ NMR (400 MHz, DMSO-$d_6$) δ 8.33 (t, J=5.6 Hz, 1H), 8.16 (s, 2H), 7.57 (s, 1H), 6.97 (d, J=1.4 Hz, 1H), 6.87 (dd, J=8.3, 1.7 Hz, 1H), 6.81 (s, 1H), 6.60 (d, J=8.2 Hz, 1H), 4.64 (d, J=13.0 Hz, 2H), 4.13 (d, J=5.7 Hz, 2H), 3.39 (t, J=8.8 Hz, 1H), 3.27-3.12 (m, 2H), 2.89 (s, 2H), 2.77 (dd, J=12.7, 2.0 Hz, 1H), 2.32-2.27 (m, 1H), 2.19 (s, 3H), 1.69 (d, J=11.4 Hz, 2H), 1.42 (dt, J=13.2, 6.6 Hz, 1H), 1.31-1.22 (m, 1H), 1.19-1.04 (m, 2H), 0.87 (d, J=6.8 Hz, 6H).

5-oxo-N-(3-(4-((4-(tert-pentyl)phenyl)amino)phenyl)propyl)pyrrolidine-3-carboxamide (624)

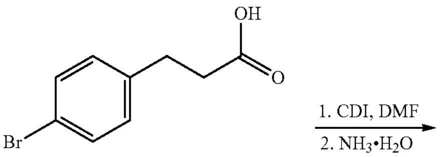

624-1

-continued

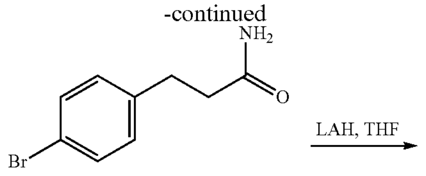

624-2

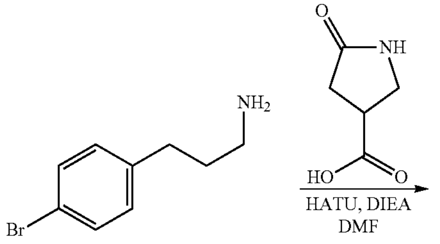

624-3

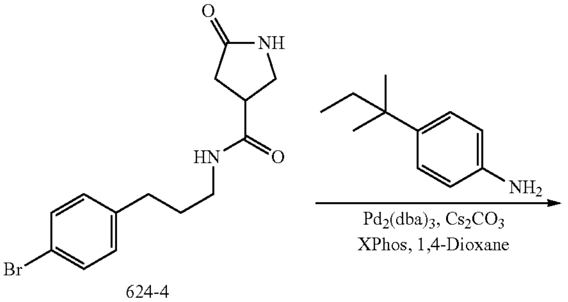

624-4

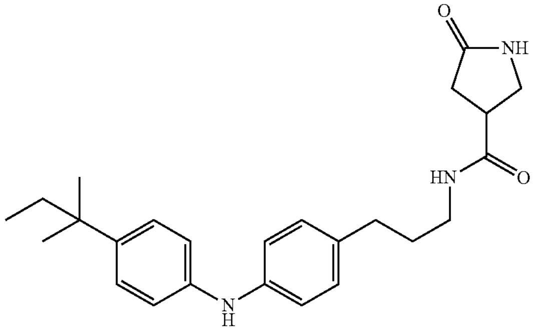

624

Step 1. 3-(4-bromophenyl)propanamide (624-2). To a solution of 3-(4-bromophenyl)propanoic acid (1.2 g, 5.26 mmol) in DMF (5 mL) was added CDI (1.7 g, 10.52 mmol) and stirred at 80° C. for overnight under nitrogen atmosphere. After cooling to room temperature, the reaction mixture was poured slowly into 28% aqueous ammonium hydroxide solution (30 ml) at 0° C. The mixture was extracted with ethyl acetate, washed with water and brine and dried over $Na_2SO_4$. Filtration followed by evaporation under reduced pressure gave 3-(4-bromophenyl)propan-1-amine (1.1 g, 92%) as a white solid. Mass (m/z): 227.9 $[M+H]^+$.

Step 2. 3-(4-bromophenyl)propan-1-amine (624-3). To a solution of 3-(4-bromophenyl)propan-1-amine (1.1 g, 4.84 mmol) in THF (15 mL) was added LAH (276 mg, 7.26 mmol) and stirred at 0° C. for 4 h under nitrogen atmosphere. The reaction mixture was poured into 1N aqueous sodium hydroxide solution (100 ml). The mixture was extracted with ethyl acetate and the organic layer was washed with water and brine and dried over magnesium sulfate. Filtration followed by evaporation under reduced pressure, then purified by flash to give 3-(4-bromophenyl) propan-1-amine (180 mg, 17%) as a white solid. Mass (m/z): 214.0 $[M+H]^+$.

Step 3. N-(3-(4-bromophenyl)propyl)-5-oxopyrrolidine-3-carboxamide (624-4). To a solution of 3-(4-bromophenyl) propan-1-amine (180 mg, 0.84 mmol), 5-oxopyrrolidine-3-carboxylic acid (163 mg, 1.26 mmol) in DMF (2 mL) was added 3-DIEA (327 mg, 2.53 mmol) and HATU (481 mg, 1.26 mmol). Then the mixture was stirred at 0° C. for 1 h under nitrogen atmosphere. The mixture was purified by flash to give N-(3-(4-bromophenyl)propyl)-5-oxopyrrolidine-3-carboxamide (138 mg, 50%) as a white solid. Mass (m/z): 325.0 $[M+H]^+$.

Step 4. 5-oxo-N-(3-(4-((4-(tert-pentyl)phenyl)amino)phenyl)propyl)pyrrolidine-3-carboxamide (624). To a solution of 4-(tert-pentyl)aniline (83 mg, 0.51 mmol) and N-(3-(4-bromophenyl)propyl)-5-oxopyrrolidine-3-carboxamide (138 mg, 3.68 mmol) in dioxane (1.5 mL) was added $Pd_2(dba)_3$ (39 mg, 0.04 mmol), Xphos (40 mg, 0.08 mmol) and $Cs_2CO_3$ (277 mg, 0.85 mmol) under nitrogen atmosphere. Then the mixture was purified by prep TLC then purified by prep HPLC to give 5-oxo-N-(3-(4-((4-(tert-pentyl)phenyl)amino)phenyl)propyl)pyrrolidine-3-carboxamide (20.8 mg, 12%) as a white solid. Mass (m/z): 408.2 $[M+H]^+$. $^1H$ NMR (400 MHz, DMSO-$d_6$) δ 8.00 (t, J=5.5 Hz, 1H), 7.90 (br, 1H), 7.56 (s, 1H), 7.20-7.12 (m, 2H), 7.07-6.99 (m, 2H), 7.02-6.91 (m, 4H), 3.40 (d, J=8.7 Hz, 1H), 3.21 (dd, J=9.3, 6.5 Hz, 1H), 3.18-3.05 (m, 2H), 3.05 (d, J=6.6 Hz, 1H), 2.49-2.44 (m, 2H), 2.27 (dd, J=8.5, 1.9 Hz, 2H), 1.72-1.61 (m, 2H), 1.57 (q, J=7.4 Hz, 2H), 1.20 (s, 6H), 0.63 (t, J=7.4 Hz, 3H).

(S)-5-oxo-N-(4-((4-(4-(trifluoromethyl)piperidin-1-yl)phenyl)amino)benzyl)pyrrolidine-3-carboxamide (625)

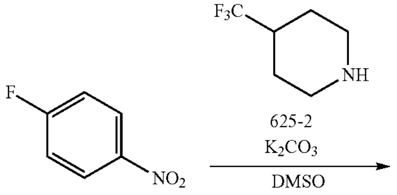

625-1

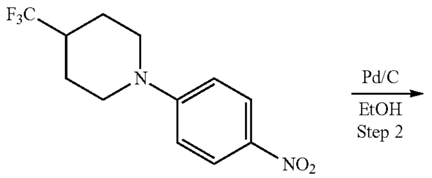

625-3

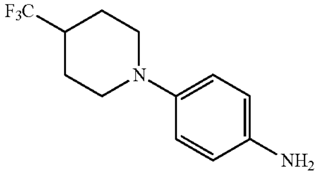

625-4

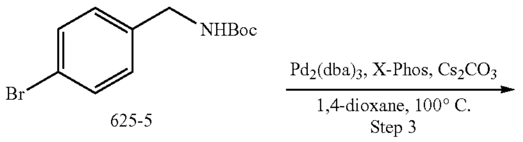

-continued

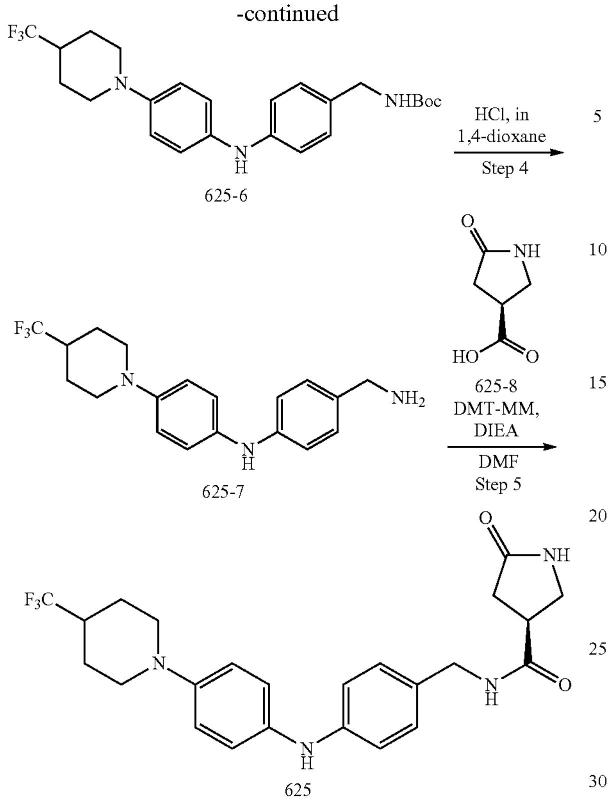

Step 1. Preparation of 1-(4-nitrophenyl)-4-(trifluoromethyl)piperidine (625-3). A solution of 1-fluoro-4-nitrobenzene (1.41 g, 10.0 mmol), 4-(trifluoromethyl)piperidine (1.99 g, 13.0 mmol) and $Cs_2CO_3$ (6.51 g, 20.0 mmol) in DMSO (50 mL) was stirred for 18 hours at r.t. After cooling to rt. 200 mL of water was added dropwise. The resulting solution was extracted with 3×100 mL of ethyl acetate. The organic layers were combined, washed with water (3×150 mL), dried and concentrated under vacuum. The residue was purified by flash column chromatography (EA/PE-1/10) to afford the desired product as a yellow solid (2.10 g, 76.6%). Mass (m/z): 275.1 $[M+H]^+$.

Step 2. Preparation of 4-(4-(trifluoromethyl)piperidin-1-yl)aniline (625-4). To a solution of 1-(4-nitrophenyl)-4-(trifluoromethyl)piperidine (1.37 g, 5.0 mmol) in EtOH (50 mL) was added 10% Pd/C (53 mg, 5.0 umol). Then the reaction was stirred overnight at rt under an atmosphere of Hydrogen. Pd/C was filtrated out. The PH of the filtration was adjusted to 8-9 with sodium carbonate solution. Then the mixture was extracted by DCM (100 mL×3). The combined organic layers were washed with brine (100 mL×3), dried over $Na_2SO_4$ and concentrated to give the desired product as yellow solid (1.04 g, 85.2%). Mass (m/z): 245.2 $[M+H]^+$.

Step 3. Preparation of tert-butyl (4-((4-(4-(trifluoromethyl)piperidin-1-yl)phenyl)amino)benzyl)carbamate (625-6). A mixture of 4-(4-(trifluoromethyl)piperidin-1-yl)aniline (878 mg, 3.6 mmol), tert-butyl (4-bromobenzyl)carbamate (858 mg, 3.0 mmol), Pd2(dba)$_3$ (27.5 mg, 0.03 mmol), X-Phos (71.55 mg, 0.15 mmol). $Cs_2CO_3$ (1.47 g, 4.5 mmol) in 1,4-dioxane (30 mL) was stirred overnight at 100° C. After cooling to rt. 100 mL of water was added. Then the mixture was extracted by DCM (100 mL×3). The combined organic layers were washed with water (100 mL×3), dried over $Na_2SO_4$ and concentrated under vacuum. The residue was purified by flash column chromatography (EA/PE=1/2) to give the desired product as yellow solid (1.03 g, 76.3%). Mass (m/z): 450.3 $[M+H]^+$.

Step 4. Preparation of 4-(aminomethyl)-N-(4-(4-(trifluoromethyl)piperidin-1-yl)phenyl)aniline (625-7). A solution of tert-butyl (4-((4-(4-(trifluoromethyl)piperidin-1-yl)phenyl)amino)benzyl)carbamate (1.03 g, 2.28 mmol) in 10 mL of a solution of HCl in 1,4-dioxane was stirred for 30 mins at rt and concentrated. 5 ml water was added. The PH of the filtration was adjusted to 8-9 with sodium carbonate solution. Then the mixture was extracted by DCM (10 mL×3). The combined organic layers were washed with water (20 mL), dried over Na2SO4 and concentrated. The residue was purified by perp-TLC (MeOH/DCM=1/10) to afford the desired product as a yellow solid. Mass (m/z): 350.2 [M+H]

Step 5. Preparation of (S)-5-oxo-N-(4-((4-(4-(trifluoromethyl)piperidin-1-yl)phenyl)amino)benzyl)pyrrolidine-3-carboxamide (625). To a solution of 4-(aminomethyl)-N-(4-(4-(trifluoromethyl)piperidin-1-yl)phenyl)aniline (146.6 mg, 0.42 mmol) and 2-(4-methylpiperazin-1-yl)acetic acid (64.5 mg, 0.5 mmol) in DMF (2 mL) was added DIEA (0.023 mL, 1.26 mmol). Followed by the addition of DMT-MM (147.4 mg, 0.5 mmol) then the reaction mixture was stirred for 3 hours at rt. 20 ml of water was added. Then the mixture was extracted by DCM (10 mL×3). The combined organic layers were washed with water (10 mL×3), dried over Na2SO4 and concentrated under vacuum. The residue was purified by prep-TLC (MeOH/DCM=1/10) to give the desired product as yellow solid (135 mg, 70.0%). 1H NMR (400 MHz, Methanol-$d_4$) δ 7.11 (d, J=8.4 Hz, 2H), 7.02 (d, J=8.4 Hz, 2H), 6.99-6.88 (m, 4H), 4.26 (s, 2H), 3.68-3.43 (m, 4H), 3.28 (m, 1H), 2.73-2.43 (m, 4H), 2.31 (m, 1H), 2.01-1.92 (m, 2H), 1.79-1.65 (m, 2H). Mass (m/z): 461.2 $[M+H]^+$.

N-(2-(dimethylamino)ethyl)-1-ethyl-N-(4-((4-(4-methylpiperidin-1-yl)phenyl)amino)benzyl)-5-oxopyrrolidine-3-carboxamide (626)

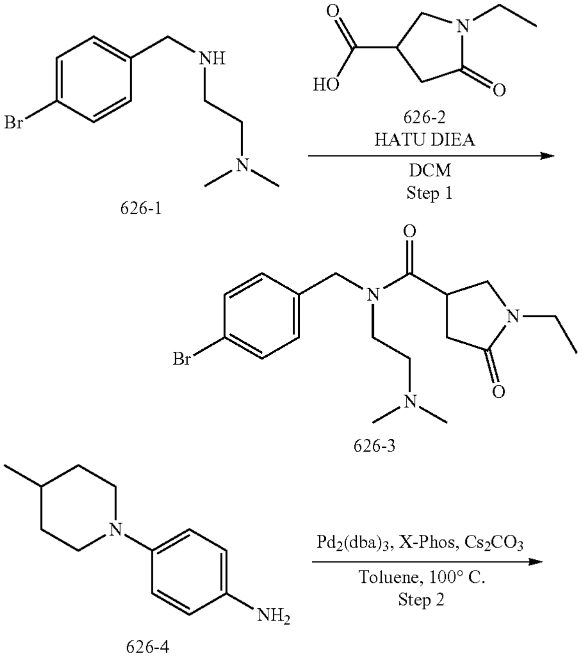

-continued

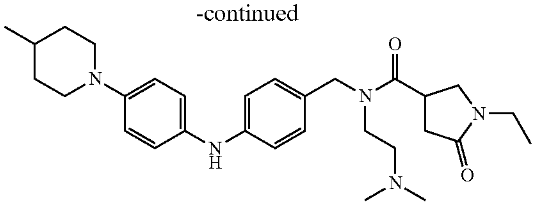

626

Step 1. Preparation of N-(4-bromobenzyl)-N-(2-(dimethylamino)ethyl)-1-ethyl-5-oxopyrrolidine-3-carboxamide (626-3). The title compound (626-3) was prepared in a total yield of 82.8% as a white solid from N1-(4-bromobenzyl)-N2,N2-dimethylethane-1,2-diamine (288 mg, 1.12 mmol), 1-ethyl-5-oxopyrrolidine-3-carboxylic acid (229 mg, 1.46 mmol), DIEA (0.293 mL, 1.68 mmol) and HATU (554 mg, 1.46 mmol) according to the procedure for 625.

Mass (m/z): 396.1 [M+H]$^+$.

Step 2. Preparation of N-(2-(dimethylamino)ethyl)-1-ethyl-N-(4-((4-(4-methylpiperidin-1-yl)phenyl)amino)benzyl)-5-oxopyrrolidine-3-carboxamide (626). The title compound 626 (16.4 mg) was prepared in a total yield of 32.4% as a white solid from N-(4-bromobenzyl)-N-(2-(dimethylamino)ethyl)-1-ethyl-5-oxopyrrolidine-3-carboxamide (39.6 mg, 0.1 mmol), 4-(4-methylpiperidin-1-yl)aniline (25 mg, 0.13 mmol), Pd2(dba)$_3$ (1.83 mg, 2 umol), X-Phos (1.91 mg, 4 umol), $Cs_2CO_3$ (48.8 mg, 0.15 mmol) according to the procedure for 625-3. $^1$H NMR (400 MHz, Methanol-d$_4$) δ 7.28-6.91 (m, 8H), 4.60 (s, 2H), 3.78-3.44 (m, 6H), 3.37 (m, 1H), 3.25-3.08 (m, 4H), 2.97 (s, 6H), 2.70-2.58 (m, 2H), 2.39-2.28 (m, 2H), 1.96-1.83 (m, 2H), 1.78 (m, 1H), 1.65-1.50 (m, 2H), 0.99 (d, J=6.4 Hz, 3H), 0.87 (t, J=6.8 Hz, 3H). Mass (m/z): 506.3 [M+H]$^+$.

1-acetyl-N-(4-((4-(4-(trifluoromethyl)piperidin-1-yl) phenyl)amino)benzyl)pyrrolidine-3-carboxamide (627)

627

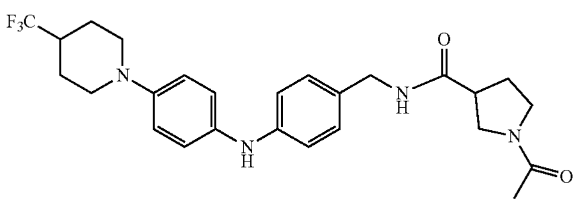

The title compound 627 (12.8 mg) was prepared in a total yield of 52.1% as a wheat powder from 4-(aminomethyl)-N-(4-(4-(trifluoromethyl)piperidin-1-yl)phenyl)aniline (17.5 mg, 0.05 mmol), 1-acetylpyrrolidine-3-carboxylic acid (10.2 mg, 0.065 mmol), DIEA (19 mg, 0.15 mmol) and HATU (25 mg, 0.065 mmol) according to the procedure for compound 625. $^1$H NMR (400 MHz, Methanol-d$_4$) δ 7.14-6.91 (m, 8H), 4.26 (s, 2H), 4.03-3.83 (m, 2H), 3.79-3.66 (m, 2H), 3.57-3.43 (m, 2H), 3.36 (m, 1H), 2.99-2.78 (m, 2H), 2.26 (s, 3H), 2.41 (m, 1H), 1.97-1.71 (m, 4H), 1.66-1.51 (m, 2H). Mass (m/z): 489.3 [M+H]$^+$.

1-(cyclopropanecarbonyl)-N-(4-((4-(4-(trifluoromethyl)piperidin-1-yl)phenyl)amino)benzyl)pyrrolidine-3-carboxamide (628)

628

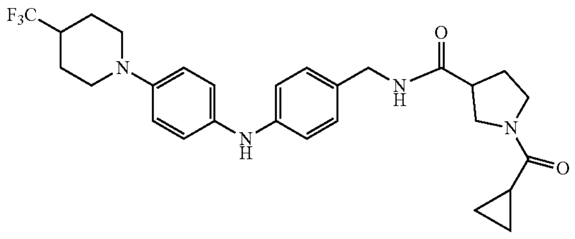

The title compound 628 (12.3 mg) was prepared in a total yield of 47.6% as a wheat powder from 4-(aminomethyl)-N-(4-(4-(trifluoromethyl)piperidin-1-yl)phenyl)aniline (17.5 mg, 0.05 mmol), 1-(cyclopropanecarbonyl)pyrrolidine-3-carboxylic acid (11.9 mg, 0.065 mmol), DIEA (19 mg, 0.15 mmol) and HATU (25 mg, 0.065 mmol) according to the procedure for compound 625. $^1$H NMR (400 MHz, Methanol-d$_4$) δ 7.15-6.88 (m, 8H), 4.28 (s, 2H), 4.05-3.69 (m, 4H), 3.59-3.44 (m, 2H), 3.35 (m, 1H), 2.97-2.78 (m, 2H), 2.42 (m, 1H), 2.11-1.98 (m, 2H), 1.97-1.71 (m, 4H), 1.66-1.51 (m, 2H), 0.89-0.75 (m, 4H). Mass (m/z): 515.2 [M+H]$^+$.

1-acetyl-N-(4-((4-(4-(trifluoromethyl)piperidin-1-yl) phenyl)amino)benzyl)azetidine-3-carboxamide (629)

629

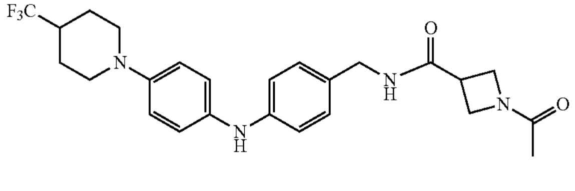

The title compound 629 (12.0 mg) was prepared in a total yield of 50.5% as a wheat powder from 4-(aminomethyl)-N-(4-(4-(trifluoromethyl)piperidin-1-yl)phenyl)aniline (17.5 mg, 0.05 mmol), 1-acetylazetidine-3-carboxylic acid (9.3 mg, 0.065 mmol), DIEA (19 mg, 0.15 mmol) and HATU (25 mg, 0.065 mmol) according to the procedure for compound 625. $^1$H NMR (400 MHz, Methanol-d$_4$) δ 7.14-6.87 (m, 8H), 4.39-4.23 (m, 4H), 4.17-3.99 (m, 2H), 3.54-3.67 (m, 2H), 3.39 (m, 1H), 2.76-2.54 (m, 2H), 2.27 (m, 1H), 2.04-1.94 (m, 2H), 1.86 (s, 3H), 1.79-1.65 (m, 2H). Mass (m/z): 475.2 [M+H]$^+$.

1-(cyclopropanecarbonyl)-N-(4-((4-(4-(trifluoromethyl)piperidin-1-yl)phenyl)amino)benzyl)azetidine-3-carboxamide (630)

630

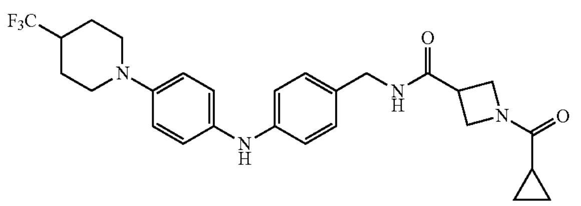

The title compound 630 (14.4 mg) was prepared in a total yield of 57.5% as a wheat powder from 4-(aminomethyl)-N-(4-(4-(trifluoromethyl)piperidin-1-yl)phenyl)aniline (17.5 mg, 0.05 mmol), 1-(cyclopropanecarbonyl)azetidine-3-carboxylic acid (11.0 mg, 0.065 mmol), DIEA (19 mg, 0.15 mmol) and HATU (25 mg, 0.065 mmol) according to the procedure for compound 625. $^1$H NMR (400 MHz, Methanol-$d_4$) δ 7.14-7.06 (m, 8H), 4.23 (s, 2H), 4.13-4.04 (m, 4H), 3.51-3.41 (m, 2H), 2.79-2.55 (m, 2H), 2.21 (m, 1H), 2.13-2.03 (m, 2H), 1.97-1.71 (m, 2H), 1.64-1.46 (m, 2H), 0.89-0.78 (m, 4H). Mass (m/z): 501.3 $[M+H]^+$.

1,1-dimethyl-3-(4-((4-(4-(trifluoromethyl)piperidin-1-yl)phenyl)amino)benzyl)urea (631)

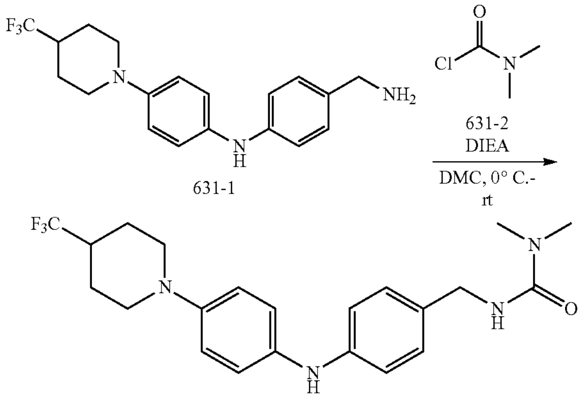

631-1

631

To a solution of 4-(aminomethyl)-N-(4-(4-(trifluoromethyl)piperidin-1-yl)phenyl)aniline (34.9 mg, 0.1 mmol) and DIEA (39.0 mg, 0.3 mmol) in DCM (2 ml) was added dropwise dimethylcarbamic chloride (12.8 mg, 0.12 mmol) at 0° C. Then the reaction was stirred for 2 hours at rt. The reaction solution was concentrated and purified by prep-TLC (MeOH/DCM=1/10) to give the desired product as yellow solid (21.0 mg, 49.9%). $^1$H NMR (400 MHz, Methanol-$d_4$) δ 7.15-7.08 (d, J=8.1 Hz, 2H), 7.06-6.82 (m, 6H), 4.24 (s, 2H), 3.70-3.52 (m, 2H), 2.91 (s, 6H), 2.56-2.78 (m, 2H), 2.27 (m, 1H), 2.03-1.93 (m, 2H), 1.79-1.64 (m, 2H). Mass (m/z): 421.3 $[M+H]^+$.

1-acetyl-N-(4-((4-(4-methylpiperidin-1-yl)phenyl)amino)benzyl)pyrrolidine-3-carboxamide (632)

632

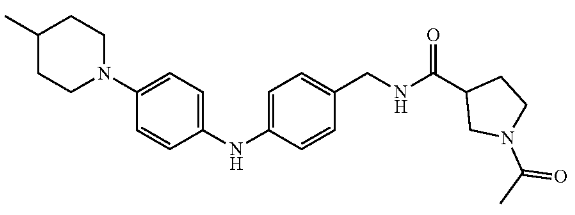

The title compound 632 (7.0 mg) was prepared in a total yield of 32.1% as a wheat powder from 4-(aminomethyl)-N-(4-(4-methylpiperidin-1-yl)phenyl)aniline (14.8 mg, 0.05 mmol), 1-acetylpyrrolidine-3-carboxylic acid (10.2 mg, 0.065 mmol), DIEA (19 mg, 0.15 mmol) and HATU (25 mg, 0.065 mmol) according to the procedure for compound 625. $^1$H NMR (400 MHz, Methanol-$d_4$) δ 7.43-6.87 (m, 8H), 4.34 (s, 2H), 4.01-3.68 (m, 4H), 3.58-3.43 (m, 2H), 3.38 (m, 1H), 3.20-2.98 (m, 2H), 2.21 (s, 3H), 2.11-1.99 (m, 2H), 1.91-1.58 (m, 5H), 1.04 (d, J=6.4 Hz, 311). Mass (m/z): 435.3 $[M+H]^4$.

1-(cyclopropanecarbonyl)-N-(4-((4-(4-methylpiperidin-1-yl)phenyl)amino)benzyl)pyrrolidine-3-carboxamide (633)

633

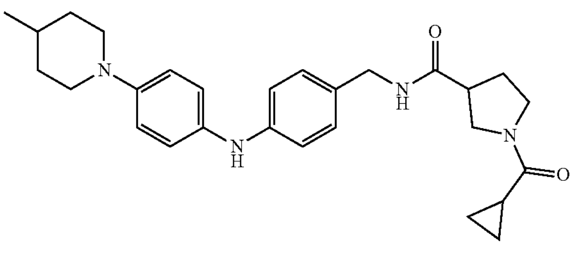

The title compound 633 (12.2 mg) was prepared in a total yield of 52.9% as a lightskyblue solid from 4-(aminomethyl)-N-(4-(4-methylpiperidin-1-yl)phenyl)aniline (14.8 mg, 0.05 mmol), 1-(cyclopropanecarbonyl)pyrrolidine-3-carboxylic acid (11.9 mg, 0.065 mmol), DIEA (19 mg, 0.15 mmol) and HATU (25 mg, 0.065 mmol) according to the procedure for compound 625. $^1$H NMR (400 MHz, Methanol-$d_4$) δ 7.46 (d, J=8.0 Hz, 2H), 7.32-7.04 (m, 6H), 4.33 (s, 2H), 4.01-3.79 (m, 2H), 3.75-3.50 (m, 6H), 3.20-2.98 (m, 2H), 2.28-2.16 (m, 1H), 2.10-1.98 (m, 2H), 1.90-1.59 (m, 4H), 1.09 (d, J=6.4 Hz, 3H), 0.91-0.76 (m, 4H). Mass (m/z): 461.3 $[M+H]^+$.

1-acetyl-N-(4-((4-(4-methylpiperidin-1-yl)phenyl)amino)benzyl)azetidine-3-carboxamide (634)

634

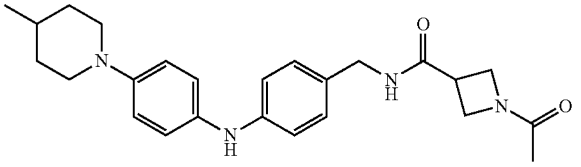

The title compound 634 (8.1 mg) was prepared in a total yield of 38.5% as a Darkgray solid r from 4-(aminomethyl)-N-(4-(4-methylpiperidin-1-yl)phenyl)aniline (14.8 mg, 0.05 mmol), 1-acetylazetidine-3-carboxylic acid (9.3 mg, 0.065 mmol), DIEA (19 mg, 0.15 mmol) and HATU (25 mg, 0.065 mmol) according to the procedure for compound 625. $^1$H NMR (400 MHz, Methanol-$d_4$) δ 7.46 (d, J=8.4 Hz, 2H), 7.23 (d, J=8.4 Hz, 2H), 7.17-7.08 (m, 4H), 4.43-4.26 (m, 4H), 4.18-3.99 (m, 2H), 3.61 (m, 1H), 3.59 (s, 3H), 2.10-2.00 (m, 2H), 1.93-1.83 (m, 3H), 1.74-1.62 (m, 2H), 1.09 (d, J=6.4 Hz, 3H). Mass (m/z): 421.3 $[M+H]^+$.

1-(cyclopropanecarbonyl)-N-(4-((4-(4-methylpiperidin-1-yl)phenyl)amino)benzyl)azetidine-3-carboxamide (635)

635

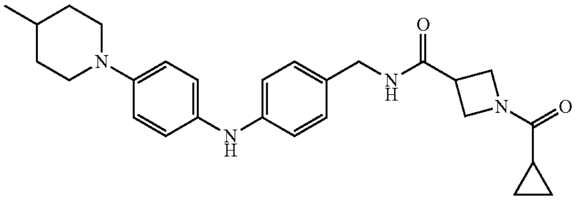

The title compound 635 (15.4 mg) was prepared in a total yield of 68.9% as a Darkgray solid r from 4-(aminomethyl)-N-(4-(4-methylpiperidin-1-yl)phenyl)aniline (14.8 mg, 0.05 mmol), 1-(cyclopropanecarbonyl)azetidine-3-carboxylic acid (11.0 mg, 0.065 mmol), DIEA (19 mg, 0.15 mmol) and HATU (25 mg, 0.065 mmol) according to the procedure for compound 625. $^1$H NMR (400 MHz, Methanol-$d_4$) δ 7.46 (d, J=8.0 Hz, 2H), 7.35-7.06 (m, 6H), 4.51-4.40 (m, 4H), 4.13-4.04 (m, 6H), 3.51-3.41 (m, 2H), 2.21 (m, 1H), 2.11-2.01 (m, 2H), 1.64-1.48 (m, 2H), 1.07 (d, J=6.4 Hz, 3H), 0.89-0.78 (m, 4H). Mass (m/z): 447.3 $[M+H]^+$.

4-oxo-4-(pyrrolidin-1-yl)-N-(4-((4-(4-(trifluoromethyl)piperidin-1-yl)phenyl)amino)benzyl)butanamide (636)

636

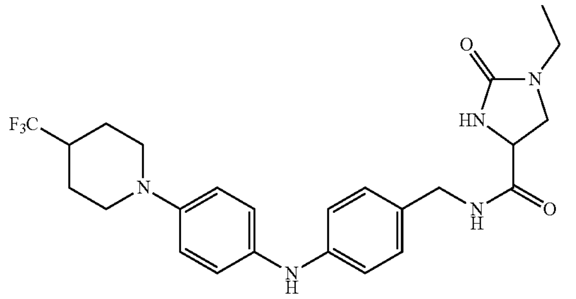

The title compound 636 (8.0 mg) was prepared in a total yield of 32.7% as a white solid from 4-(aminomethyl)-N-(4-(4-(trifluoromethyl)piperidin-1-yl)phenyl)aniline (17.5 mg, 0.05 mmol), 1-ethyl-2-oxoimidazolidine-4-carboxylic acid (10.3 mg, 0.065 mmol), DIEA (19 mg, 0.15 mmol) and HATU (25 mg, 0.065 mmol) according to the procedure for compound 625. $^1$H NMR (400 MHz, Methanol-$d_4$) δ 7.38-6.64 (m, 8H), 4.38-4.21 (m, 3H), 3.66-3.38 (m, 6H), 3.07-2.88 (m, 2H), 2.26 (m, 11H), 2.04-1.92 (m, 2H), 1.78-1.65 (m, 2H), 1.05 (t, J=7.2 Hz, 3H). Mass (m/z): 490.3 $[M+H]^+$.

5-oxo-1-propyl-N-(4-((4-(4-(trifluoromethyl)piperidin-1-yl)phenyl)amino)benzyl)pyrrolidine-3-carboxamide (637)

637

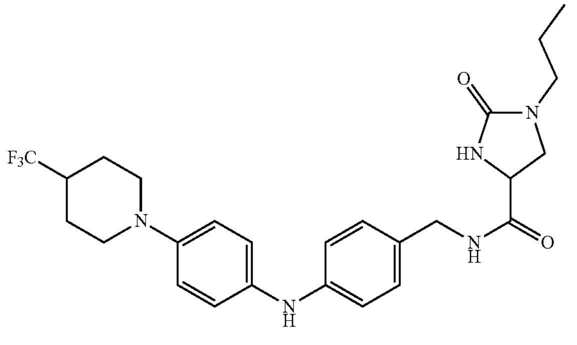

The title compound 637 (12.8 mg) was prepared in a total yield of 49.3% as a darkgray solid from 4-(aminomethyl)-N-(4-(4-(trifluoromethyl)piperidin-1-yl)phenyl)aniline (17.5 mg, 0.05 mmol), 5-oxo-1-propylpyrrolidine-3-carboxylic acid (11.1 mg, 0.065 mmol), DIEA (19 mg, 0.15 mmol) and HATU (25 mg, 0.065 mmol) according to the procedure for compound 625. $^1$H NMR (400 MHz, Methanol-$d_4$) δ 7.45-6.65 (m, 8H), 4.26 (s, 2H), 3.79-3.49 (m, 4H), 3.28-3.12 (m, 5H), 2.65-2.52 (m, 2H), 2.25 (s, 2H), 2.05-1.87 (m, 2H), 1.79-1.63 (m, 2H), 1.55 (m, 2H), 0.89 (t, J=7.2 Hz, 3H). Mass (m/z): 503.2 $[M+H]^+$.

N-(4-((4-(4-methylpiperidin-1-yl)phenyl)amino) benzyl)-5-oxo-1-propylpyrrolidine-3-carboxamide (638)

638

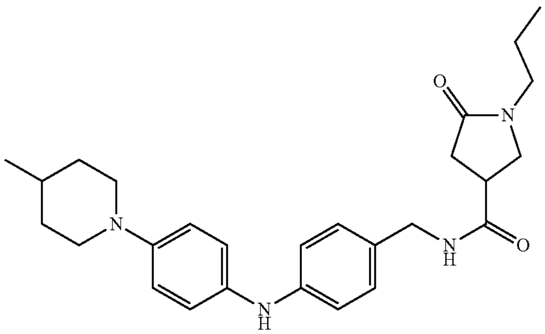

The title compound 638 (10.2 mg) was prepared in a total yield of 45.4% as a burlywood solid from 4-(aminomethyl)-N-(4-(4-methylpiperidin-1-yl)phenyl)aniline (14.8 mg, 0.05 mmol), 5-oxo-1-propylpyrrolidine-3-carboxylic acid (11.1 mg, 0.065 mmol), DIEA (19 mg, 0.15 mmol) and HATU (25 mg, 0.065 mmol) according to the procedure for compound 625. $^1$H NMR (400 MHz, Methanol-$d_4$) δ 7.46-6.71 (m, 8H), 4.28 (s, 2H), 3.76-3.47 (m, 4H), 3.28-3.13 (m, 5H), 2.65-2.54 (m, 2H), 1.78 (m, 2H), 1.62-1.48 (m, 3H), 1.38-1.33 (m, 2H), 0.99 (d, J=6.0 Hz, 3H), 0.89 (t, J=7.2 Hz, 3H). Mass (m/z): 449.3 $[M+H]^+$.

1-ethyl-N-(4-((4-(4-methylpiperidin-1-yl)phenyl) amino)benzyl)-2-oxoimidazolidine-4-carboxamide (639)

639

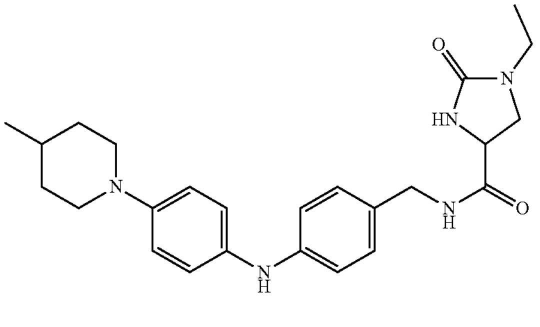

The title compound 639 (18.1 mg) was prepared in a total yield of 82.9% as a white solid from 4-(aminomethyl)-N-(4-(4-methylpiperidin-1-yl)phenyl)aniline (14.8 mg, 0.05 mmol), 1-ethyl-2-oxoimidazolidine-4-carboxylic acid (10.3 mg, 0.065 mmol), DIEA (19 mg, 0.15 mmol) and HATU (25 mg, 0.065 mmol) according to the procedure for compound 625. $^1$H NMR (400 MHz, Chloroform-d) δ 7.48-6.67 (m, 8H), 4.14 (s, 2H), 3.70-3.62 (m, 2H), 3.32-3.22 (m, 2H), 3.06 (m, 1H), 2.96-2.84 (m, 4H), 1.58-1.27 (m, 5H), 1.00 (d, J=6.0 Hz, 3H), 0.93 (t, J=7.2 Hz, 3H). Mass (m/z): 436.4 $[M+H]^+$.

1-methyl-N-(4-((4-(4-(trifluoromethyl)piperidin-1-yl)phenyl)amino)benzyl)azetidine-3-carboxamide (640)

640

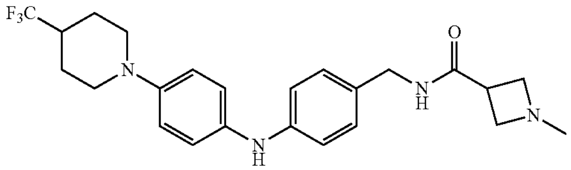

The title compound 640 (9.6 mg) was prepared in a total yield of 43.0% as a white solid from 4-(aminomethyl)-N-(4-(4-(trifluoromethyl)piperidin-1-yl)phenyl)aniline (17.5 mg, 0.05 mmol), 1-methylazetidine-3-carboxylic acid (7.5 mg, 0.065 mmol), DIEA (19 mg, 0.15 mmol) and HATU (25 mg, 0.065 mmol) according to the procedure for compound 625. $^1$H NMR (400 MHz, Methanol-$d_4$) δ 7.50-6.70 (m, 8H), 4.37-4.15 (m, 6H), 3.65-3.52 (m, 5H), 2.93 (s, 3H), 2.29 (m, 1H), 2.12-1.90 (m, 2H), 1.82-1.62 (m, 2H). Mass (m/z): 447.2 $[M+H]^+$.

1-methyl-N-(4-((4-(4-(trifluoromethyl)piperidin-1-yl)phenyl)amino)benzyl)pyrrolidine-3-carboxamide (641)

641

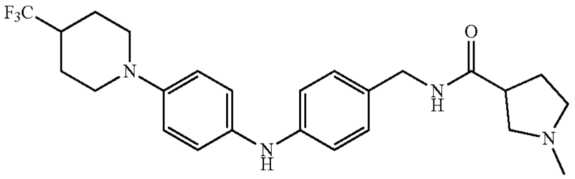

The title compound 641 (10.5 mg) was prepared in a total yield of 45.6% as a lightgray solid from 4-(aminomethyl)-N-(4-(4-(trifluoromethyl)piperidin-1-yl)phenyl)aniline (17.5 mg, 0.05 mmol), 1-methylpyrrolidine-3-carboxylic acid (8.4 mg, 0.065 mmol), DIEA (19 mg, 0.15 mmol) and HATU (25 mg, 0.065 mmol) according to the procedure for compound 625.1H NMR (400 MHz, Methanol-$d_4$) δ 7.55-6.75 (m, 8H), 4.29 (s, 2H), 3.80-3.55 (m, 3H), 3.51-3.35 (m, 4H), 3.29-3.20 (m, 2H), 2.95 (s, 3H), 2.44 (m, 1H), 2.30 (m, 1H), 2.18 (m, 1H), 2.10-1.86 (m, 2H), 1.79-1.58 (m, 2H). Mass (m/z): 461.3 $[M+H]^+$.

N-(4-((4-(4-(trifluoromethyl)piperidin-1-yl)phenyl) amino)benzyl)pyrrolidine-3-carboxamide (642)

642

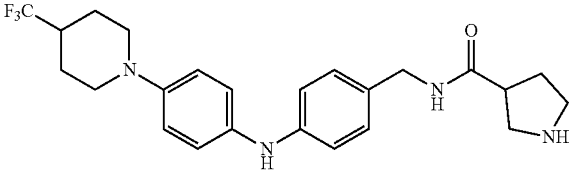

The title compound 642 (13.1 mg) was prepared in a total yield of 58.6% as a lightgray solid from 4-(aminomethyl)-N-(4-(4-(trifluoromethyl)piperidin-1-yl)phenyl)aniline (17.5 mg, 0.05 mmol), pyrrolidine-3-carboxylic acid (7.5 mg, 0.065 mmol), DIEA (19 mg, 0.15 mmol) and HATU (25 mg, 0.065 mmol) according to the procedure for compound 625.1H NMR (400 MHz, Methanol-$d_4$) δ 7.65-7.53 (m, 2H), 7.24 (d, J=8.4 Hz, 2H), 7.19-7.04 (m, 4H), 4.33 (s, 2H), 3.86-3.62 (m, 4H), 3.54-3.21 (m, 5H), 2.70 (m, 1H), 2.41-2.09 (m, 6H). Mass (m/z): 447.3 $[M+H]^+$.

N-(4-((4-(4-(trifluoromethyl)piperidin-1-yl)phenyl)amino)benzyl)azetidine-3-carboxamide (643)

643

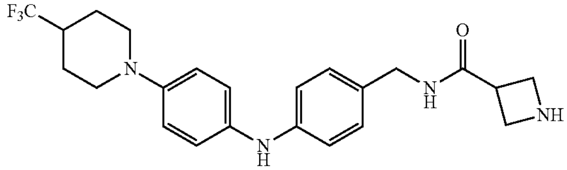

The title compound 643 (6.2 mg) was prepared in a total yield of 28.6% as a sandybrown solid from 4-(aminomethyl)-N-(4-(4-(trifluoromethyl)piperidin-1-yl)phenyl)aniline (17.5 mg, 0.05 mmol), azetidine-3-carboxylic acid (6.5 mg, 0.065 mmol), DIEA (19 mg, 0.15 mmol) and HATU (25 mg, 0.065 mmol) according to the procedure for compound 625. $^1$H NMR (400 MHz, Methanol-$d_4$) δ 7.58 (d, J=8.4 Hz, 2H), 7.24 (d, J=8.4 Hz, 2H), 7.14 (d, J=8.4 Hz, 2H), 7.11 (d, J=8.4 Hz, 2H), 4.34 (s, 2H), 4.25 (m, 4H), 3.81-3.68 (m, 5H), 2.83 (m, 1H), 2.32-2.15 (m, 4H). Mass (m/z): 433.2 $[M+H]^+$.

N-(4-((4-(4-(trifluoromethyl)piperidin-1-yl)phenyl)amino)benzyl)nicotinamide (644)

644

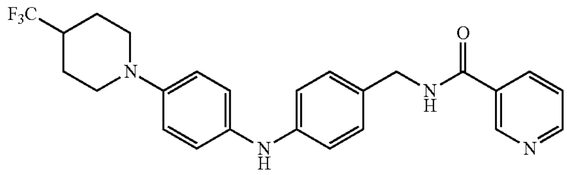

The title compound 644 (16.8 mg) was prepared in a total yield of 73.8% as a light green solid from 4-(aminomethyl)-N-(4-(4-(trifluoromethyl)piperidin-1-yl)phenyl)aniline (17.5 mg, 0.05 mmol), nicotinic acid (8.0 mg, 0.065 mmol), DIEA (19 mg, 0.15 mmol) and HATU (25 mg, 0.065 mmol) according to the procedure for compound 625. $^1$H NMR (400 MHz, Methanol-$d_4$) δ 8.98 (s, 1H), 8.67 (m, 1H), 8.25 (m, 1H), 7.59-7.50 (m, 1H), 7.28-6.84 (m, 8H), 4.48 (s, 2H), 3.84-3.45 (m, 2H), 2.91-2.41 (m, 2H), 2.26 (m, 1H), 2.10-1.91 (m, 2H), 1.80-1.63 (m, 2H). Mass (m/z): 455.3 $[M+H]^+$.

N-(4-((4-(4-(trifluoromethyl)piperidin-1-yl)phenyl)amino)benzyl)pyrrolidine-1-carboxamide (645)

645

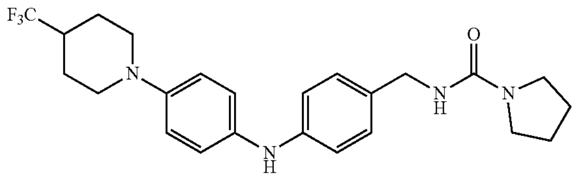

The title compound 645 (9.2 mg) was prepared in a total yield of 41.2% as a white powder from 4-(aminomethyl)-N-(4-(4-(trifluoromethyl)piperidin-1-yl)phenyl)aniline (17.5 mg, 0.05 mmol), pyrrolidine-1-carbonyl chloride (8.0 mg, 0.06 mmol), and DIEA (19 mg, 0.15 mmol) according to the procedure for compound 631. $^1$H NMR (400 MHz, Methanol-$d_4$) δ 7.45-6.65 (m, 811), 4.24 (s, 2H), 3.83-3.45 (m, 2H), 3.39-3.32 (m, 4H), 2.83-2.54 (m, 2H), 2.27 (m, 1H), 2.06-1.84 (m, 6H), 1.78-1.65 (m, 2H). Mass (m/z): 447.2 $[M+H]^+$.

6-chloro-N-(4-((4-(4-(trifluoromethyl)piperidin-1-yl)phenyl)amino)benzyl)pyrazine-2-carboxamide (646)

646

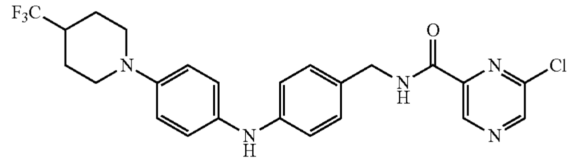

The title compound 646 (23.1 mg) was prepared in a total yield of 95.5% as a white solid from 4-(aminomethyl)-N-(4-(4-(trifluoromethyl)piperidin-1-yl)phenyl)aniline (17.5 mg, 0.05 mmol), 6-chloropyrazine-2-carboxylic acid (10.3 mg, 0.065 mmol), DIEA (19 mg, 0.15 mmol) and HATU (25 mg, 0.065 mmol) according to the procedure for compound 625. $^1$H NMR (400 MHz, Methanol-$d_4$) δ 9.16 (s, 1H), 8.83 (s, 1H), 7.32-6.67 (m, 8H), 4.48 (s, 2H), 3.81-3.46 (m, 2H), 2.91-2.42 (m, 2H), 2.25 (m, 1H), 2.02-1.88 (m, 2H), 1.78-1.62 (m, 2H). Mass (n/z): 490.2 $[M+H]^+$.

2-methyl-5-oxo-N-(4-((4-(4-(trifluoromethyl)piperidin-1-yl)phenyl)amino)benzyl)pyrrolidine-3-carboxamide (647)

647

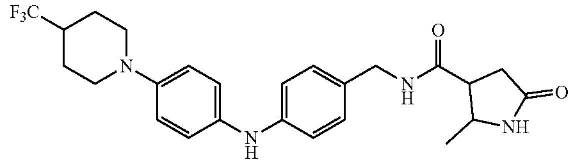

The title compound 647 (14.3 mg) was prepared in a total yield of 60.2% as a wheat powder from 4-(aminomethyl)-N-(4-(4-(trifluoromethyl)piperidin-1-yl)phenyl)aniline (17.5 mg, 0.05 mmol), 2-methyl-5-oxopyrrolidine-3-carboxylic acid (9.3 mg, 0.065 mmol), DIEA (19 mg, 0.15 mmol) and HATU (25 mg, 0.065 mmol) according to the procedure for compound 625. $^1$H NMR (400 MHz, Methanol-$d_4$) δ 7.56-6.65 (m, 8H), 4.27 (s, 2H), 3.93-3.77 (m, 2H), 3.72 (m, 1H), 3.22 (m, 1H), 2.77 (m, 1H), 2.73-2.44 (m, 2H), 2.27 (m, 1H), 2.07-1.85 (m, 2H), 1.81-1.65 (m, 2H), 1.25 (d, J=6.4 Hz, 3H). Mass (m/z): 475.3 [M+H]$^+$.

2-methyl-5-oxo-N-(4-((4-(4-(trifluoromethyl)piperidin-1-yl)phenyl)amino)benzyl)pyrrolidine-3-carboxamide (648)

648

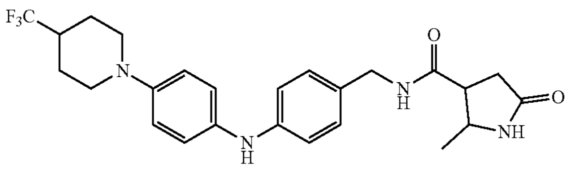

The title compound 648 (9.2 mg) was prepared in a total yield of 38.7% as a wheat powder from 4-(aminomethyl)-N-(4-(4-(trifluoromethyl)piperidin-1-yl)phenyl)aniline (17.5 mg, 0.05 mmol), 2-methyl-5-oxopyrrolidine-3-carboxylic acid (9.3 mg, 0.065 mmol), DIEA (19 mg, 0.15 mmol) and HATU (25 mg, 0.065 mmol) according to the procedure for compound 625. $^1$H NMR (400 MHz, Methanol-$d_4$) δ 7.51-6.64 (m, 8H), 4.27 (s, 2H), 4.02-3.95 (m, 2H), 3.77-3.68 (m, 1H), 3.23 (m, 1H), 2.74 (m, 1H), 2.42-2.33 (m, 2H), 2.30 (m, 1H), 2.08-1.87 (m, 2H), 1.83-1.71 (m, 2H), 1.09 (d, J=6.4 Hz, 3H). Mass (m/z): 475.3 [M+H]$^+$.

3-oxo-N-(4-((4-(4-(trifluoromethyl)piperidin-1-yl)phenyl)amino)benzyl)tetrahydro-1H-pyrrolizine-7a(5H)-carboxamide (649)

649

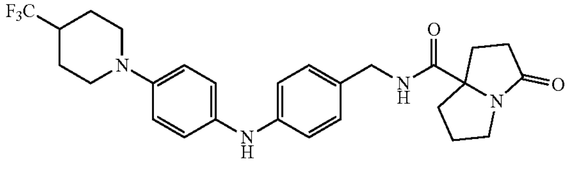

The title compound 649 (16.1 mg) was prepared in a total yield of 64.2% as a white powder from 4-(aminomethyl)-N-(4-(4-(trifluoromethyl)piperidin-1-yl)phenyl)aniline (17.5 mg, 0.05 mmol), 3-oxotetrahydro-1H-pyrrolizine-7a(5H)-carboxylic acid (10.9 mg, 0.065 mmol), DIEA (19 mg, 0.15 mmol) and HATU (25 mg, 0.065 mmol) according to the procedure for compound 625. $^1$H NMR (400 MHz, Methanol-$d_4$) δ 7.52-6.71 (m, 8H), 4.31 (s, 2H), 3.63-3.53 (m, 2H), 3.19-3.06 (m, 2H), 2.82-2.62 (m, 2H), 2.51-2.32 (m, 6H), 2.18 (m, 1H), 2.12-2.01 (m, 2H), 1.93-1.83 (m, 2H), 1.74-1.65 (m, 2H). Mass (m/z): 501.2 [M+H]$^+$.

2-oxo-N-(4-((4-(4-(trifluoromethyl)piperidin-1-yl)phenyl)amino)benzyl)Imidazolidine-4-carboxamide (650)

650

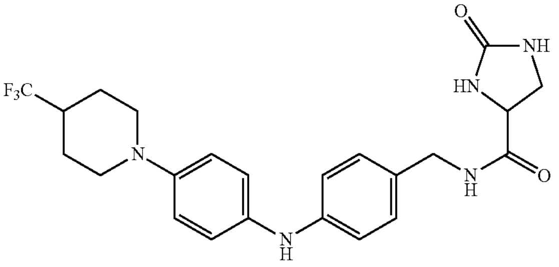

The title compound 650 (10.1 mg) was prepared in a total yield of 43.8% as a white powder from 4-(aminomethyl)-N-(4-(4-(trifluoromethyl)piperidin-1-yl)phenyl)aniline (17.5 mg, 0.05 mmol), 2-oxoimidazolidine-4-carboxylic acid (8.4 mg, 0.065 mmol), DIEA (19 mg, 0.15 mmol) and HATU (25 mg, 0.065 mmol) according to the procedure for compound 625. $^1$H NMR (400 MHz, DMSO-$d_6$) δ 7.35-6.66 (m, 8H), 4.17 (s, 2H), 4.12-4.06 (m, 1H), 3.82-3.46 (m, 2H), 3.26-3.05 (m, 2H), 2.78-2.54 (m, 2H), 2.42 (m, 1H), 1.94-1.76 (m, 2H), 1.67-1.47 (m, 2H). Mass (m/z): 462.2 [M+H]$^+$.

2-oxo-N-(4-((4-(4-(trifluoromethyl)piperidin-1-yl)phenyl)amino)benzyl)pyrrolidine-3-carboxamide (651)

651

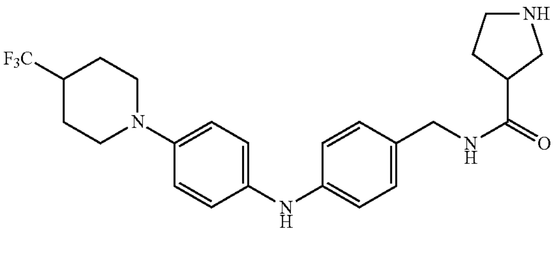

The title compound 651 (13 mg) was prepared in a total yield of 56.4% as a white powder from 4-(aminomethyl)-N-(4-(4-(trifluoromethyl)piperidin-1-yl)phenyl)aniline (17.5 mg, 0.05 mmol), 2-oxopyrrolidine-3-carboxylic acid (8.4 mg, 0.065 mmol), DIEA (19 mg, 0.15 mmol) and HATU (25 mg, 0.065 mmol) according to the procedure for compound 625. $^1$H NMR (400 MHz, DMSO-$d_6$) δ 7.23-6.72 (m, 8H), 4.18 (s, 2H), 3.72-3.51 (m, 2H), 3.31-3.12 (m, 3H), 2.73-2.52 (m, 2H), 2.42 (m, 1H), 2.32-2.08 (m, 2H), 1.95-1.80 (m, 2H), 1.66-1.48 (m, 2H). Mass (m/z): 461.2 [M+H]$^+$.

(S)-5-oxo-N-(4-((4-(4-(trifluoromethyl)piperidin-1-yl)phenyl)amino)benzyl)pyrrolidine-2-carboxamide (652)

652

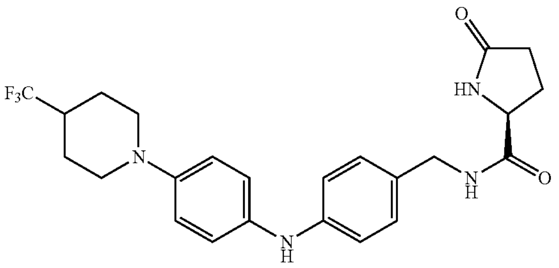

The title compound 652 (9.3 mg) was prepared in a total yield of 40.4% as a white powder from 4-(aminomethyl)-N-(4-(4-(trifluoromethyl)piperidin-1-yl)phenyl)aniline (17.5 mg, 0.05 mmol), (S)-5-oxopyrrolidine-2-carboxylic acid (8.4 mg, 0.065 mmol), DIEA (19 mg, 0.15 mmol) and HATU (25 mg, 0.065 mmol) according to the procedure for compound 625. $^1$H NMR (400 MHz, Methanol-$d_4$) δ 7.31-6.68 (m, 8H), 4.31 (s, 2H), 4.20 (m, 1H), 3.78-3.38 (m, 2H), 2.53-2.12 (m, 4H), 2.12-1.82 (m, 3H), 1.78-1.62 (m, 2H). Mass (m/z): 461.2 $[M+H]^+$.

(R)-5-oxo-N-(4-((4-(4-(trifluoromethyl)piperidin-1-yl)phenyl)amino)benzyl)pyrrolidine-2-carboxamide (653)

653

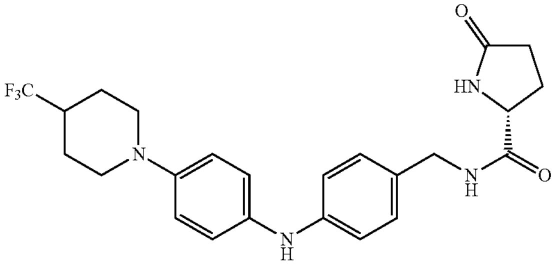

The title compound 653 (9.8 mg) was prepared in a total yield of 42.5% as a white powder from 4-(aminomethyl)-N-(4-(4-(trifluoromethyl)piperidin-1-yl)phenyl)aniline (17.5 mg, 0.05 mmol), (R)-5-oxopyrrolidine-2-carboxylic acid (8.4 mg, 0.065 mmol), DIEA (19 mg, 0.15 mmol) and HATU (25 mg, 0.065 mmol) according to the procedure for compound 625. $^1$H NMR (400 MHz, Methanol-$d_4$) δ 7.42-6.65 (m, 8H), 4.29 (s, 2H), 4.17 (m, 1H), 3.82-3.55 (m, 2H), 2.48-2.19 (m, 4H), 2.14-1.88 (m, 3H), 1.84-1.57 (m, 2H). Mass (m/z): 461.2 $[M+H]^+$.

N-(4-((4-(tert-butylamino)phenyl)amino)benzyl)-1-ethyl-5-oxopyrrolidine-3-carboxamide (654)

654

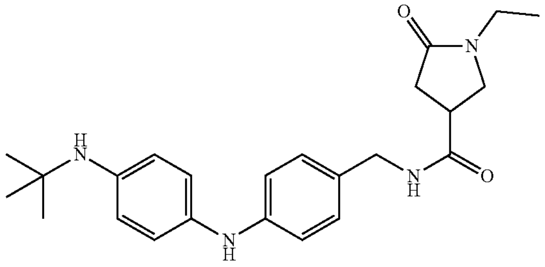

The title compound 654 (7.2 mg) was prepared in a total yield of 35.2% as a white powder from N1-(4-(aminomethyl)phenyl)-N4-(tert-butyl)benzene-1,4-diamine (13.5 mg, 0.05 mmol), 1-ethyl-5-oxopyrrolidine-3-carboxylic acid (10.2 mg, 0.065 mmol), DIEA (19 mg, 0.15 mmol) and HATU (25 mg, 0.065 mmol) according to the procedure for compound 625. $^1$H NMR (400 MHz, Methanol-$d_4$) δ 7.37-7.00 (m, 8H), 4.32 (s, 2H), 3.82-3.66 (m, 4H), 3.52 (m, 1H), 2.61 (d, J=8.4 Hz, 2H), 1.39 (s, 9H), 1.12 (t, J=7.2 Hz, 3H). Mass (m/z): 409.3 $[M+H]^+$.

(S)—N-(4-((4-(4-(trifluoromethyl)piperidin-1-yl)phenyl)amino)benzyl)pyrrolidine-2-carboxamide (655)

655

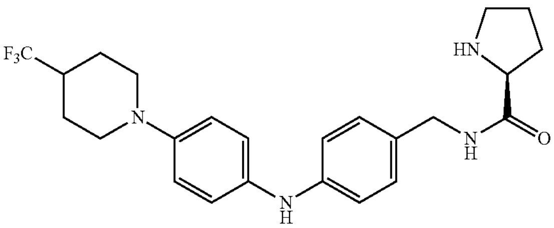

The title compound 655 (8.8 mg) was prepared in a total yield of 39.4% as a white powder from 4-(aminomethyl)-N-(4-(4-(trifluoromethyl)piperidin-1-yl)phenyl)aniline (17.5 mg, 0.05 mmol), L-proline (7.5 mg, 0.065 mmol), DIEA (19 mg, 0.15 mmol) and HATU (25 mg, 0.065 mmol) according to the procedure for compound 625. $^1$H NMR (400 MHz, DMSO-$d_6$) δ 7.11-6.81 (m, 8H), 4.20 (s, 2H), 4.12 (m, 1H), 3.68-3.54 (m, 2H), 3.26-3.12 (m, 2H), 2.68-2.55 (m, 2H), 2.41 (m, 1H), 1.95-1.76 (m, 4H), 1.71-1.44 (m, 4H). Mass (m/z): 447.3 $[M+H]^+$.

(R)—N-(4-((4-(4-(trifluoromethyl)piperidin-1-yl)phenyl)amino)benzyl)pyrrolidine-2-carboxamide (656)

656

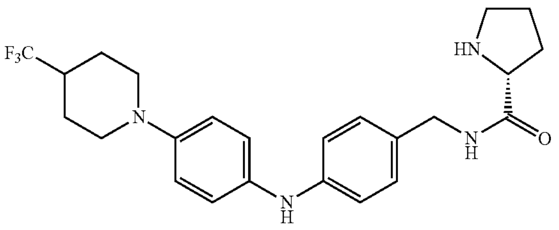

The title compound 656 (8.0 mg) was prepared in a total yield of 35.8% as a white powder from 4-(aminomethyl)-N-(4-(4-(trifluoromethyl)piperidin-1-yl)phenyl)aniline (17.5 mg, 0.05 mmol), D-proline (7.5 mg, 0.065 mmol), DIEA (19 mg, 0.15 mmol) and HATU (25 mg, 0.065 mmol) according to the procedure for compound 625. $^1$H NMR (400 MHz, DMSO-$d_6$) δ 7.12-6.82 (m, 8H), 4.22 (s, 2H), 4.14 (m, 1H), 3.66-3.55 (m, 2H), 3.25-3.03 (m, 2H), 2.68-2.55 (m, 2H), 2.40 (m, 1H), 1.98-1.76 (m, 4H), 1.73-1.48 (m, 4H). Mass (m/z): 447.3 $[M+H]^+$.

(S)-6-oxo-N-(4-((4-(4-(trifluoromethyl)piperidin-1-yl)phenyl)amino)benzyl)piperidine-2-carboxamide (657)

657

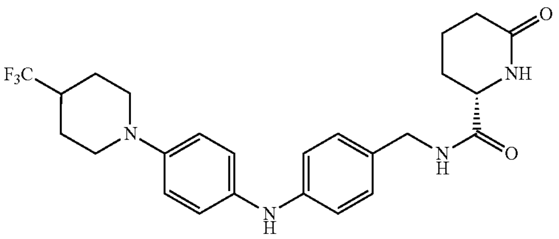

The title compound 657 (14.6 mg) was prepared in a total yield of 61.5% as a white powder from 4-(aminomethyl)-N-(4-(4-(trifluoromethyl)piperidin-1-yl)phenyl)aniline (17.5 mg, 0.05 mmol), (S)-6-oxopiperidine-2-carboxylic acid (9.3 mg, 0.065 mmol), DIEA (19 mg, 0.15 mmol) and HATU (25 mg, 0.065 mmol) according to the procedure for compound 625. $^1$H NMR (400 MHz, DMSO-$d_6$) δ 7.35-6.55 (m, 8H), 4.19 (s, 2H), 3.70 (m, 1H), 3.63-3.55 (m, 2H), 2.72-2.58 (m, 2H), 2.42 (m, 1H), 2.13 (t, J=6.4 Hz, 2H), 1.97-1.82 (m, 2H), 1.78-1.50 (m, 6H). Mass (m/z): 475.2 $[M+H]^+$.

(S)-2,6-dioxo-N-(4-((4-(4-(trifluoromethyl)piperidin-1-yl)phenyl)amino)benzyl)hexahydropyrimidine-4-carboxamide (658)

658

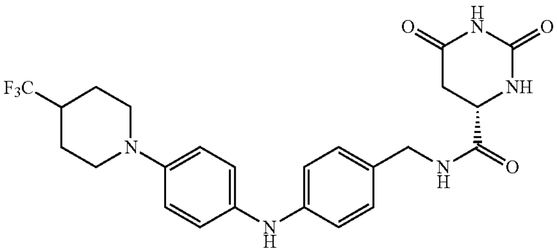

The title compound 658 (13.1 mg) was prepared in a total yield of 53.6% as a white powder from 4-(aminomethyl)-N-(4-(4-(trifluoromethyl)piperidin-1-yl)phenyl)aniline (17.5 mg, 0.05 mmol), (S)-2,6-dioxohexahydropyrimidine-4-carboxylic acid (10.3 mg, 0.065 mmol), DIE A (19 mg, 0.15 mmol) and HATU (25 mg, 0.065 mmol) according to the procedure for compound 625. $^1$H NMR (400 MHz, DMSO-$d_6$) δ 7.17-6.65 (m, 8H), 4.16 (s, 2H), 4.00 (m, 1H), 3.73-3.50 (m, 2H), 2.90-2.77 (m, 1H), 2.75-2.56 (m, 2H), 2.48-2.35 (m, 2H), 2.02-1.82 (m, 2H), 1.68-1.52 (m, 2H). Mass (m/z): 490.2 $[M+H]^+$.

(S)-1-methyl-2,6-dioxo-N-(4-((4-(4-(trifluoromethyl)piperidin-1-yl)phenyl)amino)benzyl)hexahydropyrimidine-4-carboxamide (659)

659

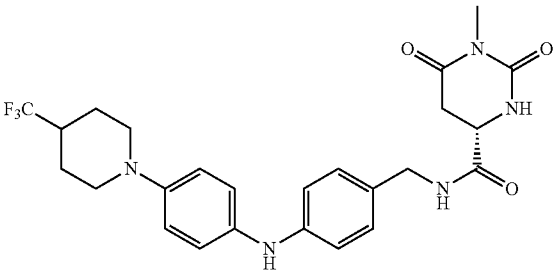

The title compound 659 (19.4 mg) was prepared in a total yield of 77.0% as a white powder from 4-(aminomethyl)-N-(4-(4-(trifluoromethyl)piperidin-1-yl)phenyl)aniline (17.5 mg, 0.05 mmol), (S)-1-methyl-2,6-dioxohexahydropyrimidine-4-carboxylic acid (11.2 mg, 0.065 mmol), DIEA (19 mg, 0.15 mmol) and HATU (25 mg, 0.065 mmol) according to the procedure for compound 625. $^1$H NMR (400 MHz, DMSO-$d_6$) δ 7.21-6.65 (m, 8H), 4.14 (s, 2H), 3.97 (m, 1H), 3.75-3.46 (m, 2H), 3.00 (m, 1H), 2.95 (s, 3H), 2.78-2.54 (m, 3H), 2.44 (m, 1H), 1.97-1.76 (m, 2H), 1.68-1.47 (m, 2H). Mass (m/z): 504.3 $[M+H]^+$.

4-oxo-N-(4-((4-(4-(trifluoromethyl)piperidin-1-yl)phenyl)amino)benzyl)imidazolidine-1-carboxamide (660)

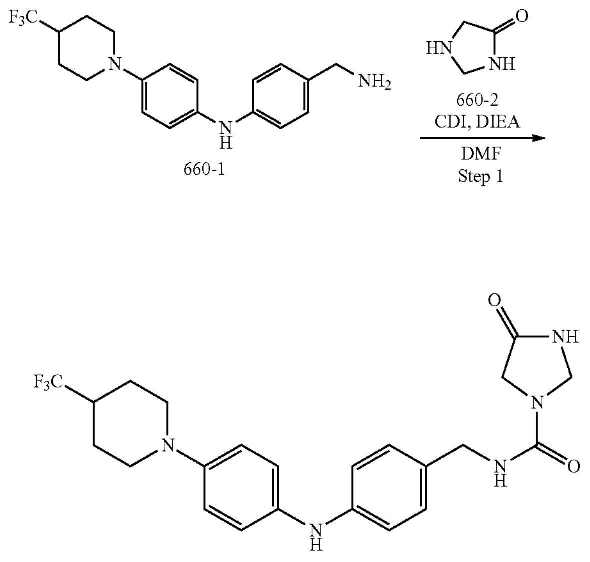

660

To a solution of 4-(aminomethyl)-N-(4-(4-(trifluoromethyl)piperidin-1-yl)phenyl)aniline (34.9 mg, 0.1 mmol) in DMF (10 mL) was added CDI (17.8 mg, 0.11 mmol). The reaction mixture was stirred for 1 hour at r.t. Then imidazolidin-4-one (9.5 mg, 0.11 mmol) and DIEA (38.7 mg, 0.3 mmol) were added and the reaction was stirred for another 3 hours. Then the solution was washed with 3×10 mL of water, dried over $Na_2SO_4$ and concentrated under vacuum. The residue was purified by prep-TLC (MeOH/DCM=1/15) to afford the desired product as a light yellow solid. (10.1 mg, 21.9%). $^1H$ NMR (400 MHz, DMSO-$d_6$) δ 7.25-6.57 (m, 8H), 4.61 (s, 2H), 4.14 (s, 2H), 3.72 (s, 2H), 3.68-3.42 (m, 2H), 2.78-2.55 (m, 2H), 2.41 (m, 1H), 1.98-1.77 (m, 2H), 1.68-1.45 (m, 2H). Mass (m/z): 462.2 $[M+H]^+$.

(R)-5-oxo-N-(4-((4-(4-(trifluoromethyl)piperidin-1-yl)phenyl)amino)benzyl)pyrrolidine-3-carboxamide (661)

661

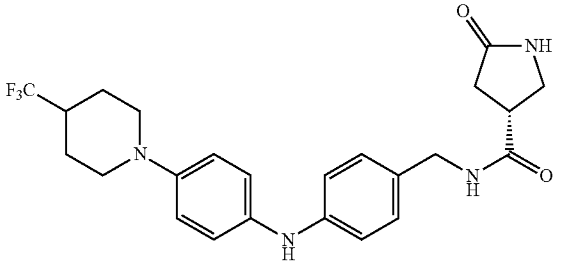

The title compound 661 (122 mg) was prepared in a total yield of 63.1% as a wheat solid from 4-(aminomethyl)-N-(4-(4-(trifluoromethyl)piperidin-1-yl)phenyl)aniline (146.6 mg, 0.42 mmol) and 2-(4-methylpiperazin-1-yl)acetic acid (64.5 mg, 0.5 mmol) in DMF (2 mL) was added DIEA (0.023 mL, 1.26 mmol) according to the procedure for compound 625. $^1H$ NMR (400 MHz, Methanol-$d_4$) δ 7.10 (d, J=8.4 Hz, 2H), 7.02 (d, J=8.4 Hz, 2H), 6.99-6.88 (m, 4H), 4.26 (s, 2H), 3.69-3.42 (m, 4H), 3.27 (m, 1H), 2.75-2.44 (m, 4H), 2.27 (m, 1H), 2.02-1.93 (m, 2H), 1.79-1.66 (m, 2H). Mass (m/z): 461.2 $[M+H]^+$.

1-(4-((4-(4-(trifluoromethyl)piperidin-1-yl)phenyl)amino)benzyl)urea (662)

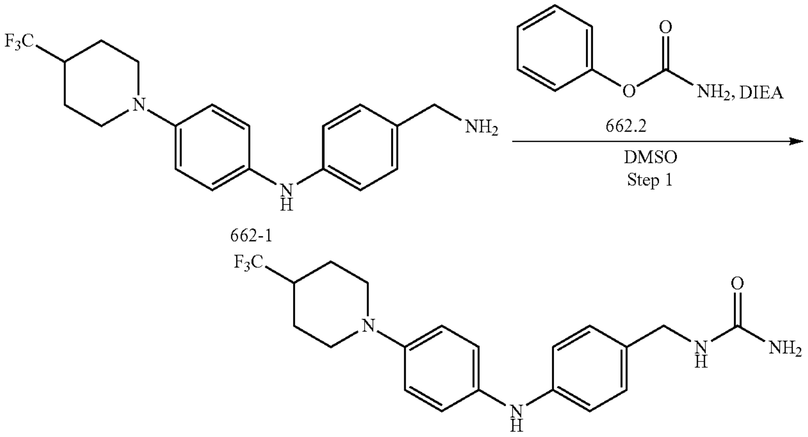

662

To a solution of 4-(aminomethyl)-N-(4-(4-(trifluoromethyl)piperidin-1-yl)phenyl)aniline (34.9 mg, 0.1 mmol) in DMSO (2 ml), DIEA (39.0 mg, 0.3 mmol) and phenyl carbamate (16.4 mg, 0.12 mmol) was added at 0° C. Then the reaction was stirred for 2 hours at rt. Then the solution was washed with 3×10 mL of water, dried over $Na_2SO_4$ and concentrated under vacuum. The residue was purified by prep-TLC (MeOH/DCM=1/15) to afford the desired product as a light yellow solid. (30.1 mg, 77.2%). $^1H$ NMR (400 MHz, DMSO-$d_6$) δ 7.05 (d, J=8.4 Hz, 2H), 6.96 (d, J=8.4 Hz, 2H), 6.91-6.85 (m, 4H), 4.04 (s, 2f), 3.65-3.56 (m, 2H), 2.68-2.55 (m, 2H), 2.41 (m, 1H), 1.95-1.81 (m, 2H), 1.63-1.50 (m, 2H). Mass (m/z): 393.2 $[M+H]^+$.

(R)-2,6-dioxo-N-(4-((4-(4-(trifluoromethyl)piperidin-1-yl)phenyl)amino)benzyl)hexahydropyrimidine-4-carboxamide (663)

663

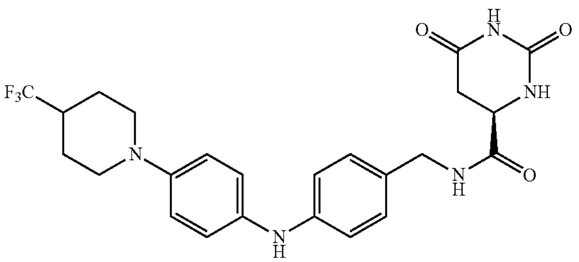

The title compound 663 (15.4 mg) was prepared in a total yield of 63.0% as a white powder from 4-(aminomethyl)-N-(4-(4-(trifluoromethyl)piperidin-1-yl)phenyl)aniline (17.5 mg, 0.05 mmol), (R)-2,6-dioxohexahydropyrimidine-4-carboxylic acid (10.3 mg, 0.065 mmol), DIEA (19 mg, 0.15 mmol) and HATU (25 mg, 0.065 mmol) according to the procedure for compound 625. $^1$H NMR (400 MHz, DMSO-$d_6$) δ 7.05 (d, J=8.4 Hz, 2H), 6.97 (d, J=8.4 Hz, 2H), 6.92-6.86 (m, 4H), 4.15 (s, 2H), 4.01 (m, 1H), 3.66-3.57 (m, 2H), 2.85 (m, 1H), 2.67-2.56 (m, 2H), 2.48-2.34 (m, 2H), 1.94-1.78 (m, 2H), 1.63-1.51 (m, 2H). Mass (n/z): 490.2 $[M+H]^+$.

(R)-6-oxo-N-(4-((4-(4-(trifluoromethyl)piperidin-1-yl)phenyl)amino)benzyl)piperidine-2-carboxamide (664)

664

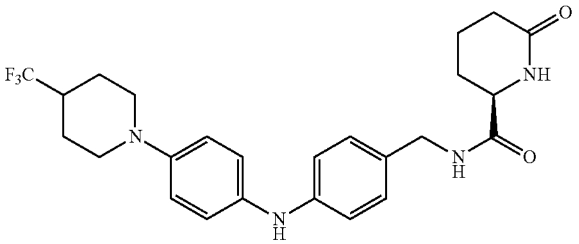

The title compound 664 (14.8 mg) was prepared in a total yield of 62.3% as a white powder from 4-(aminomethyl)-N-(4-(4-(trifluoromethyl)piperidin-1-yl)phenyl)aniline (17.5 mg, 0.05 mmol), (R)-6-oxopiperidine-2-carboxylic acid (9.3 mg, 0.065 mmol), DIEA (19 mg, 0.15 mmol) and HATU (25 mg, 0.065 mmol) according to the procedure for compound 625. $^1$H NMR (400 MHz, DMSO-$d_6$) δ 7.30-6.68 (m, 8H), 4.17 (s, 2H), 3.89 (m, 1H), 3.72-3.53 (m, 2H), 2.79-2.56 (m, 2H), 2.42 (m, 1H), 2.13 (t, J=6.4 Hz, 2H), 1.93-1.82 (m, 2H), 1.76-1.67 (m, 2H), 1.64-1.53 (m, 2H), 1.31-1.22 (m, 2H). Mass (m/z): 475.2 $[M+H]^+$.

N3-(4-((4-(4-(trifluoromethyl)piperidin-1-yl)phenyl)amino)benzyl)azetidine-1,3-dicarboxamide (665)

665

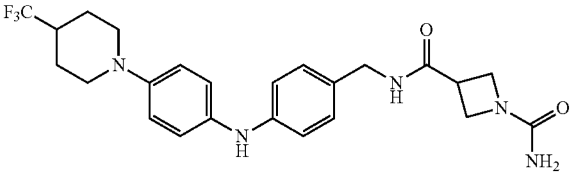

The title compound 665 (12.4 mg) was prepared in a total yield of 52.2% as a white solid from 4-(aminomethyl)-N-(4-(4-(trifluoromethyl)piperidin-1-yl)phenyl)aniline (17.5 mg, 0.05 mmol), 1-carbamoylazetidine-3-carboxylic acid (9.3 mg, 0.065 mmol), DIEA (19 mg, 0.15 mmol) and HATU (25 mg, 0.065 mmol) according to the procedure for compound 625. $^1$H NMR (400 MHz, DMSO-$d_6$) δ 7.20-6.68 (m, 8H), 4.16 (s, 2H), 3.92-3.73 (m, 4H), 3.69-3.53 (m, 2H), 3.26 (m, 1H), 2.72-2.54 (m, 2H), 2.41 (m, 1H), 1.95-1.80 (m, 2H), 1.65-1.51 (m, 2H). Mass (m/z): 476.2 $[M+H]^+$.

N-(4-((4-(4-methylpiperidin-1-yl)phenyl)amino)benzyl)-3-oxopiperazine-1-carboxamide (666)

666

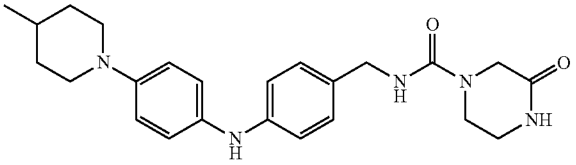

The title compound 666 (8.2 mg) was prepared in a total yield of 38.9% as a white solid from 4-(aminomethyl)-N-(4-(4-methylpiperidin-1-yl)phenyl)aniline (29 mg, 0.1 mmol), piperazin-2-one (11.0 mg, 0.11 mmol), CDI (17.8 mg, 0.11 mmol) and DIEA (38.7 mg, 0.3 mmol) according to the procedure for compound 660. $^1$H NMR (400 MHz, DMSO-$d_6$) δ 7.28-6.64 (m, 8H), 4.15 (s, 2H), 3.86 (s, 2H), 3.65-3.45 (m, 4H), 3.23-3.13 (m, 2H), 2.80-2.55 (m, 2H), 1.83-1.60 (m, 2H), 1.46 (m, 1H), 1.38-1.16 (m, 2H), 0.93 (d, J=6.4 Hz, 3H). Mass (m/z): 422.3 $[M+H]^+$.

N-(4-((4-(4-methylpiperidin-1-yl)phenyl)amino)benzyl)-2-oxoimidazolidine-4-carboxamide (667)

667

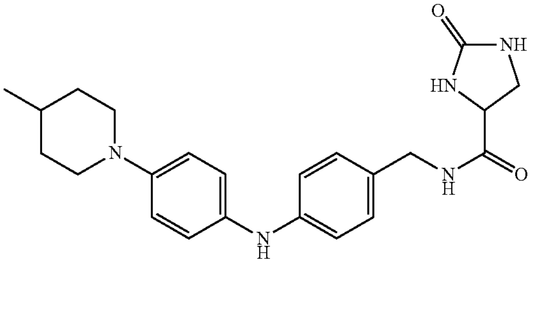

The title compound 667 (14.0 mg) was prepared in a total yield of 68.5% as a wheat powder from 4-(aminomethyl)-N-(4-(4-methylpiperidin-1-yl)phenyl)aniline (14.8 mg, 0.05 mmol), 2-oxoimidazolidine-4-carboxylic acid (8.4 mg, 0.065 mmol), DIEA (19 mg, 0.15 mmol) and HATU (25 mg, 0.065 mmol) according to the procedure for compound 625. $^1$H NMR (400 MHz, DMSO-$d_6$) δ 7.30-6.69 (m, 8H), 4.17 (s, 2H), 4.09 (m, 1H), 3.65-3.43 (m, 3H), 3.22 (m, 1H), 2.72-2.54 (m, 2H), 1.82-1.58 (m, 2H), 1.46 (m, 1H), 1.37-1.10 (m, 2H), 0.94 (d, J=6.4 Hz, 3H). Mass (m/z): 408.2 $[M+H]^+$.

(S)—N-(4-((4-(4-methylpiperidin-1-yl)phenyl)amino)benzyl)-2,6-dioxohexahydropyrimidine-4-carboxamide (668)

668

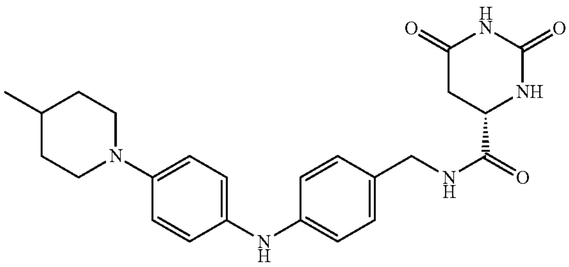

The title compound 668 (7.4 mg) was prepared in a total yield of 33.9% as a wheat powder from 4-(aminomethyl)-N-(4-(4-methylpiperidin-1-yl)phenyl)aniline (14.8 mg, 0.05 mmol), (S)-2,6-dioxohexahydropyrimidine-4-carboxylic acid (8.4 mg, 0.065 mmol), DIEA (19 mg, 0.15 mmol) and HATU (25 mg, 0.065 mmol) according to the procedure for compound 625. $^1$H NMR (400 MHz, DMSO-$d_6$) δ 7.31-6.63 (m, 8H), 4.15 (s, 2H), 4.01 (m, 11H), 3.67-3.42 (m, 3H), 2.84 (m, 1H), 2.68-2.54 (m, 211), 1.87-1.62 (m, 2H), 1.46 (m, 1H), 1.39-1.15 (m, 2H), 0.94 (d, J=6.4 Hz, 3H). Mass (m/z): 436.2 $[M+H]^+$.

N-(2-methoxy-4-((4-(4-(trifluoromethyl)piperidin-1-yl)phenyl)amino)benzyl)-5-oxopyrrolidine-3-carboxamide (669)

669

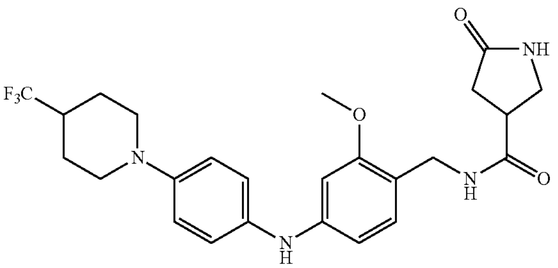

The title compound 669 (8.2 mg) was prepared in a total yield of 33.4% as a wheat powder from 4-(aminomethyl)-3-methoxy-N-(4-(4-(trifluoromethyl)piperidin-1-yl)phenyl)aniline (19.5 mg, 0.05 mmol), 5-oxopyrrolidine-3-carboxylic acid (8.4 mg, 0.065 mmol), DIEA (19 mg, 0.15 mmol) and HATU (25 mg, 0.065 mmol) according to the procedure for compound 625. $^1$H NMR (400 MHz, DMSO-$d_6$) δ 7.06-6.85 (m, 511), 6.58-6.44 (m, 2H), 4.12 (s, 2H), 3.71 (s, 3H), 3.67-3.55 (m, 211), 3.41 (m, 1H), 3.28-3.11 (m, 2H), 2.68-2.54 (m, 2H), 2.43 (m, 111), 2.32-2.23 (m, 2H), 1.95-1.80 (m, 2H), 1.65-1.48 (m, 2H). Mass (m/z): 491.2 $[M+H]^+$.

N-(2-fluoro-4-((4-(4-(trifluoromethyl)piperidin-1-yl)phenyl)amino)benzyl)-5-oxopyrrolidine-3-carboxamide (670)

670

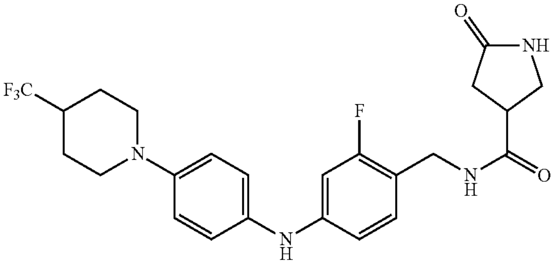

The title compound 670 (10.9 mg) was prepared in a total yield of 45.5% as a wheat solid from 4-(aminomethyl)-3-fluoro-N-(4-(4-(trifluoromethyl)piperidin-1-yl)phenyl)aniline (18.3 mg, 0.05 mmol), 5-oxopyrrolidine-3-carboxylic acid (8.4 mg, 0.065 mmol), DIEA (19 mg, 0.15 mmol) and HATU (25 mg, 0.065 mmol) according to the procedure for compound 625. $^1$H NMR (400 MHz, DMSO-$d_6$) δ 7.12-6.86 (m, 5H), 6.72-6.56 (m, 2H), 4.17 (s, 2H), 3.74-3.58 (m, 2H), 3.39 (m, 1H), 3.28-3.06 (m, 2H), 2.71-2.58 (m, 2H), 2.43 (m, 1H), 2.32-2.25 (m, 2H), 1.92-1.83 (m, 2H), 1.63-1.50 (m, 2H). Mass (m/z): 479.2 $[M+H]^+$.

1-ethyl-3-(4-((4-(4-(trifluoromethyl)piperidin-1-yl)phenyl)amino)benzyl)urea (671)

671

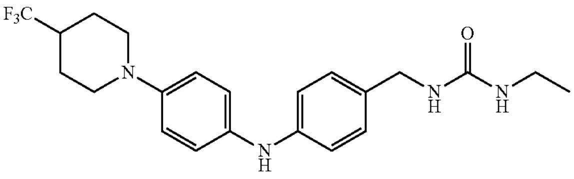

The title compound 671 (14.0 mg) was prepared in a total yield of 33.3% as a white solid from 4-(aminomethyl)-N-(4-(4-(trifluoromethyl)piperidin-1-yl)phenyl)aniline (34.9 mg, 0.1 mmol), ethanamine (4.9 mg, 0.11 mmol), CDI (17.8 mg, 0.11 mmol) and DIEA (38.7 mg, 0.3 mmol) according to the procedure for compound 660. $^1$H NMR (400 MHz, DMSO-$d_6$) δ 7.25-6.70 (m, 8H), 4.06 (s, 2H), 3.75-3.47 (m, 2H), 3.02 (q, J=7.2 Hz, 2H), 2.75-2.54 (m, 2H), 2.42 (m, 1H), 1.97-1.75 (m, 2H), 1.68-1.45 (m, 2H), 0.98 (t, J=7.2 Hz, 3H). Mass (m/z): 421.3 $[M+H]^+$.

1-(tert-butyl)-3-(4-((4-(4-(trifluoromethyl)piperidin-1-yl)phenyl)amino)benzyl)urea (672)

672

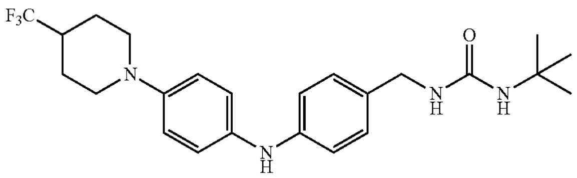

The title compound 672 (8.0 mg) was prepared in a total yield of 35.3% as a white solid from 4-(aminomethyl)-N-(4-(4-(trifluoromethyl)piperidin-1-yl)phenyl)aniline (34.9 mg, 0.1 mmol), 2-methylpropan-2-amine (10.3 mg, 0.11 mmol), CDI (17.8 mg, 0.11 mmol) and DIEA (38.7 mg, 0.3 mmol) according to the procedure for compound 660. $^1$H NMR (400 MHz, DMSO-$d_6$) δ 7.09-6.82 (m, 8H), 4.02 (s, 2H), 3.68-3.55 (m, 2H), 2.69-2.55 (m, 2H), 2.42 (m, 1H), 1.95-1.82 (m, 2H), 1.63-1.51 (m, 2H), 1.22 (s, 9H). Mass (m/z): 449.3 [M+H]$^+$.

(S)-2-oxo-N-(4-((4-(4-(trifluoromethyl)piperidin-1-yl)phenyl)amino)benzyl)imidazolidine-4-carboxamide (673)

673

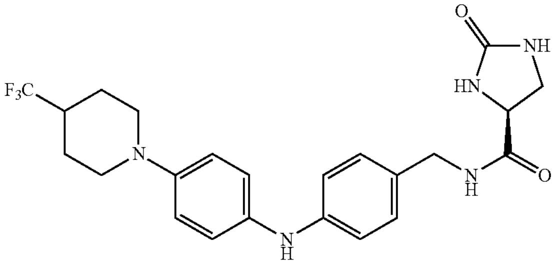

The title compound 673 (12.2 mg) was prepared in a total yield of 52.8% as a wheat solid from 4-(aminomethyl)-N-(4-(4-(trifluoromethyl)piperidin-1-yl)phenyl)aniline (17.5 mg, 0.05 mmol), (S)-2-oxoimidazolidine-4-carboxylic acid (8.5 mg, 0.065 mmol) DIEA (19 mg, 0.15 mmol) and HATU (25 mg, 0.065 mmol) according to the procedure for compound 625. $^1$H NMR (400 MHz, DMSO-$d_6$) δ 7.43-6.67 (m, 8H), 4.18 (s, 2H), 4.09 (m, 1H), 3.78-3.47 (m, 3H), 3.22 (m, 1H), 2.71-2.54 (m, 2H), 2.41 (m, 1H), 2.05-1.77 (m, 2H), 1.69-1.44 (m, 2H). Mass (m/z): 462.2 [M+H]$^+$.

(R)-2-oxo-N-(4-((4-(4-(trifluoromethyl)piperidin-1-yl)phenyl)amino)benzyl)imidazolidine-4-carboxamide (674)

674

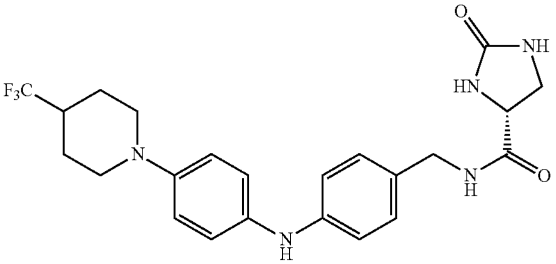

The title compound 674 (8.2 mg) was prepared in a total yield of 36.0% as a wheat solid from 4-(aminomethyl)-N-(4-(4-(trifluoromethyl)piperidin-1-yl)phenyl)aniline (17.5 mg, 0.05 mmol), (R)-2-oxoimidazolidine-4-carboxylic acid (8.5 mg, 0.065 mmol) DIEA (19 mg, 0.15 mmol) and HATU (25 mg, 0.065 mmol) according to the procedure for compound 625. $^1$H NMR (400 MHz, DMSO-$d_6$) δ 7.31-6.72 (m, 8H), 4.18 (s, 2H), 4.12 (m, 1H), 3.73-3.50 (m, 3H), 3.24 (m, 1H), 2.78-2.54 (m, 2H), 2.40 (m, 1H), 1.97-1.77 (m, 2H), 1.67-1.44 (m, 2H). Mass (m/z): 462.2 [M+H]$^+$.

1-ethyl-5-imino-N-(4-((4-(4-(trifluoromethyl)piperidin-1-yl)phenyl)amino)benzyl)pyrrolidine-3-carboxamide (675)

675

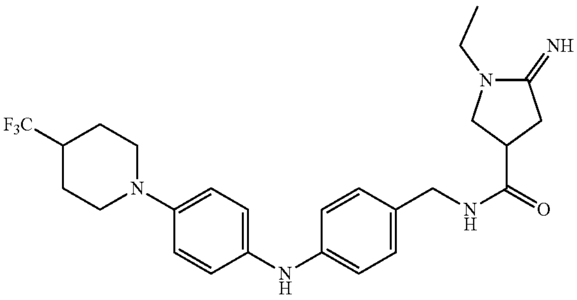

The title compound 675 (8.0 mg) was prepared in a total yield of 32.7% as a wheat solid from 4-(aminomethyl)-N-(4-(4-(trifluoromethyl)piperidin-1-yl)phenyl)aniline (17.5 mg, 0.05 mmol), 1-ethyl-5-iminopyrrolidine-3-carboxylic acid (10.1 mg, 0.065 mmol) DIEA (19 mg, 0.15 mmol) and HATU (25 mg, 0.065 mmol) according to the procedure for compound 625. $^1$H NMR (400 MHz, DMSO-$d_6$) δ 7.32-6.70 (m, 8H), 4.35 (s, 2H), 3.85-3.78 (m, 6H), 3.73 (m, 1H), 3.67-3.55 (m, 2H), 2.71-2.55 (m, 2H), 2.41 (m, 1H), 1.95-1.79 (m, 2H), 1.65-1.46 (m, 2H), 0.85 (t, J=6.8 Hz, 3H). Mass (m/z): 488.3 [M+H]$^+$.

3,5-dioxo-N-(4-((4-(4-(trifluoromethyl)piperidin-1-yl)phenyl)amino)benzyl)piperazine-1-carboxamide (676)

676

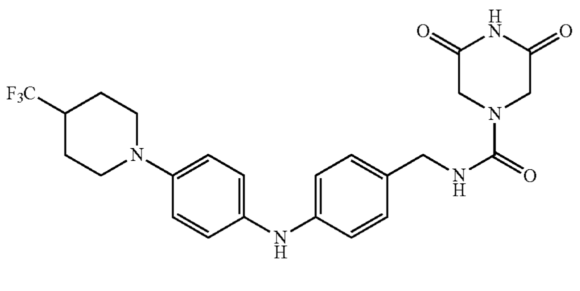

The title compound 676 (18.0 mg) was prepared in a total yield of 36.8% as a Lightgray solid from 4-(aminomethyl)-N-(4-(4-(trifluoromethyl)piperidin-1-yl)phenyl)aniline (34.9 mg, 0.1 mmol), DIEA (39.0 mg, 0.3 mmol), CDI (17.8 mg, 0.11 mmol) and piperazine-2,6-dione (12.1 mg, 0.11 mmol) according to the procedure for compound 660. $^{1}$H NMR (300 MHz, DMSO-$d_6$) δ 7.23-6.75 (m, 8H), 4.40 (s, 2H), 3.98 (s, 2H), 3.87 (s, 2H), 3.65-3.44 (m, 2H), 2.67-2.54 (m, 2H), 2.43 (m, 1H), 1.91-1.81 (m, 2H), 1.63-1.47 (m, 2H). Mass (m/z): 490.3 $[M+H]^+$.

N-(4-((4-(4-methylpiperidin-1-yl)phenyl)amino)benzyl)-3,5-dioxopiperazine-1-carboxamide (677)

677

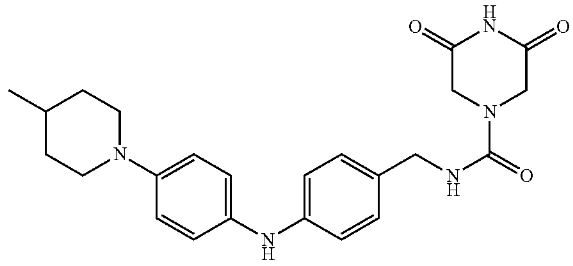

The title compound 677 (13.0 mg) was prepared in a total yield of 29.8% as a white solid from 4-(aminomethyl)-N-(4-(4-methylpiperidin-1-yl)phenyl)aniline (29 mg, 0.1 mmol), piperazine-2,6-dione (12.1 mg, 0.11 mmol), CDI (17.8 mg, 0.11 mmol) and DIEA (38.7 mg, 0.3 mmol) according to the procedure for compound 660.1H NMR (300 MHz, DMSO-$d_6$) δ 7.31-6.67 (m, 8H), 4.42 (s, 2H), 4.00 (s, 2H), 3.89 (s, 2H), 3.68-3.42 (m, 2H), 2.71-2.54 (m, 2H), 1.83-1.57 (m, 2H), 1.46 (m, 1H), 1.35-1.14 (m, 2H), 0.94 (d, J=6.0 Hz, 3H). Mass (m/z): 436.2 $[M+H]^+$.

2,6-dioxo-N-(4-((4-(4-(trifluoromethyl)piperidin-1-yl)phenyl)amino)benzyl)piperidine-4-carboxamide (678)

678

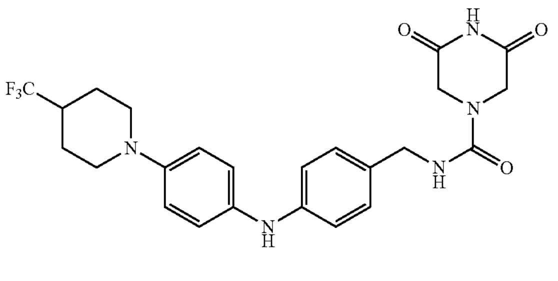

The title compound 678 (12.0 mg) was prepared in a total yield of 49.1% as a gray solid from 4-(aminomethyl)-N-(4-(4-(trifluoromethyl)piperidin-1-yl)phenyl)aniline (17.5 mg, 0.05 mmol), 2,6-dioxopiperidine-4-carboxylic acid (10.2 mg, 0.065 mmol) DIEA (19 mg, 0.15 mmol) and HATU (25 mg, 0.065 mmol) according to the procedure for compound 625. $^{1}$H NMR (400 MHz, DMSO-$d_6$) δ 7.15-6.79 (m, 8H), 4.15 (s, 2H), 3.70-3.53 (m, 2H), 2.99 (m, 1H), 2.74-2.52 (m, 6H), 2.40 (m, 1H), 1.94-1.80 (m, 2H), 1.67-1.48 (m, 2H). Mass (m/z): 489.2 $[M+H]^+$.

5-oxo-N-(4-((4-propyl-3,4-dihydro-2H-benzo[b][1,4]oxazin-7-yl)amino)benzyl)pyrrolidine-3-carboxamide (679)

679

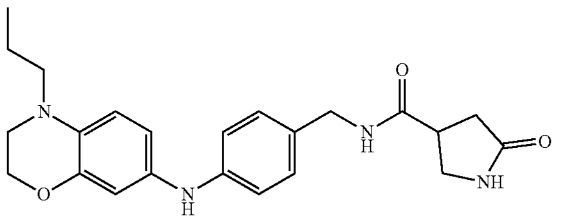

The title compound 679 (8.6 mg) was prepared in a total yield of 42.1% as a gray solid from N-(4-(aminomethyl)phenyl)-4-propyl-3,4-dihydro-2H-benzo[b][1,4]oxazin-7-amine (14.9 mg, 0.05 mmol), 5-oxopyrrolidine-3-carboxylic acid (8.4 mg, 0.065 mmol) DIEA (19 mg, 0.15 mmol) and HATU (25 mg, 0.065 mmol) according to the procedure for compound 625. $^{1}$H NMR (400 MHz, DMSO-$d_6$) δ 7.25-6.35 (m, 7H), 4.14 (s, 2H), 3.27-3.12 (m, 5H), 2.54-2.51 (m, 4H), 2.36-2.21 (m, 2H), 1.62-1.45 (m, 2H), 0.98-0.76 (m, 3H). Mass (m/z): 409.2 $[M+H]^+$.

2,4-dioxo-N-(4-((4-(4-(trifluoromethyl)piperidin-1-yl)phenyl)amino)benzyl)imidazolidine-1-carboxamide (680)

680

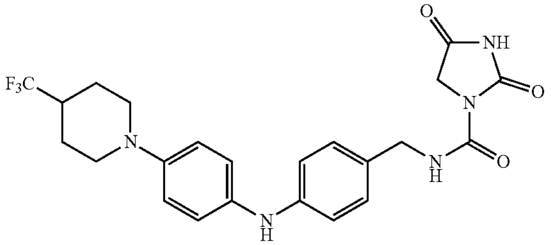

The title compound 680 (10.1 mg) was prepared in a total yield of 43.8% as a white solid from 4-(aminomethyl)-N-(4-(4-(trifluoromethyl)piperidin-1-yl)phenyl)aniline (34.9 mg, 0.1 mmol), CDI (17.8 mg, 0.11 mmol), DIEA (39.0 mg, 0.3 mmol) and imidazolidine-2,4-dione (11.0 mg, 0.11 mmol)) according to the procedure for compound 660. $^1$H NMR (300 MHz, DMSO-$d_6$) δ 7.43-6.71 (m, 8H), 4.38 (s, 2H), 4.19 (s, 2H), 3.66-3.47 (m, 2H), 2.73-2.54 (m, 2H), 2.41 (m, 1H), 1.92-1.82 (m, 2H), 1.64-1.51 (m, 2H). Mass (m/z): 476.2 $[M+H]^+$.

5-oxo-N-(4-((2-(4-(trifluoromethyl)piperidin-1-yl)phenyl)amino)benzyl)pyrrolidine-3-carboxamide (681)

681

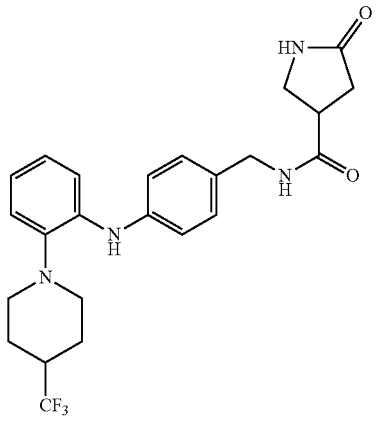

The title compound 681 (8.4 mg) was prepared in a total yield of 36.4% as a white powder from N-(4-(aminomethyl)phenyl)-2-(4-(trifluoromethyl)piperidin-1-yl)aniline (17.5 mg, 0.05 mmol), 5-oxopyrrolidine-3-carboxylic acid (8.4 mg, 0.065 mmol), DIEA (19 mg, 0.15 mmol) and HATU (25 mg, 0.065 mmol) according to the procedure for compound 625. $^1$H NMR (300 MHz, DMSO-$d_6$) δ 7.21-6.76 (m, 8H), 4.19 (s, 2H), 3.75-3.64 (m, 2H), 3.42 (m, 1H), 3.26-3.17 (m, 2H), 2.74-2.66 (m, 2H), 2.34-2.27 (m, 3H), 1.91-1.83 (m, 2H), 1.59-1.52 (m, 2H). Mass (m/z): 461.2 $[M+H]^+$.

N-(4-((4-(diethylamino)-3-fluorophenyl)amino)benzyl)-5-oxopyrrolidine-3-carboxamide (682)

682

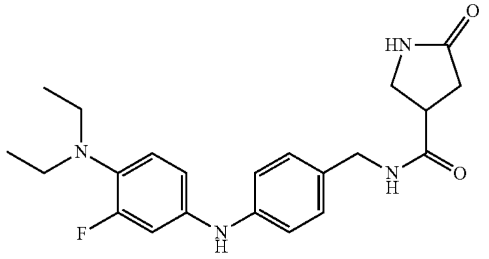

The title compound 682 (8.4 mg) was prepared in a total yield of 42.1% as a white powder from N4-(4-(aminomethyl)phenyl)-N1,N1-diethyl-2-fluorobenzene-1,4-diamine (14.5 mg, 0.05 mmol), 5-oxopyrrolidine-3-carboxylic acid (8.4 mg, 0.065 mmol), DIEA (19 mg, 0.15 mmol) and HATU (25 mg, 0.065 mmol) according to the procedure for compound 625. $^1$H NMR (400 MHz, DMSO-$d_6$) δ 7.46-6.68 (m, 7H), 4.21 (s, 2H), 3.54-3.31 (m, 5H), 3.28-3.10 (m, 2H), 2.42-2.28 (m, 2H), 0.99 (t, J=7.2 Hz, 6H). Mass (m/z): 399.2 $[M+H]^+$.

N-(4-((3-chloro-4-(diethylamino)phenyl)amino)benzyl)-5-oxopyrrolidine-3-carboxamide (683)

683

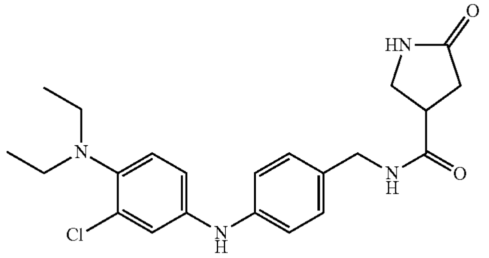

The title compound 683 (13.2 mg) was prepared in a total yield of 63.6% as a white powder from N4-(4-(aminomethyl)phenyl)-2-chloro-N1,N1-diethylbenzene-1,4-diamine (15.2 mg, 0.05 mmol), 5-oxopyrrolidine-3-carboxylic acid (8.4 mg, 0.065 mmol), DIEA (19 mg, 0.15 mmol) and HATU (25 mg, 0.065 mmol) according to the procedure for compound 625. $^1$H NMR (400 MHz, DMSO-$d_6$) δ 7.53 (s, 1H), 7.20 (d, J=8.4 Hz, 2H), 7.14-7.03 (m, 4H), 4.23 (s, 2H), 3.55-3.35 (m, 5H), 3.27-3.11 (m, 2H), 2.34-2.28 (m, 2H), 0.98 (t, J=7.2 Hz, 6H). Mass (m/z): 415.2 $[M+H]^+$.

N-(4-((4-(diethylamino)-3-methylphenyl)amino)benzyl)-5-oxopyrrolidine-3-carboxamide (684)

684

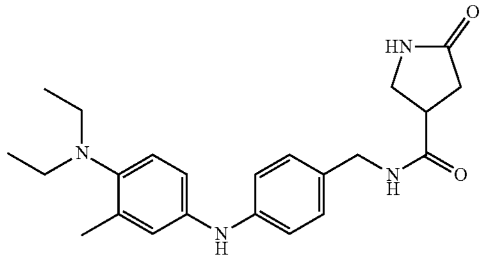

The title compound 684 (4.2 mg) was prepared in a total yield of 21.3% as a white powder from N4-(4-(aminomethyl)phenyl)-N1,N1-diethyl-2-methylbenzene-1,4-diamine (14.1 mg, 0.05 mmol), 5-oxopyrrolidine-3-carboxylic acid (8.4 mg, 0.065 mmol), DIEA (19 mg, 0.15 mmol) and HATU (25 mg, 0.065 mmol) according to the procedure for compound 625. $^1$H NMR (400 MHz, DMSO-$d_6$) δ 7.26-6.67 (m, 7H), 4.18 (s, 2H), 3.62-3.45 (m, 2H), 3.44-3.36 (m, 2H), 3.29-3.11 (m, 3H), 2.41-2.25 (m, 2H), 2.17 (s, 3H), 0.87 (t, J=7.2 Hz, 6H). Mass (m/z): 395.3 $[M+H]^+$.

N-(4-((4-(4-methylpiperidin-1-yl)phenyl)amino)benzyl)-2,6-dioxopiperidine-4-carboxamide (685)

685

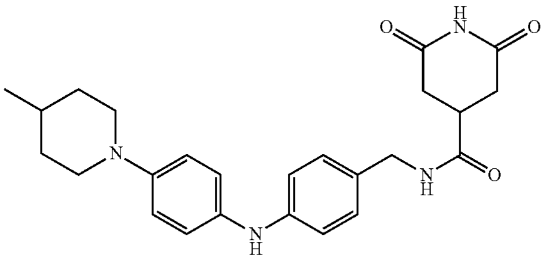

The title compound 685 (12.6 mg) was prepared in a total yield of 29.7% as a wheat powder from 4-(aminomethyl)-N(4-(4-methylpiperidin-1-yl)phenyl)aniline (14.8 mg, 0.05 mmol), 2,6-dioxopiperidine-4-carboxylic acid (10.2 mg, 0.065 mmol), DIEA (19 mg, 0.15 mmol) and HATU (25 mg, 0.065 mmol) according to the procedure for compound 625. $^1$H NMR (400 MHz, DMSO-$d_6$) δ 7.25-6.73 (m, 8H), 4.14 (s, 2H), 3.65-3.36 (m, 2H), 2.99 (m, 1H), 2.70-2.52 (m, 6H), 1.87-1.58 (m, 2H), 1.55-1.17 (m, 3H), 0.94 (d, J=6.4 Hz, 3H). Mass (m/z): 435.2 $[M+H]^+$.

N-(4-((2-(azocan-1-yl)pyrimidin-5-yl)amino)benzyl)-5-oxopyrrolidine-3-carboxamide (686)

686

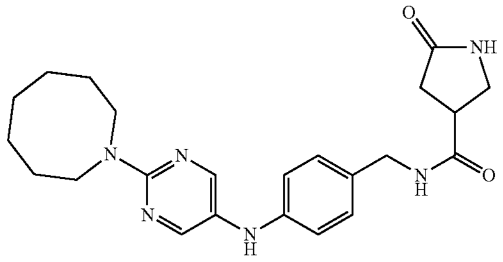

The title compound 686 (12.1 mg) was prepared in a total yield of 56.9% as a wheat powder from N-(4-(aminomethyl)phenyl)-2-(azocan-1-yl)pyrimidin-5-amine (15.7 mg, 0.05 mmol), 5-oxopyrrolidine-3-carboxylic acid (8.4 mg, 0.065 mmol), DIEA (19 mg, 0.15 mmol) and HATU (25 mg, 0.065 mmol) according to the procedure for compound 625. $^1$H NMR (400 MHz, DMSO-$d_6$) δ 8.21 (s, 2H), 7.07-6.96 (m, 2H), 6.74-6.62 (m, 2H), 4.13 (s, 2H), 3.75-3.57 (m, 4H), 3.46-3.36 (m, 1H), 3.27-3.09 (m, 2H), 2.34-2.21 (m, 2H), 1.78-1.65 (m, 4H), 1.55-1.38 (m, 6H). Mass (m/z): 423.2 $[M+H]^+$.

N-(4-((5-chloro-2-fluoro-4-(4-(trifluoromethyl)piperidin-1-yl)phenyl)amino)benzyl)-5-oxopyrrolidine-3-carboxamide (687)

687

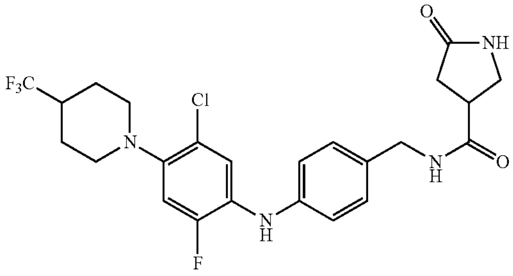

The title compound 687 (10.1 mg) was prepared in a total yield of 38.9% as a wheat powder from N-(4-(aminomethyl)phenyl)-5-chloro-2-fluoro-4-(4-(trifluoromethyl)piperidin-1-yl)aniline (25.2 mg, 0.05 mmol), 5-oxopyrrolidine-3-carboxylic acid (8.4 mg, 0.065 mmol), DIEA (19 mg, 0.15 mmol) and HATU (25 mg, 0.065 mmol) according to the procedure for compound 625. $^1$H NMR (400 MHz, Methanol-$d_4$) δ 7.25-7.17 (m, 2H), 7.13 (m, 1H), 7.06-6.93 (m, 3H), 4.32 (s, 2H), 3.66-3.46 (m, 2H), 3.26 (m, 1H), 2.70-2.46 (m, 4H), 2.32-2.16 (m, 2H), 2.08-1.98 (m, 1H), 1.94-1.85 (m, 2H), 1.77-1.63 (m, 2H). Mass (m/z): 513.2 $[M+H]^+$.

N-hydroxy-5-oxo-N-(4-((4-(4-(trifluoromethyl)piperidin-1-yl)phenyl)amino)benzyl)pyrrolidine-3-carboxamide (688)

688

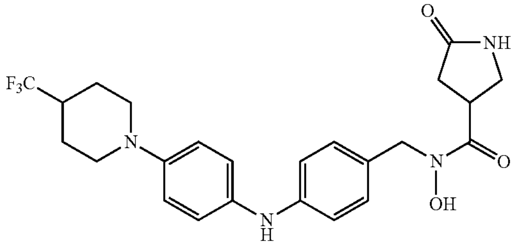

The title compound 688 (10.5 mg) was prepared in a total yield of 41.9% as a lightyellow powder from 4-((hydroxyamino)methyl)-N-(4-(4-(trifluoromethyl)piperidin-1-yl)phenyl)aniline (18.2 mg, 0.05 mmol), 5-oxopyrrolidine-3-carboxylic acid (8.4 mg, 0.065 mmol), DIEA (19 mg, 0.15 mmol) and HATU (25 mg, 0.065 mmol) according to the procedure for compound 625. $^1$H NMR (400 MHz, DMSO-$d_6$) δ 7.06 (d, J=8.4 Hz, 2H), 6.98 (d, J=8.4 Hz, 2H), 6.94-6.84 (m, 4H), 4.57 (s, 2H), 3.75-3.55 (m, 3H), 3.46 (m, 1H), 3.24 (m, 1H), 2.70-2.55 (m, 2H), 2.41 (m, 1H), 2.37-2.24 (m, 2H), 1.94-1.82 (m, 2H), 1.65-1.50 (m, 2H). Mass (m/z): 477.2 $[M+H]^+$.

N-hydroxy-2,6-dioxo-N-(4-((4-(4-(trifluoromethyl)piperidin-1-yl)phenyl)amino)benzyl)piperidine-4-carboxamide (689)

689

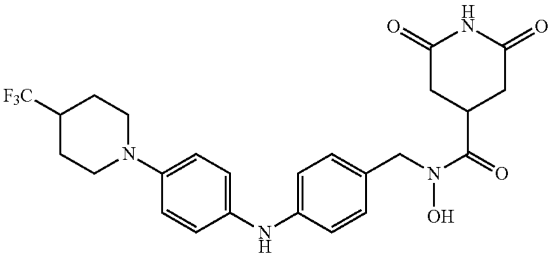

The title compound 689 (10.5 mg) was prepared in a total yield of 41.9% as a light yellow powder from 4-((hydroxyamino)methyl)-N-(4-(4-(trifluoromethyl)piperidin-1-yl)phenyl)aniline (18.2 mg, 0.05 mmol), 2,6-dioxopiperidine-4-carboxylic acid (10.2 mg, 0.065 mmol), DIEA (19 mg, 0.15 mmol) and HATU (25 mg, 0.065 mmol) according to the procedure for compound 625. $^1$H NMR (400 MHz, DMSO-$d_6$) δ 7.03 (d, J=8.4 Hz, 2H), 6.98 (d, J=8.4 Hz, 2H), 6.93-6.84 (m, 4H), 4.54 (s, 2H), 3.67-3.58 (m, 2H), 3.52 (p, J=6.0 Hz, 1H), 2.75-2.53 (m, 6H), 2.42 (m, 1H), 1.93-1.82 (m, 2H), 1.64-1.51 (m, 2H). Mass (m/z): 505.3 $[M+H]^+$.

1-acetyl-N-(4-((4-cyclohexylphenyl)amino)benzyl)azetidine-3-carboxamide (690)

690

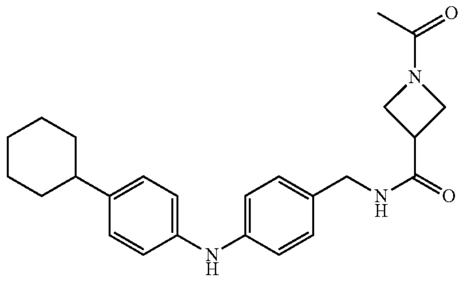

The title compound 690 (7.2 mg) was prepared in a total yield of 35.6% as a yellow powder from 4-(aminomethyl)-N-(4-cyclohexylphenyl)aniline (14.0 mg, 0.05 mmol), l-acetylazetidine-3-carboxylic acid (9.3 mg, 0.065 mmol), DIEA (19 mg, 0.15 mmol) and HATU (25 mg, 0.065 mmol) according to the procedure for compound 625. $^1$H NMR (400 MHz, DMSO-$d_6$) δ 7.17-6.88 (m, 8H), 4.19 (s, 2H), 4.17-4.06 (m, 2H), 3.95-3.79 (m, 2H), 3.33-3.28 (m, 1H), 2.39 (m, 1H), 1.87-1.65 (m, 5H), 1.73 (s, 3H), 1.39-1.13 (m, 5H). Mass (m/z): 406.3 $[M+H]^+$.

N-(4-((4-cyclohexylphenyl)amino)benzyl)-2,6-dioxopiperidine-4-carboxamide (691)

691

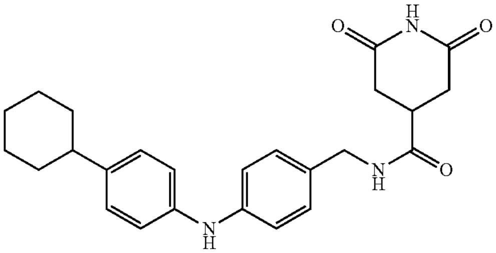

The title compound 691 (8.7 mg) was prepared in a total yield of 41.4% as a yellow powder from 4-(aminomethyl)-N-(4-cyclohexylphenyl)aniline (14.0 mg, 0.05 mmol), 2,6-dioxopiperidine-4-carboxylic acid (10.2 mg, 0.065 mmol), DIEA (19 mg, 0.15 mmol) and HATU (25 mg, 0.065 mmol) according to the procedure for compound 625. $^1$H NMR (400 MHz, DMSO-$d_6$) δ 7.12-6.91 (m, 8H), 4.15 (s, 2H), 2.99 (m, 1H), 2.72-2.52 (m, 4H), 2.39 (m, 1H), 1.83-1.63 (m, 5H), 1.43-1.13 (m, 5H). Mass (m/z): 420.2 $[M+H]^+$.

N-(4-((4-cyclohexylphenyl)amino)benzyl)azetidine-3-carboxamide (692)

692

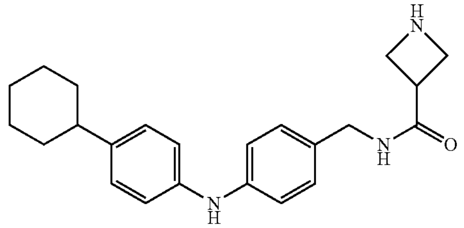

The title compound 692 (11.7 mg) was prepared in a total yield of 64.3% as a yellow powder from 4-(aminomethyl)-N-(4-cyclohexylphenyl)aniline (14.0 mg, 0.05 mmol), azetidine-3-carboxylic acid (5.1 mg, 0.065 mmol), DIEA (19 mg, 0.15 mmol) and HATU (25 mg, 0.065 mmol) according to the procedure for compound 625. $^1$H NMR (400 MHz, DMSO-$d_6$) δ 7.18-6.88 (m, 8H), 4.18 (s, 2H), 4.03-3.85 (m, 4H), 3.59 (p, J=8.4 Hz, 1H), 2.38 (m, 1H), 1.83-1.61 (m, 5H), 1.42-1.15 (m, 5H). Mass (m/z): 364.2 $[M+H]^+$.

(S)—N-hydroxy-2-oxo-N-(4-((4-(4-(trifluoromethyl)piperidin-1-yl)phenyl)amino)benzyl)imidazolidine-4-carboxamide (693)

693

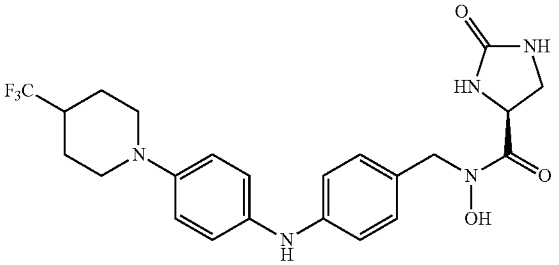

The title compound 693 (9.7 mg) was prepared in a total yield of 40.1% as a sky blue powder from 4-((hydroxyamino)methyl)-N-(4-(4-(trifluoromethyl)piperidin-1-yl)phenyl)aniline (18.2 mg, 0.05 mmol), (S)-2-oxoimidazolidine-4-carboxylic acid (8.5 mg, 0.065 mmol), DIEA (19 mg, 0.15 mmol) and HATU (25 mg, 0.065 mmol) according to the procedure for compound 625. $^1$H NMR (400 MHz, DMSO-$d_6$) δ 7.31-6.86 (m, 8H), 4.59 (s, 2H), 4.52 (m, 1H), 3.73-3.51 (m, 4H), 3.29-3.02 (m, 2H), 2.61 (m, 1H), 2.10-1.91 (m, 2H), 1.85-1.65 (m, 2H). Mass (m/z): 478.1 $[M+H]^+$.

N-(3-fluoro-4-((2-(4-(trifluoromethyl)piperidin-1-yl)pyrimidin-5-yl)amino)benzyl)-5-oxopyrrolidine-3-carboxamide (694)

694

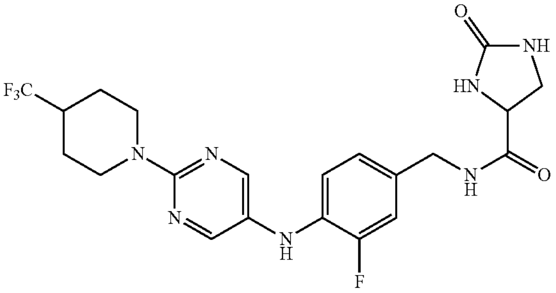

The title compound 694 (10.7 mg) was prepared in a total yield of 44.5% as a wheat solid from N-(4-(aminomethyl)-2-fluorophenyl)-2-(4-(trifluoromethyl)piperidin-1-yl)pyrimidin-5-amine (18.5 mg, 0.05 mmol), 5-oxopyrrolidine-3-carboxylic acid (8.4 mg, 0.065 mmol), DIEA (19 mg, 0.15 mmol) and HATU (25 mg, 0.065 mmol) according to the procedure for compound 625. $^1$H NMR (400 MHz, DMSO-$d_6$) δ 7.63-7.50 (m, 2H), 7.03 (m, 1H), 6.91-6.69 (m, 2H), 4.69 (s, 2H), 4.22-4.12 (m, 2H), 3.46-3.37 (m, 1H), 3.26-3.13 (m, 2H), 2.95-2.83 (m, 2H), 2.62 (m, 1H), 2.34-2.25 (m, 2H), 1.93-1.82 (m, 2H), 1.45-1.30 (m, 2H). Mass (m/z): 481.2 $[M+H]^+$.

N-(4-((4-cyclohexylphenyl)amino)benzyl)-N-hydroxy-5-oxopyrrolidine-3-carboxamide (695)

695

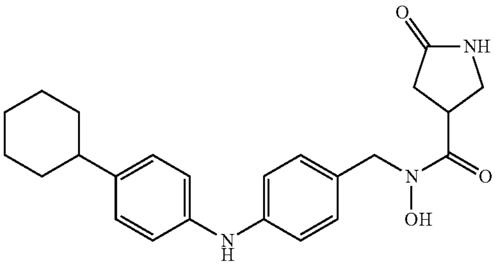

The title compound 695 (8.8 mg) was prepared in a total yield of 43.2% as a lightyellow powder from 4-cyclohexyl-N-(4-((hydroxyamino)methyl)phenyl)aniline (14.8 mg, 0.05 mmol), 5-oxopyrrolidine-3-carboxylic acid (8.4 mg, 0.065 mmol), DIEA (19 mg, 0.15 mmol) and HATU (25 mg, 0.065 mmol) according to the procedure for compound 625. $^1$H NMR (400 MHz, DMSO-$d_6$) δ 7.16-6.91 (m, 8H), 4.59 (s, 2H), 3.76-3.57 (m, 1H), 3.46 (m, 1H), 3.25 (m, 1H), 2.45-2.24 (m, 3H), 1.83-1.65 (m, 5H), 1.43-1.27 (m, 5H). Mass (m/z): 408.1 $[M+H]^+$.

N1-(4-((4-(4,4-dimethylpiperidin-1-yl)phenyl) amino)benzyl)oxalamide (696)

696

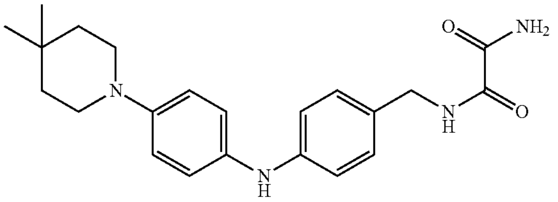

The title compound 696 (9.0 mg) was prepared in a total yield of 47.2% as a lightyellow powder from 4-(aminomethyl)-N-(4-(4,4-dimethylpiperidin-1-yl)phenyl)aniline (15.4 mg, 0.05 mmol), 2-amino-2-oxoacetic acid (4.5 mg, 0.065 mmol), DIEA (19 mg, 0.15 mmol) and HATU (25 mg, 0.065 mmol) according to the procedure for compound 625. $^{1}H$ NMR (400 MHz, DMSO-$d_6$) δ 7.06 (d, J=8.4 Hz, 2H), 6.95 (d, J=8.4 Hz, 2H), 6.90-6.80 (m, 4H), 4.17 (s, 2H), 3.08-2.94 (m, 4H), 1.52-1.36 (m, 4H), 0.94 (s, 6H). Mass (m/z): 381.3 $[M+H]^+$.

1-(4-((4-(4,4-dimethylpiperidin-1-yl)phenyl)amino) benzyl)urea (697)

697

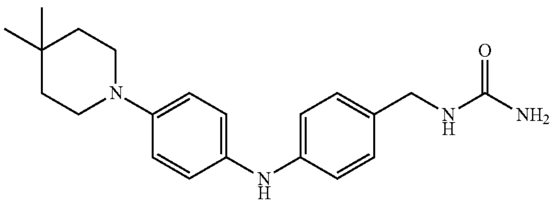

The title compound 697 (10.9 mg) was prepared in a total yield of 61.9% as a lightyellow powder from 4-(aminomethyl)-N-(4-(4,4-dimethylpiperidin-1-yl)phenyl)aniline (15.4 mg, 0.05 mmol), phenyl carbamate (8.2 mg, 0.06 mmol) and DIEA (19 mg, 0.15 mmol) according to the procedure for compound 662.1H NMR (400 MHz, DMSO-$d_6$) δ 7.35-6.67 (m, 8H), 4.04 (s, 2H), 3.31-2.69 (m, 4H), 1.55-1.37 (m, 4H), 0.95 (s, 6H). Mass (m/z): 353.2 $[M+H]^+$.

3,5-dioxo-N-(4-((4-(4-propylpiperidin-1-yl)phenyl) amino)benzyl)piperazine-1-carboxamide (698)

698

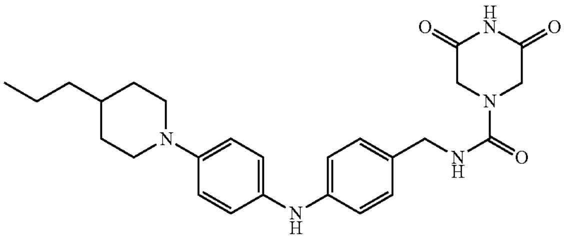

The title compound 698 (10.1 mg) was prepared in a total yield of 21.5% as a white solid from 4-(aminomethyl)-N-(4-(4-propylpiperidin-1-yl)phenyl)aniline (32.3 mg, 0.1 mmol), piperazine-2,6-dione (12.1 mg, 0.11 mmol), CDI (17.8 mg, 0.11 mmol) and DIEA (38.7 mg, 0.3 mmol) according to the procedure for compound 660. $^{1}H$ NMR (400 MHz, Methanol-$d_4$) δ 7.56-6.98 (m, 8H), 4.61 (s, 2H), 4.07 (s, 4H), 3.80-3.51 (m, 2H), 2.23-1.94 (m, 3H), 1.86-1.53 (m, 4H), 1.48-1.36 (m, 4H), 0.97 (t, J=7.2 Hz, 3H). Mass (m/z): 464.3 $[M+H]^+$.

2,4-dioxo-N-(4-((4-(4-propylpiperidin-1-yl)phenyl) amino)benzyl)imidazolidine-1-carboxamide (699)

699

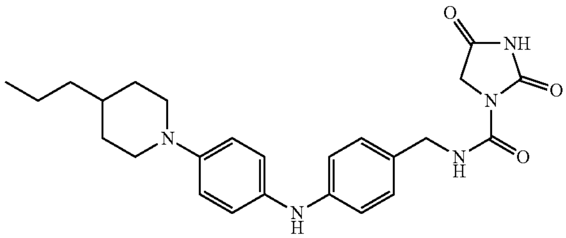

The title compound 699 (9.3 mg) was prepared in a total yield of 20.9% as a white solid from 4-(aminomethyl)-N-(4-(4-propylpiperidin-1-yl)phenyl)aniline (32.3 mg, 0.1 mmol), imidazolidine-2,4-dione (11.0 mg, 0.11 mmol), CDI (17.8 mg, 0.11 mmol) and DIEA (38.7 mg, 0.3 mmol) according to the procedure for compound 660. $^{1}H$ NMR (400 MHz, Methanol-$d_4$) δ 7.55-6.85 (m, 8H), 4.41 (s, 2H), 4.28 (s, 2H), 3.78-3.45 (m, 2H), 2.19-1.95 (m, 3H), 1.86-1.53 (m, 4H), 1.48-1.36 (m, 4H), 0.93 (t, J=7.2 Hz, 3H). Mass (m/z): 450.3 $[M+H]^+$.

N-(4-((4-(4,4-dimethylcyclohexyl)phenyl)amino) benzyl)-1-methylpyrrolidine-3-carboxamide (700)

700

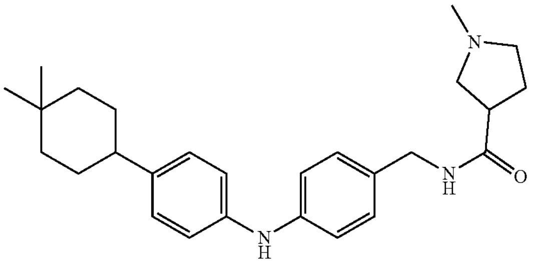

The title compound 700 (11.2 mg) was prepared in a total yield of 53.3% as a lightgray solid from 4-(aminomethyl)-N-(4-(4,4-dimethylcyclohexyl)phenyl)aniline (15.4 mg, 0.05 mmol), 1-methylpyrrolidine-3-carboxylic acid (8.4 mg, 0.065 mmol), DIEA (19 mg, 0.15 mmol) and HATU (25 mg, 0.065 mmol) according to the procedure for compound 625. $^{1}H$ NMR (400 MHz, DMSO-$d_6$) δ 7.16-6.90 (m, 8H), 4.18 (s, 2H), 3.29-3.12 (m, 3H), 2.80 (s, 3H), 2.39-2.13 (m, 2H), 2.11-1.95 (m, 1H), 1.65-1.20 (m, 10H), 0.95 (s, 6H). Mass (m/z): 420.3 $[M+H]^+$.

N-(4-((4-(4,4-dimethylcyclohexyl)phenyl)amino)benzyl)pyrrolidine-3-carboxamide (701)

701

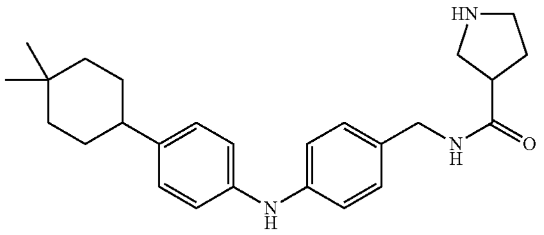

The title compound 701 (9.1 mg) was prepared in a total yield of 44.3% as a lightgray solid from 4-(aminomethyl)-N-(4-(4,4-dimethylcyclohexyl)phenyl)aniline (15.4 mg, 0.05 mmol), pyrrolidine-3-carboxylic acid (7.5 mg, 0.065 mmol), DIEA (19 mg, 0.15 mmol) and HATU (25 mg, 0.065 mmol) according to the procedure for compound 625. $^1$H NMR (400 MHz, DMSO-$d_6$) δ 7.08 (d, J=8.4 Hz, 4H), 7.01-6.94 (m, 4H), 4.17 (s, 2H), 3.31 (m, 1H), 3.22-3.04 (m, 2H), 2.29 (m, 1H), 2.13 (m, 1H), 1.93 (m, 1H), 1.62-1.48 (m, 4H), 1.47-1.39 (m, 2H), 1.37-1.16 (m, 4H), 0.94 (s, 6H). Mass (m/z): 406.3 [M+H]$^+$.

N1-(4-((4-(4-ethylpiperidin-1-yl)phenyl)amino)benzyl)oxalamide (702)

702

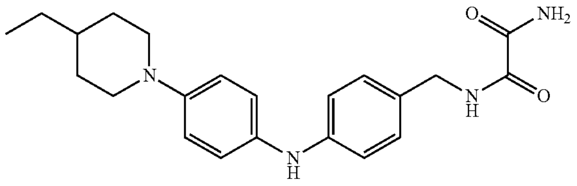

The title compound 702 (9.0 mg) was prepared in a total yield of 47.2% as a lightyellow powder from 4-(aminomethyl)-N-(4-(4-ethylpiperidin-1-yl)phenyl)aniline (15.4 mg, 0.05 mmol), 2-amino-2-oxoacetic acid (4.5 mg, 0.065 mmol), DIEA (19 mg, 0.15 mmol) and HATU (25 mg, 0.065 mmol) according to the procedure for compound 625. $^1$H NMR (400 MHz, DMSO-$d_6$) δ 7.40-6.58 (m, 8H), 4.18 (s, 2H), 3.67-3.44 (m, 2H), 2.69-2.55 (m, 2H), 2.06-1.55 (m, 2H), 1.33-1.10 (m, 5H), 0.89 (t, J=7.2 Hz, 3H). Mass (m/z): 381.2 [M+H]$^+$.

N1-(4-((4-(4-methylpiperidin-1-yl)phenyl)amino)benzyl)oxalamide (703)

703

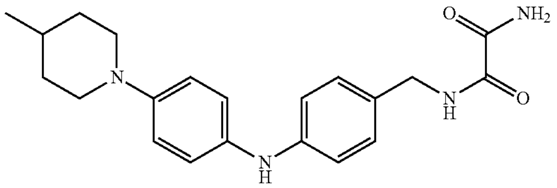

The title compound 703 (8.3 mg) was prepared in a total yield of 45.2% as a lightyellow powder from 4-(aminomethyl)-N-(4-(4-methylpiperidin-1-yl)phenyl)aniline (14.8 mg, 0.05 mmol), 2-amino-2-oxoacetic acid (4.5 mg, 0.065 mmol), DIEA (19 mg, 0.15 mmol) and HATU (25 mg, 0.065 mmol) according to the procedure for compound 625. $^1$H NMR (400 MHz, DMSO-$d_6$) δ 7.28-6.64 (m, 8H), 4.18 (s, 2H), 3.70-3.41 (m, 2H), 2.71-2.53 (m, 2H), 1.83-1.54 (m, 2H), 1.45 (m, 1H), 1.34-1.13 (m, 2H), 0.93 (d, J=6.4 Hz, 3H). Mass (m/z): 367.2 [M+H]$^+$.

1-(4-((4-(4-ethylpiperidin-1-yl)phenyl)amino)benzyl)urea (704)

704

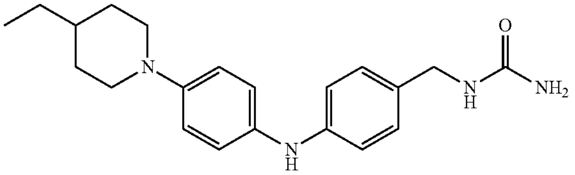

The title compound 704 (8.9 mg) was prepared in a total yield of 50.9% as a lightyellow powder from 4-(aminomethyl)-N-(4-(4-ethylpiperidin-1-yl)phenyl)aniline (15.4 mg, 0.05 mmol), phenyl carbamate (8.2 mg, 0.06 mmol) and DIEA (19 mg, 0.15 mmol) according to the procedure for compound 662.1H NMR (400 MHz, DMSO-$d_6$) δ 7.30-6.66 (m, 8H), 4.04 (s, 2H), 3.65-3.43 (m, 2H), 2.65-2.53 (m, 2H), 1.86-1.63 (m, 2H), 1.33-1.11 (m, 5H), 0.89 (t, J=7.2 Hz, 3H). Mass (m/z): 353.3 [M+H]$^+$.

1-(4-((4-(4-methylpiperidin-1-yl)phenyl)amino)benzyl)urea (705)

705

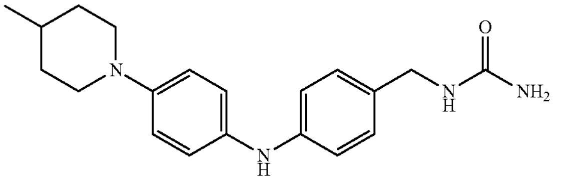

The title compound 705 (15.5 mg) was prepared in a total yield of 91.4% as a white powder from 4-(aminomethyl)-N-(4-(4-methylpiperidin-1-yl)phenyl)aniline (14.8 mg, 0.05 mmol), phenyl carbamate (8.2 mg, 0.06 mmol) and DIEA (19 mg, 0.15 mmol) according to the procedure for compound 662. $^1$H NMR (400 MHz, DMSO-$d_6$) δ 7.24-6.60 (m, 8H), 4.04 (s, 2H), 3.65-3.41 (m, 2H), 2.71-2.52 (m, 2H), 1.80-1.61 (m, 2H), 1.44 (m, 1H), 1.34-1.14 (m, 2H), 0.93 (d, J=6.4 Hz, 3H). Mass (m/z): 339.2 [M+H]$^+$.

N-(4-((4-(4,4-dimethylcyclohexyl)phenyl)amino)benzyl)-3,5-dioxopiperazine-1-carboxamide (706)

706

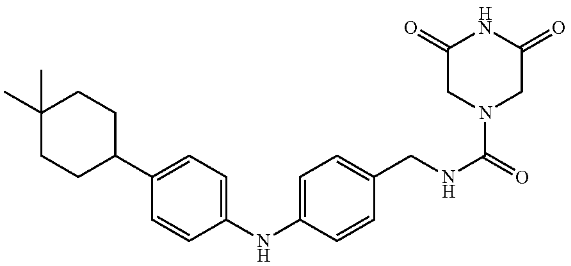

The title compound 706 (8.1 mg) was prepared in a total yield of 70.5% as a white solid from 4-(aminomethyl)-N-(4-(4,4-dimethylcyclohexyl)phenyl)aniline (30.8 mg, 0.1 mmol), piperazine-2,6-dione (12.1 mg, 0.11 mmol), CDI (17.8 mg, 0.11 mmol) and DIEA (38.7 mg, 0.3 mmol) according to the procedure for compound 660. $^1$H NMR (400 MHz, DMSO-$d_6$) δ 7.13-7.03 (m, 4H), 7.00-6.91 (m, 4H), 4.19 (s, 4H), 4.13 (s, 2H), 2.29 (m, 1H), 1.63-1.20 (m, 8H), 0.95 (s, 3H), 0.93 (s, 3H). Mass (m/z): 449.3 $[M+H]^+$.

N-(4-((3-(azepan-1-yl)-4-fluorophenyl)amino)benzyl)-5-oxopyrrolidine-3-carboxamide (707)

707

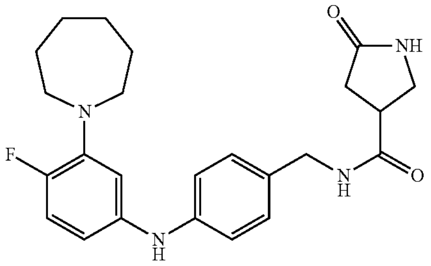

The title compound 707 (7.8 mg) was prepared in a total yield of 36.7% as a yellow powder from N-(4-(aminomethyl)phenyl)-3-(azepan-1-yl)-4-fluoroaniline (15.6 mg, 0.05 mmol), 5-oxopyrrolidine-3-carboxylic acid (8.4 mg, 0.065 mmol), DIEA (19 mg, 0.15 mmol) and HATU (25 mg, 0.065 mmol) according to the procedure for compound 625.1H NMR (400 MHz, DMSO-$d_6$) δ 7.06 (d, J=8.4 Hz, 2H), 6.94 (d, J=8.4 Hz, 2H), 6.90-6.77 (m, 1H), 6.40-6.31 (m, 1H), 6.20 (m, 1H), 4.15 (s, 2H), 3.45-3.13 (m, 4H), 2.97-2.84 (m, 2H), 2.36-2.24 (m, 2H), 2.24-2.15 (m, 1H), 1.78-1.65 (m, 2H), 1.63-1.45 (m, 4H), 1.28-1.18 (m, 2H). Mass (m/z): 425.2 $[M+H]^+$.

N-(4-((4-fluoro-3-(pyrrolidin-1-yl)phenyl)amino)benzyl)-5-oxopyrrolidine-3-carboxamide (708)

708

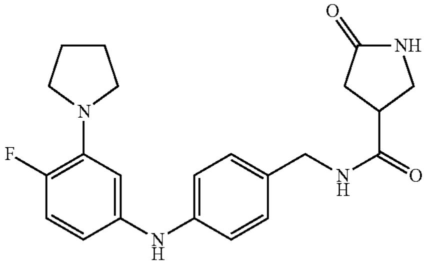

The title compound 708 (14.1 mg) was prepared in a total yield of 71.0% as a yellow powder from N-(4-(aminomethyl)phenyl)-4-fluoro-3-(pyrrolidin-1-yl)aniline (14.2 mg, 0.05 mmol), 5-oxopyrrolidine-3-carboxylic acid (8.4 mg, 0.065 mmol), DIEA (19 mg, 0.15 mmol) and HATU (25 mg, 0.065 mmol) according to the procedure for compound 625. $^1$H NMR (400 MHz, DMSO-$d_6$) δ 7.08 (d, J=8.4 Hz, 2H), 7.00-6.81 (m, 3H), 6.42-6.28 (m, 2H), 4.17 (s, 2H), 3.41 (m, 1H), 3.31-3.12 (m, 6H), 2.35-2.26 (m, 2H), 1.95-1.79 (m, 4H). Mass (m/z): 397.2 $[M+H]^+$.

N-hydroxy-N-(4-((4-(4-methylpiperidin-1-yl)phenyl)amino)benzyl)-5-oxopyrrolidine-3-carboxamide (709)

709

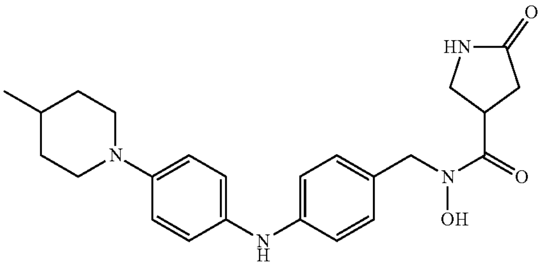

The title compound 709 (12.1 mg) was prepared in a total yield of 56.7% as a white solid from 4-((hydroxyamino)methyl)-N-(4-(4-methylpiperidin-1-yl)phenyl)aniline (15.5 mg, 0.05 mmol), 5-oxopyrrolidine-3-carboxylic acid (8.4 mg, 0.065 mmol), DIEA (19 mg, 0.15 mmol) and HATU (25 mg, 0.065 mmol) according to the procedure for compound 625. $^1$H NMR (400 MHz, DMSO-$d_6$) δ 7.30-6.99 (m, 8H), 4.63 (s, 2H), 3.74-3.62 (m, 2H), 3.56-3.41 (m, 4H), 3.26 (m, 1H), 2.39-2.28 (m, 2H), 1.95-1.84 (m, 2H), 1.77 (m, 1H), 1.62-1.49 (m, 2H), 0.99 (d, J=6.4 Hz, 3H). Mass (m/z): 423.3 $[M+H]^+$.

N-(4-((2-methyl-6-(4-(trifluoromethyl)cyclohexyl)pyridin-3-yl)amino)benzyl)-5-oxopyrrolidine-3-carboxamide (710)

710

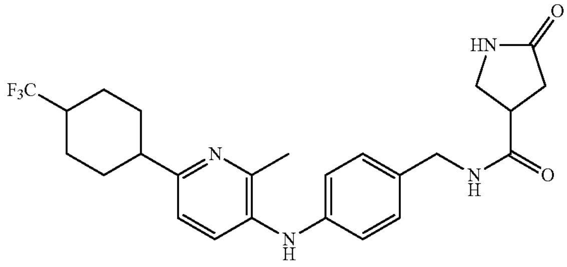

The title compound 710 (10.3 mg) was prepared in a total yield of 43.5% as a white solid from N-(4-(aminomethyl)phenyl)-2-methyl-6-(4-(trifluoromethyl)cyclohexyl)pyridin-3-amine (18.2 mg, 0.05 mmol), 5-oxopyrrolidine-3-carboxylic acid (8.4 mg, 0.065 mmol), DIEA (19 mg, 0.15 mmol) and HATU (25 mg, 0.065 mmol) according to the procedure for compound 625. $^1$H NMR (400 MHz, DMSO-$d_6$) δ 7.53-7.36 (m, 2H), 7.15-7.00 (m, 2H), 6.93-6.73 (m, 2H), 4.18 (s, 2H), 3.30-3.11 (m, 2H), 2.87 (m, 1H), 2.38 (s, 3H), 2.34-2.19 (m, 3H), 2.15-1.86 (m, 2H), 1.82-1.50 (m, 6H). Mass (m/z): 475.2 [M+H]$^+$.

N-(4-((4-(4-hydroxy-4-(trifluoromethyl)piperidin-1-yl)phenyl)amino)benzyl)-1-methylpyrrolidine-3-carboxamide (711)

711

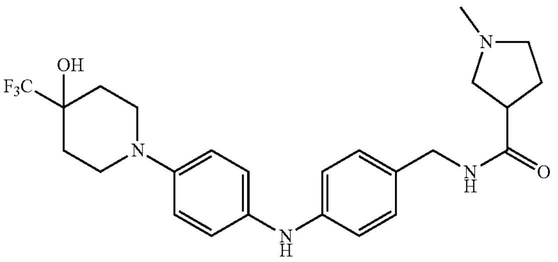

The title compound 711 (9.6 mg) was prepared in a total yield of 40.2% as a lightyellow solid from 1-(4-((4-(aminomethyl)phenyl)amino)phenyl)-4-(trifluoromethyl)piperidin-4-ol (15.4 mg, 0.05 mmol), 1-methylpyrrolidine-3-carboxylic acid (8.4 mg, 0.065 mmol), DIEA (19 mg, 0.15 mmol) and HATU (25 mg, 0.065 mmol) according to the procedure for compound 625. $^1$H NMR (400 MHz, DMSO-$d_6$) δ 7.14-6.82 (m, 8H), 4.16 (s, 2H), 3.33-3.09 (m, 6H), 2.92-2.82 (m, 2H), 2.77 (s, 3H), 2.23 (m, 1H), 2.05 (m, 1H), 1.85-1.66 (m, 4H). Mass (m/z): 477.3 [M+H]$^+$.

N-(4-((4-fluoro-6-(4-(trifluoromethyl)piperidin-1-yl)pyridin-3-yl)amino)benzyl)-5-oxopyrrolidine-3-carboxamide (712)

712

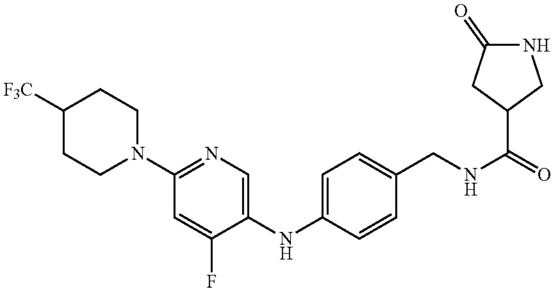

The title compound 712 (10.5 mg) was prepared in a total yield of 42.9% as a white solid from N-(4-(aminomethyl)phenyl)-4-fluoro-6-(4-(trifluoromethyl)piperidin-1-yl)pyridin-3-amine (18.4 mg, 0.05 mmol), 5-oxopyrrolidine-3-carboxylic acid (8.4 mg, 0.065 mmol), DIEA (19 mg, 0.15 mmol) and HATU (25 mg, 0.065 mmol) according to the procedure for compound 625. $^1$H NMR (400 MHz, DMSO-$d_6$) δ 7.50 (s, 1H), 7.00 (d, J=8.4 Hz, 2H), 6.85 (m, 1H), 6.59 (d, J=8.4 Hz, 2H), 4.35 (s, 2H), 4.15-4.09 (m, 2H), 3.41 (m, 1H), 3.25-3.11 (m, 2H), 2.90-2.76 (m, 2H), 2.63 (m, 1H), 2.31-2.23 (m, 2H), 1.91-1.80 (m, 2H), 1.49-1.34 (m, 2H). Mass (m/z): 480.2 [M+H]$^+$.

N-(4-((2-(2-azaspiro[3.3]heptan-2-yl)pyrimidin-5-yl)amino)benzyl)-5-oxopyrrolidine-3-carboxamide (713)

713

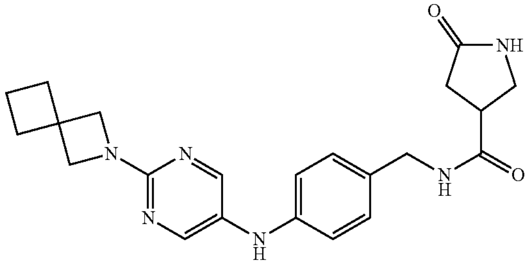

The title compound 713 (4.5 mg) was prepared in a total yield of 22.1% as a white solid from N-(4-(aminomethyl)phenyl)-2-(2-azaspiro[3.3]heptan-2-yl)pyrimidin-5-amine (14.8 mg, 0.05 mmol), 5-oxopyrrolidine-3-carboxylic acid (8.4 mg, 0.065 mmol), DIEA (19 mg, 0.15 mmol) and HATU (25 mg, 0.065 mmol) according to the procedure for compound 625. $^1$H NMR (400 MHz, DMSO-$d_6$) δ 7.66 (s, 1H), 7.58 (s, 1H), 7.03 (d, J=8.4 Hz, 2H), 6.71 (d, J=8.4 Hz, 2H), 4.13 (s, 2H), 3.96 (s, 4H), 3.38 (m, 1H), 3.27-3.11 (m, 2H), 2.31-2.25 (m, 2H), 2.17 (4, J=7.6 Hz, 4H), 1.86-1.76 (m, 2H). Mass (m/z): 407.2 [M+H]$^+$.

N-(4-((2-(2-azaspiro[3.4]octan-2-yl)pyrimidin-5-yl)amino)benzyl)-5-oxopyrrolidine-3-carboxamide (714)

714

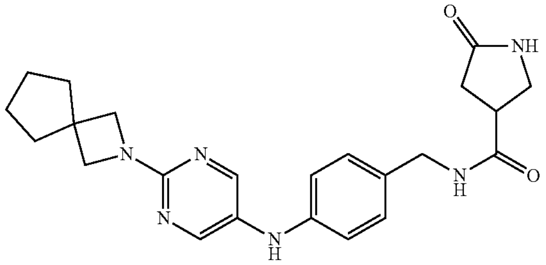

The title compound 714 (7.2 mg) was prepared in a total yield of 34.2% as a white solid from N-(4-(aminomethyl)phenyl)-2-(2-azaspiro[3.4]octan-2-yl)pyrimidin-5-amine (15.5 mg, 0.05 mmol), 5-oxopyrrolidine-3-carboxylic acid (8.4 mg, 0.065 mmol), DIEA (19 mg, 0.15 mmol) and HATU (25 mg, 0.065 mmol) according to the procedure for compound 625. $^1$H NMR (400 MHz, DMSO-$d_6$) δ 7.66 (s, 1H), 7.58 (s, 1H), 7.03 (d, J=8.4 Hz, 2H), 6.71 (d, J=8.4 Hz, 2H), 4.13 (s, 2H), 3.84 (s, 4H), 3.40 (m, 1H), 3.26-3.08 (m, 2H), 2.34-2.25 (m, 2H), 1.79 (t, J=6.8, 4H), 1.63-1.53 (m, 4H). Mass (m/z): 421.3 [M+H]$^+$.

N-(2-(2-(dimethylamino)ethyl)-4-((4-(4-(trifluoromethyl)piperidin-1-yl)phenyl)amino)benzyl)-5-oxopyrrolidine-3-carboxamide (715)

715

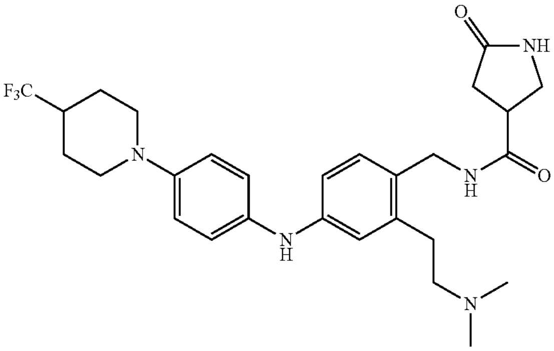

The title compound 715 (6.7 mg) was prepared in a total yield of 25.2% as a white solid from 4-(aminomethyl)-3-(2-(dimethylamino)ethyl)-N-(4-(4-(trifluoromethyl)piperidin-1-yl)phenyl)aniline (21.0 mg, 0.05 mmol). 5-oxopyrrolidine-3-carboxylic acid (8.4 mg, 0.065 mmol), DIEA (19 mg, 0.15 mmol) and HATU (25 mg, 0.065 mmol) according to the procedure for compound 625. $^1$H NMR (400 MHz, DMSO-$d_6$) δ 7.21 (s, 1H), 7.15-6.73 (m, 6H), 4.21 (s, 2H), 3.70-3.55 (m, 2H), 3.42 (m, 1H), 3.30-3.19 (m, 2H), 3.17-3.11 (m, 2H), 3.02-2.91 (m, 2H), 2.80 (s, 6H), 2.70-2.56 (m, 2H), 2.35-2.23 (m, 2H), 2.01 (m, 1H), 1.95-1.81 (m, 2H), 1.68-1.51 (m, 2H). Mass (m/z): 532.3 [M+H]$^+$.

N-(2-(2-methoxyethyl)-4-((4-(4-(trifluoromethyl)piperidin-1-yl)phenyl)amino)benzyl)-5-oxopyrrolidine-3-carboxamide (716)

716

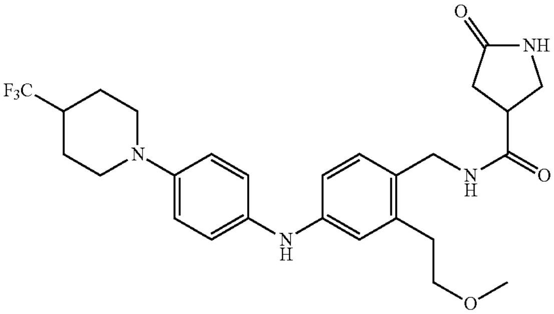

The title compound 716 (7.0 mg) was prepared in a total yield of 26.9% as a white solid from 4-(aminomethyl)-3-(2-methoxyethyl)-N-(4-(4-(trifluoromethyl)piperidin-1-yl)phenyl)aniline (20.3 mg, 0.05 mmol), 5-oxopyrrolidine-3-carboxylic acid (8.4 mg, 0.065 mmol), DIEA (19 mg, 0.15 mmol) and HATU (25 mg, 0.065 mmol) according to the procedure for compound 625. $^1$H NMR (400 MHz, DMSO-$d_6$) δ 7.05-6.66 (m, 7H), 4.18 (s, 2H), 3.68-3.55 (m, 2H), 3.47 (t, J=6.8 Hz, 2H), 3.40 (m, 1H), 3.24 (s, 3H), 3.22-3.11 (m, 2H), 2.79-2.54 (m, 4H), 2.42 (m, 1H), 2.36-2.21 (m, 2H), 1.94-1.78 (m, 2H), 1.65-1.49 (m, 2H). Mass (m/z): 519.3 [M+H]$^+$.

N-(4-((6-(4-isopropylpiperidin-1-yl)-2-methylpyridin-3-yl)amino)benzyl)-2,4-dioxoimidazolidine-1-carboxamide (717)

717

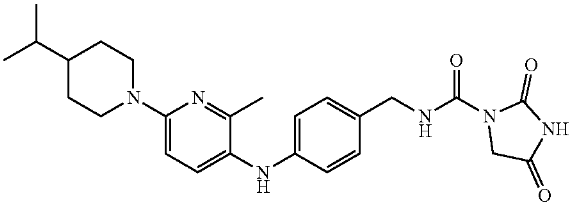

The title compound 717 (4.2 mg) was prepared in a total yield of 18.1% as a white solid from N-(4-(aminomethyl)phenyl)-6-(4-isopropylpiperidin-1-yl)-2-methylpyridin-3-amine (16.9 mg, 0.05 mmol), imidazolidine-2,4-dione (5.5 mg, 0.055 mmol), CDI (8.9 mg, 0.055 mmol) and DIEA (19.4 mg, 0.15 mmol) according to the procedure for compound 660. $^1$H NMR (400 MHz, DMSO-$d_6$) δ 7.26 (d, J=8.8 Hz, 1H), 7.05 (d, J=8.4 Hz, 2H), 6.62 (d, J=8.8 Hz, 1H), 6.51 (d, J=8.4 Hz, 2H), 4.28 (s, 2H), 4.22-4.19 (m, 2H), 4.16 (s, 2H), 2.68-2.56 (m, 2H), 2.20 (s, 3H), 1.75-1.65 (m, 2H), 1.49-1.37 (m, 1H), 1.21-1.13 (m, 3H), 0.88 (d, J=6.8 Hz, 6H). Mass (m/z): 465.3 [M+H]$^+$.

N-(4-((6-(4-isopropylpiperidin-1-yl)-2-methylpyridin-3-yl)amino)benzyl)-3,5-dioxopiperazine-1-carboxamide (718)

718

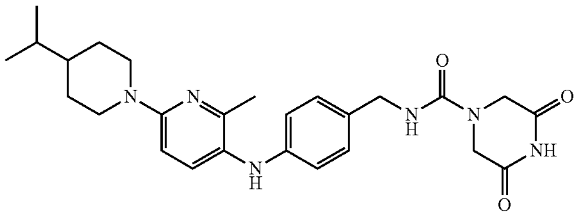

The title compound 718 (10.4 mg) was prepared in a total yield of 43.4% as a white solid from N-(4-(aminomethyl) phenyl)-6-(4-isopropylpiperidin-1-yl)-2-methylpyridin-3-amine (16.9 mg, 0.05 mmol), piperazine-2,6-dione (6.1 mg, 0.055 mmol), CDI (8.9 mg, 0.055 mmol) and DIEA (19.4 mg, 0.15 mmol) according to the procedure for compound 660. $^1H$ NMR (400 MHz, DMSO-$d_6$) δ 7.25 (d, J=8.8 Hz, 1H), 6.97 (d, J=8.4 Hz, 2H), 6.63 (d, J=8.8 Hz, 1H), 6.49 (d, J=8.4 Hz, 2H), 4.27 (s, 2H), 4.18 (s, 4H), 4.11-4.06 (m, 2H), 2.68-2.58 (m, 2H), 2.20 (s, 3H), 1.75-1.66 (m, 2H), 1.46-1.36 (m, 1H), 1.27-1.05 (m, 3H), 0.88 (d, J=6.8 Hz, 6H). Mass (m/z): 479.3 $[M+H]^+$.

N-(4-((4-(4-(2-methoxypropan-2-yl)piperidin-1-yl)-2-methylphenyl)amino)benzyl)-5-oxopyrrolidine-3-carboxamide (719)

719

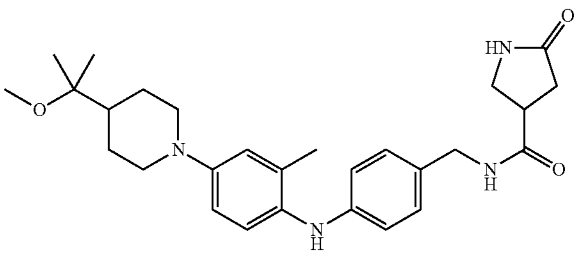

The title compound 719 (30.2 mg) was prepared in a total yield of 63.0% as a Sandybrown solid from N-(4-(aminomethyl)phenyl)-4-(4-(2-methoxypropan-2-yl)piperidin-1-yl)-2-methylaniline (36.7 mg, 0.1 mmol), 5-oxopyrrolidine-3-carboxylic acid (12.8 mg, 0.13 mmol), DIEA (39.0 mg, 0.3 mmol) and HATU (49.4 mg, 0.13 mmol) according to the procedure for compound 625. $^1H$ NMR (400 MHz, DMSO-$d_6$) δ 7.23-7.12 (m, 2H), 7.01-6.92 (m, 5H), 4.25 (s, 2H), 4.15-4.08 (m, 2H), 3.71-3.62 (m, 2H), 3.41 (m, 1H), 3.10 (s, 3H), 2.36-2.23 (m, 4H), 2.10 (s, 3H), 1.75-1.62 (m, 2H), 1.50 (m, 1H), 1.43-1.30 (m, 2H), 1.06 (s, 6H). Mass (m/z): 479.3 $[M+H]^+$.

N-(4-(aminomethyl)phenyl)-2-(4-(trifluoromethyl)piperidin-1-yl)pyrimidin-5-amine (720)

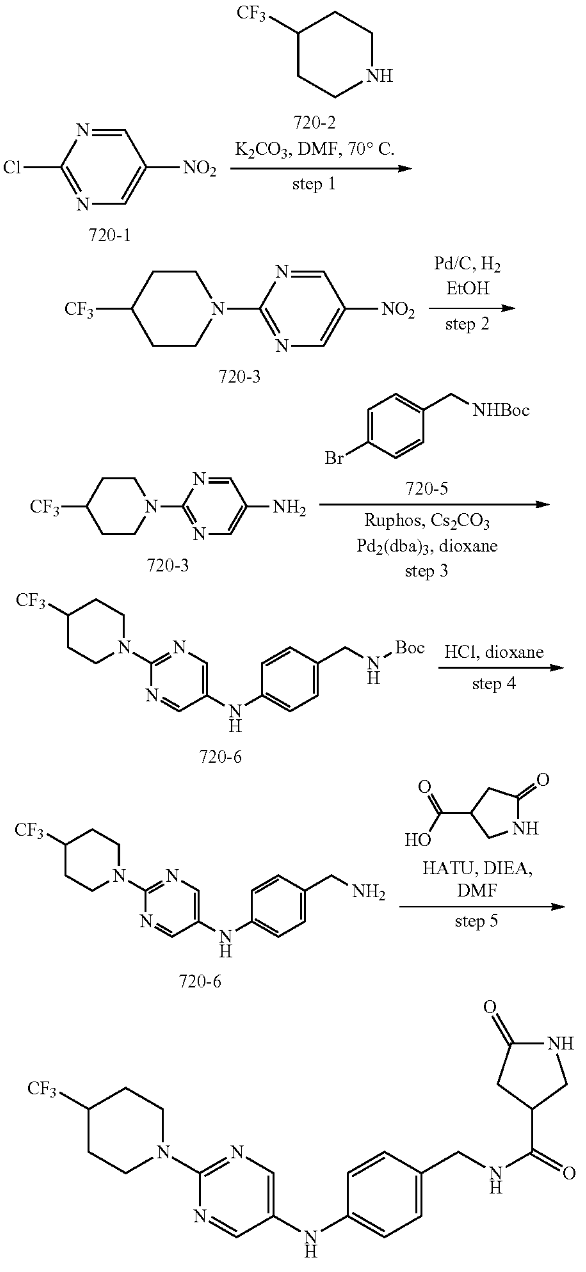

720

Step 1. Preparation of 5-nitro-2-(4-(trifluoromethyl)piperidin-1-yl)pyrimidine. To a solution of compound 720-1 (2 g, 12.6 mmol) in DMF (40 mL) was added $K_2CO_3$ (3.5 g, 25.2 mmol) and compound 720-2 (1.93 g, 12.6 mmol) at rt, then the mixture was stirred at 70° C. for 2 hrs. TLC showed the reaction was completed. The mixture was poured into $H_2O$ (150 mL). The mixture was filtered, the solid was collected and dried under reduced pressure to give 5-nitro-2-(4-(trifluoromethyl)piperidin-1-yl)pyrimidine 720-3 (2.2 g, 63% yield) as a yellow solid. MS (ESI) m/z 276.1 $[M+H]^+$.

Step 2. Preparation of 2-(4-(trifluoromethyl)piperidin-1-yl)pyrimidin-5-amine. To a solution of compound 720-3 (0.1 g, 0.4 mmol) in EtOH (5 mL) was added Pd/C (20 mg), then stirred under 1 atmosphere of $H_2$ at 25° C. for 2 hrs. Then the mixture was filtered and concentrated to give 2-(4-(trifluoromethyl)piperidin-1-yl)pyrimidin-5-amine 720-4 (0.1 g, 100% yield) as a brown solid. MS (ESI) m/z 246.1 $[M+H]^+$.

Step 3. Preparation of tert-butyl (4-((2-(4-trifluoromethyl) piperidin-1-yl)pyrimidin-5-yl)amino)benzyl)carbamate. To a stirred solution of compound 720-4 (0.1 g, 0.4 mmol) and compound 720-5 (0.12 g, 0.4 mmol) in dioxane under nitrogen was added $Cs_2CO_3$ (0.39 g, 1.2 mmol), tris(dibenzylideneacetone)dipalladium (0.037 g, 0.04 mmol) and Ruphos (38 mg, 0.08 mmol), then stirred at 90° C. for 16 hrs. Then the mixture was filtered and concentrated, the residue was purified by combi-flash with EA/PE (1:1) to afford tert-butyl (4-((2-(4-(trifluoromethyl)piperidin-1-yl)pyrimidin-5-yl)amino)benzyl)carbamate 720-6 (0.07 g, 38.5% yield) as a yellow solid. MS (ESI) m/z 452.3 $[M+H]^+$.

Step 4. Preparation of N-(4-(aminomethyl)phenyl)-2-(4-(trifluoromethyl)piperidin-1-yl)pyrimidin-5-amine. To a solution of compound 720-6 (0.07 g, 0.15 mmol) in DCM (2 mL) was added 4 N HCl in dioxane (2 mL) at rt. Then the mixture was stirred at rt for 1 h. LCMS showed the reaction was completed. The mixture was filtered, the solid was collected and dried to give N-(4-(aminomethyl)phenyl)-2-(4-(trifluoromethyl)piperidin-1-yl)pyrimidin-5-amine 720-7 (50 mg, % yield) as a brown solid. MS (ESI) m/z 352.2 $[M+H]^+$.

Step 5. Preparation of 5-oxo-N-(4-((2-(4-(trifluoromethyl)piperidin-1-yl)pyrimidin-5-yl)amino)benzyl)pyrrolidine-3-carboxamide (720) To a solution of compound 720-7 (0.05 g, 0.14 mmol), 5-oxopyrrolidine-3-carboxylic acid (22.1 mg, 0.17 mmol) in DMF (3 mL) stirred under nitrogen was added N,N,N',N'-Tetramethyl-O-(7-azabenzotriazol-1-yl)uronium (53.2 mg, 0.14 mmol) and DIEA (54 mg, 0.42 mmol). The reaction mixture was stirred at rt for 16 hrs. The mixture was poured into $H_2O$ (10 mL) and extracted with EA (10 mL*3), the organic layer was washed with brine, dried over $Na_2SO_4$, filtered and concentrated. The residue was purified by prep-HPLC to afford 720 (29 mg, 45% yield) as a yellow solid. MS (ESI) m/z 462.7 $[M+H]^+$ $^1H$ NMR (400 MHz, $CD_3OD$) δ 8.21 (s, 2H), 7.08 (d, J=8.0 Hz, 2H), 6.75 (d, J=8.0 Hz, 2H), 4.91-4.74 (m, 2H), 4.24 (s, 2H), 3.46-3.30 (m, 1H), 2.91-2.80 (m, 2H), 2.60-2.30 (m, 3H), 1.91-1.88 (m, 2H), 1.50-1.45 (m, 2H).

N-(4-((6-butylpyridin-3-yl)amino)benzyl)-5-oxopyrrolidine-3-carboxamide (721)

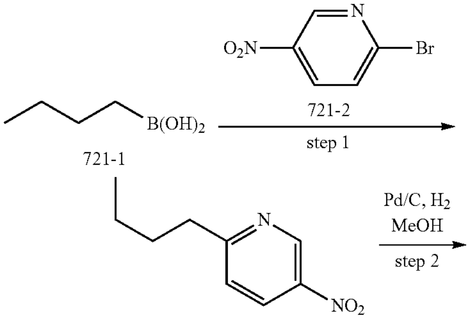

721-1

721-3

-continued

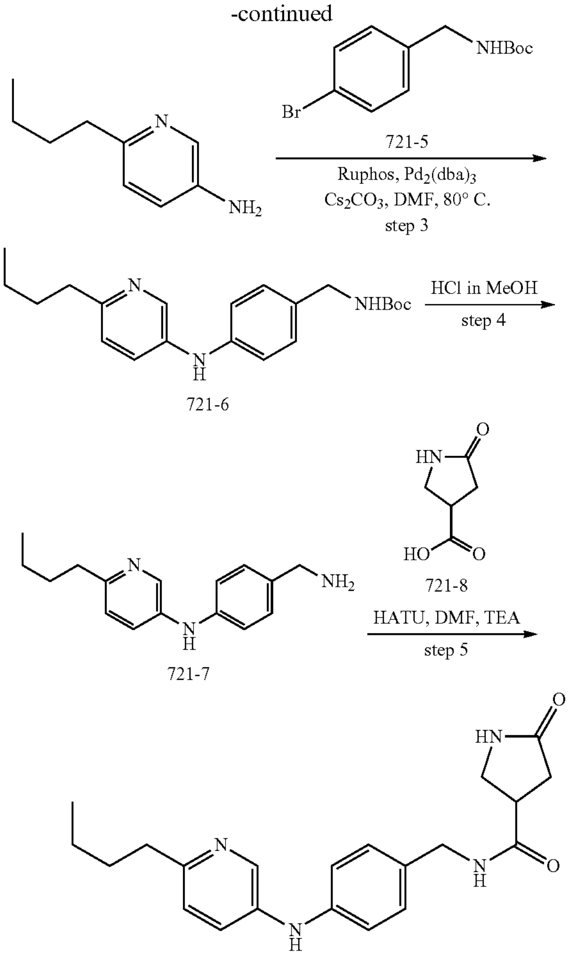

721

Step 1. Preparation of 2-butyl-5-nitropyridine (721-3) To a solution of n-butylboronic acid (1004 mg, 9.85 mmol), 2-bromo-5-nitropyridine (1000 mg, 4.93 mmol), $K_2CO_3$ (1361 mg, 9.85 mmol) in toluene/$H_2O$=10:1 (20 mL) was added palladium diacetate (110 mg, 0.49 mmol), tricyclohexyl phosphine (138 mg, 0.49 mmol), then was heated and stirred at 100° C. under $N_2$ for 16 hrs. After cooling to ambient temperature, concentrated under reduced pressure. The residue was purified by silica gel column to provide 2-butyl-5-nitropyridine 721-3 (520 mg, 58.58% yield) as a yellow solid. MS (ESI) m/z 181.2 $[M+H]^+$.

Step 2. Preparation of 6-butylpyridin-3-amine (721-4) To a solution of 2-butyl-5-nitropyridine (520 mg, 2.88 mmol) in MeOH (10 mL) was added Pd/C (200 mg, 10%), then was stirred under 1 atmosphere of $H_2$ at rt for 16 hrs, then filtered, the filtrate was concentrated under vacuum to give 6-butylpyridin-3-amine 721-4 (420 mg, 96.89% yield) as a yellow solid. MS (ESI) m/z 151.0 $[M+H]^+$.

Step 3. Preparation of tert-butyl (4-((6-butylpyridin-3-yl) amino)benzyl)carbamate (721-6) To a solution of compound 721-4 (420 mg, 2.79 mmol), compound 721-5 (1200 mg, 4.19 mmol), $Cs_2CO_3$ (1821 mg, 5.59 mmol) in 1,4-dioxane (20 mL) was added RuPhos (130 mg, 0.28 mmol), $Pd_2(dba)_3$ (256 mg, 0.28 mmol), then was heated and stirred at 90° C. under $N_2$ for 16 hrs. After cooling to ambient temperature, the mixture was concentrated under reduced pressure. The residue was purified by silica gel column to provide tert-butyl (4-((6-butylpyridin-3-yl)amino)benzyl)carbamate 721-6 (640 mg, 64.39% yield) as a yellow solid. MS (ESI) m/z 355.9 $[M+H]^+$.

Step 4. Preparation of N-(4-(aminomethyl)phenyl)-6-butylpyridin-3-amine (721-7). A solution of compound 721-6 (640 mg, 1.80 mmol) in HCl in 1,4-Dioxane (10 mL, 4 N) was stirred at rt for 16 hrs. then the solution was concentrated to dryness to give N-(4-(aminomethyl)phenyl)-6-butylpyridin-3-amine 721-7 (450 mg, 97.88% yield) as a white solid. MS (ESI) m/z 256.2 $[M+H]^+$.

Step 5. Preparation of N-(4-((6-butylpyridin-3-yl)amino)benzyl)-5-oxopyrrolidine-3-carboxamide (721). To a stirred solution of compound 721-7 (0.2 g, 0.78 mmol), 5-oxopyrrolidine-3-carboxylic acid (151 mg, 1.17 mmol) in DMF (3 mL) was added N,N,N',N'-Tetramethyl-O-(7-azabenzotriazol-1-yl)uronium (446 mg, 1.17 mmol) and TEA (237 mg, 2.35 mmol). The reaction mixture was stirred at 25° C. for 16 hrs. The mixture was poured into $H_2O$ (20 mL), extracted with EA (20 mL*2), the organic layer was washed by brine, dried over $Na_2SO_4$, filtered and concentrated. The residue was purified by prep-HPLC to afford 721 (72 mg, 25% yield) as a yellow solid. MS (ESI) m/z 367.2 $[M+H]^+$. $^1$H NMR (400 MHz, DMSO-$d_6$) δ 8.42 (s, 1H), 8.26-8.20 (m, 2H), 7.59 (s, 1H), 7.40 (dd, J=8.4, 2.8 Hz, 1H), 7.12 (dd, J=8.4, 4.8 Hz, 3H), 7.00 (d, J=8.5 Hz, 2H), 4.19 (d, J=5.8 Hz, 2H), 3.41 (s, 1H), 3.27-3.17 (m, 2H), 2.67-2.61 (m, 2H), 2.30 (dd, J=8.4, 3.3 Hz, 2H), 1.61 (dd, J=8.7, 6.5 Hz, 2H), 1.31 (dd, J=14.9, 7.4 Hz, 2H), 0.90 (t, J=7.4 Hz, 3H).

N-(4-((3-(2-aminoethoxy)-4-(4-(trifluoromethyl)piperidin-1-yl)phenyl)amino)benzyl)-5-oxopyrrolidine-3-carboxamide (722)

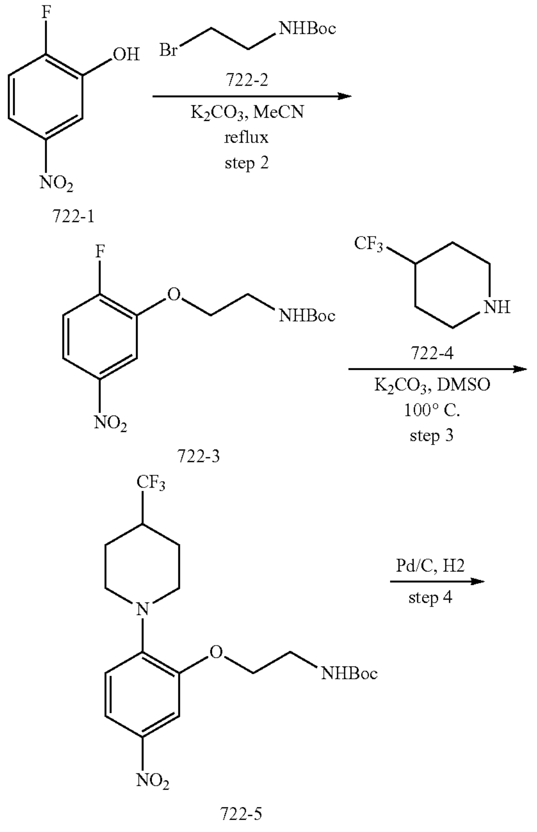

-continued

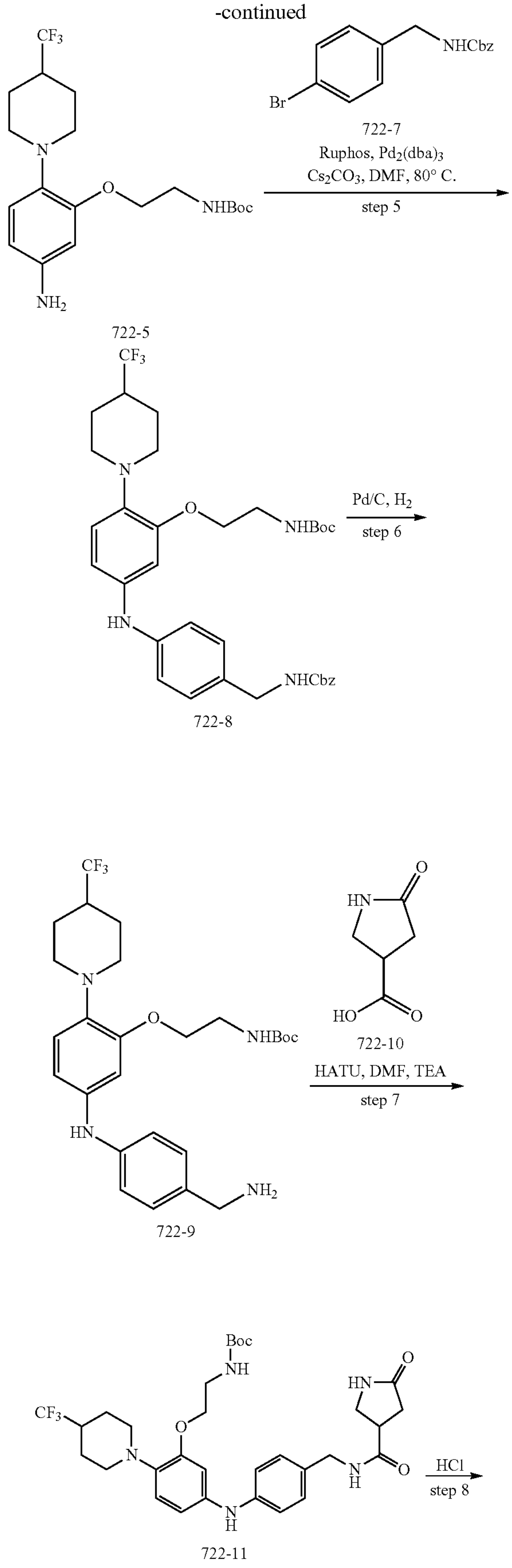

-continued

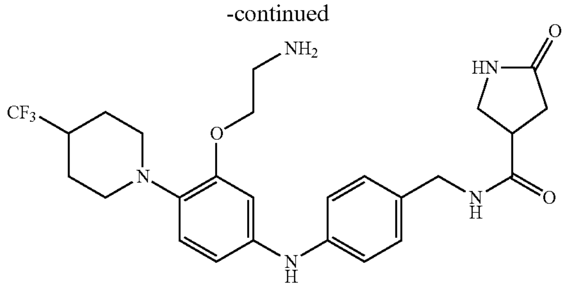

722

Step 1. Preparation of benzyl (4-bromobenzyl)carbamate (722-7) CbzCl (920 mg, 5.4 mmol) was added to a solution of (4-bromophenyl)methanamine hydrochloride (100 mg, 4.5 mmol), triethylamine (910 mg, 9.0 mmol) in DCM (50 mL), the mixture was allowed to react at 25° C. for 16 hrs, then solvent was removed under vacuum to give benzyl (4-bromobenzyl)carbamate 7 (900 mg, 62.22% yield) as a yellow solid. MS (ESI) m/z 341.6 $[M+H]^+$.

Step 2. Preparation of tert-butyl (2-(2-fluoro-5-nitrophenoxy)ethyl)carbamate (722-3) To a solution of compound 722-1 (3 g, 19.09 mmol), compound 722-2 (4.28 g, 19.09 mmol) in $CH_3CN$ (50 mL) was added $K_2CO_3$ (7.9 g, 57.29 mmol), then stirred at 80° C. for 16 hrs. After cooling to ambient temperature, filtered and concentrated, the residue was purified by combi-flash with EA/PE (1:3) to afford tert-butyl (2-(2-fluoro-5-nitrophenoxy)ethyl)carbamate 722-3 (5.3 g, 92.43% yield) as a yellow solid. MS (ESI) m/z 322.8 [M+Na]*.

Step 3. Preparation of tert-butyl (2-(5-nitro-2-(4-(trifluoromethyl)piperidin-1-yl)phenoxy)ethyl)carbamate (722-5) To a solution of 722-3 (5300 mg, 17.65 mmol), 722-4 (2703 mg, 17.65 mmol) in DMSO (50 mL) and water (2 mL) was added $K_2CO_3$ (7307 mg, 52.95 mmol), then stirred at 100° C. for 3 hrs. After cooling to ambient temperature, poured into water (150 mL), extracted with EA (50 mL*3). The combined organic layers were washed with brine (50 mL), dried over sodium sulfate, filtered and concentrated. The residue was purified by silica gel column to provide tert-butyl (2-(5-nitro-2-(4-(trifluoromethyl)piperidin-1-yl)phenoxy)ethyl)carbamate 722-5 (5100 mg, 66.67% yield) as a yellow solid. MS (ESI) m/z 434.1 $[M+H]^+$.

Step 4. Preparation of tert-butyl (2-(5-amino-2-(4-(trifluoromethyl)piperidin-1-yl)phenoxy)ethyl)carbamate (722-6) To a solution of compound 722-5 (5000 mg, 11.54 mmol) in MeOH (50 mL) was added Pd/C (1000 mg, 10%), then stirred under 1 atmosphere of $H_2$ for 16 hrs, then filtered, the filtrate was concentrated to dryness to give tert-butyl (2-(5-amino-2-(4-(trifluoromethyl)piperidin-1-yl)phenoxy)ethyl) carbamate 722-6 (5000 mg, 100% yield) as a yellow solid. MS (ESI) m/z 404.2 $[M+H]^+$.

Step 5. Preparation of tert-butyl (2-(5-((4-((((benzyloxy) carbonyl)amino)methyl)phenyl)amino)-2-(4-(trifluoromethyl)piperidin-1-yl)phenoxy)ethyl)carbamate (722-8) To a solution of compound 722-6 (190.46 mg, 0.59 mmol), compound 722-7 (200 mg, 0.4957 mmol), $Cs_2CO_3$ (323.02 mg, 0.99 mmol) in 1,4-dioxane (20 mL) was added RuPhos (23 mg, 0.04957 mmol), $Pd_2(dba)_3$ (45.39 mg, 0.04957 mmol), then was heated and stirred at 90° C. under $N_2$ for 16 hrs. After cooling to ambient temperature, concentrated under reduced pressure. The residue was purified by silica gel column to provide tert-butyl (2-(5-((4-((((benzyloxy) carbonyl)amino)methyl)phenyl)amino)-2-(4-(trifluoromethyl)piperidin-1-yl)phenoxy)ethyl)carbamate 722-8 (300 mg, 94.17% yield) as a yellow solid. MS (ESI) m/z 642.6 $[M+H]^+$.

Step 6. Preparation of tert-butyl (2-(5-((4-(aminomethyl) phenyl)amino)-2-(4-(trifluoromethyl)piperidin-1-yl)phenoxy)ethyl)carbamate (722-9) To a solution of compound 722-8 (220 mg, 0.34 mmol) in MeOH (20 mL) was added Pd/C (50 mg, 10%), then was allowed to attired at 1 atmosphere of $H_2$ for 16 hrs, then filtered, the filtrate was concentrated to dryness to give tert-butyl (2-(5-((4-(aminomethyl)phenyl)amino)-2-(4-(trifluoromethyl)piperidin-1-yl)phenoxy)ethyl)carbamate 722-9 (175 mg, 100% yield) as a yellow solid. MS (ESI) m/z 509.3 $[M+H]^+$. Step 7. Preparation of tert-butyl (2-(5-((4-((5-oxopyrrolidine-3-carboxamido)methyl)phenyl)amino)-2-(4-(trifluoromethyl)piperidin-1 -yl)phenoxy)ethyl)carbamate (722-11) To a attired solution of compound 722-9 (0.175 g, 0.3441 mmol), 5-oxopyrrolidine-3-carboxylic acid (53.31 mg, 0.41 mmol) in DMF (3 mL) was added N,N,N',N'-Tetramethyl-O-(7-azabenzotriazol-1-yl)uronium (196 mg, 0.516 mmol) and TEA (104.26 mg, 1.032 mmol). The reaction mixture was stirred at 25° C. for 16 hrs. The mixture was poured into $H_2O$ (15 mL) and extracted with EA (15 mL*3), the organic layer was washed by brine, dried over $Na_2SO_4$, filtered and concentrated. The residue was purified by silica gel column to provide tert-butyl (2-(5-((4-((5-oxopyrrolidine-3-carboxamido)methyl)phenyl)amino)-2-(4-(trifluoromethyl)piperidin-1-yl)phenoxy)ethyl)carbamate 722-11 (160 mg, 74.92% yield) as a yellow solid. MS (ESI) m/z 620.3 $[M+H]^+$.

Step 8. Preparation of N-(4-((6-butylpyridin-3-yl)amino) benzyl)-5-oxopyrrolidine-3-carboxamide (722) A solution of compound 722-11 (160 mg, 1.80 mmol) in HCl in 1,4-Dioxan (5 mL, 4 N) was stirred at 25° C. for 2 hrs. then was concentrated, the residue was purified by prep-HPLC to afford 722 (7.7 mg, 5.74% yield) as a yellow solid. MS (ESI) m/z 520.3 $[M+H]^+$.

$^1$H NMR (400 MHz, DMSO-$d_6$) δ 8.46 (t, J=5.8 Hz, 1H), 8.05 (s, 3H), 7.61 (s, 1H), 7.14 (d, J=8.4 Hz, 2H), 7.04 (d, J=8.4 Hz, 2H), 6.76 (d, J=2.3 Hz, 1H), 6.71 (dd, J=8.7, 2.3 Hz, 1H), 4.20 (d, J=3.2 Hz, 5H), 3.51 (s, 2H), 3.40 (d, J=8.7 Hz, 1H), 3.31-3.16 (m, 5H), 2.63 (s, 1H), 2.31 (d, J=8.5 Hz, 2H), 2.00 (d, J=10.5 Hz, 2H), 1.88 (s, 2H).

tert-butyl(4-((5-(4-(trifluoromethyl)piperidin-1-yl) pyrazin-2-yl)amino)benzyl) carbamate (723)

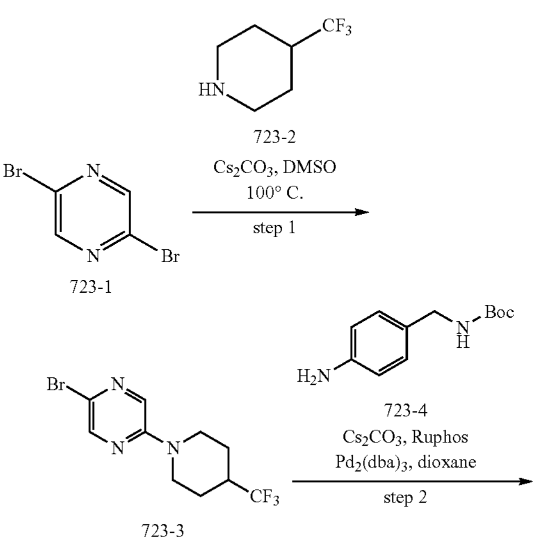

-continued

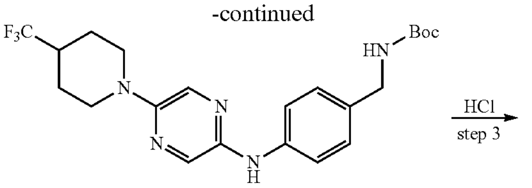

723-5

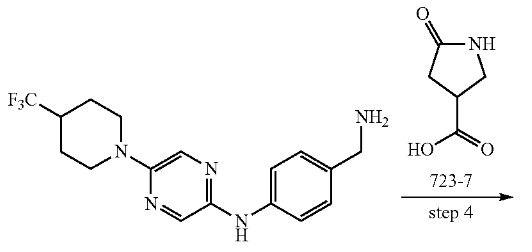

723-5

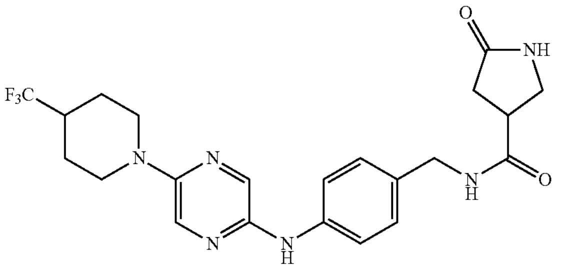

723

Step 1. Preparation of tert-butyl (4-((5-(4-(trifluoromethyl)piperidin-1-yl)pyrazin-2-yl)amino)benzyl)carbamate To a solution of compound 723-1 (3 g, 12.6 mmol) in DMSO (40 mL) was added $Cs_2CO_3$ (6.16 g, 18.9 mmol) and compound 723-2 (1.93 g, 12.6 mmol) at 25° C. Then the mixture was stirred at 100° C. for 2 hrs. LCMS showed the reaction was completed. The mixture was poured into $H_2O$ (120 mL). The mixture was filtered, the solid was collected and dried to give tert-butyl (4-((5-(4-(trifluoromethyl)piperidin-1-yl)pyrazin-2-yl)amino)benzyl)carbamate 723-3 (4 g, 100% yield) as a yellow solid. MS (ESI) m/z 310.0 $[M+H]^+$.

Step 2. Preparation of tert-butyl (4-((5-(4-(trifluoromethyl)piperidin-1-yl)pyrazin-2-yl)amino)benzyl)carbamate To a mixture solution of compound 723-3 (0.5 g, 1.6 mmol), compound 723-4 (0.39 g, 1.76 mmol) and dicyclohexyl (2',6'-diisopropoxybiphenyl-2-yl)phosphine (0.15 g, 0.32 mmol) in dioxane under nitrogen was added $Cs_2CO_3$ (1.04 g, 3.2 mmol) and tris(dibenzylideneacetone)dipalladium (0.15 g, 0.16 mmol). The reaction mixture was stirred at 90° C. for 16 hrs. Then the mixture was filtered and concentrated. The residue was purified by combi-flash with EA/PE (1:1) to afford to give tert-butyl (4-((5-(4-(trifluoromethyl) piperidin-1-yl)pyrazin-2-yl)amino)benzyl)carbamate 723-5 (0.3 g, 69.8% yield) as a yellow solid. MS (ESI) m/z 452.3 $[M+H]^+$.

Step 3. Preparation of N-(4-(aminomethyl)phenyl)-5-(4-(trifluoromethyl)piperidin-1-yl)pyrazin-2-amine To a solution of compound 723-5 (0.1 g, 0.22 mmol) in DCM (2 mL) was added 4 N HCl in dioxane (2 mL) at rt. Then the mixture was stirred at rt for 1 h. LCMS showed the reaction was completed. The mixture was filtered and dried to give N-(4-(aminomethyl)phenyl)-5-(4-(trifluoromethyl)piperidin-1-yl)pyrazin-2-amine 723-6 (70 mg, 89.7% yield) as a brown solid. MS (ESI) m/z 351.8 $[M+H]^4$.

Step 4. Preparation of 5-oxo-N-(4-((5-(4-(trifluoromethyl)piperidin-1-yl)pyrazin-2-yl)amino)benzyl)pyrrolidine-3-carboxamide (723) To a stirred solution of compound 723-6 (0.1 g, 0.3 mmol), 5-oxopyrrolidine-3-carboxylic acid 723-7 (40 mg, 0.3 mmol) in DMF (3 mL) under nitrogen was added N,N,N',N'-Tetramethyl-O-(7-azabenzotriazol-1-yl) uronium (110 mg, 0.3 mmol) and DIEA (0.06 g, 0.45 mmol). The reaction mixture was stirred at rt for 16 hrs. The mixture was poured into $H_2O$ (10 mL) and extracted with EA (10 mL*3), the organic layer was washed with brine, dried over $Na_2SO_4$, filtered and concentrated, the residue was purified by prep-HPLC to give 723 (40 mg) as a yellow solid. MS (ESI) m/z 463.2 $[M+H]^+$. $^1H$ NMR (300 MHz, $CD_3OD$) δ 7.88-7.75 (m, 2H), 7.37 (d, J=8.4 Hz, 2H), 7.11 (d, J=8.4 Hz, 2H), 4.25 (s, 2H), 4.14 (d, J=12.6 Hz, 2H), 3.50-3.40 (m, 2H), 2.74 (t, J=12.6 Hz, 2H), 2.61-2.30 (m, 4H), 1.91 (d, J=12.6 Hz, 2H), 1.66-1.52 (m, 2H).

N-(4-((2,2-dimethyl-2,3-dihydro-1H-inden-5-yl) amino) benzyl)-5-oxopyrrolidine-3-carboxamide (724)

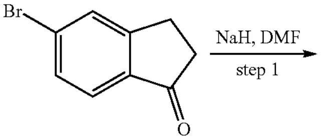

724-1

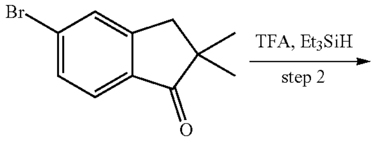

724-2

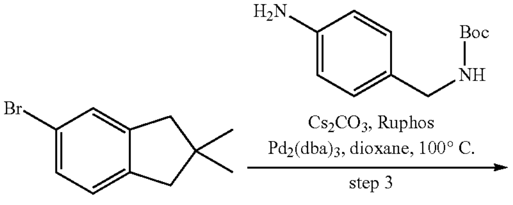

724-3

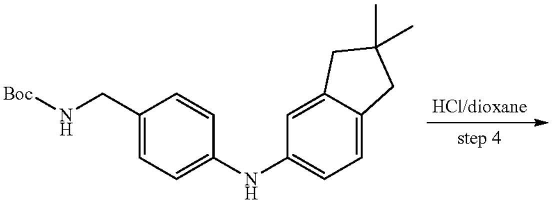

724-4

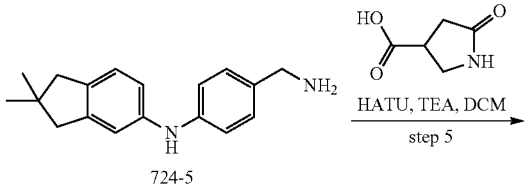

724-5

-continued

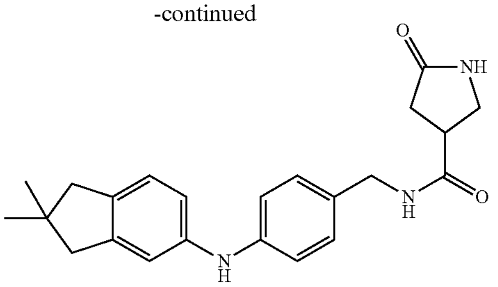

724

Step 1. Preparation of 5-bromo-2,2-dimethyl-2,3-dihydro-1H-Inden-1-one. To a solution of compound 724-1 (3 g, 14.2 mmol) in DMF (40 mL) was added NaH (0.78 g, 32.6 mmol) at 0° C. Then the mixture was stirred at 25° C. for 30 mins. Then was added Mel (4.44 g, 31.2 mmol). TLC showed the reaction was completed. The mixture was poured into $H_2O$ (120 mL) and extracted with EA (50 mL*3), the organic layer was washed with brine, dried over $Na_2SO_4$, filtered and concentrated to dryness to give 5-bromo-2,2-dimethyl-2,3-dihydro-1H-inden-1-one 724-2 (2.4 g, 70.6% yield) as a yellow oil.

Step 2. Preparation of 5-bromo-2,2-dimethyl-2,3-dihydro-1H-indene To a solution of compound 724-2 (2.4 g, 10 mmol) in TFA (10 mL) was added $Et_3SiH$ (10 mL). The reaction mixture was stirred at 70° C. for 2 hrs. Then the mixture was poured into $H_2O$ (50 mL) and extracted with EA (30 mL*2), the organic layer was washed with brine, dried over $Na_2SO_4$, filtered and concentrated. The residue was purified by combi-flash with EA/PE (1:4) to afford to give 5-bromo-2,2-dimethyl-2,3-dihydro-1H-indene 724-3 (2 g, 80% yield) as a yellow solid. $^1H$ NMR (400 MHz, $CD_3OD$) δ7.28 (s, 1H), 7.24-7.20 (m, 1H), 7.01 (d, J=7.9 Hz, 1H), 2.69 (s, 2H), 2.64 (s, 2H), 1.13 (s, 6H).

Step 3. Preparation of tert-butyl (4-((2,2-dimethyl-2,3-dihydro-1H-inden-5-yl)amino) benzyl)carbamate (724-4) A mixture solution of 5-bromo-2,2-dimethyl-2,3-dihydro-1H-indene (1 g, 4.4 mmol), tert-butyl (4-((2,2-dimethyl-2,3-dihydro-1H-inden-5-yl)amino)benzyl)carbamate (1.08 g, 4.8 mmol), $Cs_2CO_3$ (4.3 g, 13.2 mmol), Ruphos (410 mg, 0.8 mmol) and $Pd_2(dba)_3$ (400 mg, 0.4 mmol)) in dioxane (50 mL) was stirred at 100° C. under $N_2$ for 16 hrs. Then the solvent was removed under reduced pressure, the residue was diluted with EA (50 mL), washed with water (50 mL×3), dried with $Na_2SO_4$, filtered and evaporated. The residue was purified by column chromatography to give tert-butyl (4-((2,2-dimethyl-2,3-dihydro-1H-inden-5-yl) amino)benzyl)carbamate 724-4 (900 mg, 52.27%). Mass (m/z): 366.7 $[M+H]^+$.

Step 4. Preparation of N-(4-((2,2-dimethyl-2,3-dihydro-1H-inden-5-yl)amino)benzyl)-5-oxopyrrolidine-3-carboxamide (724-5) A solution of tert-butyl (4-((2,2-dimethyl-2,3-dihydro-1H-inden-5-yl)amino)benzyl)carbamate (900 mg, 2.45 mmol) in 4 N HCl dioxane was stirred at rt for 2 hrs. Then the solvent was removed under vacuo to give N-(4-((2,2-dimethyl-2,3-dihydro-1H-inden-5-yl)amino) benzyl)-5-oxopyrrolidine-3-carboxamide 724-5 (800 mg, 98.7%). Mass (m/z): 366.7 $[M+H]^+$.

Step 5. Preparation of N-(4-((2,2-dimethyl-2,3-dihydro-1H-inden-5-yl)amino)benzyl)-5-oxopyrrolidine-3-carboxamide (724) A mixture solution of N-(4-((2,2-dimethyl-2,3-dihydro-1H-inden-5-yl)amino)benzyl)-5-oxopyrrolidine-3-carboxamide (200 mg, 0.66 mmol), 5-oxopyrrolidine-3-carboxylic acid (103 mg, 0.8 mmol), TEA (258 mg, 1.99 mmol) and HATU (506 mg, 1.33 mmol) in DCM (20 mL) was stirred at rt for 2 hrs. Then the solvent was removed under vacuo, the residue was diluted with EA (20 mL), washed with water (20 mL×3), dried with $Na_2SO_4$, filtered and evaporated. The residue was purified by column chromatography to give 724 (90 mg). Mass (m/z): 377.8 $[M+H]^+$. $^1H$ NMR (400 MHz, $CD_3OD$) δ 7.13-7.08 (m, 2H), 7.01-6.94 (m, 3H), 6.88 (s, 1H), 6.82 (dd, J=8.0, 2.1 Hz, 1H), 4.27 (s, 2H), 3.57 (dd, J=9.9, 8.9 Hz, 1H), 3.48 (dd, J=9.9, 6.5 Hz, 1H), 2.65 (dd, J=5.8, 2.9 Hz, 4H), 2.53 (qd, J=16.9, 8.6 Hz, 2H), 1.14 (s, 6H).

(S)—N-(4-((2,2-dimethyl-2,3-dihydro-1H-inden-5-yl)amino)benzyl)-2-oxoimidazolidine-4-carboxamide (725)

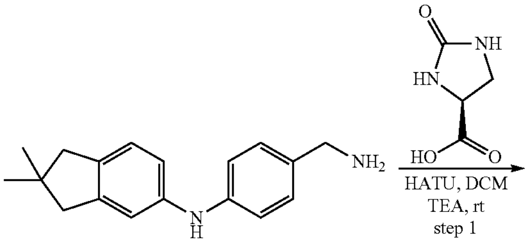

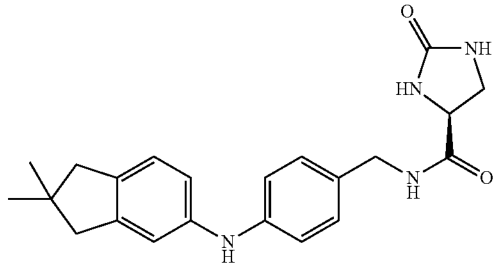

725

Step 1. Preparation of tert-butyl (4-((2,2-dimethyl-2,3-dihydro-1H-inden-5-yl)amino)benzyl)carbamate (725) A mixture solution of N-(4-((2,2-dimethyl-2,3-dihydro-1H-inden-5-yl)amino)benzyl)-5-oxopyrrolidine-3-carboxamide (200 mg, 0.66 mmol), (S)-2-oxoimidazolidine-4-carboxylic acid (103 mg, 0.8 mmol), TEA (258 mg, 1.99 mmol) and HATU (506 mg, 1.33 mmol) in DCM (20 mL) was stirred at rt for 2 hrs. Then the solvent was removed under vacuo, the residue was diluted with EA (20 mL), washed with water (10 mL×3), dried with $Na_2SO_4$, filtered and evaporated. The residue was purified by prep-HPLC to get 725 (61 mg, 21.47%). Mass (m/z): 378.8 $[M+H]^+$. $^1H$ NMR (400 MHz, $CD_3OD$) δ 7.15-7.10 (m, 2H), 7.01-6.94 (m, 3H), 6.88 (s, 1H), 6.82 (dd, J=8.0, 2.1 Hz, 1H), 4.31 (s, 2H), 4.29-4.26 (m, 1H), 3.78 (dd, J=10.1, 9.4 Hz, 1H), 3.43 (dd, J=9.3, 6.5 Hz, 1H), 2.66-2.62 (m, 4H), 1.14 (s, 6H).

N-(4-((3,5-difluoro-4-(piperidin-1-yl)phenyl)amino) benzyl)-5-oxopyrrolidine-3-carboxamide (726)

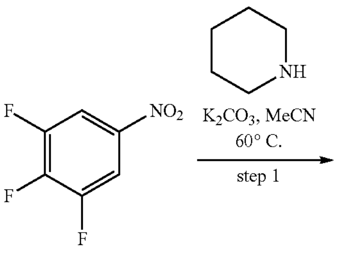

726-1

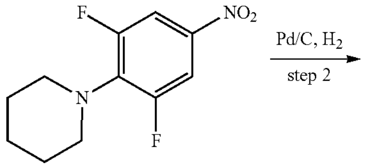

726-2

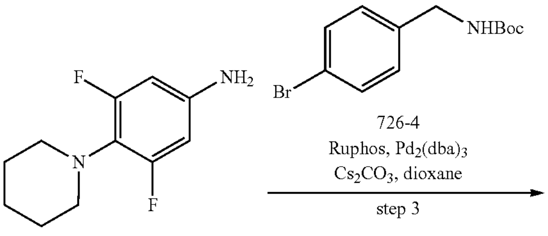

726-3

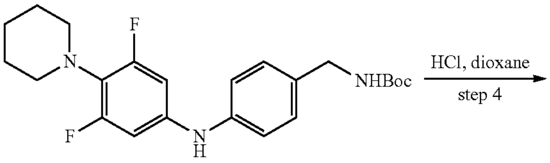

726-5

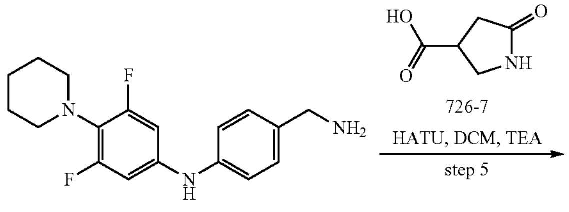

726-6

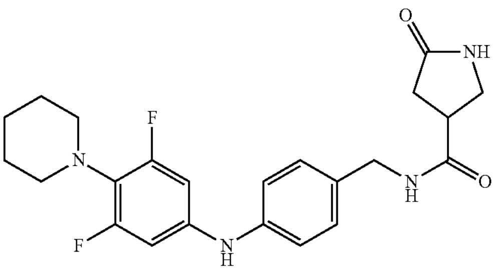

726

Step 1. Preparation of 1-(2,6-difluoro-4-nitrophenyl)piperidine (726-2) A mixture solution of 1,2,3-trifluoro-5-nitrobenzene (1 g, 5.65 mmol), piperidine (962 mg, 11.3 mmol) and $K_2CO_3$ (2.36 g, 16.8 mmol) in acetonitrile (50 mL) was stirred at 60° C. for 2 hrs. Then the residue was diluted with EA (200 mL), washed with water (100 mL×3), dried with Na2SO4, filtered and evaporated. The residue was purified by column chromatography to afford 1-(2,6-difluoro-4-nitrophenyl)piperidine 726-2 (1.5 g, 100/u).

Step 2. Preparation of 3,5-difluoro-4-(piperidin-1-yl)aniline (726-3) To a solution of 1-(2,6-difluoro-4-nitrophenyl) piperidine (1.5 g, 5.6 mmol) in THF was added Pd/C (200 mg), then the mixture was stirred for 16 h at rt under 1 atmosphere of $H_2$. Then filtered, the filtrate was concentrated under vacuo to afford 3,5-difluoro-4-(piperidin-1-yl) aniline 726-3 (1.3 g, 98.39%). Mass (m/z): 212.9 $[M+H]^+$.

Step 3. Preparation of tert-butyl (4-((3,5-difluoro-4-(piperidin-1-yl)phenyl)amino)benzyl)carbamate (726-5) A mixture solution of 3,5-difluoro-4-(piperidin-1-yl)aniline (500 mg, 2.36 mmol), tert-butyl (4-bromobenzyl)carbamate (809 g, 2.83 mmol), $Cs_2CO_3$ (2.3 g, 7.07 mmol), Ruphos (220 mg, 0.47 mmol) and $Pd_2(dba)_3$ (216 mg, 0.24 mmol)) in dioxane (50 mL) was stirred for 16 h at 100° C. under $N_2$. Then the solvent was removed under vacuo, the residue was diluted with EA (50 mL), washed with water (50 mL×3), dried with $Na_2SO_4$, filtered and evaporated. The residue was purified by column chromatography to give tert-butyl (4-((3,5-difluoro-4-(piperidin-1-yl)phenyl)amino)benzyl)carbamate 726-5 (1.2 g, 97.6%). Mass (m/z): 417.8 $[M+H]^+$.

Step 4. Preparation of N-(4-(aminomethyl)phenyl)-3,5-difluoro-4-(piperidin-1-yl)aniline (726-6) A solution of tert-butyl (4-((3,5-difluoro-4-(piperidin-1-yl)phenyl)amino)benzyl)carbamate (1.2 g, 2.3 mmol) in 4 N HCl in dioxane (50 mL) was stirred at rt for 2 hrs. Then the solvent was re moved under vacuo to give N-(4-(aminomethyl)phenyl)-3,5-difluoro-4-(piperidin-1-yl)aniline 726-6 (1 g, 96.55%). Mass (m/z): 317.8 $[M+H]^+$.

Step 5. Preparation of N-(4-((3,5-difluoro-4-(piperidin-1-yl)phenyl)amino)benzyl)-5-oxopyrrolidine-3-carboxamide (726) A mixture solution of N-(4-(aminomethyl)phenyl)-3,5-difluoro-4-(piperidin-1-yl)aniline (100 mg, 0.28 mmol), 5-oxopyrrolidine-3-carboxylic acid (44 mg, 0.34 mmol), TEA (86 mg, 0.85 mmol) and HATU (216 mg, 0.57 mmol) in DCM (20 mL) was stirred at rt for 2 hrs. Then the solvent was removed under vacuo, the residue was diluted with EA (20 mL), washed with water (10 mL×3), dried with $Na_2SO_4$, filtered and evaporated. The residue was purified by prep-H PLC to give 726 (45.6 mg, 37.44%). Mass (m/z): 429.2 $[M+H]^+$. $^1H$ NMR (400 MHz, $CD_3OD$) δ 7.21 (d, J=8.4 Hz, 2H), 7.05 (d, J=8.1 Hz, 2H), 6.54 (d, J=11.6 Hz, 2H), 4.31 (s, 2H), 3.58 (dd, J=9.8, 8.9 Hz, 11H), 3.49 (dd, J=9.9, 6.4 Hz, 1H), 3.12 (br, 4H), 2.58-2.47 (m, 2H), 1.70 (br, 4H), 1.58 (br, 2H).

(R)—N-(4-((3,5-difluoro-4-(piperidin-1-yl)phenyl) amino)benzyl)pyrrolidine-2-carboxamide (727)

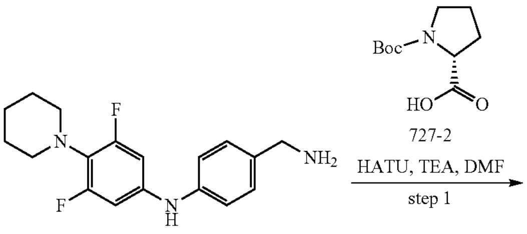

727-1

-continued

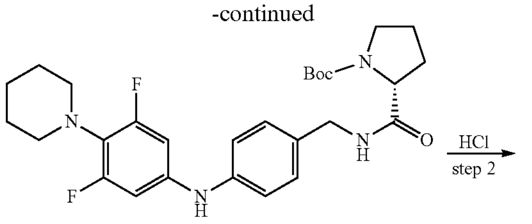

727-3

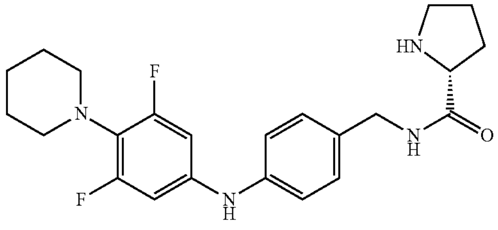

727

Step 1. Preparation of tert-butyl (R)-2-((4-((3,5-difluoro-4-(piperidin-1-yl)phenyl)amino)benzyl)carbamoyl)pyrrolidine-1-carboxylate (727-3) To a stirred solution of compound 727-1 (0.1 g, 0.3151 mmol), compound 727-2 (68.14 mg, 0.3151 mmol) in DMF (3 mL) was added N,N,N',N'-Tetramethyl-O-(7-azabenzotriazol-1-yl)uronium (119.8 mg, 0.3151 mmol) and TEA (95.6 mg, 0.9453 mmol). The reaction mixture was stirred at 25° C. for 2 hrs. The mixture was poured into $H_2O$ (10 mL) and extracted with EA (15 mL*2), the organic layer was washed by brine, dried over $Na_2SO4$, filtered and concentrated. The residue was purified by silica gel column to provide tert-butyl (R)-2-((4-((3,5-difluoro-4-(piperidin-1-yl)phenyl)amino)benzyl)carbamoyl)pyrrolidine-1-carboxylate 727-3 (90 mg, 55.38% yield) as a yellow solid. MS (ESI) m/z 620.3 $[M+H]^+$.

Step 2. Preparation of (R)—N-(4-((3,5-difluoro-4-(piperidin-1-yl)phenyl)amino)benzyl)pyrrolidine-2-carboxamide (727) A solution of compound 727-3 (160 mg, 1.80 mmol) in HCl in 1,4-Dioxane (5 mL, 4 N) was stirred at 25° C. for 2 hrs. then concentrated, the residue was purified by prep-HPLC to afford 727 (16.7 mg, 23.09% yield) as a yellow solid. MS (ESI) m/z 414.7 $[M+H]^+$. $^1H$ NMR (400 MHz, DMSO-$d_6$) δ 8.49 (s, 1H), 8.37 (s, 1H), 8.19 (s, 1H), 7.16 (d, J=8.4 Hz, 2H), 7.04 (d, J=8.5 Hz, 2H), 6.56 (d, J=11.7 Hz, 2H), 4.22 (d, J=5.9 Hz, 2H), 3.71 (d, J=6.6 Hz, 2H), 2.93 (d, J=5.0 Hz, 6H), 2.54 (d, J=5.0 Hz, 1H), 2.06 (d, J=11.1 Hz, 1H), 1.68 (dd, J=11.4, 5.3 Hz, 4H), 1.60-1.45 (m, 6H).

N-(2-fluoro-4-((2-(4-isopropylpiperidin-1-yl)pyrimidin-5-yl)amino)benzyl)-5-oxopyrrolidine-3-carboxamide (728)

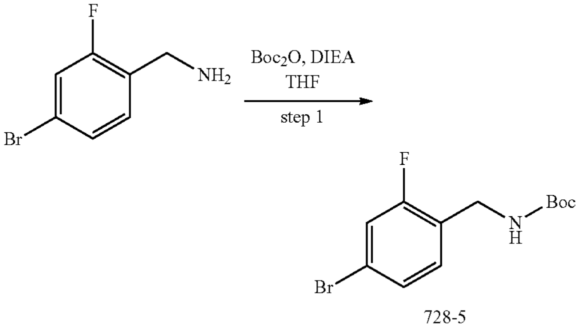

728-5

-continued

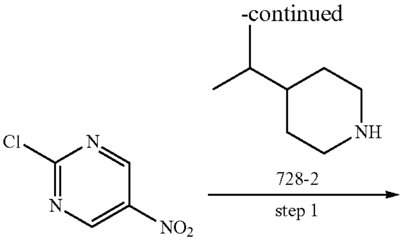

728-1

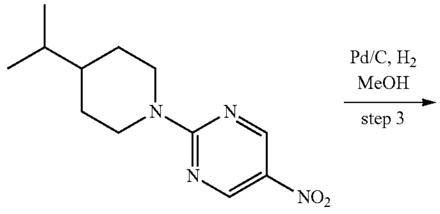

728-3

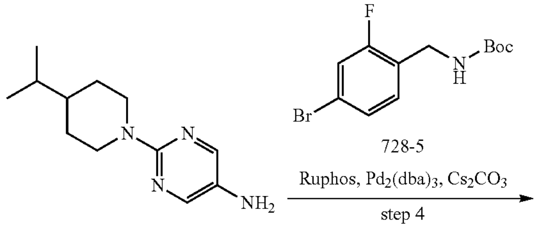

728-4

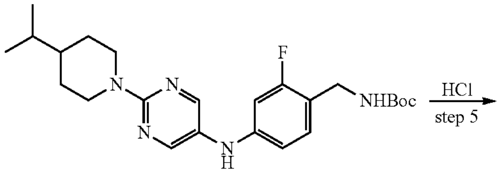

728-6

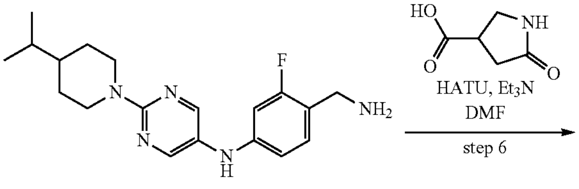

728-7

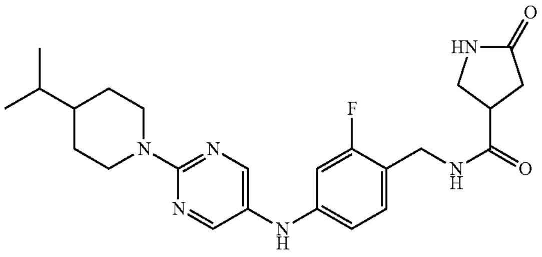

728

Step 1. Preparation of tert-butyl (4-bromo-2-fluorobenzyl)carbamate (728-5) (Boc)2O (427.9 mg, 1.96 mmol) was added to a solution of (4-bromo-2-fluorophenyl)methanamine (200 mg, 0.98 mmol), DIEA (380 mg, 2.94 mmol) in THF (10 mL), then was stirred at rt for 16 hrs, the solvent was removed under vacuum, the residue was purified by combi-flash with EA/PE (1:3) to afford to give tert-butyl (4-bromo-2-fluorobenzyl)carbamate 728-5 (0.18 g, 60.17% yield) as a yellow solid. MS (ESI) m/z 326 $[M+Na]^+$.

Step 2. Preparation of 2-(4-isopropylpiperidin-1-yl)-5-nitropyrimidine (728-3) To a solution of compound 728-1 (3 g, 18.8 mmol), compound 728-2 (2.39 g, 18.8 mmol) in 1,4-dioxane (50 mL) was added $Cs_2CO_3$ (12.25 g, 37.61 mmol), then stirred at 100° C. for 2 hrs. After cooling to ambient temperature, filtered and concentrated. The residue was purified by combi-flash with EA/PE (1:3) to afford to give 2-(4-isopropylpiperidin-1-yl)-5-nitropyrimidine 728-3 (3.6 g, 76.48% yield) as a yellow solid. MS (ESI) m/z 251.2 $[M+H]^+$.

Step 3. Preparation of 2-(4-isopropylpiperidin-1-yl)pyrimidin-5-amine (728-4) To a solution of compound 728-3 (3600 mg, 14.4 mmol) in EtOAc (50 mL) was added Pd/C (360 mg, 10%), then was stirred under 1 atmosphere of $H_2$ for 16 hrs, then filtered, solvent was removed under vacuum to give 2-(4-isopropylpiperidin-1-yl)pyrimidin-5-amine 728-4 (3000 mg, 94.44% yield) as a yellow solid. MS (ESI) m/z 221.0 $[M+H]^+$.

Step 4. Preparation of tert-butyl (2-fluoro-4-((2-(4-isopropylpiperidin-1-yl)pyrimidin-5-yl)amino)benzyl)carbamate (728-6) To a solution of compound 728-4 (100 mg, 0.45 mmol), compound 728-5 (138.5 mg, 0.45 mmol), $Cs_2CO_3$ (295.8 mg, 0.90 mmol) in toluene (20 mL) was added RuPhos (42 mg, 0.091 mmol), $Pd2(dba)_3$ (41.5 mg, 0.04539 mmol), then was heated and stirred at 80° C. under $N_2$ for 16 hrs. After cooling to ambient temperature, concentrated under reduced pressure. The residue was purified by silica gel column to provide tert-butyl (2-fluoro-4-((2-(4-isopropylpiperidin-1-yl)pyrimidin-5-yl)amino)benzyl)carbamate 728-6 (110 mg, 54.64% yield) as a yellow solid. MS (ESI) m/z 443.8 $[M+H]^+$.

Step 5. Preparation of N-(4-(aminomethyl)-3-fluorophenyl)-2-(4-isopropylpiperidin-1-yl)pyrimidin-5-amine (728-7) A solution of compound 728-6 (110 mg, 0.25 mmol) in HCl in 1,4-Dioxane (10 mL, 4 N) was stirred at 25° C. for 1 h. then concentrated to dryness to give N-(4-(aminomethyl)-3-fluorophenyl)-2-(4-isopropylpiperidin-1-yl)pyrimidin-5-amine 728-7 (95 mg, 100% yield) as a white solid. MS (ESI) m/z 343.8 $[M+H]^+$.

Step 6. Preparation of N-(2-fluoro-4-((2-(4-isopropylpiperidin-1-yl)pyrimidin-5-yl)amino)benzyl)-5-oxopyrrolidine-3-carboxamide (728) To a stirred solution of compound 728-7 (95 mg, 0.25 mmol), 5-oxopyrrolidine-3-carboxylic acid (32 mg, 0.25 mmol) in DMF (3 mL) was added N,N,N',N'-Tetramethyl-O-(7-azabenzotriazol-1-yl)uronium (95 mg, 0.25 mmol) and TEA (75.9 mg, 0.75 mmol). The reaction mixture was stirred at 25° C. for 16 hrs. The mixture was poured into $H_2O$ (10 mL) and extracted with EA (10 mL*3), the organic layer was washed by brine, dried over $Na_2SO_4$, filtered and concentrated. The residue was purified by prep-HPLC to afford 728 (35.3 mg, 31% yield) as a yellow solid. MS (ESI) m/z 455.2 $[M+H]^+$.

$^1H$ NMR (400 MHz, DMSO-$d_6$) δ 8.29 (t, J=5.6 Hz, 1H), 8.19 (s, 2H), 7.81 (s, 1H), 7.53 (s, 1H), 7.03 (t, J=8.6 Hz, 1H), 6.48 (dd, J=8.3, 2.2 Hz, 1H), 6.40 (dd, J=12.6, 2.2 Hz, 1H), 4.62 (d, J=13.1 Hz, 2H), 4.12 (d, J=5.5 Hz, 2H), 3.34 (t, J=8.5 Hz, 1H), 3.19-3.11 (m, 2H), 2.73 (td, J=12.8, 2.4 Hz, 2H), 2.23 (dd, J=8.5, 1.9 Hz, 2H), 1.66 (d, J=10.7 Hz, 2H), 1.39 (dd, J=13.2, 6.6 Hz, 1H), 1.24-1.04 (m, 3H), 0.83 (d, J=6.8 Hz, 6H).

N-(4-((3,5-difluoro-4-(4-(trifluoromethyl)piperidin-1-yl)phenyl)amino)benzyl)-2-oxopyrrolidine-3-carboxamide (729)

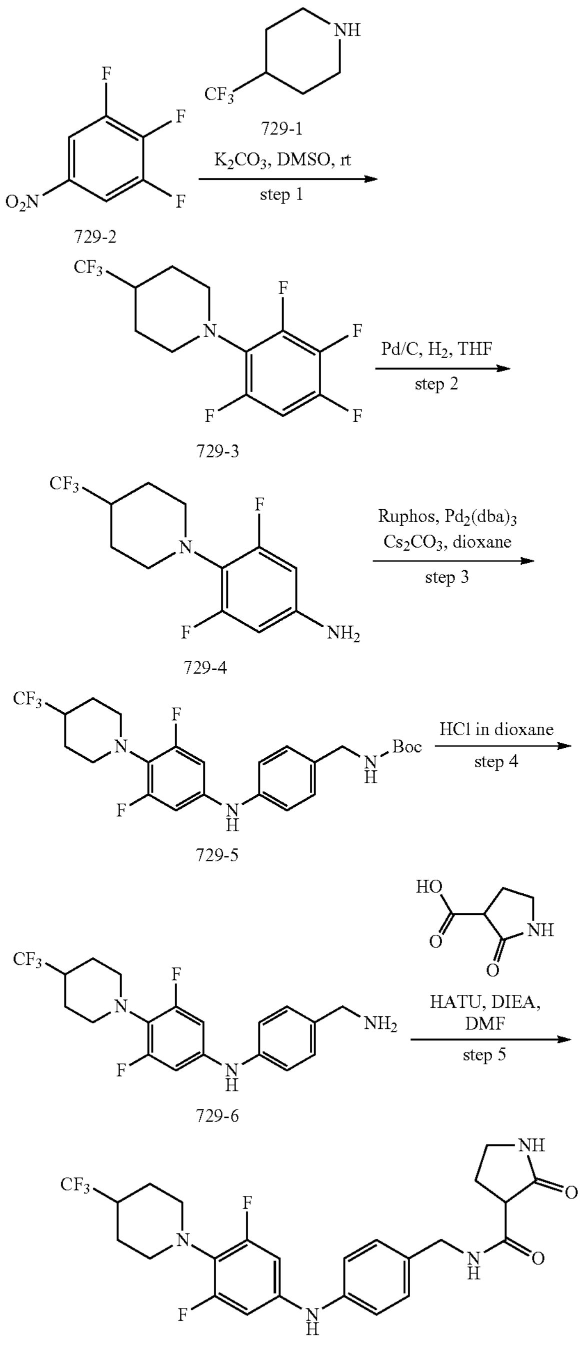

Step 1. Preparation of 1-(2,6-difluoro-4-nitrophenyl)-4-(trifluoro methyl)piperidine To a solution of compound 729-1 (4.75 g, 31 mmol) in DMSO (50 mL) was added $K_2CO_3$ (5.8 g, 42.3 mmol) and 1,2,3-trifluoro-5-nitrobenzene 729-2 (5 g, 28.2 mmol) at rt. Then the mixture was stirred at rt for 4 hrs. TLC showed the reaction was completed. The mixture was filtered and dried to give 1-(2,6- difluoro-4-nitrophenyl)-4-(trifluoro methyl)piperidine 729-3 (6 g, 68.5% yield) as a yellow solid. MS (ESI) m/z 310.07 $[M+H]^+$.

Step 2. Preparation of 3,5-difluoro-4-(4-(trifluoromethyl) piperidin-1-yl)aniline To a solution of compound 729-3 (6 g, 19.3 mmol) in THF (100 mL) was added Pd/C (1 g) at 25° C. Then the mixture was stirred at 25° C. under 1 atmosphere of $H_2$ overnight. Then the mixture was filtered and concentrated. The residue was purified by combi-flash with EA/PE (1:0) to afford to give 3,5-difluoro-4-(4-(trifluoromethyl)piperidin-1-yl)aniline 729-4 (3.5 g, 64% yield) as a brown solid. MS (ESI) m/z 281.2 $[M+H]^+$.

Step 3. Preparation of tert-butyl (4-((3,5-difluoro-4-(4-(trifluoromethyl)piperidin-1-yl)phenyl)amino)benzyl)carbamate To a stirred solution of compound 729-4 (3.5 g, 12.5 mmol), tert-butyl (4-bromobenzyl)carbamate (3.59 g, 12.5 mmol) and dicyclohexyl(2',6'-diisopropoxybiphenyl-2-yl) phosphine (1.17 g, 2.5 mmol) in dioxane under nitrogen was added $Cs_2CO_3$ (8.15 g, 25 mmol) and tris(dibenzylideneacetone)dipalladium (1.14 g, 1.25 mmol). The reaction mixture was stirred at 90° C. for 16 hrs. Then the mixture was filtered and concentrated. The residue was purified by combi-flash with EA/PE (1:1) to afford to give tert-butyl (4-((3,5-difluoro-4-(4-(trifluoromethyl)piperidin-1-yl)phenyl)amino)benzyl)carbamate 729-5 (1.2 g, 19.8% yield) as a yellow solid. MS (ESI) m/z 485.6 $[M+H]^+$.

Step 4. Preparation of N-(4-(aminomethyl)phenyl)-3,5-difluoro-4-(4-(trifluoromethyl)piperidin-1-yl)aniline To a solution of compound 729-5 (1.2 g, 2.5 mmol) in DCM (5 mL) was added 4 N HCl in dioxane (5 mL) at 25° C. Then the mixture was stirred at 25° C. for 1 h. LCMS showed the reaction was completed. The mixture was concentrated to give N-(4-(aminomethyl)phenyl)-3,5-difluoro-4-(4-(trifluoromethyl)piperidin-1-yl)aniline 729-6 (1 g, 100% yield) as a brown solid. MS (ESI) m/z 385.7 $[M+H]^+$ Step 5. Preparation of N-(4-((3,5-difluoro-4-(4-(trifluoromethyl)piperidin-1-yl)phenyl)amino)benzyl)-2-oxopyrrolidine-3-carboxamide (729) To a mixture solution of compound 729-6 (0.1 g, 0.3 mmol), 2-oxopyrrolidine-3-carboxylic acid (0.04 g, 0.3 mmol) and HATU (0.11 g, 0.3 mmol) in DMF (3 mL) was added DIEA (0.06 g, 0.45 mmol). The reaction mixture was stirred at 25° C. for 6 hrs. The mixture was poured into $H_2O$ (10 mL) and extracted with EA (10 mL*3), the organic layer was washed with brine, dried over $Na_2SO_4$, filtered and concentrated, The residue was purified by combi-flash with EA/PE (1:1) to afford to give 729 (0.0782 g, 60.7% yield) as a yellow solid. MS (ESI) m/z 496.2 $[M+H]^{+1}$H NMR (400 MHz, $CD_3OD$) δ 7.25-7.19 (m, 2H), 7.05-7.00 (m, 2H), 6.55-6.46 (m, 2H), 4.40-4.27 (m, 2H), 3.46-3.26 (m, 2H), 3.15-3.00 (m, 4H), 2.46-2.13 (m, 3H), 1.90-1.79 (m, 2H), 1.71-1.61 (m, 2H).

(S)—N-(4-((3,5-difluoro-4-(4-(trifluoromethyl)piperidin-1-yl)phenyl)amino)benzyl)-2,6-dioxohexahydropyrimidine-4-carboxamide (730)

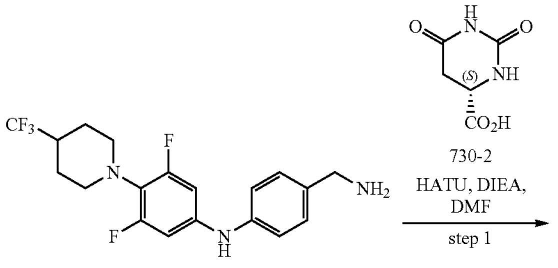

730-1

-continued

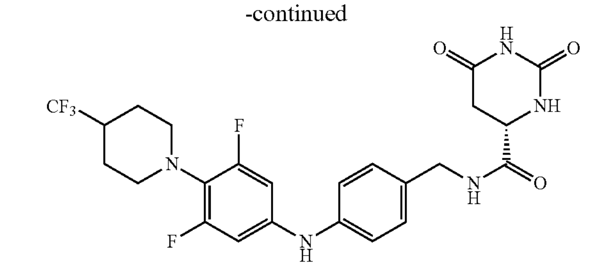

730

To a solution of 730-1 (100 mg, 0.26 mmol) and (S)-2,6-dioxohexahydropyrimidine-4-carboxylic acid (49.24 mg, 0.31 mmol) in DMF (5 mL) was added HATU (148 mg, 0.39 mmol), DIEA (134.15 mg, 1.04 mmol). Then the reaction mixture was stirred for 16 hours at rt. 10 mL of water was added to the mixture, extracted by EA (10 mL×3). The combined organic layers were washed with brine (10 mL×3), dried over $Na_2SO_4$ and concentrated under vacuum. The residue was purified by perp-TLC to afford the desired product 730 as a white solid. (30.8 mg). Mass (m/z): 526, $2[M+H]^+$. $^1$H NMR (400 MHz, $CD_3OD$) δ 7.20 (d, J=8.4 Hz, 2H), 7.04 (d, J=8.4 Hz, 211), 6.53 (d, J=11.6 Hz, 2H), 4.36-4.30 (m, 2H), 4.15 (dd, J=6.8, 4.4 Hz, 1H), 3.10 (d, J=12.0 Hz, 4H), 2.92 (dd, J=16.8, 7.0 Hz, 1H), 2.73 (dd, J=16.8, 4.4 Hz, 1H), 2.26-2.18 (m, 1H), 1.88 (d, J=12.2 Hz, 2H), 1.75-1.65 (m, 2H).

(S)—N-(4-((3,5-difluoro-4-(4-(trifluoromethyl)piperidin-1-yl)phenyl)amino)benzyl)-2,6-dioxohexahydropyrimidine-4-carboxamide (731)

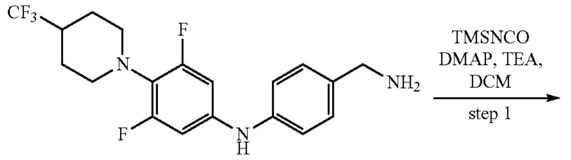

731-1

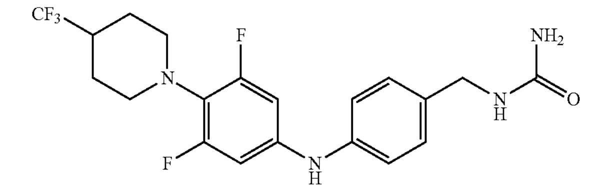

731

To a solution of 731-1 (100 mg, 0.26 mmol) and TMSNCO (29.89 mg, 0.26 mmol) in DCM (5 mL) was added TEA (105 mg, 1.04 mmol), DMAP (6.3 mg, 0.05 mmol). Then the reaction mixture was stirred for 16 hours at rt. 10 mL of water was added to the mixture, extracted with EA (10 mL×3). The combined organic layers were washed with brine (10 mL×3), dried over $Na_2SO_4$ and concentrated under vacuum. The residue was purified by perp-TLC to afford 731 as a white solid. (40.8 mg). Mass (m/z): 429.2 $[M+H]^+$. $^1$H NMR (400 MHz, $CD_3OD$) δ 7.21 (d, J=8.6 Hz, 2H), 7.07-7.00 (m, 2H), 6.56-6.48 (m, 2H), 4.23 (s, 2H), 3.15-3.03 (m, 4H), 2.30-2.20 (m, 1H), 1.87 (d, J=13.6 Hz, 2H), 1.70 (d, J=4.8 Hz, 2H).

(S)—N-(4-((3,5-difluoro-4-(piperidin-1-yl)phenyl)amino)benzyl)-6-oxopiperidine-2-carboxamide (732)

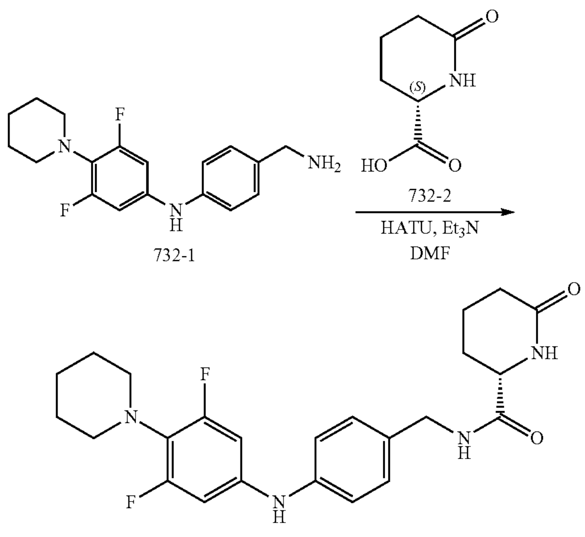

732-1 732-2 732

Step 1. Preparation of (S)—N-(4-((3,5-difluoro-4-(piperidin-1-yl)phenyl)amino)benzyl)-6-oxopiperidine-2-carboxamide (732) To a solution of compound 732-1 (0.1 g, 0.315 mmol), compound 732-2 (45 mg, 0.315 mmol) in DMF (3 mL) under nitrogen was added N,N,N',N'-Tetramethyl-O-(7-azabenzotriazol-1-yl)uronium (120 mg, 0.315 mmol) and TEA (96 mg, 0.94 mmol). The reaction mixture was stirred at 25° C. for 2 hrs. The mixture was poured into $H_2O$ (10 mL) and extracted with EA (10 mL*3), the organic layer was washed by brine, dried over $Na_2SO_4$, filtered and concentrated. The residue was purified by prep-HPLC to afford 732 (45.2 mg, 32.4% yield) as a yellow solid. MS (ESI) m/z 443.2 $[M+H]^+$. $^1H$ NMR (400 MHz, DMSO-$d_6$) S 8.38 (dd, J=11.5, 5.4 Hz, 2H), 7.52 (d, J=2.5 Hz, 1H), 7.18 (d, J=8.5 Hz, 2H), 7.03 (d, J=8.5 Hz, 2H), 6.55 (d, J=11.7 Hz, 2H), 4.22 (dd, J=10.2, 5.9 Hz, 2H), 3.91-3.88 (m, 1H), 2.94 (d, J=5.3 Hz, 4H), 2.13 (t, J=6.5 Hz, 2H), 1.90-1.85 (m, 1H), 1.71 (dd, J=11.0, 4.3 Hz, 2H), 1.57 (s, 5H), 1.49 (d, J=4.0 Hz, 2H).

N-(4-((3,5-difluoro-4-(4-methylpiperidin-1-yl)phenyl)amino)benzyl)-5-oxopyrrolidine-3-carboxamide (733)

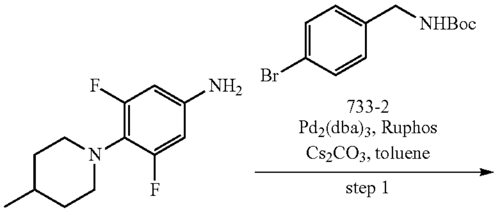

733-1 733-2

-continued

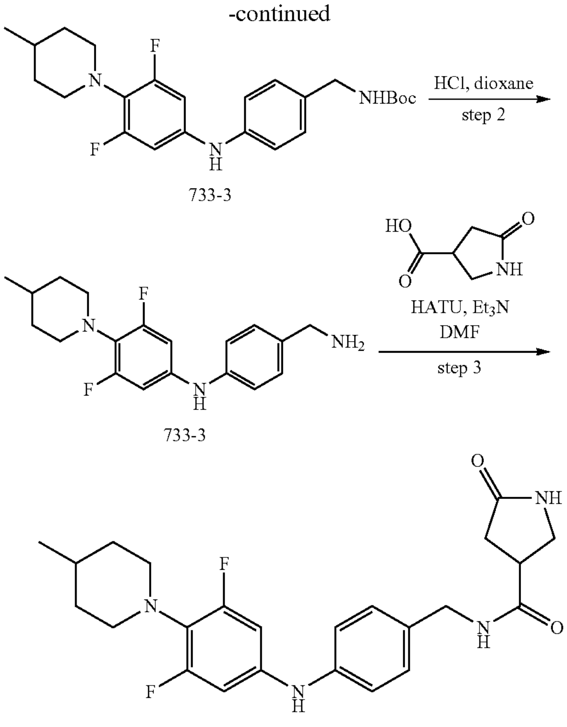

733-3 733-3 733

Step 1. Preparation of tert-butyl (4-((3,5-difluoro-4-(4-methylpiperidin-1-yl)phenyl)amino)benzyl)carbamate (733-3) To a solution of compound 733-1 (150 mg, 0.66 mmol), compound 733-2 (190 mg, 0.66 mmol), $Cs_2CO_3$ (431 mg, 1.33 mmol) in toluene (20 mL) was added RuPhos (61 mg, 0.13 mmol), $Pd_2(dba)_3$ (61 mg, 0.066 mmol), then was heated and stirred at 90° C. under $N_2$ for 16 hrs. After cooling to ambient temperature, concentrated under reduced pressure. The residue was purified by silica gel column to provide tert-butyl (4-((3,5-difluoro-4-(4-methylpiperidin-1-yl)phenyl)amino)benzyl)carbamate 733-3 (200 mg, 69.92% yield) as a yellow solid. MS (ESI) m/z 432.3 $[M+H]^+$.

Step 2. Preparation of N-(4-(aminomethyl)phenyl)-3,5-difluoro-4-(4-methylpiperidin-1-yl)aniline (733-4) A solution of compound 733-3 (200 mg, 0.46 mmol) in HCl in 1,4-Dioxane (5 mL, 4N) was stirred at 25° C. for 16 hrs. concentrated to dryness to give N-(4-(aminomethyl)phenyl)-3,5-difluoro-4-(4-methylpiperidin-1-yl)aniline 733-4 (150 mg, 97.65% yield) as a white solid. MS (ESI) m/z 332.2 $[M+H]^+$.

Step 3. Preparation of N-(4-((3,5-difluoro-4-(4-methylpiperidin-1-yl)phenyl)amino)benzyl)-5-oxopyrrolidine-3-carboxamide (733) To a stirred solution of compound 733-4 (0.15 g, 0.45 mmol), 5-oxopyrrolidine-3-carboxylic acid (58 mg, 0.45 mmol) in DMF (3 mL) under nitrogen was added N,N,N',N'-Tetramethyl-O-(7-azabenzotriazol-1-yl)uronium (172 mg, 0.45 mmol) and TEA (137 mg, 1.35 mmol). The reaction mixture was stirred at 25° C. for 2 hrs. The mixture was poured into $H_2O$ (10 mL) and extracted with EA (10 mL*3), the organic layer was washed by brine, dried over $Na_2SO_4$, filtered and concentrated. The residue was purified by prep-HPLC to afford 733 (81.6 mg, 40.4% yield) as a yellow solid. MS (ESI) m/z 443.2 $[M+H]^+$. $^1H$ NMR (400 MHz, DMSO-$d_6$) δ 8.42 (s, 1H), 8.36 (s, 1H), 7.58 (s, 1H), 7.16 (d, J=8.5 Hz, 2H), 7.04 (d, J=8.5 Hz, 2H), 6.56 (d, J=11.7 Hz, 2H), 4.21 (d, J=5.8 Hz, 2H), 3.41 (t, J=8.6 Hz, 1H), 3.27-3.17 (m, 2H), 2.95 (d, J=7.7 Hz, 4H), 2.30 (dd, J=8.4, 3.4 Hz, 2H), 1.62 (d, J=12.1 Hz, 2H), 1.46-1.39 (m, 1H), 1.24 (dd, J=17.2, 10.5 Hz, 2H), 0.94 (d, J=6.5 Hz, 3H).

The invention claimed is:

1. A compound of formula I, or a pharmaceutically acceptable salt, hydrate or stereoisomer thereof:

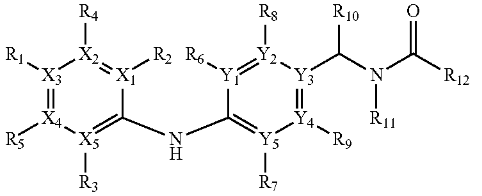

I wherein:

R1 is NR'R", wherein R' and R" are independently selected from substituted or unsubstituted C1-C9 alkyl, and substituted or unsubstituted C5-C12 aryl, or wherein R' and R" are linked to form a substituted or unsubstituted 4- to 9-membered heterocycle containing 1 to 4 heteroatoms selected from N, O, and S;

R2-R9 are independently H, halogen, C1-C6 alkoxy, amino, C1-C6 alkylamino, di-(C1-C6 alkyl)amino, or substituted or unsubstituted C1-C6 alkyl;

R10 is H, halogen, C1-C6 alkoxy, amino, C1-C6 alkylamino, di-(C1-C6 alkyl)amino, or unsubstituted C1-C6 alkyl;

R11 is H, OH, or substituted or unsubstituted C1-C4 alkyl;

R12 is C1-C6 alkoxy, amino, C1-C6 alkylamino, di-(C1-C6 alkyl)amino, C1-C6 alkanoyl, carbamoyl, carboxyl, amido, substituted or unsubstituted C1-C6 alkyl, substituted or unsubstituted C3-C9 cycloalkyl, or substituted or unsubstituted 3- to 9-membered heterocycloalkyl containing 1 to 3 heteroatoms selected from N, O, and S;

R11 and R12 are optionally joined to form a substituted or unsubstituted 3- to 18-membered heterocycle containing 1 to 4 heteroatoms selected from N, O, and S; and X1-X5 and Y1-Y5 are C;

wherein the substituents are in a number ranging from 0 to 3, each independently selected from halogen, —R', —OR', =O, =NR', =N—OR', —NR'R", —SR', —SiR'R"R"', —OC(O)R', —C(O)R', —CO2R', —CONR'R", —OC(O)NR'R", —NR"C(O)R', —NR'—C(O)NR"R"', —NR'—SO2NR"', —NR"CO2R', —NH—C(NH2)=NH, —NR'C(NH2)=NH, —NH—C(NH2)=NR', —S(O)R', —SO2R', —SO2NR'R", —NR"SO2R, —CN, —NO2, —N3, —CH(Ph)2, perfluoro(C1-C4)alkoxy, and perfluoro(C1-C4)alkyl; wherein R', R" and R"' each independently refer to hydrogen, unsubstituted (C1-C8) alkyl, (C1-C8)alkyl substituted with one to three halogens, unsubstituted C6-C14 aryl, C6-C14 aryl substituted with one to three halogens, unsubstituted C1-C6 alkyl, C1-C6 alkoxy, C1-C6 thioalkoxy groups, or C6-C14 aryl-(C1-C4)alkyl groups, wherein when R' and R" are attached to the same nitrogen atom, they are optionally combined with the nitrogen atom to form a 5-, 6- or 7-membered ring.

2. The compound, pharmaceutically acceptable salt, hydrate, or stereoisomer of claim 1, wherein:

R1 is NR'R", forming substituted or unsubstituted piperidin-1-yl;

R2-R9 are independently H, halogen, or substituted or unsubstituted C1-C6 alkyl;

R10 is H, halogen, or unsubstituted C1-C4 alkyl;

R11 is H, OH, or substituted or unsubstituted C1-C4 alkyl;

R12 is 1-ethyl-pyrrolidin-2-one-4-yl; and

R11-R12 are optionally joined in a substituted or unsubstituted 3- to 10-membered heterocycle containing 1 to 3 heteroatoms selected from N, O, and S.

3. The compound, pharmaceutically acceptable salt, hydrate, or stereoisomer of claim 1, wherein:

R1 is NR'R", wherein R' and R" are independently substituted or unsubstituted C1-C9 alkyl, and linked to form a substituted or unsubstituted C4-C9 heterocycle containing 1 to 4 heteroatoms selected from N, O, and S.

4. The compound, pharmaceutically acceptable salt, hydrate, or stereoisomer of claim 1, wherein:

R1 is NR'R", forming substituted or unsubstituted piperidin-1-yl.

5. The compound, pharmaceutically acceptable salt, hydrate, or stereoisomer of claim 1, wherein:

R1 is NR'R", forming piperidin-1-yl, 4-methyl piperidin-1-yl, or 4-$CF_3$ piperidin-1-yl.

6. The compound, pharmaceutically acceptable salt, hydrate, or stereoisomer of claim 4, wherein:

R2-R9 are independently H, halogen, or substituted or unsubstituted C1-C6 alkyl; and R10 is H, halogen, or unsubstituted C1-C6 alkyl.

7. The compound, pharmaceutically acceptable salt, hydrate, or stereoisomer of claim 4, wherein:

R2-R10 are H.

8. The compound, pharmaceutically acceptable salt, hydrate, or stereoisomer of claim 7, wherein:

R11 is H or OH.

9. The compound, pharmaceutically acceptable salt, hydrate, or stereoisomer of claim 7, wherein:

R11 is H.

10. The compound, pharmaceutically acceptable salt, hydrate, or stereoisomer of claim 9, wherein:

R12 is substituted or unsubstituted C3-C9 cycloalkyl, or substituted or unsubstituted 3- to 9-membered heterocycloalkyl containing 1 to 3 heteroatoms selected from N, O, and S.

11. The compound, pharmaceutically acceptable salt, hydrate, or stereoisomer of claim 6, wherein:

R12 is pyrrolidin-2-one-4-yl, 1-methyl-pyrrolidin-2-one-4-yl, or 1-ethyl-pyrrolidin-2-one-4-yl.

12. The compound, pharmaceutically acceptable salt, hydrate, or stereoisomer of claim 6, wherein:

R11-R12 are joined in a substituted or unsubstituted 3- to 10-membered heterocycle containing 1 to 4 heteroatoms selected from N, O, and S.

13. The compound, pharmaceutically acceptable salt, hydrate, or stereoisomer of claim 6, wherein:

R11-R12 are joined in a 5- to 6-membered heterocycle containing 1 to 3 heteroatoms selected from N, O, and S.

14. The compound, pharmaceutically acceptable salt, hydrate, or stereoisomer of claim 1, wherein the compound has a structure selected from:

-continued
40
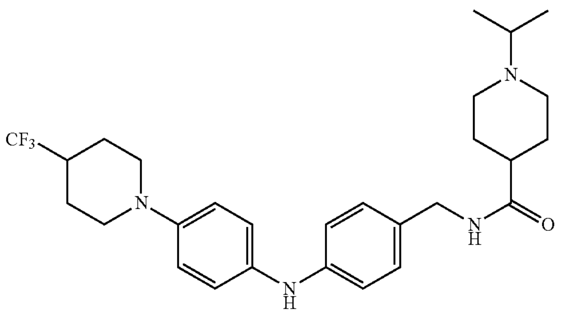
42
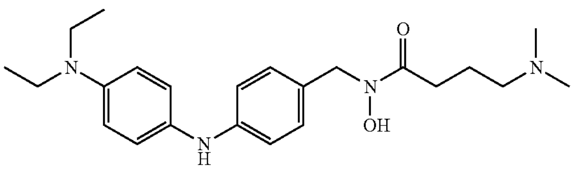
44
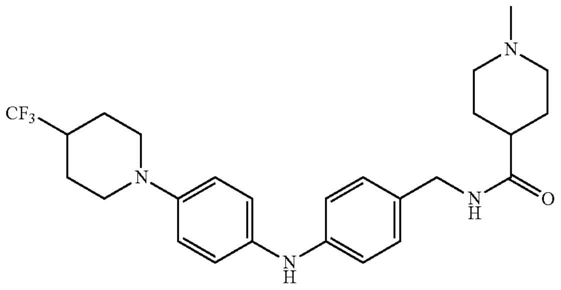
50
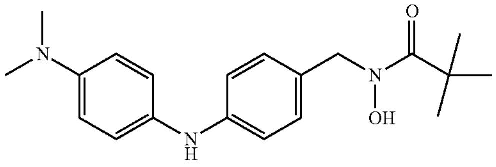
59
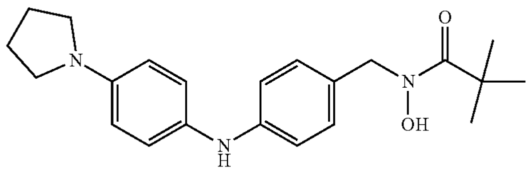
79
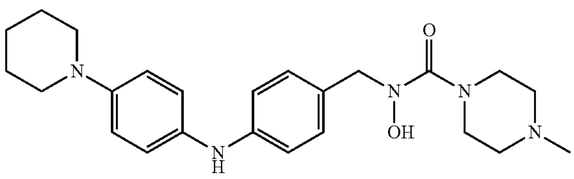
100
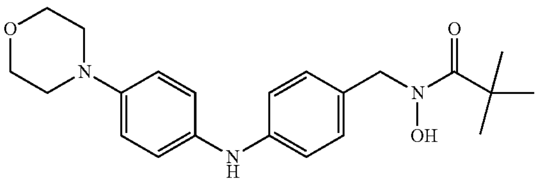
106
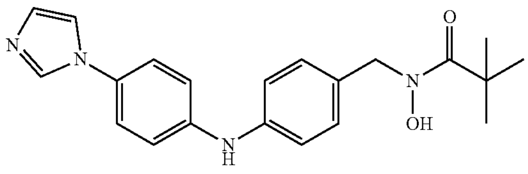
124
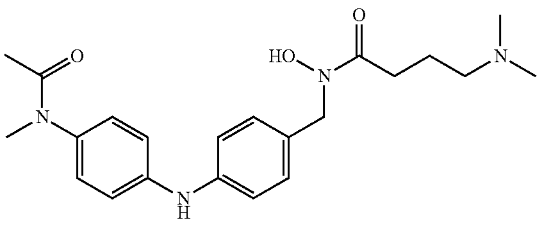
136
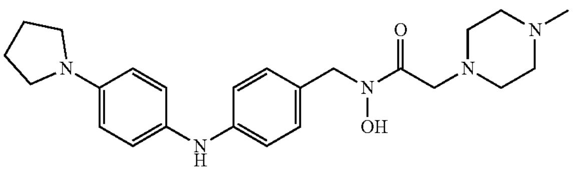
138
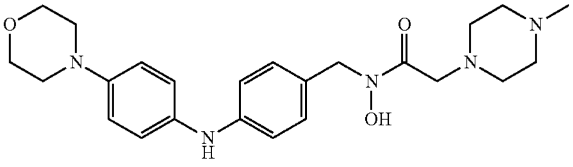
139
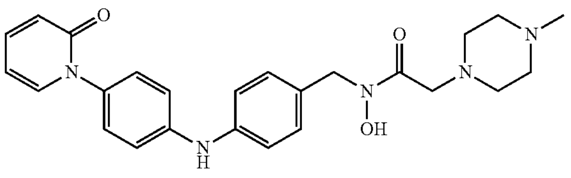
141
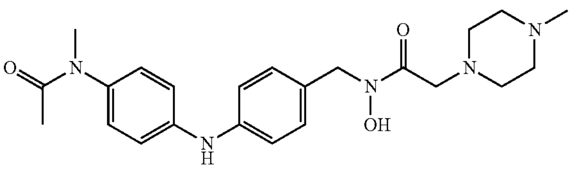
146
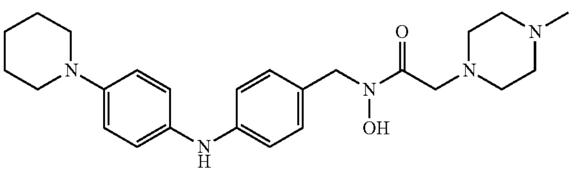
148
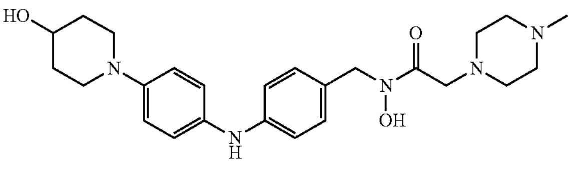

-continued
155
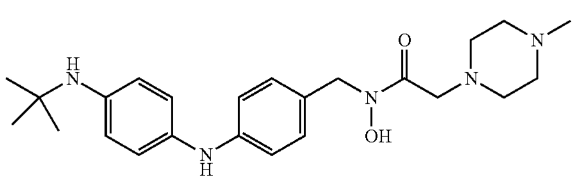
156
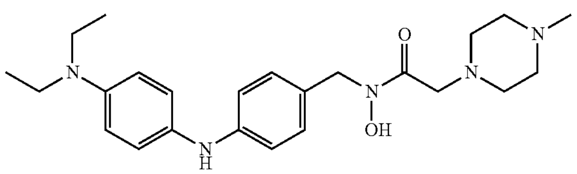
160
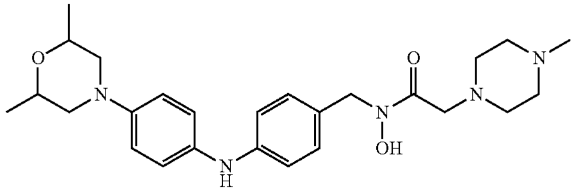
161
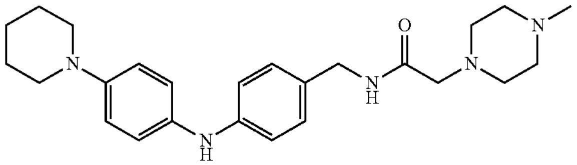
162
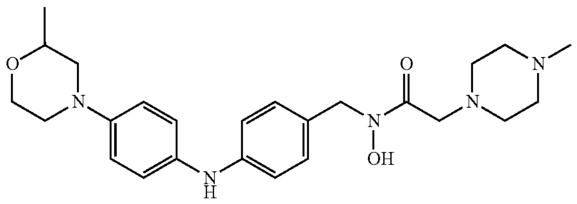 [SMILES: CN1CCN(CC(=O)N(O)Cc2ccc(Nc3ccc(N4CCOCC4)cc3)cc2)CC1]
164
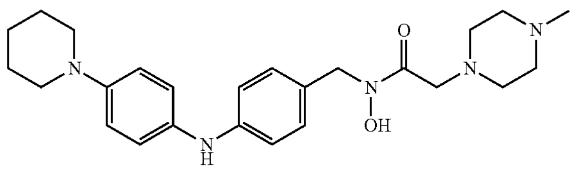
165
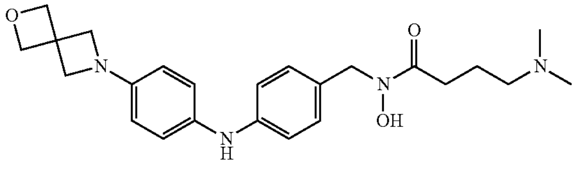
-continued
166
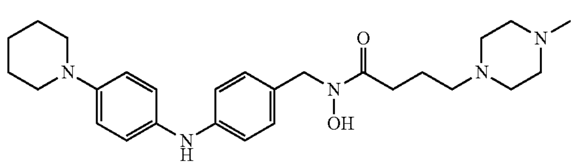
167
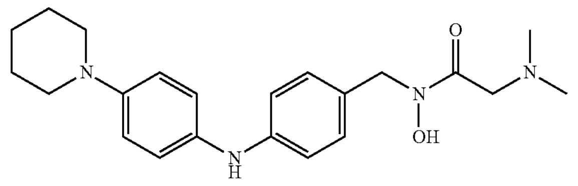
168
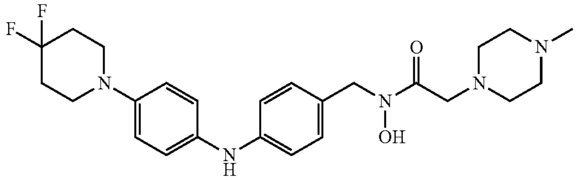
169
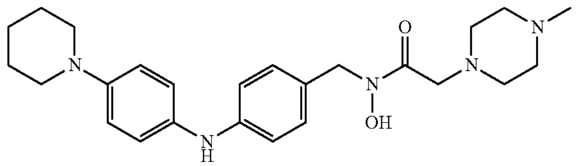
171
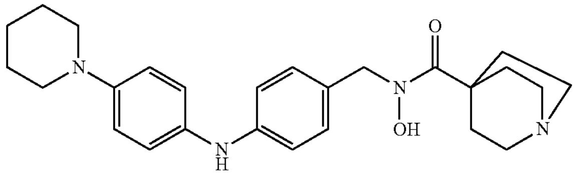
172
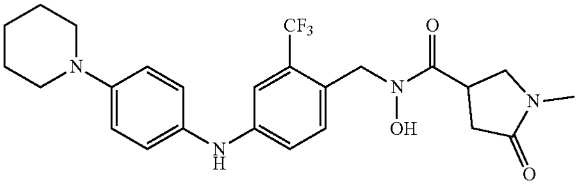
173
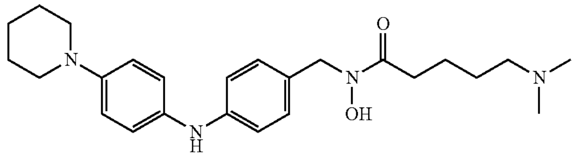
174
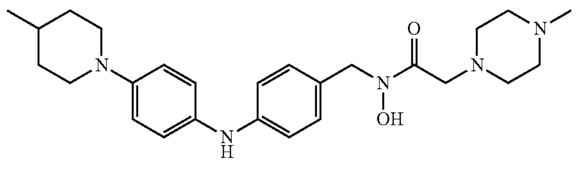

-continued
175
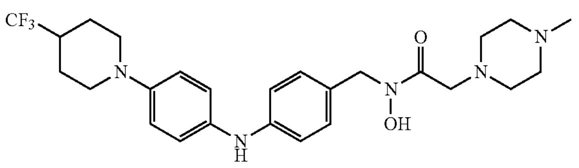
176
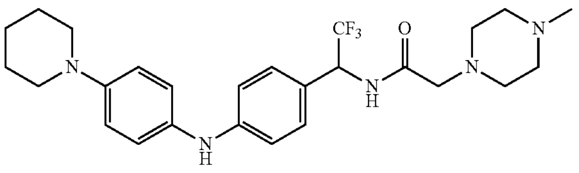
177
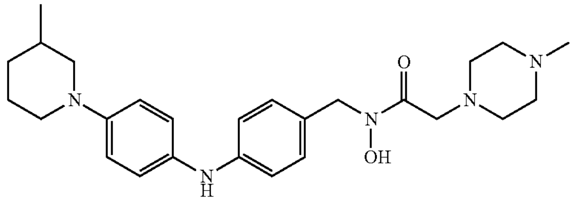
178
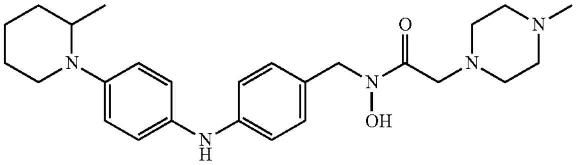
179
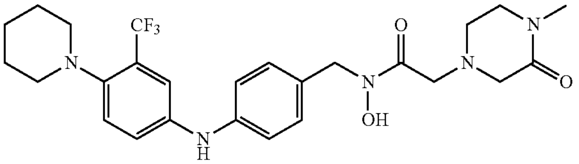
180
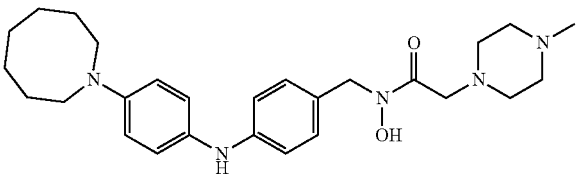
181
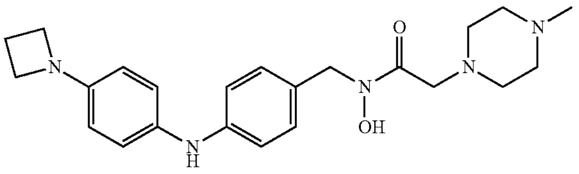
182
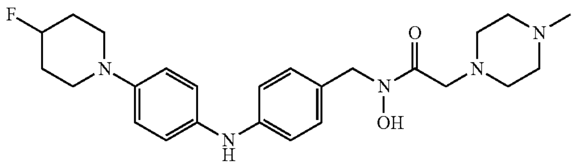
-continued
183
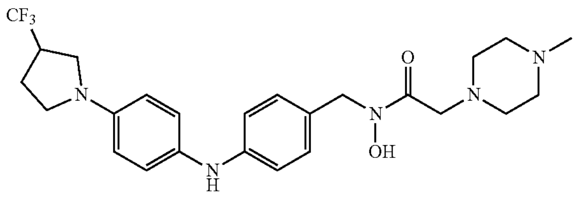
184
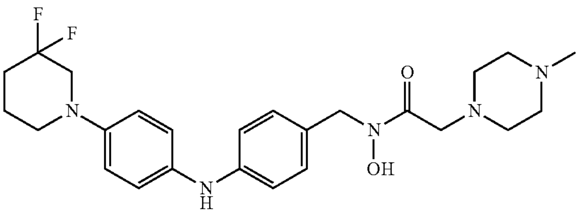
185
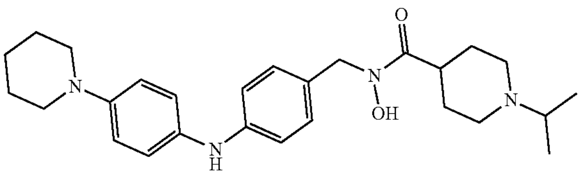
186
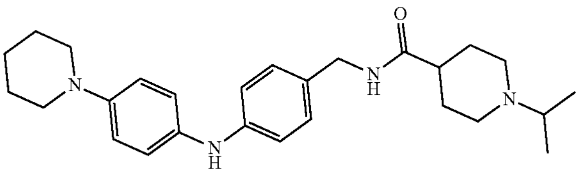
187
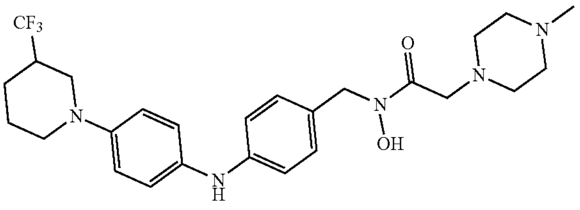
188
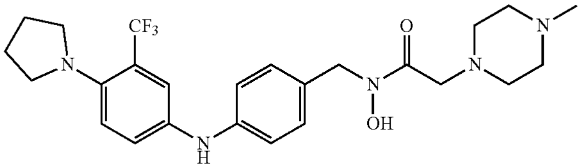
189
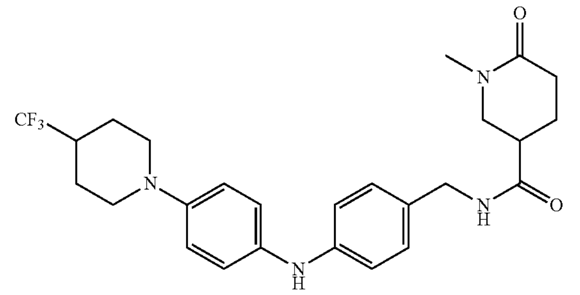

-continued
190
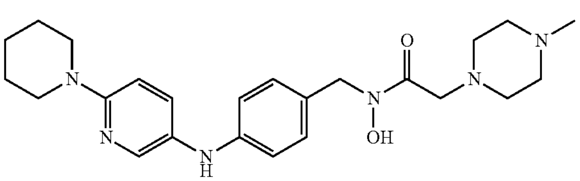
191
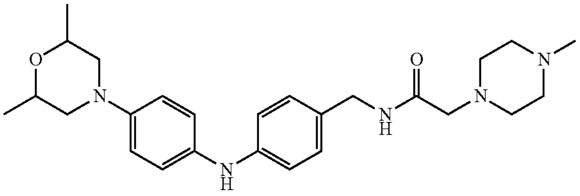
192
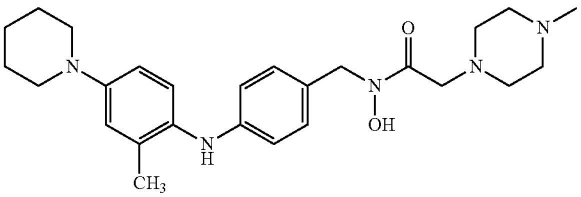
193
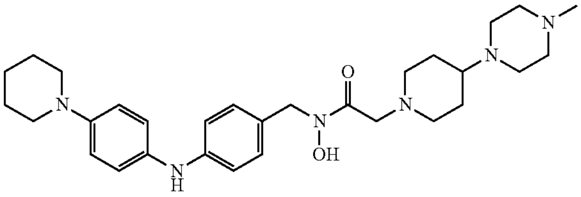
195
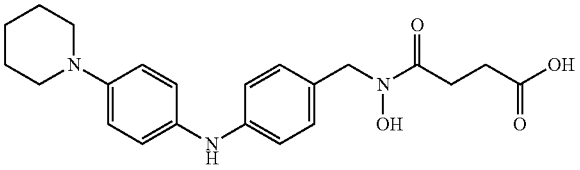
196
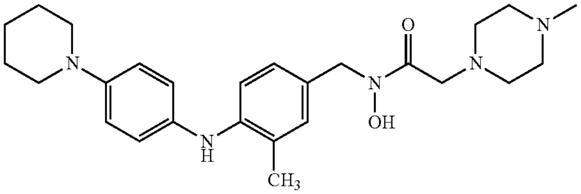
197
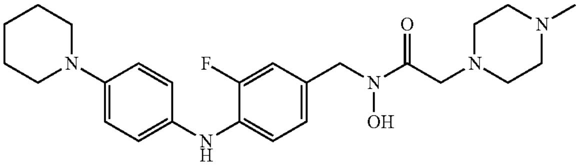
-continued
198
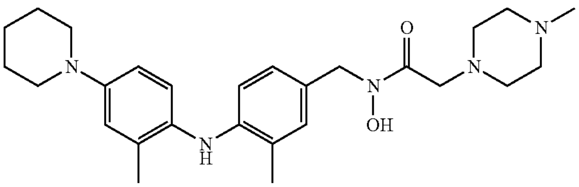
201
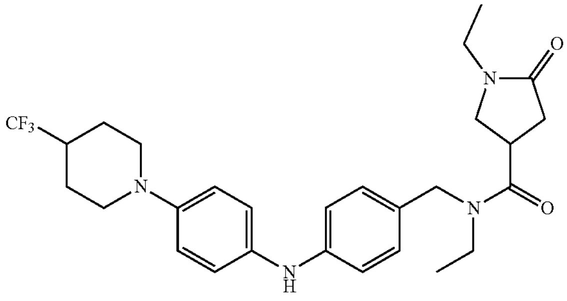
202
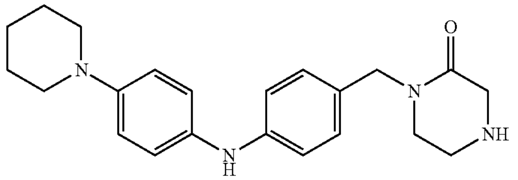
203
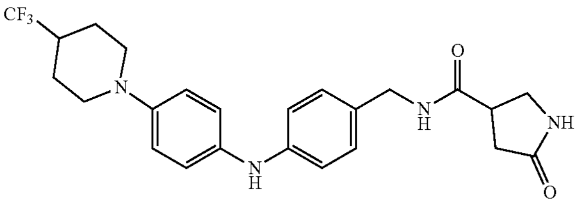
204
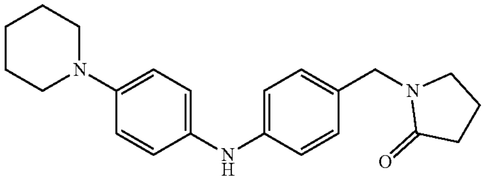
205
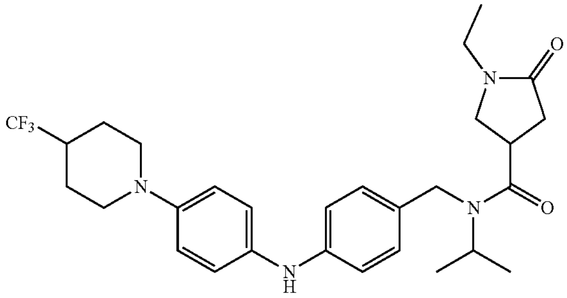

206
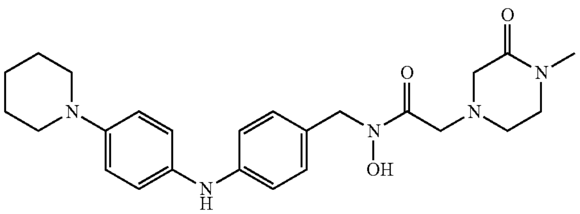
207
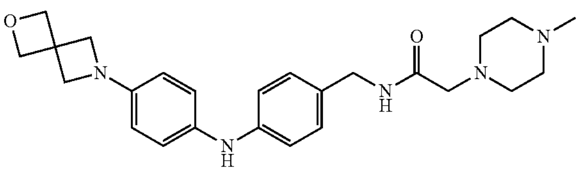
208
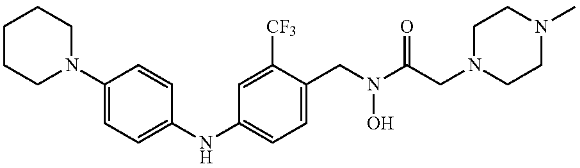
209
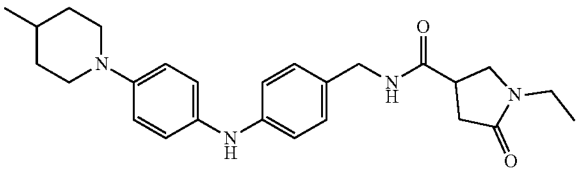
210
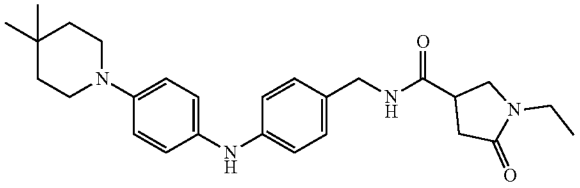
211
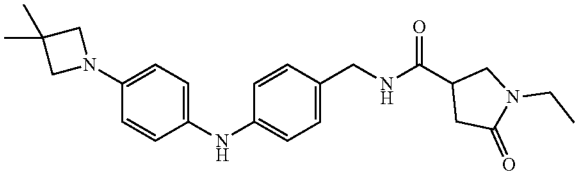
212
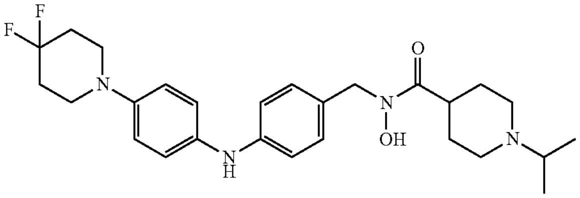
214
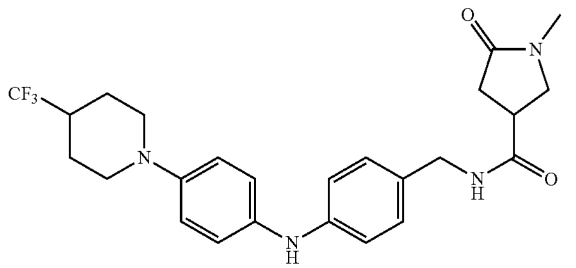
215
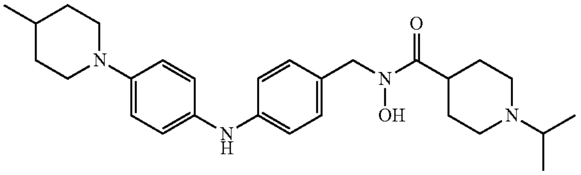
217
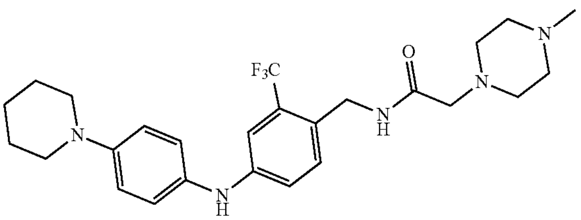
219
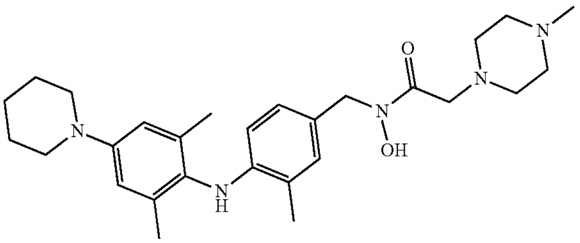
220
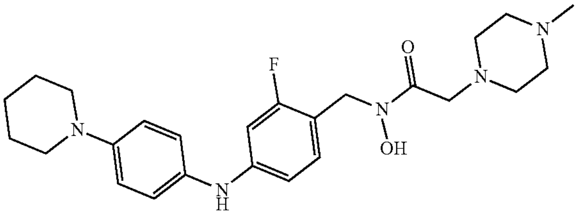
221
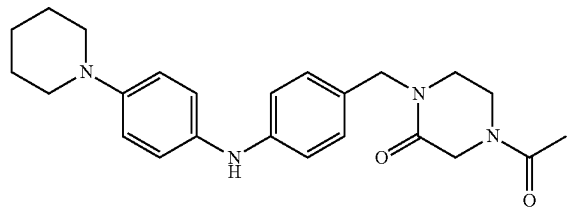

-continued
223
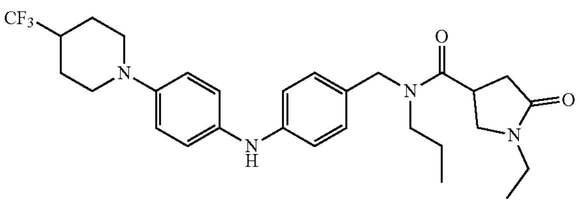
224
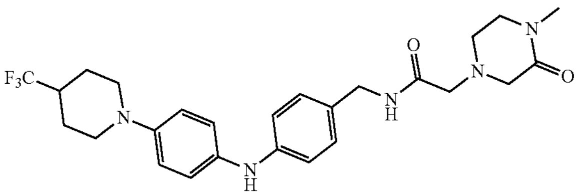
225
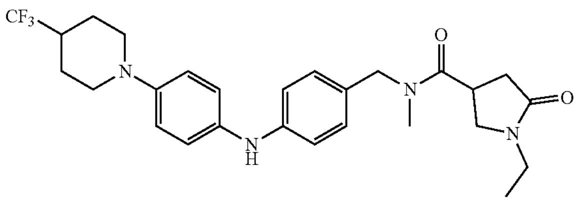
226
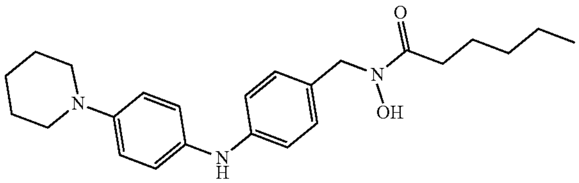
227
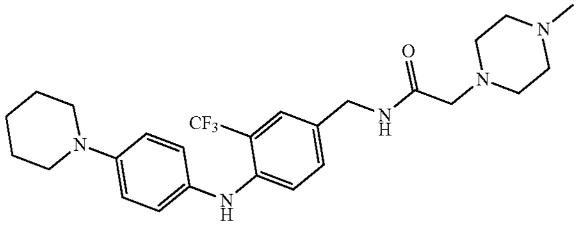
228
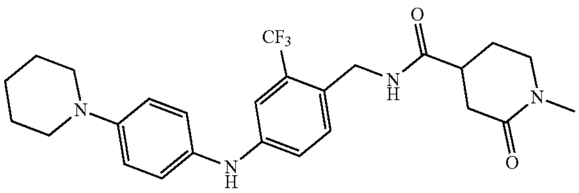
229
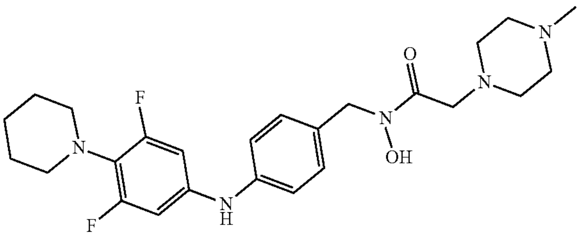
-continued
230
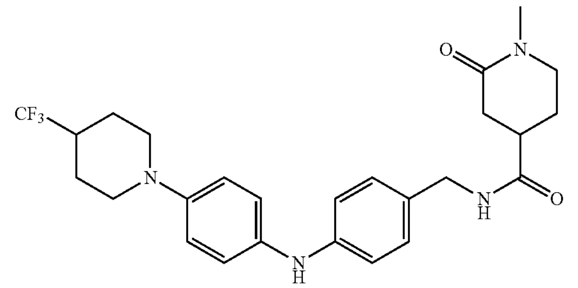
231
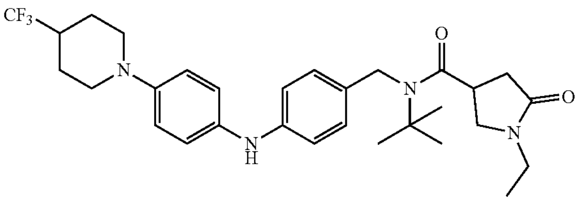
232
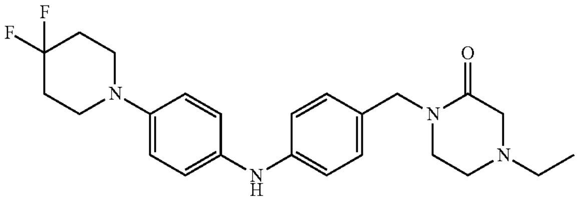
233
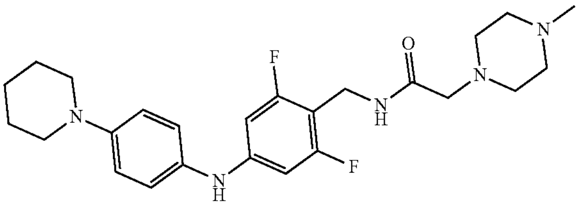
234
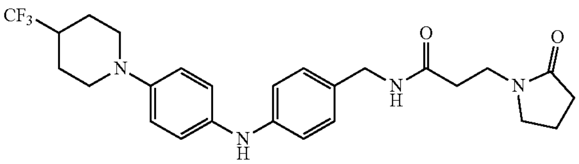
235
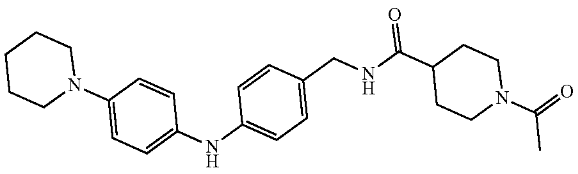
237
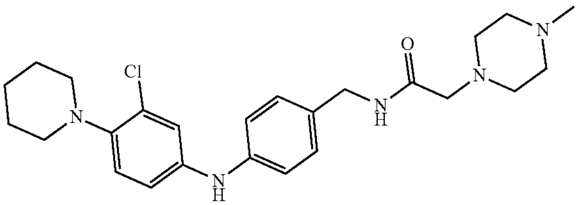

-continued
238
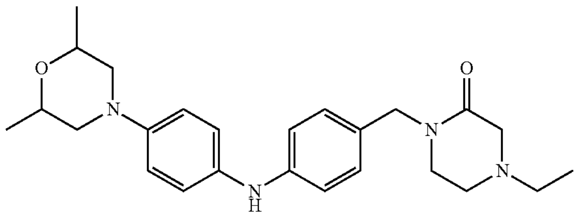
239
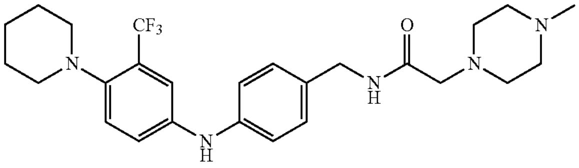
240
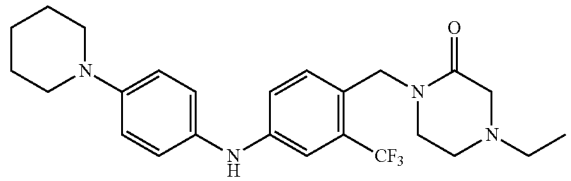
241
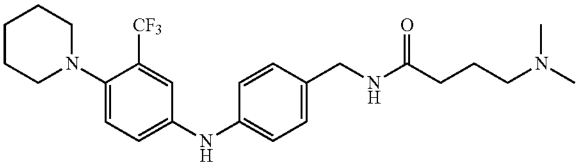
242
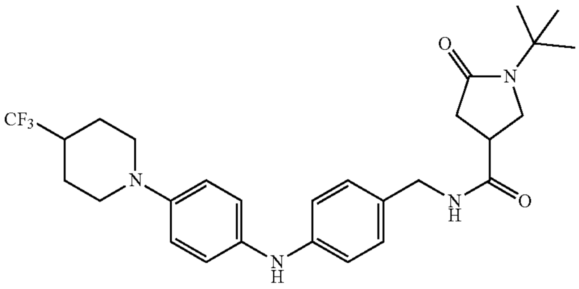
243
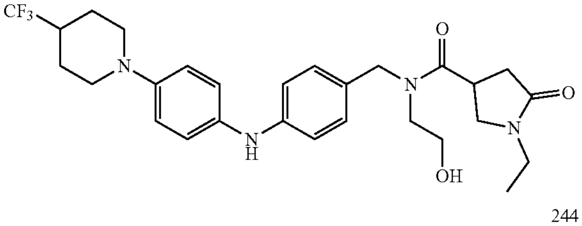
244
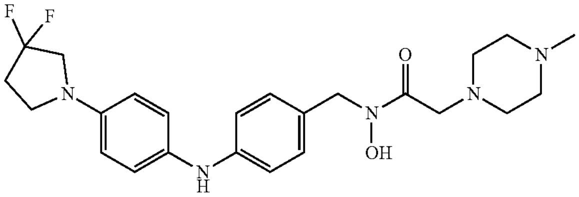
-continued
245
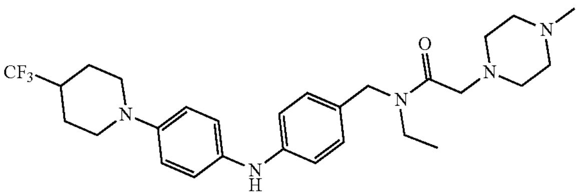
246
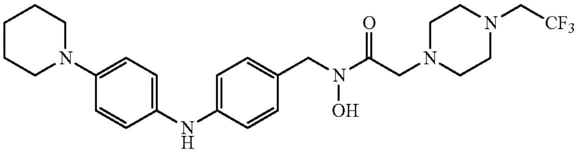
247
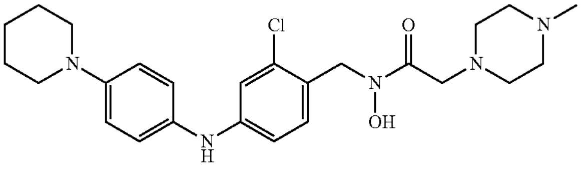
248
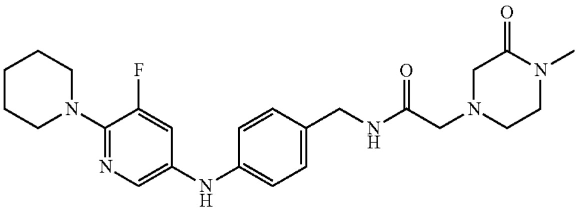
250
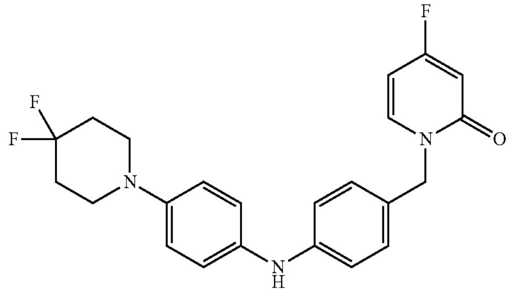
251
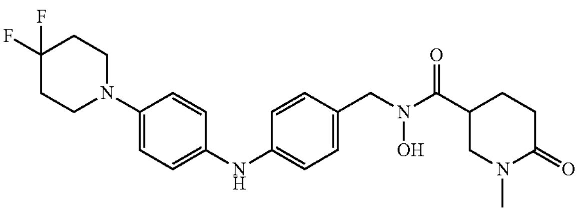
252
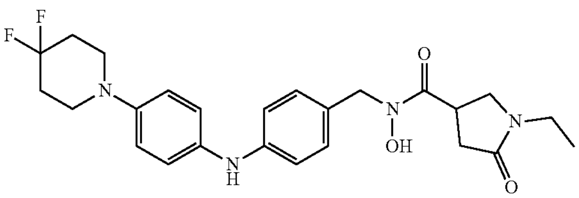

-continued
253
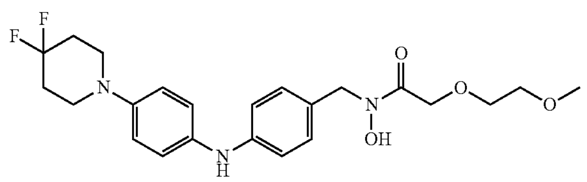
257
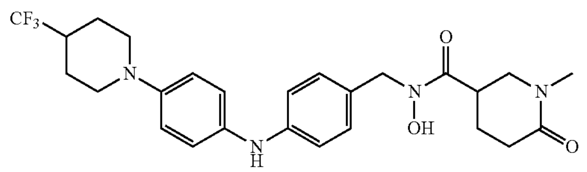
258
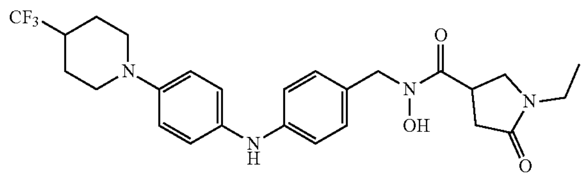
259
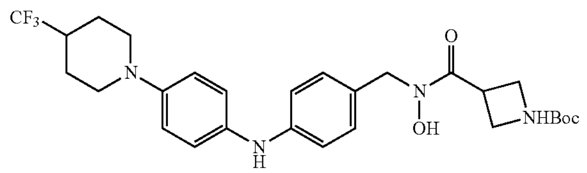
260
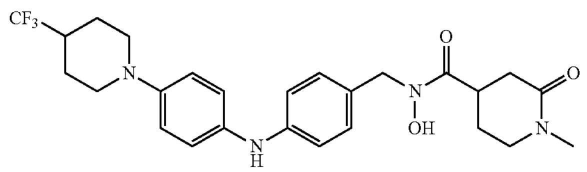
261
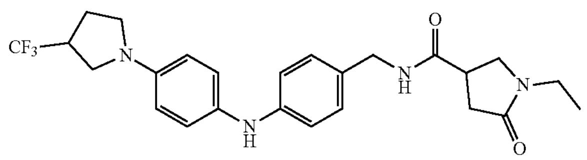
262
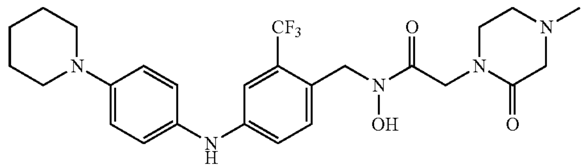
263
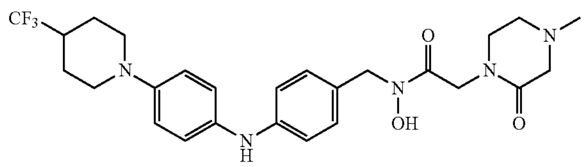
-continued
264
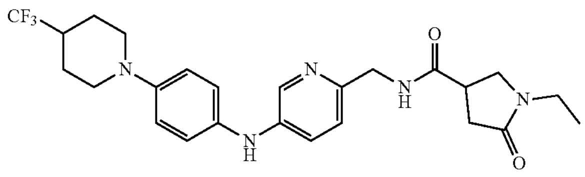
268
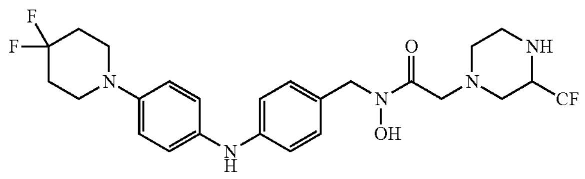
269
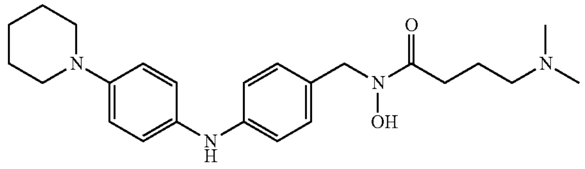
273
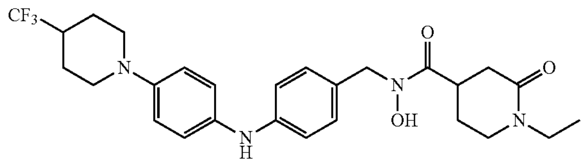
274
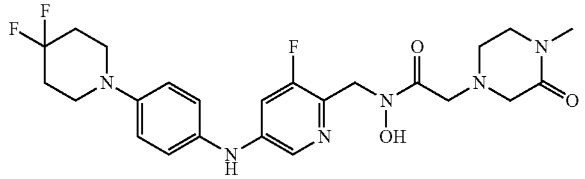
276
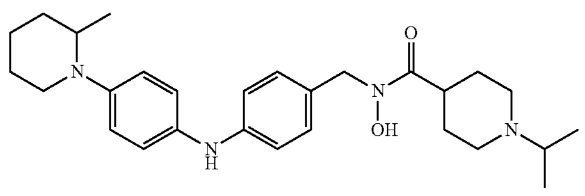
277
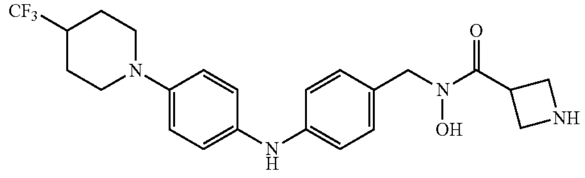
278
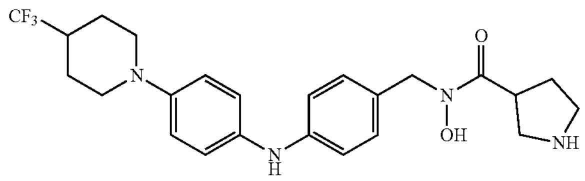

-continued
279
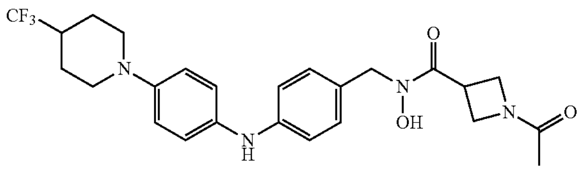
281
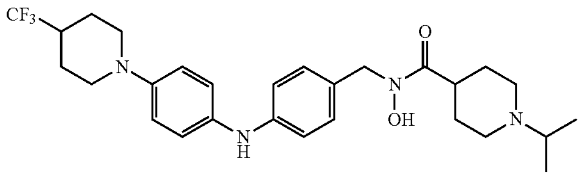
282
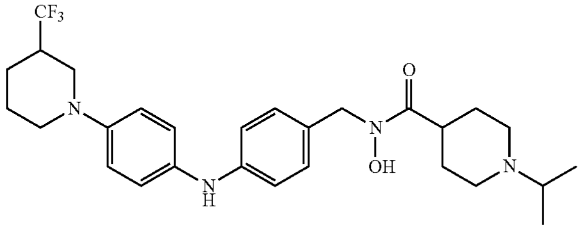
283
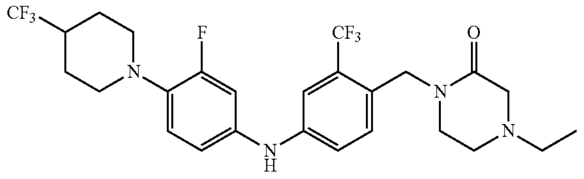
284
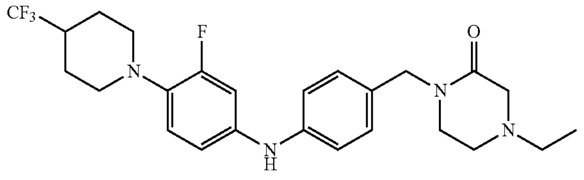
285
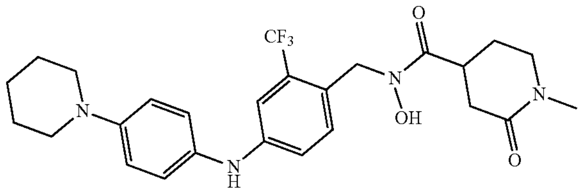
286
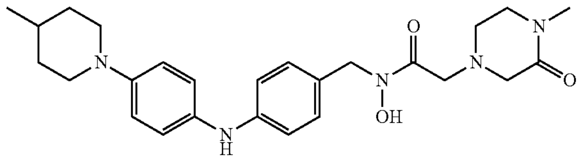
-continued
289
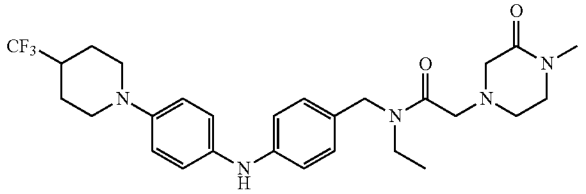
290
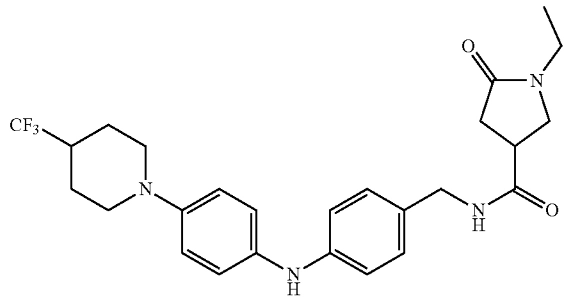
291
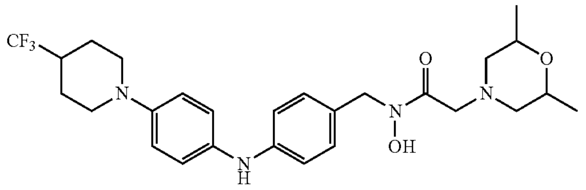
292
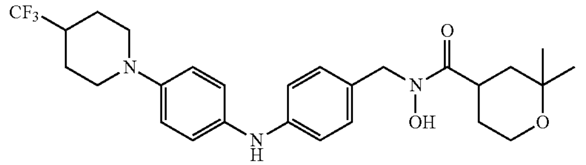
293
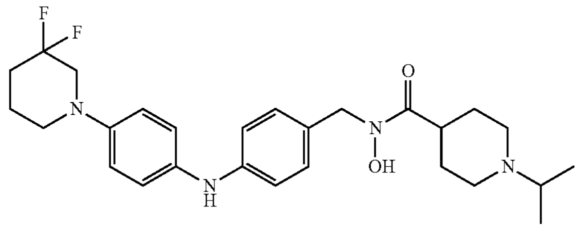
294
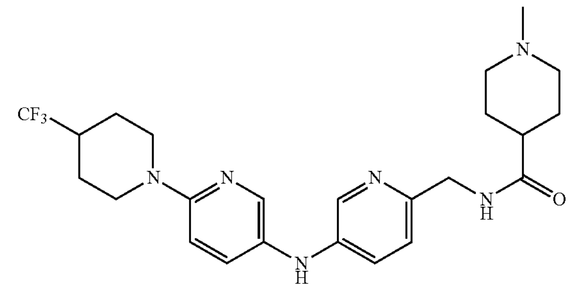

-continued
295
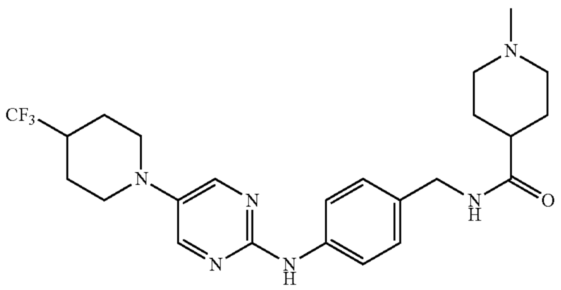
296
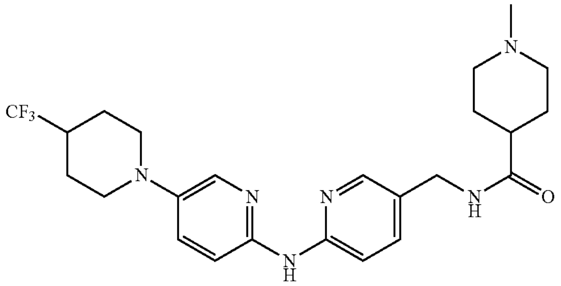
297
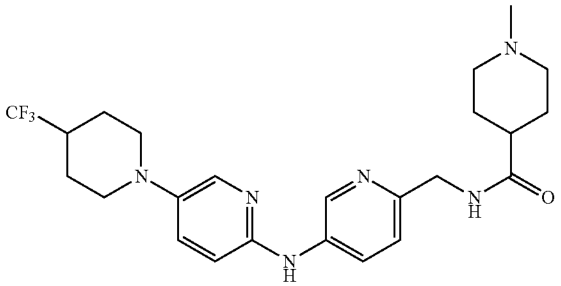
298
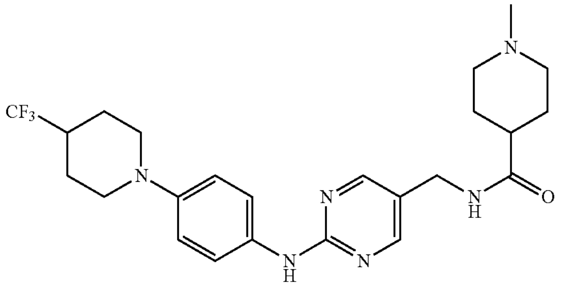
299
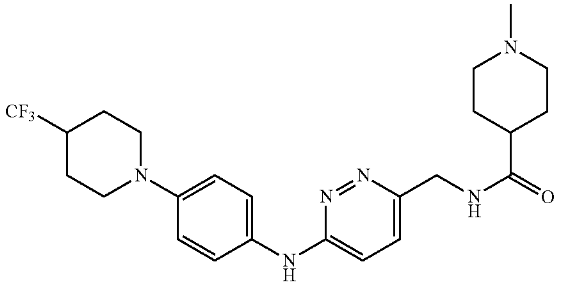
-continued
300
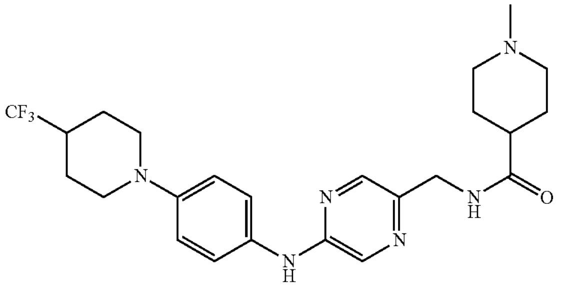
301
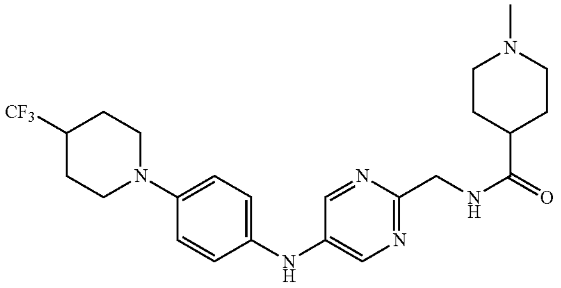
302
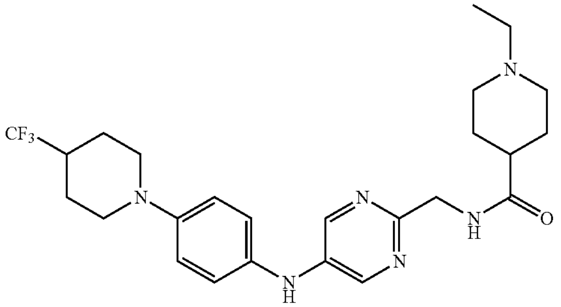
303
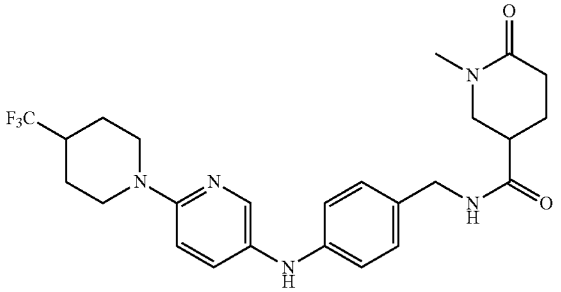
304
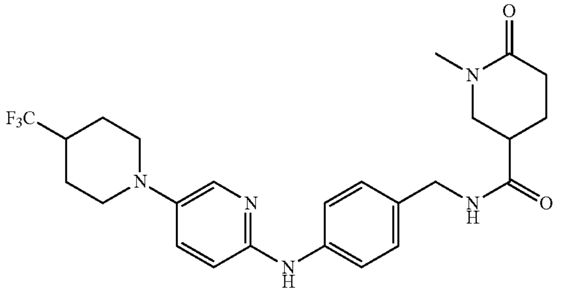

-continued
305
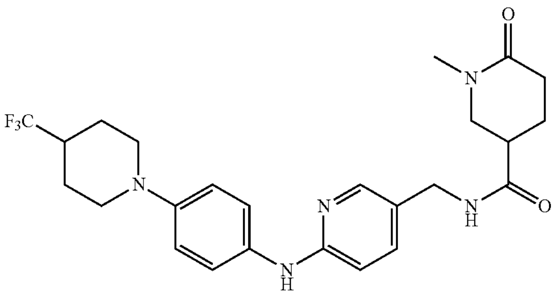
306
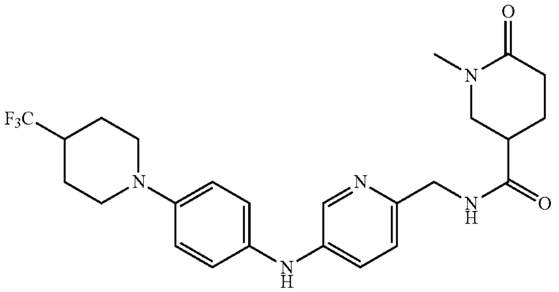
307
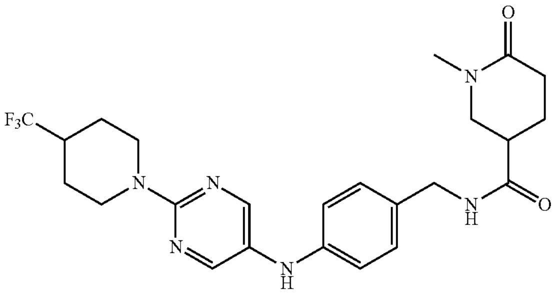
308
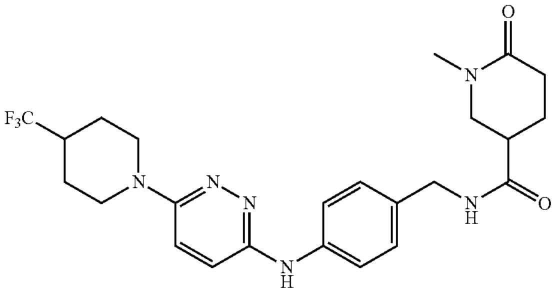
309
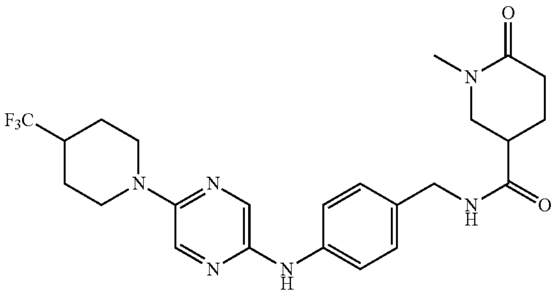
-continued
310
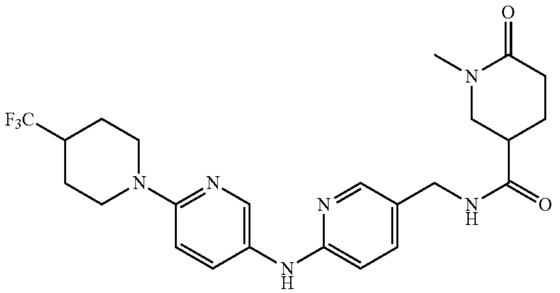
311
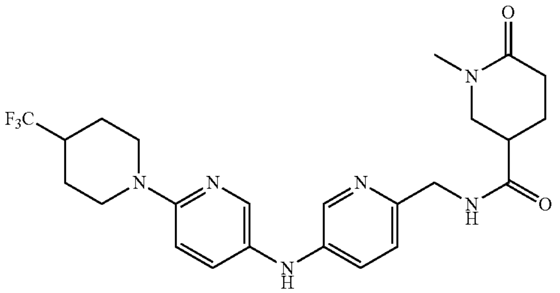
312
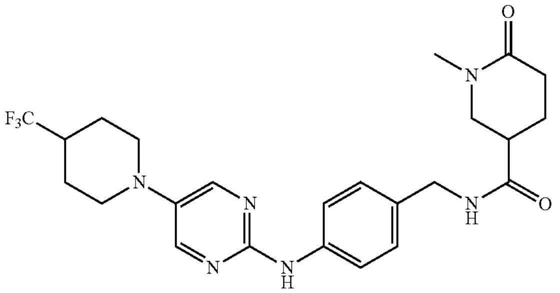
313
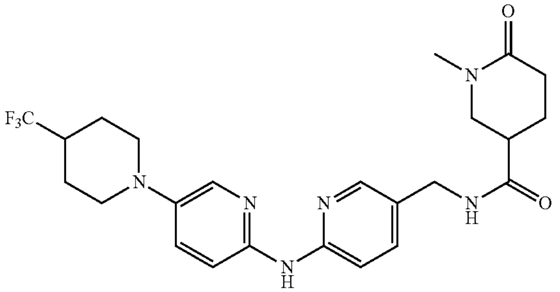
314
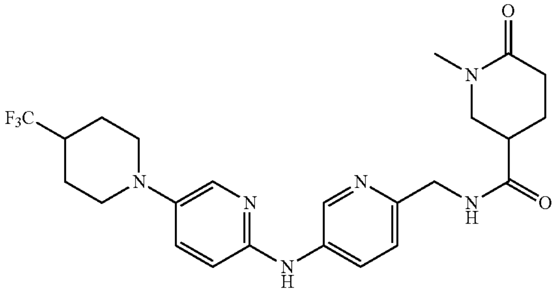

-continued
315
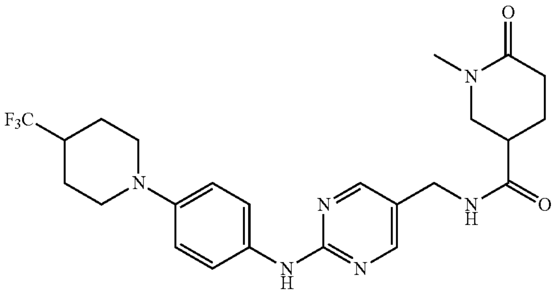
316
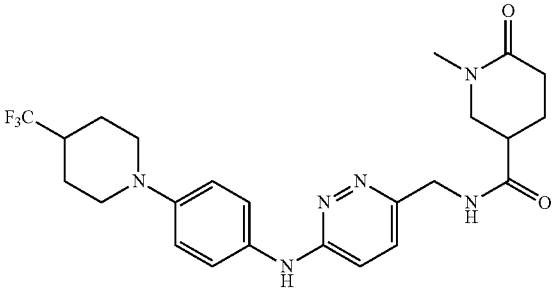
317
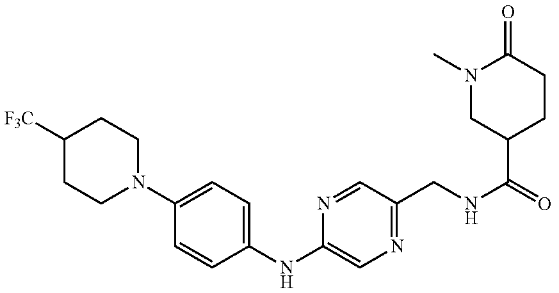
318
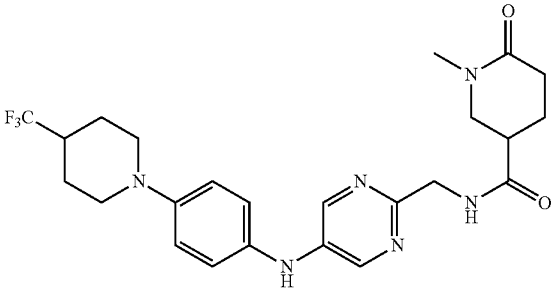
319
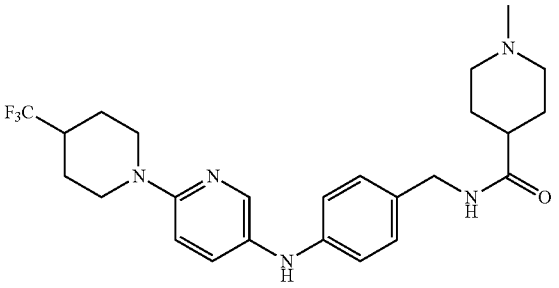
-continued
320
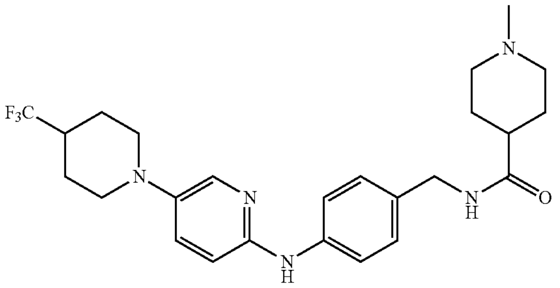
321
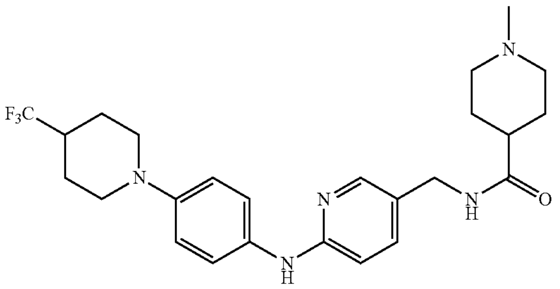
322
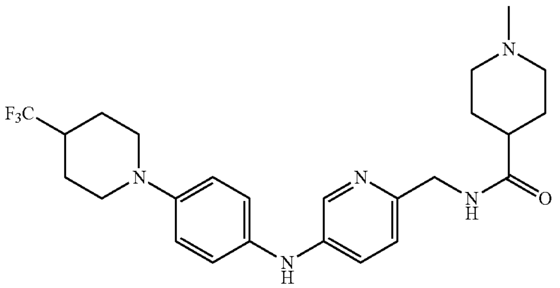
323
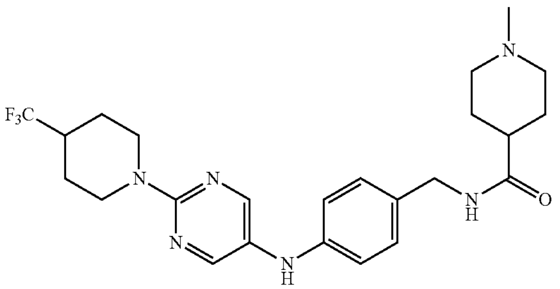
324
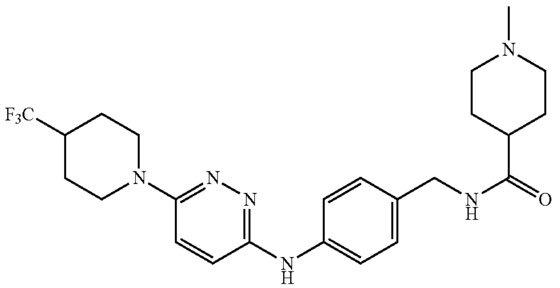

-continued
325
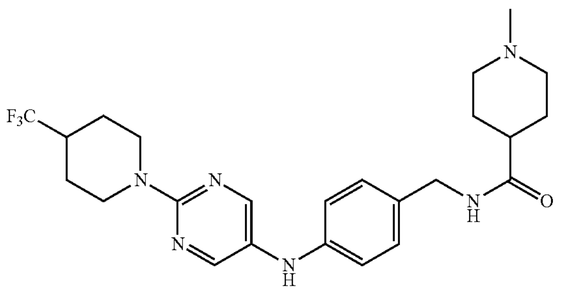
326
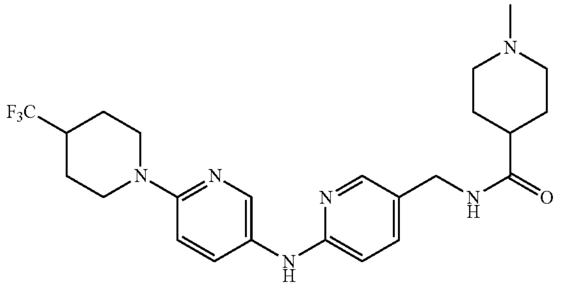
327
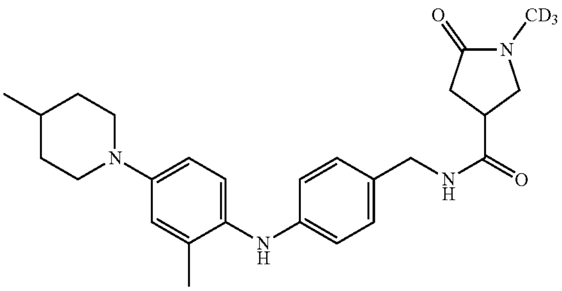
328
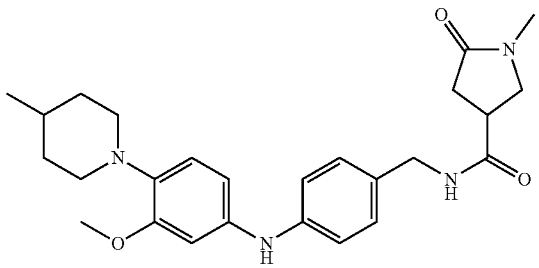
329
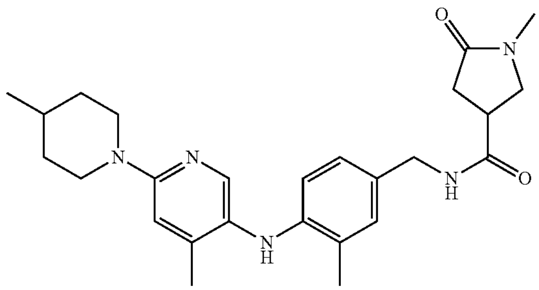
-continued
330
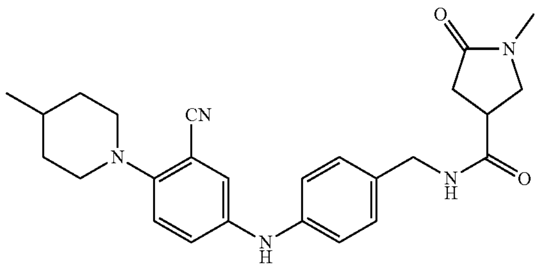
332
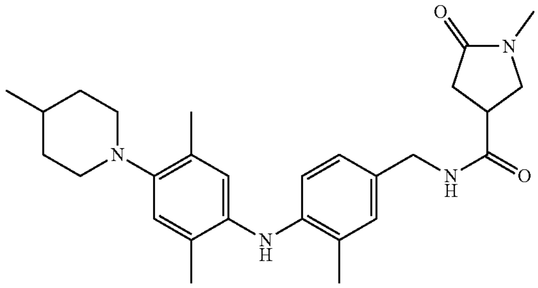
333
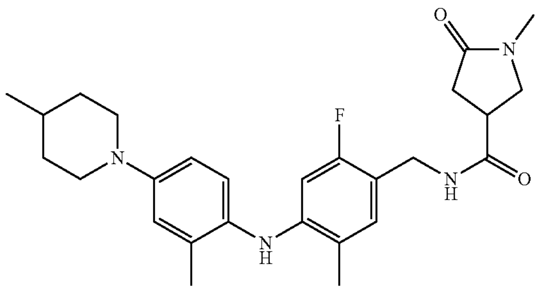
335
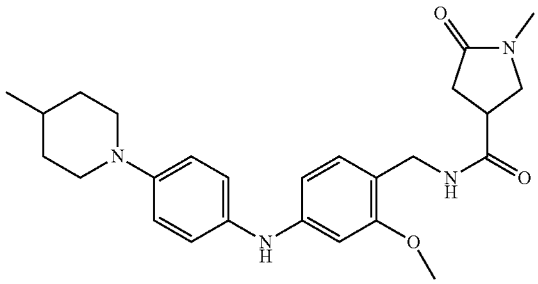
336
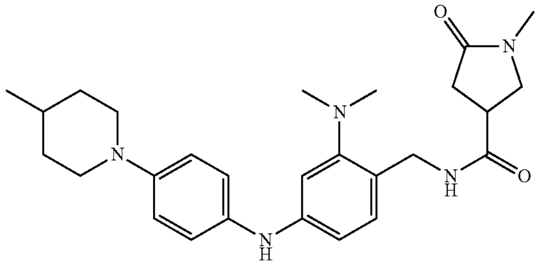

337
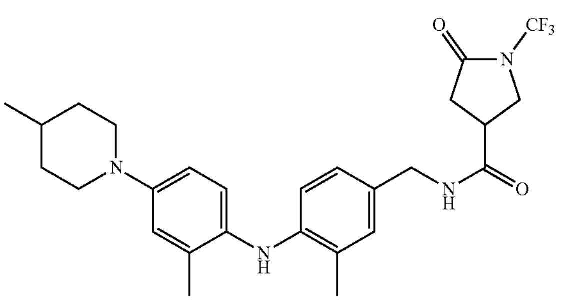
338
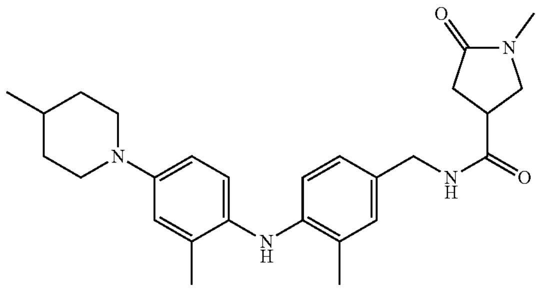
339
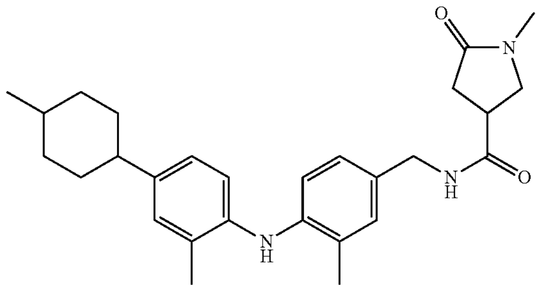
341
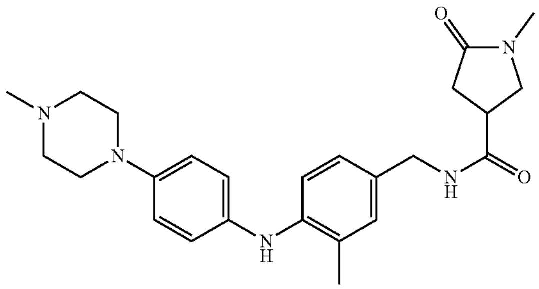
350
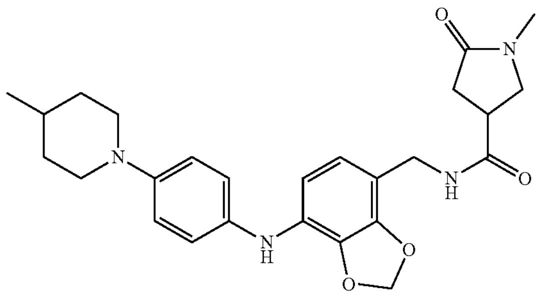
356
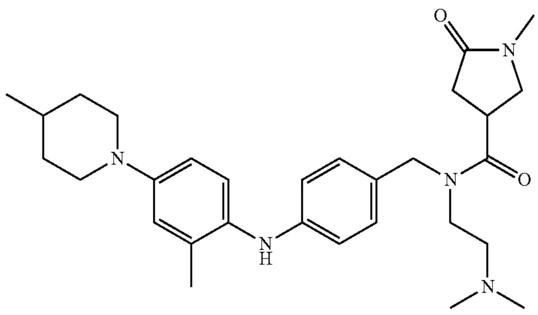
361
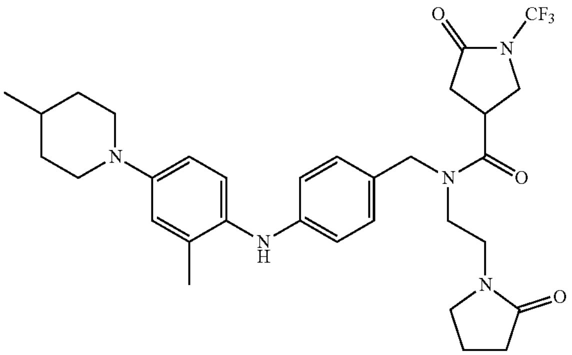
362
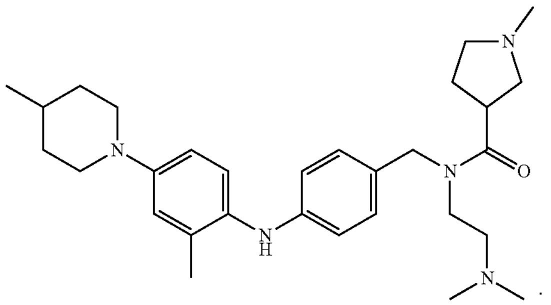
15. The compound, pharmaceutically acceptable salt, hydrate, or stereoisomer of claim 14, wherein the compound has a structure selected from:
203
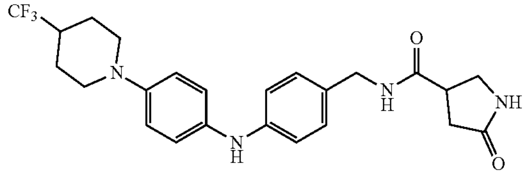

-continued
189
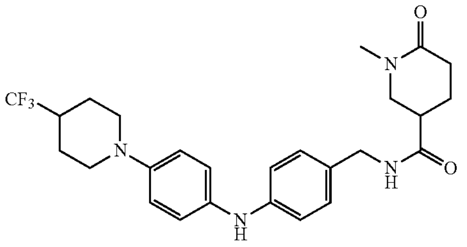
279
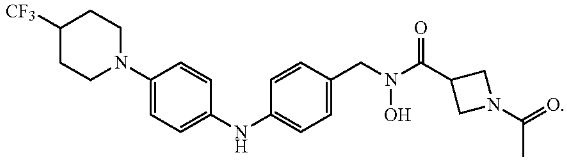
16. The compound, pharmaceutically acceptable salt, hydrate, or stereoisomer of claim 1, wherein the compound has a structure selected from:
363
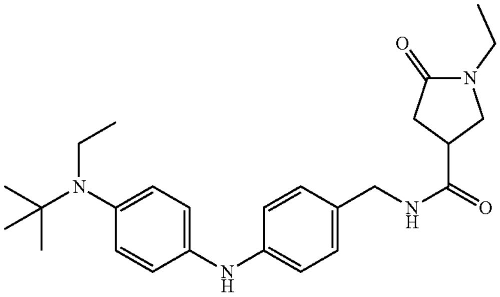
364
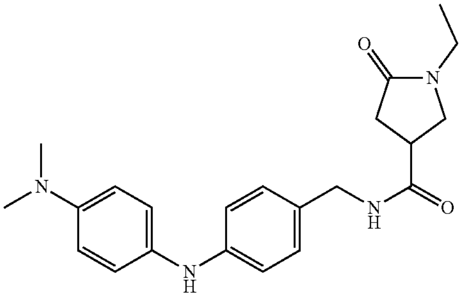
365
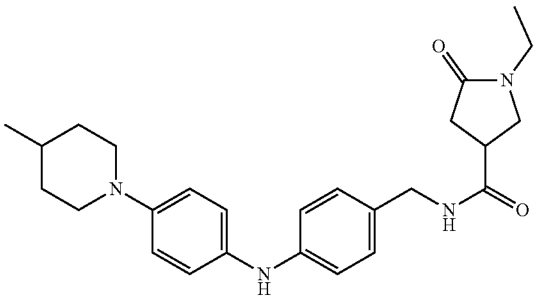
-continued
366
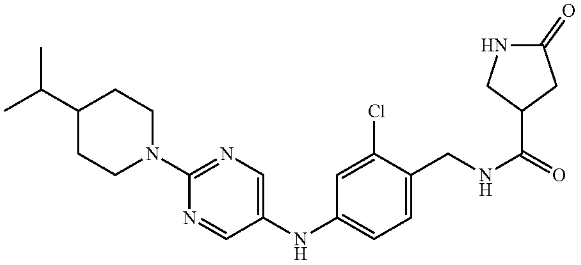
367
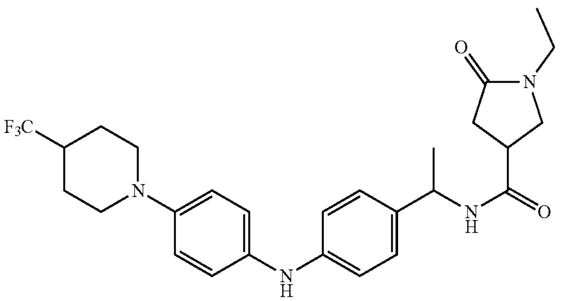
368
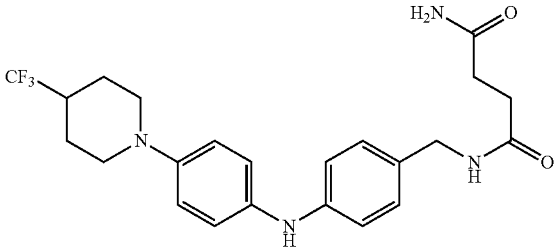
370
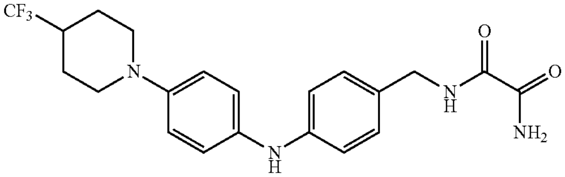
371
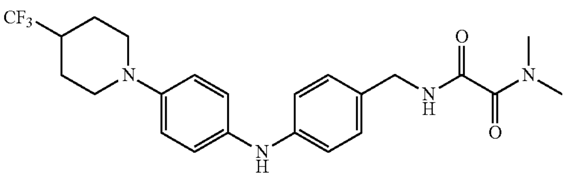
372
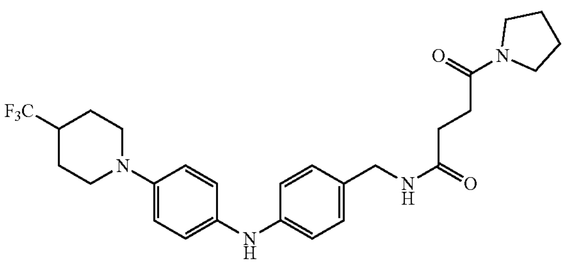

-continued
373
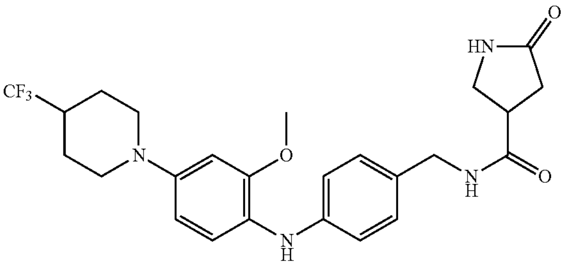
374
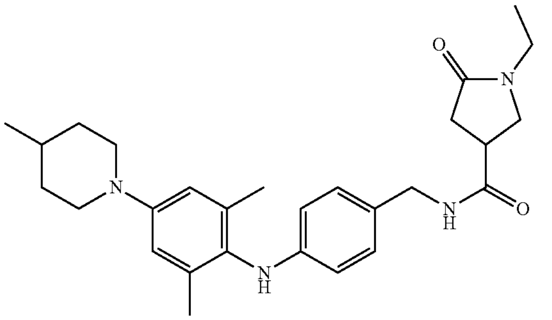
375
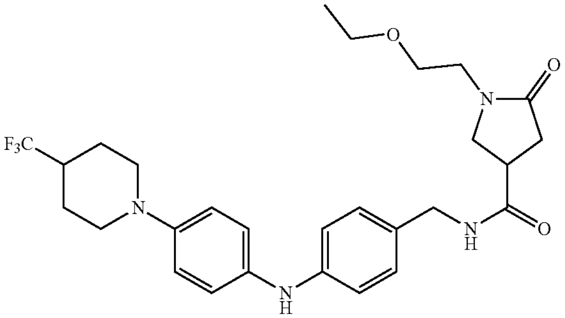
376
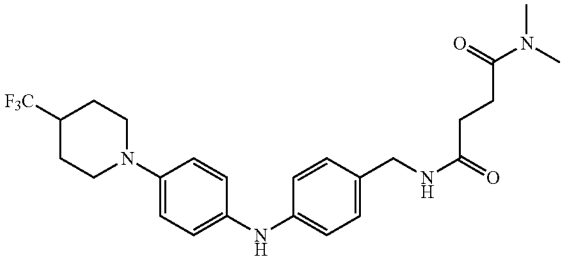
377
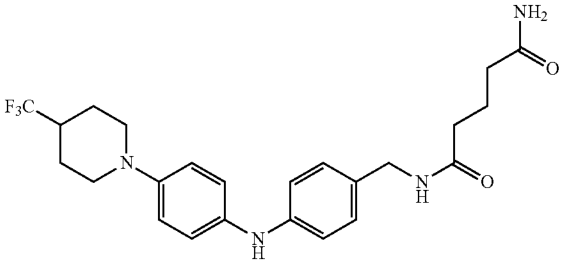
-continued
378
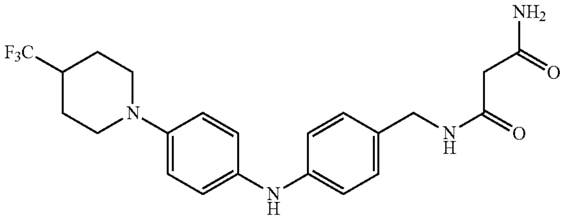
379
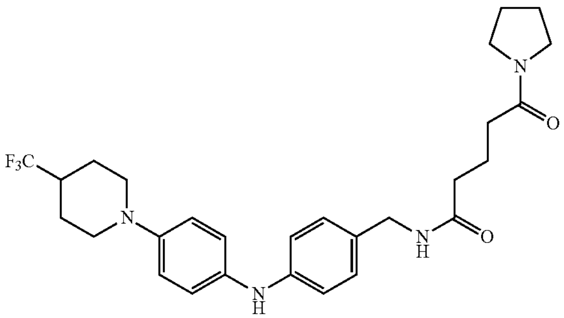
380
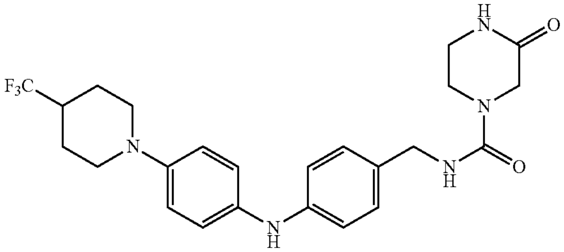
381
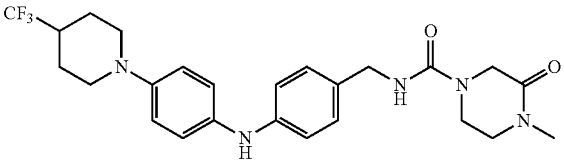
382
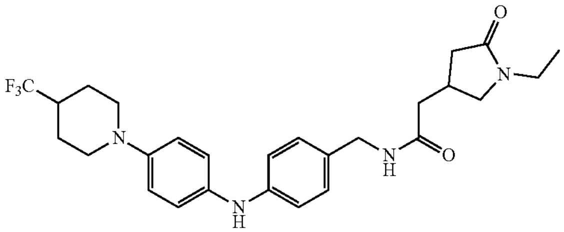
383
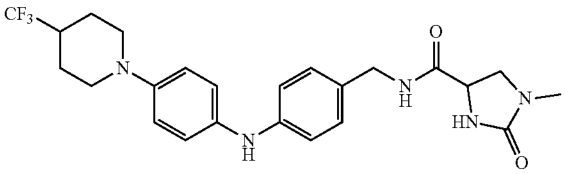

384
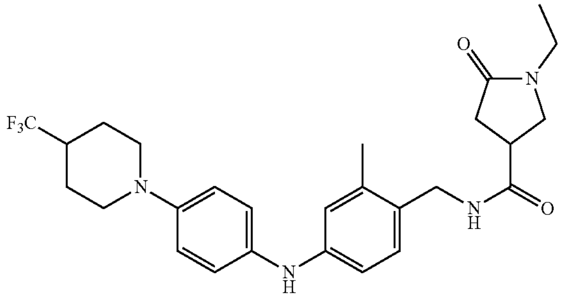
385
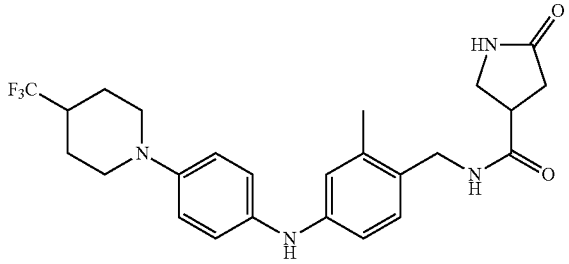
386
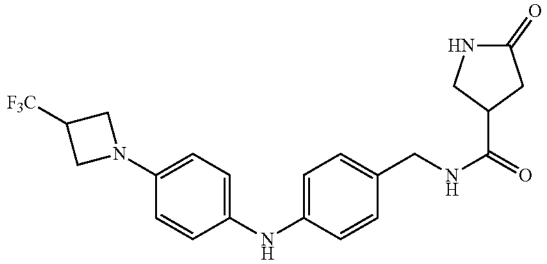
387
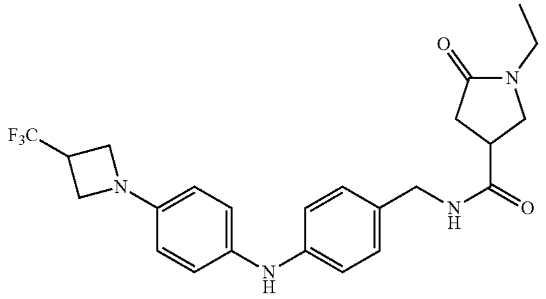
388
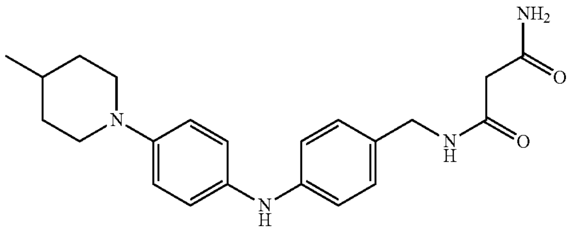
389
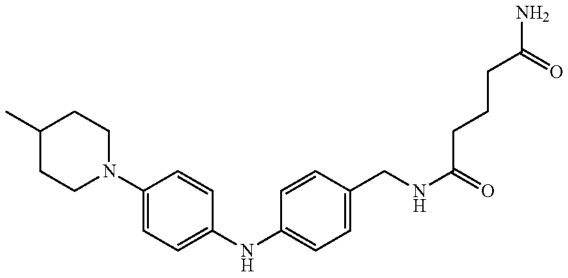
390
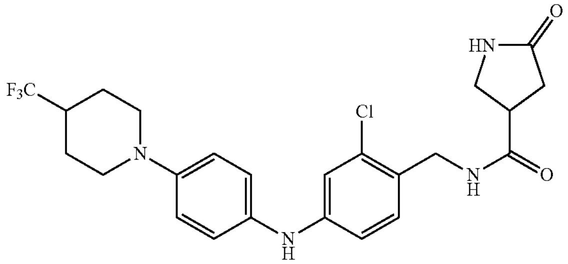
391
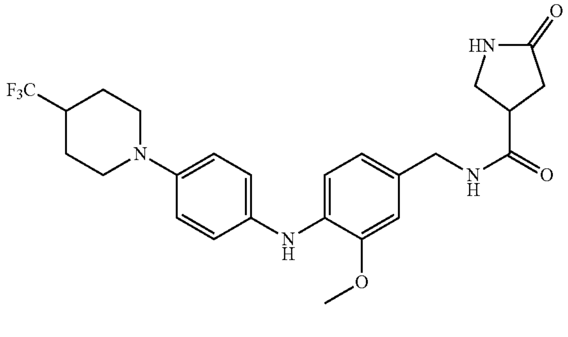
393
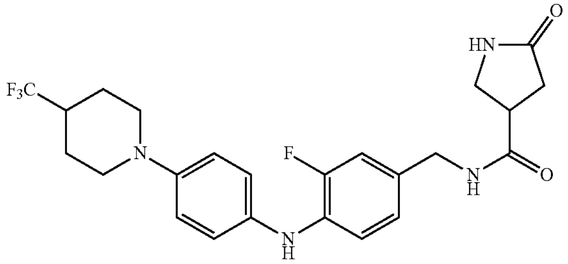
395
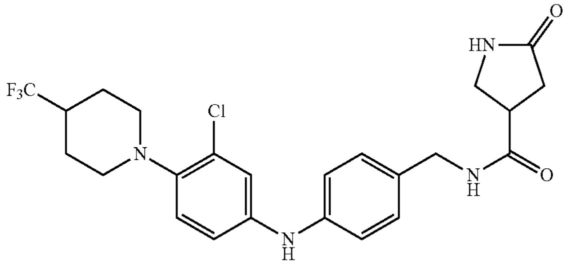

-continued
396
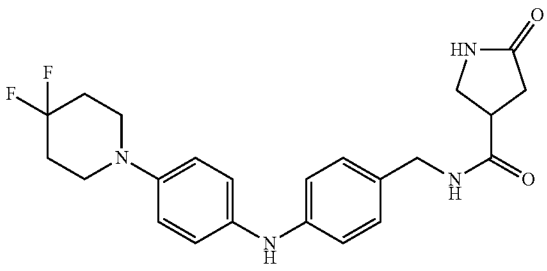
397
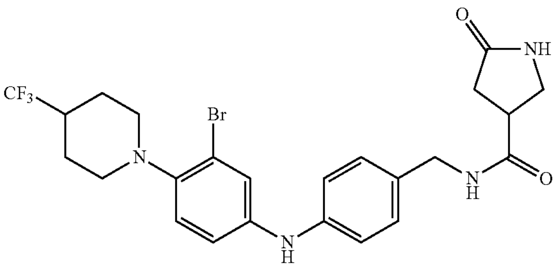
398
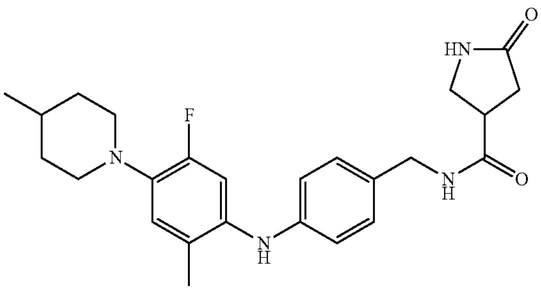
399
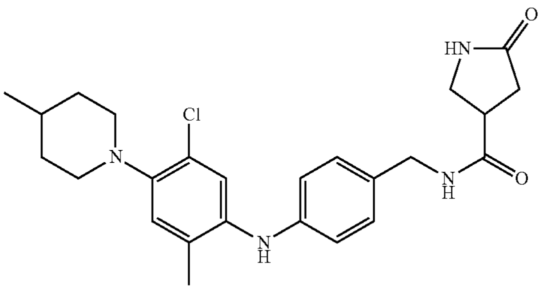
400
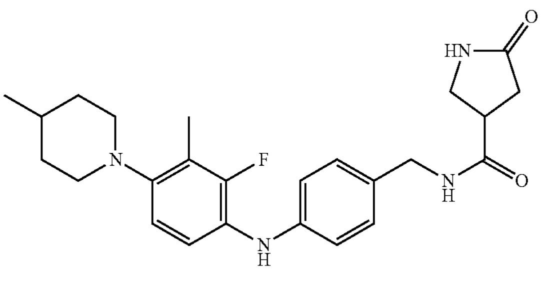
-continued
401
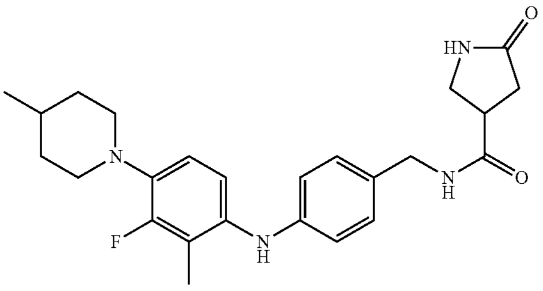
402
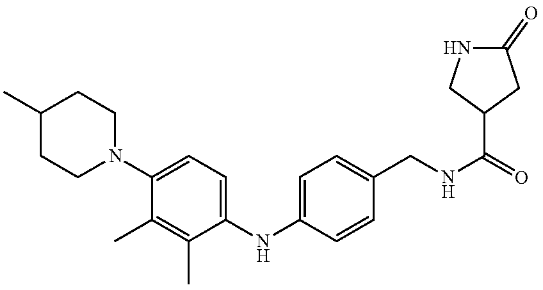
403
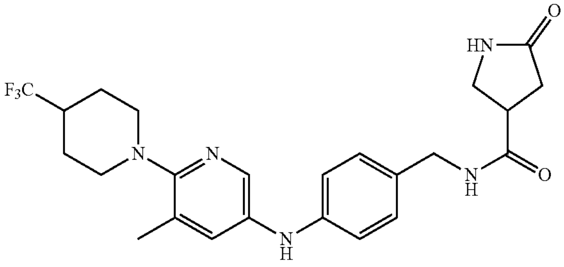
404
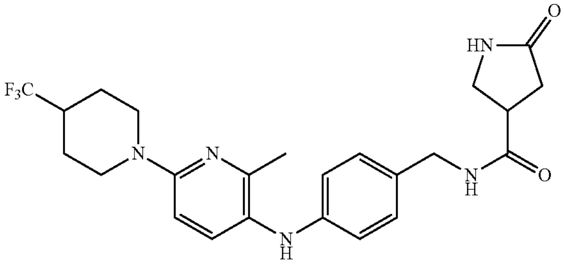
406
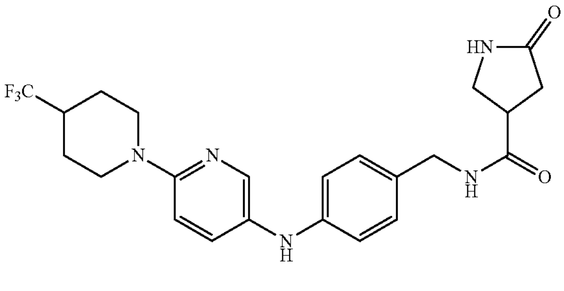

-continued
407
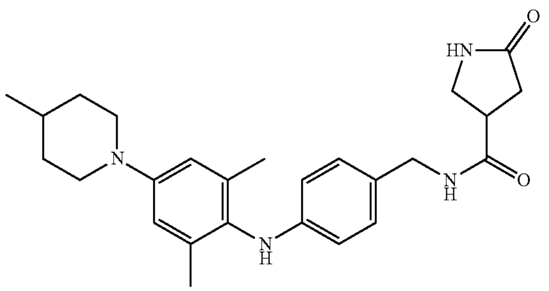
408
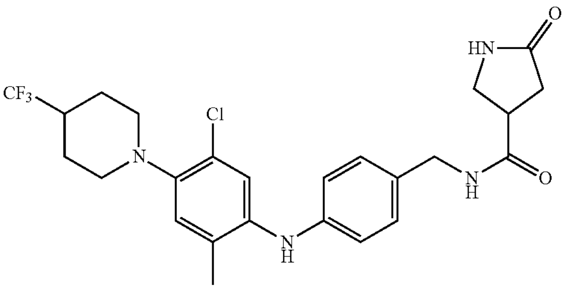
409
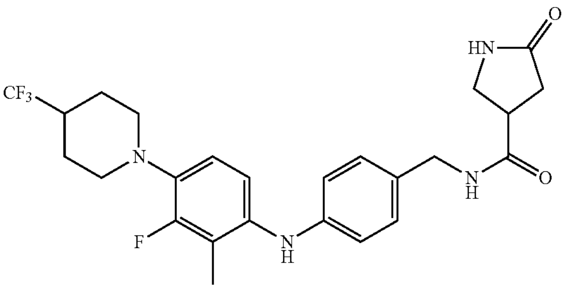
410
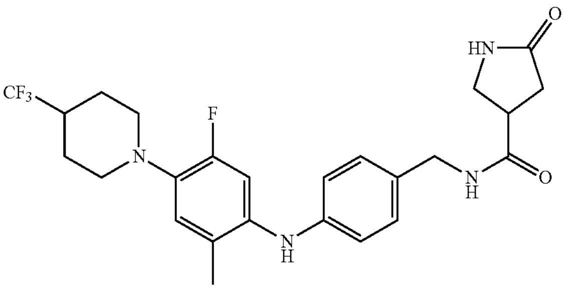
411
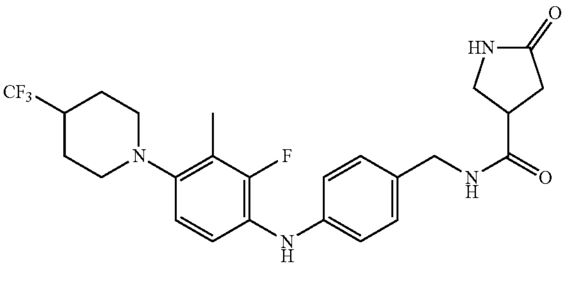
-continued
412
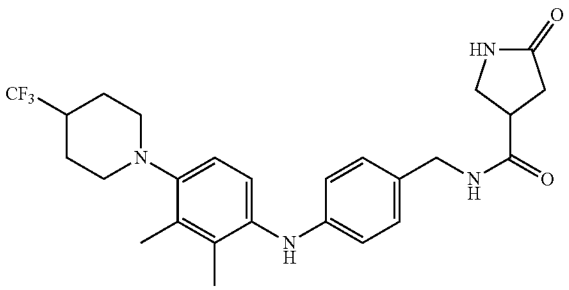
415
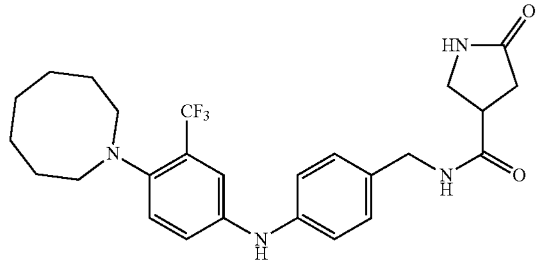
416
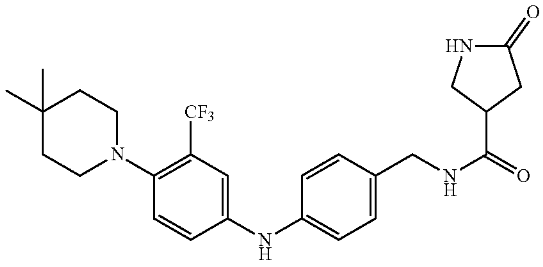
419
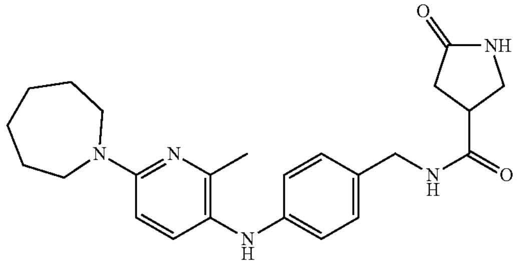
420
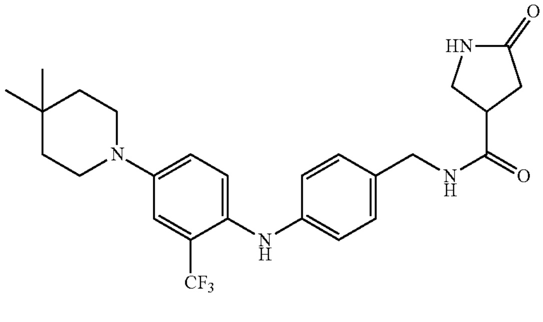

-continued
421
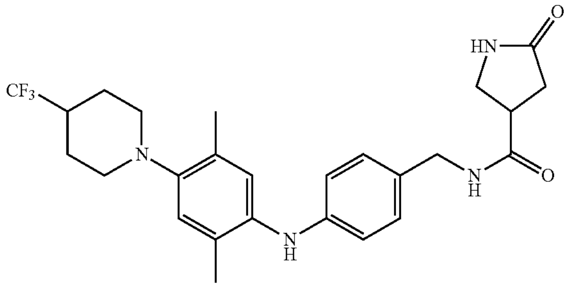
422
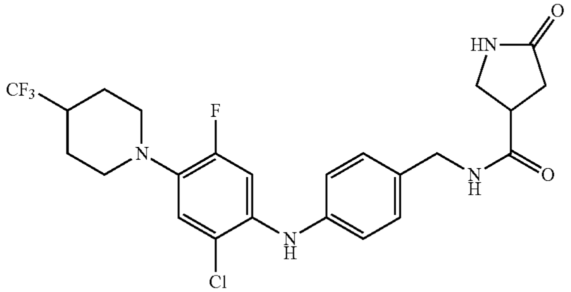
427
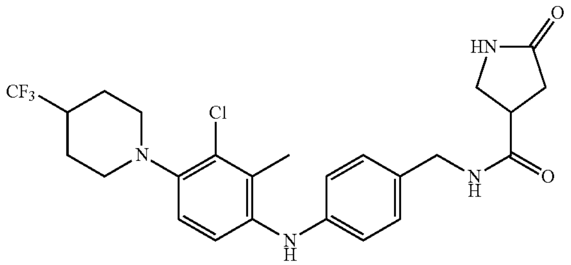
429
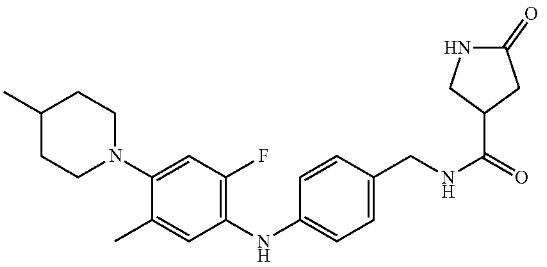
430
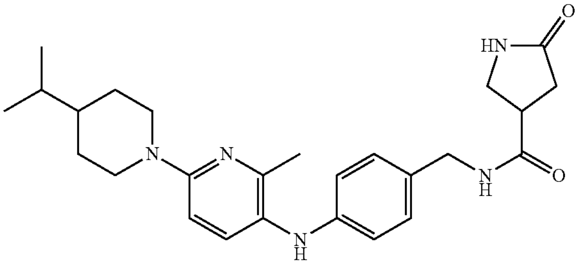
-continued
431
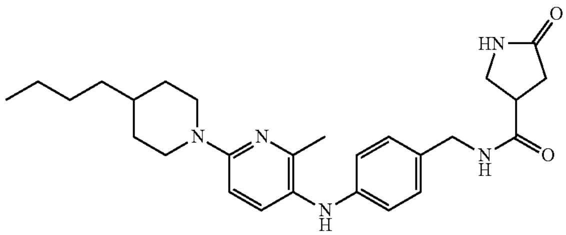
432
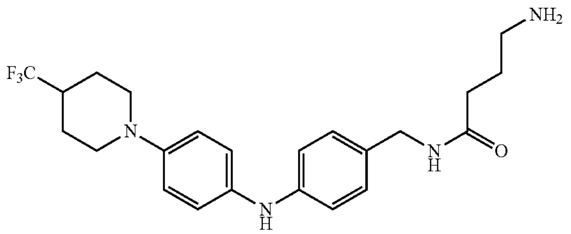
433
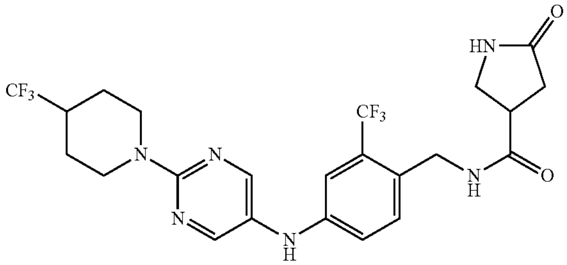
437
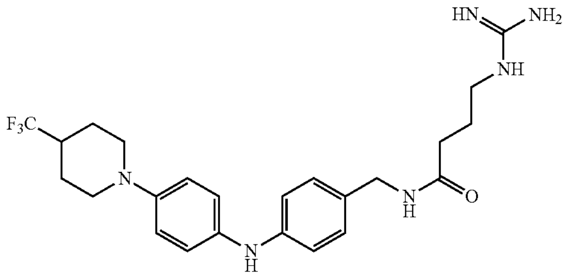
438
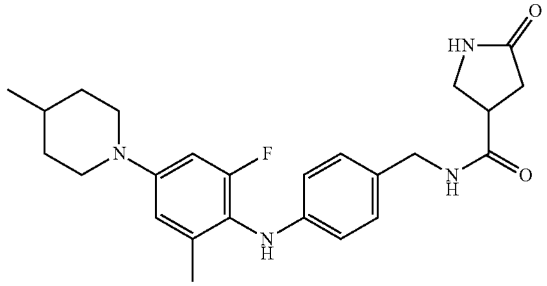

-continued
439
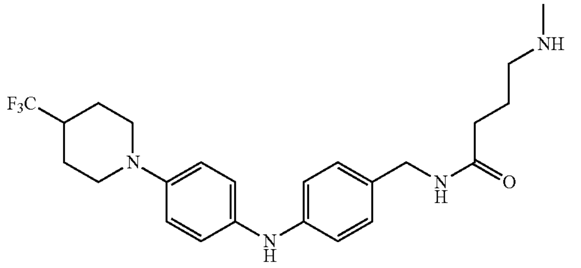
443
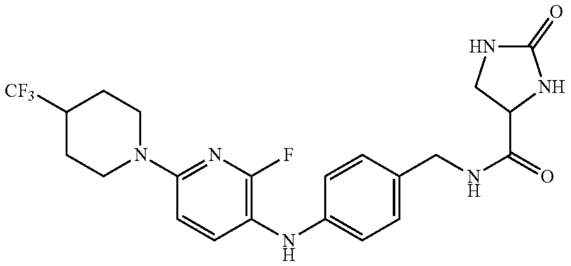
444
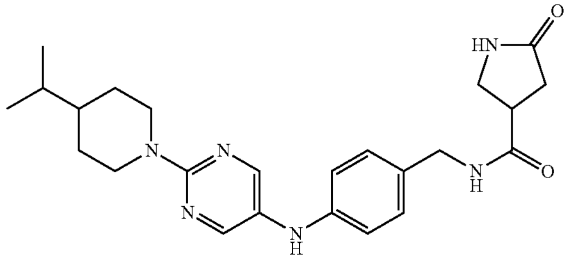
445
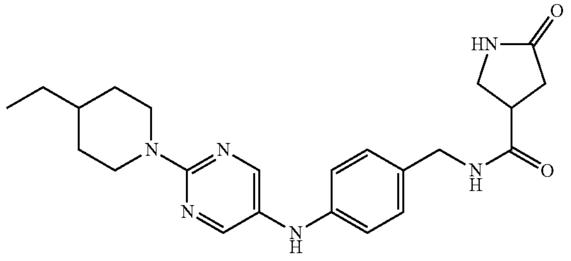
446
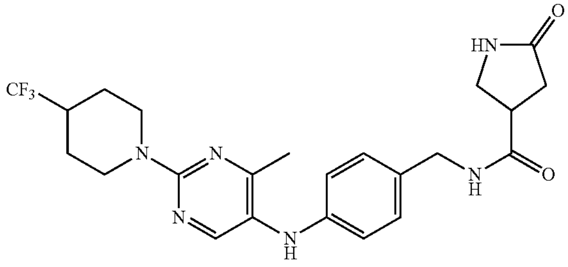
-continued
448
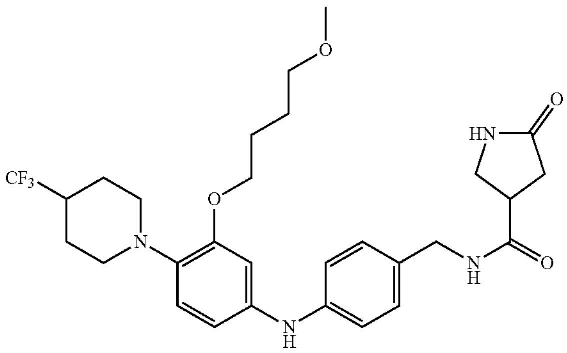
449
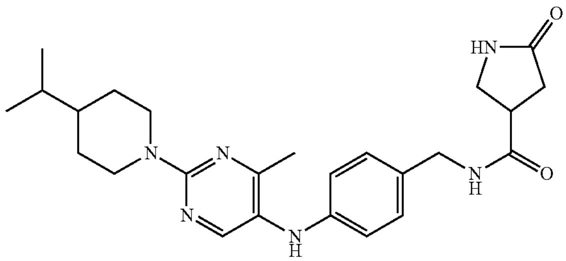
450
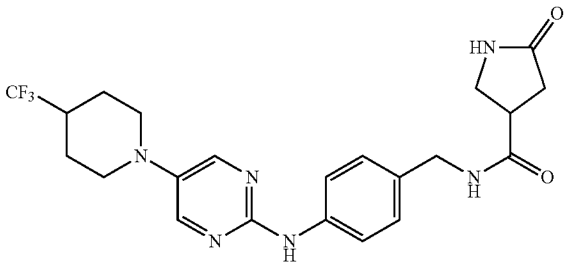
451
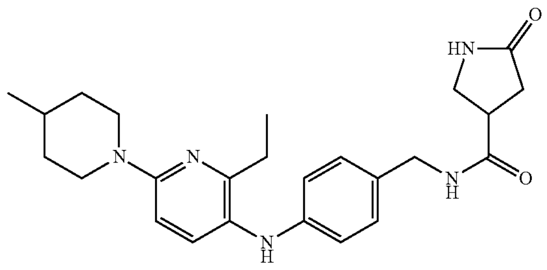
453
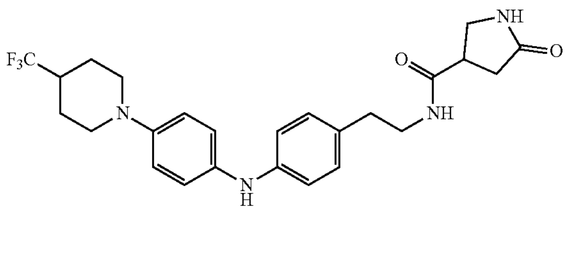

-continued
454
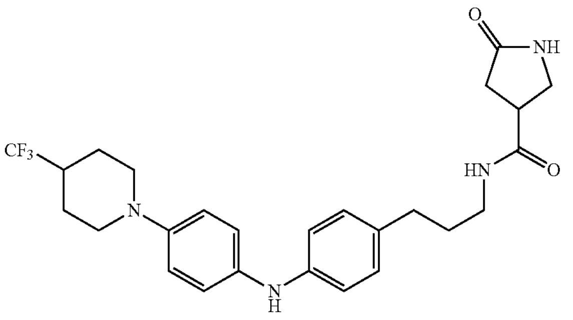
455
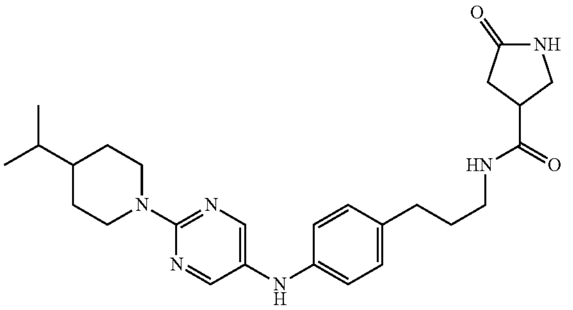
456
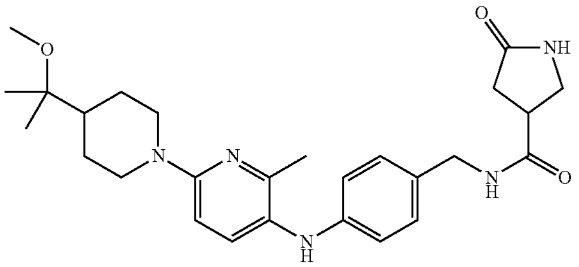
457
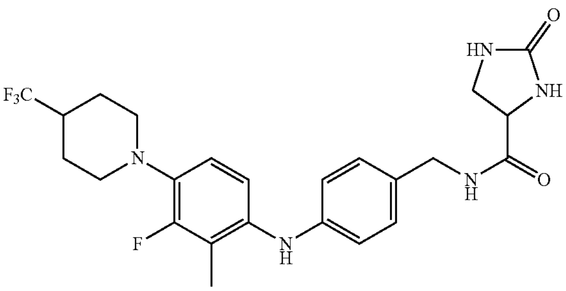
-continued
458
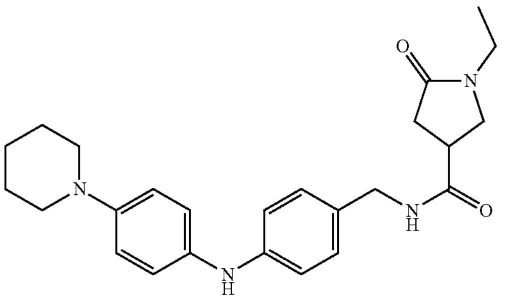
459
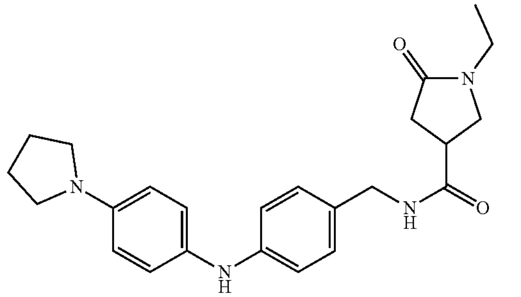
460
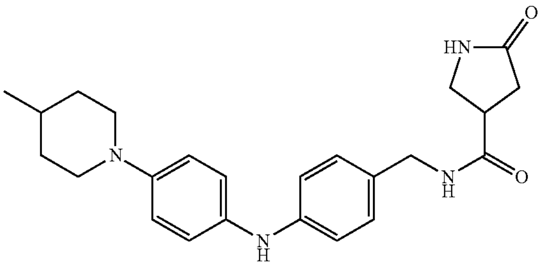
461
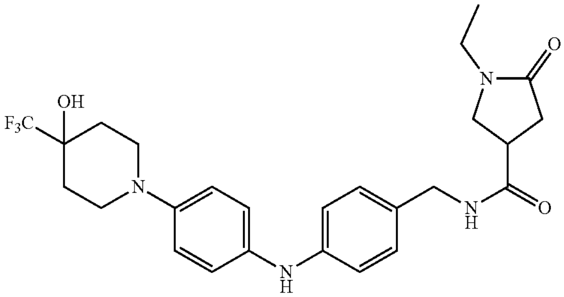
462
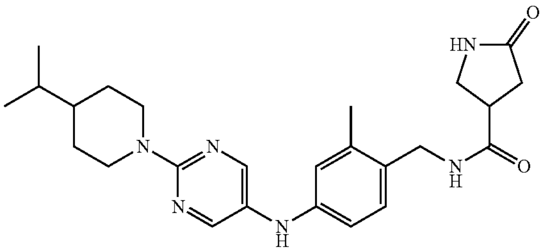

-continued
463
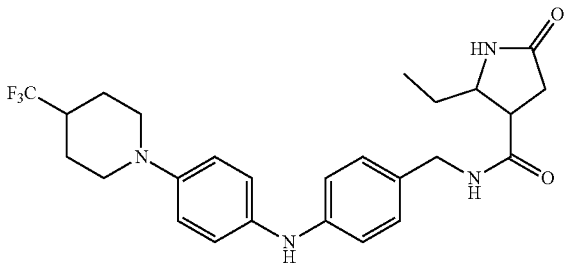
464
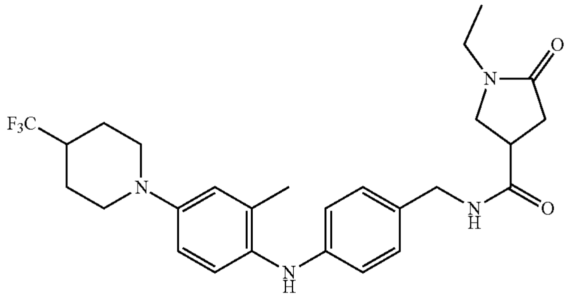
465
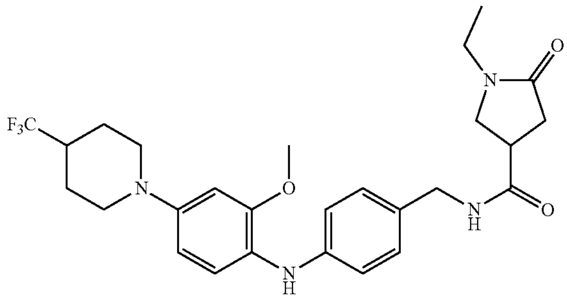
466
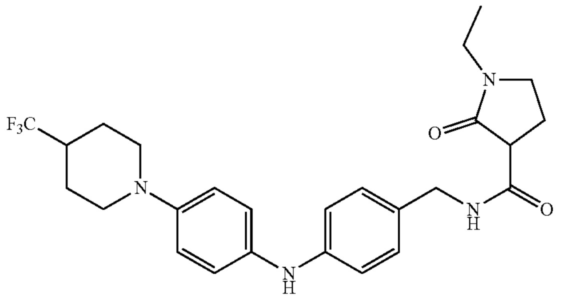
467
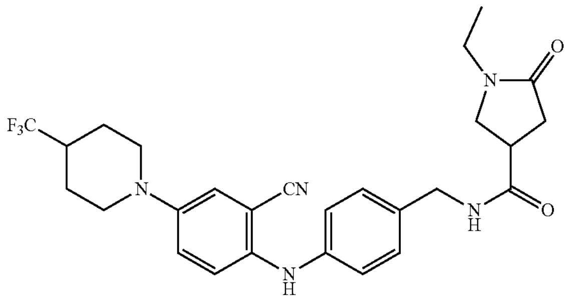
-continued
468
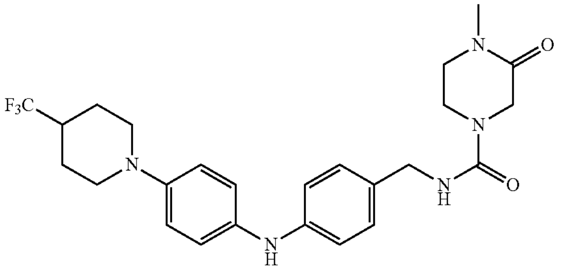
469
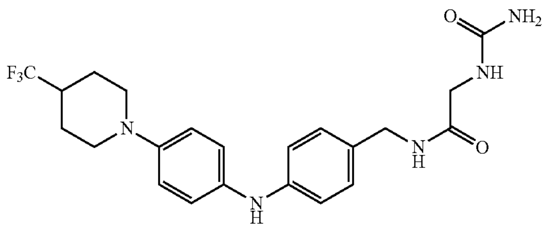
470
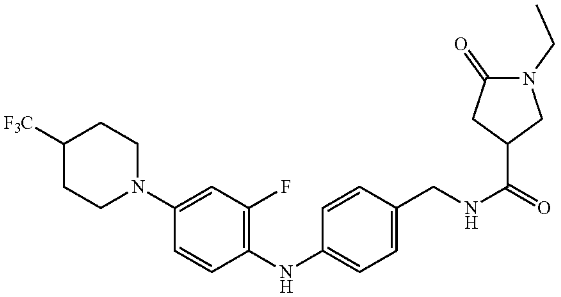
471
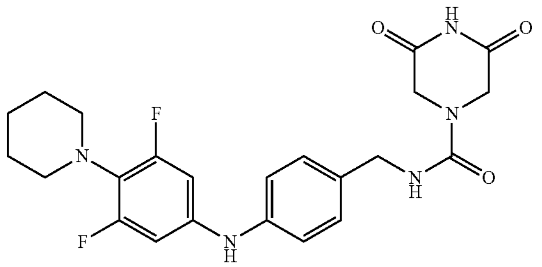
472
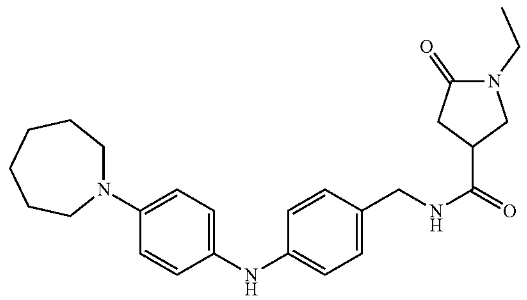

-continued
475
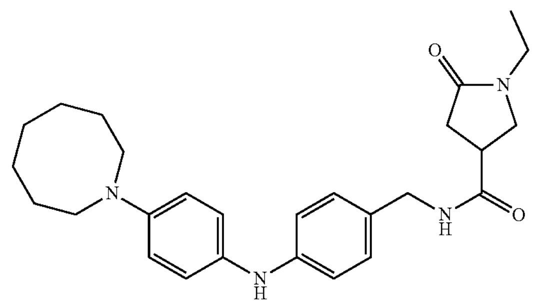
476
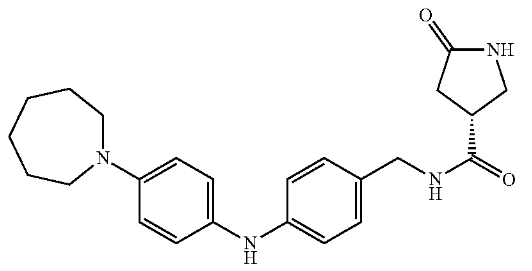
477
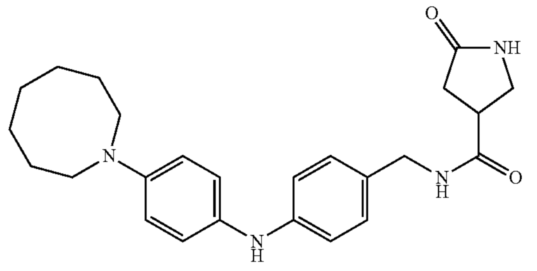
478
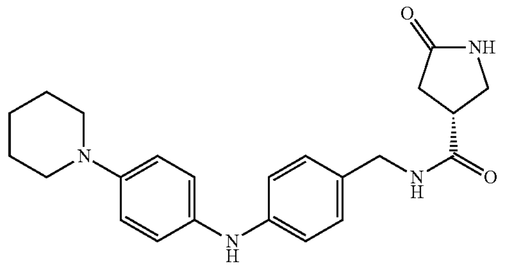
479
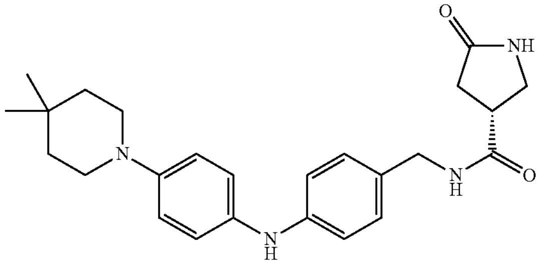
-continued
480
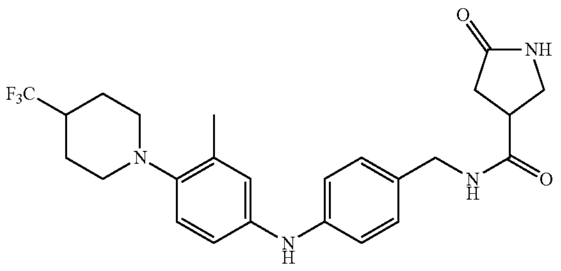
481
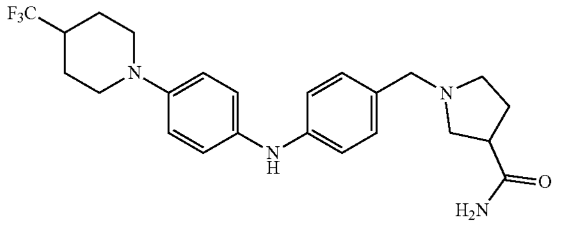
483
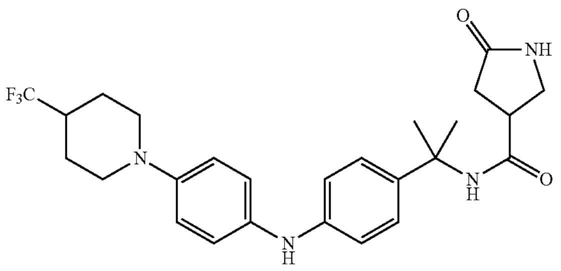
484
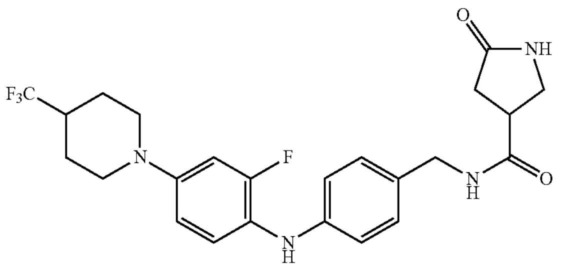
485
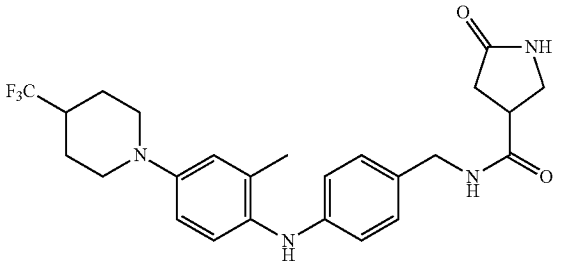

-continued
486
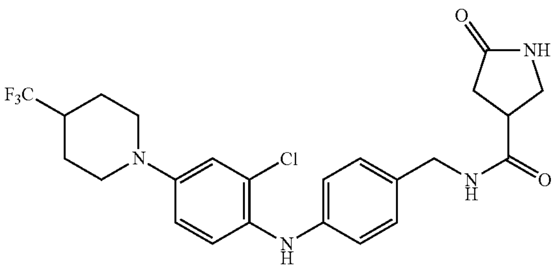
487
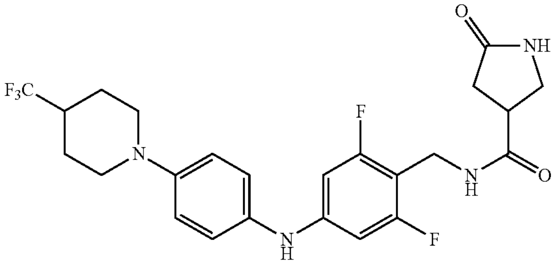
488
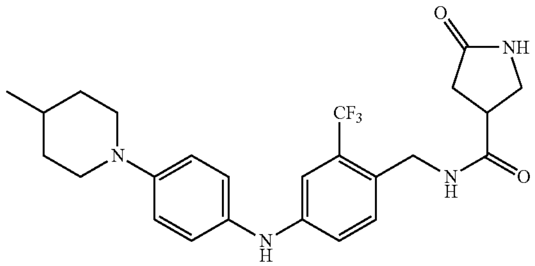
489
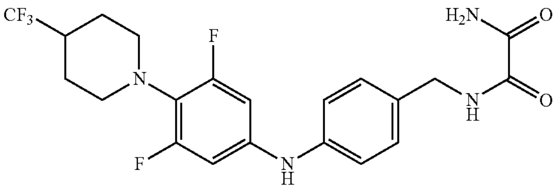
491
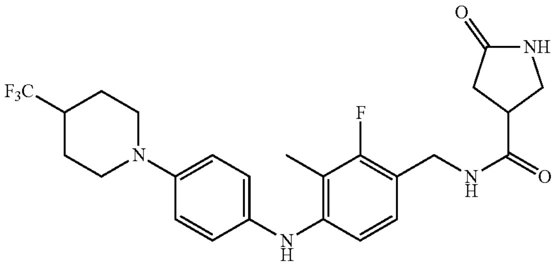
-continued
492
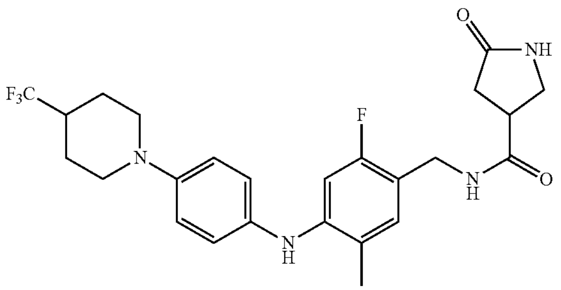
493
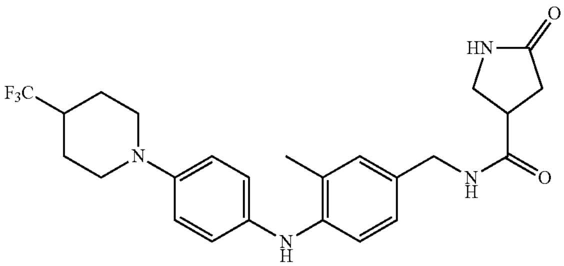
495
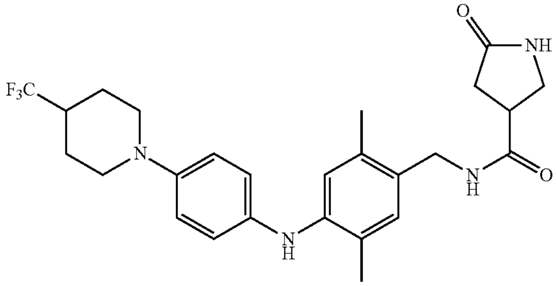
496
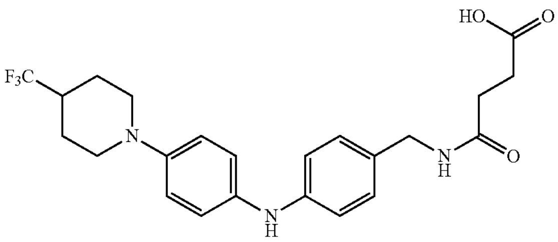
497
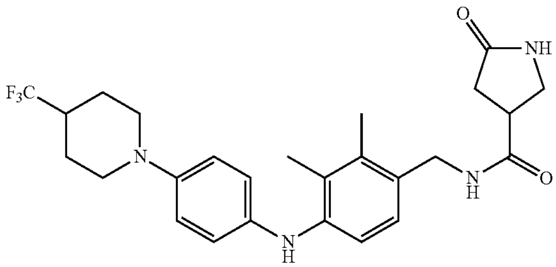

498
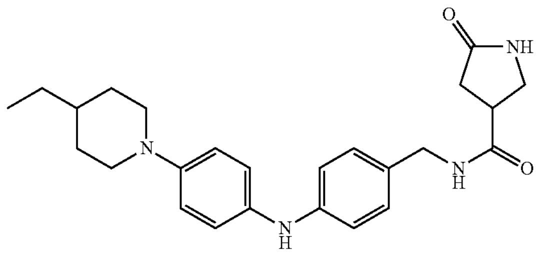
499
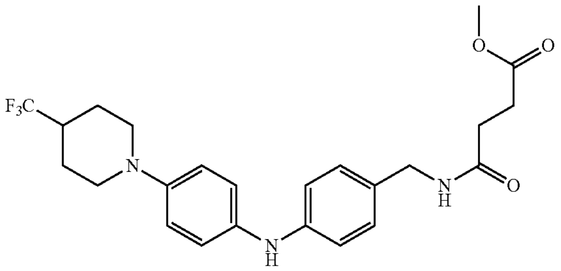
500
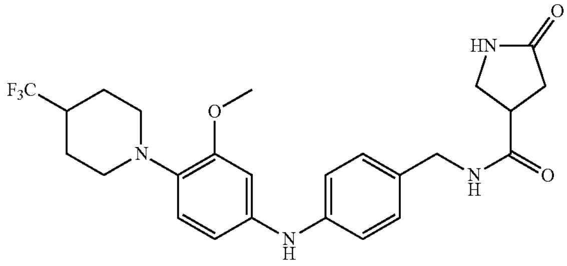
501
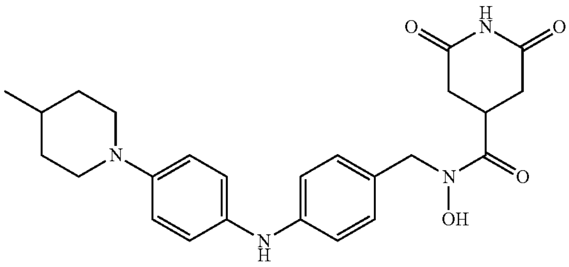
502
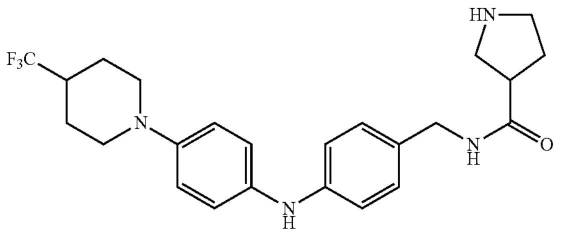
503
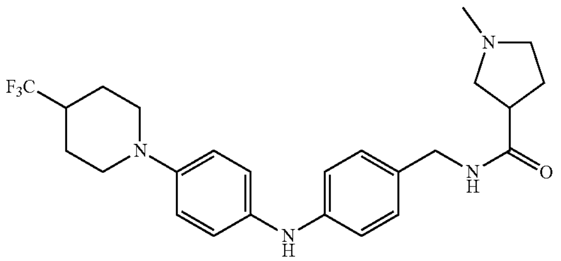
504
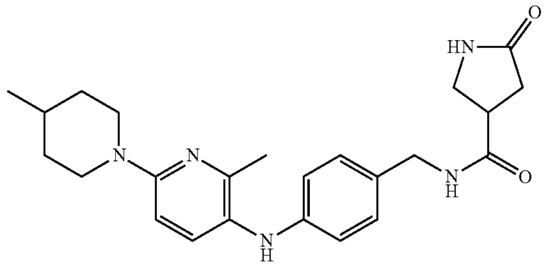
505
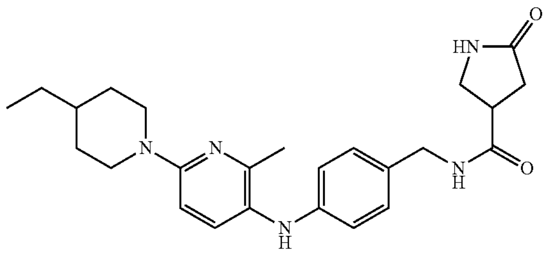
506
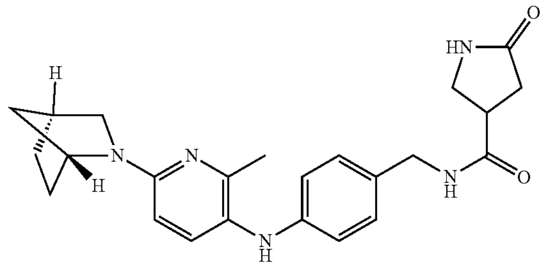
507
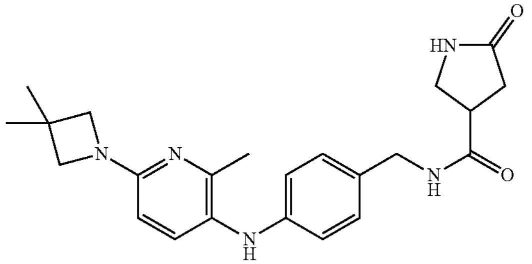

-continued
508
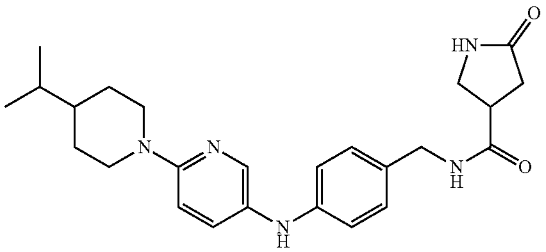
509
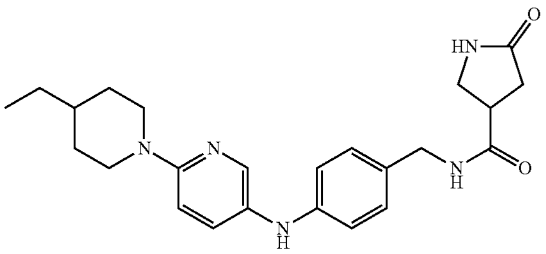
510
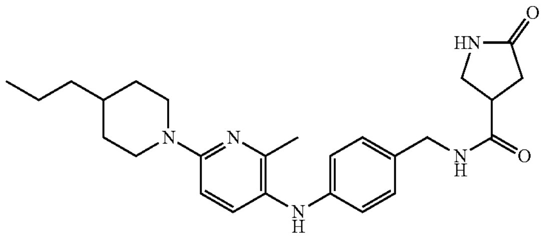
511
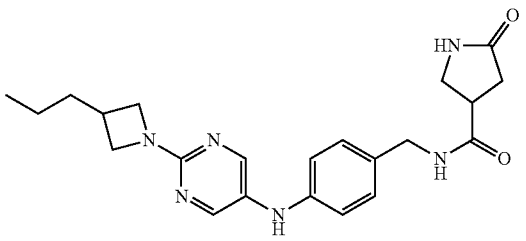
512
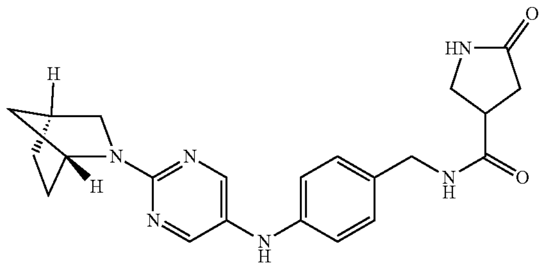
513
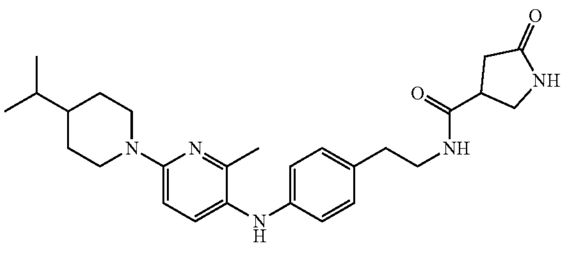
-continued
514
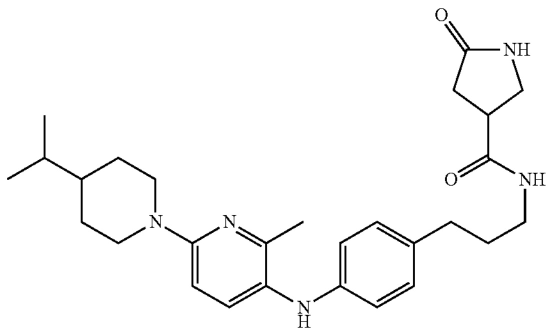
515
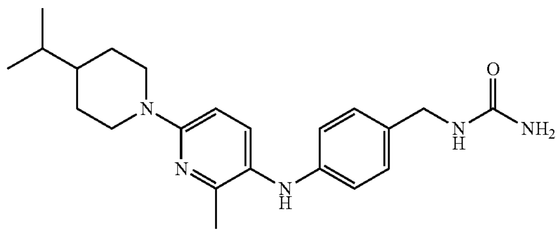
516
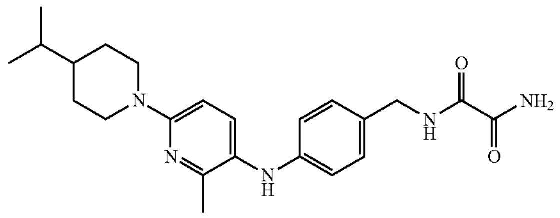
517
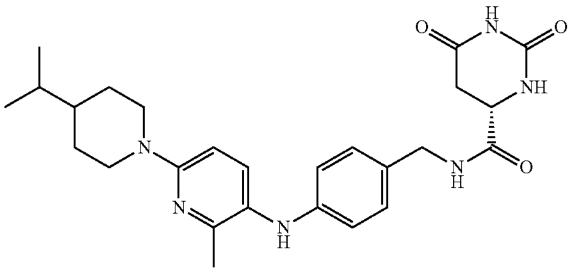
518
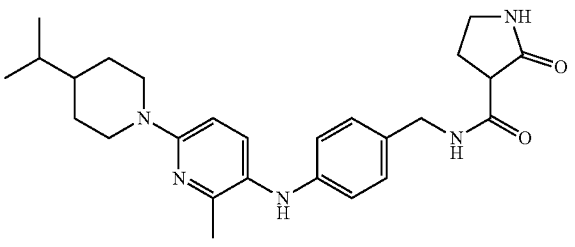

-continued
519
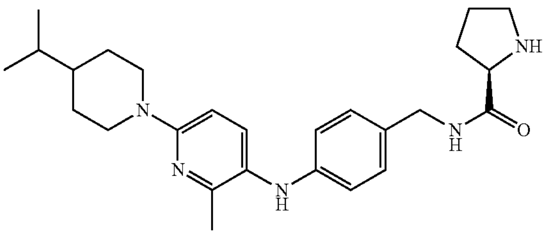
520
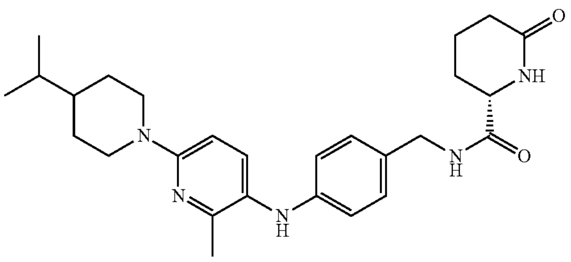
521
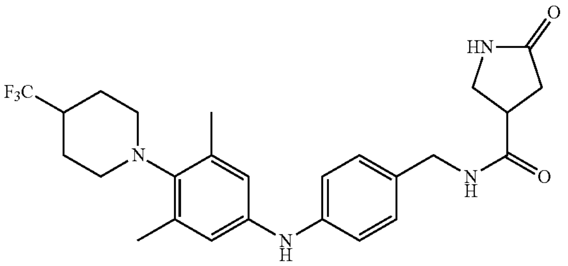
522
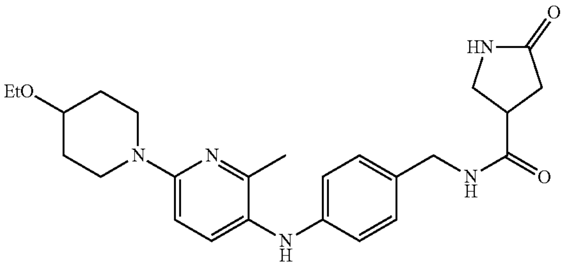
523
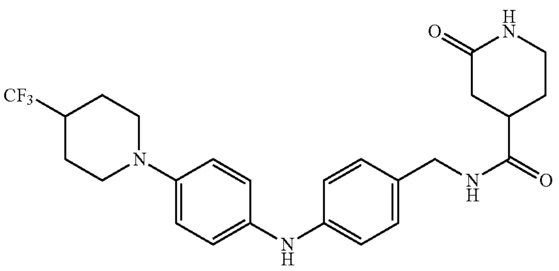
-continued
524
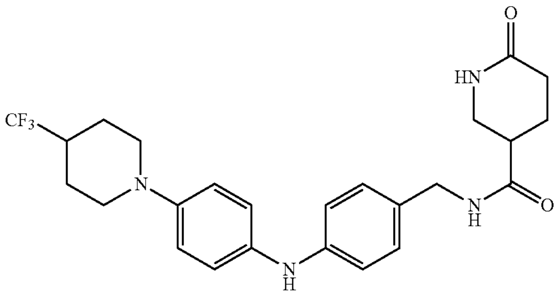
525
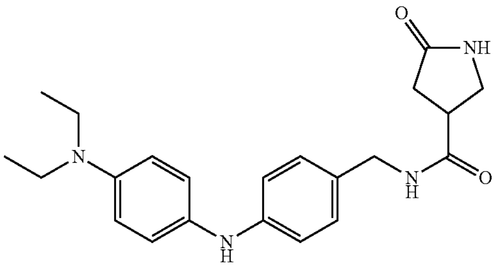
526
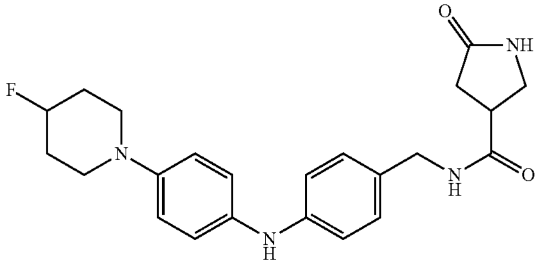
527
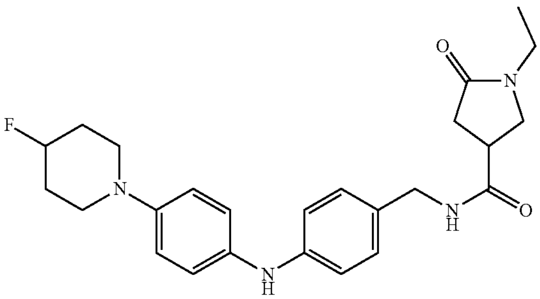
528
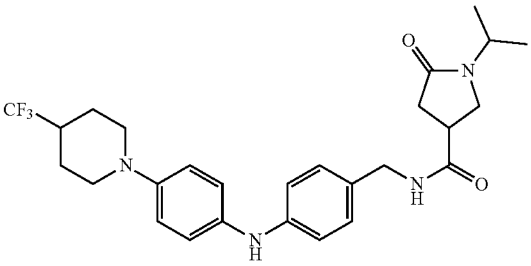

-continued
529
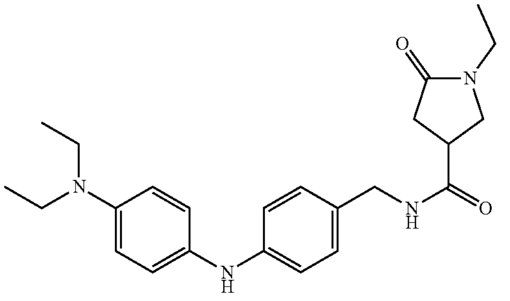
530
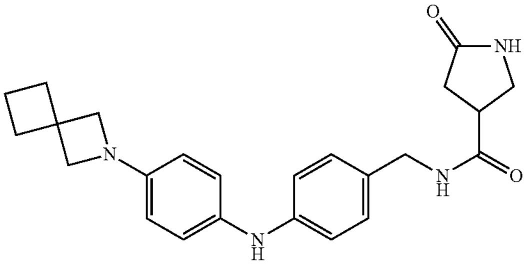
531
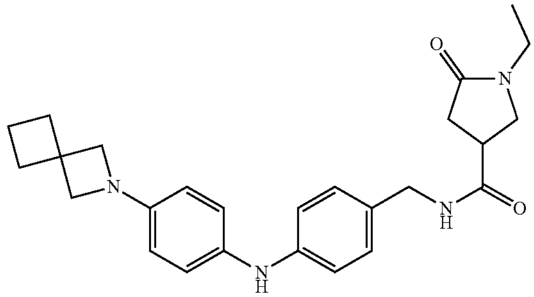
532
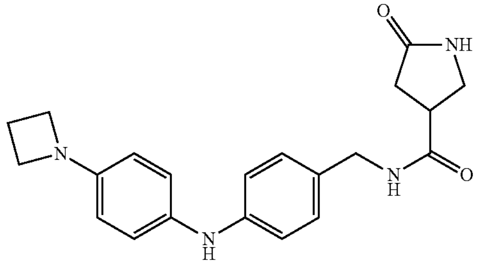
533
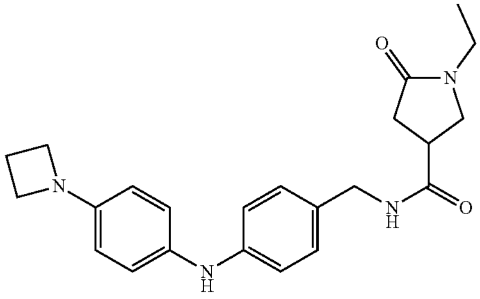
-continued
538
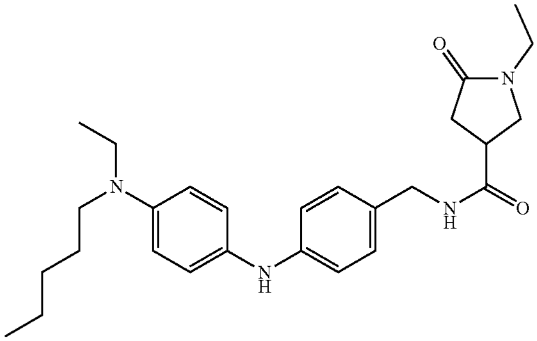
539
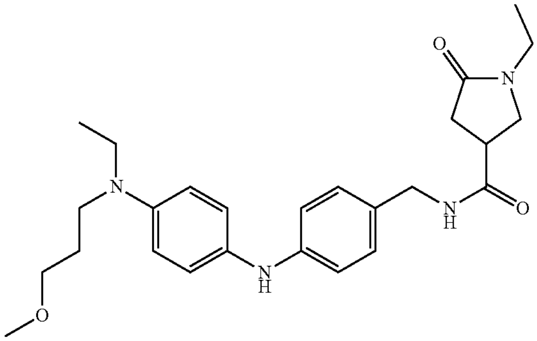
540
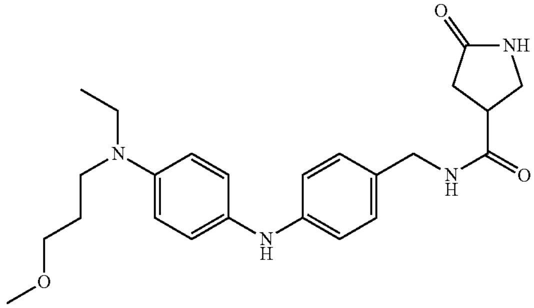
543
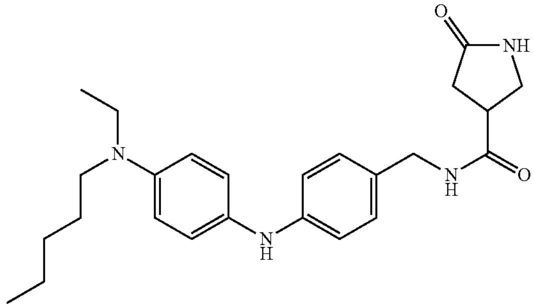

-continued
546
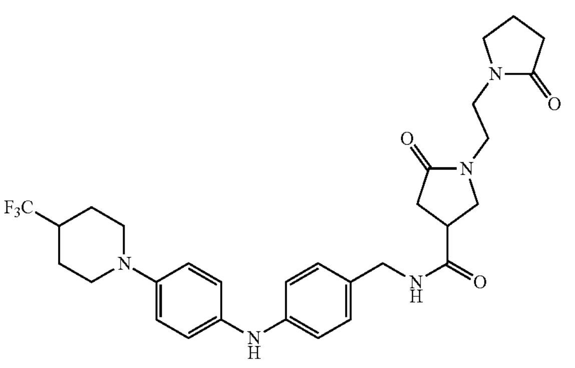
549
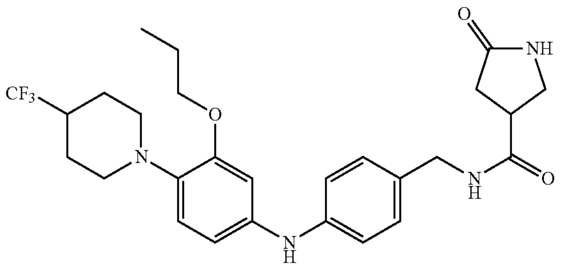
550
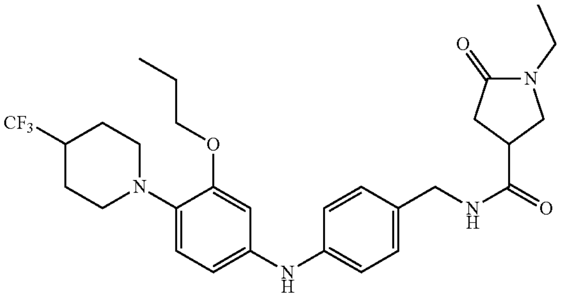
551
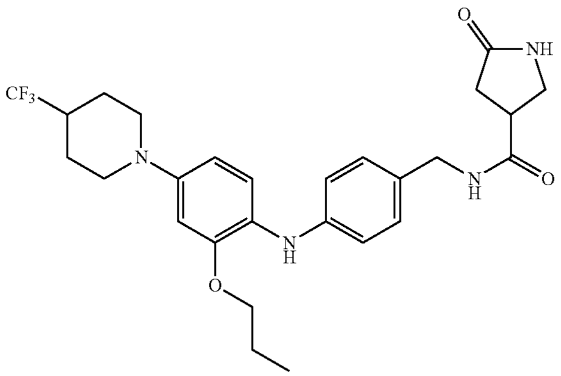
-continued
552
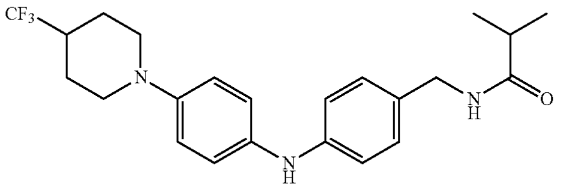
553
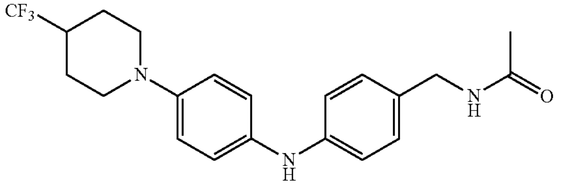
554
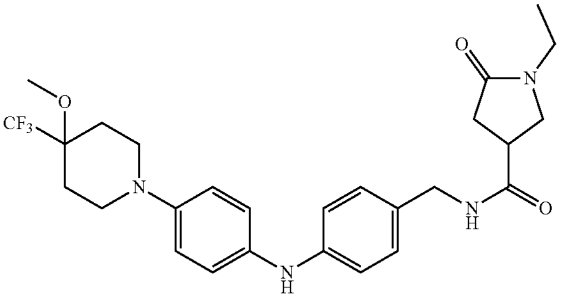
555
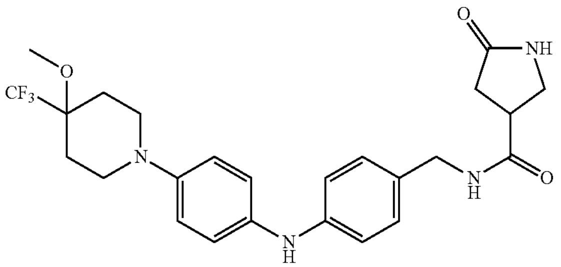
558
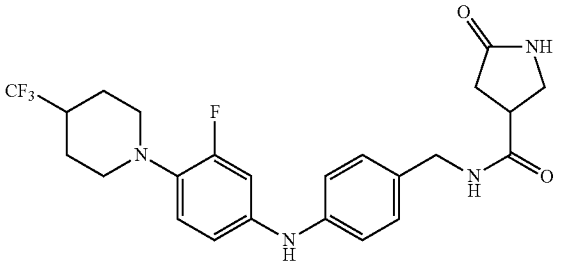
559
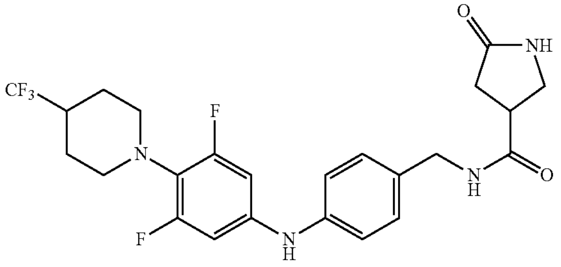

-continued
560
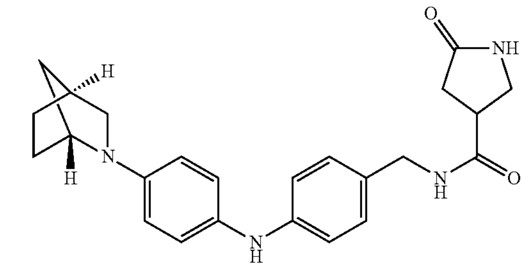
561
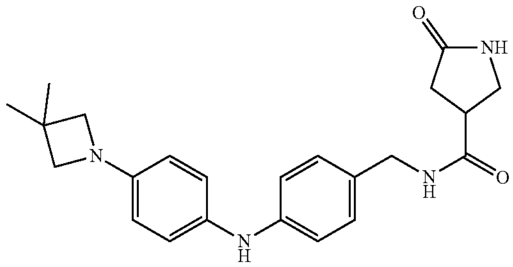
562
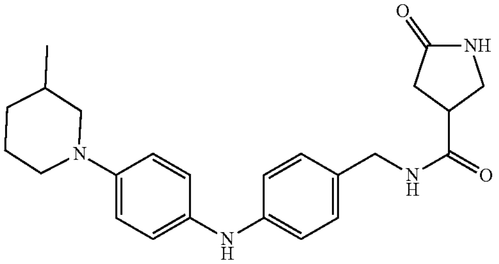
563
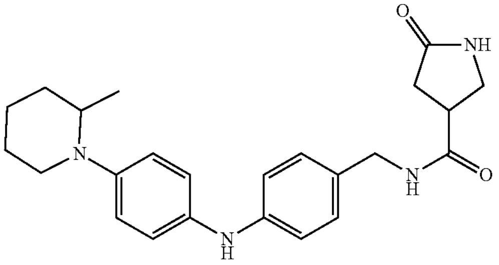
564
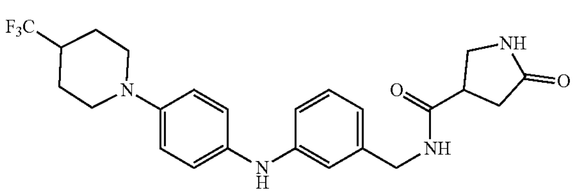
565
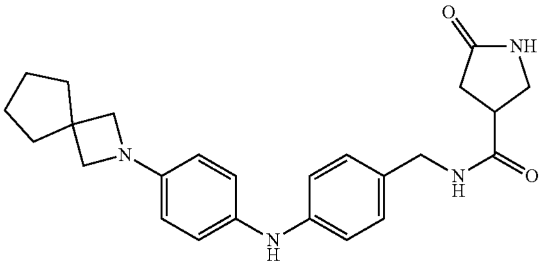
-continued
566
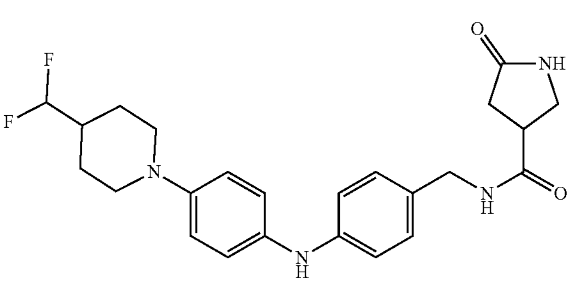
567
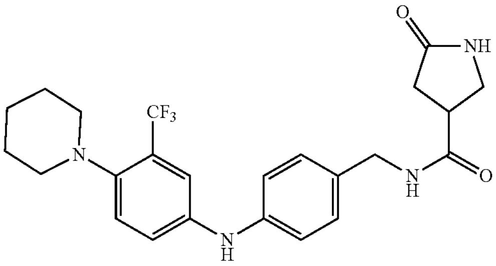
568
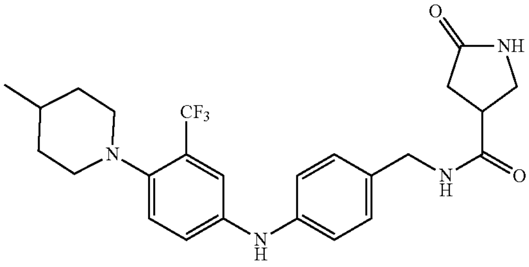
569
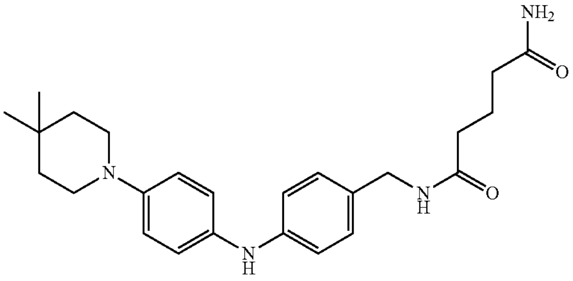
570
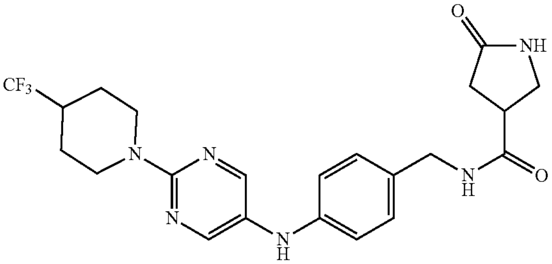

571
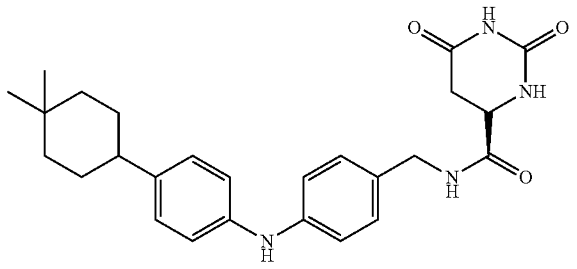
572
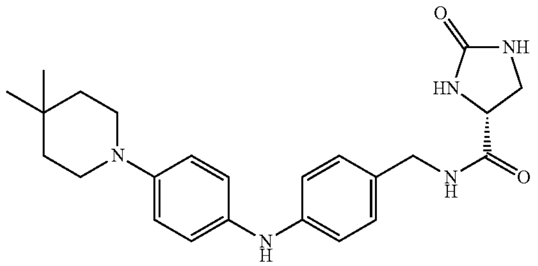
573
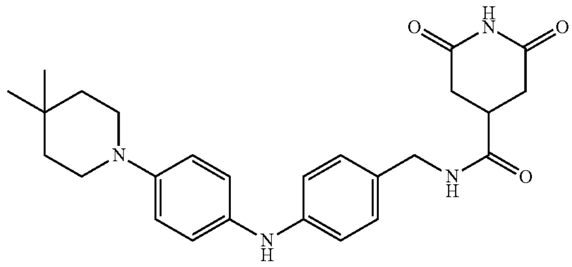
574
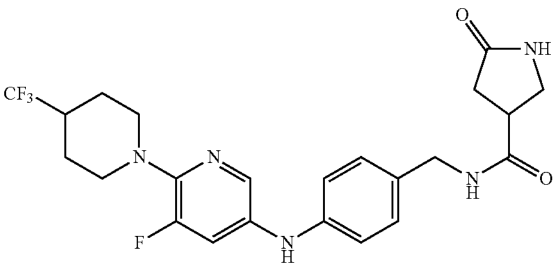
575
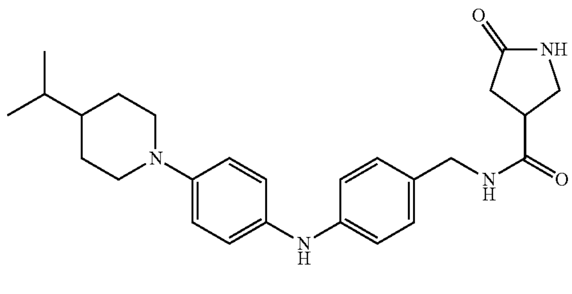
576
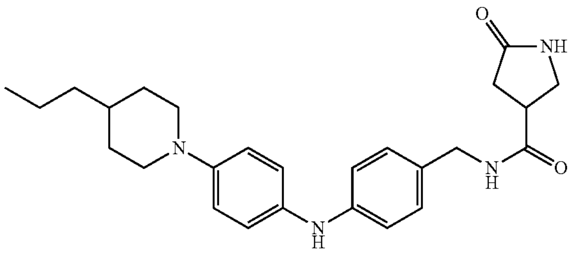
577
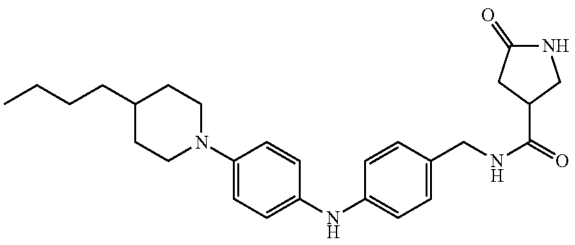
578
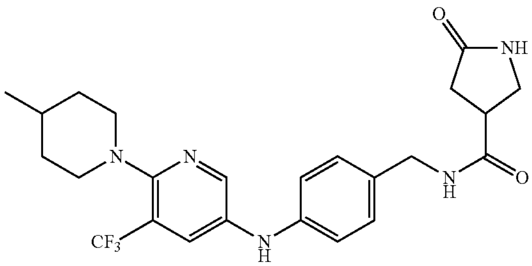
579
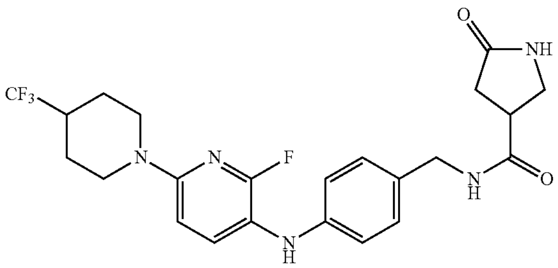
580
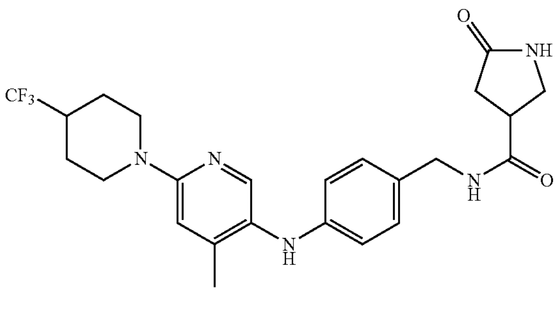

-continued
581
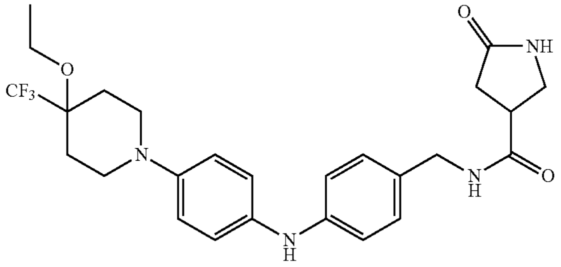
582
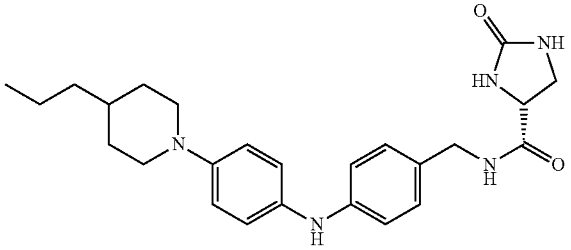
583
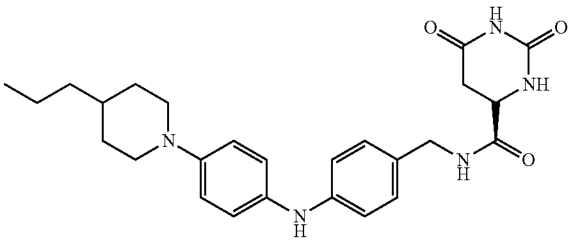
584
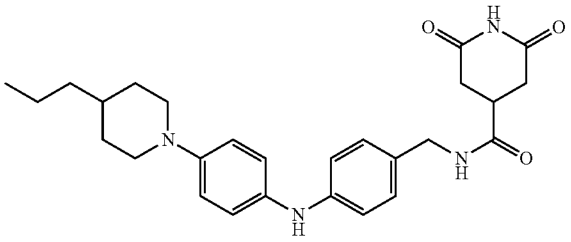
585
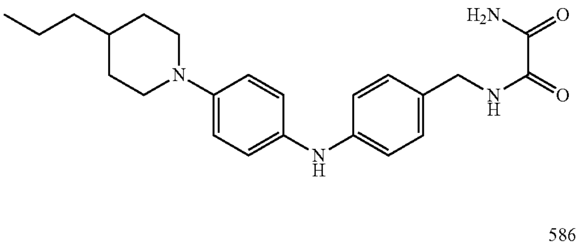
586
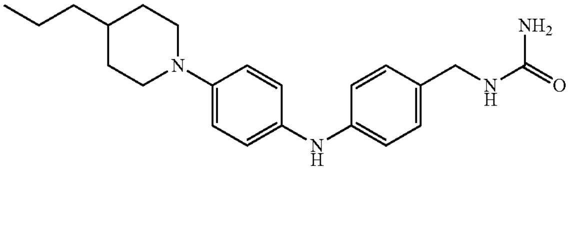
-continued
589
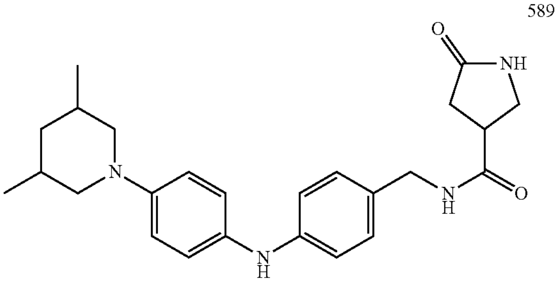
590
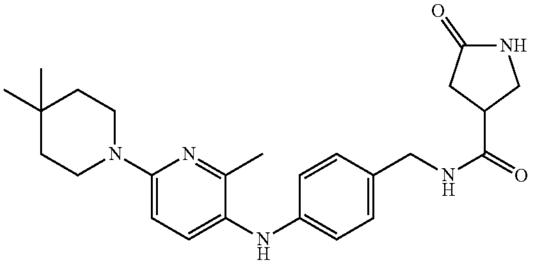
591
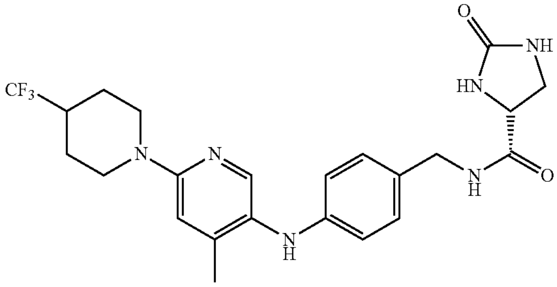
592
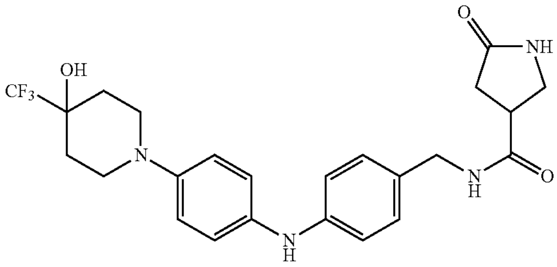
593
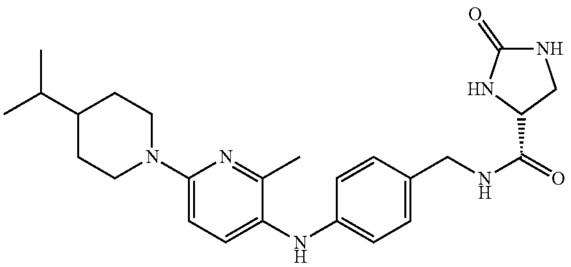

-continued
594
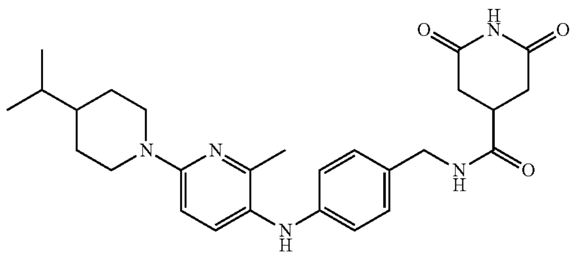
595
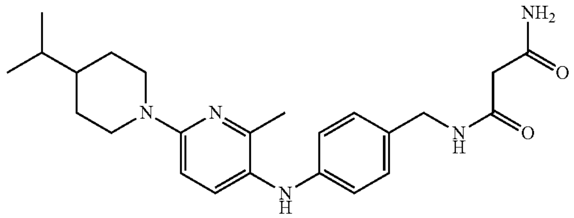
596
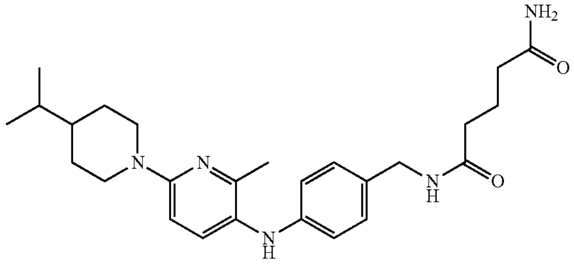
597
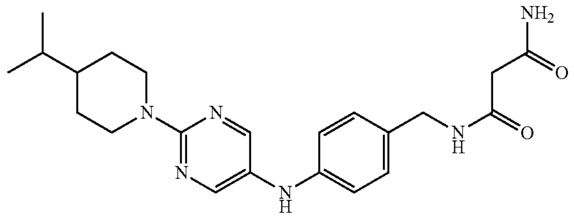
598
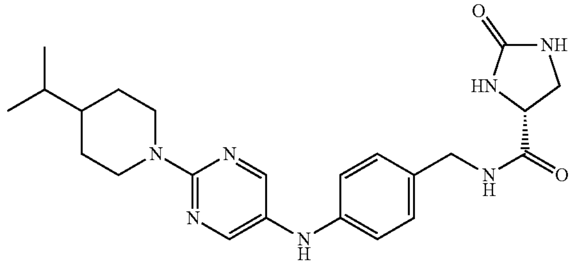
599
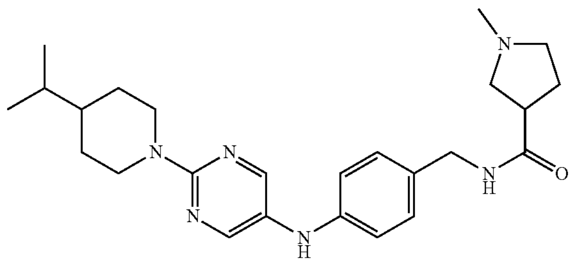
-continued
600
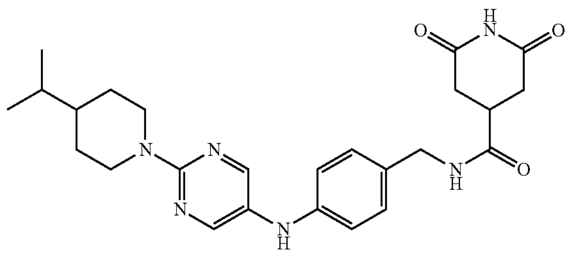
601
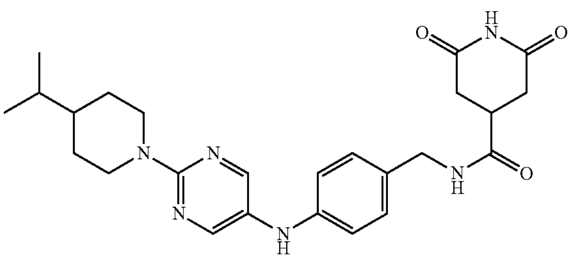
603
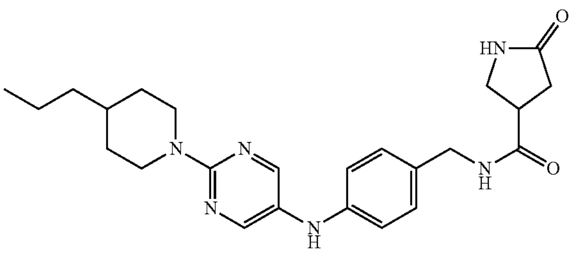
604
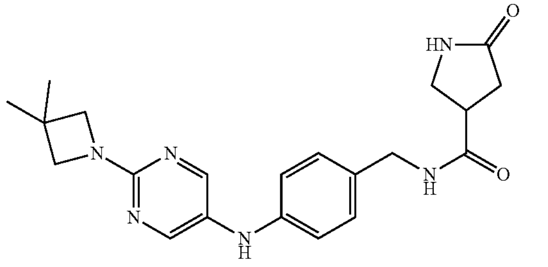
605
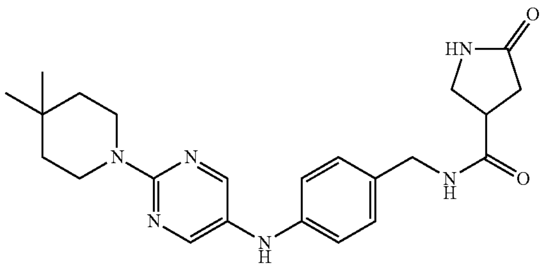

606
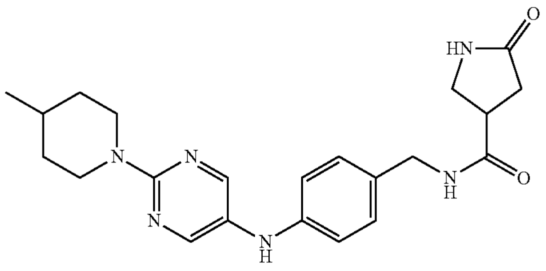
607
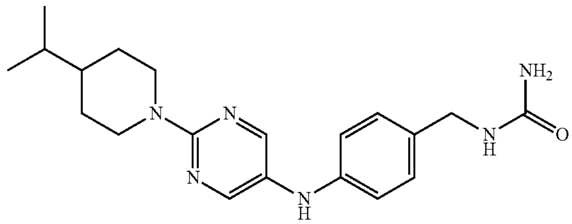
608
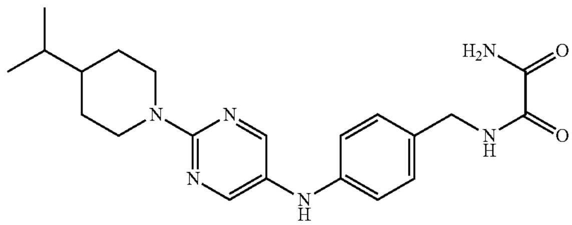
609
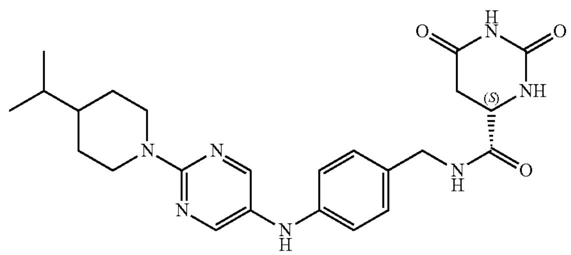
610
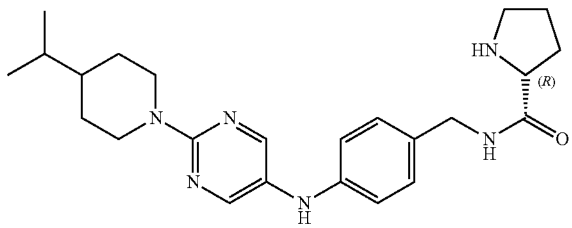
611
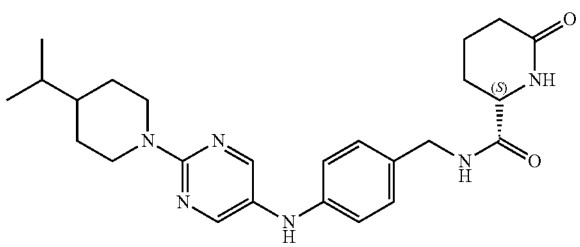
612
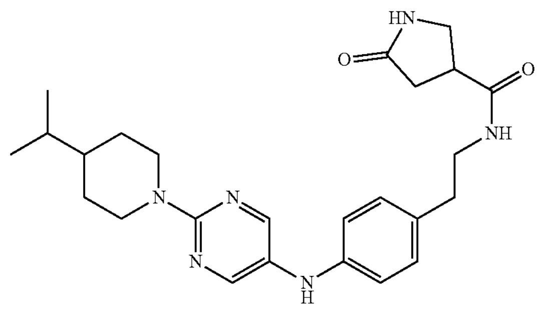
613
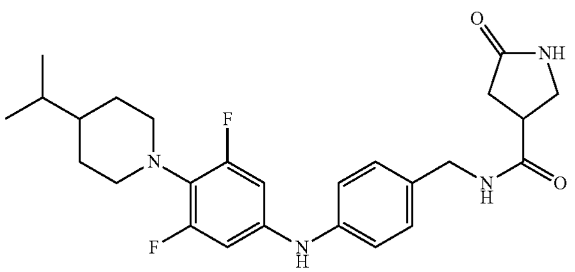
614
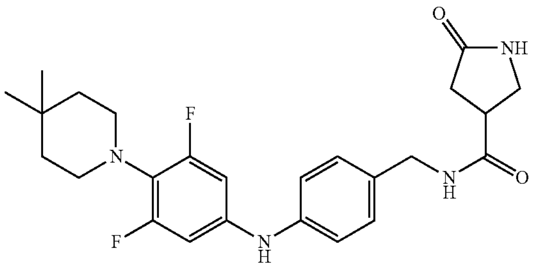
615
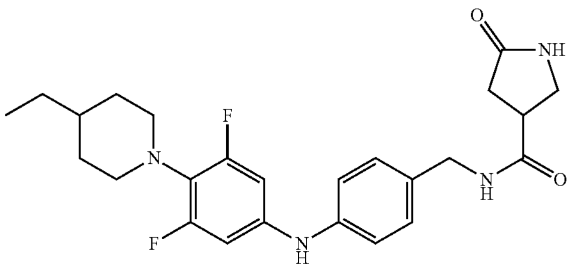
616
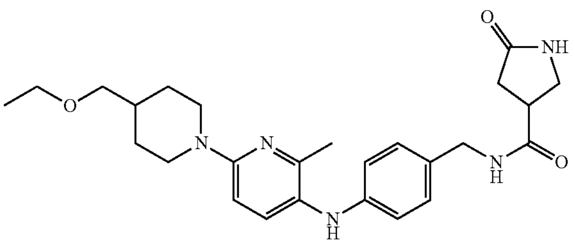

-continued
617
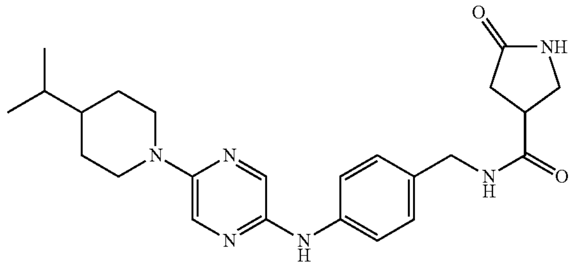
623
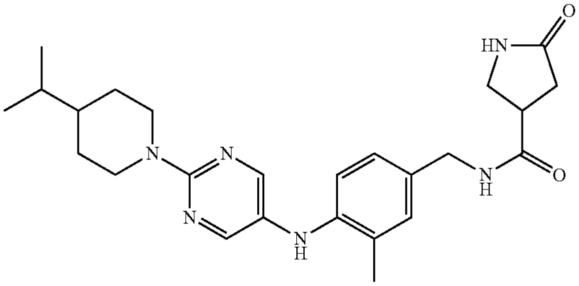
625
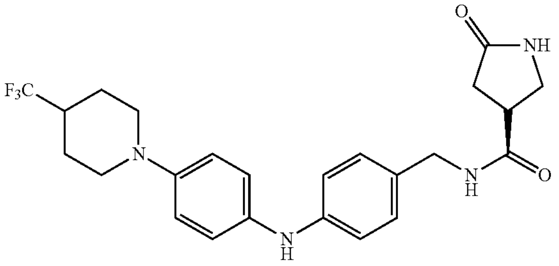
626
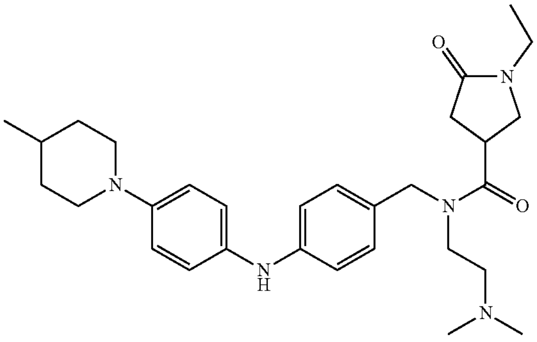
627
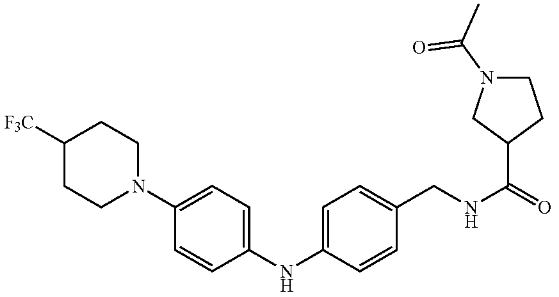
-continued
629
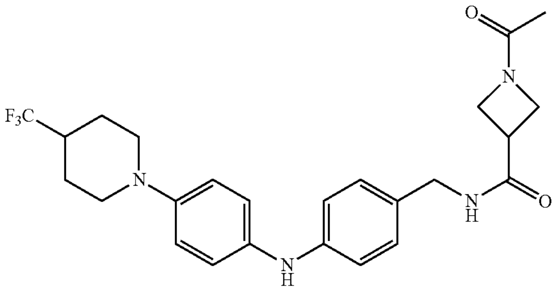
631
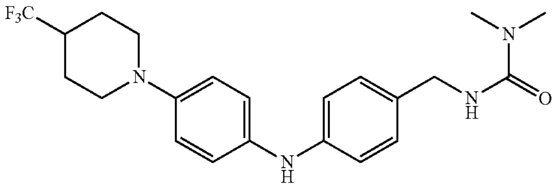
632
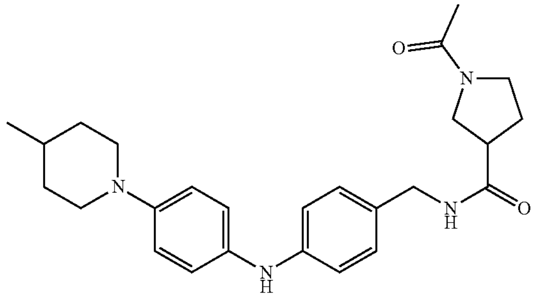
634
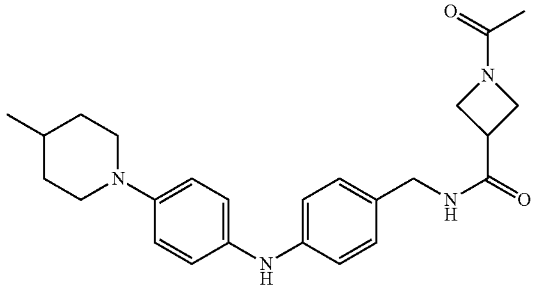
636
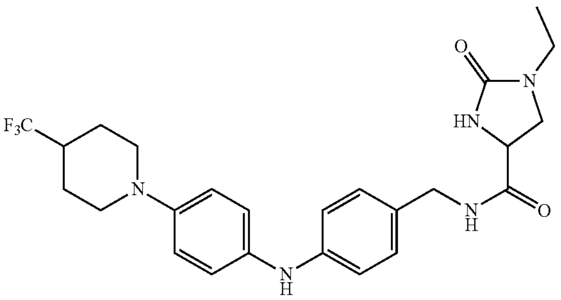

-continued
637
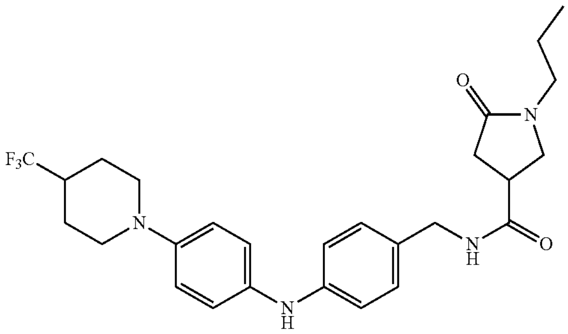
638
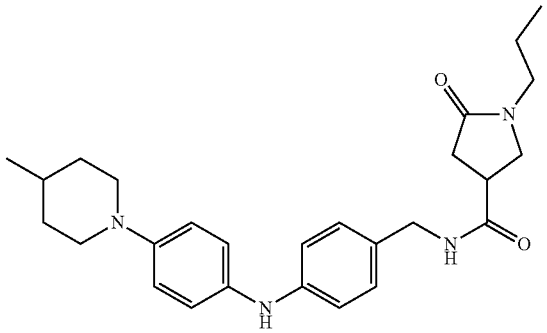
639
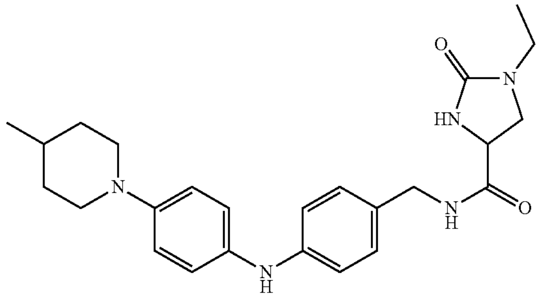
640
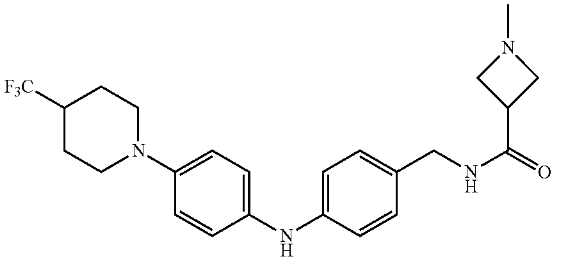
641
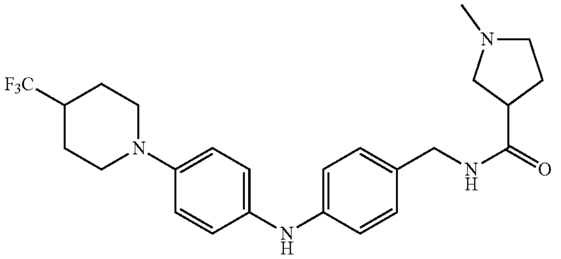
-continued
642
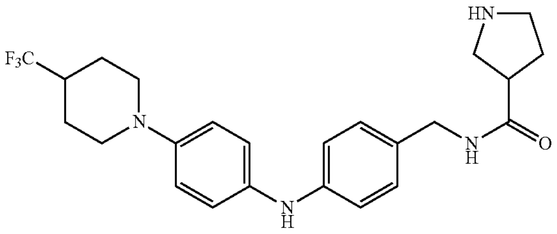
643
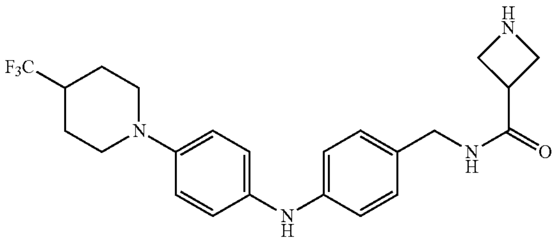
645
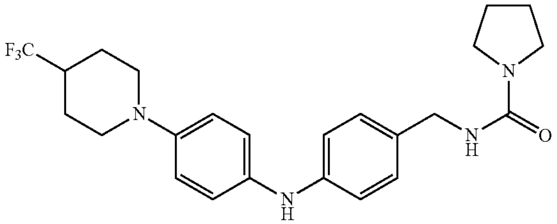
647
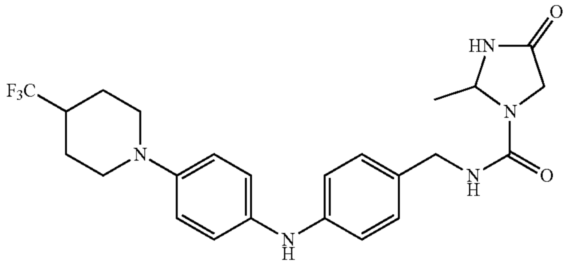
648
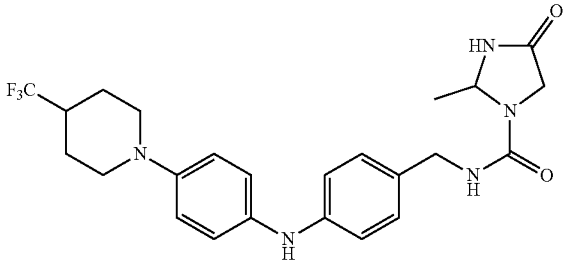

-continued
649
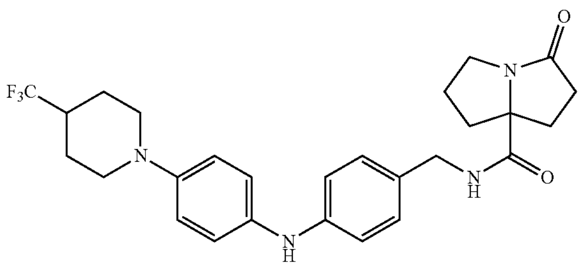
650
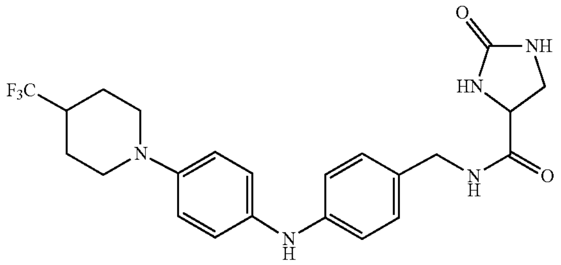
651
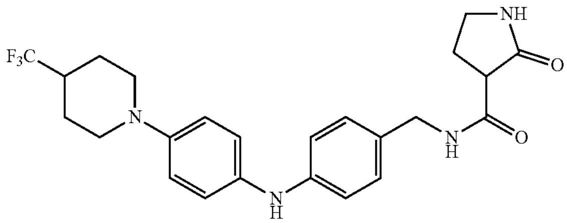
652
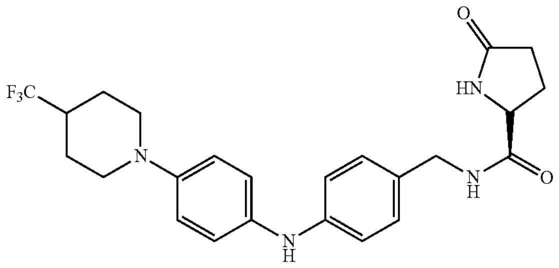
653
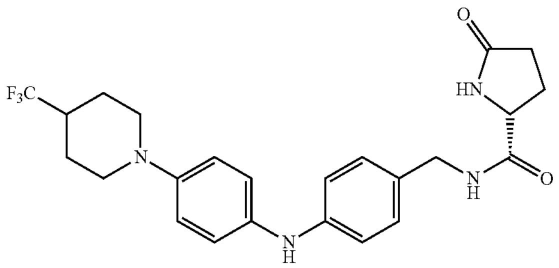
-continued
655
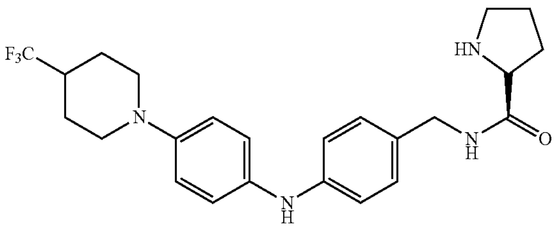
656
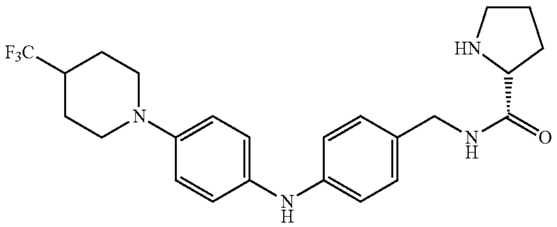
657
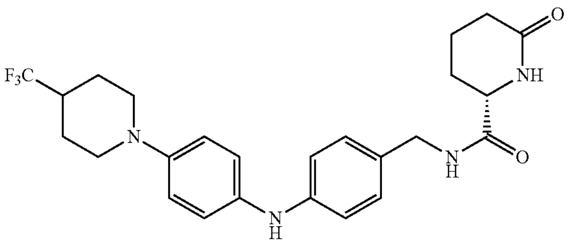
658
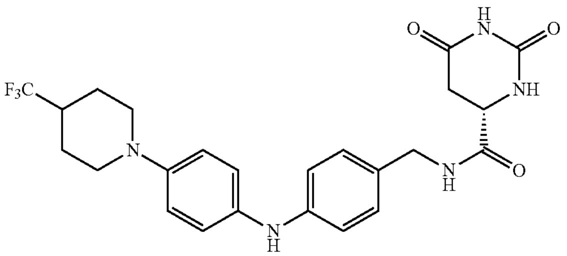
659
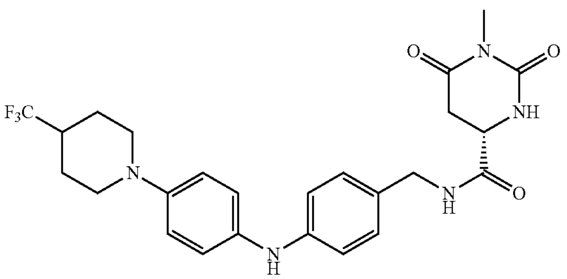
660
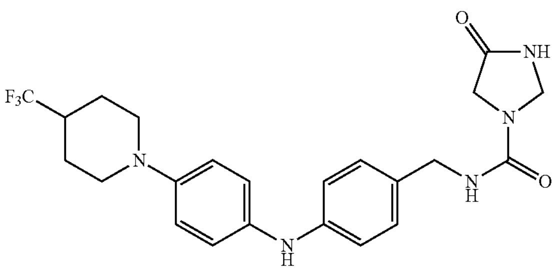

-continued
661
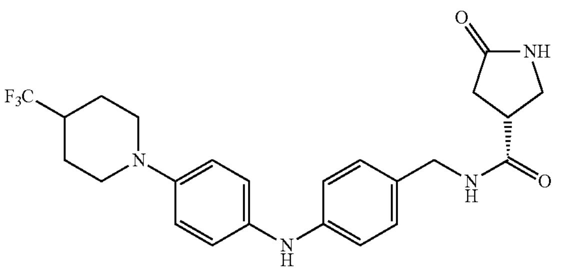
662
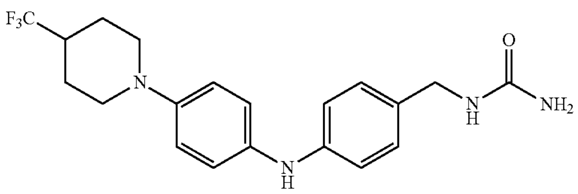
663
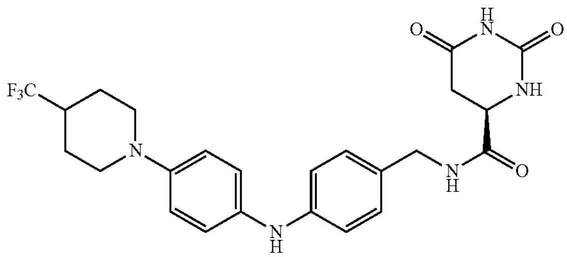
664
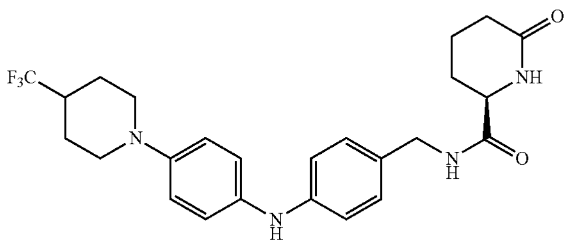
665
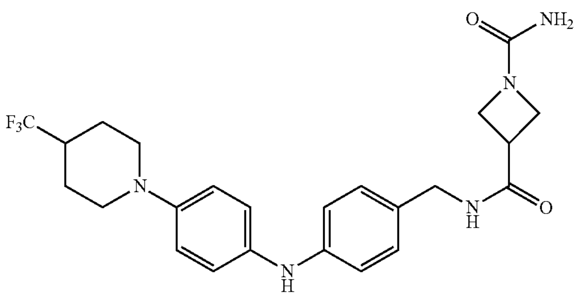
-continued
666
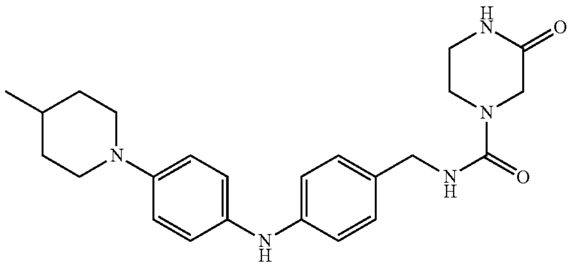
667
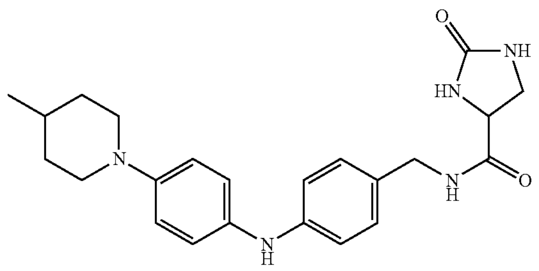
668
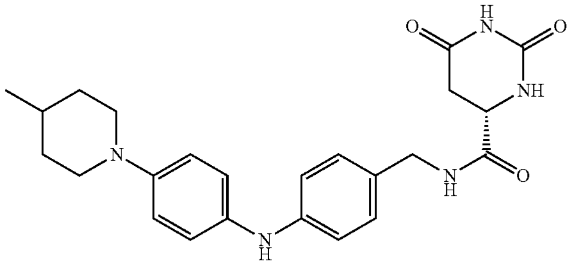
669
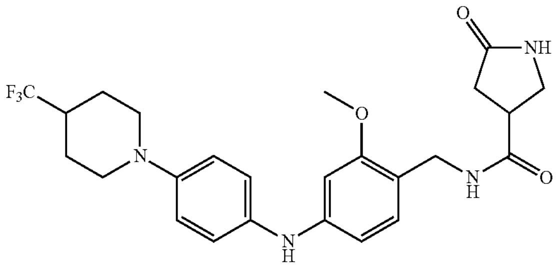
670
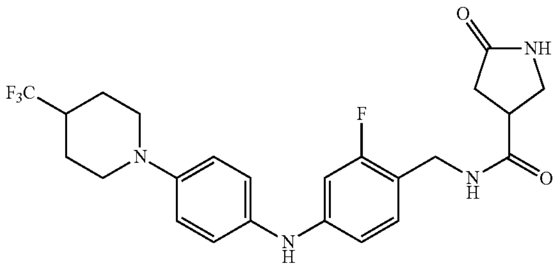

-continued
671
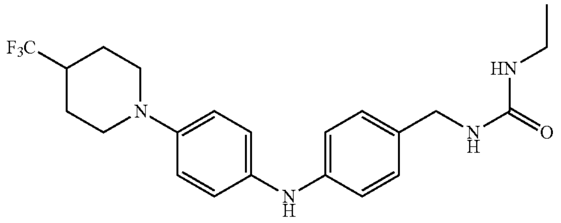
672
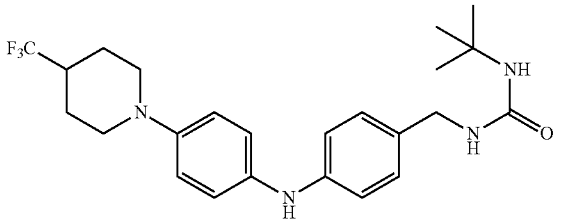
673
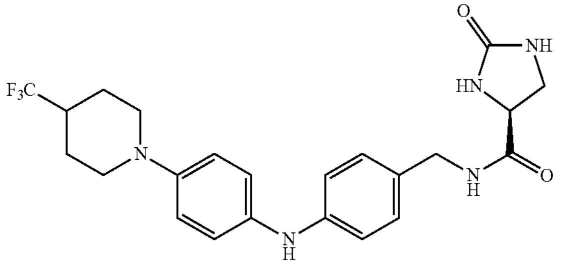
674
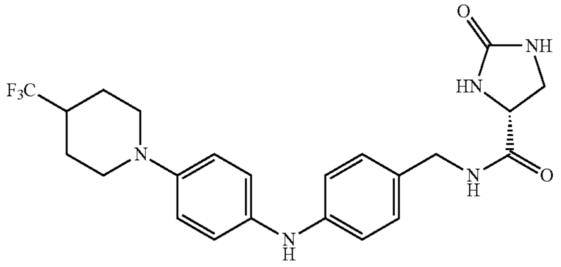
675
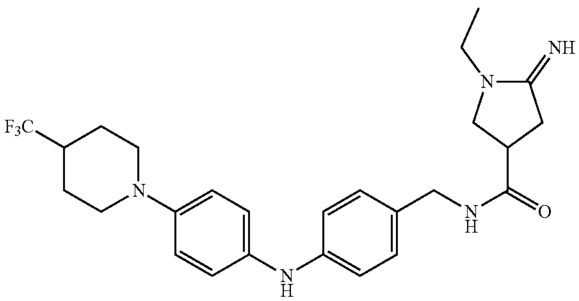
-continued
676
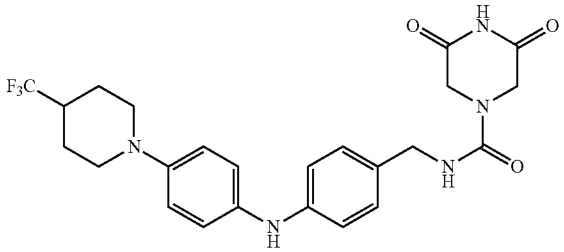
677
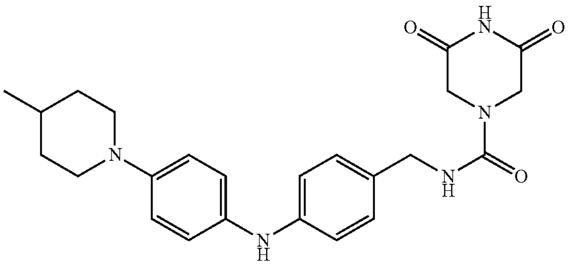
678
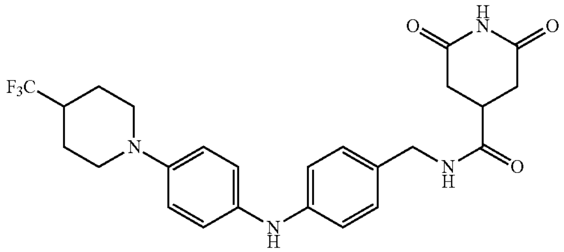
680
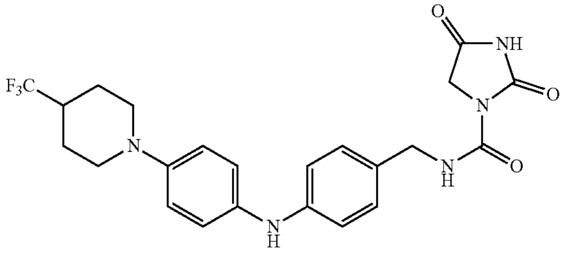
682
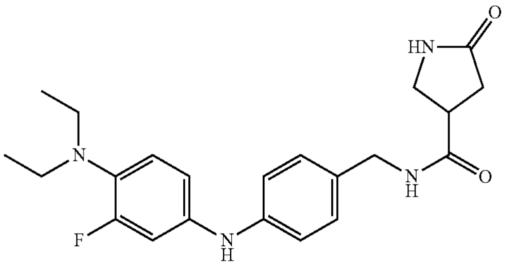

-continued
683
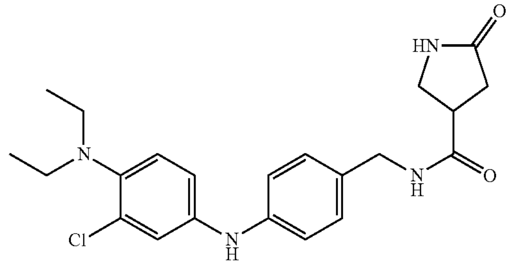
684
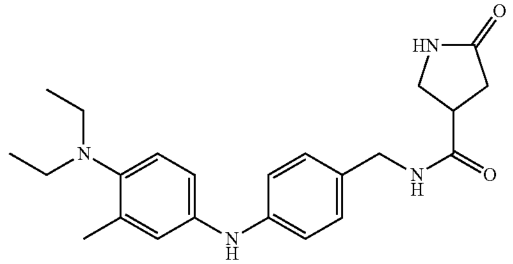
685
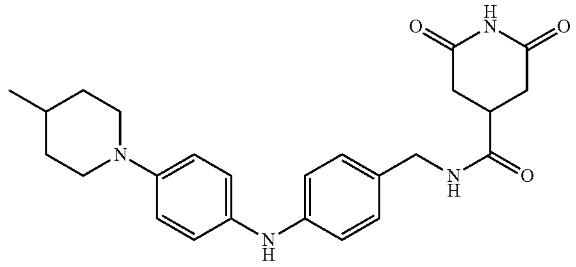
686
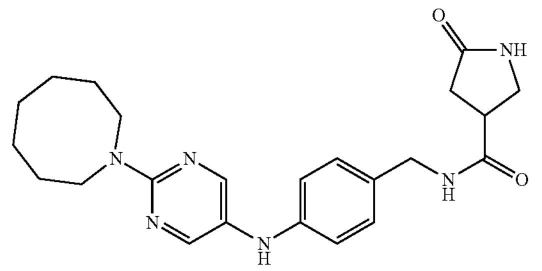
687
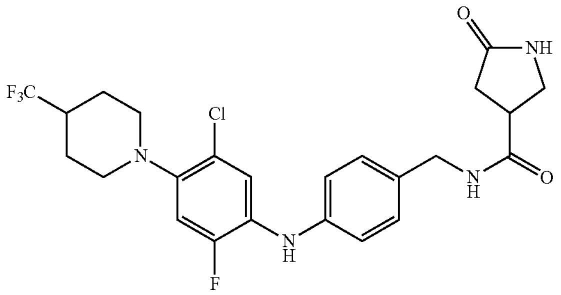
-continued
688
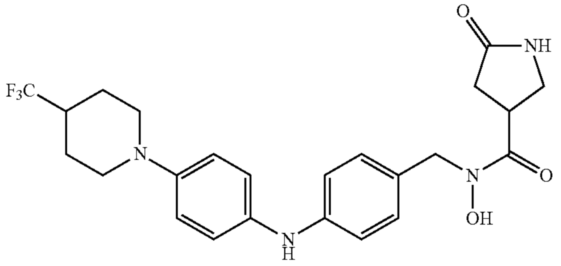
689
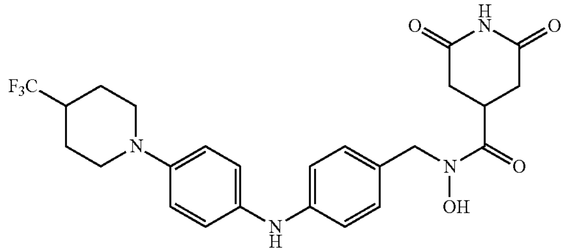
693
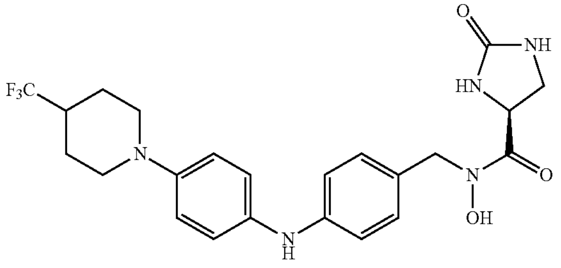
694
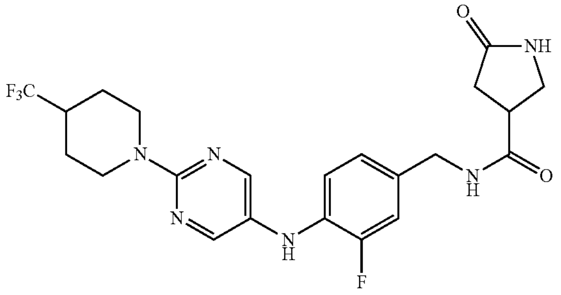
696
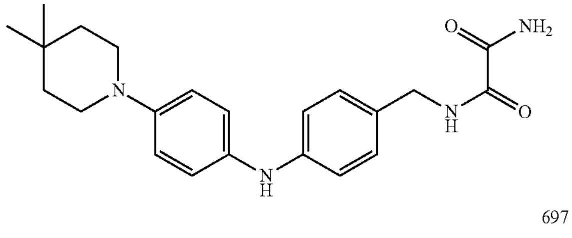
697
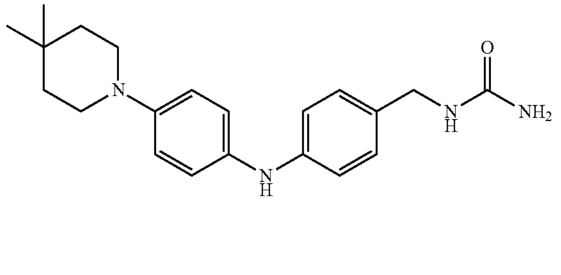

-continued
698
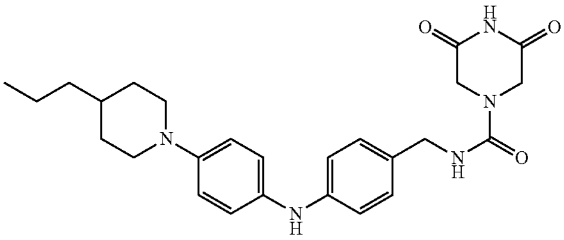
699
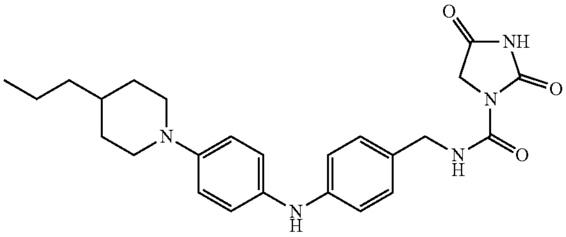
702
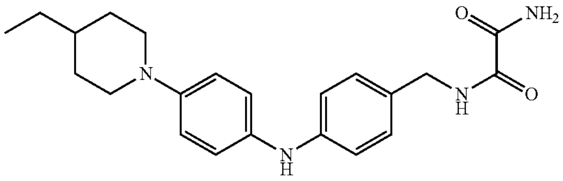
703
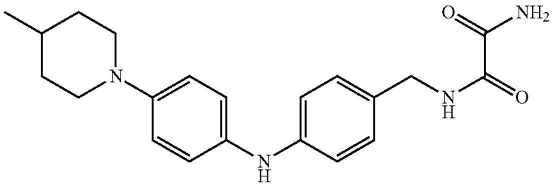
704
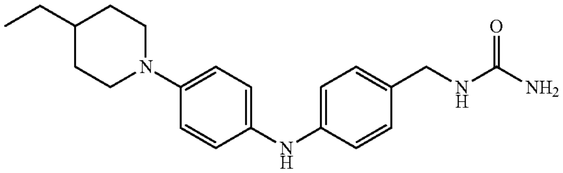
705
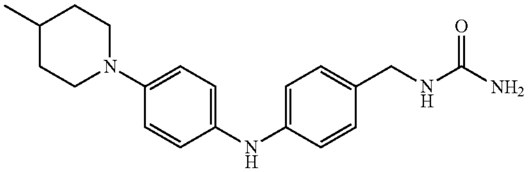
-continued
709
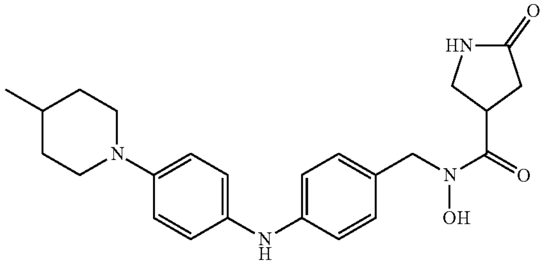
710
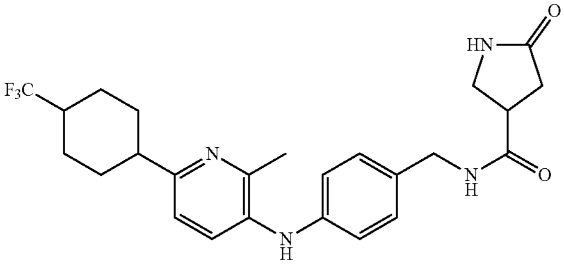
711
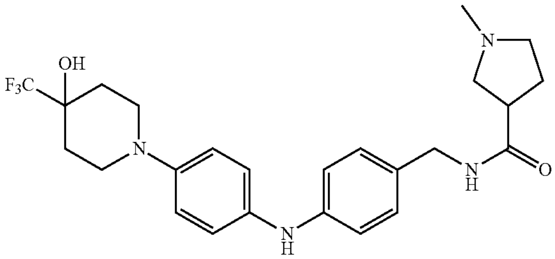
712
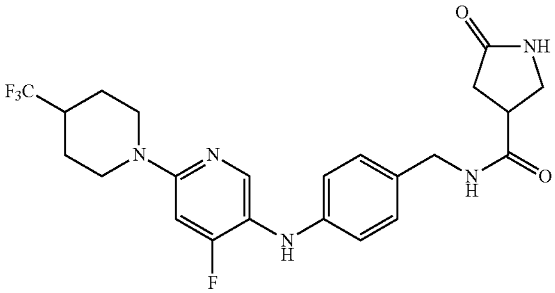
713
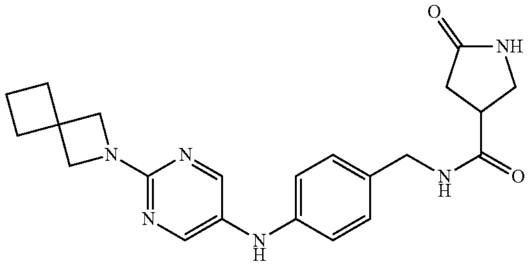

-continued
714
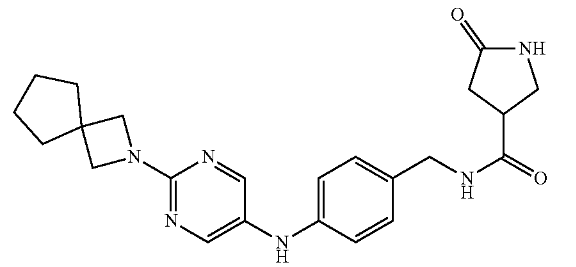
715
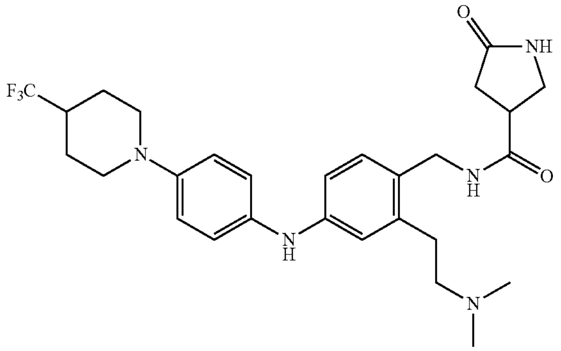
716
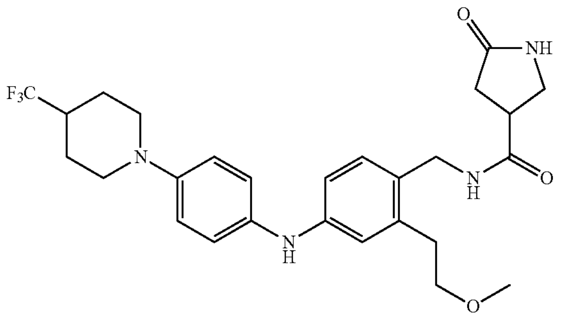
717
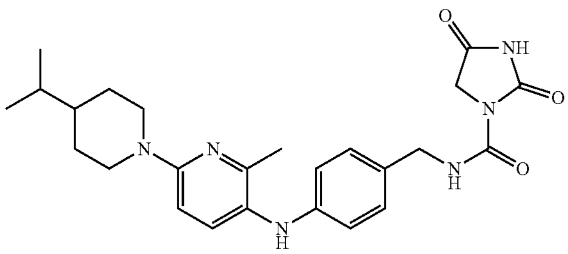
718
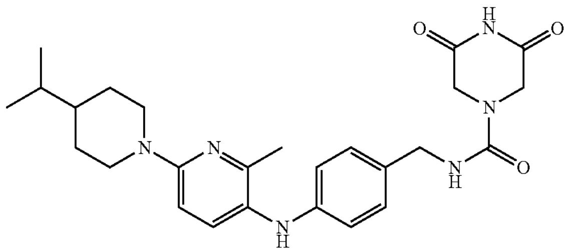
-continued
719
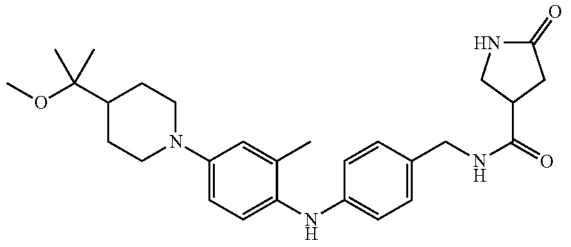
720
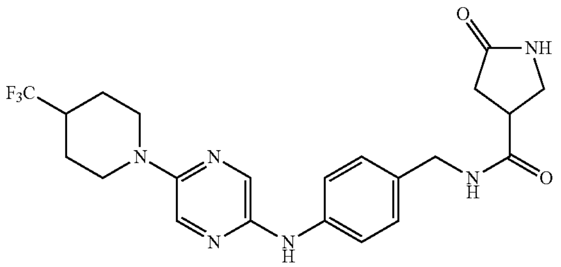
722
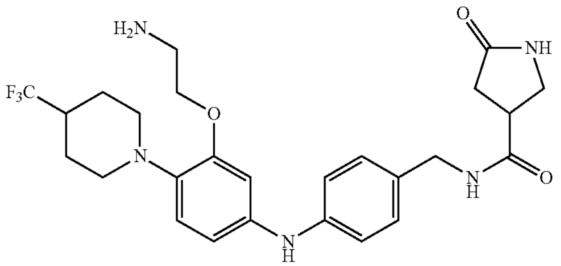
723
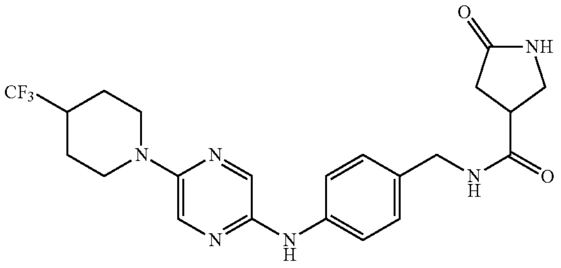
726
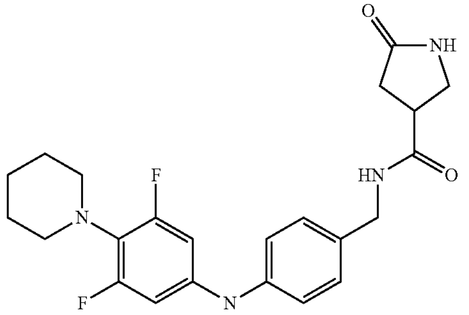

-continued
727
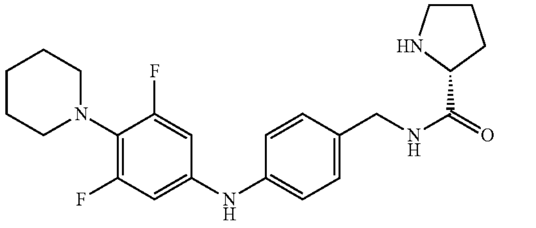
728
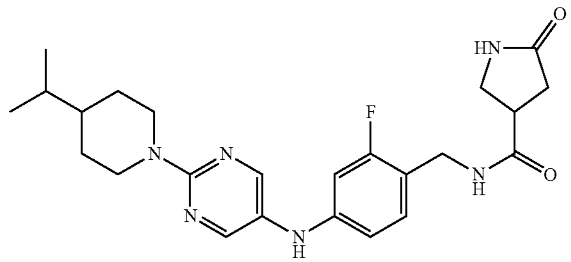
729
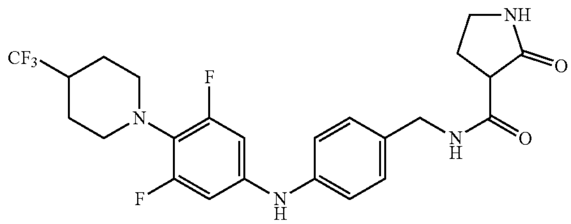
730
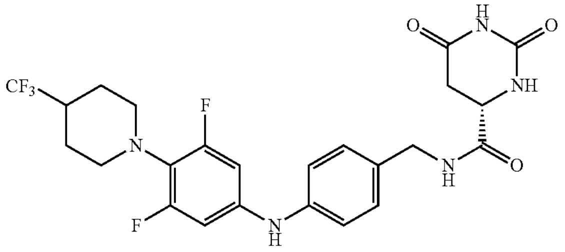
731
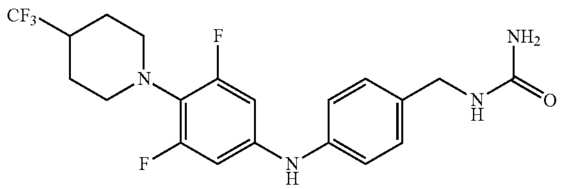
732
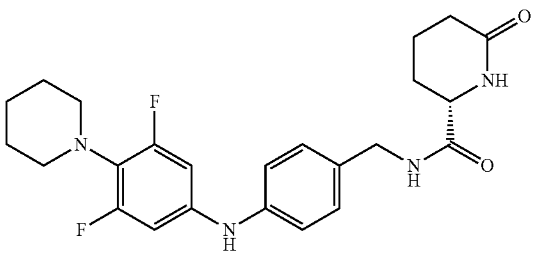
-continued
733
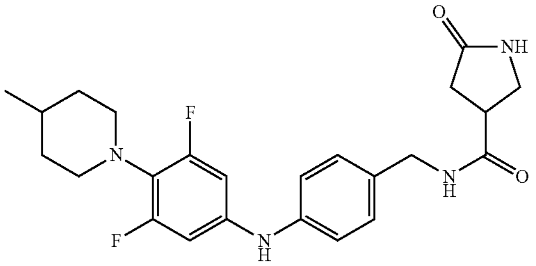
17. The compound, pharmaceutically acceptable salt, hydrate, or stereoisomer of claim 16, wherein the compound has a structure selected from:
625
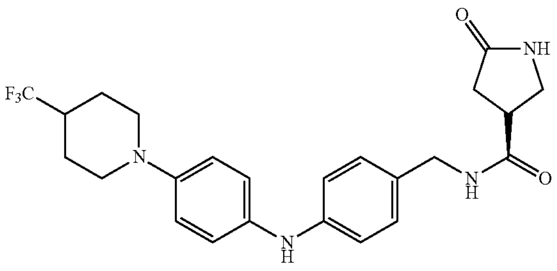
661
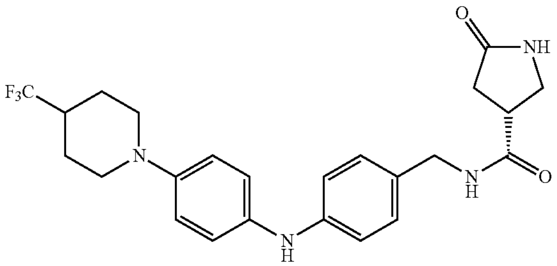
652
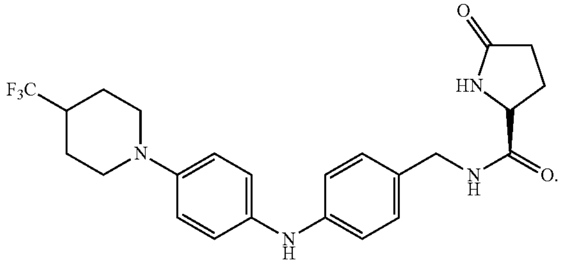
444
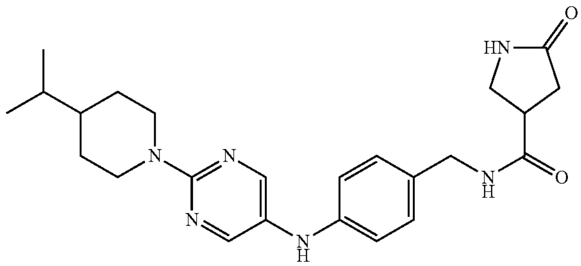

-continued

559

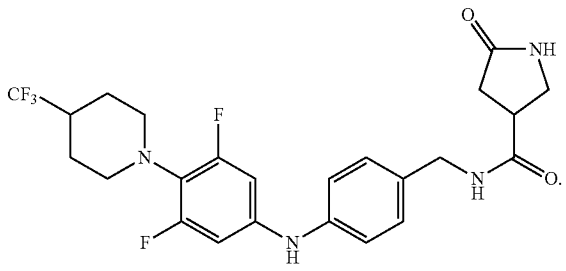

18. The compound, pharmaceutically acceptable salt, hydrate, or stereoisomer of claim 16, wherein the compound has a structure selected from:

370

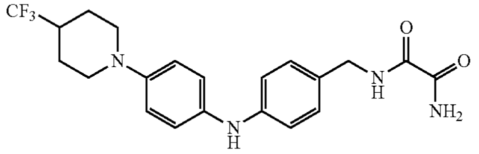

377

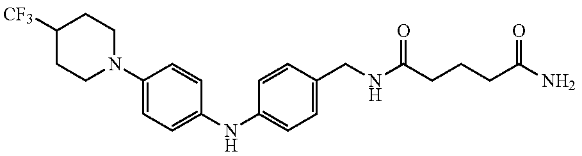

-continued

378

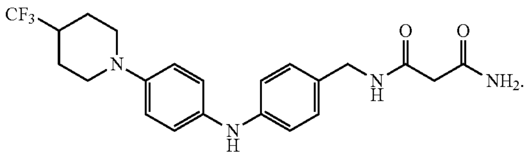

19. A pharmaceutical composition comprising a therapeutically effective amount of the compound, pharmaceutically acceptable salt, hydrate, or stereoisomer of claim 1 and one or more pharmaceutically acceptable excipients, in predetermined, unit dosage form.

20. A method of inhibiting ferroptosis activity, or modulating or inhibiting a disease associated with ferroptosis dysregulation in a person in need thereof, comprising administering to the person a therapeutically effective amount of the compound, pharmaceutically acceptable salt, hydrate, or stereoisomer of claim 1, wherein the disease associated with ferroptosis dysregulationin is selected from muscular dystrophy, ischemia and ischemia reperfusion injury, diabetes, and cancer-chemo/radiation therapy-induced cell-death.

* * * * *